US012624018B1

(12) United States Patent
VanHuis et al.

(10) Patent No.: US 12,624,018 B1
(45) **Date of Patent: *May 12, 2026**

(54) INHIBITORS OF RIPK2 AND MEDICAL USES THEREOF

(71) Applicant: Odyssey Therapeutics, Inc., Boston, MA (US)

(72) Inventors: Chad VanHuis, Hartland, MI (US); Shifeng Pan, San Diego, CA (US); Dominik K. Koelmel, Ann Arbor, MI (US); Robert Aversa, Watertown, MA (US); Clarke Taylor, Ann Arbor, MI (US); Marta Wlodarska, Cambridge, MA (US)

(73) Assignee: Odyssey Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/316,575

(22) Filed: Sep. 2, 2025

Related U.S. Application Data

(63) Continuation of application No. 19/131,704, filed as application No. PCT/US2023/080859 on Nov. 22, 2023.

(Continued)

(51) Int. Cl.

| | |
|---|---|
| ***C07D 401/12*** | (2006.01) |
| ***A61K 31/4709*** | (2006.01) |
| ***A61K 31/496*** | (2006.01) |
| ***A61K 31/497*** | (2006.01) |
| ***A61K 31/4995*** | (2006.01) |
| ***A61K 31/501*** | (2006.01) |
| ***A61K 31/506*** | (2006.01) |
| ***A61K 31/517*** | (2006.01) |
| ***A61K 31/519*** | (2006.01) |
| ***A61K 31/5377*** | (2006.01) |
| ***A61K 31/5386*** | (2006.01) |
| ***A61K 31/541*** | (2006.01) |
| ***A61K 31/675*** | (2006.01) |
| ***C07B 59/00*** | (2006.01) |
| ***C07D 401/14*** | (2006.01) |
| ***C07D 403/12*** | (2006.01) |

(Continued)

(52) U.S. Cl.

CPC ........ *C07D 401/12* (2013.01); *A61K 31/4709* (2013.01); *A61K 31/496* (2013.01); *A61K 31/497* (2013.01); *A61K 31/4995* (2013.01); *A61K 31/501* (2013.01); *A61K 31/506* (2013.01); *A61K 31/517* (2013.01); *A61K 31/519* (2013.01); *A61K 31/5377* (2013.01); *A61K 31/5386* (2013.01); *A61K 31/541* (2013.01); *A61K 31/675* (2013.01); *C07B 59/002* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/12* (2013.01); *C07D 417/14* (2013.01); *C07D 451/06* (2013.01); *C07D 487/08* (2013.01); *C07D 491/107* (2013.01); *C07D 498/08* (2013.01); *C07F 9/65583* (2013.01); *C07F 9/65685* (2013.01); *C07K 16/2839* (2013.01)

(58) Field of Classification Search

CPC ........... B81B 2201/042; B81B 3/0021; G02B 26/001; G06F 3/1212; G06F 3/1247; G06F 3/1277; G06F 3/1285

See application file for complete search history.

(56) References Cited

U.S. PATENT DOCUMENTS

| | | | |
|---|---|---|---|
| 7,973,164 | B2 | 7/2011 | Jung et al. |
| 8,153,643 | B2 | 4/2012 | Ple et al. |

(Continued)

FOREIGN PATENT DOCUMENTS

| | | | |
|---|---|---|---|
| CN | 113563260 | A | 10/2021 |
| WO | WO-98/28269 | A1 | 7/1998 |

(Continued)

OTHER PUBLICATIONS

Khan et al (Am J Physiol Gastrointest Liver Physiol 291: G803-G811, 2006). (Year: 2006).*

(Continued)

*Primary Examiner* — Jean P Cornet
(74) *Attorney, Agent, or Firm* — FOLEY HOAG LLP

(57) ABSTRACT

The present disclosure relates to RIPK2 inhibitors represented by structural formula (I):

(I)

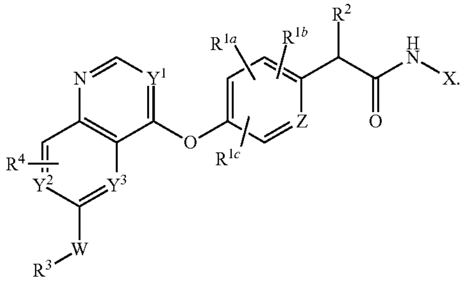

The disclosure further relates to pharmaceutical composition comprising the RIPK2 inhibitors and methods of treatment of conditions such as inflammatory diseases, autoimmune diseases, granulomatous disease, neurodegenerative disease, and cancer.

11 Claims, 1 Drawing Sheet

Related U.S. Application Data

(60) Provisional application No. 63/544,884, filed on Oct. 19, 2023, provisional application No. 63/468,591, filed on May 24, 2023, provisional application No. 63/443,760, filed on Feb. 7, 2023, provisional application No. 63/427,317, filed on Nov. 22, 2022.

(51) Int. Cl.

| | |
|---|---|
| ***C07D 403/14*** | (2006.01) |
| ***C07D 405/14*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 451/06*** | (2006.01) |
| ***C07D 487/08*** | (2006.01) |
| ***C07D 491/107*** | (2006.01) |
| ***C07D 498/08*** | (2006.01) |
| ***C07F 9/6558*** | (2006.01) |
| ***C07F 9/6568*** | (2006.01) |
| ***C07K 16/28*** | (2006.01) |

(56) References Cited

U.S. PATENT DOCUMENTS

| | | | |
|---|---|---|---|
| 9,163,017 | B2 | 10/2015 | Degoey et al. |
| 10,357,477 | B2 | 7/2019 | Chen et al. |
| 2005/0171171 | A1 | 8/2005 | Mehta et al. |

FOREIGN PATENT DOCUMENTS

| | | | | | |
|---|---|---|---|---|---|
| WO | WO-98/57937 | A2 | | 12/1998 | |
| WO | WO-99/32111 | A1 | | 7/1999 | |
| WO | WO-02/24656 | A1 | | 3/2002 | |
| WO | WO-02/094793 | A1 | | 11/2002 | |
| WO | WO-2006/040520 | A1 | | 4/2006 | |
| WO | WO-2007/099317 | A1 | | 9/2007 | |
| WO | WO-2007/099323 | A2 | | 9/2007 | |
| WO | WO-2007099326 | A1 | * | 9/2007 | ................ A61P 3/10 |
| WO | WO-2007/113548 | A1 | | 10/2007 | |
| WO | WO-2007/113565 | A1 | | 10/2007 | |
| WO | WO-2019/232275 | A1 | | 12/2019 | |
| WO | WO-2020/139748 | A1 | | 7/2020 | |
| WO | WO-2020/198026 | A1 | | 10/2020 | |
| WO | WO-2021/226547 | A2 | | 11/2021 | |
| WO | WO-2024/112854 | A1 | | 5/2024 | |
| WO | WO-2025/085928 | A1 | | 4/2025 | |

OTHER PUBLICATIONS

International Search Report and Written Opinion for International Application No. PCT/US25/31212 dated Sep. 29, 2025.

International Search Report and Written Opinion for International Application No. PCT/US25/31234 dated Sep. 29, 2025.

Wu et al., "Design, synthesis, and structure-activity relationship of novel RIPK2 inhibitors." Bioorganic & Medicinal Chemistry Letters 75 (2022): 128968.

Haile et al., "Discovery of a first-in-class receptor interacting protein 2 (RIP2) kinase specific clinical candidate, 2-((4-(benzo [d] thiazol-5-ylamino)-6-(tert-butylsulfonyl) quinazolin-7-yl) oxy) ethyl dihydrogen phosphate, for the treatment of inflammatory diseases." J Med Chem (2019); 62(14): 6482-6494.

International Search Report and Written Opinion for International Application No. PCT/US23/80859 dated Feb. 6, 2024.

Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors", Journal of Medicinal Chemistry, 2018, 61, 8797-8810.

Suebsuwong et al., "Receptor-interacting protein kinase 2 (RIPK2) and nucleotide-binding oligomerization domain (NOD) cell signaling inhibitors based on a 3, 5-diphenyl-2-aminopyridine scaffold." European Journal of Medicinal Chemistry 200 (2020): 112417.

Topal et al., "RIPK2 NODs to XIAP and IBD", Seminars in Cell and Developmental Biology, 109 (2021) 144-150.

* cited by examiner

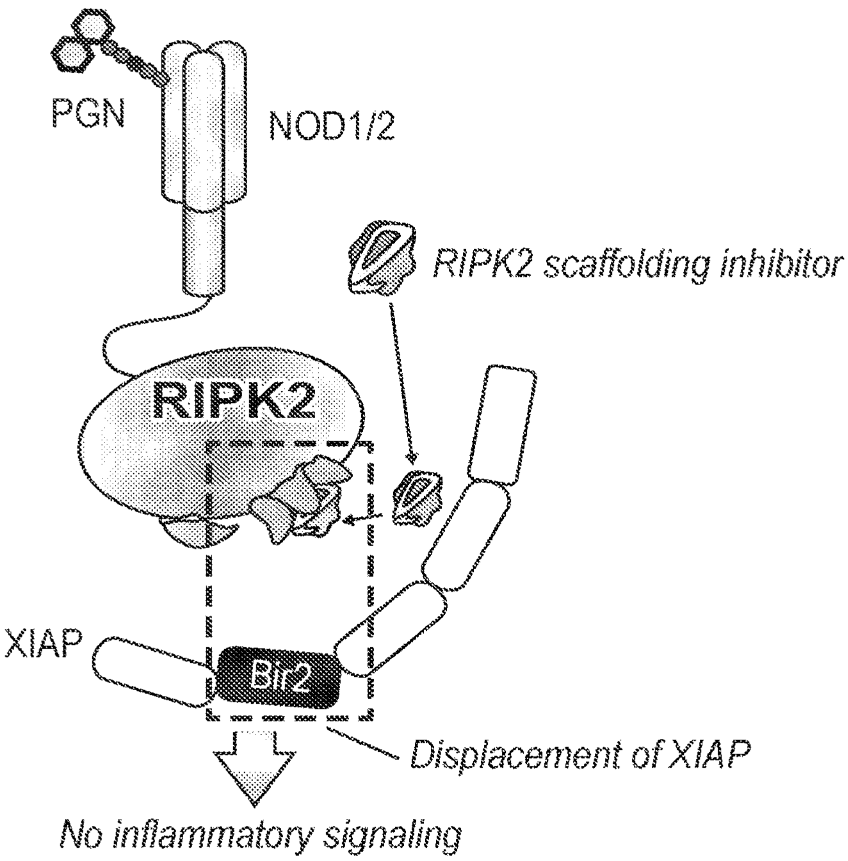
PGN
NOD1/2
RIPK2 scaffolding inhibitor
RIPK2
XIAP
Bir2
Displacement of XIAP
No inflammatory signaling

INHIBITORS OF RIPK2 AND MEDICAL USES THEREOF

RELATED APPLICATIONS

This application is a continuation of U.S. application Ser. No. 19/131,704, filed May 21, 2025, which is the U.S. National Stage of International Application No. PCT/US2023/080859, filed Nov. 22, 2023, which claims the benefit of priority to U.S. Provisional Patent Application No. 63/544,884, filed Oct. 19, 2023; U.S. Provisional Patent Application No. 63/468,591, filed May 24, 2023; U.S. Provisional Patent Application No. 63/443,760, filed Feb. 7, 2023; and U.S. Provisional Patent Application No. 63/427,317, filed Nov. 22, 2022. The entire teachings of the above applications are incorporated herein by reference.

BACKGROUND OF THE INVENTION

Autoinflammatory disorders are diseases characterized by systemic and organ-specific inflammation due to abnormalities in the innate immune system. These abnormalities are associated with numerous inflammatory disorders such as inflammatory bowel disease (including Crohn's disease and ulcerative colitis), sarcoidosis, inflammatory arthritis, peritonitis, multiple sclerosis, rheumatoid arthritis, and Wegener's granulomatosis. These disorders affect millions of people.

NOD1 and NOD2 (nucleotide-binding oligomerization domains 1 and 2) are members of the NOD-like receptor (NLR) family, which represent important components of the mammalian innate immune system, serving as intracellular receptors for peptidoglycan (PGN), a component of bacterial cell walls. NOD1 and NOD2 detect the presence of intracellular bacteria by binding to PGN fragments. Heredity polymorphisms in the genes encoding NOD1 and NOD2 have been associated with inflammatory disorders. Once activated, NOD signaling leads to activation of NF-kB and MAP kinases, resulting in the transcription of pro-inflammatory kinases and the induction of autophagy.

NOD1 and NOD2 require RIPK2 as a common scaffolding (adaptor) protein to propagate downstream signals that lead to aberrant proinflammatory innate immune activation. In particular, RIPK2 is needed for NF-kB activation and subsequent cytokine production. Inhibition of RIPK2 resolves abnormal inflammation states such as intestinal inflammation. Accordingly, inhibitors of RIPK2 have potential to act as therapeutic agents, for example, to reduce or resolve inflammation for inflammatory disorders such as inflammatory bowel disease (including Crohn's disease and ulcerative colitis), sarcoidosis, inflammatory arthritis, peritonitis, multiple sclerosis, rheumatoid arthritis, and Wegener's granulomatosis.

In the context of malignant transformation, knockdown of RIPK2 downregulated RNA expression of E-cadherin and vimentin, proteins involved in epithelial-to-mesenchymal transition (EMT) and the promotion of the metastatic phenotype indicating that RIPK2 is involved in cell migration and metastasis.

Accordingly inhibitors of RIPK2 activity which can block RIPK2-dependent pro-inflammatory signaling and thereby provide a therapeutic benefit in auto-inflammatory diseases and other disorders characterized by increased and/or dysregulated RIPK2 activity are needed.

A description of example embodiments of the invention follows.

SUMMARY OF THE INVENTION

In a first embodiment, the present invention relates a compound represented by structural formula (I):

or a pharmaceutically acceptable salt thereof:

(I)

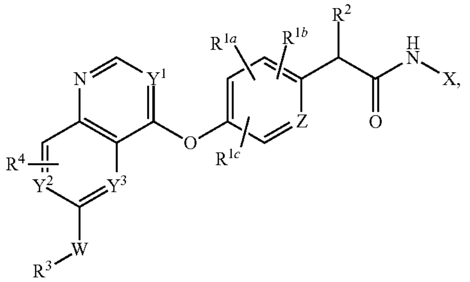

wherein:

- $R^{1a}$, $R^{1b}$, and $R^{1c}$ are each independently selected from H, halogen, CN, and $C_{1-6}$ alkyl;
- $R^2$ is H or $C_{1-3}$ alkyl;
- $R^3$ is selected from halogen, 4- to 10-membered heterocyclyl, 5-12 membered heteroaryl, $S(=O)_2R^5$, $S(=O)(=NR^6)(R^7)$, $QR^7$, $C(=O)NR^8R^9$, $NH(C=O)R^5$, CN, $NR^8R^9$, $P(=O)R^{8a}R^{9a}$;
- $R^4$ is selected from H, halogen, $C_{1-6}$ alkyl, and $C_{1-6}$ alkoxy;
- $R^5$ is selected from $NR^{10}R^{11}$, $C_{1-6}$ alkyl, $C_{3-6}$ cycloalkyl, and 4- to 10-membered heterocyclyl;
- $R^6$ is selected from H, CN, and $C_{1-6}$ alkyl;
- $R^7$ is selected from $C_{1-6}$ alkyl, $C_{3-6}$ cycloalkyl, and 4- to 10-membered heterocyclyl, 5-12 membered heteroaryl, or
- $R^6$ and $R^7$ taken together with the nitrogen and sulfur atoms to which they are attached form 4- to 10-membered heterocyclyl;
- Q is selected from O, S, —S(=O)—, and —C(=O)—;
- $R^8$ and $R^9$ are each independently selected from H, $C_{1-6}$ alkyl, $C_{1-6}$ deuteroalkyl, $C_{3-6}$ cycloalkyl, and 4- to 10-membered heterocyclyl, or
- $R^8$ and $R^9$ taken together with the nitrogen atom to which they are attached form 4- to 10-membered heterocyclyl;
- $R^{8a}$ and $R^{9b}$ are each independently $C_{1-6}$ alkyl, or
- $R^{8a}$ and $R^{9a}$ taken together with the phosphorus atom to which they are attached form 4- to 10-membered heterocyclyl;
- $R^{10}$ and $R^{11}$ are each independently H or $C_{1-6}$ alkyl, or
- $R^{10}$ and $R^{11}$ taken together with the nitrogen to which they are attached form 4- to 10-membered heterocyclyl;
- W is selected from O, $NR^2$, $O(C_{1-2}$ alkylene), $NH(C_{1-2}$ alkylene), $C_{1-2}$ alkylene, $C_{3-6}$ cycloalkylene, and a bond;
- X is a moiety represented by one of the following structural formulas:

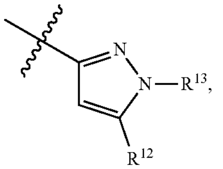
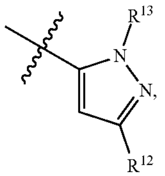
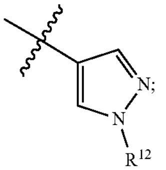
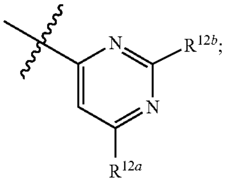
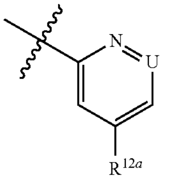
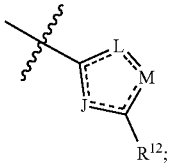

$Y^1$ is CH or N;

$Y^2$ and $Y^3$ are each independently $CR^4$ or N;

U is $CR^{12b}$ or N;

Z is $CR^{1b}$ or N;

L, M, and J are each independently selected from N, O, or S, provided that two of L, M, and J are N;

$R^{12}$ is selected from $C_{3-6}$ alkyl, $C_{3-6}$ cycloalkyl, $C_{5-12}$ bridged bicyclic carbocyclyl, and 4- to 10-membered heterocyclyl;

$R^{12a}$ is selected from $C_{1-6}$ alkyl, $C_{1-6}$ deuteroalkyl, $C_{3-6}$ cycloalkyl, $C_{5-12}$ bridged bicyclic carbocyclyl, and 4- to 10-membered heterocyclyl;

$R^{12b}$ and $R^{13}$ are each independently H or $C_{1-6}$ alkyl; and is a single bond or a double bond, wherein each $C_{1-6}$ alkyl, $C_{1-3}$ alkyl, $C_{1-2}$ alkylene, $C_{3-6}$ alkyl, $C_{3-6}$ cycloalkyl, $C_{1-6}$ alkoxy, $C_{5-12}$ bridged bicyclic carbocyclyl, 5-12 membered heteroaryl, and 4- to 10-membered heterocyclyl is optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{1-6}$ deuteroalkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, ($C_{1-6}$) alkylamino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 8-membered heterocyclyl, and 5- to 12-membered heteroaryl, wherein $R^{14}$, $R^{15}$, $R^{18}$, $R^{18a}$, $R^{20}$, $R^{20a}$, $R^{24}$, and $R^{27}$ are each independently hydrogen or $C_{1-6}$ alkyl;

$R^{16}$ and $R^{17}$ are each independently selected from hydrogen, $C_{1-6}$ alkyl, hydroxy($C_{1-6}$)alkyl, and halo($C_{1-6}$)alkyl;

$R^{19}$ and $R^{23}$ are each independently $C_{1-6}$ alkyl or halo($C_{1-6}$)alkyl;

$R^{21}$, $R^{22}$, $R^{25}$ and $R^{26}$ are each independently selected from H, $C_{1-6}$ alkyl, $C_{1-3}$ alkoxy($C_{1-6}$)alkyl, hydroxy($C_{1-6}$)alkyl, cyano($C_{1-6}$)alkyl, amino($C_{1-6}$)alkyl, $C_{1-3}$ alkylamino($C_{1-6}$)alkyl, and di($C_{1-3}$)alkylamino($C_{1-6}$)alkyl; or $R^{21}$ and $R^{22}$ or $R^{25}$ and $R^{26}$, together with the nitrogen to which they are attached, form a 3-8 membered ring optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 10-membered heterocyclyl, and 5- to 12-membered heteroaryl.

provided that when $Y^2$ is CH substituted with $R^4$ and $R^4$ is optionally substituted $C_{1-6}$ alkoxy, W—$R^3$ is not CN or optionally substituted $C_{1-6}$ alkoxy; and provided that when $Y^1$, $Y^2$ and $Y^3$ are each CH, then W—$R^3$ is not F.

In a second embodiment, the present invention relates to a pharmaceutical composition comprising a compound or pharmaceutically acceptable salt thereof described herein with respect to the first embodiment and various aspects thereof, and a pharmaceutically acceptable excipient.

In a third embodiment, the present invention relates to a method of treating a disease or disorder, comprising administering to a subject in need thereof a therapeutically effective amount of a compound or a pharmaceutically acceptable salt of the compound described herein with respect to the first embodiment and various aspects thereof (e.g., a Compound of Formula (I) or a pharmaceutically acceptable salt thereof) or a pharmaceutical composition described herein with respect to the second embodiment and various aspects thereof, wherein the disease or disorder is selected from inflammatory diseases, autoimmune diseases, granulomatous diseases, cancer and neurodegenerative diseases.

In a fourth embodiment, the present relates to a method of treating a RIP2 kinase-mediated disease or disorder, comprising administering to a subject in need thereof a therapeutically effective amount of a compound described herein with respect to the first embodiment and various aspects thereof (e.g., a Compound of Formula (I) or a pharmaceutically acceptable salt thereof) or a pharmaceutical composition described herein with respect to the second embodiment and various aspects thereof. In one aspect, the RIP2 kinase-mediated disease or disorder is a disease or disorder wherein inhibition of RIP2 kinase would provide benefit. In a particular aspect, the disease or disorder is selected from an inflammatory disease, autoimmune disease, granulomatous disease, cancer, and neurodegenerative disease.

In a fifth embodiment, the present invention relates to the use of a compound of Formula (I) or a pharmaceutically acceptable salt thereof in the manufacture of a medicament for use in treating RIP2 kinase-mediated diseases or disorders (e.g., inflammatory diseases, autoimmune diseases, granulomatous diseases, cancer or neurodegenerative diseases).

In a sixth embodiment, the present invention relates to a compound of Formula (I) or a pharmaceutically acceptable salt thereof for use in treating RIP2 kinase-mediated diseases and disorders ((e.g., inflammatory diseases, autoimmune diseases, granulomatous diseases, cancer or neurodegenerative diseases).

BRIEF DESCRIPTION OF THE DRAWINGS

The FIGURE is a schematic representation illustrating how a RIPK2 scaffolding inhibitor locks RIPK2 in an inactive conformation, preventing interaction with XIAP and leading to complete pathway inhibition.

DETAILED DESCRIPTION OF THE INVENTION

RIP Kinases

Protein kinases constitute a large family of structurally related enzymes that are responsible for the control of a wide variety of signal transduction processes in the cell. They have been shown to be key regulators in most cellular functions including proliferation, cell metabolism, cell survival, apoptosis, DNA damage repair, and cell motility. Uncontrolled signaling due to defective control of protein phosphorylation has been implicated in a number of diseases, including, for example, cancer, inflammation, allergies, immune diseases, CNS disorders, and angiogenesis.

Amongst the families of protein kinases, one particular example is the Receptor-Interacting Serine/Threonine Kinases including RIPK2. RIPK2 is composed of an N-terminal kinase domain and a C-terminal caspase-recruitment domain (CARD) linked via an intermediate (IM) region. The CARD domain of RIP2 kinase mediates interaction with other CARD-containing proteins, such as NOD1 and NOD2. NOD1 and NOD2 are cytoplasmic receptors which are activated by specific bacterial peptidoglycan motifs and play a key role in innate immune surveillance. Upon intracellular bacterial exposure, NOD1 or NOD2 binds to RIPK2 to coordinate NF-kB (nuclear factor k B)-mediated cytokine responses. Once associated with NOD1/2, RIPK2 undergoes autophosphorylation on Tyr 474 (Y474), and acts as a molecular scaffold to bring together other kinases (TAK1, IKKb involved in NF-kB, and MAPK activation).

Both NOD1/2 and RIPK2 are NF-kB regulated genes, and as such, their activation causes a positive feedback loop in which activation of NOD1/2:RIPK2 stimulates further activation and further inflammation. Additionally, NOD1/2 and RIPK2 expression are stimulated by a variety of mediators of inflammation, including TNF (Tumor Necrosis Factor) and IFN (Interferon). In addition to NF-kB pathway activation, the NOD1/2:RIPK2 complex stimulates autophagy, bactericidal activity, MHC Class II presentation and MAPK (Mitogen-Activated Protein Kinase) activation. Overall, this pathway modulates the innate immune system to help tailor the adaptive immune response to eradicate the offending pathogen.

Dysregulation of RIPK2-dependent signaling has been linked to autoinflammatory diseases. Patients with loss-of-function NOD2 alleles are prone to the development of Crohn's disease (CD), an inflammatory disorder of the gastrointestinal tract. NOD2/RIPK2 pathway is involved in the pathogenesis of inflammatory bowel disease (IBD). Both NOD2 and RIPK2 are upregulated in colon biopsies from CD patients as well as ulcerative colitis (UC) pediatric population. A selective RIPK2 inhibitor has been shown to block the spontaneous pro-inflammatory cytokines secretion from UC/CD patient's biopsies. This result underlines that RIPK2 activation in the UC/CD patient's mucosa leads to the pro-inflammatory status of these biopsies.

Rheumatoid arthritis (RA) is a disease where NOD2/RIPK2 plays a role. NOD2/RIPK2 pathway has been shown to be upregulated in immune cells of RA patients, suggesting that RIPK2 inhibition could be beneficial in this population.

Gain-of-function NOD2 mutations have been genetically linked to other inflammatory diseases, such as Blau Syndrome/Early Onset Sarcoidosis (EOS), a pediatric granulomatous disease characterized by uveitis, dermatitis, and arthritis. Broad genotyping of young patients suffering from allergic rhinitis and atopic dermatitis highlighted common NOD2 polymorphism with Crohn's as probable leading cause of the excessive immune response against skin tissues observed. Mutations in NOD1 have been associated with asthma and early-onset and extra-intestinal inflammatory bowel disease. Genetic and functional studies have also suggested a role for RIP2-dependent signaling in a variety of other granulomatous disorders, such as sarcoidosis.

Metabolic syndrome, a pathology closely related to obesity and overweight, results from a chronic inflammation and is characterized by hypertension, hyperglycemia and lipolysis dysfunction. Activation of the immune system through NOD1 pathway was observed in patients suffering from metabolic syndrome. A recent functional study highlighting the impact of RIPK2 inhibitors on lipolysis suggested a role for RIP2-dependent signaling in dysglycemia and lipolysis.

In cardiac hypertrophy, a complex and multifactorial pathology, inflammation was shown as important hallmark of the disease, notably through the activation of NF-kB signaling. Knockout studies of RIPK2 on hypertrophic heart mice models suggested a role of RIPK2 in the regulation of the inflammation and subsequent tissue fibrosis and hypertrophy.

Beyond immuno-inflammatory diseases, RIPK2 modulation has also been described in several cancers. In triple negative breast cancer (TNBC), RIPK2 high expression has been associated to worse progression-free survival as well as a worse overall survival. It has been shown that RIPK2 knockdown increases docetaxel sensitivity and decreases tumor and lung metastasis. Another study focusing on a new cancer gene cassette on breast cancer patients' chromosome 8 discovered RIPK2 coamplification with other tested oncogenes (such as MYC). TNBC biopsies performed in order to find druggable kinases beyond HER2 demonstrated that RIPK2 was hyper-phosphorylated in basal-like and luminal B breast cancer biopsies suggesting that this pathway could be activated in these type of TNBC. More recently, phospho-RIPK2 levels as well as NF-kB activity were shown elevated in biopsies of Inflammatory Breast Cancer. 34 head and neck squamous cell carcinoma cell lines showed that RIPK2 knockdown led to cell death, indicating central roles of the protein for cell survival. It has been proposed that RIPK2 promotes glioma cell growth by regulating TRAF3 and activating the NF-kB pathway and p38 signaling.

A new role for RIPK2 in osteosarcoma invasion was demonstrated when Gefitinib, via RIPK2 inhibition, prevented progression of pulmonary metastasis. Further, non-canonical NF-kB plays a pivotal role in non-Hodgkin's lymphoma. Finally, using a three-dimensional lymphatic endothelial cell tube formation, RIPK2 was identified as a kinase involved in lymphatic vessel remodeling, a key factor for the metastatic spread of cancer. Taken together these data strongly support the development of RIPK2 inhibitors in oncology.

RIPK2 and RIP2 kinase are used interchangeably herein and refer to Receptor-interacting protein kinase 2.

XIAP (X-linked inhibitor of apoptosis protein) ubiquitinates RIPK2 following NOD2 stimulation, and the interaction between the XIAP BIR2 domain and the RIPK2 kinase domain is needed for NOD2 signaling (FIG. 1). While the kinase function of RIPK2 is dispensable for downstream signaling, its ability to recruit and activate XIAP is needed for RIPK2 ubiquitination and signal transduction. Therefore, inhibition of RIPK2 by a scaffolding inhibitor that binds to RIPK2 and prevents interaction with XIAP can block proinflammatory responses in vitro and in vivo.

Compounds described herein have been shown to be RIPK2 scaffolding inhibitors. FIG. 1 shows how RIPK2 scaffolding inhibitor can lock RIPK2 in an inactive conformation, preventing interaction with XIAP and leading to complete pathway inhibition. Blocking scaffolding is beneficial for inhibition of RIPK2 activation in response to the microbiota. The disclosed RIPK2 scaffolding inhibitors can be used, for example, to abrogate pathogenic responses to microbiota from which inflammatory intestinal and rheumatic diseases can originate.

Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions*, Wiley Interscience, New York, 1981; Wilen et al., *Tetrahedron* 33:2725 (1977); Eliel, E. L. *Stereochemistry of Carbon Compounds*, McGraw-Hill, NY, 1962; and Wilen, S. H., *Tables of Resolving Agents and Optical Resolutions* p. 268, E. L. Eliel, Ed., Univ. of Notre Dame Press, Notre Dame, IN 1972. The invention additionally encompasses compounds as individual isomers substantially free of other isomers, and alternatively, as mixtures of various isomers.

In a formula, ∿∿∿ is a single bond where the stereochemistry of the moieties immediately attached thereto is not specified, - - - is absent or a single bond, and ═══ or ═══ is a single or double bond. An asterisk (*) next to an atom indicates that the atom is a stereocenter of unknown absolute configuration. For example, in a pair of enantiomers each can be depicted by a chemical structure with an asterisk (*) next to the stereocenter, which would indicate that the absolute configuration for the stereocenter of a given enantiomer is not defined.

Unless otherwise stated, structures depicted herein are also meant to include all isomeric (e.g., enantiomeric, diastereomeric, and geometric (or conformational)) forms of the structure; for example, the R and S configurations for each stereocenter. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example, "$C_{1-6}$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $—CF_3$, Bn).

The term "haloalkyl" refers to a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $—CHF_2$, $—CH_2F$, $—CF_3$, $—CH_2CF_3$, $—CF_2CF_3$, $—CF_2CF_2CF_3$, $—CCl_3$, $—CFCl_2$, $—CF_2Cl$, and the like.

The term "deuteroalkyl" refers to an alkyl group, wherein one or more of the hydrogen atoms are independently replaced by deuterium. In some embodiments, the deuteroalkyl moiety has 1 to 8 carbon atoms ("$C_{1-8}$ deuteroalkyl"). In some embodiments, the deuteroalkyl moiety has 1 to 6 carbon atoms ("$C_{1-6}$ deuteroalkyl"). In some embodiments, the deuteroalkyl moiety has 1 to 4 carbon atoms ("$C_{1-4}$ deuteroalkyl"). In some embodiments, the deuteroalkyl moiety has 1 to 3 carbon atoms ("$C_{1-3}$ deuteroalkyl"). In some embodiments, the deuteroalkyl moiety has 1 to 2 carbon atoms ("$C_{1-2}$ deuteroalkyl"). In some embodiments, the deuteroalkyl moiety is $C_1$, $C_2$, $C_3$, $C_4$, $C_5$, or $C_6$ deuteroalkyl. A deuteroalkyl moiety having n carbon atoms can have from 1 to 2n+1 deuterium atoms. Examples of deuteroalkyl groups include $—CHD_2$, $—CH_2D$, $—CD_3$, $—CH_2CD_3$, $—CD_2CD_3$, $—CD_2CD_2CD_3$, $—CH(CD_3)_2$, $—CD(CD_3)_2$, $—C(CD_3)_3$, and the like.

The term "hydroxyalkyl" is a substituted alkyl group, wherein one or more of the hydrogen atoms are independently replaced by a hydroxyl. In some embodiments, the hydroxyalkyl moiety has 1 to 8 carbon atoms ("$C_{1-8}$ hydroxyalkyl"). In some embodiments, the hydroxyalkyl moiety has 1 to 6 carbon atoms ("$C_{1-6}$ hydroxyalkyl"). In some embodiments, the hydroxyalkyl moiety has 1 to 4 carbon atoms ("$C_{1-4}$ hydroxyalkyl"). In some embodiments, the hydroxyalkyl moiety has 1 to 3 carbon atoms ("$C_{1-3}$ hydroxyalkyl"). In some embodiments, the hydroxyalkyl moiety has 1 to 2 carbon atoms ("$C_{1-2}$ hydroxyalkyl").

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "haloalkoxy" refers to a haloalkyl group, as defined herein, appended to the parent molecular moiety through an oxygen atom. In some embodiments, the alkoxy moiety has 1 to 8 carbon atoms ("$C_{1-8}$ haloalkoxy"). In some embodiments, the alkoxy moiety has 1 to 6 carbon atoms ("$C_{1-6}$ haloalkoxy"). In some embodiments, the alkoxy moiety has 1 to 4 carbon atoms ("$C_{1-4}$ haloalkoxy"). In some embodiments, the alkoxy moiety has 1 to 3 carbon atoms ("$C_{1-3}$ haloalkoxy"). In some embodiments, the alkoxy moiety has 1 to 2 carbon atoms ("$C_{1-2}$ haloalkoxy"). Representative examples of haloalkoxy include, but are not limited to, difluoromethoxy, trifluoromethoxy, and 2,2,2-trifluoroethoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and lor more heteroatoms within the parent chain ("hetero$C_{1-18}$ alkyl"). In some embodiments, a heteroalkyl group is a saturated group having 1 to 16 carbon atoms and/or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and lor more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═CHCH$_3$ or

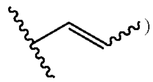

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl").

In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and lor more heteroatoms within the parent chain ("hetero$C_{2-9}$ alkynyl"). In some embodiments, a heteroalkynyl group has 2 to 8 carbon atoms, at least one triple bond, and lor more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like.

Exemplary $C_{3-8}$ carbocyclyl groups include, without limitation, the aforementioned $C_{3-8}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 4-10 membered non-aromatic ring system having ring carbon atoms and 1-4 ring heteroatoms, wherein each heteroatom is independently selected from nitrogen, oxygen, and sulfur ("4-10 membered heterocyclyl"). In some embodiments, a heterocyclyl group is a 4-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-12 membered aromatic ring system having ring carbon atoms and 1-4 ring heteroatoms provided in the aromatic ring system, wherein each heteroatom is independently selected from nitrogen, oxygen, and sulfur ("5-12 membered heteroaryl"). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, alkoxy, heteroalkyl, heteroalkenyl, heteroalkynyl, carbocyclyl, cycloalkyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3{}^+X^-$, $—N(OR^{cc})R^{bb}$, —SH, $—SR^{aa}$, $—SSR^{cc}$, $—C(=O)R^{aa}$, $—CO_2H$, —CHO, $—C(OR^{cc})_3$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2Ra$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3$, $—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}P(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3{}^+X^-$, $—P(OR^{cc})_3{}^+X^-$, $—P(R^{cc})_4$, $—P(OR^{cc})_2$, $—OP(R^{cc})_2$, $—OP(R^{cc})_3{}^+X^-$, $—OP(OR^{cc})_2$, $—OP(OR^{cc})_3{}^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein X is a counterion; or two geminal hydrogens on a carbon atom are replaced with the group =O, =S, $=NN(R^{bb})_2$, $NNR^{bb}C(=O)R^{aa}$, $=NNR^{bb}C(=O)OR^{aa}$, $=NNR^{bb}S(=O)_2R^{aa}$, $=NR^{bb}$ or $=NOR^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; each instance of $R^{bb}$ is, independently, selected from hydrogen, —OH, $—OR^{aa}$, $—N(R^{cc})_2$, —CN, $—C(=O)R^{a}$, $—C(=O)N(R^{cc})_2$, $—CO_2Ra$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein X is a counterion; each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; each instance of $R^{dd}$ is, independently, selected from halogen, —CN, —$NO_2$, —$N_3$, —$SO_2H$, —$SO_3H$, —OH, —$OR^{cc}$, —$ON(R^{ff})_2$, —$N(R^{ff})_2$, —$N(R^{ff})_3X^-$, —$N(OR^{ee})R^{ff}$, —SH, —$SR^{ee}$, —$SSR^{ee}$, —C(═O)$R^{ee}$, —$CO_2H$, —$CO_2R^{cc}$, —OC(═O)$R^{ee}$, —$OCO_2R^{ee}$, —C(═O)N(R)$_2$, —OC(═O)$N(R^{ff})_2$, —$NR^{ff}$C(═O)$R^{ee}$, —$NR^{ff}CO_2R^{ee}$—$N^{ee}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —NRC(═$NR^{ff}$)$N(R^{ff})_2$, —$NR^{ff}SO_2R^{ee}$, —$SO_2N(R^{ff})_2$, —$SO_2R^{cc}$, —$SO_2OR^{cc}$, —$OSO_2R^{ee}$, —S(═O)$R^{cc}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$—OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein X is a counterion; each instance of $R^{cc}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), —$OCO_2(C_{1-6}$ alkyl), —C(═O)$NH_2$, —C(═O)$N(C_{1-6}$ alkyl$)_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2(C_{1-6}$ alkyl), —NHC(═O)$N(C_{1-6}$ alkyl$)_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)$N(C_{1-6}$ alkyl$)_2$, —C(═NH)NH($C_{1-6}$ alkyl), —C(═NH)$NH_2$, —OC(═NH)$N(C_{1-6}$ alkyl$)_2$, —OC(═NH)NH($C_{1-6}$ alkyl), —OC(═NH)$NH_2$, —NHC(═NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2(C_{1-6}$ alkyl), —$SO_2O(C_{1-6}$ alkyl), —$OSO_2(C_{1-6}$ alkyl), —SO($C_{1-6}$ alkyl), —$Si(C_{1-6}$ alkyl$)_3$, —$OSi(C_{1-6}$ alkyl$)_3$, —C(═S)$N(C_{1-6}$ alkyl$)_2$, —C(═S)NH($C_{1-6}$ alkyl), —C(═S)$NH_2$, —C(═O)S($C_{1-6}$ alkyl), —C(═S)$SC_{1-6}$ alkyl, —SC(═S)$SC_{1-6}$ alkyl, —P(═O)$(OC_{1-6}$ alkyl$)_2$, —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^a$, —$ON(R^{bb})_2$, —OC(═O)$SR^{aa}$, —OC(═O)$R^{aa}$, —$OCO_2R^{aa}$, —OC(═O)$N(R^{bb})_2$, —OC(═$NR^{bb}$)$R^{aa}$, —OC(═$NR^{bb}$)$OR^{aa}$, —OC(═$NR^{bb}$)$N(R^{bb})_2$, —OS(═O)$R^{aa}$, —$OSO_2R^{aa}$, —$OSi(R^{aa})_3$, —$OP(R^{cc})_2$, —$OP(R^{cc})_3{}^+X^-$, —$OP(OR^{cc})_2$, —$OP(OR^{cc})_3{}^+X^-$, —OP(═O)$(R^{aa})_2$, —OP(═O)$(OR^{cc})_2$, and —OP(═O)$(N(R^{bb})_2)_2$, wherein $X^-$, $R^{aa}$, $R^{bb}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted ammino group.

The term "monosubstituted amino" refers to an amino group wherein the nitrogen atom directly attached to the parent molecule is substituted with one hydrogen and one group other than hydrogen, and includes groups selected from —$NH(R^{bb})$, —NHC(═O)$R^{aa}$, —$NHCO_2R^{aa}$, —NHC(═O)$N(R^{bb})_2$, —NHC(═$NR^b$)$N(R^{bb})_2$, —$NHSO_2R^{aa}$, —NHP(═O)$(OR^{cc})_2$, and —NHP(═O)$(N(R^{bb})_2)_2$, wherein $R^{aa}$, $R^{bb}$, and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}$C(═O)$R^{aa}$, —$NR^{bb}CO_2R^{aa}$, —$NR^{bb}$C(═O)$N(R^{bb})_2$, —$NR^{bb}$C(═$NR^{bb}$)$N(R^{bb})_2$, —$NR^{bb}SO_2R^{aa}$, —$NR^{bb}$P(═O)$(OR^{cc})_2$, and —$NR^{bb}$P(═O)$(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})_2$ and —$N(R^{bb})_3{}^+X^-$, wherein $R^{bb}$ and $X^-$ are as defined herein.

The term "sulfonyl" refers to a group selected from $—SO_2N(R^{bb})_2$, $—SO_2R^{aa}$, and $SO_2OR^{aa}$, wherein $R^{aa}$ and $R^{bb}$ are as defined herein.

The term "sulfinyl" refers to the group $—S(═O)R^{aa}$, wherein $R^{aa}$ is as defined herein.

The term "acyl" refers to a group having the general formula $—C(═O)R^{X1}$, $—C(═O)OR^{X1}$, $—C(═O)—O—C(═O)R^{X1}$, $—C(═O)SR^{X1}$, $—C(═O)N(R^{X1})_2$, $—C(═S)R^{X1}$, $—C(═S)N(R^{X1})_2$, $—C(═S)O(R^{X1})$, $—C(═S)S(R^{X1})$, $—C(═NR^{X1})R^{X1}$, $—C(═NR^{X1})OR^{X1}$, $—C(═NR^{X1})SR^{X1}$, and $—C(═NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di alkylamino, mono- or di-heteroalkylamino, mono- or di-arylamino, or mono- or di heteroarylamino; or two $R^{X1}$ groups taken together form a 5- to 6-membered heterocyclic ring.

Exemplary acyl groups include aldehydes (—CHO), carboxylic acids ($—CO_2H$), ketones, acyl halides, esters, amides, imines, carbonates, carbamates, and ureas. Acyl substituents include, butare not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (e.g., $—C(═O)R^{aa}$), carboxylic acids (e.g., $—CO_2H$), aldehydes(CHO), esters (e.g., $—CO_2R^{aa}$, $—C(═O)SR^{aa}$, $—C(═S)SR^{aa}$), amides (e.g., $—C(═O)N(R^{bb})_2$, $C(═O)NR^{bb}SO_2R^{aa}$, $—C(═S)N(R^{bb})_2$, and imines (e.g., $—C(═NR^{bb})R^{aa}$, $—C(═NR^{bb})OR^{aa}$), $C(═NR^{bb})N(R^{bb})_2$, wherein $R^{aa}$ and $R^{bb}$ are as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{bb})R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)(OR^{cc})_2$, $—P(═O)(R^{aa})_2$, $—P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or a 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, $—OR^{aa}$, $—N(R^{cc}h$, $—C(═O)R^{aa}$, $—C(═O)N(R^{cc})_2$, $—CO_2R^{aa}$, $—SO_2R^{aa}$, $—C(═NR^{cc})R^{aa}$, $—C(═NR^{cc})OR^{a}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., $—C(═O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o nitrophenylacetamide, o-nitrophenoxyacetamide, acetoacetamide, (N'-dithiobenzyloxyacylamina)acetamide, 3-(p-hydroxypheny1)propanamide, 3-(o-nitrophen y1)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o nitrocinnamide, N-acetylmethionine derivative, o-nitrobenzamide and o (benzoyloxymethyl)benzamide.

Nitrogen protecting groups such as carbamate groups (e.g., $—C(═O)OR^{aa}$) include, but are not limited to, methyl carbamate, ethyl carbamate, 9-fluorenylmethyl carbamate (Fmoc), 9-(2-sulfa)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p (dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p (phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), -trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10) acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasu$^{cc}$inimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methox ybenzylideneamine, N-diphenylmethyleneamine, N-[(2-pyridy1)mesityl]methyleneamine, N—(N',N'-dimethylaminomethylene)amine, N,N'-isopropylidenediamine, N-p nitrobenzylideneamine, N-salicylideneamine, N-5-chlorosalicylideneamine, N-(5-chloro-2-hydrox yphen y1)phenylmethyleneamine, N-cyclohex ylideneamine, N-(5,5-dimethyl-3-oxo-1-cyclohexenyl)amine, N-borane derivative, N-diphenylborinic acid derivative, N [phenyl(pent$^{aa}$-cylchromium- or tungsten)acyl]amine, N-copper chelate, N-zinc chelate, N nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$Ra, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymeth yl (SEMOR), tetrahydropyranyl (THP), 3-bromotetrahydropyranyl, tetrahydrothiopyranyl, 1-methoxycyclohexy1, 4-methoxytetrahydropyrany1 (MTHP), 4-methoxytetrahydrothiopyrany1, 4-methoxytetrahydrothiopyranyl S,S-dioxide, 1-[(2-chloro-4-meth y1)pheny1]-4-methox ypiperidin-4-yl (CTMP), 1,4-dioxan-2-yl, tetrahydrofuranyl, tetrahydrothiofuranyl, 2,3,3a,4,5,6,7,7a octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacy loxyphen y1)diphen ylmethyl, 4,4',4"-tris(4,5-dichlorophthalimidopheny1)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TEMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethox y)ethy1, 4-(meth ylthiomethox y)butyrate, 2-(methylthiomethox ymethyl)benzoate, 2,6-dichloro-4-methylphenoxyacetate, 2,6-dichloro-4-(1,1,3,3-tetramethylbutyl)phenox yacetate, 2,4-bis(1,1-dimethylpropyl)phenox yacetate, chlorodiphenylacetate, isobutyrate, monosu$^{cc}$inoate, (E)-2-methyl-2-butenoate, o (methoxyacyl)benzoate, a-naphthoate, nitrate, alkyl N,N,N',N'-tetramethylphosphorodiamidate, alkyl N-phenylcarbamate, borate, dimethylphosphinothioyl, alkyl2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)$SR^{a}$, —C(═O)$R^{aa}$, —$CO_2$Ra, —C(═O)$N(R^{bb})_2$, —C(═$NR^{bb}$)$R^{aa}$, —C(═$NR^{bb}$)$OR^{aa}$, —C(═$NR^{bb}$)$N(R^{bb})_2$, —S(═O)$R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —P(═O)$(R^{aa})_2$, —P(═O)$(OR^{cc})_2$, and —P(═O)$(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" as used herein can be an anionic counterion or a cationic counterion.

An "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary anionic counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary anionic counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "cationic counterion" is a positively charged group associated with a negatively charged group in order to maintain electronic neutrality. A cationic counterion may be monovalent (i.e., including one formal positive charge). A cationic counterion may also be multivalent (i.e., including more than one formal positive charge), such as divalent or trivalent. Exemplary cationic counterions include, for example, cations of metals, such as alkali metals and alkaline earth metals, as well as $NH_4^+$, $NH_3(C_{1-6}alkyl)^+$, $NH_2(C_{1-6}alkyl)_2^+$, $NH(C_{1-6}alkyl)_3^+$, and $N^+(C_{1-6}alkyl)_4$ cations, where the $C_{1-6}$alkyl can be optionally substituted as discussed above. Representative cations of alkali and alkaline earth metals include $Li^+$, $Na^+$, $K^+$, $Mg^{2+}$, and $Ca^{2+}$, and the like.

Formulation and Administration

Another embodiment of the invention is a composition comprising a compound of the invention (e.g, a compound of Formula (I)), or a pharmaceutically acceptable salt thereof, and a pharmaceutically acceptable carrier, adjuvant, or vehicle. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.). In a particular embodiment the subject is a human, for example, a adult male of female or a male of female child.

As used herein, an amount of a compound described herein (e.g., a compound of Formula (I)) that is effective to treat a disorder, or a "therapeutically effective amount" refers to an amount of the compound which is effective, upon single or multiple dose administration to a subject or a cell, in curing, alleviating, relieving or improving one or more symptoms of a disorder.

As used herein, an amount of a compound effective to prevent a disorder, or a "prophylactically effective amount" of the compound refers to an amount effective, upon single- or multiple-dose administration to the subject, in preventing or delaying the onset or recurrence of a disorder or one or more symptoms of the disorder.

For administration to human subjects, the total daily dose of the compounds of Formula (I) is typically in the range of about 0.1 mg to about 3000 mg depending on the route of administration. For example, oral administration can require a total daily dose of from about 1 mg to about 3000 mg, while an intravenous dose can only require a total daily dose of from about 0.1 mg to about 300 mg. The total daily dose may be administered in a single or divided doses (e.g., 2, 3, 4, 5 or 6 times per day at evenly space or randomly spaced intervals) or on an as needed basis. The typical daily dose can fall outside the ranges above based on the discretion of the physician or drug prescriber. Although these dosages are based on an average human subject having a mass of about 60 kg to 70 kg, the physician will be able to determine the appropriate dose for a subject (e.g., an infant) whose mass falls outside this weight range.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

"Pharmaceutically or pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethylamine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the invention can also be in micro-encapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound of the invention can be provided in an extended (or "delayed" or "sustained") release composition. This delayed-release composition comprises a compound of the invention in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intravenous administration.

In some embodiments, pharmaceutically acceptable compositions of this invention are formulated for topical administration.

The amount of compounds of the present invention that can be combined with the carrier materials to produce a composition in a single dosage form will vary depending upon the host treated, the particular mode of administration and the activity of the compound employed. Preferably, compositions should be formulated so that a dosage of between 0.01-100 mg/kg body weight/day of the inhibitor can be administered to a patient receiving the composition.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-a-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

The pharmaceutical compositions of this invention are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agent(s) can be administered separately, as part of a multiple dose regimen, from the compounds of this invention. Alternatively, the additional agent(s) can be part of a single dosage form, mixed together with the compound of this invention in a single composition.

The compounds described herein can, for example, be administered by injection, intravenously, intraarterially, intraocularly, intravitreally, subdermally, orally, buccally, nasally, transmucosally, topically, in an ophthalmic preparation, or by inhalation, with a dosage ranging from about 0.5 to about 100 mg/kg of body weight or, alternatively, in a dosage ranging from about 1 mg to about 1000 mg/dose, every 4 to 120 hours, or according to the requirements of the particular drug. The methods herein contemplate administration of an effective amount of a compound of the invention, or a composition thereof, to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

Uses of Compounds and Pharmaceutically Acceptable Compositions

As used herein, "RIPK2-mediated" disease, disorder or condition means any disease or other deleterious condition in which RIPK2 plays a role. Accordingly, another embodiment of the present invention relates to treating, for example, lessening the severity of, a RIPK2-mediated disorder or condition. RIPK2-mediated disorders include inflammatory disorders, autoimmune disorders, granulomatous diseases, neurodegenerative disorders, and cancer. Specific examples of RIPK2-mediated disorders are set forth in detail below.

Compounds provided by this invention are also useful as tools, for example, to study RIPK2 modulation in biological and pathological phenomena, to study cancer or for the identification and/or comparative evaluation of RIPK2 modulators. Accordingly, in particular embodiments, the present invention provides a method for studying an effect of a compound described herein, or a salt or composition thereof, on a sample, the method comprising contacting a sample comprising cells in culture or RIPK2 with the compound, or the salt or composition thereof, and measuring the effect of the compound, or salt or composition thereof, on the cells or RIPK2. For example, the compounds described herein can be used as a standard or control substance in binding assays (e.g., competitive binding assays) to identify or evaluate potential RIPK2 modulators or as a discovery tool to probe the role of RIPK2 modulation in certain disorders or conditions, such as those described herein, including inflammatory disorders, autoimmune disorders, and other RIPK2-mediated disorders or conditions.

In a certain embodiment, the present invention relates to a method of treating a disease or disorder, comprising administering to a subject in need thereof a therapeutically effective amount of a compound of Formula (I) as described herein or a pharmaceutically acceptable salt thereof or a pharmaceutical composition described herein, wherein the disease or disorder is selected from inflammatory diseases, autoimmune diseases, granulomatous diseases, cancer and neurodegenerative diseases.

In some embodiments, compounds and compositions described herein are useful for treating inflammatory disorders in a subject in need thereof. Thus, in certain embodiments, the present invention provides a method for treating an inflammatory disorder, comprising the step of administering to a subject in need thereof a therapeutically effective amount of a compound of the present invention (e.g., a Compound of Formula (I)), or pharmaceutically acceptable salt or composition thereof.

In certain aspects, the inflammatory disease can include, but is not limited to uveitis, interleukin-1 converting enzyme fever syndrome, dermatitis, acute lung injury, type 2 diabetes mellitus, arthritis, inflammatory bowel disorder (IBD), ischemia reperfusion injury in a solid organ transplant, sepsis, liver disease, allergic disease, and graft versus host disease.

In certain instances, the inflammatory disease is an IBD. For example, the IBD is selected from ulcerative colitis, Crohn's disease, early-onset IBD, and extraintestinal IBD.

Alternatively, the inflammatory disease can include but is not limited to rheumatoid arthritis, inflammatory arthritis, peritonitis, ischemia reperfusion injury in kidney transplant, non-alcohol steatohepatitis, alcohol steatohepatitis, insulin-resistant type 2 diabetes, allergic rhinitis, asthma, atopic dermatitis, Sjogren's syndrome, ankylosing spondylitis, pemphigus vulgaris, idiopathic plasmacytic lymphadenopathy, atherosclerosis, myocardial infarction, thrombosis, a-synucleinopathy, Parkinson's disease, dementia with Lewy body, multiple system atrophy, Alzheimer's disease, amyotrophic lateral sclerosis, and chronic obstructive pulmonary disease.

In a particular embodiment, the disease or disorder is an autoimmune disease. For example, the autoimmune disease can include, but is not limited to systemic lupus erythematosus, lupus nephritis, psoriasis, diabetes mellitus type 1, Goodpasture's syndrome, Guillain-Barre Syndrome, Hashimoto's disease, Grave's disease, immune thrombocytopenic purpura, and multiple sclerosis (including relapsing-remitting MS, secondary-progressive MS, primary-progressive MS, progressive-relapsing MS).

In a further embodiment, the disease or disorder is a granulomatous disease. For example, the granulomatous disease is selected from sarcoidosis, Blau syndrome, Wegner's granulomatosis, Behcet's disease, and interstitial pulmonary disease.

In another embodiment, the disease or disorder is a neurodegenerative disorder. For example, the neurological disorder is selected from Alzheimer's disease, amyotrophic lateral sclerosis (ALS/Lou Gehrig's Disease), Parkinson's disease, multiple sclerosis, diabetic neurophathy, polyglutamine (polyQ) diseases, stroke, Fahr disease, Menke's disease, Wilson's disease, cerebral ischemia, a prion disorder, dementia, corticobasal degeneration, progressive supranuclear palsy, spinocerebellar atrophies, brain injury and spinal cord injury.

In yet another embodiment, the disease or disorder is cancer. For example, the cancer is selected from a hematological cancer such as leukemia (e.g., acute myeloid leukemia, chronic myelogenous leukemia), lymphoma (e.g., non-Hodgkin's Lymphoma, Hodgkin's Lymphoma, diffuse large B-cell lymphoma), myeloma (e.g., multiple myeloma), myelodysplastic syndrome, myelofibrosis), breast cancer, brain cancer (e.g., glioblastoma), colorectal cancer, esophageal cancer, head and neck cancer, melanoma, pancreatic cancer, prostate cancer, stomach cancer, bone cancer, ovarian cancer, uterine cancer, renal cancer, liver cancer and lung cancer. The cancer can be a soft tissue cancer, including but not limited to, a sarcoma selected from the group consisting of a fibrosarcoma and liposarcoma (e.g., a dedifferentiated liposarcoma and a pleomorphic liposarcoma)

The compounds and compositions described herein can also be administered to cells in culture, e.g., in vitro or ex vivo, or to a subject, e.g., in vivo, to treat, prevent, and/or diagnose a variety of disorders, including those described herein below.

The compounds of this invention can be used alone or in combination with other therapeutic agents. Combination therapies according to the present invention comprise the administration of a therapeutically effective amount of at least one compound of the invention, and a therapeutically effective amount of at least one other therapeutically active agent (a second agent). For example, combination therapies according to the present invention comprise the administration of at least one compound of the invention and at least one other therapeutically active agent to a subject in need of treatment for a given disease or disorder, for example, the inflammatory diseases, autoimmune diseases, granulomatous diseases, cancers and neurodegenerative diseases described herein.

The compounds of the invention and the other therapeutically active agent can be administered together in a single pharmaceutical composition or separately and, when administered separately this can occur simultaneously or sequentially in any order. The amounts of the compounds of the invention and other therapeutically active agents and the relative timings of administration can be selected in order to achieve the desired combined therapeutic effect. Thus in a further aspect, there is provided a combination comprising a compound of the invention together with one or more other therapeutically active agents.

In certain embodiments, the invention relates to a method of treating a subject suffering from an inflammatory disorder as described herein comprising administering to the subject an effective amount of a compound represented by Formula (I) or a pharmaceutically acceptable salt thereof and an anti-inflammatory agent and/or an anti-TNF agent.

In a particular embodiment, the invention relates to a method of treating a subject suffering from Crohn's disease as described herein comprising administering to the subject an effective amount of a compound represented by Formula (I) or a pharmaceutically acceptable salt thereof and optionally an anti-inflammatory agent and/or an anti-TNF agent.

In another embodiment, the invention relates to a method of treating a subject suffering from an autoimmune disorder as described herein comprising administering to the subject atherapeutically effective amount of a compound represented by Formula (I) or a pharmaceutically acceptable salt thereof and an autoimmune agent such as, but not limited to, an anti-TNF agent.

Suitable anti-inflammatory/autoimmune agents include 5-aminosalicyclic acid and mesalamine preparations, sulfasalazine, hydroxycloroquine, thiopurines (azathioprin, mercaptopurin), methotrexate, cyclophosphamide, cyclosporine, calcineurin inhibitors (cyclosporine, pimecrolimus, tacrolimus), mycophenolic acid (CellCept®), mTOR inhibitors (temsirolimus, everolimus), JAK inhibitors (tofacitinib), (Xeljan®)), Syk inhibitors (fostamatinib), corticosteroids, particularly low-dose corticosteroids (such as prednisone (Deltasone®) and bundesonide) and anti-inflammatory biologics such as anti-IL6R mAbs (Actemra® (tocilizumab)), anti-IL6 biologics, anti-IL I (anakinra (Kineret®), canakinumab (Ilaris®), rilonacept (Arcalyst®)), anti- or IL12 or and IL23 biologics (ustekinumab (Stelara®)), anti-IL 17 biologics (secukinumab), anti-CD22 (epratuzumab), anti-integrin agents(natalizumab (Tysabri®)), vedolizumab (Entyvio®)), anti-IFNa (sifalimumab), anti-CD20 mAbs (rituximab (Rituxan®) and ofatumumab (Arzerra®)), and other agents, such as abatacept (Orencia®), anakinra (Kineret®), canakinumab (Ilaris®), rilonacept (Arcalyst®), secukinumab, epratuzumab, sifalimumab, and belimumab (Benlysta®), CD4 biologics and other cytokine inhibitors or biologics to T-cell or B-cell receptors or interleukins.

Examples of suitable anti-TNF agents include the anti-TNF biologics such as Enbrel® (etanecerpt), Humira® (adalimumab), Remicade® (infliximab), Cimzia® (certolizumab), and Simponi® (golimumab).

In some embodiments, the second agent and the compound represented by Structural Formula (I) are administered simultaneously. When administered simultaneously, the second agent and the compound can be administered in the same formulation or in different formulations. Alternatively, the compound and the additional anti-inflammatory/autoimmune agent can be administered separately.

In a particular embodiment, the invention relates to a method of treating a subject suffering from a neurodegenerative disease as described herein such as Parkinson's comprising administering to the subject an effective amount of a compound represented by Formula (I) or a pharmaceutically acceptable salt thereof and optionally one or more additional therapeutic agents typically used in the treatment of Parkinson's. Such additional therapeutic agents include, but are not limited to levodopa, carbodopa or a combination thereof, pramipexole, ropinirole, rotigotine, selegiline, rasagiline, entacapone, tolcapone, benztropine, trihexyphenidyl, or amantadine, or a pharmaceutically acceptable salt thereof.

In a particular embodiment, the invention relates to a method of treating a subject suffering from a neurodegenerative disease as described herein such as Alzheimer's comprising administering to the subject an effective amount of a compound represented by Formula (I) or a pharmaceutically acceptable salt thereof and optionally one or more additional therapeutic agents typically used in the treatment of Alzheimer's disease. Such additional therapeutic agents include, but are not limited to donepezil, galantamine, memantine, rivastigmine, anti-Abeta (amyloid beta) therapies including aducanumab, crenezumab, solanezumab, and gantenerumab, small molecule inhibitors of BACEl including verubecestat, AZD3293 (LY3314814), elenbecestat (E2609), LY2886721, PF-05297909, JNJ-54861911, TAK-070, VTP-37948, HPP854, CTS-21166, or anti-tau therapies such as LMTM (leuco-methylthioninium-bis (hydromethanesulfonate)), or a pharmaceutically acceptable salt thereof.

In certain embodiments, the invention relates to a method of treating a subject with cancer comprising administering to the subject an effective amount of a compound represented by Formula (I) or a pharmaceutically acceptable salt thereof and an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agents suitable for use in the methods described herein include any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents.

In one embodiment, the anti-cancer agents that can be used in methods described herein include, but are not limited to, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin and adriamycin and a combination thereof.

In one embodiment, the anti-cancer agent and the compound represented by Structural Formula (I) are administered contemporaneously. When administered contemporaneously, the anti-cancer agent and the compound can be administered in the same formulation or in different formulations. Alternatively, the compound and the additional anti-cancer agent can be administered separately at different times.

In a first embodiment, the present invention relates to a compound represented by structural formula (I):

or a pharmaceutically acceptable salt thereof:

(I)

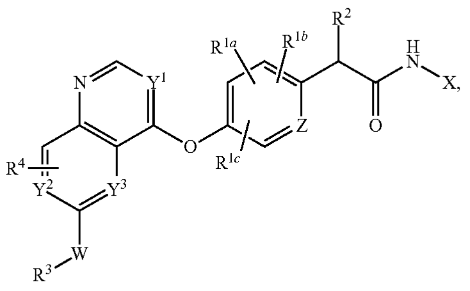

wherein:

$R^{1a}$, $R^{1b}$, and $R^{1c}$ are each independently selected from H, halogen, CN, and $C_{1-6}$ alkyl;

$R^2$ is H or $C_{1-3}$ alkyl;

$R^3$ is selected from halogen, 4- to 10-membered heterocyclyl, 5-12 membered heteroaryl, $S(=O)_2R^5$, $S(=O)(=NR^6)(R^7)$, $QR^7$, $C(=O)NR^8R^9$, $NH(C=O)R^5$, CN, $NR^8R^9$, $P(=O)R^{8a}R^{9a}$;

$R^4$ is selected from H, halogen, $C_{1-6}$ alkyl, and $C_{1-6}$ alkoxy;

$R^5$ is selected from $NR^{10}R^{11}$, $C_{1-6}$ alkyl, $C_{3-6}$ cycloalkyl, and 4- to 10-membered heterocyclyl;

$R^6$ is selected from H, CN, and $C_{1-6}$ alkyl;

$R^7$ is selected from $C_{1-6}$ alkyl, $C_{3-6}$ cycloalkyl, and 4- to 10-membered heterocyclyl, 5-12 membered heteroaryl, or $R^6$ and $R^7$ taken together with the nitrogen and sulfur atoms to which they are attached form 4- to 10-membered heterocyclyl;

Q is selected from O, S, —S(=O)—, and —C(=O)—;

$R^8$ and $R^9$ are each independently selected from H, $C_{1-6}$ alkyl, $C_{1-6}$ deuteroalkyl, $C_{3-6}$ cycloalkyl, and 4- to 10-membered heterocyclyl, or $R^8$ and $R^9$ taken together with the nitrogen atom to which they are attached form 4- to 10-membered heterocyclyl;

$R^{8a}$ and $R^{9b}$ are each independently $C_{1-6}$ alkyl, or $R^{8a}$ and $R^{9a}$ taken together with the phosphorus atom to which they are attached form 4- to 10-membered heterocyclyl;

$R^{10}$ and $R^{11}$ are each independently H or $C_{1-6}$ alkyl, or $R^{10}$ and $R^{11}$ taken together with the nitrogen to which they are attached form 4- to 10-membered heterocyclyl;

W is selected from O, $NR^2$, $O(C_{1-2}$ alkylene), $NH(C_{1-2}$ alkylene), $C_{1-2}$ alkylene, $C_{3-6}$ cycloalkylene, and a bond;

X is a moiety represented by one of the following structural formulas:

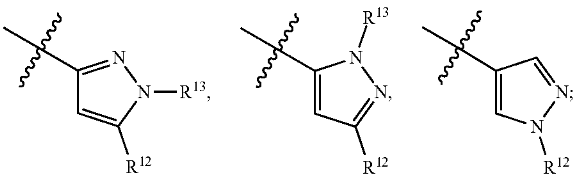

-continued

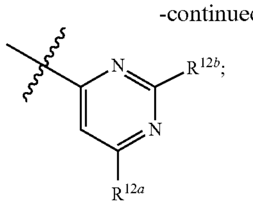

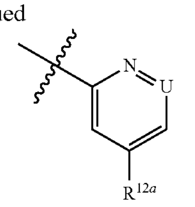

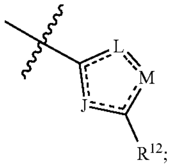

$Y^1$ is CH or N;

$Y^2$ and $Y^3$ are each independently $CR^4$ or N;

U is $CR^{12b}$ or N;

Z is $CR^{1b}$ or N;

L, M, and J are each independently selected from N, O, or S, provided that two of L, M, and J are N;

$R^{12}$ is selected from $C_{3-6}$ alkyl, $C_{3-6}$ cycloalkyl, $C_{5-12}$ bridged bicyclic carbocyclyl, and 4- to 10-membered heterocyclyl;

$R^{12a}$ is selected from $C_{1-6}$ alkyl, $C_{1-6}$ deuteroalkyl, $C_{3-6}$ cycloalkyl, $C_{5-12}$ bridged bicyclic carbocyclyl, and 4- to 10-membered heterocyclyl;

$R^{12b}$ and $R^{13}$ are each independently H or $C_{1-6}$ alkyl; and is a single bond or a double bond, wherein each $C_{1-6}$ alkyl, $C_{1-3}$ alkyl, $C_{1-2}$ alkylene, $C_{3-6}$ alkyl, $C_{3-6}$ cycloalkyl, $C_{1-6}$ alkoxy, $C_{5-12}$ bridged bicyclic carbocyclyl, 5-12 membered heteroaryl, and 4- to 10-membered heterocyclyl is optionally substituted with 1 to 3 substituents independently selected from deuterium, oxo, F, Cl, Br, CN, $OR^{14}$, $SR^{aa}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{1-6}$ deuteroalkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, ($C_{1-6}$) alkylamino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$) alkoxy, $C_{1-6}$ alkoxy($C_{1-3}$)alkyl, $C_{6-12}$ aryl, 4- to 8-membered heterocyclyl, and 5- to 12-membered heteroaryl, wherein $R^{14}$, $R^{15}$, $R^{18}$, $R^{18a}$, $R^{20}$, $R^{20a}$, $R^{24}$, and $R^{27}$ are each independently hydrogen or $C_{1-6}$ alkyl;

$R^{16}$ and $R^{17}$ are each independently selected from hydrogen, $C_{1-6}$ alkyl, hydroxy($C_{1-6}$)alkyl, and halo($C_{1-6}$)alkyl;

$R^{19}$ and $R^{23}$ are each independently $C_{1-6}$ alkyl or halo($C_{1-6}$)alkyl;

$R^{21}$, $R^{22}$, $R^{25}$ and $R^{26}$ are each independently selected from H, $C_{1-6}$ alkyl, $C_{1-3}$ alkoxy($C_{1-6}$)alkyl, hydroxy ($C_{1-6}$)alkyl, cyano($C_{1-6}$)alkyl, amino($C_{1-6}$)alkyl, $C_{1-3}$ alkylamino($C_{1-6}$)alkyl, and di($C_{1-3}$)alkylamino($C_{1-6}$) alkyl; or $R^{21}$ and $R^{22}$ or $R^{25}$ and $R^{26}$, together with the nitrogen to which they are attached, form a 3-8 membered ring optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino ($C_{1-6}$)alkyl, cyano($C_{1-6}$)alkyl, $C_{1-3}$ alkylcarbonylamino ($C_{1-6}$)alkyl, $C_{1-3}$ alkoxy, halo($C_{1-3}$)alkoxy, $C_{1-6}$ alkoxy ($C_{1-3}$)alkyl, $C_{6-12}$ aryl, 4- to 10-membered heterocyclyl, and 5- to 12-membered heteroaryl.

provided that when $Y^2$ is CH substituted with $R^4$ and $R^4$ is optionally substituted $C_{1-6}$ alkoxy, W—$R^3$ is not CN or optionally substituted $C_{1-6}$ alkoxy; and provided that when $Y^1$, $Y^2$ and $Y^3$ are each CH, then W—$R^3$ is not F.

For example, the present invention relates to a compound represented by structural formula (I):

or a pharmaceutically acceptable salt thereof:

(I)

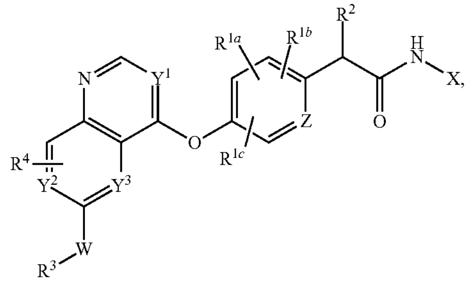

wherein:

$R^{1a}$, $R^{1b}$, and $R^{1c}$ are each independently selected from H, halogen, CN, and $C_{1-6}$ alkyl;

$R^2$ is H or $C_{1-3}$ alkyl;

$R^3$ is selected from halogen, 4- to 10-membered heterocyclyl, 5-12 membered heteroaryl, $S(=O)_2R^5$, $S(=O)(=NR^6)(R^7)$, $QR^7$, $C(=O)NR^8R^9$, $NH(C=O)R^5$, CN, $NR^8R^9$, $P(=O)R^{8a}R^{9a}$;

$R^4$ is selected from H, halogen, $C_{1-6}$ alkyl, and $C_{1-6}$ alkoxy;

$R^5$ is selected from $NR^{10}R^{11}$, $C_{1-6}$ alkyl, $C_{3-6}$ cycloalkyl, and 4- to 10-membered heterocyclyl;

$R^6$ is selected from H, CN, and $C_{1-6}$ alkyl;

$R^7$ is selected from $C_{1-6}$ alkyl, $C_{3-6}$ cycloalkyl, and 4- to 10-membered heterocyclyl, 5-12 membered heteroaryl, or $R^6$ and $R^7$ taken together with the nitrogen and sulfur atoms to which they are attached form 4- to 10-membered heterocyclyl;

Q is selected from O, S, —S(=O)—, and —C(=O)—;

$R^8$ and $R^9$ are each independently selected from H, $C_{1-6}$ alkyl, $C_{3-6}$ cycloalkyl, and 4- to 10-membered heterocyclyl, or $R^8$ and $R^9$ taken together with the nitrogen atom to which they are attached form 4- to 10-membered heterocyclyl;

$R^{8a}$ and $R^{9b}$ are each independently $C_{1-6}$ alkyl, or $R^{8a}$ and $R^{9a}$ taken together with the phosphorus atom to which they are attached form 4- to 10-membered heterocyclyl;

$R^{10}$ and $R^{11}$ are each independently H or $C_{1-6}$ alkyl, or $R^{10}$ and $R^{11}$ taken together with the nitrogen to which they are attached form 4- to 10-membered heterocyclyl;

W is selected from O, $NR^2$, O($C_{1-2}$ alkylene), NH($C_{1-2}$ alkylene), $C_{1-2}$ alkylene, and a bond;

X is a moiety represented by one of the following structural formulas:

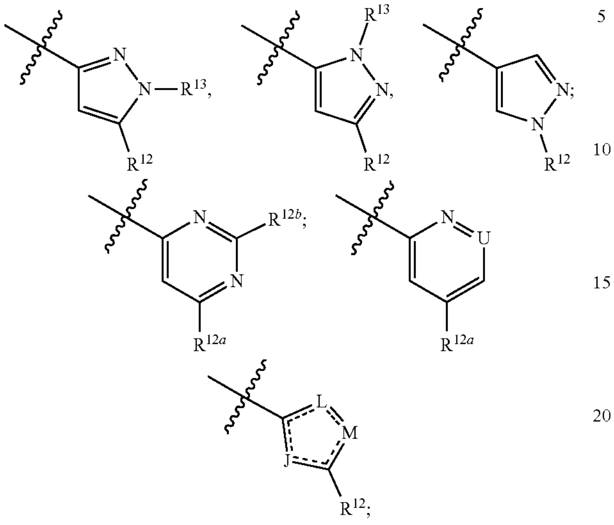

$Y^1$ is CH or N;

$Y^2$ and $Y^3$ are each independently $CR^4$ or N;

U is $CR^{12b}$ or N;

Z is $CR^{1b}$ or N;

L, M, and J are each independently selected from N, O, or S, provided that two of L, M, and J are N;

$R^{12}$ is selected from $C_{3-6}$ alkyl, $C_{3-6}$ cycloalkyl, $C_{5-12}$ bridged bicyclic carbocyclyl, and 4- to 10-membered heterocyclyl;

$R^{12a}$ is selected from $C_{1-6}$ alkyl, $C_{3-6}$ cycloalkyl, $C_{5-12}$ bridged bicyclic carbocyclyl, and 4- to 10-membered heterocyclyl;

$R^{12b}$ and $R^{13}$ are each independently H or $C_{1-6}$ alkyl; and is a single bond or a double bond, wherein each $C_{1-6}$ alkyl, $C_{1-3}$ alkyl, $C_{1-2}$ alkylene, $C_{3-6}$ alkyl, $C_{3-6}$ cycloalkyl, $C_{1-6}$ alkoxy, $C_{5-12}$ bridged bicyclic carbocyclyl, 5-12 membered heteroaryl, and 4- to 10-membered heterocyclyl is optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 8-membered heterocyclyl, and 5- to 12-membered heteroaryl, wherein $R^{14}$, $R^{15}$, $R^{18}$, $R^{18a}$, $R^{20}$, $R^{20a}$, $R^{24}$, and $R^{27}$ are each independently hydrogen or $C_{1-6}$ alkyl;

$R^{16}$ and $R^{17}$ are each independently selected from hydrogen, $C_{1-6}$ alkyl, hydroxy($C_{1-6}$)alkyl, and halo($C_{1-6}$)alkyl;

$R^{19}$ and $R^{23}$ are each independently $C_{1-6}$ alkyl or halo($C_{1-6}$)alkyl;

$R^{21}$, $R^{22}$, $R^{25}$ and $R^{26}$ are each independently selected from H, $C_{1-6}$ alkyl, $C_{1-3}$ alkoxy($C_{1-6}$)alkyl, hydroxy($C_{1-6}$)alkyl, cyano($C_{1-6}$)alkyl, amino($C_{1-6}$)alkyl, $C_{1-3}$ alkylamino($C_{1-6}$)alkyl, and di($C_{1-3}$)alkylamino($C_{1-6}$)alkyl; or $R^{21}$ and $R^{22}$ or $R^{25}$ and $R^{26}$, together with the nitrogen to which they are attached, form a 3-8 membered ring optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 10-membered heterocyclyl, and 5- to 12-membered heteroaryl.

provided that when $Y^2$ is CH substituted with $R^4$ and $R^4$ is optionally substituted $C_{1-6}$ alkoxy, W—$R^3$ is not CN or optionally substituted $C_{1-6}$ alkoxy; and provided that when $Y^1$, $Y^2$ and $Y^3$ are each CH, then W—$R^3$ is not F.

In a first aspect of the first embodiment, $R^3$ is selected from 4- to 10-membered heterocyclyl, 5-10 membered heteroaryl, $S(=O)_2R^5$, $-S(=O)(=NR^6)(R^7)$, and $C(=O)NR^8R^9$. For example, $R^3$ is selected from 4- to 10-membered heterocyclyl, $S(=O)_2R^5$, and $C(=O)NR^8R^9$.

In a second aspect of the first embodiment, W is selected from NH, N($C_{1-2}$ alkylene), O($C_{1-2}$ alkylene), and $C_{1-2}$ alkylene. For example, W is O. Alternatively, W is a bond. Alternatively yet, W is a $C_{3-6}$ cycloalkylene. The remainder of features and example features of the second aspect is as described above with respect to the first aspect of the first embodiment.

In a third aspect of the first embodiment, $R^3$ is a 4- to 6-membered heterocyclyl optionally substituted with 1 to 3 substituents independently selected from deuterium, oxo, F, Cl, Br, CN, $OR^{14}$, $SR^1$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 8-membered heterocyclyl, and 5- to 12-membered heteroaryl, wherein $R^{14}$, $R^{15}$, $R^{18}$, $R^{18a}$, $R^{20}$, $R^{20a}$, $R^{24}$, and $R^{27}$ are each independently hydrogen or $C_{1-6}$ alkyl;

$R^{16}$ and $R^{17}$ are each independently selected from hydrogen, $C_{1-6}$ alkyl, hydroxy($C_{1-6}$)alkyl, and halo($C_{1-6}$)alkyl;

$R^{19}$ and $R^{23}$ are each independently $C_{1-6}$ alkyl or halo($C_{1-6}$)alkyl;

$R^{21}$, $R^{22}$, $R^{25}$ and $R^{26}$ are each independently selected from H, $C_{1-6}$ alkyl, $C_{1-3}$ alkoxy($C_{1-6}$)alkyl, hydroxy($C_{1-6}$)alkyl, cyano($C_{1-6}$)alkyl, amino($C_{1-6}$)alkyl, $C_{1-3}$ alkylamino($C_{1-6}$)alkyl, and di($C_{1-3}$)alkylamino($C_{1-6}$)alkyl; or $R^{21}$ and $R^{22}$ or $R^{25}$ and $R^{26}$, together with the nitrogen to which they are attached, form a 3-8 membered ring optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino $(C_{1-6})$alkyl, cyano$(C_{1-6})$alkyl, $C_{1-3}$ alkylcarbonylamino $(C_{1-6})$alkyl, $C_{1-3}$ alkoxy, halo$(C_{1-3})$alkoxy, $C_{1-6}$ alkoxy $(C_{1-3})$alkyl, $C_{6-12}$ aryl, 4- to 10-membered heterocyclyl, and 5- to 12-membered heteroaryl. For example, $R^3$ is an unsubstituted 4- to 6-membered heterocyclyl. Alternatively, $R^3$ is 4- to 6-membered heterocyclyl substituted with 1 to 3 substituents independently selected from oxo, F, Cl, Br, CN, $OR^{14}$, $SR^{15}$, $NR^{16}R^{17}$, 4- to 10-membered heterocyclyl, and $C_{1-6}$ alkyl. For example $R^3$ is substituted with oxo. In some embodiments, $R^3$ is a saturated 4- to 6-membered heterocyclyl. For example, $R^3$ is a moiety represented by structural formula

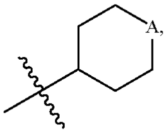

wherein:

A is O or $NR^{28}$; and $R^{28}$ is selected from H, $C_{1-6}$ alkyl, $C_{3-6}$ cycloalkyl, and 4- to 6-membered heterocyclyl, wherein each $C_{1-6}$ alkyl, $C_{3-6}$ cycloalkyl, and 4- to 6-membered heterocyclyl is optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo$(C_{1-6})$alkyl, $C_{1-3}$ alkylsulfonylaminoalkyl, hydroxy$(C_{1-6})$alkyl, amino $(C_{1-6})$alkyl, cyano$(C_{1-6})$alkyl, $C_{1-3}$ alkylcarbonylamino $(C_{1-6})$alkyl, $C_{1-3}$ alkoxy, halo$(C_{1-3})$alkoxy, $C_{1-6}$ alkoxy $(C_{1-3})$alkyl, $C_{6-12}$ aryl, 4- to 8-membered heterocyclyl, and 5- to 12-membered heteroaryl, wherein $R^{14}$, $R^{15}$, $R^{18}$, $R^{18a}$, $R^{20}$, $R^{20a}$, $R^{24}$, and $R^{27}$ are each independently hydrogen or $C_{1-6}$ alkyl;

$R^{16}$ and $R^{17}$ are each independently selected from hydrogen, $C_{1-6}$ alkyl, hydroxy$(C_{1-6})$alkyl, and halo$(C_{1-6})$alkyl;

$R^{19}$ and $R^{23}$ are each independently $C_{1-6}$ alkyl or halo$(C_{1-6})$alkyl;

$R^{21}$, $R^{22}$, $R^{25}$ and $R^{26}$ are each independently H, $C_{1-6}$ alkyl, $C_{1-3}$ alkoxy$(C_{1-6})$alkyl, hydroxy$(C_{1-6})$alkyl, cyano$(C_{1-6})$alkyl, amino$(C_{1-6})$alkyl, $C_{1-3}$ alkylamino $(C_{1-6})$alkyl, and di$(C_{1-3})$alkylamino$(C_{1-6})$alkyl; or $R^{21}$ and $R^{22}$ or $R^{25}$ and $R^{26}$, together with the nitrogen to which they are attached, form a 3-8 membered ring optionally substituted with 1 to 3 substituents independently selected from deuterium, oxo, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo$(C_{1-6})$alkyl, $C_{1-3}$ alkylsulfonylaminoalkyl, hydroxy$(C_{1-6})$alkyl, cyano $(C_{1-6})$alkyl, $C_{1-3}$ alkylcarbonylamino$(C_{1-6})$alkyl, $C_{1-3}$ alkoxy, halo$(C_{1-3})$alkoxy, $C_{1-6}$ alkoxy$(C_{1-3})$alkyl, $C_{6-12}$ aryl, 4- to 10-membered heterocyclyl, and 5- to 12-membered heteroaryl. In some embodiments, $R^3$ is a moiety represented by one of the following structural formulas:

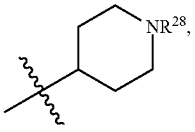, 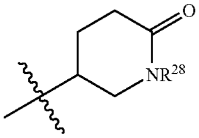, wherein $R^{28}$ is H or $C_{1-3}$ alkyl.

The remainder of features and example features of the third aspect is as described above with respect to the first through second aspects of the first embodiment.

In a fourth aspect of the first embodiment, $R^3$ is $S(=O)_2R^5$. For example, $R^5$ is $C_{1-6}$ alkyl, such as $C_{1-3}$ alkyl. $R^5$ can methyl, ethyl, propyl, isopropyl, butyl, isobutyl, tert-butyl, pentyl, neopentyl, or hexyl. Alternatively, $R^5$ is $C_{3-6}$ cycloalkyl, such as cyclopropyl, cyclobutyl, cyclopentyl, or cyclohexyl. In some embodiments, $R^5$ is optionally substituted 4- to 6-membered heterocyclyl. In some embodiments, $R^5$ is $NR^{10}R^{11}$. For example, $R^{10}$ and $R^{11}$ are each independently $C_{1-6}$ alkyl, such as such as methyl, ethyl, propyl, isopropyl, butyl, isobutyl, tert-butyl, pentyl, neopentyl, or hexyl. Alternatively, $R^{10}$ is H and $R^{11}$ is $C_{1-6}$ alkyl, such as methyl, ethyl, propyl, isopropyl, butyl, isobutyl, tert-butyl, pentyl, neopentyl, or hexyl. Alternatively yet, $R^{10}$ and $R^{11}$ are each H. The remainder of features and example features of the fourth aspect is as described above with respect to the first through third aspects of the first embodiment.

In a fifth aspect of the first embodiment, $R^3$ is $(R^7)S(=O)(NR^6)$. For example, $R^7$ is $C_{1-6}$ alky, such as methyl, ethyl, propyl, isopropyl, butyl, isobutyl, tert-butyl, pentyl, neopentyl, or hexyl, or $C_{3-6}$ cycloalkyl, cyclopropyl, cyclobutyl, cyclopentyl, or cyclohexyl. Alternatively, $R^6$ and $R^7$ taken together with the nitrogen and sulfur atoms to which they are attached form a 4- to 10-membered heterocyclyl. The remainder of features and example features of the fifth aspect is as described above with respect to the first through fourth aspects of the first embodiment.

In a sixth aspect of the first embodiment, $R^3$ is $C(=O)NR^8R^9$. For example, $R^8$ is H and $R^9$ is $C_{1-3}$ alkyl, such as methyl, ethyl, propyl, or isopropyl. Alternatively, $R^8$ and $R^9$ are each independently $C_{1-3}$ alkyl, such as methyl, ethyl, propyl, or isopropyl. Alternatively yet, $R^8$ and $R^9$ are H. The remainder of features and example features of the sixth aspect is as described above with respect to the first through fifth aspects of the first embodiment.

In a seventh aspect of the first embodiment, $R^3$ is selected from $QR^7$, $NH(C=O)R^5$, CN, and $NR^8R^9$. For example, $R^3$ is $QR^7$. For example, $R^7$ is $C_{1-6}$ alkyl, such as methyl, ethyl, propyl, isopropyl, butyl, isobutyl, tert-butyl, pentyl, neopentyl, or hexyl. Alternatively, Q is O. Alternatively yet, Q is S. In some embodiments, Q is —C(=O)—. The remainder of features and example features of the seventh aspect is as described above with respect to the first through sixth aspects of the first embodiment.

In an eighth aspect of the first embodiment, $R^3$ is halogen. For example, $R^3$ is Cl. Alternatively, $R^3$ is F. The remainder of features and example features of the eighth aspect is as described above with respect to the first through seventh aspects of the first embodiment.

In a ninth aspect of the first embodiment, $R^3$ is $P(=O)R^{8a}R^{9a}$. For example, $R^{8a}$ and $R^{9b}$ are each independently $C_{1-3}$ alkyl, such as methyl, ethyl, propyl, or isopropyl. In some embodiments, $R^{8a}$ and $R^{9b}$ are each methyl or ethyl. Alternatively, $R^{8a}$ and $R^{9a}$ taken together with the phosphorus atom to which they are attached form 4- to 10-membered heterocyclyl. In a ninth aspect of the first embodiment, the compound is represented by structural formula (Ia):

(Ia)

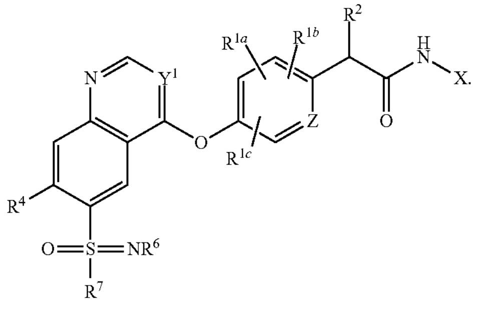

The remainder of features and example features of the ninth aspect is as described above with respect to the first through eighth aspects of the first embodiment.

In a tenth aspect of the first embodiment, the compound is represented by structural formula (Ib):

(Ib)

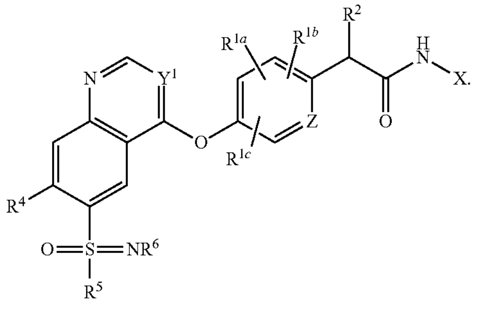

The remainder of features and example features of the tenth aspect is as described above with respect to the first through ninth aspects of the first embodiment.

In an eleventh aspect of the first embodiment, the compound is represented by structural formula (Ic):

(Ic)

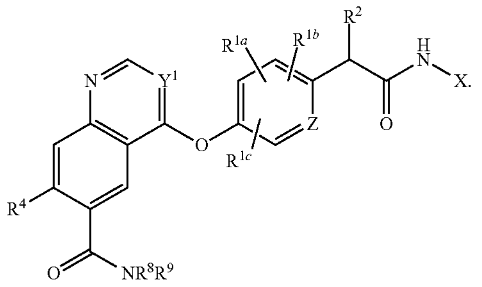

The remainder of features and example features of the eleventh aspect is as described above with respect to the first through ninth through tenth aspects of the first embodiment.

In a twelfth aspect of the first embodiment, the compound is represented by structural formula (Id):

(Id)

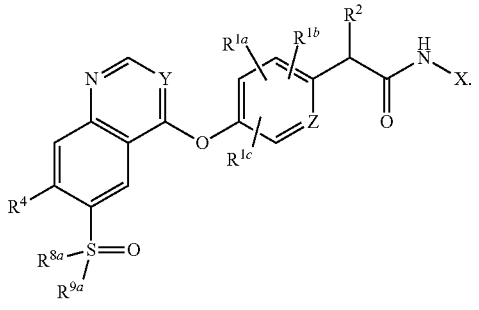

The remainder of features and example features of the twelfth aspect is as described above with respect to the first through eleventh aspects of the first embodiment.

In a thirteenth aspect of the first embodiment, the compound is represented by structural formula (Ie):

(Ie)

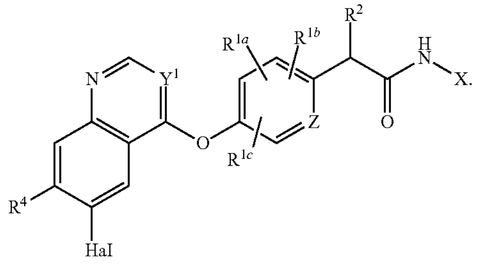

The remainder of features and example features of the thirteenth aspect is as described above with respect to the first through twelfth aspects of the first embodiment.

In a fourteenth aspect of the first embodiment, the compound is represented by structural formula (If):

(If)

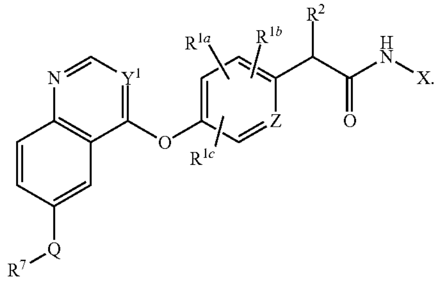

The remainder of features and example features of the fourteenth aspect is as described above with respect to the first through thirteenth aspects of the first embodiment.

In a fifteenth aspect of the first embodiment, $R^4$ is H. The remainder of features and example features of the fifteenth aspect is as described above with respect to the first through fourteenth aspects of the first embodiment.

In a sixteenth aspect of the first embodiment, $R^4$ is $C_{1-6}$ alkoxy, such as $C_{1-4}$ alkoxy. For example, $R^4$ is methoxy, ethoxy, propoxy, isopropoxy, butoxy, isobutoxy, or tert-butoxy, such as methoxy. The remainder of features and example features of the sixteenth aspect is as described above with respect to the first through fifteenth aspects of the first embodiment.

In a seventeenth aspect of the first embodiment, X is a moiety represented by the following structural formula:

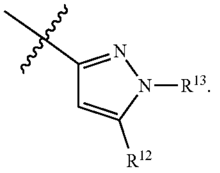

For example, $R^{13}$ is H. Alternatively, $R^{13}$ is $C_{1-6}$ alkyl, such as methyl, ethyl, propyl, isopropyl, butyl, isobutyl, tert-butyl, pentyl, neopentyl, or hexyl. The remainder of features and example features of the seventeenth aspect is as described above with respect to the first through sixteenth aspects of the first embodiment.

In an eighteenth aspect of the first embodiment, X is a moiety represented by the following structural formula:

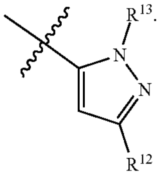

For example, $R^{13}$ is H. Alternatively, $R^{13}$ is $C_{1-6}$ alkyl, such as methyl, ethyl, propyl, isopropyl, butyl, isobutyl, tert-butyl, pentyl, neopentyl, or hexyl. The remainder of features and example features of the eighteenth aspect is as described above with respect to the seventeenth aspect of the first embodiment.

In a nineteenth aspect of the first embodiment, X is a moiety represented by the following structural formula:

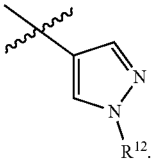

The remainder of features and example features of the nineteenth aspect is as described above with respect to the first through eighteenth aspects of the first embodiment.

In a twentieth aspect of the first embodiment, X is a moiety represented by one of the following structural formulas:

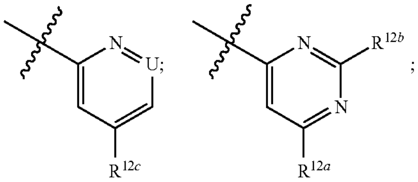

-continued

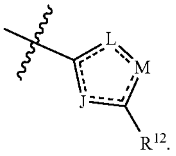

For example, X is a moiety represented by the structural formula

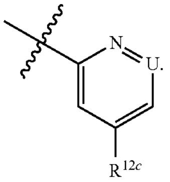

Alternatively, X is a moiety represented by the structural formula

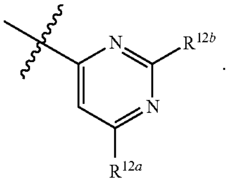

In some embodiments, X is a moiety represented by the structural formula

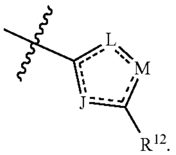

In some embodiments, X is a moiety represented by one of the following structural formulas:

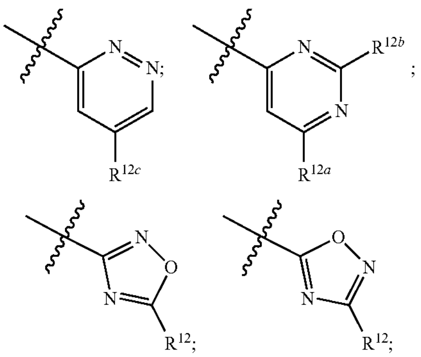

-continued

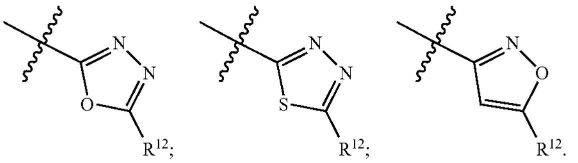

The remainder of features and example features of the twentieth aspect is as described above with respect to the first through nineteenth aspects of the first embodiment.

In a twenty-first aspect of the first embodiment, $R^{12}$ is an optionally substituted $C_{3-6}$ alkyl, such as such as propyl, isopropyl, butyl, isobutyl, tert-butyl, pentyl, neopentyl, or hexyl. For example $R^{12}$ is propyl, isopropyl, butyl, isobutyl, tert-butyl. In some embodiments, $R^{12}$ is tert-butyl. In some embodiments, $R^{12}$ is unsubstituted tert-butyl. In some embodiments, $R^{12}$ is an isopropyl substituted with 1 to 3 substituents independently selected from deuterium, $CF_3$, F, Cl, Br, CN, $OR^{14}$, $SR^{15}$, $NR^{16}R^{17}$, $S(O)R^{18}$, $S(O)_2R^{18a}$, $NR^{19}S(=O)R^{20}$, $C(=O)OR^{20a}$, $C(=O)NR^{21}R^{22}$, $NR^{23}C(=O)R^{24}$, $C(=S)NR^{25}R^{26}$, $C(=O)R^{27}$, $C_{1-6}$ alkyl, $C_{3-8}$ cycloalkyl, $C_{2-6}$ alkenyl, halo($C_{1-6}$)alkyl, $C_{1-3}$ alkylsulfonylaminoalkyl, hydroxy($C_{1-6}$)alkyl, amino($C_{1-6}$)alkyl, cyano($C_{1-6}$)alkyl, $C_{1-3}$ alkylcarbonylamino($C_{1-6}$)alkyl, $C_{1-3}$ alkoxy, halo($C_{1-3}$)alkoxy, $C_{1-6}$ alkoxy($C_{1-3}$)alkyl, $C_{6-12}$ aryl, 4- to 10-membered heterocyclyl, and 5- to 12-membered heteroaryl. The remainder of features and example features of the twenty-first aspect is as described above with respect to the first through twentieth aspects of the first embodiment.

In a twenty-second aspect of the first embodiment, $R^{12}$ is selected is a moiety represented by one of the following structural formulas:

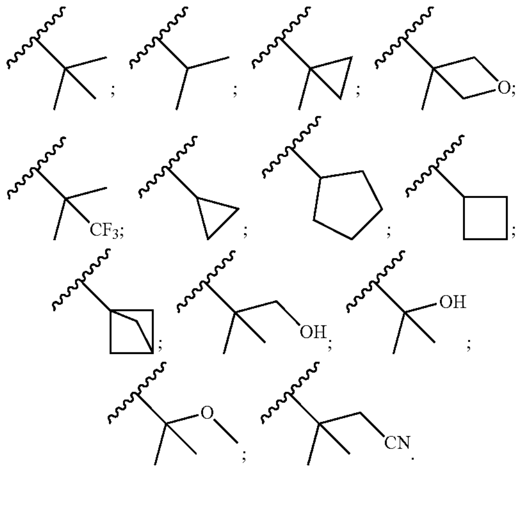

For example, $R^{12}$ is selected is a moiety represented by one of the following structural formulas:

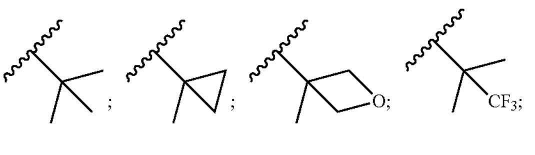

-continued

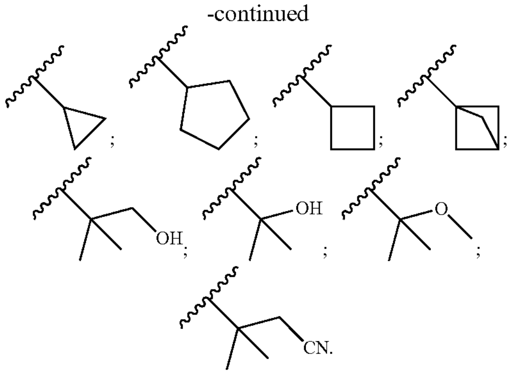

The remainder of features and example features of the twenty-second aspect is as described above with respect to the first through twenty-first aspects of the first embodiment.

In a twenty-third aspect of the first embodiment, $R^{1a}$ is halogen or a $C_{1-3}$ alkyl. For example, $R^{1a}$ is $C_{1-3}$ alkyl, such as methyl, ethyl, propyl, or isopropyl. Alternatively, $R^{1a}$ is halogen. In some embodiments, $R^{1a}$ is selected from H, F, Cl, $CH_3$, $CHF_2$, $CF_3$, and $CD_3$. For example, $R^{1a}$ is selected from F, $CH_3$, and $CHF_2$. The remainder of the values and example values of the variables of the twenty-third aspect are as described above with respect to the first through the twenty-second aspects of the first embodiment.

In a twenty-fourth aspect of the first embodiment, $R^{1b}$ is halogen or a $C_{1-3}$ alkyl. For example, $R^{1b}$ is $C_{1-3}$ alkyl, such as methyl, ethyl, propyl, or isopropyl. Alternatively, $R^{1b}$ is halogen. In some embodiments, $R^{1b}$ is selected from H, F, Cl, $CH_3$, $CHF_2$, $CF_3$, and $CD_3$. For example, $R^{1b}$ is selected from F, $CH_3$, and $CHF_2$. The remainder of the values and example values of the variables of the twenty-fourth aspect are as described above with respect to the first through the twenty-third aspects of the first embodiment.

In a twenty-fifth aspect of the first embodiment, $R^{1c}$ is H or halogen. For example, $R^{1c}$ is H. Alternatively, $R^{1c}$ halogen. For example, $R^{1c}$ is F. The remainder of the values and example values of the variables of the twenty-fifth aspect are as described above with respect to the first through the twenty-fourth aspects of the first embodiment.

In a twenty-fifth aspect of the first embodiment, the compound is represented by structural formula (Ig):

(Ig)

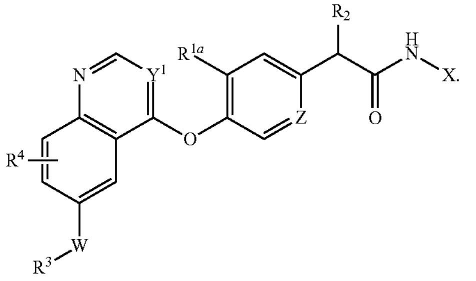

The remainder of the values and example values of the variables of the twenty-fifth aspect are as described above with respect to the first through the twenty-fourth aspects of the first embodiment.

In a twenty-seventh aspect of the first embodiment, the compound is represented by structural formula (Ih), (Ii), or (Ij):

(Ih)

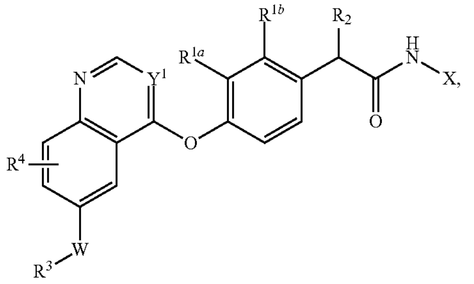

(Ii)

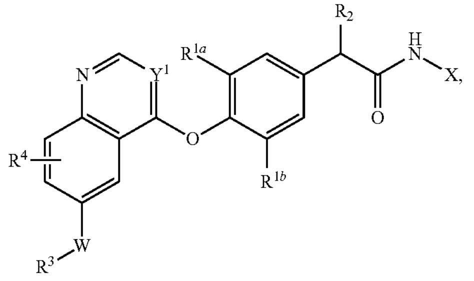

(Ij)

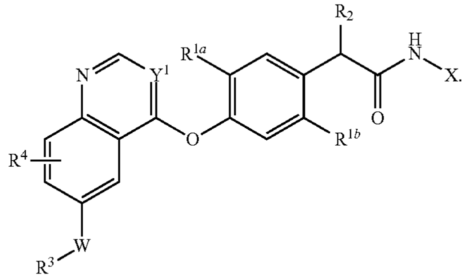

For example, the compound is represented by structural formula (Ih). Alternatively, the compound is represented by structural formula (Ii). Alternatively yet, the compound is represented by structural formula (Ij). The remainder of the values and example values of the variables of the twenty-seventh aspect are as described above with respect to the first through the twenty-sixth aspects of the first embodiment.

In a twenty-eighth aspect of the first embodiment, $Y^1$ is CH. Alternatively, $Y^1$ is N. The remainder of the values and example values of the variables of the twenty-eighth aspect are as described above with respect to the first through the twenty-seventh aspects of the first embodiment.

In a twenty-ninth aspect of the first embodiment, Z is CH. Alternatively, Z is N. The remainder of the values and example values of the variables of the twenty-ninth aspect are as described above with respect to the first through the twenty-eighth aspects of the first embodiment.

In a thirtieth aspect of the first embodiment, $R^2$ is H. Alternatively, $R^2$ is $C_{1-3}$ alkyl. For example, $R^2$ is methyl, ethyl, propyl, or isopropyl. The remainder of the values and example values of the variables of the thirtieth aspect are as described above with respect to the first through the twenty-ninth aspects of the first embodiment.

In a thirty-first aspect of the first embodiment, the compound is represented by structural formula (Ik):

(Ik)

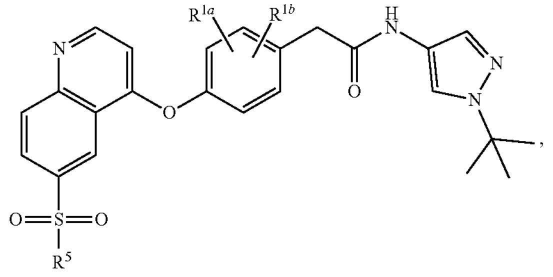

wherein $R^5$ is $C_{1-3}$ alkyl. For example, $R^5$ is methyl, ethyl, propyl, or isopropyl. The remainder of the values and example values of the variables of the thirty-first aspect are as described above with respect to the first through the thirtieth aspects of the first embodiment.

In a thirty-second aspect of the first embodiment, the compound is represented by structural formula (Il):

(Il)

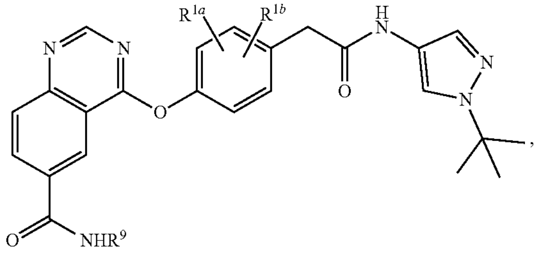

wherein $R^9$ is $C_{1-3}$ alkyl. For example, $R^9$ is methyl, ethyl, propyl, or isopropyl. The remainder of the values and example values of the variables of the thirty-second aspect are as described above with respect to the first through the thirtieth aspects of the first embodiment.

In a thirty-third aspect of the first embodiment, the compound is represented by structural formula (Im):

(Im)

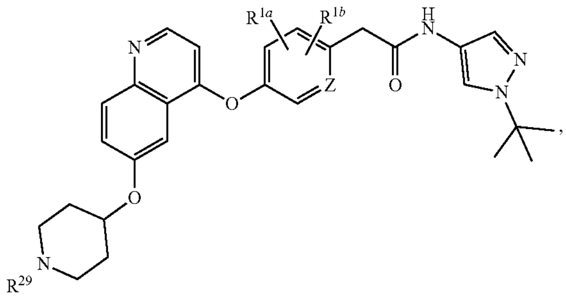

wherein $R^{29}$ is $C_{1-3}$ alkyl. For example, $R^{29}$ is methyl, ethyl, propyl, or isopropyl. The remainder of the values and example values of the variables of the thirty-third aspect are as described above with respect to the first through the thirtieth aspects of the first embodiment.

In a thirty-fourth aspect of the first embodiment, the compound is selected from the compounds in Table 1.
TABLE 1
| Compound number | Structure |
| --- | --- |
| 1 | 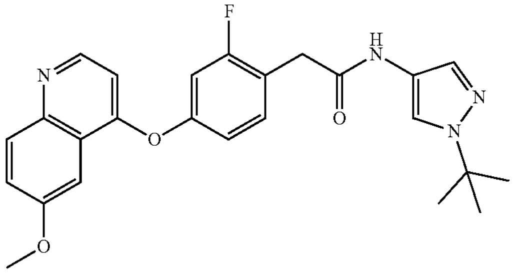 [SMILES: COc1ccc2nccc(Oc3ccc(CC(=O)Nc4cnn(C(C)(C)C)c4)c(F)c3)c2c1] |
| 2 | 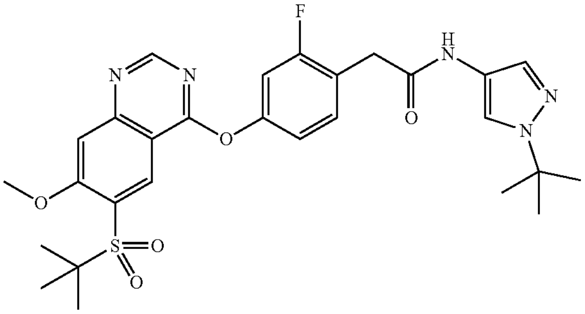 [SMILES: COc1cc2ncnc(Oc3ccc(CC(=O)Nc4cnn(C(C)(C)C)c4)c(F)c3)c2cc1S(=O)(=O)C(C)(C)C] |
| 3 | 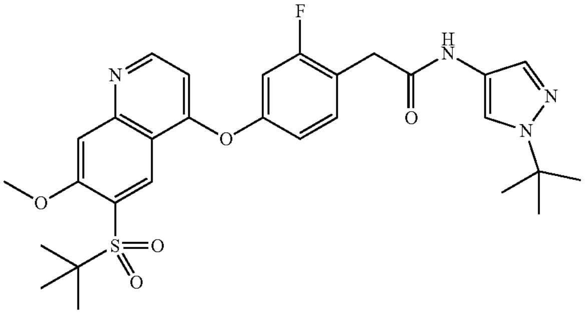 [SMILES: COc1cc2nccc(Oc3ccc(CC(=O)Nc4cnn(C(C)(C)C)c4)c(F)c3)c2cc1S(=O)(=O)C(C)(C)C] |
| 4 | 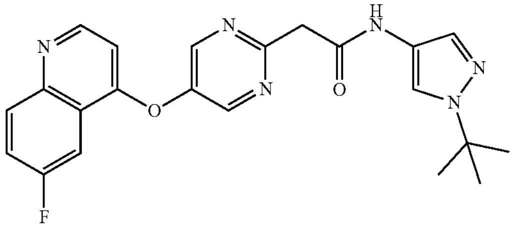 [SMILES: CC(C)(C)n1cc(NC(=O)Cc2ncc(Oc3ccnc4ccc(F)cc34)cn2)cn1] |
| 5 | 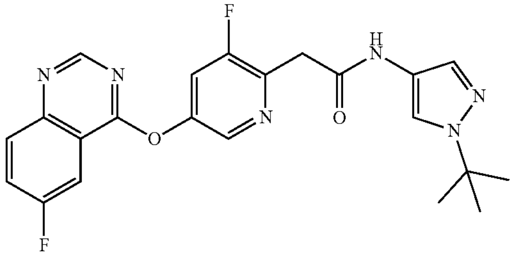 [SMILES: CC(C)(C)n1cc(NC(=O)Cc2ncc(Oc3ncnc4ccc(F)cc34)cc2F)cn1] |

TABLE 1-continued
| Compound number | Structure |
| --- | --- |
| 6 | 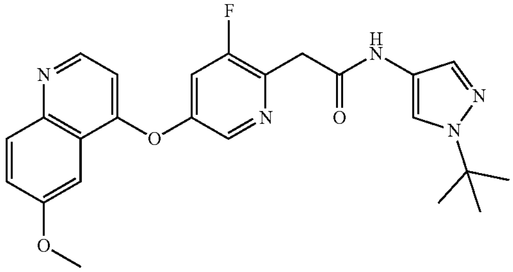 [SMILES: COc1ccc2nccc(Oc3cnc(CC(=O)Nc4cnn(C(C)(C)C)c4)c(F)c3)c2c1] |
| 7 | 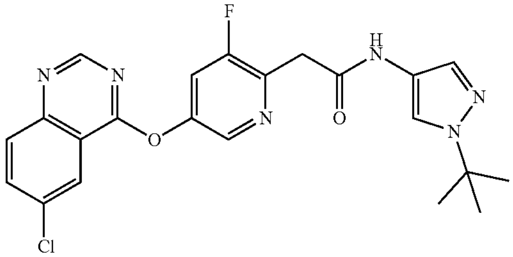 |
| 8 | 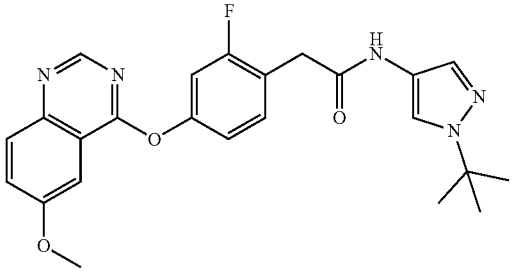 [SMILES: COc1ccc2ncnc(Oc3ccc(CC(=O)Nc4cnn(C(C)(C)C)c4)c(F)c3)c2c1] |
| 9 | 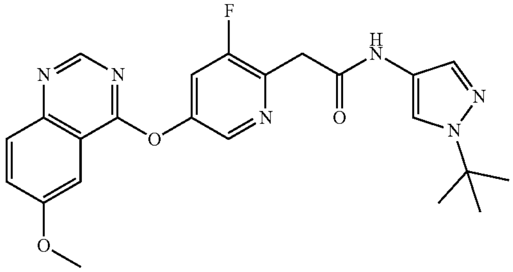 [SMILES: COc1ccc2ncnc(Oc3cnc(CC(=O)Nc4cnn(C(C)(C)C)c4)c(F)c3)c2c1] |
| 10 | 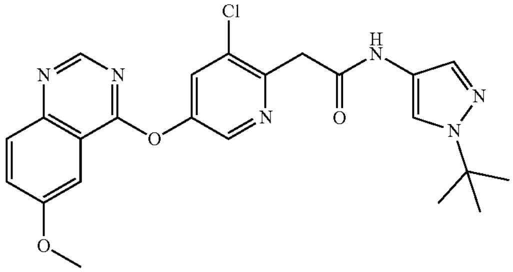 |

TABLE 1-continued
| Compound number | Structure |
|---|---|
| 11 | 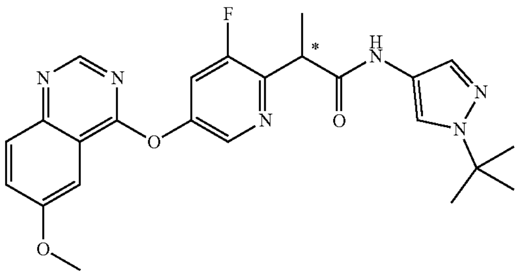 [SMILES: COc1ccc2ncnc(Oc3cnc(C(C)C(=O)Nc4cnn(C(C)(C)C)c4)c(F)c3)c2c1] enantiomer 1 |
| 12 | 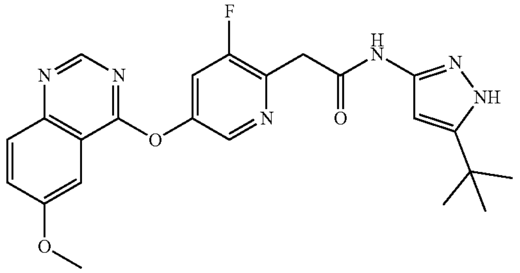 [SMILES: COc1ccc2ncnc(Oc3cnc(CC(=O)Nc4cc(C(C)(C)C)[nH]n4)c(F)c3)c2c1] |
| 13 | 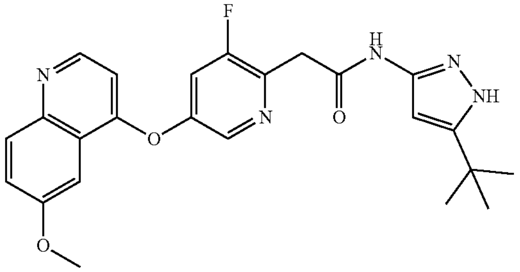 [SMILES: COc1ccc2nccc(Oc3cnc(CC(=O)Nc4cc(C(C)(C)C)[nH]n4)c(F)c3)c2c1] |
| 14 | 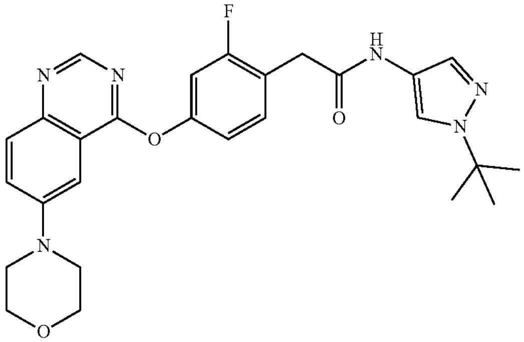 [SMILES: CC(C)(C)n1cc(NC(=O)Cc2ccc(Oc3ncnc4ccc(N5CCOCC5)cc34)cc2F)cn1] |
| 15 | 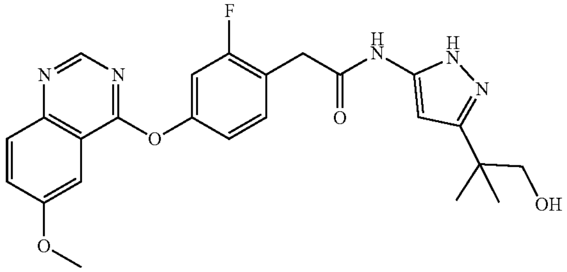 [SMILES: COc1ccc2ncnc(Oc3ccc(CC(=O)Nc4cc(C(C)(C)CO)n[nH]4)c(F)c3)c2c1] |

TABLE 1-continued
| Compound number | Structure |
|---|---|
| 16 | 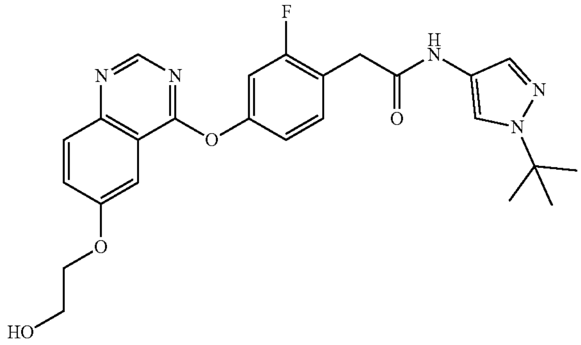 [SMILES: CC(C)(C)n1cc(NC(=O)Cc2ccc(Oc3ncnc4ccc(OCCO)cc34)cc2F)cn1] |
| 17 | 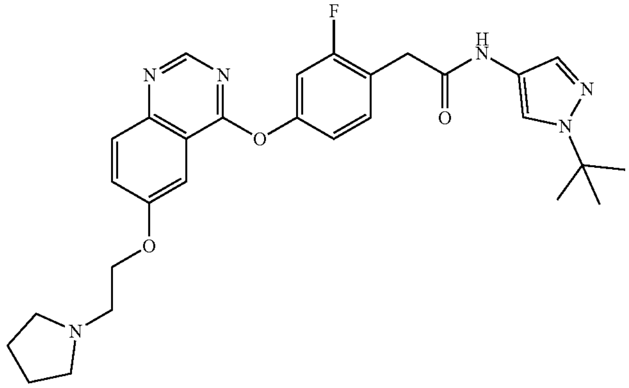 [SMILES: CC(C)(C)n1cc(NC(=O)Cc2ccc(Oc3ncnc4ccc(OCCN5CCCC5)cc34)cc2F)cn1] |
| 18 | 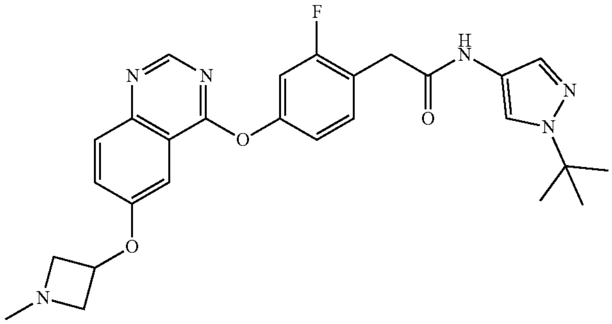 [SMILES: CN1CC(Oc2ccc3ncnc(Oc4ccc(CC(=O)Nc5cnn(C(C)(C)C)c5)c(F)c4)c3c2)C1] |
| 19 | 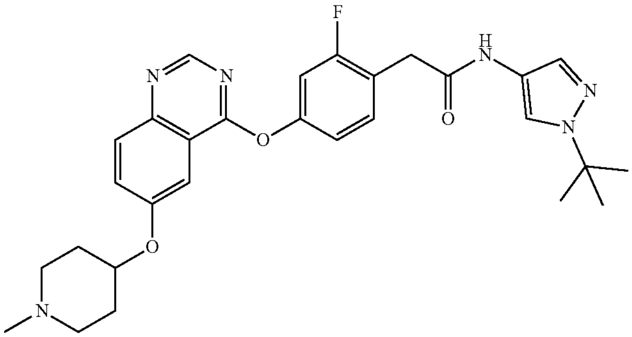 [SMILES: CN1CCC(Oc2ccc3ncnc(Oc4ccc(CC(=O)Nc5cnn(C(C)(C)C)c5)c(F)c4)c3c2)CC1] |

TABLE 1-continued
| Compound number | Structure |
| --- | --- |
| 20 | 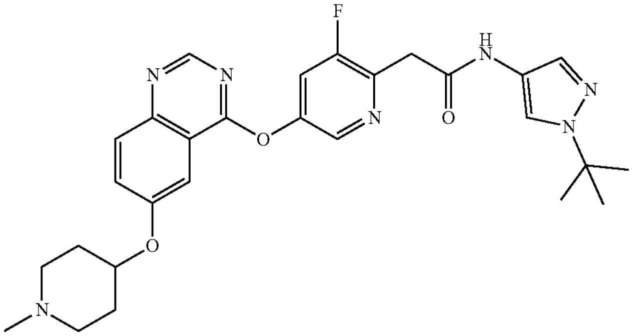 |
| 21 | 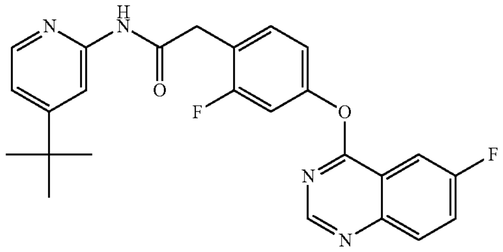 [SMILES: CC(C)(C)c1ccnc(NC(=O)Cc2ccc(Oc3ncnc4ccc(F)cc34)cc2F)c1] |
| 22 | 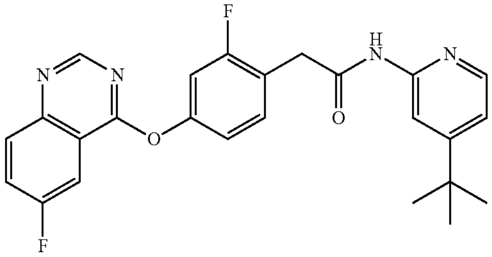 [SMILES: CC(C)(C)c1ccnc(NC(=O)Cc2ccc(Oc3ncnc4ccc(F)cc34)cc2F)c1] |
| 23 | 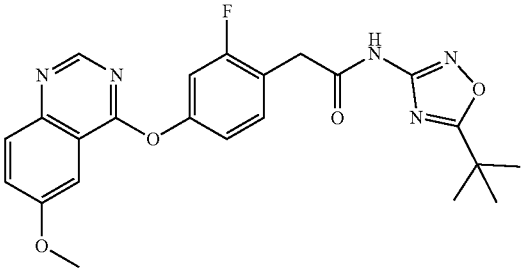 [SMILES: COc1ccc2ncnc(Oc3ccc(CC(=O)Nc4noc(C(C)(C)C)n4)c(F)c3)c2c1] |
| 24 | 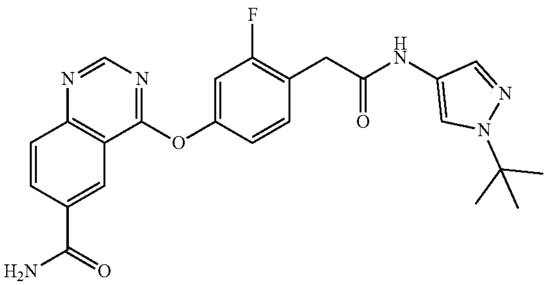 [SMILES: CC(C)(C)n1cc(NC(=O)Cc2ccc(Oc3ncnc4ccc(C(N)=O)cc34)cc2F)cn1] |

TABLE 1-continued
| Compound number | Structure |
| --- | --- |
| 25 | 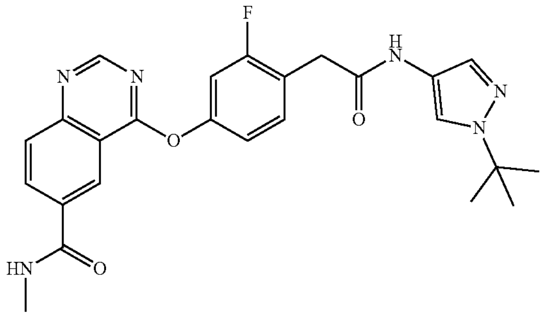 [SMILES: CNC(=O)c1ccc2ncnc(Oc3ccc(CC(=O)Nc4cnn(C(C)(C)C)c4)c(F)c3)c2c1] |
| 26 | 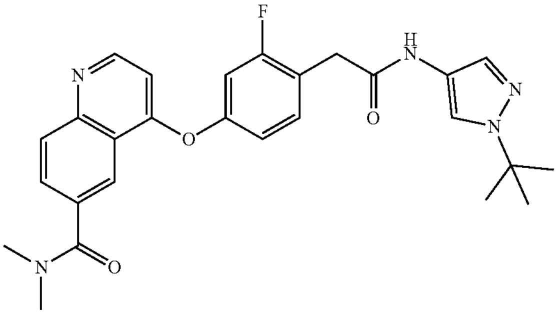 [SMILES: CN(C)C(=O)c1ccc2nccc(Oc3ccc(CC(=O)Nc4cnn(C(C)(C)C)c4)c(F)c3)c2c1] |
| 27 | 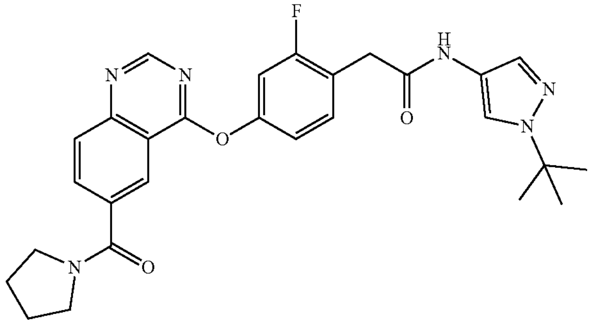 [SMILES: CC(C)(C)n1cc(NC(=O)Cc2ccc(Oc3ncnc4ccc(C(=O)N5CCCC5)cc34)cc2F)cn1] |
| 28 | 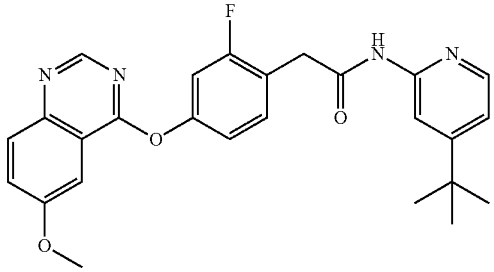 [SMILES: COc1ccc2ncnc(Oc3ccc(CC(=O)Nc4cc(C(C)(C)C)ccn4)c(F)c3)c2c1] |
| 29 | 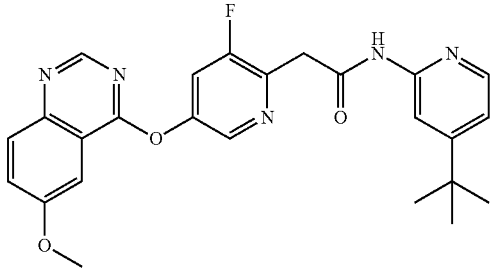 [SMILES: COc1ccc2ncnc(Oc3cnc(CC(=O)Nc4cc(C(C)(C)C)ccn4)c(F)c3)c2c1] |

TABLE 1-continued
| Compound number | Structure |
|---|---|
| 30 | 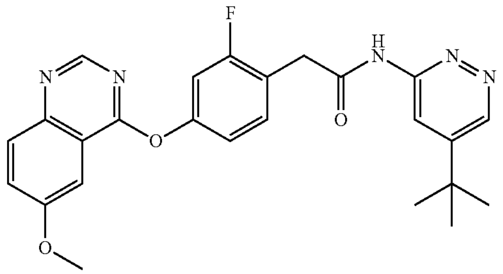 [SMILES: COc1ccc2ncnc(Oc3ccc(CC(=O)Nc4cc(C(C)(C)C)cnn4)c(F)c3)c2c1] |
| 31 | 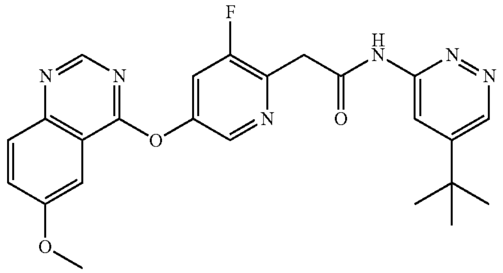 [SMILES: COc1ccc2ncnc(Oc3cnc(CC(=O)Nc4cc(C(C)(C)C)cnn4)c(F)c3)c2c1] |
| 32 | 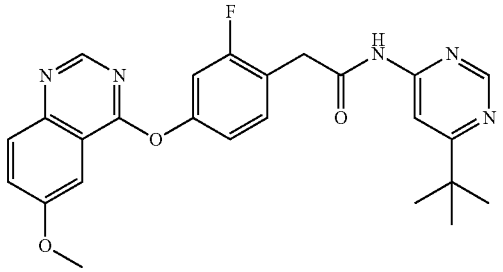 [SMILES: COc1ccc2ncnc(Oc3ccc(CC(=O)Nc4cc(C(C)(C)C)ncn4)c(F)c3)c2c1] |
| 33 | 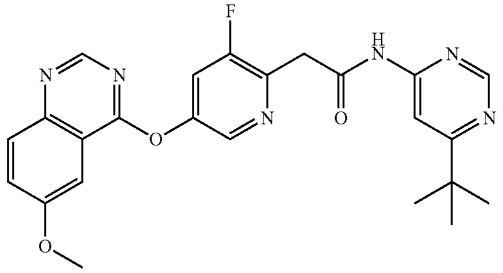 [SMILES: COc1ccc2ncnc(Oc3cnc(CC(=O)Nc4cc(C(C)(C)C)ncn4)c(F)c3)c2c1] |
| 34 | 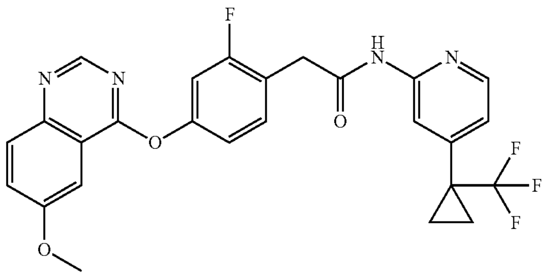 [SMILES: COc1ccc2ncnc(Oc3ccc(CC(=O)Nc4cc(C5(C(F)(F)F)CC5)ccn4)c(F)c3)c2c1] |

TABLE 1-continued
| Compound number | Structure |
|---|---|
| 35 | 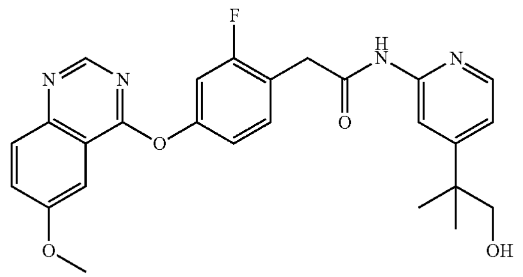 [SMILES: COc1ccc2ncnc(Oc3ccc(CC(=O)Nc4cc(C(C)(C)CO)ccn4)c(F)c3)c2c1] |
| 36 | 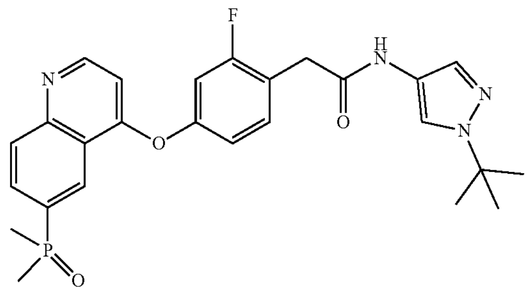 [SMILES: CC(C)(C)n1cc(NC(=O)Cc2ccc(Oc3ccnc4ccc(P(C)(C)=O)cc34)cc2F)cn1] |
| 37 | 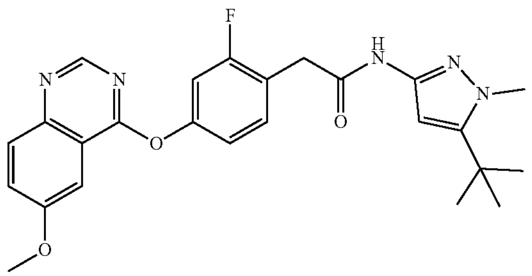 [SMILES: COc1ccc2ncnc(Oc3ccc(CC(=O)Nc4cc(C(C)(C)C)n(C)n4)c(F)c3)c2c1] |
| 38 | 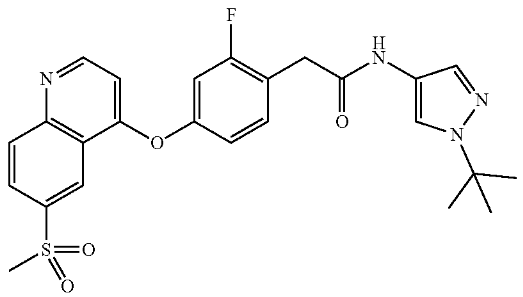 [SMILES: CC(C)(C)n1cc(NC(=O)Cc2ccc(Oc3ccnc4ccc(S(C)(=O)=O)cc34)cc2F)cn1] |
| 39 | 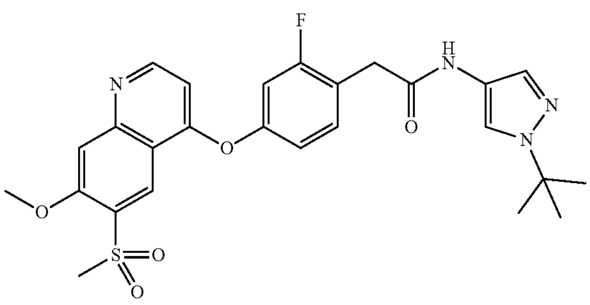 [SMILES: COc1cc2nccc(Oc3ccc(CC(=O)Nc4cnn(C(C)(C)C)c4)c(F)c3)c2cc1S(C)(=O)=O] |

TABLE 1-continued
| Compound number | Structure |
|---|---|
| 40 | 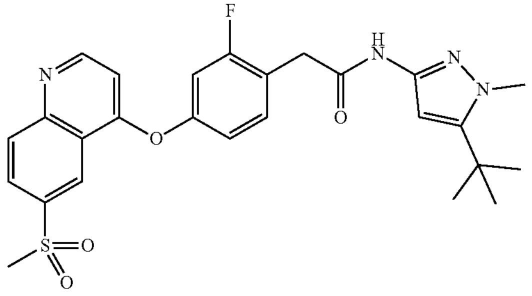 [SMILES: Cn1nc(NC(=O)Cc2ccc(Oc3ccnc4ccc(S(C)(=O)=O)cc34)cc2F)cc1C(C)(C)C] |
| 41 | 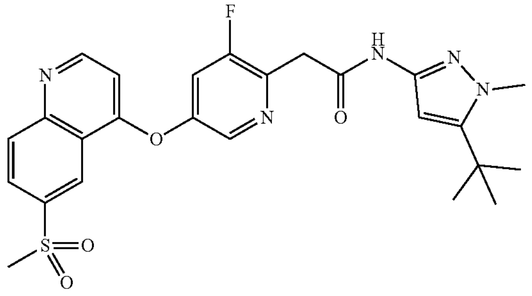 [SMILES: Cn1nc(NC(=O)Cc2ncc(Oc3ccnc4ccc(S(C)(=O)=O)cc34)cc2F)cc1C(C)(C)C] |
| 42 | 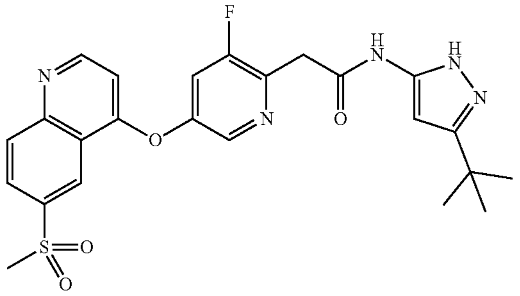 [SMILES: CC(C)(C)c1cc(NC(=O)Cc2ncc(Oc3ccnc4ccc(S(C)(=O)=O)cc34)cc2F)[nH]n1] |
| 43 | 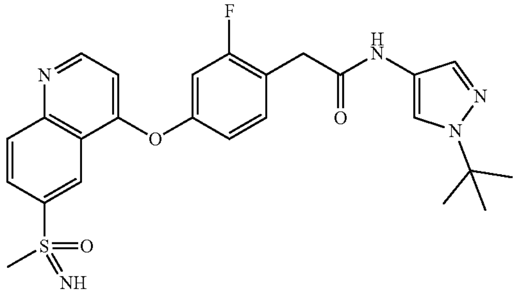 [SMILES: CC(C)(C)n1cc(NC(=O)Cc2ccc(Oc3ccnc4ccc(S(C)(=N)=O)cc34)cc2F)cn1] |
| 44 | 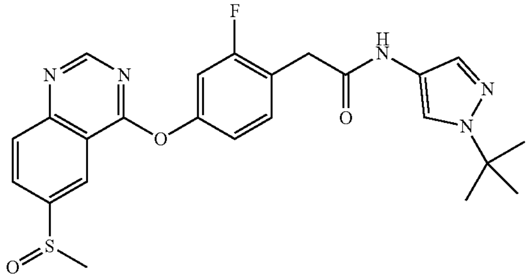 [SMILES: CS(=O)c1ccc2ncnc(Oc3ccc(CC(=O)Nc4cnn(C(C)(C)C)c4)c(F)c3)c2c1] |

TABLE 1-continued
| Compound number | Structure |
|---|---|
| 45 | 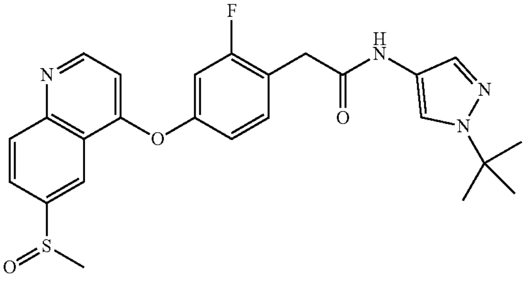 [SMILES: CS(=O)c1ccc2nccc(Oc3ccc(CC(=O)Nc4cnn(C(C)(C)C)c4)c(F)c3)c2c1] |
| 46 | 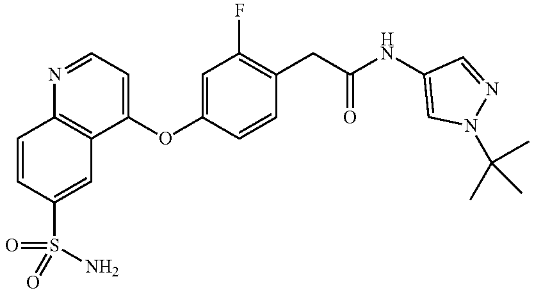 [SMILES: CC(C)(C)n1cc(NC(=O)Cc2ccc(Oc3ccnc4ccc(S(N)(=O)=O)cc34)cc2F)cn1] |
| 47 | 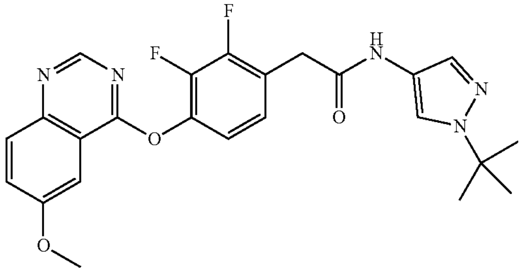 [SMILES: COc1ccc2ncnc(Oc3ccc(CC(=O)Nc4cnn(C(C)(C)C)c4)c(F)c3F)c2c1] |
| 48 | 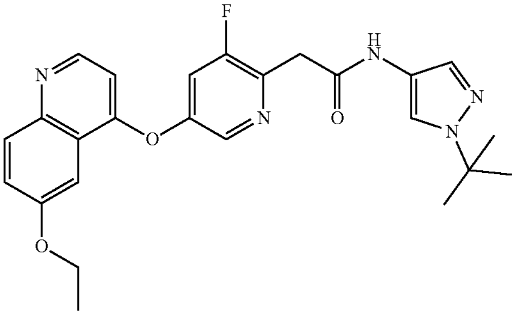 [SMILES: CCOc1ccc2nccc(Oc3cnc(CC(=O)Nc4cnn(C(C)(C)C)c4)c(F)c3)c2c1] |
| 49 | 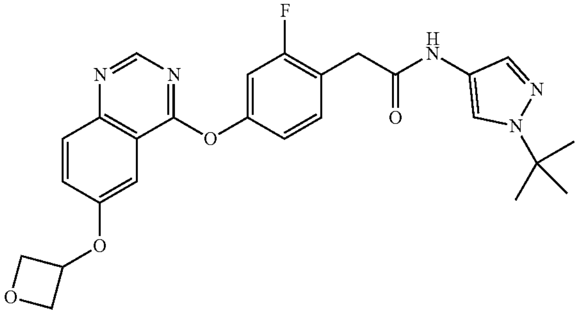 [SMILES: CC(C)(C)n1cc(NC(=O)Cc2ccc(Oc3ncnc4ccc(OC5COC5)cc34)cc2F)cn1] |

TABLE 1-continued
| Compound number | Structure |
| --- | --- |
| 50 | 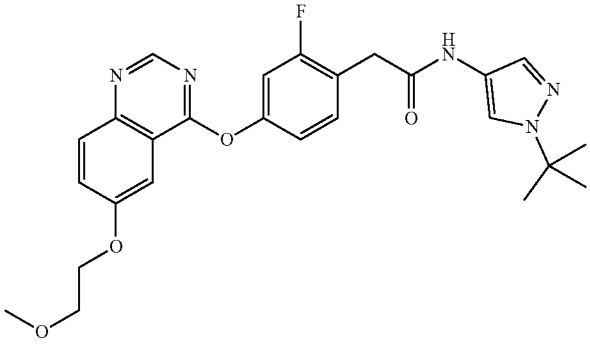 [SMILES: COCCOc1ccc2ncnc(Oc3ccc(CC(=O)Nc4cnn(C(C)(C)C)c4)c(F)c3)c2c1] |
| 51 | 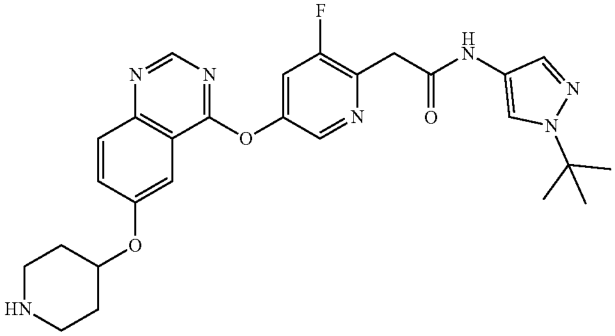 [SMILES: CC(C)(C)n1cc(NC(=O)Cc2ncc(Oc3ncnc4ccc(OC5CCNCC5)cc34)cc2F)cn1] |
| 52 | 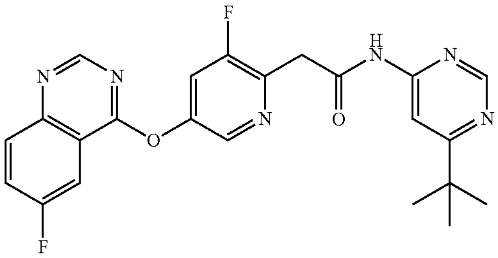 [SMILES: CC(C)(C)c1cc(NC(=O)Cc2ncc(Oc3ncnc4ccc(F)cc34)cc2F)ncn1] |
| 53 | 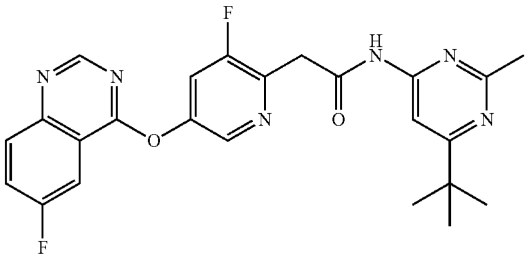 [SMILES: Cc1nc(NC(=O)Cc2ncc(Oc3ncnc4ccc(F)cc34)cc2F)cc(C(C)(C)C)n1] |
| 54 | 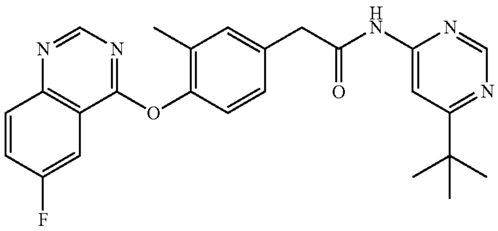 [SMILES: Cc1cc(CC(=O)Nc2cc(C(C)(C)C)ncn2)ccc1Oc1ncnc2ccc(F)cc12] |

TABLE 1-continued
| Compound number | Structure |
|---|---|
| 55 | 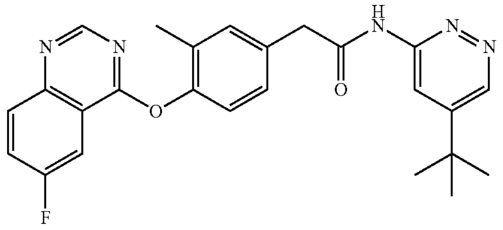 [SMILES: Cc1cc(CC(=O)Nc2cc(C(C)(C)C)cnn2)ccc1Oc1ncnc2ccc(F)cc12] |
| 56 | 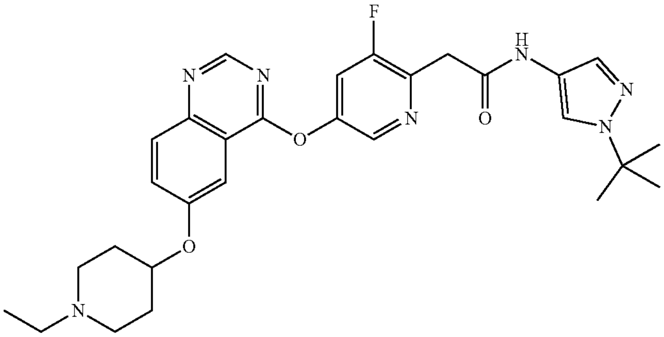 [SMILES: CCN1CCC(Oc2ccc3ncnc(Oc4cnc(CC(=O)Nc5cnn(C(C)(C)C)c5)c(F)c4)c3c2)CC1] |
| 57 | 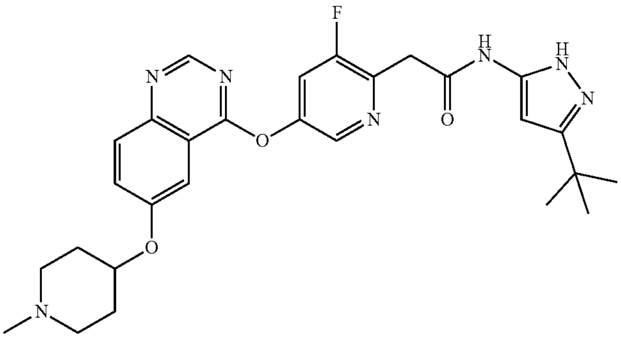 [SMILES: CN1CCC(Oc2ccc3ncnc(Oc4cnc(CC(=O)Nc5cc(C(C)(C)C)n[nH]5)c(F)c4)c3c2)CC1] |
| 58 | 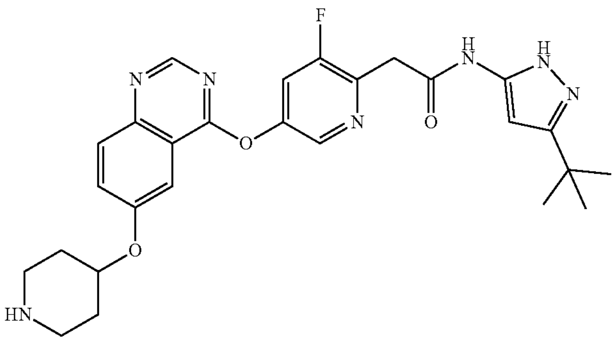 |

TABLE 1-continued
| Compound number | Structure |
|---|---|
| 59 | 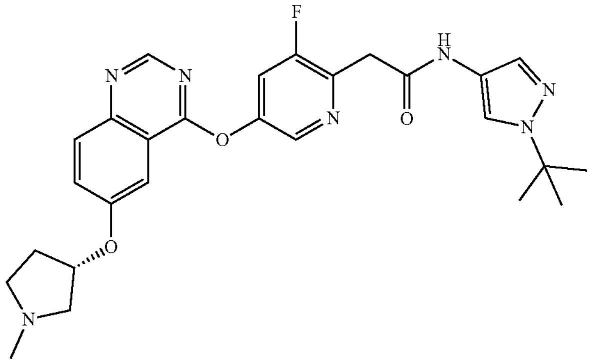 [SMILES: CN1CC[C@H](Oc2ccc3ncnc(Oc4cnc(CC(=O)Nc5cnn(C(C)(C)C)c5)c(F)c4)c3c2)C1] |
| 60 | 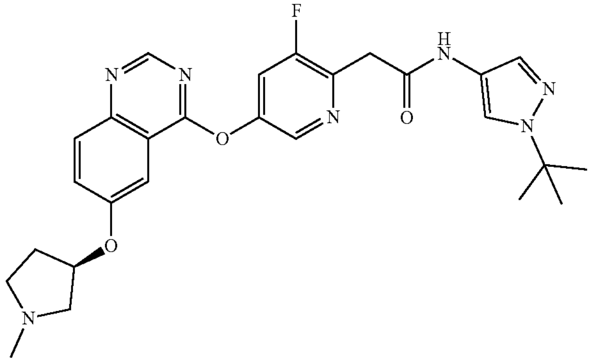 [SMILES: CN1CC[C@@H](Oc2ccc3ncnc(Oc4cnc(CC(=O)Nc5cnn(C(C)(C)C)c5)c(F)c4)c3c2)C1] |
| 61 | 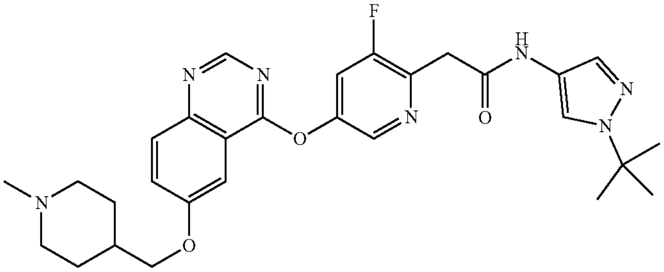 [SMILES: CN1CCC(COc2ccc3ncnc(Oc4cnc(CC(=O)Nc5cnn(C(C)(C)C)c5)c(F)c4)c3c2)CC1] |
| 62 | 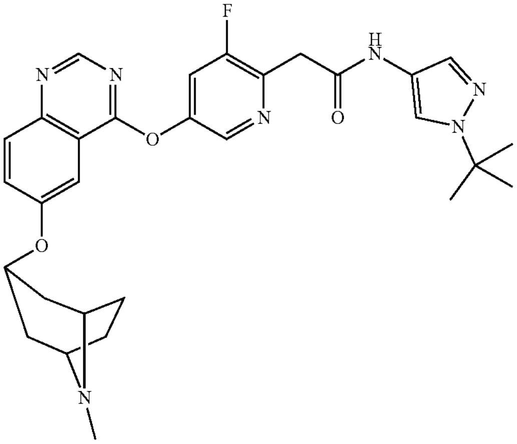 [SMILES: CN1C2CCC1CC(Oc1ccc3ncnc(Oc4cnc(CC(=O)Nc5cnn(C(C)(C)C)c5)c(F)c4)c3c1)C2] |

TABLE 1-continued
| Compound number | Structure |
|---|---|
| 63 | 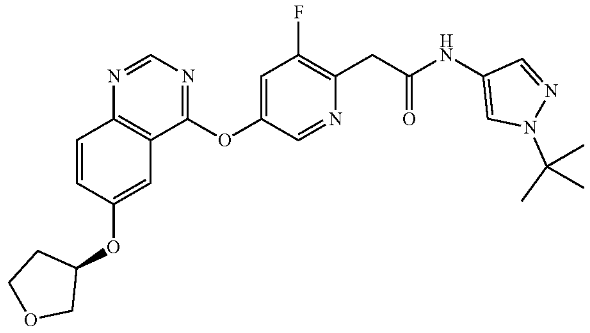 [SMILES: CC(C)(C)n1cc(NC(=O)Cc2ncc(Oc3ncnc4ccc(O[C@@H]5CCOC5)cc34)cc2F)cn1] |
| 64 | 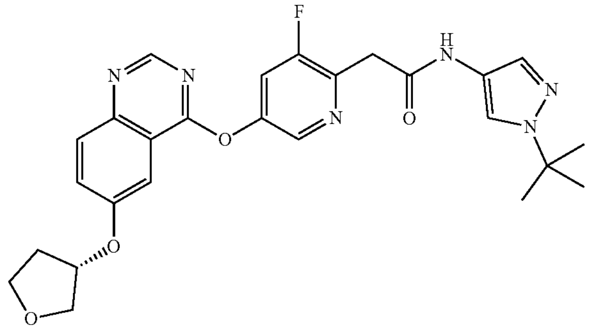 [SMILES: CC(C)(C)n1cc(NC(=O)Cc2ncc(Oc3ncnc4ccc(O[C@H]5CCOC5)cc34)cc2F)cn1] |
| 65 | 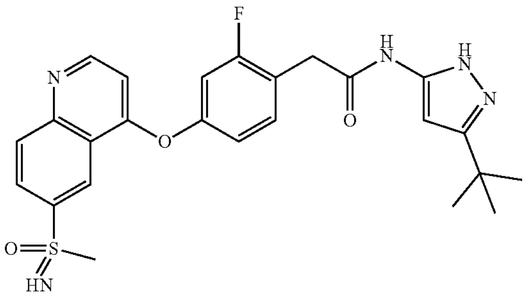 [SMILES: CC(C)(C)c1cc(NC(=O)Cc2ccc(Oc3ccnc4ccc(S(C)(=N)=O)cc34)cc2F)[nH]n1] |
| 66 | 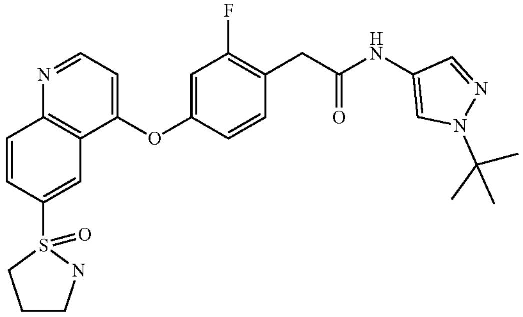 |

TABLE 1-continued
| Compound number | Structure |
|---|---|
| 67 | 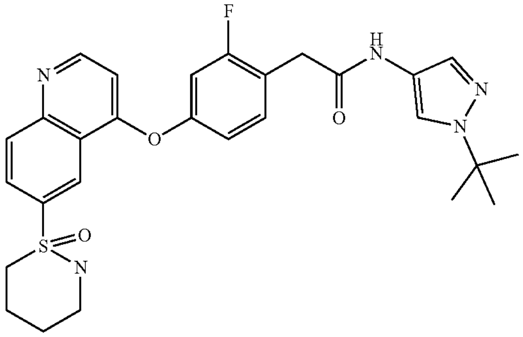 |
| 68 | 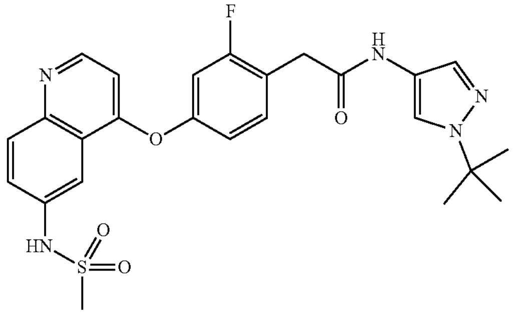 [SMILES: CC(C)(C)n1cc(NC(=O)Cc2ccc(Oc3ccnc4ccc(NS(C)(=O)=O)cc34)cc2F)cn1] |
| 69 | 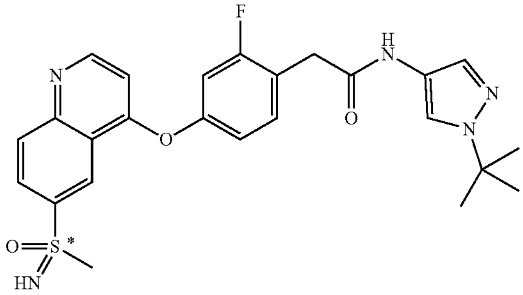 [SMILES: CC(C)(C)n1cc(NC(=O)Cc2ccc(Oc3ccnc4ccc(S(C)(=N)=O)cc34)cc2F)cn1]<br>enantiomer 1 |
| 70 | 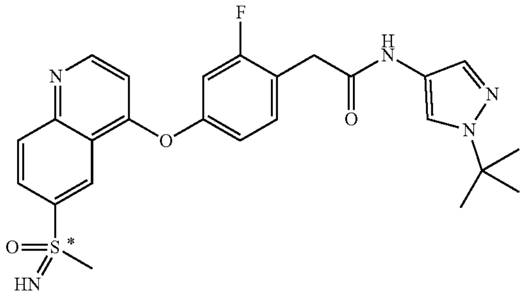 [SMILES: CC(C)(C)n1cc(NC(=O)Cc2ccc(Oc3ccnc4ccc(S(C)(=N)=O)cc34)cc2F)cn1]<br>enantiomer 2 |

TABLE 1-continued
| Compound number | Structure |
|---|---|
| 71 | 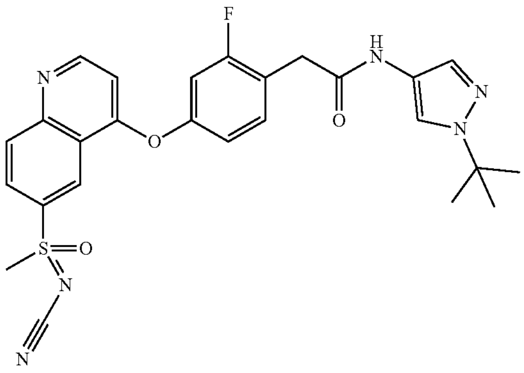 [SMILES: CC(C)(C)n1cc(NC(=O)Cc2ccc(Oc3ccnc4ccc(S(C)(=O)=NC#N)cc34)cc2F)cn1] |
| 72 | 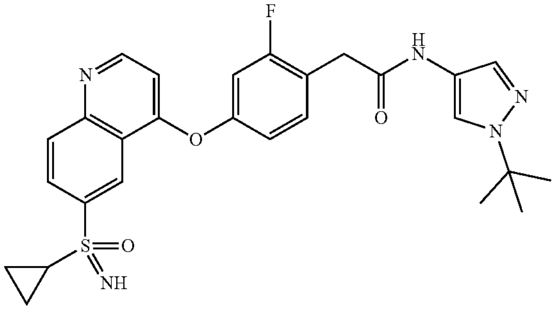 [SMILES: CC(C)(C)n1cc(NC(=O)Cc2ccc(Oc3ccnc4ccc(S(=N)(=O)C5CC5)cc34)cc2F)cn1] |
| 73 | 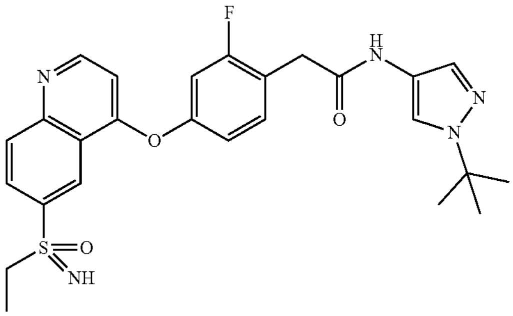 [SMILES: CCS(=N)(=O)c1ccc2nccc(Oc3ccc(CC(=O)Nc4cnn(C(C)(C)C)c4)c(F)c3)c2c1] |
| 74 | 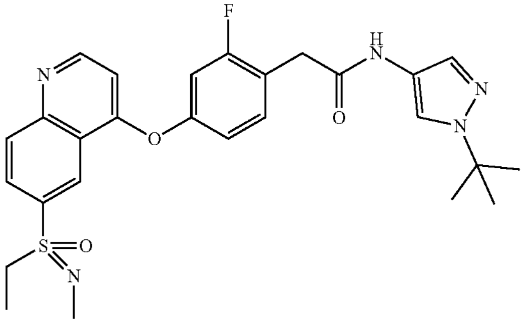 [SMILES: CCS(=O)(=NC)c1ccc2nccc(Oc3ccc(CC(=O)Nc4cnn(C(C)(C)C)c4)c(F)c3)c2c1] |

TABLE 1-continued
| Compound number | Structure |
| --- | --- |
| 75 | 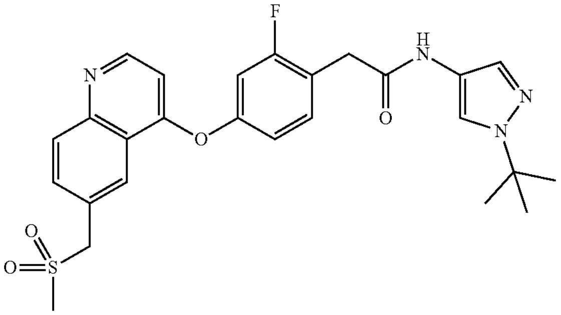 [SMILES: CC(C)(C)n1cc(NC(=O)Cc2ccc(Oc3ccnc4ccc(CS(C)(=O)=O)cc34)cc2F)cn1] |
| 76 | 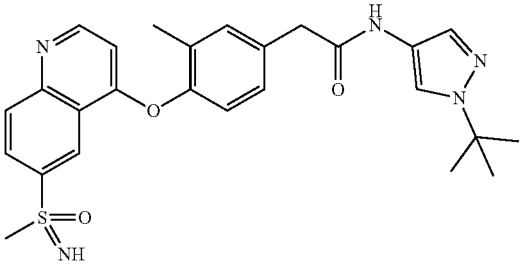 [SMILES: Cc1cc(CC(=O)Nc2cnn(C(C)(C)C)c2)ccc1Oc1ccnc2ccc(S(C)(=N)=O)cc12] |
| 77 | 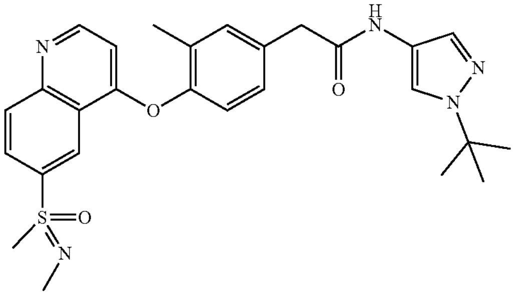 [SMILES: CN=S(C)(=O)c1ccc2nccc(Oc3ccc(CC(=O)Nc4cnn(C(C)(C)C)c4)cc3C)c2c1] |
| 78 | 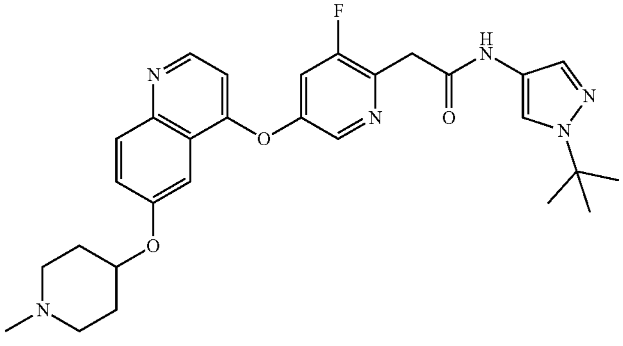 [SMILES: CN1CCC(Oc2ccc3nccc(Oc4cnc(CC(=O)Nc5cnn(C(C)(C)C)c5)c(F)c4)c3c2)CC1] |
| 79 | 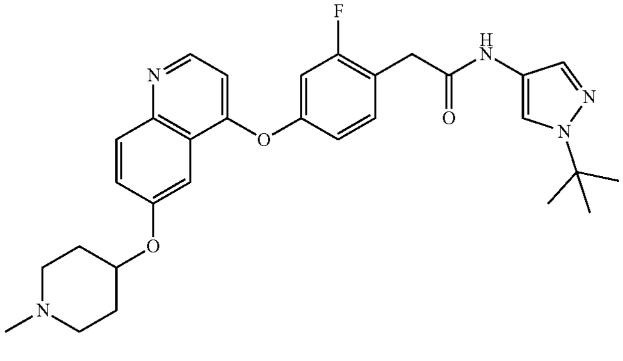 [SMILES: CN1CCC(Oc2ccc3nccc(Oc4ccc(CC(=O)Nc5cnn(C(C)(C)C)c5)c(F)c4)c3c2)CC1] |

TABLE 1-continued
| Compound number | Structure |
|---|---|
| 80 | 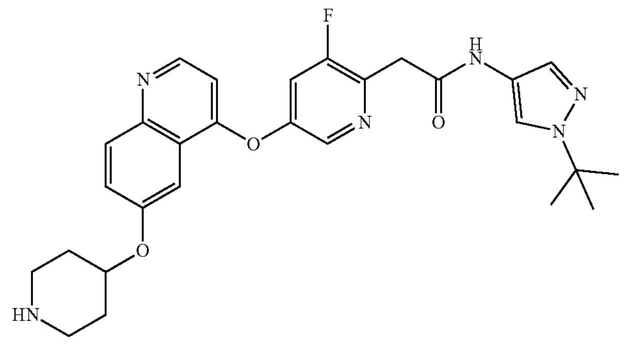 |
| 81 | 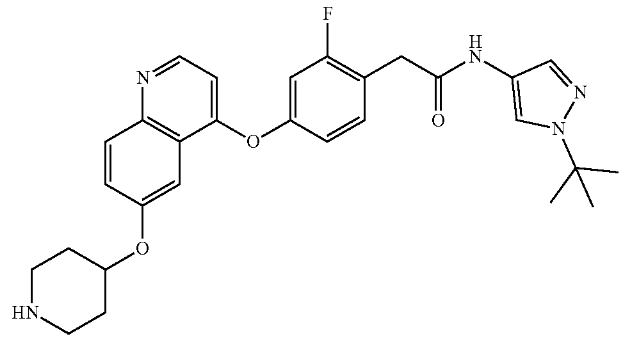 [SMILES: CC(C)(C)n1cc(NC(=O)Cc2ccc(Oc3ccnc4ccc(OC5CCNCC5)cc34)cc2F)cn1] |
| 82 | 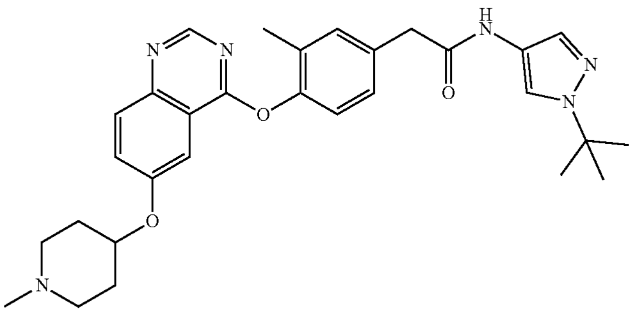 [SMILES: Cc1cc(CC(=O)Nc2cnn(C(C)(C)C)c2)ccc1Oc1ncnc2ccc(OC3CCN(C)CC3)cc12] |
| 83 | 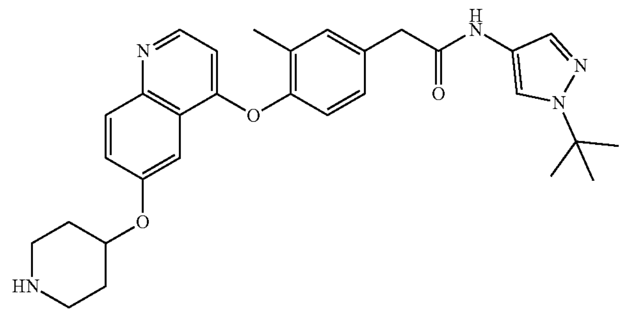 [SMILES: Cc1cc(CC(=O)Nc2cnn(C(C)(C)C)c2)ccc1Oc1ccnc2ccc(OC3CCNCC3)cc12] |

TABLE 1-continued
| Compound number | Structure |
|---|---|
| 84 | 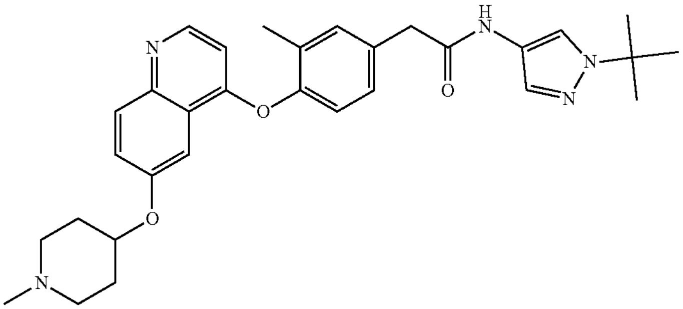 [SMILES: Cc1cc(CC(=O)Nc2cnn(C(C)(C)C)c2)ccc1Oc1ccnc2ccc(OC3CCN(C)CC3)cc12] |
| 85 | 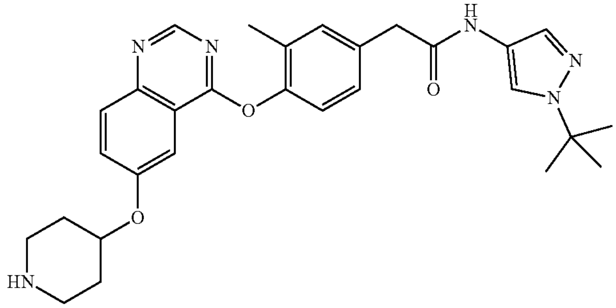 [SMILES: Cc1cc(CC(=O)Nc2cnn(C(C)(C)C)c2)ccc1Oc1ncnc2ccc(OC3CCNCC3)cc12] |
| 86 | 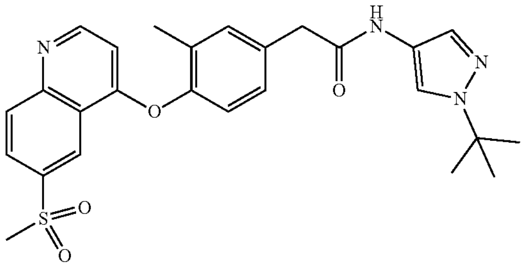 [SMILES: Cc1cc(CC(=O)Nc2cnn(C(C)(C)C)c2)ccc1Oc1ccnc2ccc(S(C)(=O)=O)cc12] |
| 87 | 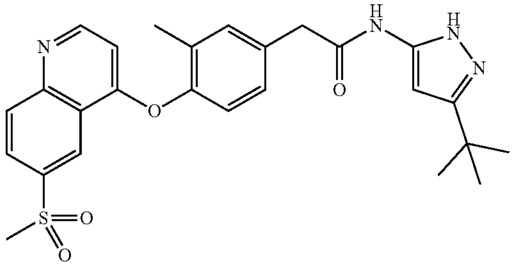 [SMILES: Cc1cc(CC(=O)Nc2cc(C(C)(C)C)n[nH]2)ccc1Oc1ccnc2ccc(S(C)(=O)=O)cc12] |
| 88 | 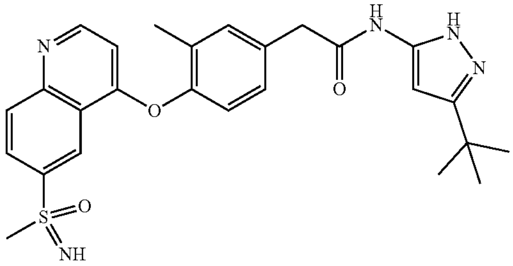 [SMILES: Cc1cc(CC(=O)Nc2cc(C(C)(C)C)n[nH]2)ccc1Oc1ccnc2ccc(S(C)(=N)=O)cc12] |

TABLE 1-continued
| Compound number | Structure |
| --- | --- |
| 89 | 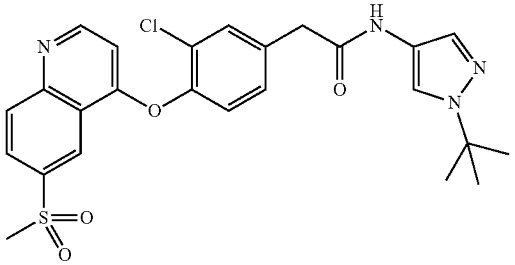 [SMILES: CC(C)(C)n1cc(NC(=O)Cc2ccc(Oc3ccnc4ccc(S(C)(=O)=O)cc34)c(Cl)c2)cn1] |
| 90 | 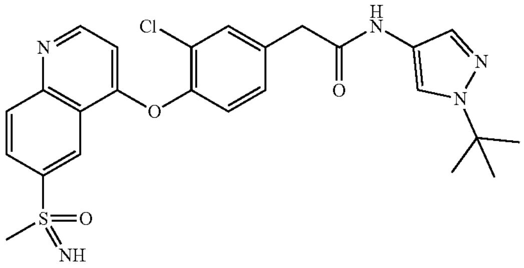 [SMILES: CC(C)(C)n1cc(NC(=O)Cc2ccc(Oc3ccnc4ccc(S(C)(=N)=O)cc34)c(Cl)c2)cn1] |
| 91 | 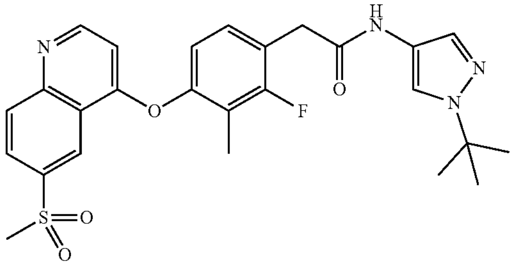 [SMILES: Cc1c(Oc2ccnc3ccc(S(C)(=O)=O)cc23)ccc(CC(=O)Nc2cnn(C(C)(C)C)c2)c1F] |
| 92 | 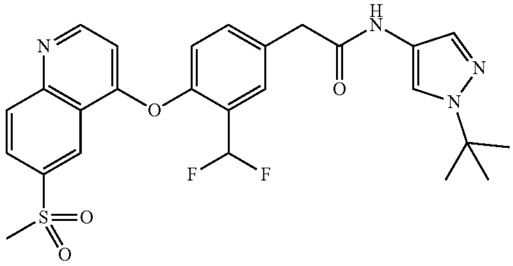 [SMILES: CC(C)(C)n1cc(NC(=O)Cc2ccc(Oc3ccnc4ccc(S(C)(=O)=O)cc34)c(C(F)F)c2)cn1] |
| 93 | 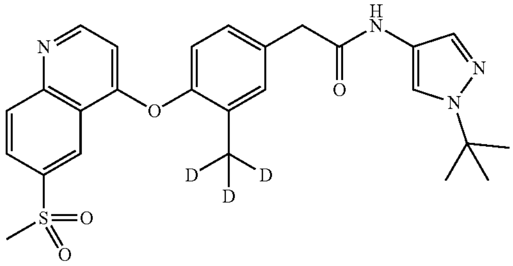 [SMILES: [2H]C([2H])([2H])c1cc(CC(=O)Nc2cnn(C(C)(C)C)c2)ccc1Oc1ccnc2ccc(S(C)(=O)=O)cc12] |

TABLE 1-continued
| Compound number | Structure |
| --- | --- |
| 94 | 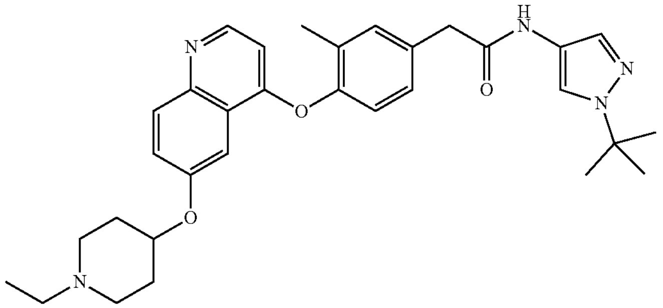 [SMILES: CCN1CCC(Oc2ccc3nccc(Oc4ccc(CC(=O)Nc5cnn(C(C)(C)C)c5)cc4C)c3c2)CC1] |
| 95 | 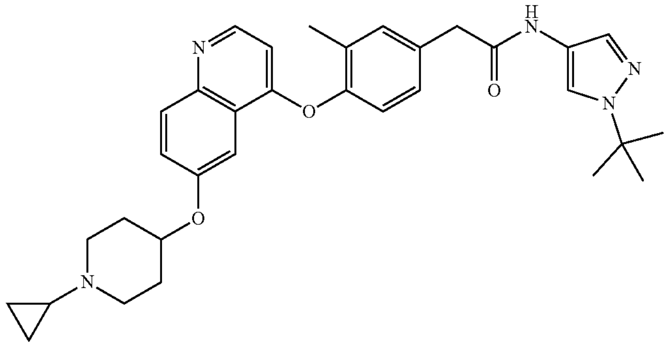 [SMILES: Cc1cc(CC(=O)Nc2cnn(C(C)(C)C)c2)ccc1Oc1ccnc2ccc(OC3CCN(C4CC4)CC3)cc12] |
| 96 | 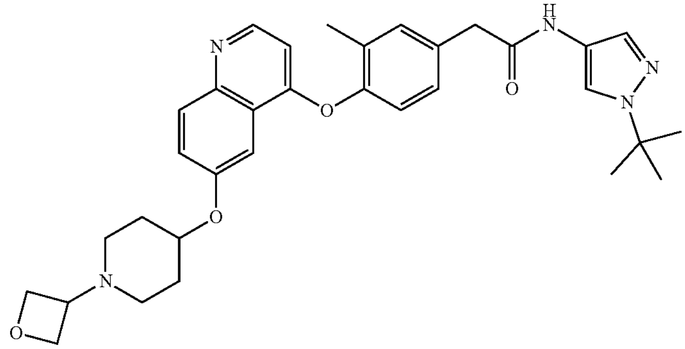 [SMILES: Cc1cc(CC(=O)Nc2cnn(C(C)(C)C)c2)ccc1Oc1ccnc2ccc(OC3CCN(C4COC4)CC3)cc12] |
| 97 | 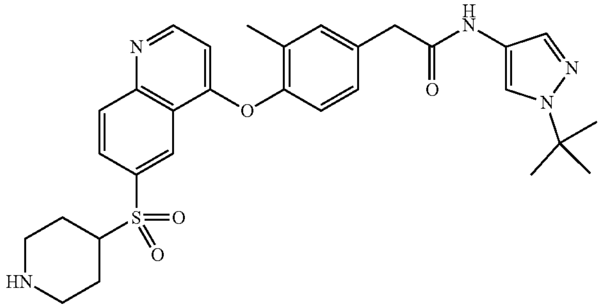 [SMILES: Cc1cc(CC(=O)Nc2cnn(C(C)(C)C)c2)ccc1Oc1ccnc2ccc(S(=O)(=O)C3CCNCC3)cc12] |

TABLE 1-continued
| Compound number | Structure |
|---|---|
| 98 | 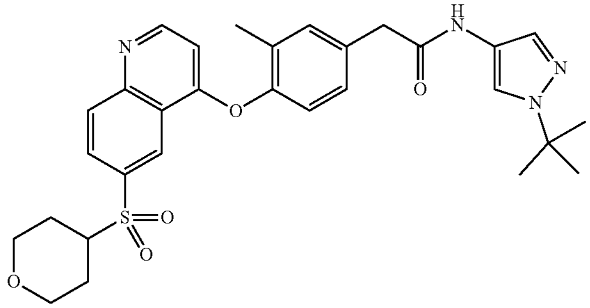 [SMILES: Cc1cc(CC(=O)Nc2cnn(C(C)(C)C)c2)ccc1Oc1ccnc2ccc(S(=O)(=O)C3CCOCC3)cc12] |
| 99 | 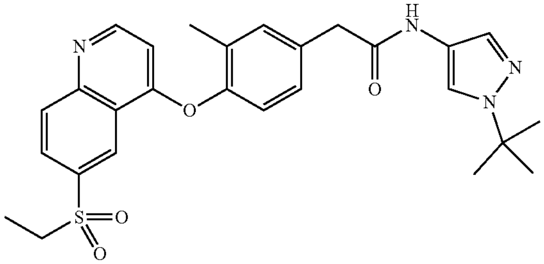 [SMILES: CCS(=O)(=O)c1ccc2nccc(Oc3ccc(CC(=O)Nc4cnn(C(C)(C)C)c4)cc3C)c2c1] |
| 100 | 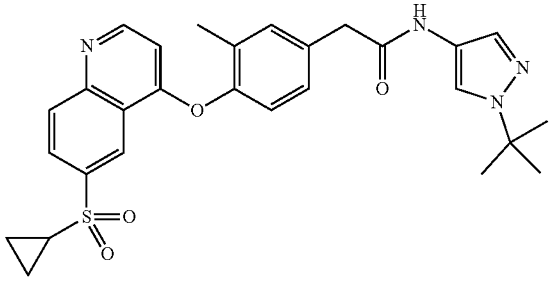 [SMILES: Cc1cc(CC(=O)Nc2cnn(C(C)(C)C)c2)ccc1Oc1ccnc2ccc(S(=O)(=O)C3CC3)cc12] |
| 101 | 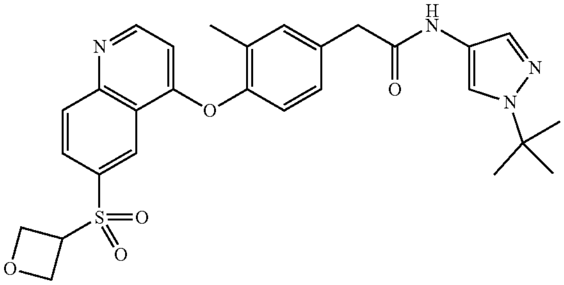 [SMILES: Cc1cc(CC(=O)Nc2cnn(C(C)(C)C)c2)ccc1Oc1ccnc2ccc(S(=O)(=O)C3COC3)cc12] |
| 102 | 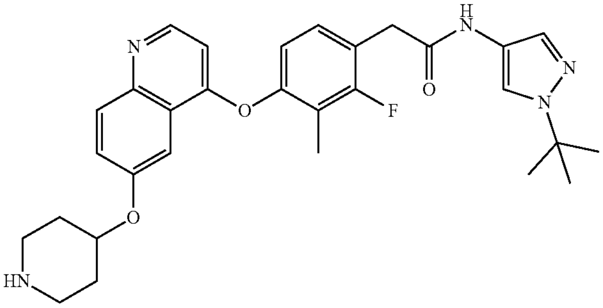 [SMILES: Cc1c(Oc2ccnc3ccc(OC4CCNCC4)cc23)ccc(CC(=O)Nc2cnn(C(C)(C)C)c2)c1F] |

TABLE 1-continued
| Compound number | Structure |
| --- | --- |
| 103 | 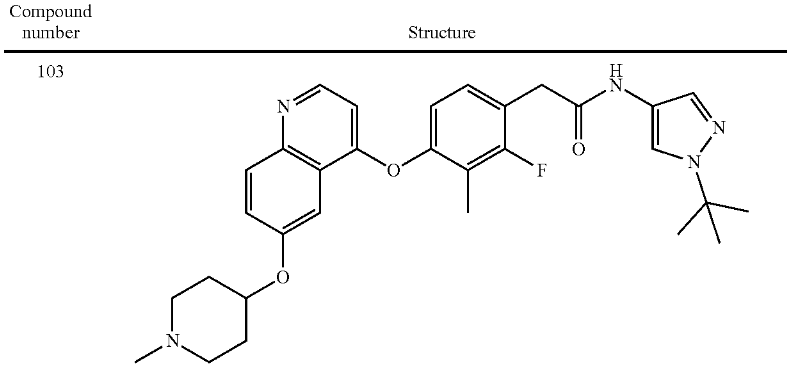 |
| 104 | 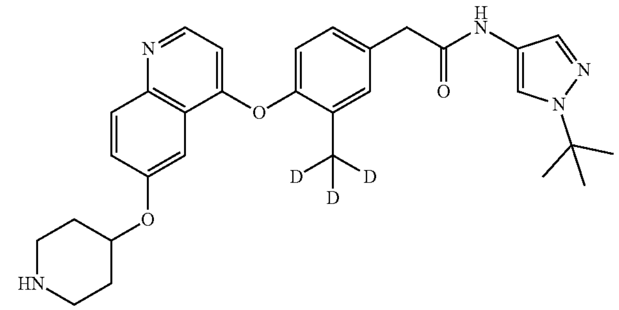 [SMILES: [2H]C([2H])([2H])c1cc(CC(=O)Nc2cnn(C(C)(C)C)c2)ccc1Oc1ccnc2ccc(OC3CCNCC3)cc12] |
| 105 | 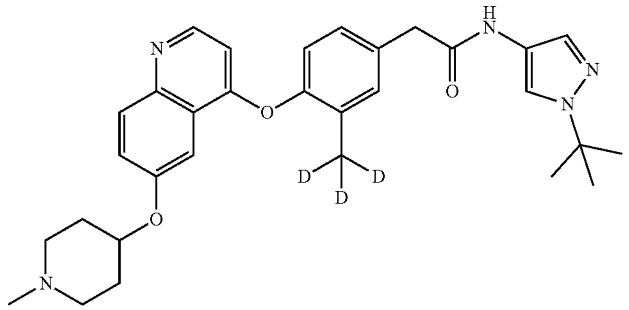 [SMILES: [2H]C([2H])([2H])c1cc(CC(=O)Nc2cnn(C(C)(C)C)c2)ccc1Oc1ccnc2ccc(OC3CCN(C)CC3)cc12] |
| 106 | 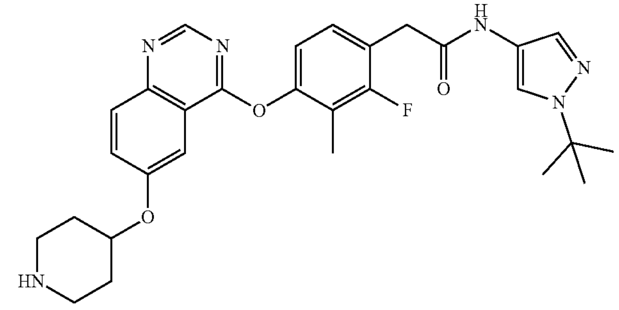 |
| 107 | 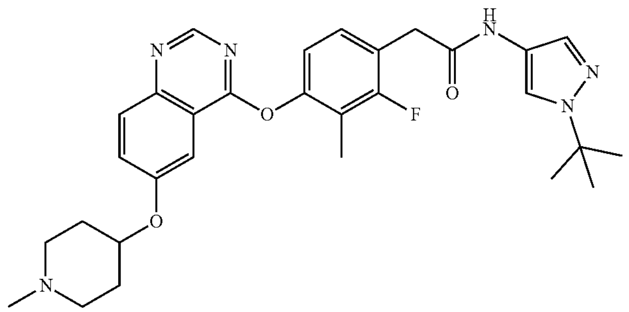 [SMILES: Cc1c(Oc2ncnc3ccc(OC4CCN(C)CC4)cc23)ccc(CC(=O)Nc2cnn(C(C)(C)C)c2)c1F] |

TABLE 1-continued
| Compound number | Structure |
|---|---|
| 108 | 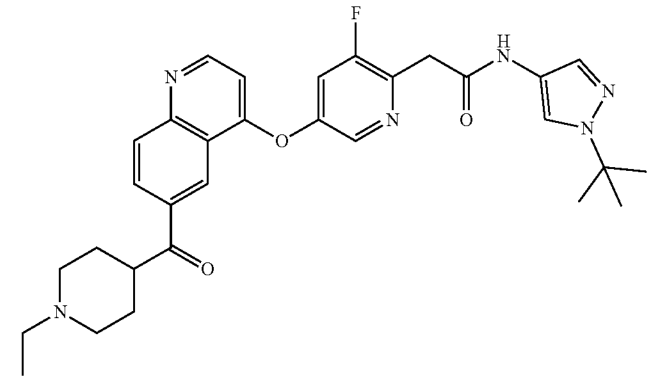 [SMILES: CCN1CCC(C(=O)c2ccc3nccc(Oc4cnc(CC(=O)Nc5cnn(C(C)(C)C)c5)c(F)c4)c3c2)CC1] |
| 109 | 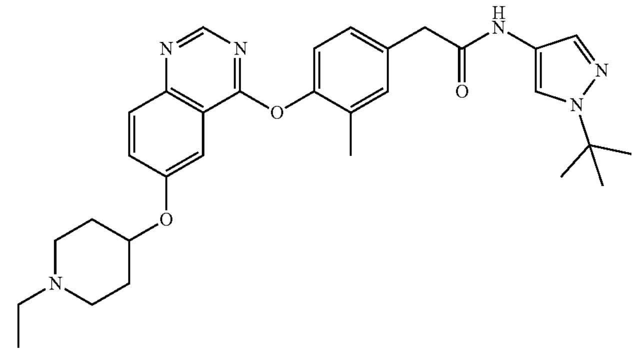 [SMILES: CCN1CCC(Oc2ccc3ncnc(Oc4ccc(CC(=O)Nc5cnn(C(C)(C)C)c5)cc4C)c3c2)CC1] |
| 110 | 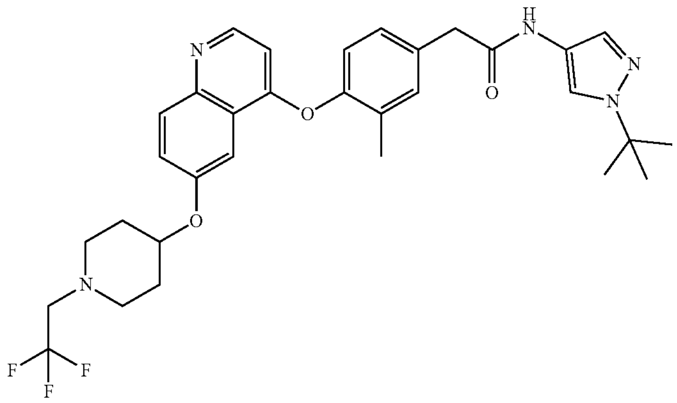 [SMILES: Cc1cc(CC(=O)Nc2cnn(C(C)(C)C)c2)ccc1Oc1ccnc2ccc(OC3CCN(CC(F)(F)F)CC3)cc12] |
| 111 | 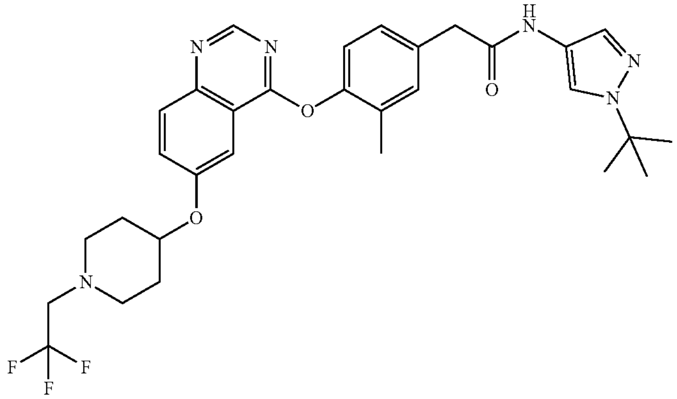 [SMILES: Cc1cc(CC(=O)Nc2cnn(C(C)(C)C)c2)ccc1Oc1ncnc2ccc(OC3CCN(CC(F)(F)F)CC3)cc12] |

TABLE 1-continued
| Compound number | Structure |
|---|---|
| 112 | 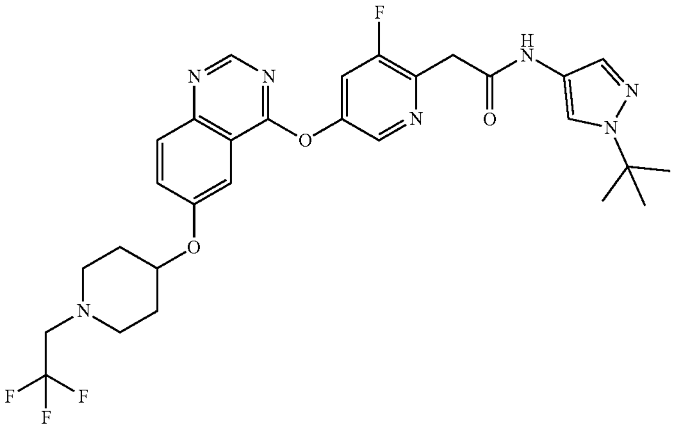 [SMILES: CC(C)(C)n1cc(NC(=O)Cc2ncc(Oc3ncnc4ccc(OC5CCN(CC(F)(F)F)CC5)cc34)cc2F)cn1] |
| 113 | 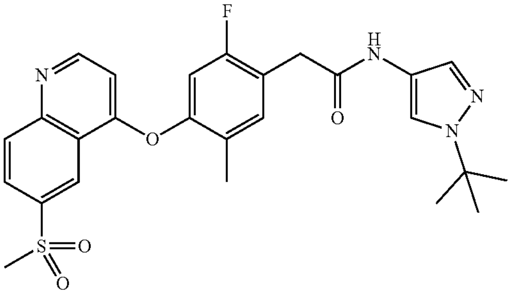 [SMILES: Cc1cc(CC(=O)Nc2cnn(C(C)(C)C)c2)c(F)cc1Oc1ccnc2ccc(S(C)(=O)=O)cc12] |
| 114 | 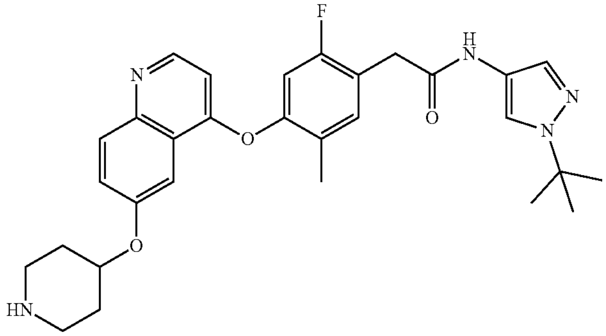 [SMILES: Cc1cc(CC(=O)Nc2cnn(C(C)(C)C)c2)c(F)cc1Oc1ccnc2ccc(OC3CCNCC3)cc12] |
| 115 | 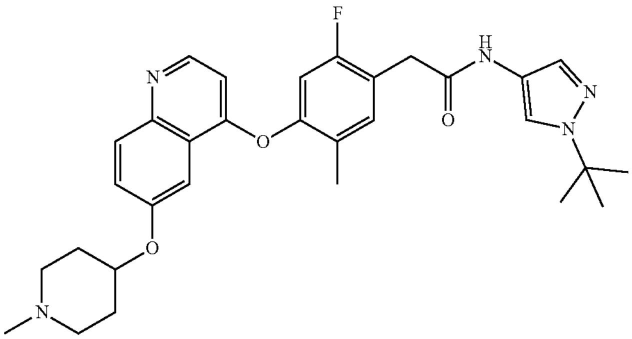 [SMILES: Cc1cc(CC(=O)Nc2cnn(C(C)(C)C)c2)c(F)cc1Oc1ccnc2ccc(OC3CCN(C)CC3)cc12] |

TABLE 1-continued
| Compound number | Structure |
|---|---|
| 116 | 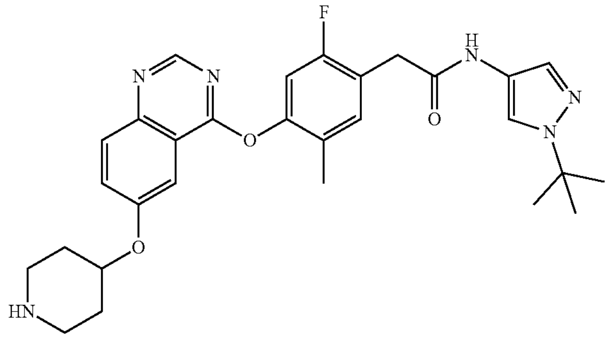 |
| 117 | 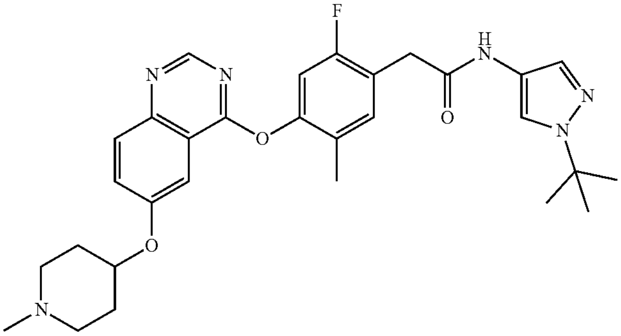 [SMILES: Cc1cc(CC(=O)Nc2cnn(C(C)(C)C)c2)c(F)cc1Oc1ncnc2ccc(OC3CCN(C)CC3)cc12] |
| 118 | 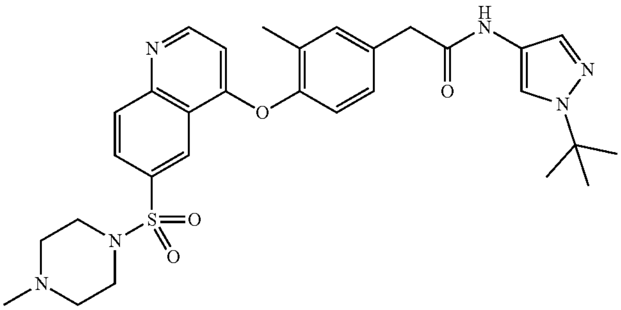 [SMILES: Cc1cc(CC(=O)Nc2cnn(C(C)(C)C)c2)ccc1Oc1ccnc2ccc(S(=O)(=O)N3CCN(C)CC3)cc12] |
| 119 | 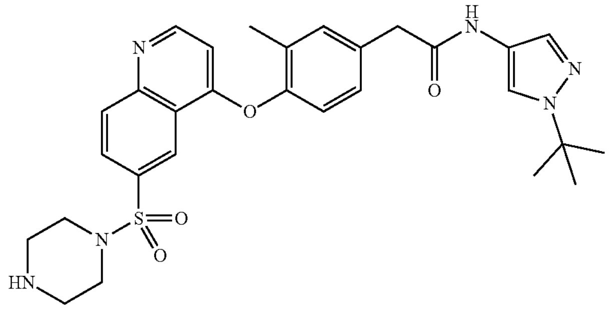 [SMILES: Cc1cc(CC(=O)Nc2cnn(C(C)(C)C)c2)ccc1Oc1ccnc2ccc(S(=O)(=O)N3CCNCC3)cc12] |

TABLE 1-continued
| Compound number | Structure |
|---|---|
| 120 | 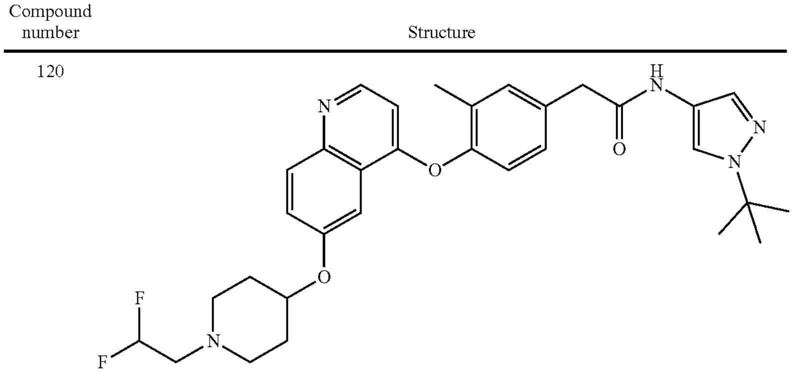 |
| 121 | 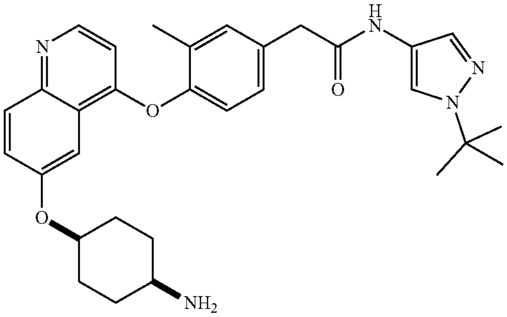 |
| 122 | 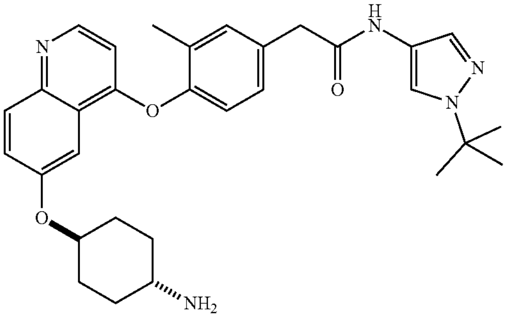 |
| 123 | 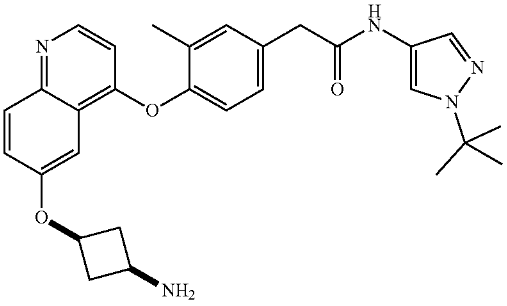 |
| 124 | 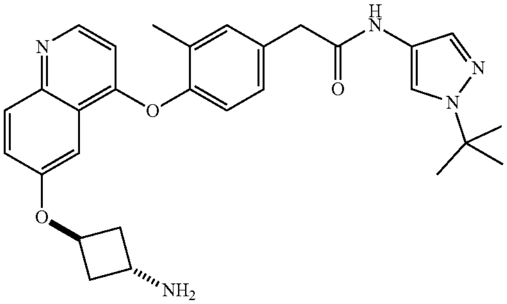 |

TABLE 1-continued
| Compound number | Structure |
|---|---|
| 125 | 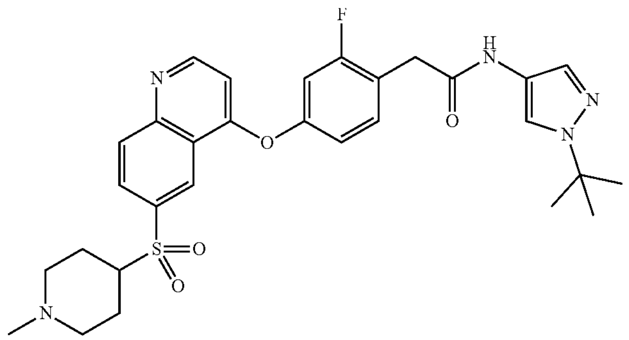 [SMILES: CN1CCC(S(=O)(=O)c2ccc3nccc(Oc4ccc(CC(=O)Nc5cnn(C(C)(C)C)c5)c(F)c4)c3c2)CC1] |
| 126 | 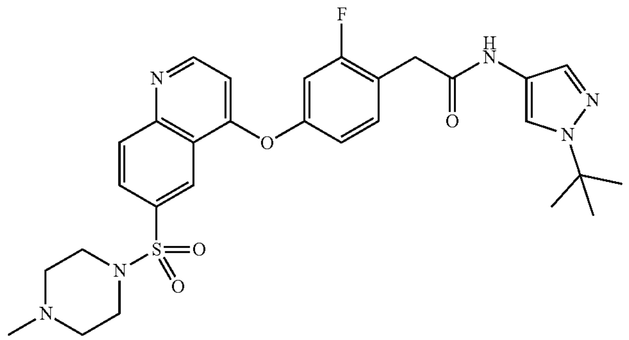 [SMILES: CN1CCN(S(=O)(=O)c2ccc3nccc(Oc4ccc(CC(=O)Nc5cnn(C(C)(C)C)c5)c(F)c4)c3c2)CC1] |
| 127 | 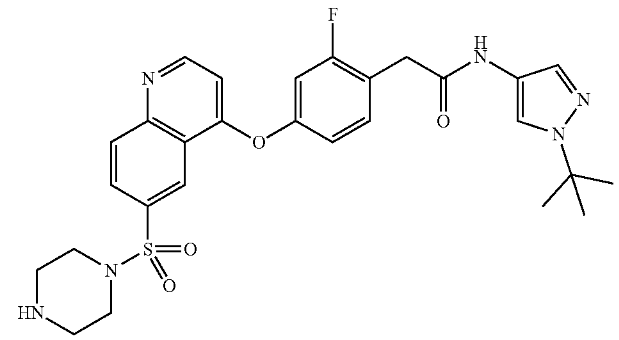 [SMILES: CC(C)(C)n1cc(NC(=O)Cc2ccc(Oc3ccnc4ccc(S(=O)(=O)N5CCNCC5)cc34)cc2F)cn1] |
| 128 | 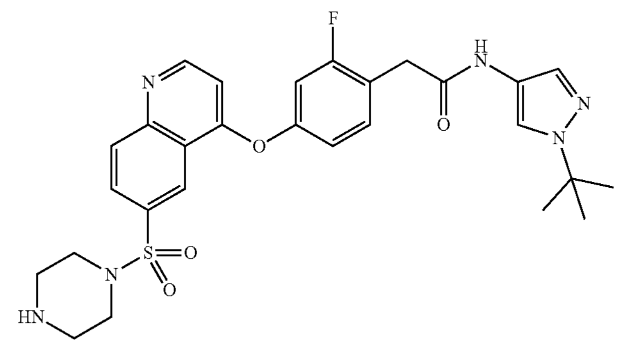 [SMILES: CC(C)(C)n1cc(NC(=O)Cc2ccc(Oc3ccnc4ccc(S(=O)(=O)N5CCNCC5)cc34)cc2F)cn1] |

TABLE 1-continued
| Compound number | Structure |
|---|---|
| 129 | 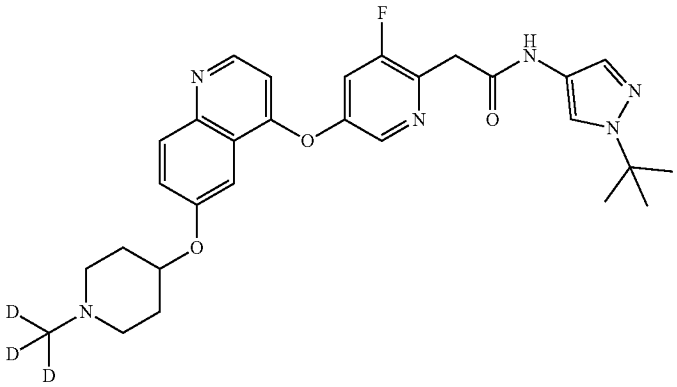 [SMILES: [2H]C([2H])([2H])N1CCC(Oc2ccc3nccc(Oc4cnc(CC(=O)Nc5cnn(C(C)(C)C)c5)c(F)c4)c3c2)CC1] |
| 130 | 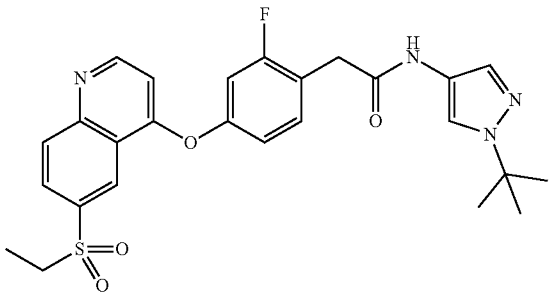 [SMILES: CCS(=O)(=O)c1ccc2nccc(Oc3ccc(CC(=O)Nc4cnn(C(C)(C)C)c4)c(F)c3)c2c1] |
| 131 | 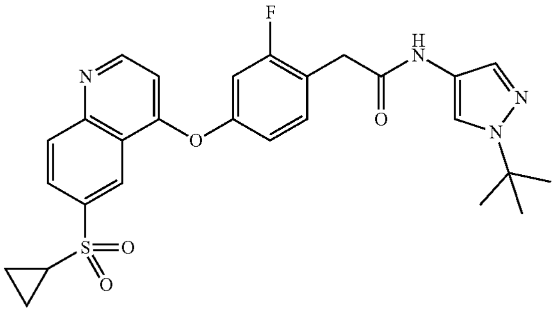 [SMILES: CC(C)(C)n1cc(NC(=O)Cc2ccc(Oc3ccnc4ccc(S(=O)(=O)C5CC5)cc34)cc2F)cn1] |
| 132 | 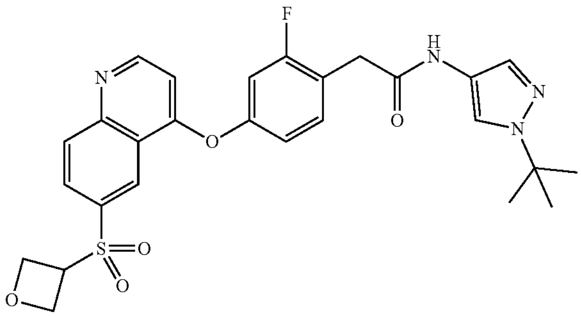 [SMILES: CC(C)(C)n1cc(NC(=O)Cc2ccc(Oc3ccnc4ccc(S(=O)(=O)C5COC5)cc34)cc2F)cn1] |

TABLE 1-continued
| Compound number | Structure |
|---|---|
| 133 | 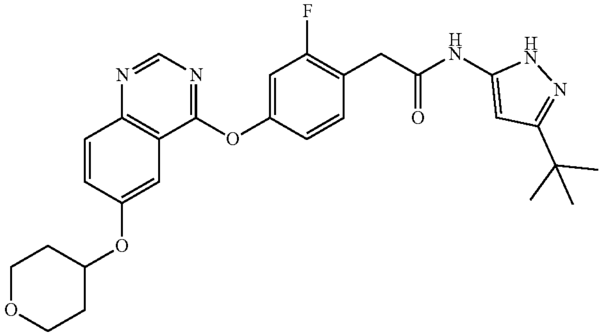 [SMILES: CC(C)(C)c1cc(NC(=O)Cc2ccc(Oc3ncnc4ccc(OC5CCOCC5)cc34)cc2F)[nH]n1] |
| 134 | 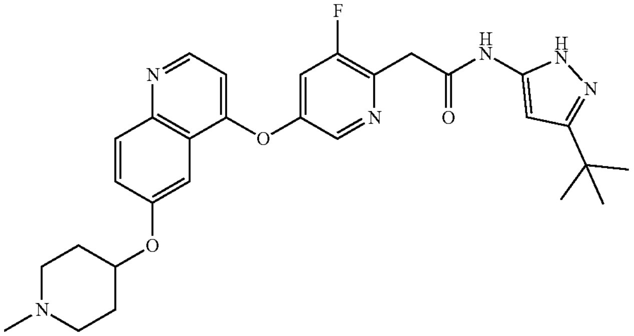 [SMILES: CN1CCC(Oc2ccc3nccc(Oc4cnc(CC(=O)Nc5cc(C(C)(C)C)n[nH]5)c(F)c4)c3c2)CC1] |
| 135 | 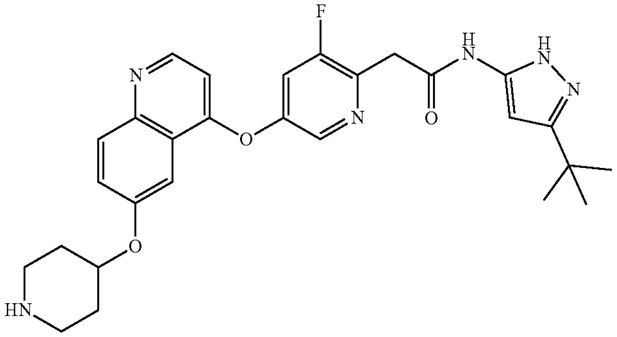 |
| 136 | 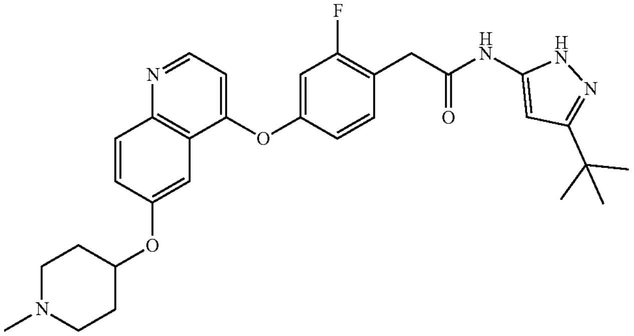 [SMILES: CN1CCC(Oc2ccc3nccc(Oc4ccc(CC(=O)Nc5cc(C(C)(C)C)n[nH]5)c(F)c4)c3c2)CC1] |

TABLE 1-continued
| Compound number | Structure |
|---|---|
| 137 | 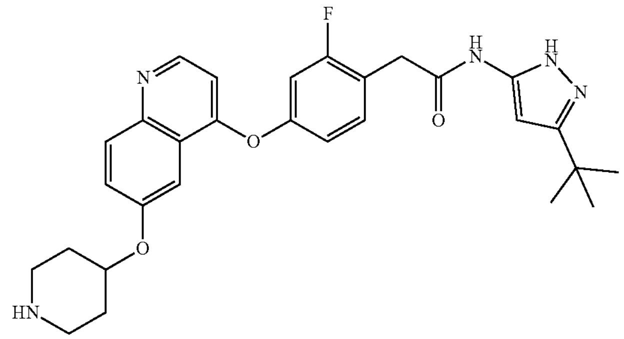 [SMILES: CC(C)(C)c1cc(NC(=O)Cc2ccc(Oc3ccnc4ccc(OC5CCNCC5)cc34)cc2F)[nH]n1] |
| 138 | 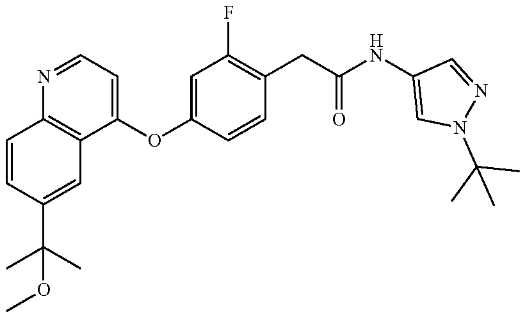 [SMILES: COC(C)(C)c1ccc2nccc(Oc3ccc(CC(=O)Nc4cnn(C(C)(C)C)c4)c(F)c3)c2c1] |
| 139 | 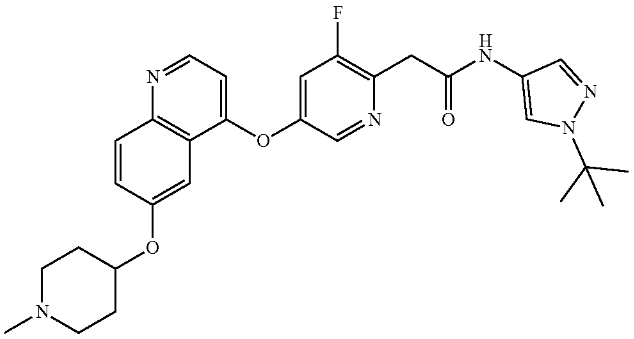 |
| 140 | 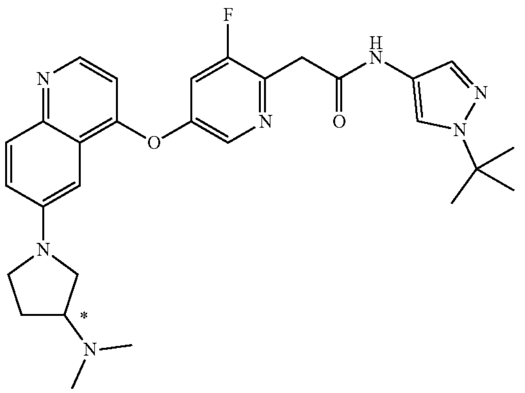 [SMILES: CN(C)C1CCN(c2ccc3nccc(Oc4cnc(CC(=O)Nc5cnn(C(C)(C)C)c5)c(F)c4)c3c2)C1] enantiomer 1 |

TABLE 1-continued
| Compound number | Structure |
| --- | --- |
| 141 | 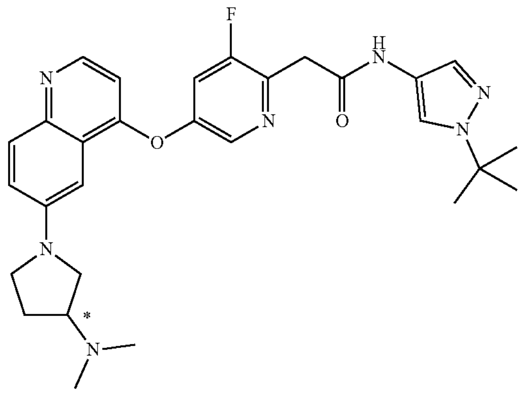 [SMILES: CN(C)C1CCN(c2ccc3nccc(Oc4cnc(CC(=O)Nc5cnn(C(C)(C)C)c5)c(F)c4)c3c2)C1] enantiomer 2 |
| 142 | 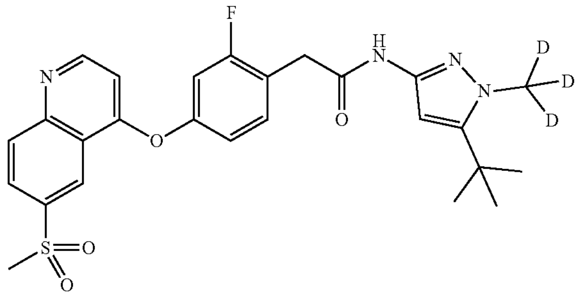 [SMILES: [2H]C([2H])([2H])n1nc(NC(=O)Cc2ccc(Oc3ccnc4ccc(S(C)(=O)=O)cc34)cc2F)cc1C(C)(C)C] |
| 143 | 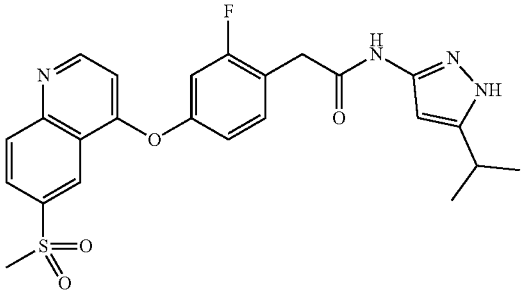 [SMILES: CC(C)c1cc(NC(=O)Cc2ccc(Oc3ccnc4ccc(S(C)(=O)=O)cc34)cc2F)n[nH]1] |
| 144 | 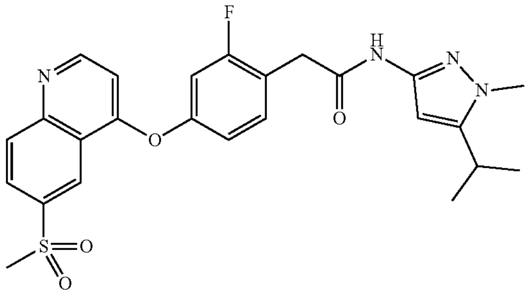 [SMILES: CC(C)c1cc(NC(=O)Cc2ccc(Oc3ccnc4ccc(S(C)(=O)=O)cc34)cc2F)nn1C] |

TABLE 1-continued
| Compound number | Structure |
| --- | --- |
| 145 | 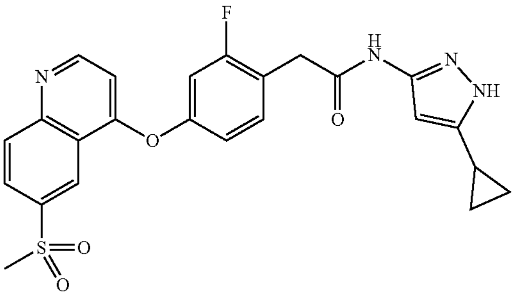 [SMILES: CS(=O)(=O)c1ccc2nccc(Oc3ccc(CC(=O)Nc4cc(C5CC5)[nH]n4)c(F)c3)c2c1] |
| 146 | 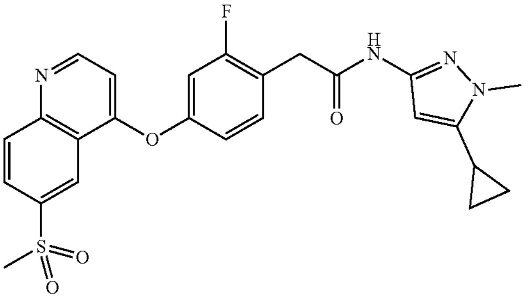 [SMILES: Cn1nc(NC(=O)Cc2ccc(Oc3ccnc4ccc(S(C)(=O)=O)cc34)cc2F)cc1C1CC1] |
| 147 | 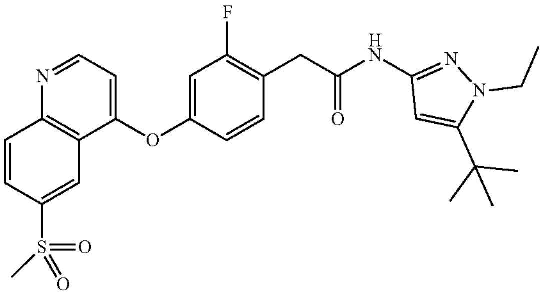 [SMILES: CCn1nc(NC(=O)Cc2ccc(Oc3ccnc4ccc(S(C)(=O)=O)cc34)cc2F)cc1C(C)(C)C] |
| 148 | 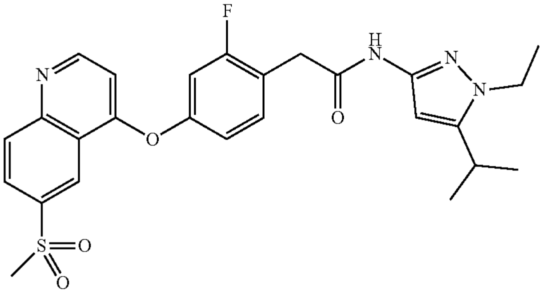 [SMILES: CCn1nc(NC(=O)Cc2ccc(Oc3ccnc4ccc(S(C)(=O)=O)cc34)cc2F)cc1C(C)C] |
| 149 | 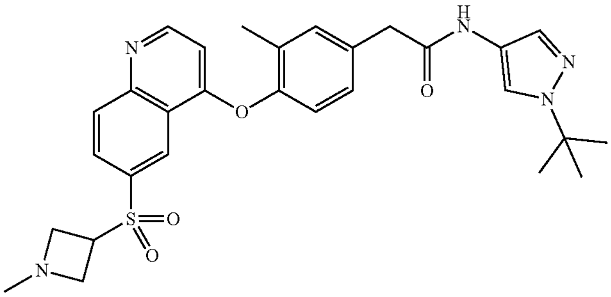 [SMILES: Cc1cc(CC(=O)Nc2cnn(C(C)(C)C)c2)ccc1Oc1ccnc2ccc(S(=O)(=O)C3CN(C)C3)cc12] |

TABLE 1-continued
| Compound number | Structure |
| --- | --- |
| 150 | 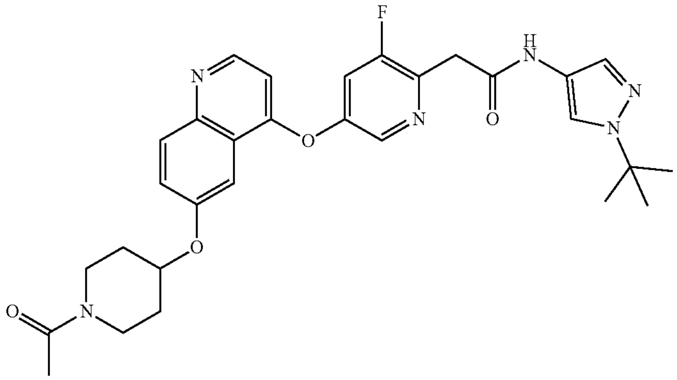 [SMILES: CC(=O)N1CCC(Oc2ccc3nccc(Oc4cnc(CC(=O)Nc5cnn(C(C)(C)C)c5)c(F)c4)c3c2)CC1] |
| 151 | 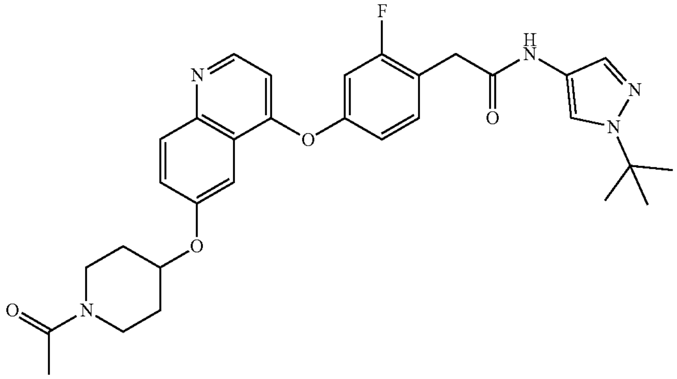 [SMILES: CC(=O)N1CCC(Oc2ccc3nccc(Oc4ccc(CC(=O)Nc5cnn(C(C)(C)C)c5)c(F)c4)c3c2)CC1] |
| 152 | 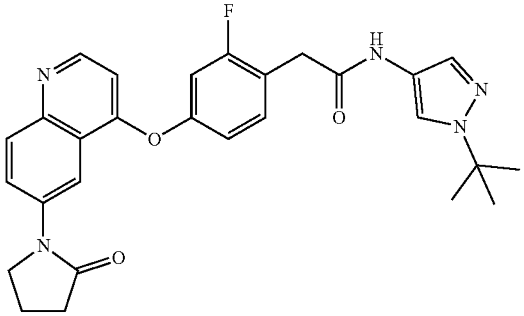 [SMILES: CC(C)(C)n1cc(NC(=O)Cc2ccc(Oc3ccnc4ccc(N5CCCC5=O)cc34)cc2F)cn1] |
| 153 | 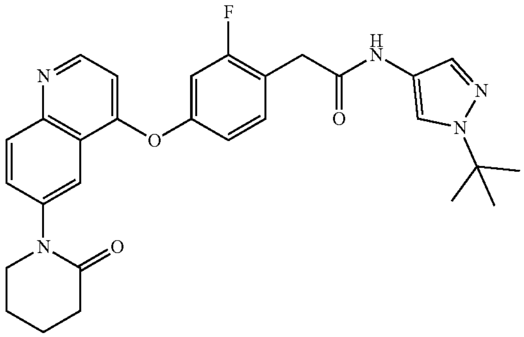 [SMILES: CC(C)(C)n1cc(NC(=O)Cc2ccc(Oc3ccnc4ccc(N5CCCCC5=O)cc34)cc2F)cn1] |

TABLE 1-continued
| Compound number | Structure |
|---|---|
| 154 | 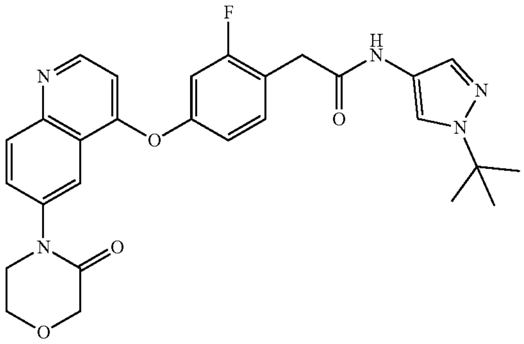 [SMILES: CC(C)(C)n1cc(NC(=O)Cc2ccc(Oc3ccnc4ccc(N5CCOCC5=O)cc34)cc2F)cn1] |
| 155 | 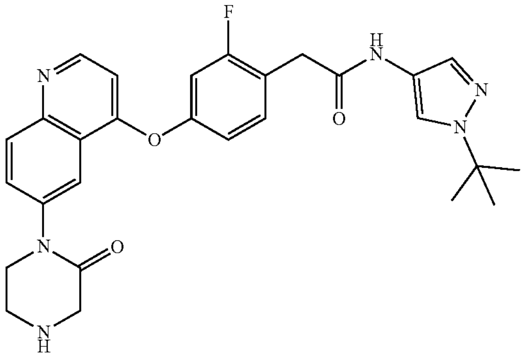 [SMILES: CC(C)(C)n1cc(NC(=O)Cc2ccc(Oc3ccnc4ccc(N5CCNCC5=O)cc34)cc2F)cn1] |
| 156 | 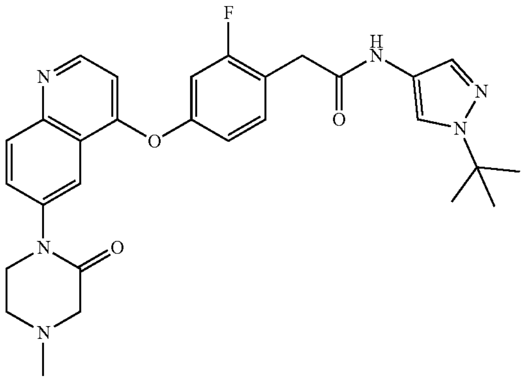 [SMILES: CN1CCN(c2ccc3nccc(Oc4ccc(CC(=O)Nc5cnn(C(C)(C)C)c5)c(F)c4)c3c2)C(=O)C1] |
| 157 | 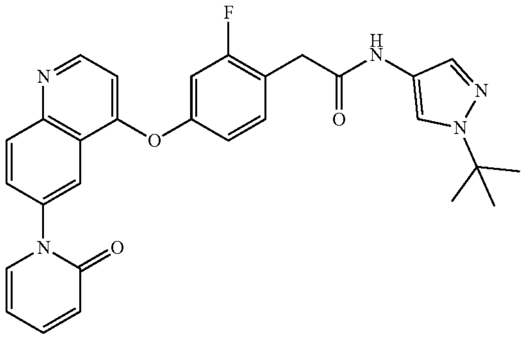 [SMILES: CC(C)(C)n1cc(NC(=O)Cc2ccc(Oc3ccnc4ccc(-n5ccccc5=O)cc34)cc2F)cn1] |

TABLE 1-continued
| Compound number | Structure |
| --- | --- |
| 158 | 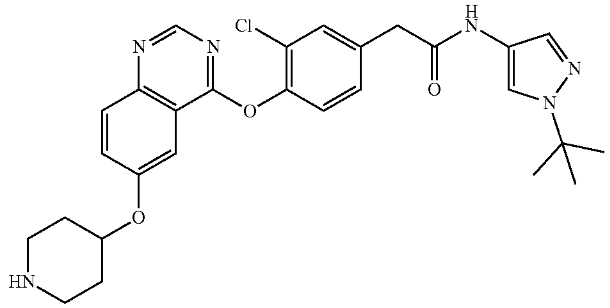 |
| 159 | 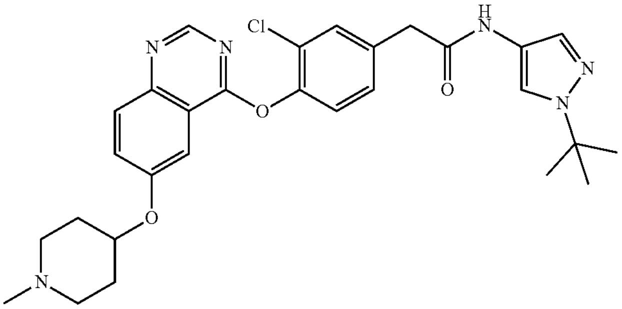 |
| 160 | 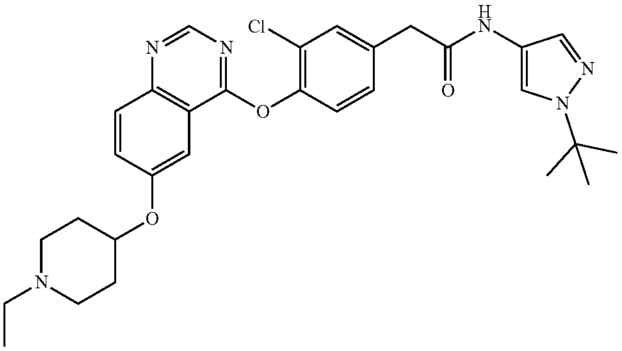 [SMILES: CCN1CCC(Oc2ccc3ncnc(Oc4ccc(CC(=O)Nc5cnn(C(C)(C)C)c5)cc4Cl)c3c2)CC1] |
| 161 | 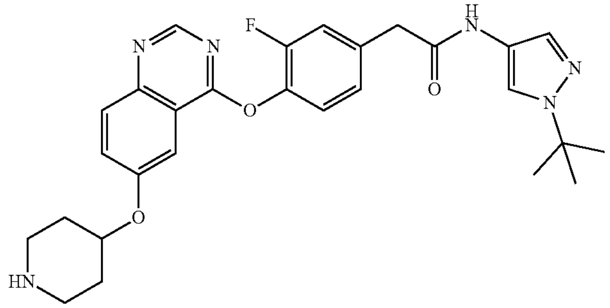 [SMILES: CC(C)(C)n1cc(NC(=O)Cc2ccc(Oc3ncnc4ccc(OC5CCNCC5)cc34)c(F)c2)cn1] |

TABLE 1-continued
| Compound number | Structure |
|---|---|
| 162 | 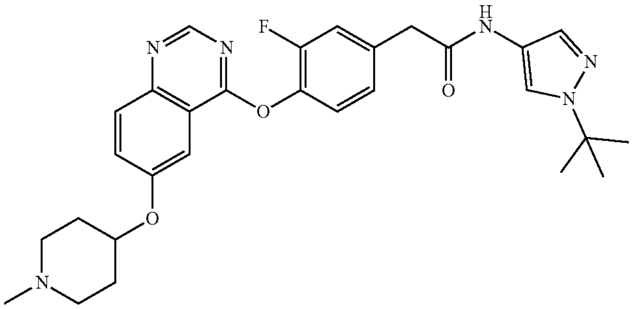 [SMILES: CN1CCC(Oc2ccc3ncnc(Oc4ccc(CC(=O)Nc5cnn(C(C)(C)C)c5)cc4F)c3c2)CC1] |
| 163 | 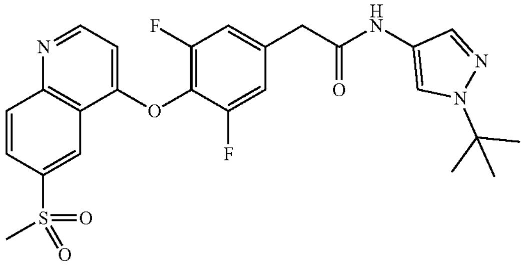 [SMILES: CC(C)(C)n1cc(NC(=O)Cc2cc(F)c(Oc3ccnc4ccc(S(C)(=O)=O)cc34)c(F)c2)cn1] |
| 164 | 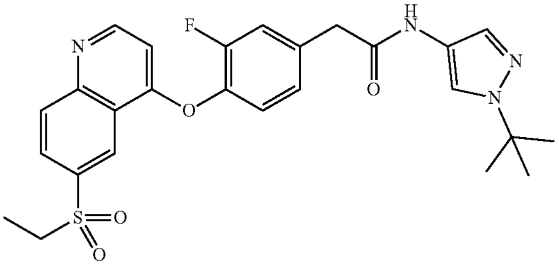 [SMILES: CCS(=O)(=O)c1ccc2nccc(Oc3ccc(CC(=O)Nc4cnn(C(C)(C)C)c4)cc3F)c2c1] |
| 165 | 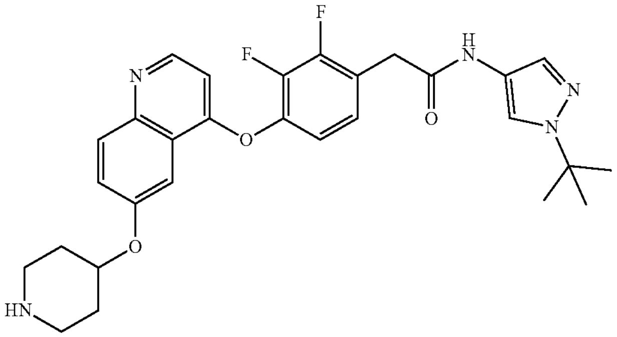 [SMILES: CC(C)(C)n1cc(NC(=O)Cc2ccc(Oc3ccnc4ccc(OC5CCNCC5)cc34)c(F)c2F)cn1] |
| 166 | 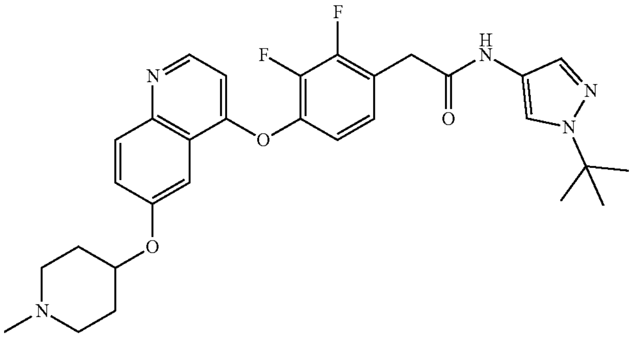 [SMILES: CN1CCC(Oc2ccc3nccc(Oc4ccc(CC(=O)Nc5cnn(C(C)(C)C)c5)c(F)c4F)c3c2)CC1] |

TABLE 1-continued
| Compound number | Structure |
|---|---|
| 167 | 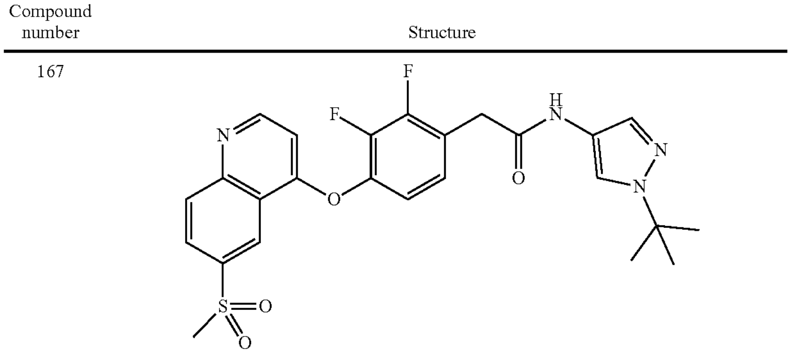 |
| 168 | 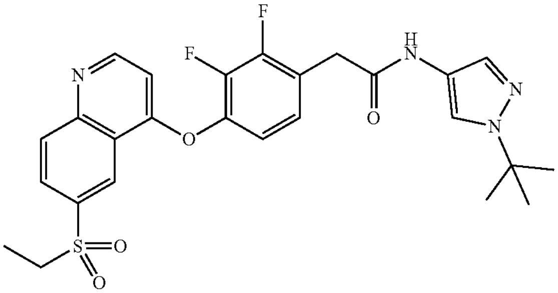 |
| 169 | 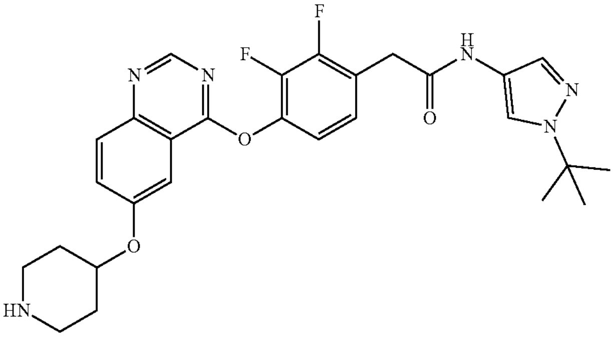 [SMILES: CC(C)(C)n1cc(NC(=O)Cc2ccc(Oc3ncnc4ccc(OC5CCNCC5)cc34)c(F)c2F)cn1] |
| 170 | 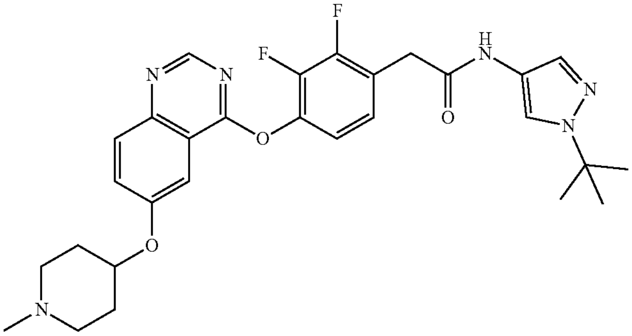 [SMILES: CN1CCC(Oc2ccc3ncnc(Oc4ccc(CC(=O)Nc5cnn(C(C)(C)C)c5)c(F)c4F)c3c2)CC1] |
| 171 | 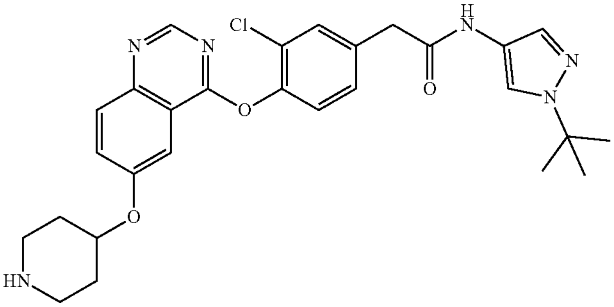 [SMILES: CC(C)(C)n1cc(NC(=O)Cc2ccc(Oc3ncnc4ccc(OC5CCNCC5)cc34)c(Cl)c2)cn1] |

TABLE 1-continued
| Compound number | Structure |
|---|---|
| 172 | 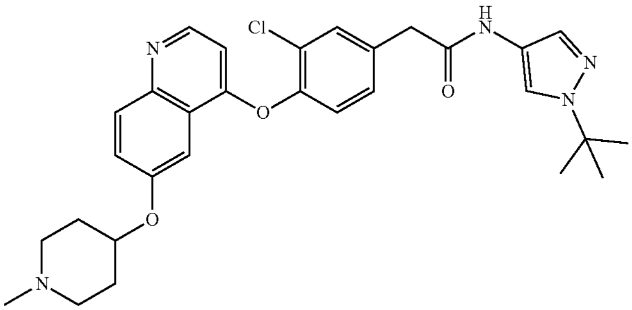 |
| 173 | 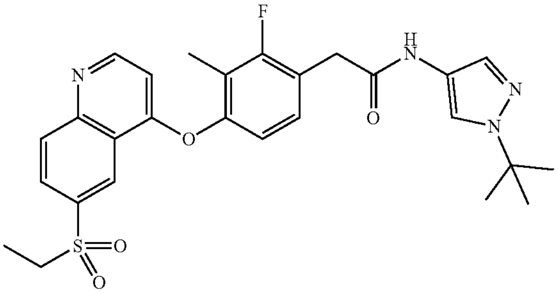 [SMILES: CCS(=O)(=O)c1ccc2nccc(Oc3ccc(CC(=O)Nc4cnn(C(C)(C)C)c4)c(F)c3C)c2c1] |
| 174 | 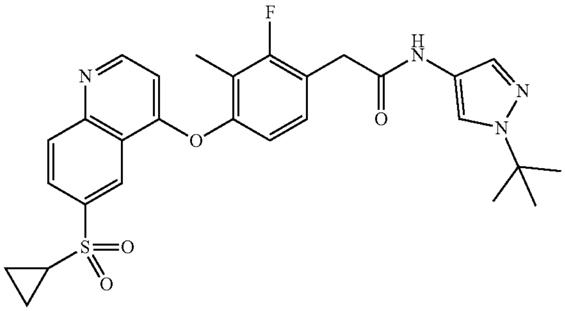 [SMILES: Cc1c(Oc2ccnc3ccc(S(=O)(=O)C4CC4)cc23)ccc(CC(=O)Nc2cnn(C(C)(C)C)c2)c1F] |
| 175 | 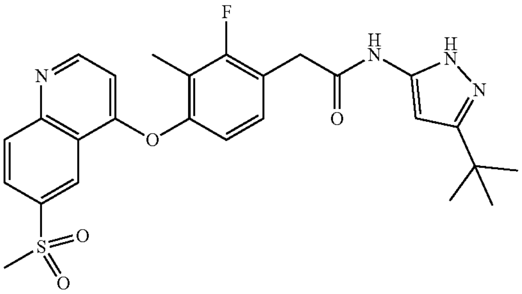 [SMILES: Cc1c(Oc2ccnc3ccc(S(C)(=O)=O)cc23)ccc(CC(=O)Nc2cc(C(C)(C)C)n[nH]2)c1F] |

TABLE 1-continued
| Compound number | Structure |
|---|---|
| 176 | 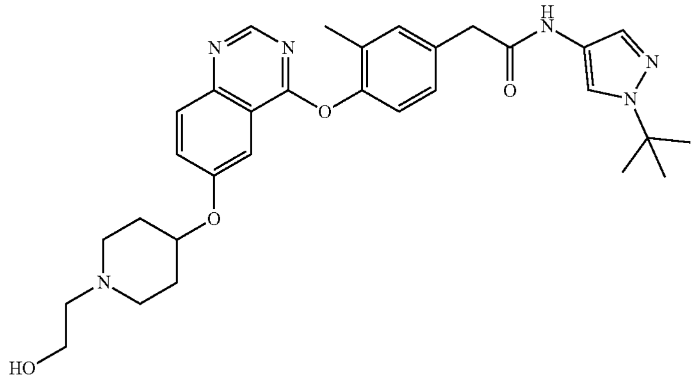 [SMILES: Cc1cc(CC(=O)Nc2cnn(C(C)(C)C)c2)ccc1Oc1ncnc2ccc(OC3CCN(CCO)CC3)cc12] |
| 177 | 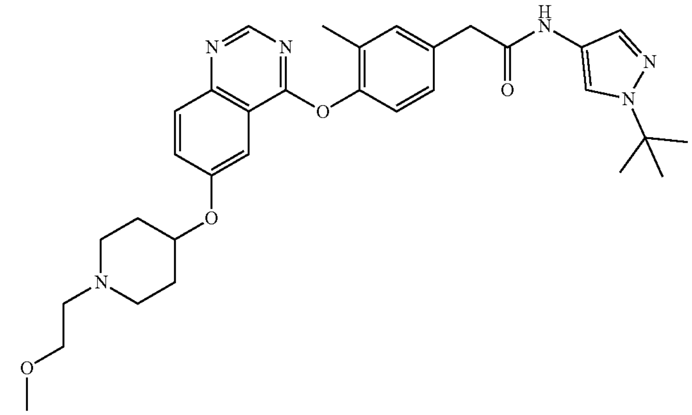 [SMILES: COCCN1CCC(Oc2ccc3ncnc(Oc4ccc(CC(=O)Nc5cnn(C(C)(C)C)c5)cc4C)c3c2)CC1] |
| 178 | 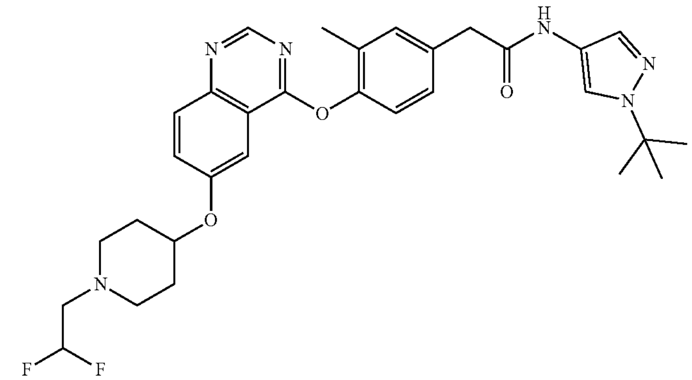 [SMILES: Cc1cc(CC(=O)Nc2cnn(C(C)(C)C)c2)ccc1Oc1ncnc2ccc(OC3CCN(CC(F)F)CC3)cc12] |
| 179 | 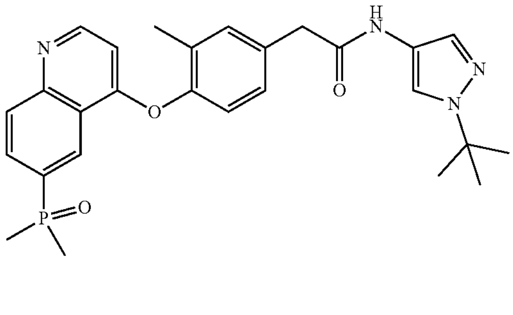 [SMILES: Cc1cc(CC(=O)Nc2cnn(C(C)(C)C)c2)ccc1Oc1ccnc2ccc(P(C)(C)=O)cc12] |

TABLE 1-continued
| Compound number | Structure |
| --- | --- |
| 180 | 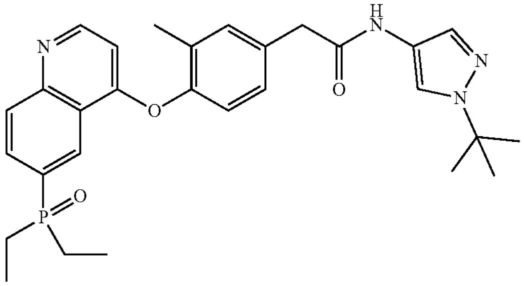 [SMILES: CCP(=O)(CC)c1ccc2nccc(Oc3ccc(CC(=O)Nc4cnn(C(C)(C)C)c4)cc3C)c2c1] |
| 181 | 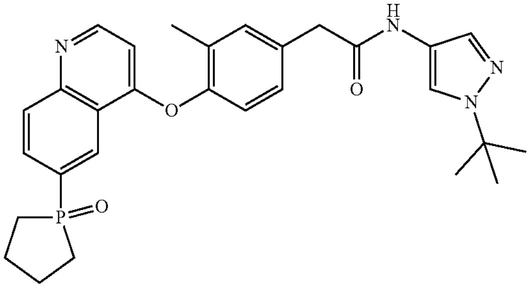 [SMILES: Cc1cc(CC(=O)Nc2cnn(C(C)(C)C)c2)ccc1Oc1ccnc2ccc(P3(=O)CCCC3)cc12] |
| 182 | 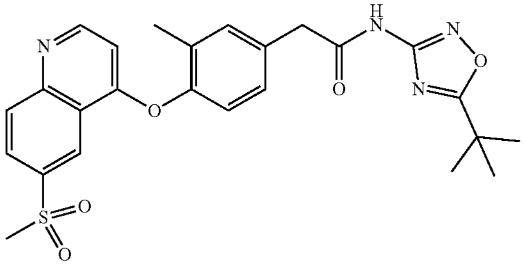 [SMILES: Cc1cc(CC(=O)Nc2noc(C(C)(C)C)n2)ccc1Oc1ccnc2ccc(S(C)(=O)=O)cc12] |
| 183 | 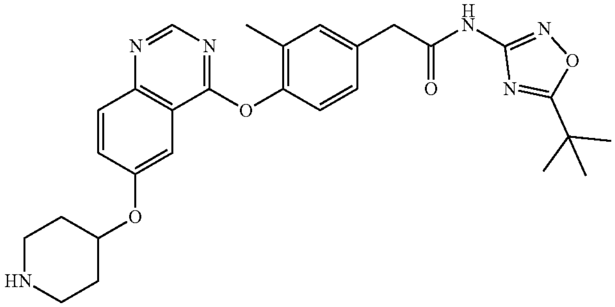 [SMILES: Cc1cc(CC(=O)Nc2noc(C(C)(C)C)n2)ccc1Oc1ncnc2ccc(OC3CCNCC3)cc12] |
| 184 | 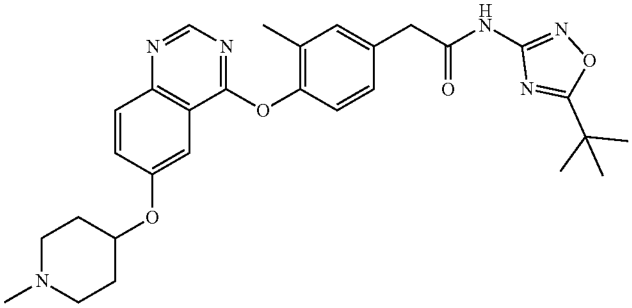 [SMILES: Cc1cc(CC(=O)Nc2noc(C(C)(C)C)n2)ccc1Oc1ncnc2ccc(OC3CCN(C)CC3)cc12] |

TABLE 1-continued
| Compound number | Structure |
| --- | --- |
| 185 | 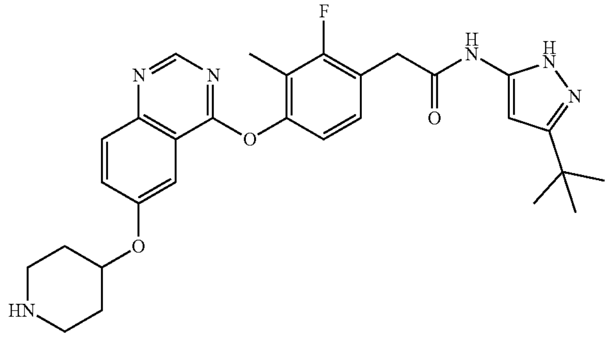 [SMILES: Cc1c(Oc2ncnc3ccc(OC4CCNCC4)cc23)ccc(CC(=O)Nc2cc(C(C)(C)C)n[nH]2)c1F] |
| 186 | 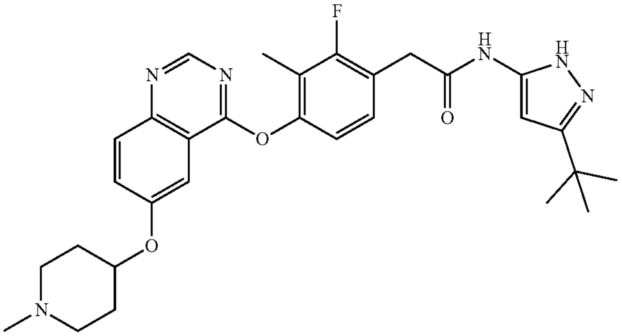 [SMILES: Cc1c(Oc2ncnc3ccc(OC4CCN(C)CC4)cc23)ccc(CC(=O)Nc2cc(C(C)(C)C)n[nH]2)c1F] |
| 187 | 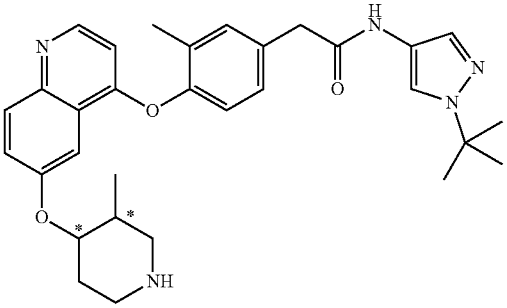 racemic mixture of trans isomers |
| 188 | 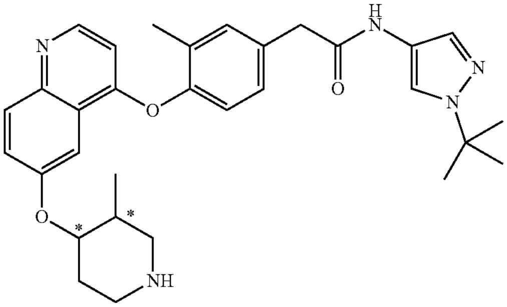 racemic mixture of cis isomers |

TABLE 1-continued
| Compound number | Structure |
|---|---|
| 189 | 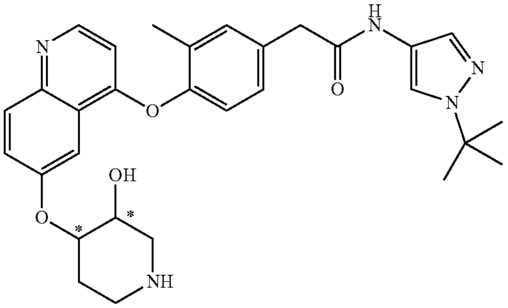 [SMILES: Cc1cc(CC(=O)Nc2cnn(C(C)(C)C)c2)ccc1Oc1ccnc2ccc(OC3CCNCC3O)cc12] racemic mixture of trans isomers |
| 190 | 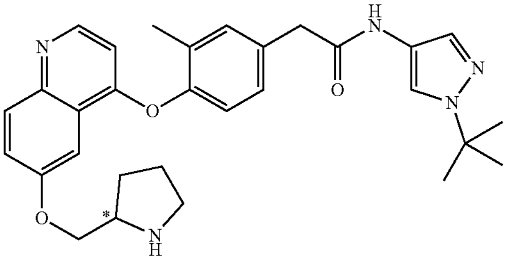 [SMILES: Cc1cc(CC(=O)Nc2cnn(C(C)(C)C)c2)ccc1Oc1ccnc2ccc(OCC3CCCN3)cc12] enantiomer 2 |
| 191 | 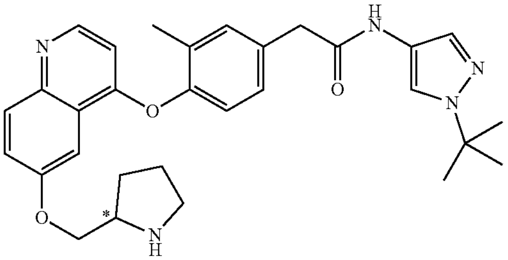 [SMILES: Cc1cc(CC(=O)Nc2cnn(C(C)(C)C)c2)ccc1Oc1ccnc2ccc(OCC3CCCN3)cc12] enantiomer 1 |
| 192 | 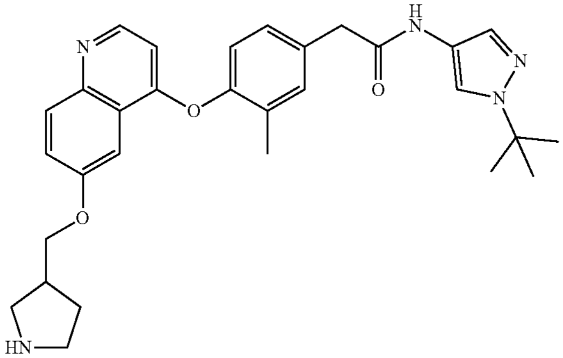 [SMILES: Cc1cc(CC(=O)Nc2cnn(C(C)(C)C)c2)ccc1Oc1ccnc2ccc(OCC3CCNC3)cc12] |

TABLE 1-continued
| Compound number | Structure |
|---|---|
| 193 | 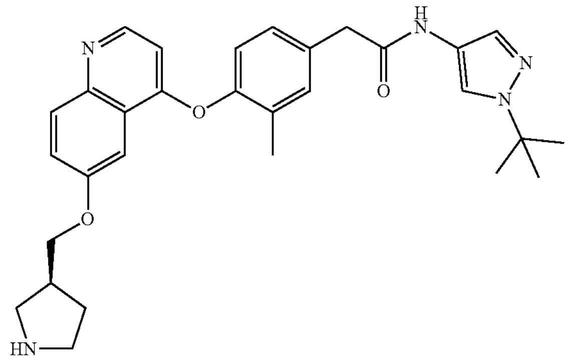 [SMILES: Cc1cc(CC(=O)Nc2cnn(C(C)(C)C)c2)ccc1Oc1ccnc2ccc(OC[C@H]3CCNC3)cc12] |
| 194 | 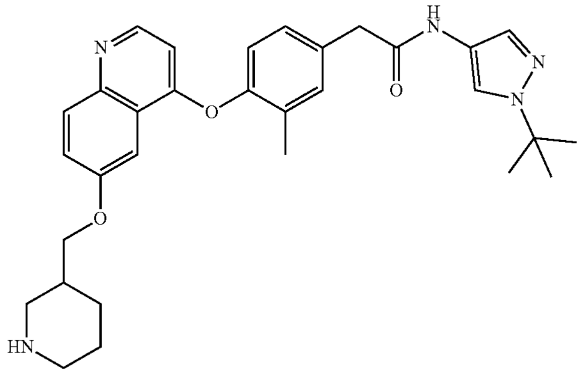 [SMILES: Cc1cc(CC(=O)Nc2cnn(C(C)(C)C)c2)ccc1Oc1ccnc2ccc(OCC3CCCNC3)cc12] |
| 195 | 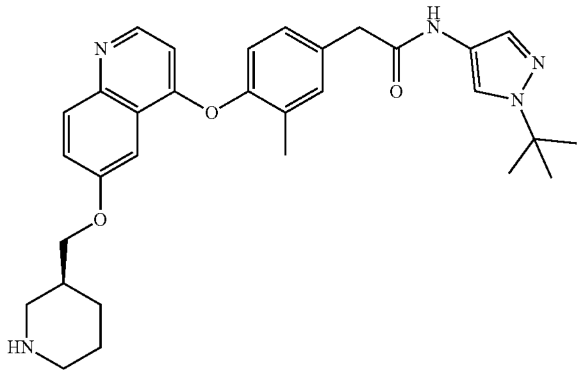 [SMILES: Cc1cc(CC(=O)Nc2cnn(C(C)(C)C)c2)ccc1Oc1ccnc2ccc(OC[C@H]3CCCNC3)cc12] |
| 196 | 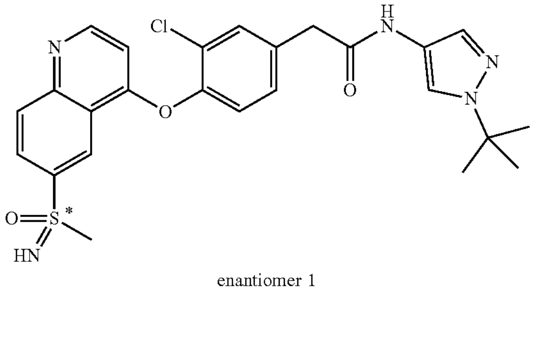 enantiomer 1 |

TABLE 1-continued
| Compound number | Structure |
|---|---|
| 197 | 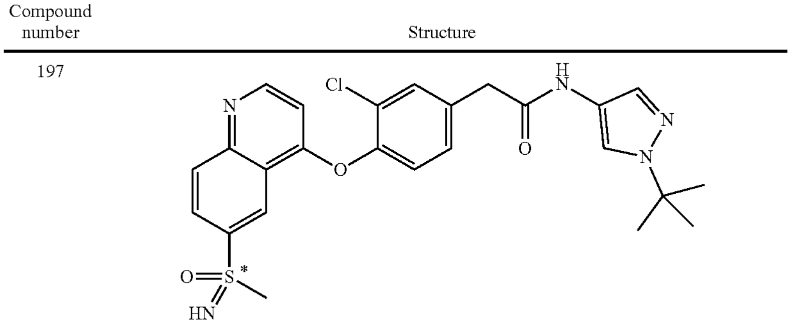 enantiomer 2 |
| 198 | 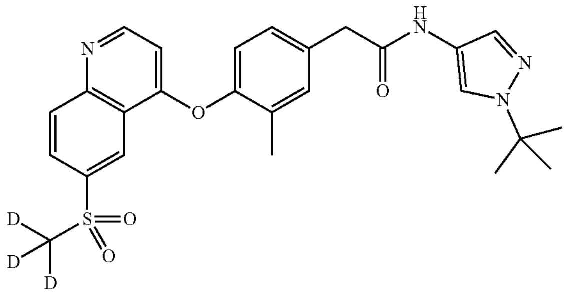 [SMILES: [2H]C([2H])([2H])S(=O)(=O)c1ccc2nccc(Oc3ccc(CC(=O)Nc4cnn(C(C)(C)C)c4)cc3C)c2c1] |
| 199 | 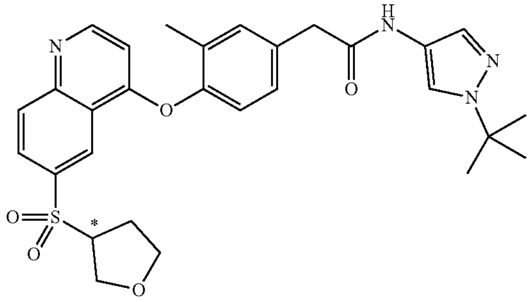 enantiomer 1 |
| 200 | 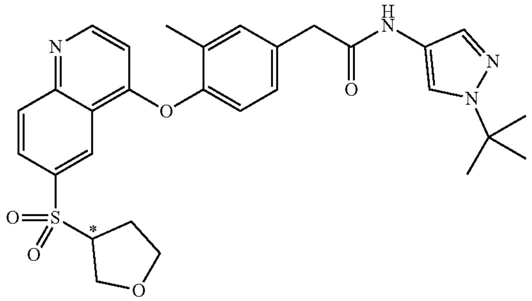 [SMILES: Cc1cc(CC(=O)Nc2cnn(C(C)(C)C)c2)ccc1Oc1ccnc2ccc(S(=O)(=O)C3CCOC3)cc12] enantiomer 2 |
| 201 | 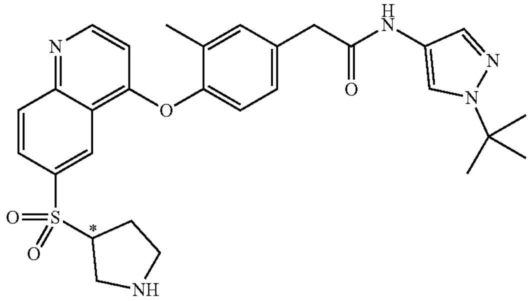 [SMILES: Cc1cc(CC(=O)Nc2cnn(C(C)(C)C)c2)ccc1Oc1ccnc2ccc(S(=O)(=O)C3CCNC3)cc12] enantiomer 1 |

TABLE 1-continued
| Compound number | Structure |
| --- | --- |
| 202 | 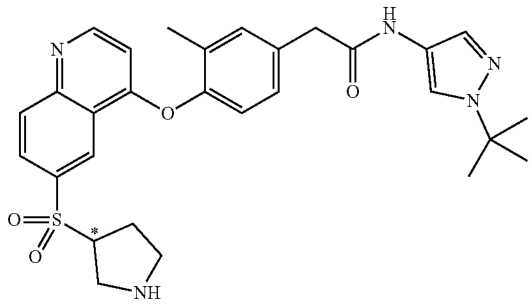 [SMILES: Cc1cc(CC(=O)Nc2cnn(C(C)(C)C)c2)ccc1Oc1ccnc2ccc(S(=O)(=O)C3CCNC3)cc12] enantiomer 2 |
| 203 | 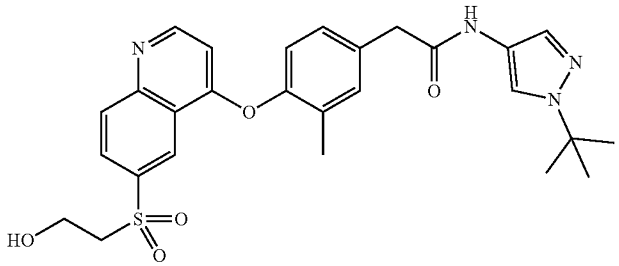 [SMILES: Cc1cc(CC(=O)Nc2cnn(C(C)(C)C)c2)ccc1Oc1ccnc2ccc(S(=O)(=O)CCO)cc12] |
| 204 | 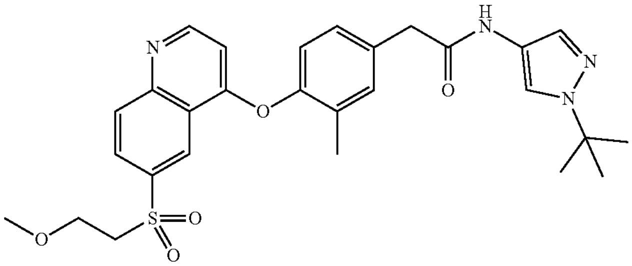 [SMILES: COCCS(=O)(=O)c1ccc2nccc(Oc3ccc(CC(=O)Nc4cnn(C(C)(C)C)c4)cc3C)c2c1] |
| 205 | 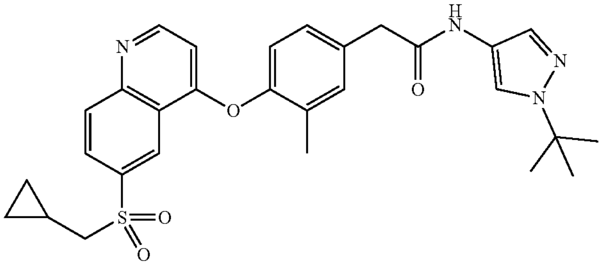 [SMILES: Cc1cc(CC(=O)Nc2cnn(C(C)(C)C)c2)ccc1Oc1ccnc2ccc(S(=O)(=O)CC3CC3)cc12] |
| 206 | 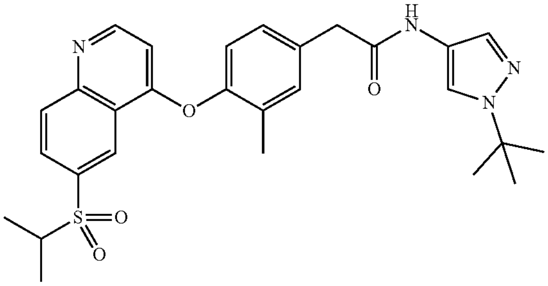 [SMILES: Cc1cc(CC(=O)Nc2cnn(C(C)(C)C)c2)ccc1Oc1ccnc2ccc(S(=O)(=O)C(C)C)cc12] |

TABLE 1-continued
| Compound number | Structure |
| --- | --- |
| 207 | 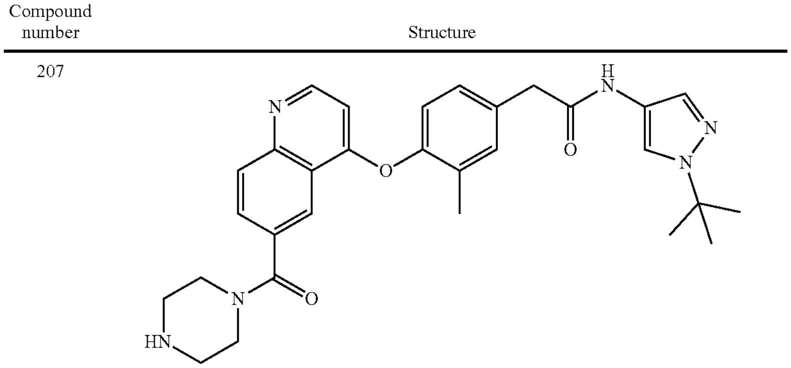 |
| 208 | 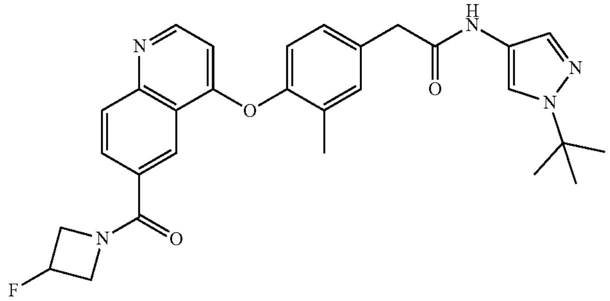 [SMILES: Cc1cc(CC(=O)Nc2cnn(C(C)(C)C)c2)ccc1Oc1ccnc2ccc(C(=O)N3CC(F)C3)cc12] |
| 209 | 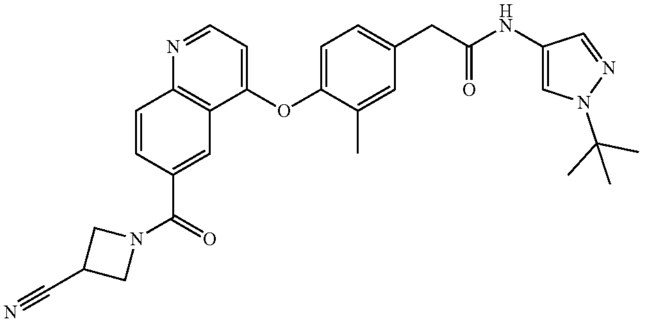 [SMILES: Cc1cc(CC(=O)Nc2cnn(C(C)(C)C)c2)ccc1Oc1ccnc2ccc(C(=O)N3CC(C#N)C3)cc12] |
| 210 | 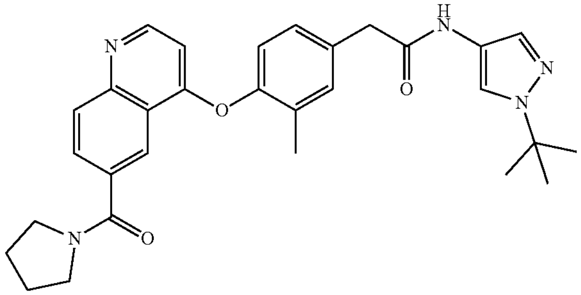 [SMILES: Cc1cc(CC(=O)Nc2cnn(C(C)(C)C)c2)ccc1Oc1ccnc2ccc(C(=O)N3CCCC3)cc12] |
| 211 | 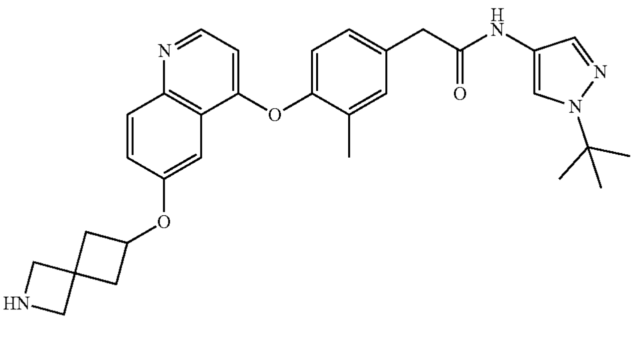 [SMILES: Cc1cc(CC(=O)Nc2cnn(C(C)(C)C)c2)ccc1Oc1ccnc2ccc(OC3CC4(CNC4)C3)cc12] |

TABLE 1-continued
| Compound number | Structure |
|---|---|
| 212 | 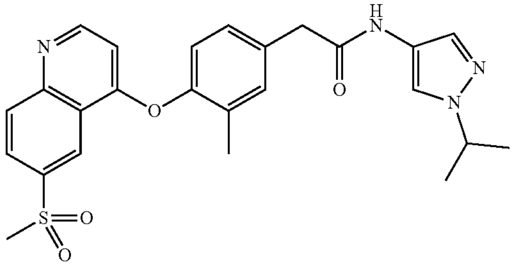 [SMILES: Cc1cc(CC(=O)Nc2cnn(C(C)C)c2)ccc1Oc1ccnc2ccc(S(C)(=O)=O)cc12] |
| 213 | 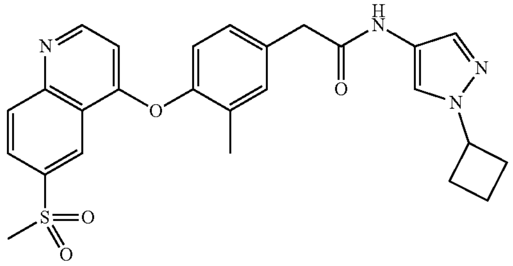 [SMILES: Cc1cc(CC(=O)Nc2cnn(C3CCC3)c2)ccc1Oc1ccnc2ccc(S(C)(=O)=O)cc12] |
| 214 | 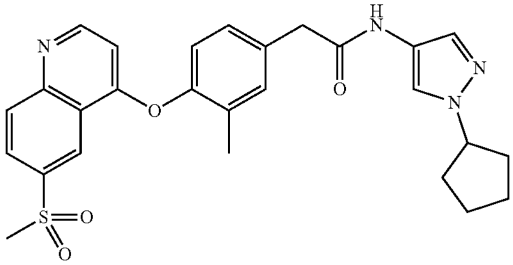 [SMILES: Cc1cc(CC(=O)Nc2cnn(C3CCCC3)c2)ccc1Oc1ccnc2ccc(S(C)(=O)=O)cc12] |
| 215 | 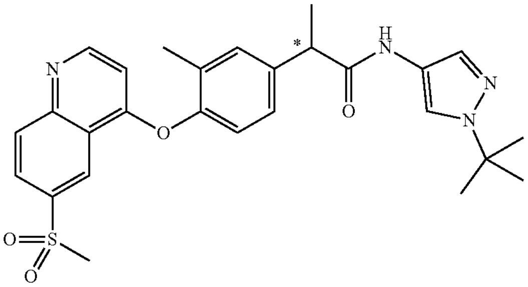 [SMILES: Cc1cc(C(C)C(=O)Nc2cnn(C(C)(C)C)c2)ccc1Oc1ccnc2ccc(S(C)(=O)=O)cc12]<br>enantiomer 1 |
| 216 | 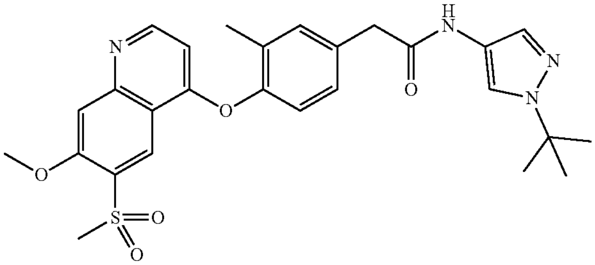 [SMILES: COc1cc2nccc(Oc3ccc(CC(=O)Nc4cnn(C(C)(C)C)c4)cc3C)c2cc1S(C)(=O)=O] |

TABLE 1-continued
| Compound number | Structure |
| --- | --- |
| 217 | 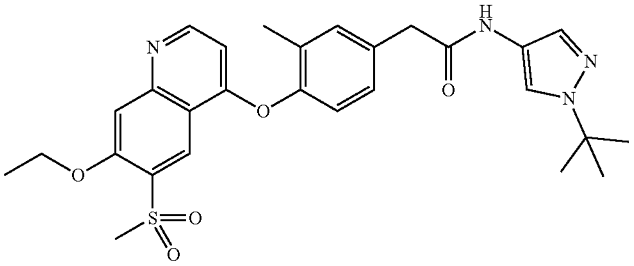 [SMILES: CCOc1cc2nccc(Oc3ccc(CC(=O)Nc4cnn(C(C)(C)C)c4)cc3C)c2cc1S(C)(=O)=O] |
| 218 | 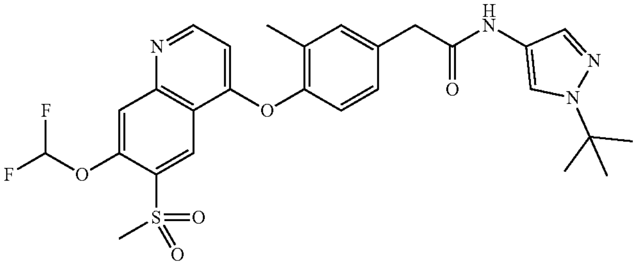 [SMILES: Cc1cc(CC(=O)Nc2cnn(C(C)(C)C)c2)ccc1Oc1ccnc2cc(OC(F)F)c(S(C)(=O)=O)cc12] |
| 219 | 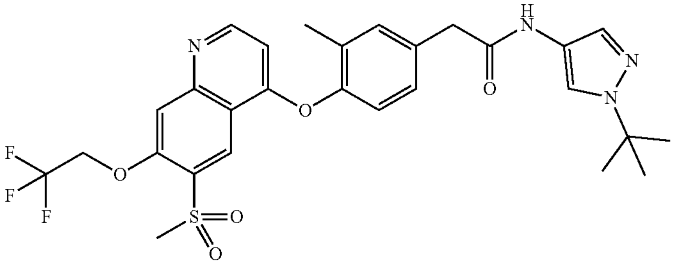 [SMILES: Cc1cc(CC(=O)Nc2cnn(C(C)(C)C)c2)ccc1Oc1ccnc2cc(OCC(F)(F)F)c(S(C)(=O)=O)cc12] |
| 220 | 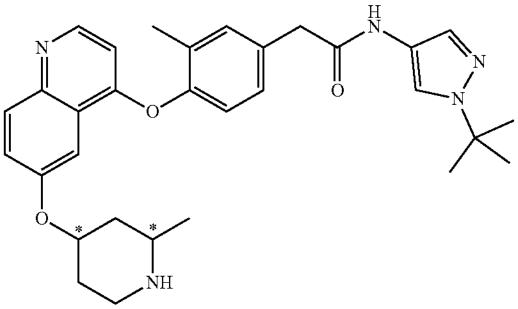 [SMILES: Cc1cc(CC(=O)Nc2cnn(C(C)(C)C)c2)ccc1Oc1ccnc2ccc(OC3CCNC(C)C3)cc12] racemic mixture of cis isomers |
| 221 | 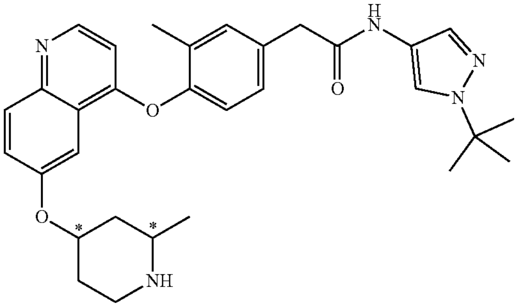 [SMILES: Cc1cc(CC(=O)Nc2cnn(C(C)(C)C)c2)ccc1Oc1ccnc2ccc(OC3CCNC(C)C3)cc12] racemic mixture of trans isomers |

TABLE 1-continued
| Compound number | Structure |
| --- | --- |
| 222 | 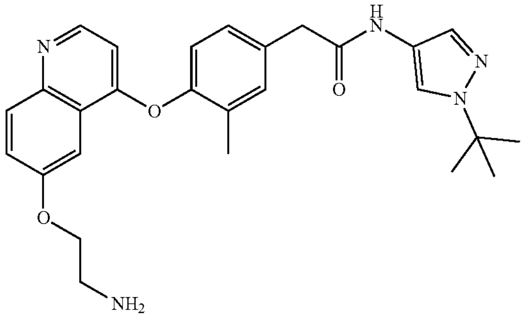 [SMILES: Cc1cc(CC(=O)Nc2cnn(C(C)(C)C)c2)ccc1Oc1ccnc2ccc(OCCN)cc12] |
| 223 | 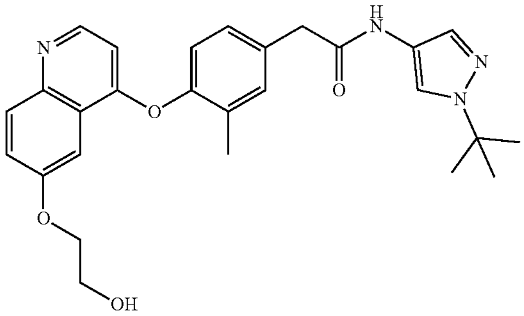 [SMILES: Cc1cc(CC(=O)Nc2cnn(C(C)(C)C)c2)ccc1Oc1ccnc2ccc(OCCO)cc12] |
| 224 | 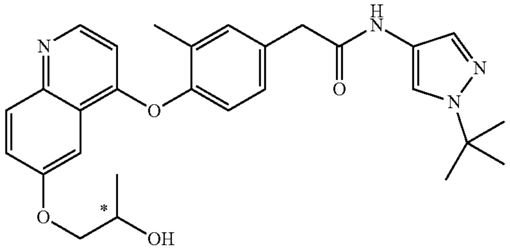 [SMILES: Cc1cc(CC(=O)Nc2cnn(C(C)(C)C)c2)ccc1Oc1ccnc2ccc(OCC(C)O)cc12]<br>enantiomer 1 |
| 225 | 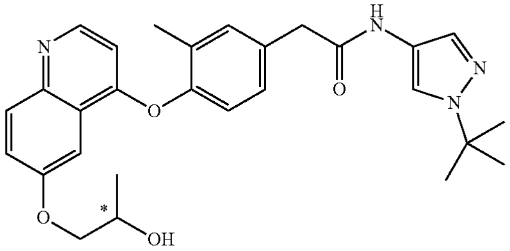 [SMILES: Cc1cc(CC(=O)Nc2cnn(C(C)(C)C)c2)ccc1Oc1ccnc2ccc(OCC(C)O)cc12]<br>enantiomer 2 |
| 226 | 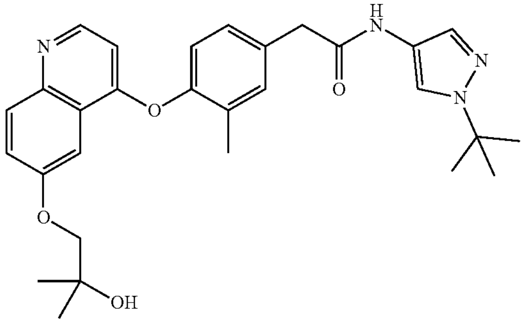 [SMILES: Cc1cc(CC(=O)Nc2cnn(C(C)(C)C)c2)ccc1Oc1ccnc2ccc(OCC(C)(C)O)cc12] |

TABLE 1-continued
| Compound number | Structure |
| --- | --- |
| 227 | 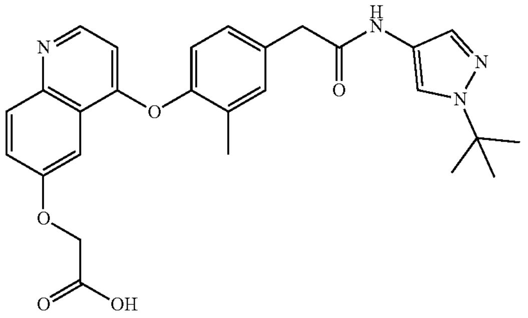 [SMILES: Cc1cc(CC(=O)Nc2cnn(C(C)(C)C)c2)ccc1Oc1ccnc2ccc(OCC(=O)O)cc12] |
| 228 | 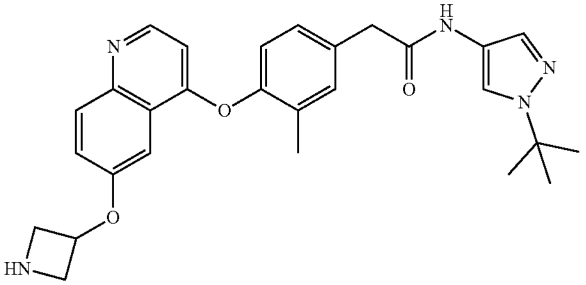 [SMILES: Cc1cc(CC(=O)Nc2cnn(C(C)(C)C)c2)ccc1Oc1ccnc2ccc(OC3CNC3)cc12] |
| 229 | 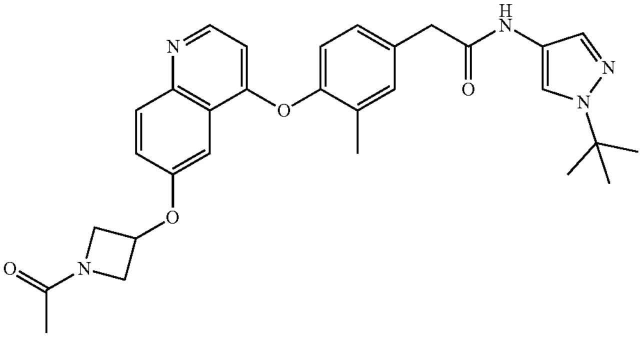 [SMILES: CC(=O)N1CC(Oc2ccc3nccc(Oc4ccc(CC(=O)Nc5cnn(C(C)(C)C)c5)cc4C)c3c2)C1] |
| 230 | 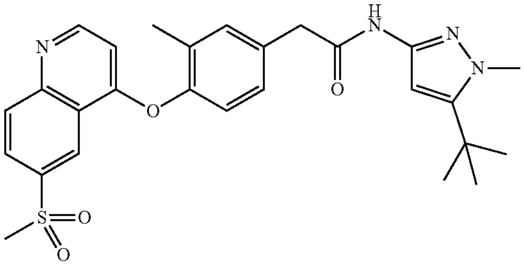 [SMILES: Cc1cc(CC(=O)Nc2cc(C(C)(C)C)n(C)n2)ccc1Oc1ccnc2ccc(S(C)(=O)=O)cc12] |
| 231 | 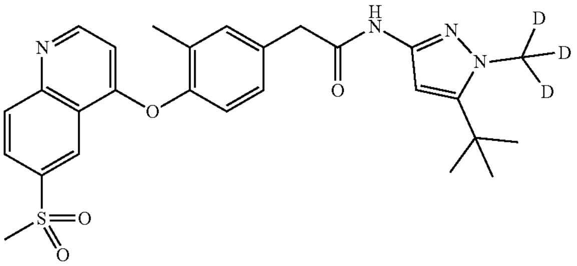 [SMILES: [2H]C([2H])([2H])n1nc(NC(=O)Cc2ccc(Oc3ccnc4ccc(S(C)(=O)=O)cc34)c(C)c2)cc1C(C)(C)C] |

TABLE 1-continued
| Compound number | Structure |
| --- | --- |
| 232 | 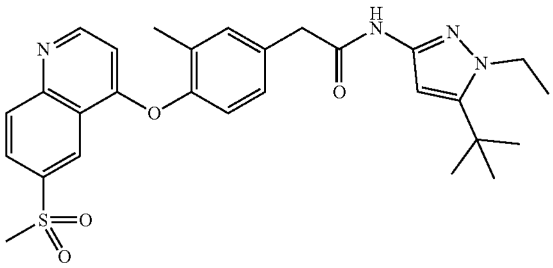 [SMILES: CCn1nc(NC(=O)Cc2ccc(Oc3ccnc4ccc(S(C)(=O)=O)cc34)c(C)c2)cc1C(C)(C)C] |
| 233 | 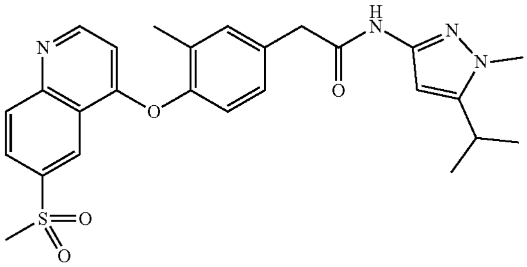 [SMILES: Cc1cc(CC(=O)Nc2cc(C(C)C)n(C)n2)ccc1Oc1ccnc2ccc(S(C)(=O)=O)cc12] |
| 234 | 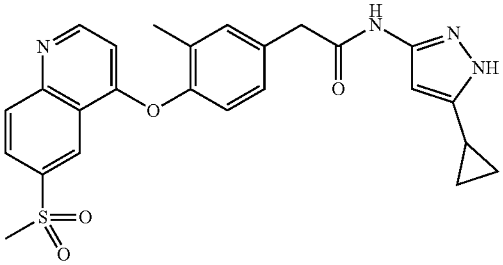 [SMILES: Cc1cc(CC(=O)Nc2cc(C3CC3)[nH]n2)ccc1Oc1ccnc2ccc(S(C)(=O)=O)cc12] |
| 235 | 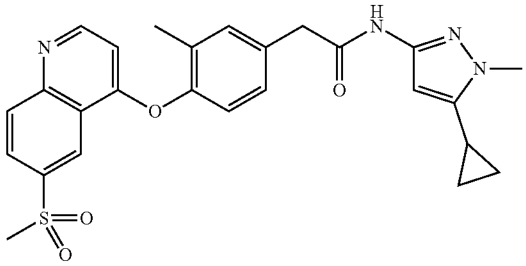 [SMILES: Cc1cc(CC(=O)Nc2cc(C3CC3)n(C)n2)ccc1Oc1ccnc2ccc(S(C)(=O)=O)cc12] |
| 236 | 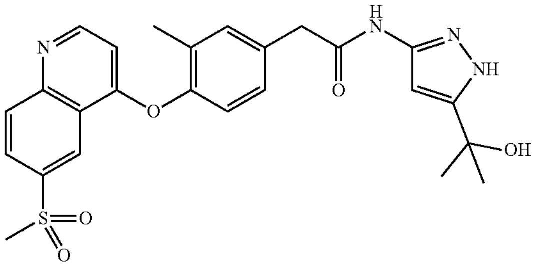 [SMILES: Cc1cc(CC(=O)Nc2cc(C(C)(C)O)[nH]n2)ccc1Oc1ccnc2ccc(S(C)(=O)=O)cc12] |

TABLE 1-continued
| Compound number | Structure |
|---|---|
| 237 | 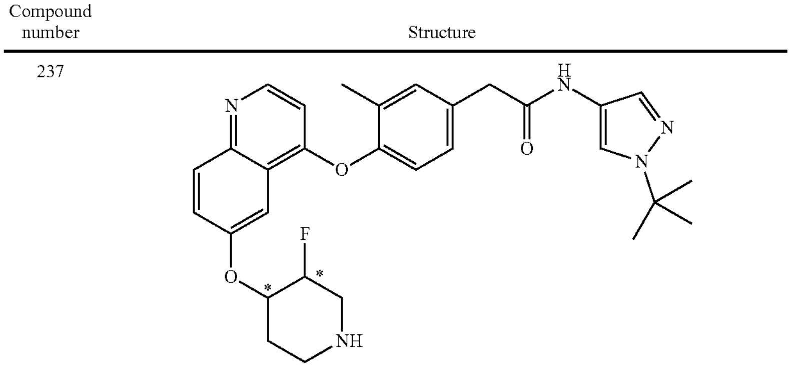 racemic mixture of trans isomers |
| 238 | 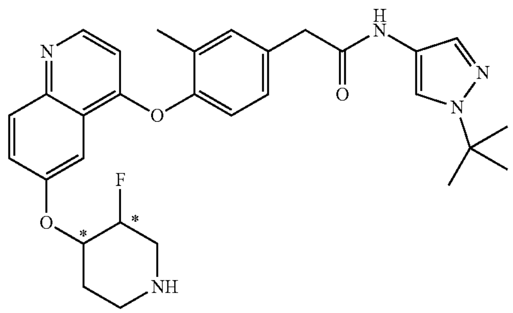 racemic mixture of cis isomers |
| 239 | 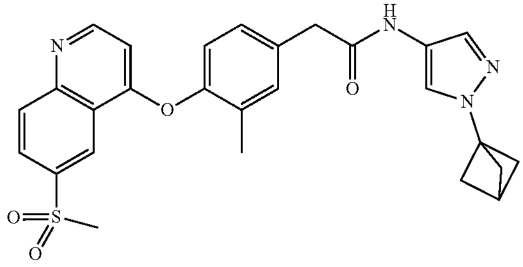 [SMILES: Cc1cc(CC(=O)Nc2cnn(C34CC(C3)C4)c2)ccc1Oc1ccnc2ccc(S(C)(=O)=O)cc12] |
| 240 | 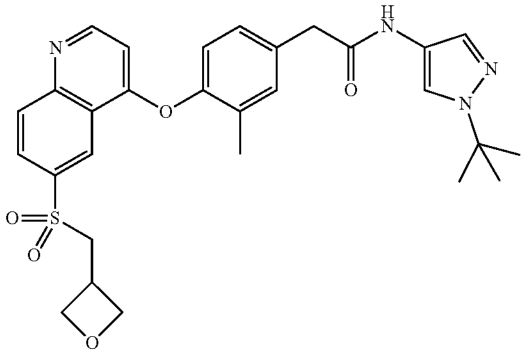 [SMILES: Cc1cc(CC(=O)Nc2cnn(C(C)(C)C)c2)ccc1Oc1ccnc2ccc(S(=O)(=O)CC3COC3)cc12] |
| 241 | 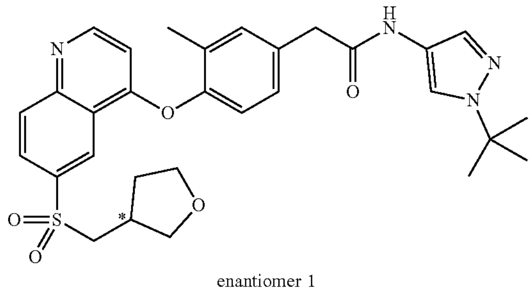 enantiomer 1 |

TABLE 1-continued
| Compound number | Structure |
|---|---|
| 242 | 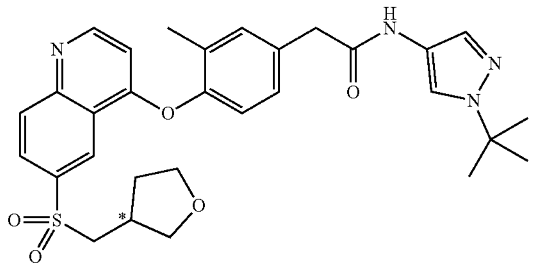 [SMILES: Cc1cc(CC(=O)Nc2cnn(C(C)(C)C)c2)ccc1Oc1ccnc2ccc(S(=O)(=O)CC3CCOC3)cc12] enantiomer 2 |
| 243 | 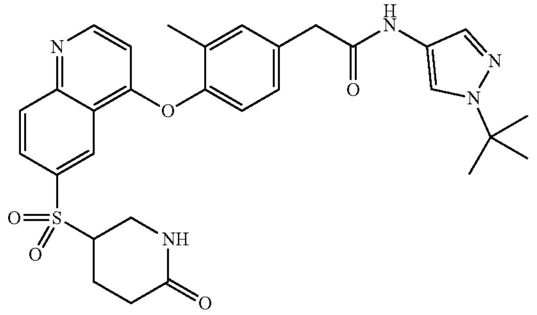 [SMILES: Cc1cc(CC(=O)Nc2cnn(C(C)(C)C)c2)ccc1Oc1ccnc2ccc(S(=O)(=O)C3CCC(=O)NC3)cc12] |
| 244 | 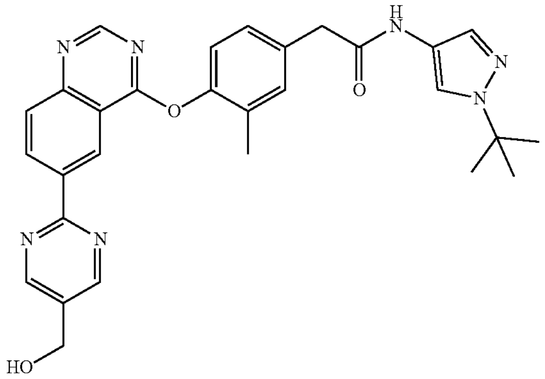 [SMILES: Cc1cc(CC(=O)Nc2cnn(C(C)(C)C)c2)ccc1Oc1ncnc2ccc(-c3ncc(CO)cn3)cc12] |
| 245 | 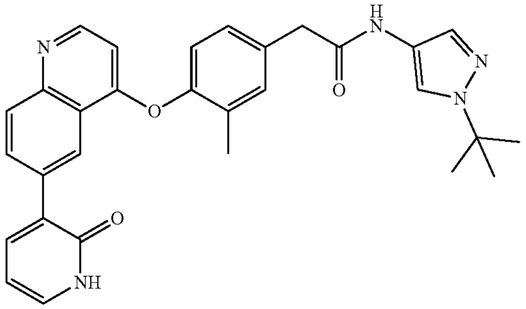 [SMILES: Cc1cc(CC(=O)Nc2cnn(C(C)(C)C)c2)ccc1Oc1ccnc2ccc(-c3ccc[nH]c3=O)cc12] |

TABLE 1-continued
| Compound number | Structure |
|---|---|
| 246 | 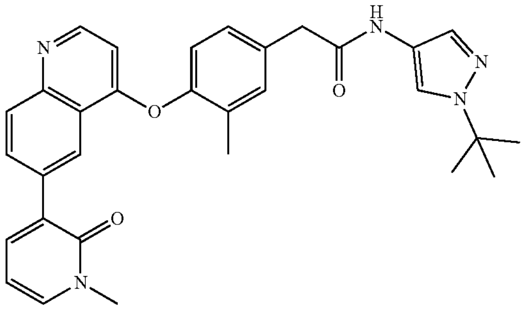 [SMILES: Cc1cc(CC(=O)Nc2cnn(C(C)(C)C)c2)ccc1Oc1ccnc2ccc(-c3cccn(C)c3=O)cc12] |
| 247 | 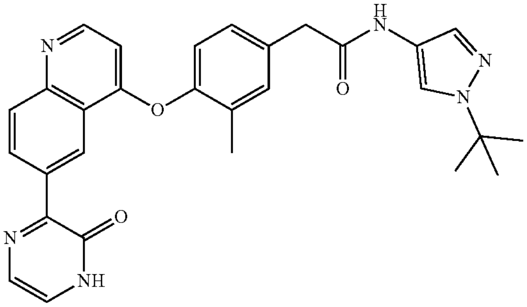 [SMILES: Cc1cc(CC(=O)Nc2cnn(C(C)(C)C)c2)ccc1Oc1ccnc2ccc(-c3ncc[nH]c3=O)cc12] |
| 248 | 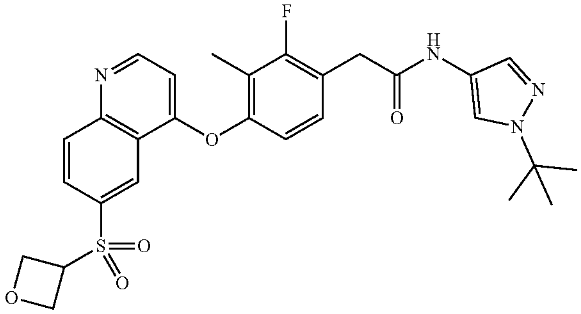 [SMILES: Cc1c(Oc2ccnc3ccc(S(=O)(=O)C4COC4)cc23)ccc(CC(=O)Nc2cnn(C(C)(C)C)c2)c1F] |
| 249 | 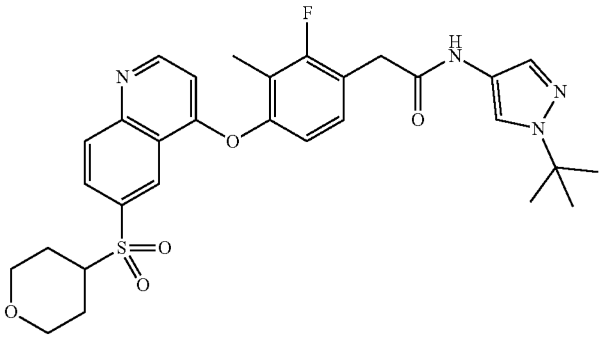 [SMILES: Cc1c(Oc2ccnc3ccc(S(=O)(=O)C4CCOCC4)cc23)ccc(CC(=O)Nc2cnn(C(C)(C)C)c2)c1F] |

TABLE 1-continued
| Compound number | Structure |
| --- | --- |
| 250 | 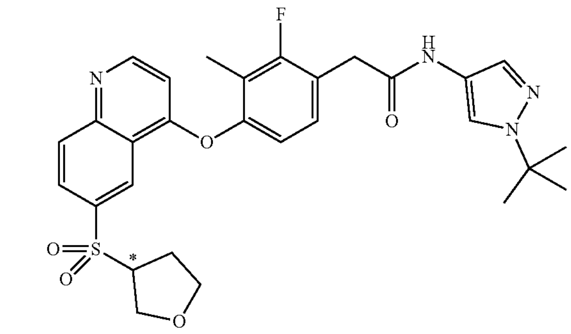 [SMILES: Cc1c(Oc2ccnc3ccc(S(=O)(=O)C4CCOC4)cc23)ccc(CC(=O)Nc2cnn(C(C)(C)C)c2)c1F] enantiomer 1 |
| 251 | 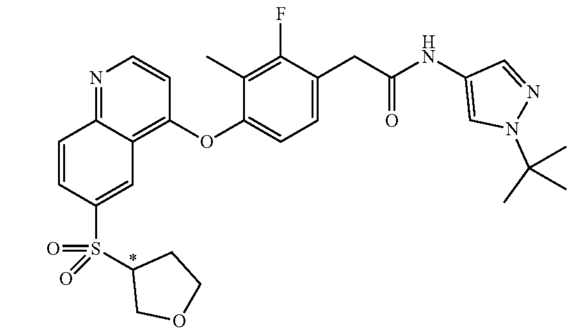 [SMILES: Cc1c(Oc2ccnc3ccc(S(=O)(=O)C4CCOC4)cc23)ccc(CC(=O)Nc2cnn(C(C)(C)C)c2)c1F] enantiomer 2 |
| 252 | 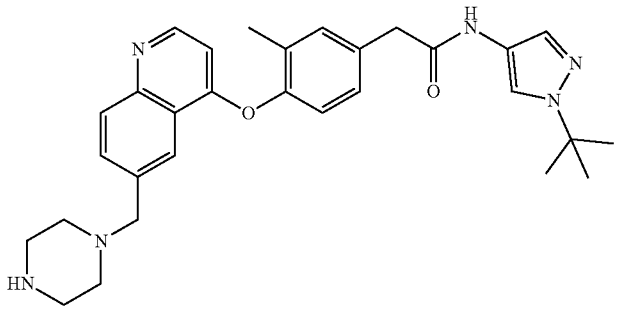 [SMILES: Cc1cc(CC(=O)Nc2cnn(C(C)(C)C)c2)ccc1Oc1ccnc2ccc(CN3CCNCC3)cc12] |
| 253 | 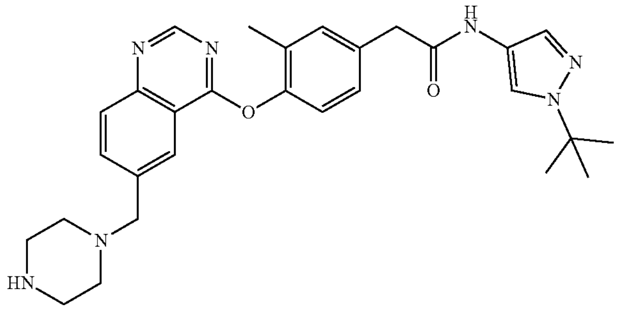 [SMILES: Cc1cc(CC(=O)Nc2cnn(C(C)(C)C)c2)ccc1Oc1ncnc2ccc(CN3CCNCC3)cc12] |

TABLE 1-continued
| Compound number | Structure |
|---|---|
| 254 | 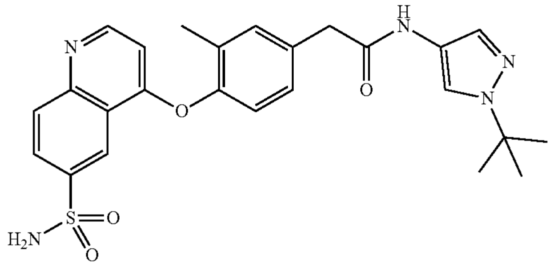 [SMILES: Cc1cc(CC(=O)Nc2cnn(C(C)(C)C)c2)ccc1Oc1ccnc2ccc(S(N)(=O)=O)cc12] |
| 255 | 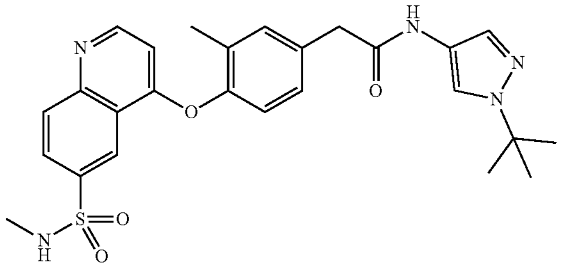 [SMILES: CNS(=O)(=O)c1ccc2nccc(Oc3ccc(CC(=O)Nc4cnn(C(C)(C)C)c4)cc3C)c2c1] |
| 256 | 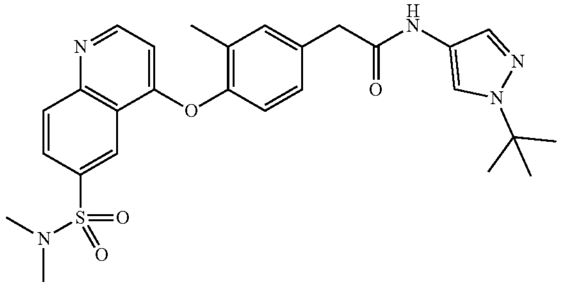 [SMILES: Cc1cc(CC(=O)Nc2cnn(C(C)(C)C)c2)ccc1Oc1ccnc2ccc(S(=O)(=O)N(C)C)cc12] |
| 257 | 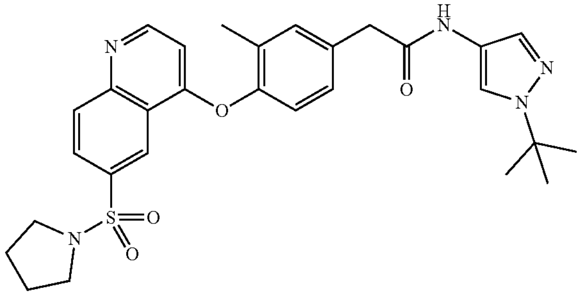 [SMILES: Cc1cc(CC(=O)Nc2cnn(C(C)(C)C)c2)ccc1Oc1ccnc2ccc(S(=O)(=O)N3CCCC3)cc12] |
| 258 | 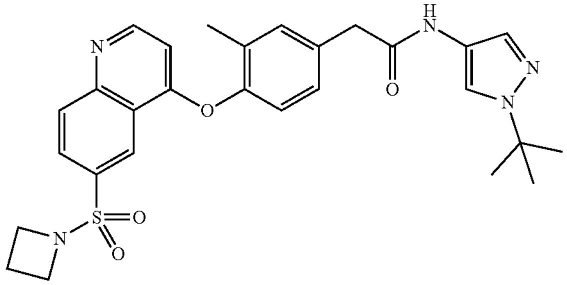 [SMILES: Cc1cc(CC(=O)Nc2cnn(C(C)(C)C)c2)ccc1Oc1ccnc2ccc(S(=O)(=O)N3CCC3)cc12] |

TABLE 1-continued
| Compound number | Structure |
| --- | --- |
| 259 | 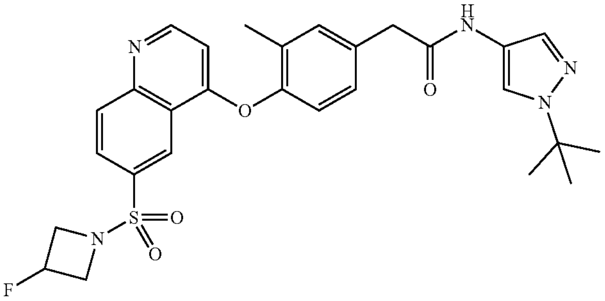 [SMILES: Cc1cc(CC(=O)Nc2cnn(C(C)(C)C)c2)ccc1Oc1ccnc2ccc(S(=O)(=O)N3CC(F)C3)cc12] |
| 260 | 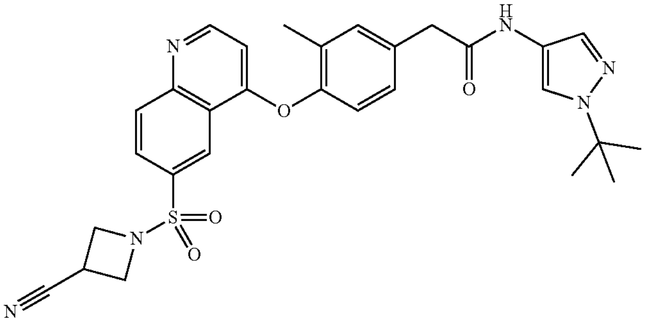 [SMILES: Cc1cc(CC(=O)Nc2cnn(C(C)(C)C)c2)ccc1Oc1ccnc2ccc(S(=O)(=O)N3CC(C#N)C3)cc12] |
| 261 | 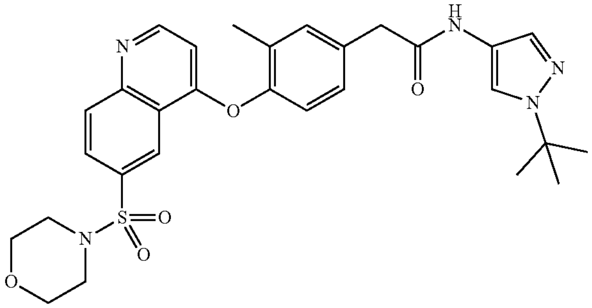 [SMILES: Cc1cc(CC(=O)Nc2cnn(C(C)(C)C)c2)ccc1Oc1ccnc2ccc(S(=O)(=O)N3CCOCC3)cc12] |
| 262 | 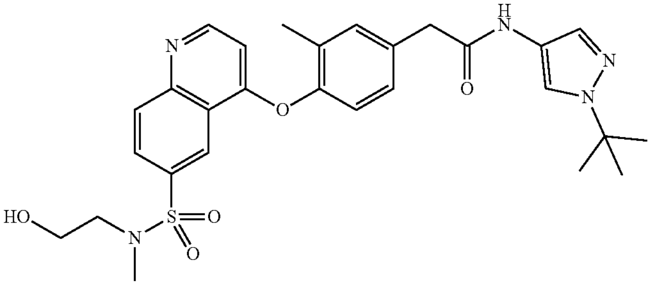 [SMILES: Cc1cc(CC(=O)Nc2cnn(C(C)(C)C)c2)ccc1Oc1ccnc2ccc(S(=O)(=O)N(C)CCO)cc12] |
| 263 | 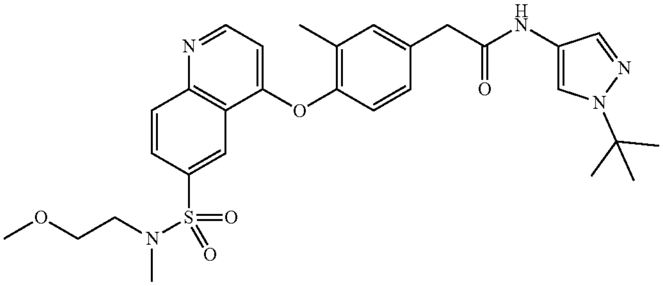 [SMILES: COCCN(C)S(=O)(=O)c1ccc2nccc(Oc3ccc(CC(=O)Nc4cnn(C(C)(C)C)c4)cc3C)c2c1] |

TABLE 1-continued
| Compound number | Structure |
|---|---|
| 264 | 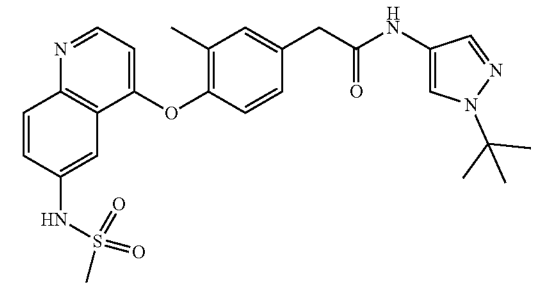 [SMILES: Cc1cc(CC(=O)Nc2cnn(C(C)(C)C)c2)ccc1Oc1ccnc2ccc(NS(C)(=O)=O)cc12] |
| 265 | 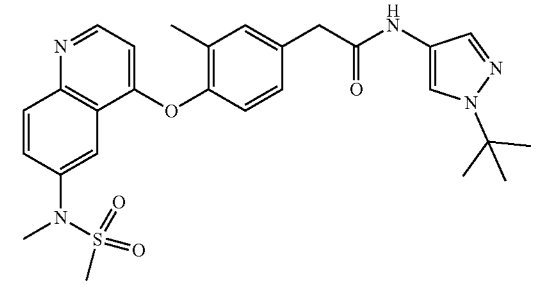 [SMILES: Cc1cc(CC(=O)Nc2cnn(C(C)(C)C)c2)ccc1Oc1ccnc2ccc(N(C)S(C)(=O)=O)cc12] |
| 266 | 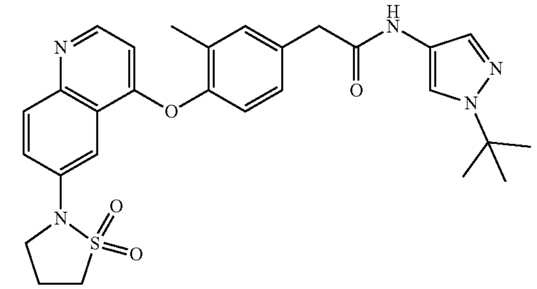 [SMILES: Cc1cc(CC(=O)Nc2cnn(C(C)(C)C)c2)ccc1Oc1ccnc2ccc(N3CCCS3(=O)=O)cc12] |
| 267 | 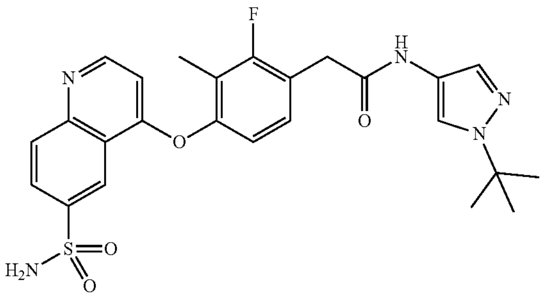 [SMILES: Cc1c(Oc2ccnc3ccc(S(N)(=O)=O)cc23)ccc(CC(=O)Nc2cnn(C(C)(C)C)c2)c1F] |
| 268 | 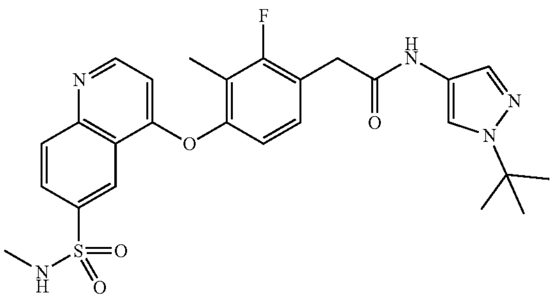 [SMILES: CNS(=O)(=O)c1ccc2nccc(Oc3ccc(CC(=O)Nc4cnn(C(C)(C)C)c4)c(F)c3C)c2c1] |

TABLE 1-continued
| Compound number | Structure |
| --- | --- |
| 269 | 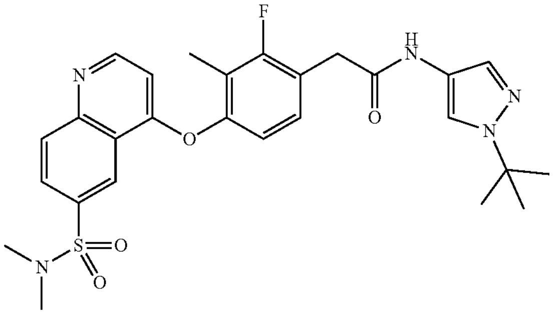 [SMILES: Cc1c(Oc2ccnc3ccc(S(=O)(=O)N(C)C)cc23)ccc(CC(=O)Nc2cnn(C(C)(C)C)c2)c1F] |
| 270 | 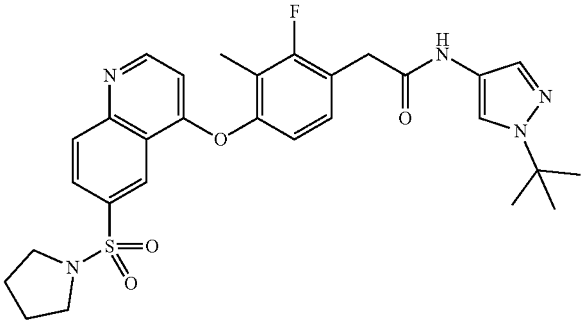 [SMILES: Cc1c(Oc2ccnc3ccc(S(=O)(=O)N4CCCC4)cc23)ccc(CC(=O)Nc2cnn(C(C)(C)C)c2)c1F] |
| 271 | 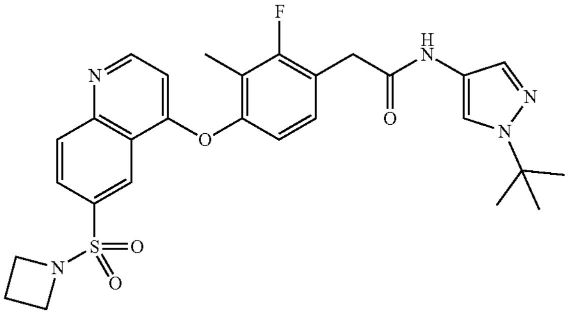 [SMILES: Cc1c(Oc2ccnc3ccc(S(=O)(=O)N4CCC4)cc23)ccc(CC(=O)Nc2cnn(C(C)(C)C)c2)c1F] |
| 272 | 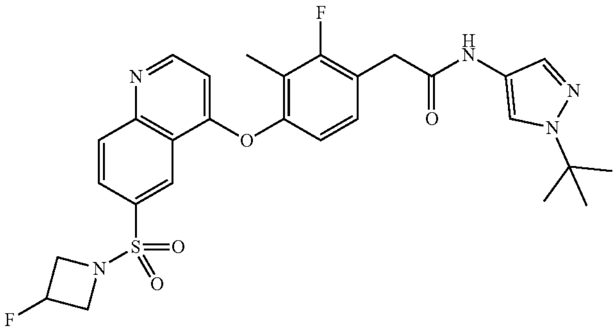 [SMILES: Cc1c(Oc2ccnc3ccc(S(=O)(=O)N4CC(F)C4)cc23)ccc(CC(=O)Nc2cnn(C(C)(C)C)c2)c1F] |

TABLE 1-continued
| Compound number | Structure |
|---|---|
| 273 | 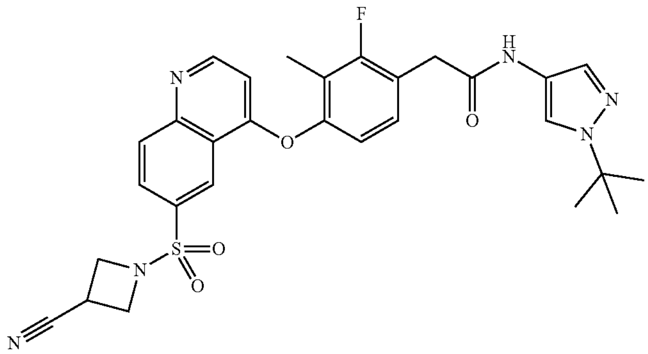 [SMILES: Cc1c(Oc2ccnc3ccc(S(=O)(=O)N4CC(C#N)C4)cc23)ccc(CC(=O)Nc2cnn(C(C)(C)C)c2)c1F] |
| 274 | 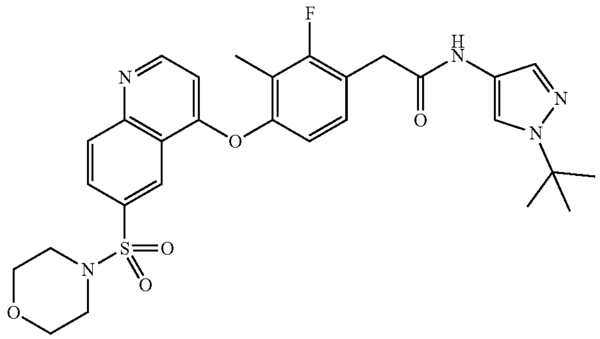 [SMILES: Cc1c(Oc2ccnc3ccc(S(=O)(=O)N4CCOCC4)cc23)ccc(CC(=O)Nc2cnn(C(C)(C)C)c2)c1F] |
| 275 | 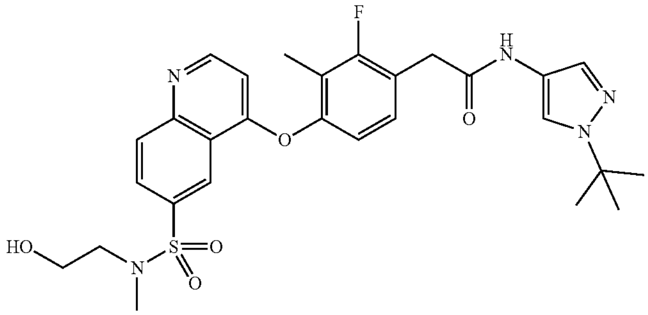 [SMILES: Cc1c(Oc2ccnc3ccc(S(=O)(=O)N(C)CCO)cc23)ccc(CC(=O)Nc2cnn(C(C)(C)C)c2)c1F] |
| 276 | 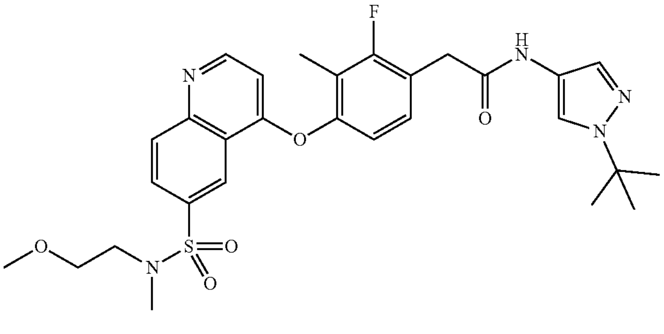 [SMILES: COCCN(C)S(=O)(=O)c1ccc2nccc(Oc3ccc(CC(=O)Nc4cnn(C(C)(C)C)c4)c(F)c3C)c2c1] |

TABLE 1-continued
| Compound number | Structure |
|---|---|
| 277 | 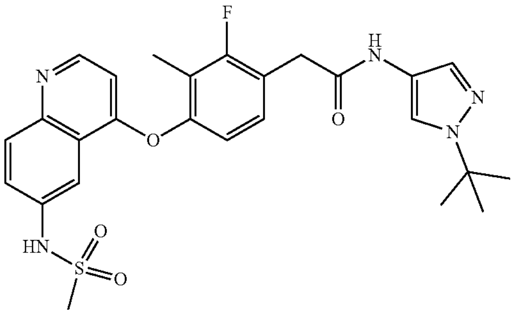 [SMILES: Cc1c(Oc2ccnc3ccc(NS(C)(=O)=O)cc23)ccc(CC(=O)Nc2cnn(C(C)(C)C)c2)c1F] |
| 278 | 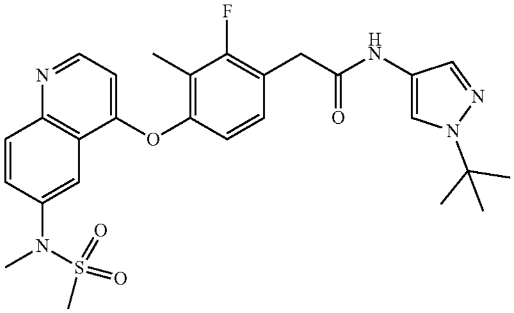 [SMILES: Cc1c(Oc2ccnc3ccc(N(C)S(C)(=O)=O)cc23)ccc(CC(=O)Nc2cnn(C(C)(C)C)c2)c1F] |
| 279 | 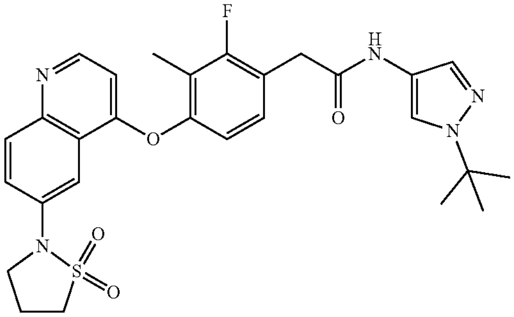 [SMILES: Cc1c(Oc2ccnc3ccc(N4CCCS4(=O)=O)cc23)ccc(CC(=O)Nc2cnn(C(C)(C)C)c2)c1F] |
| 280 | 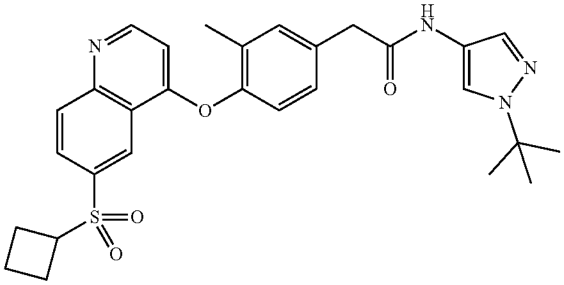 [SMILES: Cc1cc(CC(=O)Nc2cnn(C(C)(C)C)c2)ccc1Oc1ccnc2ccc(S(=O)(=O)C3CCC3)cc12] |
| 281 | 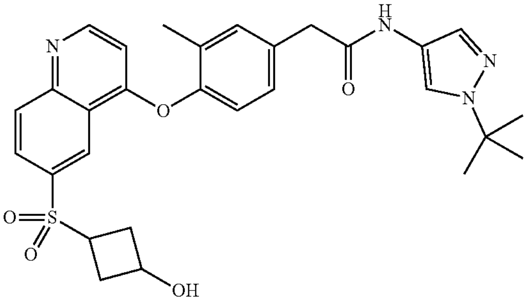 [SMILES: Cc1cc(CC(=O)Nc2cnn(C(C)(C)C)c2)ccc1Oc1ccnc2ccc(S(=O)(=O)C3CC(O)C3)cc12] |

TABLE 1-continued
| Compound number | Structure |
| --- | --- |
| 282 | 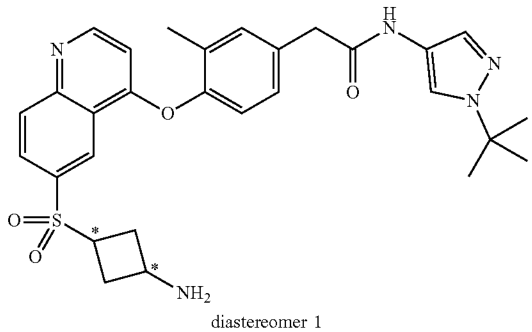 diastereomer 1 |
| 283 | 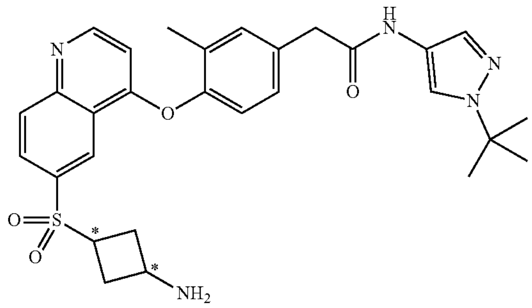 [SMILES: Cc1cc(CC(=O)Nc2cnn(C(C)(C)C)c2)ccc1Oc1ccnc2ccc(S(=O)(=O)C3CC(N)C3)cc12] diastereomer 2 |
| 284 | 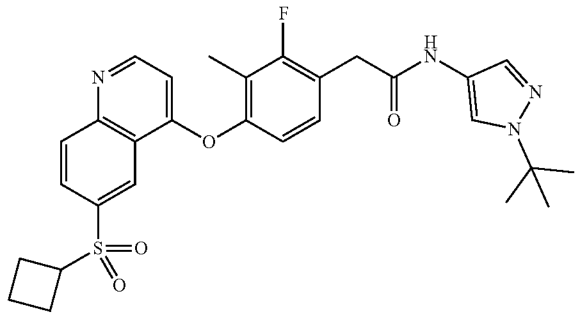 [SMILES: Cc1c(Oc2ccnc3ccc(S(=O)(=O)C4CCC4)cc23)ccc(CC(=O)Nc2cnn(C(C)(C)C)c2)c1F] |
| 285 | 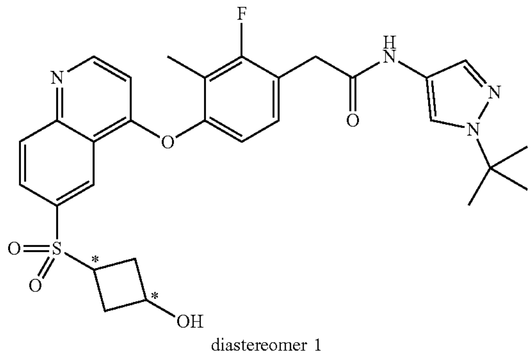 diastereomer 1 |

TABLE 1-continued
| Compound number | Structure |
|---|---|
| 286 | 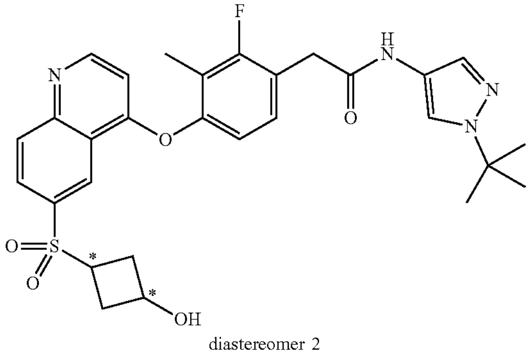 diastereomer 2 |
| 287 | 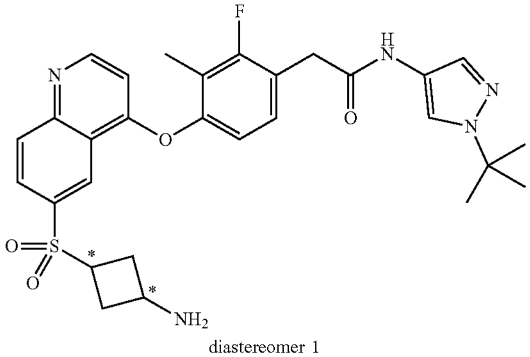 diastereomer 1 |
| 288 | 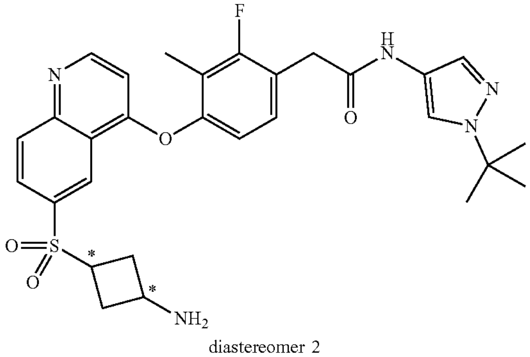 diastereomer 2 |
| 289 | 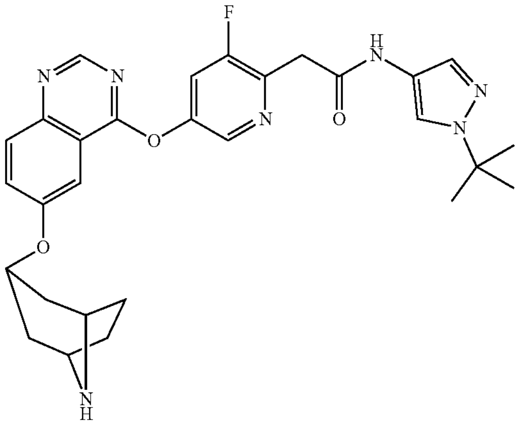 [SMILES: CC(C)(C)n1cc(NC(=O)Cc2ncc(Oc3ncnc4ccc(OC5CC6CCC(C5)N6)cc34)cc2F)cn1] |

TABLE 1-continued
| Compound number | Structure |
|---|---|
| 290 | 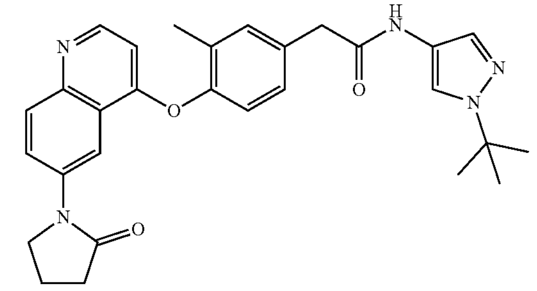 [SMILES: Cc1cc(CC(=O)Nc2cnn(C(C)(C)C)c2)ccc1Oc1ccnc2ccc(N3CCCC3=O)cc12] |
| 291 | 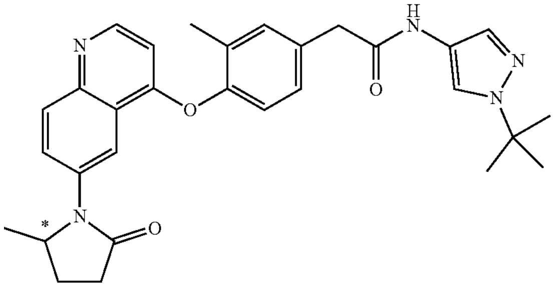 [SMILES: Cc1cc(CC(=O)Nc2cnn(C(C)(C)C)c2)ccc1Oc1ccnc2ccc(N3C(=O)CCC3C)cc12] enantiomer 1 |
| 292 | 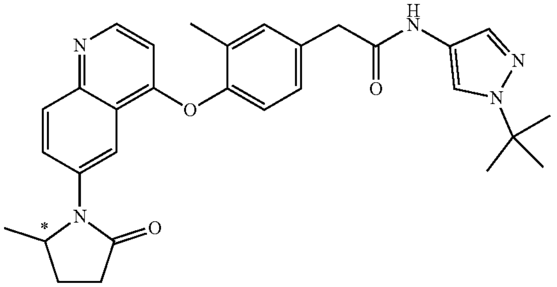 [SMILES: Cc1cc(CC(=O)Nc2cnn(C(C)(C)C)c2)ccc1Oc1ccnc2ccc(N3C(=O)CCC3C)cc12] enantiomer 2 |
| 293 | 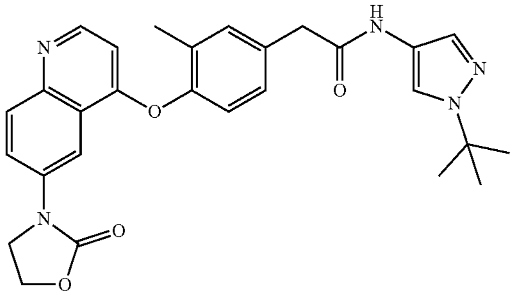 [SMILES: Cc1cc(CC(=O)Nc2cnn(C(C)(C)C)c2)ccc1Oc1ccnc2ccc(N3CCOC3=O)cc12] |
| 294 | 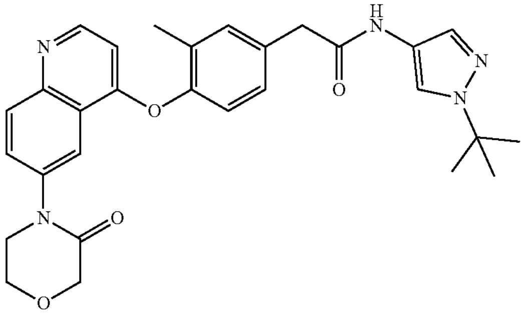 [SMILES: Cc1cc(CC(=O)Nc2cnn(C(C)(C)C)c2)ccc1Oc1ccnc2ccc(N3CCOCC3=O)cc12] |

TABLE 1-continued
| Compound number | Structure |
|---|---|
| 295 | 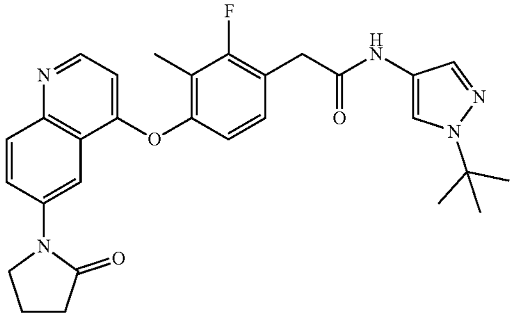 [SMILES: Cc1c(Oc2ccnc3ccc(N4CCCC4=O)cc23)ccc(CC(=O)Nc2cnn(C(C)(C)C)c2)c1F] |
| 296 | 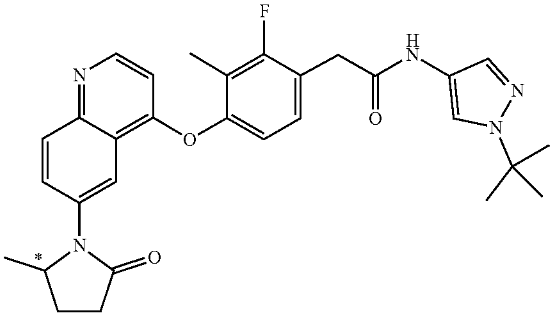 [SMILES: Cc1c(Oc2ccnc3ccc(N4C(=O)CCC4C)cc23)ccc(CC(=O)Nc2cnn(C(C)(C)C)c2)c1F]<br>enantiomer 1 |
| 297 | 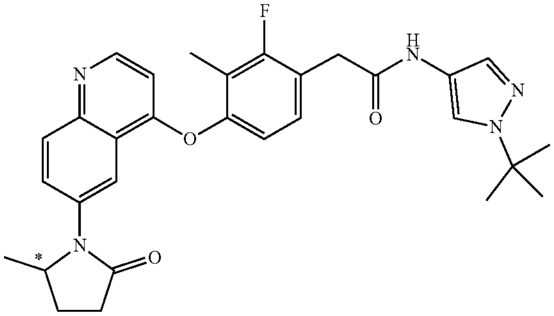 [SMILES: Cc1c(Oc2ccnc3ccc(N4C(=O)CCC4C)cc23)ccc(CC(=O)Nc2cnn(C(C)(C)C)c2)c1F]<br>enantiomer 2 |
| 298 | 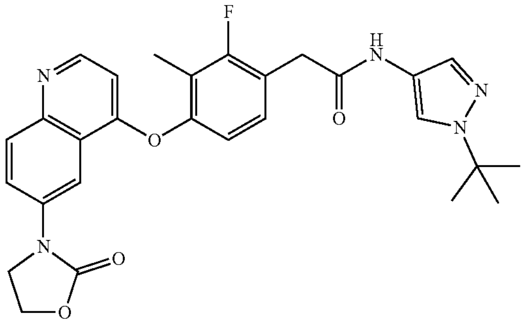 [SMILES: Cc1c(Oc2ccnc3ccc(N4CCOC4=O)cc23)ccc(CC(=O)Nc2cnn(C(C)(C)C)c2)c1F] |

TABLE 1-continued
| Compound number | Structure |
| --- | --- |
| 299 | 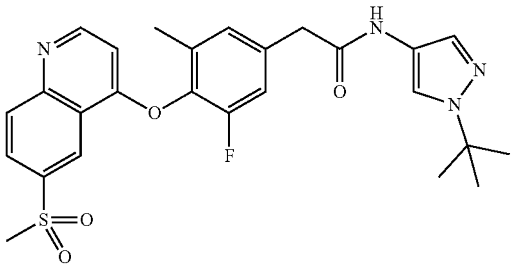 [SMILES: Cc1cc(CC(=O)Nc2cnn(C(C)(C)C)c2)cc(F)c1Oc1ccnc2ccc(S(C)(=O)=O)cc12] |
| 300 | 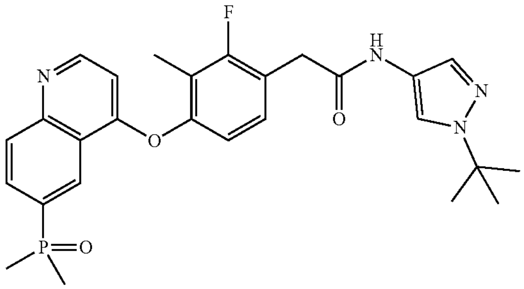 [SMILES: Cc1c(Oc2ccnc3ccc(P(C)(C)=O)cc23)ccc(CC(=O)Nc2cnn(C(C)(C)C)c2)c1F] |
| 301 | 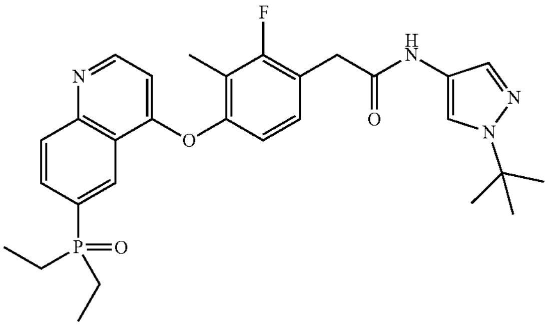 [SMILES: CCP(=O)(CC)c1ccc2nccc(Oc3ccc(CC(=O)Nc4cnn(C(C)(C)C)c4)c(F)c3C)c2c1] |
| 302 | 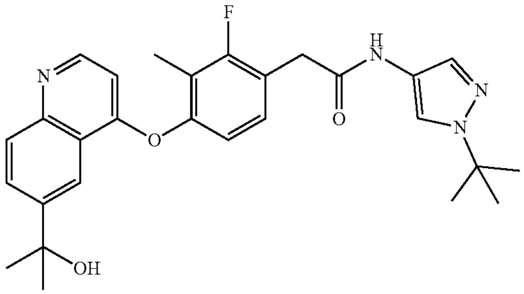 [SMILES: Cc1c(Oc2ccnc3ccc(C(C)(C)O)cc23)ccc(CC(=O)Nc2cnn(C(C)(C)C)c2)c1F] |
| 303 | 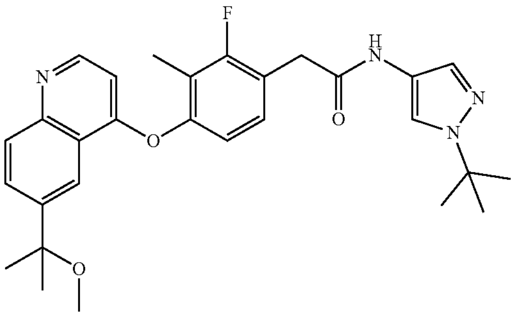 [SMILES: COC(C)(C)c1ccc2nccc(Oc3ccc(CC(=O)Nc4cnn(C(C)(C)C)c4)c(F)c3C)c2c1] |

TABLE 1-continued
| Compound number | Structure |
| --- | --- |
| 304 | 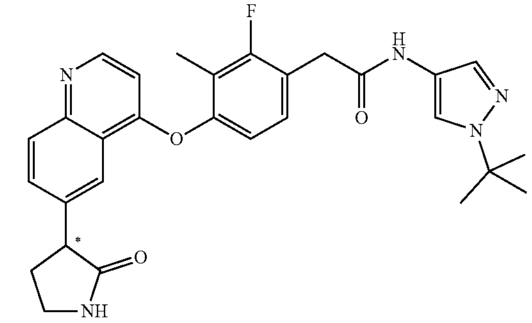 [SMILES: Cc1c(Oc2ccnc3ccc(C4CCNC4=O)cc23)ccc(CC(=O)Nc2cnn(C(C)(C)C)c2)c1F] enantiomer 1 |
| 305 | 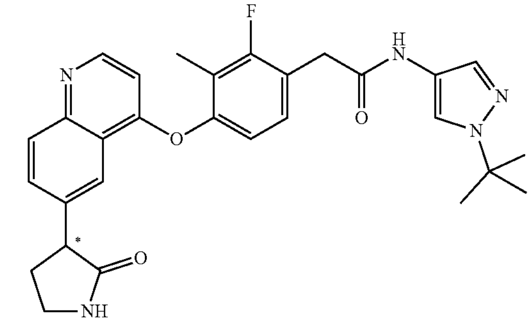 [SMILES: Cc1c(Oc2ccnc3ccc(C4CCNC4=O)cc23)ccc(CC(=O)Nc2cnn(C(C)(C)C)c2)c1F] enantiomer 2 |
| 306 | 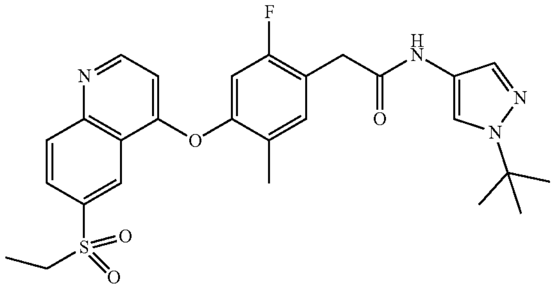 [SMILES: CCS(=O)(=O)c1ccc2nccc(Oc3cc(F)c(CC(=O)Nc4cnn(C(C)(C)C)c4)cc3C)c2c1] |
| 307 | 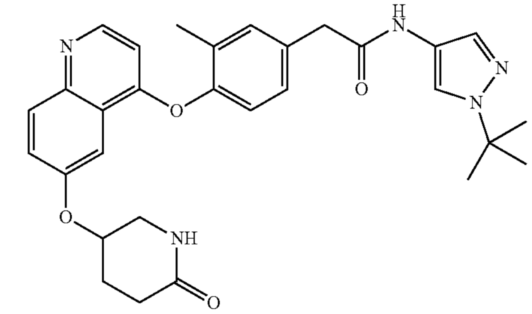 [SMILES: Cc1cc(CC(=O)Nc2cnn(C(C)(C)C)c2)ccc1Oc1ccnc2ccc(OC3CCC(=O)NC3)cc12] |

TABLE 1-continued
| Compound number | Structure |
|---|---|
| 308 | 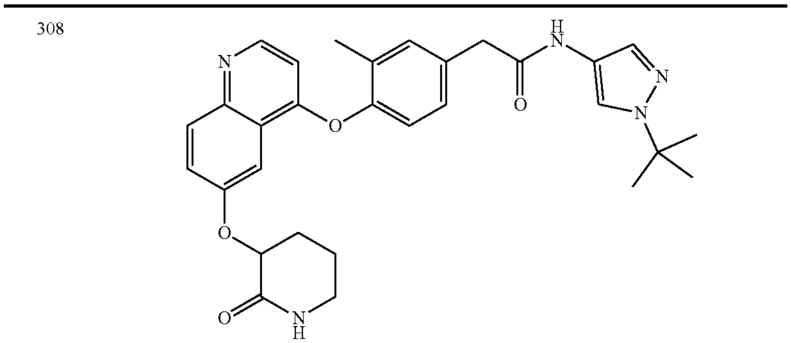 |
| 309 | 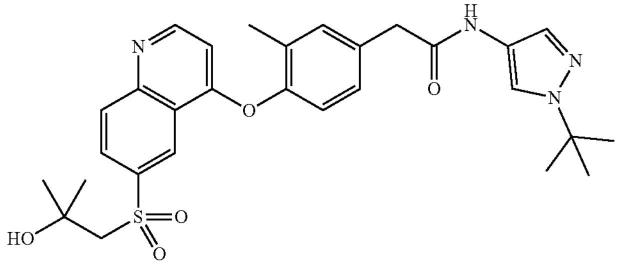 [SMILES: Cc1cc(CC(=O)Nc2cnn(C(C)(C)C)c2)ccc1Oc1ccnc2ccc(S(=O)(=O)CC(C)(C)O)cc12] |
| 310 | 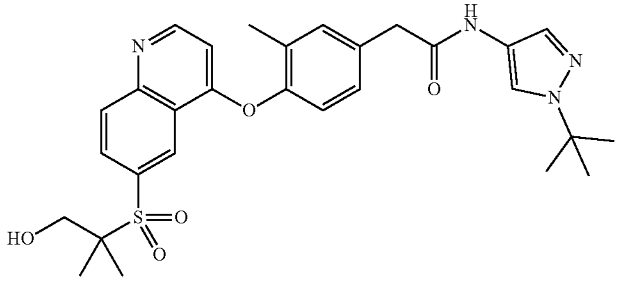 [SMILES: Cc1cc(CC(=O)Nc2cnn(C(C)(C)C)c2)ccc1Oc1ccnc2ccc(S(=O)(=O)C(C)(C)CO)cc12] |
| 311 | 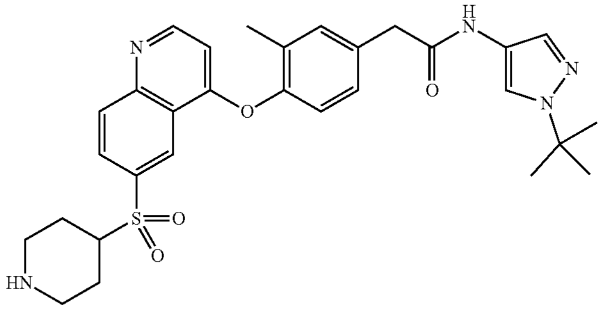 [SMILES: Cc1cc(CC(=O)Nc2cnn(C(C)(C)C)c2)ccc1Oc1ccnc2ccc(S(=O)(=O)C3CCNCC3)cc12] |
| 312 | 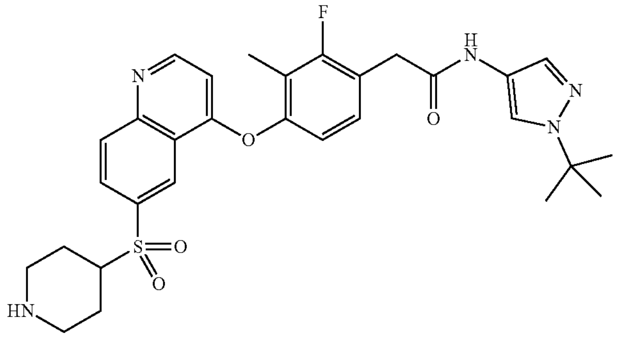 [SMILES: Cc1c(Oc2ccnc3ccc(S(=O)(=O)C4CCNCC4)cc23)ccc(CC(=O)Nc2cnn(C(C)(C)C)c2)c1F] |

TABLE 1-continued
| Compound number | Structure |
| --- | --- |
| 313 | 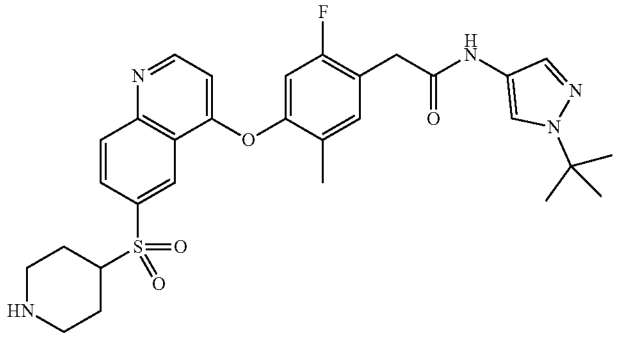 [SMILES: Cc1cc(CC(=O)Nc2cnn(C(C)(C)C)c2)c(F)cc1Oc1ccnc2ccc(S(=O)(=O)C3CCNCC3)cc12] |
| 314 | 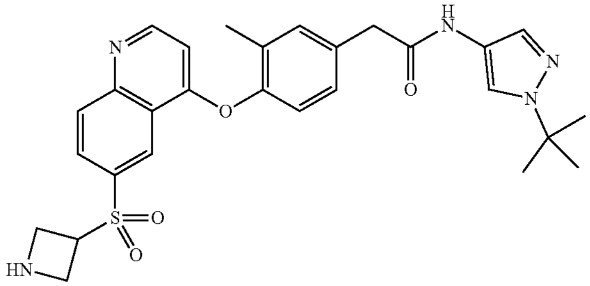 [SMILES: Cc1cc(CC(=O)Nc2cnn(C(C)(C)C)c2)ccc1Oc1ccnc2ccc(S(=O)(=O)C3CNC3)cc12] |
| 315 | 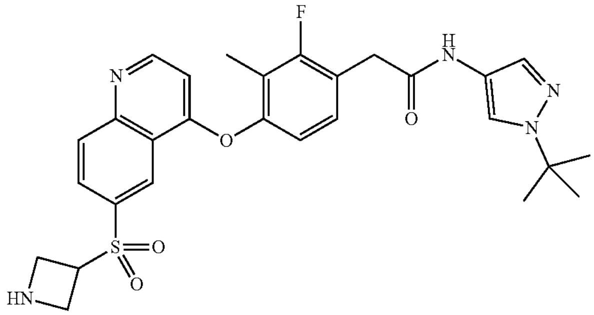 [SMILES: Cc1c(Oc2ccnc3ccc(S(=O)(=O)C4CNC4)cc23)ccc(CC(=O)Nc2cnn(C(C)(C)C)c2)c1F] |
| 316 | 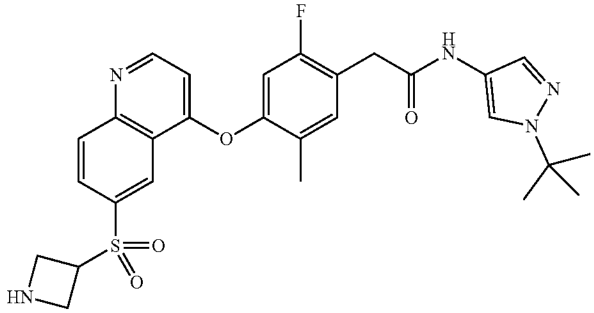 [SMILES: Cc1cc(CC(=O)Nc2cnn(C(C)(C)C)c2)c(F)cc1Oc1ccnc2ccc(S(=O)(=O)C3CNC3)cc12] |

TABLE 1-continued
| Compound number | Structure |
|---|---|
| 317 | 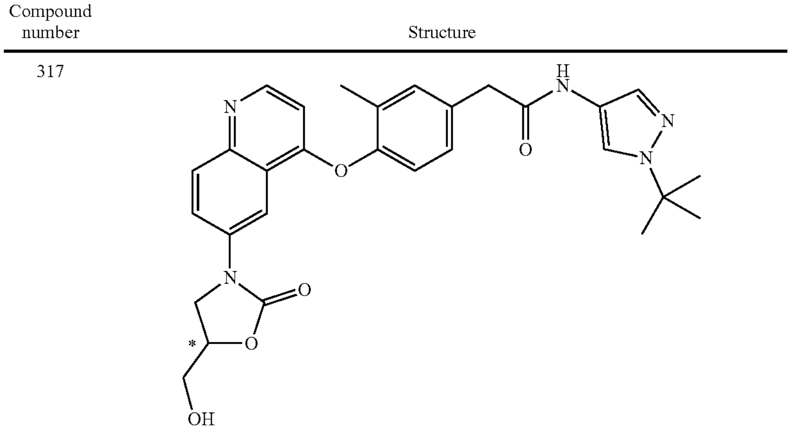 enantiomer 1 |
| 318 | 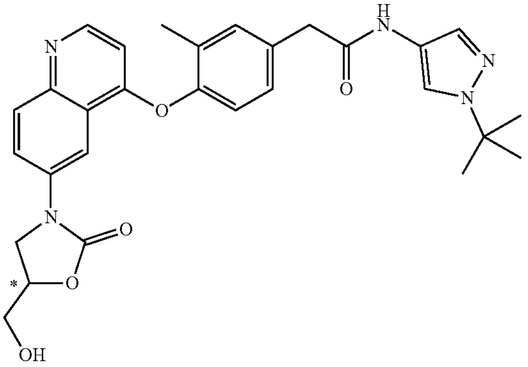 [SMILES: Cc1cc(CC(=O)Nc2cnn(C(C)(C)C)c2)ccc1Oc1ccnc2ccc(N3CC(CO)OC3=O)cc12] enantiomer 2 |
| 319 | 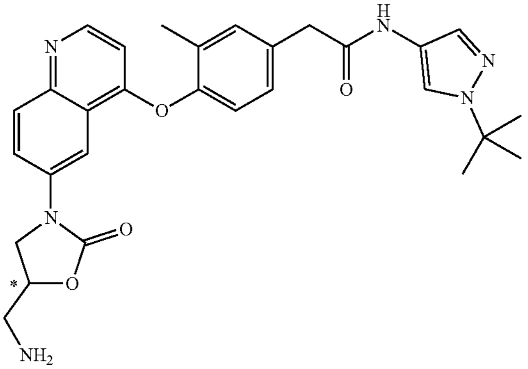 [SMILES: Cc1cc(CC(=O)Nc2cnn(C(C)(C)C)c2)ccc1Oc1ccnc2ccc(N3CC(CN)OC3=O)cc12] enantiomer 1 |
| 320 | 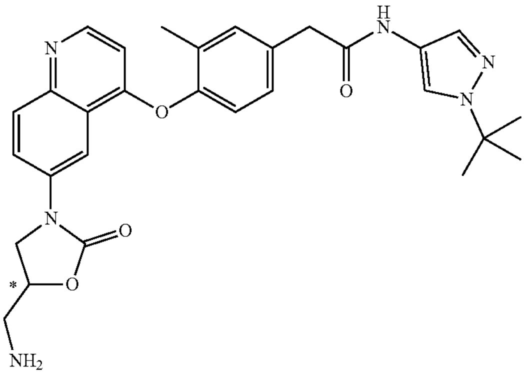 [SMILES: Cc1cc(CC(=O)Nc2cnn(C(C)(C)C)c2)ccc1Oc1ccnc2ccc(N3CC(CN)OC3=O)cc12] enantiomer 2 |

TABLE 1-continued
| Compound number | Structure |
| --- | --- |
| 321 | 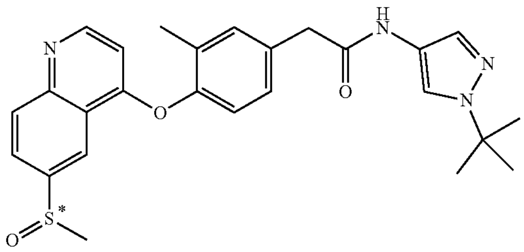 [SMILES: Cc1cc(CC(=O)Nc2cnn(C(C)(C)C)c2)ccc1Oc1ccnc2ccc(S(C)=O)cc12] enantiomer 1 |
| 322 | 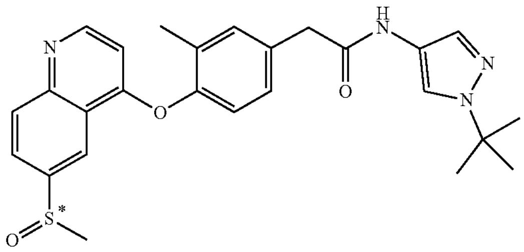 [SMILES: Cc1cc(CC(=O)Nc2cnn(C(C)(C)C)c2)ccc1Oc1ccnc2ccc(S(C)=O)cc12] enantiomer 2 |
| 323 | 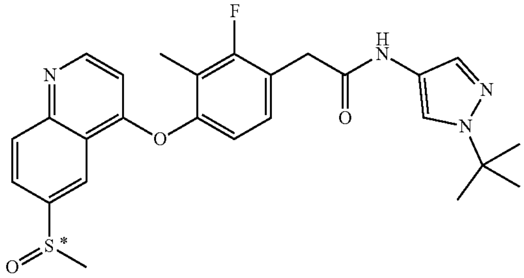 [SMILES: Cc1c(Oc2ccnc3ccc(S(C)=O)cc23)ccc(CC(=O)Nc2cnn(C(C)(C)C)c2)c1F] enantiomer 1 |
| 324 | 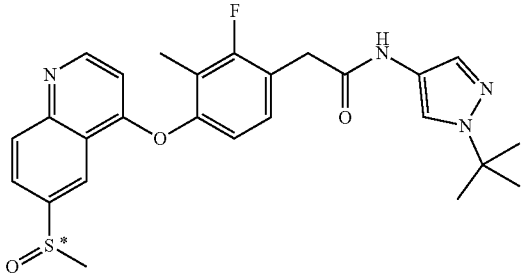 [SMILES: Cc1c(Oc2ccnc3ccc(S(C)=O)cc23)ccc(CC(=O)Nc2cnn(C(C)(C)C)c2)c1F] enantiomer 2 |
| 325 | 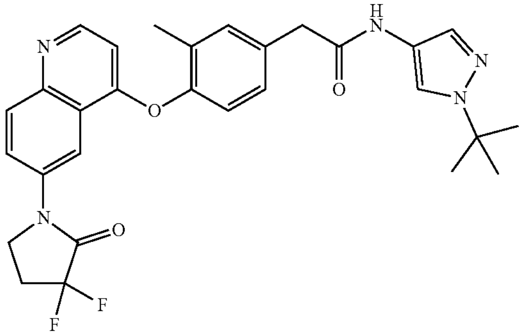 [SMILES: Cc1cc(CC(=O)Nc2cnn(C(C)(C)C)c2)ccc1Oc1ccnc2ccc(N3CCC(F)(F)C3=O)cc12] |

TABLE 1-continued
| Compound number | Structure |
|---|---|
| 326 | 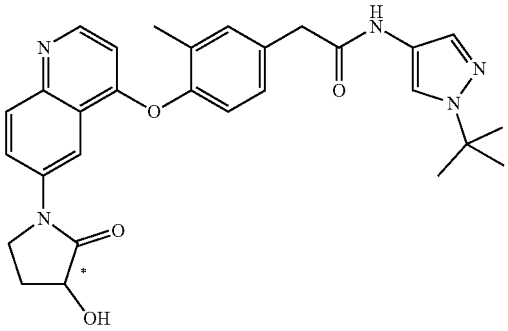 [SMILES: Cc1cc(CC(=O)Nc2cnn(C(C)(C)C)c2)ccc1Oc1ccnc2ccc(N3CCC(O)C3=O)cc12]<br>enantiomer 1 |
| 327 | 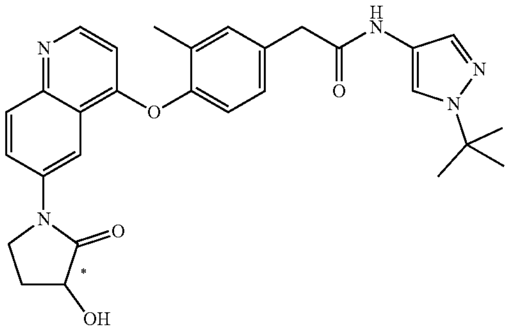 [SMILES: Cc1cc(CC(=O)Nc2cnn(C(C)(C)C)c2)ccc1Oc1ccnc2ccc(N3CCC(O)C3=O)cc12]<br>enantiomer 2 |
| 328 | 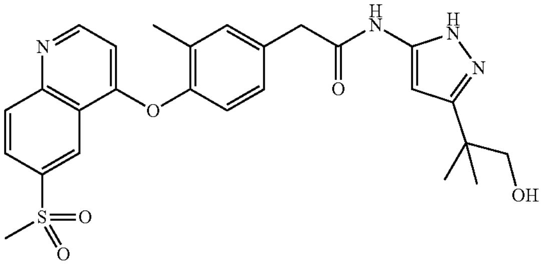 [SMILES: Cc1cc(CC(=O)Nc2cc(C(C)(C)CO)n[nH]2)ccc1Oc1ccnc2ccc(S(C)(=O)=O)cc12] |
| 329 | 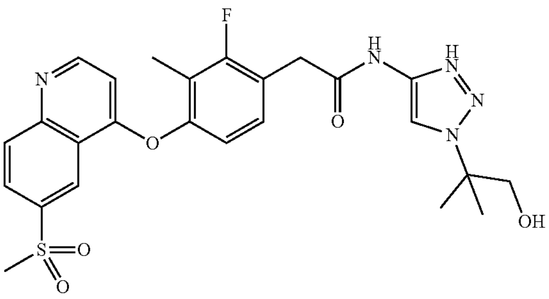 |
| 330 | 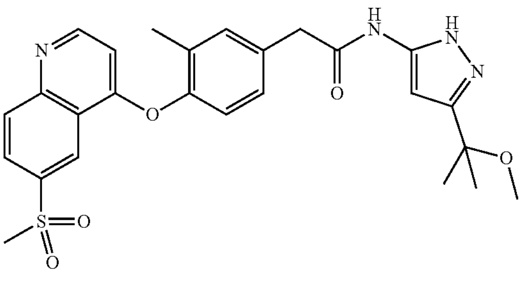 [SMILES: COC(C)(C)c1cc(NC(=O)Cc2ccc(Oc3ccnc4ccc(S(C)(=O)=O)cc34)c(C)c2)[nH]n1] |

TABLE 1-continued
| Compound number | Structure |
| --- | --- |
| 331 | 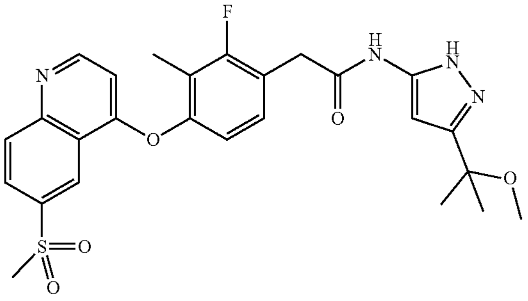 [SMILES: COC(C)(C)c1cc(NC(=O)Cc2ccc(Oc3ccnc4ccc(S(C)(=O)=O)cc34)c(C)c2F)[nH]n1] |
| 332 | 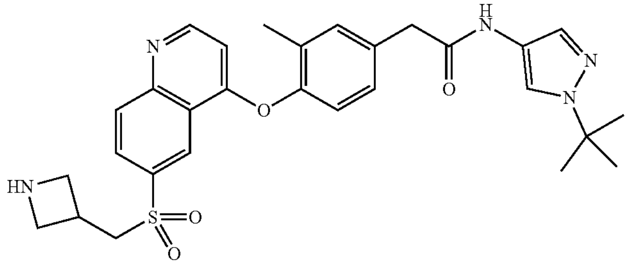 [SMILES: Cc1cc(CC(=O)Nc2cnn(C(C)(C)C)c2)ccc1Oc1ccnc2ccc(S(=O)(=O)CC3CNC3)cc12] |
| 333 | 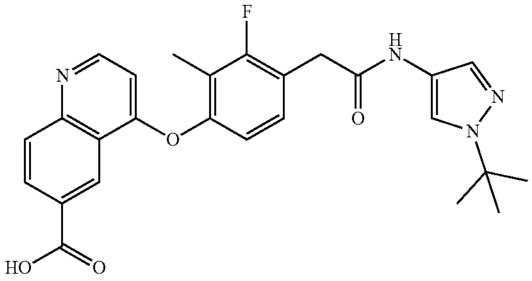 [SMILES: Cc1c(Oc2ccnc3ccc(C(=O)O)cc23)ccc(CC(=O)Nc2cnn(C(C)(C)C)c2)c1F] |
| 334 | 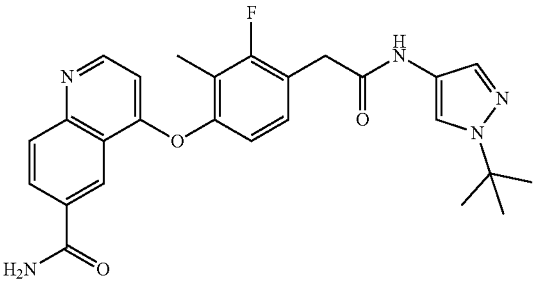 [SMILES: Cc1c(Oc2ccnc3ccc(C(N)=O)cc23)ccc(CC(=O)Nc2cnn(C(C)(C)C)c2)c1F] |
| 335 | 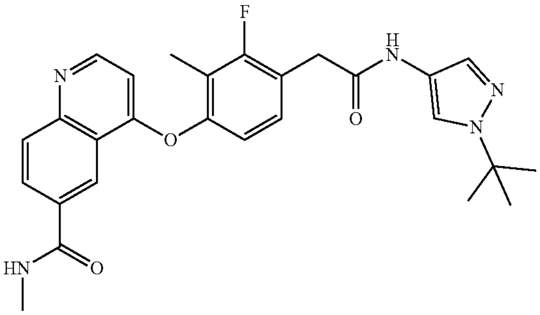 [SMILES: CNC(=O)c1ccc2nccc(Oc3ccc(CC(=O)Nc4cnn(C(C)(C)C)c4)c(F)c3C)c2c1] |

TABLE 1-continued
| Compound number | Structure |
|---|---|
| 336 | 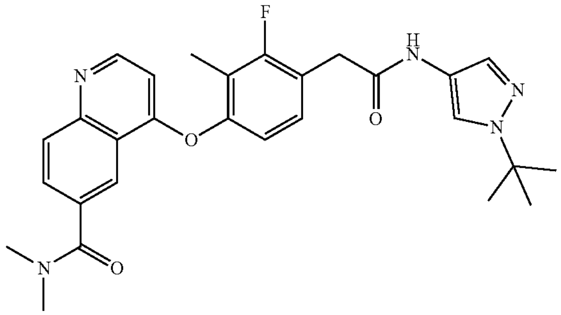 [SMILES: Cc1c(Oc2ccnc3ccc(C(=O)N(C)C)cc23)ccc(CC(=O)Nc2cnn(C(C)(C)C)c2)c1F] |
| 337 | 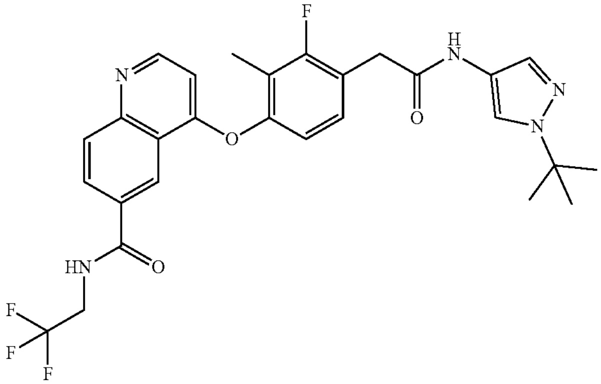 [SMILES: Cc1c(Oc2ccnc3ccc(C(=O)NCC(F)(F)F)cc23)ccc(CC(=O)Nc2cnn(C(C)(C)C)c2)c1F] |
| 338 | 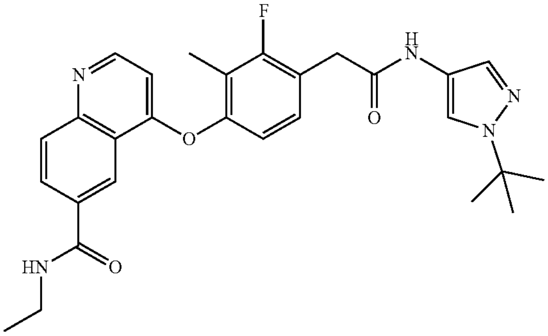 [SMILES: CCNC(=O)c1ccc2nccc(Oc3ccc(CC(=O)Nc4cnn(C(C)(C)C)c4)c(F)c3C)c2c1] |
| 339 | 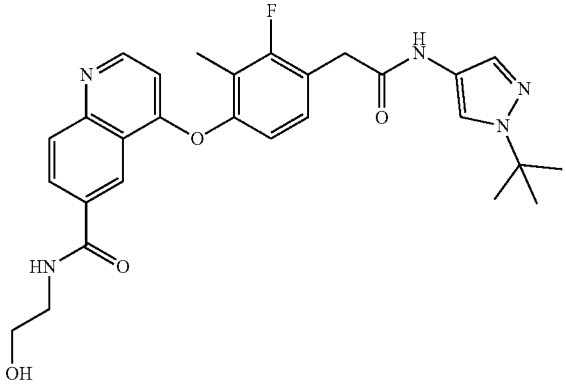 [SMILES: Cc1c(Oc2ccnc3ccc(C(=O)NCCO)cc23)ccc(CC(=O)Nc2cnn(C(C)(C)C)c2)c1F] |

TABLE 1-continued
| Compound number | Structure |
|---|---|
| 340 | 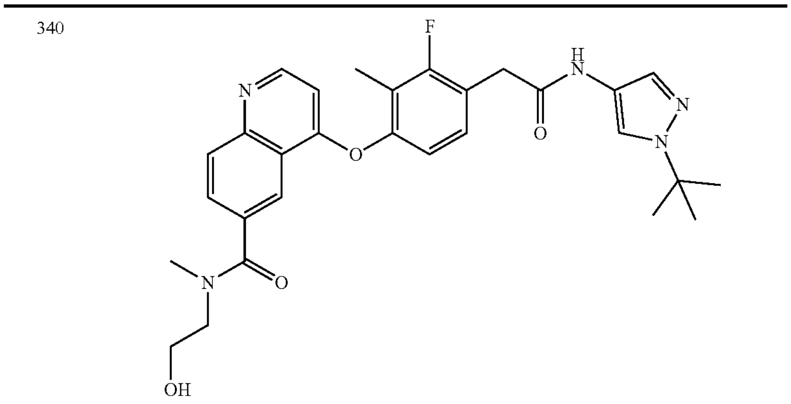 |
| 341 | 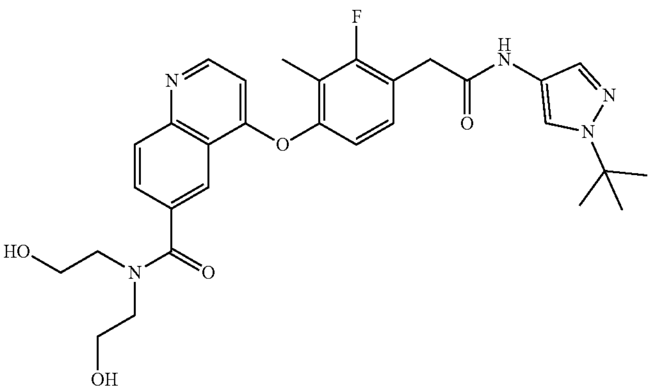 [SMILES: Cc1c(Oc2ccnc3ccc(C(=O)N(CCO)CCO)cc23)ccc(CC(=O)Nc2cnn(C(C)(C)C)c2)c1F] |
| 342 | 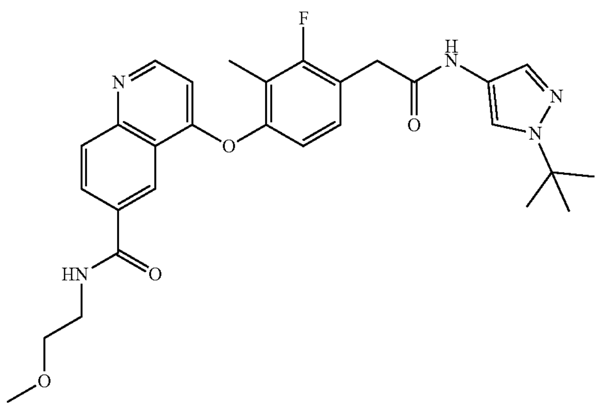 [SMILES: COCCNC(=O)c1ccc2nccc(Oc3ccc(CC(=O)Nc4cnn(C(C)(C)C)c4)c(F)c3C)c2c1] |
| 343 | 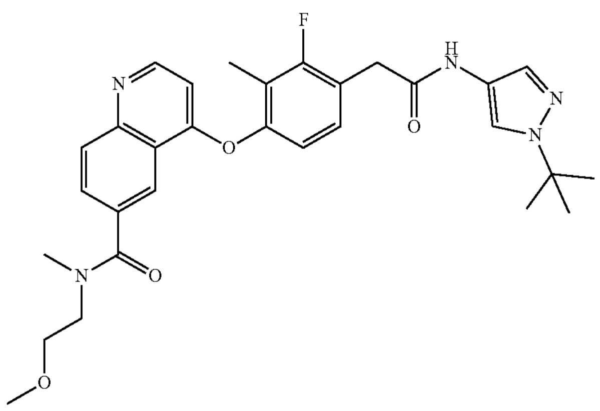 [SMILES: COCCN(C)C(=O)c1ccc2nccc(Oc3ccc(CC(=O)Nc4cnn(C(C)(C)C)c4)c(F)c3C)c2c1] |

TABLE 1-continued
| Compound number | Structure |
|---|---|
| 344 | 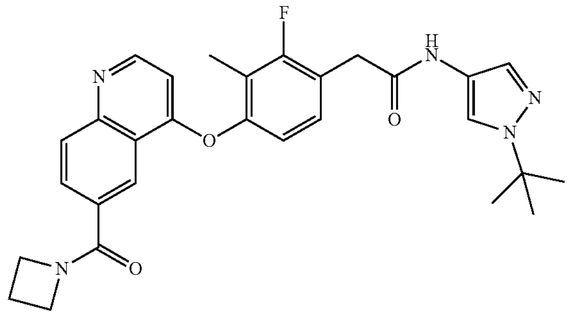 [SMILES: Cc1c(Oc2ccnc3ccc(C(=O)N4CCC4)cc23)ccc(CC(=O)Nc2cnn(C(C)(C)C)c2)c1F] |
| 345 | 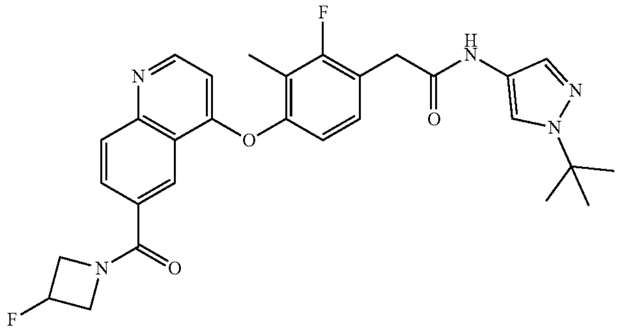 [SMILES: Cc1c(Oc2ccnc3ccc(C(=O)N4CC(F)C4)cc23)ccc(CC(=O)Nc2cnn(C(C)(C)C)c2)c1F] |
| 346 | 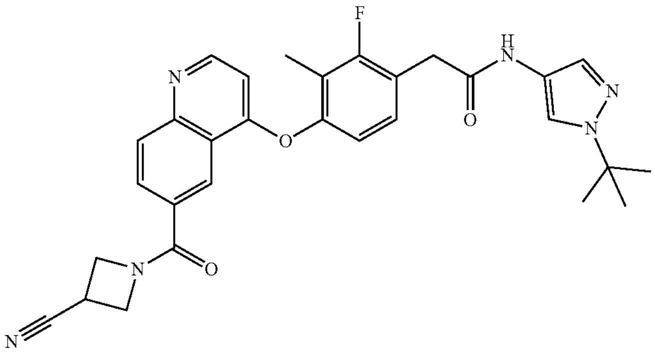 [SMILES: Cc1c(Oc2ccnc3ccc(C(=O)N4CC(C#N)C4)cc23)ccc(CC(=O)Nc2cnn(C(C)(C)C)c2)c1F] |
| 347 | 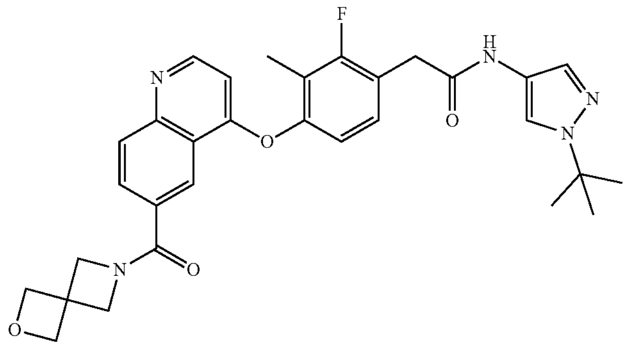 [SMILES: Cc1c(Oc2ccnc3ccc(C(=O)N4CC5(COC5)C4)cc23)ccc(CC(=O)Nc2cnn(C(C)(C)C)c2)c1F] |

TABLE 1-continued
| Compound number | Structure |
|---|---|
| 348 | 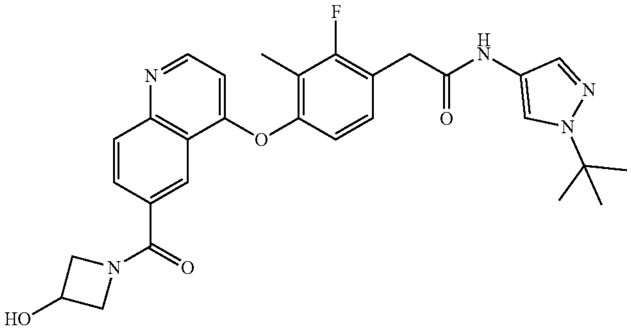 [SMILES: Cc1c(Oc2ccnc3ccc(C(=O)N4CC(O)C4)cc23)ccc(CC(=O)Nc2cnn(C(C)(C)C)c2)c1F] |
| 349 | 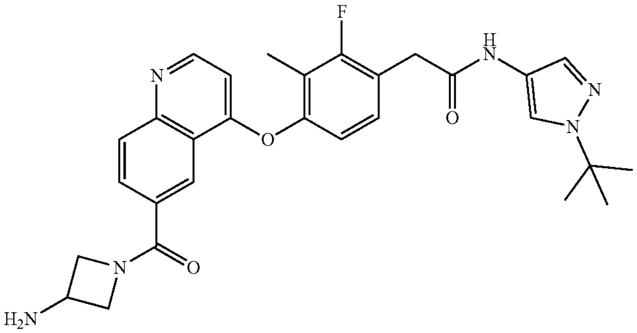 [SMILES: Cc1c(Oc2ccnc3ccc(C(=O)N4CC(N)C4)cc23)ccc(CC(=O)Nc2cnn(C(C)(C)C)c2)c1F] |
| 350 | 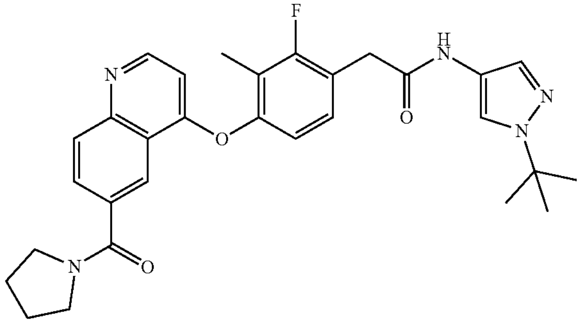 [SMILES: Cc1c(Oc2ccnc3ccc(C(=O)N4CCCC4)cc23)ccc(CC(=O)Nc2cnn(C(C)(C)C)c2)c1F] |
| 351 | 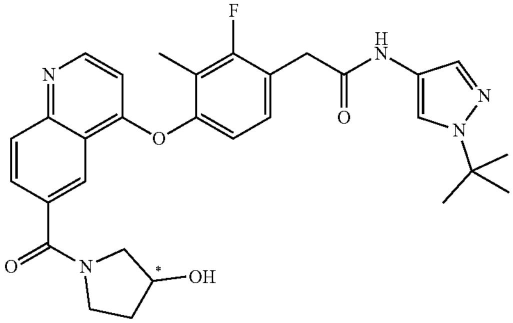 [SMILES: Cc1c(Oc2ccnc3ccc(C(=O)N4CCC(O)C4)cc23)ccc(CC(=O)Nc2cnn(C(C)(C)C)c2)c1F] enantiomer 1 |

TABLE 1-continued
| Compound number | Structure |
|---|---|
| 352 | 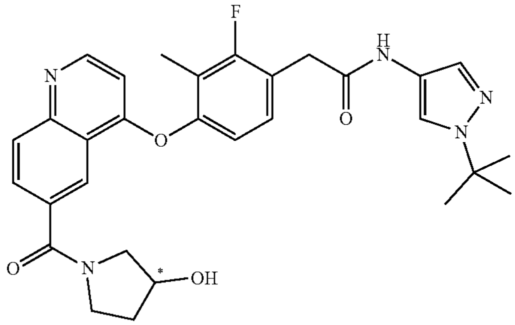 [SMILES: Cc1c(Oc2ccnc3ccc(C(=O)N4CCC(O)C4)cc23)ccc(CC(=O)Nc2cnn(C(C)(C)C)c2)c1F] enantiomer 2 |
| 353 | 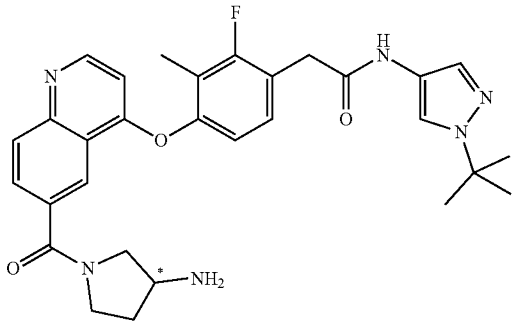 enantiomer 1 |
| 354 | 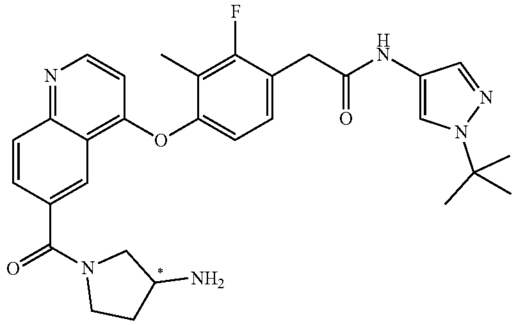 [SMILES: Cc1c(Oc2ccnc3ccc(C(=O)N4CCC(N)C4)cc23)ccc(CC(=O)Nc2cnn(C(C)(C)C)c2)c1F] enantiomer 2 |
| 355 | 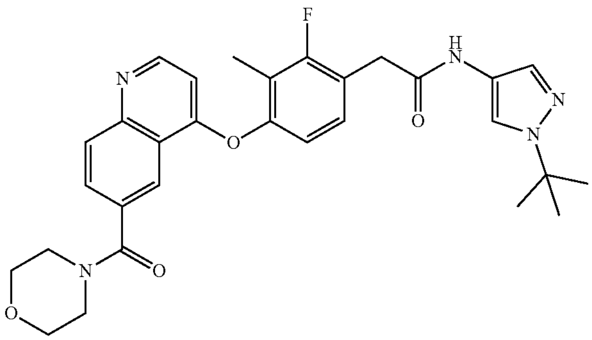 [SMILES: Cc1c(Oc2ccnc3ccc(C(=O)N4CCOCC4)cc23)ccc(CC(=O)Nc2cnn(C(C)(C)C)c2)c1F] |

TABLE 1-continued
| Compound number | Structure |
| --- | --- |
| 356 | 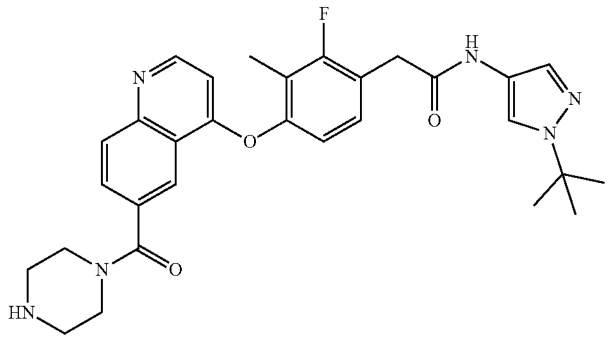 [SMILES: Cc1c(Oc2ccnc3ccc(C(=O)N4CCNCC4)cc23)ccc(CC(=O)Nc2cnn(C(C)(C)C)c2)c1F] |
| 357 | 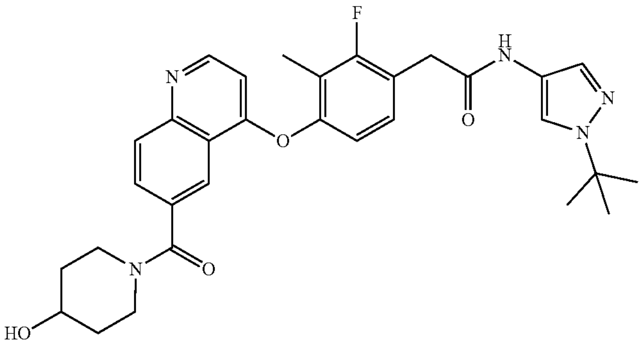 [SMILES: Cc1c(Oc2ccnc3ccc(C(=O)N4CCC(O)CC4)cc23)ccc(CC(=O)Nc2cnn(C(C)(C)C)c2)c1F] |
| 358 | 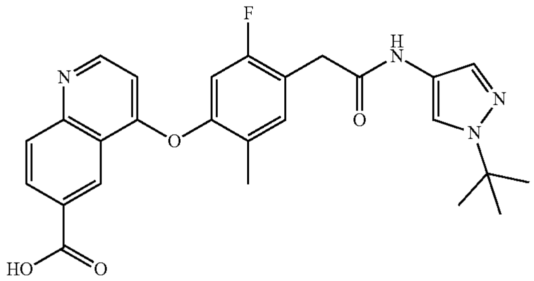 [SMILES: Cc1cc(CC(=O)Nc2cnn(C(C)(C)C)c2)c(F)cc1Oc1ccnc2ccc(C(=O)O)cc12] |
| 359 | 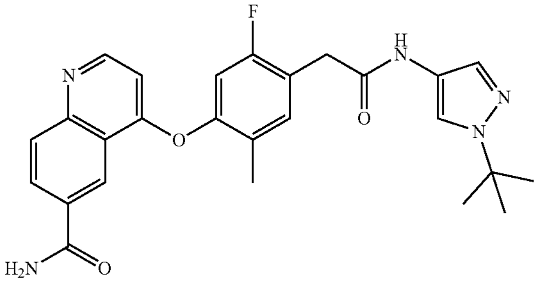 |
| 360 | 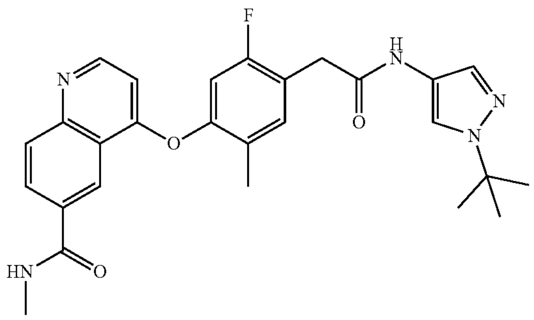 [SMILES: CNC(=O)c1ccc2nccc(Oc3cc(F)c(CC(=O)Nc4cnn(C(C)(C)C)c4)cc3C)c2c1] |

TABLE 1-continued
| Compound number | Structure |
|---|---|
| 361 | 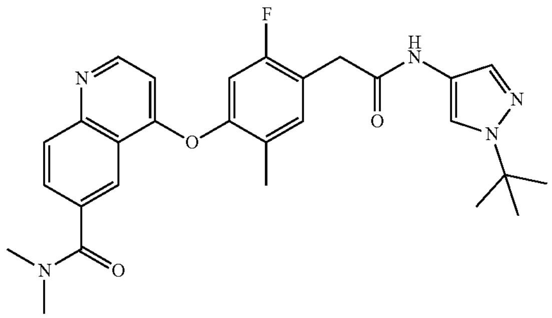 [SMILES: Cc1cc(CC(=O)Nc2cnn(C(C)(C)C)c2)c(F)cc1Oc1ccnc2ccc(C(=O)N(C)C)cc12] |
| 362 | 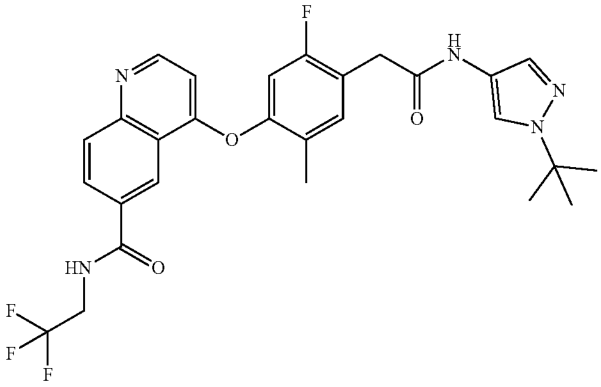 [SMILES: Cc1cc(CC(=O)Nc2cnn(C(C)(C)C)c2)c(F)cc1Oc1ccnc2ccc(C(=O)NCC(F)(F)F)cc12] |
| 363 | 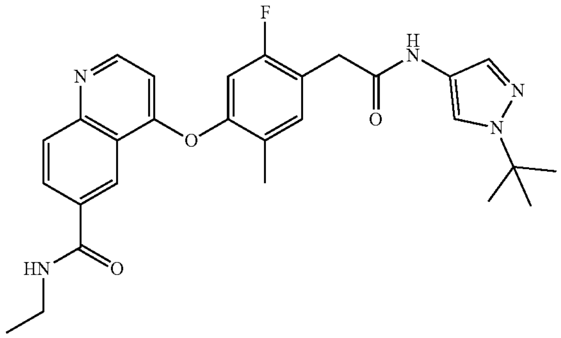 [SMILES: CCNC(=O)c1ccc2nccc(Oc3cc(F)c(CC(=O)Nc4cnn(C(C)(C)C)c4)cc3C)c2c1] |
| 364 | 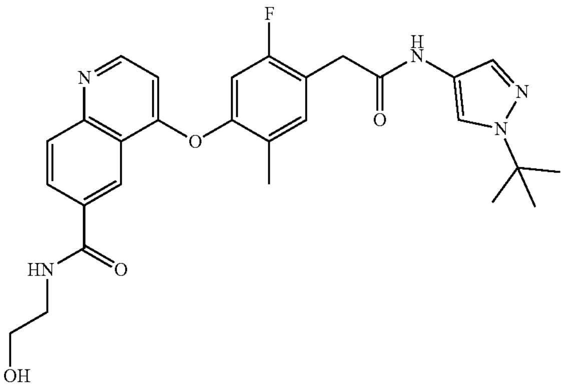 [SMILES: Cc1cc(CC(=O)Nc2cnn(C(C)(C)C)c2)c(F)cc1Oc1ccnc2ccc(C(=O)NCCO)cc12] |

TABLE 1-continued
| Compound number | Structure |
|---|---|
| 365 | 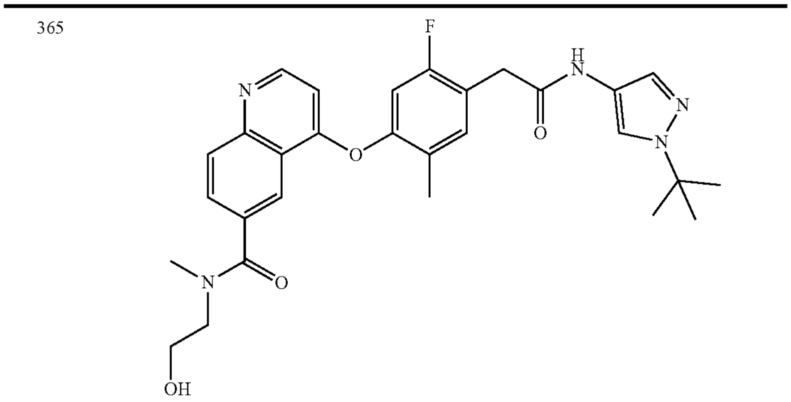 |
| 366 | 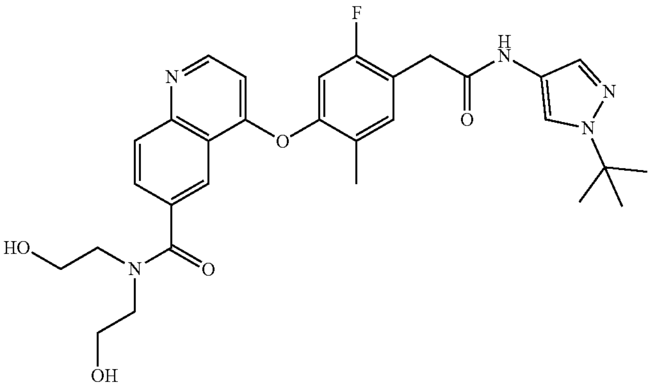 [SMILES: Cc1cc(CC(=O)Nc2cnn(C(C)(C)C)c2)c(F)cc1Oc1ccnc2ccc(C(=O)N(CCO)CCO)cc12] |
| 367 | 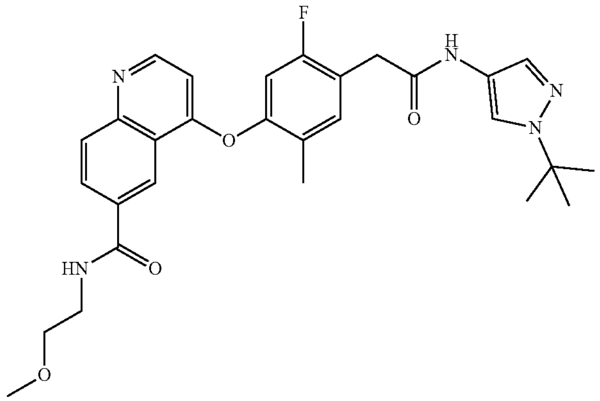 [SMILES: COCCNC(=O)c1ccc2nccc(Oc3cc(F)c(CC(=O)Nc4cnn(C(C)(C)C)c4)cc3C)c2c1] |
| 368 | 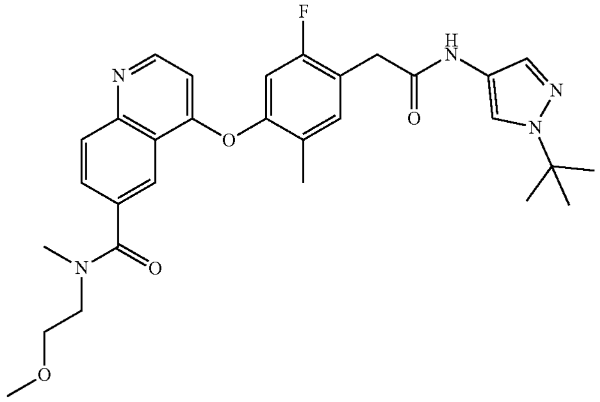 [SMILES: COCCN(C)C(=O)c1ccc2nccc(Oc3cc(F)c(CC(=O)Nc4cnn(C(C)(C)C)c4)cc3C)c2c1] |

TABLE 1-continued
| Compound number | Structure |
| --- | --- |
| 369 | 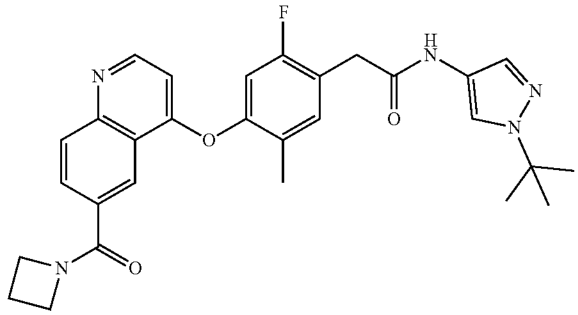 [SMILES: Cc1cc(CC(=O)Nc2cnn(C(C)(C)C)c2)c(F)cc1Oc1ccnc2ccc(C(=O)N3CCC3)cc12] |
| 370 | 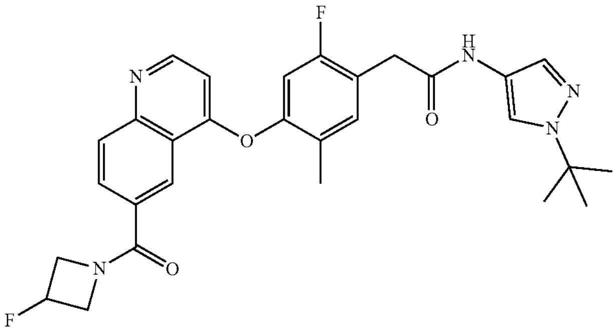 [SMILES: Cc1cc(CC(=O)Nc2cnn(C(C)(C)C)c2)c(F)cc1Oc1ccnc2ccc(C(=O)N3CC(F)C3)cc12] |
| 371 | 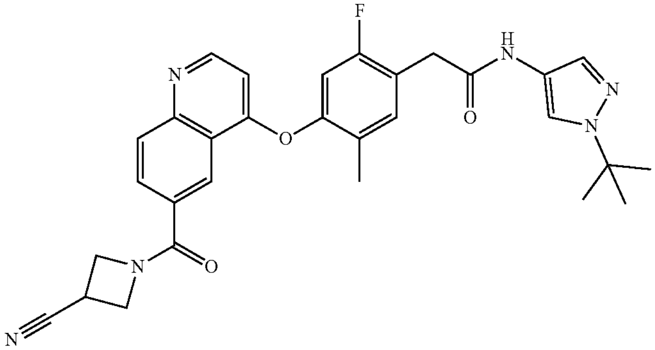 [SMILES: Cc1cc(CC(=O)Nc2cnn(C(C)(C)C)c2)c(F)cc1Oc1ccnc2ccc(C(=O)N3CC(C#N)C3)cc12] |
| 372 | 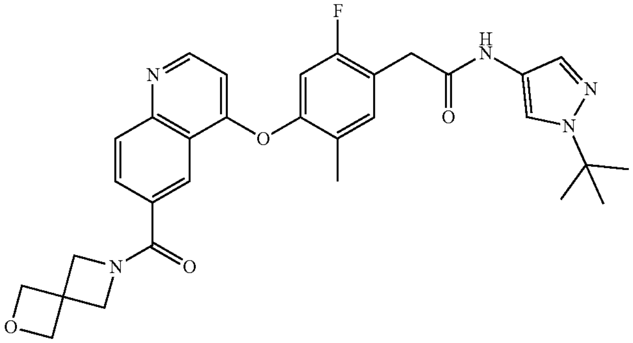 [SMILES: Cc1cc(CC(=O)Nc2cnn(C(C)(C)C)c2)c(F)cc1Oc1ccnc2ccc(C(=O)N3CC4(COC4)C3)cc12] |

TABLE 1-continued
| Compound number | Structure |
| --- | --- |
| 373 | 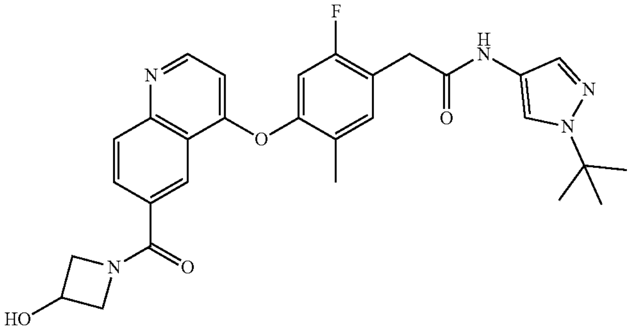 [SMILES: Cc1cc(CC(=O)Nc2cnn(C(C)(C)C)c2)c(F)cc1Oc1ccnc2ccc(C(=O)N3CC(O)C3)cc12] |
| 374 | 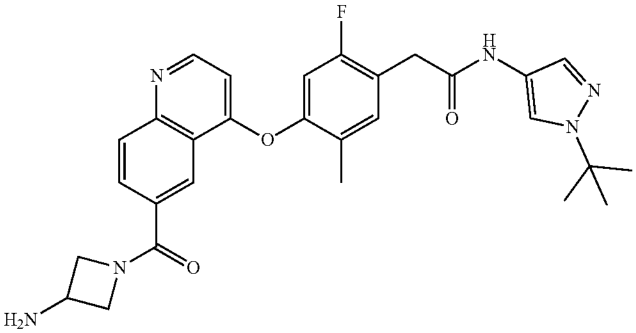 [SMILES: Cc1cc(CC(=O)Nc2cnn(C(C)(C)C)c2)c(F)cc1Oc1ccnc2ccc(C(=O)N3CC(N)C3)cc12] |
| 375 | 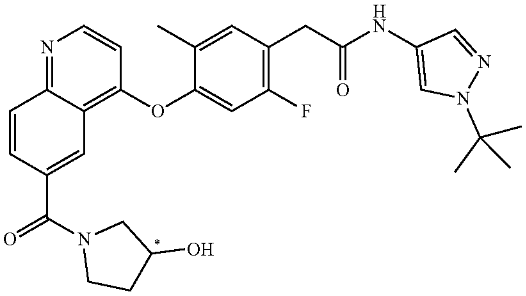 [SMILES: Cc1cc(CC(=O)Nc2cnn(C(C)(C)C)c2)c(F)cc1Oc1ccnc2ccc(C(=O)N3CCC(O)C3)cc12] enantiomer 1 |
| 376 | 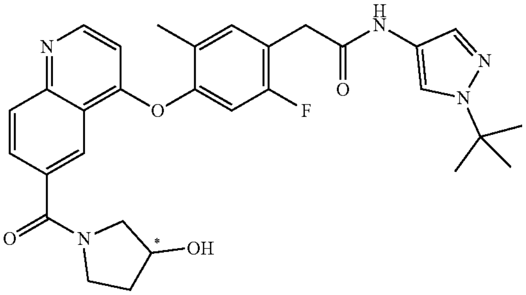 [SMILES: Cc1cc(CC(=O)Nc2cnn(C(C)(C)C)c2)c(F)cc1Oc1ccnc2ccc(C(=O)N3CCC(O)C3)cc12] enantiomer 2 |

TABLE 1-continued
| Compound number | Structure |
|---|---|
| 377 | 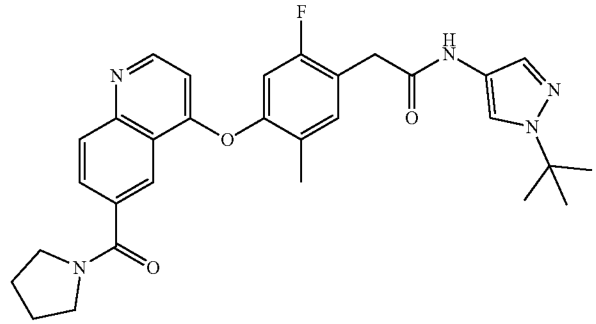 [SMILES: Cc1cc(CC(=O)Nc2cnn(C(C)(C)C)c2)c(F)cc1Oc1ccnc2ccc(C(=O)N3CCCC3)cc12] |
| 378 | 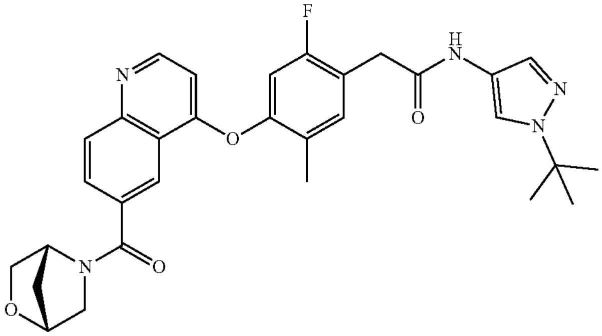 [SMILES: Cc1cc(CC(=O)Nc2cnn(C(C)(C)C)c2)c(F)cc1Oc1ccnc2ccc(C(=O)N3C[C@H]4C[C@@H]3CO4)cc12] |
| 379 | 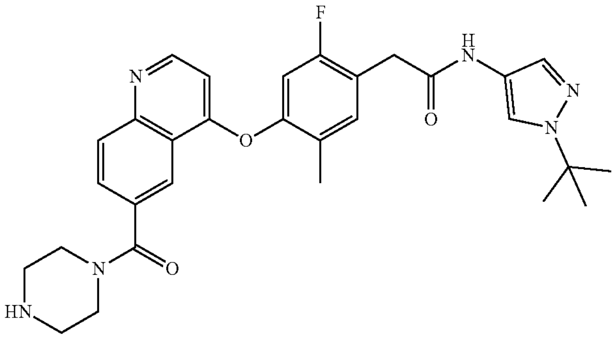 [SMILES: Cc1cc(CC(=O)Nc2cnn(C(C)(C)C)c2)c(F)cc1Oc1ccnc2ccc(C(=O)N3CCNCC3)cc12] |
| 380 | 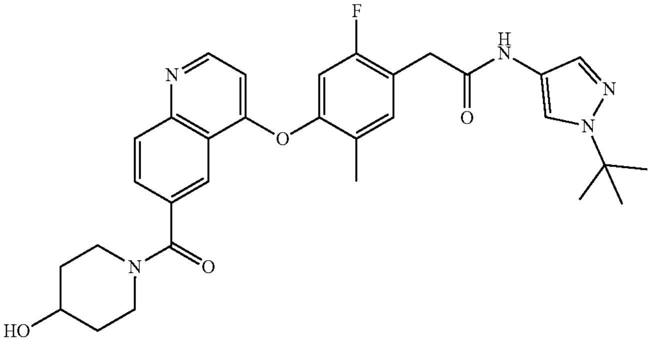 [SMILES: Cc1cc(CC(=O)Nc2cnn(C(C)(C)C)c2)c(F)cc1Oc1ccnc2ccc(C(=O)N3CCC(O)CC3)cc12] |

TABLE 1-continued
| Compound number | Structure |
| --- | --- |
| 381 | 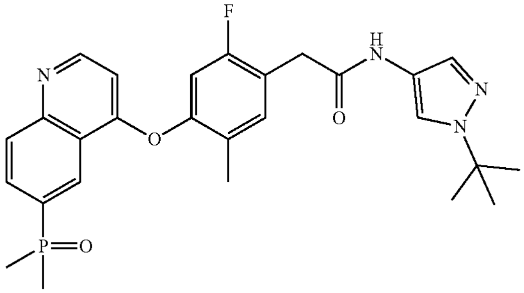 [SMILES: Cc1cc(CC(=O)Nc2cnn(C(C)(C)C)c2)c(F)cc1Oc1ccnc2ccc(P(C)(C)=O)cc12] |
| 382 | 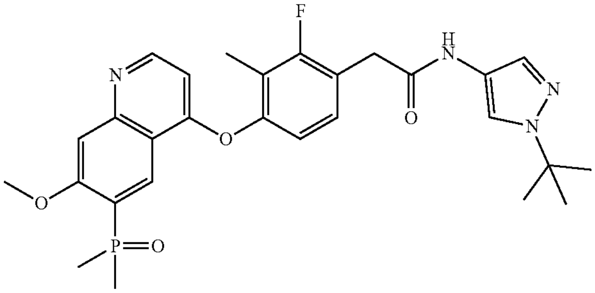 [SMILES: COc1cc2nccc(Oc3ccc(CC(=O)Nc4cnn(C(C)(C)C)c4)c(F)c3C)c2cc1P(C)(C)=O] |
| 383 | 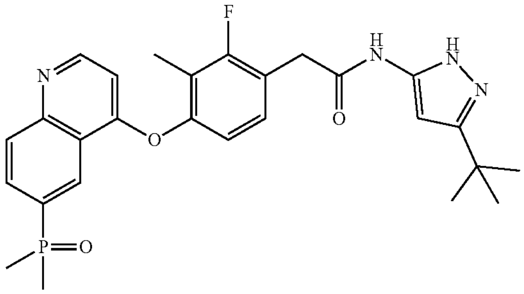 [SMILES: Cc1c(Oc2ccnc3ccc(P(C)(C)=O)cc23)ccc(CC(=O)Nc2cc(C(C)(C)C)n[nH]2)c1F] |
| 384 | 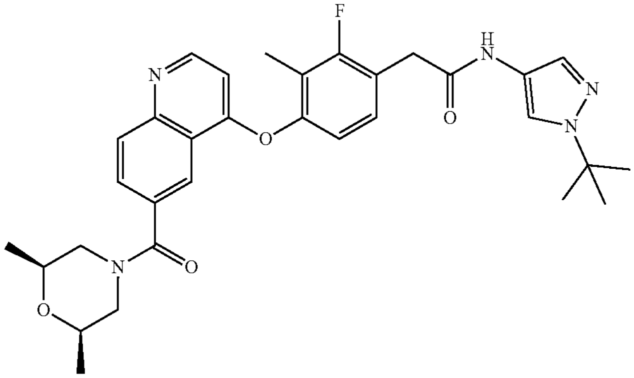 [SMILES: Cc1c(Oc2ccnc3ccc(C(=O)N4C[C@@H](C)O[C@@H](C)C4)cc23)ccc(CC(=O)Nc2cnn(C(C)(C)C)c2)c1F] |

TABLE 1-continued
| Compound number | Structure |
|---|---|
| 385 | 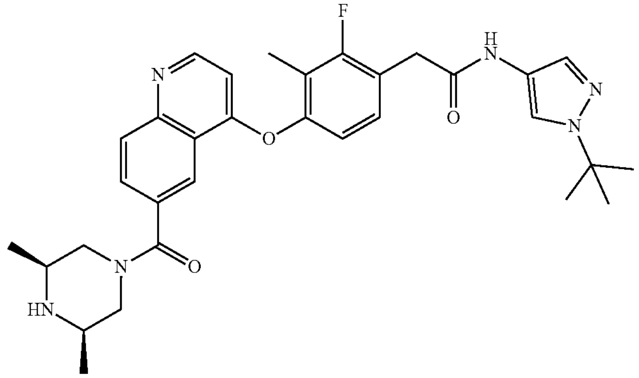 [SMILES: Cc1c(Oc2ccnc3ccc(C(=O)N4C[C@@H](C)N[C@@H](C)C4)cc23)ccc(CC(=O)Nc2cnn(C(C)(C)C)c2)c1F] |
| 386 | 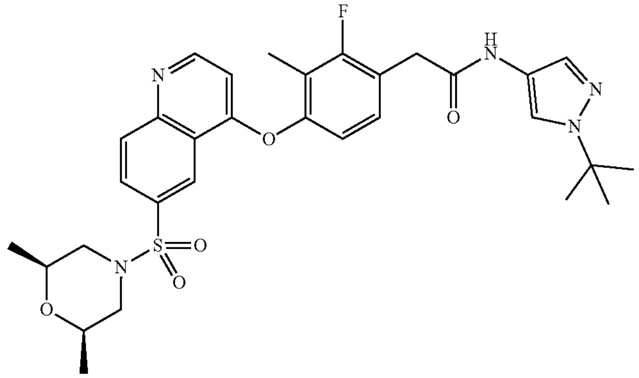 [SMILES: Cc1c(Oc2ccnc3ccc(S(=O)(=O)N4C[C@@H](C)O[C@@H](C)C4)cc23)ccc(CC(=O)Nc2cnn(C(C)(C)C)c2)c1F] |
| 387 | 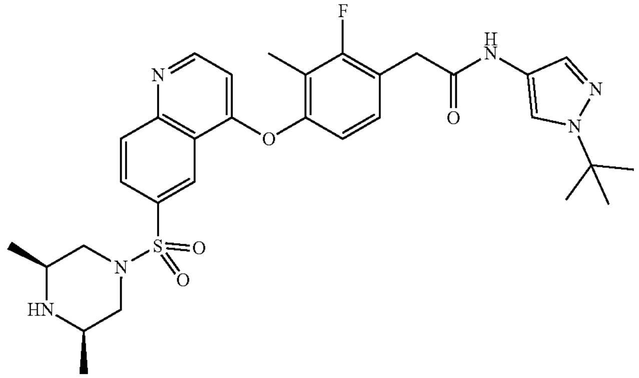 [SMILES: Cc1c(Oc2ccnc3ccc(S(=O)(=O)N4C[C@@H](C)N[C@@H](C)C4)cc23)ccc(CC(=O)Nc2cnn(C(C)(C)C)c2)c1F] |
| 388 | 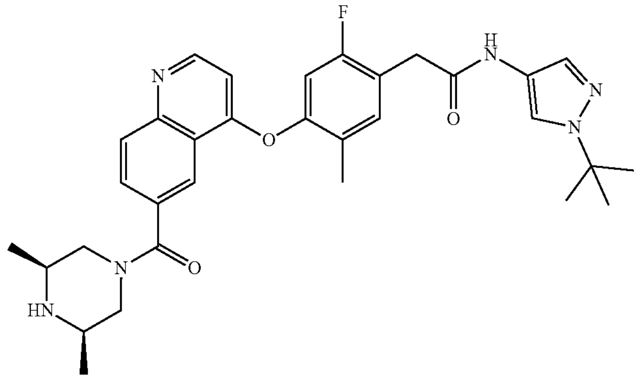 [SMILES: Cc1cc(CC(=O)Nc2cnn(C(C)(C)C)c2)c(F)cc1Oc1ccnc2ccc(C(=O)N3C[C@@H](C)N[C@@H](C)C3)cc12] |

TABLE 1-continued
| Compound number | Structure |
|---|---|
| 389 | 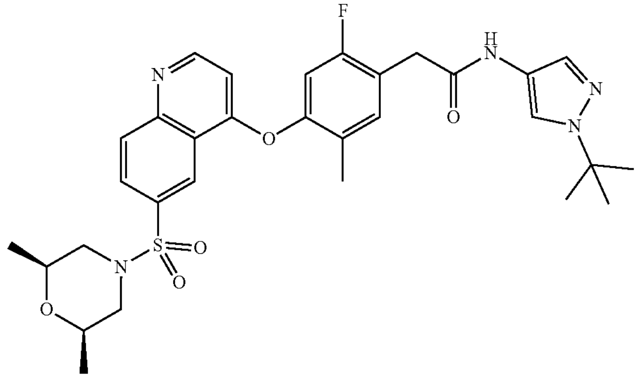 [SMILES: Cc1cc(CC(=O)Nc2cnn(C(C)(C)C)c2)c(F)cc1Oc1ccnc2ccc(S(=O)(=O)N3C[C@@H](C)O[C@@H](C)C3)cc12] |
| 390 | 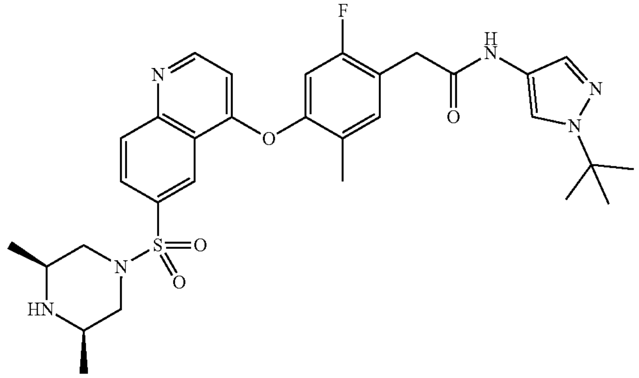 [SMILES: Cc1cc(CC(=O)Nc2cnn(C(C)(C)C)c2)c(F)cc1Oc1ccnc2ccc(S(=O)(=O)N3C[C@@H](C)N[C@@H](C)C3)cc12] |
| 391 | 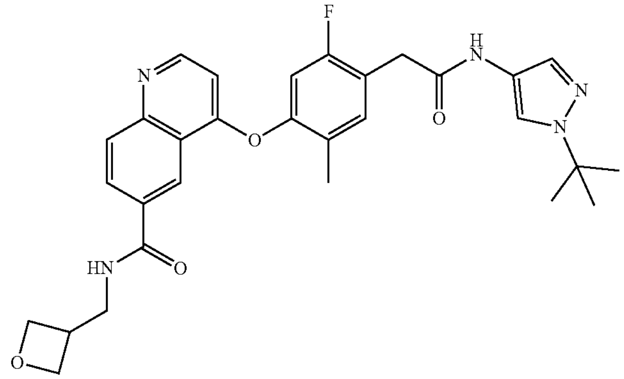 [SMILES: Cc1cc(CC(=O)Nc2cnn(C(C)(C)C)c2)c(F)cc1Oc1ccnc2ccc(C(=O)NCC3COC3)cc12] |
| 392 | 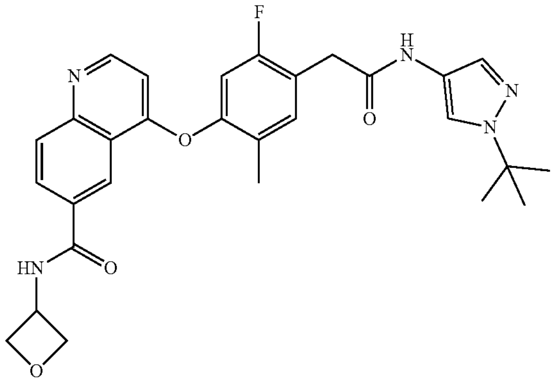 [SMILES: Cc1cc(CC(=O)Nc2cnn(C(C)(C)C)c2)c(F)cc1Oc1ccnc2ccc(C(=O)NC3COC3)cc12] |

TABLE 1-continued
| Compound number | Structure |
|---|---|
| 393 | 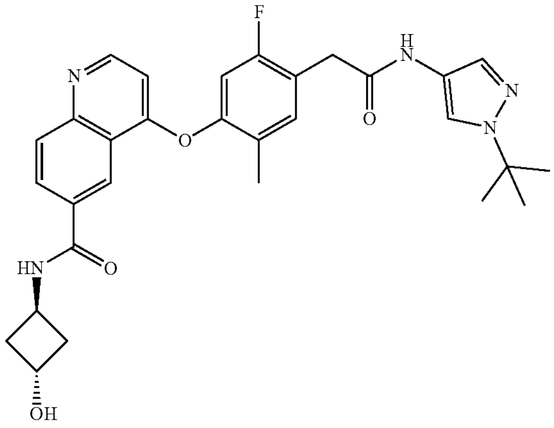 [SMILES: Cc1cc(CC(=O)Nc2cnn(C(C)(C)C)c2)c(F)cc1Oc1ccnc2ccc(C(=O)N[C@H]3C[C@H](O)C3)cc12] |
| 394 | 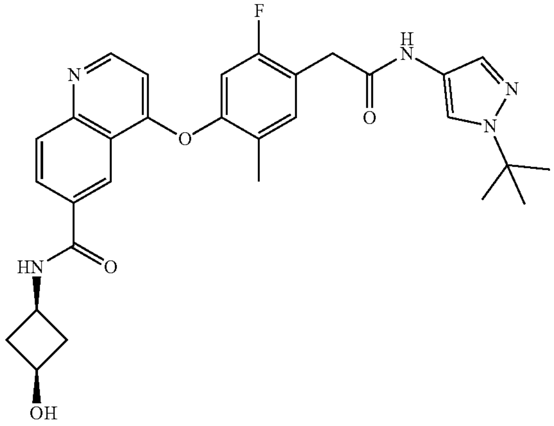 [SMILES: Cc1cc(CC(=O)Nc2cnn(C(C)(C)C)c2)c(F)cc1Oc1ccnc2ccc(C(=O)N[C@H]3C[C@@H](O)C3)cc12] |
| 395 | 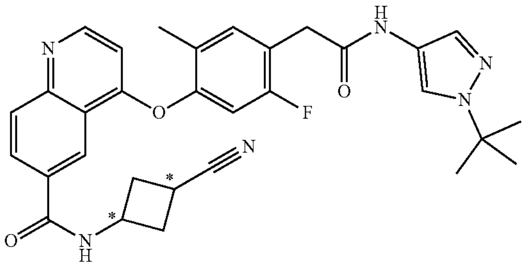 [SMILES: Cc1cc(CC(=O)Nc2cnn(C(C)(C)C)c2)c(F)cc1Oc1ccnc2ccc(C(=O)NC3CC(C#N)C3)cc12]<br>diastereomer 2 |
| 396 | 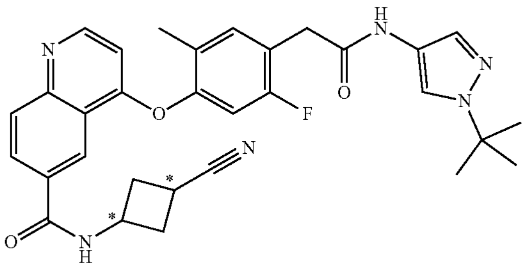 [SMILES: Cc1cc(CC(=O)Nc2cnn(C(C)(C)C)c2)c(F)cc1Oc1ccnc2ccc(C(=O)NC3CC(C#N)C3)cc12]<br>diastereomer 1 |

TABLE 1-continued
| Compound number | Structure |
|---|---|
| 397 | 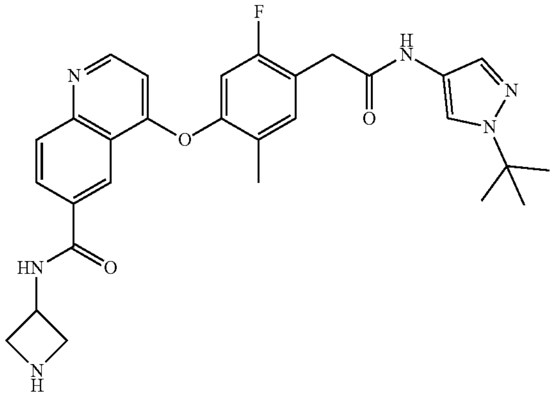 [SMILES: Cc1cc(CC(=O)Nc2cnn(C(C)(C)C)c2)c(F)cc1Oc1ccnc2ccc(C(=O)NC3CNC3)cc12] |
| 398 | 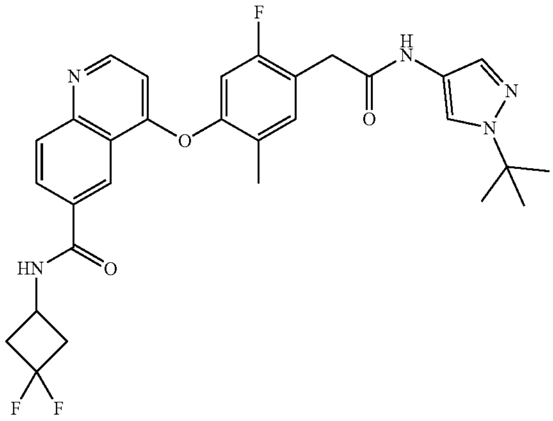 [SMILES: Cc1cc(CC(=O)Nc2cnn(C(C)(C)C)c2)c(F)cc1Oc1ccnc2ccc(C(=O)NC3CC(F)(F)C3)cc12] |
| 399 | 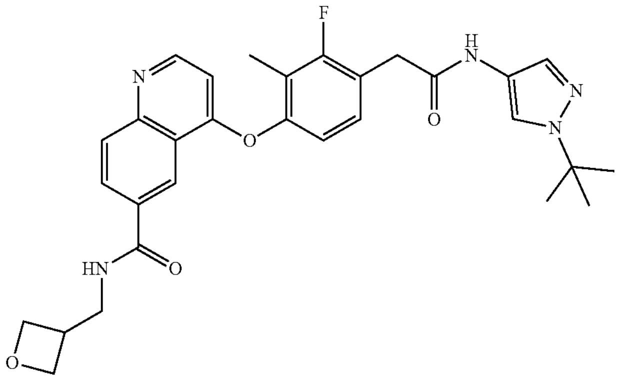 [SMILES: Cc1c(Oc2ccnc3ccc(C(=O)NCC4COC4)cc23)ccc(CC(=O)Nc2cnn(C(C)(C)C)c2)c1F] |
| 400 | 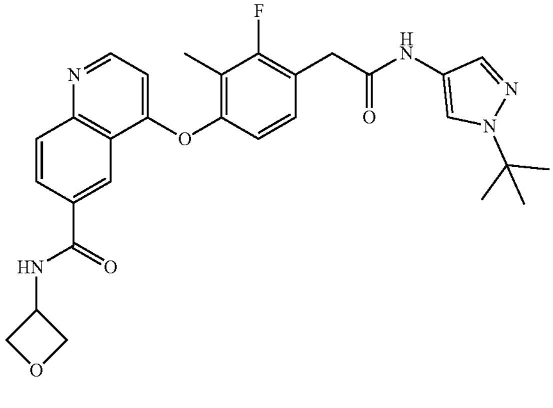 [SMILES: Cc1c(Oc2ccnc3ccc(C(=O)NC4COC4)cc23)ccc(CC(=O)Nc2cnn(C(C)(C)C)c2)c1F] |

TABLE 1-continued
| Compound number | Structure |
|---|---|
| 401 | 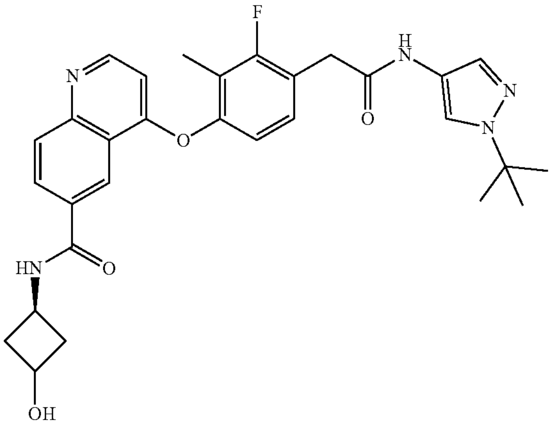 |
| 402 | 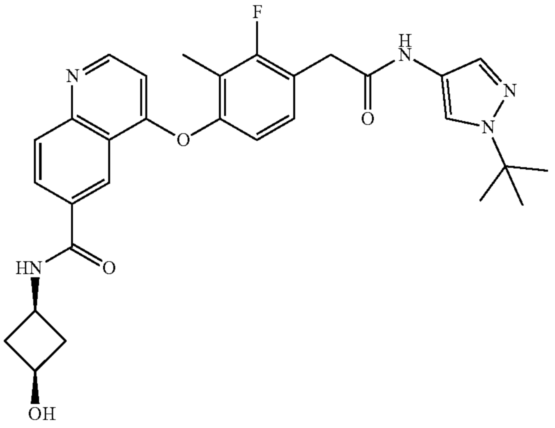 [SMILES: Cc1c(Oc2ccnc3ccc(C(=O)N[C@H]4C[C@@H](O)C4)cc23)ccc(CC(=O)Nc2cnn(C(C)(C)C)c2)c1F] |
| 403 | 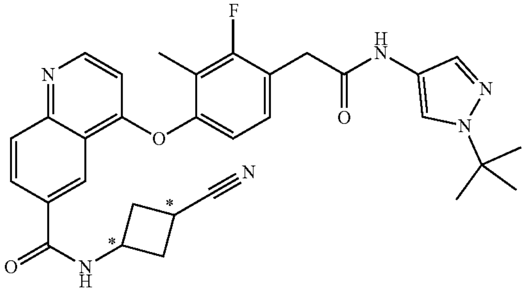 [SMILES: Cc1c(Oc2ccnc3ccc(C(=O)NC4CC(C#N)C4)cc23)ccc(CC(=O)Nc2cnn(C(C)(C)C)c2)c1F] diastereomer 1 |
| 404 | 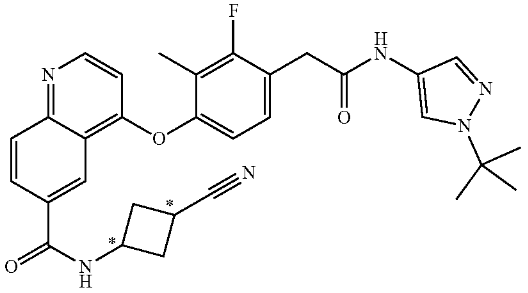 [SMILES: Cc1c(Oc2ccnc3ccc(C(=O)NC4CC(C#N)C4)cc23)ccc(CC(=O)Nc2cnn(C(C)(C)C)c2)c1F] diastereomer 2 |

TABLE 1-continued
| Compound number | Structure |
|---|---|
| 405 | 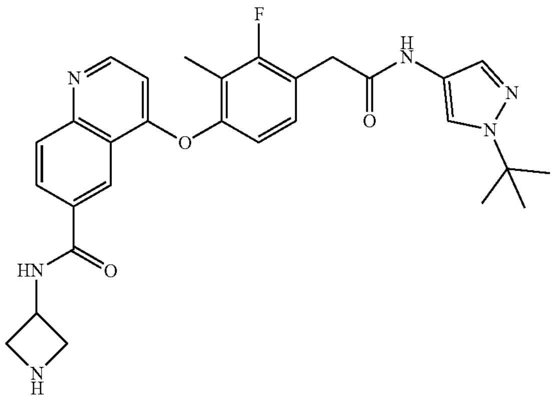 [SMILES: Cc1c(Oc2ccnc3ccc(C(=O)NC4CNC4)cc23)ccc(CC(=O)Nc2cnn(C(C)(C)C)c2)c1F] |
| 406 | 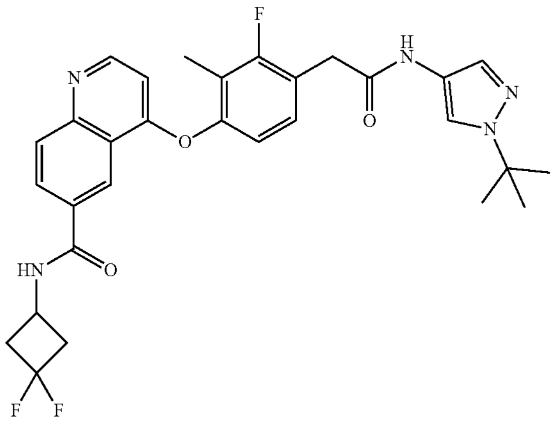 [SMILES: Cc1c(Oc2ccnc3ccc(C(=O)NC4CC(F)(F)C4)cc23)ccc(CC(=O)Nc2cnn(C(C)(C)C)c2)c1F] |
| 407 | 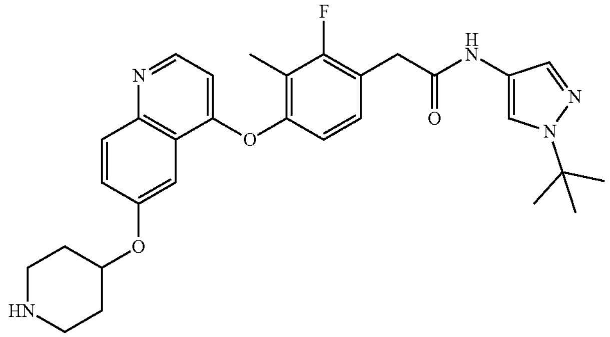 |
| 408 | 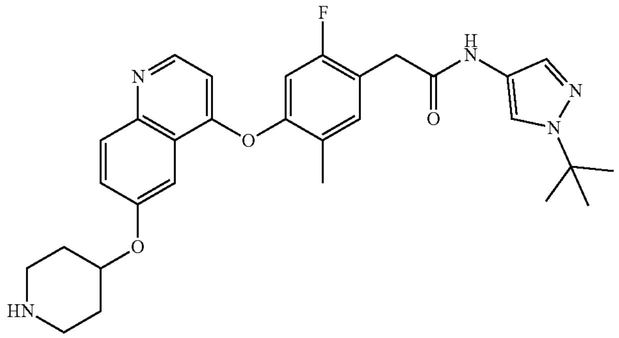 [SMILES: Cc1cc(CC(=O)Nc2cnn(C(C)(C)C)c2)c(F)cc1Oc1ccnc2ccc(OC3CCNCC3)cc12] |

TABLE 1-continued
| Compound number | Structure |
| --- | --- |
| 409 | 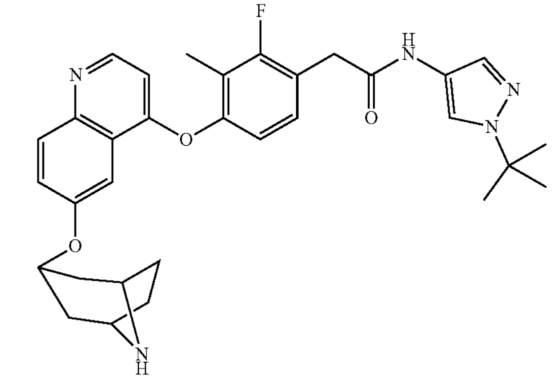 [SMILES: Cc1c(Oc2ccnc3ccc(OC4CC5CCC(C4)N5)cc23)ccc(CC(=O)Nc2cnn(C(C)(C)C)c2)c1F] |
| 410 | 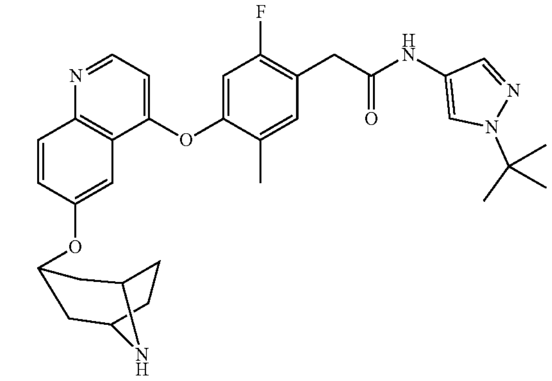 [SMILES: Cc1cc(CC(=O)Nc2cnn(C(C)(C)C)c2)c(F)cc1Oc1ccnc2ccc(OC3CC4CCC(C3)N4)cc12] |
| 411 | 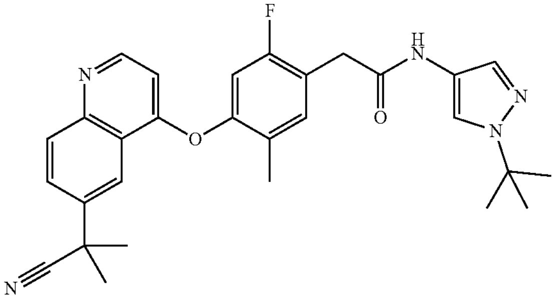 [SMILES: Cc1cc(CC(=O)Nc2cnn(C(C)(C)C)c2)c(F)cc1Oc1ccnc2ccc(C(C)(C)C#N)cc12] |
| 412 | 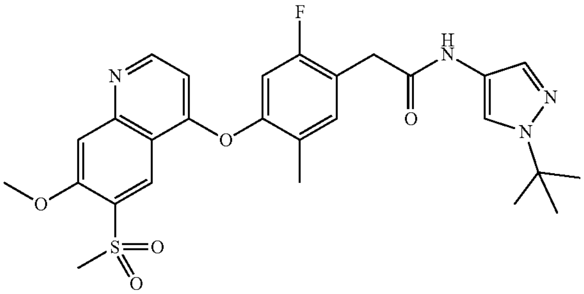 [SMILES: COc1cc2nccc(Oc3cc(F)c(CC(=O)Nc4cnn(C(C)(C)C)c4)cc3C)c2cc1S(C)(=O)=O] |

TABLE 1-continued
| Compound number | Structure |
|---|---|
| 413 | 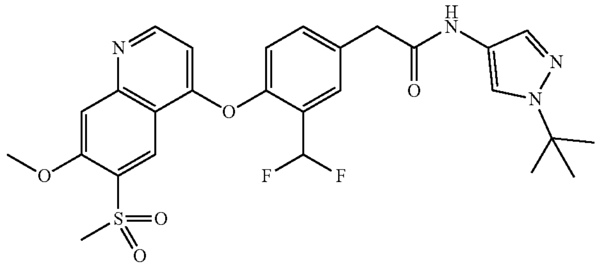 [SMILES: COc1cc2nccc(Oc3ccc(CC(=O)Nc4cnn(C(C)(C)C)c4)cc3C(F)F)c2cc1S(C)(=O)=O] |
| 414 | 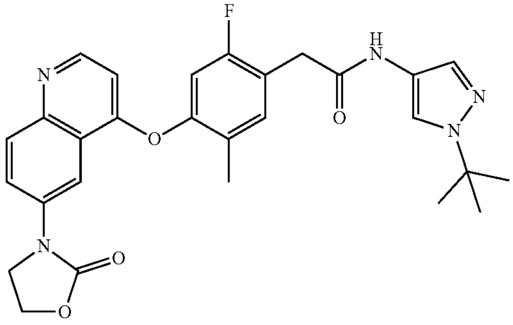 [SMILES: Cc1cc(CC(=O)Nc2cnn(C(C)(C)C)c2)c(F)cc1Oc1ccnc2ccc(N3CCOC3=O)cc12] |
| 415 | 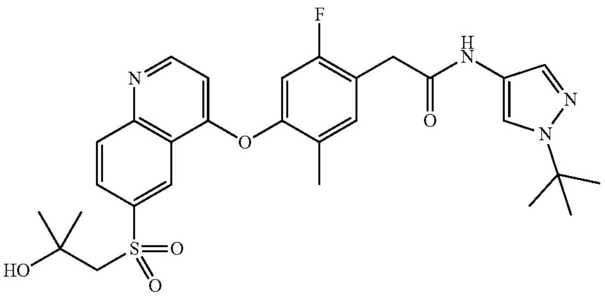 [SMILES: Cc1cc(CC(=O)Nc2cnn(C(C)(C)C)c2)c(F)cc1Oc1ccnc2ccc(S(=O)(=O)CC(C)(C)O)cc12] |
| 416 | 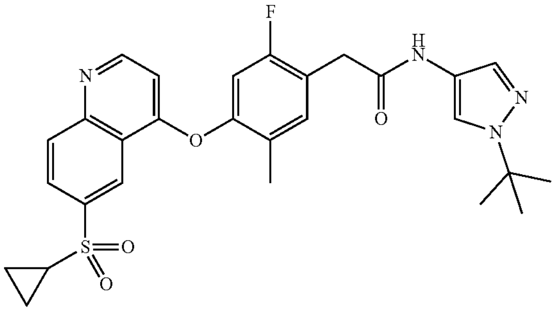 [SMILES: Cc1cc(CC(=O)Nc2cnn(C(C)(C)C)c2)c(F)cc1Oc1ccnc2ccc(S(=O)(=O)C3CC3)cc12] |
| 417 | 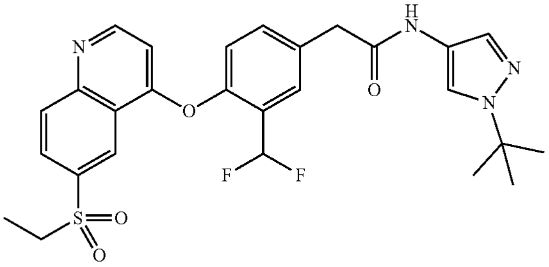 [SMILES: CCS(=O)(=O)c1ccc2nccc(Oc3ccc(CC(=O)Nc4cnn(C(C)(C)C)c4)cc3C(F)F)c2c1] |

TABLE 1-continued
| Compound number | Structure |
|---|---|
| 418 | 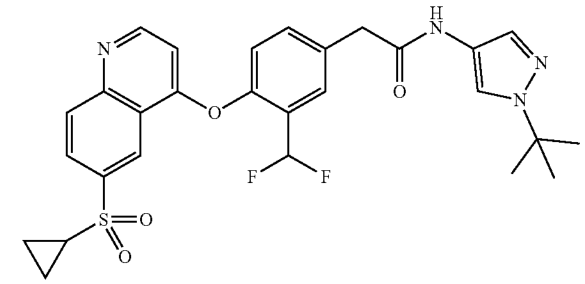 [SMILES: CC(C)(C)n1cc(NC(=O)Cc2ccc(Oc3ccnc4ccc(S(=O)(=O)C5CC5)cc34)c(C(F)F)c2)cn1] |
| 419 | 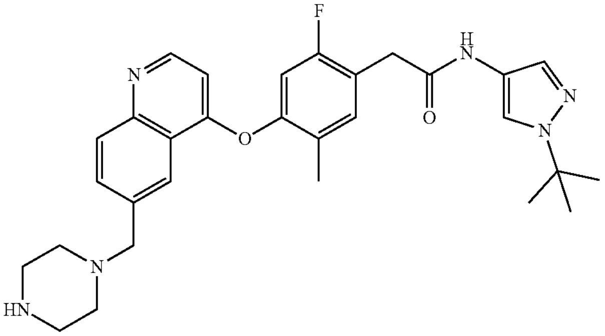 |
| 420 | 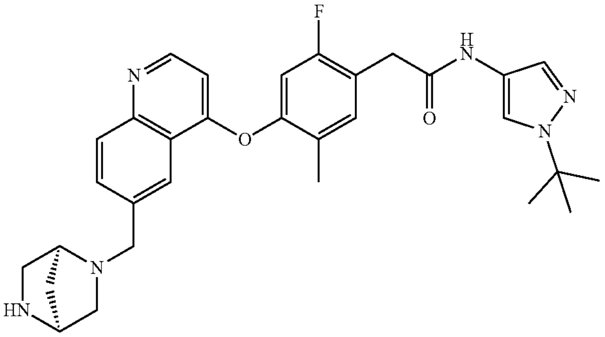 [SMILES: Cc1cc(CC(=O)Nc2cnn(C(C)(C)C)c2)c(F)cc1Oc1ccnc2ccc(CN3C[C@@H]4C[C@H]3CN4)cc12] |
| 421 | 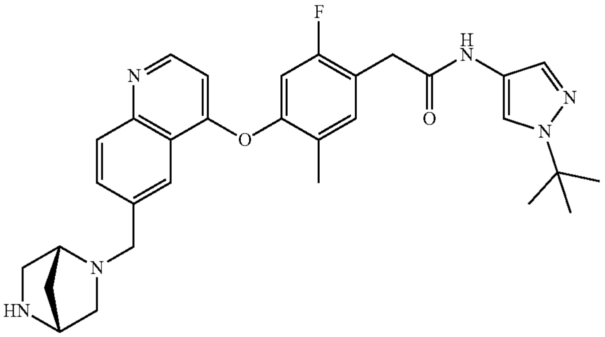 [SMILES: Cc1cc(CC(=O)Nc2cnn(C(C)(C)C)c2)c(F)cc1Oc1ccnc2ccc(CN3C[C@H]4C[C@@H]3CN4)cc12] |

TABLE 1-continued
| Compound number | Structure |
|---|---|
| 422 | 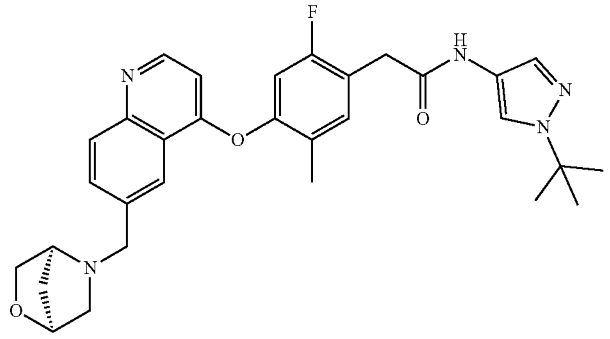 [SMILES: Cc1cc(CC(=O)Nc2cnn(C(C)(C)C)c2)c(F)cc1Oc1ccnc2ccc(CN3C[C@@H]4C[C@H]3CO4)cc12] |
| 423 | 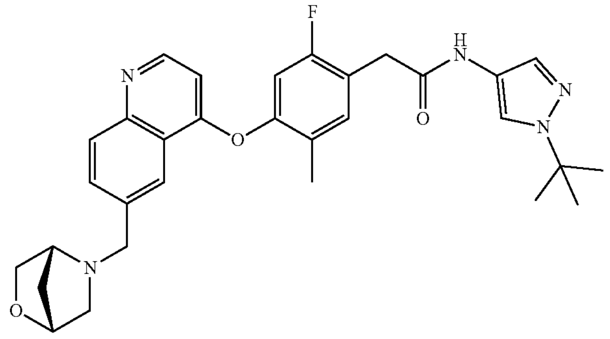 [SMILES: Cc1cc(CC(=O)Nc2cnn(C(C)(C)C)c2)c(F)cc1Oc1ccnc2ccc(CN3C[C@H]4C[C@@H]3CO4)cc12] |
| 424 | 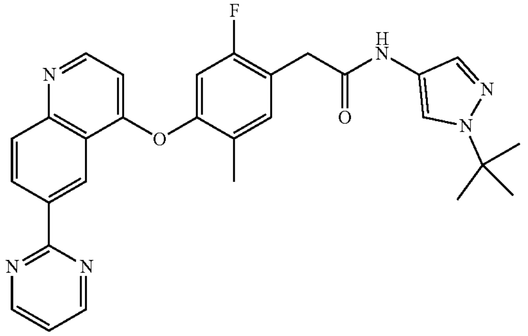 [SMILES: Cc1cc(CC(=O)Nc2cnn(C(C)(C)C)c2)c(F)cc1Oc1ccnc2ccc(-c3ncccn3)cc12] |
| 425 | 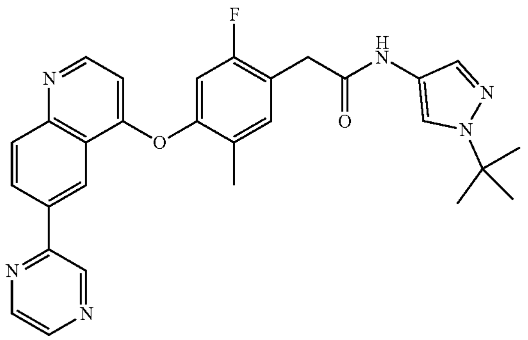 [SMILES: Cc1cc(CC(=O)Nc2cnn(C(C)(C)C)c2)c(F)cc1Oc1ccnc2ccc(-c3cnccn3)cc12] |

TABLE 1-continued
| Compound number | Structure |
|---|---|
| 426 | 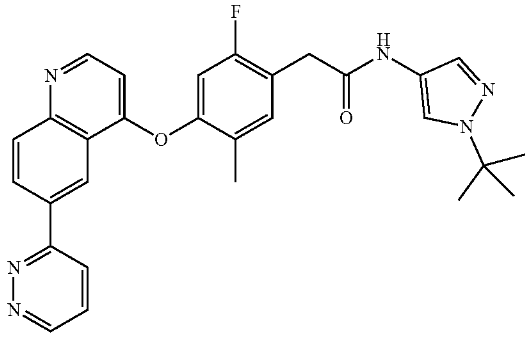 [SMILES: Cc1cc(CC(=O)Nc2cnn(C(C)(C)C)c2)c(F)cc1Oc1ccnc2ccc(-c3cccnn3)cc12] |
| 427 | 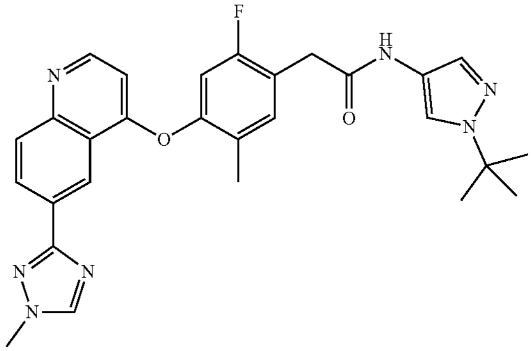 [SMILES: Cc1cc(CC(=O)Nc2cnn(C(C)(C)C)c2)c(F)cc1Oc1ccnc2ccc(-c3ncn(C)n3)cc12] |
| 428 | 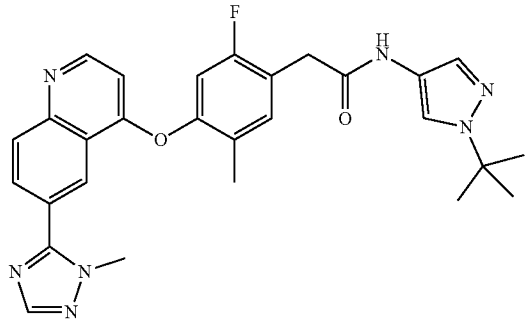 [SMILES: Cc1cc(CC(=O)Nc2cnn(C(C)(C)C)c2)c(F)cc1Oc1ccnc2ccc(-c3ncnn3C)cc12] |
| 429 | 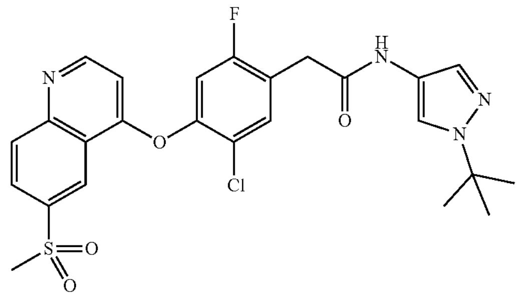 [SMILES: CC(C)(C)n1cc(NC(=O)Cc2cc(Cl)c(Oc3ccnc4ccc(S(C)(=O)=O)cc34)cc2F)cn1] |

TABLE 1-continued
| Compound number | Structure |
|---|---|
| 430 | 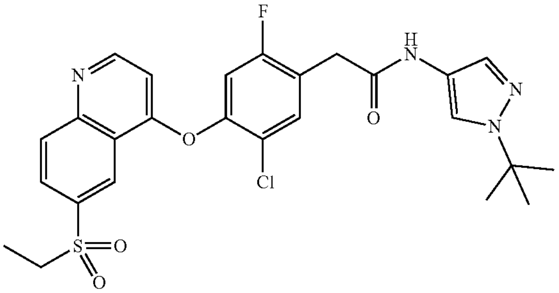 [SMILES: CCS(=O)(=O)c1ccc2nccc(Oc3cc(F)c(CC(=O)Nc4cnn(C(C)(C)C)c4)cc3Cl)c2c1] |
| 431 | 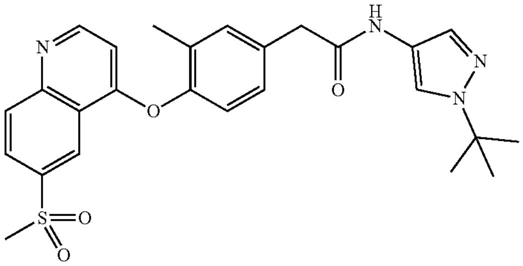 [SMILES: Cc1cc(CC(=O)Nc2cnn(C(C)(C)C)c2)ccc1Oc1ccnc2ccc(S(C)(=O)=O)cc12] |
| 432 | 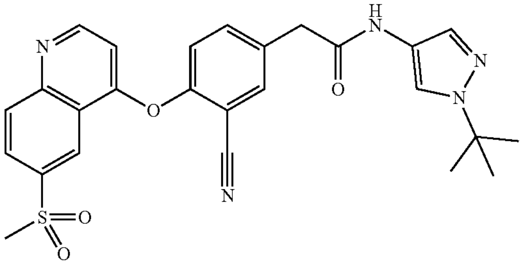 [SMILES: CC(C)(C)n1cc(NC(=O)Cc2ccc(Oc3ccnc4ccc(S(C)(=O)=O)cc34)c(C#N)c2)cn1] |
| 433 | 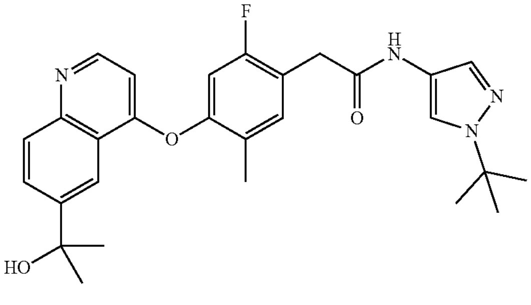 [SMILES: Cc1cc(CC(=O)Nc2cnn(C(C)(C)C)c2)c(F)cc1Oc1ccnc2ccc(C(C)(C)O)cc12] |
| 434 | 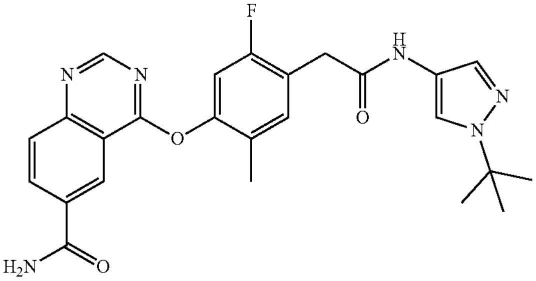 [SMILES: Cc1cc(CC(=O)Nc2cnn(C(C)(C)C)c2)c(F)cc1Oc1ncnc2ccc(C(N)=O)cc12] |

TABLE 1-continued
| Compound number | Structure |
|---|---|
| 435 | 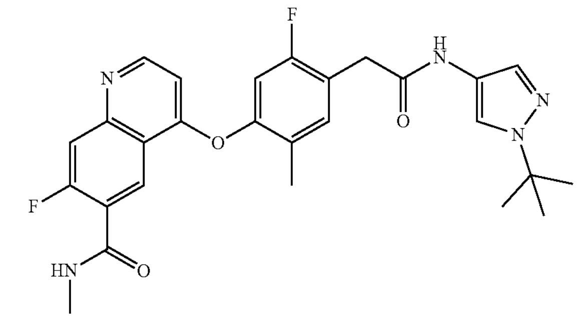 [SMILES: CNC(=O)c1cc2c(Oc3cc(F)c(CC(=O)Nc4cnn(C(C)(C)C)c4)cc3C)ccnc2cc1F] |
| 436 | 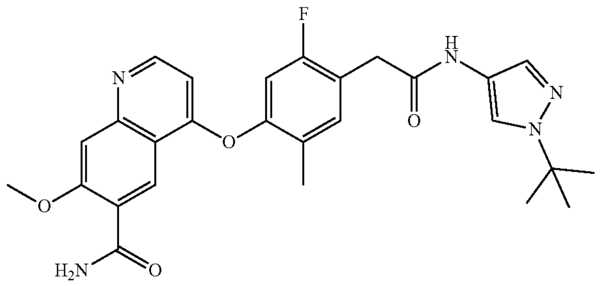 [SMILES: COc1cc2nccc(Oc3cc(F)c(CC(=O)Nc4cnn(C(C)(C)C)c4)cc3C)c2cc1C(N)=O] |
| 437 | 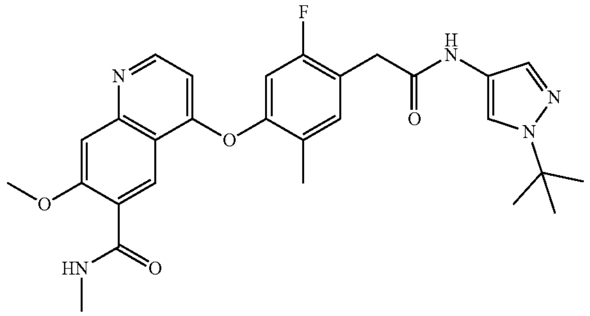 [SMILES: CNC(=O)c1cc2c(Oc3cc(F)c(CC(=O)Nc4cnn(C(C)(C)C)c4)cc3C)ccnc2cc1OC] |
| 438 | 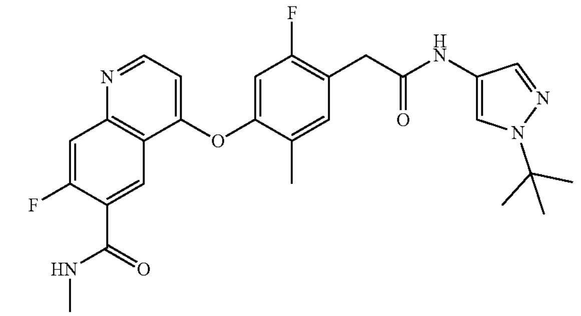 [SMILES: CNC(=O)c1cc2c(Oc3cc(F)c(CC(=O)Nc4cnn(C(C)(C)C)c4)cc3C)ccnc2cc1F] |
| 439 | 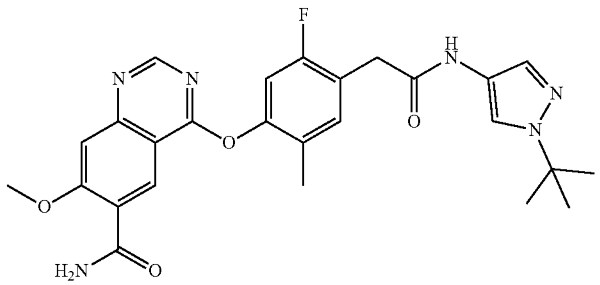 |

TABLE 1-continued
| Compound number | Structure |
|---|---|
| 440 | 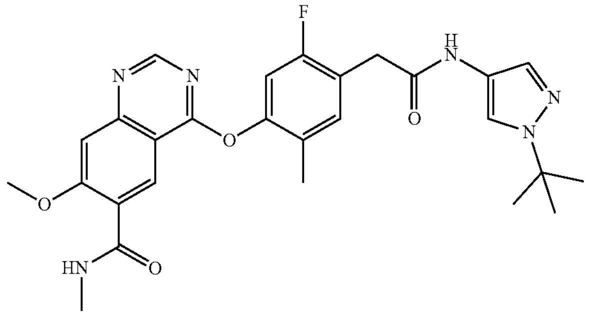 [SMILES: CNC(=O)c1cc2c(Oc3cc(F)c(CC(=O)Nc4cnn(C(C)(C)C)c4)cc3C)ncnc2cc1OC] |
| 441 | 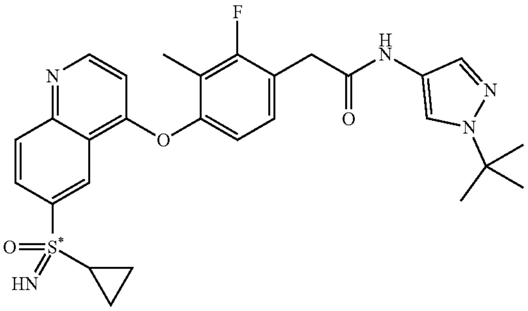 enantiomer 1 |
| 442 | 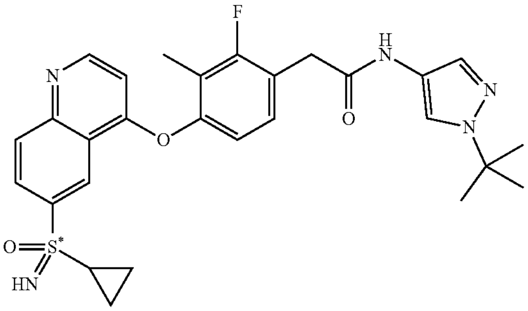 enantiomer 2 |
| 443 | 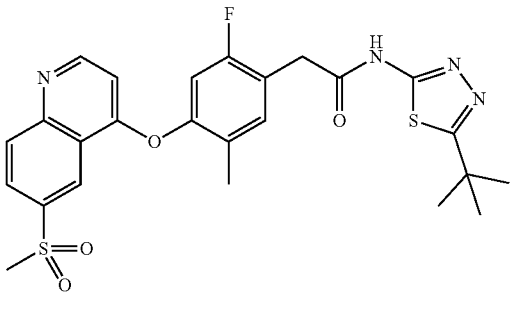 [SMILES: Cc1cc(CC(=O)Nc2nnc(C(C)(C)C)s2)c(F)cc1Oc1ccnc2ccc(S(C)(=O)=O)cc12] |

TABLE 1-continued
| Compound number | Structure |
|---|---|
| 444 | 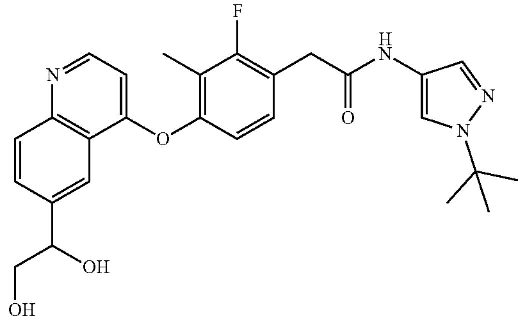 [SMILES: Cc1c(Oc2ccnc3ccc(C(O)CO)cc23)ccc(CC(=O)Nc2cnn(C(C)(C)C)c2)c1F] |
| 445 | 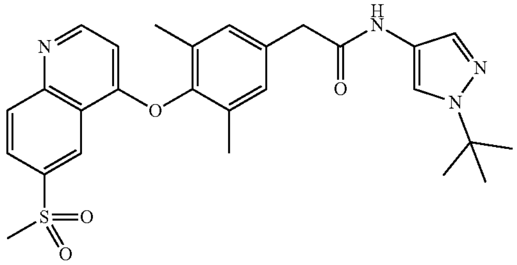 [SMILES: Cc1cc(CC(=O)Nc2cnn(C(C)(C)C)c2)cc(C)c1Oc1ccnc2ccc(S(C)(=O)=O)cc12] |
| 446 | 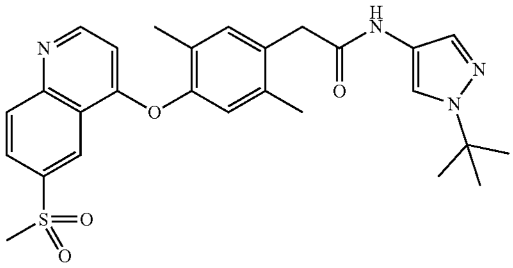 [SMILES: Cc1cc(Oc2ccnc3ccc(S(C)(=O)=O)cc23)c(C)cc1CC(=O)Nc1cnn(C(C)(C)C)c1] |
| 447 | 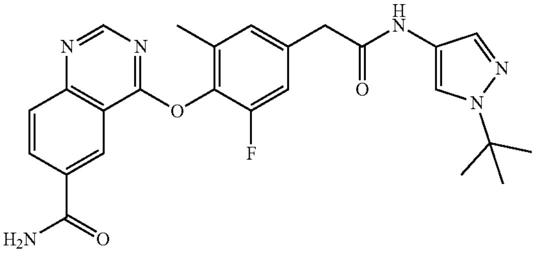 |
| 448 | 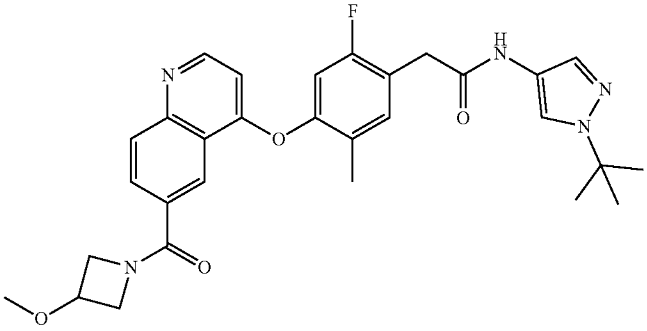 [SMILES: COC1CN(C(=O)c2ccc3nccc(Oc4cc(F)c(CC(=O)Nc5cnn(C(C)(C)C)c5)cc4C)c3c2)C1] |

TABLE 1-continued
| Compound number | Structure |
| --- | --- |
| 449 | 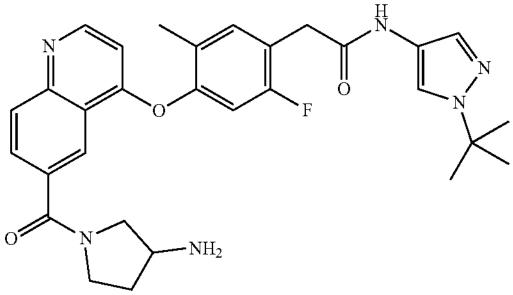 [SMILES: Cc1cc(CC(=O)Nc2cnn(C(C)(C)C)c2)c(F)cc1Oc1ccnc2ccc(C(=O)N3CCC(N)C3)cc12] |
| 450 | 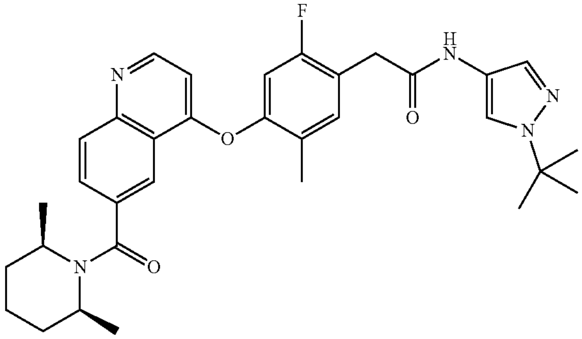 [SMILES: Cc1cc(CC(=O)Nc2cnn(C(C)(C)C)c2)c(F)cc1Oc1ccnc2ccc(C(=O)N3[C@H](C)CCC[C@@H]3C)cc12] |
| 451 | 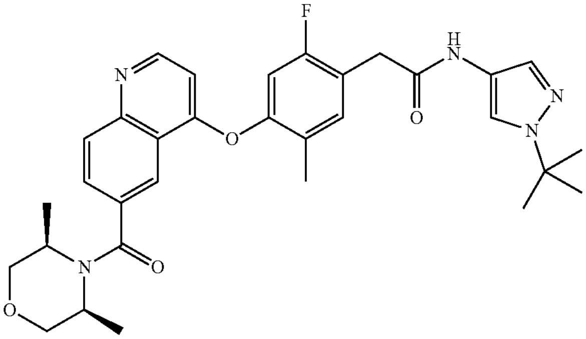 [SMILES: Cc1cc(CC(=O)Nc2cnn(C(C)(C)C)c2)c(F)cc1Oc1ccnc2ccc(C(=O)N3[C@H](C)COC[C@@H]3C)cc12] |
| 452 | 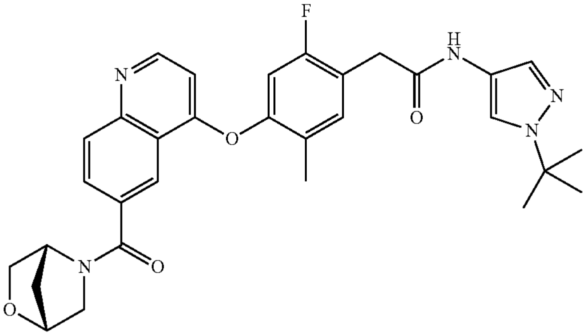 [SMILES: Cc1cc(CC(=O)Nc2cnn(C(C)(C)C)c2)c(F)cc1Oc1ccnc2ccc(C(=O)N3C[C@H]4C[C@@H]3CO4)cc12] |

TABLE 1-continued
| Compound number | Structure |
| --- | --- |
| 453 | 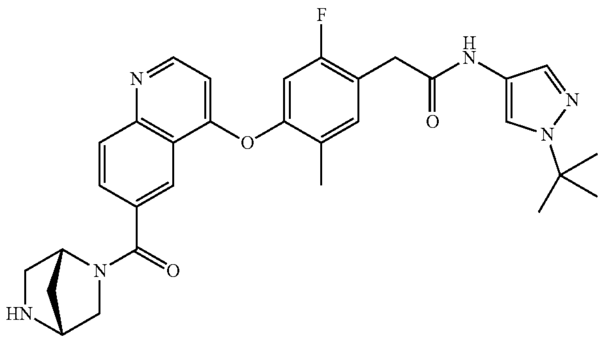 [SMILES: Cc1cc(CC(=O)Nc2cnn(C(C)(C)C)c2)c(F)cc1Oc1ccnc2ccc(C(=O)N3C[C@H]4C[C@@H]3CN4)cc12] |
| 454 | 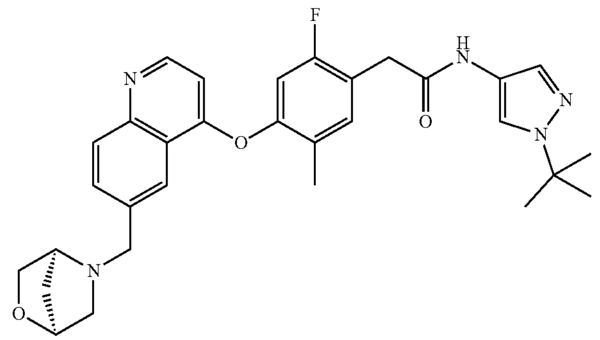 [SMILES: Cc1cc(CC(=O)Nc2cnn(C(C)(C)C)c2)c(F)cc1Oc1ccnc2ccc(CN3C[C@@H]4C[C@H]3CO4)cc12] |
| 455 | 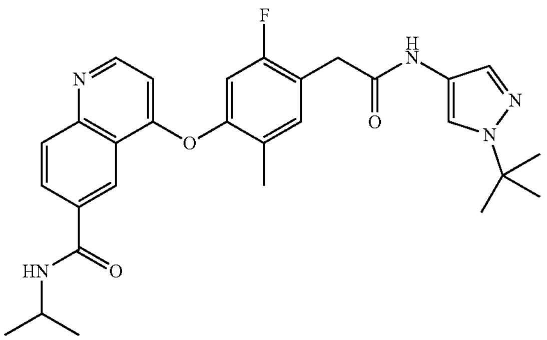 [SMILES: Cc1cc(CC(=O)Nc2cnn(C(C)(C)C)c2)c(F)cc1Oc1ccnc2ccc(C(=O)NC(C)C)cc12] |
| 456 | 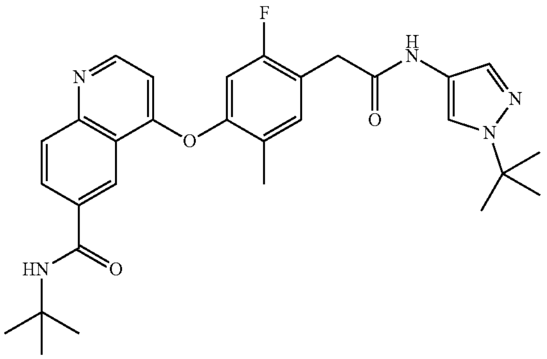 [SMILES: Cc1cc(CC(=O)Nc2cnn(C(C)(C)C)c2)c(F)cc1Oc1ccnc2ccc(C(=O)NC(C)(C)C)cc12] |

TABLE 1-continued
| Compound number | Structure |
| --- | --- |
| 457 | 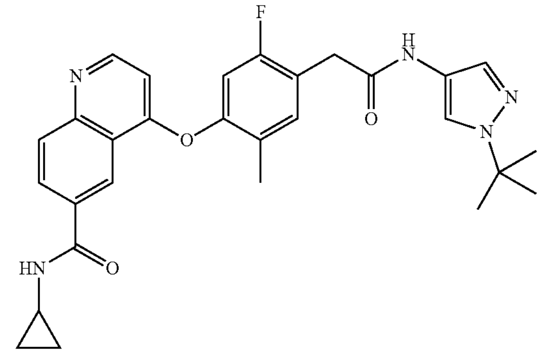 [SMILES: Cc1cc(CC(=O)Nc2cnn(C(C)(C)C)c2)c(F)cc1Oc1ccnc2ccc(C(=O)NC3CC3)cc12] |
| 458 | 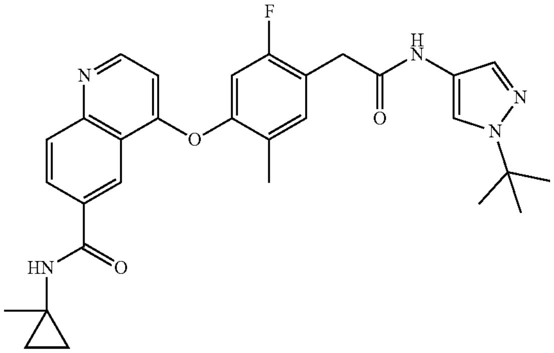 [SMILES: Cc1cc(CC(=O)Nc2cnn(C(C)(C)C)c2)c(F)cc1Oc1ccnc2ccc(C(=O)NC3(C)CC3)cc12] |
| 459 | 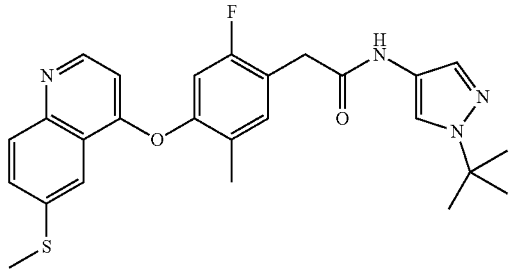 [SMILES: CSc1ccc2nccc(Oc3cc(F)c(CC(=O)Nc4cnn(C(C)(C)C)c4)cc3C)c2c1] |
| 460 | 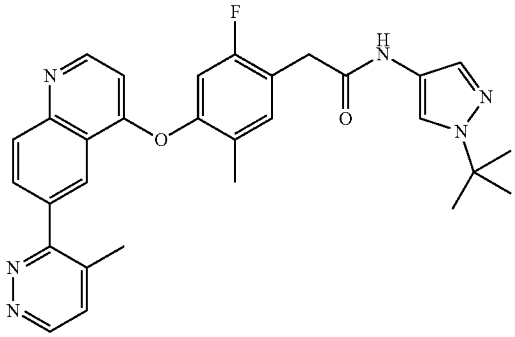 [SMILES: Cc1cc(CC(=O)Nc2cnn(C(C)(C)C)c2)c(F)cc1Oc1ccnc2ccc(-c3nnccc3C)cc12] |

TABLE 1-continued
| Compound number | Structure |
| --- | --- |
| 461 | 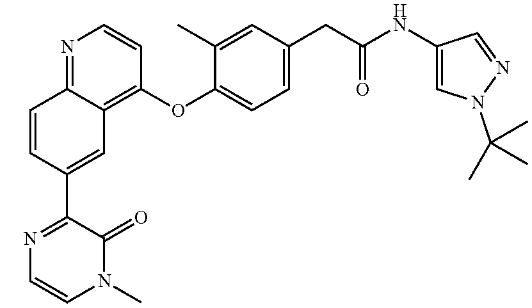 [SMILES: Cc1cc(CC(=O)Nc2cnn(C(C)(C)C)c2)ccc1Oc1ccnc2ccc(-c3nccn(C)c3=O)cc12] |
| 462 | 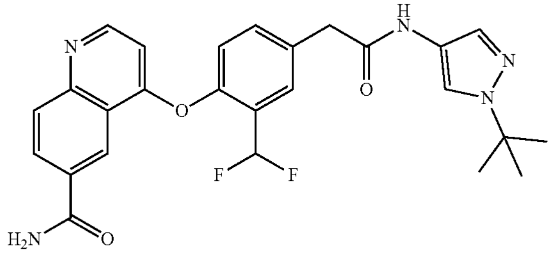 [SMILES: CC(C)(C)n1cc(NC(=O)Cc2ccc(Oc3ccnc4ccc(C(N)=O)cc34)c(C(F)F)c2)cn1] |
| 463 | 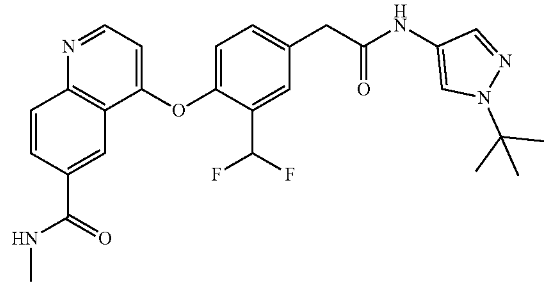 [SMILES: CNC(=O)c1ccc2nccc(Oc3ccc(CC(=O)Nc4cnn(C(C)(C)C)c4)cc3C(F)F)c2c1] |
| 464 | 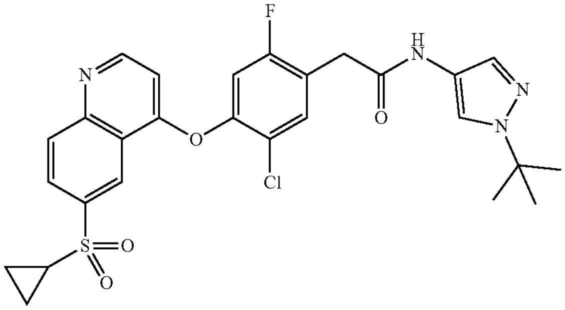 [SMILES: CC(C)(C)n1cc(NC(=O)Cc2cc(Cl)c(Oc3ccnc4ccc(S(=O)(=O)C5CC5)cc34)cc2F)cn1] |
| 465 | 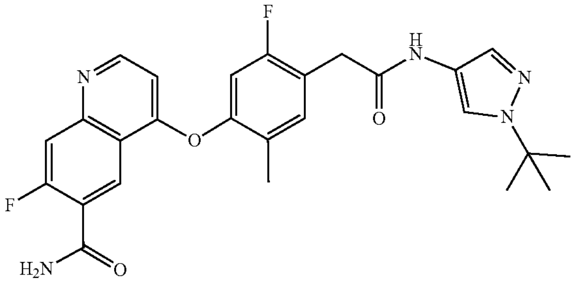 [SMILES: Cc1cc(CC(=O)Nc2cnn(C(C)(C)C)c2)c(F)cc1Oc1ccnc2cc(F)c(C(N)=O)cc12] |

TABLE 1-continued
| Compound number | Structure |
|---|---|
| 466 | 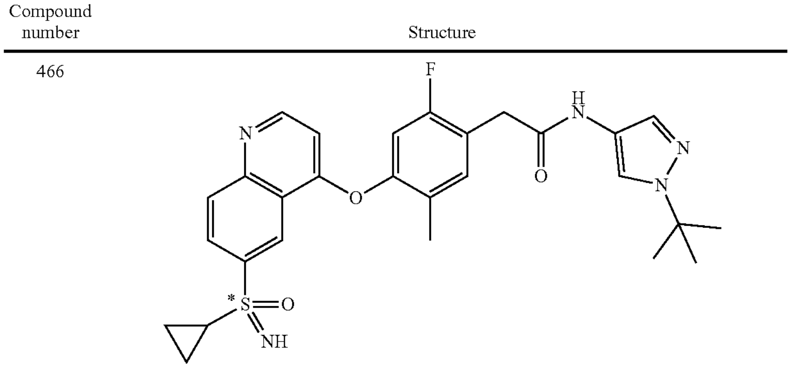 enantiomer 1 |
| 467 | 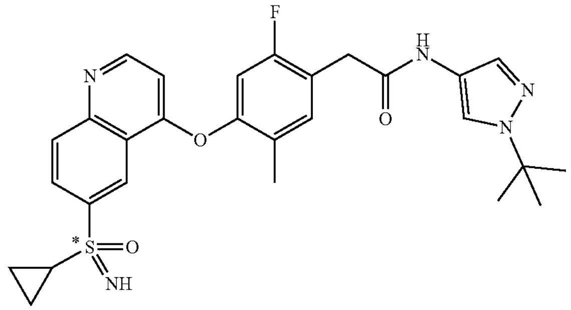 enantiomer 2 |
| 468 | 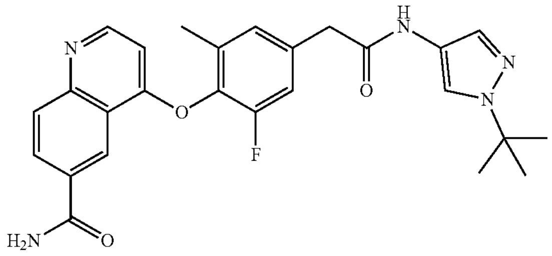 |
| 469 | 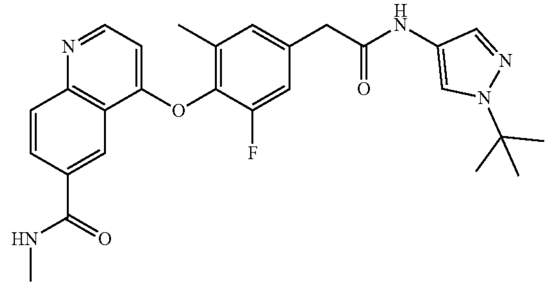 |
| 470 | 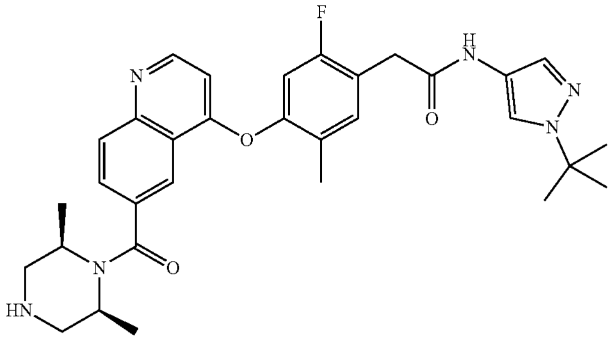 [SMILES: Cc1cc(CC(=O)Nc2cnn(C(C)(C)C)c2)c(F)cc1Oc1ccnc2ccc(C(=O)N3[C@H](C)CNC[C@@H]3C)cc12] |

TABLE 1-continued
| Compound number | Structure |
|---|---|
| 471 | 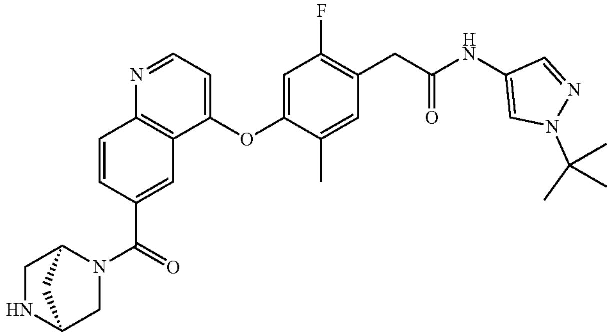 [SMILES: Cc1cc(CC(=O)Nc2cnn(C(C)(C)C)c2)c(F)cc1Oc1ccnc2ccc(C(=O)N3C[C@@H]4C[C@H]3CN4)cc12] |
| 472 | 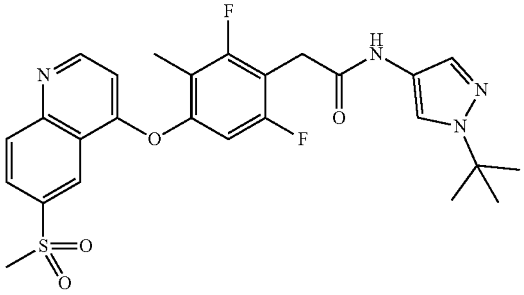 [SMILES: Cc1c(Oc2ccnc3ccc(S(C)(=O)=O)cc23)cc(F)c(CC(=O)Nc2cnn(C(C)(C)C)c2)c1F] |
| 473 | 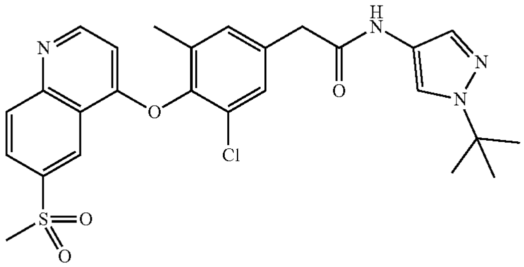 [SMILES: Cc1cc(CC(=O)Nc2cnn(C(C)(C)C)c2)cc(Cl)c1Oc1ccnc2ccc(S(C)(=O)=O)cc12] |
| 474 | 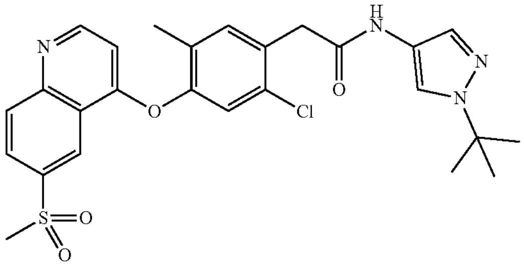 [SMILES: Cc1cc(CC(=O)Nc2cnn(C(C)(C)C)c2)c(Cl)cc1Oc1ccnc2ccc(S(C)(=O)=O)cc12] |
| 475 | 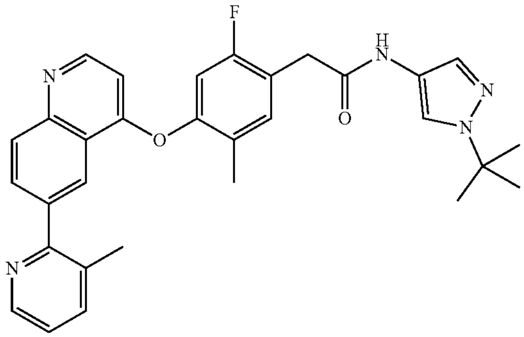 [SMILES: Cc1cc(CC(=O)Nc2cnn(C(C)(C)C)c2)c(F)cc1Oc1ccnc2ccc(-c3ncccc3C)cc12] |

TABLE 1-continued
| Compound number | Structure |
| --- | --- |
| 476 | 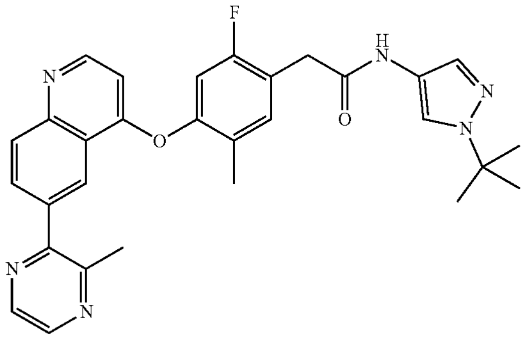 |
| 477 | 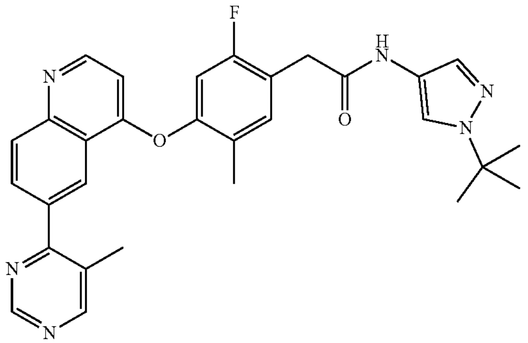 [SMILES: Cc1cc(CC(=O)Nc2cnn(C(C)(C)C)c2)c(F)cc1Oc1ccnc2ccc(-c3ncncc3C)cc12] |
| 478 | 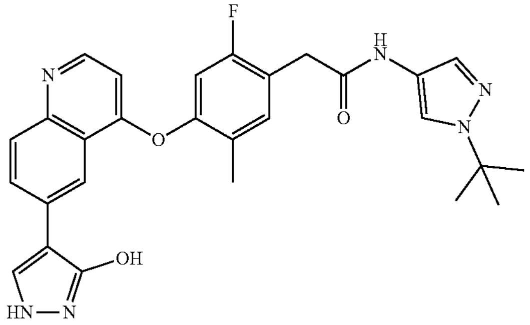 [SMILES: Cc1cc(CC(=O)Nc2cnn(C(C)(C)C)c2)c(F)cc1Oc1ccnc2ccc(-c3c[nH]nc3O)cc12] |
| 479 | 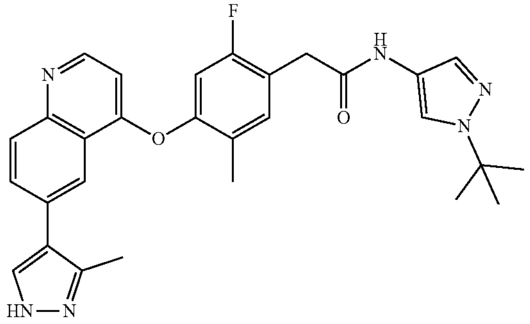 [SMILES: Cc1cc(CC(=O)Nc2cnn(C(C)(C)C)c2)c(F)cc1Oc1ccnc2ccc(-c3c[nH]nc3C)cc12] |

TABLE 1-continued
| Compound number | Structure |
|---|---|
| 480 | 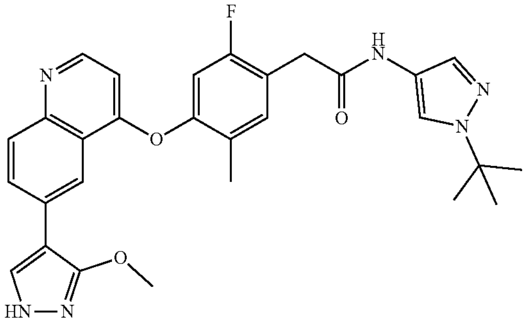 [SMILES: COc1n[nH]cc1-c1ccc2nccc(Oc3cc(F)c(CC(=O)Nc4cnn(C(C)(C)C)c4)cc3C)c2c1] |
| 481 | 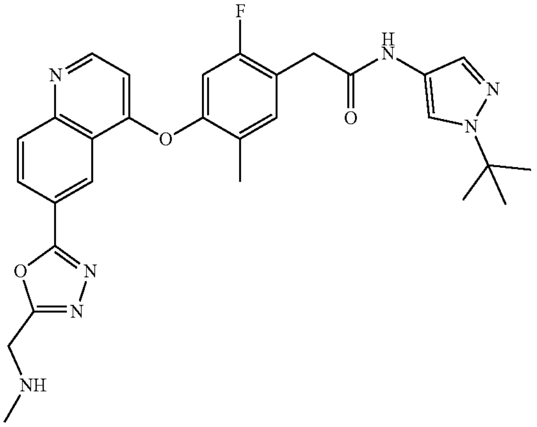 [SMILES: CNCc1nnc(-c2ccc3nccc(Oc4cc(F)c(CC(=O)Nc5cnn(C(C)(C)C)c5)cc4C)c3c2)o1] |
| 482 | 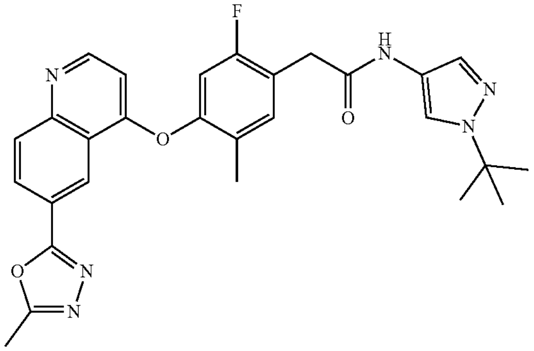 [SMILES: Cc1nnc(-c2ccc3nccc(Oc4cc(F)c(CC(=O)Nc5cnn(C(C)(C)C)c5)cc4C)c3c2)o1] |
| 483 | 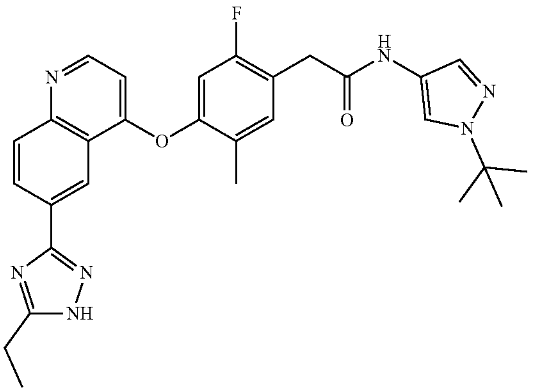 [SMILES: CCc1nc(-c2ccc3nccc(Oc4cc(F)c(CC(=O)Nc5cnn(C(C)(C)C)c5)cc4C)c3c2)n[nH]1] |

TABLE 1-continued
| Compound number | Structure |
|---|---|
| 484 | 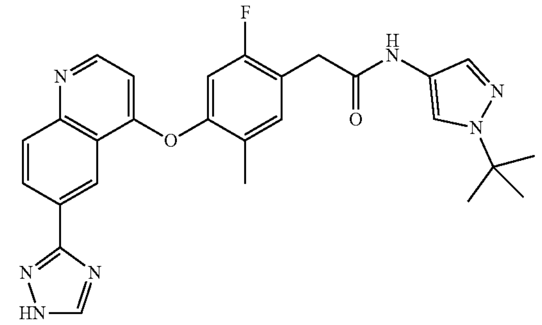 [SMILES: Cc1cc(CC(=O)Nc2cnn(C(C)(C)C)c2)c(F)cc1Oc1ccnc2ccc(-c3nc[nH]n3)cc12] |
| 485 | 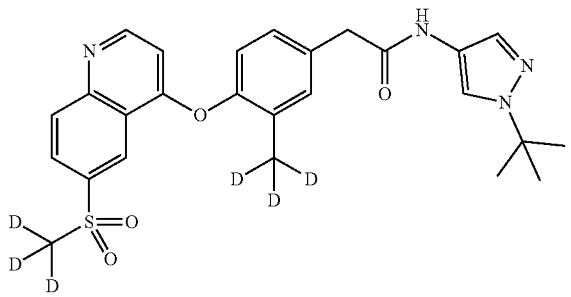 [SMILES: [2H]C([2H])([2H])c1cc(CC(=O)Nc2cnn(C(C)(C)C)c2)ccc1Oc1ccnc2ccc(S(=O)(=O)C([2H])([2H])[2H])cc12] |
| 486 | 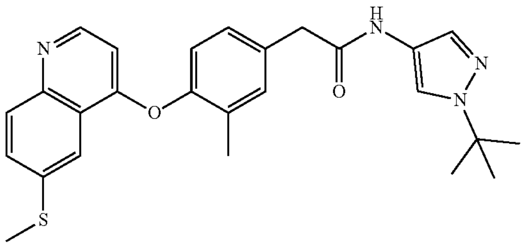 [SMILES: CSc1ccc2nccc(Oc3ccc(CC(=O)Nc4cnn(C(C)(C)C)c4)cc3C)c2c1] |
| 487 | 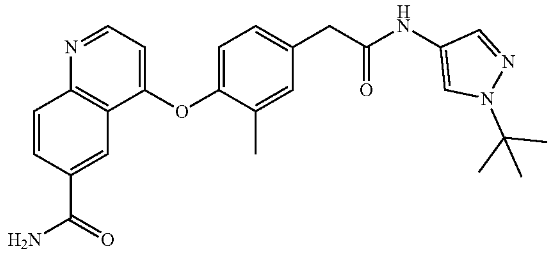 [SMILES: Cc1cc(CC(=O)Nc2cnn(C(C)(C)C)c2)ccc1Oc1ccnc2ccc(C(N)=O)cc12] |
| 488 | 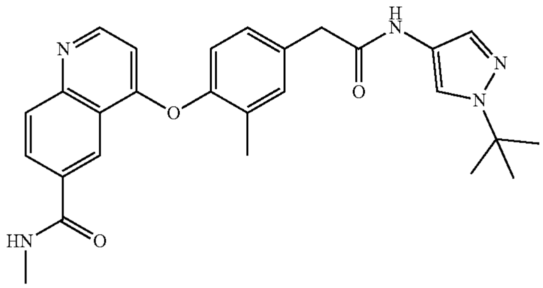 [SMILES: CNC(=O)c1ccc2nccc(Oc3ccc(CC(=O)Nc4cnn(C(C)(C)C)c4)cc3C)c2c1] |

TABLE 1-continued
| Compound number | Structure |
|---|---|
| 489 | 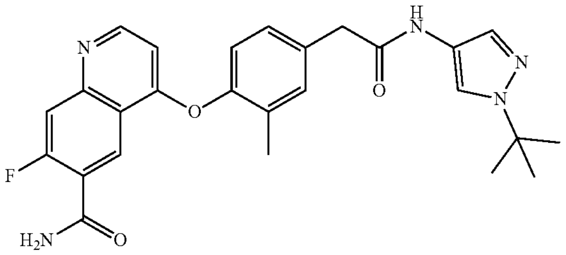 [SMILES: Cc1cc(CC(=O)Nc2cnn(C(C)(C)C)c2)ccc1Oc1ccnc2cc(F)c(C(N)=O)cc12] |
| 490 | 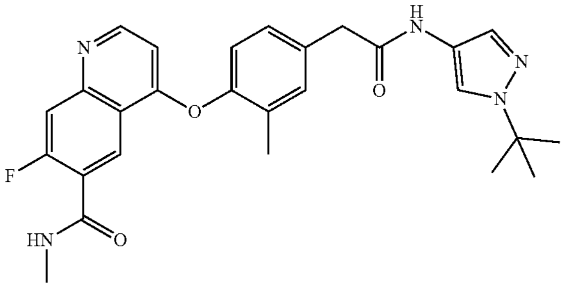 [SMILES: CNC(=O)c1cc2c(Oc3ccc(CC(=O)Nc4cnn(C(C)(C)C)c4)cc3C)ccnc2cc1F] |
| 491 | 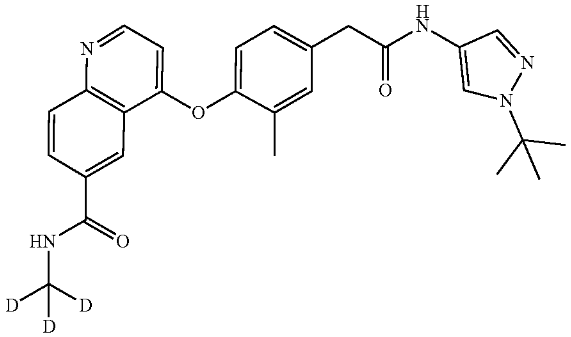 [SMILES: [2H]C([2H])([2H])NC(=O)c1ccc2nccc(Oc3ccc(CC(=O)Nc4cnn(C(C)(C)C)c4)cc3C)c2c1] |
| 492 | 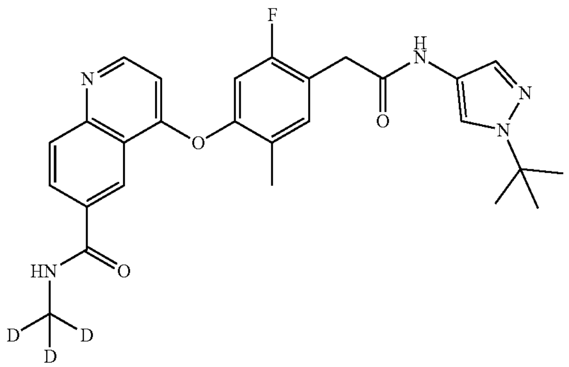 [SMILES: [2H]C([2H])([2H])NC(=O)c1ccc2nccc(Oc3cc(F)c(CC(=O)Nc4cnn(C(C)(C)C)c4)cc3C)c2c1] |

TABLE 1-continued
| Compound number | Structure |
| --- | --- |
| 493 | 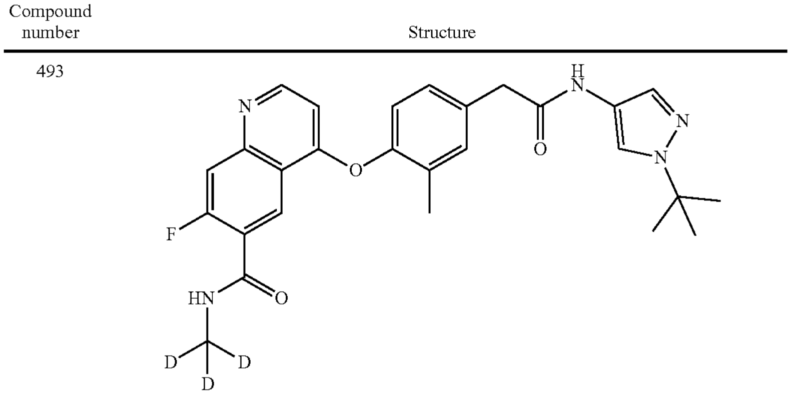 |
| 494 | 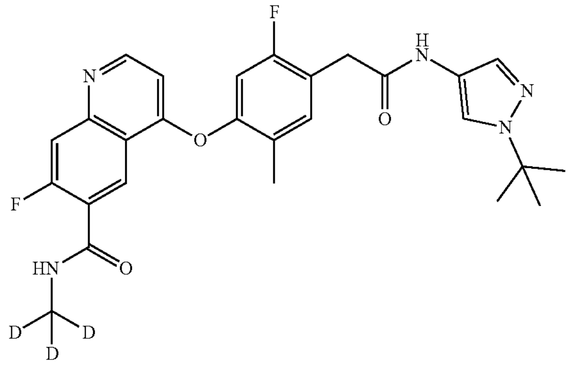 [SMILES: [2H]C([2H])([2H])NC(=O)c1cc2c(Oc3cc(F)c(CC(=O)Nc4cnn(C(C)(C)C)c4)cc3C)ccnc2cc1F] |
| 495 | 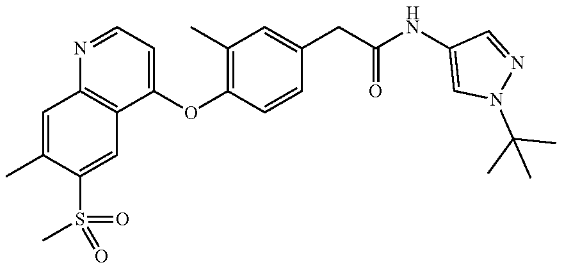 [SMILES: Cc1cc(CC(=O)Nc2cnn(C(C)(C)C)c2)ccc1Oc1ccnc2cc(C)c(S(C)(=O)=O)cc12] |
| 496 | 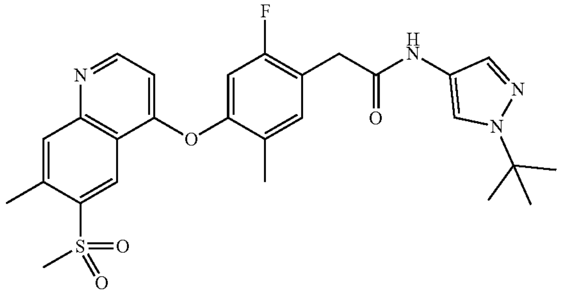 [SMILES: Cc1cc(CC(=O)Nc2cnn(C(C)(C)C)c2)c(F)cc1Oc1ccnc2cc(C)c(S(C)(=O)=O)cc12] |
| 497 | 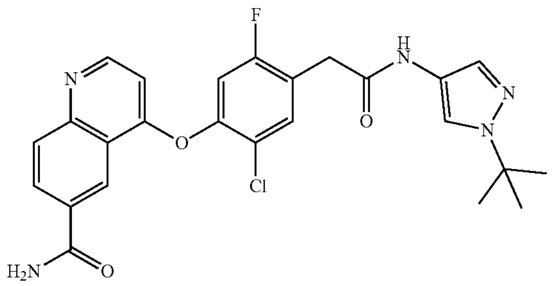 [SMILES: CC(C)(C)n1cc(NC(=O)Cc2cc(Cl)c(Oc3ccnc4ccc(C(N)=O)cc34)cc2F)cn1] |

TABLE 1-continued
| Compound number | Structure |
|---|---|
| 498 | 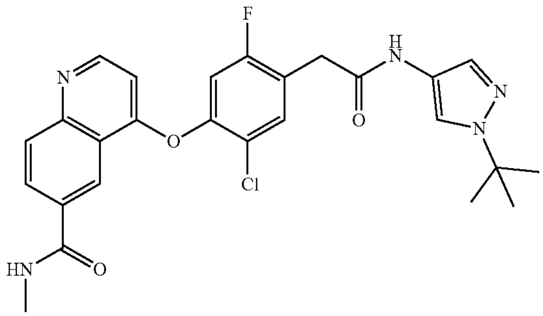 |
| 499 | 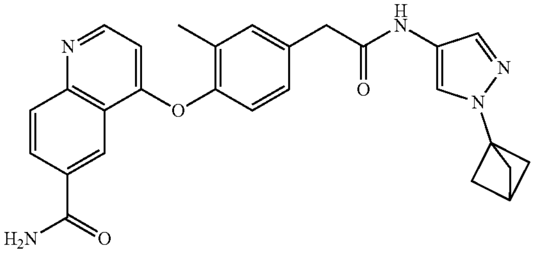 [SMILES: Cc1cc(CC(=O)Nc2cnn(C34CC(C3)C4)c2)ccc1Oc1ccnc2ccc(C(N)=O)cc12] |
| 500 | 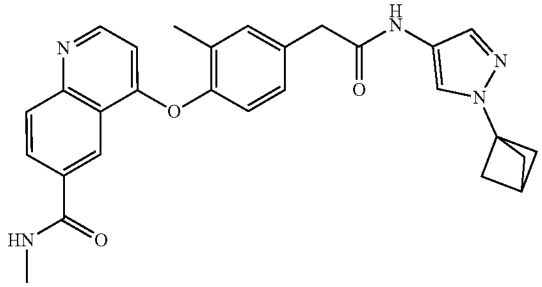 [SMILES: CNC(=O)c1ccc2nccc(Oc3ccc(CC(=O)Nc4cnn(C56CC(C5)C6)c4)cc3C)c2c1] |
| 501 | 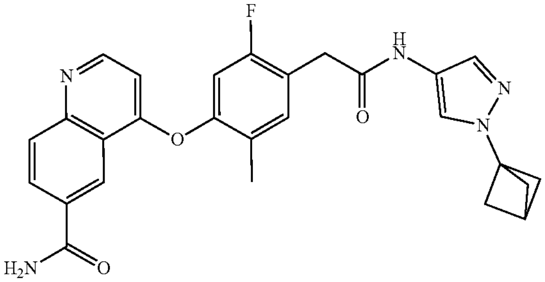 [SMILES: Cc1cc(CC(=O)Nc2cnn(C34CC(C3)C4)c2)c(F)cc1Oc1ccnc2ccc(C(N)=O)cc12] |
| 502 | 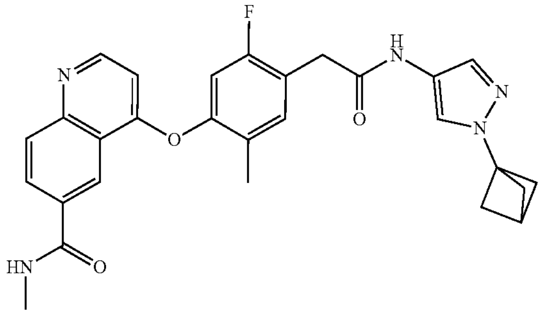 [SMILES: CNC(=O)c1ccc2nccc(Oc3cc(F)c(CC(=O)Nc4cnn(C56CC(C5)C6)c4)cc3C)c2c1] |

TABLE 1-continued
| Compound number | Structure |
| --- | --- |
| 503 | 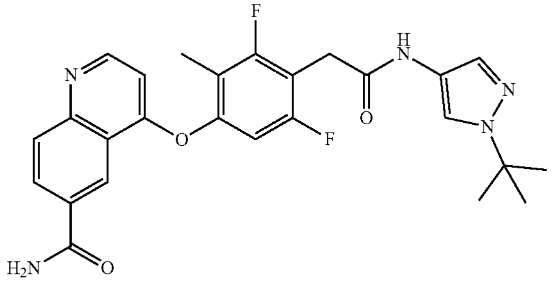 [SMILES: Cc1c(Oc2ccnc3ccc(C(N)=O)cc23)cc(F)c(CC(=O)Nc2cnn(C(C)(C)C)c2)c1F] |
| 504 | 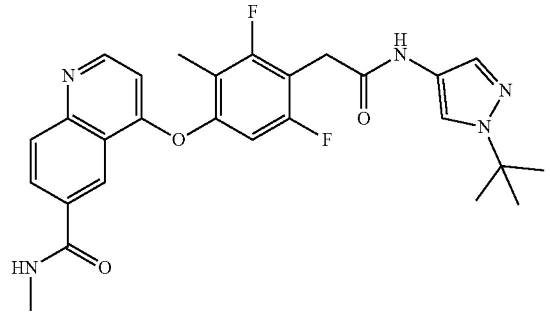 [SMILES: CNC(=O)c1ccc2nccc(Oc3cc(F)c(CC(=O)Nc4cnn(C(C)(C)C)c4)c(F)c3C)c2c1] |
| 505 | 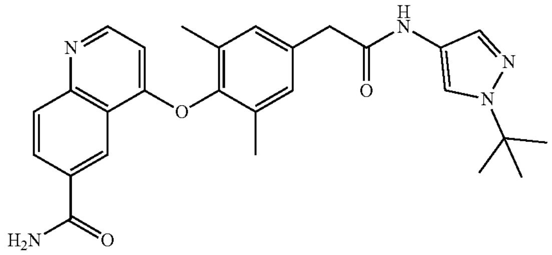 |
| 506 | 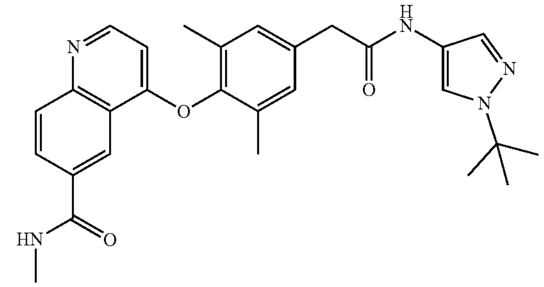 [SMILES: CNC(=O)c1ccc2nccc(Oc3c(C)cc(CC(=O)Nc4cnn(C(C)(C)C)c4)cc3C)c2c1] |
| 507 | 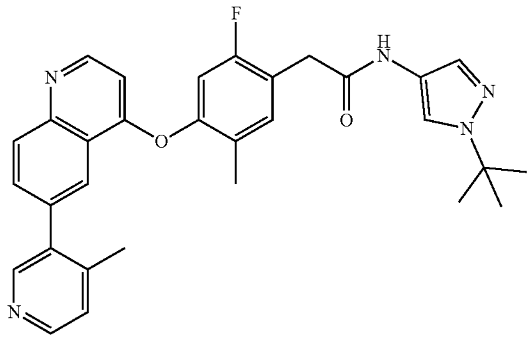 [SMILES: Cc1cc(CC(=O)Nc2cnn(C(C)(C)C)c2)c(F)cc1Oc1ccnc2ccc(-c3cnccc3C)cc12] |

TABLE 1-continued
| Compound number | Structure |
|---|---|
| 508 | 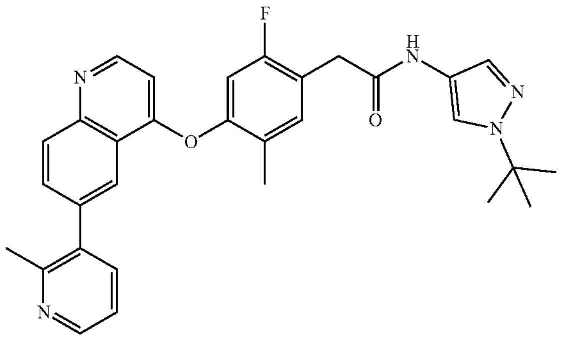 [SMILES: Cc1cc(CC(=O)Nc2cnn(C(C)(C)C)c2)c(F)cc1Oc1ccnc2ccc(-c3cccnc3C)cc12] |
| 509 | 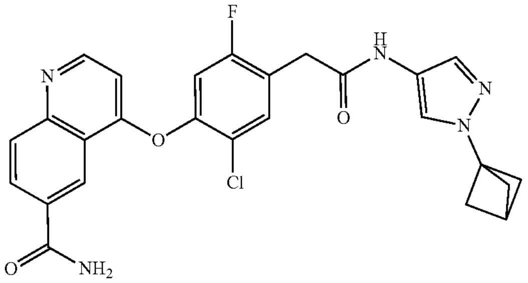 [SMILES: NC(=O)c1ccc2nccc(Oc3cc(F)c(CC(=O)Nc4cnn(C56CC(C5)C6)c4)cc3Cl)c2c1] |
| 510 | 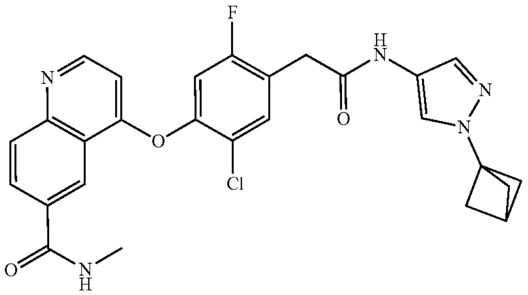 [SMILES: CNC(=O)c1ccc2nccc(Oc3cc(F)c(CC(=O)Nc4cnn(C56CC(C5)C6)c4)cc3Cl)c2c1] |
| 511 | 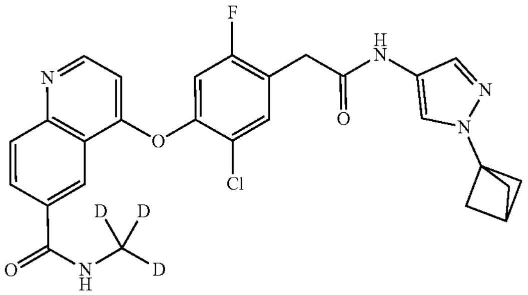 [SMILES: [2H]C([2H])([2H])NC(=O)c1ccc2nccc(Oc3cc(F)c(CC(=O)Nc4cnn(C56CC(C5)C6)c4)cc3Cl)c2c1] |
| 512 | 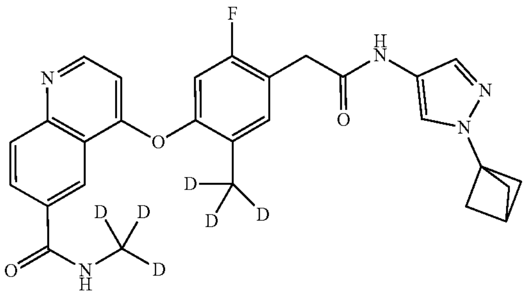 [SMILES: [2H]C([2H])([2H])NC(=O)c1ccc2nccc(Oc3cc(F)c(CC(=O)Nc4cnn(C56CC(C5)C6)c4)cc3C([2H])([2H])[2H])c2c1] |

TABLE 1-continued
| Compound number | Structure |
| --- | --- |
| 513 | 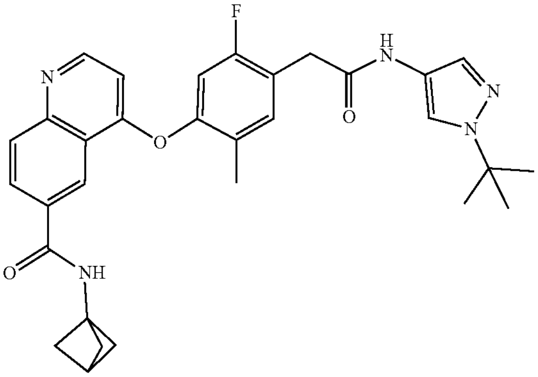 [SMILES: Cc1cc(CC(=O)Nc2cnn(C(C)(C)C)c2)c(F)cc1Oc1ccnc2ccc(C(=O)NC34CC(C3)C4)cc12] |
| 514 | 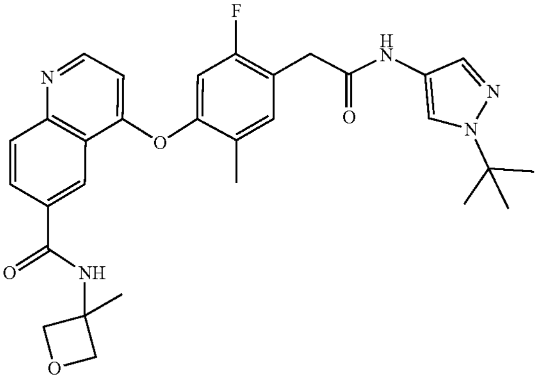 [SMILES: Cc1cc(CC(=O)Nc2cnn(C(C)(C)C)c2)c(F)cc1Oc1ccnc2ccc(C(=O)NC3(C)COC3)cc12] |
| 515 | 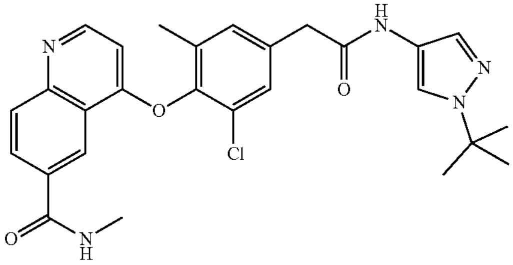 [SMILES: CNC(=O)c1ccc2nccc(Oc3c(C)cc(CC(=O)Nc4cnn(C(C)(C)C)c4)cc3Cl)c2c1] |
| 516 | 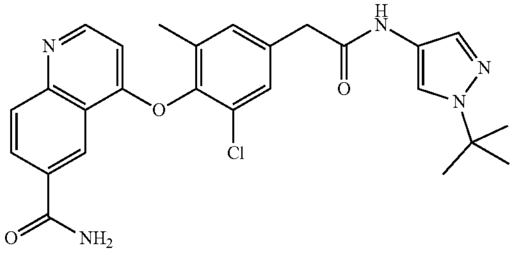 [SMILES: Cc1cc(CC(=O)Nc2cnn(C(C)(C)C)c2)cc(Cl)c1Oc1ccnc2ccc(C(N)=O)cc12] |

TABLE 1-continued
| Compound number | Structure |
|---|---|
| 517 | 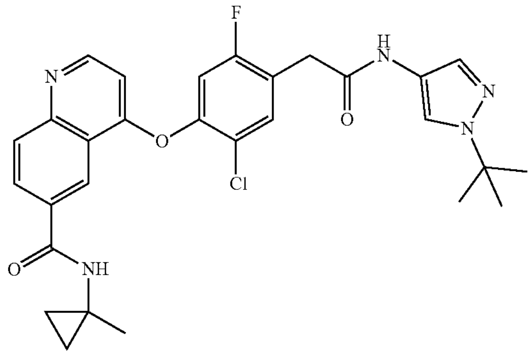 [SMILES: CC1(NC(=O)c2ccc3nccc(Oc4cc(F)c(CC(=O)Nc5cnn(C(C)(C)C)c5)cc4Cl)c3c2)CC1] |
| 518 | 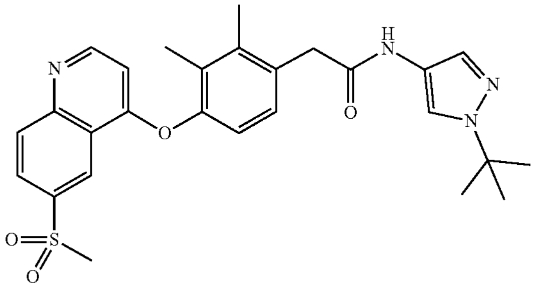 [SMILES: Cc1c(CC(=O)Nc2cnn(C(C)(C)C)c2)ccc(Oc2ccnc3ccc(S(C)(=O)=O)cc23)c1C] |
| 519 | 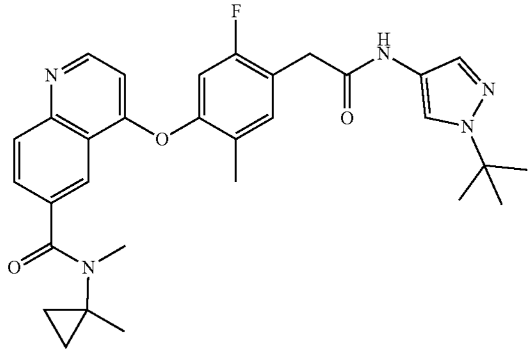 [SMILES: Cc1cc(CC(=O)Nc2cnn(C(C)(C)C)c2)c(F)cc1Oc1ccnc2ccc(C(=O)N(C)C3(C)CC3)cc12] |
| 520 | 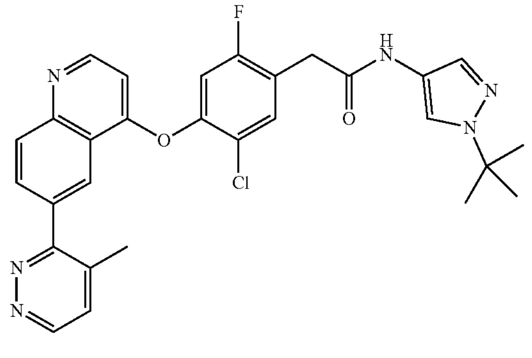 [SMILES: Cc1ccnnc1-c1ccc2nccc(Oc3cc(F)c(CC(=O)Nc4cnn(C(C)(C)C)c4)cc3Cl)c2c1] |

TABLE 1-continued
| Compound number | Structure |
| --- | --- |
| 521 | 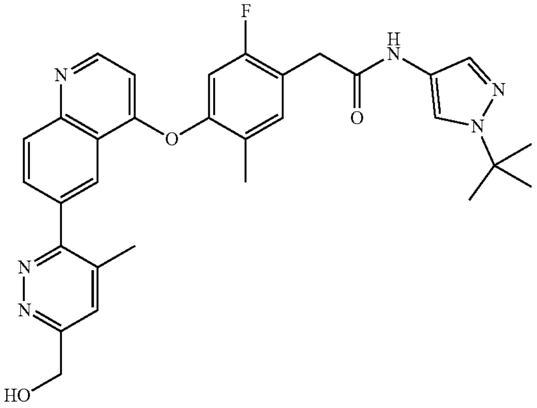 [SMILES: Cc1cc(CC(=O)Nc2cnn(C(C)(C)C)c2)c(F)cc1Oc1ccnc2ccc(-c3nnc(CO)cc3C)cc12] |
| 522 | 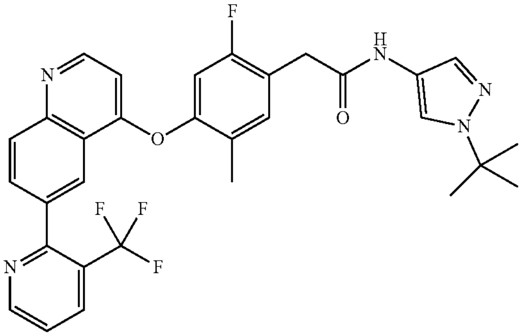 [SMILES: Cc1cc(CC(=O)Nc2cnn(C(C)(C)C)c2)c(F)cc1Oc1ccnc2ccc(-c3ncccc3C(F)(F)F)cc12] |
| 523 | 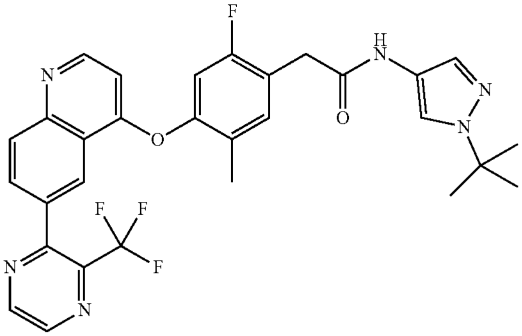 [SMILES: Cc1cc(CC(=O)Nc2cnn(C(C)(C)C)c2)c(F)cc1Oc1ccnc2ccc(-c3nccnc3C(F)(F)F)cc12] |
| 524 | 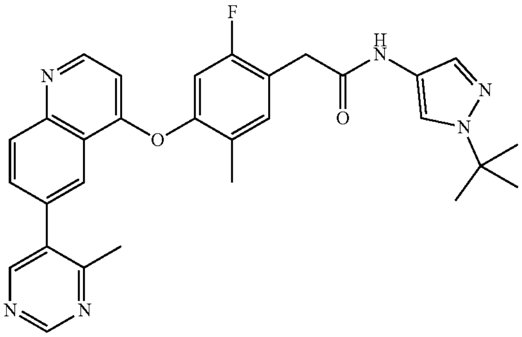 [SMILES: Cc1cc(CC(=O)Nc2cnn(C(C)(C)C)c2)c(F)cc1Oc1ccnc2ccc(-c3cncnc3C)cc12] |

TABLE 1-continued
| Compound number | Structure |
|---|---|
| 525 | 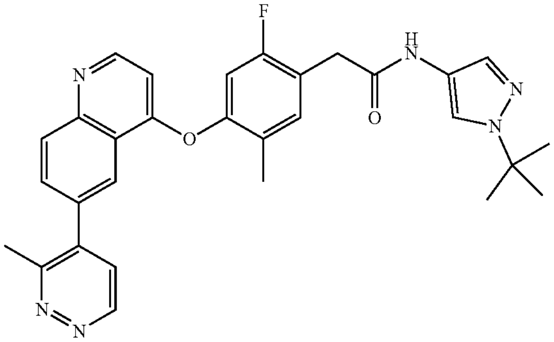 [SMILES: Cc1cc(CC(=O)Nc2cnn(C(C)(C)C)c2)c(F)cc1Oc1ccnc2ccc(-c3ccnnc3C)cc12] |
| 526 | 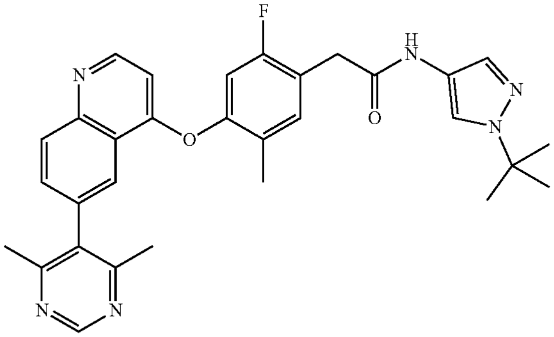 [SMILES: Cc1cc(CC(=O)Nc2cnn(C(C)(C)C)c2)c(F)cc1Oc1ccnc2ccc(-c3c(C)ncnc3C)cc12] |
| 527 | 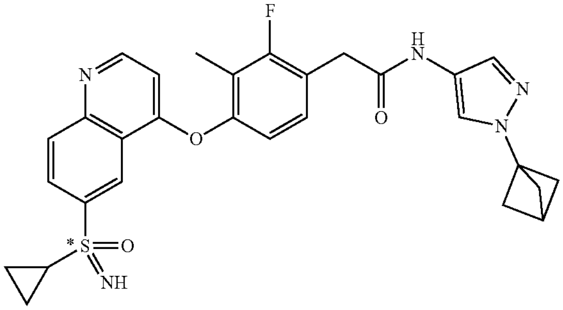 [SMILES: Cc1c(Oc2ccnc3ccc(S(=N)(=O)C4CC4)cc23)ccc(CC(=O)Nc2cnn(C34CC(C3)C4)c2)c1F] enantiomer 1 |
| 528 | 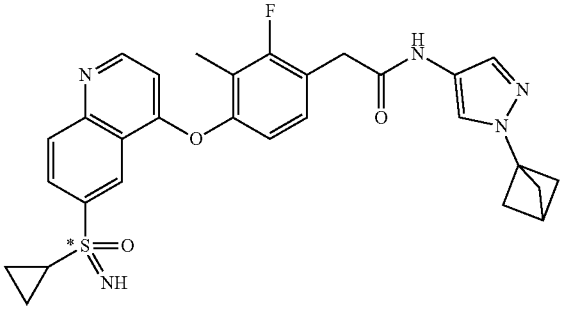 [SMILES: Cc1c(Oc2ccnc3ccc(S(=N)(=O)C4CC4)cc23)ccc(CC(=O)Nc2cnn(C34CC(C3)C4)c2)c1F] enantiomer 2 |

TABLE 1-continued
| Compound number | Structure |
|---|---|
| 529 | 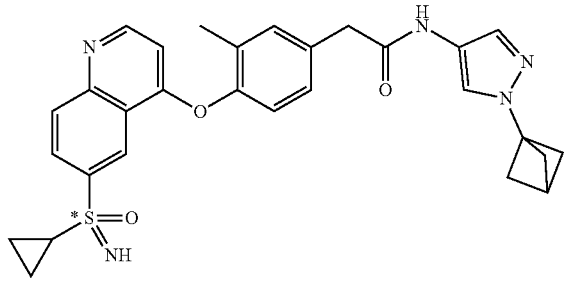 [SMILES: Cc1cc(CC(=O)Nc2cnn(C34CC(C3)C4)c2)ccc1Oc1ccnc2ccc(S(=N)(=O)C3CC3)cc12] enantiomer 1 |
| 530 | 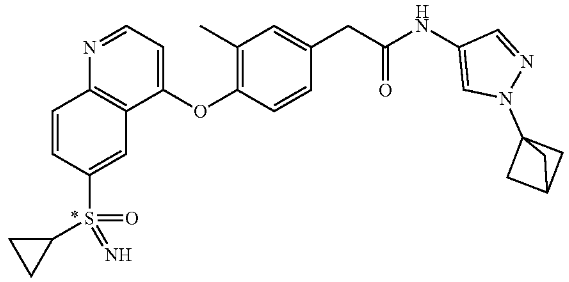 [SMILES: Cc1cc(CC(=O)Nc2cnn(C34CC(C3)C4)c2)ccc1Oc1ccnc2ccc(S(=N)(=O)C3CC3)cc12] enantiomer 2 |
| 531 | 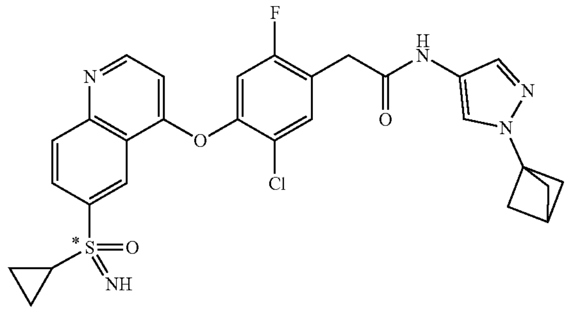 [SMILES: N=S(=O)(c1ccc2nccc(Oc3cc(F)c(CC(=O)Nc4cnn(C56CC(C5)C6)c4)cc3Cl)c2c1)C1CC1] enantiomer 1 |
| 532 | 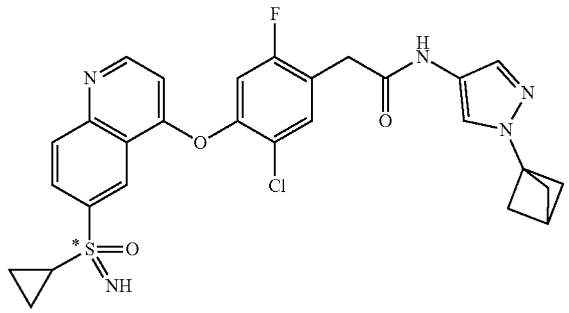 [SMILES: N=S(=O)(c1ccc2nccc(Oc3cc(F)c(CC(=O)Nc4cnn(C56CC(C5)C6)c4)cc3Cl)c2c1)C1CC1] enantiomer 2 |

TABLE 1-continued
| Compound number | Structure |
|---|---|
| 533 | 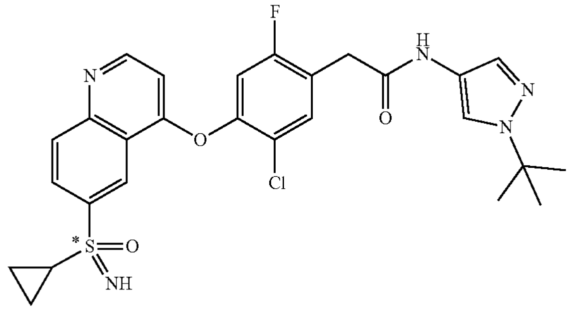 [SMILES: CC(C)(C)n1cc(NC(=O)Cc2cc(Cl)c(Oc3ccnc4ccc(S(=N)(=O)C5CC5)cc34)cc2F)cn1] enantiomer 1 |
| 534 | 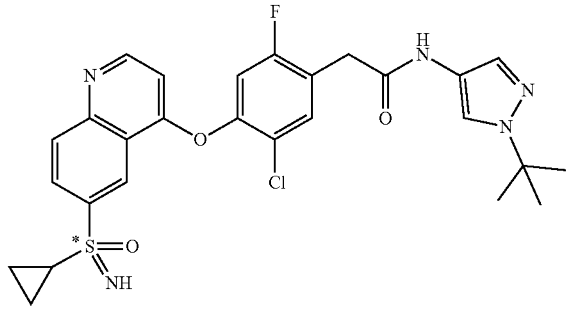 [SMILES: CC(C)(C)n1cc(NC(=O)Cc2cc(Cl)c(Oc3ccnc4ccc(S(=N)(=O)C5CC5)cc34)cc2F)cn1] enantiomer 2 |
| 535 | 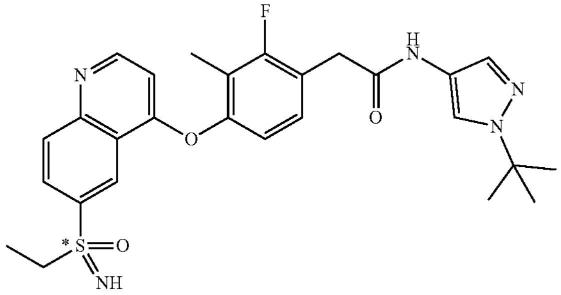 [SMILES: CCS(=N)(=O)c1ccc2nccc(Oc3ccc(CC(=O)Nc4cnn(C(C)(C)C)c4)c(F)c3C)c2c1] enantiomer 1 |
| 536 | 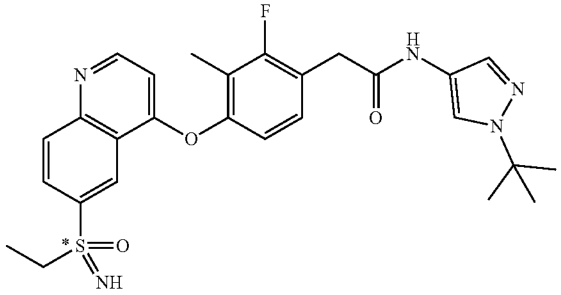 [SMILES: CCS(=N)(=O)c1ccc2nccc(Oc3ccc(CC(=O)Nc4cnn(C(C)(C)C)c4)c(F)c3C)c2c1] enantiomer 2 |

TABLE 1-continued
| Compound number | Structure |
|---|---|
| 537 | 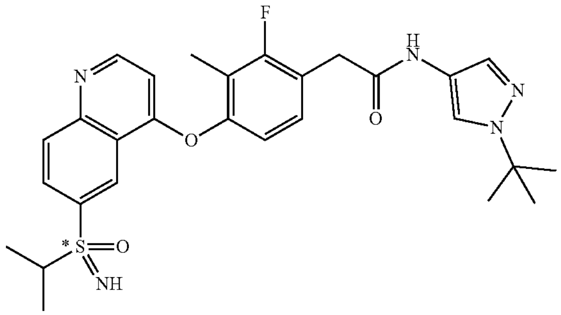 [SMILES: Cc1c(Oc2ccnc3ccc(S(=N)(=O)C(C)C)cc23)ccc(CC(=O)Nc2cnn(C(C)(C)C)c2)c1F] enantiomer 1 |
| 538 | 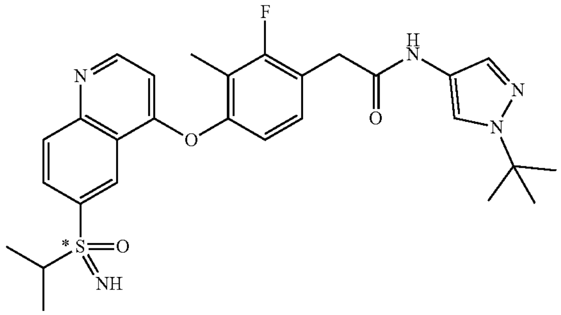 [SMILES: Cc1c(Oc2ccnc3ccc(S(=N)(=O)C(C)C)cc23)ccc(CC(=O)Nc2cnn(C(C)(C)C)c2)c1F] enantiomer 2 |
| 539 | 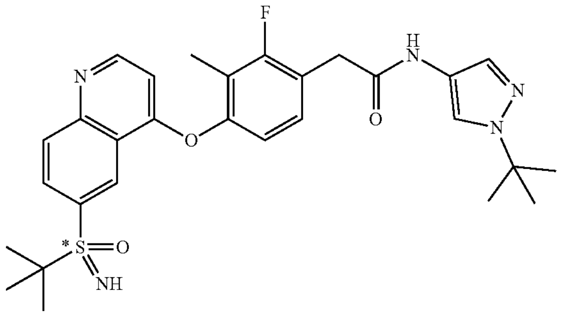 [SMILES: Cc1c(Oc2ccnc3ccc(S(=N)(=O)C(C)(C)C)cc23)ccc(CC(=O)Nc2cnn(C(C)(C)C)c2)c1F] enantiomer 1 |
| 540 | 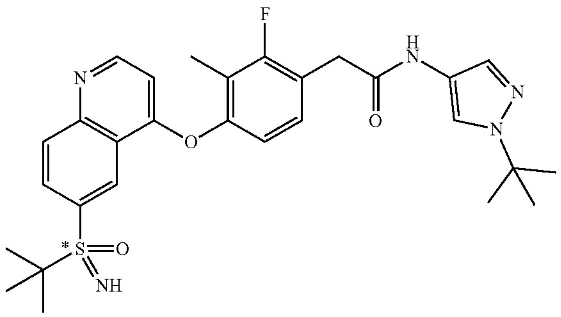 [SMILES: Cc1c(Oc2ccnc3ccc(S(=N)(=O)C(C)(C)C)cc23)ccc(CC(=O)Nc2cnn(C(C)(C)C)c2)c1F] enantiomer 2 |

TABLE 1-continued
| Compound number | Structure |
| --- | --- |
| 541 | 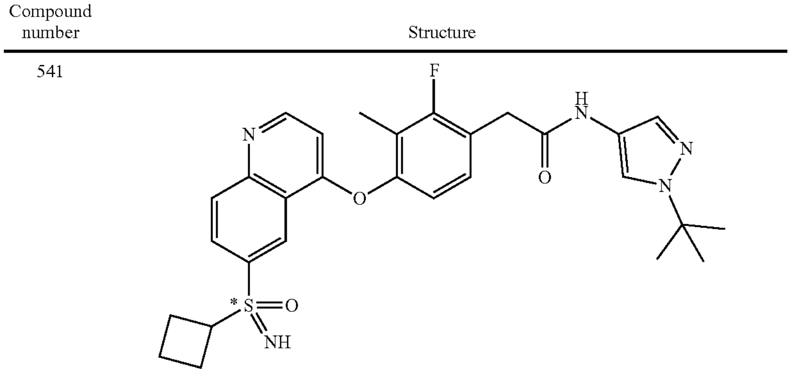 enantiomer 1 |
| 542 | 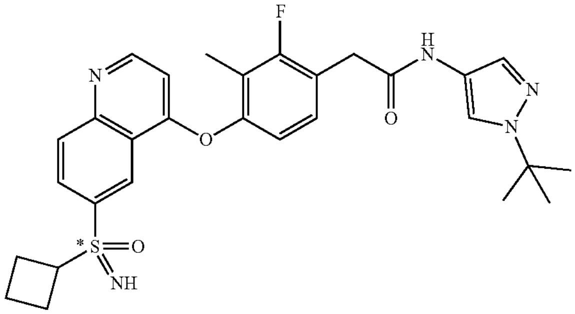 [SMILES: Cc1c(Oc2ccnc3ccc(S(=N)(=O)C4CCC4)cc23)ccc(CC(=O)Nc2cnn(C(C)(C)C)c2)c1F] enantiomer 2 |
| 543 | 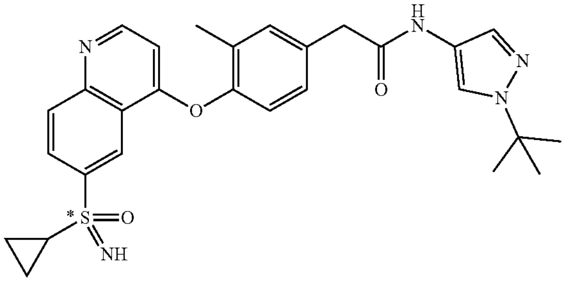 [SMILES: Cc1cc(CC(=O)Nc2cnn(C(C)(C)C)c2)ccc1Oc1ccnc2ccc(S(=N)(=O)C3CC3)cc12] enantiomer 1 |
| 544 | 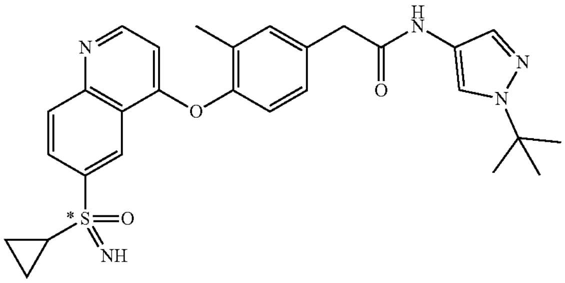 [SMILES: Cc1cc(CC(=O)Nc2cnn(C(C)(C)C)c2)ccc1Oc1ccnc2ccc(S(=N)(=O)C3CC3)cc12] enantiomer 2 |
| 545 | 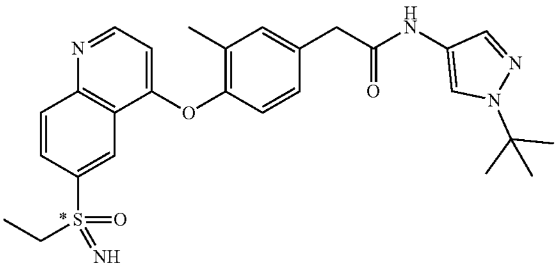 [SMILES: CCS(=N)(=O)c1ccc2nccc(Oc3ccc(CC(=O)Nc4cnn(C(C)(C)C)c4)cc3C)c2c1] enantiomer 1 |

TABLE 1-continued
| Compound number | Structure |
|---|---|
| 546 | 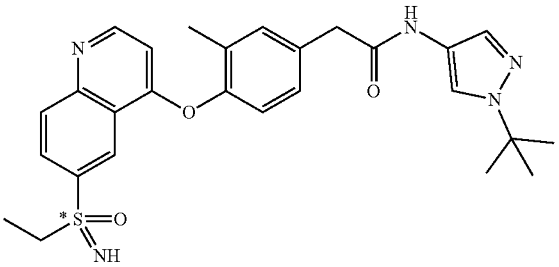 [SMILES: CCS(=N)(=O)c1ccc2nccc(Oc3ccc(CC(=O)Nc4cnn(C(C)(C)C)c4)cc3C)c2c1] enantiomer 2 |
| 547 | 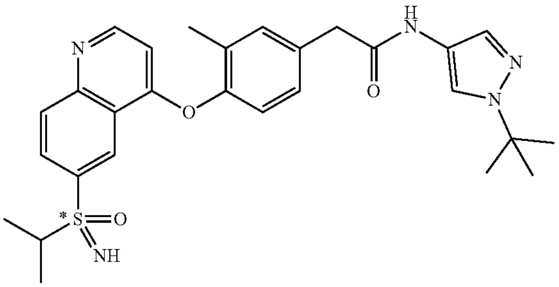 [SMILES: Cc1cc(CC(=O)Nc2cnn(C(C)(C)C)c2)ccc1Oc1ccnc2ccc(S(=N)(=O)C(C)C)cc12] enantiomer 1 |
| 548 | 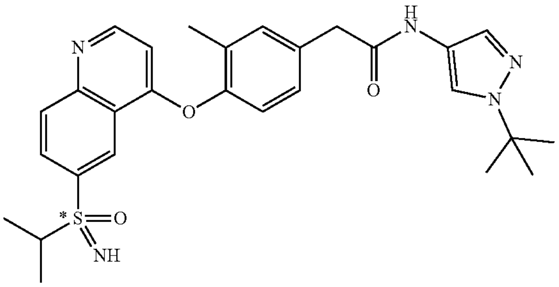 [SMILES: Cc1cc(CC(=O)Nc2cnn(C(C)(C)C)c2)ccc1Oc1ccnc2ccc(S(=N)(=O)C(C)C)cc12] enantiomer 2 |
| 549 | 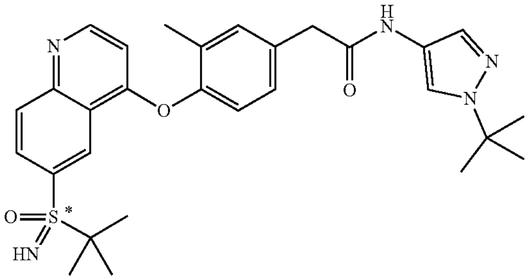 [SMILES: Cc1cc(CC(=O)Nc2cnn(C(C)(C)C)c2)ccc1Oc1ccnc2ccc(S(=N)(=O)C(C)(C)C)cc12] enantiomer 1 |
| 550 | 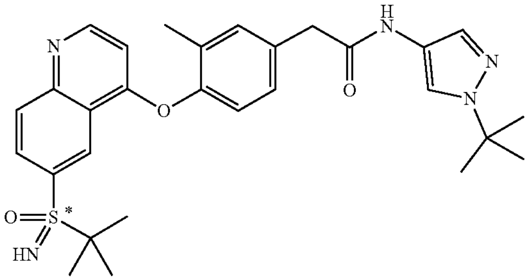 [SMILES: Cc1cc(CC(=O)Nc2cnn(C(C)(C)C)c2)ccc1Oc1ccnc2ccc(S(=N)(=O)C(C)(C)C)cc12] enantiomer 2 |

TABLE 1-continued
| Compound number | Structure |
|---|---|
| 551 | 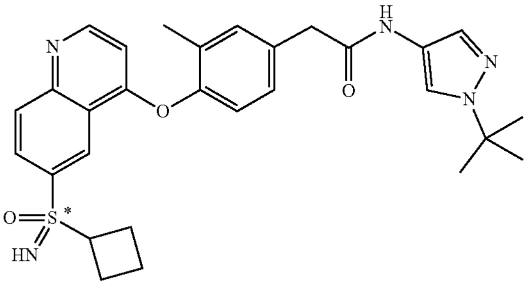 [SMILES: Cc1cc(CC(=O)Nc2cnn(C(C)(C)C)c2)ccc1Oc1ccnc2ccc(S(=N)(=O)C3CCC3)cc12] enantiomer 1 |
| 552 | 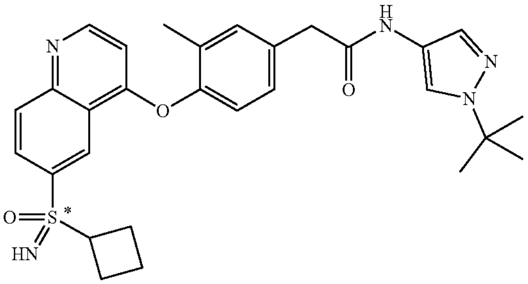 [SMILES: Cc1cc(CC(=O)Nc2cnn(C(C)(C)C)c2)ccc1Oc1ccnc2ccc(S(=N)(=O)C3CCC3)cc12] enantiomer 2 |
| 553 | 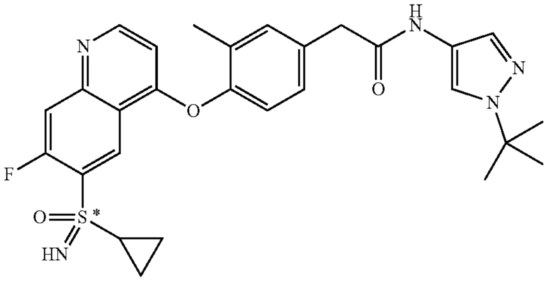 [SMILES: Cc1cc(CC(=O)Nc2cnn(C(C)(C)C)c2)ccc1Oc1ccnc2cc(F)c(S(=N)(=O)C3CC3)cc12] enantiomer 1 |
| 554 | 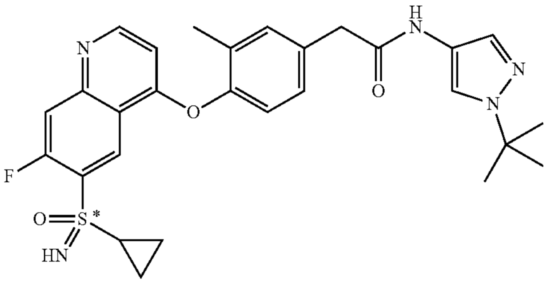 [SMILES: Cc1cc(CC(=O)Nc2cnn(C(C)(C)C)c2)ccc1Oc1ccnc2cc(F)c(S(=N)(=O)C3CC3)cc12] enantiomer 2 |

TABLE 1-continued
| Compound number | Structure |
|---|---|
| 555 | 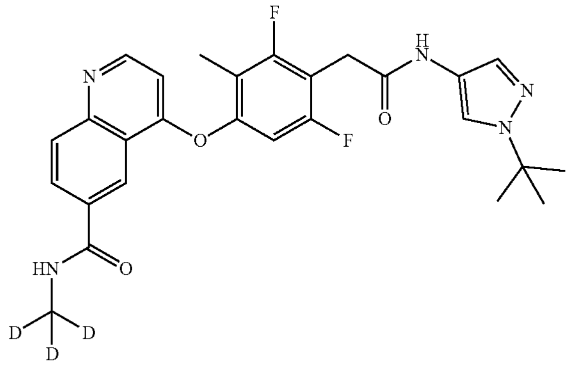 [SMILES: [2H]C([2H])([2H])NC(=O)c1ccc2nccc(Oc3cc(F)c(CC(=O)Nc4cnn(C(C)(C)C)c4)c(F)c3C)c2c1] enantiomer 1 |
| 556 | 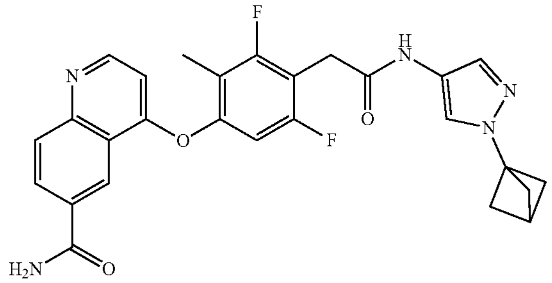 [SMILES: Cc1c(Oc2ccnc3ccc(C(N)=O)cc23)cc(F)c(CC(=O)Nc2cnn(C34CC(C3)C4)c2)c1F] |
| 557 | 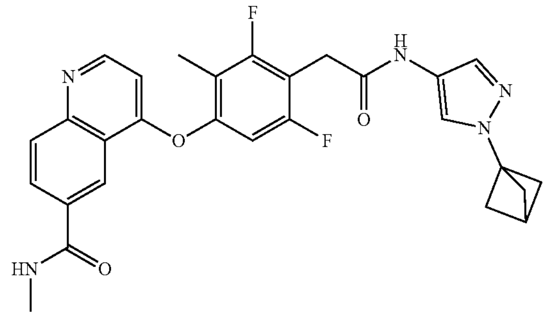 [SMILES: CNC(=O)c1ccc2nccc(Oc3cc(F)c(CC(=O)Nc4cnn(C56CC(C5)C6)c4)c(F)c3C)c2c1] |
| 558 | 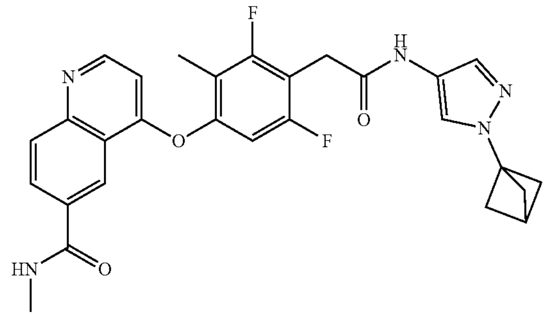 [SMILES: CNC(=O)c1ccc2nccc(Oc3cc(F)c(CC(=O)Nc4cnn(C56CC(C5)C6)c4)c(F)c3C)c2c1] |

TABLE 1-continued
| Compound number | Structure |
|---|---|
| 559 | 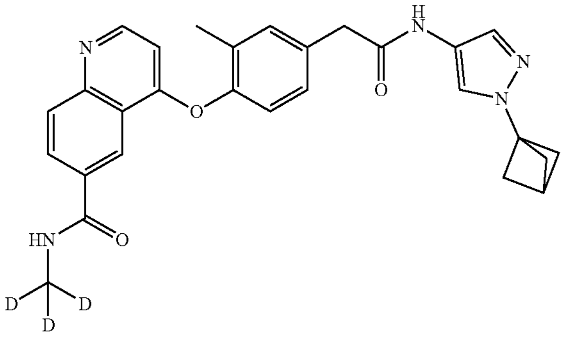 [SMILES: [2H]C([2H])([2H])NC(=O)c1ccc2nccc(Oc3ccc(CC(=O)Nc4cnn(C56CC(C5)C6)c4)cc3C)c2c1] |
| 560 | 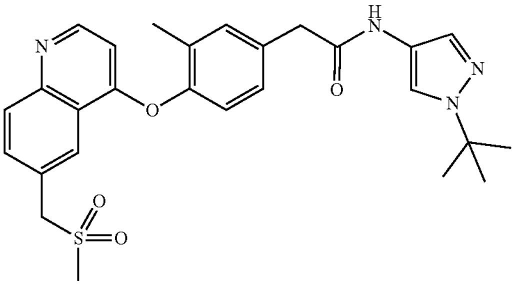 [SMILES: Cc1cc(CC(=O)Nc2cnn(C(C)(C)C)c2)ccc1Oc1ccnc2ccc(CS(C)(=O)=O)cc12] |
| 561 | 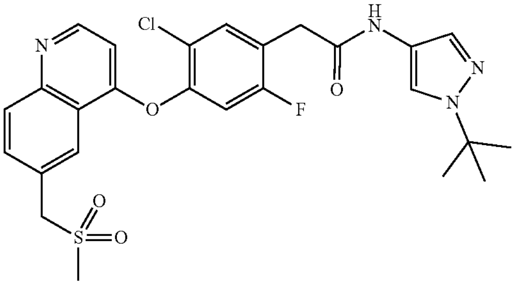 [SMILES: CC(C)(C)n1cc(NC(=O)Cc2cc(Cl)c(Oc3ccnc4ccc(CS(C)(=O)=O)cc34)cc2F)cn1] |
| 562 | 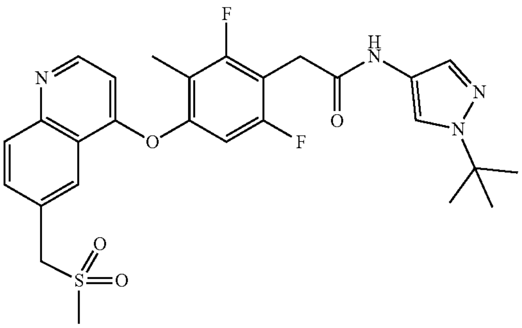 [SMILES: Cc1c(Oc2ccnc3ccc(CS(C)(=O)=O)cc23)cc(F)c(CC(=O)Nc2cnn(C(C)(C)C)c2)c1F] |

TABLE 1-continued
| Compound number | Structure |
|---|---|
| 563 | 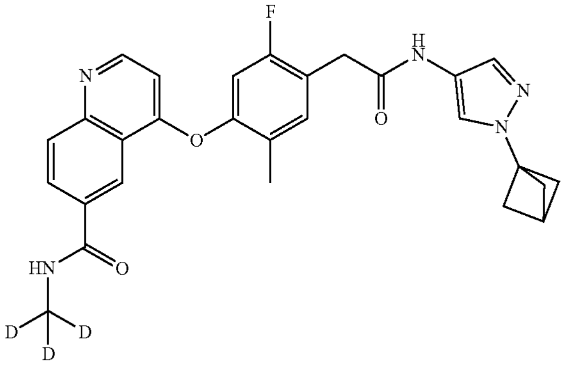 [SMILES: [2H]C([2H])([2H])NC(=O)c1ccc2nccc(Oc3cc(F)c(CC(=O)Nc4cnn(C56CC(C5)C6)c4)cc3C)c2c1] |
| 564 | 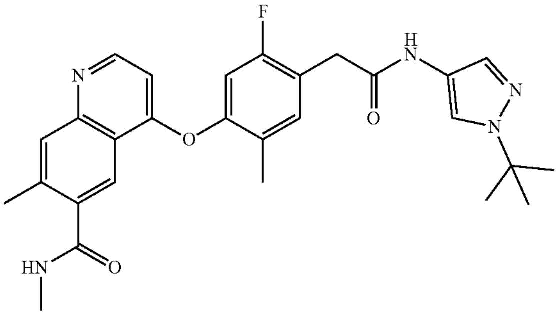 [SMILES: CNC(=O)c1cc2c(Oc3cc(F)c(CC(=O)Nc4cnn(C(C)(C)C)c4)cc3C)ccnc2cc1C] |
| 565 | 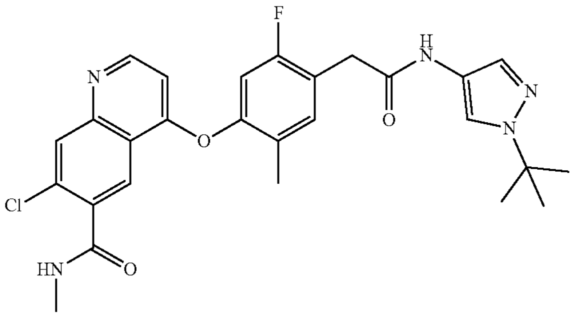 [SMILES: CNC(=O)c1cc2c(Oc3cc(F)c(CC(=O)Nc4cnn(C(C)(C)C)c4)cc3C)ccnc2cc1Cl] |
| 566 | 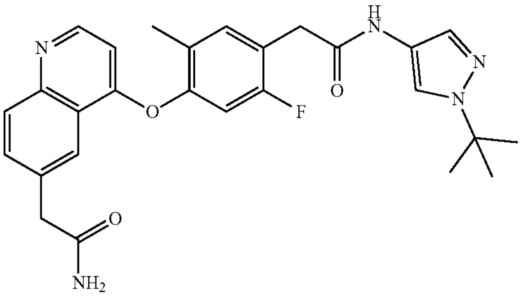 [SMILES: Cc1cc(CC(=O)Nc2cnn(C(C)(C)C)c2)c(F)cc1Oc1ccnc2ccc(CC(N)=O)cc12] |

TABLE 1-continued
| Compound number | Structure |
| --- | --- |
| 567 | 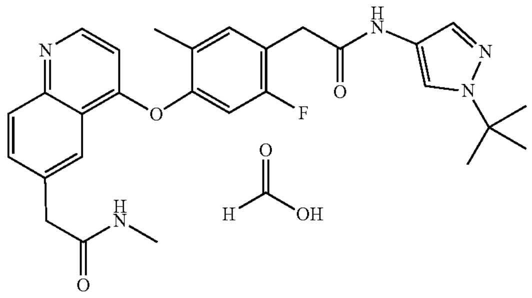 |
| 568 | 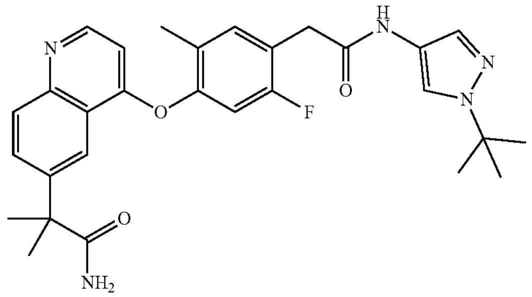 [SMILES: Cc1cc(CC(=O)Nc2cnn(C(C)(C)C)c2)c(F)cc1Oc1ccnc2ccc(C(C)(C)C(N)=O)cc12] |
| 569 | 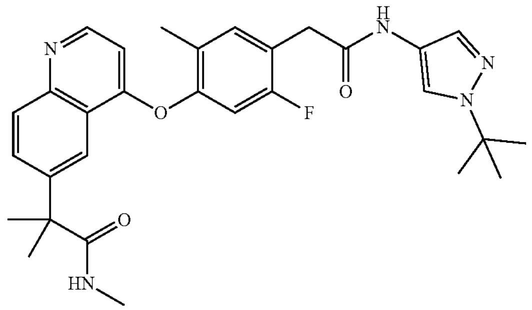 [SMILES: CNC(=O)C(C)(C)c1ccc2nccc(Oc3cc(F)c(CC(=O)Nc4cnn(C(C)(C)C)c4)cc3C)c2c1] |
| 570 | 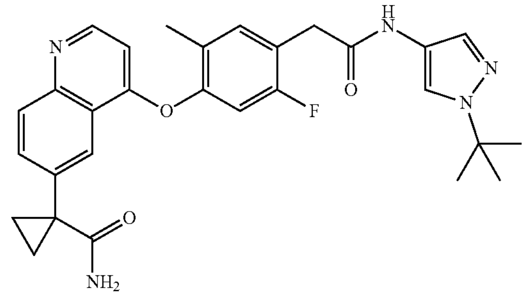 |
| 571 | 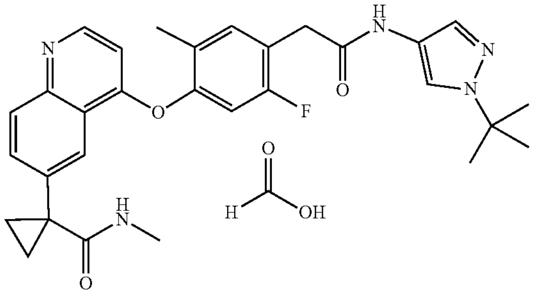 |

TABLE 1-continued
| Compound number | Structure |
| --- | --- |
| 572 | 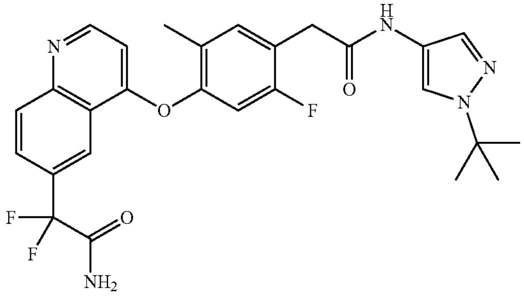 [SMILES: Cc1cc(CC(=O)Nc2cnn(C(C)(C)C)c2)c(F)cc1Oc1ccnc2ccc(C(F)(F)C(N)=O)cc12] |
| 573 | 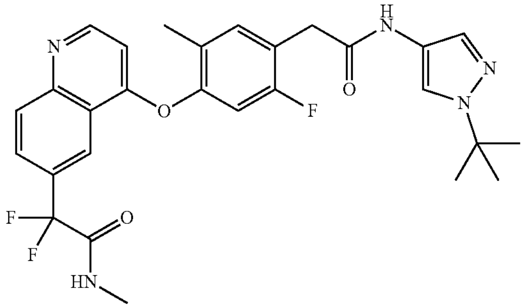 [SMILES: CNC(=O)C(F)(F)c1ccc2nccc(Oc3cc(F)c(CC(=O)Nc4cnn(C(C)(C)C)c4)cc3C)c2c1] |
| 574 | 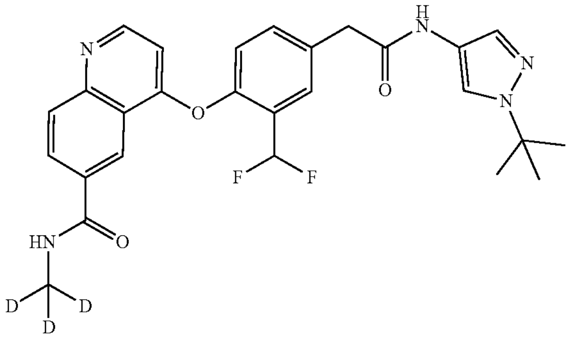 [SMILES: [2H]C([2H])([2H])NC(=O)c1ccc2nccc(Oc3ccc(CC(=O)Nc4cnn(C(C)(C)C)c4)cc3C(F)F)c2c1] |
| 575 | 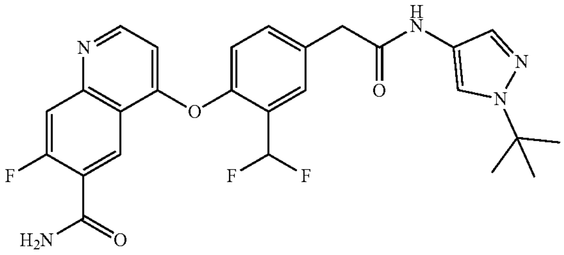 [SMILES: CC(C)(C)n1cc(NC(=O)Cc2ccc(Oc3ccnc4cc(F)c(C(N)=O)cc34)c(C(F)F)c2)cn1] |
| 576 | 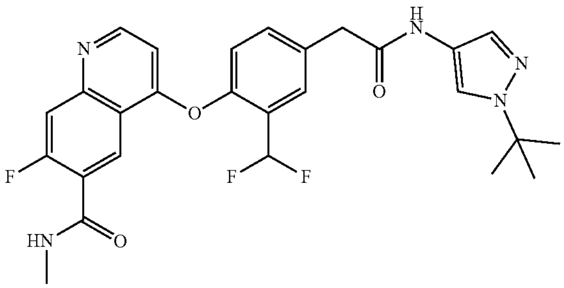 [SMILES: CNC(=O)c1cc2c(Oc3ccc(CC(=O)Nc4cnn(C(C)(C)C)c4)cc3C(F)F)ccnc2cc1F] |

TABLE 1-continued
| Compound number | Structure |
|---|---|
| 577 | 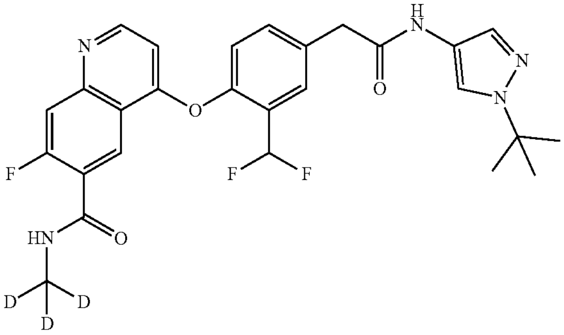 [SMILES: [2H]C([2H])([2H])NC(=O)c1cc2c(Oc3ccc(CC(=O)Nc4cnn(C(C)(C)C)c4)cc3C(F)F)ccnc2cc1F] |
| 578 | 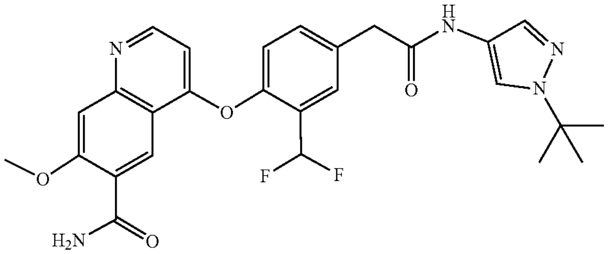 |
| 579 | 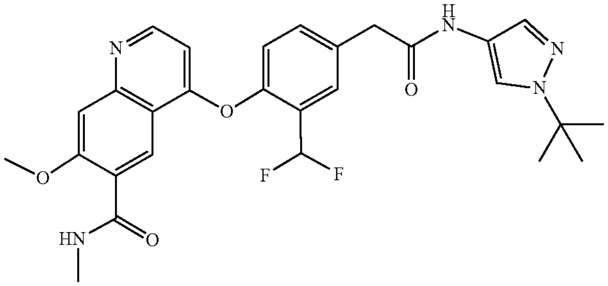 [SMILES: CNC(=O)c1cc2c(Oc3ccc(CC(=O)Nc4cnn(C(C)(C)C)c4)cc3C(F)F)ccnc2cc1OC] |
| 580 | 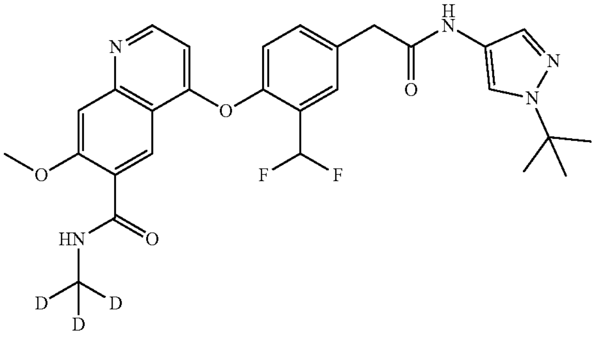 [SMILES: [2H]C([2H])([2H])NC(=O)c1cc2c(Oc3ccc(CC(=O)Nc4cnn(C(C)(C)C)c4)cc3C(F)F)ccnc2cc1OC] |
| 581 | 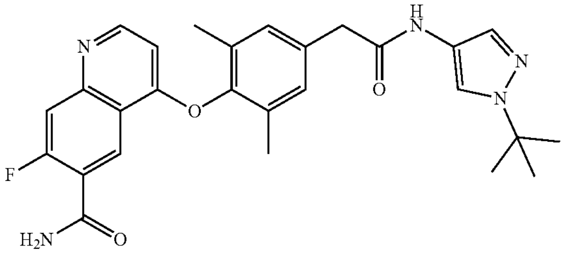 [SMILES: Cc1cc(CC(=O)Nc2cnn(C(C)(C)C)c2)cc(C)c1Oc1ccnc2cc(F)c(C(N)=O)cc12] |

TABLE 1-continued
| Compound number | Structure |
|---|---|
| 582 | 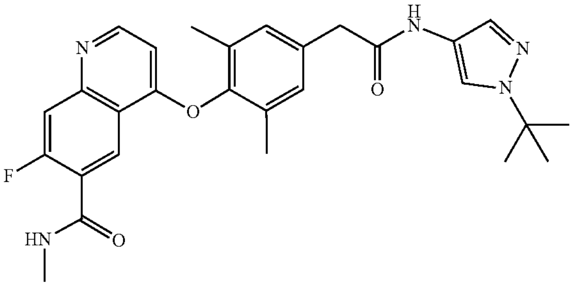 [SMILES: CNC(=O)c1cc2c(Oc3c(C)cc(CC(=O)Nc4cnn(C(C)(C)C)c4)cc3C)ccnc2cc1F] |
| 583 | 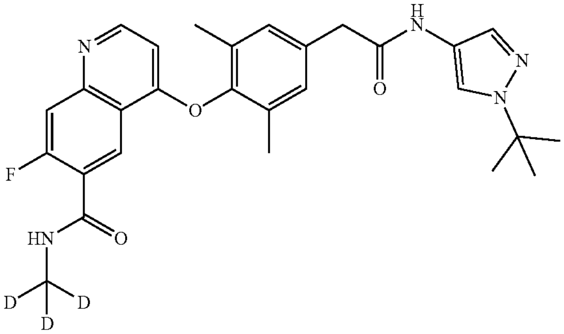 [SMILES: [2H]C([2H])([2H])NC(=O)c1cc2c(Oc3c(C)cc(CC(=O)Nc4cnn(C(C)(C)C)c4)cc3C)ccnc2cc1F] |
| 584 | 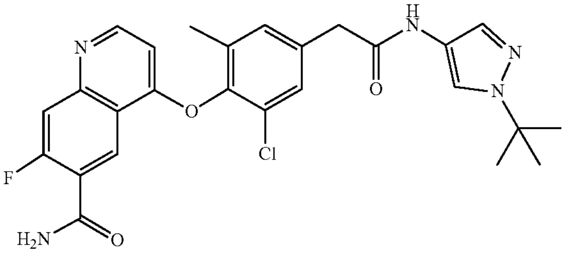 [SMILES: Cc1cc(CC(=O)Nc2cnn(C(C)(C)C)c2)cc(Cl)c1Oc1ccnc2cc(F)c(C(N)=O)cc12] |
| 585 | 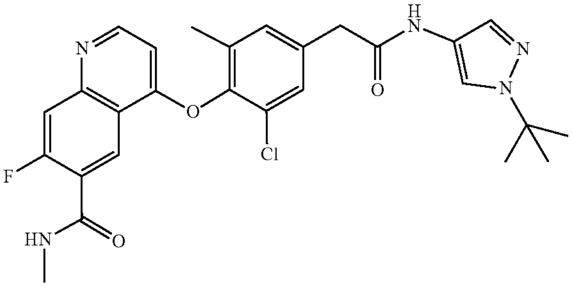 [SMILES: CNC(=O)c1cc2c(Oc3c(C)cc(CC(=O)Nc4cnn(C(C)(C)C)c4)cc3Cl)ccnc2cc1F] |
| 586 | 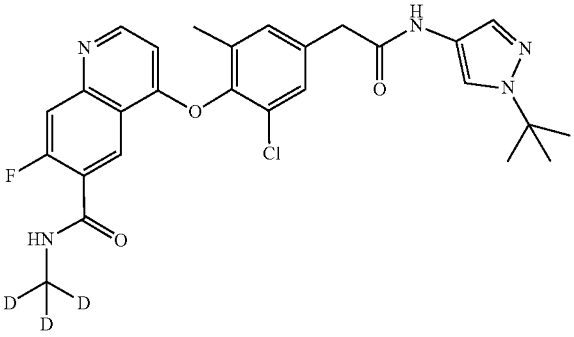 |

TABLE 1-continued
| Compound number | Structure |
|---|---|
| 587 | 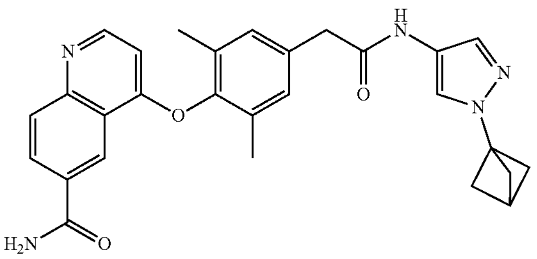 [SMILES: Cc1cc(CC(=O)Nc2cnn(C34CC(C3)C4)c2)cc(C)c1Oc1ccnc2ccc(C(N)=O)cc12] |
| 588 | 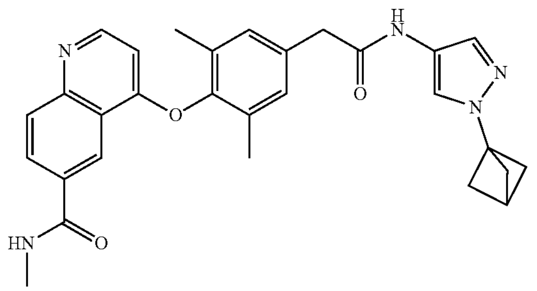 [SMILES: CNC(=O)c1ccc2nccc(Oc3c(C)cc(CC(=O)Nc4cnn(C56CC(C5)C6)c4)cc3C)c2c1] |
| 589 | 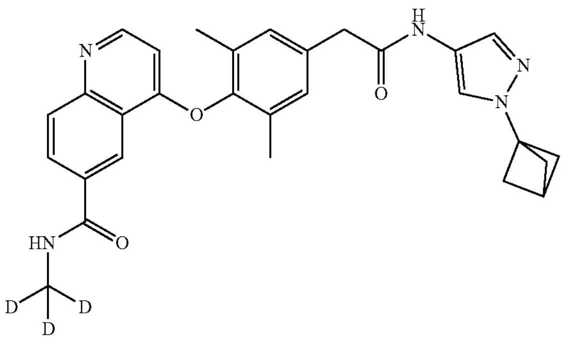 [SMILES: [2H]C([2H])([2H])NC(=O)c1ccc2nccc(Oc3c(C)cc(CC(=O)Nc4cnn(C56CC(C5)C6)c4)cc3C)c2c1] |
| 590 | 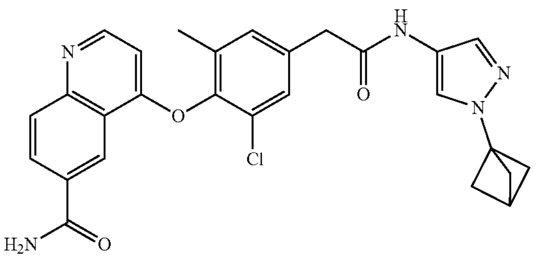 [SMILES: Cc1cc(CC(=O)Nc2cnn(C34CC(C3)C4)c2)cc(Cl)c1Oc1ccnc2ccc(C(N)=O)cc12] |
| 591 | 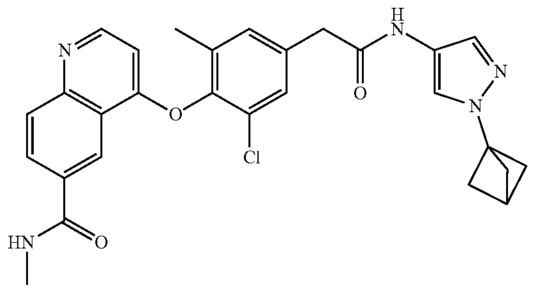 [SMILES: CNC(=O)c1ccc2nccc(Oc3c(C)cc(CC(=O)Nc4cnn(C56CC(C5)C6)c4)cc3Cl)c2c1] |

TABLE 1-continued
| Compound number | Structure |
| --- | --- |
| 592 | 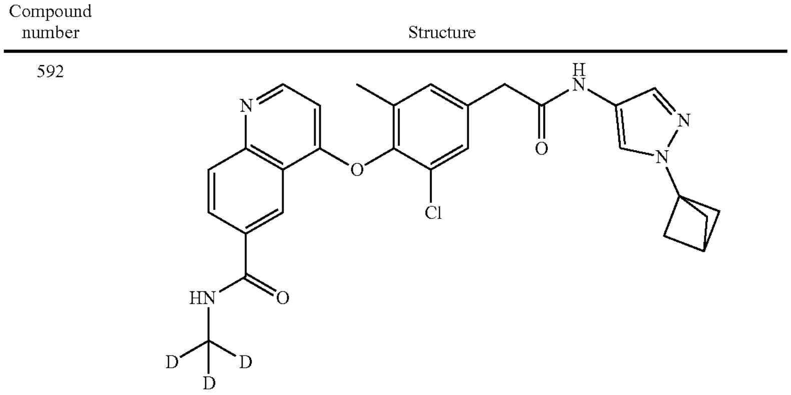 |
| 593 | 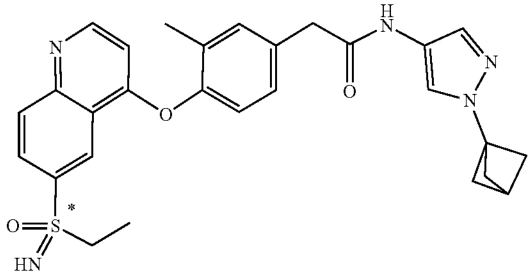 [SMILES: CCS(=N)(=O)c1ccc2nccc(Oc3ccc(CC(=O)Nc4cnn(C56CC(C5)C6)c4)cc3C)c2c1]<br>enantiomer 2 |
| 594 | 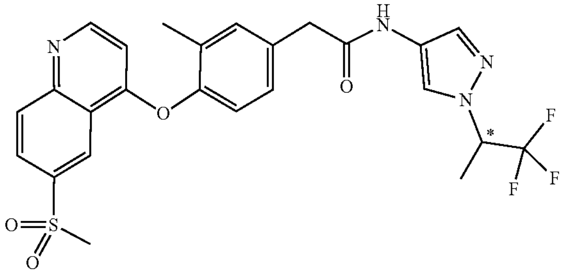 [SMILES: Cc1cc(CC(=O)Nc2cnn(C(C)C(F)(F)F)c2)ccc1Oc1ccnc2ccc(S(C)(=O)=O)cc12]<br>enantiomer 1 |
| 595 | 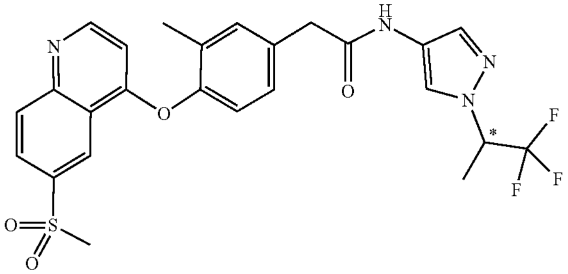 [SMILES: Cc1cc(CC(=O)Nc2cnn(C(C)C(F)(F)F)c2)ccc1Oc1ccnc2ccc(S(C)(=O)=O)cc12]<br>enantiomer 2 |
| 596 | 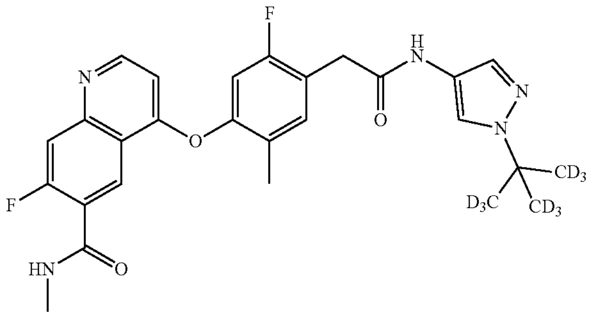 [SMILES: [2H]C([2H])([2H])C(n1cc(NC(=O)Cc2cc(C)c(Oc3ccnc4cc(F)c(C(=O)NC)cc34)cc2F)cn1)(C([2H])([2H])[2H])C([2H])([2H])[2H]] |

TABLE 1-continued
| Compound number | Structure |
|---|---|
| 597 | 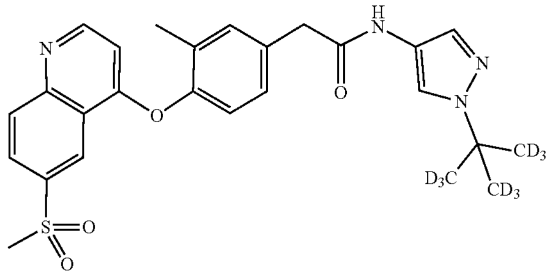 [SMILES: [2H]C([2H])([2H])C(n1cc(NC(=O)Cc2ccc(Oc3ccnc4ccc(S(C)(=O)=O)cc34)c(C)c2)cn1)(C([2H])([2H])[2H])C([2H])([2H])[2H]] |
| 598 | 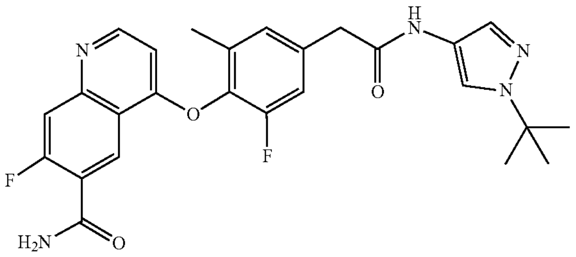 [SMILES: Cc1cc(CC(=O)Nc2cnn(C(C)(C)C)c2)cc(F)c1Oc1ccnc2cc(F)c(C(N)=O)cc12] |
| 599 | 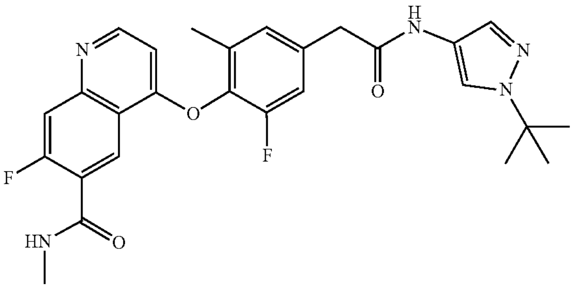 |
| 600 | 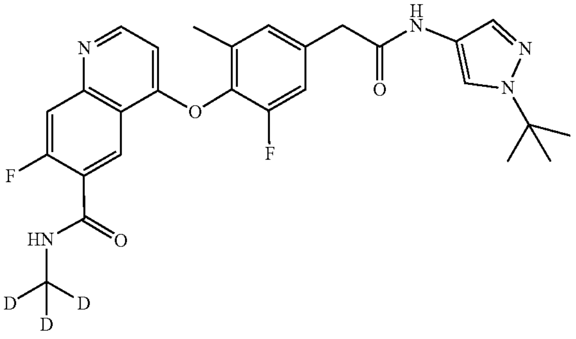 [SMILES: [2H]C([2H])([2H])NC(=O)c1cc2c(Oc3c(C)cc(CC(=O)Nc4cnn(C(C)(C)C)c4)cc3F)ccnc2cc1F] |
| 601 | 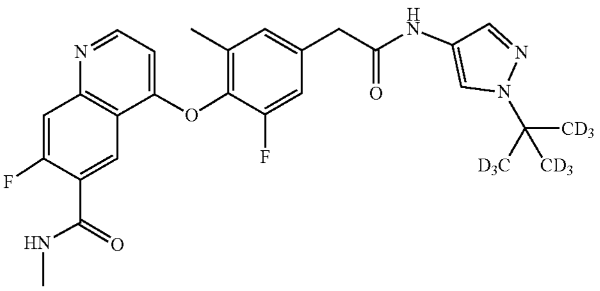 [SMILES: [2H]C([2H])([2H])C(n1cc(NC(=O)Cc2cc(C)c(Oc3ccnc4cc(F)c(C(=O)NC)cc34)c(F)c2)cn1)(C([2H])([2H])[2H])C([2H])([2H])[2H]] |

TABLE 1-continued
| Compound number | Structure |
| --- | --- |
| 602 | 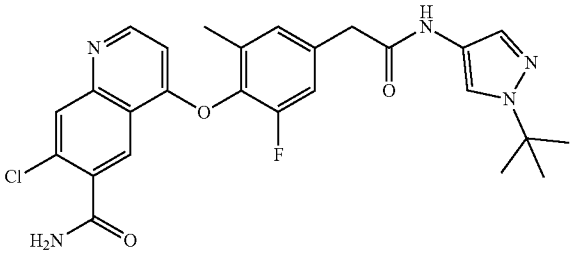 [SMILES: Cc1cc(CC(=O)Nc2cnn(C(C)(C)C)c2)cc(F)c1Oc1ccnc2cc(Cl)c(C(N)=O)cc12] |
| 603 | 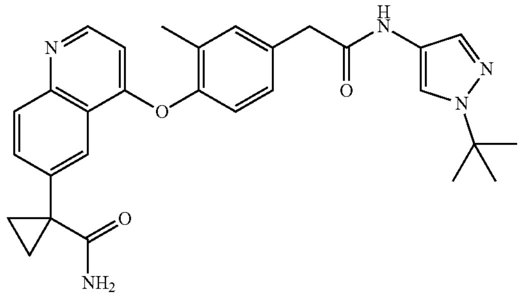 [SMILES: Cc1cc(CC(=O)Nc2cnn(C(C)(C)C)c2)ccc1Oc1ccnc2ccc(C3(C(N)=O)CC3)cc12] |
| 604 | 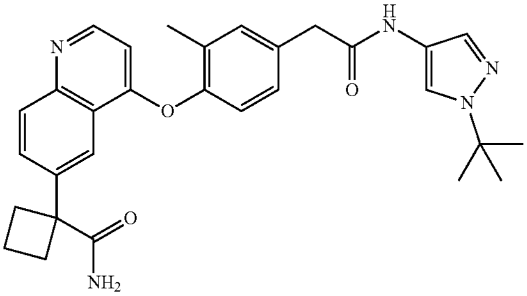 [SMILES: Cc1cc(CC(=O)Nc2cnn(C(C)(C)C)c2)ccc1Oc1ccnc2ccc(C3(C(N)=O)CCC3)cc12] |
| 605 | 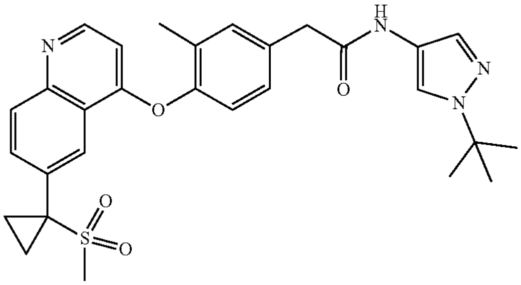 [SMILES: Cc1cc(CC(=O)Nc2cnn(C(C)(C)C)c2)ccc1Oc1ccnc2ccc(C3(S(C)(=O)=O)CC3)cc12] |
| 606 | 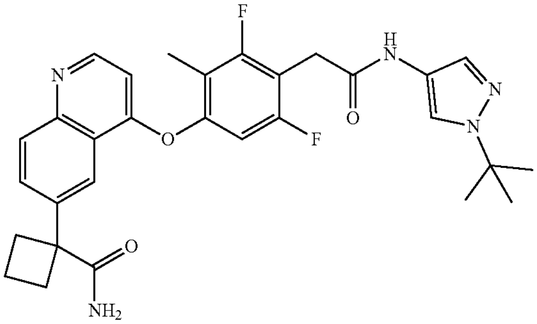 [SMILES: Cc1c(Oc2ccnc3ccc(C4(C(N)=O)CCC4)cc23)cc(F)c(CC(=O)Nc2cnn(C(C)(C)C)c2)c1F] |

TABLE 1-continued
| Compound number | Structure |
|---|---|
| 607 | 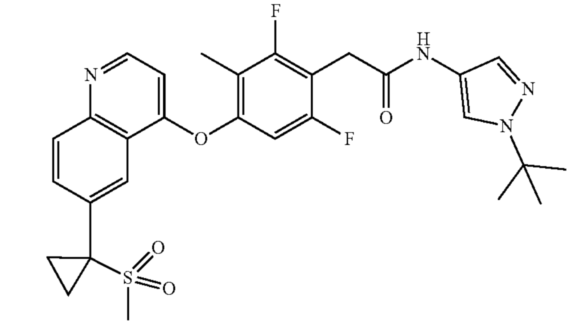 [SMILES: Cc1c(Oc2ccnc3ccc(C4(S(C)(=O)=O)CC4)cc23)cc(F)c(CC(=O)Nc2cnn(C(C)(C)C)c2)c1F] |
| 608 | 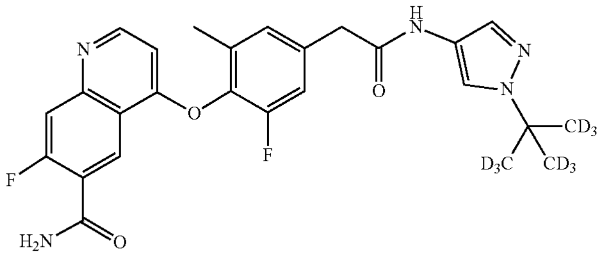 [SMILES: [2H]C([2H])([2H])C(n1cc(NC(=O)Cc2cc(C)c(Oc3ccnc4cc(F)c(C(N)=O)cc34)c(F)c2)cn1)(C([2H])([2H])[2H])C([2H])([2H])[2H]] |
| 609 | 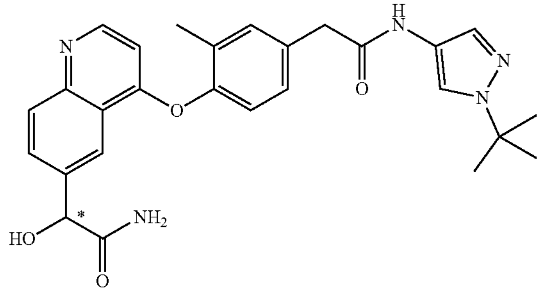 [SMILES: Cc1cc(CC(=O)Nc2cnn(C(C)(C)C)c2)ccc1Oc1ccnc2ccc(C(O)C(N)=O)cc12] enantiomer 1 |
| 610 | 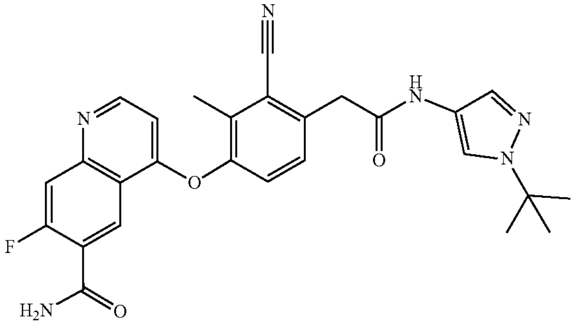 [SMILES: Cc1c(Oc2ccnc3cc(F)c(C(N)=O)cc23)ccc(CC(=O)Nc2cnn(C(C)(C)C)c2)c1C#N] |

TABLE 1-continued
| Compound number | Structure |
|---|---|
| 611 | 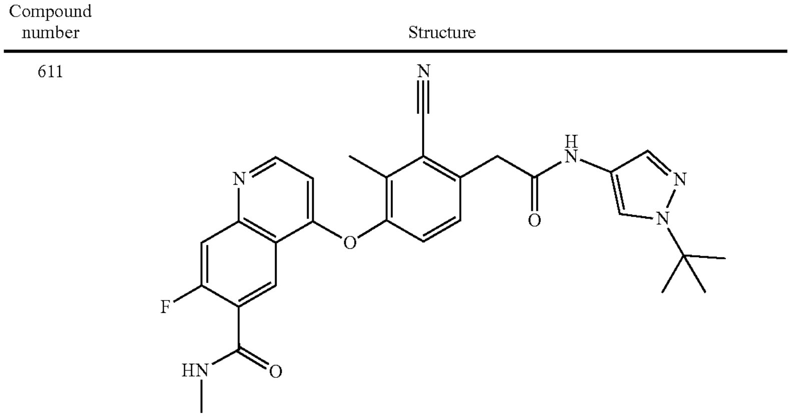 |
| 612 | 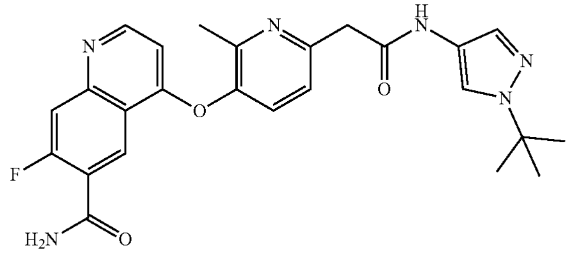 [SMILES: Cc1nc(CC(=O)Nc2cnn(C(C)(C)C)c2)ccc1Oc1ccnc2cc(F)c(C(N)=O)cc12] |
| 613 | 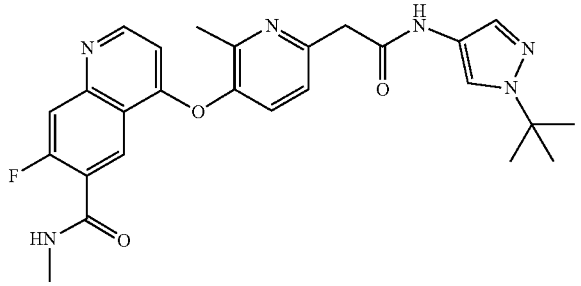 [SMILES: CNC(=O)c1cc2c(Oc3ccc(CC(=O)Nc4cnn(C(C)(C)C)c4)nc3C)ccnc2cc1F] |
| 614 | 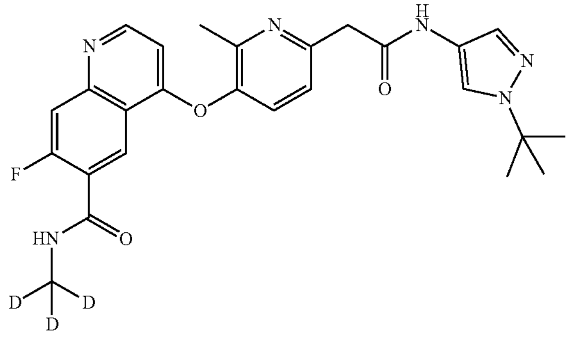 [SMILES: [2H]C([2H])([2H])NC(=O)c1cc2c(Oc3ccc(CC(=O)Nc4cnn(C(C)(C)C)c4)nc3C)ccnc2cc1F] |
| 615 | 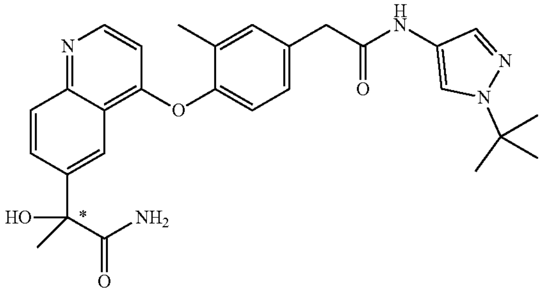 [SMILES: Cc1cc(CC(=O)Nc2cnn(C(C)(C)C)c2)ccc1Oc1ccnc2ccc(C(C)(O)C(N)=O)cc12]<br>enantiomer 1 |

TABLE 1-continued
| Compound number | Structure |
|---|---|
| 616 | 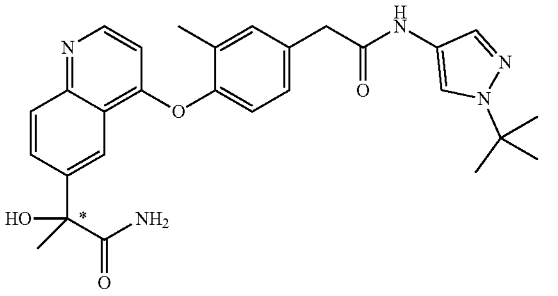 [SMILES: Cc1cc(CC(=O)Nc2cnn(C(C)(C)C)c2)ccc1Oc1ccnc2ccc(C(C)(O)C(N)=O)cc12] enantiomer 2 |
| 617 | 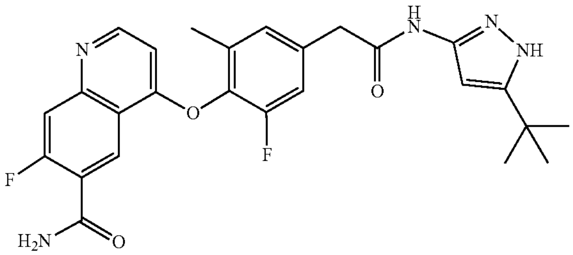 [SMILES: Cc1cc(CC(=O)Nc2cc(C(C)(C)C)[nH]n2)cc(F)c1Oc1ccnc2cc(F)c(C(N)=O)cc12] |
| 618 | 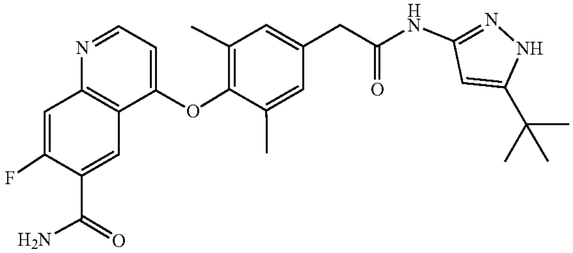 [SMILES: Cc1cc(CC(=O)Nc2cc(C(C)(C)C)[nH]n2)cc(C)c1Oc1ccnc2cc(F)c(C(N)=O)cc12] |
| 619 | 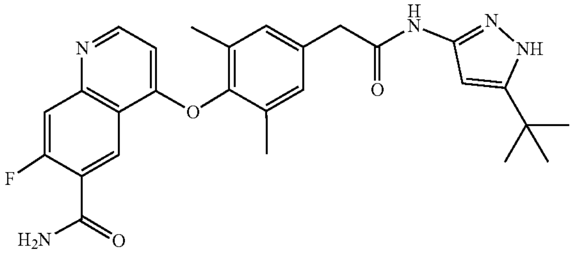 [SMILES: Cc1cc(CC(=O)Nc2cc(C(C)(C)C)[nH]n2)cc(C)c1Oc1ccnc2cc(F)c(C(N)=O)cc12] |
| 620 | 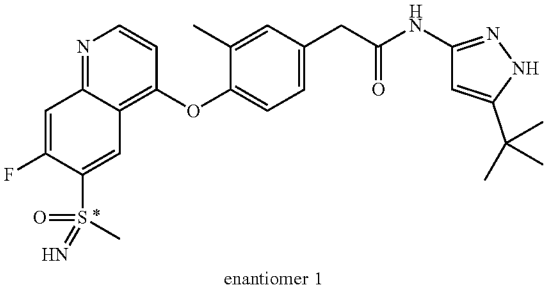 enantiomer 1 |

TABLE 1-continued
| Compound number | Structure |
|---|---|
| 621 | 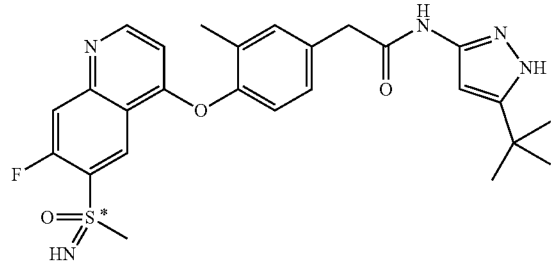 [SMILES: Cc1cc(CC(=O)Nc2cc(C(C)(C)C)[nH]n2)ccc1Oc1ccnc2cc(F)c(S(C)(=N)=O)cc12] enantiomer 2 |
| 622 | 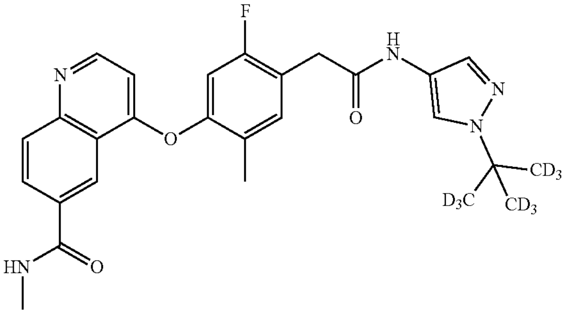 [SMILES: [2H]C([2H])([2H])C(n1cc(NC(=O)Cc2cc(C)c(Oc3ccnc4ccc(C(=O)NC)cc34)cc2F)cn1)(C([2H])([2H])[2H])C([2H])([2H])[2H]] |
In a thirty-fifth aspect of the first embodiment, the compound is selected from the compounds in Table 2.
TABLE 2
| Compound number | Structure |
|---|---|
| 2 | 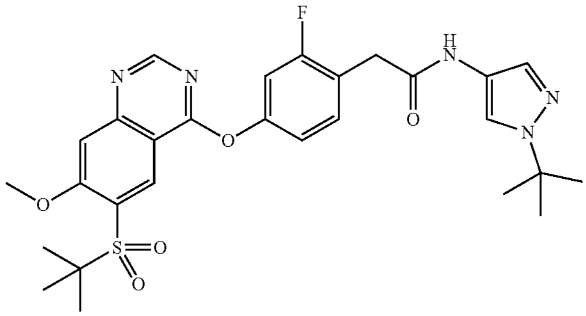 [SMILES: COc1cc2ncnc(Oc3ccc(CC(=O)Nc4cnn(C(C)(C)C)c4)c(F)c3)c2cc1S(=O)(=O)C(C)(C)C] |
| 3 | 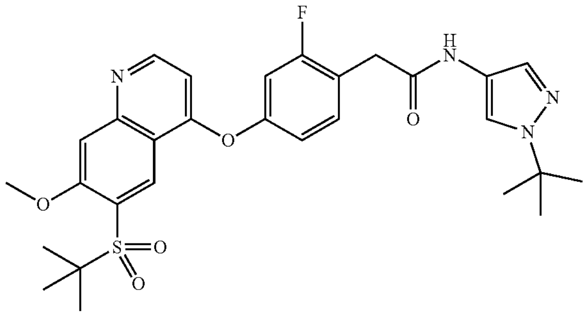 [SMILES: COc1cc2nccc(Oc3ccc(CC(=O)Nc4cnn(C(C)(C)C)c4)c(F)c3)c2cc1S(=O)(=O)C(C)(C)C] |

TABLE 2-continued
| Compound number | Structure |
| --- | --- |
| 40 | 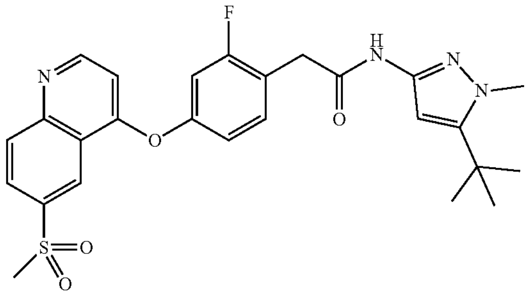 [SMILES: Cn1nc(NC(=O)Cc2ccc(Oc3ccnc4ccc(S(C)(=O)=O)cc34)cc2F)cc1C(C)(C)C] |
| 46 | 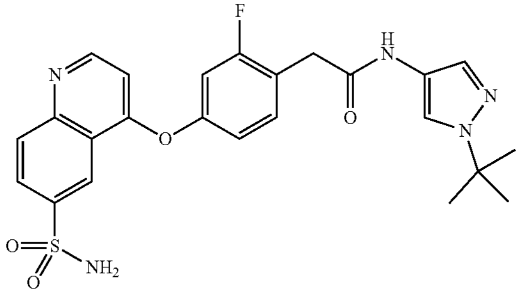 [SMILES: CC(C)(C)n1cc(NC(=O)Cc2ccc(Oc3ccnc4ccc(S(N)(=O)=O)cc34)cc2F)cn1] |
| 66 | 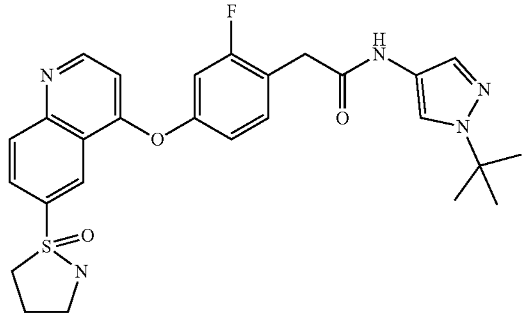 |
| 67 | 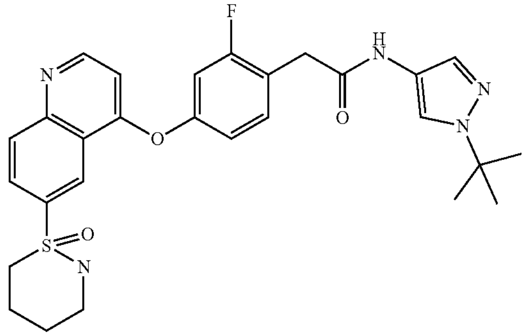 |
| 72 | 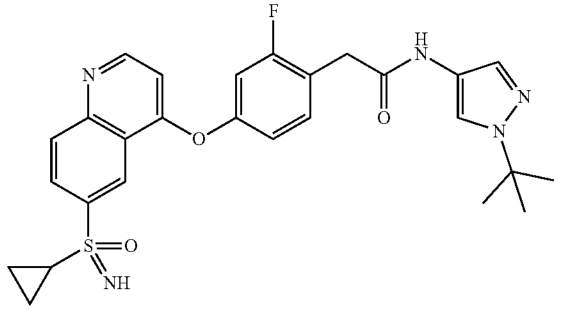 [SMILES: CC(C)(C)n1cc(NC(=O)Cc2ccc(Oc3ccnc4ccc(S(=N)(=O)C5CC5)cc34)cc2F)cn1] |

TABLE 2-continued
| Compound number | Structure |
| --- | --- |
| 79 | 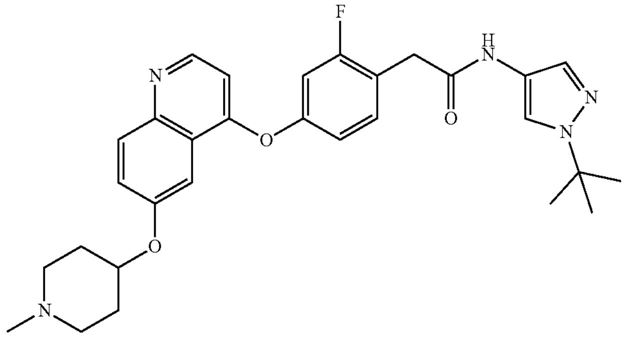 [SMILES: CN1CCC(Oc2ccc3nccc(Oc4ccc(CC(=O)Nc5cnn(C(C)(C)C)c5)c(F)c4)c3c2)CC1] |
| 81 | 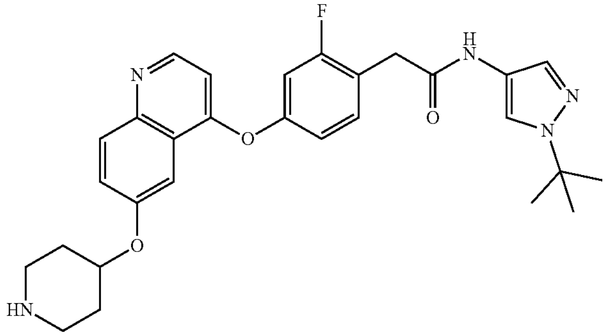 [SMILES: CC(C)(C)n1cc(NC(=O)Cc2ccc(Oc3ccnc4ccc(OC5CCNCC5)cc34)cc2F)cn1] |
| 82 | 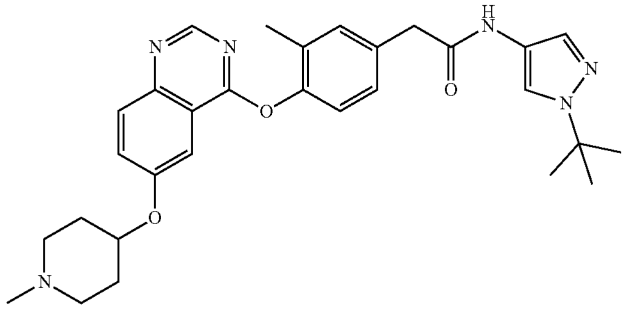 [SMILES: Cc1cc(CC(=O)Nc2cnn(C(C)(C)C)c2)ccc1Oc1ncnc2ccc(OC3CCN(C)CC3)cc12] |
| 83 | 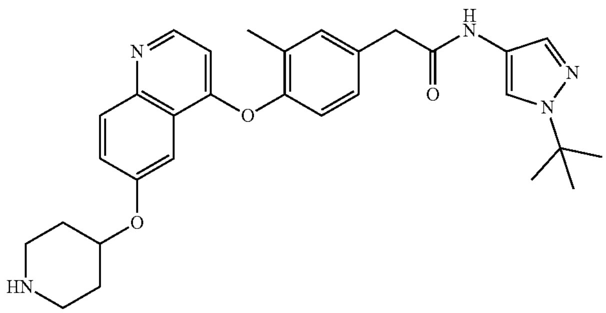 |

TABLE 2-continued
| Compound number | Structure |
| --- | --- |
| 86 | 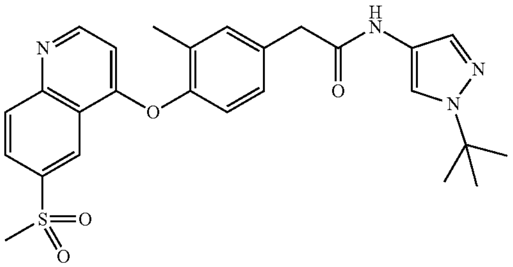 [SMILES: Cc1cc(CC(=O)Nc2cnn(C(C)(C)C)c2)ccc1Oc1ccnc2ccc(S(C)(=O)=O)cc12] |
| 87 | 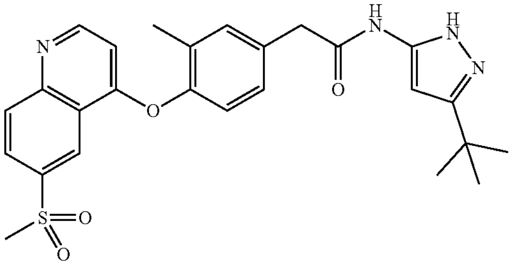 [SMILES: Cc1cc(CC(=O)Nc2cc(C(C)(C)C)n[nH]2)ccc1Oc1ccnc2ccc(S(C)(=O)=O)cc12] |
| 89 | 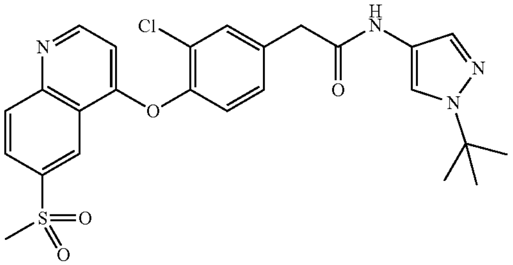 [SMILES: CC(C)(C)n1cc(NC(=O)Cc2ccc(Oc3ccnc4ccc(S(C)(=O)=O)cc34)c(Cl)c2)cn1] |
| 91 | 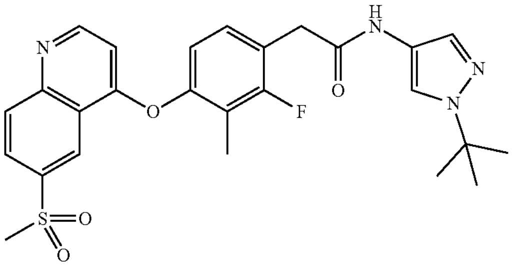 [SMILES: Cc1c(Oc2ccnc3ccc(S(C)(=O)=O)cc23)ccc(CC(=O)Nc2cnn(C(C)(C)C)c2)c1F] |
| 93 | 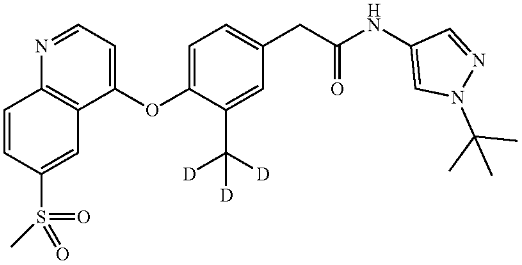 [SMILES: [2H]C([2H])([2H])c1cc(CC(=O)Nc2cnn(C(C)(C)C)c2)ccc1Oc1ccnc2ccc(S(C)(=O)=O)cc12] |

TABLE 2-continued
| Compound number | Structure |
|---|---|
| 94 | 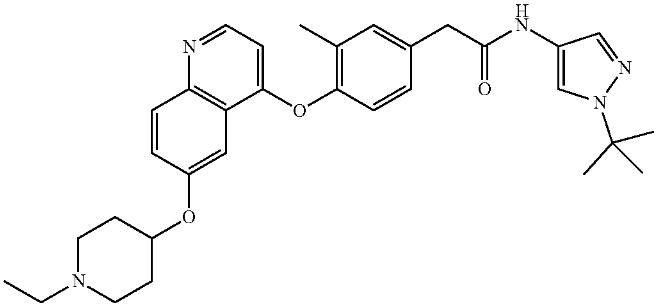 [SMILES: CCN1CCC(Oc2ccc3nccc(Oc4ccc(CC(=O)Nc5cnn(C(C)(C)C)c5)cc4C)c3c2)CC1] |
| 95 | 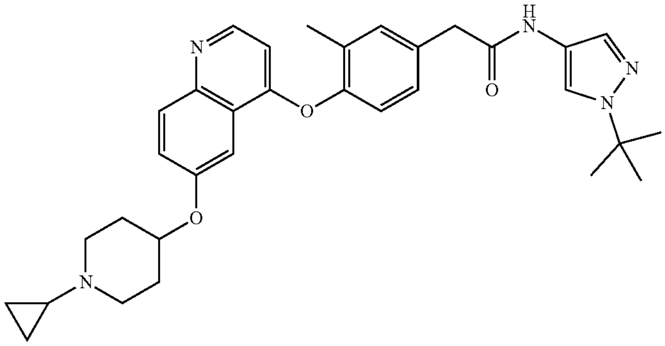 [SMILES: Cc1cc(CC(=O)Nc2cnn(C(C)(C)C)c2)ccc1Oc1ccnc2ccc(OC3CCN(C4CC4)CC3)cc12] |
| 96 | 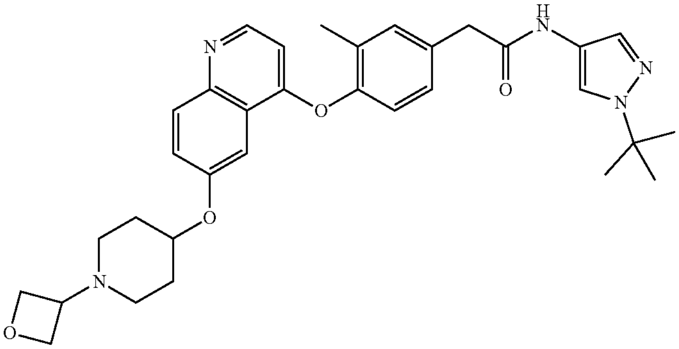 [SMILES: Cc1cc(CC(=O)Nc2cnn(C(C)(C)C)c2)ccc1Oc1ccnc2ccc(OC3CCN(C4COC4)CC3)cc12] |
| 97 | 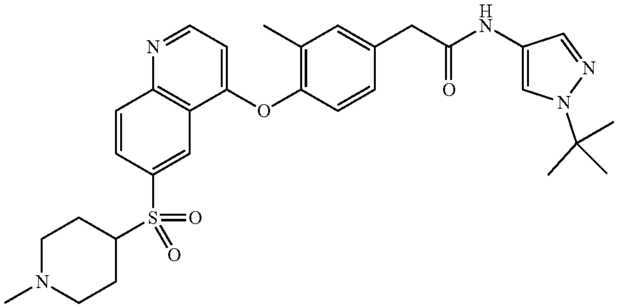 [SMILES: Cc1cc(CC(=O)Nc2cnn(C(C)(C)C)c2)ccc1Oc1ccnc2ccc(S(=O)(=O)C3CCN(C)CC3)cc12] |

TABLE 2-continued
| Compound number | Structure |
| --- | --- |
| 98 | 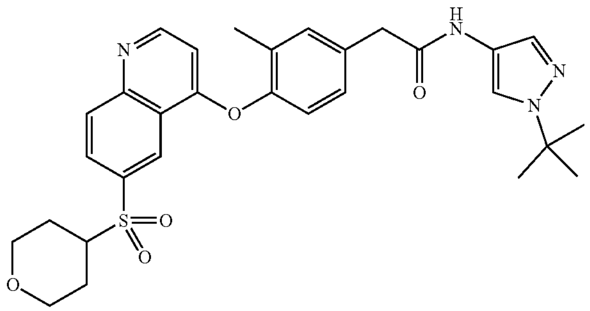 [SMILES: Cc1cc(CC(=O)Nc2cnn(C(C)(C)C)c2)ccc1Oc1ccnc2ccc(S(=O)(=O)C3CCOCC3)cc12] |
| 99 | 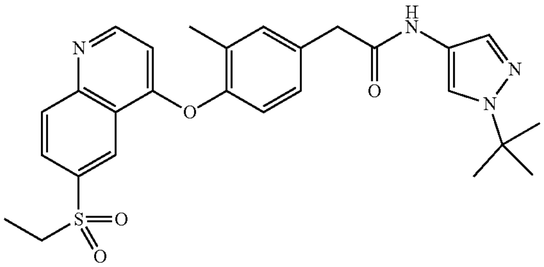 [SMILES: CCS(=O)(=O)c1ccc2nccc(Oc3ccc(CC(=O)Nc4cnn(C(C)(C)C)c4)cc3C)c2c1] |
| 100 | 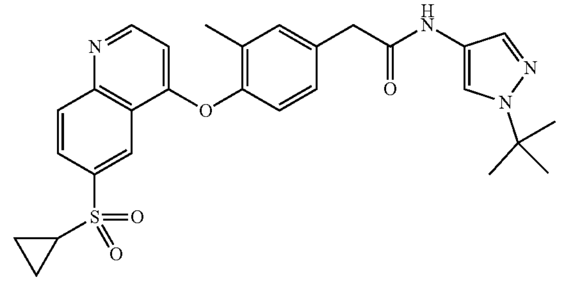 [SMILES: Cc1cc(CC(=O)Nc2cnn(C(C)(C)C)c2)ccc1Oc1ccnc2ccc(S(=O)(=O)C3CC3)cc12] |
| 101 | 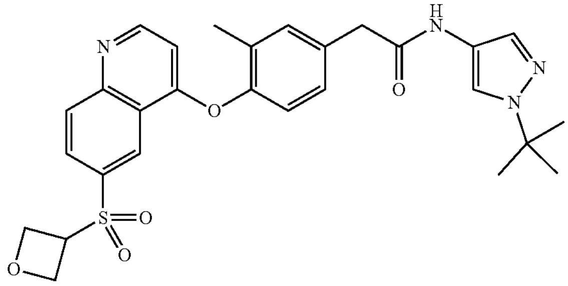 [SMILES: Cc1cc(CC(=O)Nc2cnn(C(C)(C)C)c2)ccc1Oc1ccnc2ccc(S(=O)(=O)C3COC3)cc12] |
| 102 | 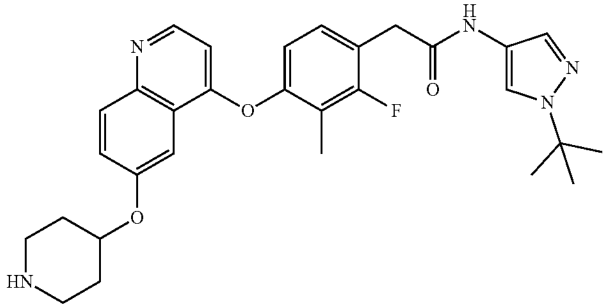 [SMILES: Cc1c(Oc2ccnc3ccc(OC4CCNCC4)cc23)ccc(CC(=O)Nc2cnn(C(C)(C)C)c2)c1F] |

TABLE 2-continued
| Compound number | Structure |
|---|---|
| 103 | 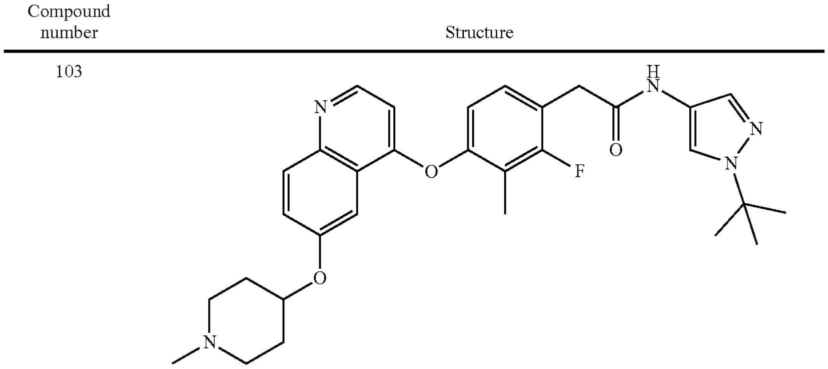 |
| 104 | 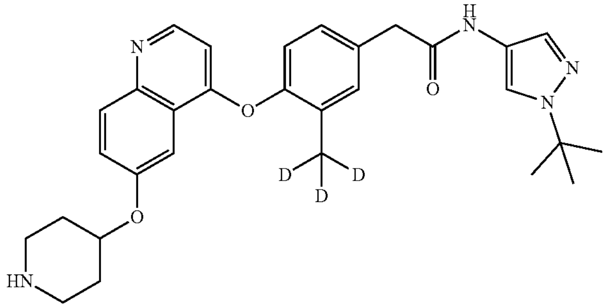 [SMILES: [2H]C([2H])([2H])c1cc(CC(=O)Nc2cnn(C(C)(C)C)c2)ccc1Oc1ccnc2ccc(OC3CCNCC3)cc12] |
| 105 | 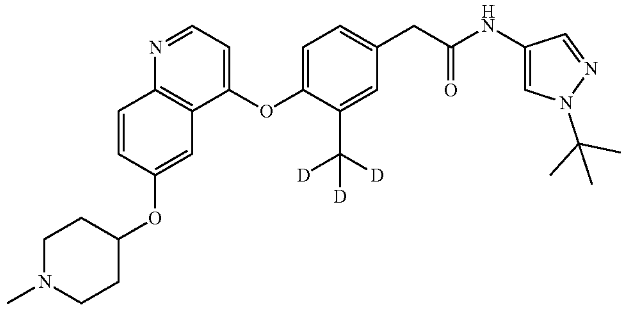 [SMILES: [2H]C([2H])([2H])c1cc(CC(=O)Nc2cnn(C(C)(C)C)c2)ccc1Oc1ccnc2ccc(OC3CCN(C)CC3)cc12] |
| 106 | 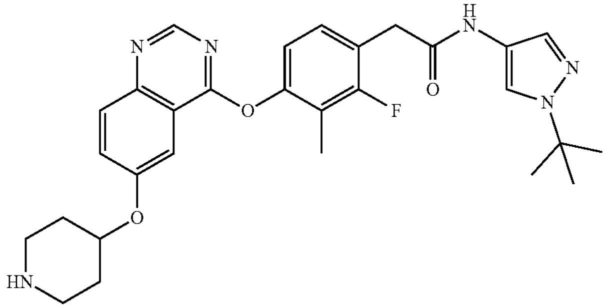 [SMILES: Cc1c(Oc2ncnc3ccc(OC4CCNCC4)cc23)ccc(CC(=O)Nc2cnn(C(C)(C)C)c2)c1F] |
| 107 | 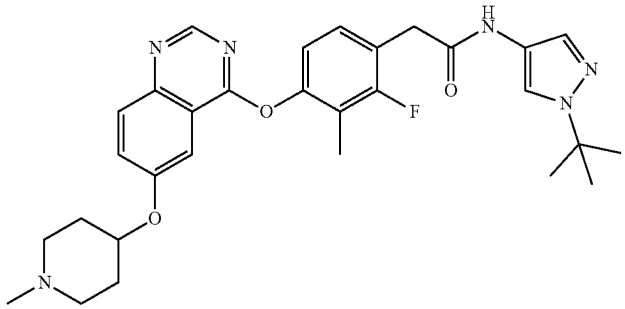 [SMILES: Cc1c(Oc2ncnc3ccc(OC4CCN(C)CC4)cc23)ccc(CC(=O)Nc2cnn(C(C)(C)C)c2)c1F] |

TABLE 2-continued
| Compound number | Structure |
| --- | --- |
| 113 | 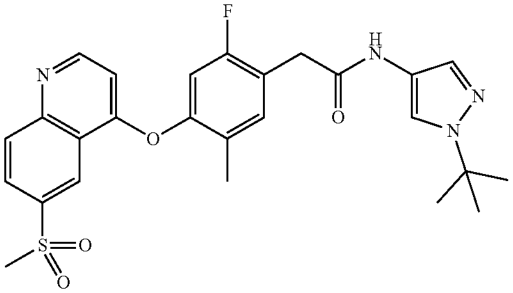 [SMILES: Cc1cc(CC(=O)Nc2cnn(C(C)(C)C)c2)c(F)cc1Oc1ccnc2ccc(S(C)(=O)=O)cc12] |
| 114 | 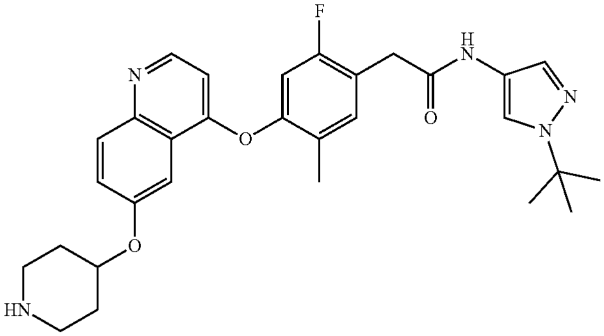 [SMILES: Cc1cc(CC(=O)Nc2cnn(C(C)(C)C)c2)c(F)cc1Oc1ccnc2ccc(OC3CCNCC3)cc12] |
| 115 | 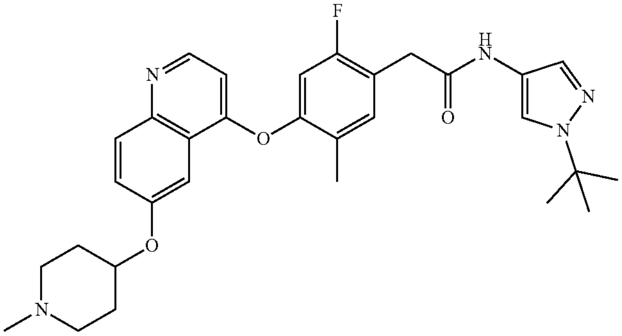 [SMILES: Cc1cc(CC(=O)Nc2cnn(C(C)(C)C)c2)c(F)cc1Oc1ccnc2ccc(OC3CCN(C)CC3)cc12] |
| 118 | 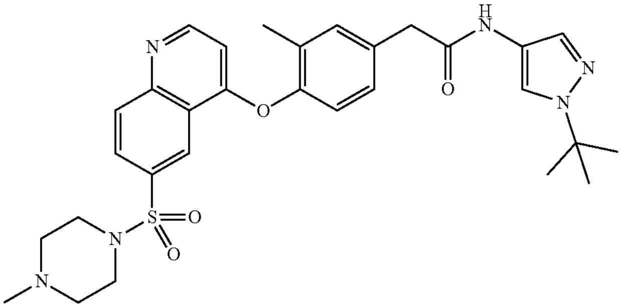 [SMILES: Cc1cc(CC(=O)Nc2cnn(C(C)(C)C)c2)ccc1Oc1ccnc2ccc(S(=O)(=O)N3CCN(C)CC3)cc12] |

TABLE 2-continued
| Compound number | Structure |
|---|---|
| 119 | 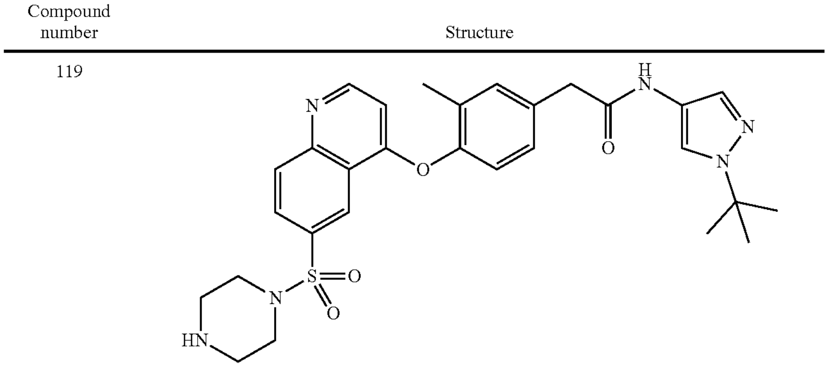 |
| 120 | 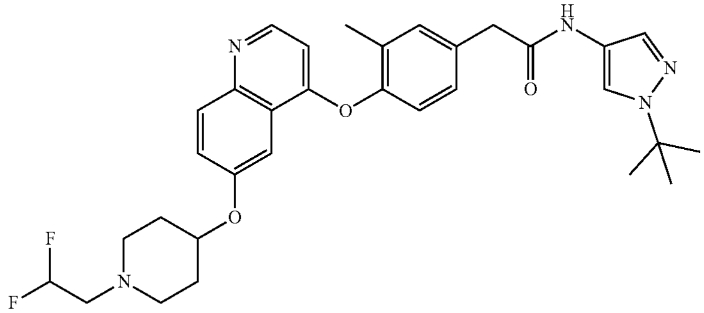 [SMILES: Cc1cc(CC(=O)Nc2cnn(C(C)(C)C)c2)ccc1Oc1ccnc2ccc(OC3CCN(CC(F)F)CC3)cc12] |
| 121 | 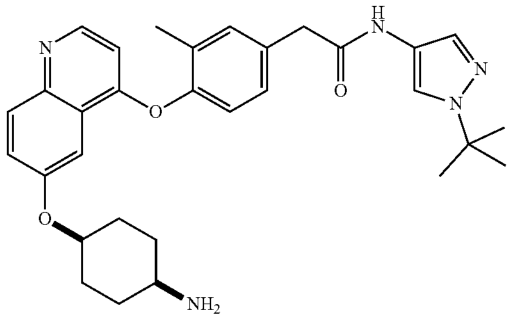 |
| 122 | 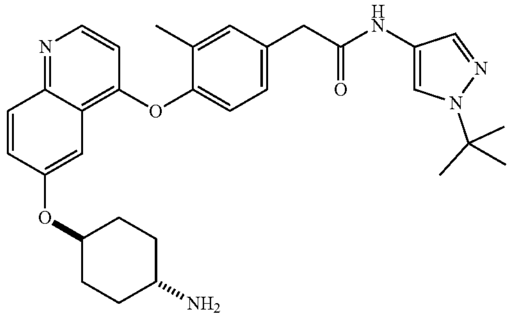 |
| 123 | 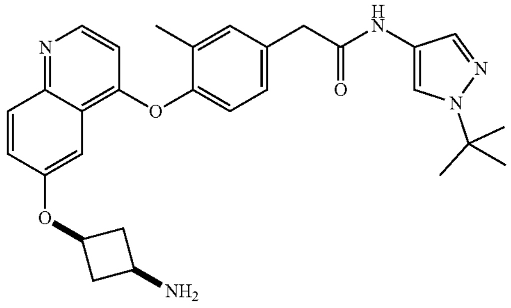 |

TABLE 2-continued
| Compound number | Structure |
|---|---|
| 124 | 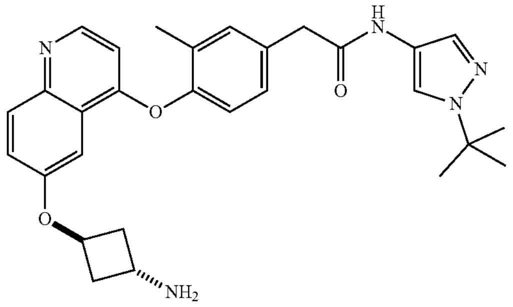 |
| 125 | 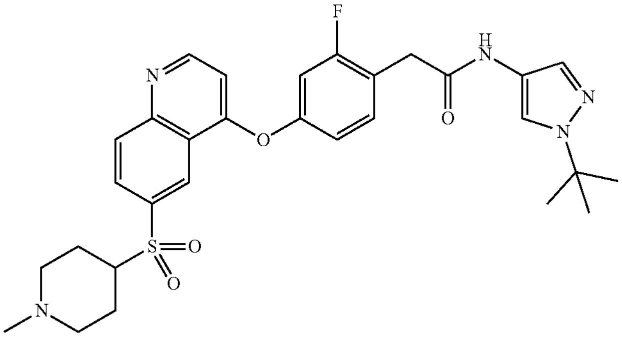 [SMILES: CN1CCC(S(=O)(=O)c2ccc3nccc(Oc4ccc(CC(=O)Nc5cnn(C(C)(C)C)c5)c(F)c4)c3c2)CC1] |
| 127 | 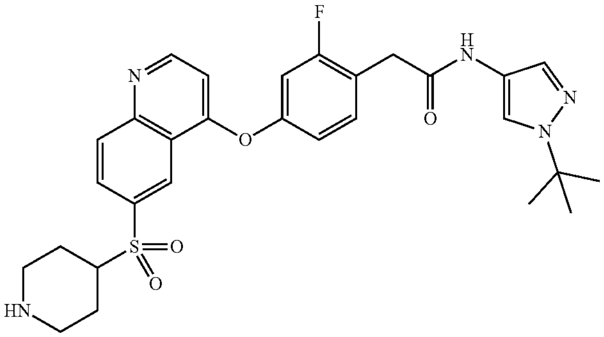 [SMILES: CC(C)(C)n1cc(NC(=O)Cc2ccc(Oc3ccnc4ccc(S(=O)(=O)N5CCNCC5)cc34)cc2F)cn1] |
| 128 | 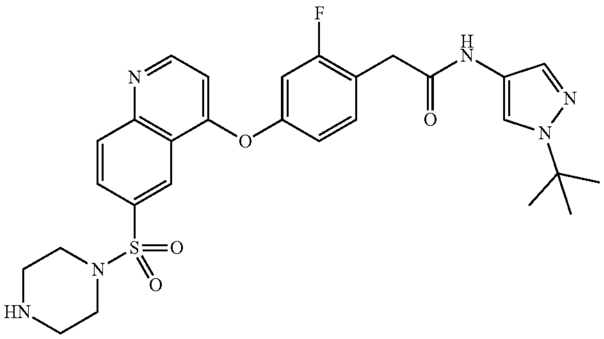 |

TABLE 2-continued
| Compound number | Structure |
|---|---|
| 130 | 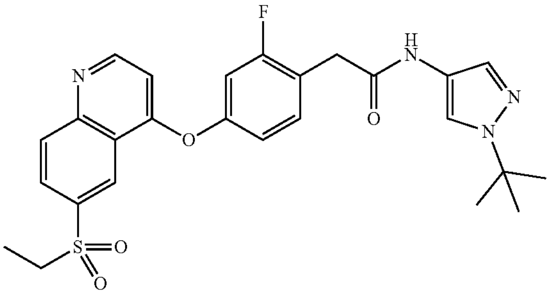 [SMILES: CCS(=O)(=O)c1ccc2nccc(Oc3ccc(CC(=O)Nc4cnn(C(C)(C)C)c4)c(F)c3)c2c1] |
| 131 | 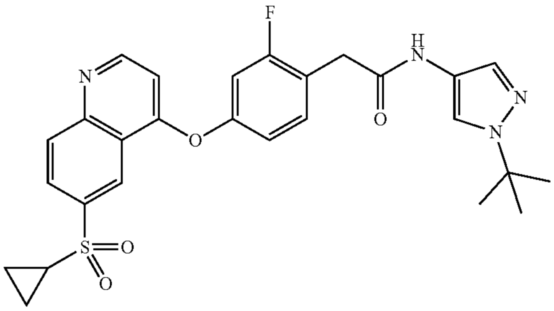 |
| 132 | 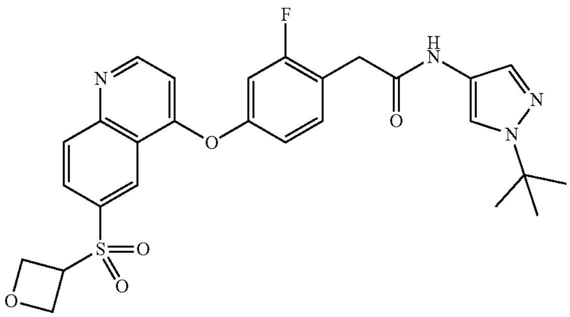 [SMILES: CC(C)(C)n1cc(NC(=O)Cc2ccc(Oc3ccnc4ccc(S(=O)(=O)C5COC5)cc34)cc2F)cn1] |
| 134 | 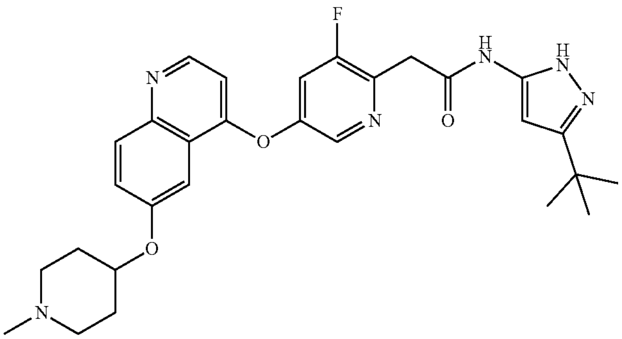 |

TABLE 2-continued
| Compound number | Structure |
|---|---|
| 135 | 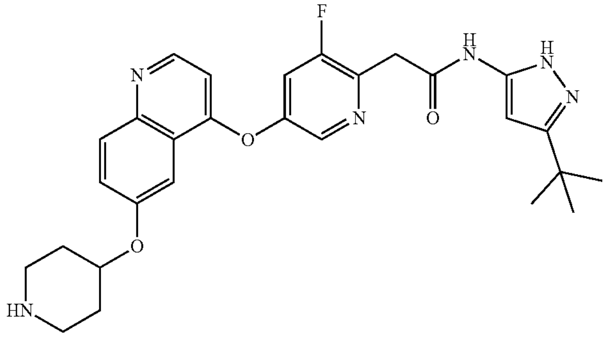 [SMILES: CC(C)(C)c1cc(NC(=O)Cc2ccc(Oc3ccnc4ccc(OC5CCNCC5)cc34)cc2F)[nH]n1] |
| 136 | 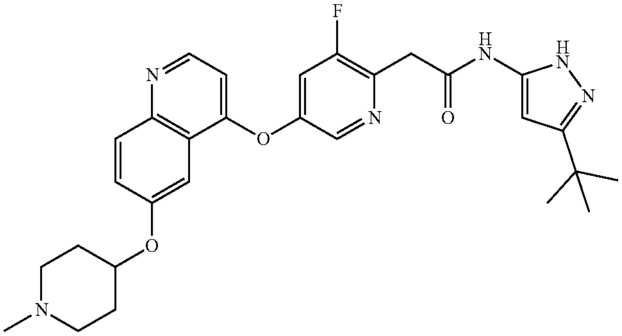 |
| 137 | 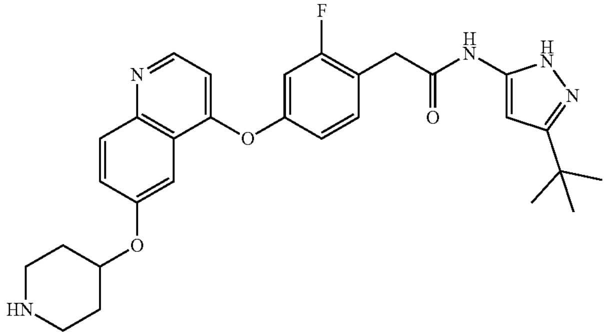 |
| 142 | 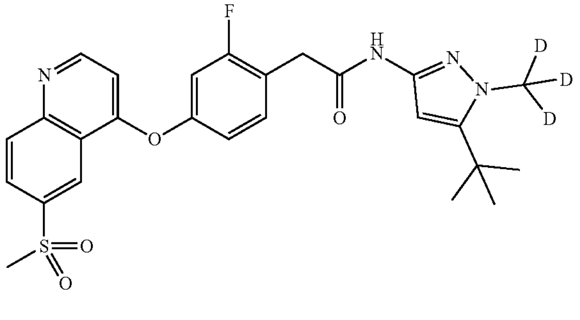 [SMILES: [2H]C([2H])([2H])n1nc(NC(=O)Cc2ccc(Oc3ccnc4ccc(S(C)(=O)=O)cc34)cc2F)cc1C(C)(C)C] |

TABLE 2-continued
| Compound number | Structure |
|---|---|
| 143 | 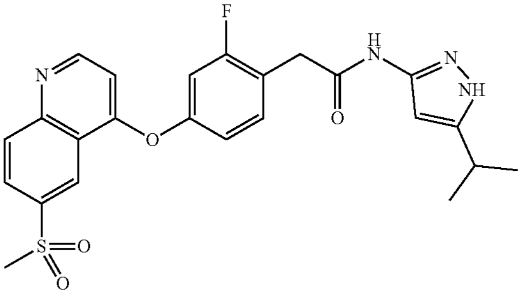 [SMILES: CC(C)c1cc(NC(=O)Cc2ccc(Oc3ccnc4ccc(S(C)(=O)=O)cc34)cc2F)n[nH]1] |
| 144 | 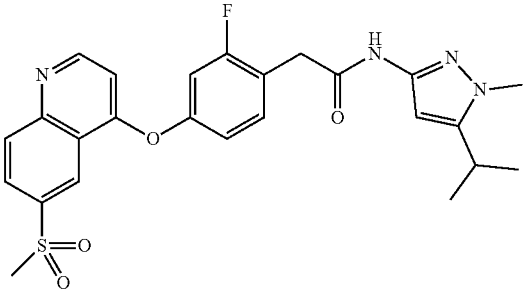 [SMILES: CC(C)c1cc(NC(=O)Cc2ccc(Oc3ccnc4ccc(S(C)(=O)=O)cc34)cc2F)nn1C] |
| 147 | 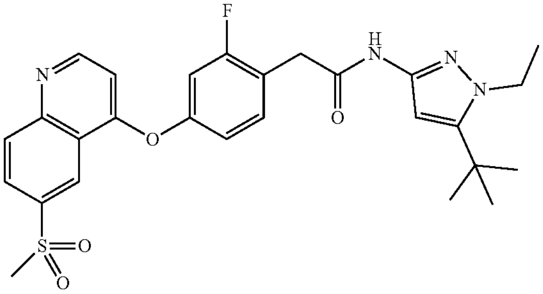 [SMILES: CCn1nc(NC(=O)Cc2ccc(Oc3ccnc4ccc(S(C)(=O)=O)cc34)cc2F)cc1C(C)(C)C] |
| 149 | 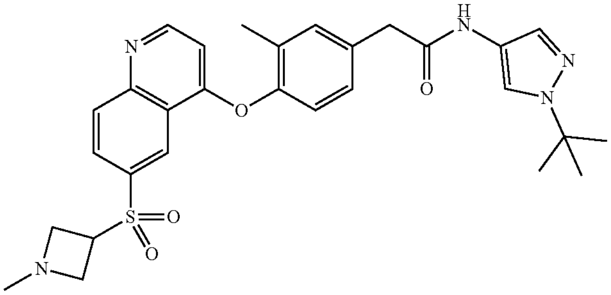 [SMILES: Cc1cc(CC(=O)Nc2cnn(C(C)(C)C)c2)ccc1Oc1ccnc2ccc(S(=O)(=O)C3CN(C)C3)cc12] |
| 152 | 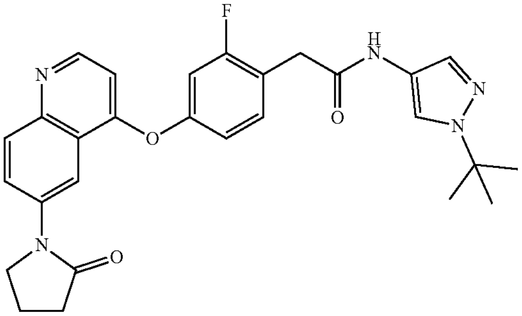 [SMILES: CC(C)(C)n1cc(NC(=O)Cc2ccc(Oc3ccnc4ccc(N5CCCC5=O)cc34)cc2F)cn1] |

TABLE 2-continued
| Compound number | Structure |
| --- | --- |
| 158 | 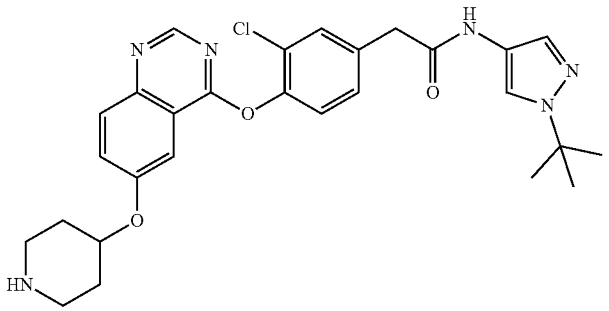 |
| 161 | 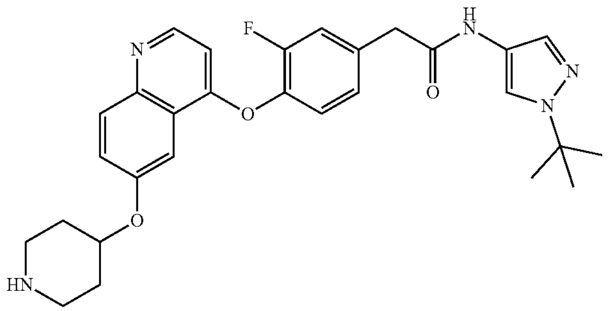 |
| 162 | 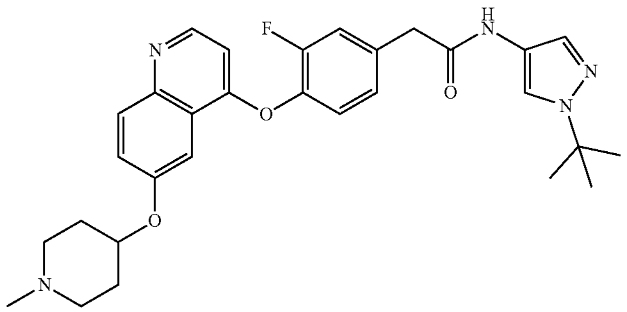 [SMILES: CN1CCC(Oc2ccc3nccc(Oc4ccc(CC(=O)Nc5cnn(C(C)(C)C)c5)cc4F)c3c2)CC1] |
| 163 | 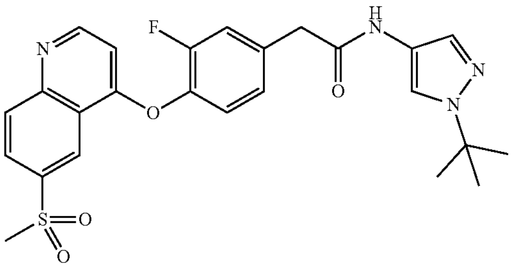 [SMILES: CC(C)(C)n1cc(NC(=O)Cc2ccc(Oc3ccnc4ccc(S(C)(=O)=O)cc34)c(F)c2)cn1] |
| 164 | 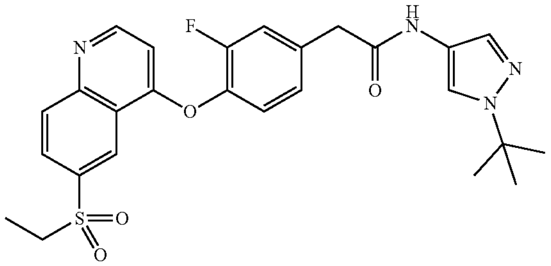 [SMILES: CCS(=O)(=O)c1ccc2nccc(Oc3ccc(CC(=O)Nc4cnn(C(C)(C)C)c4)cc3F)c2c1] |

TABLE 2-continued
| Compound number | Structure |
| --- | --- |
| 165 | 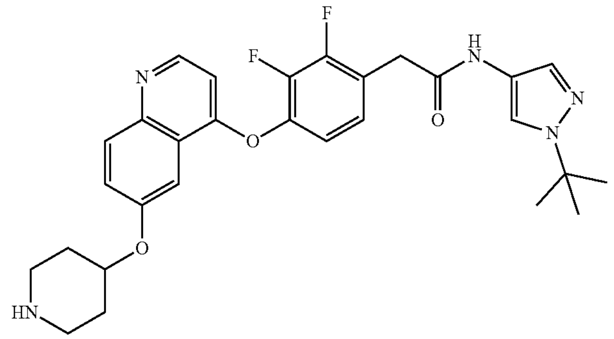 [SMILES: CC(C)(C)n1cc(NC(=O)Cc2ccc(Oc3ccnc4ccc(OC5CCNCC5)cc34)c(F)c2F)cn1] |
| 166 | 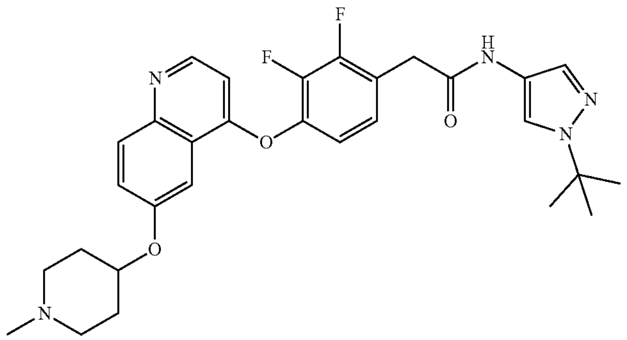 [SMILES: CN1CCC(Oc2ccc3nccc(Oc4ccc(CC(=O)Nc5cnn(C(C)(C)C)c5)c(F)c4F)c3c2)CC1] |
| 167 | 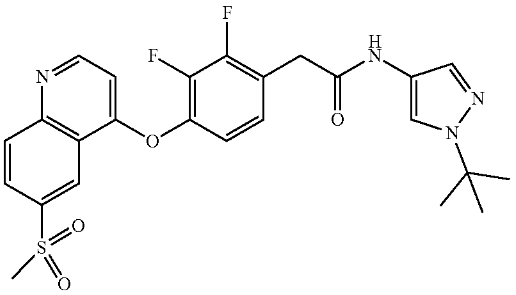 [SMILES: CC(C)(C)n1cc(NC(=O)Cc2ccc(Oc3ccnc4ccc(S(C)(=O)=O)cc34)c(F)c2F)cn1] |
| 168 | 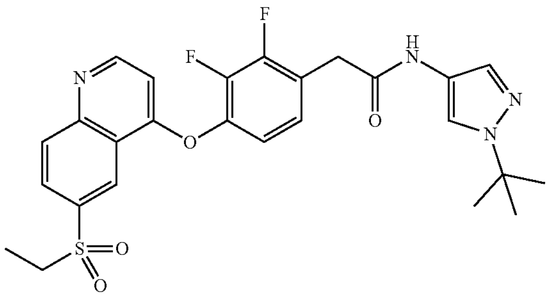 [SMILES: CCS(=O)(=O)c1ccc2nccc(Oc3ccc(CC(=O)Nc4cnn(C(C)(C)C)c4)c(F)c3F)c2c1] |

TABLE 2-continued
| Compound number | Structure |
|---|---|
| 169 | 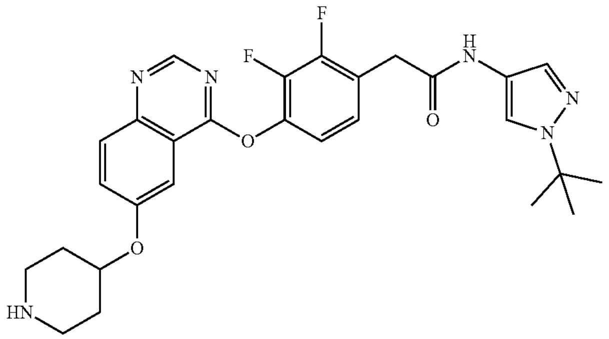 [SMILES: CC(C)(C)n1cc(NC(=O)Cc2ccc(Oc3ncnc4ccc(OC5CCNCC5)cc34)c(F)c2F)cn1] |
| 170 | 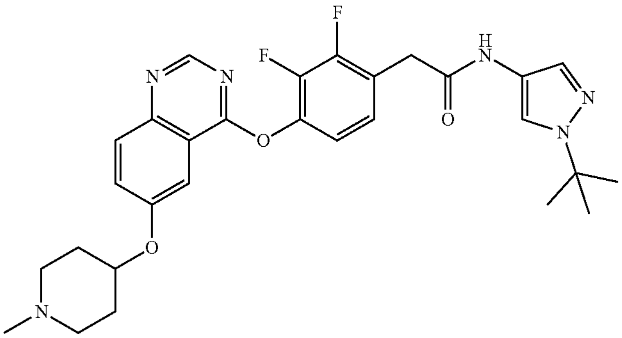 [SMILES: CN1CCC(Oc2ccc3ncnc(Oc4ccc(CC(=O)Nc5cnn(C(C)(C)C)c5)c(F)c4F)c3c2)CC1] |
| 171 | 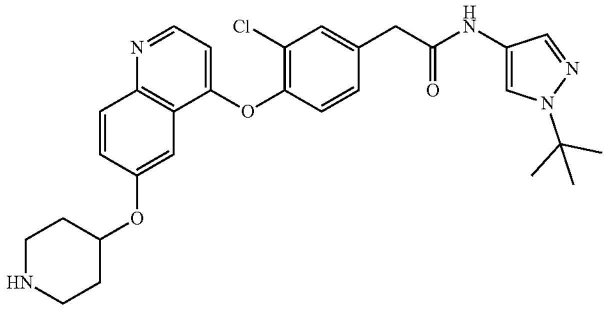 |
| 172 | 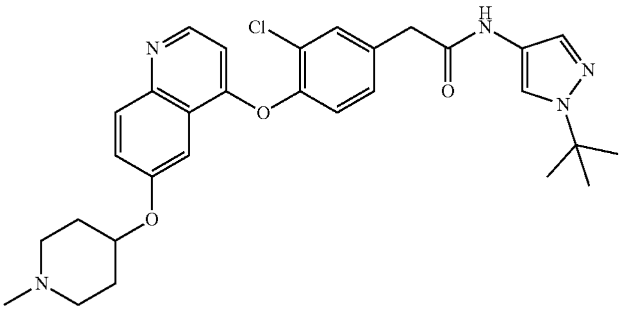 [SMILES: CN1CCC(Oc2ccc3nccc(Oc4ccc(CC(=O)Nc5cnn(C(C)(C)C)c5)cc4Cl)c3c2)CC1] |

TABLE 2-continued
| Compound number | Structure |
| --- | --- |
| 173 | 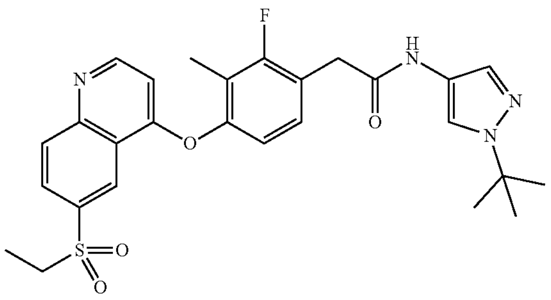 [SMILES: CCS(=O)(=O)c1ccc2nccc(Oc3ccc(CC(=O)Nc4cnn(C(C)(C)C)c4)c(F)c3C)c2c1] |
| 174 | 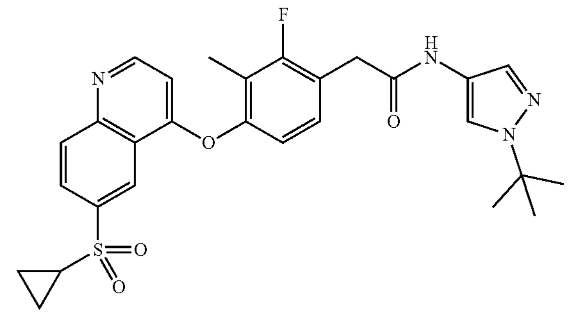 [SMILES: Cc1c(Oc2ccnc3ccc(S(=O)(=O)C4CC4)cc23)ccc(CC(=O)Nc2cnn(C(C)(C)C)c2)c1F] |
| 175 | 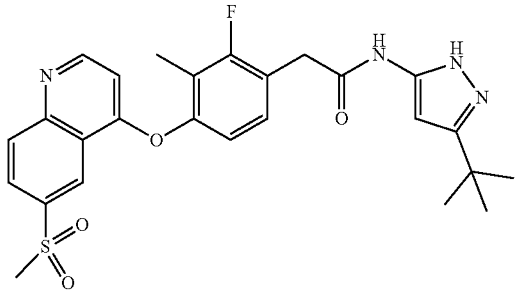 [SMILES: Cc1c(Oc2ccnc3ccc(S(C)(=O)=O)cc23)ccc(CC(=O)Nc2cc(C(C)(C)C)n[nH]2)c1F] |
| 179 | 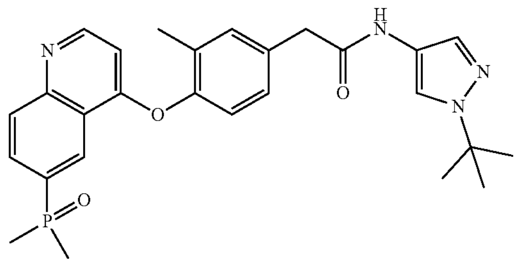 [SMILES: Cc1cc(CC(=O)Nc2cnn(C(C)(C)C)c2)ccc1Oc1ccnc2ccc(P(C)(C)=O)cc12] |
| 180 | 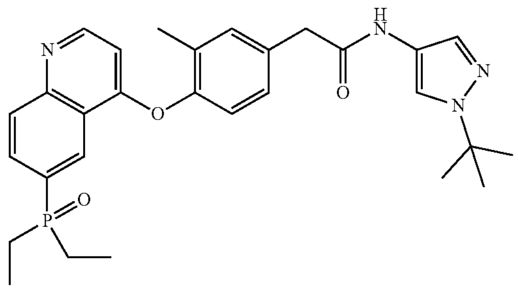 [SMILES: CCP(=O)(CC)c1ccc2nccc(Oc3ccc(CC(=O)Nc4cnn(C(C)(C)C)c4)cc3C)c2c1] |

TABLE 2-continued
| Compound number | Structure |
|---|---|
| 181 | 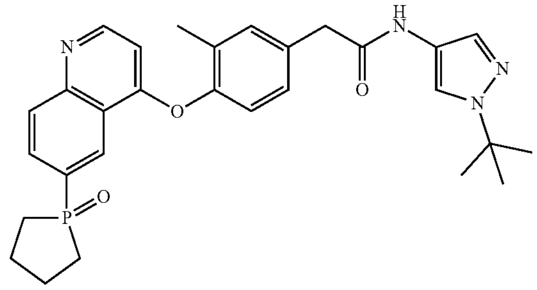 [SMILES: Cc1cc(CC(=O)Nc2cnn(C(C)(C)C)c2)ccc1Oc1ccnc2ccc(P3(=O)CCCC3)cc12] |
| 182 | 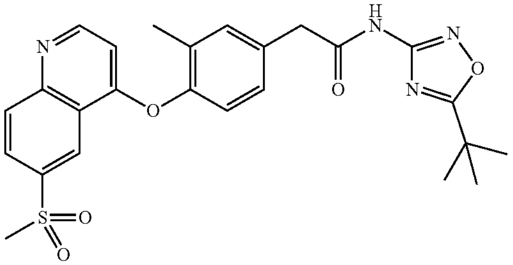 [SMILES: Cc1cc(CC(=O)Nc2noc(C(C)(C)C)n2)ccc1Oc1ccnc2ccc(S(C)(=O)=O)cc12] |
| 185 | 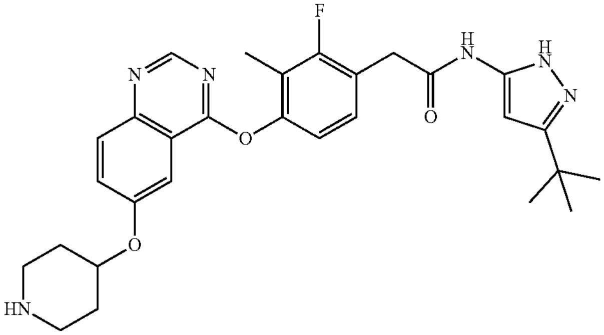 [SMILES: Cc1c(Oc2ncnc3ccc(OC4CCNCC4)cc23)ccc(CC(=O)Nc2cc(C(C)(C)C)n[nH]2)c1F] |
| 186 | 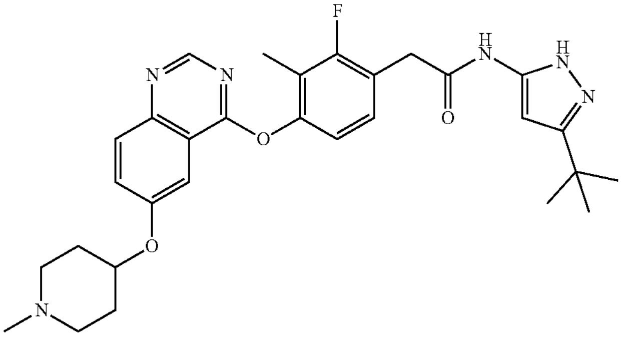 [SMILES: Cc1c(Oc2ncnc3ccc(OC4CCN(C)CC4)cc23)ccc(CC(=O)Nc2cc(C(C)(C)C)n[nH]2)c1F] |
| 187 | 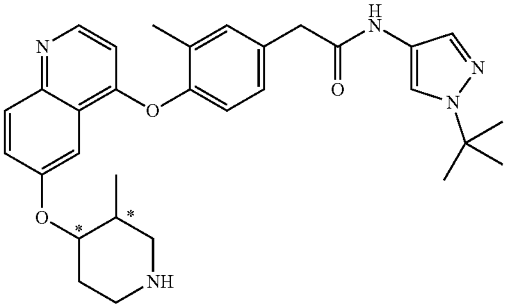 |

TABLE 2-continued
| Compound number | Structure |
| --- | --- |
| | racemic mixture of trans isomers |
| 188 | 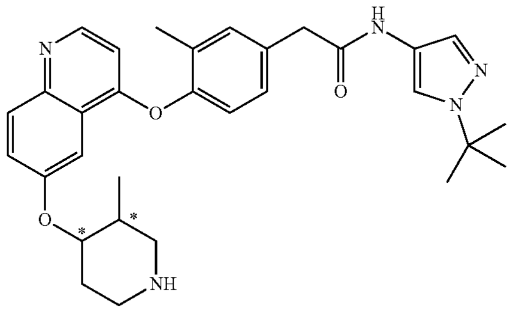 racemic mixture of cis isomers |
| 190 | 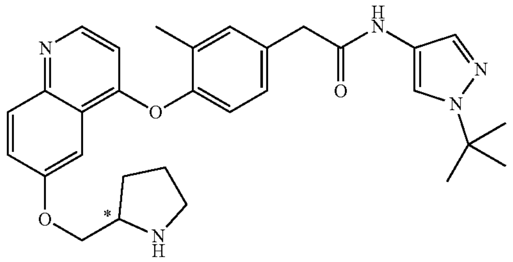 [SMILES: Cc1cc(CC(=O)Nc2cnn(C(C)(C)C)c2)ccc1Oc1ccnc2ccc(OCC3CCCN3)cc12] enantiomer 2 |
| 191 | 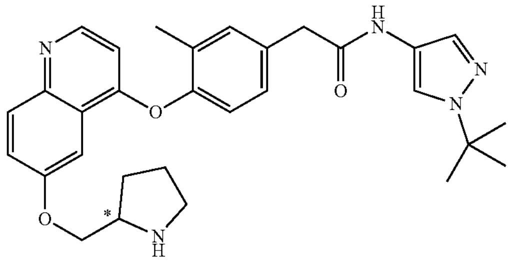 [SMILES: Cc1cc(CC(=O)Nc2cnn(C(C)(C)C)c2)ccc1Oc1ccnc2ccc(OCC3CCCN3)cc12] enantiomer 1 |
| 193 | 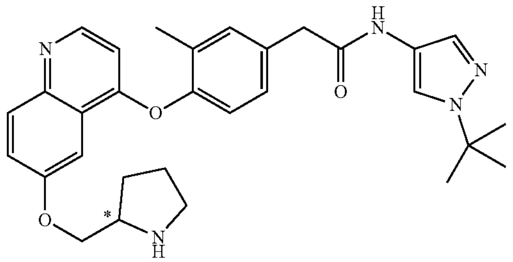 [SMILES: Cc1cc(CC(=O)Nc2cnn(C(C)(C)C)c2)ccc1Oc1ccnc2ccc(OCC3CCCN3)cc12] enantiomer 2 |

TABLE 2-continued
| Compound number | Structure |
| --- | --- |
| 194 | 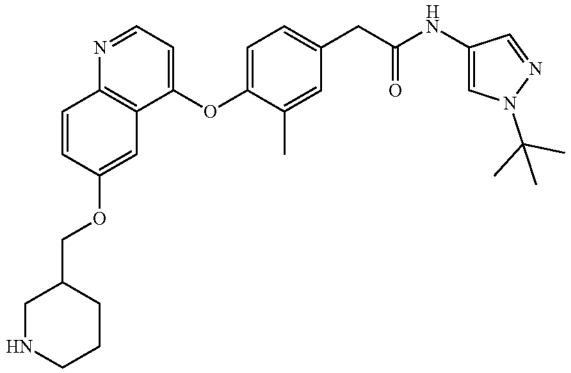 [SMILES: Cc1cc(CC(=O)Nc2cnn(C(C)(C)C)c2)ccc1Oc1ccnc2ccc(OCC3CCCNC3)cc12] |
| 195 | 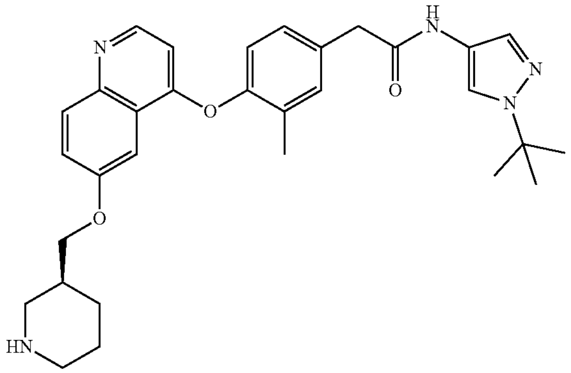 [SMILES: Cc1cc(CC(=O)Nc2cnn(C(C)(C)C)c2)ccc1Oc1ccnc2ccc(OC[C@H]3CCCNC3)cc12] |
| 197 | 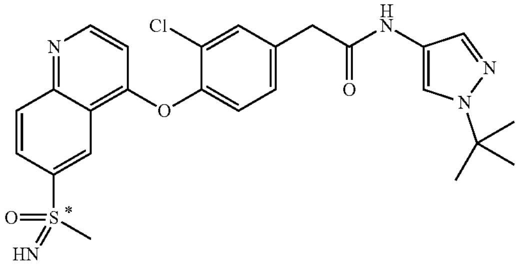 [SMILES: CC(C)(C)n1cc(NC(=O)Cc2ccc(Oc3ccnc4ccc(S(C)(=N)=O)cc34)c(Cl)c2)cn1] enantiomer 2 |
| 198 | 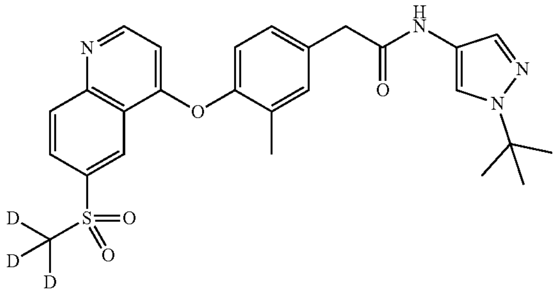 [SMILES: [2H]C([2H])([2H])S(=O)(=O)c1ccc2nccc(Oc3ccc(CC(=O)Nc4cnn(C(C)(C)C)c4)cc3C)c2c1] |

TABLE 2-continued
| Compound number | Structure |
|---|---|
| 199 | 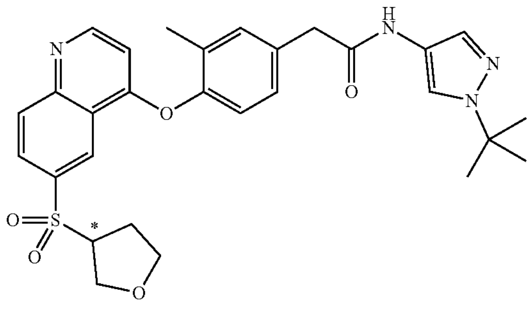 [SMILES: Cc1cc(CC(=O)Nc2cnn(C(C)(C)C)c2)ccc1Oc1ccnc2ccc(S(=O)(=O)C3CCOC3)cc12]<br>enantiomer 1 |
| 200 | 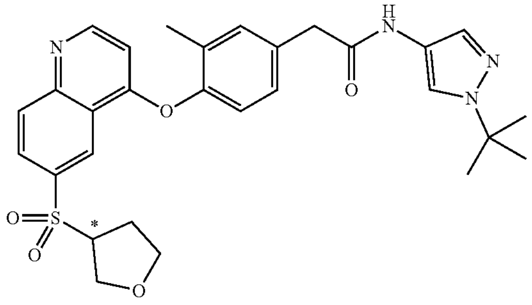 [SMILES: Cc1cc(CC(=O)Nc2cnn(C(C)(C)C)c2)ccc1Oc1ccnc2ccc(S(=O)(=O)C3CCOC3)cc12]<br>enantiomer 2 |
| 201 | 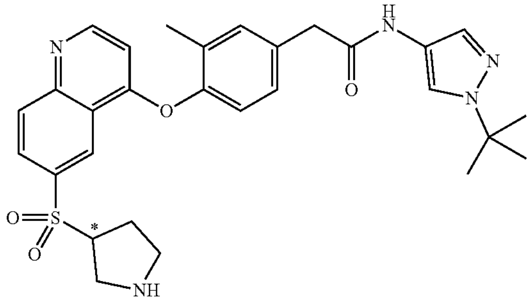 [SMILES: Cc1cc(CC(=O)Nc2cnn(C(C)(C)C)c2)ccc1Oc1ccnc2ccc(S(=O)(=O)C3CCNC3)cc12]<br>enantiomer 1 |
| 202 | 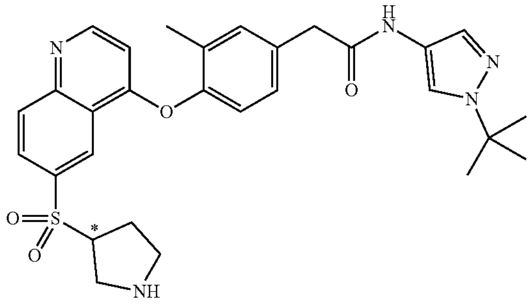<br>enantiomer 2 |

TABLE 2-continued
| Compound number | Structure |
|---|---|
| 203 | 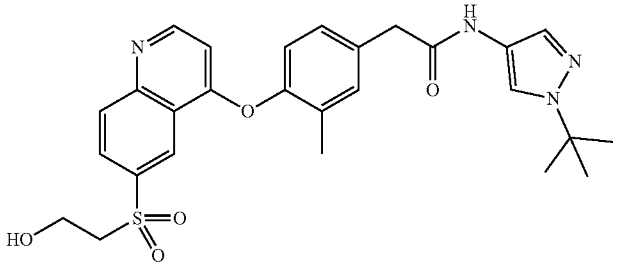 [SMILES: Cc1cc(CC(=O)Nc2cnn(C(C)(C)C)c2)ccc1Oc1ccnc2ccc(S(=O)(=O)CCO)cc12] |
| 204 | 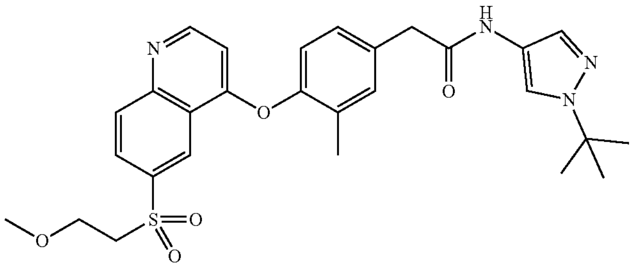 [SMILES: COCCS(=O)(=O)c1ccc2nccc(Oc3ccc(CC(=O)Nc4cnn(C(C)(C)C)c4)cc3C)c2c1] |
| 205 | 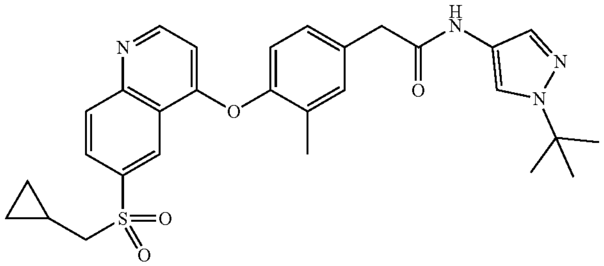 [SMILES: Cc1cc(CC(=O)Nc2cnn(C(C)(C)C)c2)ccc1Oc1ccnc2ccc(S(=O)(=O)CC3CC3)cc12] |
| 206 | 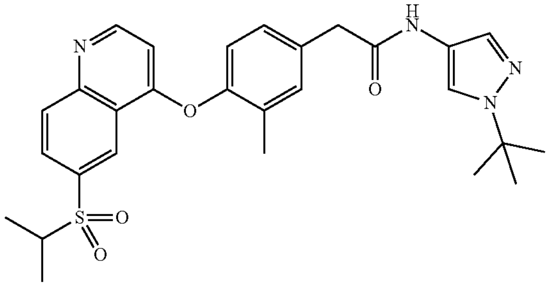 [SMILES: Cc1cc(CC(=O)Nc2cnn(C(C)(C)C)c2)ccc1Oc1ccnc2ccc(S(=O)(=O)C(C)C)cc12] |
| 207 | 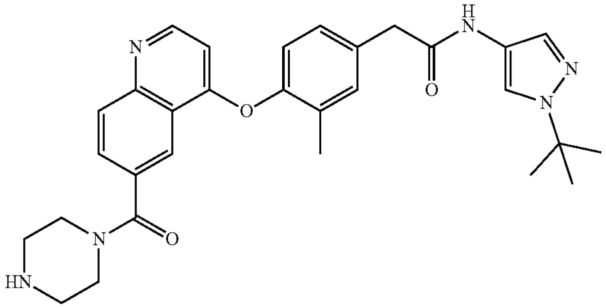 [SMILES: Cc1cc(CC(=O)Nc2cnn(C(C)(C)C)c2)ccc1Oc1ccnc2ccc(C(=O)N3CCNCC3)cc12] |

TABLE 2-continued
| Compound number | Structure |
| --- | --- |
| 208 | 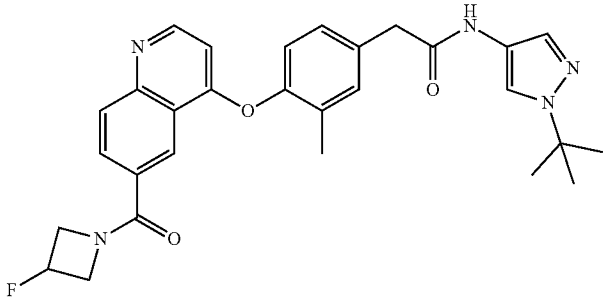 [SMILES: Cc1cc(CC(=O)Nc2cnn(C(C)(C)C)c2)ccc1Oc1ccnc2ccc(C(=O)N3CC(F)C3)cc12] |
| 209 | 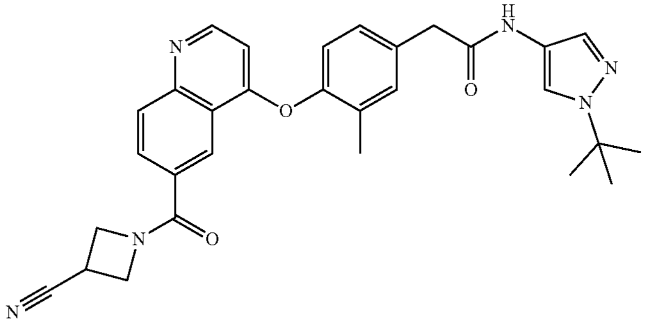 [SMILES: Cc1cc(CC(=O)Nc2cnn(C(C)(C)C)c2)ccc1Oc1ccnc2ccc(C(=O)N3CC(C#N)C3)cc12] |
| 210 | 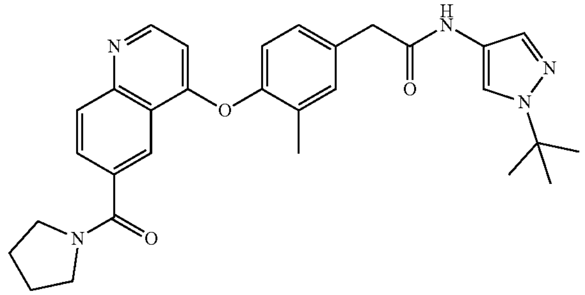 [SMILES: Cc1cc(CC(=O)Nc2cnn(C(C)(C)C)c2)ccc1Oc1ccnc2ccc(C(=O)N3CCCC3)cc12] |
| 211 | 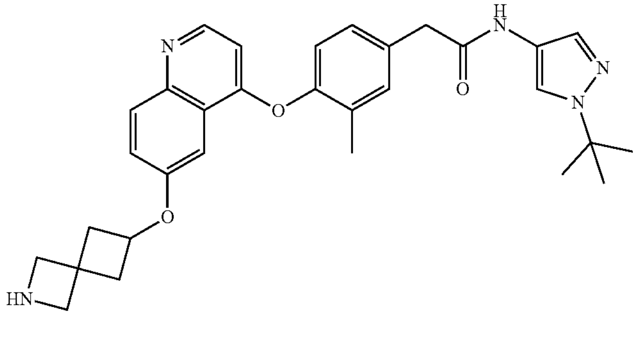 [SMILES: Cc1cc(CC(=O)Nc2cnn(C(C)(C)C)c2)ccc1Oc1ccnc2ccc(OC3CC4(CNC4)C3)cc12] |
| 212 | 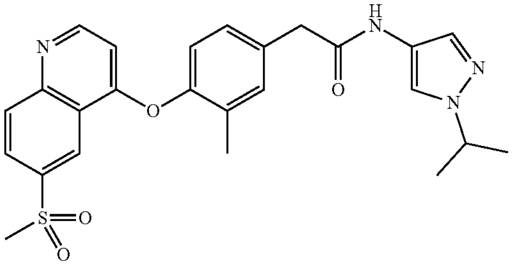 [SMILES: Cc1cc(CC(=O)Nc2cnn(C(C)C)c2)ccc1Oc1ccnc2ccc(S(C)(=O)=O)cc12] |

TABLE 2-continued
| Compound number | Structure |
|---|---|
| 214 | 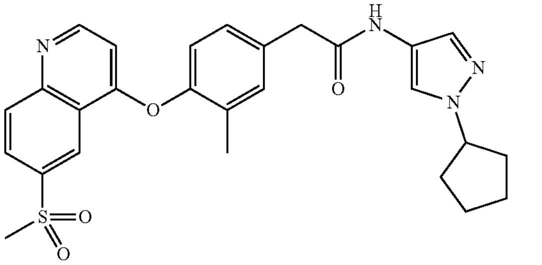 [SMILES: Cc1cc(CC(=O)Nc2cnn(C3CCCC3)c2)ccc1Oc1ccnc2ccc(S(C)(=O)=O)cc12] |
| 216 | 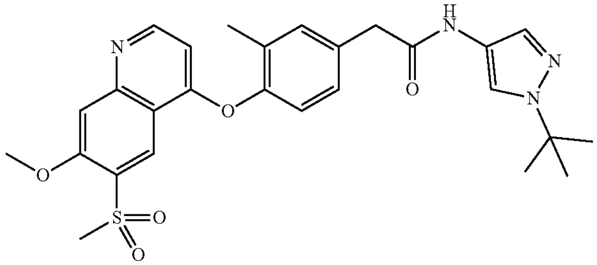 [SMILES: COc1cc2nccc(Oc3ccc(CC(=O)Nc4cnn(C(C)(C)C)c4)cc3C)c2cc1S(C)(=O)=O] |
| 217 | 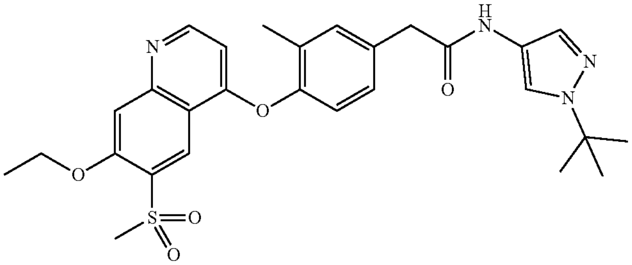 [SMILES: CCOc1cc2nccc(Oc3ccc(CC(=O)Nc4cnn(C(C)(C)C)c4)cc3C)c2cc1S(C)(=O)=O] |
| 218 | 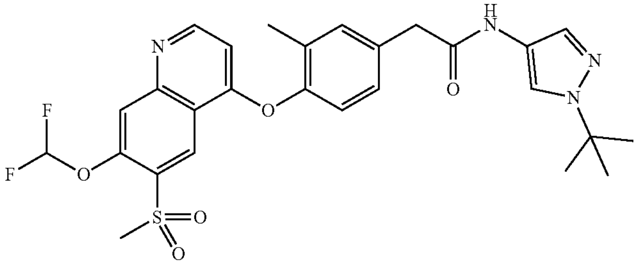 [SMILES: Cc1cc(CC(=O)Nc2cnn(C(C)(C)C)c2)ccc1Oc1ccnc2cc(OC(F)F)c(S(C)(=O)=O)cc12] |
| 220 | 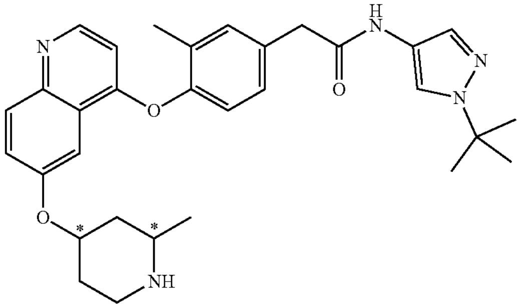 [SMILES: Cc1cc(CC(=O)Nc2cnn(C(C)(C)C)c2)ccc1Oc1ccnc2ccc(OC3CCNC(C)C3)cc12] racemic mixture of cis isomers |

TABLE 2-continued
| Compound number | Structure |
| --- | --- |
| 221 | 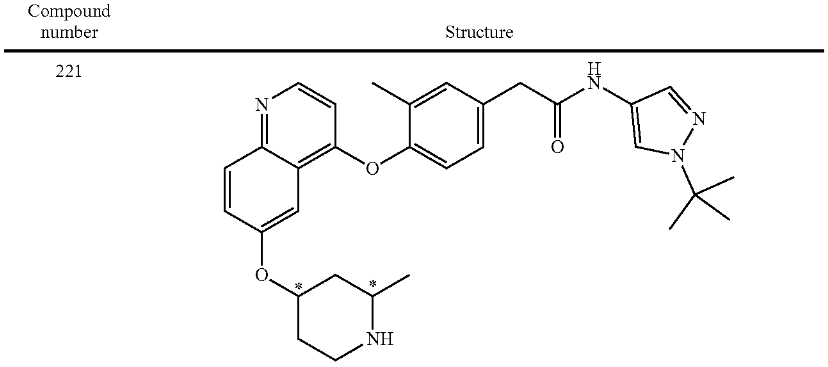 racemic mixture of trans isomers |
| 222 | 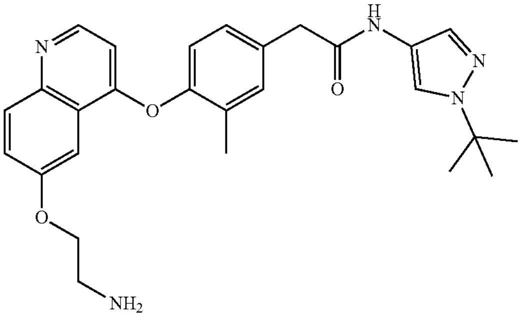 [SMILES: Cc1cc(CC(=O)Nc2cnn(C(C)(C)C)c2)ccc1Oc1ccnc2ccc(OCCN)cc12] |
| 223 | 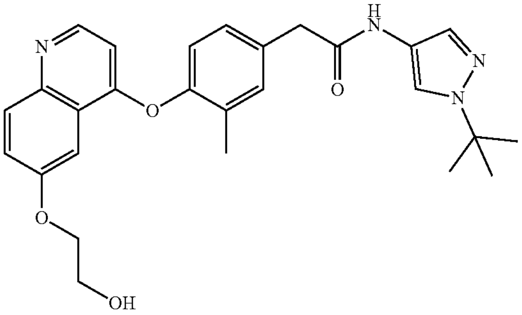 [SMILES: Cc1cc(CC(=O)Nc2cnn(C(C)(C)C)c2)ccc1Oc1ccnc2ccc(OCCO)cc12] |
| 224 | 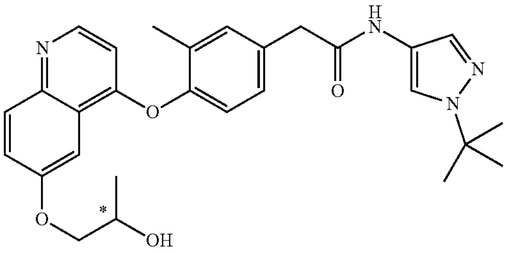 [SMILES: Cc1cc(CC(=O)Nc2cnn(C(C)(C)C)c2)ccc1Oc1ccnc2ccc(OCC(C)O)cc12] enantiomer 1 |
| 225 | 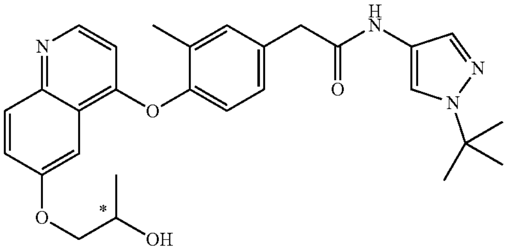 [SMILES: Cc1cc(CC(=O)Nc2cnn(C(C)(C)C)c2)ccc1Oc1ccnc2ccc(OCC(C)O)cc12] enantiomer 2 |

TABLE 2-continued
| Compound number | Structure |
| --- | --- |
| 226 | 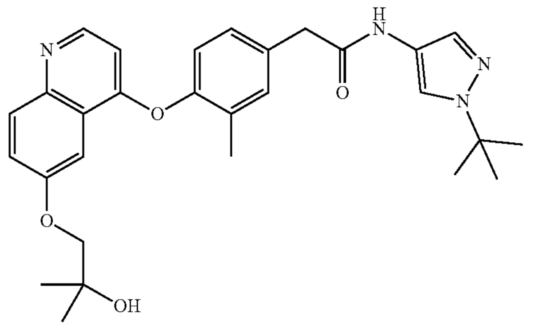 [SMILES: Cc1cc(CC(=O)Nc2cnn(C(C)(C)C)c2)ccc1Oc1ccnc2ccc(OCC(C)(C)O)cc12] |
| 230 | 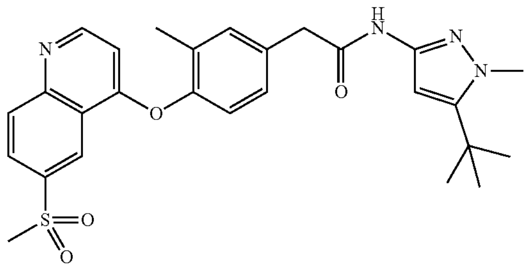 [SMILES: Cc1cc(CC(=O)Nc2cc(C(C)(C)C)n(C)n2)ccc1Oc1ccnc2ccc(S(C)(=O)=O)cc12] |
| 231 | 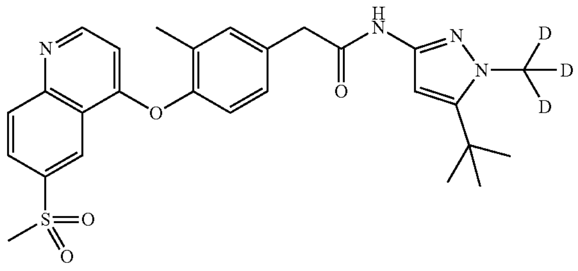 [SMILES: [2H]C([2H])([2H])n1nc(NC(=O)Cc2ccc(Oc3ccnc4ccc(S(C)(=O)=O)cc34)c(C)c2)cc1C(C)(C)C] |
| 232 | 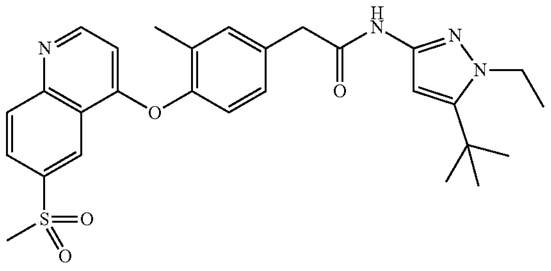 [SMILES: CCn1nc(NC(=O)Cc2ccc(Oc3ccnc4ccc(S(C)(=O)=O)cc34)c(C)c2)cc1C(C)(C)C] |
| 233 | 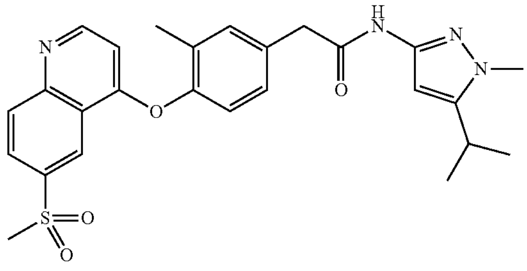 [SMILES: Cc1cc(CC(=O)Nc2cc(C(C)C)n(C)n2)ccc1Oc1ccnc2ccc(S(C)(=O)=O)cc12] |

TABLE 2-continued
| Compound number | Structure |
| --- | --- |
| 234 | 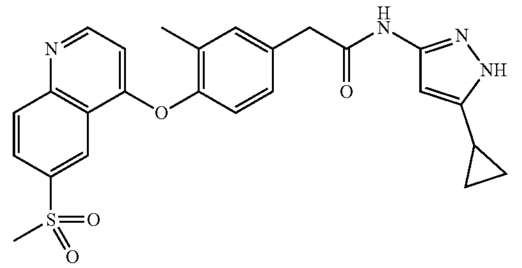 [SMILES: Cc1cc(CC(=O)Nc2cc(C3CC3)[nH]n2)ccc1Oc1ccnc2ccc(S(C)(=O)=O)cc12] |
| 235 | 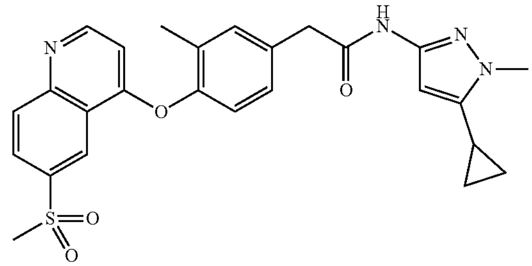 [SMILES: Cc1cc(CC(=O)Nc2cc(C3CC3)n(C)n2)ccc1Oc1ccnc2ccc(S(C)(=O)=O)cc12] |
| 237 | 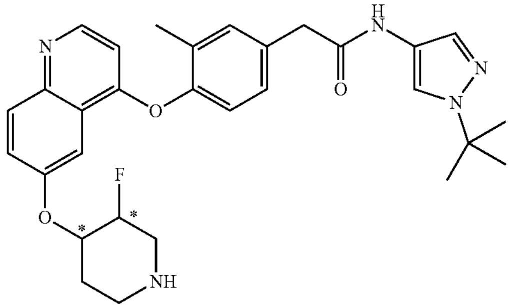 [SMILES: Cc1cc(CC(=O)Nc2cnn(C(C)(C)C)c2)ccc1Oc1ccnc2ccc(OC3CCNCC3F)cc12] racemic mixture of trans isomers |
| 238 | 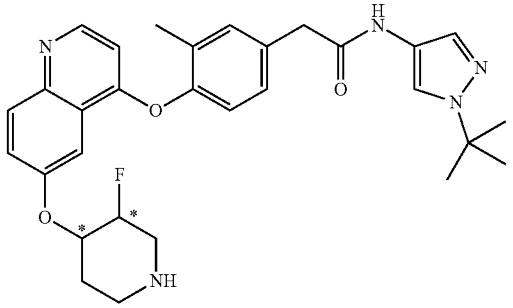 racemic mixture of cis isomers |
| 239 | 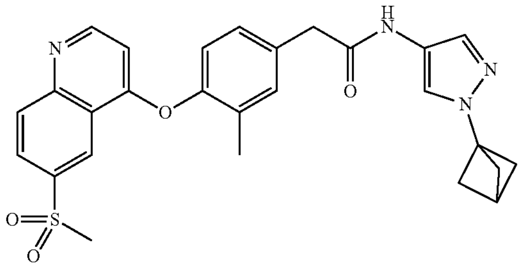 [SMILES: Cc1cc(CC(=O)Nc2cnn(C34CC(C3)C4)c2)ccc1Oc1ccnc2ccc(S(C)(=O)=O)cc12] |

TABLE 2-continued
| Compound number | Structure |
|---|---|
| 240 | 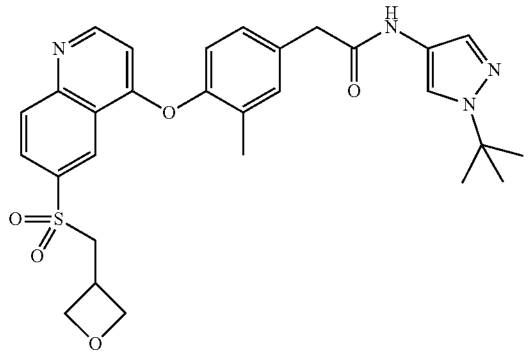 [SMILES: Cc1cc(CC(=O)Nc2cnn(C(C)(C)C)c2)ccc1Oc1ccnc2ccc(S(=O)(=O)CC3COC3)cc12] |
| 242 | 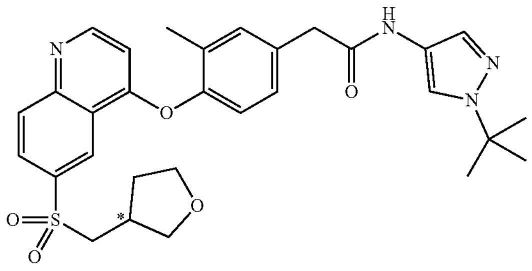 [SMILES: Cc1cc(CC(=O)Nc2cnn(C(C)(C)C)c2)ccc1Oc1ccnc2ccc(S(=O)(=O)CC3CCOC3)cc12]<br>enantiomer 2 |
| 243 | 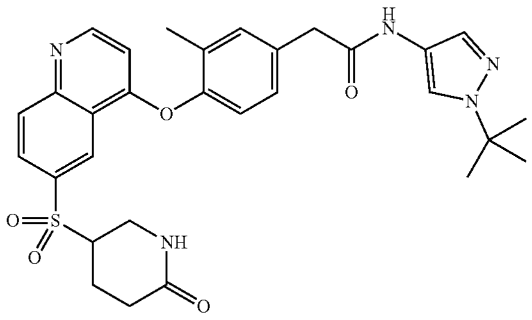 [SMILES: Cc1cc(CC(=O)Nc2cnn(C(C)(C)C)c2)ccc1Oc1ccnc2ccc(S(=O)(=O)C3CCC(=O)NC3)cc12] |
| 244 | 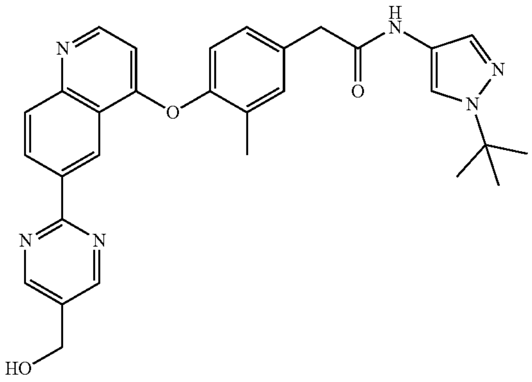 [SMILES: Cc1cc(CC(=O)Nc2cnn(C(C)(C)C)c2)ccc1Oc1ccnc2ccc(-c3ncc(CO)cn3)cc12] |

TABLE 2-continued
| Compound number | Structure |
|---|---|
| 247 | 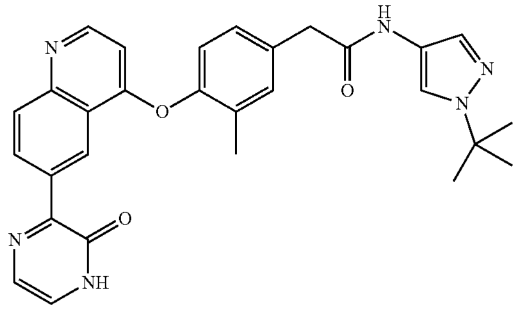 [SMILES: Cc1cc(CC(=O)Nc2cnn(C(C)(C)C)c2)ccc1Oc1ccnc2ccc(-c3ncc[nH]c3=O)cc12] |
| 248 | 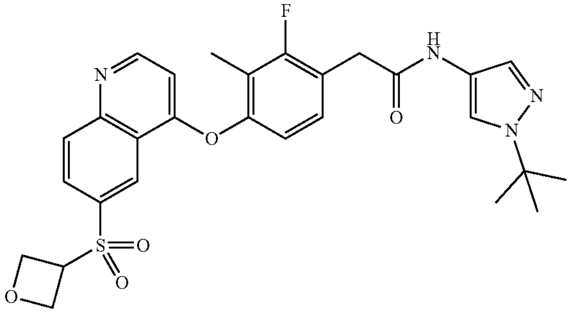 [SMILES: Cc1c(Oc2ccnc3ccc(S(=O)(=O)C4COC4)cc23)ccc(CC(=O)Nc2cnn(C(C)(C)C)c2)c1F] |
| 249 | 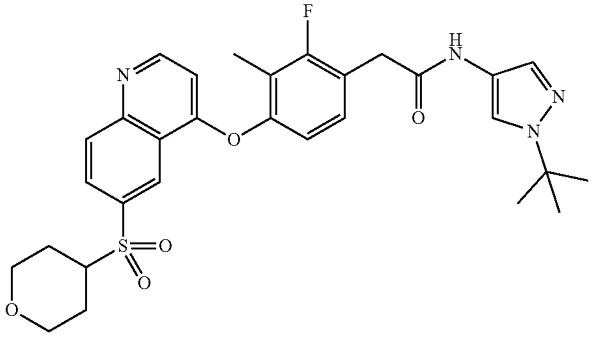 [SMILES: Cc1c(Oc2ccnc3ccc(S(=O)(=O)C4CCOCC4)cc23)ccc(CC(=O)Nc2cnn(C(C)(C)C)c2)c1F] |
| 252 | 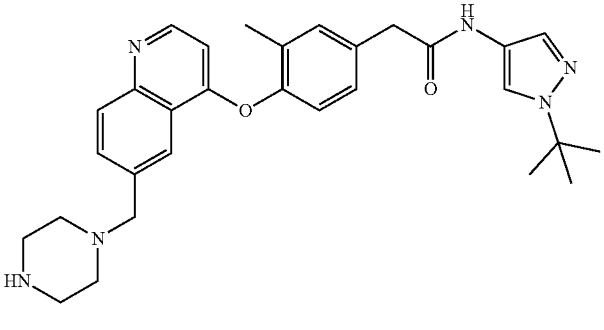 |

TABLE 2-continued
| Compound number | Structure |
|---|---|
| 253 | 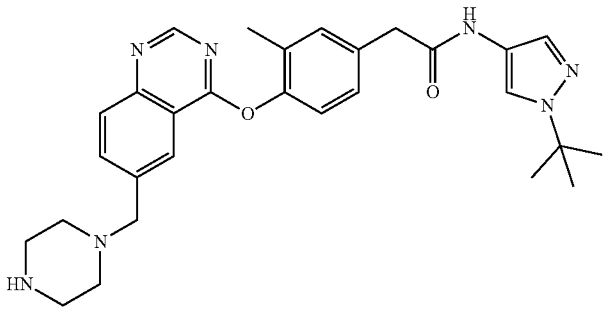 |
| 255 | 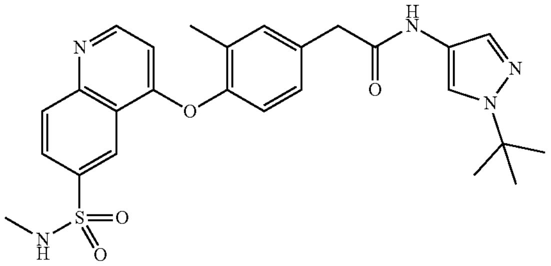 [SMILES: CNS(=O)(=O)c1ccc2nccc(Oc3ccc(CC(=O)Nc4cnn(C(C)(C)C)c4)cc3C)c2c1] |
| 256 | 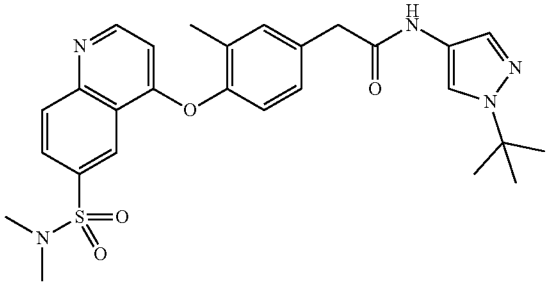 [SMILES: Cc1cc(CC(=O)Nc2cnn(C(C)(C)C)c2)ccc1Oc1ccnc2ccc(S(=O)(=O)N(C)C)cc12] |
| 257 | 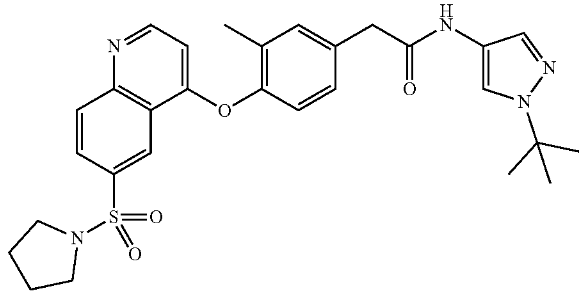 [SMILES: Cc1cc(CC(=O)Nc2cnn(C(C)(C)C)c2)ccc1Oc1ccnc2ccc(S(=O)(=O)N3CCCC3)cc12] |
| 259 | 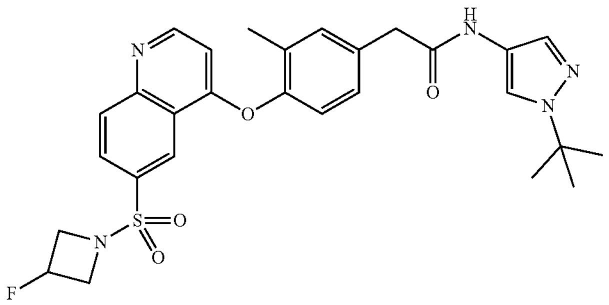 [SMILES: Cc1cc(CC(=O)Nc2cnn(C(C)(C)C)c2)ccc1Oc1ccnc2ccc(S(=O)(=O)N3CC(F)C3)cc12] |

TABLE 2-continued
| Compound number | Structure |
|---|---|
| 261 | 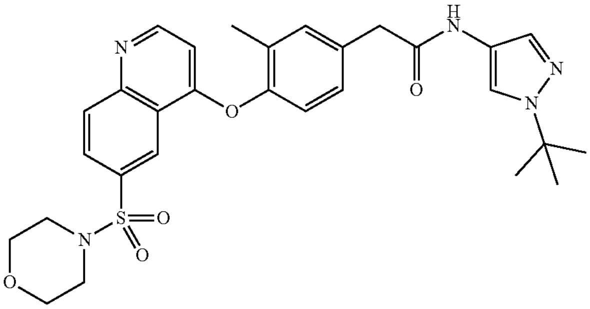 [SMILES: Cc1cc(CC(=O)Nc2cnn(C(C)(C)C)c2)ccc1Oc1ccnc2ccc(S(=O)(=O)N3CCOCC3)cc12] |
| 262 | 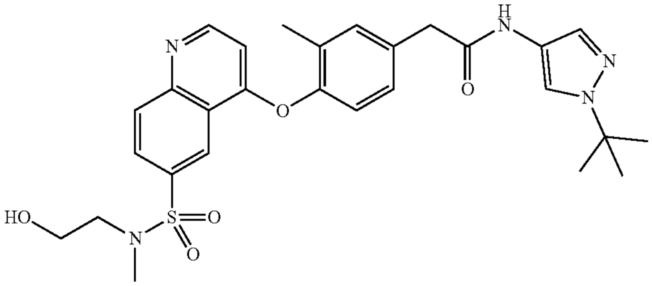 [SMILES: Cc1cc(CC(=O)Nc2cnn(C(C)(C)C)c2)ccc1Oc1ccnc2ccc(S(=O)(=O)N(C)CCO)cc12] |
| 264 | 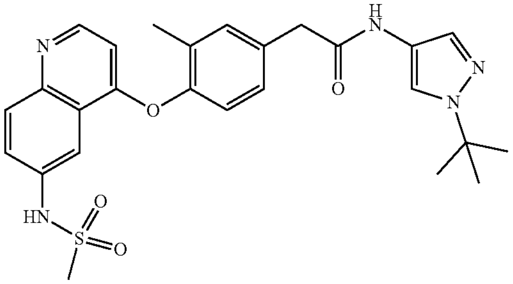 [SMILES: Cc1cc(CC(=O)Nc2cnn(C(C)(C)C)c2)ccc1Oc1ccnc2ccc(NS(C)(=O)=O)cc12] |
| 265 | 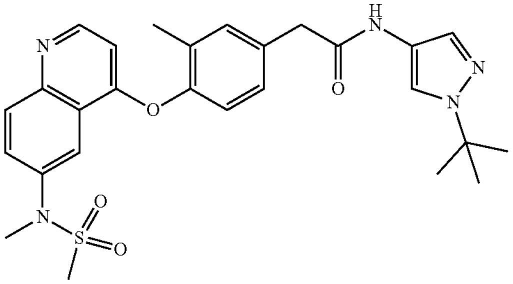 [SMILES: Cc1cc(CC(=O)Nc2cnn(C(C)(C)C)c2)ccc1Oc1ccnc2ccc(N(C)S(C)(=O)=O)cc12] |
| 267 | 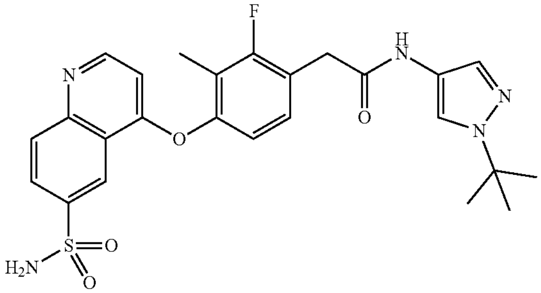 [SMILES: Cc1c(Oc2ccnc3ccc(S(N)(=O)=O)cc23)ccc(CC(=O)Nc2cnn(C(C)(C)C)c2)c1F] |

TABLE 2-continued
| Compound number | Structure |
|---|---|
| 269 | 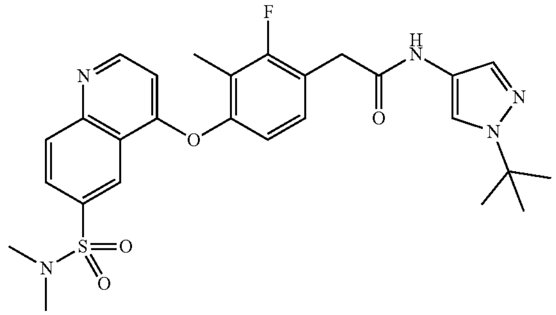 [SMILES: Cc1c(Oc2ccnc3ccc(S(=O)(=O)N(C)C)cc23)ccc(CC(=O)Nc2cnn(C(C)(C)C)c2)c1F] |
| 270 | 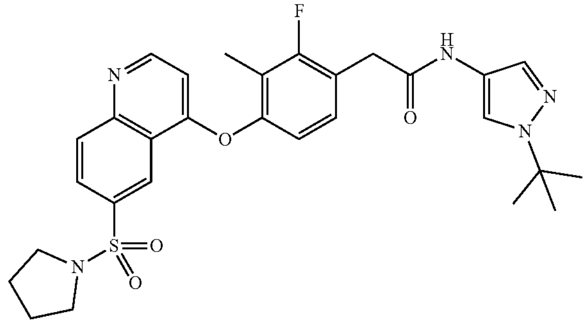 [SMILES: Cc1c(Oc2ccnc3ccc(S(=O)(=O)N4CCCC4)cc23)ccc(CC(=O)Nc2cnn(C(C)(C)C)c2)c1F] |
| 271 | 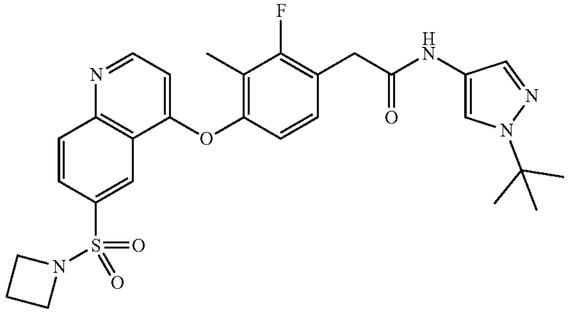 [SMILES: Cc1c(Oc2ccnc3ccc(S(=O)(=O)N4CCC4)cc23)ccc(CC(=O)Nc2cnn(C(C)(C)C)c2)c1F] |
| 272 | 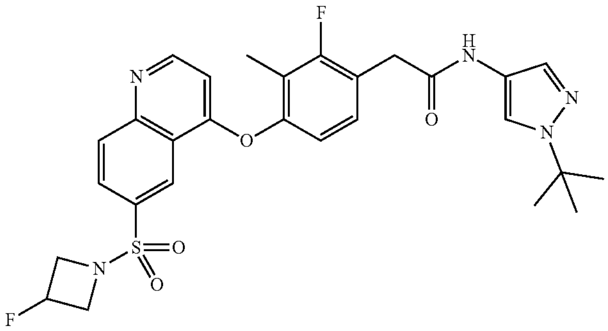 [SMILES: Cc1c(Oc2ccnc3ccc(S(=O)(=O)N4CC(F)C4)cc23)ccc(CC(=O)Nc2cnn(C(C)(C)C)c2)c1F] |

TABLE 2-continued
| Compound number | Structure |
|---|---|
| 274 | 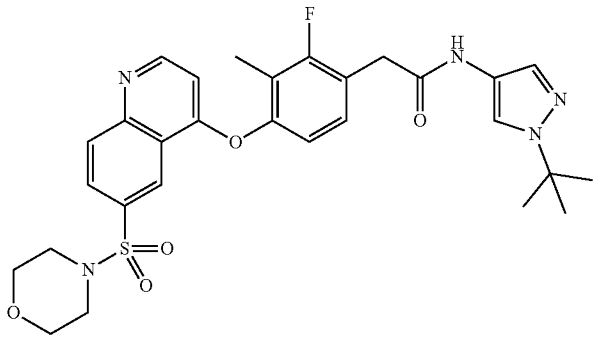 [SMILES: Cc1c(Oc2ccnc3ccc(S(=O)(=O)N4CCOCC4)cc23)ccc(CC(=O)Nc2cnn(C(C)(C)C)c2)c1F] |
| 275 | 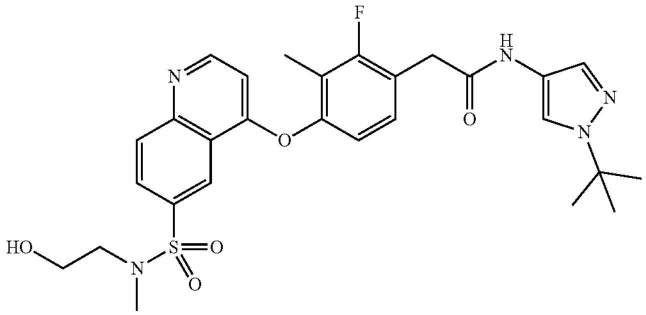 [SMILES: Cc1c(Oc2ccnc3ccc(S(=O)(=O)N(C)CCO)cc23)ccc(CC(=O)Nc2cnn(C(C)(C)C)c2)c1F] |
| 276 | 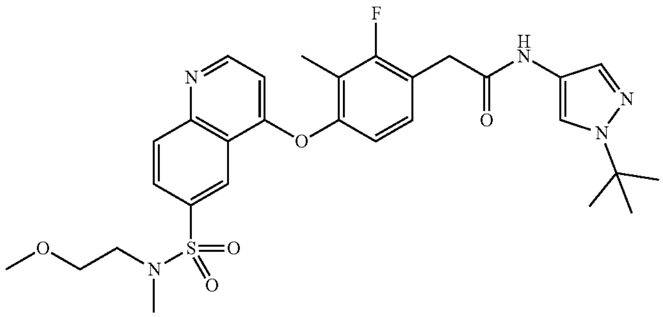 [SMILES: COCCN(C)S(=O)(=O)c1ccc2nccc(Oc3ccc(CC(=O)Nc4cnn(C(C)(C)C)c4)c(F)c3C)c2c1] |
| 277 | 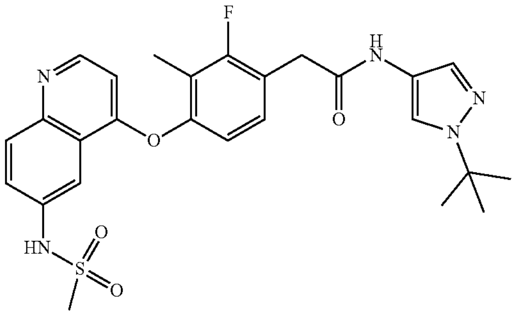 [SMILES: Cc1c(Oc2ccnc3ccc(NS(C)(=O)=O)cc23)ccc(CC(=O)Nc2cnn(C(C)(C)C)c2)c1F] |

TABLE 2-continued
| Compound number | Structure |
| --- | --- |
| 279 | 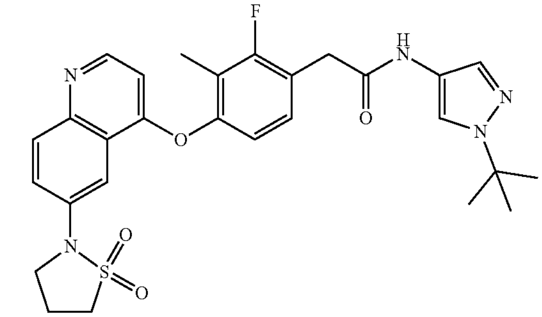 [SMILES: Cc1c(Oc2ccnc3ccc(N4CCCS4(=O)=O)cc23)ccc(CC(=O)Nc2cnn(C(C)(C)C)c2)c1F] |
| 280 | 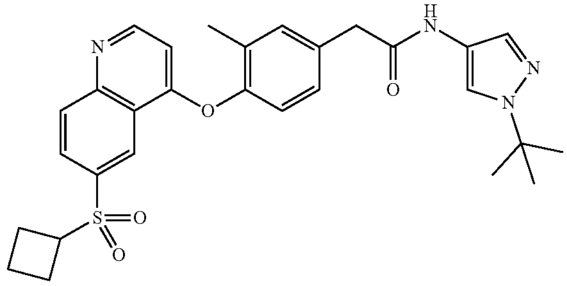 [SMILES: Cc1cc(CC(=O)Nc2cnn(C(C)(C)C)c2)ccc1Oc1ccnc2ccc(S(=O)(=O)C3CCC3)cc12] |
| 281 | 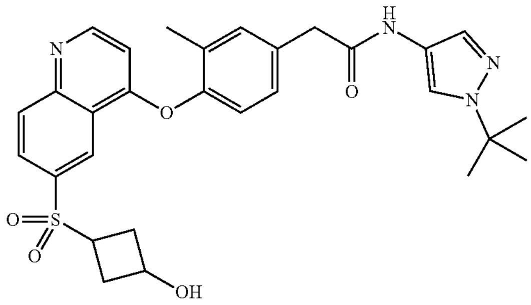 [SMILES: Cc1cc(CC(=O)Nc2cnn(C(C)(C)C)c2)ccc1Oc1ccnc2ccc(S(=O)(=O)C3CC(O)C3)cc12] |
| 282 | 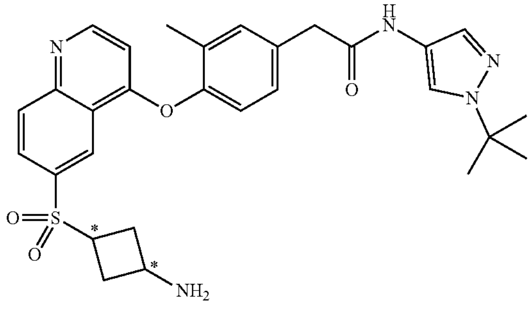 [SMILES: Cc1cc(CC(=O)Nc2cnn(C(C)(C)C)c2)ccc1Oc1ccnc2ccc(S(=O)(=O)C3CC(N)C3)cc12]<br>diastereomer 1 |

TABLE 2-continued
| Compound number | Structure |
| --- | --- |
| 283 | 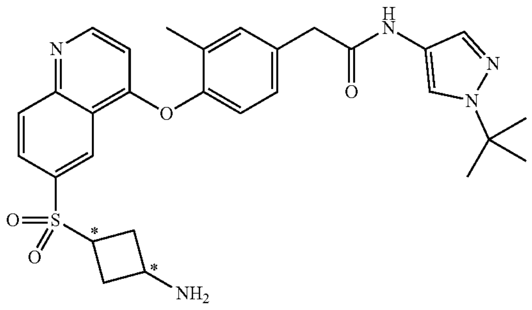 [SMILES: Cc1cc(CC(=O)Nc2cnn(C(C)(C)C)c2)ccc1Oc1ccnc2ccc(S(=O)(=O)C3CC(N)C3)cc12] diastereomer 2 |
| 285 | 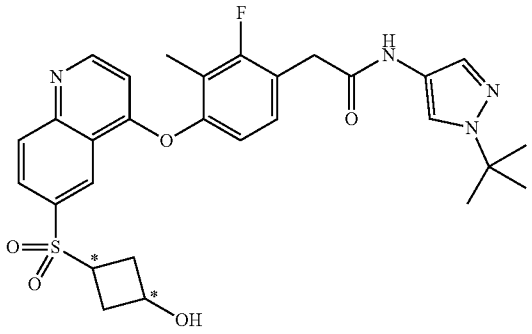 [SMILES: Cc1c(Oc2ccnc3ccc(S(=O)(=O)C4CC(O)C4)cc23)ccc(CC(=O)Nc2cnn(C(C)(C)C)c2)c1F] diastereomer 1 |
| 464 | 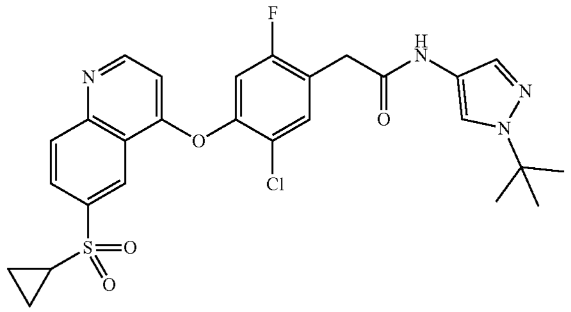 [SMILES: CC(C)(C)n1cc(NC(=O)Cc2cc(Cl)c(Oc3ccnc4ccc(S(=O)(=O)C5CC5)cc34)cc2F)cn1] |
| 465 | 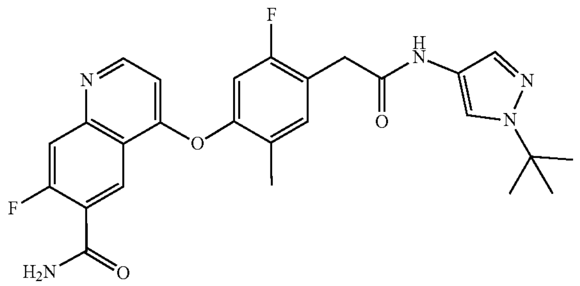 [SMILES: Cc1cc(CC(=O)Nc2cnn(C(C)(C)C)c2)c(F)cc1Oc1ccnc2cc(F)c(C(N)=O)cc12] |

TABLE 2-continued
| Compound number | Structure |
|---|---|
| 472 | 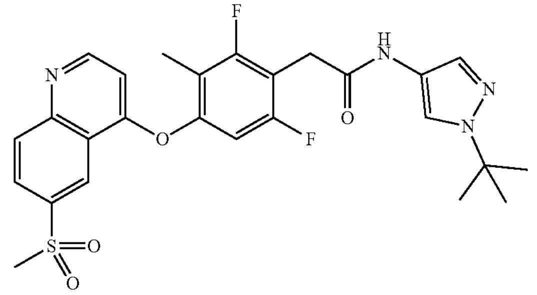 [SMILES: Cc1c(Oc2ccnc3ccc(S(C)(=O)=O)cc23)cc(F)c(CC(=O)Nc2cnn(C(C)(C)C)c2)c1F] |
| 480 | 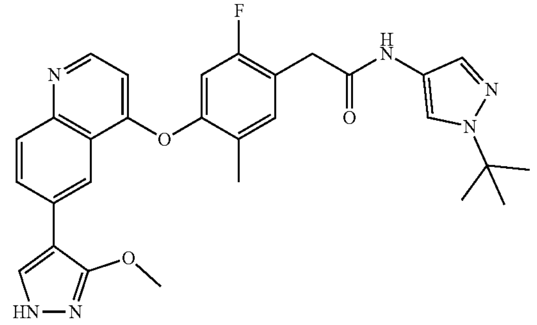 [SMILES: COc1n[nH]cc1-c1ccc2nccc(Oc3cc(F)c(CC(=O)Nc4cnn(C(C)(C)C)c4)cc3C)c2c1] |
| 482 | 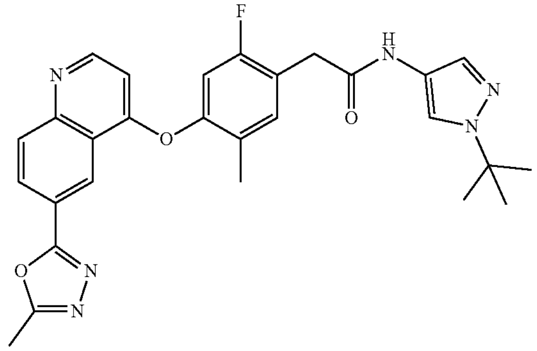 [SMILES: Cc1nnc(-c2ccc3nccc(Oc4cc(F)c(CC(=O)Nc5cnn(C(C)(C)C)c5)cc4C)c3c2)o1] |
| 483 | 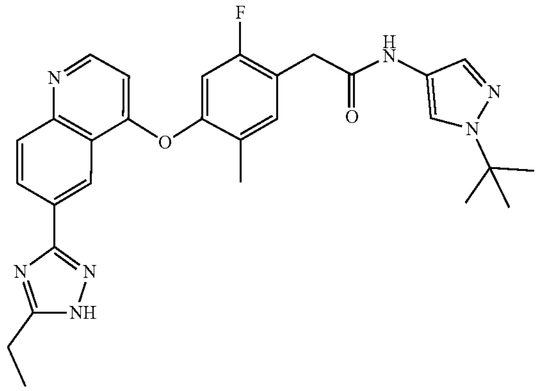 [SMILES: CCc1nc(-c2ccc3nccc(Oc4cc(F)c(CC(=O)Nc5cnn(C(C)(C)C)c5)cc4C)c3c2)n[nH]1] |

TABLE 2-continued
| Compound number | Structure |
|---|---|
| 484 | 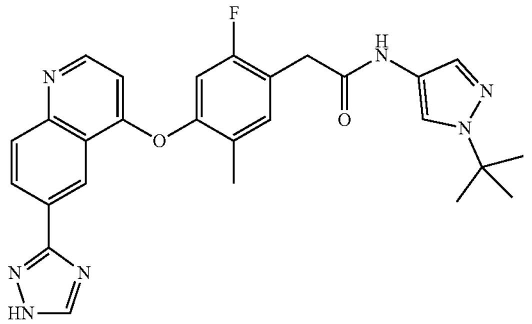 [SMILES: Cc1cc(CC(=O)Nc2cnn(C(C)(C)C)c2)c(F)cc1Oc1ccnc2ccc(-c3nc[nH]n3)cc12] |
| 485 | 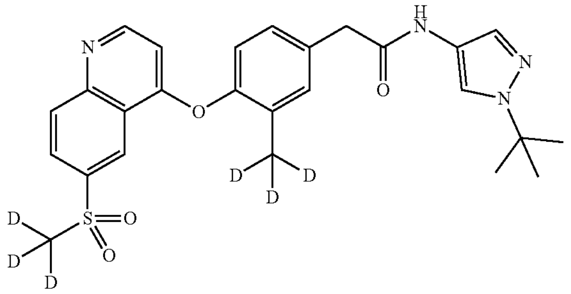 [SMILES: [2H]C([2H])([2H])c1cc(CC(=O)Nc2cnn(C(C)(C)C)c2)ccc1Oc1ccnc2ccc(S(=O)(=O)C([2H])([2H])[2H])cc12] |
| 487 | 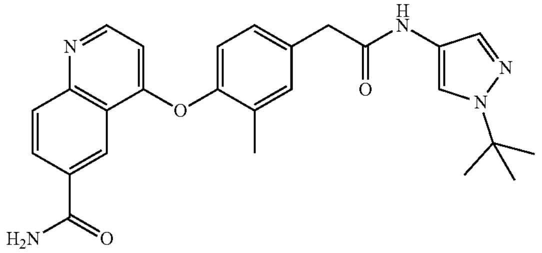 [SMILES: Cc1cc(CC(=O)Nc2cnn(C(C)(C)C)c2)ccc1Oc1ccnc2ccc(C(N)=O)cc12] |
| 488 | 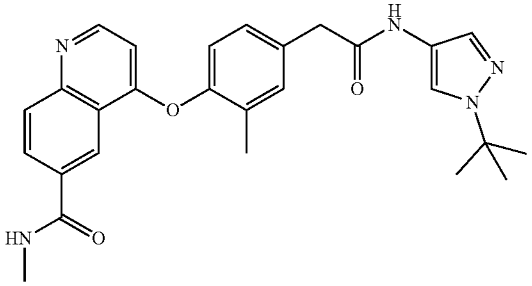 [SMILES: CNC(=O)c1ccc2nccc(Oc3ccc(CC(=O)Nc4cnn(C(C)(C)C)c4)cc3C)c2c1] |
| 489 | 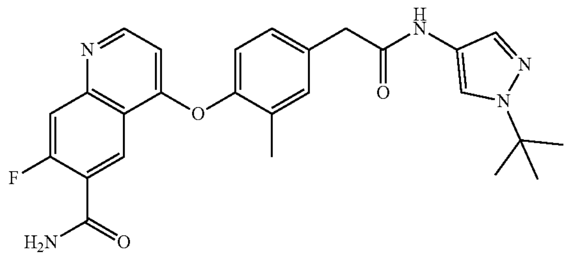 [SMILES: Cc1cc(CC(=O)Nc2cnn(C(C)(C)C)c2)ccc1Oc1ccnc2cc(F)c(C(N)=O)cc12] |

TABLE 2-continued
| Compound number | Structure |
| --- | --- |
| 490 | 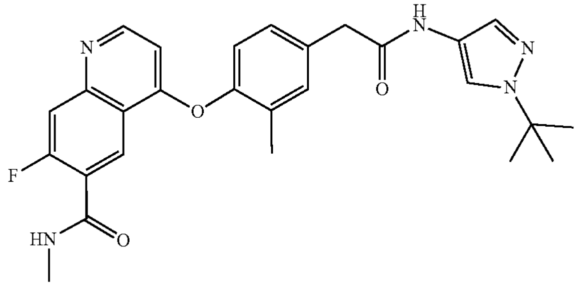 [SMILES: CNC(=O)c1cc2c(Oc3ccc(CC(=O)Nc4cnn(C(C)(C)C)c4)cc3C)ccnc2cc1F] |
| 491 | 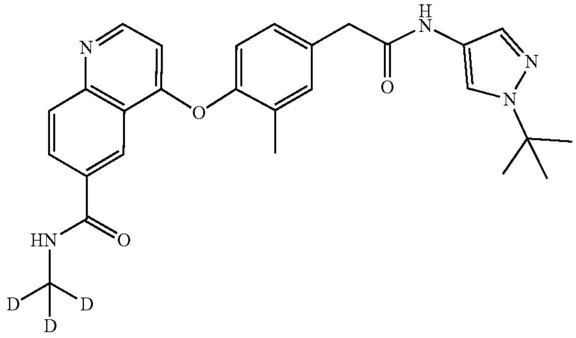 [SMILES: [2H]C([2H])([2H])NC(=O)c1ccc2nccc(Oc3ccc(CC(=O)Nc4cnn(C(C)(C)C)c4)cc3C)c2c1] |
| 500 | 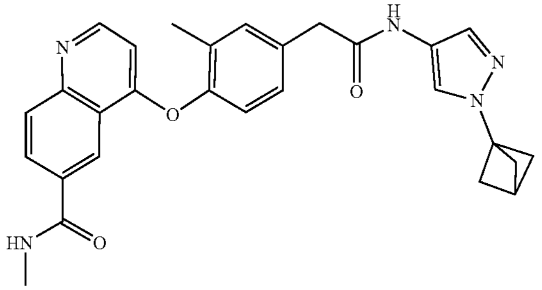 [SMILES: CNC(=O)c1ccc2nccc(Oc3ccc(CC(=O)Nc4cnn(C56CC(C5)C6)c4)cc3C)c2c1] |
| 502 | 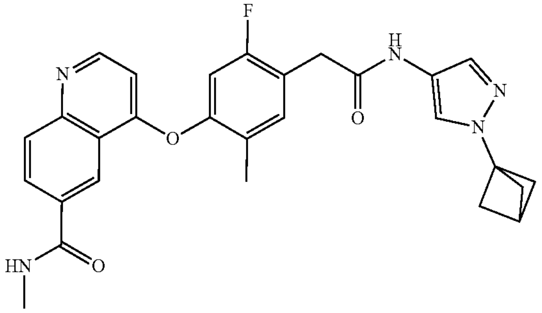 [SMILES: CNC(=O)c1ccc2nccc(Oc3cc(F)c(CC(=O)Nc4cnn(C56CC(C5)C6)c4)cc3C)c2c1] |
| 503 | 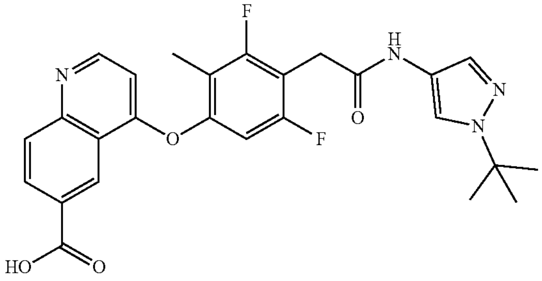 [SMILES: Cc1c(Oc2ccnc3ccc(C(=O)O)cc23)cc(F)c(CC(=O)Nc2cnn(C(C)(C)C)c2)c1F] |

TABLE 2-continued
| Compound number | Structure |
| --- | --- |
| 504 | 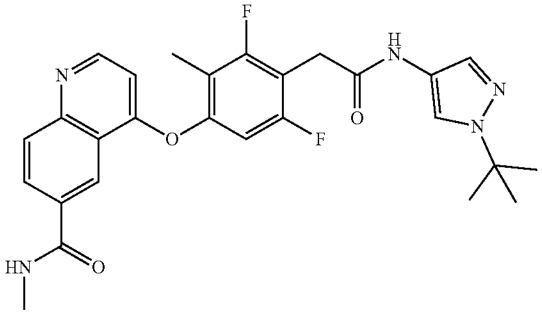 [SMILES: CNC(=O)c1ccc2nccc(Oc3cc(F)c(CC(=O)Nc4cnn(C(C)(C)C)c4)c(F)c3C)c2c1] |
| 507 | 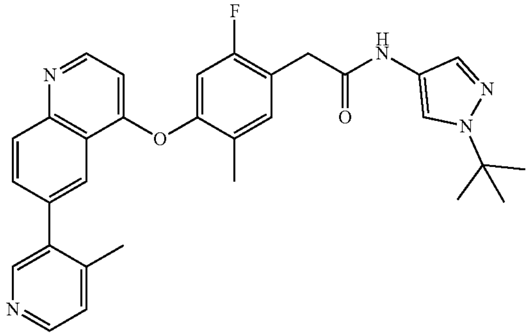 [SMILES: Cc1cc(CC(=O)Nc2cnn(C(C)(C)C)c2)c(F)cc1Oc1ccnc2ccc(-c3cnccc3C)cc12] |
| 516 | 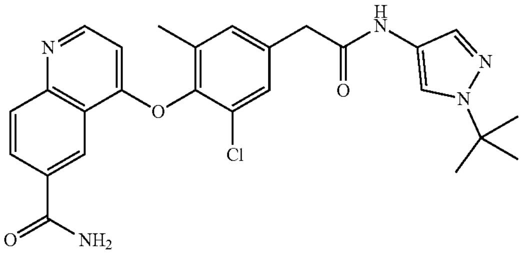 [SMILES: Cc1cc(CC(=O)Nc2cnn(C(C)(C)C)c2)cc(Cl)c1Oc1ccnc2ccc(C(N)=O)cc12] |
| 519 | 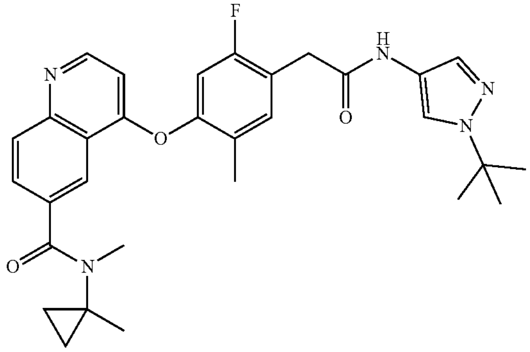 [SMILES: Cc1cc(CC(=O)Nc2cnn(C(C)(C)C)c2)c(F)cc1Oc1ccnc2ccc(C(=O)N(C)C3(C)CC3)cc12] |

TABLE 2-continued
| Compound number | Structure |
|---|---|
| 520 | 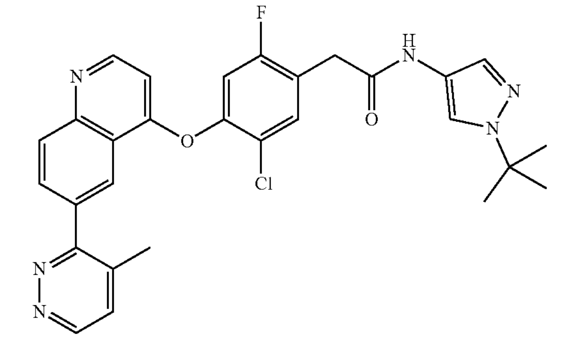 [SMILES: Cc1ccnnc1-c1ccc2nccc(Oc3cc(F)c(CC(=O)Nc4cnn(C(C)(C)C)c4)cc3Cl)c2c1] |
| 524 | 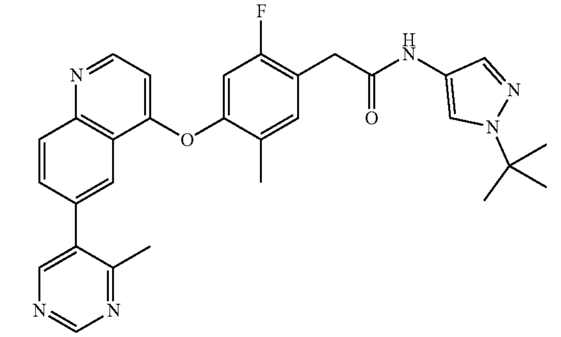 [SMILES: Cc1cc(CC(=O)Nc2cnn(C(C)(C)C)c2)c(F)cc1Oc1ccnc2ccc(-c3cncnc3C)cc12] |
| 542 | 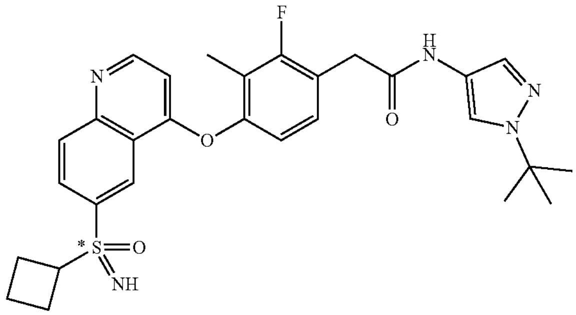 [SMILES: Cc1c(Oc2ccnc3ccc(S(=N)(=O)C4CCC4)cc23)ccc(CC(=O)Nc2cnn(C(C)(C)C)c2)c1F]<br>enantiomer 2 |
| 287 | 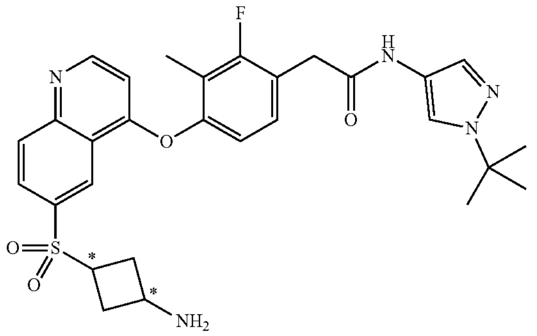 [SMILES: Cc1c(Oc2ccnc3ccc(S(=O)(=O)C4CC(N)C4)cc23)ccc(CC(=O)Nc2cnn(C(C)(C)C)c2)c1F]<br>diastereomer 1 |

TABLE 2-continued
| Compound number | Structure |
|---|---|
| 288 | 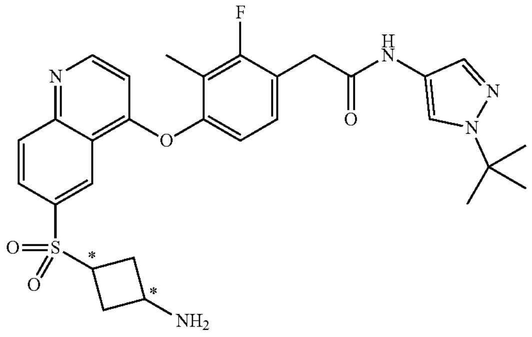 [SMILES: Cc1c(Oc2ccnc3ccc(S(=O)(=O)C4CC(N)C4)cc23)ccc(CC(=O)Nc2cnn(C(C)(C)C)c2)c1F] diastereomer 2 |
| 290 | 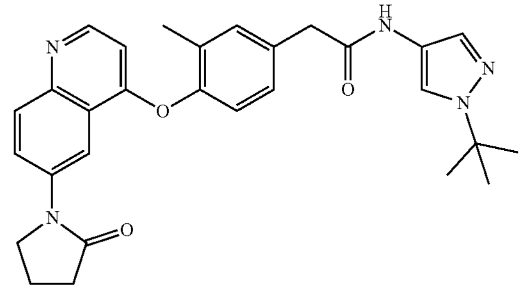 [SMILES: Cc1cc(CC(=O)Nc2cnn(C(C)(C)C)c2)ccc1Oc1ccnc2ccc(N3CCCC3=O)cc12] |
| 291 | 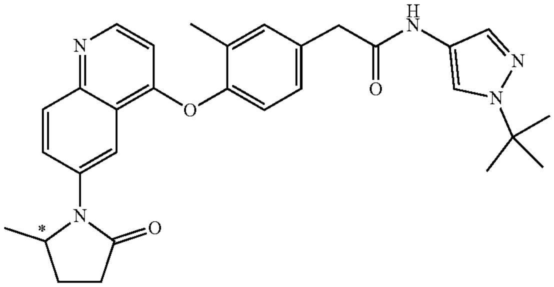 [SMILES: Cc1cc(CC(=O)Nc2cnn(C(C)(C)C)c2)ccc1Oc1ccnc2ccc(N3C(=O)CCC3C)cc12] enantiomer 1 |
| 293 | 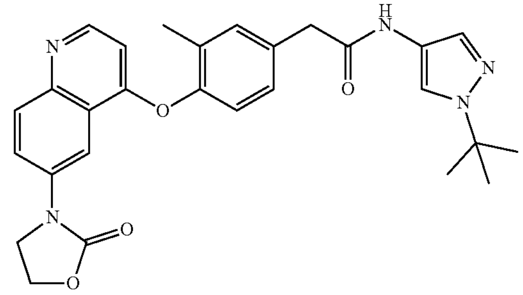 [SMILES: Cc1cc(CC(=O)Nc2cnn(C(C)(C)C)c2)ccc1Oc1ccnc2ccc(N3CCOC3=O)cc12] |

TABLE 2-continued
| Compound number | Structure |
|---|---|
| 295 | 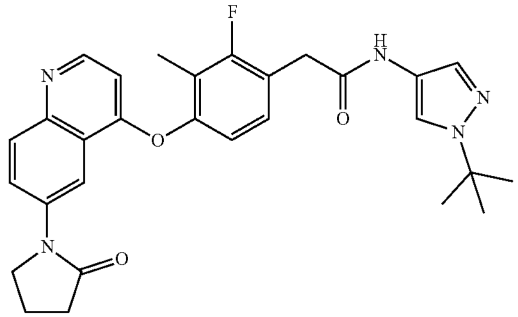 [SMILES: Cc1c(Oc2ccnc3ccc(N4CCCC4=O)cc23)ccc(CC(=O)Nc2cnn(C(C)(C)C)c2)c1F] |
| 296 | 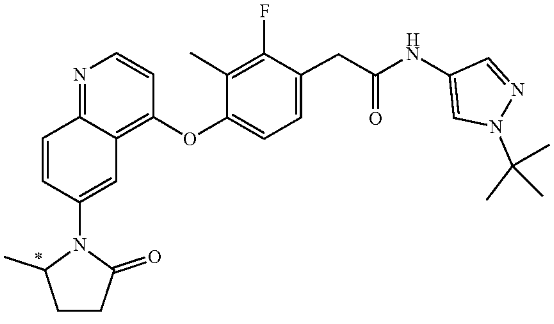 [SMILES: Cc1c(Oc2ccnc3ccc(N4C(=O)CCC4C)cc23)ccc(CC(=O)Nc2cnn(C(C)(C)C)c2)c1F]<br>enantimer 1 |
| 297 | 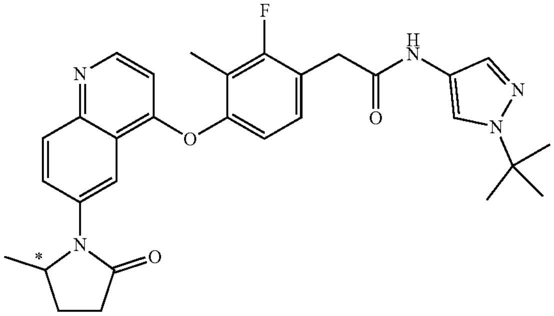 [SMILES: Cc1c(Oc2ccnc3ccc(N4C(=O)CCC4C)cc23)ccc(CC(=O)Nc2cnn(C(C)(C)C)c2)c1F]<br>enantiomer 2 |
| 298 | 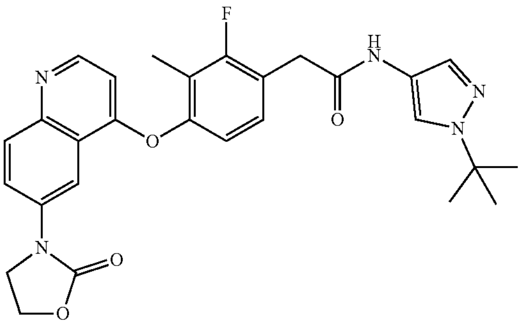 [SMILES: Cc1c(Oc2ccnc3ccc(N4CCOC4=O)cc23)ccc(CC(=O)Nc2cnn(C(C)(C)C)c2)c1F] |

TABLE 2-continued
| Compound number | Structure |
|---|---|
| 299 | 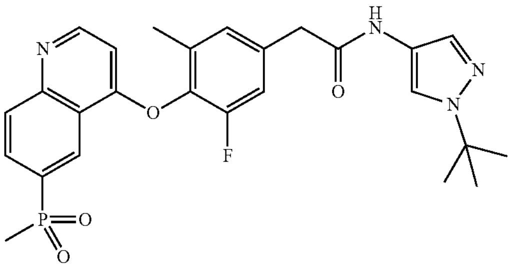 |
| 300 | 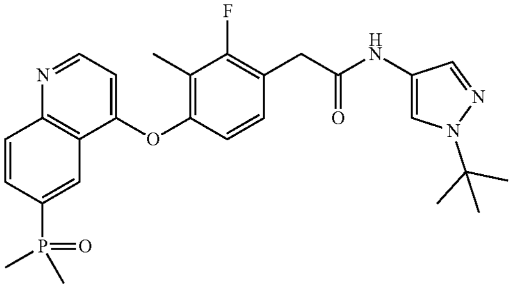 [SMILES: Cc1c(Oc2ccnc3ccc(P(C)(C)=O)cc23)ccc(CC(=O)Nc2cnn(C(C)(C)C)c2)c1F] |
| 302 | 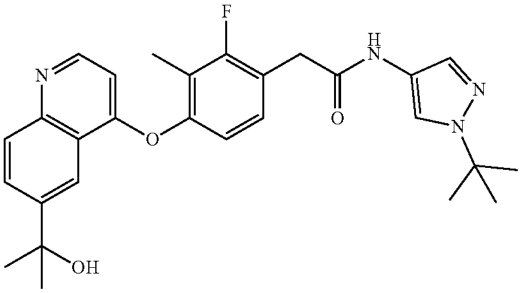 [SMILES: Cc1c(Oc2ccnc3ccc(C(C)(C)O)cc23)ccc(CC(=O)Nc2cnn(C(C)(C)C)c2)c1F] |
| 303 | 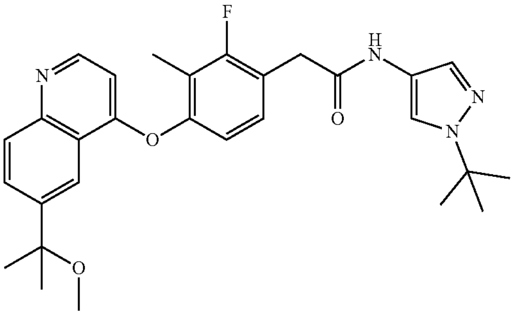 [SMILES: COC(C)(C)c1ccc2nccc(Oc3ccc(CC(=O)Nc4cnn(C(C)(C)C)c4)c(F)c3C)c2c1] |
| 304 | 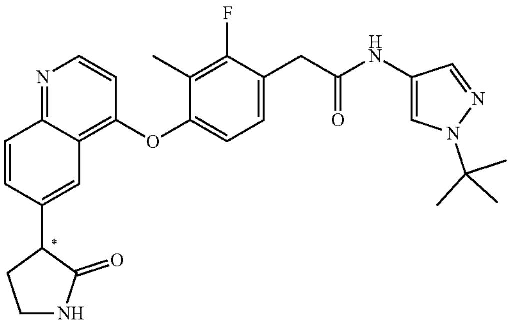 [SMILES: Cc1c(Oc2ccnc3ccc(C4CCNC4=O)cc23)ccc(CC(=O)Nc2cnn(C(C)(C)C)c2)c1F]<br>enantiomer 1 |

TABLE 2-continued
| Compound number | Structure |
|---|---|
| 305 | 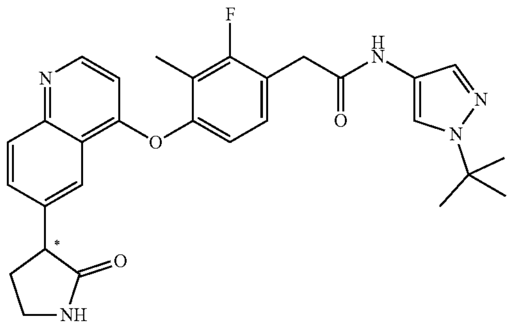 [SMILES: Cc1c(Oc2ccnc3ccc(C4CCNC4=O)cc23)ccc(CC(=O)Nc2cnn(C(C)(C)C)c2)c1F] enantiomer 2 |
| 306 | 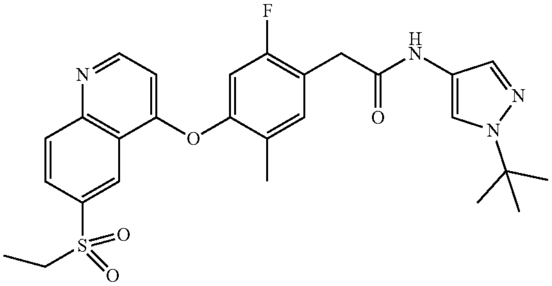 [SMILES: CCS(=O)(=O)c1ccc2nccc(Oc3cc(F)c(CC(=O)Nc4cnn(C(C)(C)C)c4)cc3C)c2c1] |
| 307 | 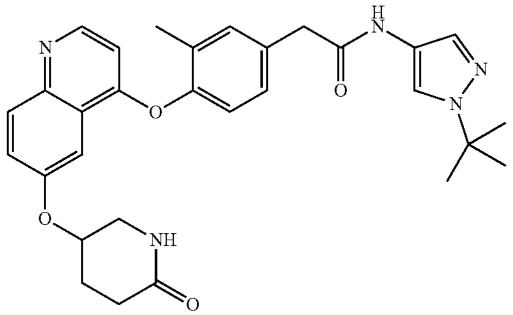 [SMILES: Cc1cc(CC(=O)Nc2cnn(C(C)(C)C)c2)ccc1Oc1ccnc2ccc(OC3CCC(=O)NC3)cc12] |
| 309 | 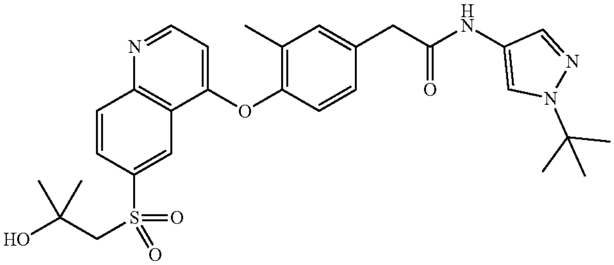 [SMILES: Cc1cc(CC(=O)Nc2cnn(C(C)(C)C)c2)ccc1Oc1ccnc2ccc(S(=O)(=O)CC(C)(C)O)cc12] |
| 310 | 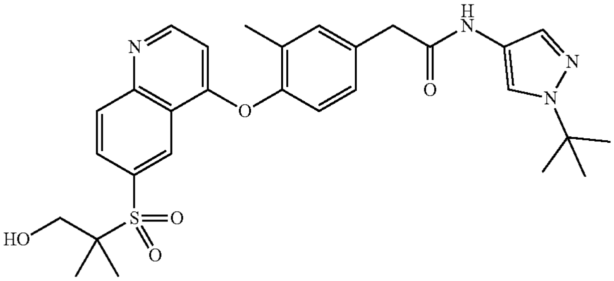 [SMILES: Cc1cc(CC(=O)Nc2cnn(C(C)(C)C)c2)ccc1Oc1ccnc2ccc(S(=O)(=O)C(C)(C)CO)cc12] |

TABLE 2-continued
| Compound number | Structure |
|---|---|
| 311 | 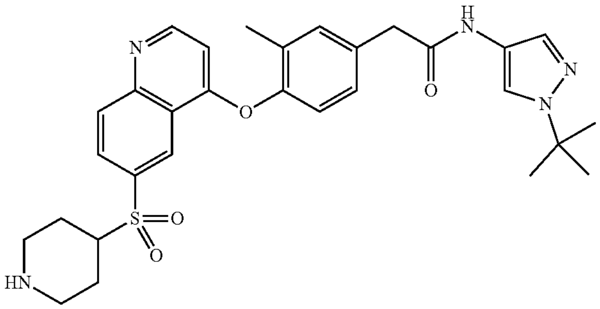 [SMILES: Cc1cc(CC(=O)Nc2cnn(C(C)(C)C)c2)ccc1Oc1ccnc2ccc(S(=O)(=O)C3CCNCC3)cc12] |
| 312 | 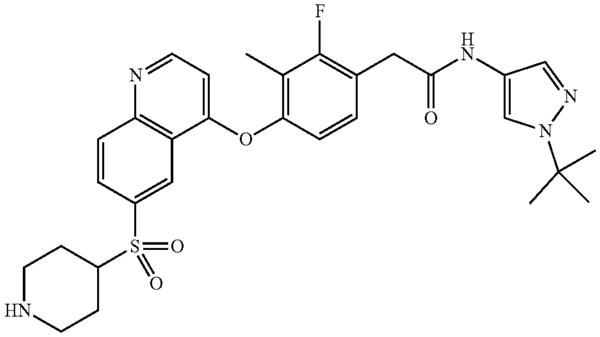 [SMILES: Cc1c(Oc2ccnc3ccc(S(=O)(=O)C4CCNCC4)cc23)ccc(CC(=O)Nc2cnn(C(C)(C)C)c2)c1F] |
| 313 | 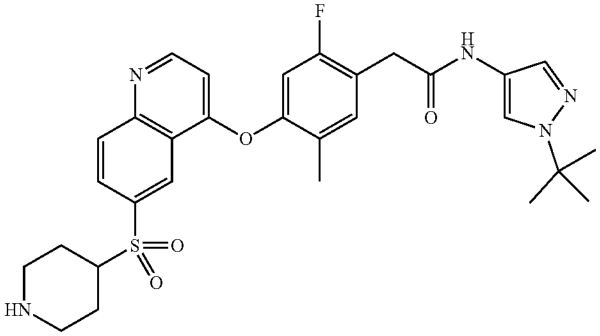 [SMILES: Cc1cc(CC(=O)Nc2cnn(C(C)(C)C)c2)c(F)cc1Oc1ccnc2ccc(S(=O)(=O)C3CCNCC3)cc12] |
| 314 | 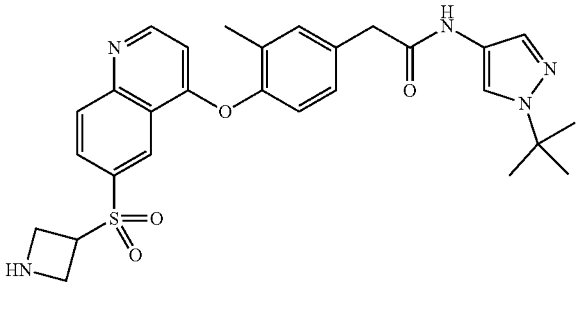 [SMILES: Cc1cc(CC(=O)Nc2cnn(C(C)(C)C)c2)ccc1Oc1ccnc2ccc(S(=O)(=O)C3CNC3)cc12] |

TABLE 2-continued
| Compound number | Structure |
| --- | --- |
| 315 | 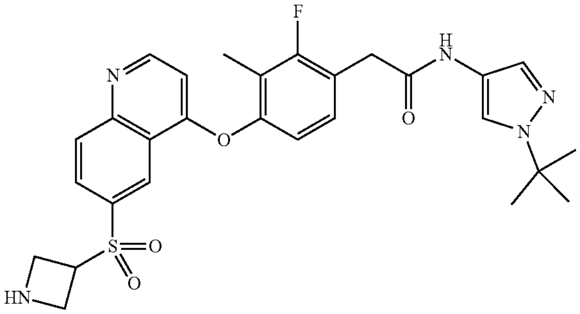 [SMILES: Cc1c(Oc2ccnc3ccc(S(=O)(=O)C4CNC4)cc23)ccc(CC(=O)Nc2cnn(C(C)(C)C)c2)c1F] |
| 316 | 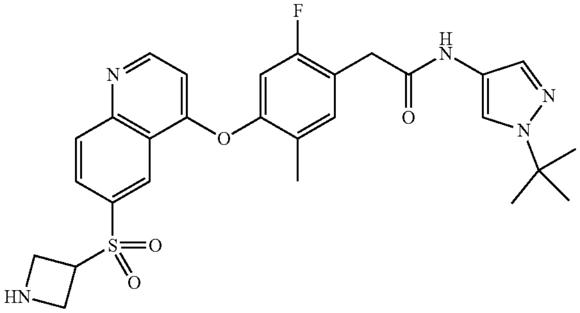 [SMILES: Cc1cc(CC(=O)Nc2cnn(C(C)(C)C)c2)c(F)cc1Oc1ccnc2ccc(S(=O)(=O)C3CNC3)cc12] |
| 317 | 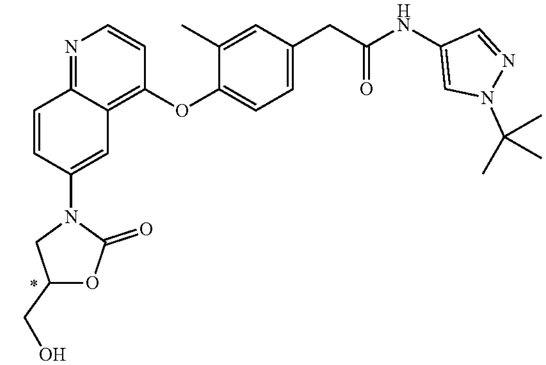 [SMILES: Cc1cc(CC(=O)Nc2cnn(C(C)(C)C)c2)ccc1Oc1ccnc2ccc(N3CC(CO)OC3=O)cc12]<br>enantiomer 1 |
| 318 | 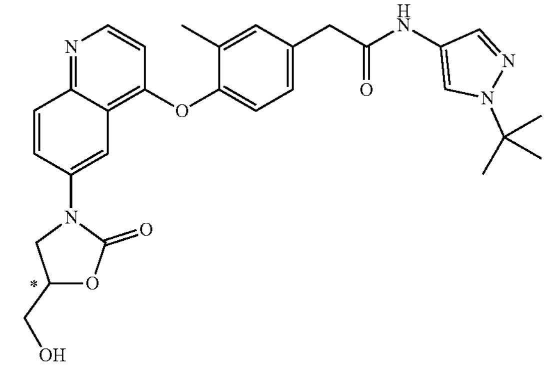 [SMILES: Cc1cc(CC(=O)Nc2cnn(C(C)(C)C)c2)ccc1Oc1ccnc2ccc(N3CC(CO)OC3=O)cc12]<br>enantiomer 2 |

TABLE 2-continued
| Compound number | Structure |
|---|---|
| 319 | 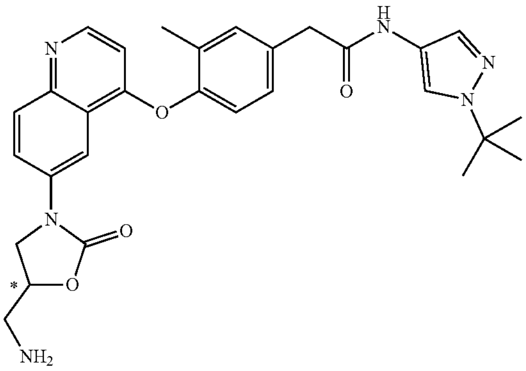 [SMILES: Cc1cc(CC(=O)Nc2cnn(C(C)(C)C)c2)ccc1Oc1ccnc2ccc(N3CC(CN)OC3=O)cc12] enantiomer 1 |
| 320 | 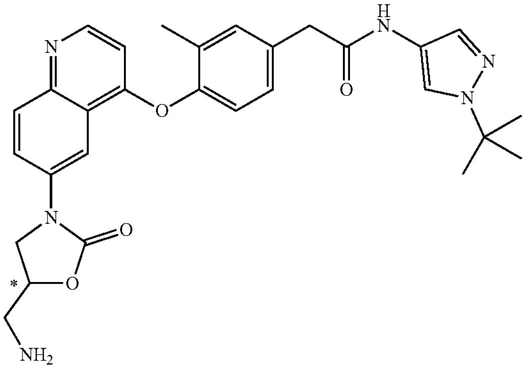 enantiomer 2 |
| 321 | 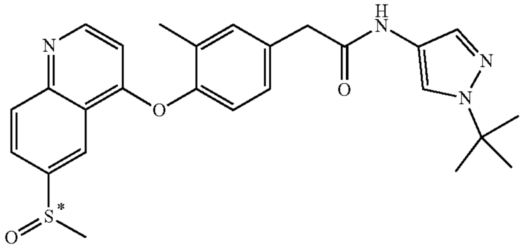 [SMILES: Cc1cc(CC(=O)Nc2cnn(C(C)(C)C)c2)ccc1Oc1ccnc2ccc(S(C)=O)cc12] enantiomer 1 |
| 322 | 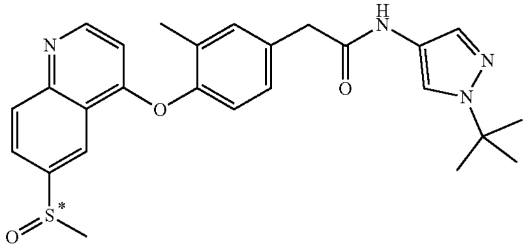 [SMILES: Cc1cc(CC(=O)Nc2cnn(C(C)(C)C)c2)ccc1Oc1ccnc2ccc(S(C)=O)cc12] enantiomer 2 |

TABLE 2-continued
| Compound number | Structure |
|---|---|
| 323 | 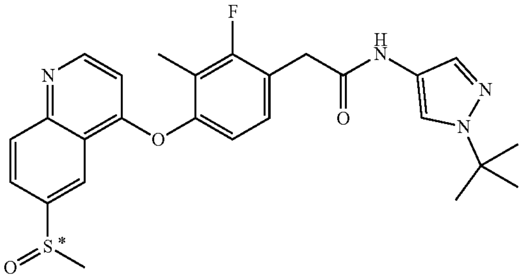 [SMILES: Cc1c(Oc2ccnc3ccc(S(C)=O)cc23)ccc(CC(=O)Nc2cnn(C(C)(C)C)c2)c1F] enantiomer 1 |
| 324 | 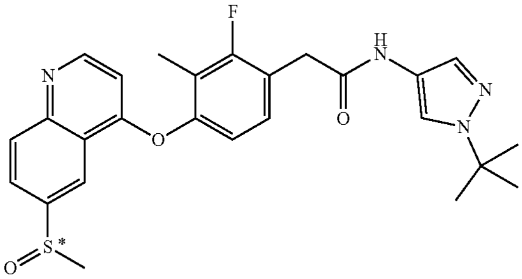 [SMILES: Cc1c(Oc2ccnc3ccc(S(C)=O)cc23)ccc(CC(=O)Nc2cnn(C(C)(C)C)c2)c1F] enantiomer 2 |
| 325 | 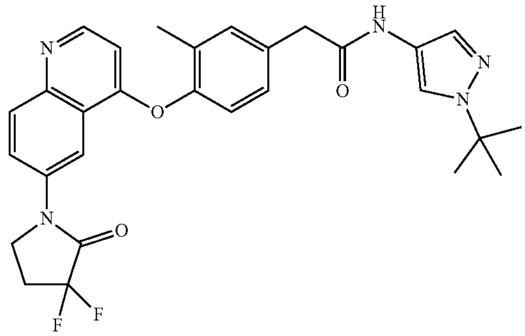 [SMILES: Cc1cc(CC(=O)Nc2cnn(C(C)(C)C)c2)ccc1Oc1ccnc2ccc(N3CCC(F)(F)C3=O)cc12] |
| 326 | 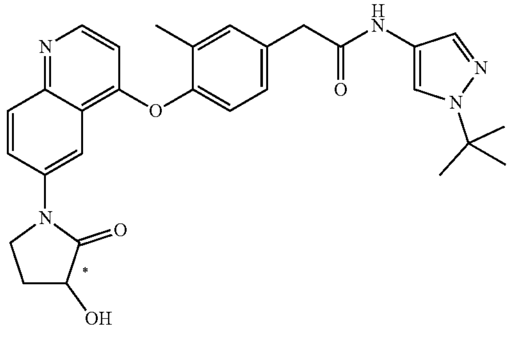 [SMILES: Cc1cc(CC(=O)Nc2cnn(C(C)(C)C)c2)ccc1Oc1ccnc2ccc(N3CCC(O)C3=O)cc12] enantiomer 1 |

TABLE 2-continued
| Compound number | Structure |
|---|---|
| 327 | 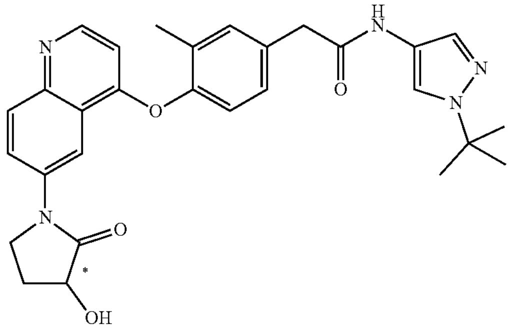 [SMILES: Cc1cc(CC(=O)Nc2cnn(C(C)(C)C)c2)ccc1Oc1ccnc2ccc(N3CCC(O)C3=O)cc12] enantiomer 2 |
| 329 | 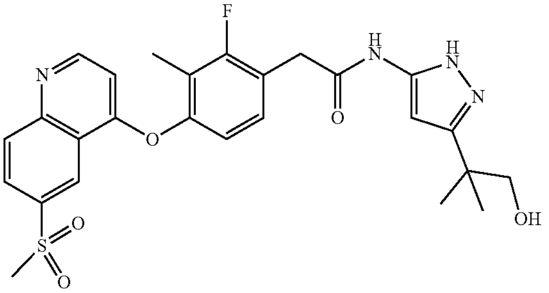 [SMILES: Cc1c(Oc2ccnc3ccc(S(C)(=O)=O)cc23)ccc(CC(=O)Nc2cc(C(C)(C)CO)n[nH]2)c1F] |
| 330 | 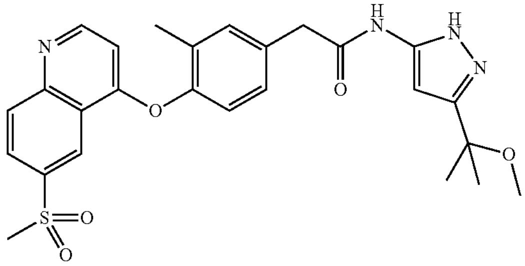 [SMILES: COC(C)(C)c1cc(NC(=O)Cc2ccc(Oc3ccnc4ccc(S(C)(=O)=O)cc34)c(C)c2)[nH]n1] |
| 331 | 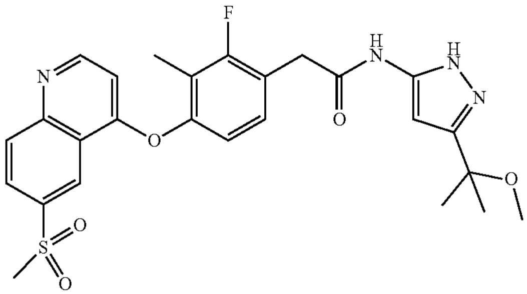 [SMILES: COC(C)(C)c1cc(NC(=O)Cc2ccc(Oc3ccnc4ccc(S(C)(=O)=O)cc34)c(C)c2F)[nH]n1] |
| 332 | 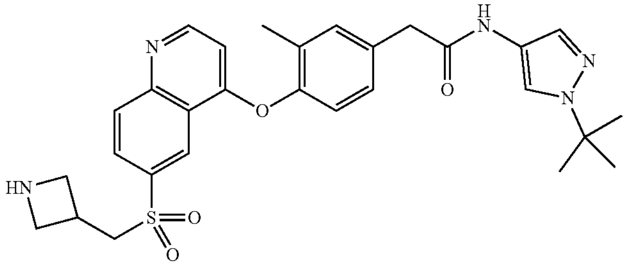 [SMILES: Cc1cc(CC(=O)Nc2cnn(C(C)(C)C)c2)ccc1Oc1ccnc2ccc(S(=O)(=O)CC3CNC3)cc12] |

TABLE 2-continued
| Compound number | Structure |
| --- | --- |
| 333 | 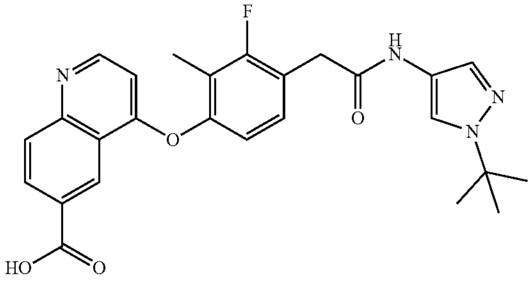 [SMILES: Cc1c(Oc2ccnc3ccc(C(=O)O)cc23)ccc(CC(=O)Nc2cnn(C(C)(C)C)c2)c1F] |
| 334 | 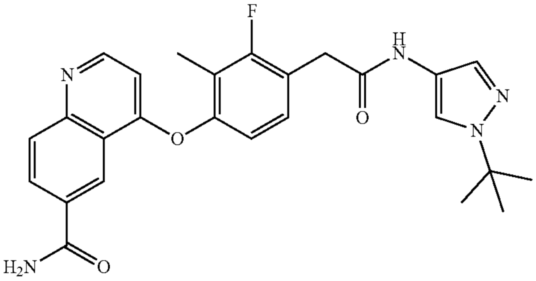 [SMILES: Cc1c(Oc2ccnc3ccc(C(N)=O)cc23)ccc(CC(=O)Nc2cnn(C(C)(C)C)c2)c1F] |
| 335 | 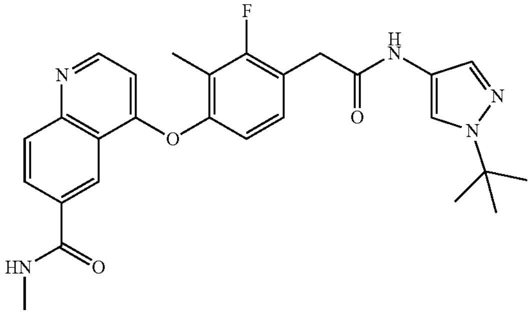 [SMILES: CNC(=O)c1ccc2nccc(Oc3ccc(CC(=O)Nc4cnn(C(C)(C)C)c4)c(F)c3C)c2c1] |
| 336 | 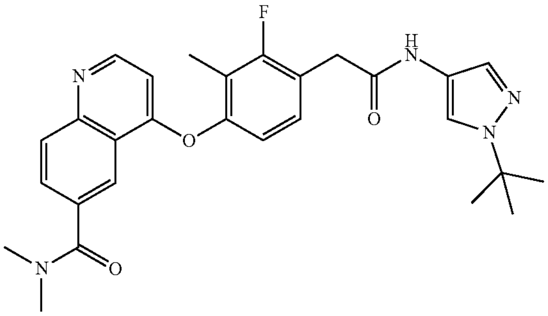 [SMILES: Cc1c(Oc2ccnc3ccc(C(=O)N(C)C)cc23)ccc(CC(=O)Nc2cnn(C(C)(C)C)c2)c1F] |

TABLE 2-continued
| Compound number | Structure |
|---|---|
| 337 | 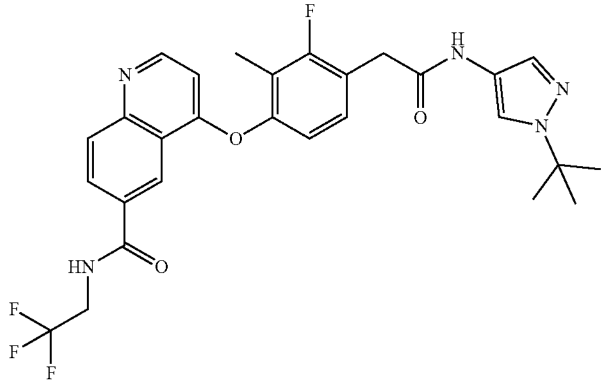 [SMILES: Cc1c(Oc2ccnc3ccc(C(=O)NCC(F)(F)F)cc23)ccc(CC(=O)Nc2cnn(C(C)(C)C)c2)c1F] |
| 338 | 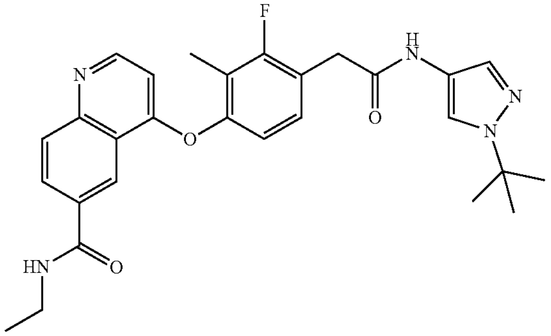 [SMILES: CCNC(=O)c1ccc2nccc(Oc3ccc(CC(=O)Nc4cnn(C(C)(C)C)c4)c(F)c3C)c2c1] |
| 339 | 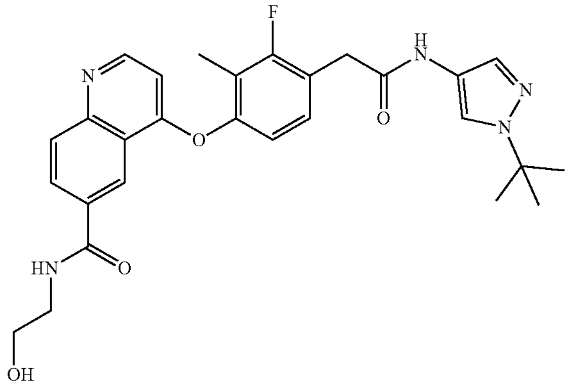 [SMILES: Cc1c(Oc2ccnc3ccc(C(=O)NCCO)cc23)ccc(CC(=O)Nc2cnn(C(C)(C)C)c2)c1F] |
| 340 | 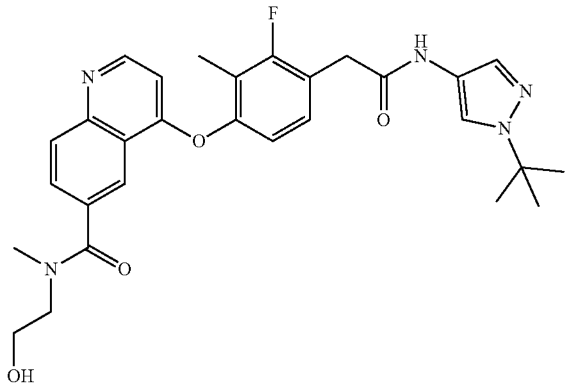 [SMILES: Cc1c(Oc2ccnc3ccc(C(=O)N(C)CCO)cc23)ccc(CC(=O)Nc2cnn(C(C)(C)C)c2)c1F] |

TABLE 2-continued
| Compound number | Structure |
| --- | --- |
| 341 | 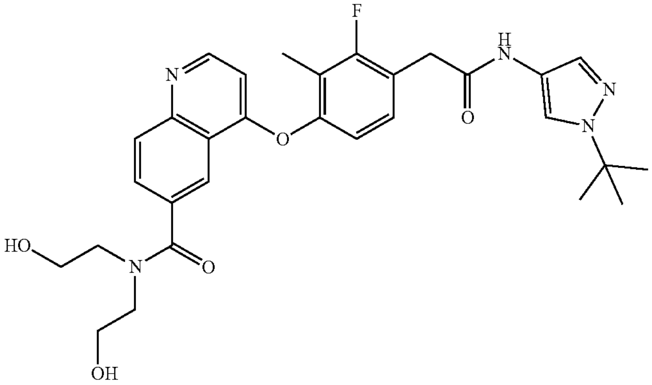 [SMILES: Cc1c(Oc2ccnc3ccc(C(=O)N(CCO)CCO)cc23)ccc(CC(=O)Nc2cnn(C(C)(C)C)c2)c1F] |
| 342 | 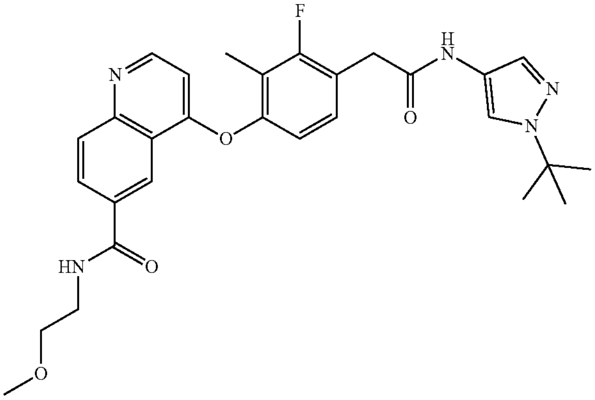 [SMILES: COCCNC(=O)c1ccc2nccc(Oc3ccc(CC(=O)Nc4cnn(C(C)(C)C)c4)c(F)c3C)c2c1] |
| 343 | 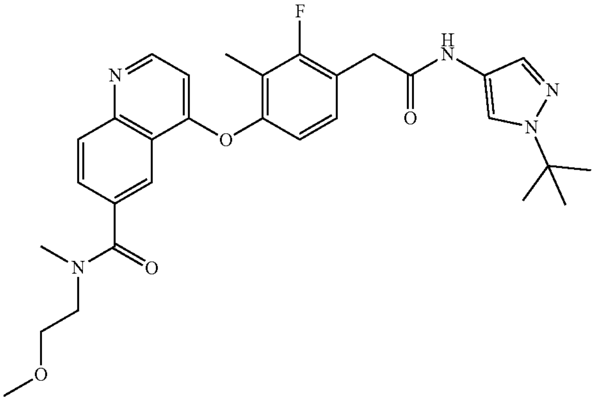 [SMILES: COCCN(C)C(=O)c1ccc2nccc(Oc3ccc(CC(=O)Nc4cnn(C(C)(C)C)c4)c(F)c3C)c2c1] |
| 344 | 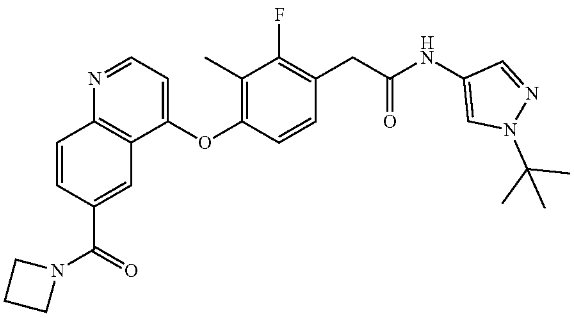 [SMILES: Cc1c(Oc2ccnc3ccc(C(=O)N4CCC4)cc23)ccc(CC(=O)Nc2cnn(C(C)(C)C)c2)c1F] |

TABLE 2-continued
| Compound number | Structure |
|---|---|
| 345 | 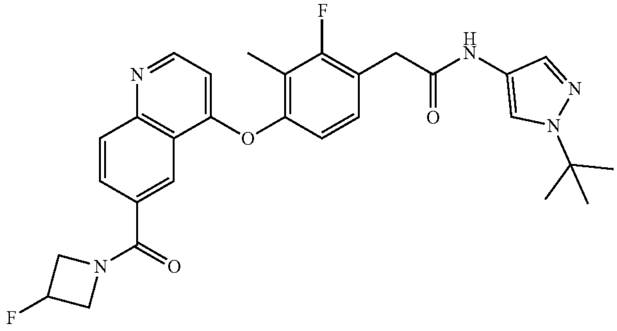 [SMILES: Cc1c(Oc2ccnc3ccc(C(=O)N4CC(F)C4)cc23)ccc(CC(=O)Nc2cnn(C(C)(C)C)c2)c1F] |
| 346 | 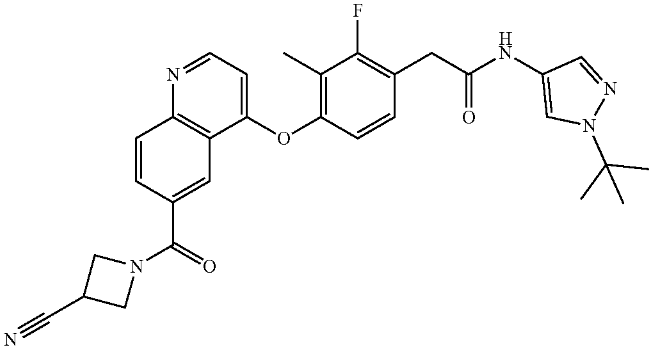 [SMILES: Cc1c(Oc2ccnc3ccc(C(=O)N4CC(C#N)C4)cc23)ccc(CC(=O)Nc2cnn(C(C)(C)C)c2)c1F] |
| 347 | 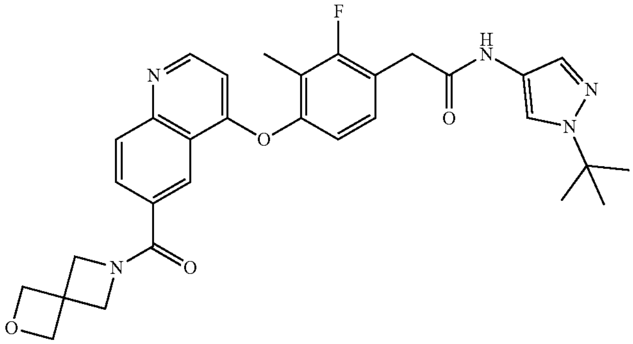 [SMILES: Cc1c(Oc2ccnc3ccc(C(=O)N4CC5(COC5)C4)cc23)ccc(CC(=O)Nc2cnn(C(C)(C)C)c2)c1F] |
| 348 | 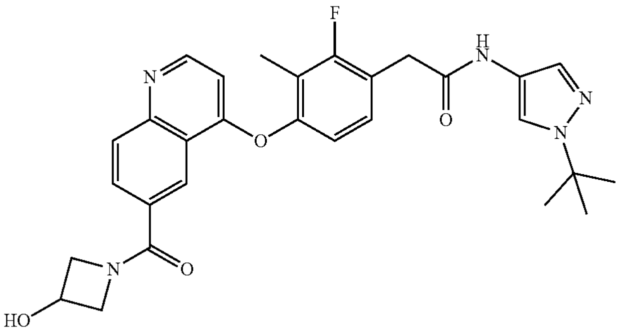 [SMILES: Cc1c(Oc2ccnc3ccc(C(=O)N4CC(O)C4)cc23)ccc(CC(=O)Nc2cnn(C(C)(C)C)c2)c1F] |

TABLE 2-continued
| Compound number | Structure |
|---|---|
| 349 | 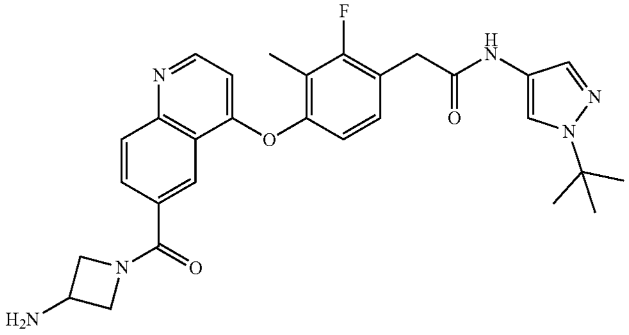 [SMILES: Cc1c(Oc2ccnc3ccc(C(=O)N4CC(N)C4)cc23)ccc(CC(=O)Nc2cnn(C(C)(C)C)c2)c1F] |
| 350 | 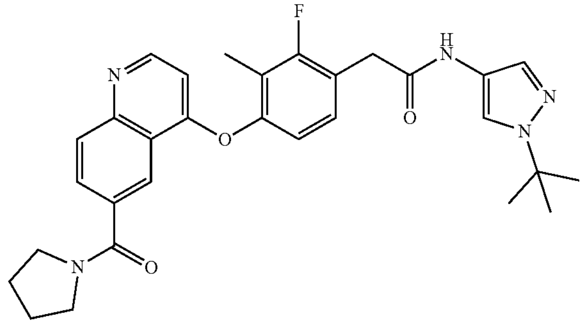 [SMILES: Cc1c(Oc2ccnc3ccc(C(=O)N4CCCC4)cc23)ccc(CC(=O)Nc2cnn(C(C)(C)C)c2)c1F] |
| 351 | 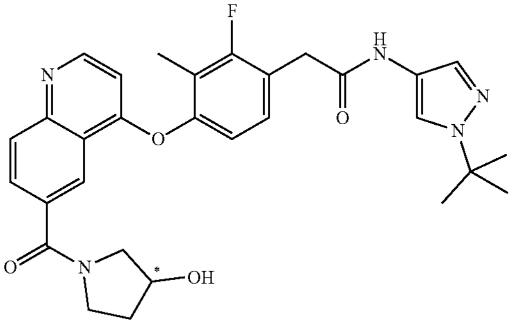 [SMILES: Cc1c(Oc2ccnc3ccc(C(=O)N4CCC(O)C4)cc23)ccc(CC(=O)Nc2cnn(C(C)(C)C)c2)c1F] enantiomer 1 |
| 352 | 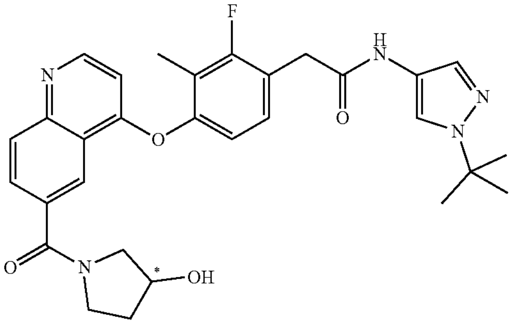 enantiomer 2 |

TABLE 2-continued
| Compound number | Structure |
| --- | --- |
| 353 | 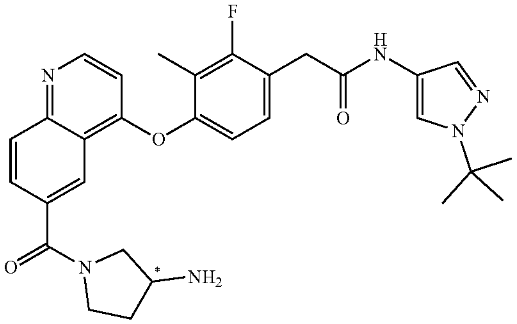 [SMILES: Cc1c(Oc2ccnc3ccc(C(=O)N4CCC(N)C4)cc23)ccc(CC(=O)Nc2cnn(C(C)(C)C)c2)c1F]<br>enantiomer 1 |
| 354 | 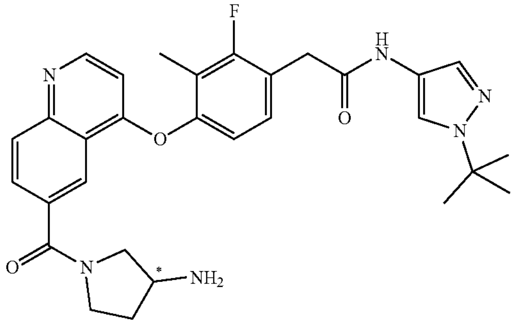 [SMILES: Cc1c(Oc2ccnc3ccc(C(=O)N4CCC(N)C4)cc23)ccc(CC(=O)Nc2cnn(C(C)(C)C)c2)c1F]<br>enantiomer 2 |
| 355 | 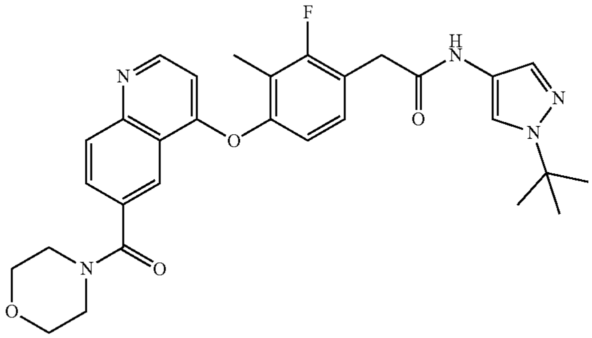 [SMILES: Cc1c(Oc2ccnc3ccc(C(=O)N4CCOCC4)cc23)ccc(CC(=O)Nc2cnn(C(C)(C)C)c2)c1F] |
| 356 | 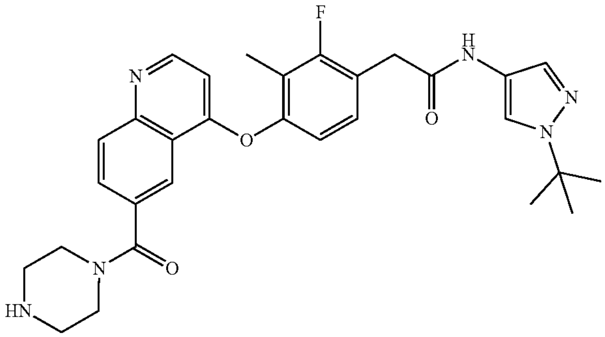 [SMILES: Cc1c(Oc2ccnc3ccc(C(=O)N4CCNCC4)cc23)ccc(CC(=O)Nc2cnn(C(C)(C)C)c2)c1F] |

TABLE 2-continued
| Compound number | Structure |
|---|---|
| 357 | 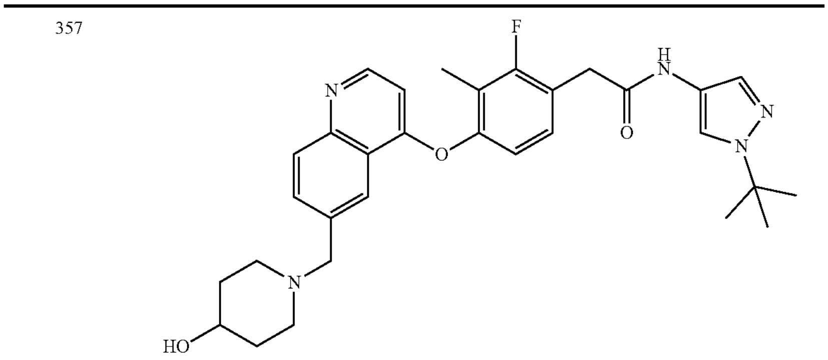 |
| 358 | 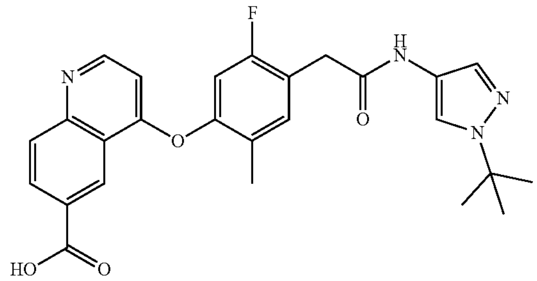 [SMILES: Cc1cc(CC(=O)Nc2cnn(C(C)(C)C)c2)c(F)cc1Oc1ccnc2ccc(C(=O)O)cc12] |
| 359 | 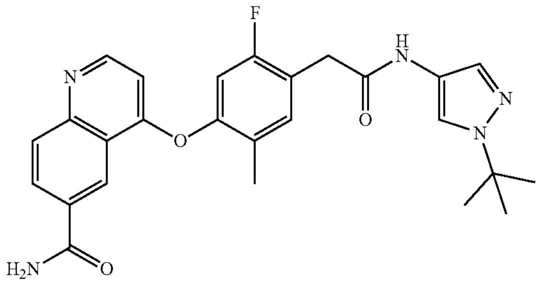 |
| 360 | 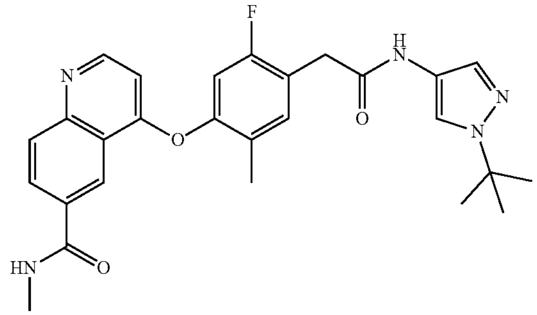 [SMILES: CNC(=O)c1ccc2nccc(Oc3cc(F)c(CC(=O)Nc4cnn(C(C)(C)C)c4)cc3C)c2c1] |
| 363 | 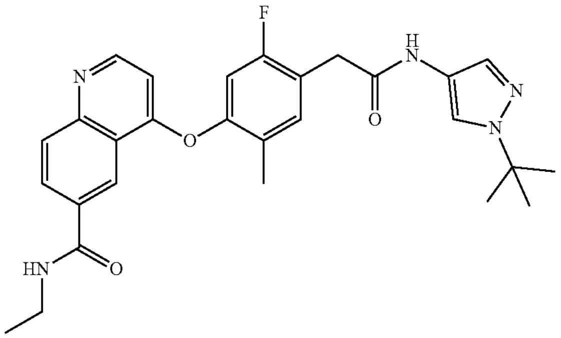 [SMILES: CCNC(=O)c1ccc2nccc(Oc3cc(F)c(CC(=O)Nc4cnn(C(C)(C)C)c4)cc3C)c2c1] |

TABLE 2-continued
| Compound number | Structure |
|---|---|
| 364 | 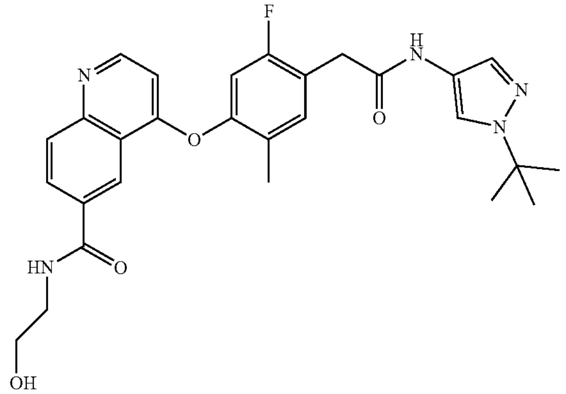 [SMILES: Cc1cc(CC(=O)Nc2cnn(C(C)(C)C)c2)c(F)cc1Oc1ccnc2ccc(C(=O)NCCO)cc12] |
| 365 | 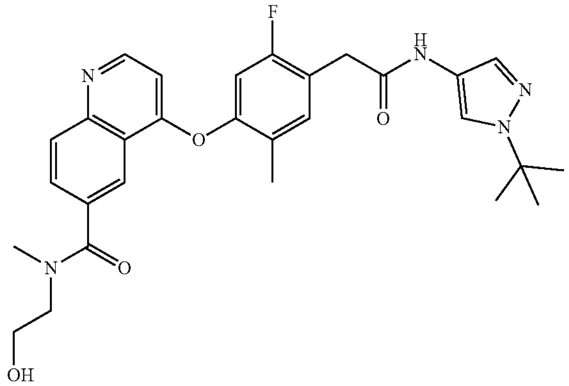 [SMILES: Cc1cc(CC(=O)Nc2cnn(C(C)(C)C)c2)c(F)cc1Oc1ccnc2ccc(C(=O)N(C)CCO)cc12] |
| 366 | 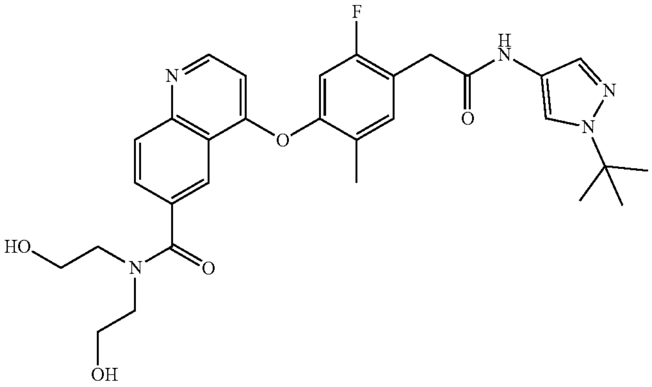 [SMILES: Cc1cc(CC(=O)Nc2cnn(C(C)(C)C)c2)c(F)cc1Oc1ccnc2ccc(C(=O)N(CCO)CCO)cc12] |
| 367 | 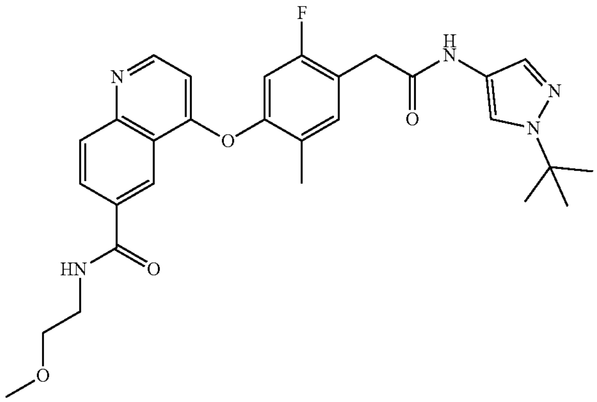 [SMILES: COCCNC(=O)c1ccc2nccc(Oc3cc(F)c(CC(=O)Nc4cnn(C(C)(C)C)c4)cc3C)c2c1] |

TABLE 2-continued
| Compound number | Structure |
|---|---|
| 370 | 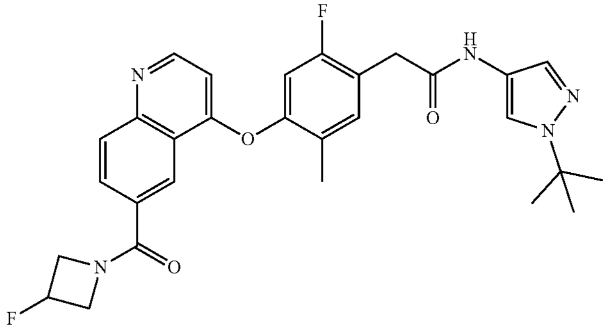 [SMILES: Cc1cc(CC(=O)Nc2cnn(C(C)(C)C)c2)c(F)cc1Oc1ccnc2ccc(C(=O)N3CC(F)C3)cc12] |
| 371 | 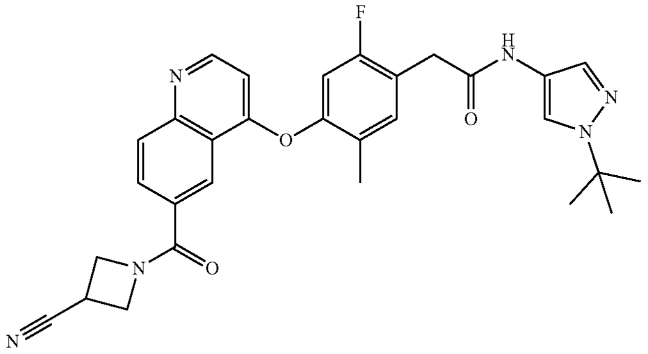 [SMILES: Cc1cc(CC(=O)Nc2cnn(C(C)(C)C)c2)c(F)cc1Oc1ccnc2ccc(C(=O)N3CC(C#N)C3)cc12] |
| 372 | 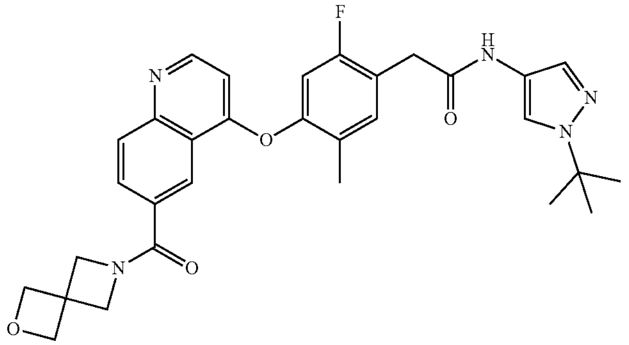 [SMILES: Cc1cc(CC(=O)Nc2cnn(C(C)(C)C)c2)c(F)cc1Oc1ccnc2ccc(C(=O)N3CC4(COC4)C3)cc12] |
| 373 | 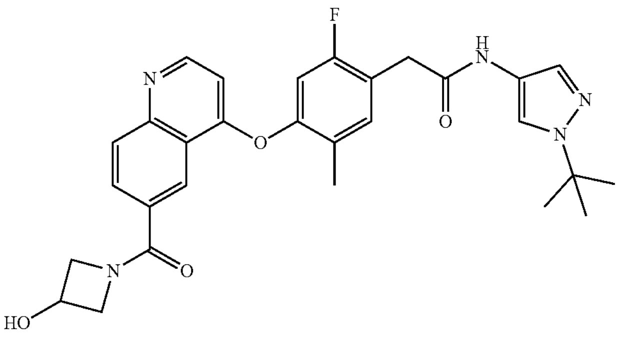 [SMILES: Cc1cc(CC(=O)Nc2cnn(C(C)(C)C)c2)c(F)cc1Oc1ccnc2ccc(C(=O)N3CC(O)C3)cc12] |

TABLE 2-continued
| Compound number | Structure |
|---|---|
| 374 | 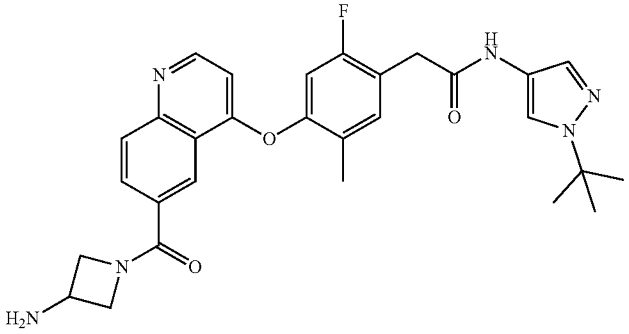 [SMILES: Cc1cc(CC(=O)Nc2cnn(C(C)(C)C)c2)c(F)cc1Oc1ccnc2ccc(C(=O)N3CC(N)C3)cc12] |
| 375 | 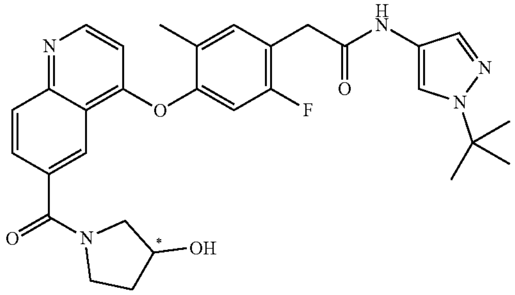<br>enantiomer 1 |
| 376 | 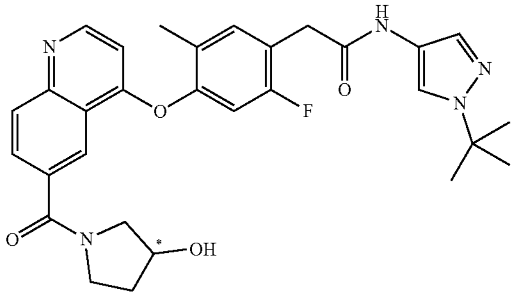<br>enantiomer 2 |
| 377 | 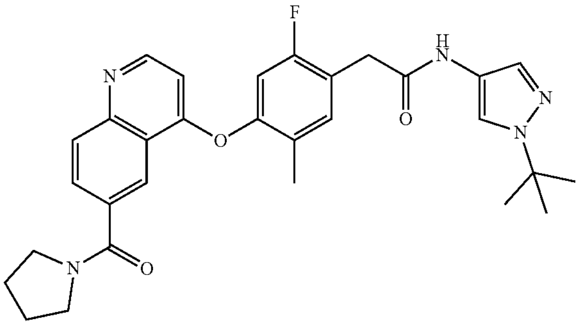 [SMILES: Cc1cc(CC(=O)Nc2cnn(C(C)(C)C)c2)c(F)cc1Oc1ccnc2ccc(C(=O)N3CCCC3)cc12] |

TABLE 2-continued
| Compound number | Structure |
| --- | --- |
| 379 | 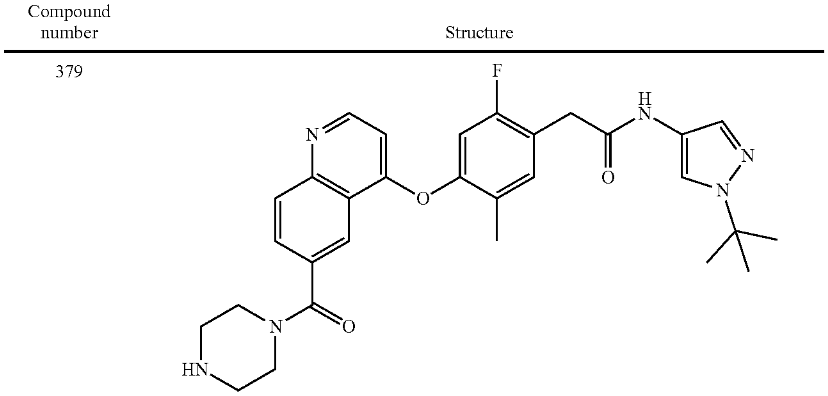 |
| 380 | 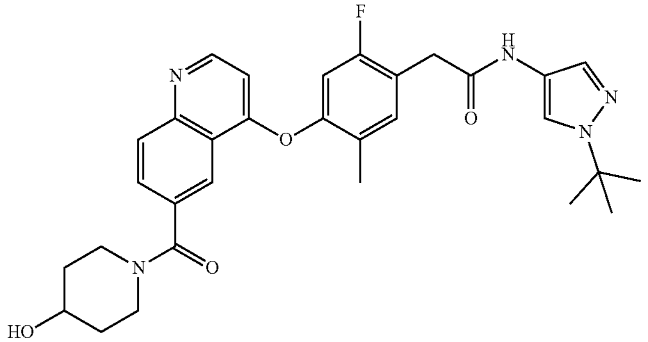 [SMILES: Cc1cc(CC(=O)Nc2cnn(C(C)(C)C)c2)c(F)cc1Oc1ccnc2ccc(C(=O)N3CCC(O)CC3)cc12] |
| 381 | 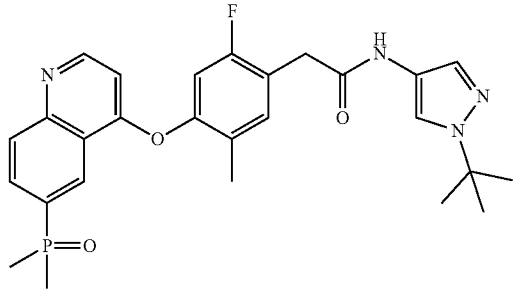 [SMILES: Cc1cc(CC(=O)Nc2cnn(C(C)(C)C)c2)c(F)cc1Oc1ccnc2ccc(P(C)(C)=O)cc12] |
| 382 | 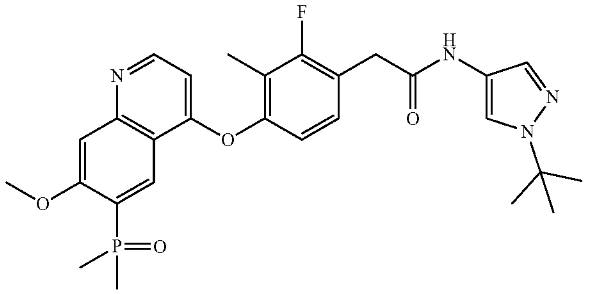 [SMILES: COc1cc2nccc(Oc3ccc(CC(=O)Nc4cnn(C(C)(C)C)c4)c(F)c3C)c2cc1P(C)(C)=O] |
| 383 | 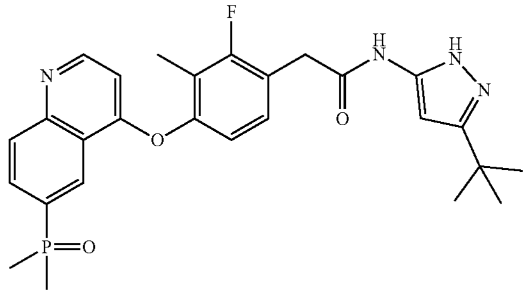 [SMILES: Cc1c(Oc2ccnc3ccc(P(C)(C)=O)cc23)ccc(CC(=O)Nc2cc(C(C)(C)C)n[nH]2)c1F] |

TABLE 2-continued
| Compound number | Structure |
| --- | --- |
| 385 | 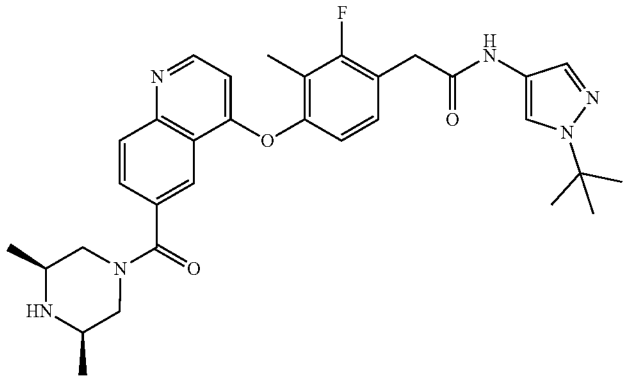 [SMILES: Cc1c(Oc2ccnc3ccc(C(=O)N4C[C@@H](C)N[C@@H](C)C4)cc23)ccc(CC(=O)Nc2cnn(C(C)(C)C)c2)c1F] |
| 387 | 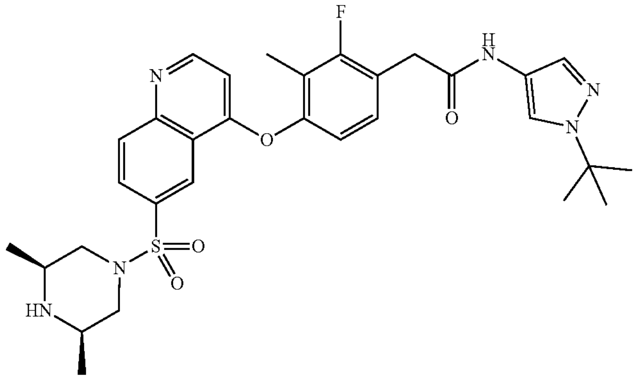 |
| 391 | 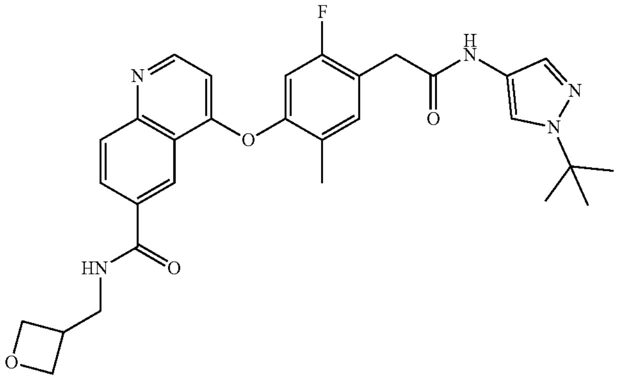 [SMILES: Cc1cc(CC(=O)Nc2cnn(C(C)(C)C)c2)c(F)cc1Oc1ccnc2ccc(C(=O)NCC3COC3)cc12] |
| 392 | 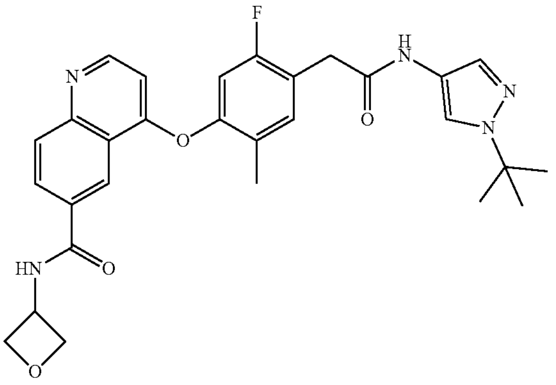 [SMILES: Cc1cc(CC(=O)Nc2cnn(C(C)(C)C)c2)c(F)cc1Oc1ccnc2ccc(C(=O)NC3COC3)cc12] |

TABLE 2-continued
| Compound number | Structure |
|---|---|
| 393 | 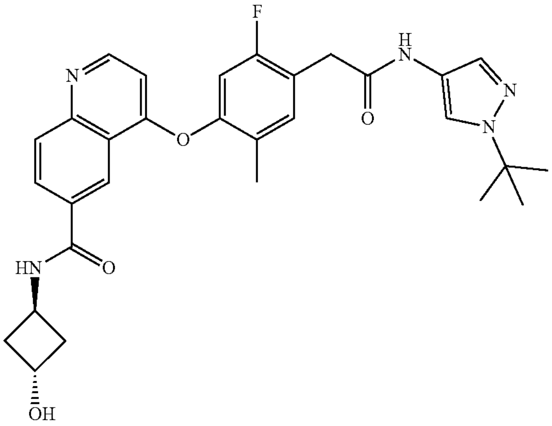 [SMILES: Cc1cc(CC(=O)Nc2cnn(C(C)(C)C)c2)c(F)cc1Oc1ccnc2ccc(C(=O)N[C@H]3C[C@H](O)C3)cc12] |
| 394 | 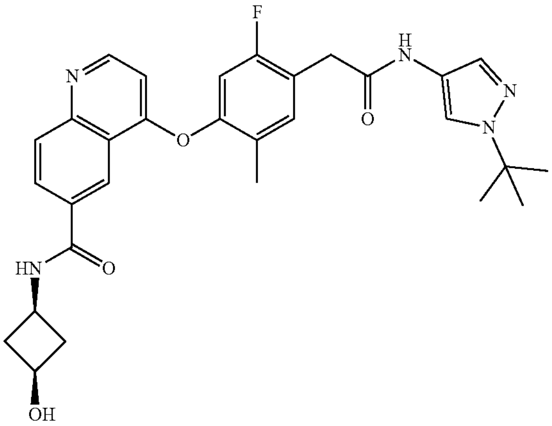 [SMILES: Cc1cc(CC(=O)Nc2cnn(C(C)(C)C)c2)c(F)cc1Oc1ccnc2ccc(C(=O)N[C@H]3C[C@@H](O)C3)cc12] |
| 395 | 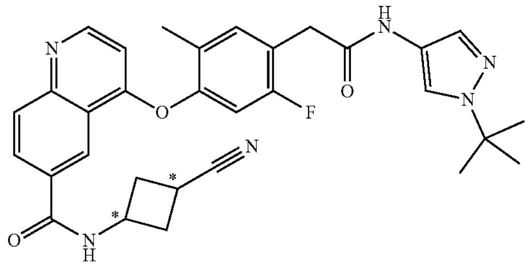 [SMILES: Cc1cc(CC(=O)Nc2cnn(C(C)(C)C)c2)c(F)cc1Oc1ccnc2ccc(C(=O)NC3CC(C#N)C3)cc12] diastereomer 2 |
| 396 | 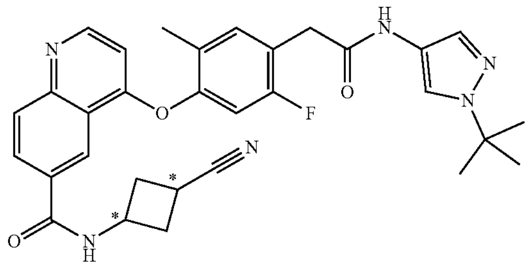 [SMILES: Cc1cc(CC(=O)Nc2cnn(C(C)(C)C)c2)c(F)cc1Oc1ccnc2ccc(C(=O)NC3CC(C#N)C3)cc12] diastereomer 1 |

TABLE 2-continued
| Compound number | Structure |
|---|---|
| 397 | 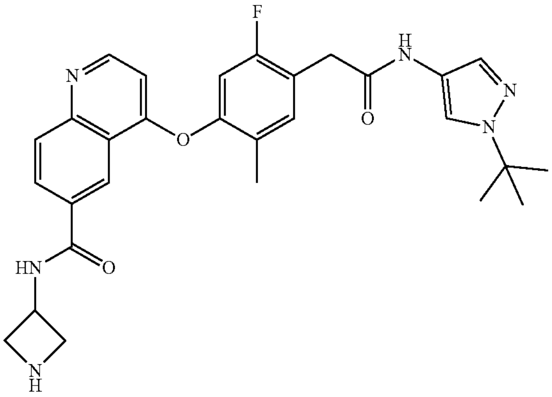 [SMILES: Cc1cc(CC(=O)Nc2cnn(C(C)(C)C)c2)c(F)cc1Oc1ccnc2ccc(C(=O)NC3CNC3)cc12] |
| 398 | 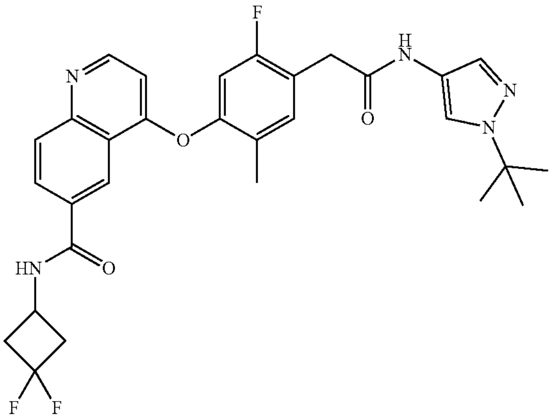 [SMILES: Cc1cc(CC(=O)Nc2cnn(C(C)(C)C)c2)c(F)cc1Oc1ccnc2ccc(C(=O)NC3CC(F)(F)C3)cc12] |
| 399 | 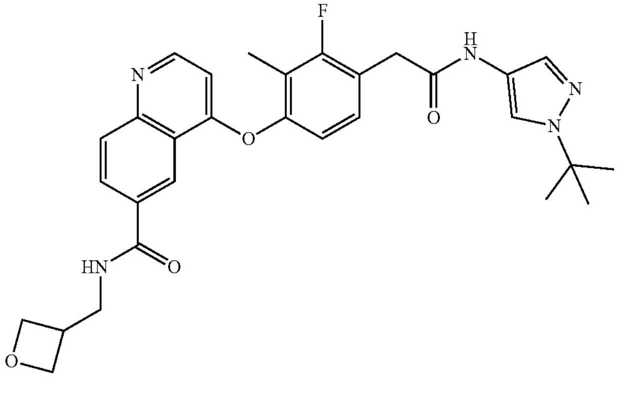 [SMILES: Cc1c(Oc2ccnc3ccc(C(=O)NCC4COC4)cc23)ccc(CC(=O)Nc2cnn(C(C)(C)C)c2)c1F] |
| 400 | 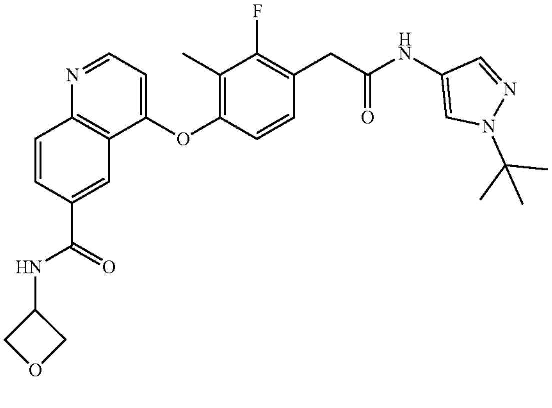 [SMILES: Cc1c(Oc2ccnc3ccc(C(=O)NC4COC4)cc23)ccc(CC(=O)Nc2cnn(C(C)(C)C)c2)c1F] |

TABLE 2-continued
| Compound number | Structure |
|---|---|
| 401 | 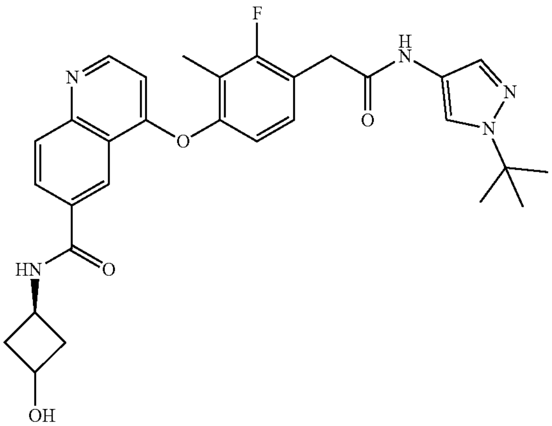 |
| 402 | 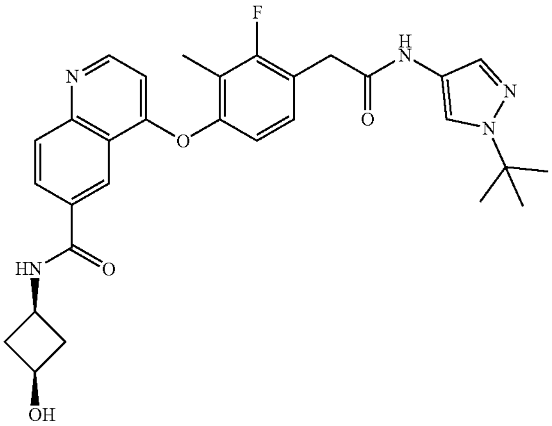 [SMILES: Cc1c(Oc2ccnc3ccc(C(=O)N[C@H]4C[C@@H](O)C4)cc23)ccc(CC(=O)Nc2cnn(C(C)(C)C)c2)c1F] |
| 403 | 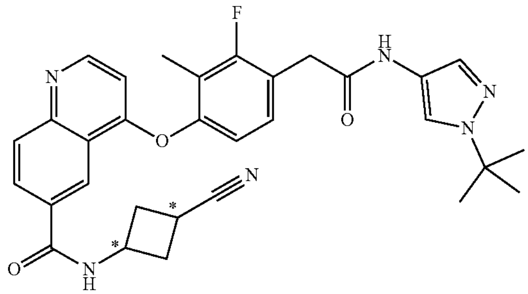 [SMILES: Cc1c(Oc2ccnc3ccc(C(=O)NC4CC(C#N)C4)cc23)ccc(CC(=O)Nc2cnn(C(C)(C)C)c2)c1F] diastereomer 1 |
| 404 | 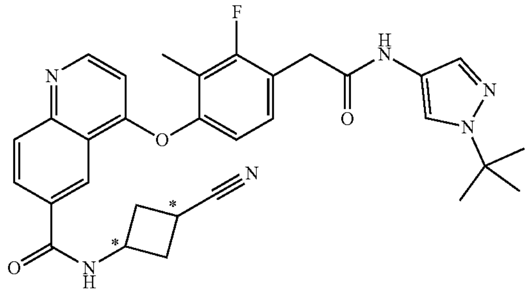 [SMILES: Cc1c(Oc2ccnc3ccc(C(=O)NC4CC(C#N)C4)cc23)ccc(CC(=O)Nc2cnn(C(C)(C)C)c2)c1F] diastereomer 2 |

TABLE 2-continued
| Compound number | Structure |
| --- | --- |
| 405 | 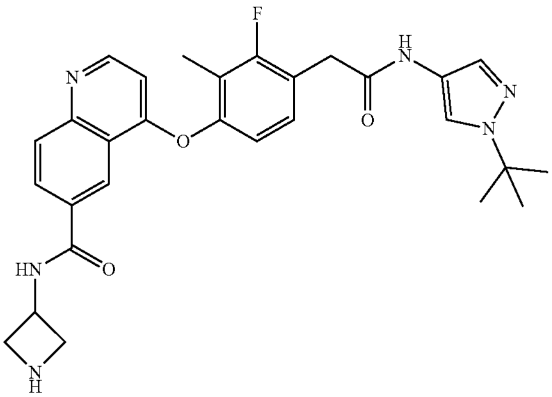 [SMILES: Cc1c(Oc2ccnc3ccc(C(=O)NC4CNC4)cc23)ccc(CC(=O)Nc2cnn(C(C)(C)C)c2)c1F] |
| 406 | 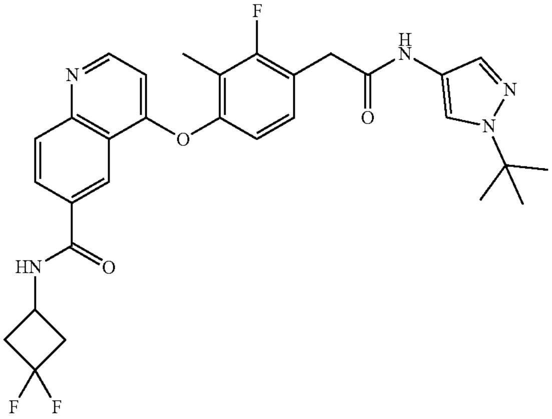 [SMILES: Cc1c(Oc2ccnc3ccc(C(=O)NC4CC(F)(F)C4)cc23)ccc(CC(=O)Nc2cnn(C(C)(C)C)c2)c1F] |
| 407 | 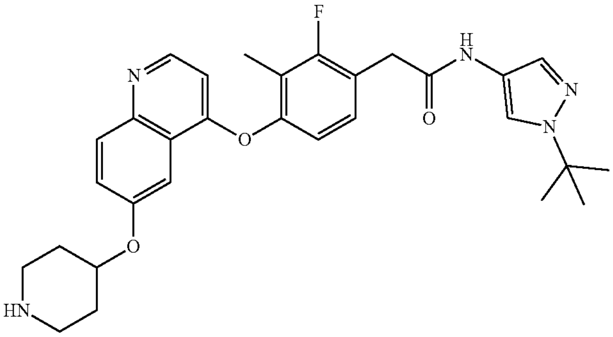 [SMILES: Cc1c(Oc2ccnc3ccc(OC4CCNCC4)cc23)ccc(CC(=O)Nc2cnn(C(C)(C)C)c2)c1F] |
| 408 | 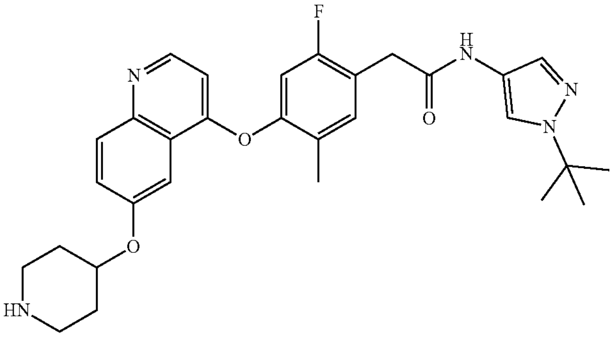 [SMILES: Cc1cc(CC(=O)Nc2cnn(C(C)(C)C)c2)c(F)cc1Oc1ccnc2ccc(OC3CCNCC3)cc12] |

TABLE 2-continued
| Compound number | Structure |
|---|---|
| 409 | 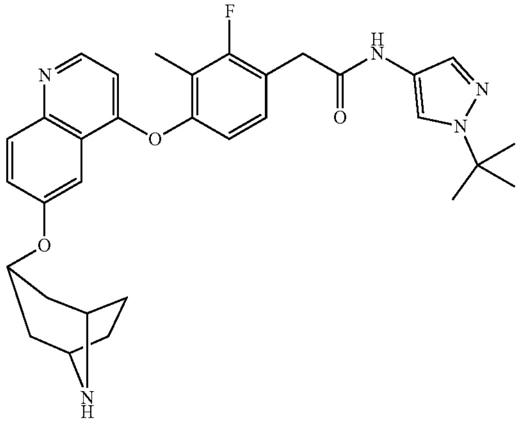 [SMILES: Cc1c(Oc2ccnc3ccc(OC4CC5CCC(C4)N5)cc23)ccc(CC(=O)Nc2cnn(C(C)(C)C)c2)c1F] |
| 410 | 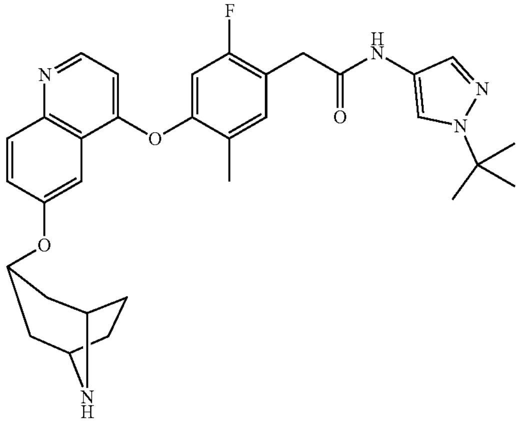 [SMILES: Cc1cc(CC(=O)Nc2cnn(C(C)(C)C)c2)c(F)cc1Oc1ccnc2ccc(OC3CC4CCC(C3)N4)cc12] |
| 411 | 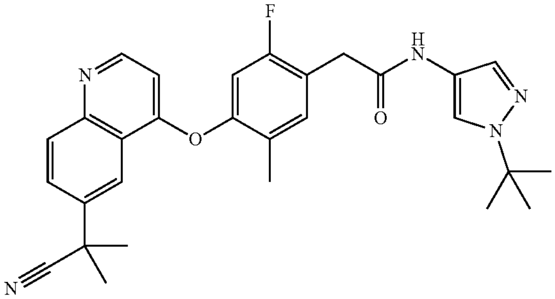 [SMILES: Cc1cc(CC(=O)Nc2cnn(C(C)(C)C)c2)c(F)cc1Oc1ccnc2ccc(C(C)(C)C#N)cc12] |
| 412 | 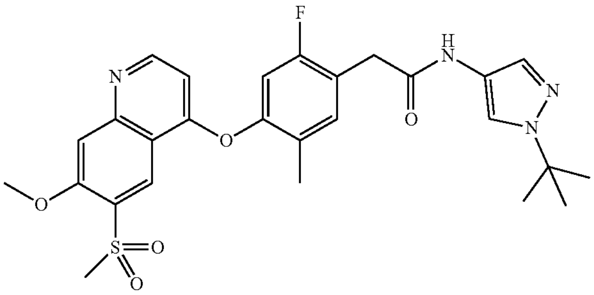 [SMILES: COc1cc2nccc(Oc3cc(F)c(CC(=O)Nc4cnn(C(C)(C)C)c4)cc3C)c2cc1S(C)(=O)=O] |

TABLE 2-continued
| Compound number | Structure |
|---|---|
| 413 | 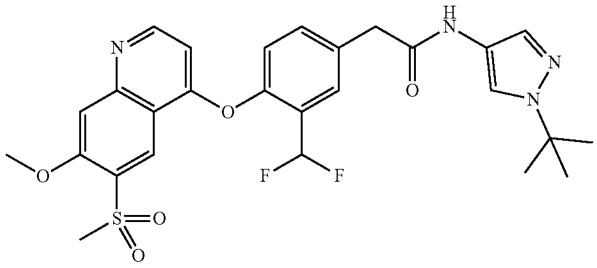 [SMILES: COc1cc2nccc(Oc3ccc(CC(=O)Nc4cnn(C(C)(C)C)c4)cc3C(F)F)c2cc1S(C)(=O)=O] |
| 414 | 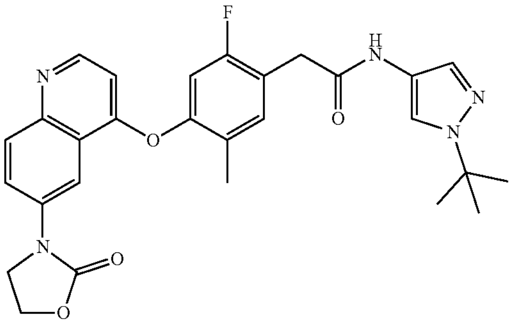 [SMILES: Cc1cc(CC(=O)Nc2cnn(C(C)(C)C)c2)c(F)cc1Oc1ccnc2ccc(N3CCOC3=O)cc12] |
| 415 | 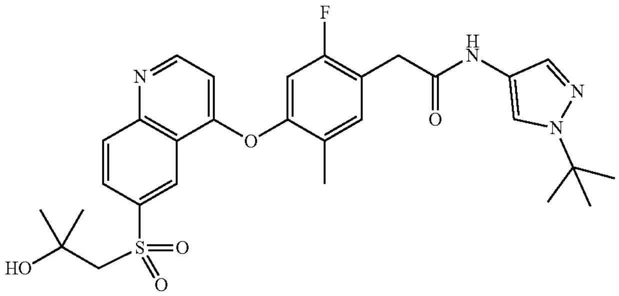 [SMILES: Cc1cc(CC(=O)Nc2cnn(C(C)(C)C)c2)c(F)cc1Oc1ccnc2ccc(S(=O)(=O)CC(C)(C)O)cc12] |
| 416 | 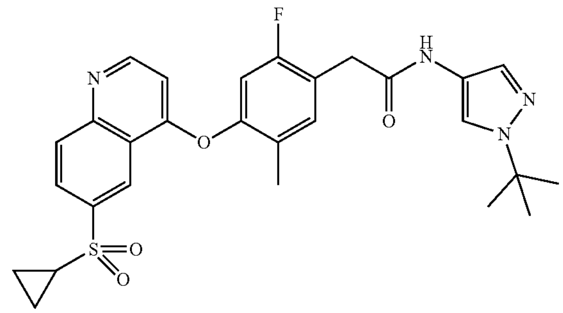 [SMILES: Cc1cc(CC(=O)Nc2cnn(C(C)(C)C)c2)c(F)cc1Oc1ccnc2ccc(S(=O)(=O)C3CC3)cc12] |
| 417 | 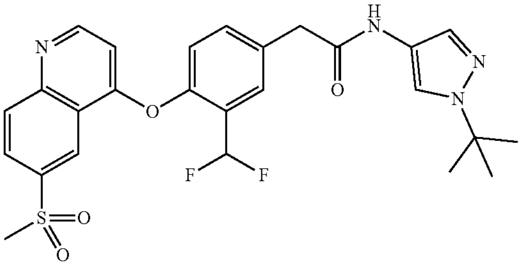 [SMILES: CC(C)(C)n1cc(NC(=O)Cc2ccc(Oc3ccnc4ccc(S(C)(=O)=O)cc34)c(C(F)F)c2)cn1] |

TABLE 2-continued
| Compound number | Structure |
|---|---|
| 418 | 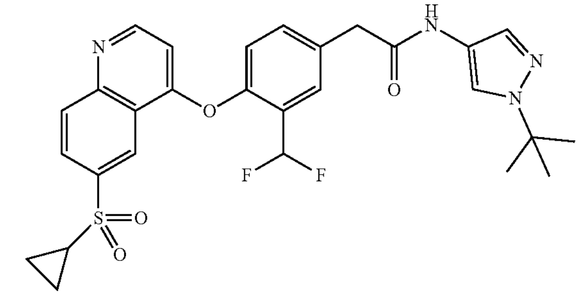 [SMILES: CC(C)(C)n1cc(NC(=O)Cc2ccc(Oc3ccnc4ccc(S(=O)(=O)C5CC5)cc34)c(C(F)F)c2)cn1] |
| 419 | 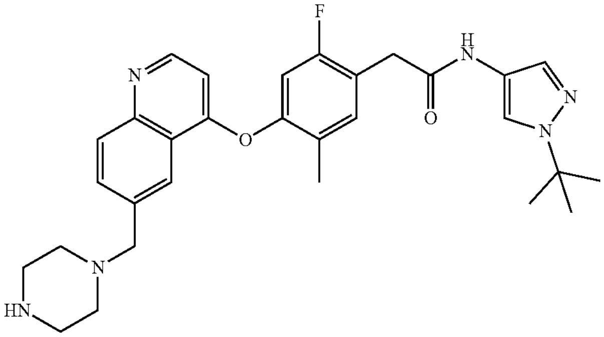 [SMILES: Cc1cc(CC(=O)Nc2cnn(C(C)(C)C)c2)c(F)cc1Oc1ccnc2ccc(CN3CCNCC3)cc12] |
| 420 | 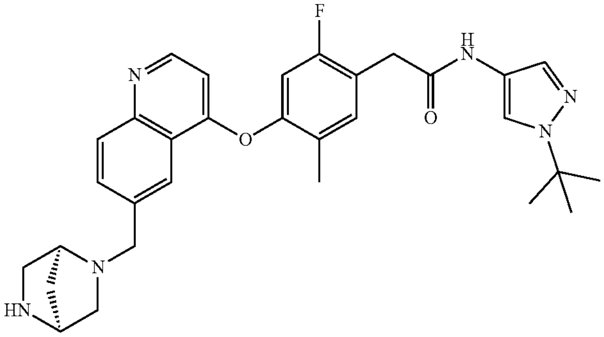 [SMILES: Cc1cc(CC(=O)Nc2cnn(C(C)(C)C)c2)c(F)cc1Oc1ccnc2ccc(CN3C[C@@H]4C[C@H]3CN4)cc12] |
| 421 | 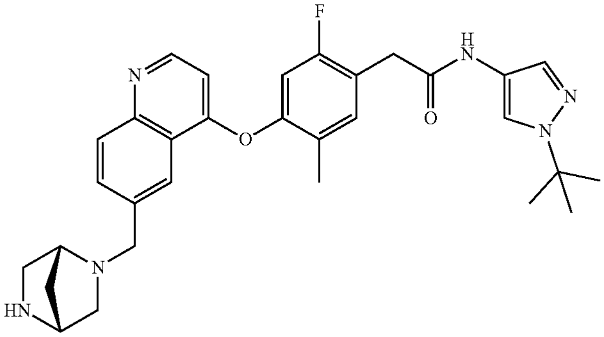 [SMILES: Cc1cc(CC(=O)Nc2cnn(C(C)(C)C)c2)c(F)cc1Oc1ccnc2ccc(CN3C[C@H]4C[C@@H]3CN4)cc12] |

TABLE 2-continued
| Compound number | Structure |
|---|---|
| 422 | 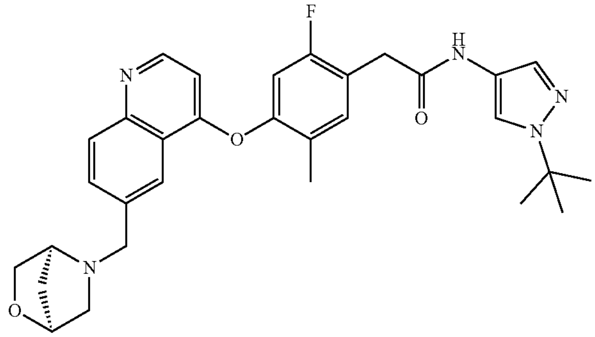 [SMILES: Cc1cc(CC(=O)Nc2cnn(C(C)(C)C)c2)c(F)cc1Oc1ccnc2ccc(CN3C[C@@H]4C[C@H]3CO4)cc12] |
| 423 | 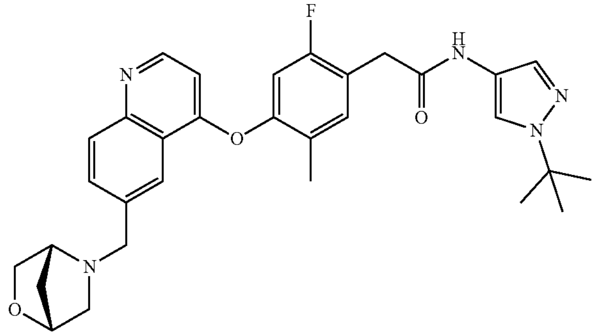 [SMILES: Cc1cc(CC(=O)Nc2cnn(C(C)(C)C)c2)c(F)cc1Oc1ccnc2ccc(CN3C[C@H]4C[C@@H]3CO4)cc12] |
| 424 | 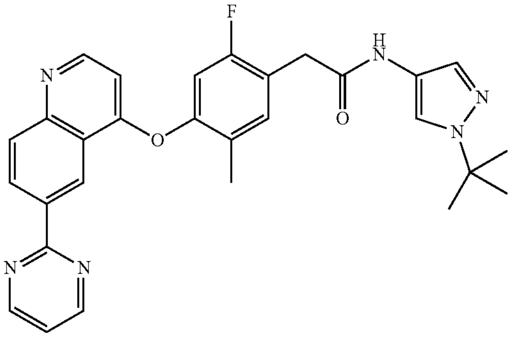 [SMILES: Cc1cc(CC(=O)Nc2cnn(C(C)(C)C)c2)c(F)cc1Oc1ccnc2ccc(-c3ncccn3)cc12] |
| 425 | 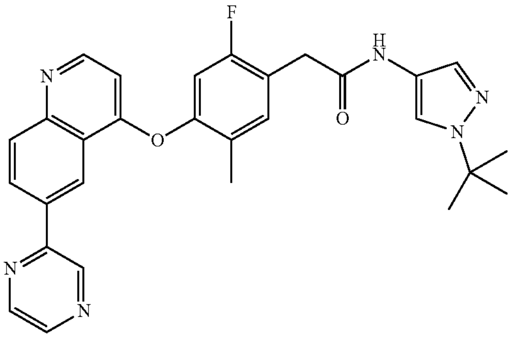 [SMILES: Cc1cc(CC(=O)Nc2cnn(C(C)(C)C)c2)c(F)cc1Oc1ccnc2ccc(-c3cnccn3)cc12] |

TABLE 2-continued
| Compound number | Structure |
| --- | --- |
| 426 | 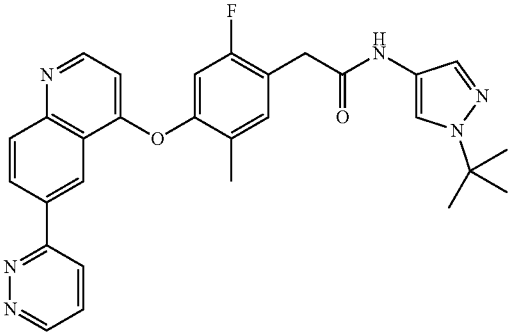 [SMILES: Cc1cc(CC(=O)Nc2cnn(C(C)(C)C)c2)c(F)cc1Oc1ccnc2ccc(-c3cccnn3)cc12] |
| 427 | 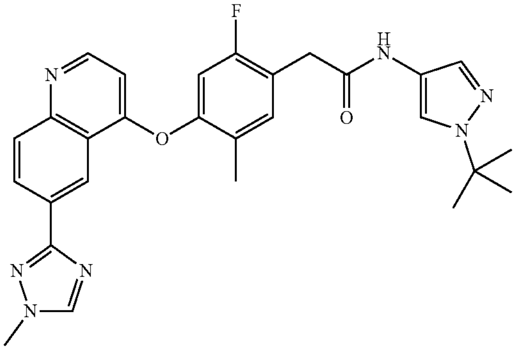 [SMILES: Cc1cc(CC(=O)Nc2cnn(C(C)(C)C)c2)c(F)cc1Oc1ccnc2ccc(-c3ncn(C)n3)cc12] |
| 428 | 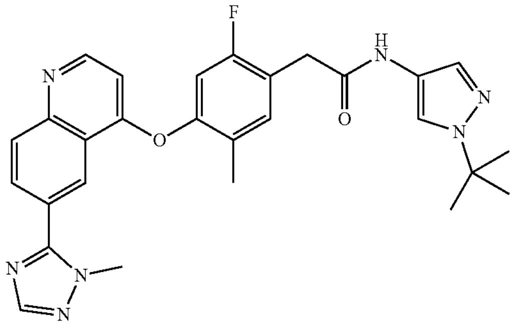 [SMILES: Cc1cc(CC(=O)Nc2cnn(C(C)(C)C)c2)c(F)cc1Oc1ccnc2ccc(-c3ncnn3C)cc12] |
| 429 | 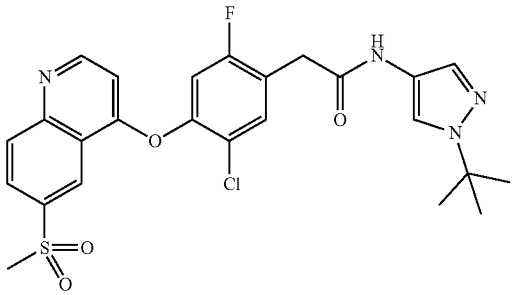 [SMILES: CC(C)(C)n1cc(NC(=O)Cc2cc(Cl)c(Oc3ccnc4ccc(S(C)(=O)=O)cc34)cc2F)cn1] |

TABLE 2-continued
| Compound number | Structure |
| --- | --- |
| 430 | 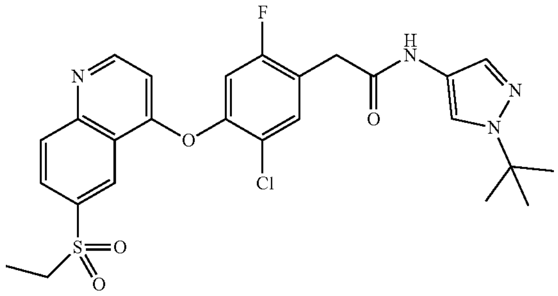 [SMILES: CCS(=O)(=O)c1ccc2nccc(Oc3cc(F)c(CC(=O)Nc4cnn(C(C)(C)C)c4)cc3Cl)c2c1] |
| 431 | 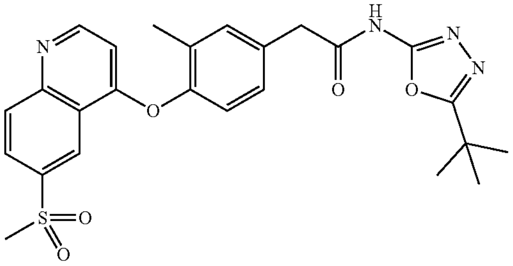 [SMILES: Cc1cc(CC(=O)Nc2nnc(C(C)(C)C)o2)ccc1Oc1ccnc2ccc(S(C)(=O)=O)cc12] |
| 433 | 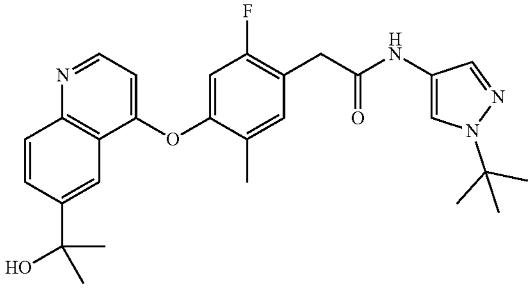 [SMILES: Cc1cc(CC(=O)Nc2cnn(C(C)(C)C)c2)c(F)cc1Oc1ccnc2ccc(C(C)(C)O)cc12] |
| 435 | 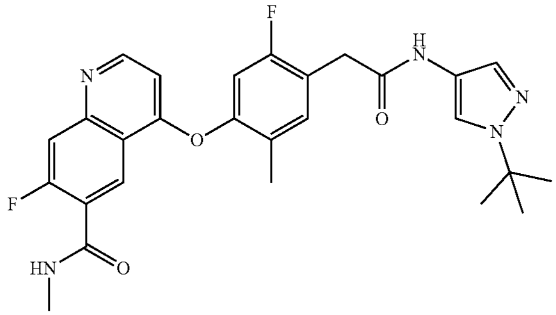 [SMILES: CNC(=O)c1cc2c(Oc3cc(F)c(CC(=O)Nc4cnn(C(C)(C)C)c4)cc3C)ccnc2cc1F] |
| 436 | 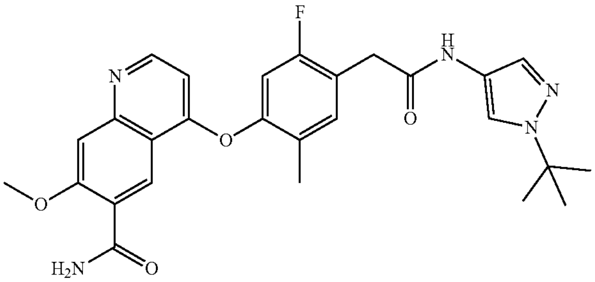 [SMILES: COc1cc2nccc(Oc3cc(F)c(CC(=O)Nc4cnn(C(C)(C)C)c4)cc3C)c2cc1C(N)=O] |

TABLE 2-continued
| Compound number | Structure |
| --- | --- |
| 437 | 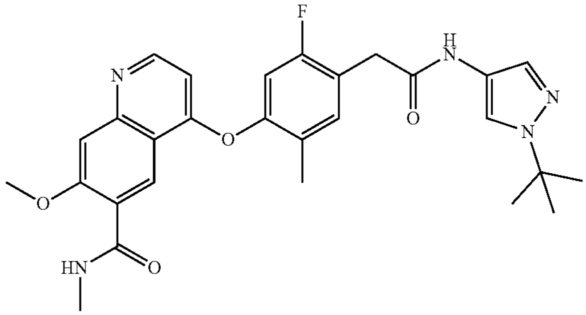 [SMILES: CNC(=O)c1cc2c(Oc3cc(F)c(CC(=O)Nc4cnn(C(C)(C)C)c4)cc3C)ccnc2cc1OC] |
| 439 | 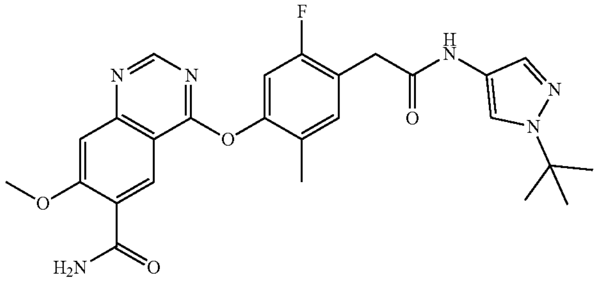 |
| 440 | 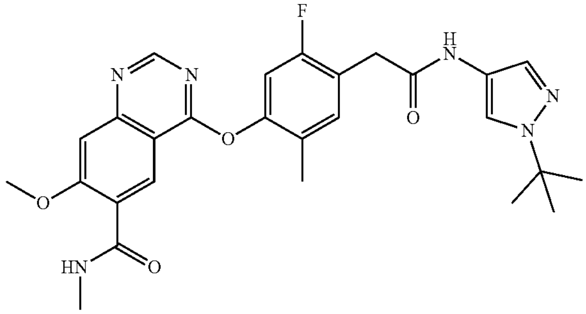 [SMILES: CNC(=O)c1cc2c(Oc3cc(F)c(CC(=O)Nc4cnn(C(C)(C)C)c4)cc3C)ncnc2cc1OC] |
| 441 | 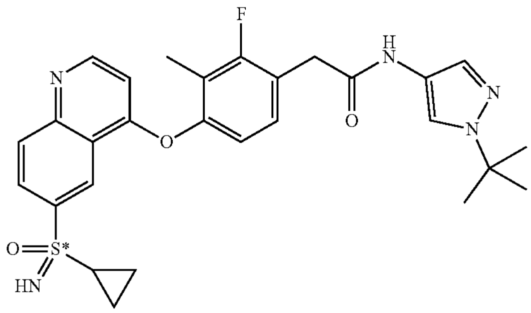<br>enantiomer 1 |

TABLE 2-continued
| Compound number | Structure |
|---|---|
| 442 | 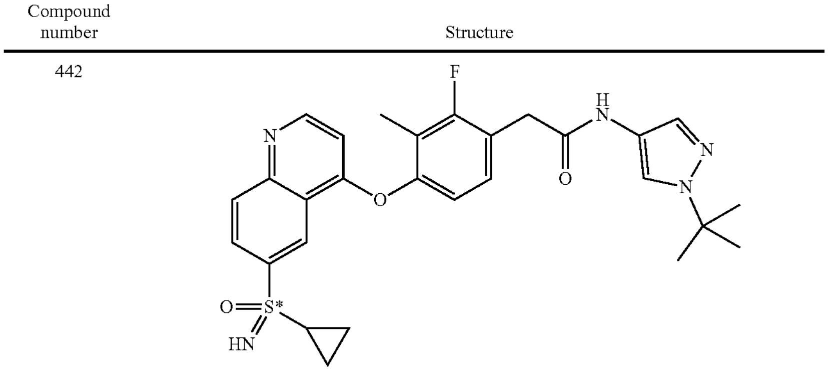<br>enantiomer 2 |
| 444 | 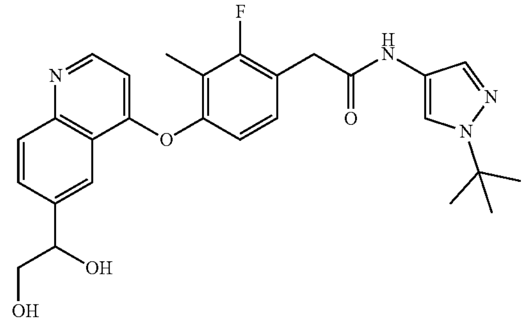 [SMILES: Cc1c(Oc2ccnc3ccc(C(O)CO)cc23)ccc(CC(=O)Nc2cnn(C(C)(C)C)c2)c1F] |
| 445 | 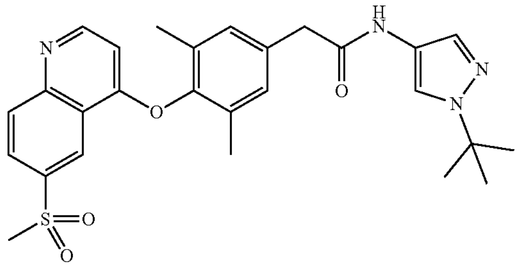 [SMILES: Cc1cc(CC(=O)Nc2cnn(C(C)(C)C)c2)cc(C)c1Oc1ccnc2ccc(S(C)(=O)=O)cc12] |
| 448 | 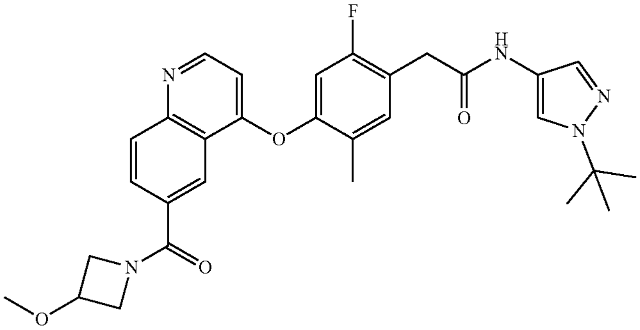 [SMILES: COC1CN(C(=O)c2ccc3nccc(Oc4cc(F)c(CC(=O)Nc5cnn(C(C)(C)C)c5)cc4C)c3c2)C1] |
| 449 | 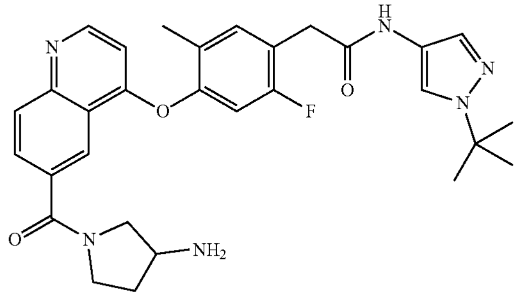 |

TABLE 2-continued
| Compound number | Structure |
| --- | --- |
| 451 | 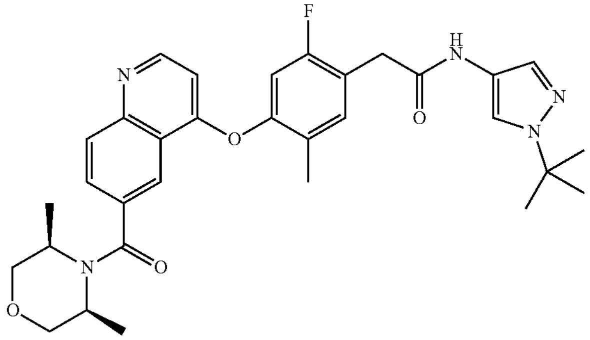 [SMILES: Cc1cc(CC(=O)Nc2cnn(C(C)(C)C)c2)c(F)cc1Oc1ccnc2ccc(C(=O)N3[C@H](C)COC[C@@H]3C)cc12] |
| 452 | 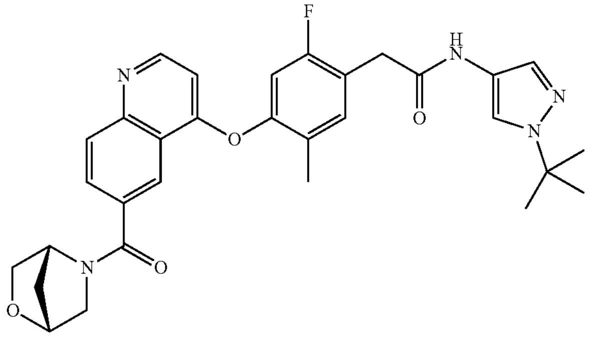 [SMILES: Cc1cc(CC(=O)Nc2cnn(C(C)(C)C)c2)c(F)cc1Oc1ccnc2ccc(C(=O)N3C[C@H]4C[C@@H]3CO4)cc12] |
| 453 | 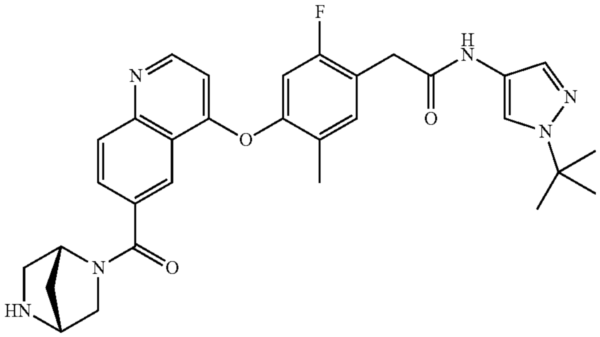 [SMILES: Cc1cc(CC(=O)Nc2cnn(C(C)(C)C)c2)c(F)cc1Oc1ccnc2ccc(C(=O)N3C[C@H]4C[C@@H]3CN4)cc12] |
| 454 | 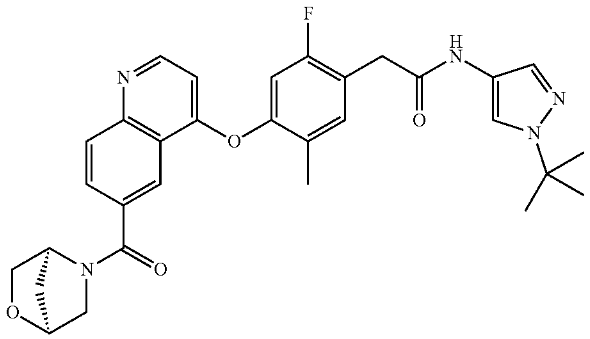 [SMILES: Cc1cc(CC(=O)Nc2cnn(C(C)(C)C)c2)c(F)cc1Oc1ccnc2ccc(C(=O)N3C[C@@H]4C[C@H]3CO4)cc12] |

TABLE 2-continued
| Compound number | Structure |
|---|---|
| 455 | 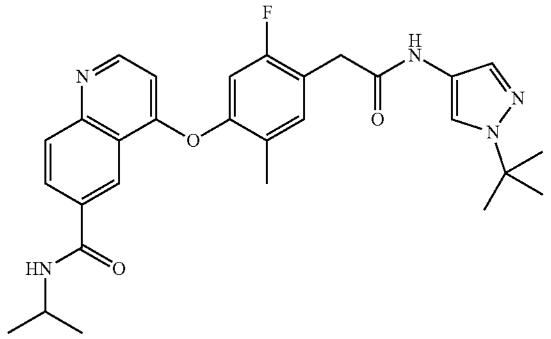 [SMILES: Cc1cc(CC(=O)Nc2cnn(C(C)(C)C)c2)c(F)cc1Oc1ccnc2ccc(C(=O)NC(C)C)cc12] |
| 456 | 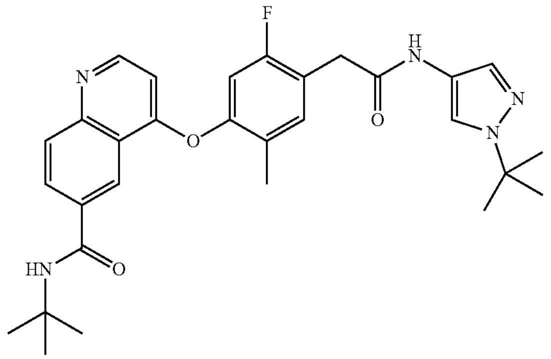 [SMILES: Cc1cc(CC(=O)Nc2cnn(C(C)(C)C)c2)c(F)cc1Oc1ccnc2ccc(C(=O)NC(C)(C)C)cc12] |
| 457 | 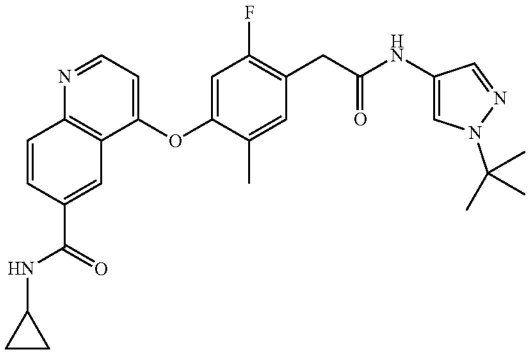 [SMILES: Cc1cc(CC(=O)Nc2cnn(C(C)(C)C)c2)c(F)cc1Oc1ccnc2ccc(C(=O)NC3CC3)cc12] |
| 458 | 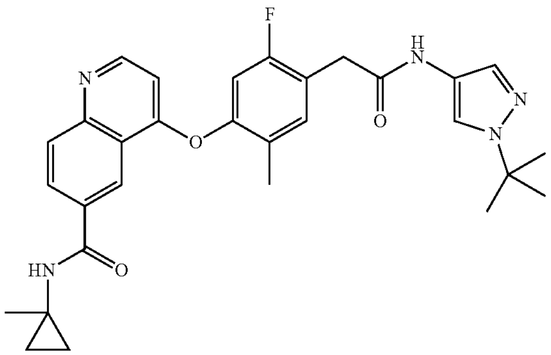 [SMILES: Cc1cc(CC(=O)Nc2cnn(C(C)(C)C)c2)c(F)cc1Oc1ccnc2ccc(C(=O)NC3(C)CC3)cc12] |

TABLE 2-continued
| Compound number | Structure |
| --- | --- |
| 459 | 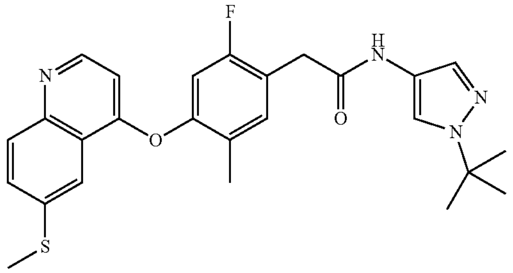 [SMILES: CSc1ccc2nccc(Oc3cc(F)c(CC(=O)Nc4cnn(C(C)(C)C)c4)cc3C)c2c1] |
| 460 | 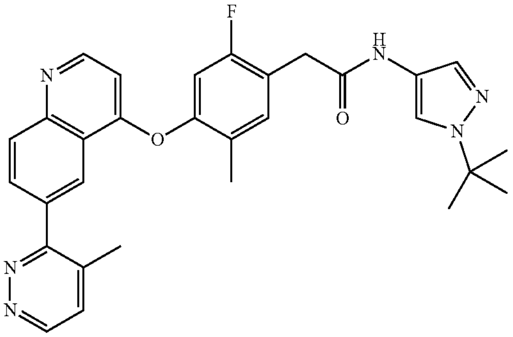 [SMILES: Cc1cc(CC(=O)Nc2cnn(C(C)(C)C)c2)c(F)cc1Oc1ccnc2ccc(-c3nnccc3C)cc12] |
| 286 | 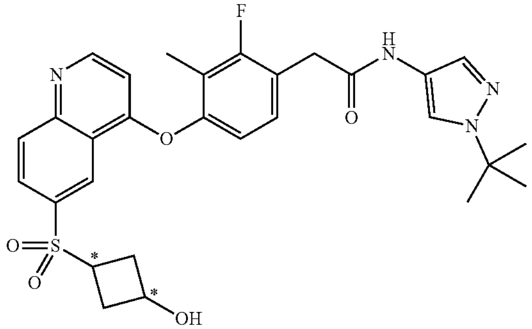 [SMILES: Cc1c(Oc2ccnc3ccc(S(=O)(=O)C4CC(O)C4)cc23)ccc(CC(=O)Nc2cnn(C(C)(C)C)c2)c1F]<br>diastereomer 2 |
| 548 | 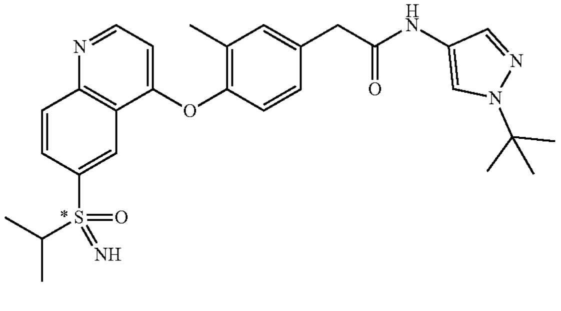 [SMILES: Cc1cc(CC(=O)Nc2cnn(C(C)(C)C)c2)ccc1Oc1ccnc2ccc(S(=N)(=O)C(C)C)cc12]<br>enantiomer 2 |

TABLE 2-continued
| Compound number | Structure |
| --- | --- |
| 555 | 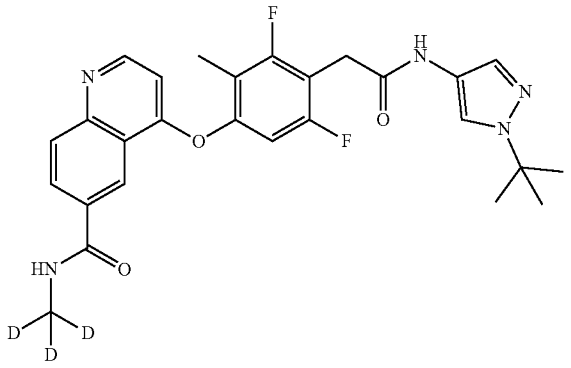 [SMILES: [2H]C([2H])([2H])NC(=O)c1ccc2nccc(Oc3cc(F)c(CC(=O)Nc4cnn(C(C)(C)C)c4)c(F)c3C)c2c1] |
| 556 | 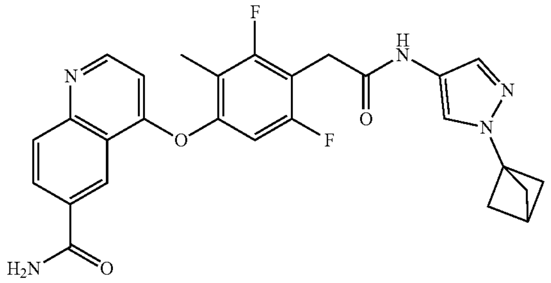 [SMILES: Cc1c(Oc2ccnc3ccc(C(N)=O)cc23)cc(F)c(CC(=O)Nc2cnn(C34CC(C3)C4)c2)c1F] |
| 557 | 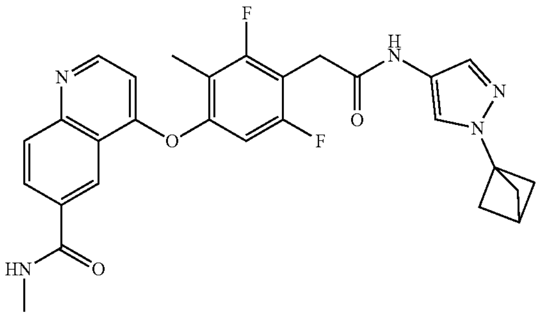 [SMILES: CNC(=O)c1ccc2nccc(Oc3cc(F)c(CC(=O)Nc4cnn(C56CC(C5)C6)c4)c(F)c3C)c2c1] |
| 558 | 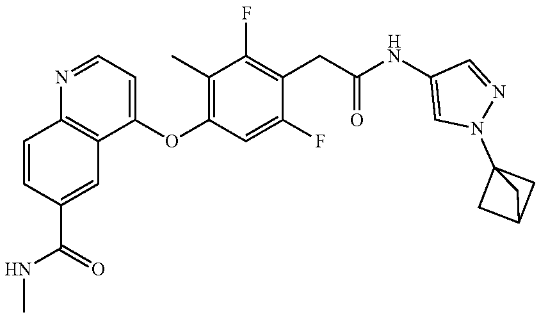 [SMILES: CNC(=O)c1ccc2nccc(Oc3cc(F)c(CC(=O)Nc4cnn(C56CC(C5)C6)c4)c(F)c3C)c2c1] |

TABLE 2-continued
| Compound number | Structure |
| --- | --- |
| 559 | 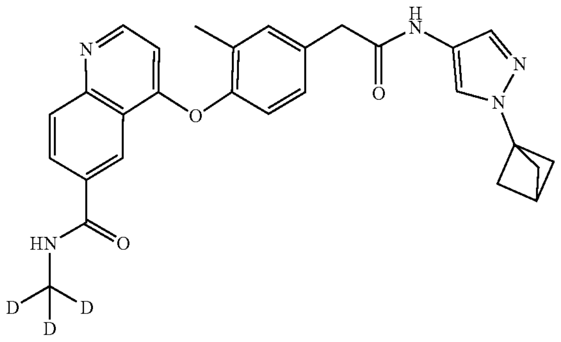 [SMILES: [2H]C([2H])([2H])NC(=O)c1ccc2nccc(Oc3ccc(CC(=O)Nc4cnn(C56CC(C5)C6)c4)cc3C)c2c1] |
| 578 | 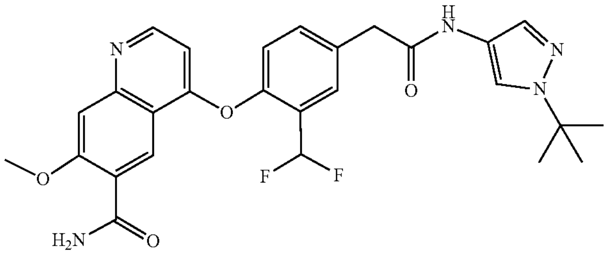 [SMILES: COc1cc2nccc(Oc3ccc(CC(=O)Nc4cnn(C(C)(C)C)c4)cc3C(F)F)c2cc1C(N)=O] |
| 579 | 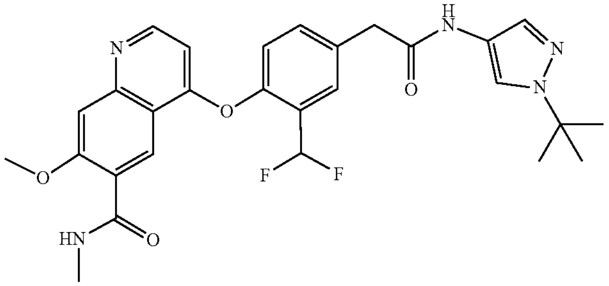 [SMILES: CNC(=O)c1cc2c(Oc3ccc(CC(=O)Nc4cnn(C(C)(C)C)c4)cc3C(F)F)ccnc2cc1OC] |
| 582 | 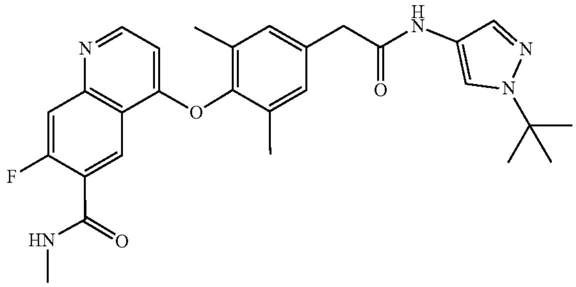 [SMILES: CNC(=O)c1cc2c(Oc3c(C)cc(CC(=O)Nc4cnn(C(C)(C)C)c4)cc3C)ccnc2cc1F] |
| 585 | 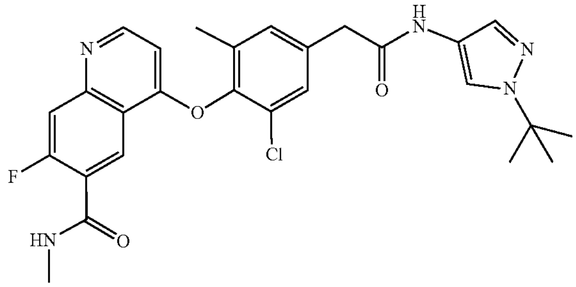 [SMILES: CNC(=O)c1cc2c(Oc3c(C)cc(CC(=O)Nc4cnn(C(C)(C)C)c4)cc3Cl)ccnc2cc1F] |

TABLE 2-continued
| Compound number | Structure |
| --- | --- |
| 586 | 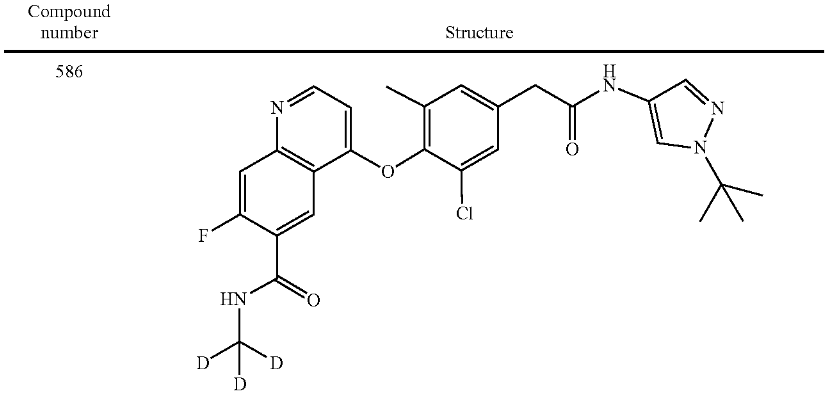 |
| 596 | 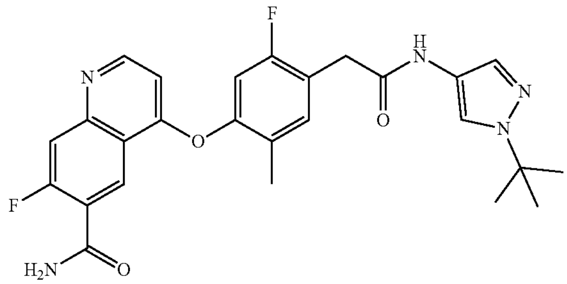 [SMILES: Cc1cc(CC(=O)Nc2cnn(C(C)(C)C)c2)c(F)cc1Oc1ccnc2cc(F)c(C(N)=O)cc12] |
| 606 | 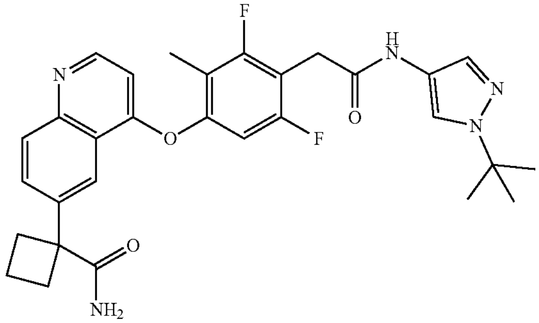 [SMILES: Cc1c(Oc2ccnc3ccc(C4(C(N)=O)CCC4)cc23)cc(F)c(CC(=O)Nc2cnn(C(C)(C)C)c2)c1F] |
| 611 | 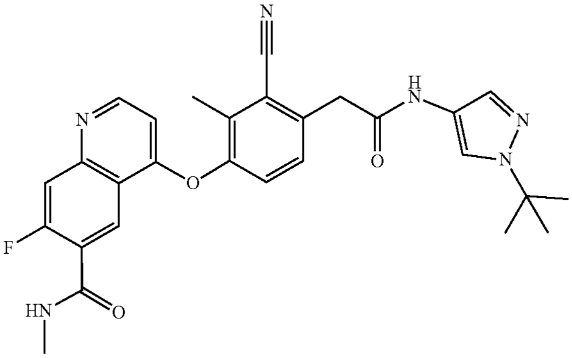 [SMILES: CNC(=O)c1cc2c(Oc3ccc(CC(=O)Nc4cnn(C(C)(C)C)c4)c(C#N)c3C)ccnc2cc1F] |
| 618 | 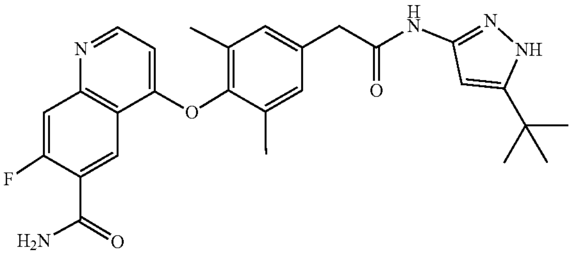 |

TABLE 2-continued
| Compound number | Structure |
| --- | --- |
| 527 | 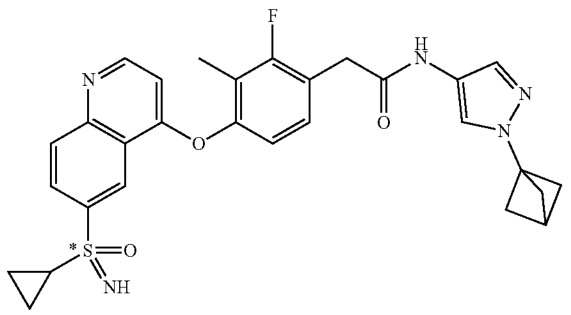 [SMILES: Cc1c(Oc2ccnc3ccc(S(=N)(=O)C4CC4)cc23)ccc(CC(=O)Nc2cnn(C34CC(C3)C4)c2)c1F] enantiomer 1 |
| 528 | 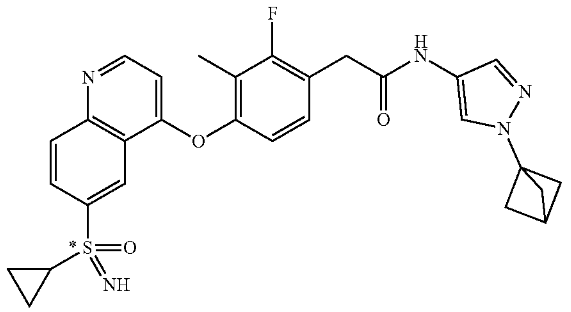 [SMILES: Cc1c(Oc2ccnc3ccc(S(=N)(=O)C4CC4)cc23)ccc(CC(=O)Nc2cnn(C34CC(C3)C4)c2)c1F] enantiomer 2 |
| 535 | 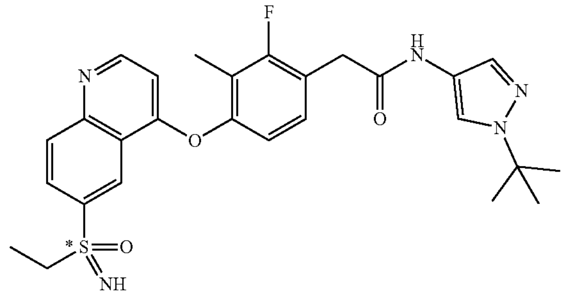 [SMILES: CCS(=N)(=O)c1ccc2nccc(Oc3ccc(CC(=O)Nc4cnn(C(C)(C)C)c4)c(F)c3C)c2c1] enantiomer 1 |
| 536 | 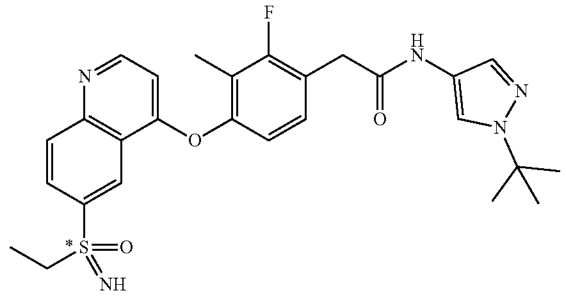 [SMILES: CCS(=N)(=O)c1ccc2nccc(Oc3ccc(CC(=O)Nc4cnn(C(C)(C)C)c4)c(F)c3C)c2c1] enantiomer 2 |

TABLE 2-continued
| Compound number | Structure |
|---|---|
| 537 | 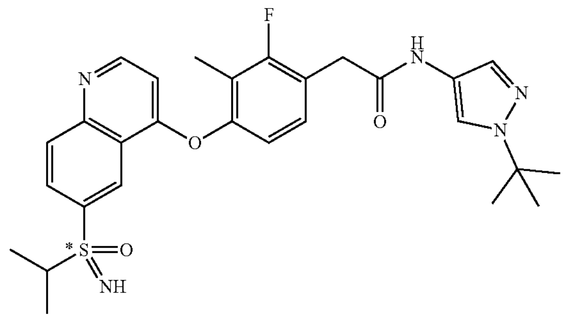 [SMILES: Cc1c(Oc2ccnc3ccc(S(=N)(=O)C(C)C)cc23)ccc(CC(=O)Nc2cnn(C(C)(C)C)c2)c1F] enantiomer 1 |
| 538 | 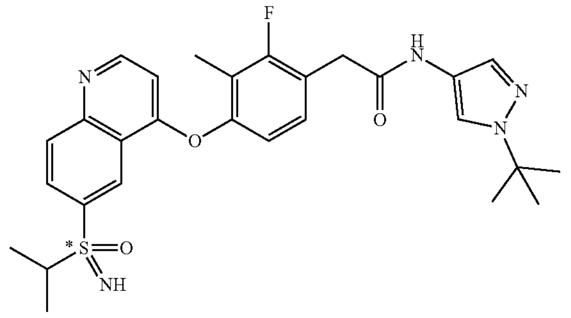 [SMILES: Cc1c(Oc2ccnc3ccc(S(=N)(=O)C(C)C)cc23)ccc(CC(=O)Nc2cnn(C(C)(C)C)c2)c1F] enantiomer 2 |
| 540 | 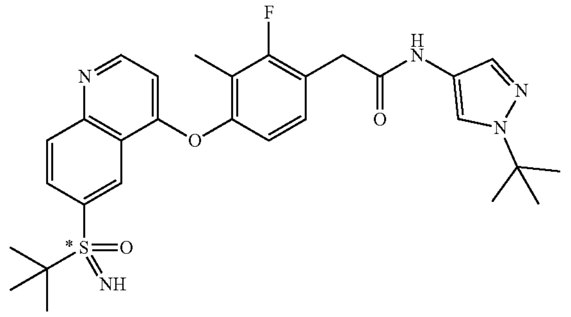 [SMILES: Cc1c(Oc2ccnc3ccc(S(=N)(=O)C(C)(C)C)cc23)ccc(CC(=O)Nc2cnn(C(C)(C)C)c2)c1F] enantiomer 2 |
| 541 | 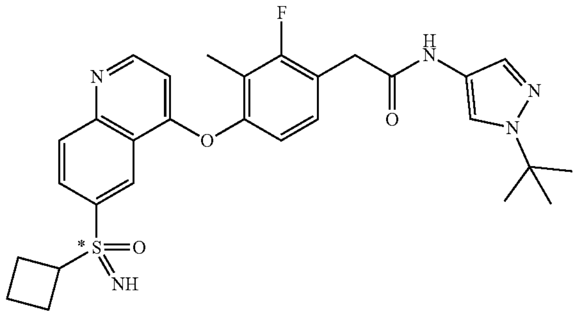 [SMILES: Cc1c(Oc2ccnc3ccc(S(=N)(=O)C4CCC4)cc23)ccc(CC(=O)Nc2cnn(C(C)(C)C)c2)c1F] enantiomer 1 |
In a thirty-sixth aspect of the first embodiment, the compound is selected from the compounds in Table 3.

TABLE 3
| Compound # | Structure | Compound # | Structure |
| --- | --- | --- | --- |
| 86 | 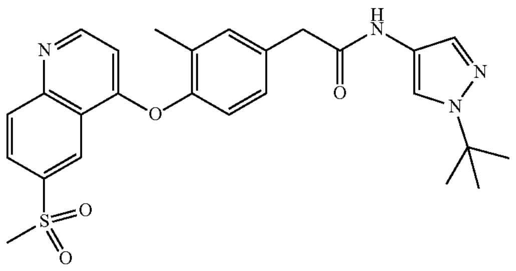 [SMILES: Cc1cc(CC(=O)Nc2cnn(C(C)(C)C)c2)ccc1Oc1ccnc2ccc(S(C)(=O)=O)cc12] | 360 | 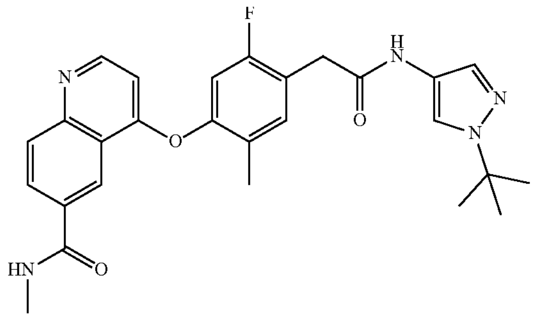 [SMILES: CNC(=O)c1ccc2nccc(Oc3cc(F)c(CC(=O)Nc4cnn(C(C)(C)C)c4)cc3C)c2c1] |
| 91 | 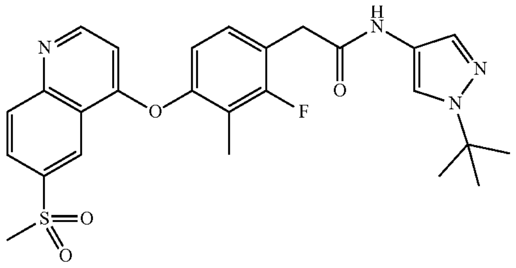 [SMILES: Cc1c(Oc2ccnc3ccc(S(C)(=O)=O)cc23)ccc(CC(=O)Nc2cnn(C(C)(C)C)c2)c1F] | 416 | 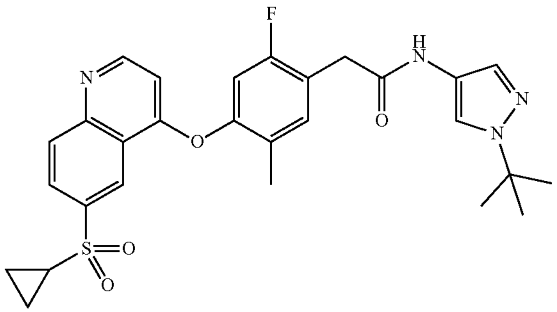 [SMILES: Cc1cc(CC(=O)Nc2cnn(C(C)(C)C)c2)c(F)cc1Oc1ccnc2ccc(S(=O)(=O)C3CC3)cc12] |
| 92 | 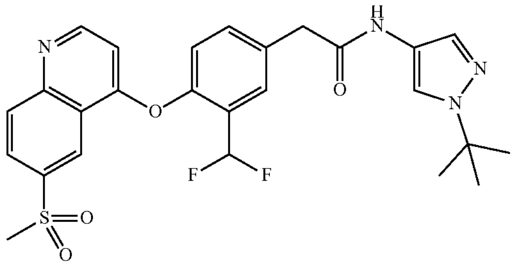 [SMILES: CC(C)(C)n1cc(NC(=O)Cc2ccc(Oc3ccnc4ccc(S(C)(=O)=O)cc34)c(C(F)F)c2)cn1] | 417 | 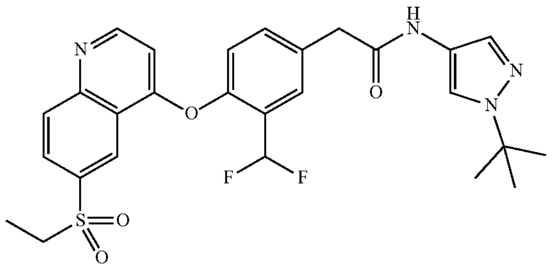 [SMILES: CCS(=O)(=O)c1ccc2nccc(Oc3ccc(CC(=O)Nc4cnn(C(C)(C)C)c4)cc3C(F)F)c2c1] |

TABLE 3-continued
| Compound # | Structure | Compound # | Structure |
|---|---|---|---|
| 99 | 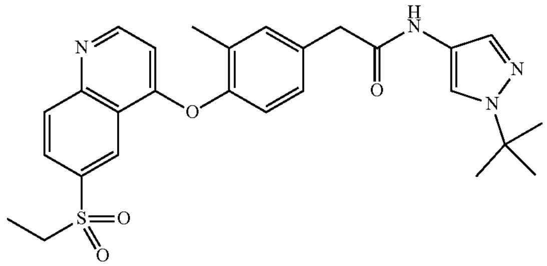 [SMILES: CCS(=O)(=O)c1ccc2nccc(Oc3ccc(CC(=O)Nc4cnn(C(C)(C)C)c4)cc3C)c2c1] | 429 | 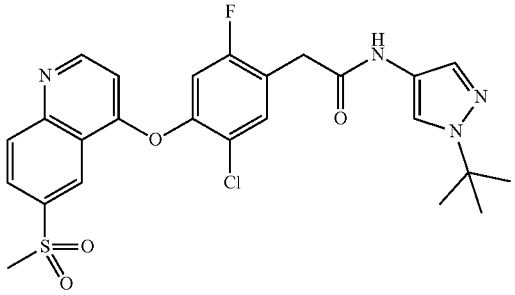 [SMILES: CC(C)(C)n1cc(NC(=O)Cc2cc(Cl)c(Oc3ccnc4ccc(S(C)(=O)=O)cc34)cc2F)cn1] |
| 100 | 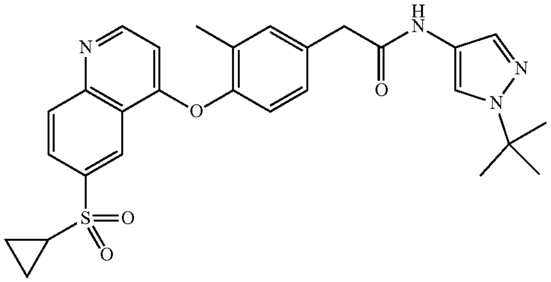 [SMILES: Cc1cc(CC(=O)Nc2cnn(C(C)(C)C)c2)ccc1Oc1ccnc2ccc(S(=O)(=O)C3CC3)cc12] | 430 | 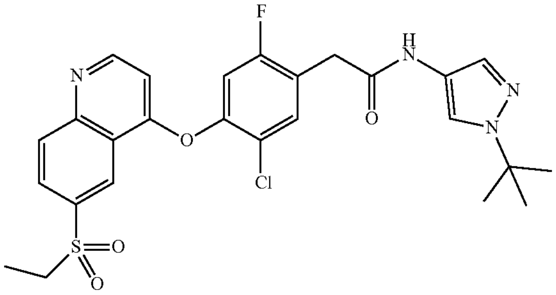 [SMILES: CCS(=O)(=O)c1ccc2nccc(Oc3cc(F)c(CC(=O)Nc4cnn(C(C)(C)C)c4)cc3Cl)c2c1] |
| 173 | 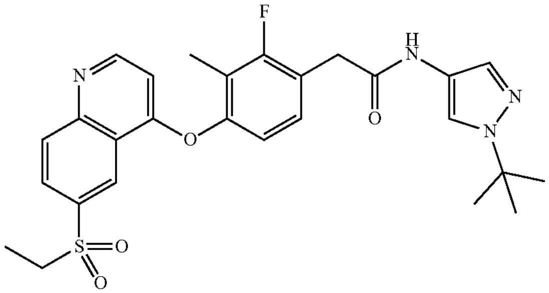 [SMILES: CCS(=O)(=O)c1ccc2nccc(Oc3ccc(CC(=O)Nc4cnn(C(C)(C)C)c4)c(F)c3C)c2c1] | 435 | 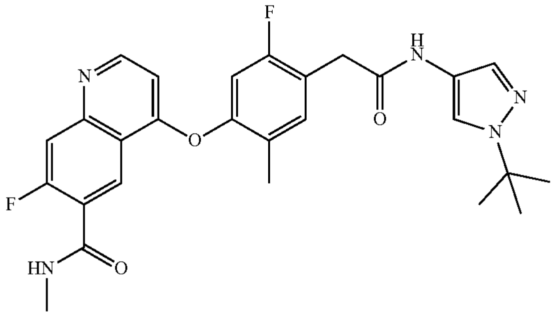 [SMILES: CNC(=O)c1cc2c(Oc3cc(F)c(CC(=O)Nc4cnn(C(C)(C)C)c4)cc3C)ccnc2cc1F] |

TABLE 3-continued
| Compound # | Structure | Compound # | Structure |
|---|---|---|---|
| 239 | 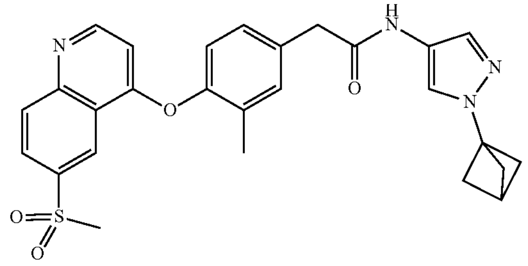 [SMILES: Cc1cc(CC(=O)Nc2cnn(C34CC(C3)C4)c2)ccc1Oc1ccnc2ccc(S(C)(=O)=O)cc12] | 441 | 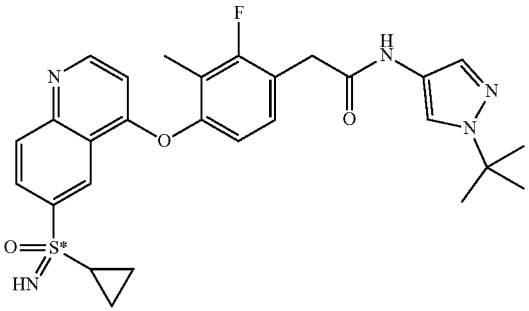<br>enantiomer 1 |
| 299 | 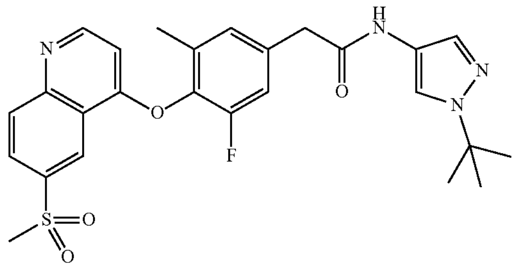 [SMILES: Cc1cc(CC(=O)Nc2cnn(C(C)(C)C)c2)cc(F)c1Oc1ccnc2ccc(S(C)(=O)=O)cc12] | 442 | 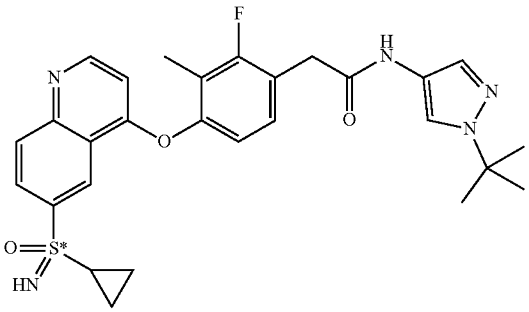<br>enantiomer 2 |
| 359 | 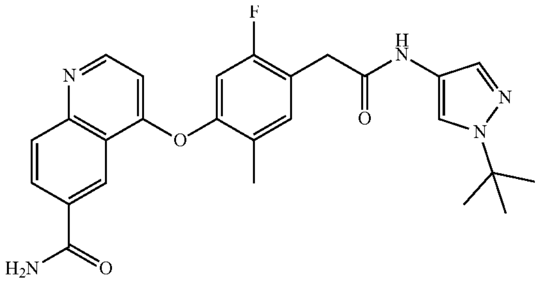 | 445 | 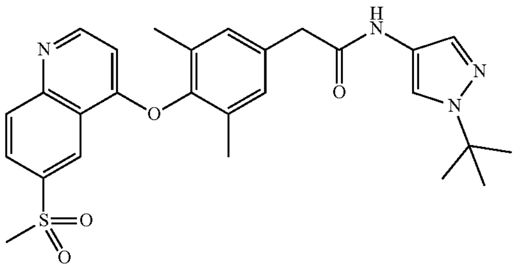 |

TABLE 3-continued
| Compound # | Structure | Compound # | Structure |
|---|---|---|---|
| 462 | 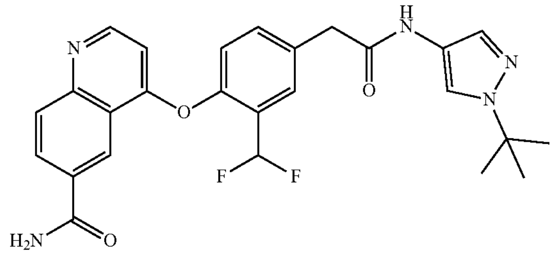 [SMILES: CC(C)(C)n1cc(NC(=O)Cc2ccc(Oc3ccnc4ccc(C(N)=O)cc34)c(C(F)F)c2)cn1] | 490 | 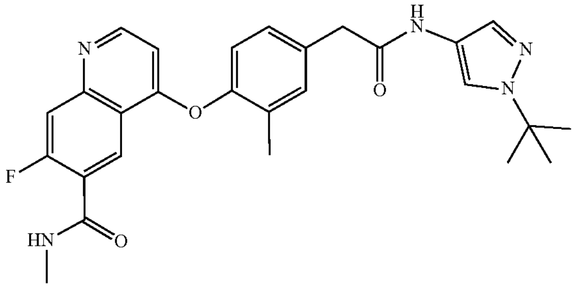 [SMILES: CNC(=O)c1cc2c(Oc3ccc(CC(=O)Nc4cnn(C(C)(C)C)c4)cc3C)ccnc2cc1F] |
| 463 | 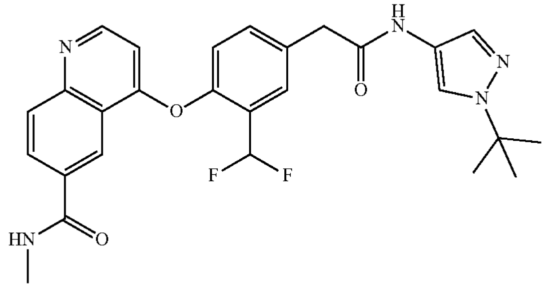 [SMILES: CNC(=O)c1ccc2nccc(Oc3ccc(CC(=O)Nc4cnn(C(C)(C)C)c4)cc3C(F)F)c2c1] | 497 | 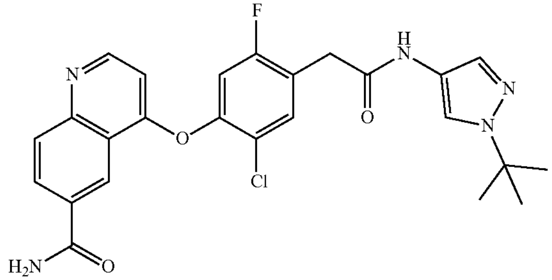 |
| 465 | 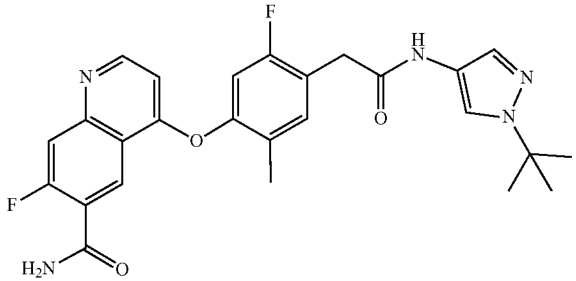 | 498 | 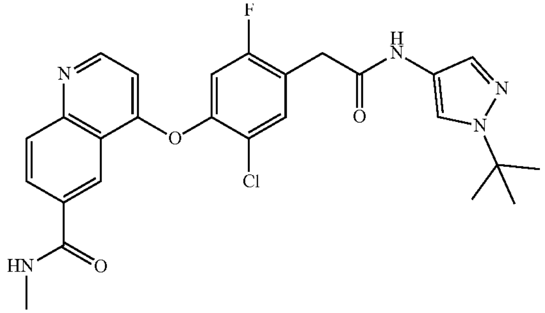 [SMILES: CNC(=O)c1ccc2nccc(Oc3cc(F)c(CC(=O)Nc4cnn(C(C)(C)C)c4)cc3Cl)c2c1] |

TABLE 3-continued
| Compound # | Structure | Compound # | Structure |
|---|---|---|---|
| 466 | 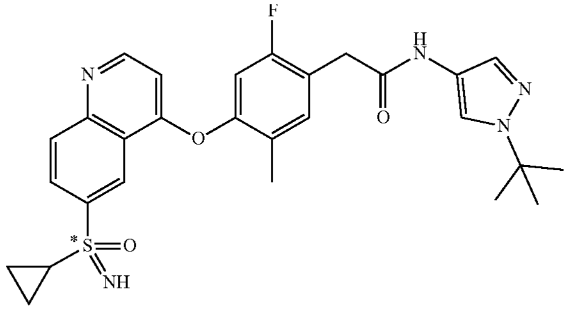 enantiomer 1 | 503 | 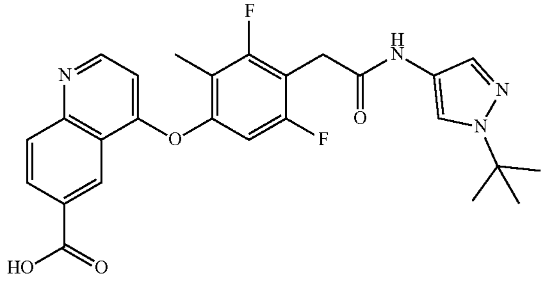 [SMILES: Cc1c(Oc2ccnc3ccc(C(=O)O)cc23)cc(F)c(CC(=O)Nc2cnn(C(C)(C)C)c2)c1F] |
| 467 | 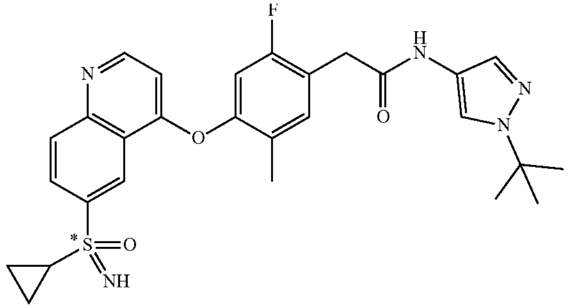 enantiomer 2 | 504 | 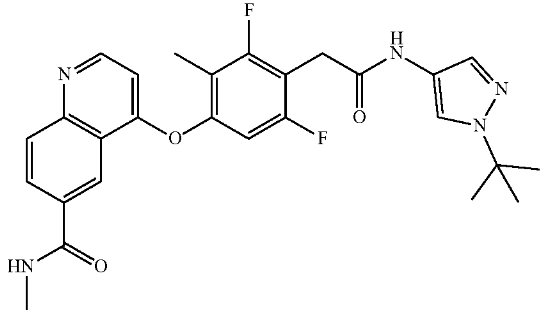 [SMILES: CNC(=O)c1ccc2nccc(Oc3cc(F)c(CC(=O)Nc4cnn(C(C)(C)C)c4)c(F)c3C)c2c1] |
| 468 | 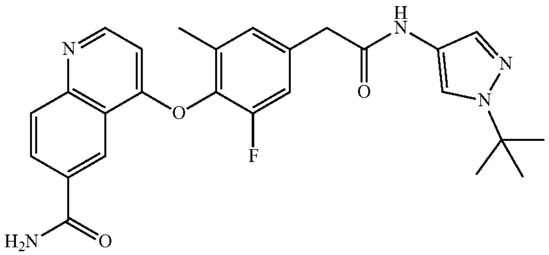 | 543 | 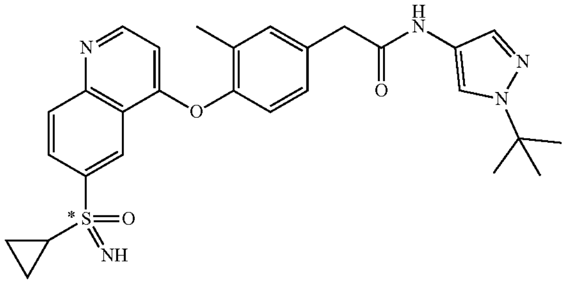 [SMILES: Cc1cc(CC(=O)Nc2cnn(C(C)(C)C)c2)ccc1Oc1ccnc2ccc(S(=N)(=O)C3CC3)cc12] enantiomer 1 |

TABLE 3-continued
| Compound # | Structure | Compound # | Structure |
|---|---|---|---|
| 469 | 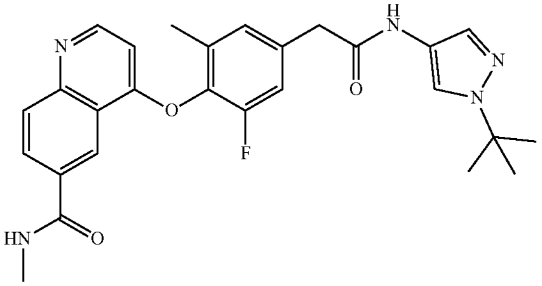 [SMILES: CNC(=O)c1ccc2nccc(Oc3c(C)cc(CC(=O)Nc4cnn(C(C)(C)C)c4)cc3F)c2c1] | 544 | 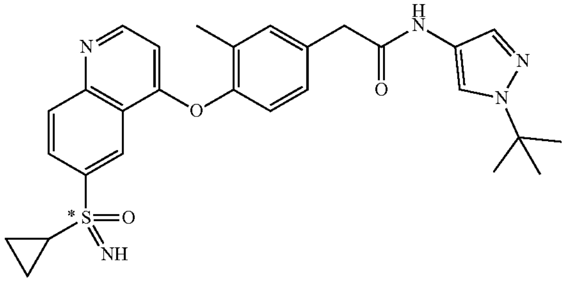 [SMILES: Cc1cc(CC(=O)Nc2cnn(C(C)(C)C)c2)ccc1Oc1ccnc2ccc(S(=N)(=O)C3CC3)cc12] enantiomer 2 |
| 487 | 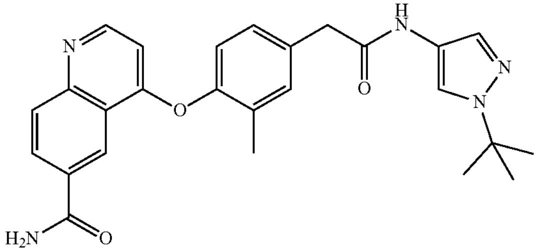 | 575 | 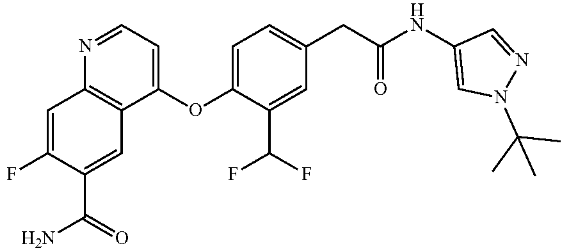 |
| 488 | 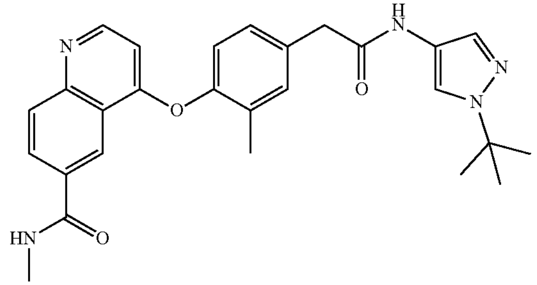 [SMILES: CNC(=O)c1ccc2nccc(Oc3ccc(CC(=O)Nc4cnn(C(C)(C)C)c4)cc3C)c2c1] | 576 | 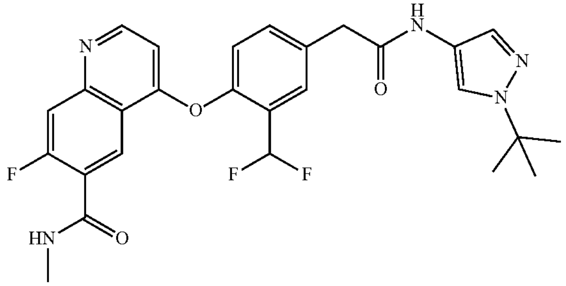 |

TABLE 3-continued
| Compound # | Structure | Compound # | Structure |
|---|---|---|---|
| 489 | 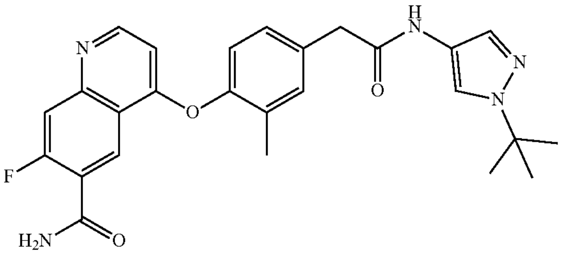 | 598 | 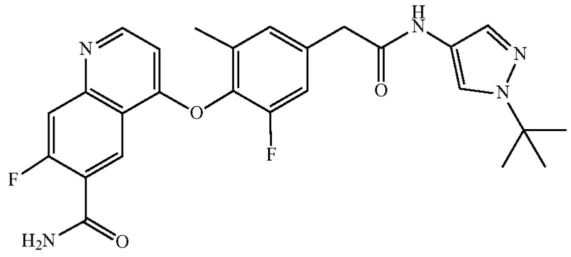 |
| | | 599 | 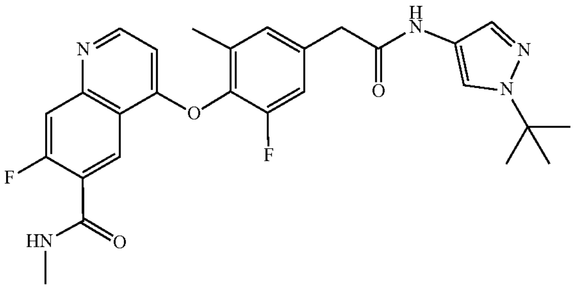 [SMILES: CNC(=O)c1cc2c(Oc3c(C)cc(CC(=O)Nc4cnn(C(C)(C)C)c4)cc3F)ccnc2cc1F] |

In a thirty-sixth aspect of the first embodiment, the compound is represented by structural formula (In):

(In)

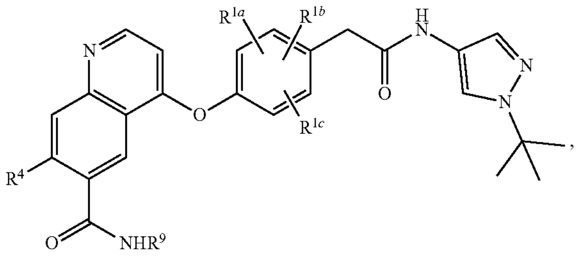

wherein: $R^{1a}$ is selected from $C_{1-3}$ alkyl, halogen, and H; $nR^{1b}$ and $R^4$ is each independently halogen or H; $R^{1c}$ is selected from $C_{1-3}$ haloalkyl, halogen, and H; and $R^9$ is H or $C_{1-3}$ alkyl. The remainder of features and example features of the thirty-sixth aspect is as described above with respect to the first through the thirty-second aspects of the first embodiment.

In a second embodiment, the present invention relates to a pharmaceutical composition comprising a compound described herein with respect to the first embodiment and various aspects thereof, and a pharmaceutically acceptable excipient.

In a third embodiment, the present invention relates to method of treating a disease or disorder, comprising administering to a subject in need thereof a therapeutically effective amount of a compound described herein with respect to the first embodiment and various aspects thereof or a pharmaceutical composition described herein with respect to the second embodiment and various aspects thereof, wherein the disease or disorder is selected from inflammatory diseases, autoimmune diseases, granulomatous diseases, cancer and neurodegenerative diseases.

In a first aspect of the third embodiment, the disease or disorder is an inflammatory disease. For example, the inflammatory disease is selected from uveitis, interleukin-1 converting enzyme fever syndrome, dermatitis, acute lung injury, type 2 diabetes mellitus, arthritis, inflammatory bowel disorder (IBD), ischemia reperfusion injury in a solid organ transplant, sepsis, liver disease, allergic disease, and graft versus host disease. For example, the inflammatory disease is an TBD. For example, the IBD is selected from ulcerative colitis, Crohn's disease, early-onset TBD, and extraintestinal IBD. Alternatively, the inflammatory disease is selected from rheumatoid arthritis, inflammatory arthritis, peritonitis, ischemia reperfusion injury in kidney transplant, non-alcohol steatohepatitis, alcohol steatohepatitis, insulin-resistant type 2 diabetes, allergic rhinitis, asthma, atopic dermatitis, Sjogren's syndrome, ankylosing spondylitis, pemphigus vulgaris, idiopathic plasmacytic lymphadenopathy, atherosclerosis, myocardial infarction, thrombosis, a-synucleinopathy, Parkinson's disease, dementia with Lewy body, multiple system atrophy, Alzheimer's disease, amyotrophic lateral sclerosis, and chronic obstructive pulmonary disease.

In a second aspect of the third embodiment, the disease or disorder is an autoimmune disease. For example, the autoimmune disease is selected from systemic lupus erythematosus, lupus nephritis, psoriasis, immune thrombocytopenic purpura, and multiple sclerosis.

In a third aspect of the third embodiment, the disease or disorder is a granulomatous disease. For example, the granulomatous disease is selected from sarcoidosis, Blau syndrome, Wegner's granulomatosis, Behcet's disease, and interstitial pulmonary disease.

In a fourth aspect of the third embodiment, the disease or disorder is cancer. For example, the cancer is selected from leukemia, breast cancer, brain cancer, colorectal cancer, head and neck cancer, melanoma, pancreatic cancer, prostate cancer, ovarian cancer, renal cancer, and lung cancer.

In a fifth aspect of the third embodiment, the disease or disorder the disease or disorder is a neurodegenerative disease. For example, the neurodegenerative disease is selected from Alzheimer's disease, amyotrophic lateral sclerosis (ALS/Lou Gehrig's Disease), Parkinson's disease, multiple sclerosis, diabetic neurophathy, polyglutamine (polyQ) diseases, stroke, Fahr disease, Menke's disease, Wilson's disease, cerebral ischemia, a prion disorder, dementia, corticobasal degeneration, progressive supranuclear palsy, spinocerebellar atrophies, brain injury, and spinal cord injury.

In a sixth aspect of the third embodiment, the method further comprises administering a therapeutically effective amount of a second agent. In some embodiments, the second agent is an anti-inflammatory agent or an anti-autoimmune agent. For example, in certain embodiments, the second agent is selected from anti-TNF agent, anti-IL-23 agent, anti-integrin agent, and JAK inhibitor. In some embodiments, the second agent is anti-TNF agent. In some embodiments, the second agent is anti-IL-23 agent. In some embodiments, the second agent is anti-integrin agent. In some embodiments, the second agent is JAK inhibitor. The remainder of features and example features of the sixth aspect is as described above with respect to the first through the fifth aspects of the third embodiment.

In a sixth aspect of the third embodiment, the second agent and the compound are administered together in a single pharmaceutical composition. The remainder of features and example features of the seventh aspect is as described above with respect to the first through the sixth aspects of the third embodiment.

In a sixth aspect of the third embodiment, the second agent and the compound are administered separately. In some embodiments, the second agent and the compound are administered separately at the same time. In some embodiments, the second agent and the compound are administered separately at different times. The remainder of features and example features of the seventh aspect is as described above with respect to the first through the sixth aspects of the third embodiment.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those skilled in the art.

The following General Schemes depict synthetic sequences for Examples 1-47.

General Scheme 1
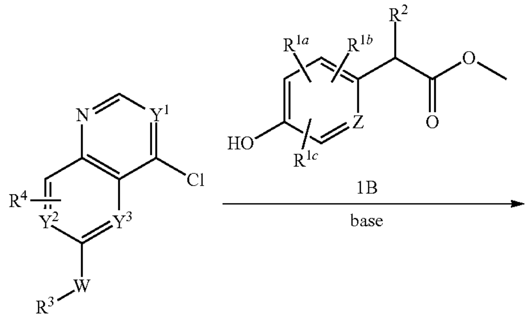
1A
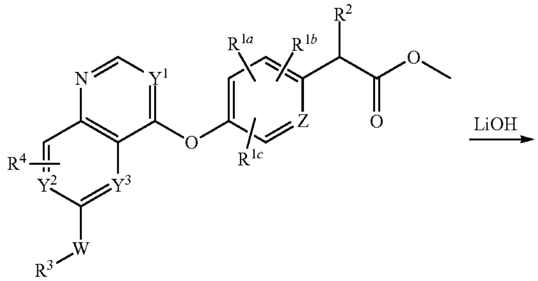
1C
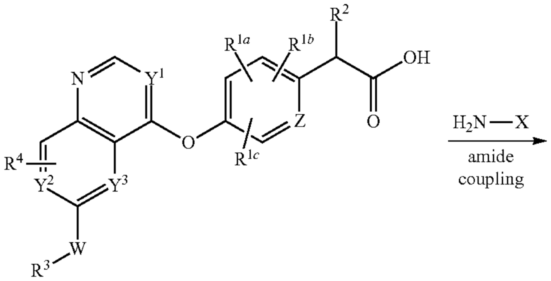
1D
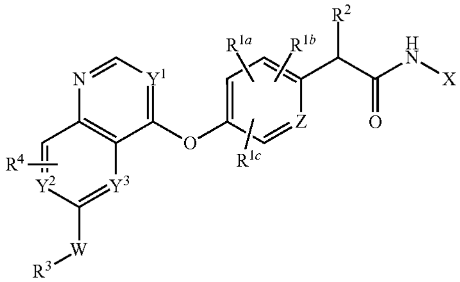
1E
General Scheme 2
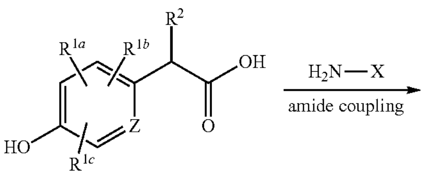
2A
-continued
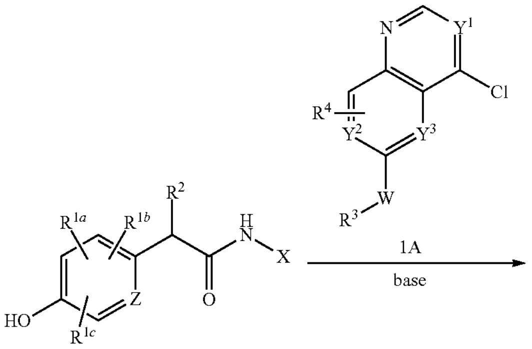
2B
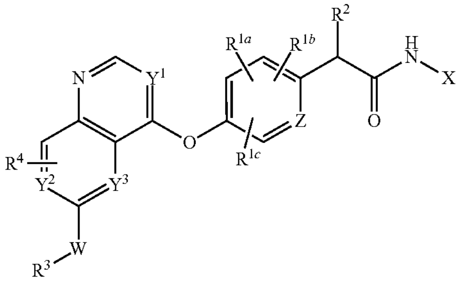
1E
General Scheme 3
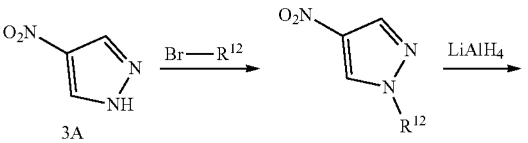
3A
3B
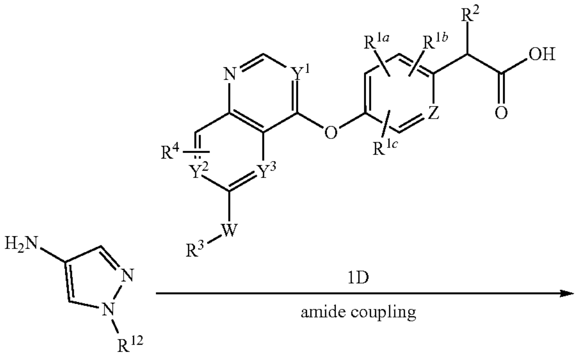
3C
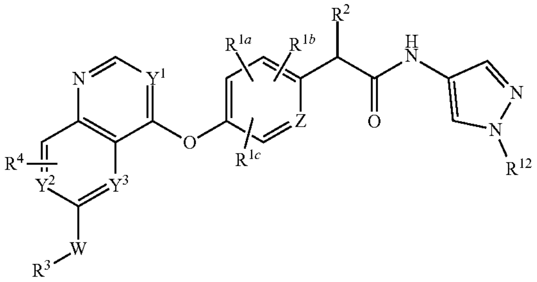
3D General Scheme 4
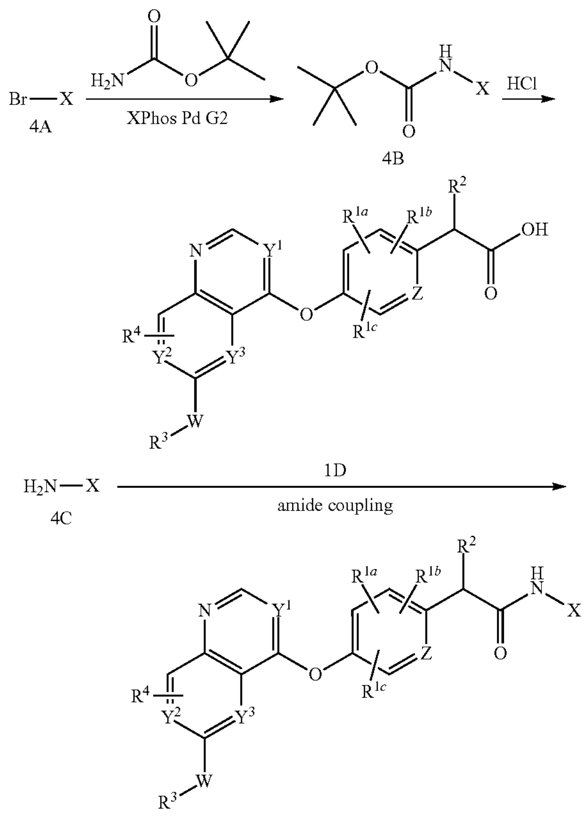
4A 4B 4C 1E
General Scheme 5
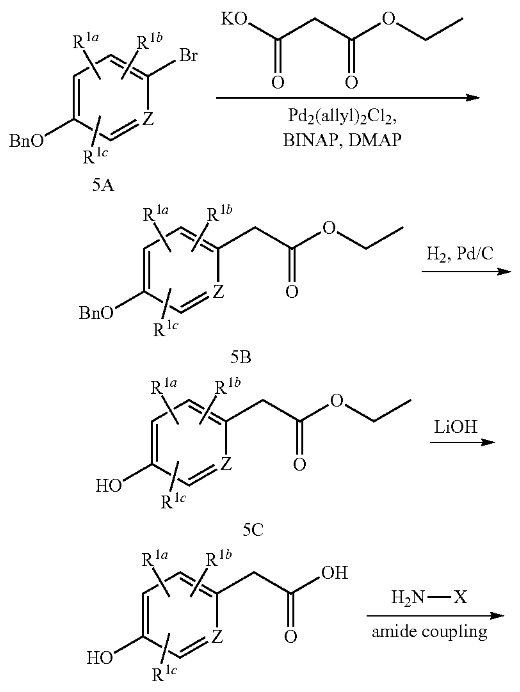
5A 5B 5C 5D
-continued
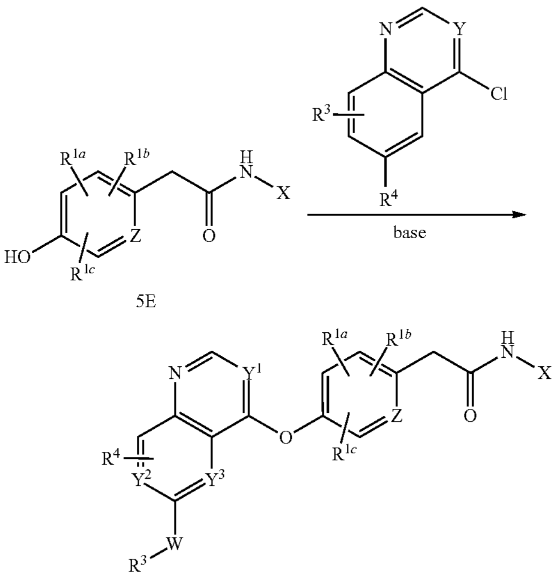
5E 5F
General Scheme 6
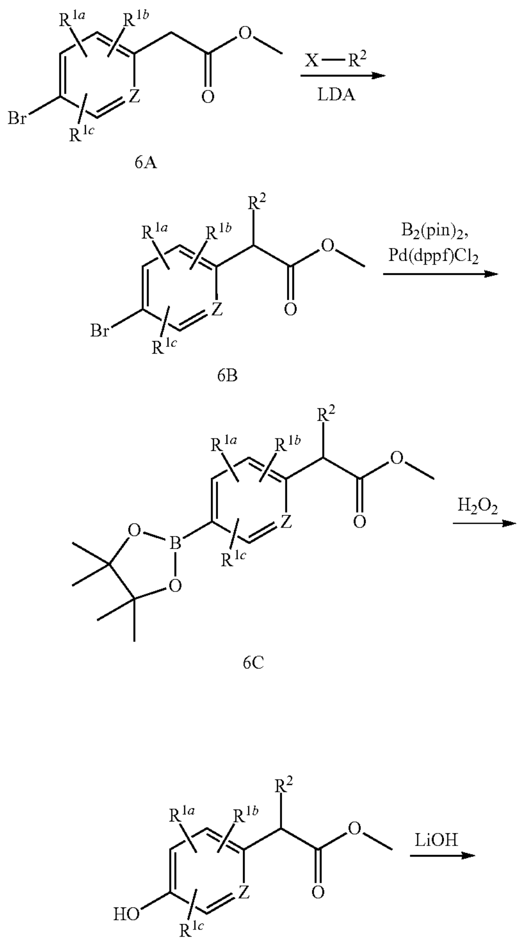
6A 6B 6C 1B -continued
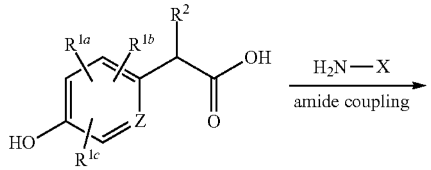
2A
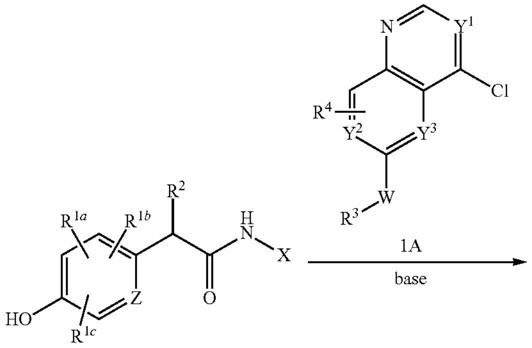
2B
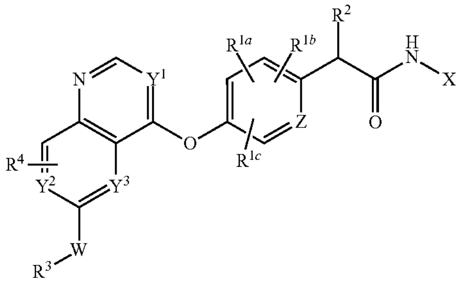
1E
General Scheme 7
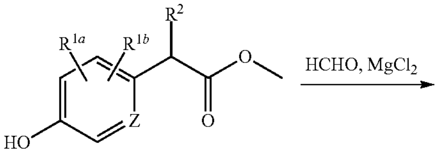
7A
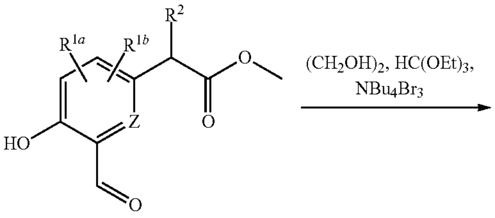
7B
-continued
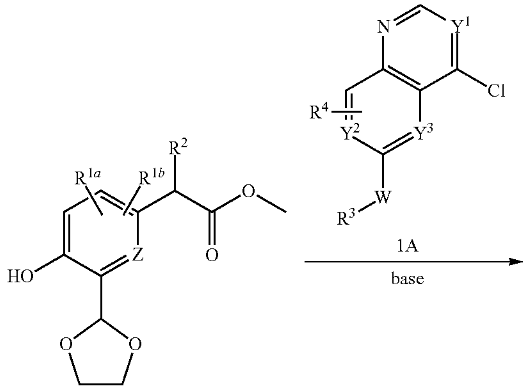
7C
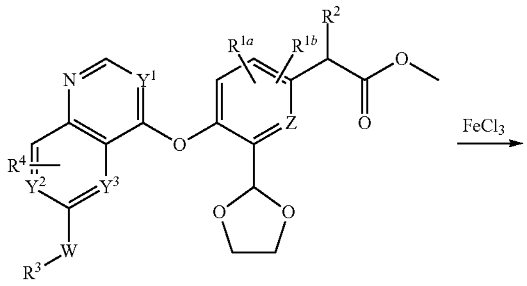
7D
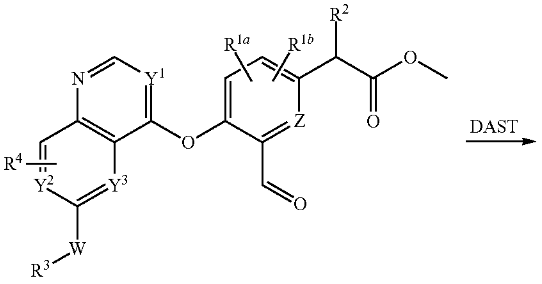
7E
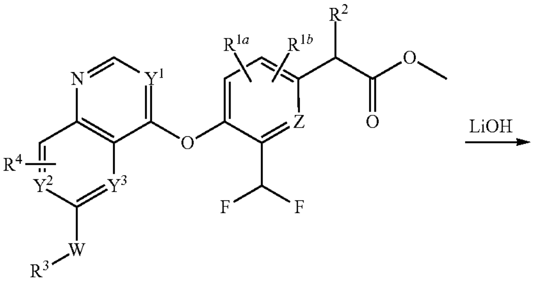
7F
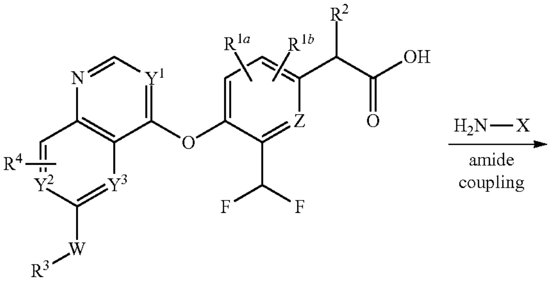
7G -continued
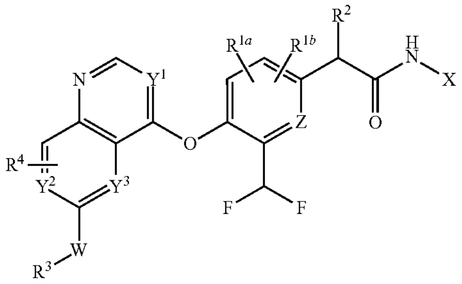
7H
-continued
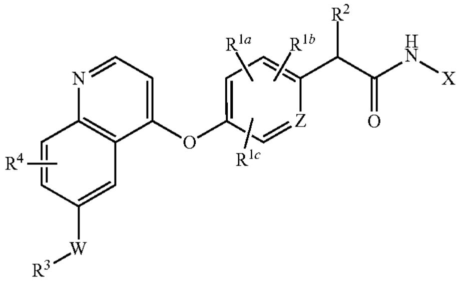
8E
General Scheme 8
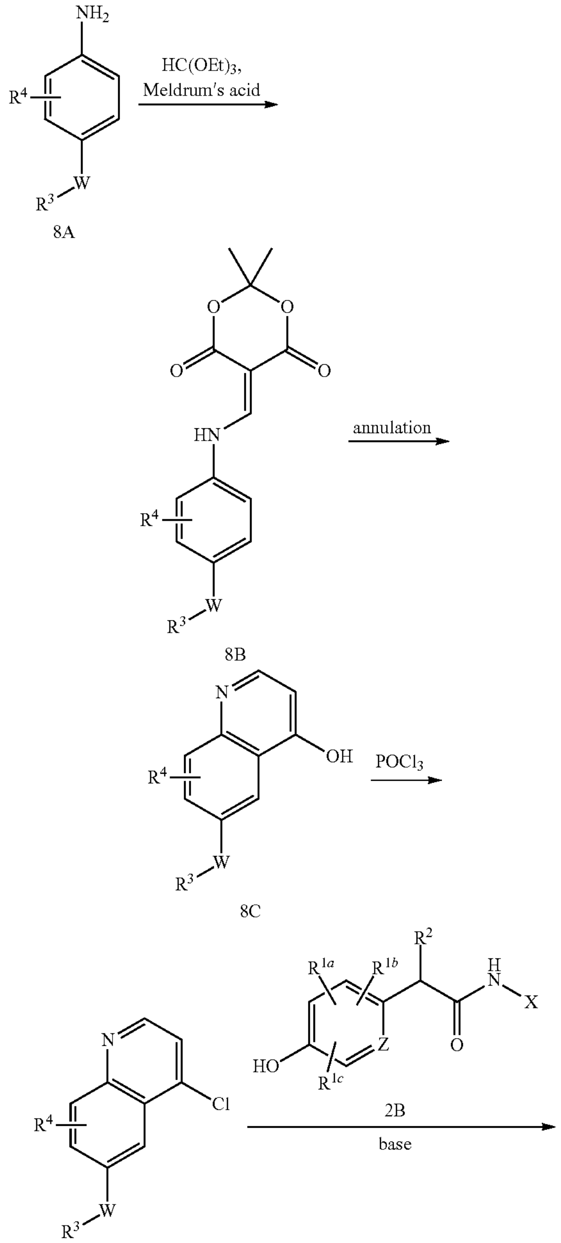
8A 8B 8C 8D
General Scheme 9
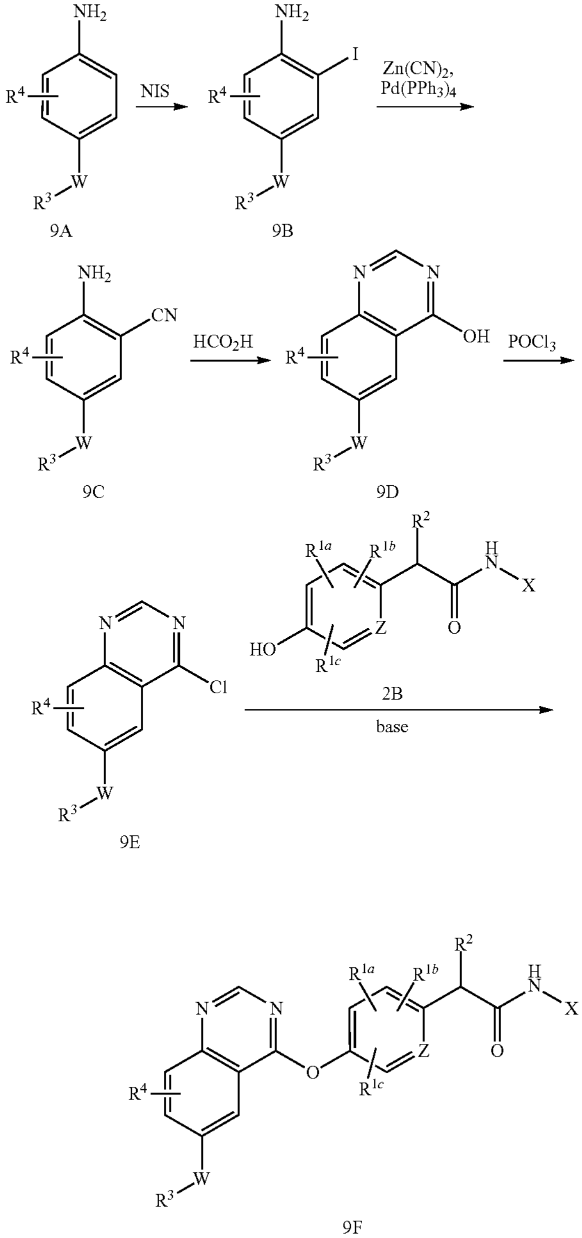
9A 9B 9C 9D 9E 9F General Scheme 10
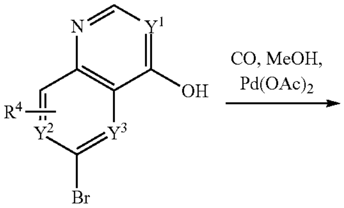
10A
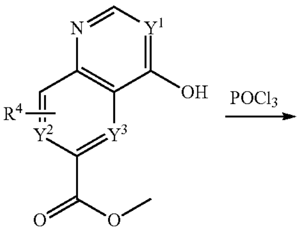
10B
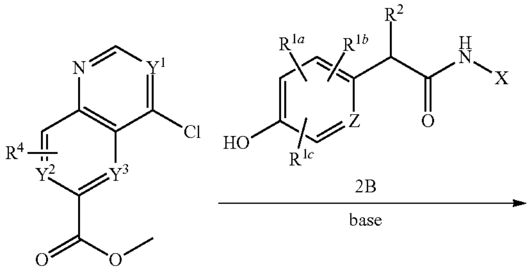
10C
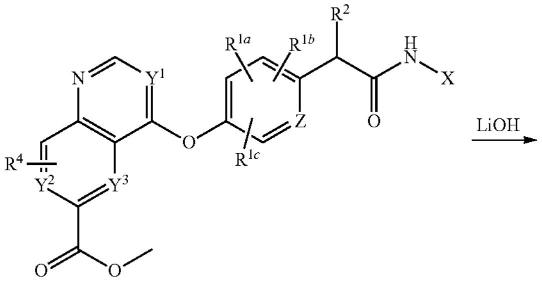
10D
-continued
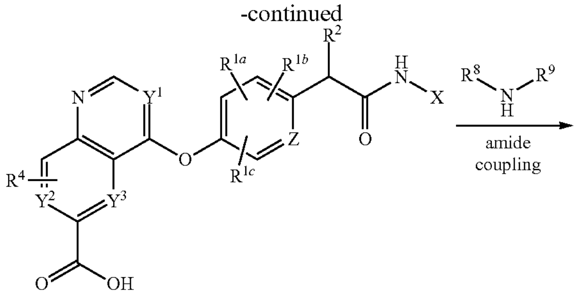
10E
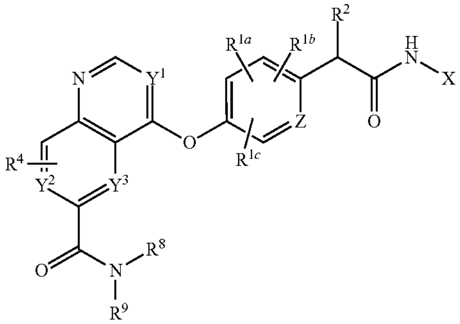
10F
General Scheme 11
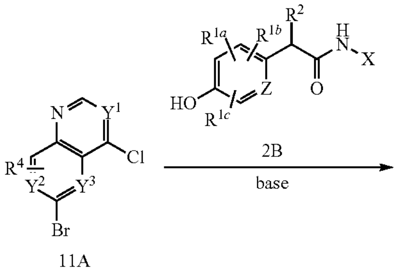
11A
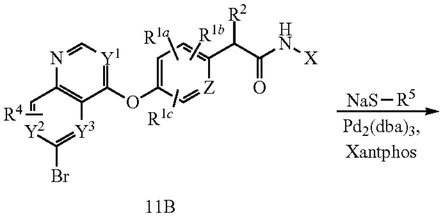
11B
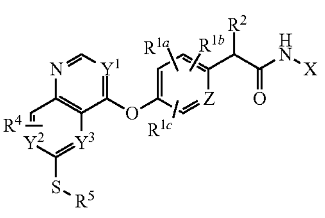
11C
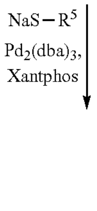
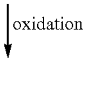

-continued
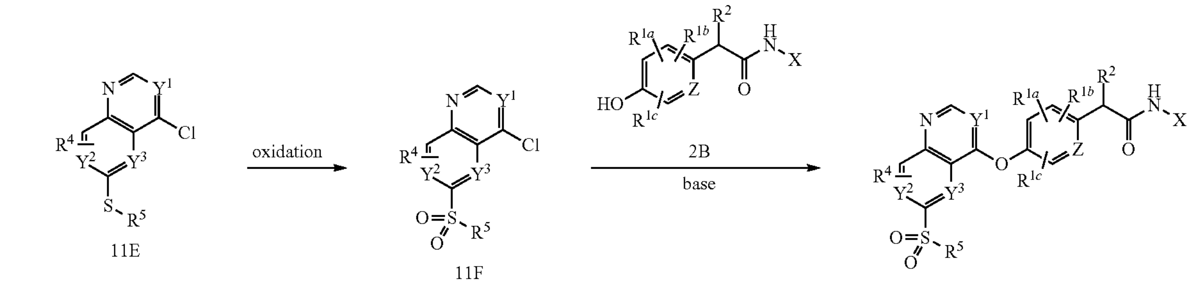
11E 11F 11D
General Scheme 12
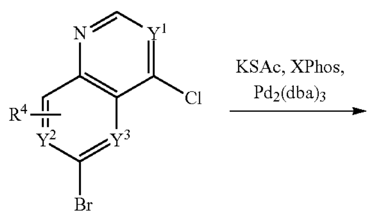
11A
-continued
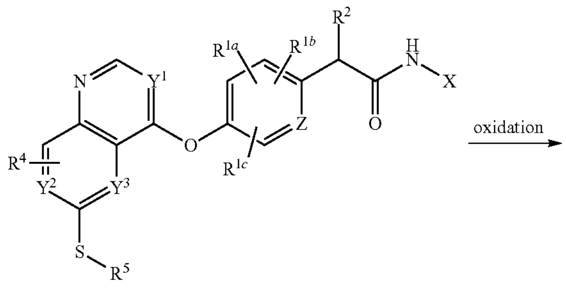
11C
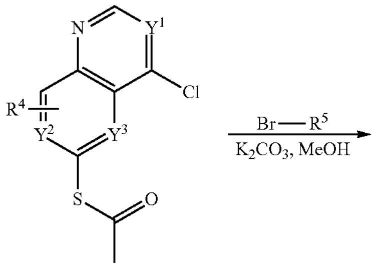
12A
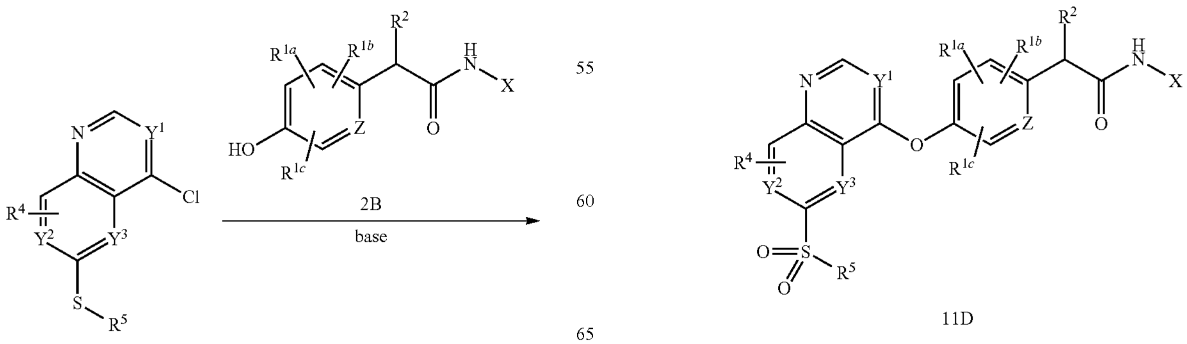
11E 11D General Scheme 13
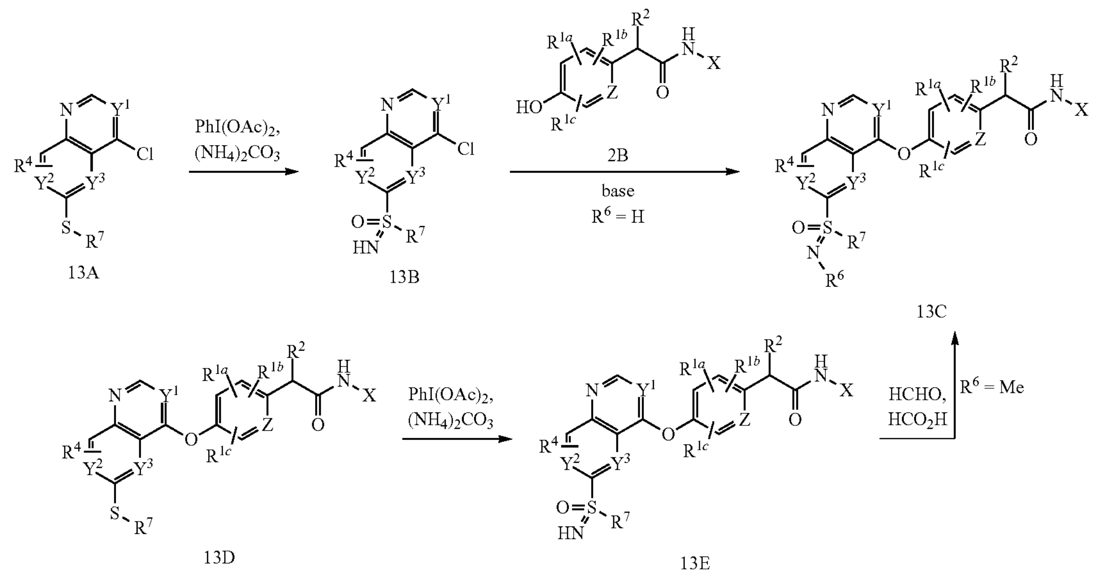
General Scheme 14
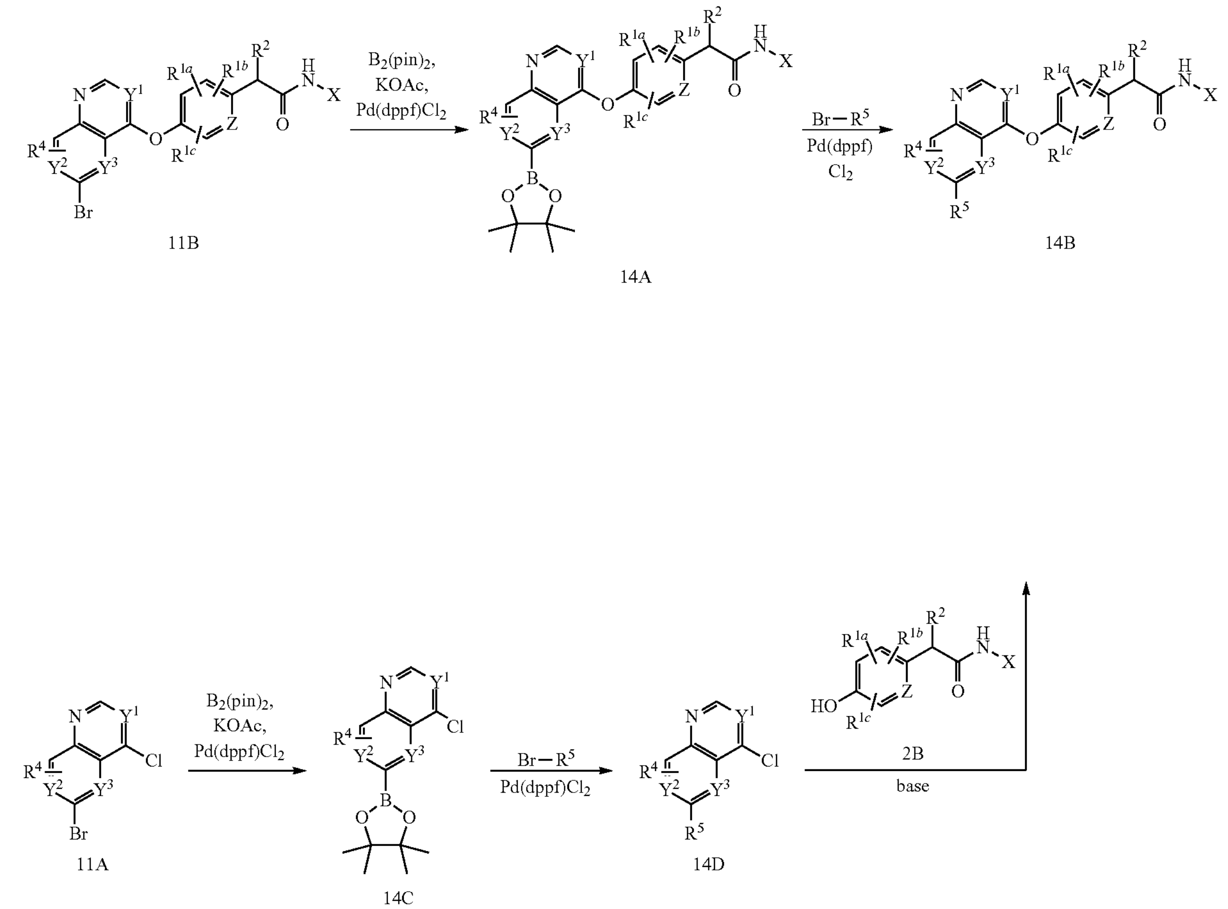

General Scheme 15
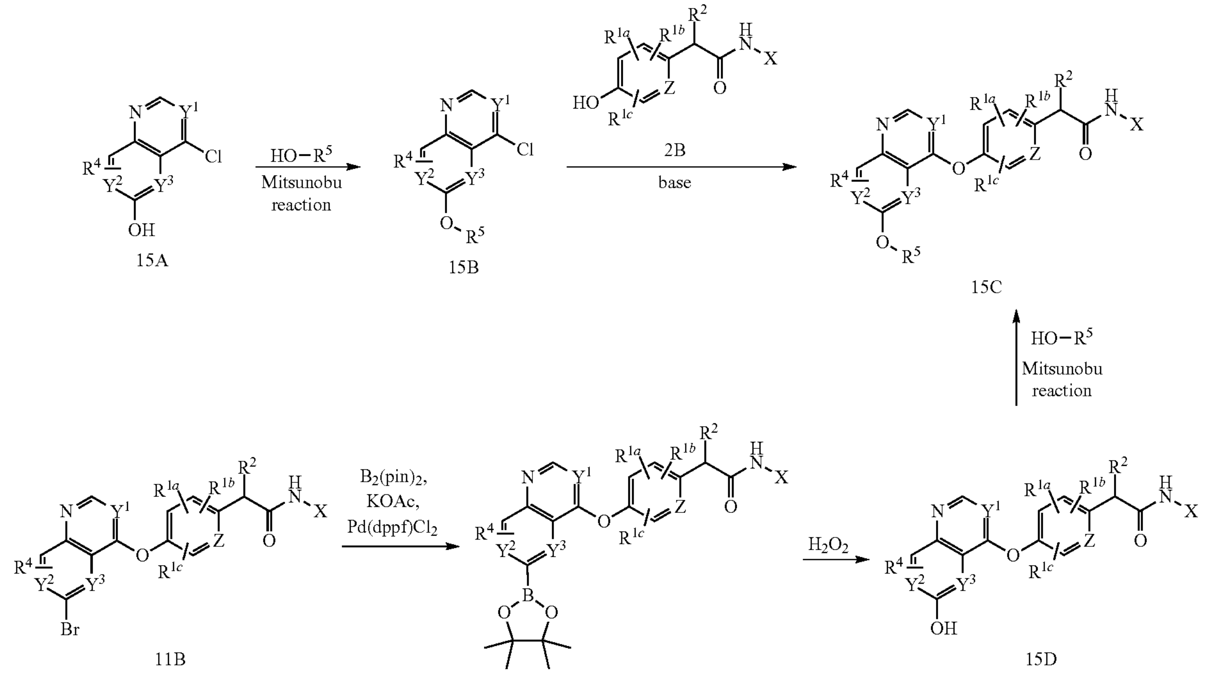
15A 15B 15C 11B 14A 15D
General Scheme 16
-continued
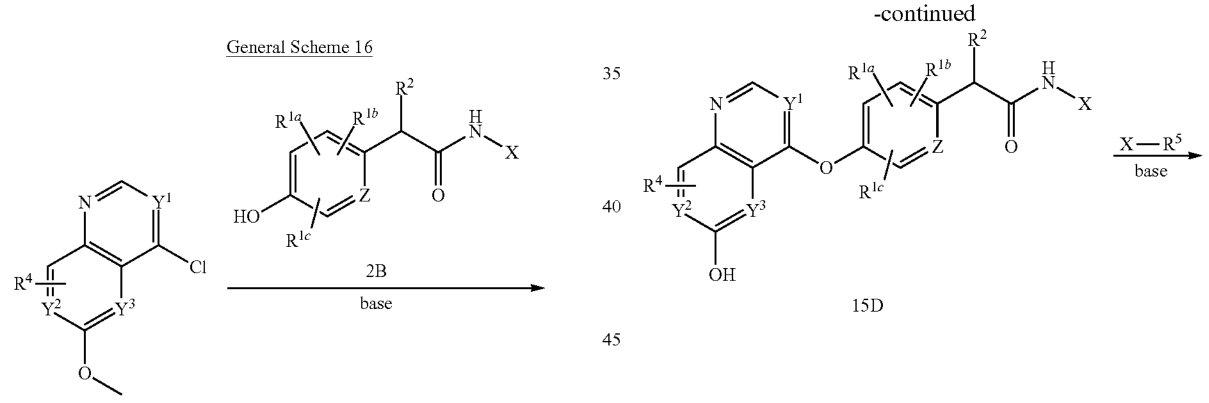
16A 15D
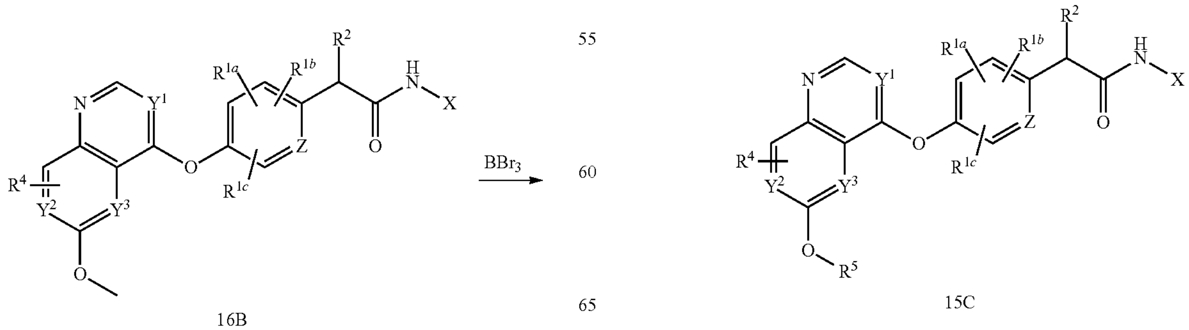
16B 15C General Scheme 17
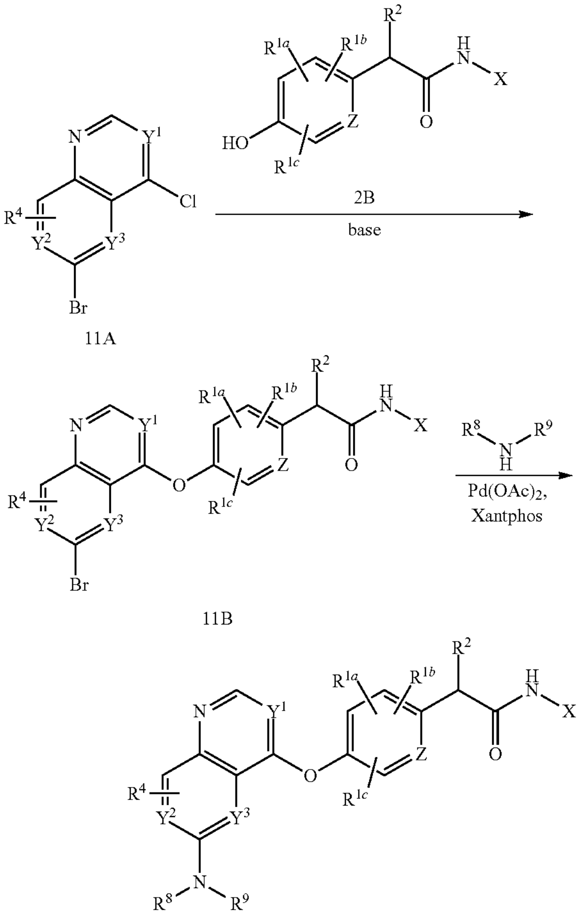
11A
11B
17A
General Scheme 18
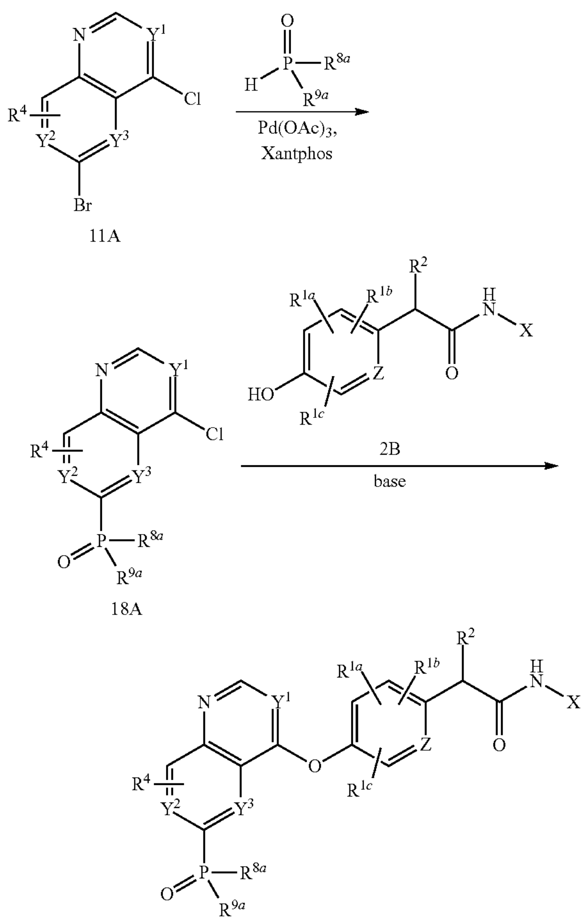
11A
18A
18B
General Scheme 19
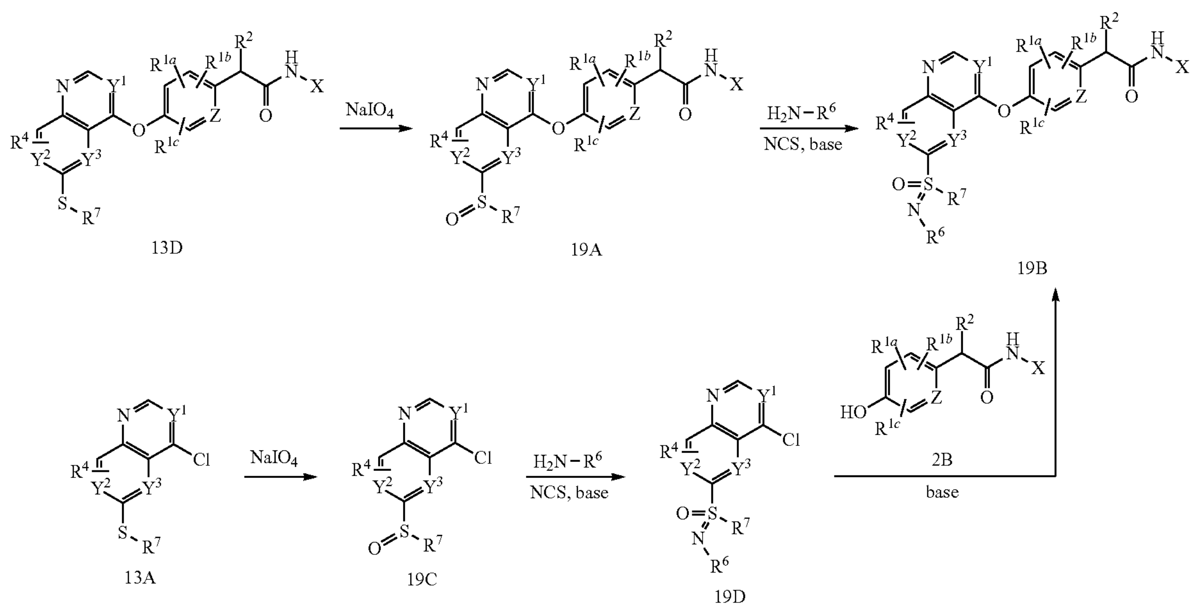
13D
19A
19B
13A
19C
19D General Scheme 20
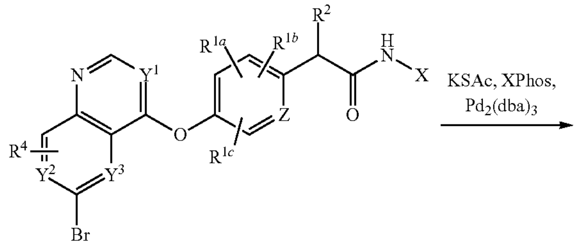
11B
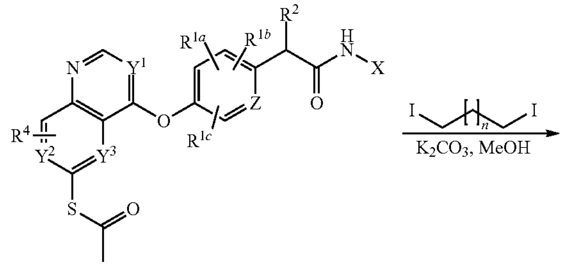
20A
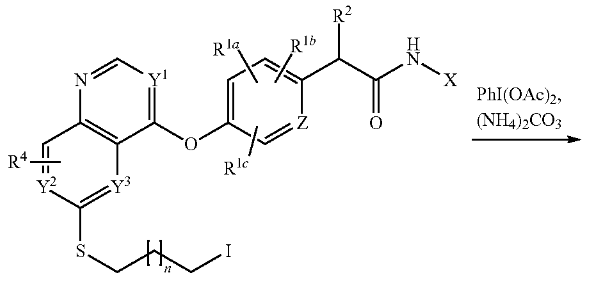
20B
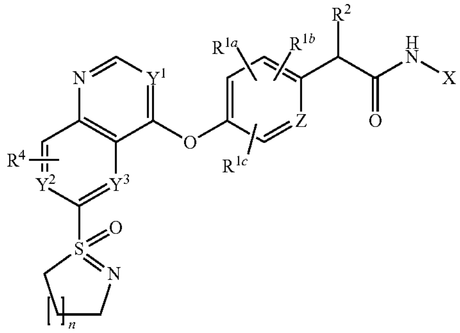
20C
General Scheme 21
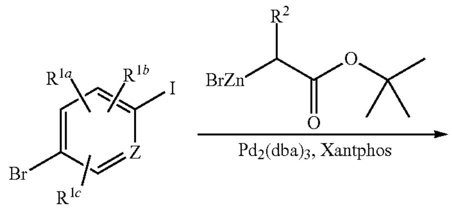
21A
-continued
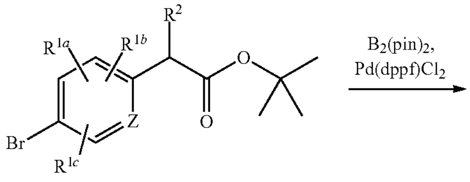
21B
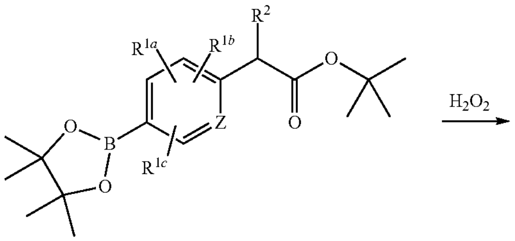
21C
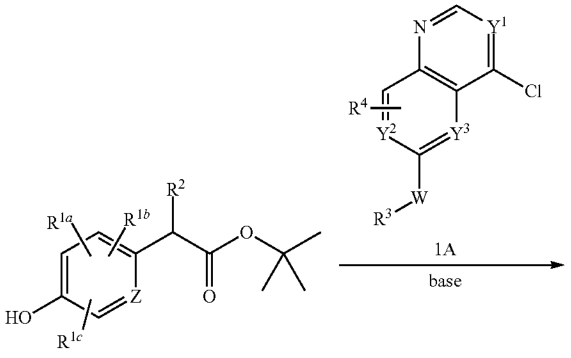
21D
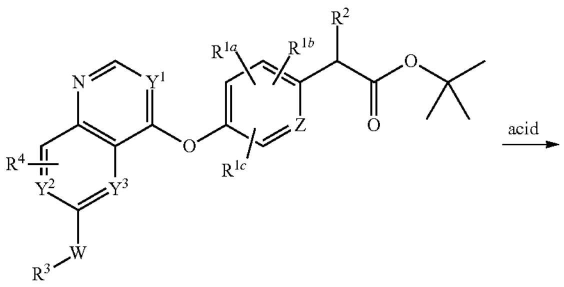
21E
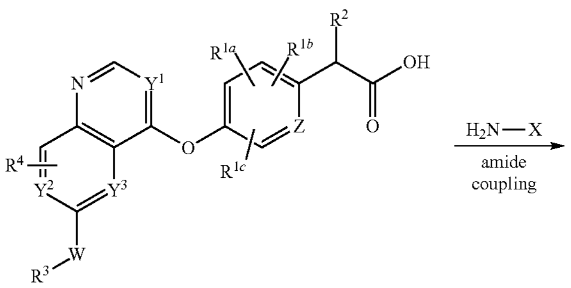
1D -continued
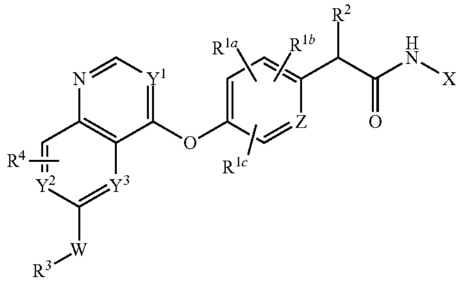
1E
General Scheme 22
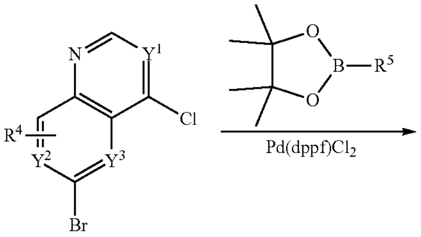
11A
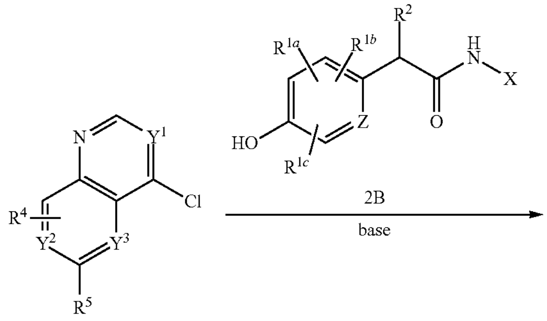
14D
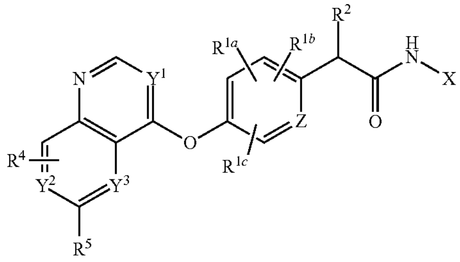
14B
General Scheme 23
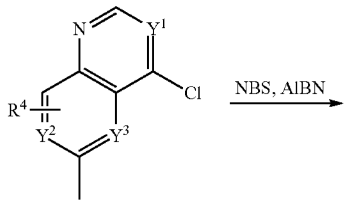
23A
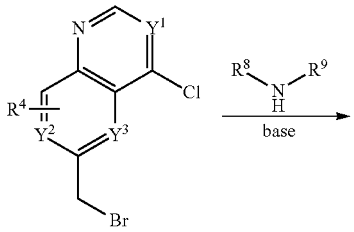
23B
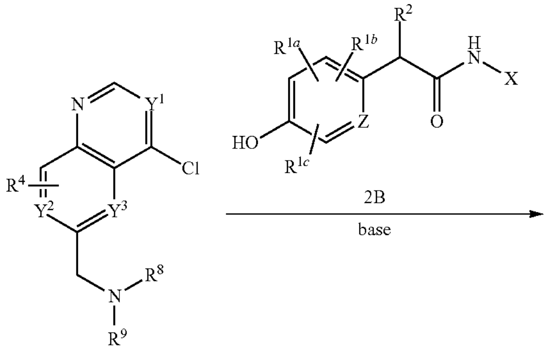
23C
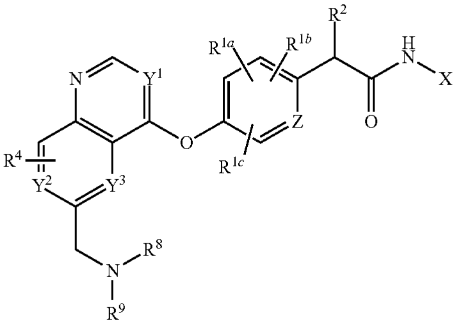
23D
General Scheme 24
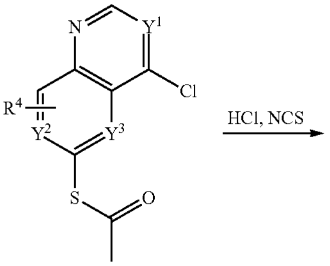
12A -continued

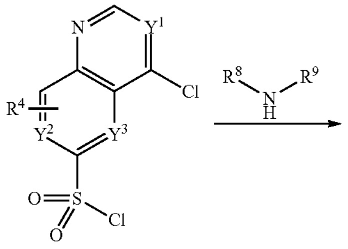

24A

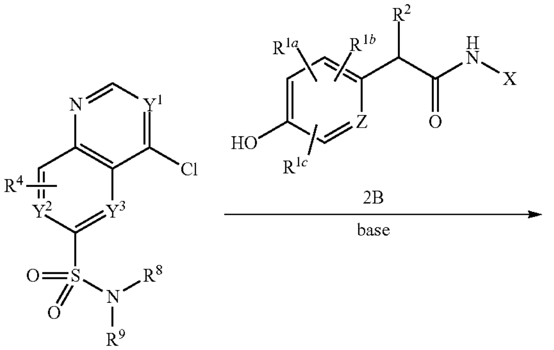

24B

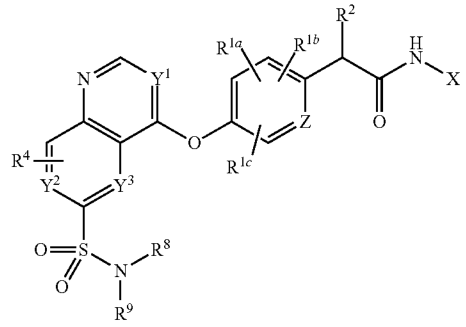

24C

General Scheme 25

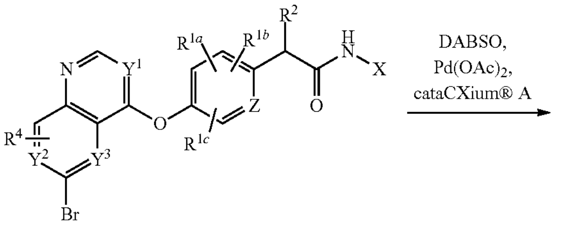

11B

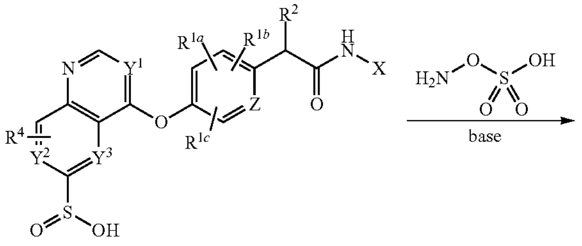

25A

-continued

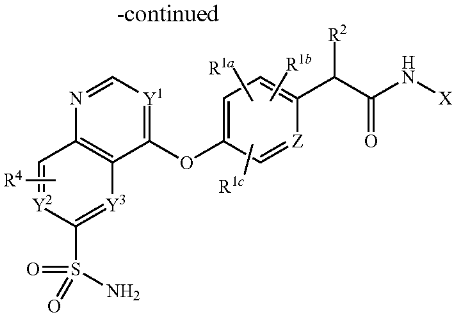

25B

Example 1—Synthesis of N-(1-(tert-butyl)-1H-pyrazol-4-yl)-2-(4-((6-(dimethylphosphoryl)quinolin-4-yl)oxy)-2-fluorophenyl)acetamide (Compound 36); Prepared According to General Scheme 18

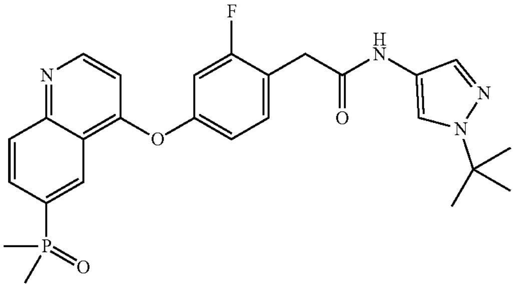 [SMILES: CC(C)(C)n1cc(NC(=O)Cc2ccc(Oc3ccnc4ccc(P(C)(C)=O)cc34)cc2F)cn1]

Part I—Synthesis of (4-chloroquinolin-6-yl)dimethylphosphine Oxide

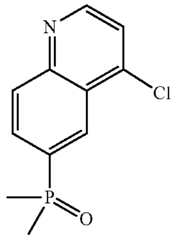

Xantphos (1.7 g, 2.94 mmol, 0.20 equiv.), $Pd_2(dba)_3$ (2.69 g, 2.94 mmol, 0.20 equiv.) and triethylamine (9.5 g, 73.5 mmol, 5.00 equiv.) were added to a solution of 6-bromo-4-chloroquinoline (commercially available, 4.0 g, 14.7 mmol, 1.00 equiv.) and dimethylphosphine oxide (1.72 g, 22.1 mmol, 1.50 equiv.) in 1,4-dioxane (40 mL) under an inert atmosphere of nitrogen. Subsequently, the reaction mixture was heated to 110° C. overnight. The solvent was removed under reduced pressure and the crude product was purified by reversed-phase flash chromatography (column: C18 silica gel; mobile phase A: water, mobile phase B: ACN, gradient: 0-30% B in 30 min; wavelength: 210 nm). The title compound was obtained as an off-white solid (500 mg, 12%).

Part II—Synthesis of N-(1-(tert-butyl)-1H-pyrazol-4-yl)-2-(4-((6-(dimethylphosphoryl)quinolin-4-yl)oxy)-2-fluorophenyl)acetamide (Compound 36)

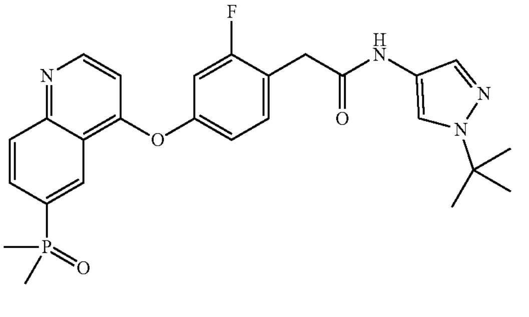 [SMILES: CC(C)(C)n1cc(NC(=O)Cc2ccc(Oc3ccnc4ccc(P(C)(C)=O)cc34)cc2F)cn1]

(4-Chloroquinolin-6-yl)dimethylphosphine oxide (164.5 mg, 0.687 mmol, 1.00 equiv.), $Cs_2CO_3$ (447.4 mg, 1.37 mmol, 2.00 equiv.), copper(I) iodide (52.3 mg, 0.275 mmol, 0.40 equiv.), and N,N-dimethylglycine (42.5 mg, 0.412 mmol, 0.60 equiv.) were added to a solution of N-(1-(tert-butyl)-1H-pyrazol-4-yl)-2-(2-fluoro-4-hydroxyphenyl)acetamide (200 mg, 0.687 mmol, 1.00 equiv., can be synthesized as described in Part II of Example 9) in 1,4-dioxane (2 mL) under an inert atmosphere of nitrogen. Subsequently, the reaction mixture was heated to 100° C. overnight. The solvent was removed under reduced pressure and the crude product was purified by reversed-phase flash chromatography (column: C18 silica gel; mobile phase A: water, mobile phase B: ACN, gradient: 10-60% B in 50 min; wavelength: 210 nm). The title compound was obtained as an off-white solid (77.7 mg, 23%). LCMS (ESI) calculated for $C_{26}H_{29}FN_4O_3P$ $(M+H)^+$: 495.2, found: 495.1. $^1H$ NMR (400 MHz, DMSO-$d_6$) 310.23 (s, 1H), 8.82 (d, J=5.2 Hz, 1H), 8.75 (dd, J=12.6, 1.4 Hz, 1H), 8.15-8.13 (m, 2H), 7.94 (s, 1H), 7.55 (t, J=8.5 Hz, 1H), 7.45 (s, 1H), 7.34 (dd, J=10.4, 2.4 Hz, 1H), 7.18 (dd, J=8.4, 2.4 Hz, 1H), 6.75 (d, J=5.2 Hz, 1H), 3.71 (s, 2H), 1.76 (d, J=13.4 Hz, 6H), 1.49 (s, 9H).

Example 2—Preparation of Additional Phosphine Oxide Compounds

Compounds in the table below were prepared based on experimental procedures described in Example 1 and the detailed description.

| No. | Structure | Name | $^1H$ NMR | Observed m/z |
|---|---|---|---|---|
| 179 | 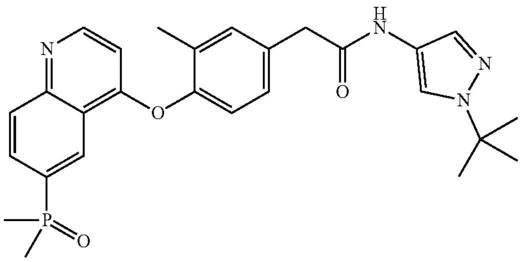 [SMILES: Cc1cc(CC(=O)Nc2cnn(C(C)(C)C)c2)ccc1Oc1ccnc2ccc(P(C)(C)=O)cc12] | N-(1-(tert-butyl)-1H-pyrazol-4-yl)-2-(4-((6-(dimethylphosphoryl) quinolin-4-yl)oxy)-3-methylphenyl) acetamide | (400 MHz, DMSO-$d_6$) δ 10.22 (s, 1H), 8.91-8.87 (m, 2H), 8.32-8.19 (m, 2H), 7.95 (d, J = 0.7 Hz, 1H), 7.48-7.40 (m, 2H), 7.34 (d, J = 8.3 Hz, 1H), 7.26 (d, J = 8.2 Hz, 1H), 6.64 (d, J = 6.5 Hz, 1H), 3.63 (s, 2H), 2.15 (s, 3H), 1.80 (d, J = 13.6 Hz, 6H), 1.49 (s, 9H) | 491.1 $(M + H)^+$ |
| 180 | 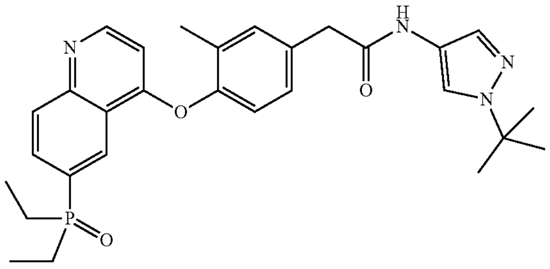 [SMILES: CCP(=O)(CC)c1ccc2nccc(Oc3ccc(CC(=O)Nc4cnn(C(C)(C)C)c4)cc3C)c2c1] | N-(1-(tert-butyl)-1H-pyrazol-4-yl)-2-(4-((6-(diethylphosphoryl) quinolin-4-yl)oxy)-3-methylphenyl) acetamide | (300 MHz, DMSO-$d_6$) δ 10.21 (s, 1H), 8.86-8.67 (m, 2H), 8.17-8.01 (m, 2H), 7.95 (s, 1H), 7.46 (s, 1H), 7.38 (s, 1H), 7.34-7.19 (m, 2H), 6.47 (d, J = 5.2 Hz, 1H), 3.61 (s, 2H), 2.13 (s, 3H), 2.11-1.95 (m, 4H), 1.49 (s, 9H), 0.98 (dt, J = 16.6, 7.6 Hz, 6H) | 519.1 $(M + H)^+$ |
| 181 | 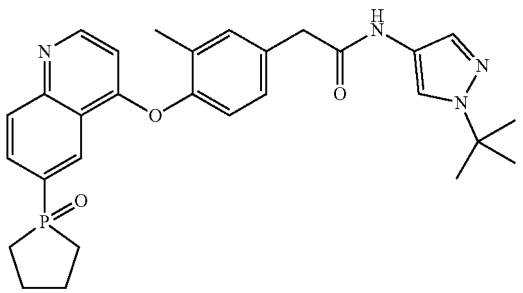 [SMILES: Cc1cc(CC(=O)Nc2cnn(C(C)(C)C)c2)ccc1Oc1ccnc2ccc(P3(=O)CCCC3)cc12] | N-(1-(tert-butyl)-1H-pyrazol-4-yl)-2-(3-methyl-4-((6-(1-oxidophospholan-1-yl)quinolin-4-yl)oxy)phenyl) acetamide | (400 MHz, DMSO-$d_6$) δ 10.21 (s, 1H), 8.83 (dd, J = 12.8, 1.7 Hz, 1H), 8.76 (d, J = 5.2 Hz, 1H), 8.16 (dd, J = 8.6, 2.5 Hz, 1H), 8.02 (d, J = 1.7 Hz, 1H), 7.95 (d, J = 0.7 Hz, 1H), 7.46 (d, J = 0.7 Hz, 1H), 7.39 (d, J = 2.2 Hz, 1H), 7.33-7.29 (m, 1H), 7.21 (d, J = 8.2 Hz, 1H), 6.49 (d, J = 5.2 Hz, 1H), 3.62 (s, 2H), 2.13 (s, 3H), 2.12-1.87 (m, 8H), 1.49 (s, 9H) | 517.1 $(M + H)^+$ |

-continued

| No. | Structure | Name | $^1$H NMR | Observed m/z |
|---|---|---|---|---|
| 300 | 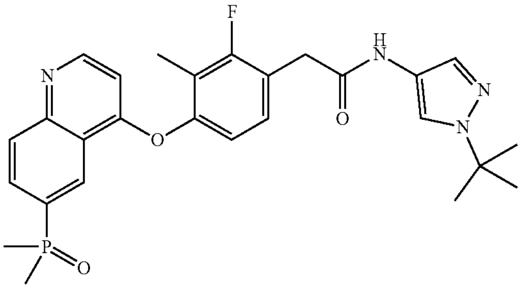 [SMILES: Cc1c(Oc2ccnc3ccc(P(C)(C)=O)cc23)ccc(CC(=O)Nc2cnn(C(C)(C)C)c2)c1F] | N-(1-(tert-butyl)-1H-pyrazol-4-yl)-2-(4-((6-(dimethylphosphoryl) quinolin-4-yl)oxy)-2-fluoro-3-methylphenyl) acetamide | (300 MHz, DMSO-$d_6$) δ 10.24 (s, 1H), 8.87-8.75 (m, 2H), 8.20-8.11 (m, 2H), 7.95 (s, 1H), 7.46 (s, 1H), 7.39 (t, J = 8.5 Hz, 1H), 7.13 (d, J = 8.4 Hz, 1H), 6.56 (d, J = 5.2 Hz, 1H), 3.72 (s, 2H), 2.08 (s, 3H), 1.78 (d, J = 13.4 Hz, 6H), 1.49 (s, 9H) | 509.2 $(M + H)^+$ |
| 301 | 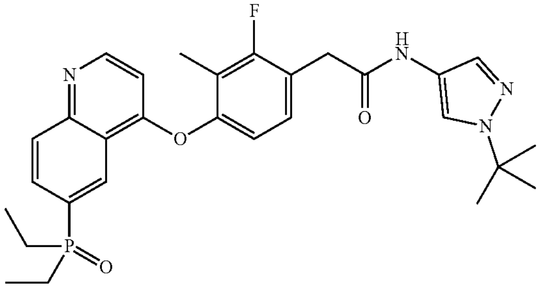 [SMILES: CCP(=O)(CC)c1ccc2nccc(Oc3ccc(CC(=O)Nc4cnn(C(C)(C)C)c4)c(F)c3C)c2c1] | N-(1-(tert-butyl)-1H-pyrazol-4-yl)-2-(4-((6-(diethylphosphoryl) quinolin-4-yl)oxy)-2-fluoro-3-methylphenyl) acetamide | (300 MHz, DMSO-$d_6$) δ 10.24 (s, 1H), 8.85-8.73 (m, 2H), 8.19-8.03 (m, 2H), 7.95 (d, J = 0.7 Hz, 1H), 7.46 (d, J = 0.7 Hz, 1H), 7.39 (t, J = 8.4 Hz, 1H), 7.19-7.11 (m, 1H), 6.56 (d, J = 5.2 Hz, 1H), 3.72 (s, 2H), 2.16-1.97 (m, 7H), 1.49 (s, 9H), 0.99 (dt, J = 16.8, 7.6 Hz, 6H) | 537.1 $(M + H)^+$ |
| 381 | 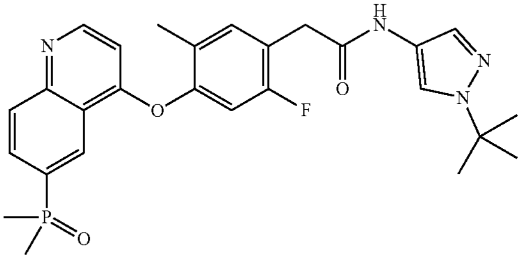 [SMILES: Cc1cc(CC(=O)Nc2cnn(C(C)(C)C)c2)c(F)cc1Oc1ccnc2ccc(P(C)(C)=O)cc12] | N-(1-(tert-butyl)-1H-pyrazol-4-yl)-2-(4-((6-(dimethylphosphoryl) quinolin-4-yl)oxy)-2-fluoro-5-methylphenyl) acetamide | | 531.2 $(M + Na)^+$ |
| 382 | 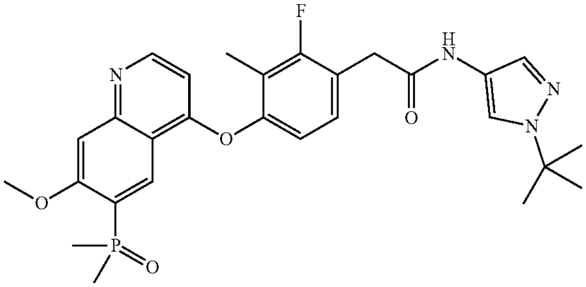 [SMILES: COc1cc2nccc(Oc3ccc(CC(=O)Nc4cnn(C(C)(C)C)c4)c(F)c3C)c2cc1P(C)(C)=O] | N-(1-(tert-butyl)-1H-pyrazol-4-yl)-2-(4-((6-(dimethylphosphoryl)-7-methoxyquinolin-4-yl)oxy)-2-fluoro-3-methylphenyl) acetamide | | 539.2 $(M + H)^+$ |
| 383 | 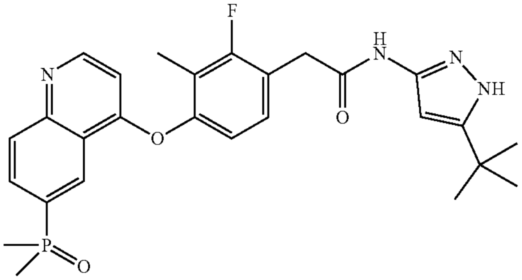 [SMILES: Cc1c(Oc2ccnc3ccc(P(C)(C)=O)cc23)ccc(CC(=O)Nc2cc(C(C)(C)C)[nH]n2)c1F] | N-(5-(tert-butyl)-1H-pyrazol-3-yl)-2-(4-((6-(dimethylphosphoryl) quinolin-4-yl)oxy)-2-fluoro-3-methylphenyl) acetamide | | 509.2 $(M + H)^+$ |

Example 3—Synthesis of N-(1-(tert-butyl)-1H-pyrazol-4-yl)-2-(2-fluoro-4-((6-(S-methylsulfonimidoyl)quinolin-4-yl)oxy)phenyl)acetamide (Compounds 69 and 70); Prepared According to General Scheme 13

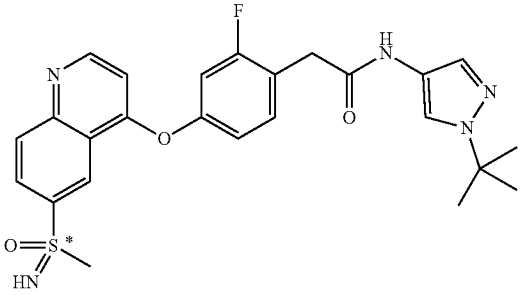 [SMILES: CC(C)(C)n1cc(NC(=O)Cc2ccc(Oc3ccnc4ccc(S(C)(=N)=O)cc34)cc2F)cn1]

(Diacetoxyiodo)benzene (1.29 g, 4.01 mmol, 3.00 equiv.) and $(NH_4)_2CO_3$ (384.7 mg, 4.01 mmol, 3.00 equiv.) were added to a solution of N-(1-(tert-butyl)-1H-pyrazol-4-yl)-2-(2-fluoro-4-((6-(methylthio)quinolin-4-yl)oxy)phenyl)acetamide (620 mg, 1.34 mmol, 1.00 equiv., can be synthesized according to Parts I and II of Example 32) in MeOH (6.2 mL) under an inert atmosphere of nitrogen. The reaction mixture was stirred for 10 min at room temperature. Subsequently, the crude product was purified by reversed-phase flash chromatography (column: C18 silica gel; mobile phase A: water, mobile phase B: ACN, gradient: 10-50% B in 60 min; wavelength: 210 nm). The racemic title compound was obtained as an off-white solid (180 mg, 27%). The two enantiomers were separated by chiral chromatography (column: CHIRALPAK IA-3, 4.6×50 mm, 3 μm; mobile phase A: MTBE (0.1% DEA), mobile phase B: MeOH:DCM (1:1), isocratic separation with 20% B). The title compounds (compound 69 (enantiomer 1): 48.8 mg, 7.6%; compound 70 (enantiomer 2): 50.4 mg, 7.8%) were obtained as off-white solids (retention time (enantiomer 1): 3.14 min, retention time (enantiomer 2): 3.59 min, column: CHIRAL Cellulose-SB, 4.6×100 mm, 3 μm; mobile phase A: MTBE (0.1% DEA), mobile phase B: MeOH/DCM (1:1), isocratic separation with 20% B, flow rate: 1.0 mL/min, wavelength: 254 nm). LCMS (ESI) calculated for $C_{25}H_{27}FN_5O_3S$ (M+H)+: 496.2, found: 495.9. $^1H$ NMR (400 MHz, DMSO-$d_6$) (310.23 (s, 1H), 8.91-8.82 (m, 2H), 8.31-8.20 (m, 2H), 7.94 (d, J=0.8 Hz, 1H), 7.57 (t, J=8.5 Hz, 1H), 7.46 (s, 1H), 7.36 (dd, J=10.4, 2.4 Hz, 1H), 7.20 (dd, J=8.4, 2.4 Hz, 1H), 6.81 (d, J=5.2 Hz, 1H), 4.52-4.44 (m, 1H), 3.72 (s, 2H), 3.20 (d, J=1.2 Hz, 3H), 1.49 (s, 9H).

Example 4—Synthesis of N-(1-(tert-butyl)-1H-pyrazol-4-yl)-2-(2-fluoro-4-((6-(N-methylethylsulfonimidoyl)quinolin-4-yl)oxy)phenyl)acetamide (Compound 74); Prepared According to General Scheme 13

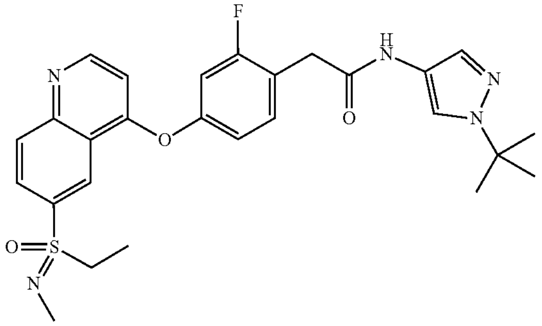 [SMILES: CCS(=O)(=NC)c1ccc2nccc(Oc3ccc(CC(=O)Nc4cnn(C(C)(C)C)c4)c(F)c3)c2c1]

Part I—Synthesis of N-(1-(tert-butyl)-1H-pyrazol-4-yl)-2-(4-((6-(ethylthio)quinolin-4-yl)oxy)-2-fluorophenyl)acetamide

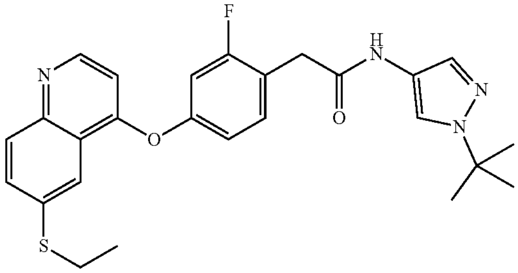 [SMILES: CCSc1ccc2nccc(Oc3ccc(CC(=O)Nc4cnn(C(C)(C)C)c4)c(F)c3)c2c1]

Sodium ethanethiolate (0.25 g, 3.02 mmol, 1.50 equiv.), triethylamine (1.02 g, 10.1 mmol, 5.00 equiv.), $Pd_2(dba)_3$ (0.37 g, 0.402 mmol, 0.20 equiv.), and Xantphos (0.23 g, 0.402 mmol, 0.20 equiv.) were added to a solution of 2-(4-((6-bromoquinolin-4-yl)oxy)-2-fluorophenyl)-N-(1-(tert-butyl)-1H-pyrazol-4-yl)acetamide (1.0 g, 2.01 mmol, 1.00 equiv., can be synthesized according to Part I in Example 32) in 1,4-dioxane (10 mL) under an inert atmosphere of nitrogen. Subsequently, the mixture was heated to 80° C. overnight. The solvent was removed under reduced pressure and the crude product was purified by column chromatography (petroleum ether/EtOAc 1:1). The title compound was obtained as a yellow solid (780 mg, 81%).

Part II—Synthesis of N-(1-(tert-butyl)-1H-pyrazol-4-yl)-2-(4-((6-(ethylsulfonimidoyl)quinolin-4-yl)oxy)-2-fluorophenyl)acetamide

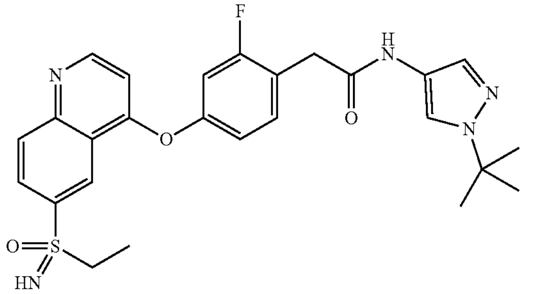

(Diacetoxyiodo)benzene (606 mg, 1.88 mmol, 3.00 equiv.) and $(NH_4)_2CO_3$ (181 mg, 1.88 mmol, 3.00 equiv.) were added to a solution of N-(1-(tert-butyl)-1H-pyrazol-4-yl)-2-(4-((6-(ethylthio)quinolin-4-yl)oxy)-2-fluorophenyl)acetamide (300 mg, 0.627 mmol, 1.00 equiv.) in MeOH (6.2 mL) under an inert atmosphere of nitrogen. The reaction mixture was stirred for 10 min at room temperature. Subsequently, the crude product was purified by reversed-phase flash chromatography (column: C18 silica gel; mobile phase A: water, mobile phase B: ACN, gradient: 10-50% B in 50 min; wavelength: 210 nm). The title compound was obtained as a light-yellow solid (21.3 mg, 6.5%).

Part III—Synthesis of N-(1-(tert-butyl)-1H-pyrazol-4-yl)-2-(2-fluoro-4-((6-(N-methylethylsulfonimidoyl)quinolin-4-yl)oxy)phenyl)acetamide (Compound 74)

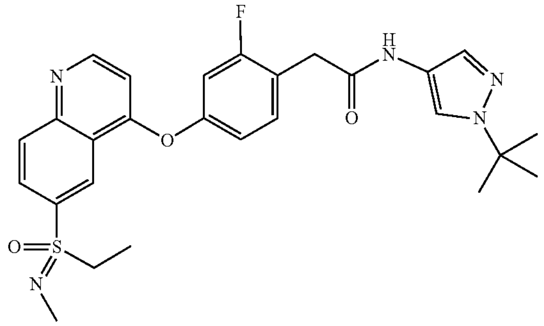 [SMILES: CCS(=O)(=NC)c1ccc2nccc(Oc3ccc(CC(=O)Nc4cnn(C(C)(C)C)c4)c(F)c3)c2c1]

A solution of N-(1-(tert-butyl)-1H-pyrazol-4-yl)-2-(4-((6-(ethylsulfonimidoyl)quinolin-4-yl)oxy)-2-fluorophenyl)acetamide (185 mg, 0.363 mmol, 1.00 equiv.) and paraformaldehyde (65.4 mg, 0.726 mmol, 2.00 equiv.) in formic acid (2 mL) was heated to 120° C. for 6 h under an inert atmosphere of nitrogen. Subsequently, the solvent was removed under reduced pressure and the crude product was purified by reversed-phase flash chromatography (column: C18 silica gel; mobile phase A: water, mobile phase B: ACN, gradient: 10-50% B in 60 min; wavelength: 210 nm). The title compound was obtained as a light-yellow solid (24.6 mg, 12%). LCMS (ESI) calculated for $C_{27}H_{31}FN_5O_3S$ $(M+H)^+$: 524.2, found: 524.0. $^1H$ NMR (400 MHz, DMSO-$d_6$) δ 10.21 (s, 1H), 8.88 (d, J=5.2 Hz, 1H), 8.73 (d, J=2.0 Hz, 1H), 8.25 (d, J=8.9 Hz, 1H), 8.10 (dd, J=8.9, 2.1 Hz, 1H), 7.94 (s, 1H), 7.55 (t, J=8.5 Hz, 1H), 7.45 (s, 1H), 7.42-7.35 (m, 1H), 7.21 (dd, J=8.3, 2.4 Hz, 1H), 6.82 (d, J=5.3 Hz, 1H), 3.71 (s, 2H), 3.39-3.65 (m, 2H), 2.54 (s, 3H), 1.49 (s, 9H), 1.13 (t, J=7.4 Hz, 3H).

Example 5—Synthesis of N-(1-(tert-butyl)-1H-pyrazol-4-yl)-2-(4-((6-(N-cyano-S-methylsulfonimidoyl)quinolin-4-yl)oxy)-2-fluorophenyl)acetamide (Compound 71); Prepared According to the Synthesis of Compound 19B in General Scheme 19

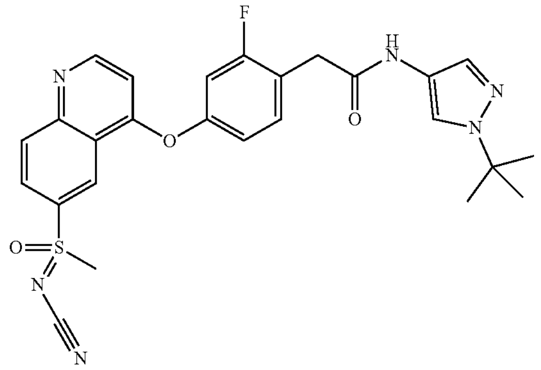 [SMILES: CC(C)(C)n1cc(NC(=O)Cc2ccc(Oc3ccnc4ccc(S(C)(=O)=NC#N)cc34)cc2F)cn1]

Cyanamide (52.7 mg, 1.25 mmol, 2.00 equiv.), potassium tert-butoxide (140.7 mg, 1.25 mmol, 2.00 equiv.), and N-chlorosuccinimide (167.4 mg, 1.25 mmol, 2.00 equiv.) were added to a solution of N-(1-(tert-butyl)-1H-pyrazol-4-yl)-2-(2-fluoro-4-((6-(methylsulfinyl)quinolin-4-yl)oxy)phenyl)acetamide (300 mg, 0.627 mmol, 1.00 equiv., can be prepared according to Example 32) in THF/water (1:1, 6 mL) and the reaction mixture was stirred at room temperature overnight. Subsequently, the crude product was purified by reversed-phase flash chromatography (column: C18 silica gel; mobile phase A: water, mobile phase B: ACN, gradient: 20-50% B in 30 min; wavelength: 210 nm). The title compound was obtained as an off-white solid (11 mg, 3.4%). LCMS (ESI) calculated for $C_{26}H_{26}FN_6O_3S$ $(M+H)^+$: 521.2, found: 521.2. $^1H$ NMR (300 MHz, DMSO-$d_6$) 310.23 (s, 1H), 9.01-8.90 (m, 2H), 8.42-8.35 (m, 2H), 7.94 (d, J=0.8 Hz, 1H), 7.58 (t, J=8.5 Hz, 1H), 7.46 (d, J=0.7 Hz, 1H), 7.41 (dd, J=10.4, 2.4 Hz, 1H), 7.28-7.19 (m, 1H), 6.88 (d, J=5.3 Hz, 1H), 3.90 (s, 3H), 3.72 (s, 2H), 1.49 (s, 9H).

Example 6—Synthesis of N-(1-(tert-butyl)-1H-pyrazol-4-yl)-2-(4-((6-(cyclopropanesulfonimidoyl)quinolin-4-yl)oxy)-2-fluoro-3-methylphenyl)acetamide (Compounds 441 and 442); Prepared According to General Scheme 13

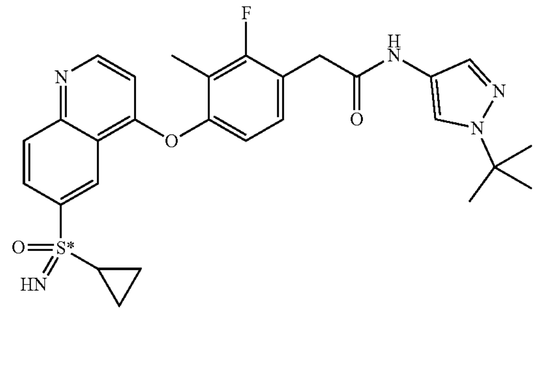

Part I—Synthesis of (4-bromo-2-fluoro-3-methylphenyl)methanol

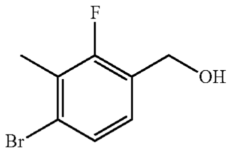

A solution of borane in THF (1 M, 388 mL, 388 mmol, 3.00 equiv.) was added to a solution of 4-bromo-2-fluoro-3-methylbenzoic acid (30.0 g, 129 mmol, 1.00 equiv.) in THF (600 mL) at 0° C. Subsequently, the mixture was stirred at room temperature overnight. Hydrochloric acid (1 M, 600 mL) was added, and the product was extracted with EtOAc (3×300 mL). The combined organic phases were washed with a saturated aqueous solution of $NaHCO_3$ and brine, dried over $Na_2SO_4$, and the solvent was removed under reduced pressure. The crude product was purified by column chromatography (petroleum ether/EtOAc 3:1). The title compound was obtained as a white solid (24.8 g, 88%).

Part II—Synthesis of 1-bromo-4-(bromomethyl)-3-fluoro-2-methylbenzene

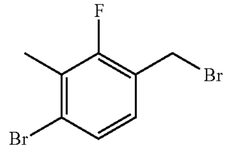

Tetrabromomethane (45.2 g, 136 mmol, 1.20 equiv.) was added to a solution of (4-bromo-2-fluoro-3-methylphenyl) methanol (24.8 g, 114 mmol, 1.00 equiv.) and triphenylphosphine (44.7 g, 171 mmol, 1.50 equiv.) in DCM (500 mL) at 0° C. Subsequently, the mixture was stirred at room temperature for 1 h. Water was added, and the product was extracted with DCM (3×300 mL). The combined organic phases were washed with brine, dried over $Na_2SO_4$, and the solvent was removed under reduced pressure. The crude product was purified by column chromatography (petroleum ether/EtOAc 80:1). The title compound was obtained as a yellow solid (29.6 g, 93%).

Part III—Synthesis of 2-(4-bromo-2-fluoro-3-methylphenyl)acetonitrile

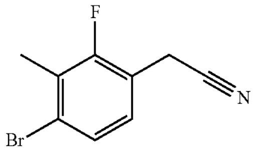

A solution of 1-bromo-4-(bromomethyl)-3-fluoro-2-methylbenzene methylbenzene (29.6 g, 106 mmol, 1.00 equiv.) and potassium cyanide (10.3 g, 158 mmol, 1.50 equiv.) in DMA (100 mL) and water (50 mL) was heated to 90° C. for 1.5 h. Subsequently, a saturated aqueous solution of $NaHCO_3$ was added and the product was extracted with EtOAc (3×300 mL). The combined organic phases were washed with brine, dried over $Na_2SO_4$, and the solvent was removed under reduced pressure. The crude product was purified by column chromatography (petroleum ether/EtOAc 50:1). The title compound was obtained as a yellow solid (19.33 g, 80%).

Part IV—Synthesis of 2-(4-bromo-2-fluoro-3-methylphenyl)acetic Acid

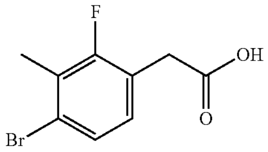

Potassium hydroxide (14.7 g, 262 mmol, 3.10 equiv.) was added to a solution of 2-(4-bromo-2-fluoro-3-methylphenyl) acetonitrile (19.3 g, 84.6 mmol, 1.00 equiv.) in EtOH (135 mL) and water (58 mL) and the mixture was heated to 90° C. for 2 h. Subsequently, the pH of the solution was brought to 4 with hydrochloric acid and the product was extracted with EtOAc (3×200 mL). The combined organic phases were washed with brine, dried over $Na_2SO_4$, and the solvent was removed under reduced pressure. The title compound (18.9 g) was used in the next reaction without further purification.

Part V—Synthesis of 2-(4-bromo-2-fluoro-3-methylphenyl)-N-(1-(tert-butyl)-1H-pyrazol-4-yl)acetamide

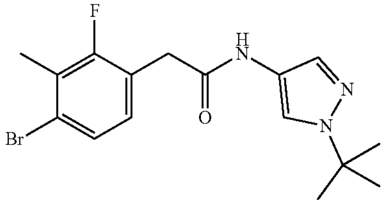 [SMILES: Cc1c(Br)ccc(CC(=O)Nc2cnn(C(C)(C)C)c2)c1F]

HATU (43.6 g, 115 mmol, 1.50 equiv.) was added to a solution of 2-(4-bromo-2-fluoro-3-methylphenyl)acetic acid (18.9 g, 76.5 mmol, 1.00 equiv.), 1-(tert-butyl)-1H-pyrazol-4-amine (10.7 g, 76.5 mmol, 1.00 equiv.), and DIPEA (29.7 g, 229 mmol, 3.00 equiv.) in DMF (378 mL) at 0° C. Subsequently, the reaction mixture was stirred at room temperature for 2 h. Water (100 mL) was added, and the product was extracted with EtOAc (3×300 mL). The combined organic phases were washed with brine (3×150 mL), dried over $Na_2SO_4$, and the solvent was removed under reduced pressure. The crude product was purified by column chromatography (petroleum ether/EtOAc 1:1). The title compound was obtained as a red solid (24 g, 85%).

Part VI—Synthesis of N-(1-(tert-butyl)-1H-pyrazol-4-yl)-2-(2-fluoro-4-hydroxy-3-methylphenyl)acetamide

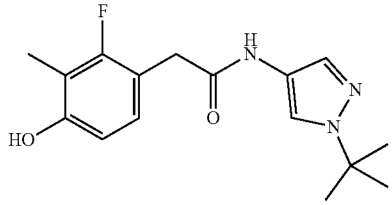 [SMILES: Cc1c(O)ccc(CC(=O)Nc2cnn(C(C)(C)C)c2)c1F]

A solution of 2-(4-bromo-2-fluoro-3-methylphenyl)-N-(1-(tert-butyl)-1H-pyrazol-4-yl)acetamide (24.0 g, 65.2 mmol, 1.00 equiv.), bis(pinacolato)diboron (33.1 g, 130 mmol, 2.00 equiv.), Pd(dppf)$Cl_2$ (4.77 g, 6.52 mmol, 0.10 equiv.), potassium acetate (12.8 g, 130 mmol, 2.00 equiv.) in 1,4-dioxane (240 mL) was heated to 90° C. for 16 h under an inert atmosphere of nitrogen. Subsequently, a solution of hydrogen peroxide (30%, 72 mL, 3.09 mol, 47.5 equiv.) was added dropwise at 0° C. The mixture was stirred at room temperature for 1 h. Water (150 mL) was added, and the product was extracted with EtOAc (3×250 mL). The combined organic phases were washed with brine, dried over $Na_2SO_4$, and the solvent was removed under reduced pressure. The crude product was purified by column chromatography (petroleum ether/EtOAc 2:1). The title compound was obtained as a green solid (17 g, 85%).

Part VII—Synthesis of 4-chloro-6-(cyclopropylthio)quinoline

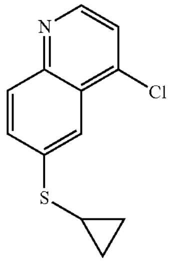 [SMILES: Clc1ccnc2ccc(SC3CC3)cc12]

A solution of 6-bromo-4-chloroquinoline (20.0 g, 82.5 mmol, 1.00 equiv.), sodium cyclopropanethiolate (9.51 g, 99.0 mmol, 1.20 equiv.), Xantphos (9.54 g, 16.5 mmol, 0.20 equiv.), $Pd_2(dba)_3$ (15.1 g, 16.5 mmol, 0.20 equiv.), and triethylamine (41.7 g, 412 mmol, 5.00 equiv.) in 1,4-dioxane (200 mL) was heated to 80° C. for 3 h under an inert atmosphere of nitrogen. Subsequently, the solvent was removed under reduced pressure, and the crude product was purified by column chromatography (petroleum ether/EtOAc 10:1). The title compound was obtained as a yellow oil (11.6 g, 56%).

Part VIII—Synthesis of (4-chloroquinolin-6-yl)(cyclopropyl)(imino)-$\lambda^6$-sulfanone

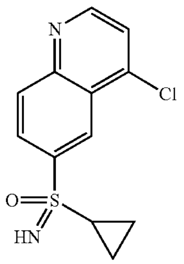 [SMILES: N=S(=O)(c1ccc2nccc(Cl)c2c1)C1CC1]

A solution of 4-chloro-6-(cyclopropylthio)quinoline (3.00 g, 12.7 mmol, 1.00 equiv.), (diacetoxyiodo)benzene (12.3 g, 38.2 mmol, 3.00 equiv.) and $(NH_4)_2CO_3$ (3.67 g, 38.2 mmol, 3.00 equiv.) in methanol (60 mL) was stirred at room temperature for 2 h. Subsequently, water (50 mL) was added, and the product was extracted with EtOAc (3×100 mL). The combined organic phases were washed with brine, dried over $Na_2SO_4$, and the solvent was removed under reduced pressure. The crude product was purified by reversed-phase flash chromatography (column: C18 silica gel; mobile phase A: water, mobile phase B: ACN, gradient: 35-65% B in 30 min; wavelength: 210 nm). The title compound was obtained as a yellow solid (1.7 g, 50%).

Part IX—Synthesis of N-(1-(tert-butyl)-1H-pyrazol-4-yl)-2-(4-((6-(cyclopropanesulfonimidoyl)quinolin-4-yl)oxy)-2-fluoro-3-methylphenyl)acetamide (Compounds 441 and 442)

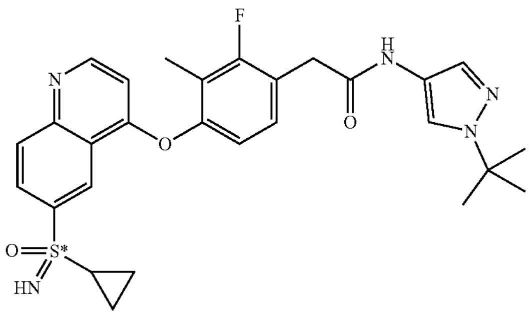

A solution of N-(1-(tert-butyl)-1H-pyrazol-4-yl)-2-(2-fluoro-4-hydroxy-3-methylphenyl)acetamide (572 mg, 1.87 mmol, 1.00 equiv.), (4-chloroquinolin-6-yl)(cyclopropyl)(imino)-$\lambda^6$-sulfanone (500 mg, 1.87 mmol, 1.00 equiv.), $Cs_2CO_3$ (285 mg, 3.75 mmol, 2.00 equiv.), CuI (285 mg, 1.50 mmol, 0.8 equiv.), and N,N-dimethylglycine (116 mg, 1.12 mmol, 0.6 equiv.) in 1,4-dioxane (10 mL) was heated to 100° C. for 16 h under an inert atmosphere of nitrogen. Subsequently, water (10 mL) was added, and the product was extracted with EtOAc (3×10 mL). The combined organic phases were washed with brine, dried over $Na_2SO_4$, and the solvent was removed under reduced pressure. The crude product was purified by reversed-phase flash chromatography (column: C18 silica gel; mobile phase A: water, mobile phase B: ACN, gradient: 25-55% B in 40 min; wavelength: 210 nm). The racemic title compound was obtained as a white solid (350 mg, 35%). The two enantiomers were separated by chiral chromatography (column: CHIRAL ART Cellulose-SC, 20×250 mm, 5 μm; mobile phase A: n-hexane/DCM (3:1), mobile phase B: isopropanol, isocratic separation with 35% B). The title compounds (compound 441 (enantiomer 1): 130.0 mg, 13%; compound 442 (enantiomer 2): 103.2 mg, 10%) were obtained as brown solids (retention time (enantiomer 1): 5.08 min, retention time (enantiomer 2): 6.70 min, column CHIRALPAK IC-3, 4.6×50 nm, 3.5 μm, mobile phase A: hexane/DCM (3:1, 0.1% DEA), mobile phase B: isopropanol, isocratic separation with 50% B, flow rate: 1.0 mL/min, wavelength: 254 nm). LCMS (ESI) calculated for $C_{28}H_{31}FN_5O_3S$ $(M+H)^+$: 536.2, found: 536.1. $^1H$ NMR (300 MHz, DMSO-$d_6$) δ 10.23 (s, 1H), 8.92-8.80 (m, 2H), 8.25-8.23 (m, 2H), 7.95 (s, 1H), 7.46 (s, 1H), 7.40 (t, J=8.4 Hz, 1H), 7.15 (d, J=8.4 Hz, 1H), 6.62 (d, J=5.2 Hz, 1H), 4.54 (s, 1H), 3.72 (s, 2H), 2.90-2.79 (m, 1H), 2.08 (s, 3H), 1.49 (s, 9H), 1.28-0.90 (m, 4H).

Example 7—Synthesis of N-(1-(tert-butyl)-1H-pyrazol-4-yl)-2-(2-fluoro-4-((6-(1-oxido-3,4,5,6-tetrahydro-1λ$^6$,2-thiazin-1-yl)quinolin-4-yl)oxy)phenyl) acetamide (Compound 67); Prepared According to General Scheme 20

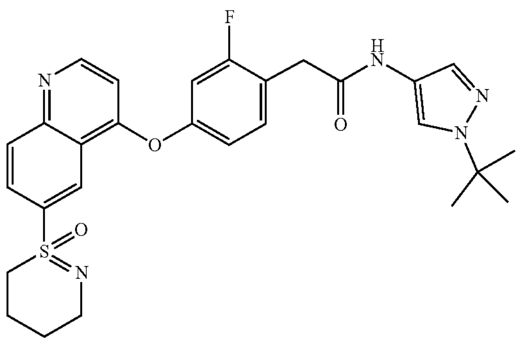 [SMILES: CC(C)(C)n1cc(NC(=O)Cc2ccc(Oc3ccnc4ccc(S5(=O)=NCCCC5)cc34)cc2F)cn1]

Part I—Synthesis of S-(4-(4-(2-((1-(tert-butyl)-1H-pyrazol-4-yl)amino)-2-oxoethyl)-3-fluorophenoxy) quinolin-6-yl) ethanethioate

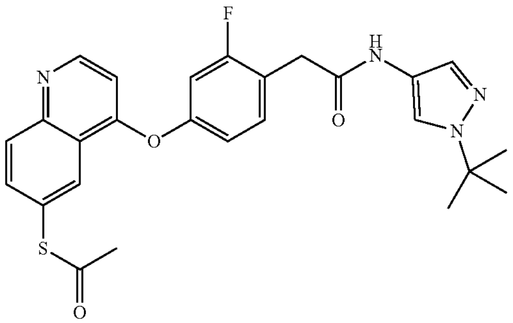 [SMILES: CC(=O)Sc1ccc2nccc(Oc3ccc(CC(=O)Nc4cnn(C(C)(C)C)c4)c(F)c3)c2c1]

A solution of 2-(4-((6-bromoquinolin-4-yl)oxy)-2-fluorophenyl)-N-(1-(tert-butyl)-1H-pyrazol-4-yl)acetamide (1.40 g, 2.82 mmol, 1.00 equiv.), potassium thioacetate (643 mg, 5.63 mmol, 2.00 equiv.), $Pd_2(dba)_3$ (129 mg, 0.141 mmol, 0.05 equiv.), Xantphos (163 mg, 0.282 mmol, 0.10 equiv.), and DIPEA (2.91 g, 22.5 mmol, 8.00 equiv.) in 1,4-dioxane (10 mL) was heated to 120° C. for 15 min under an inert atmosphere of nitrogen. Subsequently, the crude product was purified by column chromatography (petroleum ether/EtOAc 5:1). The title compound was obtained as a yellow solid (1.33 g, 96%).

Part II—Synthesis of N-(1-(tert-butyl)-1H-pyrazol-4-yl)-2-(2-fluoro-4-((6-((4-iodobutyl)thio)quinolin-4-yl)oxy)phenyl)acetamide

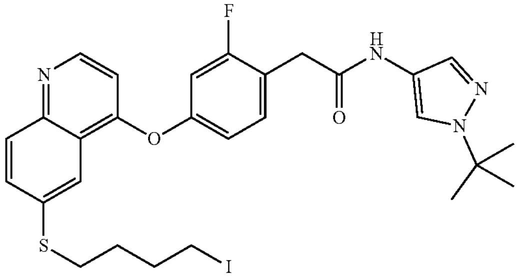 [SMILES: CC(C)(C)n1cc(NC(=O)Cc2ccc(Oc3ccnc4ccc(SCCCCI)cc34)cc2F)cn1]

1,4-Diiodobutane (629 mg, 2.03 mmol, 2.00 equiv.) and $K_2CO_3$ (302 mg, 3.05 mmol, 3.00 equiv.) were added to a solution of S-(4-(4-(2-((1-(tert-butyl)-1H-pyrazol-4-yl)amino)-2-oxoethyl)-3-fluorophenoxy)quinolin-6-yl) ethanethioate (500.0 mg, 1.02 mmol, 1.00 equiv.) in DMF (10 mL) and the mixture was stirred at room temperature for 30 min. Subsequently, water was added, and the product was extracted with EtOAc (2×20 mL). The combined organic phases were dried over $MgSO_4$, and the solvent was removed under reduced pressure. The crude product was purified by column chromatography (petroleum ether/EtOAc 1:1). The title compound was obtained as a light-yellow solid (405 mg, 63%).

Part III—Synthesis of N-(1-(tert-butyl)-1H-pyrazol-4-yl)-2-(2-fluoro-4-((6-(1-oxido-3,4,5,6-tetrahydro-1λ$^6$,2-thiazin-1-yl)quinolin-4-yl)oxy)phenyl)acetamide (Compound 67)

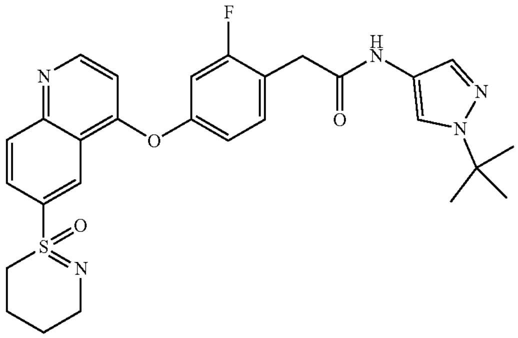 [SMILES: CC(C)(C)n1cc(NC(=O)Cc2ccc(Oc3ccnc4ccc(S5(=O)=NCCCC5)cc34)cc2F)cn1]

(Diacetoxyiodo)benzene (764 mg, 2.37 mmol, 5.00 equiv.) and $(NH_4)_2CO_3$ (137 mg, 1.42 mmol, 3.00 equiv.) were added to a solution of N-(1-(tert-butyl)-1H-pyrazol-4-yl)-2-(2-fluoro-4-((6-((4-iodobutyl)thio)quinolin-4-yl)oxy) phenyl)acetamide (300 mg, 0.474 mmol, 1.00 equiv.) in MeOH (3 mL) and the mixture was stirred overnight at room temperature. Subsequently, the crude product was purified by reversed-phase flash chromatography (column: C18 silica gel; mobile phase A: water, mobile phase B: ACN, gradient: 20-50% B in 30 min; wavelength: 210 nm). The title compound was obtained as a white solid (12.1 mg, 4.5%). LCMS (ESI) calculated for $C_{28}H_{31}FN_5O_3S$ $(M+H)^+$: 536.2, found: 536.2. $^1$H NMR (300 MHz, DMSO-$d_6$) δ 10.22 (s, 1H), 8.94-8.85 (m, 2H), 8.35-8.19 (m, 2H), 7.94 (s, 1H), 7.56 (t, J=8.5 Hz, 1H), 7.45 (s, 1H), 7.38 (dd, J=10.5, 2.1 Hz, 1H), 7.21 (dd, J=7.6, 2.2 Hz, 1H), 6.81 (d, J=5.2 Hz, 1H), 3.72 (s, 2H), 3.54-3.39 (m, 2H), 3.29-3.16 (m, 2H), 2.34-2.24 (m, 1H), 2.23-2.12 (m, 1H), 1.79-1.62 (m, 2H), 1.49 (s, 9H).

Example 8—Preparation of Additional Sulfoximine Compounds

Compounds in the table below were prepared based on experimental procedures described in Examples 3, 4 and 5 and the detailed description.

| No. | Structure | Name | $^1$H NMR | Observed m/z |
|---|---|---|---|---|
| 43 | 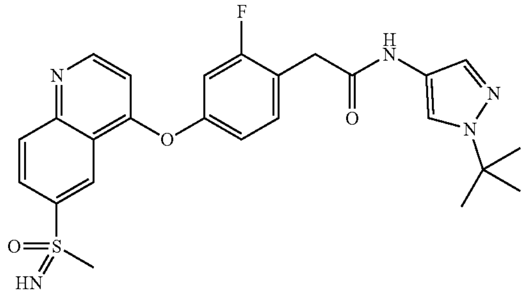 [SMILES: CC(C)(C)n1cc(NC(=O)Cc2ccc(Oc3ccnc4ccc(S(C)(=N)=O)cc34)cc2F)cn1] | N-(1-(tert-butyl)-1H-pyrazol-4-yl)-2-(2-fluoro-4-((6-(S-methylsulfonimidoyl) quinolin-4-yl)oxy) phenyl)acetamide | (300 MHz, DMSO-$d_6$) δ 10.23 (s, 1H), 8.93-8.83 (m, 2H), 8.34-8.18 (m, 2H), 7.94 (s, 1H), 7.57 (t, J = 8.5 Hz, 1H), 7.45 (s, 1H), 7.36 (dd, J = 10.4, 2.4 Hz, 1H), 7.26-7.15 (m, 1H), 6.81 (d, J = 5.2 Hz, 1H), 4.49 (s, 1H), 3.72 (s, 2H), 3.20 (s, 3H), 1.49 (s, 9H) | 496.1 $(M + H)^+$ |
| 65 | 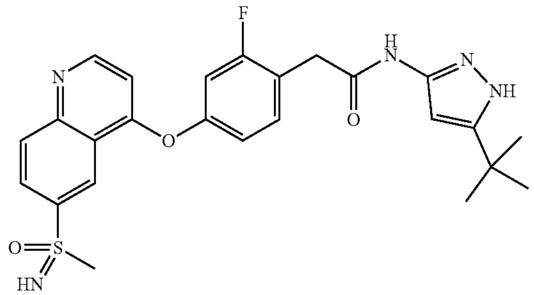 [SMILES: CC(C)(C)c1cc(NC(=O)Cc2ccc(Oc3ccnc4ccc(S(C)(=N)=O)cc34)cc2F)n[nH]1] | N-(5-(tert-butyl)-1H-pyrazol-3-yl)-2-(2-fluoro-4-((6-(S-methylsulfonimidoyl) quinolin-4-yl)oxy)phenyl) acetamide | (300 MHz, DMSO-$d_6$) δ 12.06 (s, 1H), 10.61 (s, 1H), 8.90-8.79 (m, 2H), 8.34-8.15 (m, 2H), 7.56 (t, J = 8.5 Hz, 1H), 7.35 (dd, J = 10.4, 2.4 Hz, 1H), 7.19 (dd, J = 8.6, 2.2 Hz, 1H), 6.81 (d, J = 5.2 Hz, 1H), 6.28 (s, 1H), 4.49 (s, 1H), 3.74 (s, 2H), 3.20 (s, 3H), 1.25 (s, 9H) | 496.1 |
| 66 | 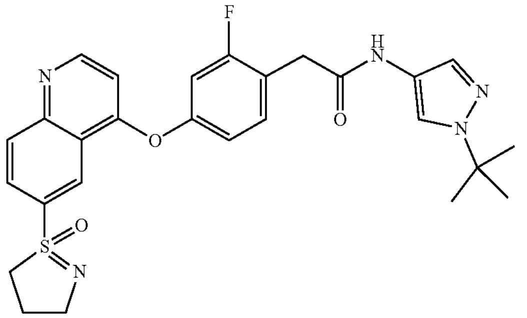 [SMILES: CC(C)(C)n1cc(NC(=O)Cc2ccc(Oc3ccnc4ccc(S5(=O)=NCCC5)cc34)cc2F)cn1] | N-(1-(tert-butyl)-1H-pyrazol-4-yl)-2-(2-fluoro-4-((6-(1-oxido-4,5-dihydro-3H-1λ$^6$-isothiazol-1-yl)quinolin-4-yl)oxy)phenyl) acetamide | (400 MHz, DMSO-$d_6$) δ 10.24 (s, 1H), 8.90 (d, J = 5.2 Hz, 1H), 8.83 (d, J = 2.2 Hz, 1H), 8.24 (d, J = 8.9 Hz, 1H), 8.15 (dd, J = 9.0, 2.1 Hz, 1H), 7.95 (s, 1H), 7.57 (t, J = 8.5 Hz, 1H), 7.46 (s, 1H), 7.38 (dd, J = 10.4, 2.4 Hz, 1H), 7.22 (dd, J = 8.3, 2.5 Hz, 1H), 6.82 (d, J = 5.2 Hz, 1H), 3.88 (dd, J = 10.9, 5.6 Hz, 1H), 3.78-3.74 (m, 1H), 3.73 (d, J = 3.6 Hz, 2H), 3.57-3.49 (m, 2H), 2.34-2.28 (m, 2H), 1.49 (s, 9H) | 522.1 $(M + H)^+$ |

-continued

| No. | Structure | Name | $^1H$ NMR | Observed m/z |
|---|---|---|---|---|
| 72 | 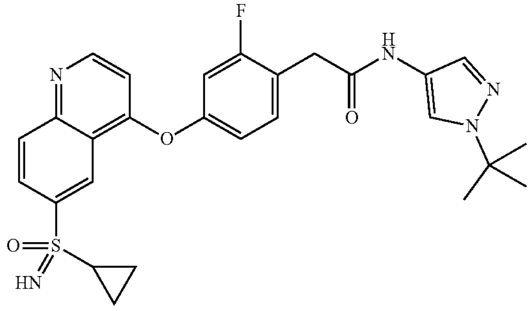 [SMILES: CC(C)(C)n1cc(NC(=O)Cc2ccc(Oc3ccnc4ccc(S(=N)(=O)C5CC5)cc34)cc2F)cn1] | N-(1-(tert-butyl)-1H-pyrazol-4-yl)-2-(4-((6-(cyclopropanesulfonimidoyl)quinolin-4-yl)oxy)-2-fluorophenyl)acetamide | (400 MHz, DMSO-$d_6$) δ 10.24 (s, 1H), 8.87 (d, J = 5.2 Hz, 1H), 8.82 (s, 1H), 8.24-8.22 (m, 2H), 7.94 (s, 1H), 7.56 (t, J = 8.5 Hz, 1H), 7.45 (s, 1H), 7.36 (dd, J = 10.5, 2.4 Hz, 1H), 7.20 (dd, J = 8.4, 2.4 Hz, 1H), 6.81 (d, J = 5.3 Hz, 1H), 4.52 (s, 1H), 3.71 (s, 2H), 2.82 (ddd, J = 12.6, 8.1, 4.7 Hz, 1H), 1.49 (s, 9H), 1.18 (dt, J = 14.1, 4.7 Hz, 1H), 1.08-1.00 (m, 1H), 1.00-0.89 (m, 2H) | 522.1 $(M + H)^+$ |
| 73 | 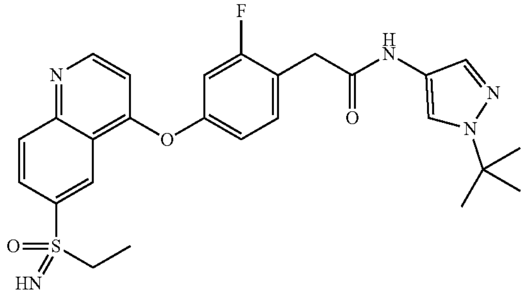 [SMILES: CCS(=N)(=O)c1ccc2nccc(Oc3ccc(CC(=O)Nc4cnn(C(C)(C)C)c4)c(F)c3)c2c1] | N-(1-(tert-butyl)-1H-pyrazol-4-yl)-2-(4-((6-(ethylsulfonimidoyl)quinolin-4-yl)oxy)-2-fluorophenyl)acetamide | (400 MHz, DMSO-$d_6$) δ 10.24 (s, 1H), 8.88 (d, J = 5.2 Hz, 1H), 8.82 (t, J = 1.4 Hz, 1H), 8.22 (d, J = 1.3 Hz, 2H), 7.94 (s, 1H), 7.56 (t, J = 8.5 Hz, 1H), 7.46 (s, 1H), 7.36 (dd, J = 10.4, 2.4 Hz, 1H), 7.20 (dd, J = 8.4, 2.4 Hz, 1H), 6.81 (d, J = 5.2 Hz, 1H), 4.48 (s, 1H), 3.72 (s, 2H), 3.27 (q, J = 7.4 Hz, 2H), 1.49 (s, 9H), 1.11 (t, J = 7.3 Hz, 3H) | 510.0 $(M + H)^+$ |
| 76 | 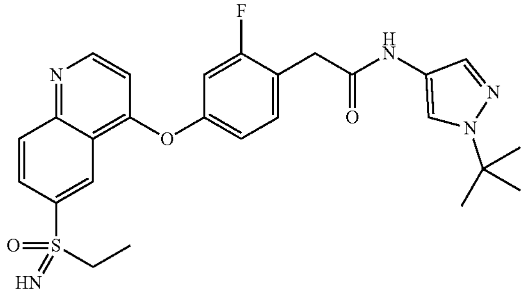 [SMILES: CCS(=N)(=O)c1ccc2nccc(Oc3ccc(CC(=O)Nc4cnn(C(C)(C)C)c4)c(F)c3)c2c1] | N-(1-(tert-butyl)-1H-pyrazol-4-yl)-2-(3-methyl-4-((6-(S-methylsulfonimidoyl)quinolin-4-yl)oxy)phenyl)acetamide | (400 MHz, DMSO-$d_6$) δ 10.20 (s, 1H), 8.93 (d, J = 2.1 Hz, 1H), 8.80 (d, J = 5.2 Hz, 1H), 8.31-8.16 (m, 2H), 7.95 (s, 1H), 7.46 (s, 1H), 7.39 (d, J = 2.1 Hz, 1H), 7.31 (dd, J = 8.2, 2.2 Hz, 1H), 7.22 (d, J = 8.2 Hz, 1H), 6.52 (d, J = 5.2 Hz, 1H), 4.49 (s, 1H), 3.61 (s, 2H), 3.21 (s, 3H), 2.13 (s, 3H), 1.49 (s, 9H) | 492.2 $(M + H)^+$ |
| 77 | 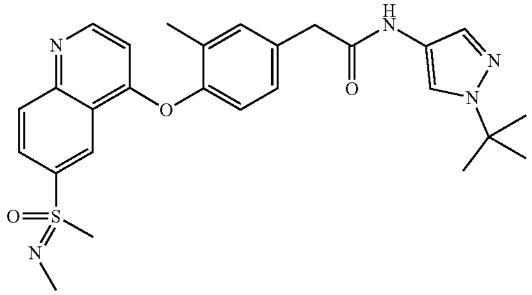 [SMILES: CN=S(C)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(4-((6-(N,S-dimethylsulfonimidoyl)quinolin-4-yl)oxy)-3-methylphenyl)acetamide | (400 MHz, DMSO-$d_6$) δ 10.23 (s, 1H), 8.90-8.77 (m, 2H), 8.29-8.10 (m, 2H), 7.95 (s, 1H), 7.46 (s, 1H), 7.39 (s, 1H), 7.34-7.20 (m, 2H), 6.53 (d, J = 5.2 Hz, 1H), 3.62 (s, 2H), 3.28 (s, 3H), 2.14 (s, 3H), 1.49 (s, 9H) | 506.2 $(M + H)^+$ |
| 88 | 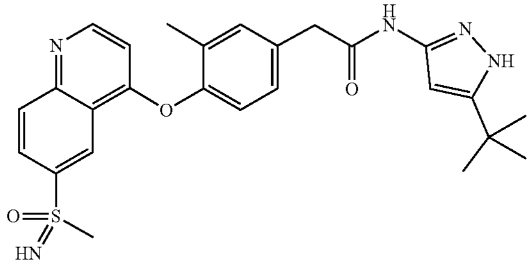 [SMILES: Cc1cc(CC(=O)Nc2cc(C(C)(C)C)[nH]n2)ccc1Oc1ccnc2ccc(S(C)(=N)=O)cc12] | N-(5-(tert-butyl)-1H-pyrazol-3-yl)-2-(3-methyl-4-((6-(S-methylsulfonimidoyl)quinolin-4-yl)oxy)phenyl)acetamide | (400 MHz, DMSO-$d_6$) δ 10.56 (s, 1H), 8.96 (d, J = 2.1 Hz, 1H), 8.82 (d, J = 5.2 Hz, 1H), 8.33-8.21 (m, 2H), 7.41 (d, J = 2.2 Hz, 1H), 7.35-7.31 (m, 1H), 7.22 (d, J = 8.2 Hz, 1H), 6.56 (d, J = 5.3 Hz, 1H), 6.29 (s, 1H), 3.64 (s, 2H), 3.30 (s, 3H), 2.13 (s, 3H), 1.24 (s, 9H) | 492.2 $(M + H)^+$ |

-continued

| No. | Structure | Name | $^1$H NMR | Observed m/z |
|---|---|---|---|---|
| 90 | 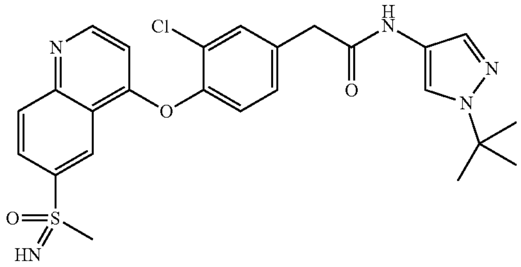 [SMILES: CC(C)(C)n1cc(NC(=O)Cc2ccc(Oc3ccnc4ccc(S(C)(=N)=O)cc34)c(Cl)c2)cn1] | N-(1-(tert-butyl)-1H-pyrazol-4-yl)-2-(3-chloro-4-((6-(S-methylsulfonimidoyl) quinolin-4-yl)oxy) phenyl)acetamide | (300 MHz, DMSO-$d_6$) δ 10.26 (s, 1H), 8.91 (s, 1H), 8.84 (d, J = 5.2 Hz, 1H), 8.32-8.22 (m, 2H), 7.96 (s, 1H), 7.69 (s, 1H), 7.57-7.41 (m, 3H), 6.61 (d, J = 5.2 Hz, 1H), 4.52 (s, 1H), 3.70 (s, 2H), 3.22 (s, 3H), 1.49 (s, 9H) | 512.1 $(M + H)^+$ |
| 196 | 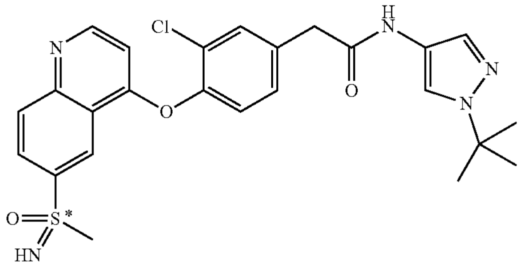 [SMILES: CC(C)(C)n1cc(NC(=O)Cc2ccc(Oc3ccnc4ccc(S(C)(=N)=O)cc34)c(Cl)c2)cn1] enantiomer 1 (retention time: 1.02 min, column: (S,S) Whelk-O1, 4.6 × 50 mm, 3.5 μm; mobile phase A: supercritical $CO_2$, mobile phase B: isopropanol (0.1% DEA), isocratic separation with 50% B, flow rate: 4.0 mL/min, wavelength: 220 nm) | N-(1-(tert-butyl)-1H-pyrazol-4-yl)-2-(3-chloro-4-((6-(S-methylsulfonimidoyl) quinolin-4-yl)oxy) phenyl)acetamide | (300 MHz, DMSO-$d_6$) δ 10.25 (s, 1H), 8.91 (d, J = 2.0 Hz, 1H), 8.84 (d, J = 5.2 Hz, 1H), 8.35-8.19 (m, 2H), 7.96 (s, 1H), 7.69 (d, J = 1.9 Hz, 1H), 7.57-7.39 (m, 3H), 6.61 (d, J = 5.2 Hz, 1H), 4.52 (s, 1H), 3.70 (s, 2H), 3.22 (s, 3H), 1.49 (s, 9H) | 512.1 $(M + H)^+$ |
| 197 | 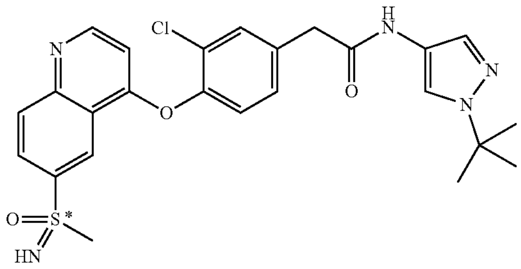 [SMILES: CC(C)(C)n1cc(NC(=O)Cc2ccc(Oc3ccnc4ccc(S(C)(=N)=O)cc34)c(Cl)c2)cn1] enantiomer 2 (retention time: 1.20 min, column: (S,S) Whelk-O1, 4.6 × 50 mm, 3.5 μm; mobile phase A: supercritical $CO_2$, mobile phase B: isopropanol (0.1% DEA), isocratic separation with 50% B, flow rate: 4.0 mL/min, wavelength: 220 nm) | N-(1-(tert-butyl)-1H-pyrazol-4-yl)-2-(3-chloro-4-((6-(S-methylsulfonimidoyl) quinolin-4-yl)oxy) phenyl)acetamide | (300 MHz, DMSO-$d_6$) δ 10.25 (s, 1H), 8.91 (d, J = 2.0 Hz, 1H), 8.85 (d, J = 5.2 Hz, 1H), 8.33-8.18 (m, 2H), 7.96 (s, 1H), 7.69 (d, J = 1.9 Hz, 1H), 7.56-7.42 (m, 3H), 6.61 (d, J = 5.2 Hz, 1H), 4.52 (s, 1H), 3.70 (s, 2H), 3.22 (s, 3H), 1.49 (s, 9H) | 534.1 $(M + Na)^+$ |

-continued

| No. | Structure | Name | $^1H$ NMR | Observed m/z |
|---|---|---|---|---|
| 466 | 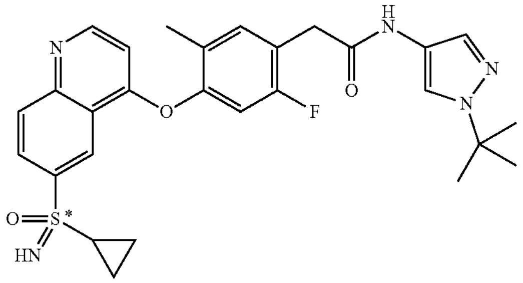 [SMILES: Cc1cc(CC(=O)Nc2cnn(C(C)(C)C)c2)c(F)cc1Oc1ccnc2ccc(S(=N)(=O)C3CC3)cc12] enantiomer 1 (retention time: 3.87 min, column: CHIRALPAK AD-3, 3.0 × 100 mm, 3 μm; mobile phase A: supercritical $CO_2$, mobile phase B: MeOH (20 mM ammonia), gradient: 10-50% B in 4 min, then hold at 50% B for 2 min, flow rate: 2.0 mL/min, wavelength: 220 nm) | N-(1-(tert-butyl)-1H-pyrazol-4-yl)-2-(4-((6-(cyclopropane-sulfonimidoyl) quinolin-4-yl)oxy)-2-fluoro-5-methylphenyl) acetamide | (300 MHz, DMSO-$d_6$) δ 10.22 (s, 1H), 8.91-8.82 (m, 2H), 8.24-8.23 (m, 2H), 7.95 (d, J = 0.8 Hz, 1H), 7.52-7.44 (m, 2H), 7.30 (d, J = 10.0 Hz, 1H), 6.62 (d, J = 5.2 Hz, 1H), 4.54 (s, 1H), 3.69 (s, 2H), 2.80-2.90 (m, 1H), 2.11 (s, 3H), 1.49 (s, 9H), 1.25-1.15 (m, 1H), 1.15-1.00 (m, 1H), 1.00-0.90 (m, 2H) | 536.2 $(M + H)^+$ |
| 467 | 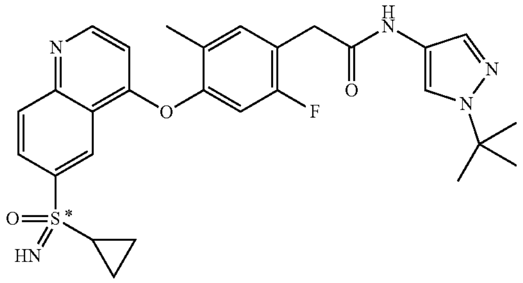 [SMILES: Cc1cc(CC(=O)Nc2cnn(C(C)(C)C)c2)c(F)cc1Oc1ccnc2ccc(S(=N)(=O)C3CC3)cc12] enantiomer 2 (retention time: 4.89 min, column: CHIRALPAK AD-3, 3.0 × 100 mm, 3 μm; mobile phase A: supercritical $CO_2$, mobile phase B: MeOH (20 mM ammonia), gradient: 10-50% B in 4 min, then hold at 50% B for 2 min, flow rate: 2.0 mL/min, wavelength: 220 nm) | N-(1-(tert-butyl)-1H-pyrazol-4-yl)-2-(4-((6-(cyclopropane-sulfonimidoyl) quinolin-4-yl)oxy)-2-fluoro-5-methylphenyl) acetamide | (300 MHz, DMSO-$d_6$) δ 10.21 (s, 1H), 8.96-8.80 (m, 2H), 8.31-8.16 (m, 2H), 7.94 (d, J = 0.7 Hz, 1H), 7.52-7.42 (m, 2H), 7.29 (d, J = 10.0 Hz, 1H), 6.62 (d, J = 5.2 Hz, 1H), 4.52 (s, 1H), 3.69 (s, 2H), 2.84 (t, J = 8.2 Hz, 1H), 2.11 (s, 3H), 1.49 (s, 9H), 1.30-1.13 (m, 1H), 1.15-1.00 (m, 1H), 1.00-0.90 (m, 2H) | 536.2 $(M + H)^+$ |

-continued

| No. | Structure | Name | $^1$H NMR | Observed m/z |
|---|---|---|---|---|
| 593 | 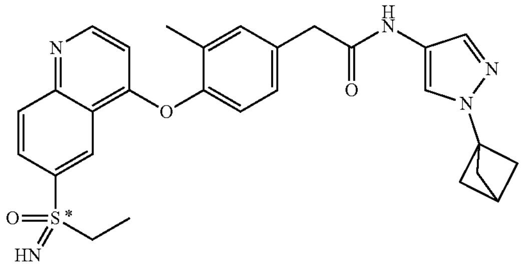 [SMILES: CCS(=N)(=O)c1ccc2nccc(Oc3ccc(CC(=O)Nc4cnn(C56CC(C5)C6)c4)cc3C)c2c1] enantiomer 2 (retention time: 3.93 min; column: CHIRAL Cellulose-SB, 4.6 × 100 mm, 3 μm; mobile phase A: MTBE (0.1% DEA), mobile phase B: EtOH, isocratic separation with 20% B, flow rate: 1.0 mL/min, wavelength: 254 nm) | N-(1-(bicyclo[1.1.1]pentan-1-yl)-1H-pyrazol-4-yl)-2-(4-((6-(ethylsulfonimidoyl)quinolin-4-yl)oxy)-3-methylphenyl)acetamide | (300 MHz, DMSO-$d_6$) δ 10.29 (s, 1H), 8.90-8.88 (m, 1H), 8.81 (d, J = 5.2 Hz, 1H), 8.23-8.21 (m, 2H), 7.91 (s, 1H), 7.47 (s, 1H), 7.39 (d, J = 2.1 Hz, 1H), 7.31 (dd, J = 8.3, 2.1 Hz, 1H), 7.24 (d, J = 8.2 Hz, 1H), 6.52 (d, J = 5.2 Hz, 1H), 4.50 (s, 1H), 3.63 (s, 2H), 3.28 (q, J = 7.4 Hz, 2H), 2.59 (s, 1H), 2.20 (s, 6H), 2.13 (s, 3H), 1.13 (t, J = 7.3 Hz, 3H) | 516.2 $(M + H)^+$ |
| 620 | 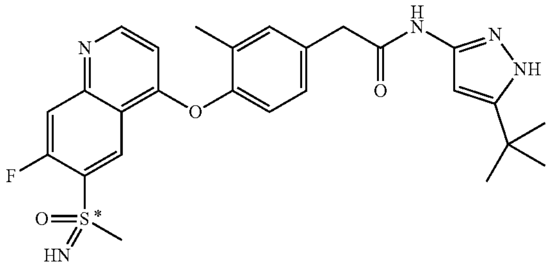 [SMILES: Cc1cc(CC(=O)Nc2cc(C(C)(C)C)[nH]n2)ccc1Oc1ccnc2cc(F)c(S(C)(=N)=O)cc12] enantiomer 1 (retention time: 1.64 min; column: CHIRALPAK IC-3, 4.6 × 50 mm, 3 μm; mobile phase A: hexane/DCM (1:1, 0.1% DEA), mobile phase B: isopropanol, isocratic separation with 30% B, flow rate: 1.0 mL/min, wavelength: 254 nm) | N-(5-(tert-butyl)-1H-pyrazol-3-yl)-2-(4-((7-fluoro-6-(S-methylsulfonimidoyl)quinolin-4-yl)oxy)-3-methylphenyl)acetamide | (300 MHz, DMSO-$d_6$) δ 12.06 (s, 1H), 10.59 (s, 1H), 8.92 (d, J = 7.9 Hz, 1H), 8.79 (d, J = 5.3 Hz, 1H), 8.00 (d, J = 11.4 Hz, 1H), 7.41 (s, 1H), 7.38-7.29 (m, 1H), 7.21 (d, J = 8.2 Hz, 1H), 6.50 (d, J = 5.3 Hz, 1H), 6.30 (s, 1H), 5.03 (s, 1H), 3.64 (s, 2H), 3.31 (d, J = 1.3 Hz, 3H), 2.13 (s, 3H), 1.25 (s, 9H) | 510.2 $(M + H)^+$ |

-continued

| No. | Structure | Name | $^1$H NMR | Observed m/z |
|---|---|---|---|---|
| 621 | 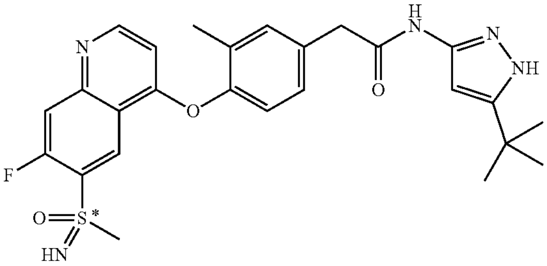 [SMILES: Cc1cc(CC(=O)Nc2cc(C(C)(C)C)[nH]n2)ccc1Oc1ccnc2cc(F)c(S(C)(=N)=O)cc12] enantiomer 2 (retention time: 2.19 min; column: CHIRALPAK IC-3, 4.6 × 50 mm, 3 μm; mobile phase A: hexane/DCM (1:1, 0.1% DEA), mobile phase B: isopropanol, isocratic separation with 30% B, flow rate: 1.0 mL/min, wavelength: 254 nm) | N-(5-(tert-butyl)-1H-pyrazol-3-yl)-2-(4-((7-fluoro-6-(S-methylsulfonimidoyl) quinolin-4-yl)oxy)-3-methylphenyl) acetamide | (300 MHz, DMSO-$d_6$) δ 12.06 (s, 1H), 10.59 (s, 1H), 8.92 (d, J = 7.9 Hz, 1H), 8.79 (d, J = 5.3 Hz, 1H), 8.00 (d, J = 11.4 Hz, 1H), 7.41 (s, 1H), 7.38-7.29 (m, 1H), 7.21 (d, J = 8.2 Hz, 1H), 6.50 (d, J = 5.3 Hz, 1H), 6.30 (s, 1H), 5.03 (s, 1H), 3.64 (s, 2H), 3.31 (d, J = 1.3 Hz, 3H), 2.13 (s, 3H), 1.25 (s, 9H) | 510.2 $(M + H)^+$ |
| 527 | 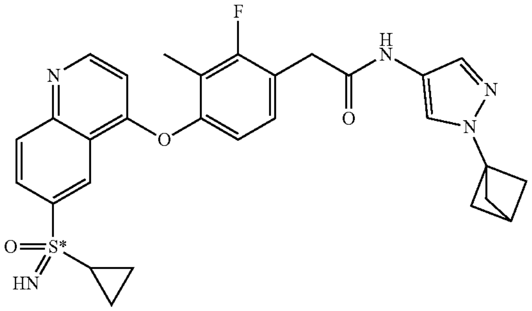 enantiomer 1 (retention time: 3.93 min, column: CHIRALPAK IC-3, 4.6 × 50 mm, 3 μm; mobile phase A: hexane/DCM (1:1, 0.1% DEA), mobile phase B: EtOH, isocratic separation with 50% B, flow rate: 1.0 mL/min, wavelength: 254 nm) | N-(1-bicyclo[1.1.1] pentan-1-yl)-1H-pyrazol-4-yl)-2-(4-((6-(cyclopropanesulfonimidoyl) quinolin-4-yl)oxy)-2-fluoro-3-methylphenyl) acetamide | (400 MHz, DMSO-$d_6$) δ 10.32 (s, 1H), 8.88 (s, 1H), 8.84 (d, J = 5.1 Hz, 1H), 8.29-8.19 (m, 2H), 7.90 (s, 1H), 7.46 (s, 1H), 7.39 (t, J = 8.4 Hz, 1H), 7.16 (d, J = 8.4 Hz, 1H), 6.61 (d, J = 5.2 Hz, 1H), 4.55 (s, 1H), 3.73 (s, 2H), 2.85 (td, J = 7.8, 4.0 Hz, 1H), 2.60 (s, 1H), 2.20 (s, 6H), 2.07 (s, 3H), 1.20-1.18 (m, 1H), 1.10-1.06 (m, 1H), 1.04-0.93 (m, 2H) | 546.1 $(M + H)^+$ |

-continued

| No. | Structure | Name | $^1H$ NMR | Observed m/z |
|---|---|---|---|---|
| 528 | 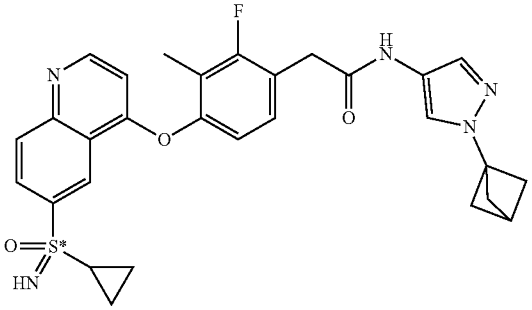 enantiomer 2 (retention time: 5.11 min, column: CHIRALPAK IC-3, 4.6 × 50 mm, 3 μm; mobile phase A: hexane/DCM (1:1, 0.1% DEA), mobile phase B: EtOH, isocratic separation with 50% B, flow rate: 1.0 mL/min, wavelength: 254 nm) | N-(1-(bicyclo[1.1.1]pentan-1-yl)-1H-pyrazol-4-yl)-2-(4-((6-(cyclopropanesulfonimidoyl)quinolin-4-yl)oxy)-2-fluoro-3-methylphenyl)acetamide | (400 MHz, DMSO-$d_6$) δ 10.32 (s, 1H), 8.88 (s, 1H), 8.84 (d, J = 5.1 Hz, 1H), 8.29-8.19 (m, 2H), 7.90 (s, 1H), 7.46 (s, 1H), 7.39 (t, J = 8.4 Hz, 1H), 7.16 (d, J = 8.4 Hz, 1H), 6.61 (d, J = 5.2 Hz, 1H), 4.55 (s, 1H), 3.73 (s, 2H), 2.85 (td, J = 7.8, 4.0 Hz, 1H), 2.60 (s, 1H), 2.20 (s, 6H), 2.07 (s, 3H), 1.20-1.18 (m, 1H), 1.10-1.06 (m, 1H), 1.04-0.93 (m, 2H) | 546.1 $(M + H)^+$ |
| 529 | 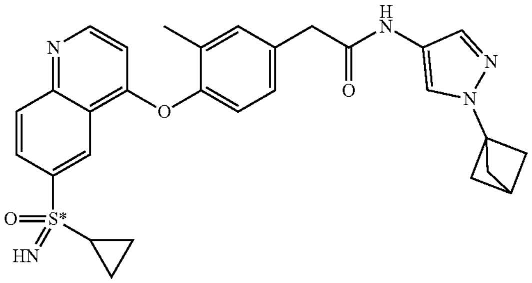 enantiomer 1 (retention time: 1.24 min, column: Lux Cellulose-4, 4.6 × 50 mm, 3 μm; mobile phase A: supercritical $CO_2$, mobile phase B: EtOH/ACN (1:1, 0.1% DEA), isocratic separation with 50% B, flow rate: 4.0 mL/min, wavelength: 220 nm) | N-(1-(bicyclo[1.1.1]pentan-1-yl)-1H-pyrazol-4-yl)-2-(4-((6-(cyclopropanesulfonimidoyl)quinolin-4-yl)oxy)-3-methylphenyl)acetamide | (300 MHz, DMSO-$d_6$) δ 10.29 (s, 1H), 8.89 (d, J= 1.8 Hz, 1H), 8.80 (d, J= 5.2 Hz, 1H), 8.29-8.16 (m, 2H), 7.91 (s, 1H), 7.46 (s, 1H), 7.39 (d, J = 2.1 Hz, 1H), 7.36-7.27 (m, 1H), 7.24 (d, J = 8.3 Hz, 1H), 6.52 (d, J = 5.2 Hz, 1H), 4.54 (s, 1H), 3.63 (s, 2H), 2.90-2.79 (m, 1H), 2.60 (s, 1H), 2.20 (s, 6H), 2.13 (s, 3H), 1.23-1.05 (m, 2H), 1.01-0.92 (m, 2H) | 528.2 $(M + H)^+$ |

-continued

| No. | Structure | Name | $^1$H NMR | Observed m/z |
|---|---|---|---|---|
| 530 | 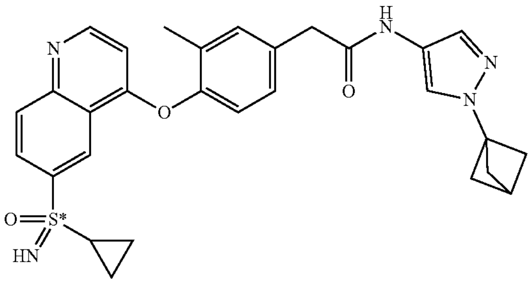 enantiomer 2 (retention time: 1.72 min, column: Lux Cellulose-4, 4.6 x 50 mm, 3 μm; mobile phase A: supercritical $CO_2$, mobile phase B: EtOH/ACN (1:1, 0.1% DEA), isocratic separation with 50% B, flow rate: 4.0 mL/min, wavelength: 220 nm) | N-(1-(bicyclo[1.1.1]pentan-1-yl)-1H-pyrazol-4-yl)-2-(4-((6-(cyclopropanesulfonimidoyl)quinolin-4-yl)oxy)-3-methylphenyl)acetamide | (300 MHz, DMSO-$d_6$) δ 10.29 (s, 1H), 8.89 (d, J = 1.8 Hz, 1H), 8.80 (d, J = 5.2 Hz, 1H), 8.29-8.16 (m, 2H), 7.91 (s, 1H), 7.46 (s, 1H), 7.39 (d, J = 2.1 Hz, 1H), 7.36-7.27 (m, 1H), 7.24 (d, J = 8.3 Hz, 1H), 6.52 (d, J = 5.2 Hz, 1H), 4.54 (s, 1H), 3.63 (s, 2H), 2.90-2.79 (m, 1H), 2.60 (s, 1H), 2.20 (s, 6H), 2.13 (s, 3H), 1.23-1.05 (m, 2H), 1.01-0.92 (m, 2H) | 528.2 $(M + H)^+$ |
| 531 | 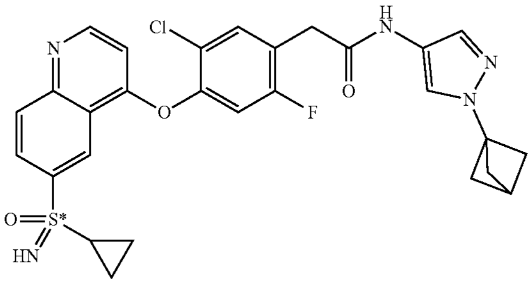 enantiomer 1 (retention time: 3.01 min, column: CHIRALPAK IA-3, 4.6 x 50 mm, 3 μm; mobile phase A: hexane (0.1% DEA), mobile phase B: isopropanol, isocratic separation with 30% B, flow rate: 1.0 mL/min, wavelength: 254 nm) | N-(1-(bicyclo[1.1.1]pentan-1-yl)-1H-pyrazol-4-yl)-2-(5-chloro-4-((6-(cyclopropanesulfonimidoyl)quinolin-4-yl)oxy)-2-fluorophenyl)acetamide | (400 MHz, DMSO-$d_6$) δ 10.33 (s, 1H), 8.91-8.82 (m, 2H), 8.28-8.23 (m, 2H), 7.90 (s, 1H), 7.82 (d, J = 7.4 Hz, 1H), 7.66 (d, J = 9.7 Hz, 1H), 7.47 (s, 1H), 6.73 (d, J = 5.2 Hz, 1H), 4.57 (s, 1H), 3.78 (s, 2H), 2.84 (tt, J = 8.3, 4.6 Hz, 1H), 2.61 (s, 1H), 2.20 (s, 6H), 1.26-1.14 (m, 1H), 1.12-0.91 (m, 3H) | 566.0 $(M + H)^+$ |

-continued

| No. | Structure | Name | $^1$H NMR | Observed m/z |
|---|---|---|---|---|
| 532 | 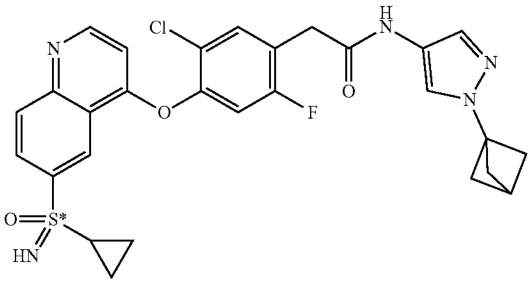 enantiomer 2 (retention time: 3.88 min, column: CHIRALPAK IA-3, 4.6 × 50 mm, 3 μm; mobile phase A: hexane (0.1% DEA), mobile phase B: isopropanol, isocratic separation with 30% B, flow rate: 1.0 mL/min, wavelength: 254 nm) | N-(1-(bicyclo[1.1.1]pentan-1-yl)-1H-pyrazol-4-yl)-2-(5-chloro-4-((6-(cyclopropanesulfonimidoyl)quinolin-4-yl)oxy)-2-fluorophenyl)acetamide | (400 MHz, DMSO-$d_6$) δ 10.33 (s, 1H), 8.91-8.82 (m, 2H), 8.28-8.23 (m, 2H), 7.90 (s, 1H), 7.82 (d, J = 7.4 Hz, 1H), 7.66 (d, J = 9.7 Hz, 1H), 7.47 (s, 1H), 6.73 (d, J = 5.2 Hz, 1H), 4.57 (s, 1H), 3.78 (s, 2H), 2.84 (tt, J = 8.3, 4.6 Hz, 1H), 2.61 (s, 1H), 2.20 (s, 6H), 1.26-1.14 (m, 1H), 1.12-0.91 (m, 3H) | 566.0 $(M + H)^+$ |
| 533 | 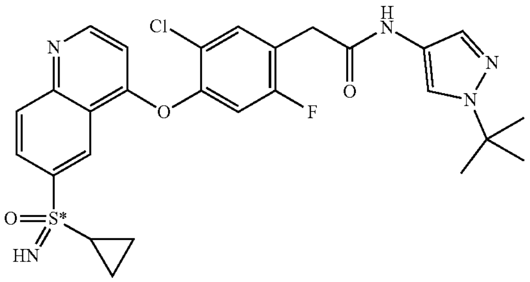 enantiomer 1 (retention time: 3.41 min, column: CHIRALPAK IA-3, 4.6 × 50 mm, 3 μm; mobile phase A: hexane (0.1% DEA), mobile phase B: isopropanol, isocratic separation with 25% B, flow rate: 1.0 mL/min, wavelength: 254 nm) | N-(1-(tert-butyl)-1H-pyrazol-4-yl)-2-(5-chloro-4-((6-(cyclopropanesulfonimidoyl)quinolin-4-yl)oxy)-2-fluorophenyl)acetamide | 400 MHz, DMSO-$d_6$) δ 10.27 (s, 1H), 8.91-8.83 (m, 2H), 8.26-8.23 (m, 2H), 7.95 (s, 1H), 7.82 (d, J = 7.4 Hz, 1H), 7.66 (d, J = 9.7 Hz, 1H), 7.46 (s, 1H), 6.73 (d, J = 5.2 Hz, 1H), 4.57 (s, 1H), 3.77 (s, 2H), 2.84 (tt, J = 8.1, 4.7 Hz, 1H), 1.49 (s, 9H), 1.26-1.14 (m, 1H), 1.14-0.91 (m, 3H) | 556.1 $(M + H)^+$ |

-continued

| No. | Structure | Name | $^{1}$H NMR | Observed m/z |
|---|---|---|---|---|
| 534 | 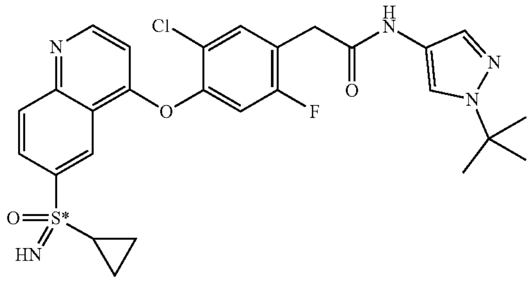 enantiomer 2 (retention time: 4.41 min, column: CHIRALPAK IA-3, 4.6 × 50 mm, 3 µm; mobile phase A: hexane (0.1% DEA), mobile phase B: isopropanol, isocratic separation with 25% B, flow rate: 1.0 mL/min, wavelength: 254 nm) | N-(1-(tert-butyl)-1H-pyrazol-4-yl)-2-(5-chloro-4-((6-(cyclopropanesulfonimidoyl)quinolin-4-yl)oxy)-2-fluorophenyl) acetamide | 400 MHz, DMSO-$d_6$) δ 10.27 (s, 1H), 8.91-8.83 (m, 2H), 8.26-8.23 (m, 2H), 7.95 (s, 1H), 7.82 (d, J = 7.4 Hz, 1H), 7.66 (d, J = 9.7 Hz, 1H), 7.46 (s, 1H), 6.73 (d, J = 5.2 Hz, 1H), 4.57 (s, 1H), 3.77 (s, 2H), 2.84 (tt, J = 8.1, 4.7 Hz, 1H), 1.49 (s, 9H), 1.26-1.14 (m, 1H), 1.14-0.91 (m, 3H) | 556.1 $(M + H)^+$ |
| 535 | 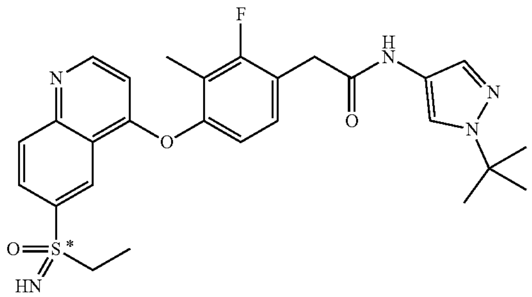 [SMILES: CCS(=N)(=O)c1ccc2nccc(Oc3ccc(CC(=O)Nc4cnn(C(C)(C)C)c4)c(F)c3C)c2c1] enantiomer 1 (retention time: 1.47 min, column: CHIRALPAK IH-3, 4.6 × 50 mm, 3 µm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(4-((6-(ethylsulfonimidoyl)quinolin-4-yl)oxy)-2-fluoro-3-methylphenyl) acetamide | (300 MHz, DMSO-$d_6$) δ 10.24 (s, 1H), 8.92-8.81 (m, 2H), 8.24-8.22 (m, 2H), 7.95 (s, 1H), 7.49-7.34 (m, 2H), 7.15 (d, J = 8.4 Hz, 1H), 6.62 (d, J = 5.2 Hz, 1H), 4.50 (s, 1H), 3.72 (s, 2H), 3.30 (q, J = 7.3 Hz, 2H), 2.07 (s, 3H), 1.49 (s, 9H), 1.14 (t, J = 7.3 Hz, 3H) | 524.1 $(M + H)^+$ |

-continued

| No. | Structure | Name | $^1H$ NMR | Observed m/z |
|---|---|---|---|---|
| 536 | 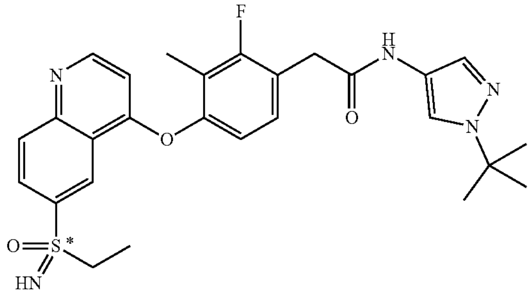 [SMILES: CCS(=N)(=O)c1ccc2nccc(Oc3ccc(CC(=O)Nc4cnn(C(C)(C)C)c4)c(F)c3C)c2c1] enantiomer 2 (retention time: 2.05 min, column: CHIRALPAK IH-3, 4.6 × 50 mm, 3 μm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(4-((6-(ethylsulfonimidoyl)quinolin-4-yl)oxy)-2-fluoro-3-methylphenyl) acetamide | (300 MHz, DMSO-$d_6$) δ 10.24 (s, 1H), 8.92-8.81 (m, 2H), 8.24-8.22 (m, 2H), 7.95 (s, 1H), 7.49-7.34 (m, 2H), 7.15 (d, J = 8.4 Hz, 1H), 6.62 (d, J = 5.2 Hz, 1H), 4.50 (s, 1H), 3.72 (s, 2H), 3.30 (q, J = 7.3 Hz, 2H), 2.07 (s, 3H), 1.50 (s, 9H), 1.14 (t, J = 7.3 Hz, 3H) | 524.1 $(M + H)^+$ |
| 537 | 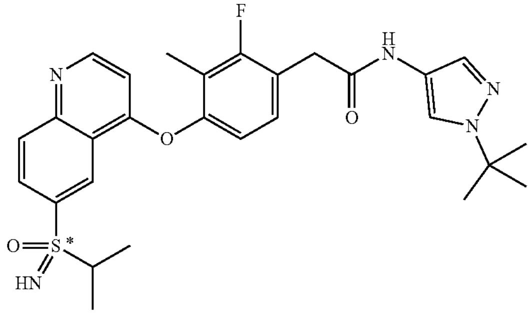 [SMILES: Cc1c(Oc2ccnc3ccc(S(=N)(=O)C(C)C)cc23)ccc(CC(=O)Nc2cnn(C(C)(C)C)c2)c1F] enantiomer 1 (retention time: 1.33 min, column: CHIRALPAK IH-3, 4.6 × 50 mm, 3 μm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-3-methyl-4-((6-(propan-2-ylsulfonimidoyl) quinolin-4-yl)oxy)phenyl) acetamide | (300 MHz, DMSO-$d_6$) δ 10.23 (s, 1H), 8.89-8.81 (m, 2H), 8.28-8.15 (m, 2H), 7.95 (s, 1H), 7.46 (s, 1H), 7.39 (t, J = 8.4 Hz, 1H), 7.16 (d, J = 8.4 Hz, 1H), 6.62 (d, J = 5.2 Hz, 1H), 4.47 (s, 1H), 3.72 (s, 2H), 3.43-3.36 (m, 1H), 2.07 (s, 3H), 1.49 (s, 9H), 1.21-1.18 (m, 6H) | 538.1 $(M + H)^+$ |

-continued

| No. | Structure | Name | $^1$H NMR | Observed m/z |
|---|---|---|---|---|
| 538 | 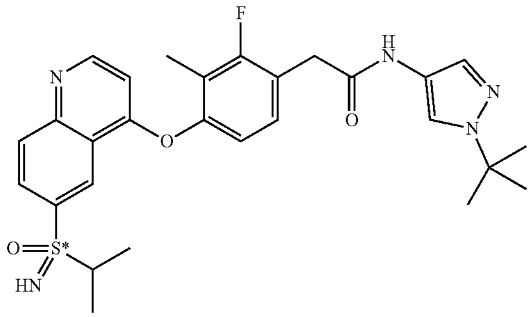 enantiomer 2 (retention time: 1.75 min, column: CHIRALPAK IH-3, 4.6 × 50 mm, 3 μm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-3-methyl-4-((6-(propan-2-ylsulfonimidoyl) quinolin-4-yl)oxy)phenyl) acetamide | (300 MHz, DMSO-$d_6$) δ 10.23 (s, 1H), 8.89-8.81 (m, 2H), 8.28-8.15 (m, 2H), 7.95 (s, 1H), 7.46 (s, 1H), 7.39 (t, J = 8.4 Hz, 1H), 7.16 (d, J = 8.4 Hz, 1H), 6.62 (d, J = 5.2 Hz, 1H), 4.47 (s, 1H), 3.72 (s, 2H), 3.43-3.36 (m, 1H), 2.07 (s, 3H), 1.49 (s, 9H), 1.21-1.18 (m, 6H) | 538.1 $(M + H)^+$ |
| 539 | 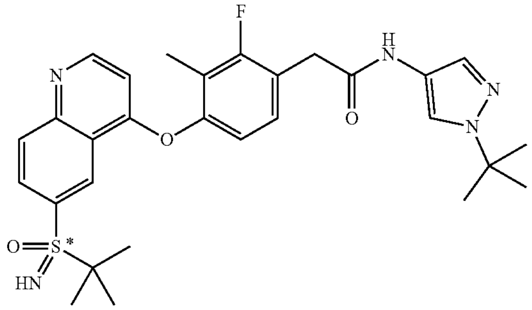 [SMILES: Cc1c(Oc2ccnc3ccc(S(=N)(=O)C(C)(C)C)cc23)ccc(CC(=O)Nc2cnn(C(C)(C)C)c2)c1F] enantiomer 1 (retention time: 2.99 min, column: CHIRAL Cellulose-SB, 4.6 × 100 mm, 3 μm; mobile phase A: MTBE (0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(2-fluoro-3-methyl-4-((6-(2-methylpropan-2-ylsulfonimidoyl) quinolin-4-yl)oxy)phenyl) acetamide | (300 MHz, DMSO-$d_6$) δ 10.23 (s, 1H), 8.90-8.81 (m, 2H), 8.28-8.14 (m, 2H), 7.95 (s, 1H), 7.46 (s, 1H), 7.39 (t, J = 8.4 Hz, 1H), 7.16 (d, J = 8.4 Hz, 1H), 6.64 (d, J = 5.2 Hz, 1H), 4.42 (s, 1H), 3.72 (s, 2H), 2.06 (s, 3H), 1.49 (s, 9H), 1.29 (s, 9H) | 552.1 $(M + H)^+$ |

-continued

| No. | Structure | Name | ¹H NMR | Observed m/z |
|---|---|---|---|---|
| 540 | 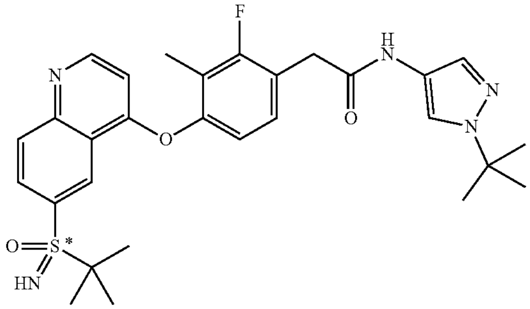 [SMILES: Cc1c(Oc2ccnc3ccc(S(=N)(=O)C(C)(C)C)cc23)ccc(CC(=O)Nc2cnn(C(C)(C)C)c2)c1F] enantiomer 2 (retention time: 3.42 min, column: CHIRAL Cellulose-SB, 4.6 × 100 mm, 3 μm; mobile phase A: MTBE (0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(2-fluoro-3-methyl-4-((6-(2-methylpropan-2-ylsulfonimidoyl) quinolin-4-yl)oxy)phenyl) acetamide | (300 MHz, DMSO-$d_6$) δ 10.22 (s, 1H), 8.90-8.81 (m, 2H), 8.28-8.14 (m, 2H), 7.95 (s, 1H), 7.46 (s, 1H), 7.39 (t, J = 8.4 Hz, 1H), 7.16 (d, J = 8.4 Hz, 1H), 6.65 (d, J = 5.2 Hz, 1H), 4.42 (s, 1H), 3.71 (s, 2H), 2.06 (s, 3H), 1.49 (s, 9H), 1.29 (s, 9H) | 552.1 $(M + H)^+$ |
| 541 | 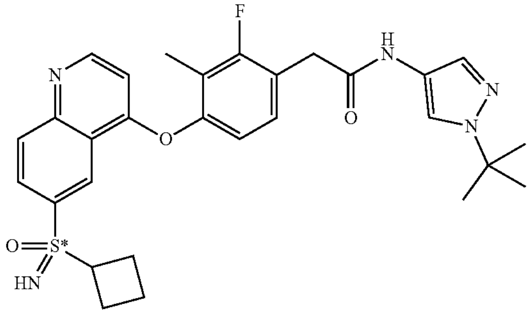 enantiomer 1 (retention time: 5.82 min, column: CHIRALPAK IH-3, 4.6 × 50 mm, 3 μm; mobile phase A: MTBE (0.1% DEA), mobile phase B: EtOH, isocratic separation with 7% B, flow rate: 1.0 mL/min, wavelength: 254 nm) | N-(1-(tert-butyl)-1H-pyrazol-4-yl)-2-(4-((6-(cyclobutanesulfonimidoyl) quinolin-4-yl) oxy)-2-fluoro-3-methylphenyl) acetamide | (300 MHz, DMSO-$d_6$) δ 10.23 (s, 1H), 8.89-8.76 (m, 2H), 8.24-8.14 (m, 2H), 7.95 (s, 1H), 7.46 (s, 1H), 7.39 (t, J = 8.4 Hz, 1H), 7.15 (d, J = 8.4 Hz, 1H), 6.61 (d, J = 5.2 Hz, 1H), 4.48 (s, 1H), 4.12-4.07 (m, 1H), 3.71 (s, 2H), 2.47-2.34 (m, 2H), 2.16-1.95 (m, 5H), 1.93-1.77 (m, 2H), 1.49 (s, 9H) | 550.1 $(M + H)^+$ |

-continued

| No. | Structure | Name | $^1H$ NMR | Observed m/z |
|---|---|---|---|---|
| 542 | 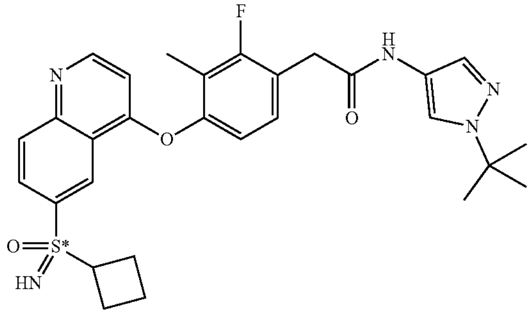 enantiomer 2 (retention time: 8.30 min, column: CHIRALPAK IH-3, 4.6 × 50 mm, 3 μm; mobile phase A: MTBE (0.1% DEA), mobile phase B: EtOH, isocratic separation with 7% B, flow rate: 1.0 mL/min, wavelength: 254 nm) | N-(1-(tert-butyl)-1H-pyrazol-4-yl)-2-(4-((6-(cyclobutanesulfonimidoyl) quinolin-4-yl) oxy)-2-fluoro-3-methylphenyl) acetamide | (300 MHz, DMSO-$d_6$) δ 10.23 (s, 1H), 8.89-8.76 (m, 2H), 8.24-8.14 (m, 2H), 7.95 (s, 1H), 7.46 (s, 1H), 7.39 (t, J = 8.4 Hz, 1H), 7.15 (d, J = 8.4 Hz, 1H), 6.61 (d, J = 5.2 Hz, 1H), 4.48 (s, 1H), 4.12-4.07 (m, 1H), 3.71 (s, 2H), 2.47-2.34 (m, 2H), 2.16-1.95 (m, 5H), 1.93-1.77 (m, 2H), 1.49 (s, 9H) | 550.1 $(M + H)^+$ |
| 543 | 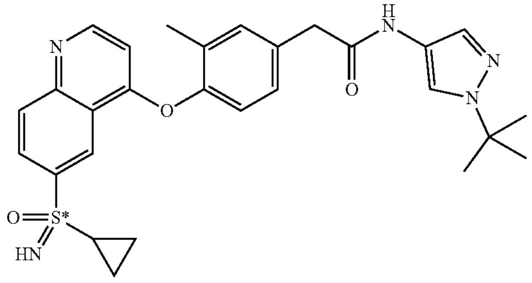 enantiomer 1 (retention time: 3.42 min, column: (R,R) Whelk-O1, 4.6 × 50 mm, 3.5 μm; mobile phase A: MTBE (0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(4-((6-(cyclopropanesulfonimidoyl) quinolin-4-yl) oxy)-3-methylphenyl) acetamide | (300 MHz, DMSO-$d_6$) δ 10.21 (s, 1H), 8.89 (dd, J = 1.9, 0.9 Hz, 1H), 8.80 (d, J = 5.2 Hz, 1H), 8.29-8.16 (m, 2H), 7.99 (s, 1H), 7.43 (s, 1H), 7.39 (d, J = 2.1 Hz, 1H), 7.36-7.28 (m, 1H), 7.24 (d, J = 8.2 Hz, 1H), 6.53 (d, J = 5.2 Hz, 1H), 4.52 (s, 1H), 3.62 (s, 2H), 2.84 (tt, J = 7.9, 4.7 Hz, 1H), 2.14 (s, 3H), 1.49 (s, 9H), 1.14-0.89 (m, 4H) | 518.2 $(M + H)^+$ |

-continued

| No. | Structure | Name | $^1$H NMR | Observed m/z |
|---|---|---|---|---|
| 544 | 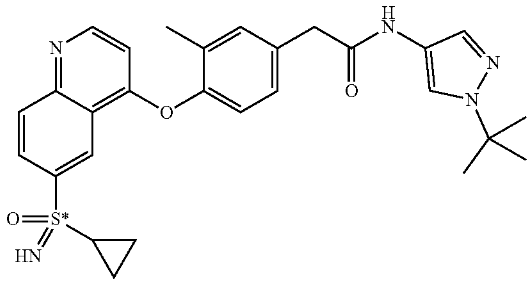 enantiomer 2 (retention time: 3.94 min, column: (R,R) Whelk-O1, 4.6 × 50 mm, 3.5 μm; mobile phase A: MTBE (0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(4-((6-(cyclopropanesulfonimidoyl) quinolin-4-yl) oxy)-3-methylphenyl) acetamide | (300 MHz, DMSO-$d_6$) δ 10.21 (s, 1H), 8.89 (dd, J = 1.9, 0.9 Hz, 1H), 8.80 (d, J = 5.2 Hz, 1H), 8.29-8.16 (m, 2H), 7.99-7.92 (m, 1H), 7.50-7.43 (m, 1H), 7.39 (d, J = 2.1 Hz, 1H), 7.36-7.28 (m, 1H), 7.24 (d, J = 8.2 Hz, 1H), 6.53 (d, J = 5.2 Hz, 1H), 4.52 (s, 1H), 3.62 (s, 2H), 2.84 (tt, J = 7.9, 4.7 Hz, 1H), 2.14 (s, 3H), 1.49 (s, 9H), 1.14-0.89 (m, 4H) | 518.2 $(M + H)^+$ |
| 545 | 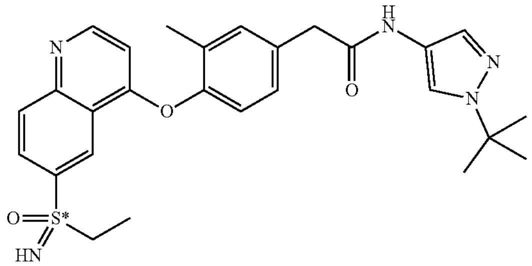 enantiomer 1 (retention time: 1.61 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(4-((6-(ethylsulfonimidoyl) quinolin-4-yl)oxy)-3-methylphenyl) acetamide | (300 MHz, DMSO-$d_6$) δ 10.22 (s, 1H), 8.89 (s, 1H), 8.81 (d, J = 5.2 Hz, 1H), 8.23-8.21 (m, 2H), 7.95 (s, 1H), 7.46 (s, 1H), 7.39 (s, 1H), 7.33-7.19 (m, 2H), 6.53 (d, J = 5.1 Hz, 1H), 4.49 (s, 1H), 3.62 (s, 2H), 3.30 (q, J = 7.3 Hz, 2H), 2.13 (s, 3H), 1.49 (s, 9H), 1.13 (t, J = 7.4 Hz, 3H) | 506.2 $(M + H)^+$ |

-continued

| No. | Structure | Name | $^{1}$H NMR | Observed m/z |
|---|---|---|---|---|
| 546 | 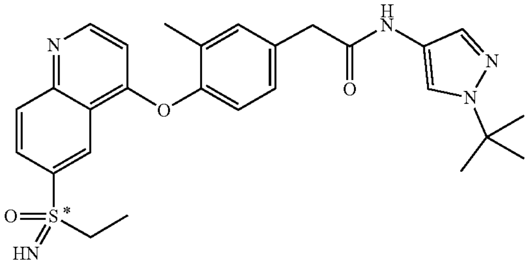 [SMILES: CCS(=N)(=O)c1ccc2nccc(Oc3ccc(CC(=O)Nc4cnn(C(C)(C)C)c4)cc3C)c2c1] enantiomer 2 (retention time: 1.68 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(4-((6-(ethylsulfonimidoyl) quinolin-4-yl)oxy)-3-methylphenyl) acetamide | (300 MHz, DMSO-$d_6$) δ 10.22 (s, 1H), 8.89 (s, 1H), 8.81 (d, J = 5.2 Hz, 1H), 8.23-8.21 (m, 2H), 7.95 (s, 1H), 7.46 (s, 1H), 7.39 (s, 1H), 7.33-7.19 (m, 2H), 6.53 (d, J = 5.1 Hz, 1H), 4.49 (s, 1H), 3.62 (s, 2H), 3.30 (q, J = 7.3 Hz, 2H), 2.13 (s, 3H), 1.49 (s, 9H), 1.13 (t, J = 7.4 Hz, 3H) | 506.2 $(M + H)^+$ |
| 547 | 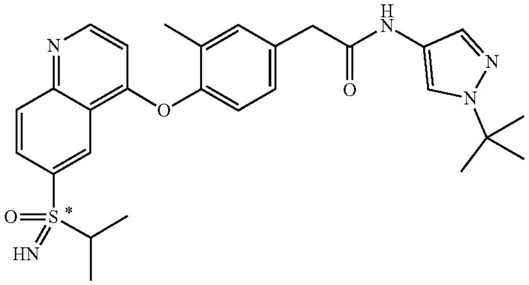 [SMILES: Cc1cc(CC(=O)Nc2cnn(C(C)(C)C)c2)ccc1Oc1ccnc2ccc(S(=N)(=O)C(C)C)cc12] enantiomer 1 (retention time: 1.55 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(3-methyl-4-((6-(propan-2-ylsulfonimidoyl) quinolin-4-yl)oxy)phenyl) acetamide | (300 MHz, DMSO-$d_6$) δ 10.21 (s, 1H), 8.90-8.77 (m, 2H), 8.21-8.19 (m, 2H), 7.96 (s, 1H), 7.46 (s, 1H), 7.39 (d, J = 2.1 Hz, 1H), 7.36-7.28 (m, 1H), 7.24 (d, J = 8.2 Hz, 1H), 6.54 (d, J = 5.2 Hz, 1H), 4.46 (s, 1H), 3.62 (s, 2H), 3.42-3.38 (m, 1H), 2.12 (s, 3H), 1.49 (s, 9H), 1.21-1.18 (m, 6H) | 520.2 $(M + H)^+$ |

-continued

| No. | Structure | Name | $^1$H NMR | Observed m/z |
|---|---|---|---|---|
| 548 | 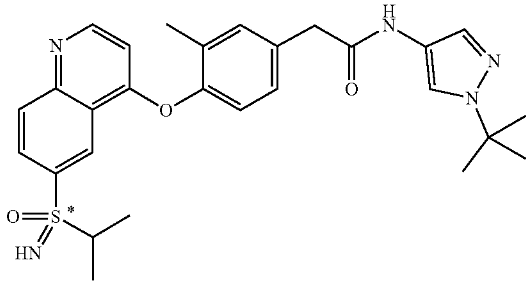 [SMILES: Cc1cc(CC(=O)Nc2cnn(C(C)(C)C)c2)ccc1Oc1ccnc2ccc(S(=N)(=O)C(C)C)cc12] enantiomer 2 (retention time: 1.61 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(3-methyl-4-((6-(propan-2-ylsulfonimidoyl) quinolin-4-yl)oxy)phenyl) acetamide | (300 MHz, DMSO-$d_6$) δ 10.21 (s, 1H), 8.90-8.77 (m, 2H), 8.21-8.19 (m, 2H), 7.96 (s, 1H), 7.46 (s, 1H), 7.39 (d, J = 2.1 Hz, 1H), 7.36-7.28 (m, 1H), 7.24 (d, J = 8.2 Hz, 1H), 6.54 (d, J = 5.2 Hz, 1H), 4.46 (s, 1H), 3.62 (s, 2H), 3.42-3.38 (m, 1H), 2.12 (s, 3H), 1.49 (s, 9H), 1.21-1.18 (m, 6H) | 520.2 $(M + H)^+$ |
| 549 | 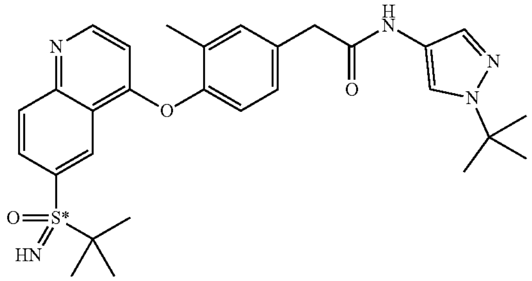 enantiomer 1 (retention time: 1.46 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(3-methyl-4-((6-(2-methylpropan-2-ylsulfonimidoyl) quinolin-4-yl)oxy)phenyl) acetamide | (400 MHz, DMSO-$d_6$) δ 10.21 (s, 1H), 8.90-8.77 (m, 2H), 8.22-8.17 (m, 2H), 7.96 (s, 1H), 7.46 (s, 1H), 7.39 (d, J = 2.1 Hz, 1H), 7.36-7.28 (m, 1H), 7.24 (d, J = 8.2 Hz, 1H), 6.54 (d, J = 5.2 Hz, 1H), 4.41 (s, 1H), 3.62 (s, 2H), 2.10 (s, 3H), 1.49 (s, 9H), 1.28 (s, 9H) | 534.1 $(M + H)^+$ |

-continued

| No. | Structure | Name | $^1$H NMR | Observed m/z |
|---|---|---|---|---|
| 550 | 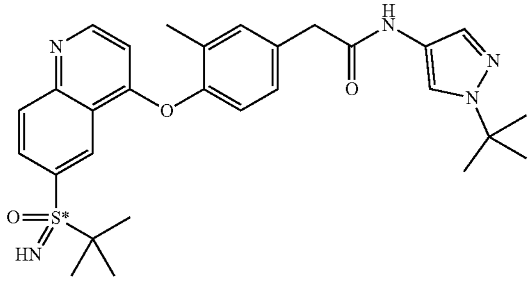 enantiomer 2 (retention time: 1.53 min, column: CHIRAL ART Cellulose-SB, 4.6 × 50 mm, 3 μm; mobile phase A: supercritical $CO_2$, mobile phase B: EtOH:ACN (1:1, 0.1% DEA), gradient: 10-50% B in 2 min, then hold at 50% B for 1 min, flow rate: 4.0 mL/min, wavelength: 220 nm) | N-(1-(tert-butyl)-1H-pyrazol-4-yl)-2-(3-methyl-4-((6-(2-methylpropan-2-ylsulfonimidoyl) quinolin-4-yl)oxy)phenyl) acetamide | (400 MHz, DMSO-$d_6$) δ 10.21 (s, 1H), 8.90-8.77 (m, 2H), 8.22-8.17 (m, 2H), 7.96 (s, 1H), 7.46 (s, 1H), 7.39 (d, J = 2.1 Hz, 1H), 7.36-7.28 (m, 1H), 7.24 (d, J = 8.2 Hz, 1H), 6.54 (d, J = 5.2 Hz, 1H), 4.41 (s, 1H), 3.62 (s, 2H), 2.10 (s, 3H), 1.49 (s, 9H), 1.28 (s, 9H) | 534.1 $(M + H)^+$ |
| 551 | 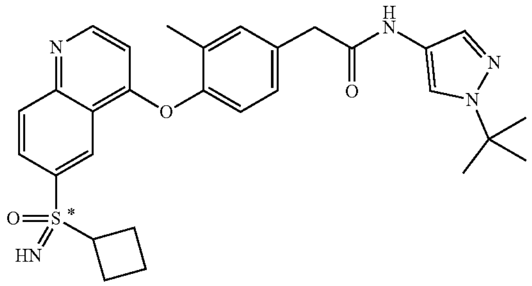 enantiomer 1 (retention time: 1.08 min, column: CHIRAL ART Cellulose-SB, 4.6 × 50 mm, 3 μm; mobile phase A: supercritical $CO_2$, mobile phase B: EtOH:ACN (1:1, 0.1% DEA), isocratic separation with 30% B, flow rate: 4.0 mL/min, wavelength: 220 nm) | N-(1-(tert-butyl)-1H-pyrazol-4-yl)-2-(4-((6-(cyclobutanesulfonimidoyl) quinolin-4-yl) oxy)-3-methylphenyl) acetamide | (300 MHz, DMSO-$d_6$) δ 10.21 (s, 1H), 8.86 (d, J = 1.9 Hz, 1H), 8.80 (d, J = 5.2 Hz, 1H), 8.25-8.12 (m, 2H), 7.95 (s, 1H), 7.46 (s, 1H), 7.39 (s, 1H), 7.35-7.20 (m, 2H), 6.53 (d, J = 5.2 Hz, 1H), 4.48 (s, 1H), 4.09 (p, J = 8.2 Hz, 1H), 3.62 (s, 2H), 2.39 (q, J = 9.5 Hz, 2H), 2.12 (s, 3H), 2.10-1.95 (m, 2H), 1.95-1.77 (m, 2H), 1.49 (s, 9H) | 532.2 $(M + H)^+$ |

-continued

| No. | Structure | Name | 1H NMR | Observed m/z |
|---|---|---|---|---|
| 552 | 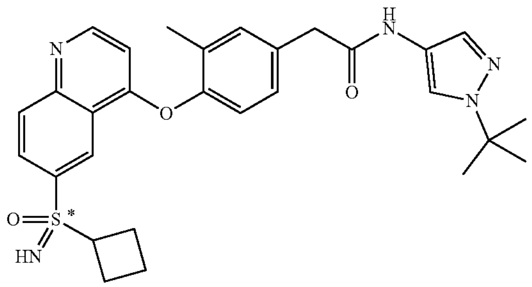 enantiomer 2 (retention time: 1.24 min, column: CHIRAL ART Cellulose-SB, 4.6 × 50 mm, 3 μm; mobile phase A: supercritical $CO_2$, mobile phase B: EtOH:ACN (1:1, 0.1% DEA), isocratic separation with 30% B, flow rate: 4.0 mL/min, wavelength: 220 nm) | N-(1-(tert-butyl)-1H-pyrazol-4-yl)-2-(4-((6-(cyclobutanesulfonimidoyl) quinolin-4-yl) oxy)-3-methylphenyl) acetamide | (300 MHz, DMSO-$d_6$) δ 10.21 (s, 1H), 8.86 (d, J = 1.9 Hz, 1H), 8.80 (d, J = 5.2 Hz, 1H), 8.25-8.12 (m, 2H), 7.95 (s, 1H), 7.46 (s, 1H), 7.39 (s, 1H), 7.35-7.20 (m, 2H), 6.53 (d, J = 5.2 Hz, 1H), 4.48 (s, 1H), 4.09 (p, J = 8.2 Hz, 1H), 3.62 (s, 2H), 2.39 (q, J = 9.5 Hz, 2H), 2.12 (s, 3H), 2.10-1.95 (m, 2H), 1.95-1.77 (m, 2H), 1.49 (s, 9H) | 532.2 $(M + H)^+$ |
| 553 | 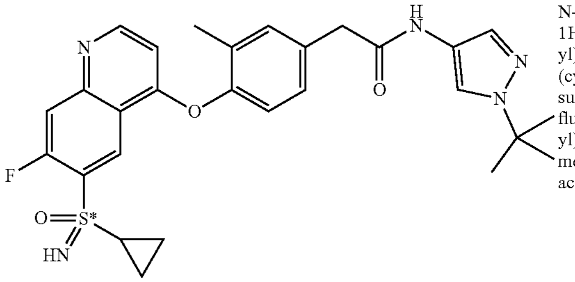 enantiomer 2 (retention time: 4.31 min, column: (R,R) Whelk-O1, 4.6 × 50 mm, 3.5 μm; mobile phase A: MTBE (0.1% DEA), mobile phase B: isopropanol, isocratic separation with 10% B, flow rate: 1.0 mL/min, wavelength: 254 nm) | N-(1-(tert-butyl)-1H-pyrazol-4-yl)-2-(4-((6-(cyclopropanesulfonimidoyl)-7-fluoroquinolin-4-yl)oxy)-3-methylphenyl) acetamide | (300 MHz, DMSO-$d_6$) δ 10.21 (s, 1H), 8.87 (d, J = 7.8 Hz, 1H), 8.79 (d, J = 5.3 Hz, 1H), 8.01 (d, J = 11.5 Hz, 1H), 7.95 (d, J = 0.7 Hz, 1H), 7.46 (d, J = 0.8 Hz, 1H), 7.39 (d, J= 2.1 Hz, 1H), 7.31 (dd, J = 8.3, 2.1 Hz, 1H), 7.23 (d, J = 8.2 Hz, 1H), 6.48 (d, J = 5.3 Hz, 1H), 5.03 (s, 1H), 3.61 (s, 2H), 2.98-2.94 (m, 1H), 2.13 (s, 3H), 1.49 (s, 9H), 1.27-1.00 (m, 4H) | 536.2 $(M + H)^+$ |

-continued

| No. | Structure | Name | $^1$H NMR | Observed m/z |
|---|---|---|---|---|
| 554 | 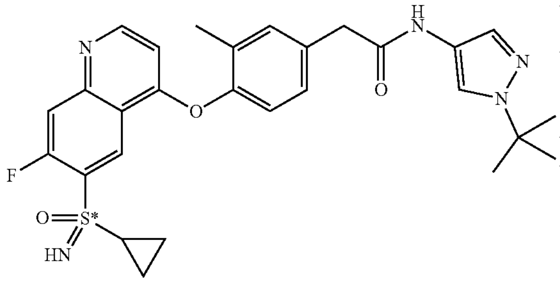 enantiomer 1 (retention time: 3.66 min, column: (R,R) Whelk-O1, 4.6 × 50 mm, 3.5 μm; mobile phase A: MTBE (0.1% DEA), mobile phase B: isopropanol, isocratic separation with 10% B, flow rate: 1.0 mL/min, wavelength: 254 nm) | N-(1-(tert-butyl)-1H-pyrazol-4-yl)-2-(4-((6-(cyclopropane-sulfonimidoyl)-7-fluoroquinolin-4-yl)oxy)-3-methylphenyl) acetamide | (300 MHz, DMSO-$d_6$) δ 10.21 (s, 1H), 8.87 (d, J = 7.8 Hz, 1H), 8.79 (d, J = 5.3 Hz, 1H), 8.01 (d, J = 11.5 Hz, 1H), 7.95 (d, J = 0.7 Hz, 1H), 7.46 (d, J = 0.8 Hz, 1H), 7.39 (d, J = 2.1 Hz, 1H), 7.31 (dd, J = 8.3, 2.1 Hz, 1H), 7.23 (d, J = 8.2 Hz, 1H), 6.48 (d, J = 5.3 Hz, 1H), 5.03 (s, 1H), 3.61 (s, 2H), 2.98-2.94 (m, 1H), 2.13 (s, 3H), 1.49 (s, 9H), 1.27-1.00 (m, 4H) | 536.2 $(M + H)^+$ |

Example 9—Synthesis of N-(1-(tert-butyl)-1H-pyrazol-4-yl)-2-(4-((6-(tert-butylsulfonyl)-7-methoxyquinazolin-4-yl)oxy)-2-fluorophenyl)acetamide (Compound 2); Prepared According to General Scheme 11

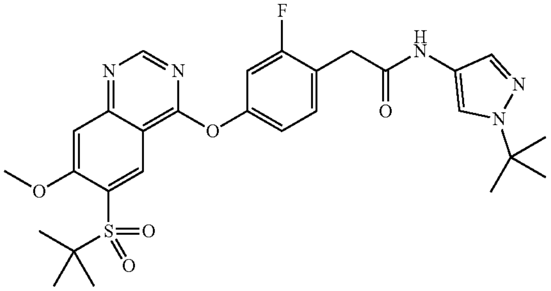 [SMILES: COc1cc2ncnc(Oc3ccc(CC(=O)Nc4cnn(C(C)(C)C)c4)c(F)c3)c2cc1S(=O)(=O)C(C)(C)C]

Part I—Synthesis of 6-bromo-7-methoxyquinazolin-4(3H)-one

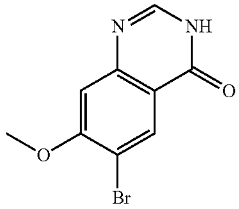

A solution of 2-amino-5-bromo-4-methoxybenzoic acid (4.80 g, 19.5 mmol, 1.00 equiv.) and ammonium acetate (30.1 g, 390 mmol, 20.0 equiv.) in trimethyl orthoformate (100 mL) was heated to 100° C. overnight. Subsequently, the solvent was removed under reduced pressure and the product was extracted with EtOAc (3×100 mL). The solvent was removed under reduced pressure. The title compound was obtained as a grey solid (4.09 g, 82% yield), which was used in the next reaction without further purification.

Part II—Synthesis of 6-(tert-butylsulfonyl)-7-methoxyquinazolin-4(3H)-one

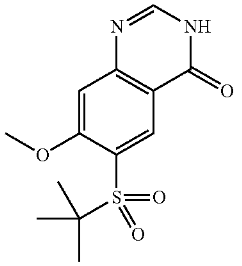 [SMILES: COc1cc2nc[nH]c(=O)c2cc1S(=O)(=O)C(C)(C)C]

A solution of 6-bromo-7-methoxyquinazolin-4(3H)-one (4.09 g, 16.1 mmol, 1.00 equiv.), 2-methylpropane-2-thiol (3.6 mL, 31.9 mmol, 2.00 equiv.), $Na_2CO_3$ (3.37 g, 30.8 mmol, 1.90 equiv.), and $Pd(PPh_3)_4$ (0.6 g, 0.483 mmol, 0.03 equiv.) in DMF (56 mL) was heated to 100° C. for 6 h under an inert atmosphere of nitrogen. Insoluble byproducts were filtered off. Water was added and the precipitated product was filtered off and washed with petroleum ether.

The thioether intermediate was dissolved in MeOH (140 mL), EtOAc (140 mL), and water (140 mL), and oxone (22.5 g, 134 mmol, 8.70 equiv.) was added. After stirring at room temperature for 16 h, the mixture was filtered and washed with a saturated aqueous solution of $NaHCO_3$. The pH of the aqueous solution was brought to 7-8 by addition of $NaHCO_3$ and the product was extracted with EtOAc. The combined organic phases were washed with saturated aqueous solution of $NaHCO_3$, dried over $MgSO_4$, and the solvent was removed under reduced pressure. The title compound was obtained as a light-yellow solid (2.57 g, 54% yield), which was used in the next reaction without further purification.

Part III—Synthesis of 6-(tert-butylsulfonyl)-4-chloro-7-methoxyquinazoline

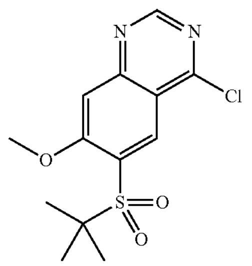 [SMILES: COc1cc2ncnc(Cl)c2cc1S(=O)(=O)C(C)(C)C]

$POCl_3$ (56.9 mg, 0.371 mmol, 1.10 equiv.) was added dropwise to a solution of 6-(tert-butylsulfonyl)-7-methoxy-quinazolin-4(3H)-one (100.0 mg, 0.337 mmol, 1.00 equiv.) and triethylamine (51.2 mg, 0.506 mmol, 1.50 equiv.) in toluene (1 mL) at room temperature. Subsequently, the reaction mixture was heated to 80° C. for 2 h. After cooling to room temperature, this reaction mixture was directly used in the next reaction.

Part IV—Synthesis of N-(1-(tert-butyl)-1H-pyrazol-4-yl)-2-(2-fluoro-4-hydroxyphenyl)acetamide

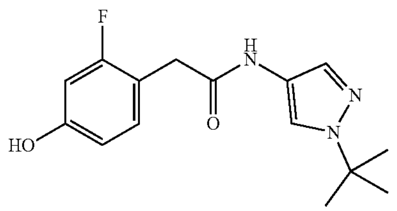 [SMILES: CC(C)(C)n1cc(NC(=O)Cc2ccc(O)cc2F)cn1]

DIPEA (2.28 g, 17.6 mmol, 3.00 equiv.) was added dropwise to a solution of (2-fluoro-4-hydroxyphenyl)acetic acid (1.0 g, 5.88 mmol, 1.00 equiv.) and 1-(tert-butyl)-1H-pyrazol-4-amine (1.23 g, 8.82 mmol, 1.10 equiv.) in DMF (10 mL) at 0° C. Subsequently, propylphosphonic anhydride (0.71 g, 17.6 mmol, 3.00 equiv.) was added dropwise to the solution and the reaction mixture was stirred for 4 h at this temperature. The solvent was removed under reduced pressure and the crude product was purified by column chromatography (hexanes/EtOAc 3:1). The title compound was obtained as a yellow solid (500 mg, 29% yield).

Part V—Synthesis of N-(1-(tert-butyl)-1H-pyrazol-4-yl)-2-(4-((6-(tert-butylsulfonyl)-7-methoxyquinazolin-4-yl)oxy)-2-fluorophenyl)acetamide (Compound 2)

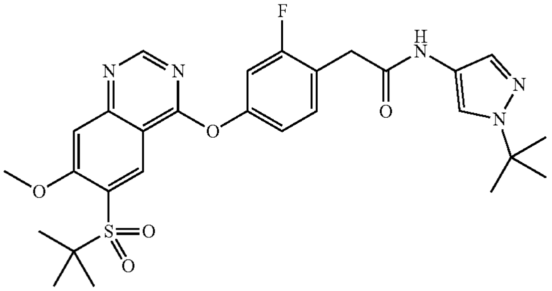 [SMILES: COc1cc2ncnc(Oc3ccc(CC(=O)Nc4cnn(C(C)(C)C)c4)c(F)c3)c2cc1S(=O)(=O)C(C)(C)C]

$K_2CO_3$ (132.0 mg, 0.954 mmol, 3.00 equiv.) was added to a solution of 6-(tert-butylsulfonyl)-4-chloro-7-methoxyquinazoline (100.0 mg, 0.318 mmol, 1.00 equiv.) and N-(1-(tert-butyl)-1H-pyrazol-4-yl)-2-(2-fluoro-4-hydroxyphenyl) acetamide (102.0 mg, 0.350 mmol, 1.10 equiv.) in DMF (2 mL). The reaction mixture was heated to 80° C. overnight. Subsequently, the crude product was purified by preparative HPLC (column: Xselect CSH C18 OBD; 30×150 mm, 5 μm; mobile phase A: water (10 mmol/L $NH_4HCO_3$), mobile phase B: ACN; flow rate: 60 mL/min; isocratic separation with 35% B for 13 min; wavelength: 220 nm; RT1: 11 min). The title compound was obtained as a white solid (10.3 mg, 5.2%). LCMS (ESI) calculated for $C_{28}H_{33}FN_5O_5S$ $(M+H)^+$: 570.2, found: 570.1. $^1H$ NMR (400 MHz, DMSO-$d_6$) δ 10.26 (d, J=8.1 Hz, 1H), 9.04-8.56 (m, 2H), 7.94 (t, J=9.9 Hz, 1H), 7.65 (t, J=6.8 Hz, 1H), 7.57-7.41 (m, 2H), 7.40-7.30 (m, 1H), 7.21 (d, J=8.3 Hz, 1H), 4.20-3.95 (m, 3H), 3.69 (d, J=8.2 Hz, 2H), 1.61-1.42 (m, 9H), 1.41-1.21 (m, 9H).

Example 10—Synthesis of N-(1-(tert-butyl)-1H-pyrazol-4-yl)-2-(4-((6-(tert-butylsulfonyl)-7-methoxyquinolin-4-yl)oxy)-2-fluorophenyl)acetamide (Compound 3); Prepared According to General Scheme 11

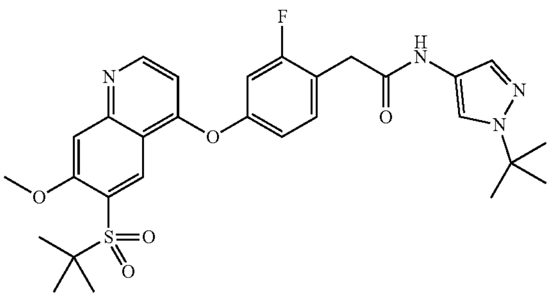 [SMILES: COc1cc2nccc(Oc3ccc(CC(=O)Nc4cnn(C(C)(C)C)c4)c(F)c3)c2cc1S(=O)(=O)C(C)(C)C]

Part I—Synthesis of 6-(tert-butylthio)-4-chloro-7-methoxyquinoline

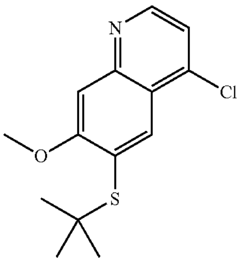 [SMILES: COc1cc2nccc(Cl)c2cc1SC(C)(C)C]

A solution of 6-bromo-4-chloro-7-methoxyquinoline (commercially available, 5.0 g, 18.3 mmol, 1.00 equiv.), 2-methylpropane-2-thiol (1.99 g, 22.0 mmol, 1.20 equiv.), $Pd(PPh_3)_4$ (0.64 g, 0.550 mmol, 0.03 equiv.) and $Na_2CO_3$ (3.89 g, 36.7 mmol, 2.00 equiv.) in DMF (50 mL) was heated to 100° C. under an inert atmosphere of nitrogen for 6 h. Subsequently, the crude product was purified by reversed-phase flash chromatography (column: C18 silica gel; mobile phase A: water (10 mmol/L $NH_4HCO_3$), mobile phase B: ACN, gradient: 40-70% B in 30 min; wavelength: 210 nm). The title compound was obtained as a yellow solid (3 g, 58%).

Part II—Synthesis of 6-(tert-butylsulfonyl)-4-chloro-7-methoxyquinoline

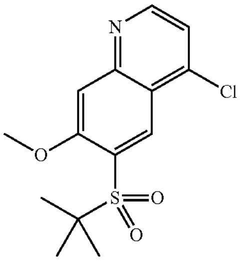 [SMILES: COc1cc2nccc(Cl)c2cc1S(=O)(=O)C(C)(C)C]

A solution of 6-(tert-butylthio)-4-chloro-7-methoxyquinoline (3.0 g, 10.6 mmol, 1.00 equiv.) and oxone (7.26 g, 42.6 mmol, 4.00 equiv.) in MeOH (90 mL), water (90 mL), and EtOAc (90 mL) was stirred for 16 h at room temperature. The product was extracted with EtOAc (3×300 mL) and the combined organic phases were washed with brine and dried over $Na_2SO_4$. The solvent was removed under reduced pressure and the crude product was purified by reversed-phase flash chromatography (column: C18 silica gel; mobile phase A: water (10 mmol/L $NH_4HCO_3$), mobile phase B: ACN, gradient: 40-70% B in 30 min; wavelength: 210 nm). The title compound was obtained as a yellow solid (1.5 g, 45%).

Part III—Synthesis of methyl 2-(4-((6-(tert-butylsulfonyl)-7-methoxyquinolin-4-yl)oxy)-2-fluorophenyl)acetate

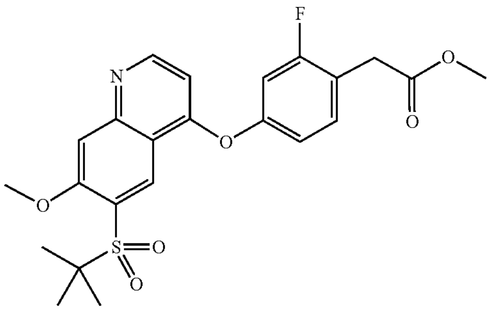

A solution of 6-(tert-butylsulfonyl)-4-chloro-7-methoxyquinoline (500.0 mg, 1.59 mmol, 1.00 equiv.) and methyl 2-(2-fluoro-4-hydroxyphenyl)acetate (293.4 mg, 1.59 mmol, 1.00 equiv.) in chlorobenzene (5 mL) was heated to 130° C. for 12 h. The reaction mixture was allowed to cool to room temperature and the crude product was purified by reversed-phase flash chromatography (column: C18 silica gel; mobile phase A: water (10 mmol/L $NH_4HCO_3$), mobile phase B: ACN, gradient: 60-90% B in 30 min; wavelength: 210 nm). The title compound was obtained as a yellow solid (300 mg, 41%).

Part IV—Synthesis of 2-(4-((6-(tert-butylsulfonyl)-7-methoxyquinolin-4-yl)oxy)-2-fluorophenyl)acetic Acid

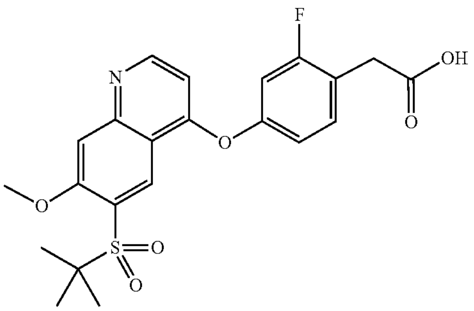 [SMILES: COc1cc2nccc(Oc3ccc(CC(=O)O)c(F)c3)c2cc1S(=O)(=O)C(C)(C)C]

A solution of methyl 2-(4-((6-(tert-butylsulfonyl)-7-methoxyquinolin-4-yl)oxy)-2-fluorophenyl)acetate (384.5 mg, 0.867 mmol, 1.00 equiv.) and LiOH (41.5 mg, 1.73 mmol, 2.00 equiv.) in THF (4 mL) and water (4 mL) was stirred at room temperature for 2 h. Subsequently, the crude product was purified by reversed-phase flash chromatography (column: C18 silica gel; mobile phase A: water (10 mmol/L $NH_4HCO_3$), mobile phase B: ACN, gradient: 20-50% B in 30 min; wavelength: 210 nm). The title compound was obtained as a yellow solid (260 mg, 67%).

Part V—Synthesis of N-(1-(tert-butyl)-1H-pyrazol-4-yl)-2-(4-((6-(tert-butylsulfonyl)-7-methoxyquinolin-4-yl)oxy)-2-fluorophenyl)acetamide (Compound 3)

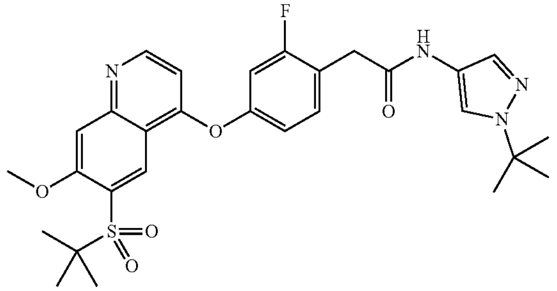 [SMILES: COc1cc2nccc(Oc3ccc(CC(=O)Nc4cnn(C(C)(C)C)c4)c(F)c3)c2cc1S(=O)(=O)C(C)(C)C]

Propylphosphonic anhydride (106.7 mg, 0.336 mmol, 3.00 equiv.) was added dropwise to a solution of 2-(4-((6-(tert-butylsulfonyl)-7-methoxyquinolin-4-yl)oxy)-2-fluorophenyl)acetic acid (50.0 mg, 0.112 mmol, 1.00 equiv.), 1-(tert-butyl)-1H-pyrazol-4-amine (15.6 mg, 0.112 mmol, 1.00 equiv.) and DIPEA (43.3 mg, 0.336 mmol, 3.00 equiv.) in DMF (0.5 mL). The reaction mixture was stirred at room temperature for 4 h. Subsequently, the crude product was purified by preparative HPLC (column: Xselect CSH C18 OBD, 30×150 mm, 5 μm; mobile phase A: water (10 mmol/L $NH_4HCO_3$), mobile phase B: ACN; flow rate: 60 mL/min; gradient: 38-43% B in 13 min; wavelength: 220 nm; RT1: 11 min). The title compound was obtained as a white solid (15 mg, 23%). LCMS (ESI) calculated for $C_{29}H_{34}FN_4O_5S$ $(M+H)^+$: 569.2, found: 569.0. $^1H$ NMR (400 MHz, DMSO-$d_6$) δ 10.23 (s, 1H), 8.81 (d, J=5.3 Hz, 1H), 8.74 (d, J=1.5 Hz, 1H), 7.97-7.92 (m, 1H), 7.68 (s, 1H), 7.54 (t, J=8.5 Hz, 1H), 7.48-7.43 (m, 1H), 7.36 (dd, J=10.4, 2.4 Hz, 1H), 7.20 (dd, J=8.2, 2.4 Hz, 1H), 6.64 (d, J=5.3 Hz, 1H), 4.03 (s, 3H), 3.71 (s, 2H), 1.49 (s, 9H), 1.32 (s, 9H).

Example 10a—Synthesis of 4-(4-(2-((1-(tert-butyl)-1H-pyrazol-4-yl)amino)-2-oxoethyl)-2-methylphenoxy)-7-fluoro-N-methylquinoline-6-carboxamide (Compound 490); Prepared According to General Scheme 8

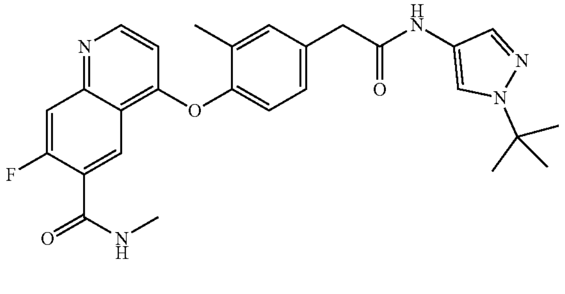 [SMILES: CNC(=O)c1cc2c(Oc3ccc(CC(=O)Nc4cnn(C(C)(C)C)c4)cc3C)ccnc2cc1F]

Part I—Synthesis of methyl 4-(((2,2-dimethyl-4,6-dioxo-1,3-dioxan-5-ylidene)methyl)amino)-2-fluorobenzoate

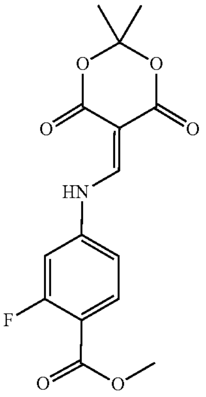 [SMILES: COC(=O)c1ccc(NC=C2C(=O)OC(C)(C)OC2=O)cc1F]

A solution of Meldrum's acid (22.0 g, 153 mmol, 1.00 equiv.) and methyl 4-amino-2-fluorobenzoate (29.7 g, 176 mmol, 1.15 equiv.) in triethyl orthoformate (220 mL) was heated to 105° C. for 2 h. Subsequently, the precipitated product was filtered off, washed with MeOH (3×20 mL) and dried under reduced pressure. The title compound was obtained as a brown solid (44 g, 89%), which was used in the next reaction without further purification.

Part II—Synthesis of methyl 7-fluoro-4-oxo-1,4-dihydroquinoline-6-carboxylate

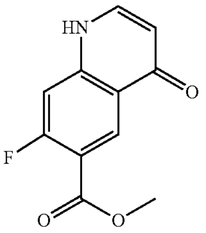 [SMILES: COC(=O)c1cc2c(=O)cc[nH]c2cc1F]

A solution of methyl 4-(((2,2-dimethyl-4,6-dioxo-1,3-dioxan-5-ylidene)methyl)amino)-2-fluorobenzoate (20.0 g, 61.9 mmol, 1.00 equiv.) in diphenyl ether (100 mL) was heated to 230° C. for 1 h. Subsequently, the precipitated product was filtered off, washed with hexane (3×100 mL), and dried under reduced pressure. The title compound was obtained as a brown solid (12 g, 88%), which was used in the next reaction without further purification.

Part III—Synthesis of methyl 4-chloro-7-fluoroquinoline-6-carboxylate

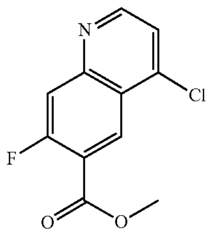 [SMILES: COC(=O)c1cc2c(Cl)ccnc2cc1F]

A solution of methyl 7-fluoro-4-oxo-1,4-dihydroquinoline-6-carboxylate (10.0 g, 45.2 mmol, 1.00 equiv.) in phosphoryl chloride (30 mL) was heated to 110° C. for 1 h. Subsequently, the reaction mixture was quenched carefully with water and the pH of the solution was brought to 8 through addition of an aqueous, saturated $Na_2CO_3$ solution. The product was extracted with EtOAc (3×200 mL). The combined organic phases were washed with brine (200 mL), dried over $Na_2SO_4$, and the solvent was removed under reduced pressure. The crude product was purified by column chromatography (petroleum ether/EtOAc 10:1). The title compound was obtained as a yellow solid (1.2 g, 11% yield).

Part IV—Synthesis of methyl 4-(4-(2-((1-(tert-butyl)-1H-pyrazol-4-yl)amino)-2-oxoethyl)-2-methylphenoxy)-7-fluoroquinoline-6-carboxylate

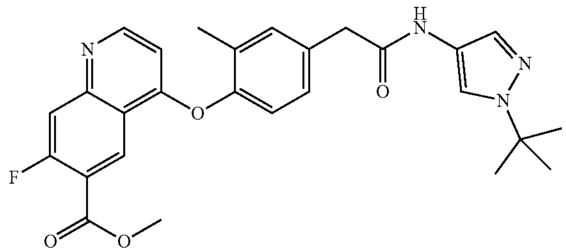 [SMILES: COC(=O)c1cc2c(Oc3ccc(CC(=O)Nc4cnn(C(C)(C)C)c4)cc3C)ccnc2cc1F]

A solution of methyl 4-chloro-7-fluoroquinoline-6-carboxylate (1.00 g, 4.17 mmol, 1.00 equiv.), N-(1-(tert-butyl)-1H-pyrazol-4-yl)-2-(4-hydroxy-3-methylphenyl)acetamide (1.20 g, 4.17 mmol, 1.00 equiv.), and $Cs_2CO_3$ (7.72 g, 8.35 mmol, 2.00 equiv.) in DMA (10 mL) was stirred at room temperature for 5 h. Subsequently, the crude product was purified by reversed-phase flash chromatography (column: C18 silica gel; mobile phase A: water (0.1% TFA), mobile phase B: ACN, gradient: 10-80% B in 50 min; wavelength: 254 nm). The title compound was obtained as a yellow solid (1.5 g, 73%).

Part V—Synthesis of 4-(4-(2-((1-(tert-butyl)-1H-pyrazol-4-yl)amino)-2-oxoethyl)-2-methylphenoxy)-7-fluoro-N-methylquinoline-6-carboxamide (Compound 490)

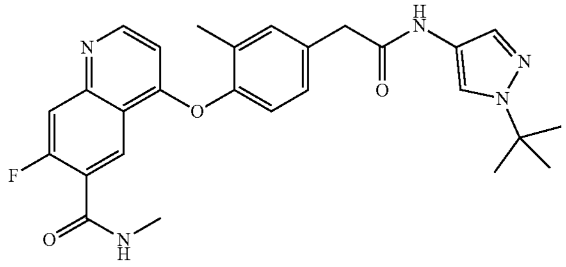 [SMILES: CNC(=O)c1cc2c(Oc3ccc(CC(=O)Nc4cnn(C(C)(C)C)c4)cc3C)ccnc2cc1F]

A solution of methylamine in MeOH (30%, 1.75 mL) was added to a solution of methyl 4-(4-(2-((1-(tert-butyl)-1H-pyrazol-4-yl)amino)-2-oxoethyl)-2-methylphenoxy)-7-fluoroquinoline-6-carboxylate (350 mg, 714 μmol, 1.00 equiv.) in MeOH (1.75 mL) and the mixture was stirred at room temperature for 3 h. Subsequently, the crude product was purified by reversed-phase flash chromatography (column: C18 silica gel; mobile phase A: water (0.100 TFA), mobile phase B: ACN, gradient: 10-50% B in 30 min; wavelength: 254 nm). The title compound was obtained as a white solid (137 g, 390%). LCMS (ESI) calculated for $C_{27}H_{29}FN_5O_3$ $(M+H)^+$: 490.2, found: 490.2. $^1H$ NMR (300 MHz, DMSO-$d_6$) δ 10.20 (s, 1H), 8.72 (d, J=5.2 Hz, 1H), 8.62 (d, J=7.8 Hz, 1H), 8.56 (d, J=4.8 Hz, 1H), 7.95 (d, J=0.7 Hz, 1H), 7.86 (d, J=11.8 Hz, 1H), 7.46 (d, J=0.7 Hz, 1H), 7.38 (d, J=2.1 Hz, 1H), 7.30 (dd, J=8.2, 2.2 Hz, 1H), 7.19 (d, J=8.2 Hz, 1H), 6.42 (d, J=5.2 Hz, 1H), 3.61 (s, 2H), 2.85 (d, J=4.6 Hz, 3H), 2.12 (s, 3H), 1.49 (s, 9H).

Example 11—Preparation of Additional 7-Substituted Quinoline and Quinazoline Compounds Compounds in the table below were prepared based on experimental procedures described in Examples 9, 10, and 10a and the detailed description.

| No. | Structure | Name | $^1H$ NMR | Observed m/z |
|---|---|---|---|---|
| 39 | 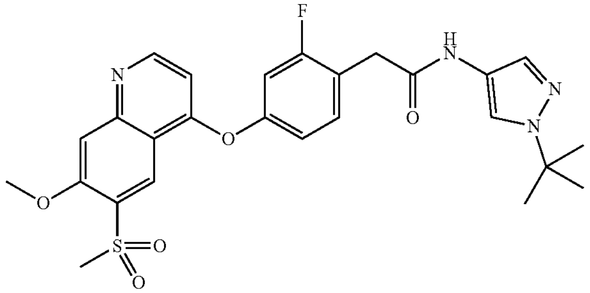 [SMILES: COc1cc2nccc(Oc3ccc(CC(=O)Nc4cnn(C(C)(C)C)c4)c(F)c3)c2cc1S(C)(=O)=O] | N-(1-(tert-butyl)-1H-pyrazol-4-yl)-2-(2-fluoro-4-((7-methoxy-6-(methylsulfonyl)quinolin-4-yl)oxy)phenyl)acetamide | (300 MHz, DMSO-$d_6$) δ 10.23 (s, 1H), 8.81 (d, J = 5.3 Hz, 1H), 8.78 (s, 1H), 7.94 (s, 1H), 7.71 (s, 1H), 7.56 (t, J = 8.5 Hz, 1H), 7.46 (s, 1H), 7.35 (dd, J = 10.3, 2.4 Hz, 1H), 7.24-7.14 (m, 1H), 6.65 (d, J = 5.3 Hz, 1H), 4.12 (s, 3H), 3.72 (s, 2H), 3.39 (s, 3H), 1.49 (s, 9H) | 527.0 $(M + H)^+$ |

-continued

| No. | Structure | Name | $^1$H NMR | Observed m/z |
|---|---|---|---|---|
| 216 | 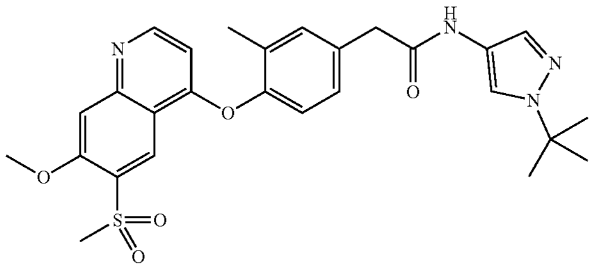 [SMILES: COc1cc2nccc(Oc3ccc(CC(=O)Nc4cnn(C(C)(C)C)c4)cc3C)c2cc1S(C)(=O)=O] | N-(1-(tert-butyl)-1H-pyrazol-4-yl)-2-(4-((7-methoxy-6-(methylsulfonyl)quinolin-4-yl)oxy)-3-methylphenyl) acetamide | (400 MHz, DMSO-$d_6$) δ 10.22 (s, 1H), 8.84 (s, 1H), 8.74 (d, J = 5.2 Hz, 1H), 7.95 (s, 1H), 7.69 (s, 1H), 7.46 (s, 1H), 7.38 (d, J = 2.2 Hz, 1H), 7.31 (dd, J = 8.2, 2.2 Hz, 1H), 7.21 (d, J = 8.2 Hz, 1H), 6.37 (d, J = 5.3 Hz, 1H), 4.12 (s, 3H), 3.61 (s, 2H), 3.40 (s, 3H), 2.12 (s, 3H), 1.49 (s, 9H) | 523.3 $(M + H)^+$ |
| 217 | 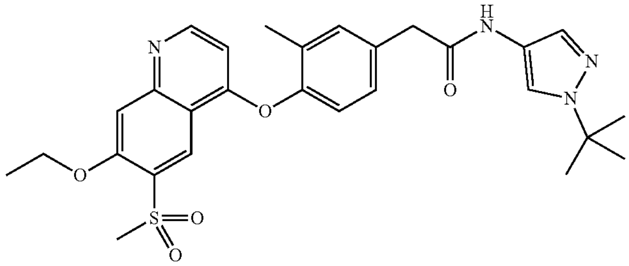 [SMILES: CCOc1cc2nccc(Oc3ccc(CC(=O)Nc4cnn(C(C)(C)C)c4)cc3C)c2cc1S(C)(=O)=O] | N-(1-(tert-butyl)-1H-pyrazol-4-yl)-2-(4-((7-ethoxy-6-(methylsulfonyl) quinolin-4-yl)oxy)-3-methylphenyl) acetamide | (300 MHz, DMSO-$d_6$) δ 10.21 (s, 1H), 8.84 (s, 1H), 8.73 (d, J = 5.3 Hz, 1H), 7.95 (s, 1H), 7.67 (s, 1H), 7.46 (s, 1H), 7.38 (s, 1H), 7.31 (d, J = 8.1 Hz, 1H), 7.21 (d, J = 8.5 Hz, 1H), 6.36 (d, J = 5.3 Hz, 1H), 4.40 (g, J = 7.1 Hz, 2H), 3.61 (s, 2H), 3.42 (s, 3H), 2.12 (s, 3H), 1.53-1.44 (m, 12H) | 537.2 $(M + H)^+$ |
| 218 | 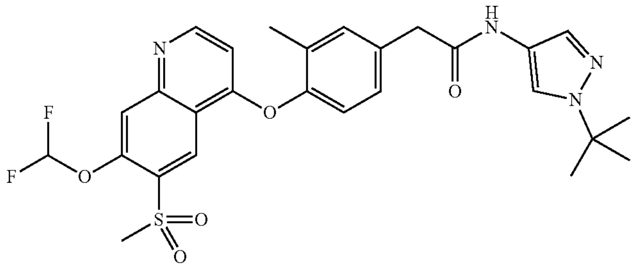 [SMILES: Cc1cc(CC(=O)Nc2cnn(C(C)(C)C)c2)ccc1Oc1ccnc2cc(OC(F)F)c(S(C)(=O)=O)cc12] | N-(1-(tert-butyl)-1H-pyrazol-4-yl)-2-(4-((7-(difluoromethoxy)-6-(methylsulfonyl) quinolin-4-yl)oxy)-3-methylphenyl) acetamide | (400 MHz, DMSO-$d_6$) δ 10.21 (s, 1H), 8.94 (s, 1H), 8.84 (d, J = 5.3 Hz, 1H), 7.96-7.94 (s, 2H), 7.69 (t, J = 72.3 Hz, 1H), 7.46 (s, 1H), 7.39 (d, J = 2.1 Hz, 1H), 7.34-7.21 (m, 2H), 6.52 (d, J = 5.3 Hz, 1H), 3.62 (s, 2H), 3.45 (s, 3H), 2.13 (s, 3H), 1.49 (s, 9H) | 559.0 $(M + H)^+$ |
| 219 | 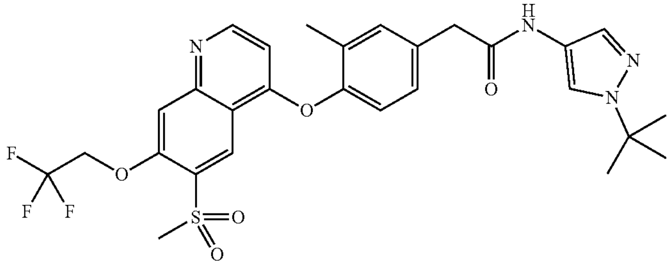 [SMILES: Cc1cc(CC(=O)Nc2cnn(C(C)(C)C)c2)ccc1Oc1ccnc2cc(OCC(F)(F)F)c(S(C)(=O)=O)cc12] | N-(1-(tert-butyl)-1H-pyrazol-4-yl)-2-(3-methyl-4-((6-(methylsulfonyl)-7-(2,2,2-trifluoroethoxy) quinolin-4-yl)oxy) phenyl)acetamide | (400 MHz, DMSO-$d_6$) δ 10.21 (s, 1H), 8.88 (s, 1H), 8.78 (d, J = 5.3 Hz, 1H), 7.95 (s, 1H), 7.87 (s, 1H), 7.46 (s, 1H), 7.39 (d, J = 2.1 Hz, 1H), 7.31 (dd, J = 8.3, 2.2 Hz, 1H), 7.22 (d, J = 8.2 Hz, 1H), 6.42 (d, J = 5.3 Hz, 1H), 5.22 (q, J = 8.7 Hz, 2H), 3.61 (s, 2H), 3.40 (s, 3H), 2.12 (s, 3H), 1.49 (s, 9H) | 591.2 $(M + H)^+$ |

-continued

| No. | Structure | Name | $^1$H NMR | Observed m/z |
|---|---|---|---|---|
| 412 | 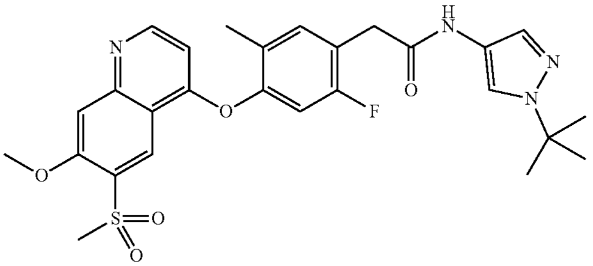 [SMILES: COc1cc2nccc(Oc3cc(F)c(CC(=O)Nc4cnn(C(C)(C)C)c4)cc3C)c2cc1S(C)(=O)=O] | N-(1-(tert-butyl)-1H-pyrazol-4-yl)-2-(2-fluoro-4-((7-methoxy-6-(methylsulfonyl) quinolin-4-yl)oxy)-5-methylphenyl) acetamide | | 541.1 $(M + H)^+$ |
| 465 | 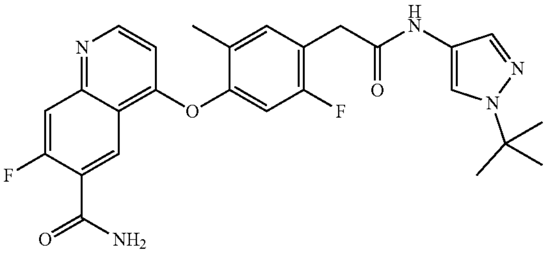 [SMILES: Cc1cc(CC(=O)Nc2cnn(C(C)(C)C)c2)c(F)cc1Oc1ccnc2cc(F)c(C(N)=O)cc12] | 4-(4-(2-((1-(tert-butyl)-1H-pyrazol-4-yl)amino)-2-oxoethyl)-5-fluoro-2-methylphenoxy)-7-fluoroquinoline-6-carboxamide | (300 MHz, DMSO-$d_6$) δ 10.21 (s, 1H), 8.75 (d, J = 5.4 Hz, 1H), 8.65 (d, J = 7.8 Hz, 1H), 8.03 (s, 1H), 7.94 (s, 1H), 7.89-7.85 (m, 2H), 7.46-7.43 (m, 2H), 7.25 (d, J = 1.8 Hz, 1H), 6.51 (d, J = 4.8 Hz, 1H), 3.68 (s, 2H), 2.10 (s, 3H), 1.49 (s, 9H) | 494.3 $(M + H)^+$ |
| 489 | 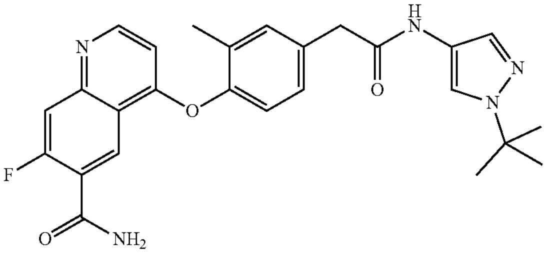 [SMILES: Cc1cc(CC(=O)Nc2cnn(C(C)(C)C)c2)ccc1Oc1ccnc2cc(F)c(C(N)=O)cc12] | 4-(4-(2-((1-(tert-butyl)-1H-pyrazol-4-yl)amino)-2-oxoethyl)-2-methylphenoxy)-7-fluoroquinoline-6-carboxamide | (400 MHz, DMSO-$d_6$) δ 10.19 (s, 1H), 8.72-8.66 (m, 2H), 8.02 (s, 1H), 7.95 (s, 1H), 7.86-7.83 (m, 2H), 7.45 (s, 1H), 7.37 (d, J = 2.2 Hz, 1H), 7.30 (dd, J = 8.2, 2.2 Hz, 1H), 7.20 (d, J = 8.2 Hz, 1H), 6.42 (d, J = 5.2 Hz, 1H), 3.61 (s, 2H), 2.12 (s, 3H), 1.49 (s, 9H) | 476.2 $(M + H)^+$ |
| 493 | 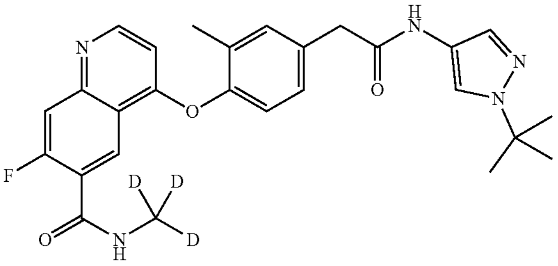 [SMILES: [2H]C([2H])([2H])NC(=O)c1cc2c(Oc3ccc(CC(=O)Nc4cnn(C(C)(C)C)c4)cc3C)ccnc2cc1F] | 4-(4-(2-((1-(tert-butyl)-1H-pyrazol-4-yl)amino)-2-oxoethyl)-2-methylphenoxy)-7-fluoro-N-(methyl-$d_3$)quinoline-6-carboxamide | (400 MHz, DMSO-$d_6$) δ 10.20 (s, 1H), 8.72 (d, J = 5.3 Hz, 1H), 8.62 (d, J = 7.8 Hz, 1H), 8.53 (s, 1H), 7.95 (d, J = 0.7 Hz, 1H), 7.86 (d, J = 11.8 Hz, 1H), 7.45 (d, J = 0.7 Hz, 1H), 7.37 (d, J = 2.2 Hz, 1H), 7.30 (dd, J = 8.3, 2.2 Hz, 1H), 7.19 (d, J = 8.2 Hz, 1H), 6.42 (d, J = 5.2 Hz, 1H), 3.61 (s, 2H), 2.12 (s, 3H), 1.49 (s, 9H) | 493.3 $(M + H)^+$ |
| 494 | 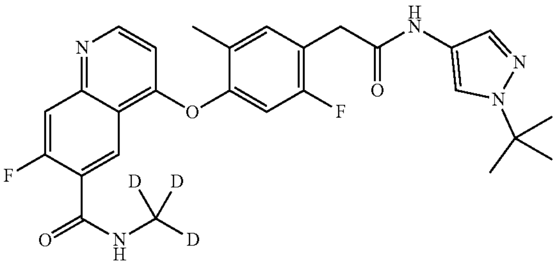 [SMILES: [2H]C([2H])([2H])NC(=O)c1cc2c(Oc3cc(F)c(CC(=O)Nc4cnn(C(C)(C)C)c4)cc3C)ccnc2cc1F] | 4-(4-(2-((1-(tert-butyl)-1H-pyrazol-4-yl)amino)-2-oxoethyl)-5-fluoro-2-methylphenoxy)-7-fluoro-N-(methyl-$d_3$)quinoline-6-carboxamide | (300 MHz, DMSO-$d_6$) δ 10.22 (s, 1H), 8.75 (d, J = 5.2 Hz, 1H), 8.61 (d, J = 7.8 Hz, 1H), 8.54 (s, 1H), 7.94 (d, J = 0.8 Hz, 1H), 7.87 (d, J = 11.8 Hz, 1H), 7.49-7.40 (m, 2H), 7.24 (d, J = 10.0 Hz, 1H), 6.51 (d, J = 5.3 Hz, 1H), 3.68 (s, 2H), 2.10 (s, 3H), 1.49 (s, 9H) | 511.3 $(M + H)^+$ |

-continued

| No. | Structure | Name | $^1$H NMR | Observed m/z |
|---|---|---|---|---|
| 495 | 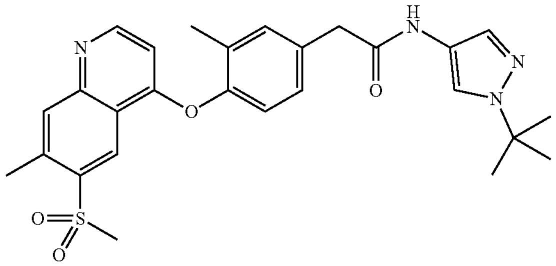 [SMILES: Cc1cc(CC(=O)Nc2cnn(C(C)(C)C)c2)ccc1Oc1ccnc2cc(C)c(S(C)(=O)=O)cc12] | N-(1-(tert-butyl)-1H-pyrazol-4-yl)-2-(3-methyl-4-((7-methyl-6-(methylsulfonyl)quinolin-4-yl)oxy)phenyl)acetamide | (300 MHz, DMSO-$d_6$) δ 10.21 (s, 1H), 8.95 (s, 1H), 8.79 (d, J = 5.2 Hz, 1H), 8.10 (s, 1H), 7.96 (s, 1H), 7.46 (s, 1H), 7.39 (s, 1H), 7.36-7.27 (m, 1H), 7.22 (d, J = 8.3 Hz, 1H), 6.47 (d, J = 5.2 Hz, 1H), 3.62 (s, 2H), 3.39 (s, 3H), 2.86 (s, 3H), 2.13 (s, 3H), 1.49 (s, 9H) | 507.2 $(M + H)^+$ |
| 496 | 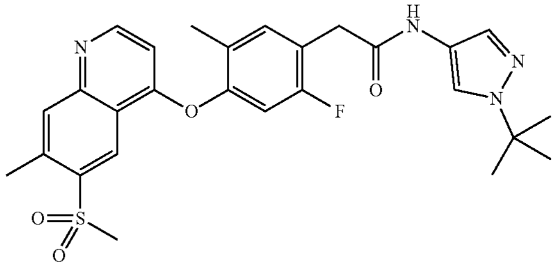 [SMILES: Cc1cc(CC(=O)Nc2cnn(C(C)(C)C)c2)c(F)cc1Oc1ccnc2cc(C)c(S(C)(=O)=O)cc12] | N-(1-(tert-butyl)-1H-pyrazol-4-yl)-2-(2-fluoro-5-methyl-4-((7-methyl-6-(methylsulfonyl)quinolin-4-yl)oxy)phenyl)acetamide | (300 MHz, DMSO-$d_6$) δ 10.23 (s, 1H), 8.94 (s, 1H), 8.83 (d, J = 5.2 Hz, 1H), 8.11 (s, 1H), 7.95 (s, 1H), 7.51-7.42 (m, 2H), 7.28 (d, J = 10.0 Hz, 1H), 6.56 (d, J = 5.2 Hz, 1H), 3.69 (s, 2H), 3.35 (s, 3H), 2.86 (s, 3H), 2.10 (s, 3H), 1.49 (s, 9H) | 525.2 $(M + H)^+$ |
| 564 | 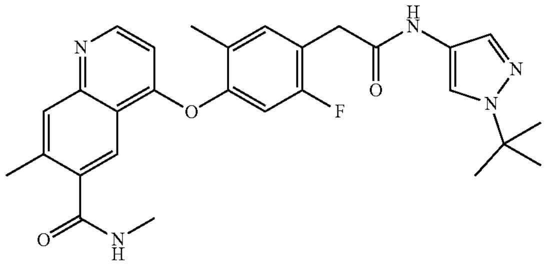 [SMILES: CNC(=O)c1cc2c(Oc3cc(F)c(CC(=O)Nc4cnn(C(C)(C)C)c4)cc3C)ccnc2cc1C] | 4-(4-(2-((1-(tert-butyl)-1H-pyrazol-4-yl)amino)-2-oxoethyl)-5-fluoro-2-methylphenoxy)-N,7-dimethylquinoline-6-carboxamide | (400 MHz, DMSO-$d_6$) δ 10.25 (s, 1H), 8.68 (d, J = 5.2 Hz, 1H), 8.52 (q, J = 4.6 Hz, 1H), 8.28 (s, 1H), 7.95 (s, 1H), 7.89 (s, 1H), 7.46-7.43 (m, 2H), 7.19 (d, J = 9.9 Hz, 1H), 6.46 (d, J = 5.2 Hz, 1H), 3.68 (s, 2H), 2.82 (d, J = 4.5 Hz, 3H), 2.55 (s, 3H), 2.09 (s, 3H), 1.49 (s, 9H) | 504.1 $(M + H)^+$ |
| 565 | 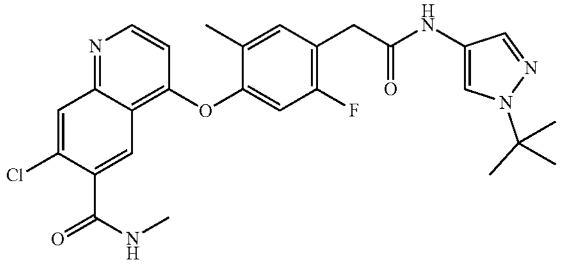 [SMILES: CNC(=O)c1cc2c(Oc3cc(F)c(CC(=O)Nc4cnn(C(C)(C)C)c4)cc3C)ccnc2cc1Cl] | 4-(4-(2-((1-(tert-butyl)-1H-pyrazol-4-yl)amino)-2-oxoethyl)-5-fluoro-2-methylphenoxy)-7-chloro-N-methylquinoline-6-carboxamide | (400 MHz, DMSO-$d_6$) δ 10.23 (s, 1H), 8.76 (d, J = 5.2 Hz, 1H), 8.64 (q, J = 4.6 Hz, 1H), 8.37 (s, 1H), 8.17 (s, 1H), 7.95 (s, 1H), 7.46-7.44 (m, 2H), 7.23 (d, J = 9.9 Hz, 1H), 6.56 (d, J = 5.2 Hz, 1H), 3.68 (s, 2H), 2.83 (d, J = 4.6 Hz, 3H), 2.10 (s, 3H), 1.49 (s, 9H) | 524.1 $(M + H)^+$ |
| 581 | 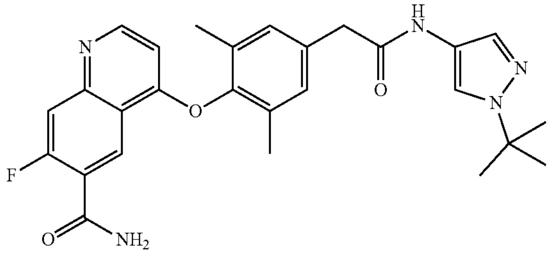 [SMILES: Cc1cc(CC(=O)Nc2cnn(C(C)(C)C)c2)cc(C)c1Oc1ccnc2cc(F)c(C(N)=O)cc12] | 4-(4-(2-((1-(tert-butyl)-1H-pyrazol-4-yl)amino)-2-oxoethyl)-2,6-dimethylphenoxy)-7-fluoroquinoline-6-carboxamide | (300 MHz, DMSO-$d_6$) δ 10.17 (s, 1H), 8.75-8.66 (m, 2H), 8.03 (s, 1H), 7.95 (d, J = 0.7 Hz, 1H), 7.87-7.83 (m, 2H), 7.45 (d, J = 0.7 Hz, 1H), 7.19 (s, 2H), 6.31 (d, J = 5.2 Hz, 1H), 3.56 (s, 2H), 2.07 (s, 6H), 1.49 (s, 9H) | 490.3 $(M + H)^+$ |

-continued

| No. | Structure | Name | $^1$H NMR | Observed m/z |
|---|---|---|---|---|
| 582 | 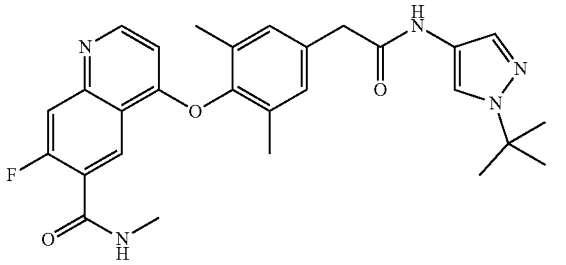 [SMILES: CNC(=O)c1cc2c(Oc3c(C)cc(CC(=O)Nc4cnn(C(C)(C)C)c4)cc3C)ccnc2cc1F] | 4-(4-(2-((1-(tert-butyl)-1H-pyrazol-4-yl)amino)-2-oxoethyl)-2,6-dimethylphenoxy)-7-fluoro-N-methylquinoline-6-carboxamide | (300 MHz, DMSO-$d_6$) δ 10.17 (s, 1H), 8.73-8.61 (m, 2H), 8.56 (s, 1H), 7.95 (d, J = 0.7 Hz, 1H), 7.86 (d, J = 11.8 Hz, 1H), 7.45 (d, J = 0.7 Hz, 1H), 7.19 (s, 2H), 6.31 (d, J = 5.2 Hz, 1H), 3.56 (s, 2H), 2.85 (d, J = 4.6 Hz, 3H), 2.06 (s, 6H), 1.49 (s, 9H) | 504.4 $(M + H)^+$ |
| 583 | 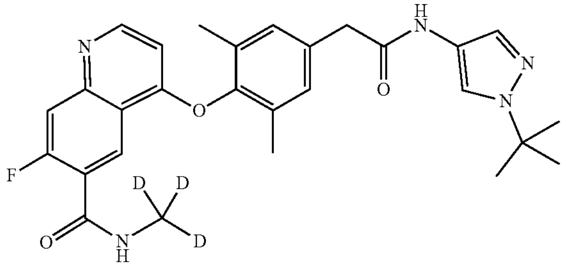 [SMILES: [2H]C([2H])([2H])NC(=O)c1cc2c(Oc3c(C)cc(CC(=O)Nc4cnn(C(C)(C)C)c4)cc3C)ccnc2cc1F] | 4-(4-(2-((1-(tert-butyl)-1H-pyrazol-4-yl)amino)-2-oxoethyl)-2,6-dimethylphenoxy)-7-fluoro-N-(methyl-$d_3$)quinoline-6-carboxamide | (300 MHz, DMSO-$d_6$) δ 10.19 (s, 1H), 8.74-8.62 (m, 2H), 8.55 (s, 1H), 7.96 (d, J = 0.8 Hz, 1H), 7.87 (d, J = 11.8 Hz, 1H), 7.46 (d, J = 0.7 Hz, 1H), 7.20 (s, 2H), 6.31 (d, J = 5.2 Hz, 1H), 3.57 (s, 2H), 2.07 (s, 6H), 1.49 (s, 9H) | 507.4 $(M + H)^+$ |
| 584 | 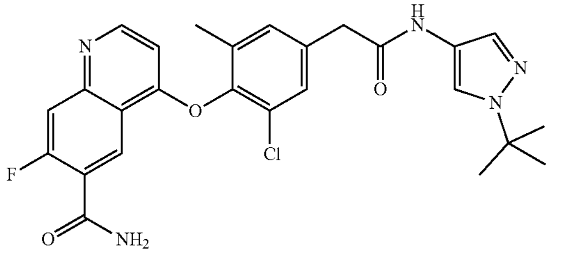 [SMILES: Cc1cc(CC(=O)Nc2cnn(C(C)(C)C)c2)cc(Cl)c1Oc1ccnc2cc(F)c(C(N)=O)cc12] | 4-(4-(2-((1-(tert-butyl)-1H-pyrazol-4-yl)amino)-2-oxoethyl)-2-chloro-6-methylphenoxy)-7-fluoroquinoline-6-carboxamide | (300 MHz, DMSO-$d_6$) δ 10.24 (s, 1H), 8.71 (dd, J = 14.7, 6.5 Hz, 2H), 8.06 (s, 1H), 7.96 (s, 1H), 7.91-7.87 (m, 2H), 7.49-7.47 (m, 2H), 7.36 (d, J = 2.1 Hz, 1H), 6.40 (d, J = 5.2 Hz, 1H), 3.65 (s, 2H), 2.16 (s, 3H), 1.49 (s, 9H) | 510.2 $(M + H)^+$ |
| 585 | 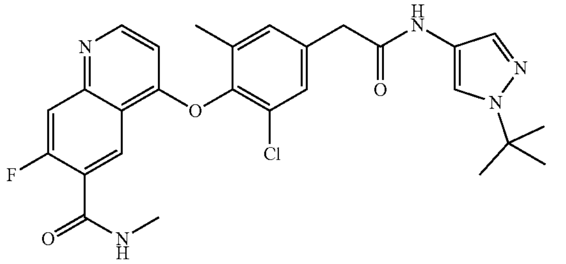 [SMILES: CNC(=O)c1cc2c(Oc3c(C)cc(CC(=O)Nc4cnn(C(C)(C)C)c4)cc3Cl)ccnc2cc1F] | 4-(4-(2-((1-(tert-butyl)-1H-pyrazol-4-yl)amino)-2-oxoethyl)-2-chloro-6-methylphenoxy)-7-fluoro-N-methylquinoline-6-carboxamide | (300 MHz, DMSO-$d_6$) δ 10.24 (s, 1H), 8.74 (d, J = 5.2 Hz, 1H), 8.66-8.59 (m, 2H), 7.96 (d, J = 0.7 Hz, 1H), 7.90 (d, J = 11.7 Hz, 1H), 7.50-7.47 (m, 2H), 7.39-7.34 (m, 1H), 6.40 (d, J = 5.2 Hz, 1H), 3.65 (s, 2H), 2.85 (d, J = 4.6 Hz, 3H), 2.16 (s, 3H), 1.49 (s, 9H) | 524.2 $(M + H)^+$ |
| 586 | 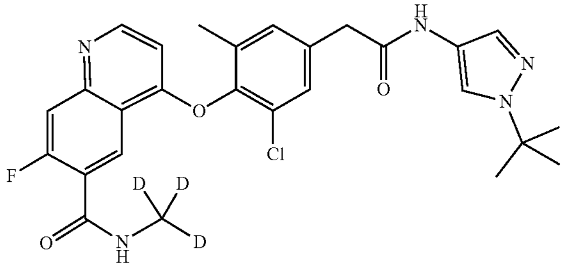 [SMILES: [2H]C([2H])([2H])NC(=O)c1cc2c(Oc3c(C)cc(CC(=O)Nc4cnn(C(C)(C)C)c4)cc3Cl)ccnc2cc1F] | 4-(4-(2-((1-(tert-butyl)-1H-pyrazol-4-yl)amino)-2-oxoethyl)-2-chloro-6-methylphenoxy)-7-fluoro-N-(methyl-$d_3$)quinoline-6-carboxamide | (300 MHz, DMSO-$d_6$) δ 10.24 (s, 1H), 8.74 (d, J = 5.2 Hz, 1H), 8.65 (d, J = 7.7 Hz, 1H), 8.57 (s, 1H), 7.96 (s, 1H), 7.90 (d, J = 11.8 Hz, 1H), 7.50-7.47 (m, 2H), 7.36 (d, J = 2.0 Hz, 1H), 6.40 (d, J = 5.2 Hz, 1H), 3.65 (s, 2H), 2.16 (s, 3H), 1.49 (s, 9H) | 527.3 $(M + H)^+$ |

-continued

| No. | Structure | Name | $^1$H NMR | Observed m/z |
|---|---|---|---|---|
| 596 | 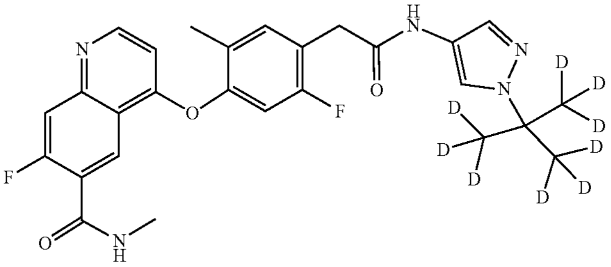 [SMILES: [2H]C([2H])([2H])C(n1cc(NC(=O)Cc2cc(C)c(Oc3ccnc4cc(F)c(C(=O)NC)cc34)cc2F)cn1)(C([2H])([2H])[2H])C([2H])([2H])[2H]] | 7-fluoro-4-(5-fluoro-2-methyl-4-(2-((1-(2-(methyl-d$_3$)propan-2-yl-1,1,1,3,3,3-d$_6$)-1H-pyrazol-4-yl)amino)-2-oxoethyl)phenoxy)-N-methylquinoline-6-carboxamide | (300 MHz, DMSO-d$_6$) δ 10.23 (s, 1H), 8.76 (d, J = 5.2 Hz, 1H), 8.63-8.59 (m, 2H), 7.97-7.83 (m, 2H), 7.46-7.44 (m, 2H), 7.25 (d, J = 10.0 Hz, 1H), 6.52 (d, J = 5.2 Hz, 1H), 3.68 (s, 2H), 2.85 (d, J = 4.6 Hz, 3H), 2.10 (s, 3H) | 517.2 (M + H)$^+$ |
| 598 | 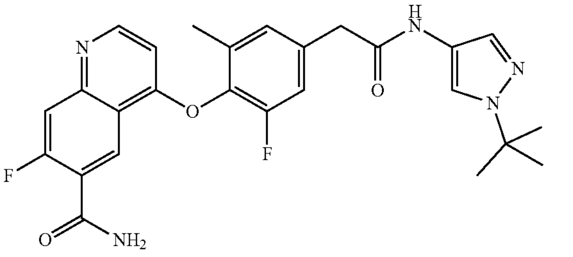 [SMILES: Cc1cc(CC(=O)Nc2cnn(C(C)(C)C)c2)cc(F)c1Oc1ccnc2cc(F)c(C(N)=O)cc12] | 4-(4-(2-((1-(tert-butyl)-1H-pyrazol-4-yl)amino)-2-oxoethyl)-2-fluoro-6-methylphenoxy)-7-fluoroquinoline-6-carboxamide | (400 MHz, DMSO-d$_6$) δ 10.22 (s, 1H), 8.75 (d, J = 5.2 Hz, 1H), 8.67 (d, J = 7.8 Hz, 1H), 8.07 (s, 1H), 7.96 (s, 1H), 7.90-7.87 (m, 2H), 7.46 (s, 1H), 7.29 (dd, J = 11.0, 2.0 Hz, 1H), 7.22 (s, 1H), 6.54-6.49 (m, 1H), 3.64 (s, 2H), 2.18 (s, 3H), 1.49 (s, 9H) | 494.1 (M + H)$^+$ |
| 599 | 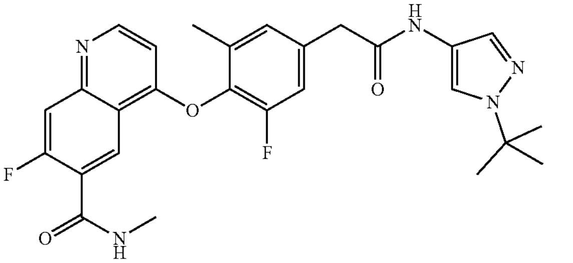 [SMILES: CNC(=O)c1cc2c(Oc3c(C)cc(CC(=O)Nc4cnn(C(C)(C)C)c4)cc3F)ccnc2cc1F] | 4-(4-(2-((1-(tert-butyl)-1H-pyrazol-4-yl)amino)-2-oxoethyl)-2-fluoro-6-methylphenoxy)-7-fluoro-N-methylquinoline-6-carboxamide | (400 MHz, DMSO-d$_6$) δ 10.22 (s, 1H), 8.75 (d, J = 5.2 Hz, 1H), 8.64-8.59 (m, 2H), 7.96 (s, 1H), 7.89 (d, J = 11.7 Hz, 1H), 7.46 (s, 1H), 7.29 (dd, J = 10.9, 2.1 Hz, 1H), 7.22 (s, 1H), 6.51 (dd, J = 5.2, 1.2 Hz, 1H), 3.64 (s, 2H), 2.85 (d, J = 4.6 Hz, 3H), 2.18 (s, 3H), 1.49 (s, 9H) | 508.1 (M + H)$^+$ |
| 600 | 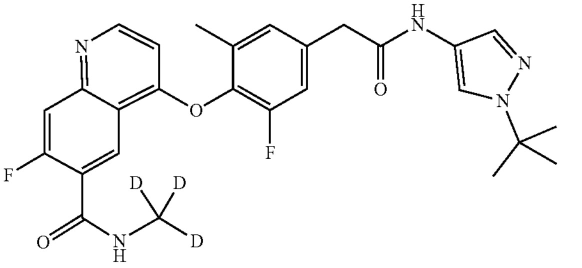 [SMILES: [2H]C([2H])([2H])NC(=O)c1cc2c(Oc3c(C)cc(CC(=O)Nc4cnn(C(C)(C)C)c4)cc3F)ccnc2cc1F] | 4-(4-(2-((1-(tert-butyl)-1H-pyrazol-4-yl)amino)-2-oxoethyl)-2-fluoro-6-methylphenoxy)-7-fluoro-N-(methyl-d$_3$)quinoline-6-carboxamide | (300 MHz, DMSO-d$_6$) δ 10.24 (s, 1H), 8.75 (d, J = 5.0 Hz, 1H), 8.64 (d, J = 7.7 Hz, 1H), 8.58 (s, 1H), 7.96 (s, 1H), 7.90 (d, J = 11.7 Hz, 1H), 7.47 (s, 1H), 7.29 (d, J = 10.9 Hz, 1H), 7.22 (s, 1H), 6.52 (d, J = 5.1 Hz, 1H), 3.65 (s, 2H), 2.18 (s, 3H), 1.20 (s, 9H) | 511.2 (M + H)$^+$ |
| 601 | 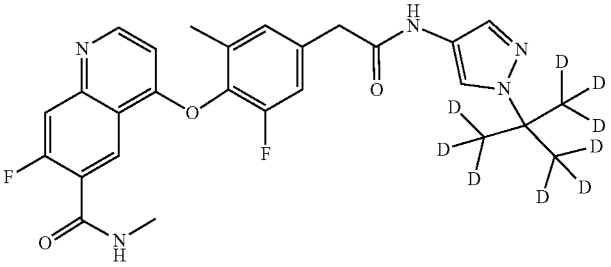 [SMILES: [2H]C([2H])([2H])C(n1cc(NC(=O)Cc2cc(C)c(Oc3ccnc4cc(F)c(C(=O)NC)cc34)c(F)c2)cn1)(C([2H])([2H])[2H])C([2H])([2H])[2H]] | 7-fluoro-4-(2-fluoro-6-methyl-4-(2-((1-(2-(methyl-d$_3$)propan-2-yl-1,1,1,3,3,3-d$_6$)-1H-pyrazol-4-yl)amino)-2-oxoethyl)phenoxy)-N-methylquinoline-6-carboxamide | (300 MHz, DMSO-d$_6$) δ 10.23 (s, 1H), 8.75 (d, J = 5.2 Hz, 1H), 8.65-8.60 (m, 2H), 7.95-7.90 (m, 2H), 7.47 (s, 1H), 7.29 (dd, J = 11.0, 2.0 Hz, 1H), 7.22 (s, 1H), 6.51 (dd, J = 5.2, 1.2 Hz, 1H), 3.65 (s, 2H), 2.85 (d, J = 4.5 Hz, 3H), 2.18 (s, 3H) | 517.2 (M + H)$^+$ |

-continued

| No. | Structure | Name | $^1$H NMR | Observed m/z |
|---|---|---|---|---|
| 602 | 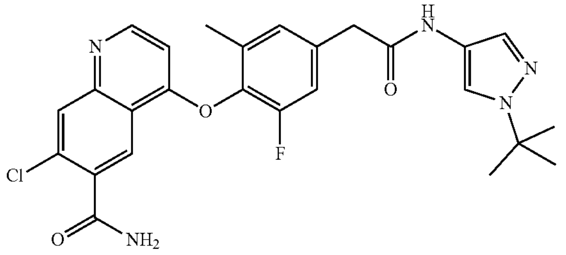 [SMILES: Cc1cc(CC(=O)Nc2cnn(C(C)(C)C)c2)cc(F)c1Oc1ccnc2cc(Cl)c(C(N)=O)cc12] | 4-(4-(2-((1-(tert-butyl)-1H-pyrazol-4-yl)amino)-2-oxoethyl)-2-fluoro-6-methylphenoxy)-7-chloroquinoline-6-carboxamide | (400 MHz, DMSO-$d_6$) δ 10.21 (s, 1H), 8.75 (d, J = 5.2 Hz, 1H), 8.42 (s, 1H), 8.19-8.17 (m, 2H), 7.96 (d, J = 0.7 Hz, 1H), 7.80 (s, 1H), 7.47 (d, J = 0.7 Hz, 1H), 7.29 (dd, J = 11.0, 2.0 Hz, 1H), 7.22 (s, 1H), 6.56 (dd, J = 5.2, 1.3 Hz, 1H), 3.64 (s, 2H), 2.18 (s, 3H), 1.50 (s, 9H) | 510.1 $(M + H)^+$ |
| 608 | 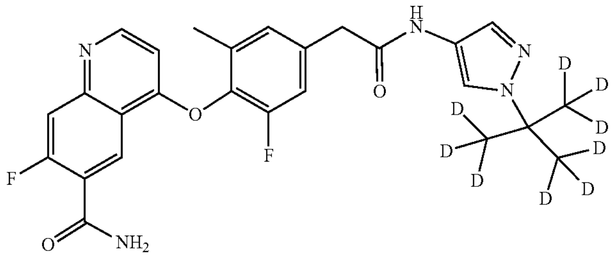 [SMILES: [2H]C([2H])([2H])C(n1cc(NC(=O)Cc2cc(C)c(Oc3ccnc4cc(F)c(C(N)=O)cc34)c(F)c2)cn1)(C([2H])([2H])[2H])C([2H])([2H])[2H]] | 7-fluoro-4-(2-fluoro-6-methyl-4-(2-((1-(2-(methyl-$d_3$)propan-2-yl-1,1,1,3,3,3-$d_6$)-1H-pyrazol-4-yl)amino)-2-oxoethyl)phenoxy)quinoline-6-carboxamide | (400 MHz, DMSO-$d_6$) δ 10.23 (s, 1H), 8.75 (d, J = 5.2 Hz, 1H), 8.68 (d, J = 7.8 Hz, 1H), 8.08 (s, 1H), 7.95 (s, 1H), 7.92-7.86 (m, 2H), 7.46 (s, 1H), 7.29 (dd, J = 11.0, 2.0 Hz, 1H), 7.22 (s, 1H), 6.51 (dd, J = 5.3, 1.2 Hz, 1H), 3.64 (s, 2H), 2.18 (s, 3H) | 503.2 $(M + H)^+$ |
| 617 | 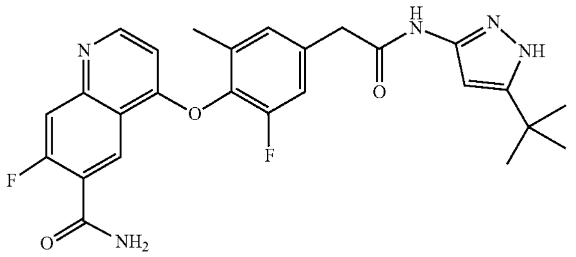 [SMILES: Cc1cc(CC(=O)Nc2cc(C(C)(C)C)[nH]n2)cc(F)c1Oc1ccnc2cc(F)c(C(N)=O)cc12] | 4-(4-(2-((5-(tert-butyl)-1H-pyrazol-3-yl)amino)-2-oxoethyl)-2-fluoro-6-methylphenoxy)-7-fluoroquinoline-6-carboxamide | (300 MHz, DMSO-$d_6$) δ 12.13 (s, 1H), 10.63 (s, 1H), 8.75 (d, J = 5.2 Hz, 1H), 8.68 (d, J = 7.7 Hz, 1H), 8.08 (s, 1H), 7.89 (d, J = 11.7 Hz, 1H), 7.88 (s, 1H), 7.35-7.23 (m, 2H), 6.52 (dd, J = 5.2, 1.2 Hz, 1H), 6.30 (s, 1H), 3.66 (s, 2H), 2.18 (s, 3H), 1.25 (s, 9H) | 494.2 $(M + H)^+$ |
| 618 | 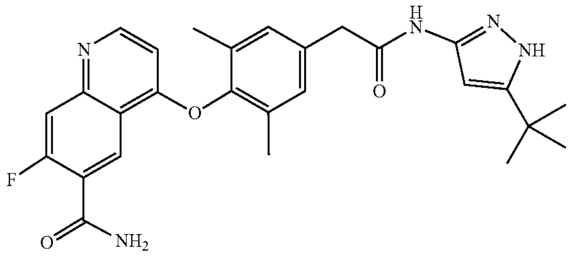 [SMILES: Cc1cc(CC(=O)Nc2cc(C(C)(C)C)[nH]n2)cc(C)c1Oc1ccnc2cc(F)c(C(N)=O)cc12] | 4-(4-(2-((5-(tert-butyl)-1H-pyrazol-3-yl)amino)-2-oxoethyl)-2,6-dimethylphenoxy)-7-fluoroquinoline-6-carboxamide | (300 MHz, DMSO-$d_6$) δ 10.59 (s, 1H), 8.75-8.66 (m, 2H), 8.05 (s, 1H), 7.87-7.83 (m, 2H), 7.21 (s, 2H), 6.36-6.27 (m, 2H), 6.04 (s, 1H), 3.59 (s, 2H), 2.07 (s, 6H), 1.25 (s, 9H) | 490.2 $(M + H)^+$ |
| 611 | 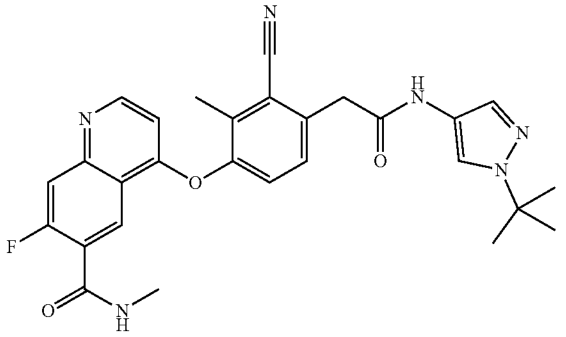 [SMILES: CNC(=O)c1cc2c(Oc3ccc(CC(=O)Nc4cnn(C(C)(C)C)c4)c(C#N)c3C)ccnc2cc1F] | 4-(4-(2-((1-(tert-butyl)-1H-pyrazol-4-yl)amino)-2-oxoethyl)-3-cyano-2-methylphenoxy)-7-fluoro-N-methylquinoline-6-carboxamide | (300 MHz, DMSO-$d_6$) δ 10.36 (s, 1H), 8.76 (d, J = 5.2 Hz, 1H), 8.65-8.59 (m, 2H), 7.98-7.85 (m, 2H), 7.61 (d, J = 8.5 Hz, 1H), 7.57-7.44 (m, 2H), 6.52 (d, J = 5.2 Hz, 1H), 3.93 (s, 2H), 2.85 (d, J = 4.6 Hz, 3H), 2.35 (s, 3H), 1.50 (s, 9H) | 515.2 $(M + H)^+$ |

-continued

| No. | Structure | Name | $^1H$ NMR | Observed m/z |
|---|---|---|---|---|
| 610 | 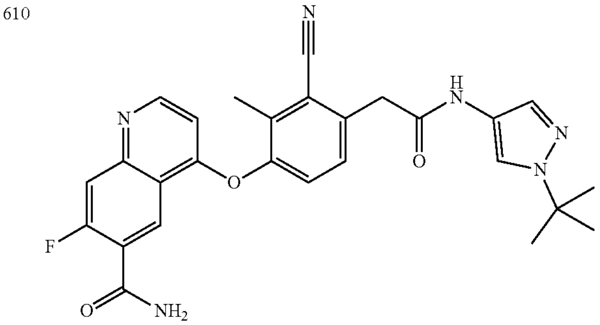 | 4-(4-(2-((1-(tert-butyl)-1H-pyrazol-4-yl)amino)-2-oxoethyl)-3-cyano-2-methylphenoxy)-7-fluoroquinoline-6-carboxamide | (300 MHz, DMSO-$d_6$) δ 10.34 (s, 1H), 8.76 (d, J = 5.2 Hz, 1H), 8.68 (d, J = 7.9 Hz, 1H), 8.05 (s, 1H), 7.95 (d, J = 0.7 Hz, 1H), 7.91-7.87 (m, 2H), 7.61 (d, J = 8.5 Hz, 1H), 7.53 (d, J = 8.4 Hz, 1H), 7.47 (d, J = 0.7 Hz, 1H), 6.52 (d, J = 5.3 Hz, 1H), 3.93 (s, 2H), 2.36 (s, 3H), 1.50 (s, 9H) | 501.2 $(M + H)^+$ |

Example 12—Synthesis of N-(1-(tert-butyl)-1H-pyrazol-4-yl)-2-(3-(difluoromethyl)-4-((6-(methylsulfonyl)quinolin-4-yl)oxy)phenyl)acetamide (Compound 92); Prepared According to General Scheme 7

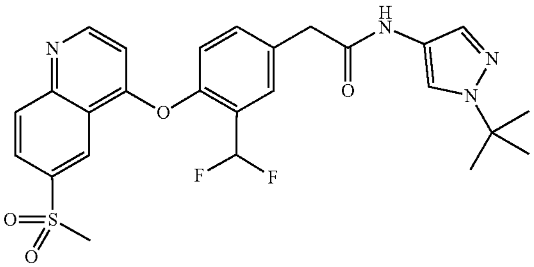 [SMILES: CC(C)(C)n1cc(NC(=O)Cc2ccc(Oc3ccnc4ccc(S(C)(=O)=O)cc34)c(C(F)F)c2)cn1]

Part I—Synthesis of methyl 2-(3-(1,3-dioxolan-2-yl)-4-hydroxyphenyl)acetate

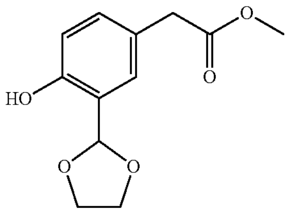 [SMILES: COC(=O)Cc1ccc(O)c(C2OCCO2)c1]

Ethylene glycol (6.39 g, 103 mmol, 4.00 equiv.), triethyl orthoformate (3.01 g, 28.3 mmol, 1.10 equiv.), and tetrabutylammonium tribromide (0.12 g, 0.257 mmol, 0.01 equiv.) were added to a solution of methyl 2-(3-formyl-4-hydroxyphenyl)acetate (5.0 g, 25.7 mmol, 1.0 equiv.) in toluene (50 mL) and the mixture was stirred at room temperature overnight. Subsequently, the reaction was quenched with water/ice (50 mL) and the product was extracted with EtOAc (3×10 mL). The combined organic phases were dried over $Na_2SO_4$, and the solvent was removed under reduced pressure. The crude product was purified by column chromatography (petroleum ether/EtOAc 5:1). The title compound was obtained as a yellow oil (2.8 g, 46%).

Part II—Synthesis of methyl 2-(3-(1,3-dioxolan-2-yl)-4-((6-(methylsulfonyl)quinolin-4-yl)oxy)phenyl) acetate

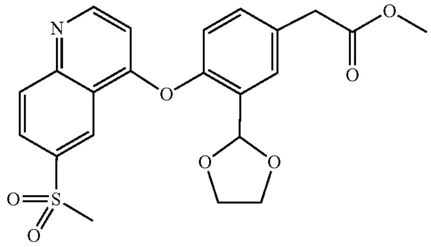 [SMILES: COC(=O)Cc1ccc(Oc2ccnc3ccc(S(C)(=O)=O)cc23)c(C2OCCO2)c1]

4-Chloro-6-(methylsulfonyl)quinoline (1.00 g, 4.18 mmol, 1.00 equiv., can be synthesized as shown in Part II of Example 30) and $Cs_2CO_3$ (2.74 g, 8.39 mmol, 2.00 equiv.) were added to a solution of methyl 2-(3-(1,3-dioxolan-2-yl)-4-hydroxyphenyl)acetate (1.0 g, 4.20 mmol, 1.00 equiv.) in NMP (10 mL) and the mixture was stirred at room temperature for 4 h. Subsequently, the reaction was quenched with water/ice (50 mL) and the product was extracted with EtOAc (3×10 mL). The combined organic phases were dried over $Na_2SO_4$, and the solvent was removed under reduced pressure. The crude product was purified by column chromatography (petroleum ether/EtOAc 1:1). The title compound was obtained as a yellow solid (600 mg, 32%).

Part III—Synthesis of methyl 2-(3-formyl-4-((6-(methylsulfonyl)quinolin-4-yl)oxy)phenyl)acetate

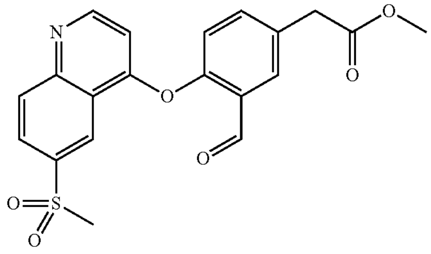 [SMILES: COC(=O)Cc1ccc(Oc2ccnc3ccc(S(C)(=O)=O)cc23)c(C=O)c1]

Iron(III) chloride (1.26 g, 4.66 mmol, 2.50 equiv.) was added to a solution of 2-(3-(1,3-dioxolan-2-yl)-4-((6-(methylsulfonyl)quinolin-4-yl)oxy)phenyl)acetate (590 mg, 1.33 mmol, 1.00 equiv.) in DCM (12 mL) and the mixture was stirred at room temperature overnight. Subsequently, the reaction was quenched with water/ice (50 mL) and the pH of the solution was adjusted to 8 with a saturated aqueous $NaHCO_3$ solution. The product was extracted with EtOAc (3×5 mL), the combined organic phases were dried over $Na_2SO_4$, and the solvent was removed under reduced pressure. The title compound (480 mg) was used in the next reaction without any further purification.

Part IV—Synthesis of methyl 2-(3-(difluoromethyl)-4-((6-(methylsulfonyl)quinolin-4-yl)oxy)phenyl)acetate

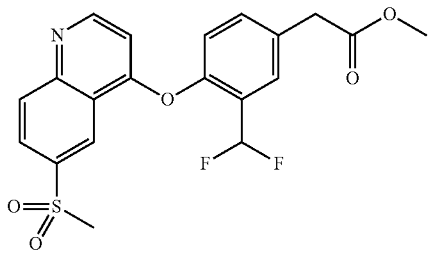 [SMILES: COC(=O)Cc1ccc(Oc2ccnc3ccc(S(C)(=O)=O)cc23)c(C(F)F)c1]

Bis(2-methoxyethyl)aminosulfur trifluoride (1.04 g, 4.71 mmol, 4.00 equiv.) was added to a solution of methyl 2-(3-formyl-4-((6-(methylsulfonyl)quinolin-4-yl)oxy)phenyl)acetate (470 mg, 1.18 mmol, 1.00 equiv.) and EtOH (10.8 mg, 0.235 mmol, 0.20 equiv.) in DCM (10 mL) at 0° C. Subsequently, the mixture was stirred overnight at room temperature. Subsequently, the reaction was quenched with water/ice and the pH of the solution was adjusted to 8 with a saturated aqueous $NaHCO_3$ solution. The product was extracted with EtOAc (3×10 mL), the combined organic phases were dried over $Na_2SO_4$, and the solvent was removed under reduced pressure. The crude product was purified by reversed-phase flash chromatography (column: C18 silica gel; mobile phase A: water, mobile phase B: ACN, gradient: 30-60% B in 30 min; wavelength: 210 nm). The title compound was obtained as a white solid (210 mg, 42%).

Part V—Synthesis of 2-(3-(difluoromethyl)-4-((6-(methylsulfonyl)quinolin-4-yl)oxy)phenyl)acetic Acid

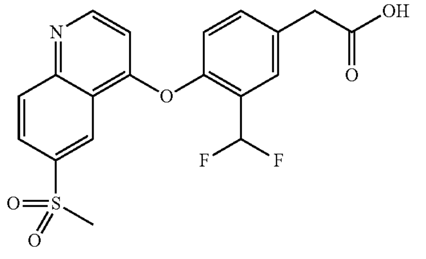 [SMILES: CS(=O)(=O)c1ccc2nccc(Oc3ccc(CC(=O)O)cc3C(F)F)c2c1]

LiOH (20.5 mg, 0.854 mmol, 2.00 equiv.) was added to a solution of methyl 2-(3-(difluoromethyl)-4-((6-(methylsulfonyl)quinolin-4-yl)oxy)phenyl)acetate (180 mg, 0.427 mmol, 1.00 equiv.) in THF (2 mL) and water (2 mL) at 0° C. Subsequently, the mixture was stirred at room temperature for 2 h. The pH of the solution was adjusted to 4 with hydrochloric acid and the crude product was purified by reversed-phase flash chromatography (column: C18 silica gel; mobile phase A: water, mobile phase B: ACN, gradient: 35-65% B in 30 min; wavelength: 210 nm). The title compound was obtained as a white solid (150 mg, 86%).

Part VI—Synthesis of N-(1-(tert-butyl)-1H-pyrazol-4-yl)-2-(3-(difluoromethyl)-4-((6-(methylsulfonyl)quinolin-4-yl)oxy)phenyl)acetamide (Compound 92)

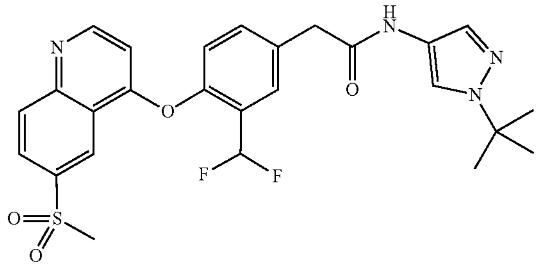 [SMILES: CC(C)(C)n1cc(NC(=O)Cc2ccc(Oc3ccnc4ccc(S(C)(=O)=O)cc34)c(C(F)F)c2)cn1]

1-(tert-Butyl)-1H-pyrazol-4-amine (41.0 mg, 0.295 mmol, 1.00 equiv.), DIPEA (114 mg, 0.885 mmol, 3.00 equiv.), and HATU (168 mg, 0.443 mmol, 1.50 equiv.) were added to a solution of 2-(3-(difluoromethyl)-4-((6-(methylsulfonyl)quinolin-4-yl)oxy)phenyl)acetic acid (120 mg, 0.295 mmol, 1.00 equiv.) in DMF (1.2 mL) at 0° C. Subsequently, the mixture was stirred at room temperature for 2 h. The reaction was quenched with water/ice (5 mL) and the product was extracted with EtOAc (3×2 mL). The combined organic phases were dried over $Na_2SO_4$, and the solvent was removed under reduced pressure. The crude product was purified by reversed-phase flash chromatography (column: C18 silica gel; mobile phase A: water (0.10 ammonia), mobile phase B: ACN, gradient: 20-50% B in 30 min; wavelength: 210 nm). The title compound was obtained as a white solid (108 mg, 69%). LCMS (ESI) calculated for $C_{26}H_{27}F_2N_4O_4(M+H)^+$: 529.2, found: 529.0. $^1H$ NMR (300 MHz, DMSO-$d_6$) 310.26 (s, 1H), 8.89-8.87 (m, 2H), 8.30-8.28 (m, 2H), 7.95 (s, 1H), 7.75 (d, J=2.0 Hz, 1H), 7.64 (d, J=8.3 Hz, 1H), 7.48-7.42 (m, 2H), 7.24 (t, J=54.0 Hz, 1H), 6.73 (d, J=5.2 Hz, 1H), 3.73 (s, 2H), 3.38 (s, 3H), 1.49 (s, 9H).

Example 13—Preparation of Additional Difluoromethylphenylene Compounds

Compounds in the table below were prepared based on experimental procedures described in Example 12 and the detailed description.

| No. | Structure | Name | $^1H$ NMR | Observed m/z |
|---|---|---|---|---|
| 413 | 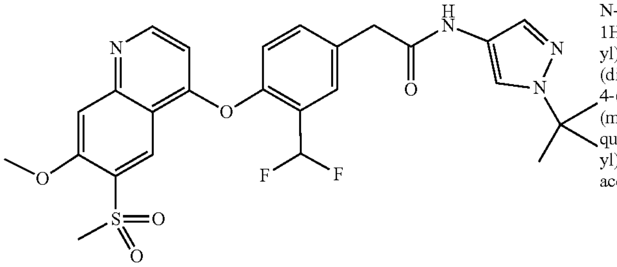 | N-(1-(tert-butyl)-1H-pyrazol-4-yl)-2-(3-(difluoromethyl)-4-((7-methoxy-6-(methylsulfonyl)quinolin-4-yl)oxy)phenyl)acetamide | | 559.0 $(M + H)^+$ |
| 417 | 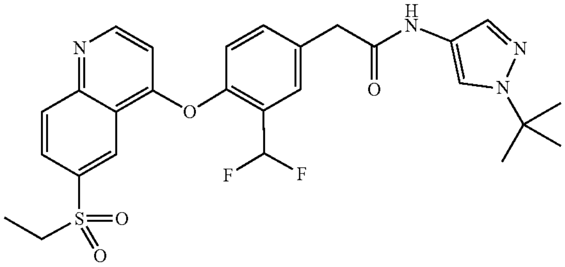 [SMILES: CCS(=O)(=O)c1ccc2nccc(Oc3ccc(CC(=O)Nc4cnn(C(C)(C)C)c4)cc3C(F)F)c2c1] | N-(1-(tert-butyl)-1H-pyrazol-4-yl)-2-(3-(difluoromethyl)-4-((6-(ethylsulfonyl)quinolin-4-yl)oxy)phenyl)acetamide | | 543.1 $(M + H)^+$ |
| 418 | 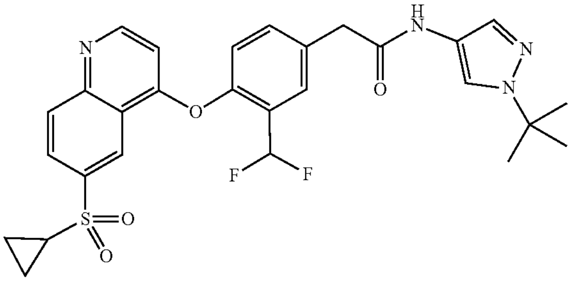 [SMILES: CC(C)(C)n1cc(NC(=O)Cc2ccc(Oc3ccnc4ccc(S(=O)(=O)C5CC5)cc34)c(C(F)F)c2)cn1] | N-(1-(tert-butyl)-1H-pyrazol-4-yl)-2-(4-((6-(cyclopropylsulfonyl)quinolin-4-yl)oxy)-3-(difluoromethyl)phenyl)acetamide | | 555.1 $(M + H)^+$ |
| 462 | 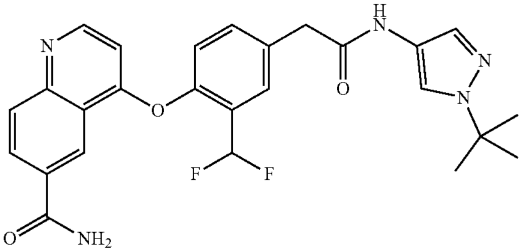 [SMILES: CC(C)(C)n1cc(NC(=O)Cc2ccc(Oc3ccnc4ccc(C(N)=O)cc34)c(C(F)F)c2)cn1] | 4-(4-(2-((1-(tert-butyl)-1H-pyrazol-4-yl)amino)-2-oxoethyl)-2-(difluoromethyl)phenoxy)quinoline-6-carboxamide | (400 MHz, DMSO-$d_6$) δ 10.29 (s, 1H), 8.91 (s, 1H), 8.77 (d, J = 5.0 Hz, 1H), 8.34 (s, 1H), 8.32-8.21 (m, 1H), 8.10 (d, J = 8.9 Hz, 1H), 7.96 (s, 1H), 7.76 (s, 1H), 7.70-7.57 (m, 2H), 7.47 (s, 1H), 7.41 (d, J = 8.5 Hz, 1H), 7.24 (t, J = 54.4 Hz, 1H), 6.64 (d, J = 5.1 Hz, 1H), 3.74 (s, 2H), 1.49 (s, 9H) | 494.0 $(M + H)^+$ |
| 463 | 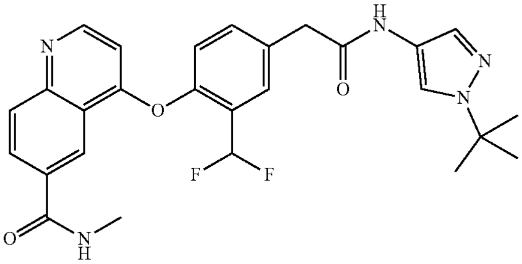 [SMILES: CNC(=O)c1ccc2nccc(Oc3ccc(CC(=O)Nc4cnn(C(C)(C)C)c4)cc3C(F)F)c2c1] | 4-(4-(2-((1-(tert-butyl)-1H-pyrazol-4-yl)amino)-2-oxoethyl)-2-(difluoromethyl)phenoxy)-N-methylquinoline-6-carboxamide | (400 MHz, DMSO-$d_6$) δ 10.29 (s, 1H), 8.85 (d, J = 2.0 Hz, 1H), 8.81-8.76 (m, 2H), 8.24 (dd, J = 8.8, 2.0 Hz, 1H), 8.10 (d, J = 8.8 Hz, 1H), 7.96 (s, 1H), 7.75 (d, J = 2.2 Hz, 1H), 7.63 (dd, J = 8.4, 2.2 Hz, 1H), 7.47 (s, 1H), 7.40 (d, J = 8.4 Hz, 1H), 7.22 (t, J = 54.4 Hz, 1H), 6.63 (d, J = 5.1 Hz, 1H), 3.73 (s, 2H), 2.86 (d, J = 4.5 Hz, 3H), 1.49 (s, 9H) | 508.1 $(M + H)^+$ |

-continued

| No. | Structure | Name | $^1$H NMR | Observed m/z |
|---|---|---|---|---|
| 574 | 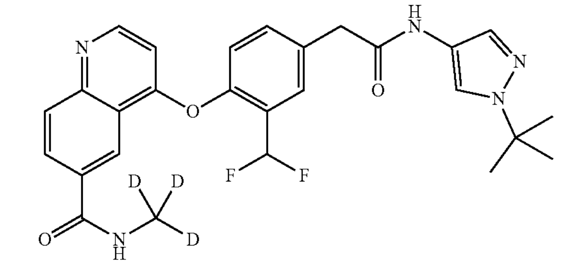 [SMILES: [2H]C([2H])([2H])NC(=O)c1ccc2nccc(Oc3ccc(CC(=O)Nc4cnn(C(C)(C)C)c4)cc3C(F)F)c2c1] | 4-(4-(2-((1-(tert-butyl)-1H-pyrazol-4-yl)amino)-2-oxoethyl)-2-(difluoromethyl) phenoxy)-N-(methyl-$d_3$)quinoline-6-carboxamide | (400 MHz, DMSO-$d_6$) δ 10.29 (s, 1H), 8.92-8.83 (m, 1H), 8.78-8.76 (m, 2H), 8.24 (d, J = 8.5 Hz, 1H), 8.10 (d, J = 8.9 Hz, 1H), 7.96 (s, 1H), 7.76 (s, 1H), 7.64 (d, J = 8.4 Hz, 1H), 7.47 (s, 1H), 7.40 (d, J = 8.4 Hz, 1H), 7.22 (t, J = 54.4 Hz, 1H), 6.63 (d, J = 5.2 Hz, 1H), 3.73 (s, 2H), 1.49 (s, 9H) | 511.1 $(M + H)^+$ |
| 578 | 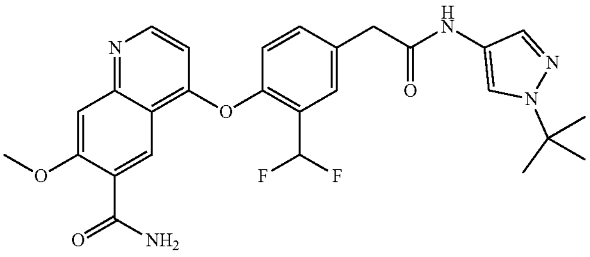 [SMILES: COc1cc2nccc(Oc3ccc(CC(=O)Nc4cnn(C(C)(C)C)c4)cc3C(F)F)c2cc1C(N)=O] | 4-(4-(2-((1-(tert-butyl)-1H-pyrazol-4-yl)amino)-2-oxoethyl)-2-(difluoromethyl) phenoxy)-7-methoxy-quinoline-6-carboxamide | (400 MHz, DMSO-$d_6$) δ 10.26 (s, 1H), 8.73-8.62 (m, 2H), 7.95 (s, 1H), 7.87 (s, 1H), 7.76 (s, 1H), 7.72 (s, 1H), 7.60 (d, J = 8.6 Hz, 1H), 7.54 (s, 1H), 7.45 (s, 1H), 7.33 (s, 1H), 7.19 (t, J = 52.0 Hz, 1H), 6.47 (d, J = 5.3 Hz, 1H), 4.03 (s, 3H), 3.71 (s, 2H), 1.48 (s, 9H) | 524.1 $(M + H)^+$ |
| 579 | 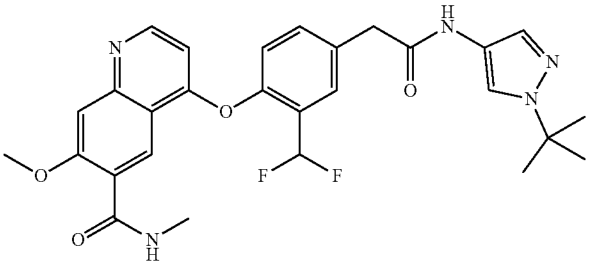 [SMILES: CNC(=O)c1cc2c(Oc3ccc(CC(=O)Nc4cnn(C(C)(C)C)c4)cc3C(F)F)ccnc2cc1OC] | 4-(4-(2-((1-(tert-butyl)-1H-pyrazol-4-yl)amino)-2-oxoethyl)-2-(difluoromethyl) phenoxy)-7-methoxy-N-methylquinoline-6-carboxamide | (400 MHz, DMSO-$d_6$) δ 10.35 (s, 1H), 8.68-8.61 (m, 2H), 8.39 (s, 1H), 7.96 (s, 1H), 7.74 (s, 1H), 7.67-7.41 (m, 3H), 7.34 (d, J = 7.5 Hz, 1H), 7.20 (t, J = 56.0 Hz, 1H), 6.49 (s, 1H), 4.03 (s, 3H), 3.73 (s, 2H), 2.84 (s, 3H), 1.48 (s, 9H) | 538.1 $(M + H)^+$ |
| 580 | 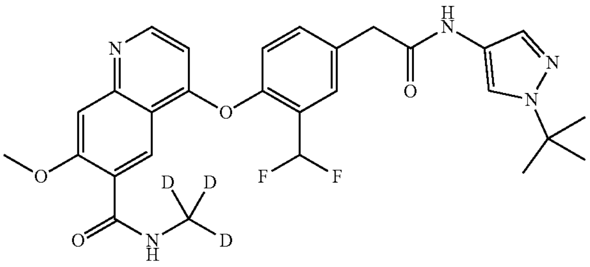 [SMILES: [2H]C([2H])([2H])NC(=O)c1cc2c(Oc3ccc(CC(=O)Nc4cnn(C(C)(C)C)c4)cc3C(F)F)ccnc2cc1OC] | 4-(4-(2-((1-(tert-butyl)-1H-pyrazol-4-yl)amino)-2-oxoethyl)-2-(difluoromethyl) phenoxy)-7-methoxy-N-(methyl-$d_3$)quinoline-6-carboxamide | (400 MHz, DMSO-$d_6$) δ 10.28 (s, 1H), 8.68 (d, J = 5.2 Hz, 1H), 8.60 (s, 1H), 8.36 (s, 1H), 7.95 (s, 1H), 7.73 (s, 1H), 7.61 (d, J = 8.4 Hz, 1H), 7.54 (s, 1H), 7.46 (s, 1H), 7.34 (d, J = 7.8 Hz, 1H), 7.19 (t, J = 54.4 Hz, 1H), 6.48 (d, J = 5.1 Hz, 1H), 4.03 (s, 3H), 3.72 (s, 2H), 1.49 (s, 9H) | 541.1 $(M + H)^+$ |
| 619 | 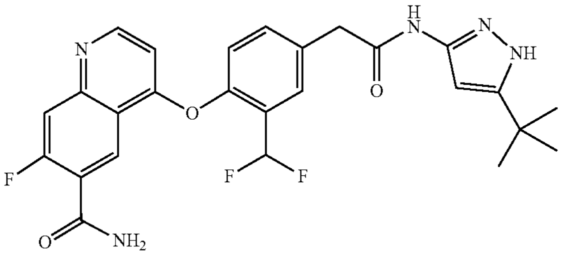 [SMILES: CC(C)(C)c1cc(NC(=O)Cc2ccc(Oc3ccnc4cc(F)c(C(N)=O)cc34)c(C(F)F)c2)n[nH]1] | 4-(4-(2-((5-(tert-butyl)-1H-pyrazol-3-yl)amino)-2-oxoethyl)-2-(difluoromethyl) phenoxy)-7-fluoroquinoline-6-carboxamide | (300 MHz, DMSO-$d_6$) δ 10.64 (s, 1H), 8.76 (d, J = 5.3 Hz, 1H), 8.65 (d, J = 7.7 Hz, 1H), 8.02 (s, 1H), 7.89-7.85 (m, 3H), 7.78-7.76 (m, 1H), 7.64 (d, J = 8.5 Hz, 1H), 7.22 (t, J = 54.3 Hz, 1H), 6.62 (d, J = 5.3 Hz, 1H), 6.29 (s, 1H), 6.05 (s, 1H), 3.74 (s, 2H), 1.25 (s, 9H) | 512.2 $(M + H)^+$ |

-continued

| No. | Structure | Name | ¹H NMR | Observed m/z |
|---|---|---|---|---|
| 576 | 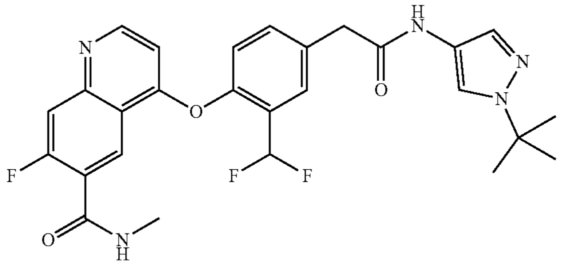 [SMILES: CNC(=O)c1cc2c(Oc3ccc(CC(=O)Nc4cnn(C(C)(C)C)c4)cc3C(F)F)ccnc2cc1F] | 4-(4-(2-((1-(tert-butyl)-1H-pyrazol-4-yl)amino)-2-oxoethyl)-2-(difluoromethyl) phenoxy)-7-fluoro-N-methylquinoline-6-carboxamide | (400 MHz, DMSO-$d_6$) δ 10.25 (s, 1H), 8.77 (d, J = 5.2 Hz, 1H), 8.60 (d, J = 7.7 Hz, 1H), 8.58-8.52 (m, 1H), 7.95 (s, 1H), 7.88 (d, J = 11.7 Hz, 1H), 7.74 (d, J = 2.2 Hz, 1H), 7.66-7.59 (m, 1H), 7.46 (s, 1H), 7.39 (d, J = 8.4 Hz, 1H), 7.23 (t, J = 54.5 Hz, 1H), 6.61 (d, J = 5.2 Hz, 1H), 3.72 (s, 2H), 2.84 (d, J = 4.6 Hz, 3H), 1.49 (s, 9H) | 526.2 $(M + H)^+$ |
| 577 | 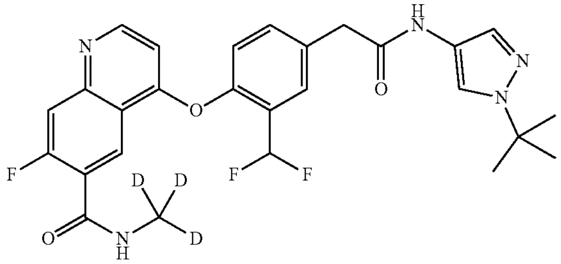 [SMILES: [2H]C([2H])([2H])NC(=O)c1cc2c(Oc3ccc(CC(=O)Nc4cnn(C(C)(C)C)c4)cc3C(F)F)ccnc2cc1F] | 4-(4-(2-((1-(tert-butyl)-1H-pyrazol-4-yl)amino)-2-oxoethyl)-2-(difluoromethyl) phenoxy)-7-fluoro-N-(methyl-$d_3$)quinoline-6-carboxamide | (400 MHz, DMSO-$d_6$) δ 10.25 (s, 1H), 8.77 (d, J = 5.2 Hz, 1H), 8.60 (d, J = 7.7 Hz, 1H), 8.53 (s, 1H), 7.95 (s, 1H), 7.88 (d, J = 11.6 Hz, 1H), 7.77-7.70 (m, 1H), 7.62 (d, J = 8.3 Hz, 1H), 7.46 (s, 1H), 7.39 (d, J = 8.4 Hz, 1H), 7.23 (t, J = 54.4 Hz, 1H), 6.61 (d, J = 5.3 Hz, 1H), 3.72 (s, 2H), 1.49 (s, 9H) | 529.2 $(M + H)^+$ |
| 575 | 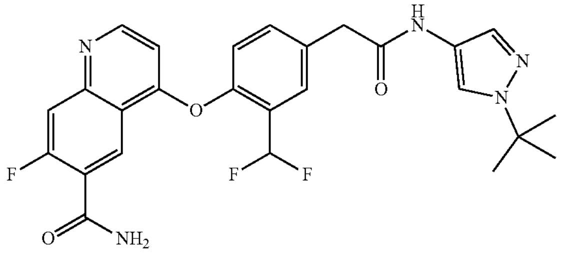 [SMILES: CC(C)(C)n1cc(NC(=O)Cc2ccc(Oc3ccnc4cc(F)c(C(N)=O)cc34)c(C(F)F)c2)cn1] | 4-(4-(2-((1-(tert-butyl)-1H-pyrazol-4-yl)amino)-2-oxoethyl)-2-(difluoromethyl) phenoxy)-7-fluoroquinoline-6-carboxamide | (400 MHz, DMSO-$d_6$) δ 10.25 (s, 1H), 8.77 (d, J = 5.2 Hz, 1H), 8.64 (d, J = 7.8 Hz, 1H), 8.02 (s, 1H), 7.97-7.93 (m, 1H), 7.91-7.81 (m, 2H), 7.74 (d, J = 2.2 Hz, 1H), 7.66-7.59 (m, 1H), 7.47-7.44 (m, 1H), 7.39 (d, J = 8.4 Hz, 1H), 7.23 (t, J = 54.4 Hz, 1H), 6.61 (d, J = 5.1 Hz, 1H), 3.72 (s, 2H), 1.49 (s, 9H) | 512.2 $(M + H)^+$ |

Example 14—Synthesis of N-(1-(tert-butyl)-1H-pyrazol-4-yl)-2-(3-fluoro-5-((6-((1-methylpiperidin-4-yl)oxy)quinazolin-4-yl)oxy)pyridin-2-yl)acetamide (Compound 20); Prepared According to General Scheme 15

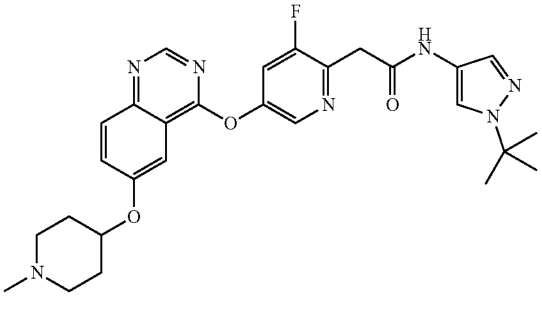 [SMILES: CN1CCC(Oc2ccc3ncnc(Oc4cnc(CC(=O)Nc5cnn(C(C)(C)C)c5)c(F)c4)c3c2)CC1]

Part I—Synthesis of N-(1-(tert-butyl)-1H-pyrazol-4-yl)-2-(3-fluoro-5-hydroxypyridin-2-yl)acetamide

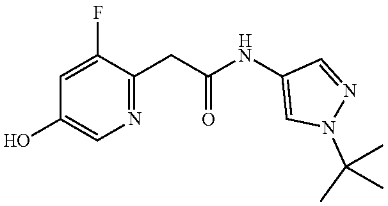 [SMILES: CC(C)(C)n1cc(NC(=O)Cc2ncc(O)cc2F)cn1]

EDC (19.7 g, 127 mmol, 1.50 equiv.) was added to a solution of 2-(3-fluoro-5-hydroxypyridin-2-yl)acetic acid (14.5 g, 84.7 mmol, 1.00 equiv.), 1-(tert-butyl)-1H-pyrazol-4-amine (11.8 g, 84.7 mmol, 1.00 equiv.), HOBt (17.2 g, 127 mmol, 1.50 equiv.), and DIPEA (32.9 g, 254 mmol, 3.00 equiv.) in THF (145 mL) and DCM (145 mL) at 0° C. and the mixture was stirred at room temperature overnight. Water (200 mL) was added, and the product was extracted with a mixture of EtOAc and 2-methyltetrahydrofuran (1:1, 5×150 mL). The combined organic phases were washed with brine, dried over $Na_2SO_4$, and the solvent was removed under reduced pressure. The crude product was purified by column chromatography (DCM/MeOH 10:1). The title compound was obtained as a brown solid (17.3 g, 70%).

Part II—Synthesis of 2-(5-((6-bromoquinazolin-4-yl)oxy)-3-fluoropyridin-2-yl)-N-(1-(tert-butyl)-1H-pyrazol-4-yl)acetamide

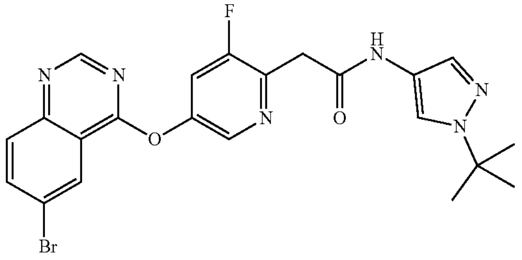

$K_2CO_3$ (3.92 g, 28.3 mmol, 3.00 equiv.) was added to a solution of 6-bromo-4-chloroquinazoline (2.3 g, 9.45 mmol, 1.00 equiv.) and N-(1-(tert-butyl)-1H-pyrazol-4-yl)-2-(3-fluoro-5-hydroxypyridin-2-yl)acetamide (2.76 g, 9.45 mmol, 1.00 equiv., can be prepared as shown in Part I of Example 15) in DMF (23 mL) under an inert atmosphere of nitrogen. The mixture was stirred at room temperature overnight. Subsequently, EtOAc (200 mL) was added, and the mixture was washed with water (2×100 mL). The organic phase was dried over $Na_2SO_4$, and the solvent was removed under reduced pressure. The title compound was obtained as a yellow solid (5.5 g), which was used in the next reaction without further purification.

Part III—Synthesis of N-(1-(tert-butyl)-1H-pyrazol-4-yl)-2-(3-fluoro-5-((6-(4,4,5,5-tetramethyl-1,3,2-dioxaborolan-2-yl)quinazolin-4-yl)oxy)pyridin-2-yl)acetamide

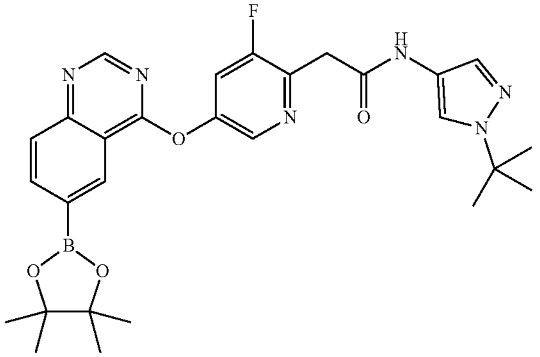 [SMILES: CC(C)(C)n1cc(NC(=O)Cc2ncc(Oc3ncnc4ccc(B5OC(C)(C)C(C)(C)O5)cc34)cc2F)cn1]

A solution of 2-(5-((6-bromoquinazolin-4-yl)oxy)-3-fluoropyridin-2-yl)-N-(1-(tert-butyl)-1H-pyrazol-4-yl)acetamide (5.0 g, 10.0 mmol, 1.00 equiv.) and bis(pinacolato) diboron (3.05 g, 12.0 mmol, 1.20 equiv.), KOAc (2.95 g, 30.0 mmol, 3.00 equiv.), and Pd(dppf)$Cl_2$ (1.1 g, 1.50 mmol, 0.15 equiv.) in 1,4-dioxane (80 mL) was heated to 70° C. for 2.5 h under an inert atmosphere of nitrogen. The mixture was diluted with EtOAc (200 mL) and washed with water (2×100 mL). Subsequently, the organic phase was dried over $Na_2SO_4$, and the solvent was removed under reduced pressure. The title compound was obtained as a brownish red solid (8.5 g), which was used in the next reaction without further purification.

Part IV—Synthesis of N-(1-(tert-butyl)-1H-pyrazol-4-yl)-2-(3-fluoro-5-((6-hydroxyquinazolin-4-yl)oxy)pyridin-2-yl)acetamide

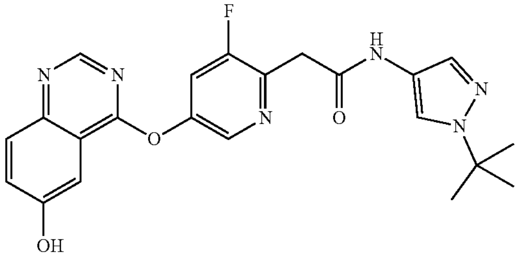 [SMILES: CC(C)(C)n1cc(NC(=O)Cc2ncc(Oc3ncnc4ccc(O)cc34)cc2F)cn1]

A solution of hydrogen peroxide in water (30%, 8 mL) was added to a solution of N-(1-(tert-butyl)-1H-pyrazol-4-yl)-2-(3-fluoro-5-((6-(4,4,5,5-tetramethyl-1,3,2-dioxaborolan-2-yl)quinazolin-4-yl)oxy)pyridin-2-yl)acetamide (8.0 g, 14.6 mmol, 1.00 equiv.) in THF (80 mL). The mixture was stirred at room temperature for 1.5 h. Subsequently, the mixture was filtered, and the solvent was removed under reduced pressure. The crude product was purified by reversed-phase flash chromatography (column: C18 silica gel; mobile phase A: water (0.1% $NH_4HCO_3$), mobile phase B: ACN, gradient: 30-70% B in 20 min; wavelength: 210 nm). The title compound was obtained as a yellowish brown solid (2 g, 48% over 3 steps).

Part V—Synthesis of N-(1-(tert-butyl)-1H-pyrazol-4-yl)-2-(3-fluoro-5-((6-((1-methylpiperidin-4-yl)oxy)quinazolin-4-yl)oxy)pyridin-2-yl)acetamide (Compound 20)

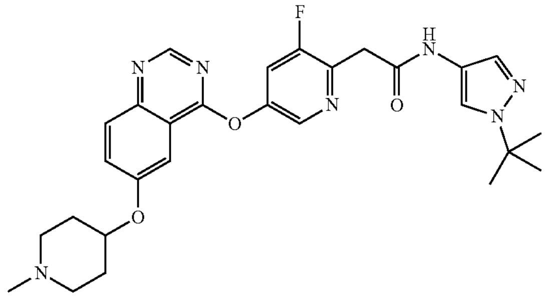 [SMILES: CN1CCC(Oc2ccc3ncnc(Oc4cnc(CC(=O)Nc5cnn(C(C)(C)C)c5)c(F)c4)c3c2)CC1]

Di-tert-butyl azodicarboxylate (844.1 mg, 3.67 mmol, 2.00 equiv.) was added to a solution of N-(1-(tert-butyl)-1H-pyrazol-4-yl)-2-(3-fluoro-5-((6-hydroxyquinazolin-4-yl)oxy)pyridin-2-yl)acetamide (800 mg, 1.83 mmol, 1.00 equiv.), 1-methylpiperidin-4-ol (316.7 mg, 2.75 mmol, 1.50 equiv.) and $PPh_3$ (961.6 mg, 3.67 mmol, 2.00 equiv.) in THF (16 mL) at 0° C. Subsequently, the mixture was stirred at room temperature for 1.5 h. EtOAc (50 mL) was added and the solution was washed with water (2×20 mL). The organic phase was dried over $Na_2SO_4$, and the solvent was removed under reduced pressure. The crude product was purified by preparative HPLC (column: Xselect CSH C18 OBD;

19×150 mm, 5 μm; mobile phase A: water (10 mmol/L $NH_4HCO_3$), mobile phase B: ACN; flow rate: 60 mL/min; gradient 25-30% B in 16 min; wavelength: 220 nm). The title compound was obtained as a white solid (130 mg, 13%). LCMS (ESI) calculated for $C_{28}H_{33}FN_7O_3(M+H)^+$: 534.3, found: 534.3. $^1H$ NMR (400 MHz, DMSO-$d_6$) δ 10.32 (s, 1H), 8.64 (s, 1H), 8.50 (d, J=1.9 Hz, 1H), 8.00 (dd, J=10.1, 2.2 Hz, 1H), 7.97 (d, J=9.1 Hz, 1H), 7.93 (d, J=0.7 Hz, 1H), 7.75-7.66 (m, 2H), 7.45 (d, J=0.7 Hz, 1H), 4.70 (dt, J=8.1, 4.2 Hz, 1H), 3.91 (d, J=2.3 Hz, 2H), 2.68-2.57 (m, 2H), 2.30-2.21 (m, 2H), 2.19 (s, 3H), 2.07-1.96 (m, 2H), 1.81-1.68 (m, 2H), 1.49 (s, 9H).

Example 15—Synthesis of N-(5-(tert-butyl)-1-methyl-1H-pyrazol-3-yl)-2-(3-fluoro-5-((6-(methylsulfonyl)quinolin-4-yl)oxy)pyridin-2-yl)acetamide (Compound 41); Prepared According to General Scheme 2

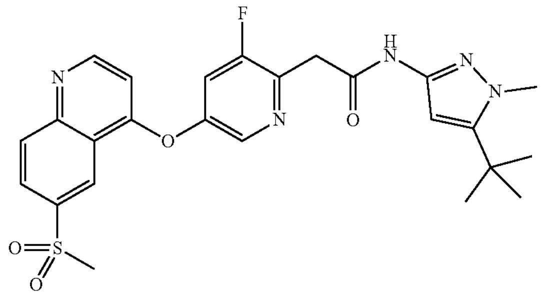 [SMILES: Cn1nc(NC(=O)Cc2ncc(Oc3ccnc4ccc(S(C)(=O)=O)cc34)cc2F)cc1C(C)(C)C]

Part I—Synthesis of 1-(tert-butyl) 3-ethyl 2-(5-bromo-3-fluoropyridin-2-yl)malonate

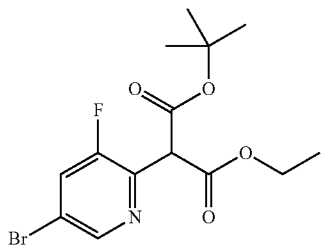 [SMILES: CCOC(=O)C(C(=O)OC(C)(C)C)c1ncc(Br)cc1F]

Sodium hydride (60 wt. %, 124 g, 3.09 mol, 1.20 equiv.) was added to a solution of tert-butyl ethyl malonate (485 g, 2.58 mol, 1.00 equiv.) in DMF (5 L) at 0° C. Subsequently, the reaction mixture was stirred at room temperature for 1 h. 5-Bromo-2,3-difluoropyridine (500 g, 2.58 mol, 1.00 equiv.) was added and the mixture was heated to 80° C. overnight. The mixture was cooled to 0° C. and a saturated, aqueous solution of $NH_4Cl$ was added. The product was extracted with EtOAc (3×5 L), and the combined organic phases were washed with brine and dried over $Na_2SO_4$. The solvent was removed under reduced pressure. The title compound (1.1 kg) was used in the next reaction without any further purification.

Part II—Synthesis of ethyl 2-(5-bromo-3-fluoropyridin-2-yl)acetate

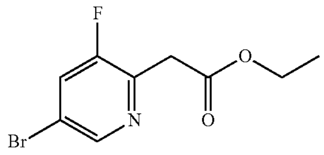

TFA (5 L) was added to a solution of 1-(tert-butyl) 3-ethyl 2-(5-bromo-3-fluoropyridin-2-yl)malonate (1.1 kg, 3.04 mol, 1.00 equiv.) in DCM (5 L) and the mixture was stirred at room temperature for 2 h. The solvent was removed under reduced pressure. Water was added and the pH of the solvent was adjusted to 7 by addition of an aqueous saturated solution of $NaHCO_3$. The product was extracted with EtOAc (3×3 L) and the combined organic phases were dried over $MgSO_4$. The solvent was removed under reduced pressure and the crude product was purified by column chromatography (petroleum ether/EtOAc 95:5). The title compound was obtained as a yellow oil (520 g, 65% over 2 steps).

Part III—Synthesis of ethyl 2-(3-fluoro-5-hydroxypyridin-2-yl)acetate

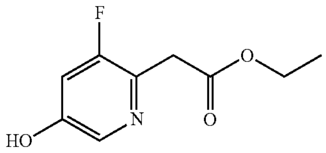

A solution of ethyl 2-(5-bromo-3-fluoropyridin-2-yl)acetate (470 g, 1.79 mol, 1.00 equiv.), Pd(dppf)$Cl_2$ (131 g, 179 mmol, 0.10 equiv.), bis(pinacolato)diboron (911 g, 3.59 mol, 2.00 equiv.), and potassium acetate (352 g, 3.59 mol, 2.00 equiv.) in 1,4-dioxane (4.7 L) was heated to 85° C. for 24 h under an inert atmosphere of nitrogen. Subsequently, a solution of hydrogen peroxide in water (30%, 470 mL, 20.2 mol, 13.3 equiv.) was added dropwise at 0° C. and the mixture was stirred at room temperature for 3 h. Water (2 L) was added, and the product was extracted with EtOAc (3×1.5 L). The combined organic phases were washed with brine, dried over $Na_2SO_4$, and the solvent was removed under reduced pressure. The crude product was purified by column chromatography (petroleum ether/EtOAc 1:1). The title compound was obtained as a colorless oil (271.1 g, 70% over 2 steps).

Part IV—Synthesis of 2-(3-fluoro-5-hydroxypyridin-2-yl)acetic Acid

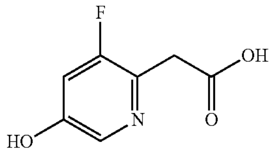 [SMILES: O=C(O)Cc1ncc(O)cc1F]

Lithium hydroxide (8.57 g, 358 mmol, 2.50 equiv.) was added to a solution of ethyl 2-(3-fluoro-5-hydroxypyridin-2-yl)acetate (28.5 g, 143 mmol, 1.00 equiv.) in THF (140 mL) and water (140 mL) and the mixture was stirred at room temperature overnight. Hydrochloric acid (3 M, 500 mL) was added, and the product was extracted with a mixture of EtOAc and 2-methyltetrahydrofuran (1:1, 6×200 mL). The combined organic phases were washed with brine, dried over $Na_2SO_4$, and the solvent was removed under reduced pressure. The title compound (14.5 g) was used in the next reaction without further purification.

Part V—Synthesis of N-(5-(tert-butyl)-1-methyl-1H-pyrazol-3-yl)-2-(3-fluoro-5-hydroxypyridin-2-yl)acetamide

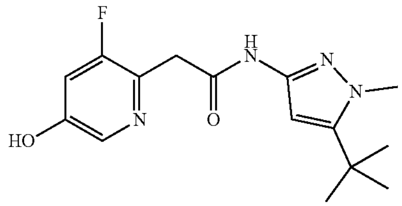 [SMILES: Cn1nc(NC(=O)Cc2ncc(O)cc2F)cc1C(C)(C)C]

HATU (9.33 g, 24.5 mmol, 1.50 equiv.) was added to a solution of 2-(3-fluoro-5-hydroxypyridin-2-yl)acetic acid (2.80 g, 16.3 mmol, 1.00 equiv.), 5-(tert-butyl)-1-methyl-1H-pyrazol-3-amine (2.76 g, 18.0 mmol, 1.10 equiv.), and triethylamine (3.31 g, 32.7 mmol, 2.00 equiv.) in DMF (28 mL) and the mixture was stirred for 1 h at room temperature. Subsequently, the solvent was removed under reduced pressure, and the crude product was purified by reversed-phase flash chromatography (column: C18 silica gel; mobile phase A: water, mobile phase B: ACN, gradient: 30-60% B in 30 min; wavelength: 210 nm). The title compound was obtained as a light-yellow solid (0.51 g, 10%).

Part VI—Synthesis of N-(5-(tert-butyl)-1-methyl-1H-pyrazol-3-yl)-2-(3-fluoro-5-((6-(methylsulfonyl)quinolin-4-yl)oxy)pyridin-2-yl)acetamide (Compound 41)

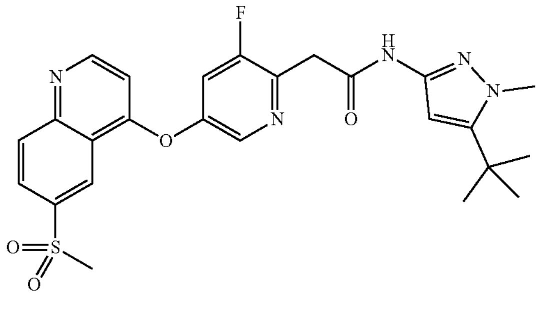 [SMILES: Cn1nc(NC(=O)Cc2ncc(Oc3ccnc4ccc(S(C)(=O)=O)cc34)cc2F)cc1C(C)(C)C]

A solution of N-(5-(tert-butyl)-1-methyl-1H-pyrazol-3-yl)-2-(3-fluoro-5-hydroxypyridin-2-yl)acetamide (200 mg, 0.653 mmol, 1.00 equiv.), 4-chloro-6-(methylsulfonyl)quinoline (158 mg, 0.653 mmol, 1.00 equiv.), $Cs_2CO_3$ (425 mg, 1.31 mmol, 2.00 equiv.), CuI (49.7 mg, 0.261 mmol, 0.40 equiv.), and N, N-dimethylglycine (40.4 mg, 0.392 mmol, 0.60 equiv.) in 1,4-dioxane (4 mL) was heated to 100° C. for 16 h under an inert atmosphere of nitrogen. Subsequently, insoluble byproducts were filtered off and the solvent was removed under reduced pressure. The crude product was purified by reversed-phase flash chromatography (column: C18 silica gel; mobile phase A: water, mobile phase B: ACN, gradient: 30-60% B in 30 min; wavelength: 210 nm). The title compound was obtained as a white solid (33.3 mg, 10%). LCMS (ESI) calculated for $C_{25}H_{27}FN_5O_4S$ $(M+H)^+$: 512.2, found: 512.1. $^1H$ NNR (300 MHz, DMSO-$d_6$) (510.64 (s, 1H), 8.93 (d, J=5.2 Hz, 1H), 8.87 (s, 1H), 8.54 (d, J=2.1 Hz, 1H), 8.31 (s, 2H), 8.03 (d, J=9.0 Hz, 1H), 6.93 (d, J=5.2 Hz, 1H), 6.30 (s, 1H), 3.95 (s, 2H), 3.81 (s, 3H), 3.38 (s, 3H), 1.31 (s, 9H).

Example 16—Preparation of Additional Pyridine Compounds

Compounds in the table below were prepared based on experimental procedures described in Example 15 and the detailed description.

| No. | Structure | Name | $^1$H NMR | Observed m/z |
|---|---|---|---|---|
| 5 | 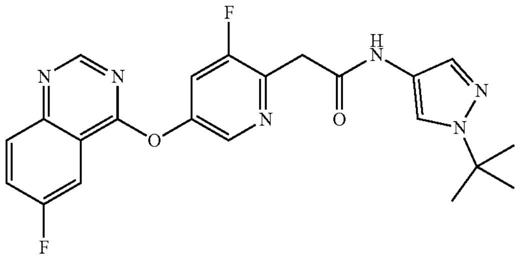 [SMILES: CC(C)(C)n1cc(NC(=O)Cc2ncc(Oc3ncnc4ccc(F)cc34)cc2F)cn1] | N-(1-(tert-butyl)-1H-pyrazol-4-yl)-2-(3-fluoro-5-((6-fluoroquinazolin-4-yl)oxy)pyridin-2-yl)acetamide | (400 MHz, DMSO-$d_6$) δ 10.32 (s, 1H), 8.79 (s, 1H), 8.52 (d, J = 1.9 Hz, 1H), 8.18-8.11 (m, 2H), 8.06-7.98 (m, 2H), 7.93 (s, 1H), 7.45 (s, 1H), 3.91 (d, J = 2.3 Hz, 2H), 1.49 (s, 9H) | 439.1 (M + H)$^+$ |
| 6 | 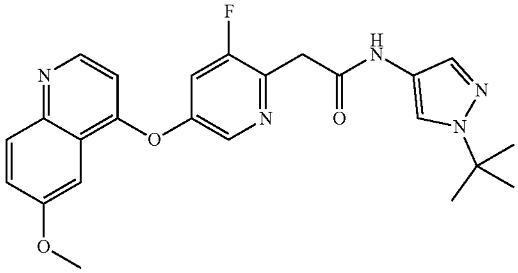 [SMILES: COc1ccc2nccc(Oc3cnc(CC(=O)Nc4cnn(C(C)(C)C)c4)c(F)c3)c2c1] | N-(1-(tert-butyl)-1H-pyrazol-4-yl)-2-(3-fluoro-5-((6-methoxyquinolin-4-yl)oxy)pyridin-2-yl)acetamide | (300 MHz, DMSO-$d_6$) δ 10.26 (s, 1H), 8.60 (s, 1H), 8.45 (s, 1H), 8.04-7.83 (m, 3H), 7.59-7.37 (m, 3H), 6.77 (s, 1H), 3.92 (s, 3H), 3.90 (s, 2H), 1.48 (s, 9H) | 450.2 (M + H)$^+$ |
| 7 | 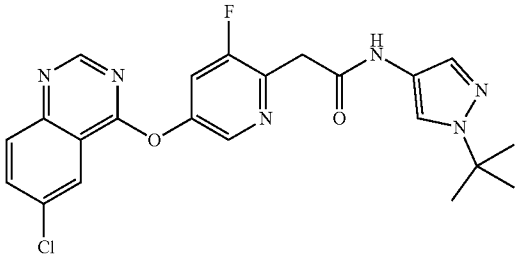 [SMILES: CC(C)(C)n1cc(NC(=O)Cc2ncc(Oc3ncnc4ccc(Cl)cc34)cc2F)cn1] | N-(1-(tert-butyl)-1H-pyrazol-4-yl)-2-(5-((6-chloroquinazolin-4-yl)oxy)-3-fluoro-pyridin-2-yl)acetamide | (400 MHz, DMSO-$d_6$) δ 10.32 (s, 1H), 8.82 (s, 1H), 8.53 (d, J = 0.7 Hz, 1H), 8.48-8.38 (m, 1H), 8.15-8.06 (m, 2H), 8.02 (dd, J = 10.0, 2.2 Hz, 1H), 7.93 (s, 1H), 7.45 (s, 1H), 3.91 (d, J = 2.3 Hz, 2H), 1.49 (s, 9H) | 455.1 (M + H)$^+$ |
| 9 | 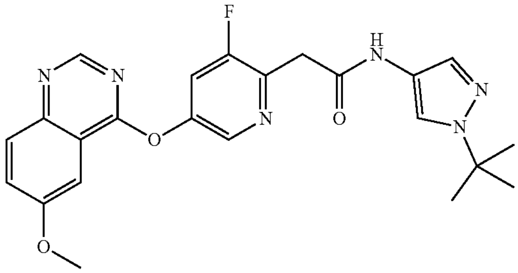 [SMILES: COc1ccc2ncnc(Oc3cnc(CC(=O)Nc4cnn(C(C)(C)C)c4)c(F)c3)c2c1] | N-(1-(tert-butyl)-1H-pyrazol-4-yl)-2-(3-fluoro-5-((6-methoxyquinazolin-4-yl)oxy)pyridin-2-yl)acetamide | (400 MHz, DMSO-$d_6$) δ 10.31 (s, 1H), 8.66 (s, 1H), 8.50 (dd, J = 2.3, 0.7 Hz, 1H), 8.01 (dd, J = 10.1, 2.2 Hz, 1H), 7.98 (d, J = 9.2 Hz, 1H), 7.93 (d, J = 0.8 Hz, 1H), 7.71 (dd, J = 9.1, 2.9 Hz, 1H), 7.65 (d, J = 2.8 Hz, 1H), 7.45 (d, J = 0.7 Hz, 1H), 3.98 (s, 3H), 3.91 (d, J = 2.3 Hz, 2H), 1.49 (s, 9H) | 451.2 (M + H)$^+$ |
| 10 | 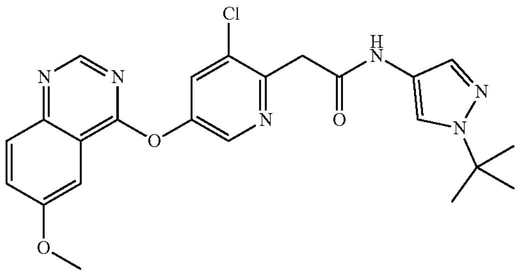 [SMILES: COc1ccc2ncnc(Oc3cnc(CC(=O)Nc4cnn(C(C)(C)C)c4)c(Cl)c3)c2c1] | N-(1-(tert-butyl)-1H-pyrazol-4-yl)-2-(3-chloro-5-((6-methoxyquinazolin-4-yl)oxy)pyridin-2-yl)acetamide | (300 MHz, DMSO-$d_6$) δ 10.28 (s, 1H), 8.66 (s, 1H), 8.60 (d, J = 2.4 Hz, 1H), 8.19 (d, J = 2.4 Hz, 1H), 7.98 (d, J = 9.2 Hz, 1H), 7.93 (s, 1H), 7.71 (dd, J = 9.1, 2.8 Hz, 1H), 7.65 (d, J = 2.8 Hz, 1H), 7.45 (s, 1H), 4.00 (s, 2H), 3.98 (s, 3H), 1.49 (s, 9H) | 467.1 (M + H)$^+$ |

-continued

| No. | Structure | Name | $^1$H NMR | Observed m/z |
|---|---|---|---|---|
| 12 | 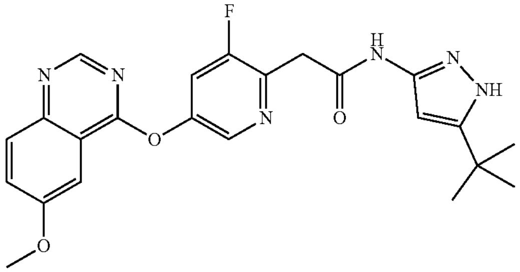 [SMILES: COc1ccc2ncnc(Oc3cnc(CC(=O)Nc4cc(C(C)(C)C)[nH]n4)c(F)c3)c2c1] | N-(5-(tert-butyl)-1H-pyrazol-3-yl)-2-(3-fluoro-5-((6-methoxyquinazolin-4-yl)oxy)pyridin-2-yl)acetamide | (400 MHz, DMSO-$d_6$) δ 12.07 (s, 1H), 10.65 (s, 1H), 8.67 (s, 1H), 8.50 (d, J = 2.1 Hz, 1H), 8.03-7.97 (m, 2H), 7.71 (dd, J = 9.1, 2.9 Hz, 1H), 7.67 (d, J = 2.8 Hz, 1H), 6.28 (d, J = 2.4 Hz, 1H), 3.99 (s, 3H), 3.95 (d, J = 1.9 Hz, 2H), 1.25 (s, 9H) | 451.0 $(M + H)^+$ |
| 13 | 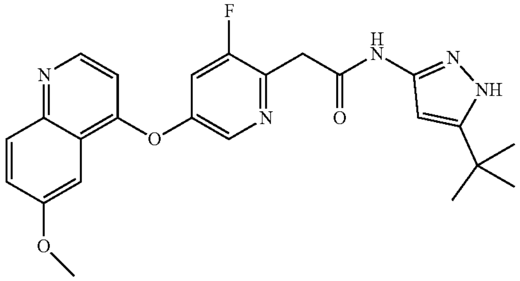 [SMILES: COc1ccc2nccc(Oc3cnc(CC(=O)Nc4cc(C(C)(C)C)[nH]n4)c(F)c3)c2c1] | N-(5-(tert-butyl)-1H-pyrazol-3-yl)-2-(3-fluoro-5-((6-methoxyquinolin-4-yl)oxy)pyridin-2-yl)acetamide | (300 MHz, DMSO-$d_6$) δ 12.07 (s, 1H), 10.63 (s, 1H), 8.61 (d, J = 5.1 Hz, 1H), 8.46 (s, 1H), 8.00 (d, J = 9.2 Hz, 1H), 7.93 (dd, J = 10.0, 2.6 Hz, 1H), 7.57 (d, J = 2.9 Hz, 1H), 7.50 (dd, J = 9.0, 2.6 Hz, 1H), 6.78 (d, J = 5.2 Hz, 1H), 6.28 (s, 1H), 4.03 (s, 3H), 3.96 (d, J = 2.3 Hz, 2H), 1.25 (s, 9H) | 450.0 $(M + H)^+$ |
| 42 | 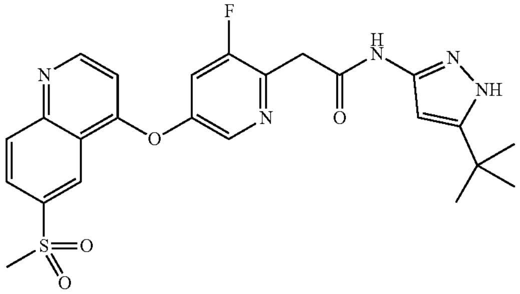 [SMILES: CC(C)(C)c1cc(NC(=O)Cc2ncc(Oc3ccnc4ccc(S(C)(=O)=O)cc34)cc2F)n[nH]1] | N-(5-(tert-butyl)-1H-pyrazol-3-yl)-2-(3-fluoro-5-((6-(methylsulfonyl) quinolin-4-yl)oxy)pyridin-2-yl)acetamide | (300 MHz, DMSO-$d_6$) δ 12.06 (s, 1H), 10.63 (s, 1H), 8.93 (d, J = 5.1 Hz, 1H), 8.87 (s, 1H), 8.53 (d, J = 1.9 Hz, 1H), 8.30 (d, J = 1.3 Hz, 2H), 8.09-7.96 (m, 1H), 6.93 (d, J = 5.3 Hz, 1H), 6.28 (s, 1H), 3.96 (s, 2H), 3.38 (s, 3H), 1.25 (s, 9H) | 498.0 $(M + H)^+$ |
| 48 | 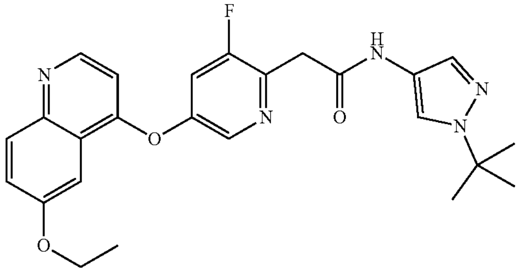 | N-(1-(tert-butyl)-1H-pyrazol-4-yl)-2-(5-((6-ethoxyquinolin-4-yl)oxy)-3-fluoropyridin-2-yl)acetamide | (400 MHz, DMSO-$d_6$) δ 10.26 (s, 1H), 8.66 (d, J = 5.4 Hz, 1H), 8.46 (d, J = 2.4 Hz, 1H), 8.05-7.90 (m, 3H), 7.59-7.44 (m, 3H), 6.84 (d, J = 5.1 Hz, 1H), 4.24-4.18 (m, 2H), 3.91 (d, J = 2.5 Hz, 2H), 1.49 (s, 9H), 1.41 (t, J = 6.9 Hz, 3H) | 464.0 $(M + H)^+$ |
| 51 | 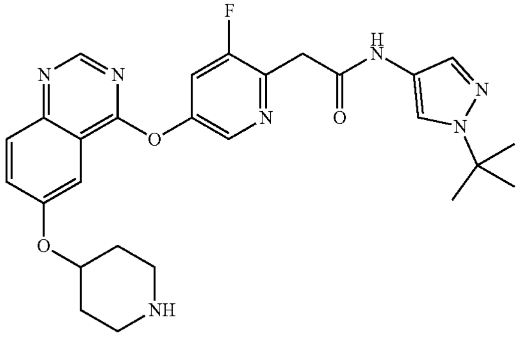 | N-(1-(tert-butyl)-1H-pyrazol-4-yl)-2-(3-fluoro-5-((6-(piperidin-4-yloxy)quinazolin-4-yl)oxy)pyridin-2-yl)acetamide | (300 MHz, DMSO-$d_6$) δ 10.30 (s, 1H), 8.64 (s, 1H), 8.49 (d, J = 2.0 Hz, 1H), 8.03-7.92 (m, 3H), 7.74-7.66 (m, 2H), 7.45 (d, J = 0.7 Hz, 1H), 4.80-4.61 (m, 1H), 3.90 (d, J = 1.8 Hz, 2H), 3.06-2.89 (m, 2H), 2.66-2.57 (m, 2H), 2.09-1.92 (m, 2H), 1.63-1.52 (m, 2H), 1.49 (s, 9H) | 520.1 $(M + H)^+$ |

-continued

| No. | Structure | Name | $^1$H NMR | Observed m/z |
|---|---|---|---|---|
| 56 | 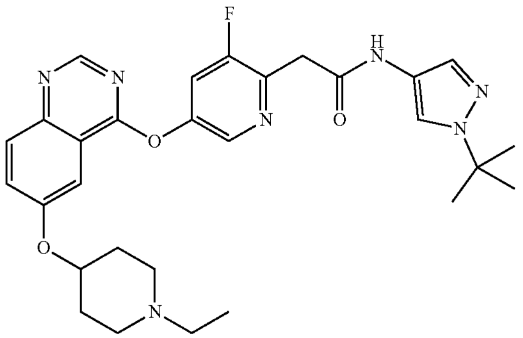 | N-(1-(tert-butyl)-1H-pyrazol-4-yl)-2-(5-((6-((1-ethylpiperidin-4-yl)oxy)quinazolin-4-yl)oxy)-3-fluoropyridin-2-yl)acetamide | (400 MHz, DMSO-$d_6$) δ 10.32 (s, 1H), 8.65 (s, 1H), 8.50 (d, J = 2.2 Hz, 1H), 8.01 (dd, J = 10.1, 2.3 Hz, 1H), 7.97 (d, J = 9.1 Hz, 1H), 7.94 (s, 1H), 7.75-7.67 (m, 2H), 7.45 (s, 1H), 4.75-4.67 (m, 1H), 3.91 (d, J = 2.3 Hz, 2H), 2.75-2.66 (m, 2H), 2.36 (q, J = 7.1 Hz, 2H), 2.33-2.23 (m, 2H), 2.08-1.99 (m, 2H), 1.78-1.66 (m, 2H), 1.49 (s, 9H), 1.01 (t, J = 7.1 Hz, 3H) | 548.2 (M + H)$^+$ |
| 57 | 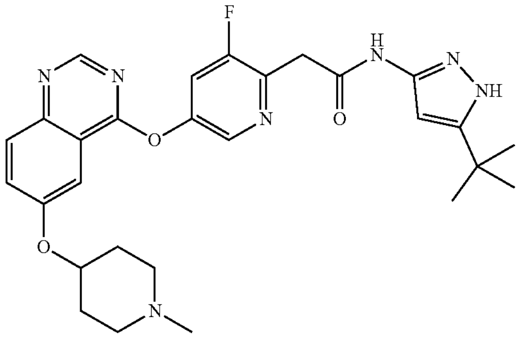 | N-(5-(tert-butyl)-1H-pyrazol-3-yl)-2-(3-fluoro-5-((6-((1-methylpiperidin-4-yl)oxy)quinazolin-4-yl)oxy)pyridin-2-yl)acetamide | (300 MHz, DMSO-$d_6$) δ 12.08 (s, 1H), 10.66 (s, 1H), 8.65 (s, 1H), 8.49 (d, J = 2.2 Hz, 1H), 8.04-7.92 (m, 2H), 7.76-7.66 (m, 2H), 6.27 (s, 1H), 4.71 (tt, J = 8.1, 3.4 Hz, 1H), 3.95 (s, 2H), 2.63 (dt, J = 9.1, 4.1 Hz, 2H), 2.33-2.23 (m, 2H), 2.20 (s, 3H), 2.07-1.97 (m, 2H), 1.83-1.66 (m, 2H), 1.25 (s, 9H) | 534.1 (M + H)$^+$ |
| 58 | 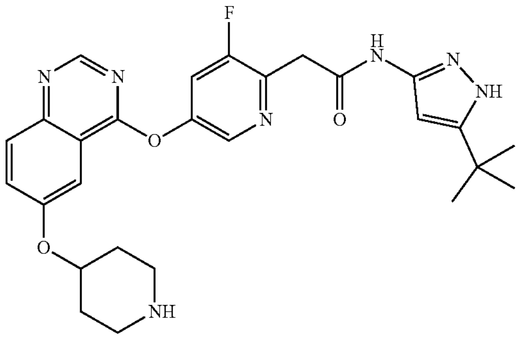 | N-(5-(tert-butyl)-1H-pyrazol-3-yl)-2-(3-fluoro-5-((6-(piperidin-4-yloxy)quinazolin-4-yl)oxy)pyridin-2-yl)acetamide | (300 MHz, DMSO-$d_6$) δ 12.06 (s, 1H), 10.63 (s, 1H), 8.64 (s, 1H), 8.49 (d, J = 2.3 Hz, 1H), 8.04-7.92 (m, 2H), 7.76-7.64 (m, 2H), 6.27 (s, 1H), 4.80-4.65 (m, 1H), 3.94 (d, J = 2.3 Hz, 2H), 2.97 (d, J = 12.6 Hz, 2H), 2.63 (t, J = 10.4 Hz, 2H), 2.00 (s, 2H), 1.54 (d, J = 10.1 Hz, 2H), 1.24 (s, 9H) | 520.1 (M + H)$^+$ |
| 59 | 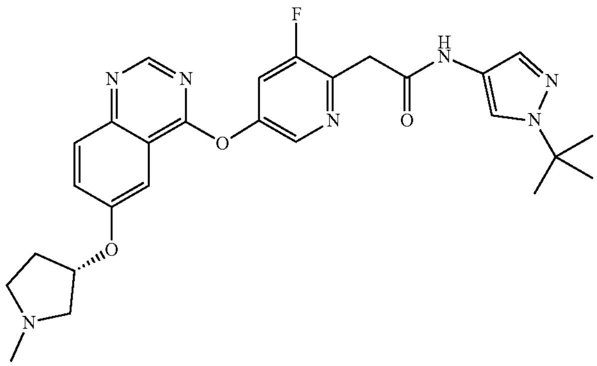 [SMILES: CN1CC[C@H](Oc2ccc3ncnc(Oc4cnc(CC(=O)Nc5cnn(C(C)(C)C)c5)c(F)c4)c3c2)C1] | (S)-N-(1-(tert-butyl)-1H-pyrazol-4-yl)-2-(3-fluoro-5-((6-((1-methylpyrrolidin-3-yl)oxy)quinazolin-4-yl)oxy)pyridin-2-yl)acetamide | (300 MHz, DMSO-$d_6$) δ 10.30 (s, 1H), 8.65 (s, 1H), 8.50 (d, J = 2.2 Hz, 1H), 8.05-7.94 (m, 2H), 7.93 (s, 1H), 7.67 (dd, J = 9.2, 2.8 Hz, 1H), 7.56 (d, J = 2.8 Hz, 1H), 7.45 (s, 1H), 5.18-5.07 (m, 1H), 3.91 (d, J = 2.3 Hz, 2H), 2.90-2.67 (m, 4H), 2.44-2.34 (m, 2H), 2.28 (s, 3H), 1.49 (s, 9H) | 520.2 (M + H)$^+$ |

-continued

| No. | Structure | Name | $^1$H NMR | Observed m/z |
|---|---|---|---|---|
| 60 | 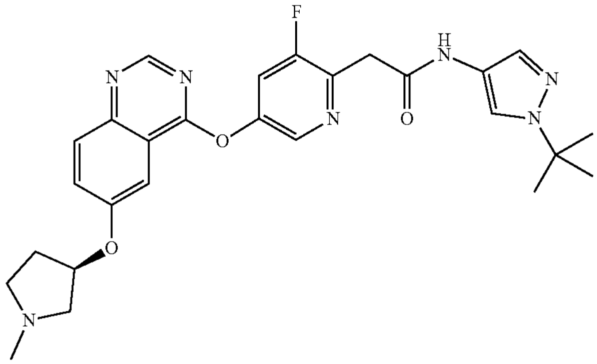 [SMILES: CN1CC[C@@H](Oc2ccc3ncnc(Oc4cnc(CC(=O)Nc5cnn(C(C)(C)C)c5)c(F)c4)c3c2)C1] | (R)-N-(1-(tert-butyl)-1H-pyrazol-4-yl)-2-(3-fluoro-5-((6-((1-methylpyrrolidin-3-yl)oxy)quinazolin-4-yl)oxy)pyridin-2-yl)acetamide | (300 MHz, DMSO-$d_6$) δ 10.33 (s, 1H), 8.66 (s, 1H), 8.51 (d, J = 2.2 Hz, 1H), 8.07-7.95 (m, 2H), 7.94 (s, 1H), 7.68 (dd, J = 9.2, 2.7 Hz, 1H), 7.57 (d, J = 2.8 Hz, 1H), 7.46 (s, 1H), 5.22-5.10 (m, 1H), 3.95-3.85 (m, 2H), 3.35 (s, 3H), 2.97-2.75 (m, 3H), 2.41-2.27 (m, 3H), 1.49 (s, 9H) | 520.0 $(M + H)^+$ |
| 61 | 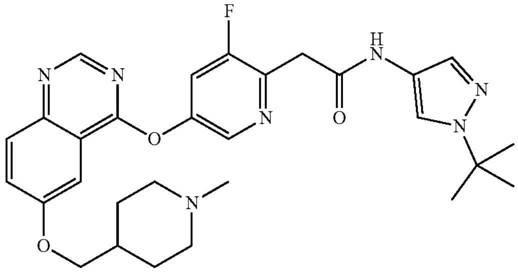 [SMILES: CN1CCC(COc2ccc3ncnc(Oc4cnc(CC(=O)Nc5cnn(C(C)(C)C)c5)c(F)c4)c3c2)CC1] | N-(1-(tert-butyl)-1H-pyrazol-4-yl)-2-(3-fluoro-5-((6-((1-methylpiperidin-4-yl)methoxy)quinazolin-4-yl)oxy)pyridin-2-yl)acetamide | (300 MHz, DMSO-$d_6$) δ 10.32 (s, 1H), 8.65 (s, 1H), 8.49 (s, 1H), 8.05-7.91 (m, 3H), 7.76-7.63 (m, 2H), 7.45 (s, 1H), 4.05 (d, J = 6.1 Hz, 1H), 3.91 (s, 2H), 2.86-2.74 (m, 2H), 2.16 (s, 3H), 1.91-1.74 (m, 4H), 1.49 (s, 9H), 1.43-1.33 (m, 4H) | 548.2 $(M + H)^+$ |
| 62 | 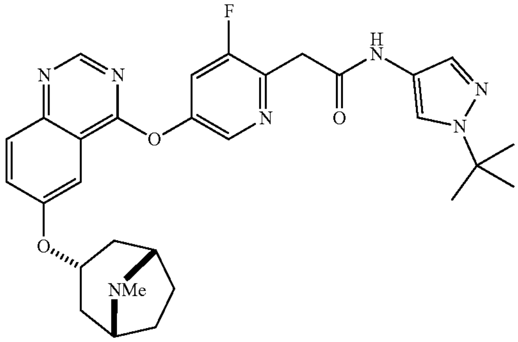 | N-(1-(tert-butyl)-1H-pyrazol-4-yl)-2-(3-fluoro-5-((6-(((1R,3r,5S)-8-methyl-8-azabicyclo[3.2.1]octan-3-yl)oxy)quinazolin-4-yl)oxy)pyridin-2-yl)acetamide | (400 MHz, DMSO-$d_6$) δ 10.31 (s, 1H), 8.64 (s, 1H), 8.50 (d, J = 2.3 Hz, 1H), 8.01 (dd, J = 10.1, 2.3 Hz, 1H), 7.97-7.92 (m, 2H), 7.72 (dd, J = 9.1, 2.8 Hz, 1H), 7.66 (d, J = 2.8 Hz, 1H), 7.45 (s, 1H), 4.84 (tt, J = 10.1, 5.7 Hz, 1H), 3.91 (d, J = 2.3 Hz, 2H), 3.22-3.14 (m, 2H), 2.23 (s, 3H), 1.99 (dd, J = 23.5, 9.5 Hz, 4H), 1.77-1.67 (m, 4H), 1.49 (s, 9H) | 560.2 $(M + H)^+$ |
| 63 | 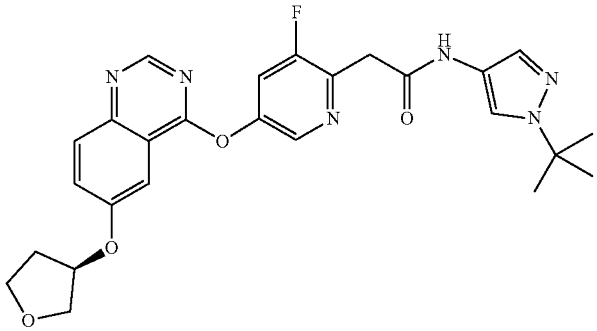 [SMILES: CC(C)(C)n1cc(NC(=O)Cc2ncc(Oc3ncnc4ccc(O[C@@H]5CCOC5)cc34)cc2F)cn1] | (R)-N-(1-(tert-butyl)-1H-pyrazol-4-yl)-2-(3-fluoro-5-((6-((tetrahydrofuran-3-yl)oxy)quinazolin-4-yl)oxy)pyridin-2-yl)acetamide | (300 MHz, DMSO-$d_6$) δ 10.33 (s, 1H), 8.66 (d, J = 3.0 Hz, 1H), 8.51 (d, J = 2.2 Hz, 1H), 8.08-7.90 (m, 3H), 7.71 (dd, J = 9.2, 2.9 Hz, 1H), 7.64 (d, J = 2.9 Hz, 1H), 7.45 (d, J = 4.4 Hz, 1H), 5.34 (s, 1H), 3.98-3.76 (m, 6H), 2.41-2.29 (m, 1H), 2.10-2.04 (m, 1H), 1.49 (s, 9H) | 507.2 $(M + H)^+$ |

-continued

| No. | Structure | Name | $^1$H NMR | Observed m/z |
|---|---|---|---|---|
| 64 | 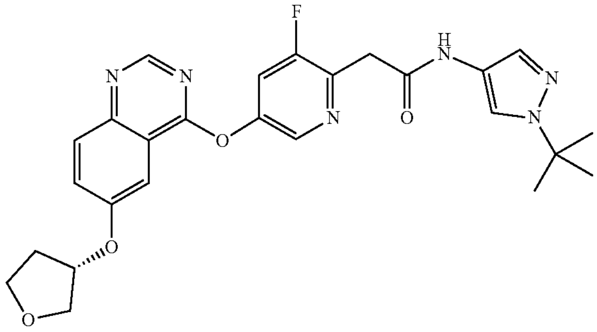 [SMILES: CC(C)(C)n1cc(NC(=O)Cc2ncc(Oc3ncnc4ccc(O[C@H]5CCOC5)cc34)cc2F)cn1] | (S)-N-(1-(tert-butyl)-1H-pyrazol-4-yl)-2-(3-fluoro-5-((6-((tetrahydrofuran-3-yl)oxy)quinazolin-4-yl)oxy)pyridin-2-yl)acetamide | (300 MHz, DMSO-$d_6$) δ 10.34 (s, 1H), 8.67 (s, 1H), 8.51 (d, J = 2.1 Hz, 1H), 8.08-7.89 (m, 3H), 7.77-7.61 (m, 2H), 7.45 (s, 1H), 5.33 (s, 1H), 4.08-3.65 (m, 6H), 2.39-2.28 (m, 1H), 2.10-2.04 (m, 1H), 1.49 (s, 9H) | 507.0 $(M + H)^+$ |
| 78 | 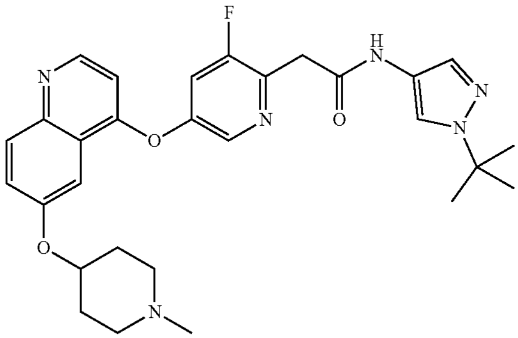 | N-(1-(tert-butyl)-1H-pyrazol-4-yl)-2-(3-fluoro-5-((6-((1-methylpiperidin-4-yl)oxy)quinolin-4-yl)oxy)pyridin-2-yl)acetamide | (400 MHz, DMSO-$d_6$) δ 10.26 (s, 1H), 8.61 (d, J = 5.1 Hz, 1H), 8.44 (d, J = 2.3 Hz, 1H), 7.99 (d, J = 9.1 Hz, 1H), 7.93-7.89 (m, 2H), 7.57-7.48 (m, 2H), 7.45 (s, 1H), 6.79 (d, J = 5.1 Hz, 1H), 4.63-4.57 (m, 1H), 3.90 (s, 2H), 2.66-2.57 (m, 2H), 2.28-2.20 (m, 2H), 2.19 (s, 3H), 2.03-1.93 (m, 2H), 1.77-1.67 (m, 2H), 1.49 (s, 9H) | 533.2 $(M + H)^+$ |
| 80 | 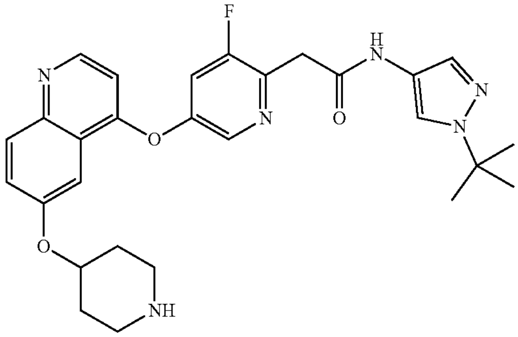 [SMILES: CC(C)(C)n1cc(NC(=O)Cc2ncc(Oc3ccnc4ccc(OC5CCNCC5)cc34)cc2F)cn1] | N-(1-(tert-butyl)-1H-pyrazol-4-yl)-2-(3-fluoro-5-((6-(piperidin-4-yloxy)quinolin-4-yl)oxy)pyridin-2-yl)acetamide | (300 MHz, DMSO-$d_6$) δ 10.28 (s, 1H), 8.61 (d, J = 5.1 Hz, 1H), 8.45 (d, J = 2.3 Hz, 1H), 8.02-7.88 (m, 3H), 7.57-7.47 (m, 2H), 7.45 (s, 1H), 6.78 (d, J = 5.1 Hz, 1H), 4.67-4.58 (m, 1H), 3.90 (d, J = 1.9 Hz, 2H), 3.04-2.92 (m, 2H), 2.67-2.57 (m, 2H), 2.03-1.92 (m, 2H), 1.60-1.51 (m, 2H), 1.49 (s, 9H) | 519.1 $(M + H)^+$ |
| 108 | 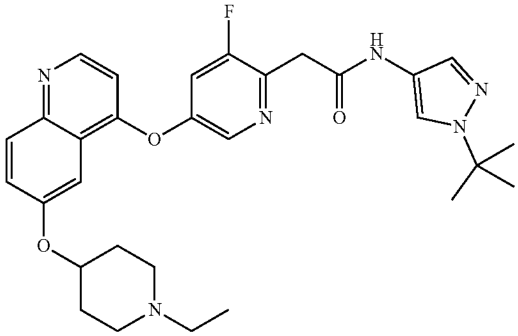 [SMILES: CCN1CCC(Oc2ccc3nccc(Oc4cnc(CC(=O)Nc5cnn(C(C)(C)C)c5)c(F)c4)c3c2)CC1] | N-(1-(tert-butyl)-1H-pyrazol-4-yl)-2-(5-((6-((1-ethylpiperidin-4-yl)oxy)quinolin-4-yl)oxy)-3-fluoropyridin-2-yl)acetamide | (300 MHz, DMSO-$d_6$) δ 10.27 (s, 1H), 8.60 (d, J = 5.1 Hz, 1H), 8.44 (d, J = 2.3 Hz, 1H), 8.01-7.88 (m, 3H), 7.57-7.47 (m, 2H), 7.45 (s, 1H), 6.78 (d, J = 5.1 Hz, 1H), 4.65-4.54 (m, 1H), 3.90 (d, J = 1.9 Hz, 2H), 2.69 (dd, J = 11.5, 6.1 Hz, 2H), 2.34 (q, J = 7.2 Hz, 2H), 2.30-2.17 (m, 2H), 2.08-1.91 (m, 2H), 1.69 (d, J = 9.3 Hz, 2H), 1.48 (s, 9H), 1.00 (t, J = 7.2 Hz, 3H) | 547.2 $(M + H)^+$ |

-continued

| No. | Structure | Name | $^1$H NMR | Observed m/z |
|---|---|---|---|---|
| 112 | 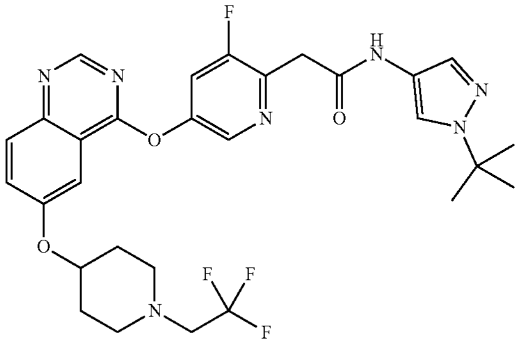 [SMILES: CC(C)(C)n1cc(NC(=O)Cc2ncc(Oc3ncnc4ccc(OC5CCN(CC(F)(F)F)CC5)cc34)cc2F)cn1] | N-(1-(tert-butyl)-1H-pyrazol-4-yl)-2-(3-fluoro-5-((6-((1-(2,2,2-trifluoroethyl)piperidin-4-yl)oxy)quinazolin-4-yl)oxy)pyridin-2-yl)acetamide | (400 MHz, DMSO-$d_6$) δ 10.32 (s, 1H), 8.65 (s, 1H), 8.50 (d, J = 2.2 Hz, 1H), 8.02-7.96 (m, 2H), 7.94 (s, 1H), 7.75-7.71 (m, 2H), 7.46 (s, 1H), 4.77-4.75 (m, 1H), 3.92-3.87 (m, 2H), 2.89 (s, 2H), 2.35-2.32 (m, 2H), 2.04-2.00 (m, 2H), 1.78-1.73 (m, 2H), 1.49 (s, 9H), 1.24 (s, 2H) | 602.1 $(M + H)^+$ |
| 129 | 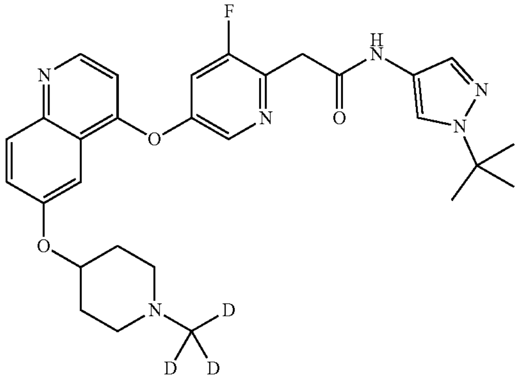 [SMILES: [2H]C([2H])([2H])N1CCC(Oc2ccc3nccc(Oc4cnc(CC(=O)Nc5cnn(C(C)(C)C)c5)c(F)c4)c3c2)CC1] | N-(1-(tert-butyl)-1H-pyrazol-4-yl)-2-(3-fluoro-5-((6-((1-(methyl-$d_3$)piperidin-4-yl)oxy)quinolin-4-yl)oxy)pyridin-2-yl)acetamide | (400 MHz, DMSO-$d_6$) δ 10.28 (s, 1H), 8.61 (d, J = 5.1 Hz, 1H), 8.46-8.40 (m, 1H), 8.02-7.87 (m, 3H), 7.58-7.48 (m, 2H), 7.45 (d, J = 0.7 Hz, 1H), 6.78 (d, J = 5.1 Hz, 1H), 4.59 (tt, J = 7.8, 3.8 Hz, 1H), 3.90 (d, J = 2.3 Hz, 2H), 2.61 (d, J = 13.0 Hz, 2H), 2.22 (t, J = 10.2 Hz, 2H), 1.98 (d, J = 13.8 Hz, 2H), 1.71 (dq, J = 8.2, 3.8 Hz, 2H), 1.48 (s, 9H) | 536.3 $(M + H)^+$ |
| 134 | 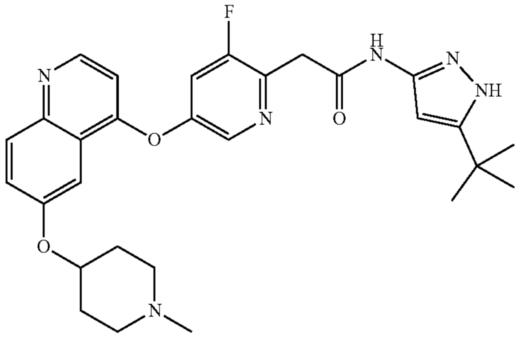 [SMILES: CN1CCC(Oc2ccc3nccc(Oc4cnc(CC(=O)Nc5cc(C(C)(C)C)[nH]n5)c(F)c4)c3c2)CC1] | N-(5-(tert-butyl)-1H-pyrazol-3-yl)-2-(3-fluoro-5-((6-((1-methylpiperidin-4-yl)oxy)quinolin-4-yl)oxy)pyridin-2-yl)acetamide | (400 MHz, DMSO-$d_6$) δ 12.07 (s, 1H), 10.63 (s, 1H), 8.60 (d, J = 5.1 Hz, 1H), 8.43 (d, J = 2.2 Hz, 1H), 7.98 (d, J = 9.1 Hz, 1H), 7.90 (dd, J = 10.2, 2.3 Hz, 1H), 7.56-7.48 (m, 2H), 6.78 (d, J = 5.1 Hz, 1H), 6.27 (s, 1H), 4.65-4.56 (m, 1H), 3.93 (d, J = 2.3 Hz, 2H), 2.66-2.57 (m, 2H), 2.24 (d, J = 13.1 Hz, 2H), 2.18 (s, 3H), 1.98 (dd, J = 12.3, 6.4 Hz, 2H), 1.76-1.64 (m, 2H), 1.24 (s, 9H) | 532.8 $(M + H)^+$ |
| 135 | 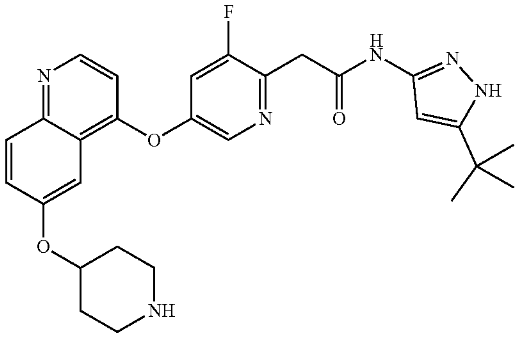 [SMILES: CC(C)(C)c1cc(NC(=O)Cc2ncc(Oc3ccnc4ccc(OC5CCNCC5)cc34)cc2F)n[nH]1] | N-(5-(tert-butyl)-1H-pyrazol-3-yl)-2-(3-fluoro-5-((6-(piperidin-4-yloxy)quinolin-4-yl)oxy)pyridin-2-yl)acetamide | (400 MHz, DMSO-$d_6$) δ 12.06 (s, 1H), 10.62 (s, 1H), 8.60 (d, J = 5.1 Hz, 1H), 8.43 (d, J = 2.3 Hz, 1H), 7.98 (d, J = 9.1 Hz, 1H), 7.90 (dd, J = 10.2, 2.3 Hz, 1H), 7.54 (d, J = 2.8 Hz, 1H), 7.50 (dd, J = 9.1, 2.8 Hz, 1H), 6.77 (d, J = 5.1 Hz, 1H), 6.27 (s, 1H), 4.62 (dt, J = 9.2, 4.8 Hz, 1H), 3.93 (d, J = 2.2 Hz, 2H), 2.95 (dd, J = 10.9, 6.4 Hz, 2H), 2.63-2.57 (m, 2H), 1.97 (d, J = 9.6 Hz, 2H), 1.58-1.45 (m, 2H), 1.24 (s, 9H) | 519.1 $(M + H)^+$ |

-continued

| No. | Structure | Name | ¹H NMR | Observed m/z |
|---|---|---|---|---|
| 138 | 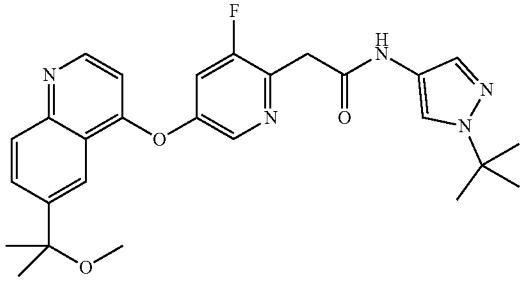 [SMILES: COC(C)(C)c1ccc2nccc(Oc3cnc(CC(=O)Nc4cnn(C(C)(C)C)c4)c(F)c3)c2c1] | N-(1-(tert-butyl)-1H-pyrazol-4-yl)-2-(3-fluoro-5-((6-(2-methoxypropan-2-yl)quinolin-4-yl)oxy)pyridin-2-yl)acetamide | (400 MHz, DMSO-$d_6$) δ 10.30 (s, 1H), 8.73 (d, J = 5.2 Hz, 1H), 8.50 (d, J = 2.3 Hz, 1H), 8.24 (d, J = 2.1 Hz, 1H), 8.06 (d, J = 8.8 Hz, 1H), 7.99 (dd, J = 10.1, 2.3 Hz, 1H), 7.95-7.88 (m, 2H), 7.46 (s, 1H), 6.76 (d, J = 5.1 Hz, 1H), 3.92 (d, J = 2.4 Hz, 2H), 3.05 (s, 3H), 1.58 (s, 6H), 1.49 (s, 9H) | 492.2 $(M + H)^+$ |
| 139 | 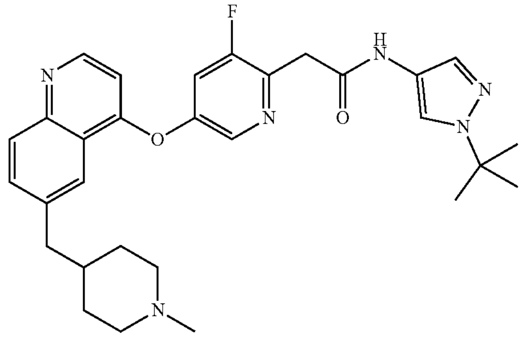 [SMILES: CN1CCC(Cc2ccc3nccc(Oc4cnc(CC(=O)Nc5cnn(C(C)(C)C)c5)c(F)c4)c3c2)CC1] | N-(1-(tert-butyl)-1H-pyrazol-4-yl)-2-(3-fluoro-5-((6-((1-methylpiperidin-4-yl)methyl)quinolin-4-yl)oxy)pyridin-2-yl)acetamide | (400 MHz, DMSO-$d_6$) δ 10.28 (s, 1H), 8.69 (d, J = 5.1 Hz, 1H), 8.47 (d, J = 2.2 Hz, 1H), 8.03 (d, J = 1.9 Hz, 1H), 7.98 (d, J = 8.6 Hz, 1H), 7.95 (dd, J = 10.1, 2.3 Hz, 1H), 7.93 (d, J = 0.7 Hz, 1H), 7.69 (dd, J = 8.6, 2.0 Hz, 1H), 7.45 (s, 1H), 6.75 (d, J = 5.1 Hz, 1H), 3.91 (s, 2H), 2.73 (t, J = 9.8 Hz, 4H), 2.11 (s, 3H), 1.77 (t, J = 11.4 Hz, 2H), 1.59-1.53 (m, 3H), 1.49 (s, 9H), 1.28-1.20 (m, 2H) | 531.2 $(M + H)^+$ |
| 140 | 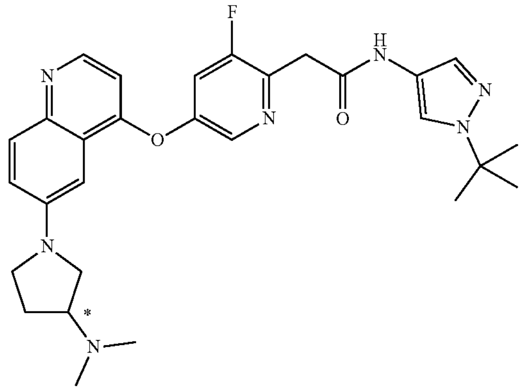 [SMILES: CN(C)C1CCN(c2ccc3nccc(Oc4cnc(CC(=O)Nc5cnn(C(C)(C)C)c5)c(F)c4)c3c2)C1] enantiomer 1 (retention time: 2.92 min, column: CHIRALPAK IA-3, 4.6 × 50 mm, 3 µm; mobile phase A: hexane (0.1% DEA), mobile phase B: EtOH, isocratic separation with 25% B, flow rate: 1.0 mL/min, wavelength: 254 nm) | N-(1-(tert-butyl)-1H-pyrazol-4-yl)-2-(5-((6-(3-(dimethylamino)pyrrolidin-1-yl)quinolin-4-yl)oxy)-3-fluoropyridin-2-yl)acetamide | (400 MHz, DMSO-$d_6$) δ 10.27 (s, 1H), 8.43-8.35 (m, 2H), 7.92 (d, J = 0.7 Hz, 1H), 7.88 (d, J = 9.2 Hz, 1H), 7.84 (dd, J = 10.2, 2.4 Hz, 1H), 7.44 (s, 1H), 7.33 (dd, J = 9.3, 2.7 Hz, 1H), 6.90 (d, J = 2.7 Hz, 1H), 6.68 (d, J = 5.0 Hz, 1H), 3.88 (d, J = 2.3 Hz, 2H), 3.63-3.48 (m, 2H), 3.40-3.35 (m, 1H), 3.16 (t, J = 8.7 Hz, 1H), 2.84 (quint, J = 7.5 Hz, 1H), 2.22 (s, 6H), 2.20-2.16 (m, 1H), 1.92-1.80 (m, 1H), 1.48 (s, 9H) | 532.1 $(M + H)^+$ |

-continued

| No. | Structure | Name | $^1$H NMR | Observed m/z |
|---|---|---|---|---|
| 141 | 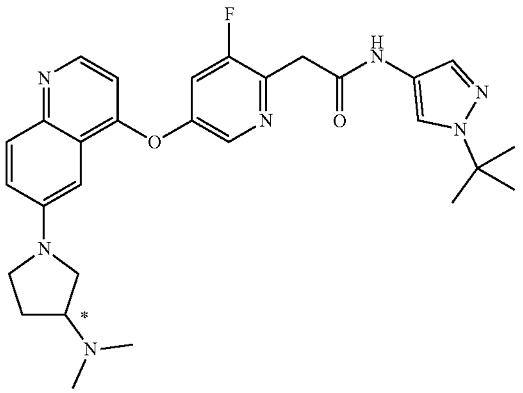 [SMILES: CN(C)C1CCN(c2ccc3nccc(Oc4cnc(CC(=O)Nc5cnn(C(C)(C)C)c5)c(F)c4)c3c2)C1] enantiomer 2 (retention time: 3.59 min, column: CHIRALPAK IA-3, 4.6 × 50 mm, 3 μm; mobile phase A: hexane (0.1% DEA), mobile phase B: EtOH, isocratic separation with 25% B, flow rate: 1.0 mL/min, wavelength: 254 nm) | N-(1-(tert-butyl)-1H-pyrazol-4-yl)-2-(5-((6-(3-(dimethylamino)pyrrolidin-1-yl)quinolin-4-yl)oxy)-3-fluoropyridin-2-yl)acetamide | (400 MHz, DMSO-$d_6$) δ 10.27 (s, 1H), 8.44-8.36 (m, 2H), 7.97-7.79 (m, 3H), 7.44 (s, 1H), 7.33 (dd, J = 9.3, 2.7 Hz, 1H), 6.90 (d, J = 2.7 Hz, 1H), 6.68 (d, J = 5.0 Hz, 1H), 3.89 (d, J = 2.3 Hz, 2H), 3.64-3.48 (m, 2H), 3.38 (dd, J = 9.8, 6.9 Hz, 1H), 3.17 (t, J = 8.7 Hz, 1H), 2.85 (quint, J = 7.4 Hz, 1H), 2.22 (s, 6H), 2.22-2.15 (m, 1H), 1.93-1.79 (m, 1H), 1.48 (s, 9H) | 532.2 $(M + H)^+$ |
| 150 | 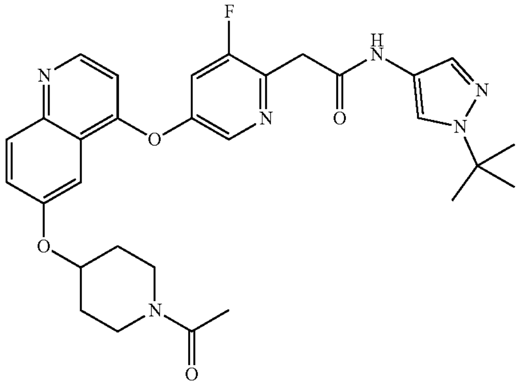 [SMILES: CC(=O)N1CCC(Oc2ccc3nccc(Oc4cnc(CC(=O)Nc5cnn(C(C)(C)C)c5)c(F)c4)c3c2)CC1] | 2-(5-((6-((1-acetylpiperidin-4-yl)oxy)quinolin-4-yl)oxy)-3-fluoropyridin-2-yl)-N-(1-(tert-butyl)-1H-pyrazol-4-yl)acetamide | (300 MHz, DMSO-$d_6$) δ 10.28 (s, 1H), 8.61 (d, J = 5.1 Hz, 1H), 8.45 (d, J = 2.2 Hz, 1H), 8.00 (d, J = 9.2 Hz, 1H), 7.95-7.89 (m, 2H), 7.62 (d, J = 2.8 Hz, 1H), 7.53 (dd, J = 9.2, 2.7 Hz, 1H), 7.45 (d, J = 0.8 Hz, 1H), 6.78 (d, J = 5.1 Hz, 1H), 4.87 (ddd, J = 11.0, 7.4, 4.0 Hz, 1H), 3.90 (s, 2H), 3.86-3.66 (m, 2H), 3.45-3.35 (m, 2H), 2.04-2.02 (m, 5H), 1.72-1.58 (m, 2H), 1.48 (s, 9H) | 561.1 $(M + H)^+$ |
| 289 | 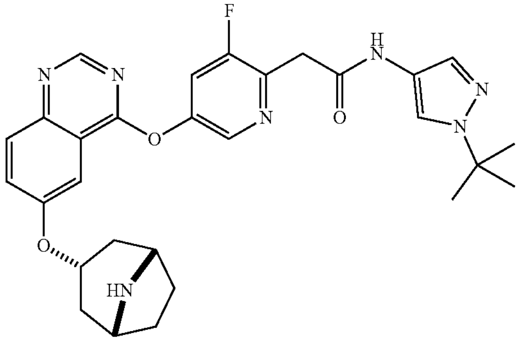 | 2-(5-((6-(((1R,3r,5S)-8-azabicyclo[3.2.1]octan-3-yl)oxy)quinazolin-4-yl)oxy)-3-fluoropyridin-2-yl)-N-(1-(tert-butyl)-1H-pyrazol-4-yl)acetamide | (300 MHz, DMSO-$d_6$) δ 10.31 (s, 1H), 8.64 (s, 1H), 8.50 (s, 1H), 8.04-7.95 (m, 2H), 7.93 (s, 1H), 7.75-7.65 (m, 2H), 7.45 (s, 1H), 4.94-4.81 (m, 1H), 3.91 (s, 2H), 3.50 (s, 2H), 2.11 (dd, J = 10.5, 5.6 Hz, 2H), 1.72 (s, 3H), 1.56 (t, J = 10.3 Hz, 2H), 1.49 (s, 9H) | 546.2 $(M + H)^+$ |

-continued

| No. | Structure | Name | $^1$H NMR | Observed m/z |
|---|---|---|---|---|
| 613 | 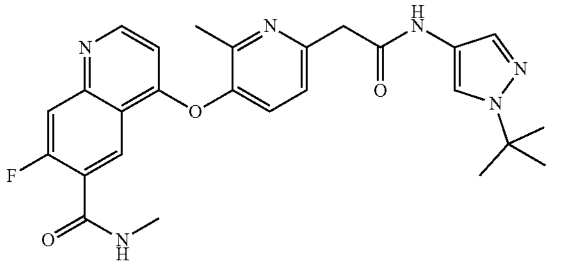 [SMILES: CNC(=O)c1cc2c(Oc3ccc(CC(=O)Nc4cnn(C(C)(C)C)c4)nc3C)ccnc2cc1F] | 4-((6-(2-((1-(tert-butyl)-1H-pyrazol-4-yl)amino)-2-oxoethyl)-2-methylpyridin-3-yl)oxy)-7-fluoro-N-methylquinoline-6-carboxamide | (400 MHz, DMSO-$d_6$) δ 10.26 (s, 1H), 8.75 (d, J = 5.2 Hz, 1H), 8.63 (d, J = 7.8 Hz, 1H), 8.59-8.54 (m, 1H), 7.95 (d, J = 0.7 Hz, 1H), 7.88 (d, J = 11.8 Hz, 1H), 7.70 (d, J = 8.3 Hz, 1H), 7.46 (d, J = 0.7 Hz, 1H), 7.41 (d, J = 8.3 Hz, 1H), 6.50 (d, J = 5.2 Hz, 1H), 3.82 (s, 2H), 2.85 (d, J = 4.6 Hz, 3H), 2.34 (s, 3H), 1.49 (s, 9H) | 491.0 (M + H)$^+$ |
| 614 | 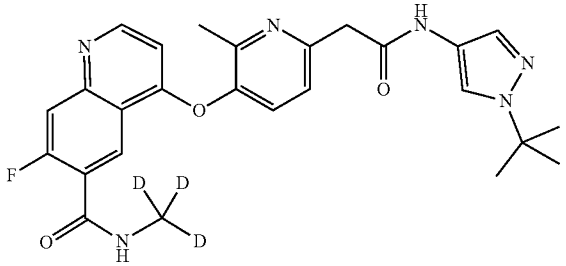 [SMILES: [2H]C([2H])([2H])NC(=O)c1cc2c(Oc3ccc(CC(=O)Nc4cnn(C(C)(C)C)c4)nc3C)ccnc2cc1F] | 4-((6-(2-((1-(tert-butyl)-1H-pyrazol-4-yl)amino)-2-oxoethyl)-2-methylpyridin-3-yl)oxy)-7-fluoro-N-(methyl-$d_3$)quinoline-6-carboxamide | (400 MHz, DMSO-$d_6$) δ 10.26 (s, 1H), 8.75 (d, J = 5.2 Hz, 1H), 8.63 (d, J = 7.8 Hz, 1H), 8.53 (s, 1H), 7.95 (s, 1H), 7.88 (d, J = 11.7 Hz, 1H), 7.70 (d, J = 8.3 Hz, 1H), 7.46 (s, 1H), 7.41 (d, J = 8.3 Hz, 1H), 6.50 (d, J = 5.2 Hz, 1H), 3.82 (s, 2H), 2.33 (s, 3H), 1.49 (s, 9H) | 494.0 (M + H)$^+$ |
| 612 | 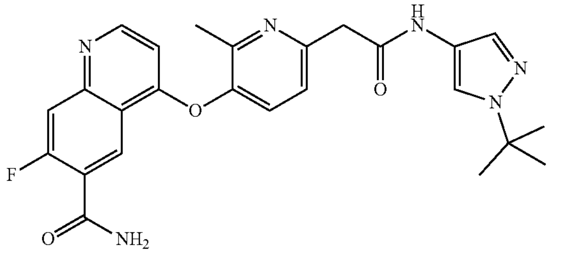 [SMILES: Cc1nc(CC(=O)Nc2cnn(C(C)(C)C)c2)ccc1Oc1ccnc2cc(F)c(C(N)=O)cc12] | 4-((6-(2-((1-(tert-butyl)-1H-pyrazol-4-yl)amino)-2-oxoethyl)-2-methylpyridin-3-yl)oxy)-7-fluoroquinoline-6-carboxamide | (300 MHz, DMSO-$d_6$) δ 10.27 (s, 1H), 8.76 (d, J = 5.2 Hz, 1H), 8.68 (d, J = 7.8 Hz, 1H), 8.04 (s, 1H), 7.98-7.82 (m, 3H), 7.72 (d, J = 8.3 Hz, 1H), 7.47 (d, J = 0.7 Hz, 1H), 7.42 (d, J = 8.3 Hz, 1H), 6.51 (d, J = 5.2 Hz, 1H), 3.83 (s, 2H), 2.34 (s, 3H), 1.49 (s, 9H) | 477.2 (M + H)$^+$ |

Example 17—Synthesis of N-(1-(tert-butyl)-1H-pyrazol-4-yl)-2-(3-methyl-4-((6-(methylsulfonyl)quinolin-4-yl)oxy)phenyl)propanamide (Compound 215); Prepared According to General Scheme 21

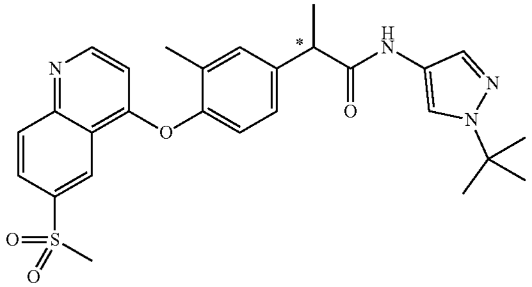 [SMILES: Cc1cc(C(C)C(=O)Nc2cnn(C(C)(C)C)c2)ccc1Oc1ccnc2ccc(S(C)(=O)=O)cc12]

Part I—Synthesis of tert-butyl 2-(4-bromo-3-methylphenyl)propanoate

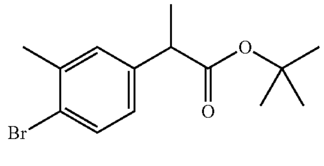 [SMILES: Cc1cc(C(C)C(=O)OC(C)(C)C)ccc1Br]

Trimethylsilyl chloride (0.52 g, 4.78 mmol, 0.05 equiv.) was added to a suspension of zinc (9.38 g, 143 mmol, 1.50 equiv.) in THF (150 mL) and the mixture was stirred for 15 min at room temperature under an inert atmosphere of nitrogen. Subsequently, a solution of tert-butyl 2-bromopropanoate (20.0 g, 95.7 mmol, 1.00 equiv.) in THF (50 mL) was added dropwise at a temperature of 50° C. After cooling to room temperature, the obtained organozinc reagent was used in the next reaction without any purification. 1-Bromo-4-iodo-2-methylbenzene (10.8 mL, 36.4 mmol 1.00 equiv.), $Pd_2(dba)_3$ (3.34 g, 3.64 mmol, 0.10 equiv.) and Xantphos (2.11 g, 3.64 mmol, 0.10 equiv.) were added to a solution of the organozinc reagent in THF (120 mL, 43.7 mmol, 1.20 equiv.) and the reaction mixture was heated to 65° C. overnight under an inert atmosphere of nitrogen. Water (150 mL) was added, and the product was extracted with EtOAc (3×200 mL). The combined organic phases were washed with brine, dried over $Na_2SO_4$, and the solvent was removed under reduced pressure. The crude product was purified by column chromatography (petroleum ether/EtOAc 100:1). The title compound was obtained as a light-yellow liquid (5.3 g, 49%).

Part II—Synthesis of tert-butyl 2-(3-methyl-4-(4,4,5,5-tetramethyl-1,3,2-dioxaborolan-2-yl)phenyl)propanoate

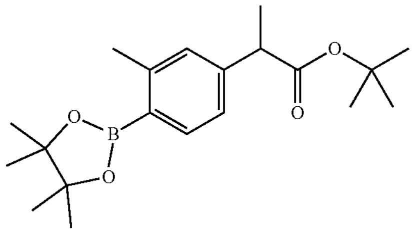 [SMILES: Cc1cc(C(C)C(=O)OC(C)(C)C)ccc1B1OC(C)(C)C(C)(C)O1]

A solution of tert-butyl 2-(4-bromo-3-methylphenyl)propanoate (5.30 g, 17.7 mmol, 1.00 equiv.), bis(pinacolato)diboron (9.03 g, 35.4 mmol, 2.00 equiv.), Pd(dppf)$Cl_2$ (1.30 g, 1.77 mmol, 0.10 equiv.) and potassium acetate (5.22 g, 53.1 mmol, 3.00 equiv.) in 1,4-dioxane (53 mL) was heated to 100° C. overnight under an inert atmosphere of nitrogen. Water (70 mL) was added, and the product was extracted with EtOAc (3×100 mL). The combined organic phases were washed with brine, dried over $Na_2SO_4$, and the solvent was removed under reduced pressure. The crude product was purified by column chromatography (petroleum ether/EtOAc 100:1). The title compound was obtained as a light-yellow liquid (4.9 g, 80%).

Part III—Synthesis of tert-butyl 2-(4-hydroxy-3-methylphenyl)propanoate

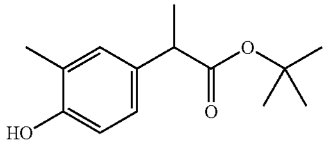 [SMILES: Cc1cc(C(C)C(=O)OC(C)(C)C)ccc1O]

A solution of hydrogen peroxide in water (1.89 g, 55.4 mmol, 4.00 equiv.) was added to a solution of tert-butyl 2-(3-methyl-4-(4,4,5,5-tetramethyl-1,3,2-dioxaborolan-2-yl)phenyl)propanoate (4.8 g, 13.9 mmol, 1.00 equiv.) in THF (33.6 mL) and the mixture was stirred at room temperature for 5 h. Subsequently, water (70 mL) was added, and the product was extracted with EtOAc (3×100 mL). The combined organic phases were washed with brine, dried over $Na_2SO_4$, and the solvent was removed under reduced pressure. The title compound was obtained as a brown oil (4.4 g), which was used in the next reaction without further purification.

Part IV—Synthesis of tert-butyl 2-(3-methyl-4-((6-(methylsulfonyl)quinolin-4-yl)oxy)phenyl)propanoate

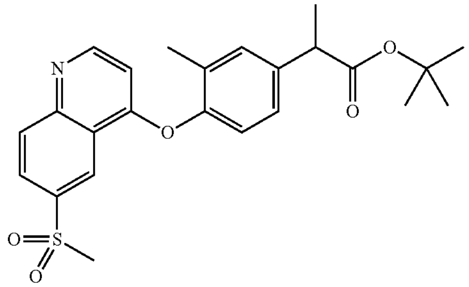 [SMILES: Cc1cc(C(C)C(=O)OC(C)(C)C)ccc1Oc1ccnc2ccc(S(C)(=O)=O)cc12]

A solution of tert-butyl 2-(4-hydroxy-3-methylphenyl)propanoate (1.0 g, 4.23 mmol, 1.00 equiv.), 4-chloro-6-(methylsulfonyl)quinoline (1.02 g, 4.23 mmol, 1.00 equiv.), and $Cs_2CO_3$ (2.76 g, 8.46 mmol, 2.00 equiv.) in NMP (20 mL) was stirred at room temperature overnight. Subsequently, insoluble byproducts were filtered off and the crude product was purified by reversed-phase flash chromatography (column: C18 silica gel; mobile phase A: water (0.1% $NH_4HCO_3$), mobile phase B: ACN, gradient: 45-75% B in 30 min; wavelength: 210 nm). The title compound was obtained as a colorless oil (1.0 g, 54%).

Part V—Synthesis of 2-(3-methyl-4-((6-(methylsulfonyl)quinolin-4-yl)oxy)phenyl)propanoic Acid

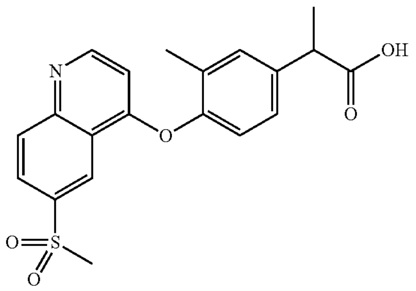 [SMILES: Cc1cc(C(C)C(=O)O)ccc1Oc1ccnc2ccc(S(C)(=O)=O)cc12]

A solution of HCl in 1,4-dioxane (4 M, 9.5 mL) was added to a solution of tert-butyl 2-(3-methyl-4-((6-(methylsulfonyl)quinolin-4-yl)oxy)phenyl)propanoate (950 mg, 2.15 mmol, 1.00 equiv.) in 1,4-dioxane (9.5 mL) and the mixture was heated to 70° C. overnight. Water (15 mL) was added, and the product was extracted with EtOAc (3×20 mL). The combined organic phases were washed with brine, dried over $Na_2SO_4$, and the solvent was removed under reduced pressure. The title compound was obtained as a white solid (800 mg, 96%), which was used in the next reaction without further purification.

Part VI—Synthesis of N-(1-(tert-butyl)-1H-pyrazol-4-yl)-2-(3-methyl-4-((6-(methylsulfonyl)quinolin-4-yl)oxy)phenyl)propanamide (Compound 215)

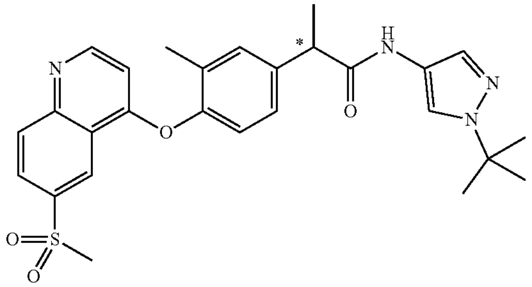 [SMILES: Cc1cc(C(C)C(=O)Nc2cnn(C(C)(C)C)c2)ccc1Oc1ccnc2ccc(S(C)(=O)=O)cc12]

TCFH (1.02 g, 3.63 mmol, 2.00 equiv.) was added to a solution of 2-(3-methyl-4-((6-(methylsulfonyl)quinolin-4-yl)oxy)phenyl)propanoic acid (700 mg, 1.82 mmol, 1.00 equiv.), 1-(tert-butyl)-1H-pyrazol-4-amine (379 mg, 2.72 mmol, 1.50 equiv.), and NMI (447 mg, 5.45 mmol, 3.00 equiv.) in ACN (7 mL) and the mixture was stirred at room temperature for 4 h. Subsequently, the crude product was purified by reversed-phase flash chromatography (column: C18 silica gel; mobile phase A: water (0.1% $NH_4HCO_3$), mobile phase B: ACN, gradient: 20-60% B in 40 min; wavelength: 210 nm). The racemic title compound was obtained as a white oil (700 mg, 76%). The two enantiomers were separated by chiral chromatography (column: CHIRAL ART Amylose-SC, 20×250 mm, 5 μm; mobile phase A: MTBE (0.5% of a 2 M solution of ammonia in MeOH), mobile phase B: EtOH). The title compound (72.4 mg, 7.9%, enantiomer 1, retention time: 1.57 min; column: CHIRALPAK IA-3, 4.6×50 mm, 3 μm; mobile phase A: MTBE (0.1% DEA), mobile phase B: EtOH, isocratic separation with 10% B, flow rate: 1.0 mL/min, wavelength: 254 nm) was obtained as a white solid. LCMS (ESI) calculated for $C_{27}H_{29}N_4O_4S$ $(M-H)^-$: 505.2, found: 505.1. $^1H$ NMR (400 MHz, DMSO-$d_6$) δ 10.15 (s, 1H), 8.89 (dd, J=1.9, 0.9 Hz, 1H), 8.83 (d, J=5.2 Hz, 1H), 8.32-8.23 (m, 2H), 7.97 (s, 1H), 7.45-7.43 (m, 2H), 7.36 (dd, J=8.3, 2.2 Hz, 1H), 7.24 (d, J=8.3 Hz, 1H), 6.55 (d, J=5.2 Hz, 1H), 3.80 (q, J=7.0 Hz, 1H), 3.38 (s, 3H), 2.15 (s, 3H), 1.48 (s, 9H), 1.45 (d, J=7.0 Hz, 3H).

Example 18—Preparation of Additional Arylpropionic Acid Compounds

Compounds in the table below were prepared based on experimental procedures described in Example 17 and the detailed description.

| No | Structure | Name | $^1H$ NMR | Observed m/z |
|---|---|---|---|---|
| 11 | 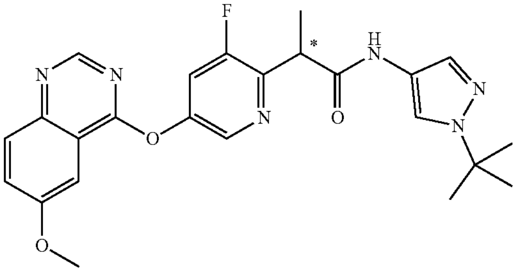 [SMILES: COc1ccc2ncnc(Oc3cnc(C(C)C(=O)Nc4cnn(C(C)(C)C)c4)c(F)c3)c2c1] enantiomer 1 (retention time: 3.45 min; column: CHIRAL Cellulose-SB, 4.6 x 100 mm, 3 μm; mobile phase A: hexane (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(3-fluoro-5-((6-methoxyquinazolin-4-yl)oxy)pyridin-2-yl)propanamide | (400 MHz, DMSO-$d_6$) δ 10.12 (s, 1H), 8.66 (s, 1H), 8.53 (d, J = 2.2 Hz, 1H), 8.01-7.96 (m, 2H), 7.94 (s, 1H), 7.71 (dd, J = 9.1, 2.8 Hz, 1H), 7.64 (d, J = 2.9 Hz, 1H), 7.45 (s, 1H), 4.20 (q, J = 7.0 Hz, 1H), 3.98 (s, 3H), 1.54 (d, J = 7.1 Hz, 3H), 1.48 (s, 9H) | 465.2 $(M + H)^+$ |

Example 19—Synthesis of N-(6-(tert-butyl)pyrimidin-4-yl)-2-(2-fluoro-4-((6-methoxyquinazolin-4-yl)oxy)phenyl)acetamide (Compound 32); Prepared According to General Scheme 4

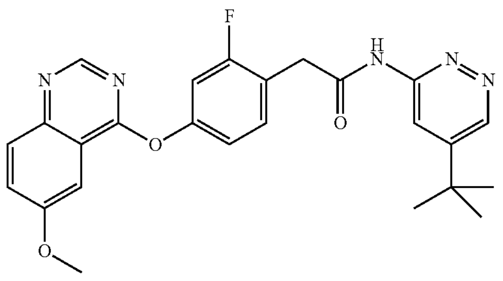

Propylphosphonic anhydride (581.5 mg, 1.83 mmol, 2.00 equiv.) was added to a solution of 2-(2-fluoro-4-((6-methoxyquinazolin-4-yl)oxy)phenyl)acetic acid (300.0 mg, 0.914 mmol, 1.00 equiv., can be prepared according to Part VI of Example 20), 6-(tert-butyl)pyrimidin-4-amine (140.9 mg, 0.932 mmol, 1.02 equiv.), and DIPEA (590.5 mg, 4.57 mmol, 5.00 equiv.) in DMF (3 mL) at 0° C. Subsequently, the reaction mixture was stirred at room temperature for 1 h. The crude product was purified by reversed-phase flash chromatography (column: C18 silica gel; mobile phase A: water (1% $NaHCO_3$), mobile phase B: ACN, gradient: 30-60% B in 30 min; wavelength: 210 nm). The title compound was obtained as a yellow solid (190 mg, 44%). LCMS (ESI) calculated for $C_{25}H_{25}FN_5O_3$ $(M+H)^+$: 462.2, found: 462.2. $^1H$ NMR (400 MHz, DMSO-$d_6$) δ 11.19 (bs, 1H), 8.85 (d, J=1.2 Hz, 1H), 8.64 (s, 1H), 8.15 (d, J=1.2 Hz, 1H), 7.95 (d, J=9.1 Hz, 1H), 7.69 (dd, J=9.1, 2.9 Hz, 1H), 7.62 (d, J=2.8 Hz, 1H), 7.51 (t, J=8.5 Hz, 1H), 7.35 (dd, J=10.5, 2.4 Hz, 1H), 7.23-7.17 (m, 1H), 3.98 (s, 3H), 3.93 (s, 2H), 1.28 (s, 9H).

Example 20—Synthesis of 2-(2-fluoro-4-((6-methoxyquinazolin-4-yl)oxy)phenyl)-N-(4-(1-(trifluoromethyl)cyclopropyl)pyridin-2-yl)acetamide (Compound 34); Prepared According to General Scheme 4

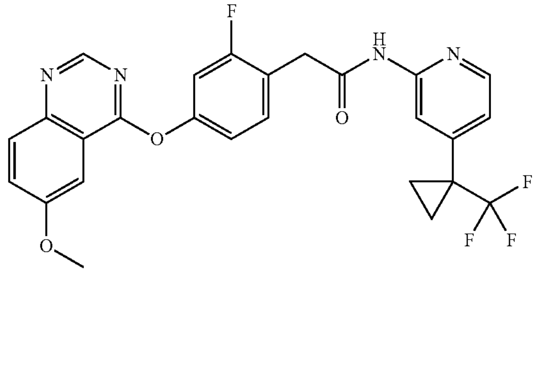 [SMILES: COc1ccc2ncnc(Oc3ccc(CC(=O)Nc4cc(C5(C(F)(F)F)CC5)ccn4)c(F)c3)c2c1]

Part I—Synthesis of 2-chloro-4-(3,3,3-trifluoroprop-1-en-2-yl)pyridine

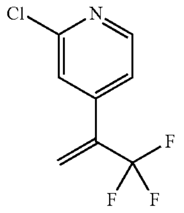

A solution of (2-chloropyridin-4-yl)boronic acid (2.00 g, 12.7 mmol, 1.00 equiv.), 2-bromo-3,3,3-trifluoroprop-1-ene (2.67 g, 15.3 mmol, 1.20 equiv.), Pd(dppf)$Cl_2$ (929 mg, 1.27 mmol, 0.10 equiv.), and $K_2CO_3$ (6.19 g, 44.5 mmol, 3.50 equiv.) in THF (20 mL) and water (10 mL) was heated to 70° C. overnight under an inert atmosphere of nitrogen. Subsequently, water was added, and the product was extracted with EtOAc (3×20 mL). The combined organic phases were washed with brine, dried over $MgSO_4$, and the solvent was removed under reduced pressure. The crude product was purified by reversed-phase flash chromatography (column: C18 silica gel; mobile phase A: water (1% $NH_4HCO_3$), mobile phase B: ACN, gradient: 50-80% B in 17 min; wavelength: 210 nm). The title compound was obtained as a yellow oil (500 mg, 19%).

Part II—Synthesis of tert-butyl (4-(3,3,3-trifluoroprop-1-en-2-yl)pyridin-2-yl)carbamate

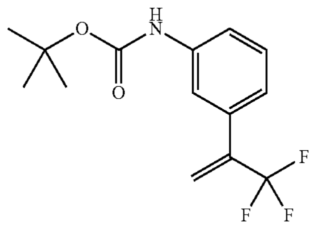 [SMILES: C=C(c1cccc(NC(=O)OC(C)(C)C)c1)C(F)(F)F]

A solution of 2-chloro-4-(3,3,3-trifluoroprop-1-en-2-yl)pyridine (1.00 g, 4.82 mmol, 1.00 equiv.), tert-butyl carbamate (1.13 g, 9.63 mmol, 2.00 equiv.), $Cs_2CO_3$ (1.87 g, 9.63 mmol, 2.00 equiv.), $Pd_2(dba)_3$ (0.44 g, 0.482 mmol, 0.10 equiv.) and XPhos (0.46 g, 0.963 mmol, 0.20 equiv.) in 1,4-dioxane (10 mL) was heated to 90° C. for 1 h under an inert atmosphere of nitrogen. EtOAc was added and the organic phase was washed with brine, dried over $MgSO_4$, and the solvent was removed under reduced pressure. The crude product was purified by column chromatography (petroleum ether/EtOAc 50:1). The title compound was obtained as a yellow solid.

Part III—Synthesis of tert-butyl (4-(1-(trifluoromethyl)cyclopropyl)pyridin-2-yl)carbamate

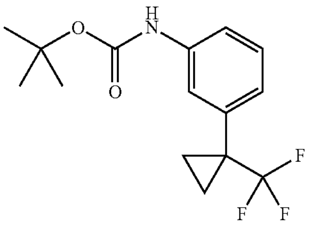 [SMILES: CC(C)(C)OC(=O)Nc1cccc(C2(C(F)(F)F)CC2)c1]

Sodium bis(trimethylsilyl)amide (1.02 g, 5.55 mmol, 1.60 equiv.) and methyl (diphenyl)sulfonium tetrafluoroborate (1.30 g, 4.50 mmol, 1.30 equiv.) were added to a solution of tert-butyl (4-(3,3,3-trifluoroprop-1-en-2-yl)pyridin-2-yl)carbamate (1.00 g, 3.47 mmol, 1.00 equiv.) in THF (10 mL) at 0° C. under an inert atmosphere of nitrogen. The mixture was stirred at this temperature for 1 h. Subsequently, the solvent was removed under reduced pressure and the crude product was purified by reversed-phase flash chromatography (column: C18 silica gel; mobile phase A: water (0.1% $NH_4HCO_3$), mobile phase B: ACN, gradient: 15-45% B in 19 min; wavelength: 210 nm). The title compound was obtained as a yellow solid (250 mg, 24%).

Part IV—Synthesis of 4-(1-(trifluoromethyl)cyclopropyl)pyridin-2-amine

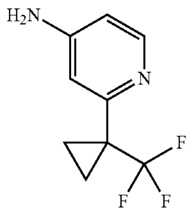 [SMILES: Nc1ccnc(C2(C(F)(F)F)CC2)c1]

A solution of HCl in 1,4-dioxane (4 M, 3.00 mL, 12.0 mmol, 18.1 equiv.) was added to a solution of tert-butyl (4-(1-(trifluoromethyl)cyclopropyl)pyridin-2-yl)carbamate (200 mg, 0.662 mmol, 1.00 equiv.) in 1,4-dioxane (1 mL) and the mixture was stirred at room temperature for 1 h. The solvent was removed under reduced pressure and the crude product was purified by reversed-phase flash chromatography (column: C18 silica gel; mobile phase A: water (0.1% $NH_4HCO_3$), mobile phase B: ACN, gradient: 10-50% B in 20 min; wavelength: 210 nm). The title compound was obtained as a yellow solid (120 mg, 90%).

Part V—Synthesis of methyl 2-(2-fluoro-4-((6-methoxyquinazolin-4-yl)oxy)phenyl)acetate

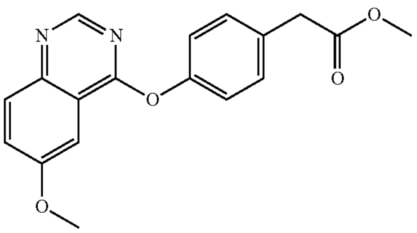 [SMILES: COC(=O)Cc1ccc(Oc2ncnc3ccc(OC)cc23)cc1]

A solution of 4-chloro-6-methoxyquinazoline (10.0 g, 51.4 mmol, 1.00 equiv.), methyl 2-(2-fluoro-4-hydroxyphenyl)acetate (10.4 g, 56.5 mmol, 1.10 equiv.), and $K_2CO_3$ (21.3 g, 154 mmol, 3.00 equiv.) in DMF (104 mL) was heated to 60° C. for 2 h. Subsequently, EtOAc (300 mL) was added, and the organic phase was washed with brine (3×100 mL) and dried over $Na_2SO_4$. The solvent was removed under reduced pressure and the crude product was purified by column chromatography (petroleum ether/EtOAc 1:1). The title compound was obtained as an off-white solid (16 g, 90%).

Part VI—Synthesis of 2-(2-fluoro-4-((6-methoxyquinazolin-4-yl)oxy)phenyl)acetic Acid

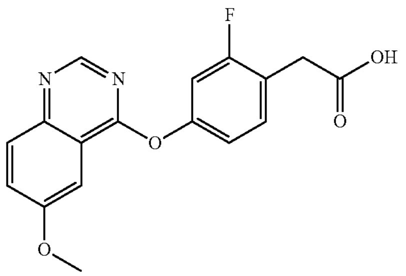 [SMILES: COc1ccc2ncnc(Oc3ccc(CC(=O)O)c(F)c3)c2c1]

A solution of lithium hydroxide monohydrate (2.75 g, 65.4 mmol, 1.40 equiv.) in water (16 mL) was added to a solution of methyl 2-(2-fluoro-4-((6-methoxyquinazolin-4-yl)oxy)phenyl)acetate (16.0 g, 46.7 mmol, 1.00 equiv.) in THF (160 mL) and the mixture was stirred at room temperature for 6 h. The precipitated product was filtered off, washed with water (50 mL), and dried under reduced pressure. The compound was obtained as an off-white solid (12.3 g), which was used in the next reaction without further purification.

Part VII—Synthesis of 2-(2-fluoro-4-((6-methoxy-quinazolin-4-yl)oxy)phenyl)-N-(4-(1-(trifluoromethyl)cyclopropyl)pyridin-2-yl)acetamide (34)

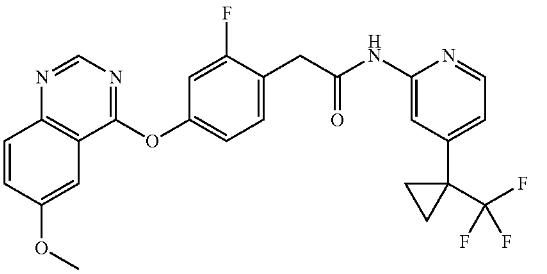 [SMILES: COc1ccc2ncnc(Oc3ccc(CC(=O)Nc4cc(C5(C(F)(F)F)CC5)ccn4)c(F)c3)c2c1]

Propylphosphonic anhydride (260 mg, 0.816 mmol, 1.50 equiv.) was added to a solution of 2-(2-fluoro-4-((6-methoxyquinazolin-4-yl)oxy)phenyl)acetic acid (179 mg, 0.544 mmol, 1.00 equiv.), 4-(1-(trifluoromethyl)cyclopropyl)pyridin-2-amine (110 mg, 0.544 mmol, 1.00 equiv.), and DIPEA (352 mg, 2.72 mmol, 5.00 equiv.) in DMF (1.1 mL) at 0° C. Subsequently, the mixture was stirred overnight at room temperature. The crude product was purified by reversed-phase flash chromatography (column: C18 silica gel; mobile phase A: water (0.1% $NaHCO_3$), mobile phase B: ACN, gradient: 35-65% B in 17 min; wavelength: 210 nm). The title compound was obtained as a white solid (7.5 mg, 2.5%). LCMS (ESI) calculated for $C_{26}H_{21}F_4N_4O_3$ $(M+H)^+$: 513.2, found: 513.0. $^1H$ NMR (300 MHz, DMSO-$d_6$) δ 10.96 (s, 1H), 8.64 (s, 1H), 8.36 (d, J=5.2 Hz, 1H), 8.24 (s, 1H), 7.96 (d, J=9.1 Hz, 1H), 7.72-7.61 (m, 2H), 7.50 (d, J=8.7 Hz, 1H), 7.35 (d, J=10.8 Hz, 1H), 7.20 (d, J=8.7 Hz, 2H), 3.98 (s, 3H), 3.89 (s, 2H), 1.24 (s, 2H), 1.20 (s, 2H).

Example 21—Preparation of Aminoheteroaryl Compounds

Compounds in the table below were prepared based on experimental procedures described in Examples 19 and 20 and the detailed description.

| No. | Structure | Name | $^1H$ NMR | Observed m/z |
|---|---|---|---|---|
| 21 | 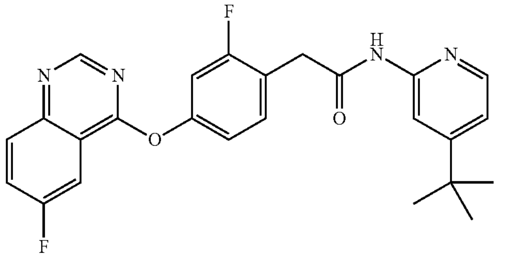 [SMILES: CC(C)(C)c1ccnc(NC(=O)Cc2ccc(Oc3ncnc4ccc(F)cc34)cc2F)c1] | N-(4-(tert-butyl)pyridin-2-yl)-2-(2-fluoro-4-((6-fluoroquinazolin-4-yl)oxy)phenyl) acetamide | (300 MHz, DMSO-$d_6$) δ 10.52 (s, 1H), 8.77 (s, 1H), 8.11 (d, J = 5.7 Hz, 2H), 8.02-7.86 (m, 2H), 7.72 (d, J = 8.6 Hz, 1H), 7.57-7.45 (m, 1H), 7.35 (d, J = 10.8 Hz, 1H), 7.22-7.12 (m, 2H), 3.92 (s, 2H), 1.32 (s, 9H) | 449.1 $(M + H)^+$ |
| 22 | 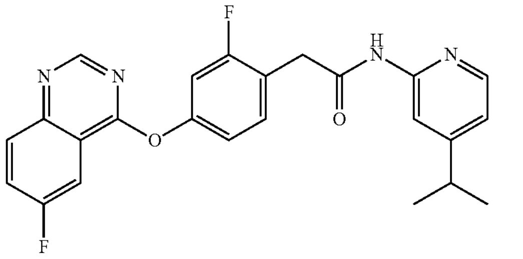 [SMILES: CC(C)c1ccnc(NC(=O)Cc2ccc(Oc3ncnc4ccc(F)cc34)cc2F)c1] | 2-(2-fluoro-4-((6-fluoroquinazolin-4-yl)oxy)phenyl)-N-(4-isopropylpyridin-2-yl)acetamide | (400 MHz, DMSO-$d_6$) δ 10.72 (s, 1H), 8.77 (s, 1H), 8.22 (d, J = 5.2 Hz, 1H), 8.15-8.07 (m, 2H), 8.03-7.95 (m, 2H), 7.52 (t, J = 8.5 Hz, 1H), 7.35 (dd, J = 10.5, 2.4 Hz, 1H), 7.21 (dd, J = 8.3, 2.3 Hz, 1H), 7.02 (dd, J = 5.2, 1.7 Hz, 1H), 3.87 (s, 2H), 2.92-2.81 (m, 1H), 1.19 (d, J = 6.8 Hz, 6H) | 435.0 $(M + H)^+$ |
| 23 | 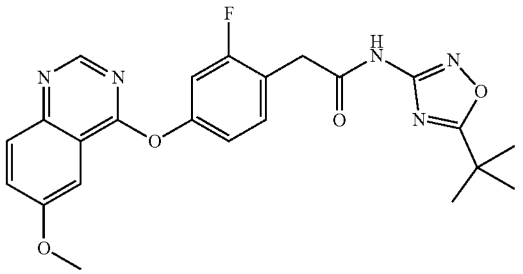 [SMILES: COc1ccc2ncnc(Oc3ccc(CC(=O)Nc4noc(C(C)(C)C)n4)c(F)c3)c2c1] | N-(5-(tert-butyl)-1,2,4-oxadiazol-3-yl)-2-(2-fluoro-4-((6-methoxy-quinazolin-4-yl)oxy)phenyl) acetamide | (400 MHz, DMSO-$d_6$) δ 11.46 (s, 1H), 8.64 (s, 1H), 7.95 (d, J = 9.1 Hz, 1H), 7.68 (dd, J = 9.1, 2.9 Hz, 1H), 7.62 (d, J = 2.8 Hz, 1H), 7.49 (t, J = 8.5 Hz, 1H), 7.34 (dd, J = 10.5, 2.4 Hz, 1H), 7.20 (dd, J = 8.3, 2.3 Hz, 1H), 3.97 (s, 3H), 3.86 (s, 2H), 1.39 (s, 9H) | 452.2 $(M + H)^+$ |

-continued

| No. | Structure | Name | $^1$H NMR | Observed m/z |
|---|---|---|---|---|
| 28 | 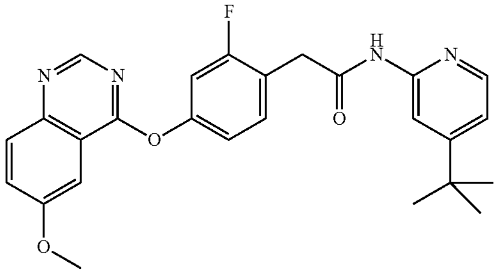 [SMILES: COc1ccc2ncnc(Oc3ccc(CC(=O)Nc4cc(C(C)(C)C)ccn4)c(F)c3)c2c1] | N-(4-(tert-butyl)pyridin-2-yl)-2-(2-fluoro-4-((6-methoxy-quinazolin-4-yl)oxy)phenyl) acetamide | (300 MHz, DMSO-$d_6$) δ 10.76 (s, 1H), 8.64 (s, 1H), 8.24 (dd, J = 5.4, 0.7 Hz, 1H), 8.19-8.15 (m, 1H), 7.95 (d, J = 9.2 Hz, 1H), 7.68 (dd, J = 9.1, 2.9 Hz, 1H), 7.63 (d, J = 2.8 Hz, 1H), 7.51 (t, J = 8.5 Hz, 1H), 7.34 (dd, J = 10.5, 2.3 Hz, 1H), 7.23-7.11 (m, 2H), 3.98 (s, 3H), 3.88 (s, 2H), 1.26 (s, 9H) | |
| 29 | 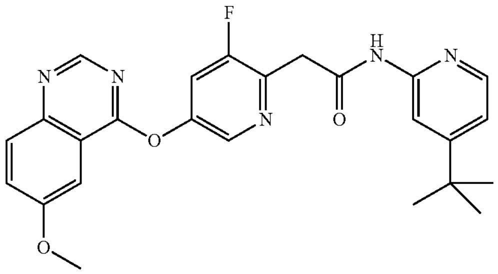 [SMILES: COc1ccc2ncnc(Oc3cnc(CC(=O)Nc4cc(C(C)(C)C)ccn4)c(F)c3)c2c1] | N-(4-(tert-butyl)pyridin-2-yl)-2-(3-fluoro-5-((6-methoxy-quinazolin-4-yl)oxy)pyridin-2-yl)acetamide | (300 MHz, DMSO-$d_6$) δ 10.81 (s, 1H), 8.67 (s, 1H), 8.52 (d, J = 2.2 Hz, 1H), 8.25 (d, J = 5.4 Hz, 1H), 8.17 (s, 1H), 8.03 (dd, J = 10.0, 2.3 Hz, 1H), 7.98 (d, J = 9.1 Hz, 1H), 7.71 (dd, J = 9.1, 2.9 Hz, 1H), 7.66 (d, J = 2.8 Hz, 1H), 7.16 (dd, J = 5.4, 1.8 Hz, 1H), 4.10 (s, 2H), 3.99 (s, 3H), 1.26 (s, 9H) | 462.2 $(M + H)^+$ |
| 30 | 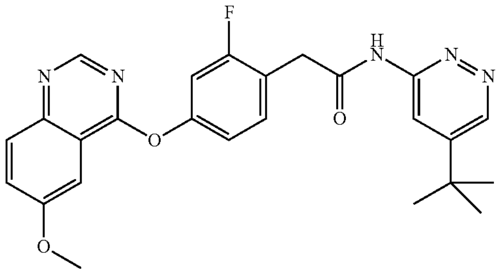 [SMILES: COc1ccc2ncnc(Oc3ccc(CC(=O)Nc4cc(C(C)(C)C)cnn4)c(F)c3)c2c1] | N-(5-(tert-butyl)pyridazin-3-yl)-2-(2-fluoro-4-((6-methoxy-quinazolin-4-yl)oxy)phenyl) acetamide | (300 MHz, DMSO-$d_6$) δ 11.40 (s, 1H), 9.12 (d, J = 2.2 Hz, 1H), 8.64 (s, 1H), 8.31 (d, J = 2.2 Hz, 1H), 7.95 (d, J = 9.1 Hz, 1H), 7.69 (dd, J = 9.1, 2.9 Hz, 1H), 7.63 (d, J = 2.8 Hz, 1H), 7.53 (t, J = 8.5 Hz, 1H), 7.35 (dd, J = 10.5, 2.3 Hz, 1H), 7.24-7.16 (m, 1H), 3.98 (s, 3H), 3.95 (s, 2H), 1.30 (s, 9H) | 462.2 $(M + H)^+$ |
| 31 | 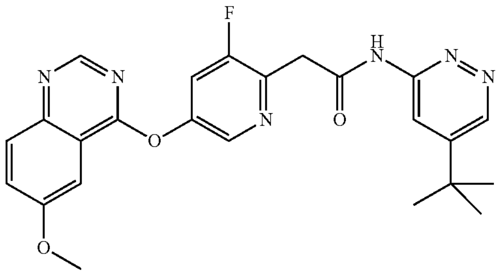 [SMILES: COc1ccc2ncnc(Oc3cnc(CC(=O)Nc4cc(C(C)(C)C)cnn4)c(F)c3)c2c1] | N-(5-(tert-butyl)pyridazin-3-yl)-2-(3-fluoro-5-((6-methoxy-quinazolin-4-yl)oxy)pyridin-2-yl)acetamide | (400 MHz, DMSO-$d_6$) δ 9.13 (d, J = 2.2 Hz, 1H), 8.67 (s, 1H), 8.53 (d, J = 2.2 Hz, 1H), 8.31 (d, J = 2.2 Hz, 1H), 8.05 (dd, J = 10.1, 2.3 Hz, 1H), 7.99 (d, J = 9.1 Hz, 1H), 7.72 (dd, J = 9.2, 2.9 Hz, 1H), 7.67 (d, J = 2.8 Hz, 1H), 4.16 (d, J = 2.3 Hz, 2H), 3.99 (s, 3H), 1.31 (s, 9H) | 462.9 $(M + H)^+$ |
| 33 | 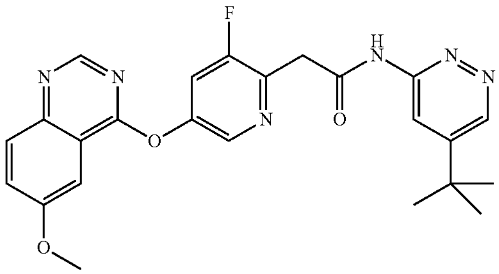 | N-(6-(tert-butyl)pyrimidin-4-yl)-2-(3-fluoro-5-((6-methoxy-quinazolin-4-yl)oxy)pyridin-2-yl)acetamide | (300 MHz, DMSO-$d_6$) δ 11.24 (s, 1H), 8.85 (d, J = 4.6 Hz, 1H), 8.67 (d, J = 4.6 Hz, 1H), 8.52 (s, 1H), 8.14 (s, 1H), 8.08-7.93 (m, 2H), 7.72-7.66 (m, 2H), 4.14 (s, 2H), 3.99 (s, 3H), 1.28 (s, 9H) | 462.9 $(M + H)^+$ |

-continued

| No. | Structure | Name | $^1$H NMR | Observed m/z |
|---|---|---|---|---|
| 35 | 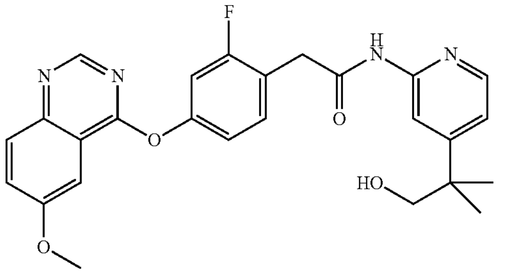 [SMILES: COc1ccc2ncnc(Oc3ccc(CC(=O)Nc4cc(C(C)(C)CO)ccn4)c(F)c3)c2c1] | 2-(2-fluoro-4-((6-methoxy-quinazolin-4-yl)oxy)phenyl)-N-(4-(1-hydroxy-2-methylpropan-2-yl)pyridin-2-yl)acetamide | (300 MHz, DMSO-$d_6$) δ 10.73 (s, 1H), 8.64 (s, 1H), 8.23 (d, J = 5.4 Hz, 1H), 8.15 (s, 1H), 7.95 (d, J = 9.1 Hz, 1H), 7.72-7.62 (m, 2H), 7.51 (t, J = 8.5 Hz, 1H), 7.34 (dd, J = 10.4, 2.4 Hz, 1H), 7.19 (dd, J = 8.3, 2.4 Hz, 1H), 7.12 (dd, J = 5.4, 1.7 Hz, 1H), 4.82-4.73 (m, 1H), 3.98 (s, 3H), 3.88 (s, 2H), 3.42 (s, 2H), 1.20 (s, 6H) | 477.0 $(M + H)^+$ |
| 52 | 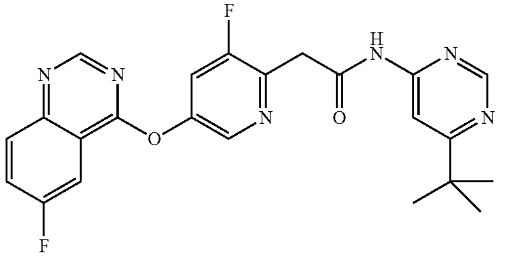 [SMILES: CC(C)(C)c1cc(NC(=O)Cc2ncc(Oc3ncnc4ccc(F)cc34)cc2F)ncn1] | N-(6-(tert-butyl)pyrimidin-4-yl)-2-(3-fluoro-5-((6-fluoroquinazolin-4-yl)oxy)pyridin-2-yl)acetamide | (300 MHz, DMSO-$d_6$) δ 11.24 (s, 1H), 8.86 (s, 1H), 8.82 (s, 1H), 8.59-8.48 (m, 2H), 8.13 (s, 1H), 8.06 (dd, J = 9.9, 2.3 Hz, 1H), 7.87 (dd, J = 10.0, 2.5 Hz, 1H), 7.76 (td, J = 9.0, 2.7 Hz, 1H), 4.14 (d, J = 2.3 Hz, 2H), 1.28 (s, 9H) | 451.1 $(M + H)^+$ |
| 53 | 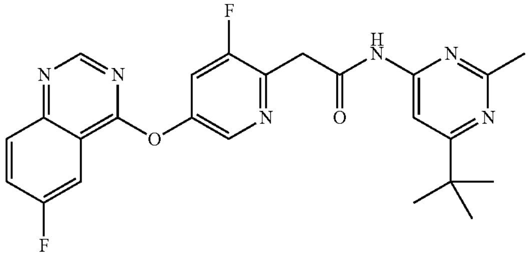 [SMILES: Cc1nc(NC(=O)Cc2ncc(Oc3ncnc4ccc(F)cc34)cc2F)cc(C(C)(C)C)n1] | N-(6-(tert-butyl)-2-methylpyrimidin-4-yl)-2-(3-fluoro-5-((6-fluoroquinazolin-4-yl)oxy)pyridin-2-yl)acetamide | (400 MHz, DMSO-$d_6$) δ 11.20 (s, 1H), 8.82 (s, 1H), 8.56-8.49 (m, 2H), 8.06 (dd, J = 10.0, 2.2 Hz, 1H), 7.95 (s, 1H), 7.87 (dd, J = 10.0, 2.6 Hz, 1H), 7.79-7.74 (m, 1H), 4.11 (d, J = 2.3 Hz, 2H), 2.54 (s, 3H), 1.27 (s, 9H) | 465.0 $(M + H)^+$ |
| 54 | 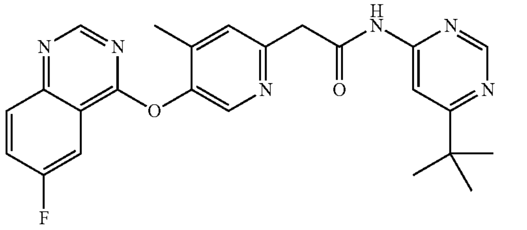 [SMILES: Cc1cc(CC(=O)Nc2cc(C(C)(C)C)ncn2)ncc1Oc1ncnc2ccc(F)cc12] | N-(6-(tert-butyl)pyrimidin-4-yl)-2-(4-((6-fluoroquinazolin-4-yl)oxy)-3-methylphenyl) acetamide | (400 MHz, DMSO-$d_6$) δ 11.15 (s, 1H), 8.84 (d, J = 1.2 Hz, 1H), 8.71 (s, 1H), 8.18-8.09 (m, 3H), 7.99 (td, J = 8.9, 2.9 Hz, 1H), 7.36-7.20 (m, 3H), 3.80 (s, 2H), 2.10 (s, 3H), 1.28 (s, 9H) | 445.9 $(M + H)^+$ |
| 55 | 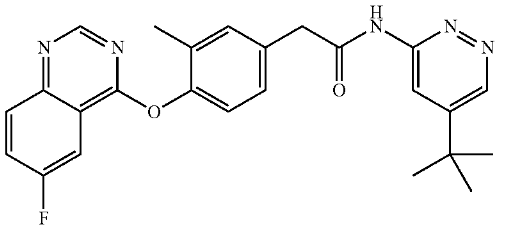 [SMILES: Cc1cc(CC(=O)Nc2cc(C(C)(C)C)cnn2)ccc1Oc1ncnc2ccc(F)cc12] | N-(5-(tert-butyl)pyridazin-3-yl)-2-(4-((6-fluoroquinazolin-4-yl)oxy)-3-methylphenyl) acetamide | (300 MHz, DMSO-$d_6$) δ 11.37 (s, 1H), 9.12 (d, J = 2.2 Hz, 1H), 8.71 (s, 1H), 8.34 (d, J = 2.2 Hz, 1H), 8.22-8.06 (m, 2H), 7.98 (td, J = 8.9, 2.9 Hz, 1H), 7.41-7.18 (m, 3H), 3.83 (s, 2H), 2.11 (s, 3H), 1.31 (s, 9H) | 446.1 $(M + H)^+$ |

-continued

| No. | Structure | Name | $^1$H NMR | Observed m/z |
|---|---|---|---|---|
| 182 | 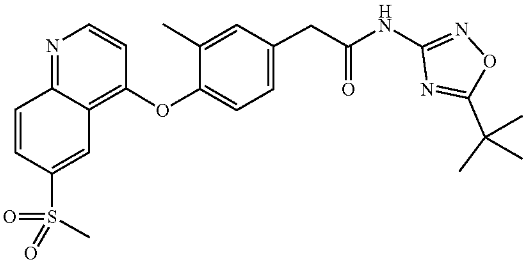 | N-(5-(tert-butyl)-1,2,4-oxadiazol-3-yl)-2-(3-methyl-4-((6-(methylsulfonyl)quinolin-4-yl)oxy)phenyl)acetamide | (400 MHz, DMSO-$d_6$) δ 11.43 (s, 1H), 8.91 (dd, J = 1.9, 0.9 Hz, 1H), 8.84 (d, J = 5.2 Hz, 1H), 8.31-8.25 (m, 2H), 7.42-7.38 (m, 1H), 7.35-7.30 (m, 1H), 7.25 (d, J = 8.2 Hz, 1H), 6.56 (d, J = 5.3 Hz, 1H), 3.76 (s, 2H), 3.39 (s, 3H), 2.14 (s, 3H), 1.38 (s, 9H) | 495.1 $(M + H)^+$ |
| 183 | 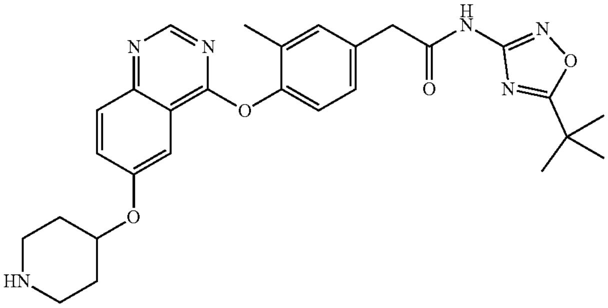 [SMILES: Cc1cc(CC(=O)Nc2noc(C(C)(C)C)n2)ccc1Oc1ncnc2ccc(OC3CCNCC3)cc12] | N-(5-(tert-butyl)-1,2,4-oxadiazol-3-yl)-2-(3-methyl-4-((6-(piperidin-4-yloxy)quinazolin-4-yl)oxy)phenyl)acetamide | (300 MHz, DMSO-$d_6$) δ 11.40 (s, 1H), 8.55 (s, 1H), 7.93 (d, J = 10.0 Hz, 1H), 7.69-7.67 (m, 2H), 7.33-7.17 (m, 3H), 4.76-4.66 (m, 1H), 3.72 (s, 2H), 3.03-2.92 (m, 2H), 2.70-2.57 (m, 2H), 2.08 (s, 3H), 2.07-1.93 (m, 2H), 1.62-1.47 (m, 2H), 1.38 (s, 9H) | 517.1 $(M + H)^+$ |
| 184 | 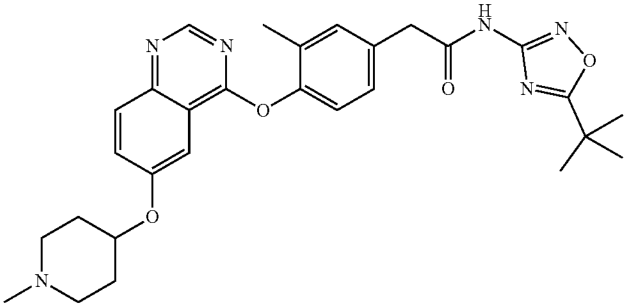 [SMILES: Cc1cc(CC(=O)Nc2noc(C(C)(C)C)n2)ccc1Oc1ncnc2ccc(OC3CCN(C)CC3)cc12] | N-(5-(tert-butyl)-1,2,4-oxadiazol-3-yl)-2-(3-methyl-4-((6-((1-methylpiperidin-4-yl)oxy)quinazolin-4-yl)oxy)phenyl)acetamide | (300 MHz, DMSO-$d_6$) δ 11.40 (s, 1H), 8.56 (s, 1H), 7.93 (d, J = 10.0 Hz, 1H), 7.69-7.67 (m, 2H), 7.30 (s, 1H), 7.27-7.19 (m, 2H), 4.73-4.64 (m, 1H), 3.72 (s, 2H), 2.68-2.59 (m, 2H), 2.30-2.23 (m, 2H), 2.19 (s, 3H), 2.08 (s, 3H), 2.05-1.95 (m, 2H), 1.81-1.68 (m, 2H), 1.38 (s, 9H) | 531.2 $(M + H)^+$ |
| 431 | 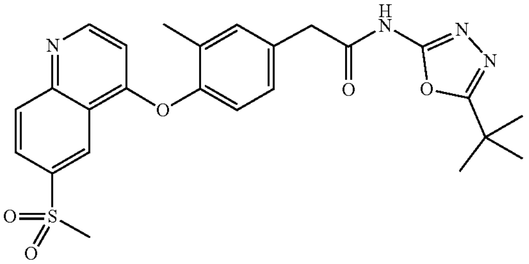 [SMILES: Cc1cc(CC(=O)Nc2nnc(C(C)(C)C)o2)ccc1Oc1ccnc2ccc(S(C)(=O)=O)cc12] | N-(5-(tert-butyl)-1,3,4-oxadiazol-2-yl)-2-(3-methyl-4-((6-(methylsulfonyl)quinolin-4-yl)oxy)phenyl)acetamide | | 495.0 $(M + H)^+$ |
| 443 | 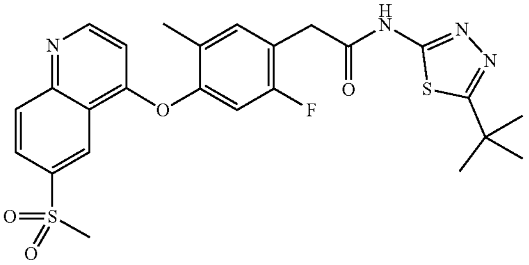 [SMILES: Cc1cc(CC(=O)Nc2nnc(C(C)(C)C)s2)c(F)cc1Oc1ccnc2ccc(S(C)(=O)=O)cc12] | N-(5-(tert-butyl)-1,3,4-thiadiazol-2-yl)-2-(2-fluoro-5-methyl-4-((6-(methylsulfonyl)quinolin-4-yl)oxy)phenyl)acetamide | | 529.2 $(M + H)^+$ |

Example 22—Synthesis of N-(1-(tert-butyl)-1H-pyrazol-4-yl)-2-(2-fluoro-4-((6-(2-hydroxyethoxy)quinazolin-4-yl)oxy)phenyl)acetamide (Compound 16); Prepared According to General Scheme 16

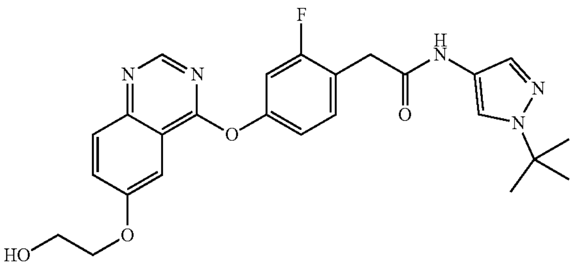 [SMILES: CC(C)(C)n1cc(NC(=O)Cc2ccc(Oc3ncnc4ccc(OCCO)cc34)cc2F)cn1]

Part I—Synthesis of N-(1-(tert-butyl)-1H-pyrazol-4-yl)-2-(2-fluoro-4-((6-methoxyquinazolin-4-yl)oxy)phenyl)acetamide

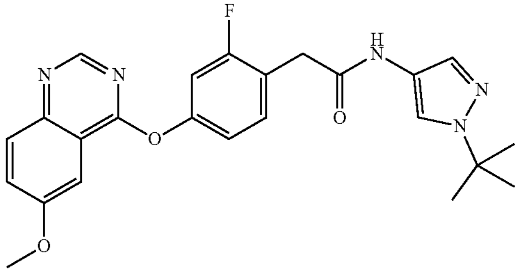 [SMILES: COc1ccc2ncnc(Oc3ccc(CC(=O)Nc4cnn(C(C)(C)C)c4)c(F)c3)c2c1]

Copper(I) iodide (0.69 g, 3.60 mmol, 1.00 equiv.) was added to a solution of N-(1-(tert-butyl)-1H-pyrazol-4-yl)-2-(2-fluoro-4-hydroxyphenyl)acetamide (1.05 g, 3.60 mmol, 1.00 equiv., can be synthesized as described in Part II of Example 9), $Cs_2CO_3$ (2.34 g, 7.19 mmol, 2.00 equiv.), N,N-dimethylglycine (0.56 g, 5.40 mmol, 1.50 equiv.), and 4-chloro-6-methoxyquinazoline (commercially available, 0.7 g, 3.60 mmol, 1.00 equiv.) in 1,4-dioxane (14 mL) under an inert atmosphere of nitrogen. The reaction mixture was heated to 100° C. for 3 h. Subsequently, the reaction mixture was filtered, and EtOAc (30 mL) was added to the solution. The organic phase was washed with water (2×20 mL) and dried over $Na_2SO_4$. The solvent was removed under reduced pressure and the crude product was purified by column chromatography (petroleum ether/EtOAc 4:1). The title compound was obtained as a brown solid (1.2 g, 74% yield).

Part II—Synthesis of N-(1-(tert-butyl)-1H-pyrazol-4-yl)-2-(2-fluoro-4-((6-hydroxyquinazolin-4-yl)oxy)phenyl)acetamide

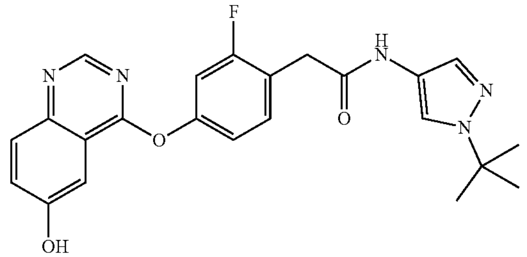

A solution of boron tribromide (1 M, 13.3 mL, 13.3 mmol, 12.0 equiv.) was added slowly to a solution of N-(1-(tert-butyl)-1H-pyrazol-4-yl)-2-(2-fluoro-4-((6-methoxyquinazolin-4-yl)oxy)phenyl)acetamide (500.0 mg, 1.11 mmol, 1.00 equiv.) in chloroform (10 mL) at 0° C. Subsequently, the reaction mixture was stirred at room temperature overnight. The solution was slowly poured into a saturated solution of $NaHCO_3$ in water (10 mL) and the product was extracted with EtOAc (20 mL). The combined organic phases were washed with water (2×10 mL) and dried over $Na_2SO_4$. The solvent was removed under reduced pressure. The title compound was obtained as a brown solid (190 mg), which was used in the next reaction without further purification.

Part III—Synthesis of N-(1-(tert-butyl)-1H-pyrazol-4-yl)-2-(4-((6-(2-((tert-butyldimethylsilyl)oxy)ethoxy)quinazolin-4-yl)oxy)-2-fluorophenyl)acetamide

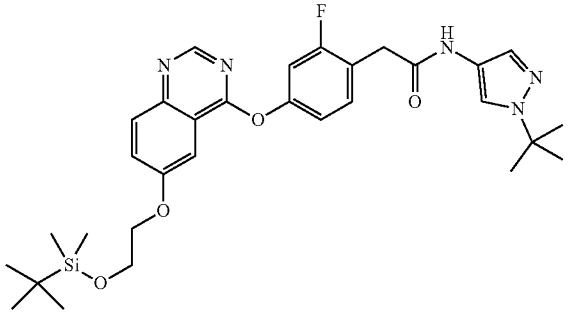 [SMILES: CC(C)(C)n1cc(NC(=O)Cc2ccc(Oc3ncnc4ccc(OCCO[Si](C)(C)C(C)(C)C)cc34)cc2F)cn1]

(2-Bromoethoxy)(tert-butyl)dimethylsilane (127.7 mg, 0.534 mmol, 1.50 equiv.) and $K_2CO_3$ (73.8 mg, 0.534 mmol, 1.50 equiv.) were added to a solution of N-(1-(tert-butyl)-1H-pyrazol-4-yl)-2-(2-fluoro-4-((6-hydroxyquinazolin-4-yl)oxy)phenyl)acetamide (155.0 mg, 0.356 mmol, 1.00 equiv.) in ACN (4.5 mL) and the mixture was heated to 80° C. for 2 h. Subsequently, the reaction mixture was diluted with EtOAc (10 mL), washed with water (2×5 mL) and dried over $Na_2SO_4$. The solvent was removed under reduced pressure. The title compound was obtained as a yellow solid (270 mg), which was used in the next reaction without further purification.

Part IV—Synthesis of N-(1-(tert-butyl)-1H-pyrazol-4-yl)-2-(2-fluoro-4-((6-(2-hydroxyethoxy)quinazolin-4-yl)oxy)phenyl)acetamide (Compound 16)

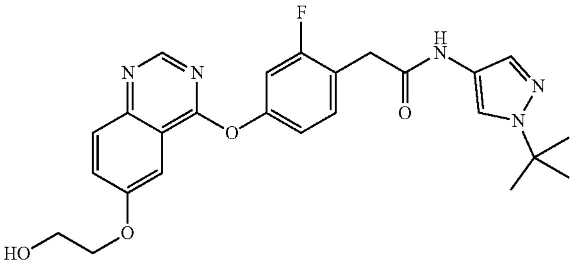 [SMILES: CC(C)(C)n1cc(NC(=O)Cc2ccc(Oc3ncnc4ccc(OCCO)cc34)cc2F)cn1]

Ammonium fluoride (389.8 mg, 10.5 mmol, 25.0 equiv.) was added to a solution of N-(1-(tert-butyl)-1H-pyrazol-4-yl)-2-(4-((6-(2-((tert-butyldimethylsilyl)oxy)ethoxy)quinazolin-4-yl)oxy)-2-fluorophenyl)acetamide (250.0 mg, 0.421 mmol, 1.00 equiv.) in MeOH (2.5 mL) and the mixture was heated to 50° C. for 2 h. Subsequently, the solution was filtered, and the crude product was purified by preparative HPLC (column: Xselect CSH C18 OBD, 30×150 mm, 5 μm; mobile phase A: water (10 mmol/L $NH_4HCO_3$), mobile phase B: ACN; flow rate: 25 mL/min; gradient: 27-31% B in 13 min, wavelength: 220 nm, RT1: 11 min). The title compound was obtained as an off-white solid (25 mg, 14% over 2 steps). LCMS (ESI) calculated for $C_{25}H_{27}FN_5O_4(M+H)^+$: 480.2, found: 480.0. $^1H$ NMR (400 MHz, DMSO-$d_6$) δ 10.25 (s, 1H), 8.63 (s, 1H), 7.97-7.95 (m, 2H), 7.70 (dd, J=9.2, 2.8 Hz, 1H), 7.63 (d, J=2.9 Hz, 1H), 7.55-7.44 (m, 2H), 7.33 (dd, J=10.5, 2.3 Hz, 1H), 7.19 (dd, J=8.3, 2.4 Hz, 1H), 5.01-4.93 (m, 1H), 4.22 (t, J=4.8 Hz, 2H), 3.81 (q, J=5.1 Hz, 2H), 3.70 (s, 2H), 1.49 (s, 9H).

Example 23—Synthesis of 2-(4-((6-(((1r,4r)-4-aminocyclohexyl)oxy)quinolin-4-yl)oxy)-3-methylphenyl)-N-(1-(tert-butyl)-1H-pyrazol-4-yl)acetamide (Compound 122); Prepared According to General Scheme 15

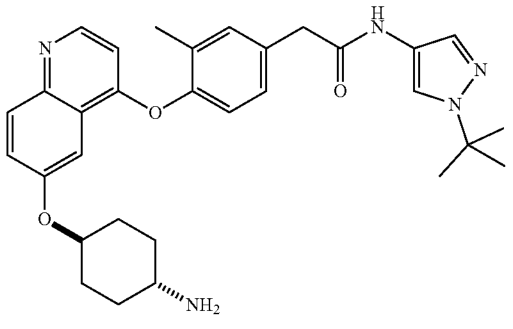

Part I—Synthesis of 4-chloroquinolin-6-ol

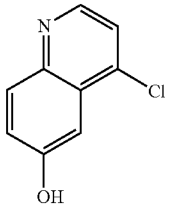 [SMILES: Oc1ccc2nccc(Cl)c2c1]

A solution of boron tribromide in DCM (1 M, 233 mL, 233 mmol, 3.00 equiv.) was added to a solution of 4-chloro-6-methoxyquinoline (commercially available, 15.0 g, 77.5 mmol, 1.00 equiv.) in DCM (150 mL) over 15 min at 0° C. Subsequently, the reaction mixture was stirred at room temperature overnight. The mixture was slowly poured into a saturated aqueous solution of $NaHCO_3$ (200 mL) and the product was extracted with EtOAc (200 mL). The organic phase was washed with water (2×100 mL), dried over $Na_2SO_4$, and the solvent was removed under reduced pressure. The title compound was obtained as an off-white solid (12.4 g), which was used in the next reaction without any further purification.

Part II—Synthesis of tert-butyl ((1r,4r)-4-((4-chloroquinolin-6-yl)oxy)cyclohexyl)carbamate

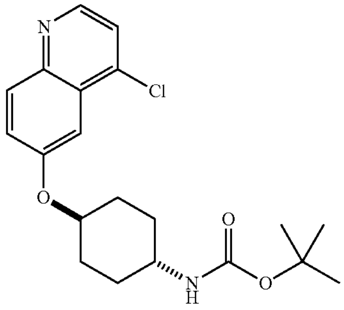 [SMILES: CC(C)(C)OC(=O)N[C@H]1CC[C@H](Oc2ccc3nccc(Cl)c3c2)CC1]

A solution of DEAD (0.97 g, 5.57 mmol, 2.00 equiv.) in THF (5 mL) was added to a solution of 4-chloroquinolin-6-ol (500 mg, 2.79 mmol, 1.00 equiv.), tert-butyl ((1s,4s)-4-hydroxycyclohexyl)carbamate (1.80 g, 8.34 mmol, 3.00 equiv., commercially available), and triphenylphosphine (3.65 g, 13.9 mmol, 5.00 equiv.) in THF (5 mL) at 0° C. Subsequently, the mixture was stirred at room temperature for 12 h. EtOAc (40 mL) was added, and the mixture was washed with water (3×20 mL) and dried over $Na_2SO_4$. The solvent was removed under reduced pressure and the product was purified by reversed-phase flash chromatography (column: C18 silica gel; mobile phase A: water (0.1% $NH_4HCO_3$), mobile phase B: ACN, gradient: 40-90% B in 20 min; wavelength: 210 nm). The title compound was obtained as a white solid (570 mg, 73%).

Part III—Synthesis of tert-butyl ((1r,4r)-4-((4-(4-(2-((1-(tert-butyl)-1H-pyrazol-4-yl)amino)-2-oxoethyl)-2-methylphenoxy)quinolin-6-yl)oxy)cyclohexyl) carbamate

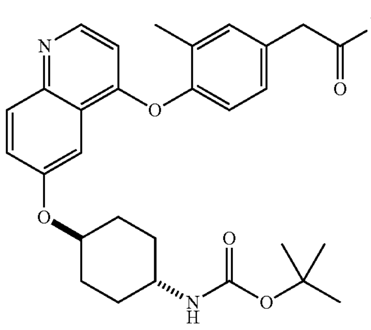

A solution of tert-butyl ((1r,4r)-4-((4-chloroquinolin-6-yl) oxy)cyclohexyl)carbamate (500 mg, 1.33 mmol, 1.00 equiv.), N-(1-(tert-butyl)-1H-pyrazol-4-yl)-2-(4-hydroxy-3-methylphenyl)acetamide (381 mg, 1.33 mmol, 1.00 equiv., can be synthesized as shown in Part III of Example 30), and DMAP (162 mg, 1.33 mmol, 1.00 equiv.) in chlorobenzene (5 mL) was heated to 130° C. for 20 h. The solvent was removed under reduced pressure and the crude product was purified by reversed-phase flash chromatography (column: C18 silica gel; mobile phase A: water (0.1% $NH_4HCO_3$), mobile phase B: ACN, gradient: 40-80% B in 30 min; wavelength: 210 nm). The title compound was obtained as a white solid (400 mg, 50%).

Part IV—Synthesis of 2-(4-((6-(((1r,4r)-4-aminocyclohexyl)oxy)quinolin-4-yl)oxy)-3-methylphenyl)-N-(1-(tert-butyl)-1H-pyrazol-4-yl)acetamide (Compound 122)

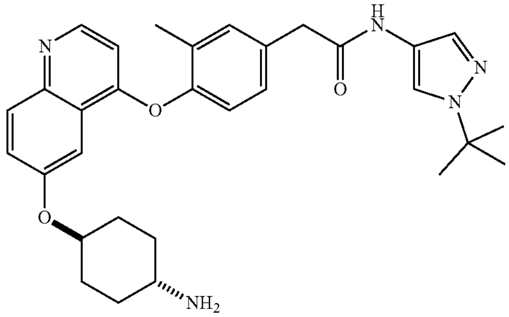

A solution of HCl in 1,4-dioxane (1 mL) was added to a solution of tert-butyl ((1r,4r)-4-((4-(4-(2-((1-(tert-butyl)-1H-pyrazol-4-yl)amino)-2-oxoethyl)-2-methylphenoxy)quinolin-6-yl)oxy)cyclohexyl)carbamate (200 mg, 0.319 mmol, 1.00 equiv.) in 1,4-dioxane (1 mL) and the mixture was stirred at room temperature for 30 min. The reaction was quenched by the addition of a saturated aqueous solution of $NaHCO_3$ (5 mL) and the product was extracted with EtOAc (3×10 mL). The combined organic phases were dried over $Na_2SO_4$, and the solvent was removed under reduced pressure. The title compound was obtained as a white solid (75 mg, 44%). LCMS (ESI) calculated for $C_{31}H_{38}N_5O_3$ $(M+H)^+$: 528.3, found: 528.2. $^1H$ NMR (400 MHz, DMSO-$d_6$) δ 10.24 (s, 1H), 8.49 (d, J=5.1 Hz, 1H), 7.97-7.91 (m, 2H), 7.60 (d, J=2.8 Hz, 1H), 7.50-7.44 (m, 2H), 7.36 (d, J=2.2 Hz, 1H), 7.28 (dd, J=8.2, 2.2 Hz, 1H), 7.15 (d, J=8.2 Hz, 1H), 6.40 (d, J=5.1 Hz, 1H), 4.50 (td, J=10.2, 4.9 Hz, 1H), 3.60 (s, 2H), 2.76 (ddd, J=10.5, 6.6, 3.9 Hz, 1H), 2.14-2.10 (m, 5H), 1.92-1.80 (m, 2H), 1.53 (td, J=7.2, 3.6 Hz, 1H), 1.49 (s, 9H), 1.47-1.42 (m, 1H), 1.36-1.21 (m, 2H).

Example 24—Synthesis of N-(1-(tert-butyl)-1H-pyrazol-4-yl)-2-(2-fluoro-3-methyl-4-((6-((1-methylpiperidin-4-yl)oxy)quinolin-4-yl)oxy)phenyl)acetamide (Compound 103); Prepared According to General Scheme 15

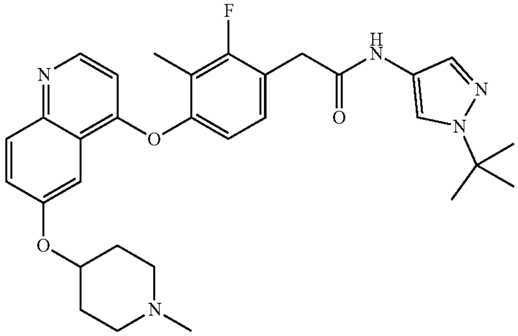 [SMILES: Cc1c(Oc2ccnc3ccc(OC4CCN(C)CC4)cc23)ccc(CC(=O)Nc2cnn(C(C)(C)C)c2)c1F]

Part I—Synthesis of 4-chloro-6-((1-methylpiperidin-4-yl)oxy)quinoline

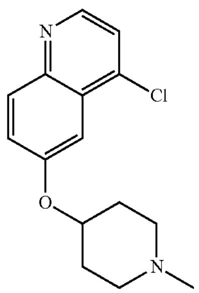 [SMILES: CN1CCC(Oc2ccc3nccc(Cl)c3c2)CC1]

Di-tert-butyl azodicarboxylate (1.28 g, 5.57 mmol, 2.00 equiv.) was added to a solution of 4-chloroquinolin-6-ol (500 mg, 2.78 mmol, 1.00 equiv.), 1-methylpiperidin-4-ol (321 mg, 2.78 mmol, 1.00 equiv.) and triphenylphosphine (1.46 g, 5.57 mmol, 2.00 equiv.) in THF (10 mL) at 0° C. Subsequently, the mixture was stirred overnight at room temperature. Water was added and the product was extracted with EtOAc (3×10 mL). The combined organic phases were washed with brine, dried over $Na_2SO_4$, and the solvent was removed under reduced pressure. The crude product was purified by column chromatography (DCM/MeOH 10:1). The title compound was obtained as a yellow liquid (480 mg, 62%).

Part II—Synthesis of N-(1-(tert-butyl)-1H-pyrazol-4-yl)-2-(2-fluoro-3-methyl-4-((6-((1-methylpiperidin-4-yl)oxy)quinolin-4-yl)oxy)phenyl)acetamide (Compound 103)

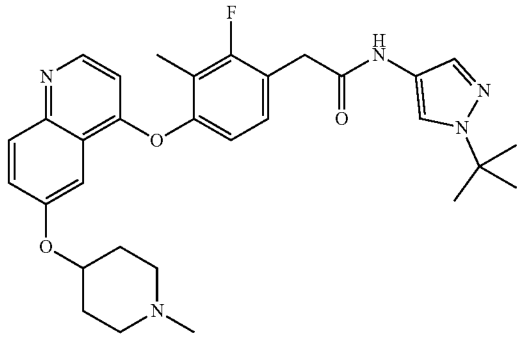

A solution of 4-chloro-6-((1-methylpiperidin-4-yl)oxy)quinoline (300 mg, 1.08 mmol, 1.00 equiv.), N-(1-(tert-butyl)-1H-pyrazol-4-yl)-2-(2-fluoro-4-hydroxy-3-methylphenyl)acetamide (330 mg, 1.08 mmol, 1.00 equiv.), $Cs_2CO_3$ (706 mg, 2.17 mmol, 2.00 equiv.), CuI (82.6 mg, 0.434 mmol, 0.40 equiv.) and N,N-dimethylglycine (67.1 mg, 0.650 mmol, 0.60 equiv.) in 1,4-dioxane (3 mL) was heated to 100° C. overnight under an inert atmosphere of nitrogen. Subsequently, water (10 mL) was added, and the product was extracted with EtOAc (3×10 mL). The combined organic phases were washed with brine, dried over $Na_2SO_4$, and the solvent was removed under reduced pressure. The crude product was purified by reversed-phase flash chromatography (column: C18 silica gel; mobile phase A: water, mobile phase B: ACN, gradient: 35-55% B in 40 min; wavelength: 210 nm). The title compound was obtained as a white solid (17.0 mg, 2.80%). LCMS (ESI) calculated for $C_{31}H_{37}FN_5O_3(M+H)^+$: 546.3, found: 546.2. $^1H$ NMR (300 MHz, DMSO-$d_6$) δ 10.23 (s, 1H), 8.54 (d, J=5.0 Hz, 1H), 8.27 (s, 1H), 8.00-7.91 (m, 2H), 7.60 (d, J=2.8 Hz, 1H), 7.50 (dd, J=9.1, 2.7 Hz, 1H), 7.46 (s, 1H), 7.34 (t, J=8.5 Hz, 1H), 7.05 (d, J=8.3 Hz, 1H), 6.49 (d, J=5.2 Hz, 1H), 4.66-4.57 (m, 1H), 3.70 (s, 2H), 2.68-2.59 (m, 2H), 2.29-2.24 (m, 2H), 2.20 (s, 3H), 2.02-1.97 (m, 2H), 1.81-1.70 (m, 5H), 1.49 (s, 9H).

Example 25—Preparation of Additional 6-Alkoxy Substituted Quinoline and Quinazoline Compounds Compounds in the table below were prepared based on experimental procedures described in Example 22, 23, and 24, and the detailed description.

| No. | Structure | Name | $^1H$ NMR | Observed m/z |
|---|---|---|---|---|
| 1 | 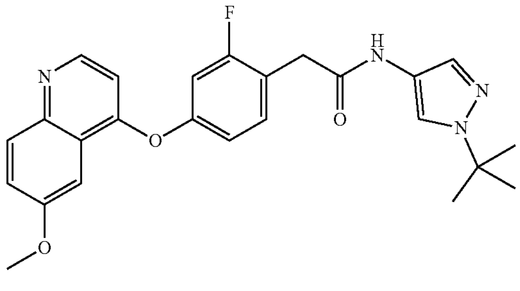 [SMILES: COc1ccc2nccc(Oc3ccc(CC(=O)Nc4cnn(C(C)(C)C)c4)c(F)c3)c2c1] | N-(1-(tert-butyl)-1H-pyrazol-4-yl)-2-(2-fluoro-4-((6-methoxy-quinolin-4-yl)oxy)phenyl) acetamide | (400 MHz, DMSO-$d_6$) δ 10.25 (s, 1H), 8.58 (d, J = 5.1 Hz, 1H), 8.00-7.90 (m, 2H), 7.57-7.42 (m, 4H), 7.26 (dd, J = 10.5, 2.4 Hz, 1H), 7.11 (dd, J = 8.4, 2.4 Hz, 1H), 6.69 (d, J = 5.1 Hz, 1H), 3.92 (s, 3H), 3.70 (s, 2H), 1.49 (s, 9H) | 449.1 (M + H)$^+$ |
| 8 | 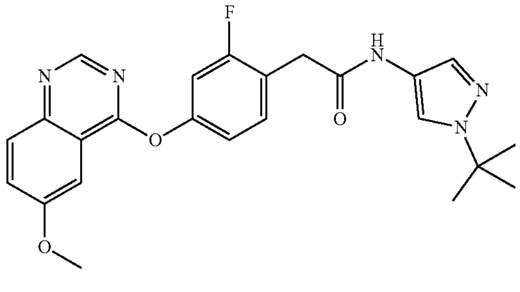 [SMILES: COc1ccc2ncnc(Oc3ccc(CC(=O)Nc4cnn(C(C)(C)C)c4)c(F)c3)c2c1] | N-(1-(tert-butyl)-1H-pyrazol-4-yl)-2-(2-fluoro-4-((6-methoxy-quinazolin-4-yl)oxy)phenyl) acetamide | (400 MHz, DMSO-$d_6$) δ 10.22 (s, 1H), 8.63 (s, 1H), 7.98-7.90 (m, 2H), 7.68 (dd, J = 9.1, 2.9 Hz, 1H), 7.62 (d, J = 2.8 Hz, 1H), 7.49 (t, J = 8.5 Hz, 1H), 7.46 (d, J = 0.7 Hz, 1H), 7.32 (dd, J = 10.5, 2.3 Hz, 1H), 7.18 (dd, J = 8.3, 2.0 Hz, 1H), 3.97 (s, 3H), 3.70 (s, 2H), 1.49 (s, 9H) | 450.1 (M + H)$^+$ |
| 15 | 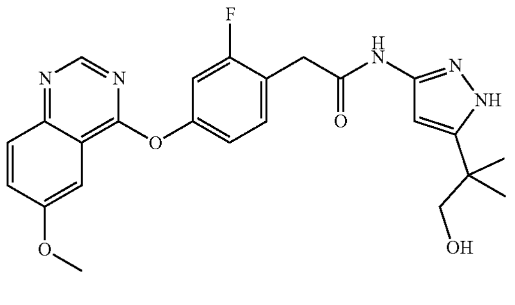 [SMILES: COc1ccc2ncnc(Oc3ccc(CC(=O)Nc4cc(C(C)(C)CO)[nH]n4)c(F)c3)c2c1] | 2-(2-fluoro-4-((6-methoxy-quinazolin-4-yl)oxy) phenyl)-N-(5-(1-hydroxy-2-methylpropan-2-yl)-1H-pyrazol-3-yl)acetamide | (400 MHz, DMSO-$d_6$) δ 11.97 (s, 1H), 10.61 (s, 1H), 8.64 (d, J = 1.2 Hz, 1H), 7.96 (d, J = 9.2 Hz, 1H), 7.69 (dd, J = 9.1, 2.9 Hz, 1H), 7.63 (d, J = 2.8 Hz, 1H), 7.49 (td, J = 8.5, 2.2 Hz, 1H), 7.32 (dd, J = 10.4, 2.1 Hz, 1H), 7.18 (dd, J = 8.1, 2.1 Hz, 1H), 6.30 (d, J = 3.4 Hz, 1H), 4.85-4.77 (m, 1H), 3.98 (s, 3H), 3.73 (s, 2H), 3.37-3.34 (m, 2H), 1.19 (d, J = 2.2 Hz, 6H) | 466.0 (M + H)$^+$ |

-continued

| No. | Structure | Name | $^1H$ NMR | Observed m/z |
|---|---|---|---|---|
| 17 | 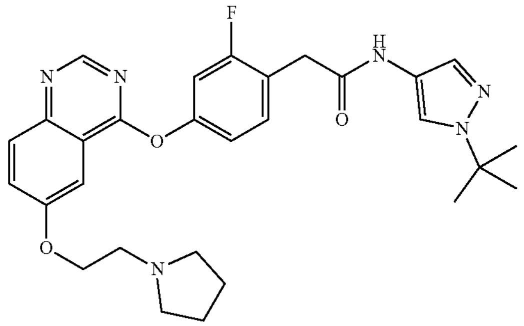 [SMILES: CC(C)(C)n1cc(NC(=O)Cc2ccc(Oc3ncnc4ccc(OCCN5CCCC5)cc34)cc2F)cn1] | N-(1-(tert-butyl)-1H-pyrazol-4-yl)-2-(2-fluoro-4-((6-(2-(pyrrolidin-1-yl)ethoxy) quinazolin-4-yl)oxy) phenyl) acetamide | (400 MHz, DMSO-$d_6$) δ 0.25 (s, 1H), 8.63 (s, 1H), 7.96-7.93 (m, 2H), 7.69 (dd, J = 9.1, 2.8 Hz, 1H), 7.66 (d, J = 2.8 Hz, 1H), 7.49 (t, J = 8.5 Hz, 1H), 7.46 (s, 1H), 7.33 (dd, J = 10.5, 2.3 Hz, 1H), 7.19 (dd, J = 8.3, 2.3 Hz, 1H), 4.29 (t, J = 5.7 Hz, 2H), 3.70 (s, 2H), 2.88 (t, J = 5.7 Hz, 2H), 2.59-2.52 (m, 4H), 1.78-1.65 (m, 4H), 1.49 (s, 9H) | 533.0 $(M + H)^+$ |
| 18 | 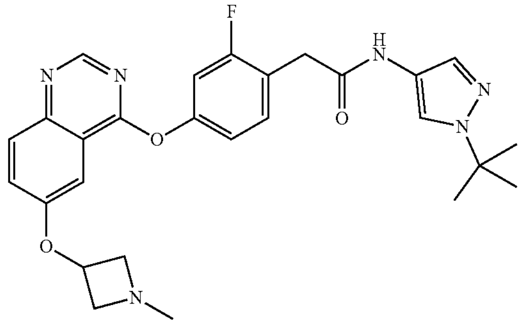 [SMILES: CN1CC(Oc2ccc3ncnc(Oc4ccc(CC(=O)Nc5cnn(C(C)(C)C)c5)c(F)c4)c3c2)C1] | N-(1-(tert-butyl)-1H-pyrazol-4-yl)-2-(2-fluoro-4-((6-((1-methyl-azetidin-3-yl)oxy) quinazolin-4-yl)oxy) phenyl) acetamide | (400 MHz, DMSO-$d_6$) δ 10.21 (s, 1H), 8.63 (s, 1H), 7.96 (d, J = 9.2 Hz, 1H), 7.93 (s, 1H), 7.66 (dd, J = 9.2, 2.8 Hz, 1H), 7.48 (t, J = 8.5 Hz, 1H), 7.45 (s, 1H), 7.41 (d, J = 2.9 Hz, 1H), 7.32 (dd, J = 10.5, 2.4 Hz, 1H), 7.18 (dd, J = 8.3, 2.3 Hz, 1H), 5.08-4.98 (m, 1H), 3.80 (dd, J = 8.3, 5.9 Hz, 2H), 3.69 (s, 2H), 3.12-3.05 (m, 2H), 2.31 (s, 3H), 1.49 (s, 9H) | 505.0 $(M + H)^+$ |
| 19 | 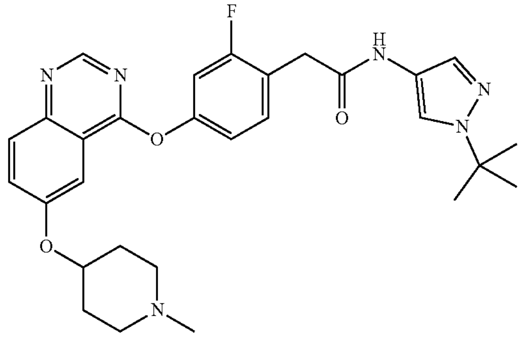 | N-(1-(tert-butyl)-1H-pyrazol-4-yl)-2-(2-fluoro-4-((6-((1-methyl-piperidin-4-yl)oxy) quinazolin-4-yl)oxy) phenyl) acetamide | (400 MHz, DMSO-$d_6$) δ 10.24 (s, 1H), 8.61 (s, 1H), 7.96-7.91 (m, 2H), 7.69 (dd, J = 9.1, 2.8 Hz, 1H), 7.65 (d, J = 2.8 Hz, 1H), 7.48 (t, J = 8.5 Hz, 1H), 7.45 (d, J = 0.7 Hz, 1H), 7.32 (dd, J = 10.5, 2.4 Hz, 1H), 7.17 (dd, J = 8.3, 2.3 Hz, 1H), 4.74-4.62 (m, 1H), 3.69 (s, 2H), 2.69-2.56 (m, 2H), 2.31-2.21 (m, 2H), 2.19 (s, 3H), 2.05-1.96 (m, 2H), 1.79-1.68 (m, 2H), 1.49 (s, 9H | 533.3 $(M + H)^+$ |
| 37 | 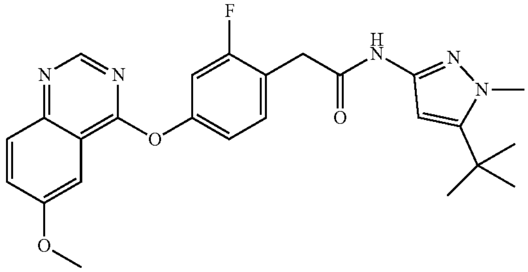 [SMILES: COc1ccc2ncnc(Oc3ccc(CC(=O)Nc4cc(C(C)(C)C)n(C)n4)c(F)c3)c2c1] | N-(5-(tert-butyl)-1-methyl-1H-pyrazol-3-yl)-2-(2-fluoro-4-((6-methoxy-quinazolin-4-yl)oxy) phenyl) acetamide | (400 MHz, DMSO-$d_6$) δ 10.60 (s, 1H), 8.63 (s, 1H), 7.95 (d, J = 9.2 Hz, 1H), 7.68 (dd, J = 9.1, 2.9 Hz, 1H), 7.62 (d, J = 2.9 Hz, 1H), 7.47 (t, J = 8.5 Hz, 1H), 7.31 (dd, J = 10.5, 2.4 Hz, 1H), 7.17 (dd, J = 8.3, 2.4 Hz, 1H), 6.30 (s, 1H), 3.97 (s, 3H), 3.80 (s, 3H), 3.71 (s, 2H), 1.31 (s, 9H) | 464.2 $(M + H)^+$ |
| 47 | 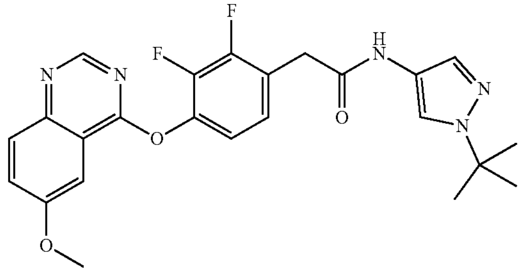 [SMILES: COc1ccc2ncnc(Oc3ccc(CC(=O)Nc4cnn(C(C)(C)C)c4)c(F)c3F)c2c1] | N-(1-(tert-butyl)-1H-pyrazol-4-yl)-2-(2,3-difluoro-4-((6-methoxy-quinazolin-4-yl)oxy)phenyl) acetamide | (400 MHz, DMSO-$d_6$) δ 10.31 (s, 1H), 8.66 (s, 1H), 8.04-7.91 (m, 2H), 7.71 (dd, J = 9.1, 2.9 Hz, 1H), 7.65 (d, J = 2.8 Hz, 1H), 7.47 (s, 1H), 7.37-7.31 (m, 2H), 3.99 (s, 3H), 3.79 (s, 2H), 1.49 (s, 9H) | 468 $(M + H)^+$ |

-continued

| No. | Structure | Name | $^1$H NMR | Observed m/z |
|---|---|---|---|---|
| 49 | 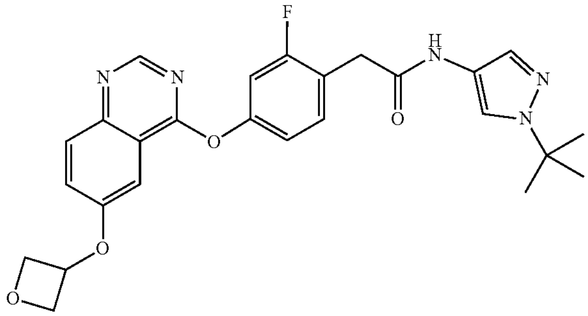 [SMILES: CC(C)(C)n1cc(NC(=O)Cc2ccc(Oc3ncnc4ccc(OC5COC5)cc34)cc2F)cn1] | N-(1-(tert-butyl)-1H-pyrazol-4-yl)-2-(2-fluoro-4-((6-(oxetan-3-yloxy) quinazolin-4-yl)oxy)phenyl) acetamide | (400 MHz, DMSO-$d_6$) δ 10.25 (s, 1H), 8.64 (s, 1H), 7.99 (d, J = 9.2 Hz, 1H), 7.94 (s, 1H), 7.70 (dd, J = 9.2, 2.8 Hz, 1H), 7.52-7.44 (m, 2H), 7.36-7.29 (m, 2H), 7.18 (dd, J = 8.4, 2.3 Hz, 1H), 5.60-5.56 (m, 1H), 5.08-4.97 (m, 2H), 4.64 (dd, J = 7.4, 4.7 Hz, 2H), 3.70 (s, 2H), 1.49 (s, 9H) | 492.2 (M + H)+ |
| 50 | 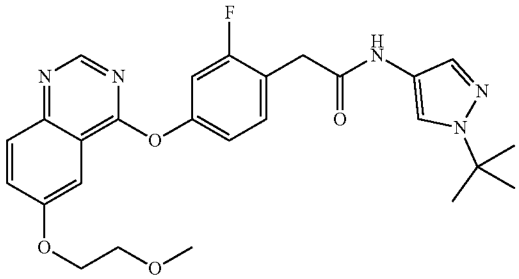 [SMILES: COCCOc1ccc2ncnc(Oc3ccc(CC(=O)Nc4cnn(C(C)(C)C)c4)c(F)c3)c2c1] | N-(1-(tert-butyl)-1H-pyrazol-4-yl)-2-(2-fluoro-4-((6-(2-methoxy-ethoxy) quinazolin-4-yl)oxy)phenyl) acetamide | (400 MHz, DMSO-$d_6$) δ 10.25 (s, 1H), 8.63 (s, 1H), 8.00-7.88 (m, 2H), 7.69 (dd, J = 9.1, 2.9 Hz, 1H), 7.64 (d, J = 2.8 Hz, 1H), 7.49 (t, J = 8.5 Hz, 1H), 7.45 (s, 1H), 7.32 (dd, J = 10.5, 2.4 Hz, 1H), 7.18 (dd, J = 8.4, 2.3 Hz, 1H), 4.35-4.26 (m, 2H), 3.79-3.72 (m, 2H), 3.70 (s, 2H), 3.34 (s, 3H), 1.49 (s, 9H) | 494.2 $(M + H)^+$ |
| 79 | 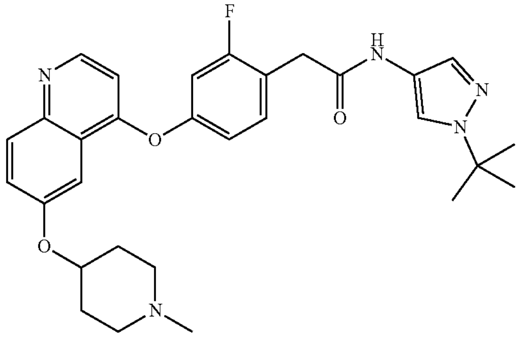 [SMILES: CN1CCC(Oc2ccc3nccc(Oc4ccc(CC(=O)Nc5cnn(C(C)(C)C)c5)c(F)c4)c3c2)CC1] | N-(1-(tert-butyl)-1H-pyrazol-4-yl)-2-(2-fluoro-4-((6-((1-methyl-piperidin-4-yl)oxy) quinolin-4-yl)oxy)phenyl) acetamide | (400 MHz, DMSO-$d_6$) δ 10.19 (s, 1H), 8.59 (d, J = 5.1 Hz, 1H), 7.97 (d, J = 9.0 Hz, 1H), 7.93 (s, 1H), 7.54-7.41 (m, 4H), 7.23 (dd, J = 10.6, 2.4 Hz, 1H), 7.08 (dd, J = 8.4, 2.4 Hz, 1H), 6.73 (d, J = 5.0 Hz, 1H), 4.56 (tt, J = 7.3, 3.2 Hz, 1H), 3.69 (s, 2H), 2.61 (t, J = 8.3 Hz, 2H), 2.22 (d, J = 10.5 Hz, 2H), 2.18 (s, 3H), 1.97 (d, J = 12.6 Hz, 2H), 1.71 (dtd, J = 12.3, 8.5, 3.4 Hz, 2H), 1.49 (s, 9H) | 532.1 $(M + H)^+$ |
| 81 | 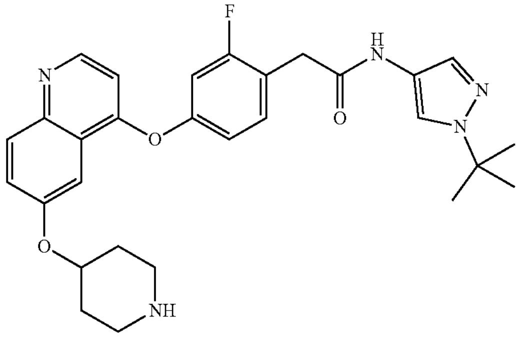 [SMILES: CC(C)(C)n1cc(NC(=O)Cc2ccc(Oc3ccnc4ccc(OC5CCNCC5)cc34)cc2F)cn1] | N-(1-(tert-butyl)-1H-pyrazol-4-yl)-2-(2-fluoro-4-((6-(piperidin-4-yloxy) quinolin-4-yl)oxy)phenyl) acetamide | (400 MHz, DMSO-$d_6$) δ 10.19 (s, 1H), 8.58 (d, J = 5.0 Hz, 1H), 7.96 (d, J = 9.1 Hz, 1H), 7.93 (s, 1H), 7.51-7.45 (m, 4H), 7.23 (dd, J = 10.6, 2.4 Hz, 1H), 7.08 (dd, J = 8.4, 2.4 Hz, 1H), 6.71 (d, J = 5.1 Hz, 1H), 4.58 (tt, J = 8.5, 3.3 Hz, 1H), 3.68 (s, 2H), 2.96 (d, J = 12.1 Hz, 2H), 2.65-2.53 (m, 2H), 1.95 (dd, J = 9.6, 5.3 Hz, 2H), 1.52 (q, J = 5.0, 4.1 Hz, 2H), 1.48 (s, 9H) | 518.0 $(M + H)^+$ |

-continued

| No. | Structure | Name | $^1$H NMR | Observed m/z |
|---|---|---|---|---|
| 82 | 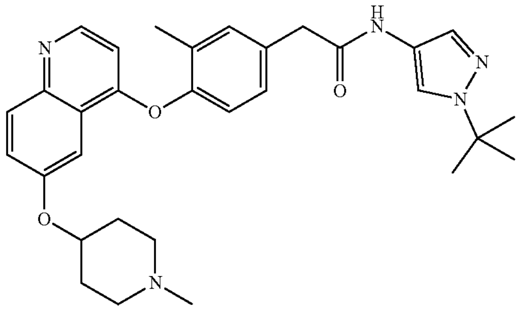 [SMILES: Cc1cc(CC(=O)Nc2cnn(C(C)(C)C)c2)ccc1Oc1ccnc2ccc(OC3CCN(C)CC3)cc12] | N-(1-(tert-butyl)-1H-pyrazol-4-yl)-2-(3-methyl-4-((6-((1-methyl-piperidin-4-yl)oxy) quinolin-4-yl)oxy)phenyl) acetamide | (400 MHz, DMSO-$d_6$) δ 10.16 (s, 1H), 8.49 (d, J = 5.1 Hz, 1H), 7.98-7.91 (m, 2H), 7.61 (d, J = 2.8 Hz, 1H), 7.48 (dd, J = 9.2, 2.8 Hz, 1H), 7.45 (d, J = 0.7 Hz, 1H), 7.35 (d, J = 2.2 Hz, 1H), 7.27 (dd, J = 8.3, 2.2 Hz, 1H), 7.14 (d, J = 8.2 Hz, 1H), 6.39 (d, J = 5.1 Hz, 1H), 4.59 (tt, J = 7.9, 3.6 Hz, 1H), 3.59 (s, 2H), 2.66-2.56 (m, 2H), 2.28-2.19 (m, 2H), 2.18 (s, 3H), 2.12 (s, 3H), 2.04-1.94 (m, 2H), 1.78-1.66 (m, 2H), 1.49 (s, 9H) | 528.0 $(M + H)^+$ |
| 83 | 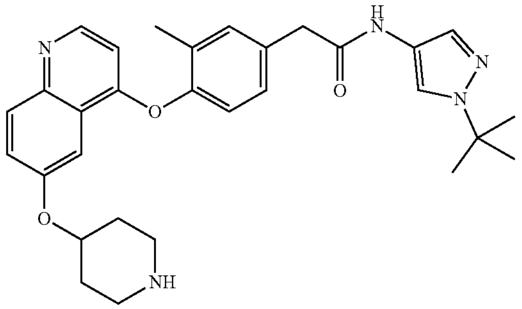 [SMILES: Cc1cc(CC(=O)Nc2cnn(C(C)(C)C)c2)ccc1Oc1ccnc2ccc(OC3CCNCC3)cc12] | N-(1-(tert-butyl)-1H-pyrazol-4-yl)-2-(3-methyl-4-((6-(piperidin-4-yloxy) quinolin-4-yl)oxy)phenyl) acetamide | (400 MHz, DMSO-$d_6$) δ 10.16 (s, 1H), 8.49 (d, J = 5.1 Hz, 1H), 7.95-7.93 (m, 2H), 7.61 (d, J = 2.8 Hz, 1H), 7.51-7.44 (m, 2H), 7.35 (d, J = 2.2 Hz, 1H), 7.27 (dd, J = 8.2, 2.2 Hz, 1H), 7.14 (d, J = 8.2 Hz, 1H), 6.39 (d, J = 5.1 Hz, 1H), 4.62 (dq, J = 8.7, 4.7 Hz, 1H), 3.59 (s, 2H), 3.04-2.90 (m, 2H), 2.69-2.54 (m, 2H), 2.11 (s, 3H), 2.04-1.93 (m, 2H), 1.60-1.50 (m, 2H), 1.49 (s, 9H | 514.0 $(M + H)^+$ |
| 84 | 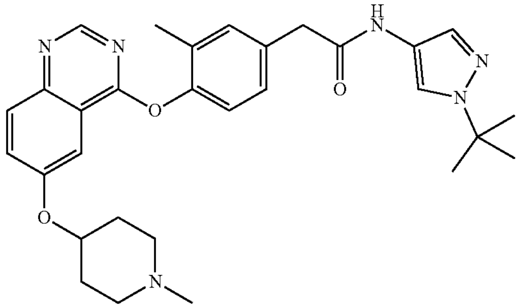 [SMILES: Cc1cc(CC(=O)Nc2cnn(C(C)(C)C)c2)ccc1Oc1ncnc2ccc(OC3CCN(C)CC3)cc12] | N-(1-(tert-butyl)-1H-pyrazol-4-yl)-2-(3-methyl-4-((6-((1-methyl-piperidin-4-yl)oxy) quinazolin-4-yl)oxy)phenyl) acetamide | (400 MHz, DMSO-$d_6$) δ 10.18 (s, 1H), 8.55 (s, 1H), 7.97-7.88 (m, 2H), 7.73-7.65 (m, 2H), 7.45 (d, J = 0.7 Hz, 1H), 7.29 (d, J = 2.1 Hz, 1H), 7.27-7.16 (m, 2H), 4.68 (tt, J = 7.8, 3.7 Hz, 1H), 3.58 (s, 2H), 2.66-2.57 (m, 2H), 2.31-2.21 (m, 2H), 2.19 (s, 3H), 2.08 (s, 3H), 2.05-1.95 (m, 2H), 1.80-1.66 (m, 2H), 1.49 (s, 9H) | 529.1 $(M + H)^+$ |
| 85 | 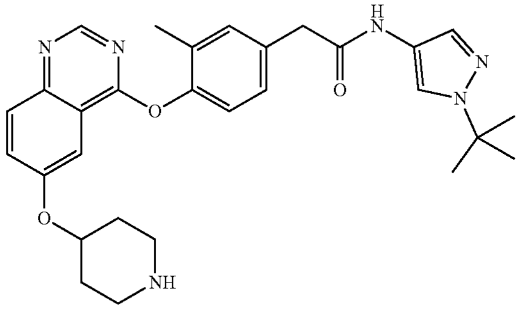 [SMILES: Cc1cc(CC(=O)Nc2cnn(C(C)(C)C)c2)ccc1Oc1ncnc2ccc(OC3CCNCC3)cc12] | N-(1-(tert-butyl)-1H-pyrazol-4-yl)-2-(3-methyl-4-((6-(piperidin-4-yloxy) quinazolin-4-yl)oxy)phenyl) acetamide | (400 MHz, DMSO-$d_6$) δ 10.18 (s, 1H), 8.54 (s, 1H), 7.97-7.88 (m, 2H), 7.70-7.66 (m, 2H), 7.45 (s, 1H), 7.29 (d, J = 2.1 Hz, 1H), 7.26-7.16 (m, 2H), 4.71 (tt, J = 8.2, 3.4 Hz, 1H), 3.58 (s, 2H), 3.03-2.93 (m, 2H), 2.69-2.60 (m, 2H), 2.07 (s, 3H), 2.01 (d, J = 12.2 Hz, 2H), 1.63-1.51 (m, 2H), 1.48 (s, 9H) | 515.1 $(M + H)^+$ |

-continued

| No. | Structure | Name | $^1$H NMR | Observed m/z |
|---|---|---|---|---|
| 94 | 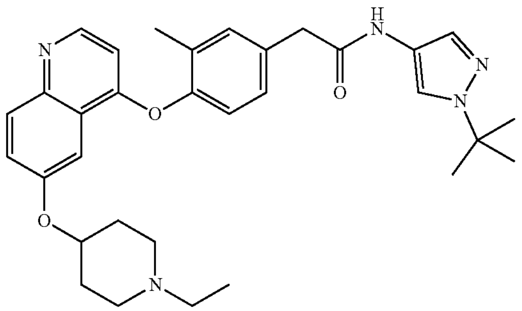 [SMILES: CCN1CCC(Oc2ccc3nccc(Oc4ccc(CC(=O)Nc5cnn(C(C)(C)C)c5)cc4C)c3c2)CC1] | N-(1-(tert-butyl)-1H-pyrazol-4-yl)-2-(4-((6-((1-ethylpiperidin-4-yl)oxy) quinolin-4-yl)oxy)-3-methylphenyl) acetamide | (400 MHz, DMSO-$d_6$) δ 10.12 (s, 1H), 8.42 (d, J = 5.1 Hz, 1H), 7.93-7.82 (m, 2H), 7.54 (d, J = 2.8 Hz, 1H), 7.45-7.36 (m, 2H), 7.28 (d, J = 2.1 Hz, 1H), 7.20 (dd, J = 8.3, 2.2 Hz, 1H), 7.08 (d, J = 8.1 Hz, 1H), 6.32 (d, J = 5.1 Hz, 1H), 4.53 (ddd, J = 11.0, 7.3, 3.3 Hz, 1H), 3.52 (s, 2H), 2.62 (t, J = 8.0 Hz, 2H), 2.26 (q, J = 7.2 Hz, 2H), 2.16 (t, J = 9.9 Hz, 2H), 2.04 (s, 3H), 1.94 (d, J = 12.5 Hz, 2H), 1.70-1.56 (m, 2H), 1.41 (s, 9H), 0.93 (t, J = 7.1 Hz, 3H) | 542.2 (M + H)$^+$ |
| 95 | 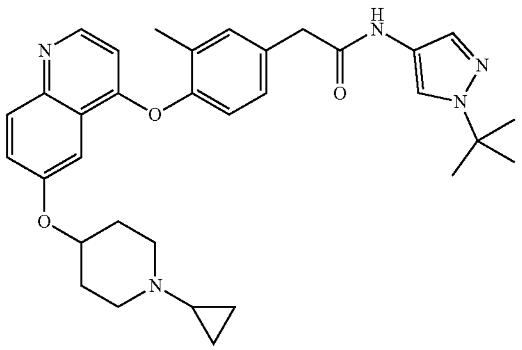 [SMILES: Cc1cc(CC(=O)Nc2cnn(C(C)(C)C)c2)ccc1Oc1ccnc2ccc(OC3CCN(C4CC4)CC3)cc12] | N-(1-(tert-butyl)-1H-pyrazol-4-yl)-2-(4-((6-((1-cyclopropyl-piperidin-4-yl)oxy) quinolin-4-yl)oxy)-3-methylphenyl) acetamide | (400 MHz, DMSO-$d_6$) δ 10.20 (s, 1H), 8.49 (d, J = 5.1 Hz, 1H), 7.98-7.90 (m, 2H), 7.62 (d, J = 2.8 Hz, 1H), 7.48 (dd, J = 9.2, 2.8 Hz, 1H), 7.45 (d, J = 0.7 Hz, 1H), 7.35 (d, J = 2.2 Hz, 1H), 7.31-7.25 (m, 1H), 7.16 (d, J = 8.2 Hz, 1H), 6.39 (d, J = 5.1 Hz, 1H), 4.62 (ddd, J = 12.1, 7.9, 3.7 Hz, 1H), 3.59 (s, 2H), 2.88-2.77 (m, 2H), 2.47 (d, J = 9.2 Hz, 2H), 2.11 (s, 3H), 2.02-1.92 (m, 2H), 1.72-1.60 (m, 3H), 1.48 (s, 9H), 0.41 (dt, J = 6.2, 3.0 Hz, 2H), 0.33-0.27 (m, 2H) | 554.1 (M + H)$^+$ |
| 96 | 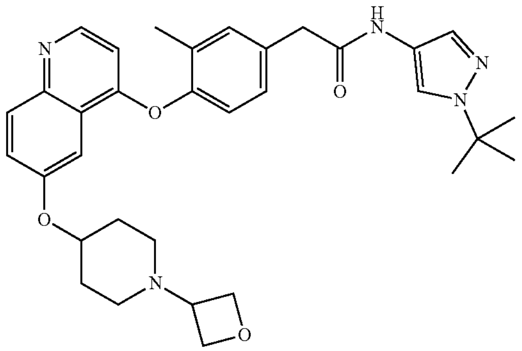 [SMILES: Cc1cc(CC(=O)Nc2cnn(C(C)(C)C)c2)ccc1Oc1ccnc2ccc(OC3CCN(C4COC4)CC3)cc12] | N-(1-(tert-butyl)-1H-pyrazol-4-yl)-2-(3-methyl-4-((6-((1-(oxetan-3-yl)piperidin-4-yl)oxy) quinolin-4-yl)oxy)phenyl) acetamide | (400 MHz, DMSO-$d_6$) δ 10.18 (s, 1H), 8.49 (d, J = 5.1 Hz, 1H), 7.99-7.85 (m, 2H), 7.62 (d, J = 2.8 Hz, 1H), 7.48 (dd, J = 9.2, 2.8 Hz, 1H), 7.45 (d, J = 0.7 Hz, 1H), 7.35 (d, J = 2.1 Hz, 1H), 7.27 (dd, J = 8.3, 2.2 Hz, 1H), 7.15 (d, J = 8.2 Hz, 1H), 6.39 (d, J = 5.1 Hz, 1H), 4.65 (ddd, J = 11.2, 7.5, 3.7 Hz, 1H), 4.53 (t, J = 6.5 Hz, 2H), 4.43 (t, J = 6.1 Hz, 2H), 3.59 (s, 2H), 3.42 (t, J = 6.5 Hz, 1H), 2.53 (s, 2H), 2.16 (t, J = 10.2 Hz, 2H), 2.11 (s, 3H), 2.02 (t, J = 7.9 Hz, 2H), 1.74 (d, J = 9.0 Hz, 2H), 1.49 (s, 9H) | 570.2 (M + H)$^+$ |
| 102 | 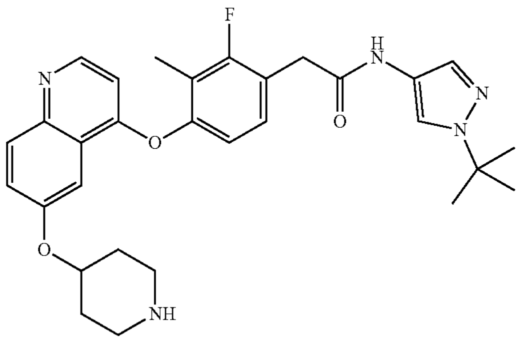 [SMILES: Cc1c(Oc2ccnc3ccc(OC4CCNCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(piperidin-4-yloxy) quinolin-4-yl)oxy)phenyl) acetamide | (300 MHz, DMSO-$d_6$) δ 10.22 (s, 1H), 8.53 (d, J = 5.1 Hz, 1H), 8.01-7.90 (m, 2H), 7.61 (d, J = 2.8 Hz, 1H), 7.50 (dd, J = 9.1, 2.8 Hz, 1H), 7.45 (s, 1H), 7.34 (t, J = 8.6 Hz, 1H), 7.05 (d, J = 8.3 Hz, 1H), 6.48 (d, J = 5.1 Hz, 1H), 4.70-4.64 (m, 1H), 3.69 (s, 2H), 3.62-3.57 (m, 4H), 3.07-2.95 (m, 1H), 2.77-2.63 (m, 2H), 2.06 (s, 3H), 1.78-1.74 (m, 2H), 1.49 (s, 9H) | 532.1 (M + H)$^+$ |

-continued

| No. | Structure | Name | $^1$H NMR | Observed m/z |
|---|---|---|---|---|
| 104 | 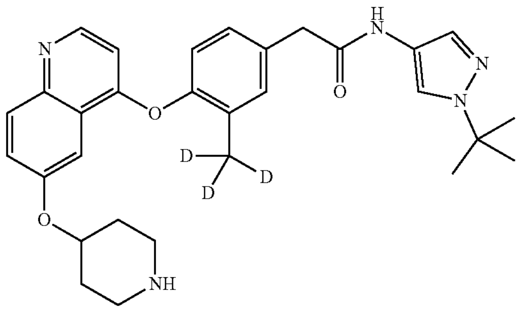 [SMILES: [2H]C([2H])([2H])c1cc(CC(=O)Nc2cnn(C(C)(C)C)c2)ccc1Oc1ccnc2ccc(OC3CCNCC3)cc12] | N-(1-(tert-butyl)-1H-pyrazol-4-yl)-2-(3-(methyl-d3)-4-((6-(piperidin-4-yloxy) quinolin-4-yl)oxy)phenyl) acetamide | (400 MHz, DMSO-$d_6$) δ 10.20 (s, 1H), 8.49 (d, J = 5.1 Hz, 1H), 7.95-7.93 (m, 2H), 7.61 (d, J = 2.7 Hz, 1H), 7.51-7.43 (m, 2H), 7.35 (d, J = 2.2 Hz, 1H), 7.27 (dd, J = 8.3, 2.2 Hz, 1H), 7.15 (d, J = 8.2 Hz, 1H), 6.38 (d, J = 5.1 Hz, 1H), 4.64 (tt, J = 8.4, 3.6 Hz, 1H), 3.59 (s, 2H), 2.98 (d, J = 12.1 Hz, 2H), 2.63 (t, J = 11.3 Hz, 2H), 1.99 (d, J = 12.4 Hz, 2H), 1.54 (d, J = 10.6 Hz, 2H), 1.48 (s, 9H) | 517.4 (M + H)$^+$ |
| 105 | 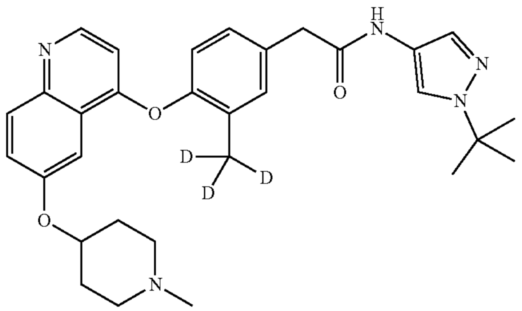 [SMILES: [2H]C([2H])([2H])c1cc(CC(=O)Nc2cnn(C(C)(C)C)c2)ccc1Oc1ccnc2ccc(OC3CCN(C)CC3)cc12] | N-(1-(tert-butyl)-1H-pyrazol-4-yl)-2-(3-(methyl-d3)-4-((6-((1-methyl-piperidin-4-yl)oxy) quinolin-4-yl)oxy)phenyl) acetamide | (400 MHz, DMSO-$d_6$) δ 10.20 (s, 1H), 8.49 (d, J = 5.1 Hz, 1H), 8.23 (s, 1H), 7.96-7.93 (m, 2H), 7.61 (d, J = 2.9 Hz, 1H), 7.48 (dd, J = 9.2, 2.8 Hz, 1H), 7.45 (s, 1H), 7.35 (d, J = 2.2 Hz, 1H), 7.27 (dd, J = 8.2, 2.2 Hz, 1H), 7.15 (d, J = 8.2 Hz, 1H), 6.39 (d, J = 5.1 Hz, 1H), 4.68-4.57 (m, 1H), 3.59 (s, 2H), 2.75-2.60 (m, 2H), 2.37-2.26 (m, 2H), 2.20 (s, 3H), 2.08-1.95 (m, 2H), 1.83-1.68 (m, 2H), 1.48 (s, 9H) | 529.2 (M − H)$^-$ |
| 106 | 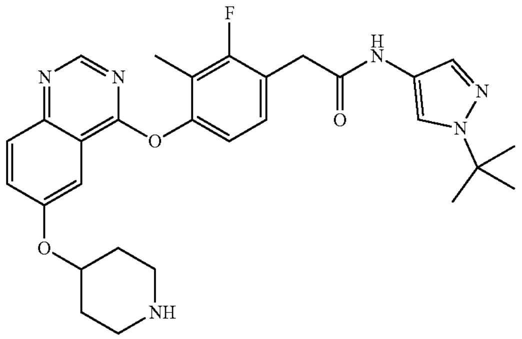 | N-(1-(tert-butyl)-1H-pyrazol-4-yl)-2-(2-fluoro-3-methyl-4-((6-(piperidin-4-yloxy) quinazolin-4-yl)oxy)phenyl) acetamide | (300 MHz, DMSO-$d_6$) δ 10.25 (s, 1H), 8.58 (s, 1H), 7.97-7.95 (m, 2H), 7.74-7.66 (m, 2H), 7.46 (s, 1H), 7.31 (t, J = 8.4 Hz, 1H), 7.12 (d, J = 8.8 Hz, 1H), 4.78-4.68 (m, 1H), 3.69 (s, 2H), 3.04-2.93 (m, 2H), 2.70-2.60 (m, 2H), 2.05-1.97 (m, 5H), 1.58-1.52 (m, 2H), 1.49 (s, 9H) | 533.2 (M + H)$^+$ |
| 107 | 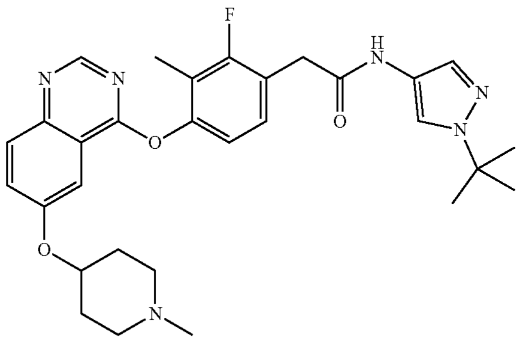 [SMILES: Cc1c(Oc2ncnc3ccc(OC4CCN(C)CC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-((1-methyl-piperidin-4-yl)oxy) quinazolin-4-yl)oxy)phenyl) acetamide | (400 MHz, DMSO-$d_6$) δ 10.25 (s, 1H), 8.59 (s, 1H), 7.97-7.94 (m, 2H), 7.76-7.68 (m, 2H), 7.46 (s, 1H), 7.31 (t, J = 8.4 Hz, 1H), 7.12 (d, J = 8.4 Hz, 1H), 4.76-4.66 (m, 1H), 3.69 (s, 2H), 2.69-2.59 (m, 2H), 2.26 (t, J = 10.0 Hz, 2H), 2.20 (s, 3H), 2.07-1.98 (m, 5H), 1.82-1.69 (m, 2H), 1.49 (s, 9H) | 547.2 (M + H)$^+$ |

-continued

| No. | Structure | Name | $^1$H NMR | Observed m/z |
|---|---|---|---|---|
| 109 | 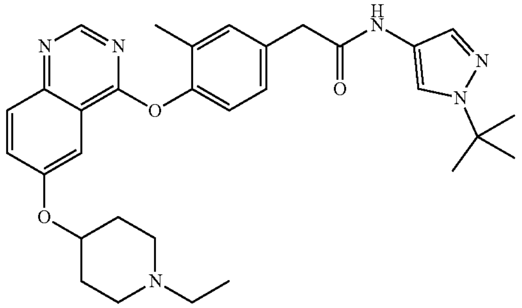 | N-(1-(tert-butyl)-1H-pyrazol-4-yl)-2-(4-((6-((1-ethyl-piperidin-4-yl)oxy) quinazolin-4-yl)oxy)-3-methylphenyl) acetamide | (400 MHz, DMSO-$d_6$) δ 10.19 (s, 1H), 8.55 (s, 1H), 7.98-7.90 (m, 2H), 7.70-7.56 (m, 2H), 7.45 (s, 1H), 7.29 (d, J = 2.1 Hz, 1H), 7.26-7.15 (m, 2H), 4.76-4.66 (m, 1H), 3.58 (s, 2H), 2.80-2.70 (m, 2H), 2.41 (q, J = 7.2 Hz, 2H), 2.34 (t, J = 10.3 Hz, 2H), 2.07 (s, 3H), 2.05-1.98 (m, 2H), 1.81-1.69 (m, 2H), 1.48 (s, 9H), 1.02 (t, J = 7.1 Hz, 3H) | 543.1 $(M + H)^+$ |
| 110 | 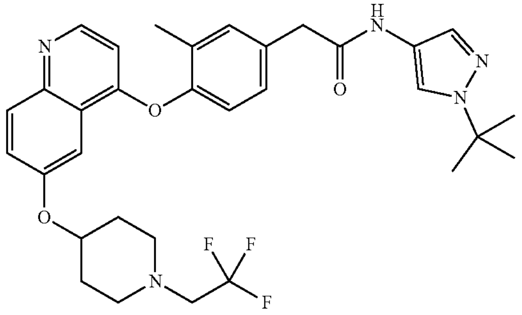 [SMILES: Cc1cc(CC(=O)Nc2cnn(C(C)(C)C)c2)ccc1Oc1ccnc2ccc(OC3CCN(CC(F)(F)F)CC3)cc12] | N-(1-(tert-butyl)-1H-pyrazol-4-yl)-2-(3-methyl-4-((6-((1-(2,2,2-trifluoroethyl) piperidin-4-yl)oxy) quinolin-4-yl)oxy)phenyl) acetamide | (400 MHz, DMSO-$d_6$) δ 10.18 (s, 1H), 8.49 (d, J = 5.1 Hz, 1H), 7.98-7.90 (m, 2H), 7.63 (d, J = 2.8 Hz, 1H), 7.49 (dd, J = 9.2, 2.8 Hz, 1H), 7.45 (d, J = 0.7 Hz, 1H), 7.35 (d, J = 2.2 Hz, 1H), 7.27 (dd, J = 8.4, 2.2 Hz, 1H), 7.15 (d, J = 8.2 Hz, 1H), 6.39 (d, J = 5.1 Hz, 1H), 4.65 (ddd, J = 11.6, 7.4, 3.4 Hz, 1H), 3.59 (s, 2H), 3.20 (q, J = 10.3 Hz, 2H), 2.89 (td, J = 6.6, 6.0, 3.2 Hz, 2H), 2.68-2.59 (m, 2H), 2.11 (s, 3H), 2.05-1.95 (m, 2H), 1.74 (ddt, J = 16.3, 7.9, 3.4 Hz, 2H), 1.49 (s, 9H) | 596.1 $(M + H)^+$ |
| 111 | 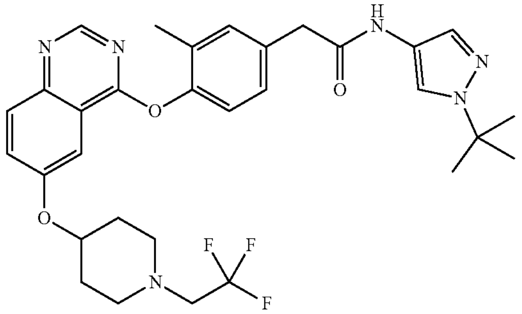 [SMILES: Cc1cc(CC(=O)Nc2cnn(C(C)(C)C)c2)ccc1Oc1ncnc2ccc(OC3CCN(CC(F)(F)F)CC3)cc12] | N-(1-(tert-butyl)-1H-pyrazol-4-yl)-2-(3-methyl-4-((6-((1-(2,2,2-trifluoroethyl) piperidin-4-yl)oxy) quinazolin-4-yl)oxy)phenyl) acetamide | (400 MHz, DMSO-$d_6$) δ 10.20 (s, 1H), 8.55 (s, 1H), 8.00-7.86 (m, 2H), 7.71-7.68 (m, 2H), 7.45 (d, J = 0.7 Hz, 1H), 7.30 (d, J = 2.1 Hz, 1H), 7.26-7.14 (m, 2H), 4.74 (ddd, J = 11.1, 7.4, 3.2 Hz, 1H), 3.58 (s, 2H), 3.21 (q, J = 10.2 Hz, 2H), 2.94-2.82 (m, 2H), 2.65 (ddd, J = 11.7, 8.6, 3.2 Hz, 2H), 2.08 (s, 3H), 2.06-1.96 (m, 2H), 1.82-1.67 (m, 2H), 1.48 (s, 9H) | 597.1 $(M + H)^+$ |
| 114 | 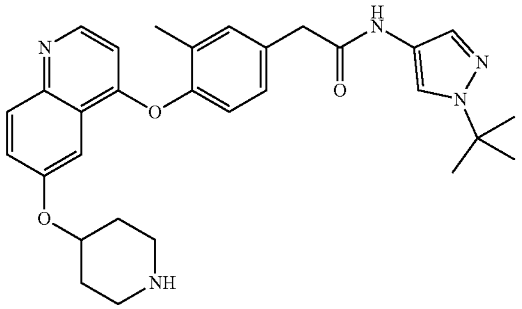 | N-(1-(tert-butyl)-1H-pyrazol-4-yl)-2-(2-fluoro-5-methyl-4-((6-(piperidin-4-yloxy) quinolin-4-yl)oxy)phenyl) acetamide | (400 MHz, DMSO-$d_6$) δ 10.24 (s, 1H), 8.53 (d, J = 5.1 Hz, 1H), 7.97-7.94 (m, 2H), 7.59 (s, 1H), 7.53-7.47 (m, 1H), 7.47-7.39 (m, 2H), 7.18 (d, J = 10.0 Hz, 1H), 6.48 (d, J = 5.0 Hz, 1H), 4.63 (s, 1H), 3.67 (s, 2H), 3.05-2.89 (m, 2H), 2.67-2.53 (m, 2H), 2.09 (s, 3H), 2.04-1.93 (m, 2H), 1.64-1.53 (m, 2H), 1.49 (s, 9H) | 532.2 $(M + H)^+$ |

-continued

| No. | Structure | Name | $^1$H NMR | Observed m/z |
|---|---|---|---|---|
| 115 | 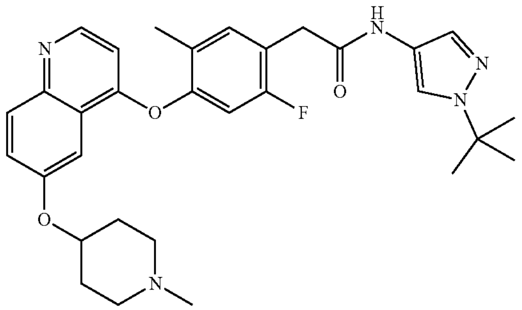 | N-(1-(tert-butyl)-1H-pyrazol-4-yl)-2-(2-fluoro-5-methyl-4-((6-((1-methyl-piperidin-4-yl)oxy) quinolin-4-yl)oxy)phenyl) acetamide | (400 MHz, DMSO-$d_6$) δ 10.19 (s, 1H), 8.53 (d, J = 5.1 Hz, 1H), 8.00-7.92 (m, 2H), 7.59 (d, J = 2.8 Hz, 1H), 7.49 (dd, J = 9.2, 2.8 Hz, 1H), 7.45 (s, 1H), 7.42 (d, J = 8.4 Hz, 1H), 7.16 (d, J = 10.1 Hz, 1H), 6.48 (d, J = 5.1 Hz, 1H), 4.68-4.56 (m, 1H), 3.66 (s, 2H), 2.62 (dt, J = 9.8, 4.9 Hz, 2H), 2.28-2.19 (m, 2H), 2.18 (s, 3H), 2.09 (s, 3H), 2.04-1.94 (m, 2H), 1.79-1.67 (m, 2H), 1.49 (s, 9H) | 546.1 $(M + H)^+$ |
| 116 | 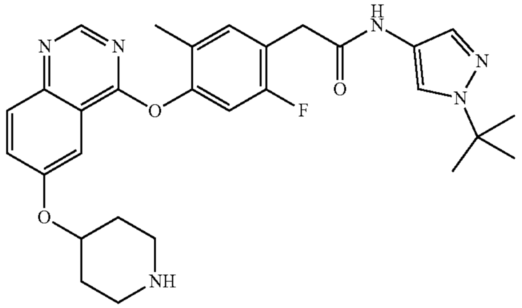 [SMILES: Cc1cc(CC(=O)Nc2cnn(C(C)(C)C)c2)c(F)cc1Oc1ncnc2ccc(OC3CCNCC3)cc12] | N-(1-(tert-butyl)-1H-pyrazol-4-yl)-2-(2-fluoro-5-methyl-4-((6-((1-methyl-piperidin-4-yl)oxy) quinazolin-4-yl)oxy)phenyl) acetamide | (300 MHz, DMSO-$d_6$) δ 10.23 (s, 1H), 8.59 (s, 1H), 7.96-7.94 (m, 2H), 7.71-7.69 (m, 2H), 7.46 (s, 1H), 7.36 (d, J = 8.3 Hz, 1H), 7.25 (d, J = 10.1 Hz, 1H), 4.72 (s, 1H), 3.66 (s, 2H), 3.38 (s, 2H), 3.03-2.93 (m, 2H), 2.64 (t, J = 10.2 Hz, 2H), 2.06 (s, 3H), 1.63-1.52 (m, 2H), 1.49 (s, 9H) | 533.2 $(M + H)^+$ |
| 117 | 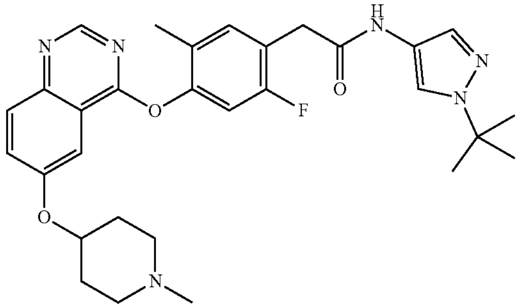 [SMILES: Cc1cc(CC(=O)Nc2cnn(C(C)(C)C)c2)c(F)cc1Oc1ncnc2ccc(OC3CCN(C)CC3)cc12] | N-(1-(tert-butyl)-1H-pyrazol-4-yl)-2-(2-fluoro-5-methyl-4-((6-((1-methyl-piperidin-4-yl)oxy) quinazolin-4-yl)oxy)phenyl) acetamide | (300 MHz, DMSO-$d_6$) δ 10.22 (s, 1H), 8.59 (s, 1H), 7.96-7.94 (m, 2H), 7.75-7.67 (m, 2H), 7.45 (s, 1H), 7.35 (d, J = 8.4 Hz, 1H), 7.24 (d, J = 10.0 Hz, 1H), 4.74-4.64 (m, 1H), 3.65 (s, 2H), 2.67-2.60 (m, 2H), 2.32-2.24 (m, 2H), 2.20 (s, 3H), 2.06 (s, 3H), 2.04-1.94 (m, 2H), 1.82-1.68 (m, 2H), 1.49 (s, 9H) | 547.2 $(M + H)^+$ |
| 120 | 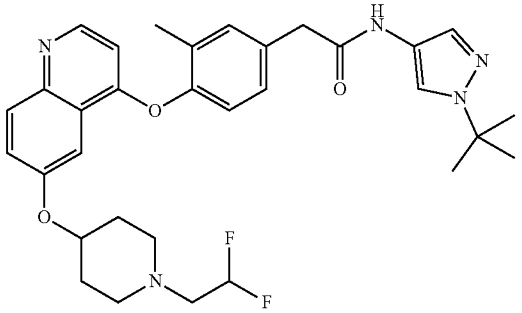 [SMILES: Cc1cc(CC(=O)Nc2cnn(C(C)(C)C)c2)ccc1Oc1ccnc2ccc(OC3CCN(CC(F)F)CC3)cc12] | N-(1-(tert-butyl)-1H-pyrazol-4-yl)-2-(4-((6-((1-(2,2-difluoroethyl) piperidin-4-yl)oxy) quinolin-4-yl)oxy)-3-methylphenyl) acetamide | (400 MHz, DMSO-$d_6$) δ 10.17 (s, 1H), 8.49 (d, J = 5.1 Hz, 1H), 7.97-7.91 (m, 2H), 7.62 (d, J = 2.8 Hz, 1H), 7.48 (dd, J = 9.2, 2.8 Hz, 1H), 7.45 (s, 1H), 7.35 (d, J = 2.2 Hz, 1H), 7.27 (dd, J = 8.3, 2.2 Hz, 1H), 7.15 (d, J = 8.2 Hz, 1H), 6.39 (d, J = 5.1 Hz, 1H), 6.14 (tt, J = 58.0, 7.2 Hz, 1H), 4.63 (td, J = 7.7, 3.7 Hz, 1H), 3.59 (s, 2H), 2.85-2.71 (m, 4H), 2.53-2.45 (m, 2H), 2.11 (s, 3H), 2.00 (dt, J = 15.0, 2.9 Hz, 2H), 1.72 (dtd, J = 12.3, 8.4, 3.5 Hz, 2H), 1.48 (s, 9H) | 578.2 $(M + H)^+$ |

-continued

| No. | Structure | Name | $^1$H NMR | Observed m/z |
|---|---|---|---|---|
| 121 | 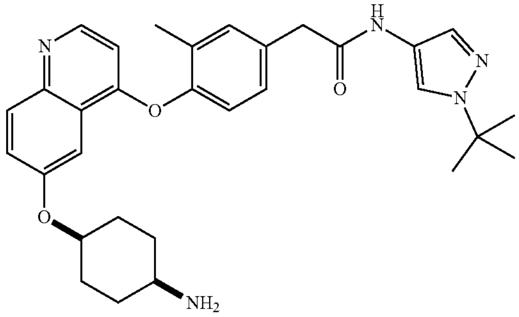 | 2-(4-((6-(((1s,4s)-4-aminocyclo-hexyl)oxy) quinolin-4-yl)oxy)-3-methyl-phenyl)-N-(1-(tert-butyl)-1H-pyrazol-4-yl)acetamide | (400 MHz, DMSO-$d_6$) δ 10.25 (s, 1H), 8.49 (d, J = 5.1 Hz, 1H), 8.02-7.91 (m, 2H), 7.63 (d, J = 2.8 Hz, 1H), 7.49 (dd, J = 9.2, 2.8 Hz, 1H), 7.46 (s, 1H), 7.36 (d, J = 2.2 Hz, 1H), 7.27 (d, J = 2.2 Hz, 1H), 7.16 (d, J = 8.2 Hz, 1H), 6.37 (d, J = 5.1 Hz, 1H), 4.75 (d, J = 3.6 Hz, 1H), 3.60 (s, 2H), 2.91-2.81 (m, 1H), 2.11 (s, 3H), 2.06-1.96 (m, 2H), 1.75-1.62 (m, 4H), 1.61-1.52 (m, 2H), 1.49 (s, 9H) | 528.2 $(M + H)^+$ |
| 123 | 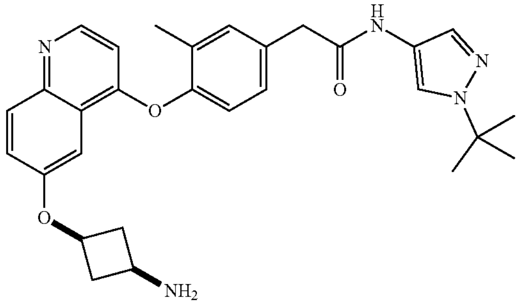 | 2-(4-((6-((1s,3s)-3-aminocyclo-butoxy) quinolin-4-yl)oxy)-3-methyl-phenyl)-N-(1-(tert-butyl)-1H-pyrazol-4-yl)acetamide | (400 MHz, DMSO-$d_6$) δ 10.71 (s, 1H), 8.99 (s, 1H), 8.70 (s, 2H), 8.50 (d, J = 8.5 Hz, 1H), 8.04 (s, 1H), 7.96 (d, J = 8.7 Hz, 1H), 7.83 (s, 1H), 7.59 (d, J = 21.1 Hz, 2H), 7.54-7.40 (m, 2H), 6.91 (s, 1H), 4.99 (s, 1H), 3.78 (s, 2H), 3.57 (s, 2H), 3.06 (s, 2H), 2.62 (s, 1H), 2.24 (s, 3H), 1.57 (s, 9H) | 500.1 $(M + H)^+$ |
| 124 | 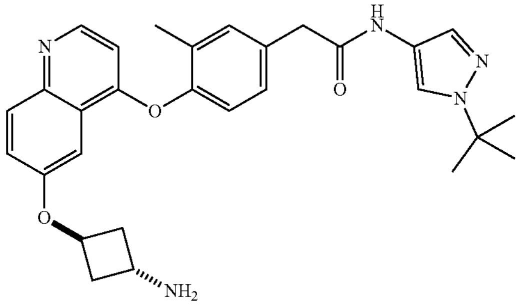 | 2-(4-((6-((1r,3r)-3-aminocyclo-butoxy) quinolin-4-yl)oxy)-3-methyl-phenyl)-N-(1-(tert-butyl)-1H-pyrazol-4-yl)acetamide | (400 MHz, DMSO-$d_6$) δ 10.22 (s, 1H), 8.49 (d, J = 5.1 Hz, 1H), 7.95-7.93 (m, 2H), 7.46 (s, 1H), 7.42-7.40 (m, 2H), 7.36 (s, 1H), 7.28 (d, J = 8.2 Hz, 1H), 7.16 (d, J = 8.1 Hz, 1H), 6.40 (d, J = 5.1 Hz, 1H), 5.04 (t, J = 5.8 Hz, 1H), 3.60 (s, 3H), 2.40-2.30 (m, 2H), 2.26-2.17 (m, 2H), 2.11 (s, 3H), 1.48 (s, 9H) | 500.1 $(M + H)^+$ |
| 133 | 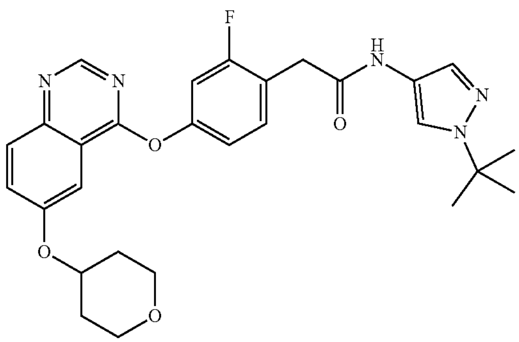 [SMILES: CC(C)(C)n1cc(NC(=O)Cc2ccc(Oc3ncnc4ccc(OC5CCOCC5)cc34)cc2F)cn1] | N-(1-(tert-butyl)-1H-pyrazol-4-yl)-2-(2-fluoro-4-((6-((tetrahydro-2H-pyran-4-yl)oxy) quinazolin-4-yl)oxy)phenyl) acetamide | (400 MHz, DMSO-$d_6$) δ 10.23 (s, 1H), 8.62 (s, 1H), 7.96-7.94 (m, 2H), 7.76-7.66 (m, 2H), 7.53-7.41 (m, 2H), 7.31 (dd, J = 10.5, 2.4 Hz, 1H), 7.18 (dd, J = 8.4, 2.3 Hz, 1H), 4.90 (dt, J = 8.6, 4.4 Hz, 1H), 3.89 (dt, J = 11.6, 4.4 Hz, 2H), 3.70 (s, 2H), 3.56 (ddd, J = 11.8, 9.3, 2.8 Hz, 2H), 2.07 (d, J = 9.3 Hz, 2H), 1.68 (dtd, J = 13.0, 9.0, 4.0 Hz, 2H), 1.49 (s, 9H) | 520.1 $(M + H)^+$ |

-continued

| No. | Structure | Name | $^1$H NMR | Observed m/z |
|---|---|---|---|---|
| 136 | 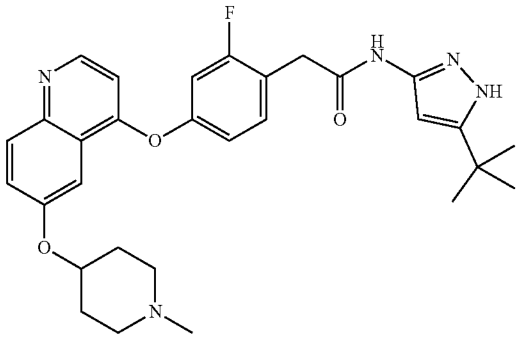 | N-(5-(tert-butyl)-1H-pyrazol-3-yl)-2-(2-fluoro-4-((6-((1-methyl-piperidin-4-yl)oxy) quinolin-4-yl)oxy)phenyl) acetamide | (400 MHz, DMSO-$d_6$) δ 12.06 (s, 1H), 10.57 (s, 1H), 8.58 (d, J = 5.1 Hz, 1H), 7.97 (d, J = 9.0 Hz, 1H), 7.53-7.45 (m, 3H), 7.22 (dd, J = 10.6, 2.4 Hz, 1H), 7.07 (dd, J = 8.4, 2.4 Hz, 1H), 6.72 (d, J = 5.1 Hz, 1H), 6.28 (s, 1H), 4.57-4.56 (m, 1H), 3.72 (s, 2H), 2.61 (d, J = 12.6 Hz, 2H), 2.22 (d, J = 11.6 Hz, 2H), 2.18 (s, 3H), 2.01-1.93 (m, 2H), 1.70 (dtd, J = 12.4, 8.6, 3.6 Hz, 2H), 1.25 (s, 9H) | 532.1 (M + H)$^+$ |
| 137 | 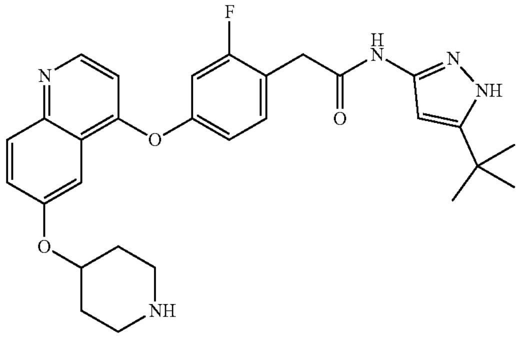 | N-(5-(tert-butyl)-1H-pyrazol-3-yl)-2-(2-fluoro-4-((6-(piperidin-4-yloxy) quinolin-4-yl)oxy)phenyl) acetamide | (400 MHz, DMSO-$d_6$) δ 12.05 (s, 1H), 10.58 (s, 1H), 8.57 (d, J = 5.1 Hz, 1H), 7.96 (d, J = 9.1 Hz, 1H), 7.51-7.46 (m, 3H), 7.23 (dd, J = 10.5, 2.4 Hz, 1H), 7.07 (dd, J = 8.4, 2.4 Hz, 1H), 6.71 (d, J = 5.0 Hz, 1H), 6.27 (s, 1H), 4.59 (dt, J = 9.1, 4.8 Hz, 1H), 3.71 (s, 2H), 2.95 (dt, J = 12.7, 4.3 Hz, 2H), 2.59 (ddd, J = 12.9, 10.1, 2.9 Hz, 2H), 1.96 (dq, J = 11.5, 3.8 Hz, 2H), 1.51 (qd, J = 9.3, 4.8 Hz, 2H), 1.24 (s, 9H) | 518.1 (M + H)$^+$ |
| 151 | 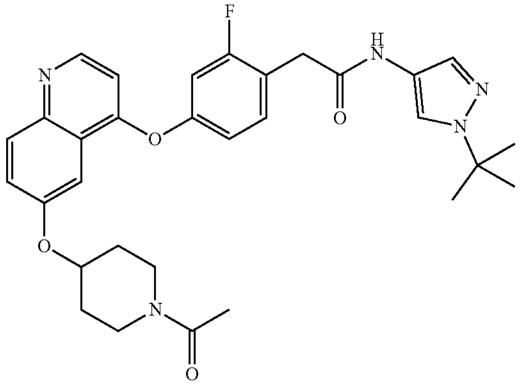 | 2-(4-((6-((1-acetyl-piperidin-4-yl)oxy) quinolin-4-yl)oxy)-2-fluoro-phenyl)-N-(1-(tert-butyl)-1H-pyrazol-4-yl)acetamide | (400 MHz, DMSO-$d_6$) δ 10.22 (s, 1H), 8.62 (d, J = 5.3 Hz, 1H), 8.00 (d, J = 9.2 Hz, 1H), 7.93 (d, J = 0.7 Hz, 1H), 7.61 (d, J = 2.8 Hz, 1H), 7.57-7.53 (m, 1H), 7.50 (d, J = 8.6 Hz, 1H), 7.45 (d, J = 0.7 Hz, 1H), 7.28-7.23 (m, 1H), 7.13-7.08 (m, 1H), 6.74 (d, J = 5.2 Hz, 1H), 4.86 (dt, J = 7.9, 4.0 Hz, 1H), 3.89-3.79 (m, 1H), 3.72-3.66 (m, 3H), 3.29 (dd, J = 8.7, 4.8 Hz, 2H), 2.02 (s, 3H), 1.98-1.91 (m, 2H), 1.73-1.64 (m, 1H), 1.62-1.55 (m, 1H), 1.48 (s, 9H) | 560.1 (M + H)$^+$ |
| 158 | 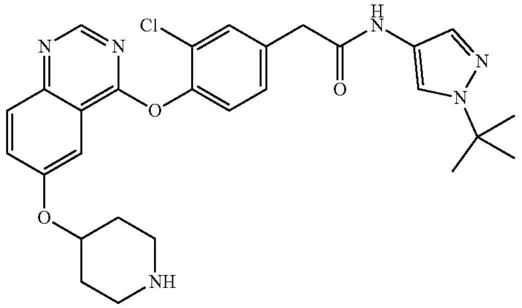 | N-(1-(tert-butyl)-1H-pyrazol-4-yl)-2-(3-chloro-4-((6-(piperidin-4-yloxy) quinazolin-4-yl)oxy)phenyl) acetamide | (400 MHz, DMSO-$d_6$) δ 10.29 (s, 1H), 8.59 (s, 1H), 7.99-7.92 (m, 2H), 7.74-7.66 (m, 2H), 7.59 (d, J = 2.0 Hz, 1H), 7.51-7.45 (m, 2H), 7.40 (dd, J = 8.3, 2.0 Hz, 1H), 4.72 (dt, J = 9.0, 4.8 Hz, 1H), 3.66 (s, 2H), 3.02-2.90 (m, 2H), 2.70-2.58 (m, 2H), 2.06-1.95 (m, 2H), 1.55 (dd, J = 11.4, 7.7 Hz, 2H), 1.49 (s, 9H) | 535.2 (M + H)$^+$ |

-continued

| No. | Structure | Name | $^1$H NMR | Observed m/z |
|---|---|---|---|---|
| 159 | 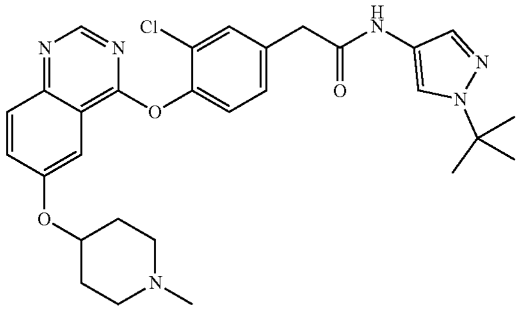 | N-(1-(tert-butyl)-1H-pyrazol-4-yl)-2-(3-chloro-4-((6-((1-methyl-piperidin-4-yl)oxy) quinazolin-4-yl)oxy)phenyl) acetamide | (400 MHz, DMSO-$d_6$) δ 10.25 (s, 1H), 8.59 (s, 1H), 7.97-7.95 (m, 2H), 7.75-7.67 (m, 2H), 7.58 (d, J = 2.0 Hz, 1H), 7.51-7.45 (m, 2H), 7.43-7.37 (m, 1H), 4.77-4.64 (m, 1H), 3.65 (s, 2H), 2.70-2.60 (m, 2H), 2.31-2.22 (m, 2H), 2.20 (s, 3H), 2.07-1.96 (m, 2H), 1.77-1.73 (m, 2H), 1.49 (s, 9H) | 549.2 $(M + H)^+$ |
| 160 | 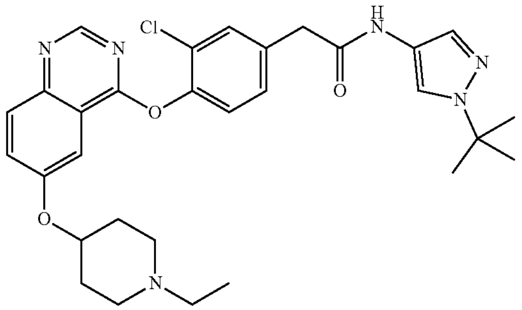 | N-(1-(tert-butyl)-1H-pyrazol-4-yl)-2-(3-chloro-4-((6-((1-ethyl-piperidin-4-yl)oxy) quinazolin-4-yl)oxy)phenyl) acetamide | (400 MHz, DMSO-$d_6$) δ 10.24 (s, 1H), 8.58 (s, 1H), 7.95-7.93 (m, 2H), 7.74-7.65 (m, 2H), 7.58 (d, J = 2.0 Hz, 1H), 7.50-7.43 (m, 2H), 7.43-7.36 (m, 1H), 4.74-4.64 (m, 1H), 3.65 (s, 2H), 2.69 (ddd, J = 11.5, 5.0, 2.2 Hz, 2H), 2.36-2.32 (m, 2H), 2.31-2.23 (m, 2H), 2.06-1.97 (m, 2H), 1.77-1.67 (m, 2H), 1.49 (s, 9H), 1.01 (t, J = 7.2 Hz, 3H) | 563.2 $(M + H)^+$ |
| 161 | 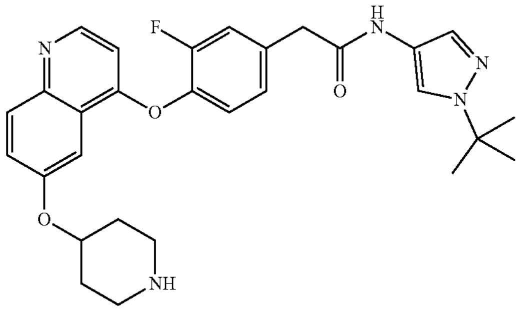 | N-(1-(tert-butyl)-1H-pyrazol-4-yl)-2-(3-fluoro-4-((6-(piperidin-4-yloxy) quinolin-4-yl)oxy)phenyl) acetamide | (300 MHz, DMSO-$d_6$) δ 10.26 (s, 1H), 8.54 (d, J = 5.1 Hz, 1H), 8.00-7.92 (m, 2H), 7.59 (s, 1H), 7.53-7.38 (m, 4H), 7.27 (dt, J = 8.6, 1.4 Hz, 1H), 6.55 (dd, J = 5.1, 1.1 Hz, 1H), 4.73-4.55 (m, 1H), 3.67 (s, 2H), 2.95 (s, 2H), 2.61 (s, 2H), 1.99 (d, J = 12.0 Hz, 2H), 1.56 (s, 2H), 1.49 (s, 9H) | 516.1 $(M - H)^-$ |
| 162 | 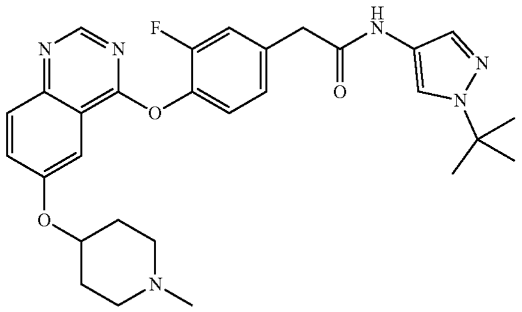 | N-(1-(tert-butyl)-1H-pyrazol-4-yl)-2-(3-fluoro-4-((6-((1-methyl-piperidin-4-yl)oxy) quinolin-4-yl)oxy)phenyl) acetamide | (400 MHz, DMSO-$d_6$) δ 10.22 (s, 1H), 8.54 (d, J = 5.1 Hz, 1H), 8.00-7.91 (m, 2H), 7.59 (d, J = 2.8 Hz, 1H), 7.49 (dd, J = 9.2, 2.8 Hz, 1H), 7.47-7.40 (m, 3H), 7.27 (d, J = 8.4 Hz, 1H), 6.58-6.54 (m, 1H), 4.63 (dt, J = 12.5, 4.7 Hz, 1H), 3.67 (s, 2H), 2.71-2.59 (m, 2H), 2.36-2.24 (m, 2H), 2.20 (s, 3H), 2.06-1.95 (m, 2H), 1.80-1.68 (m, 2H), 1.49 (s, 9H) | 530.1 $(M - H)^-$ |

-continued

| No. | Structure | Name | $^1$H NMR | Observed m/z |
|---|---|---|---|---|
| 165 | 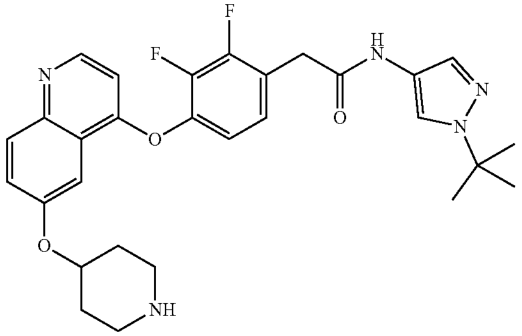 | N-(1-(tert-butyl)-1H-pyrazol-4-yl)-2-(2,3-difluoro-4-((6-(piperidin-4-yloxy) quinolin-4-yl)oxy)phenyl) acetamide | (300 MHz, DMSO-$d_6$) δ 10.25 (s, 1H), 8.58 (d, J = 5.1 Hz, 1H), 7.98 (d, J = 9.2 Hz, 1H), 7.93 (s, 1H), 7.58 (d, J = 2.8 Hz, 1H), 7.51 (dd, J = 9.2, 2.8 Hz, 1H), 7.46 (s, 1H), 7.37-7.24 (m, 2H), 6.69 (d, J = 5.1 Hz, 1H), 4.67 (dt, J = 8.9, 4.8 Hz, 1H), 3.77 (s, 2H), 3.08-2.95 (m, 2H), 2.76-2.60 (m, 2H), 2.07-1.95 (m, 2H), 1.66-1.52 (m, 2H), 1.49 (s, 9H) | 536.1 $(M + H)^+$ |
| 166 | 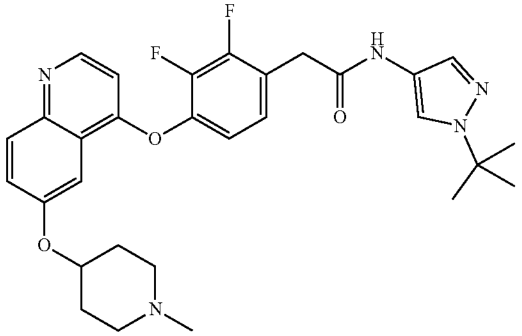 | N-(1-(tert-butyl)-1H-pyrazol-4-yl)-2-(2,3-difluoro-4-((6-((1-methyl-piperidin-4-yl)oxy) quinolin-4-yl)oxy)phenyl) acetamide | (400 MHz, DMSO-$d_6$) δ 10.28 (s, 1H), 8.60 (d, J = 5.1 Hz, 1H), 8.01 (d, J = 9.2 Hz, 1H), 7.94 (s, 1H), 7.65 (d, J = 2.8 Hz, 1H), 7.55 (dd, J = 9.2, 2.8 Hz, 1H), 7.46 (s, 1H), 7.36-7.26 (m, 2H), 6.70 (d, J = 5.1 Hz, 1H), 4.86-4.72 (m, 1H), 3.78 (s, 2H), 3.34 (s, 3H), 3.05-2.95 (m, 2H), 2.90-2.70 (m, 2H), 2.15-2.05 (m, 2H), 1.95-1.80 (m, 2H), 1.49 (s, 9H) | 550.2 $(M + H)^+$ |
| 169 | 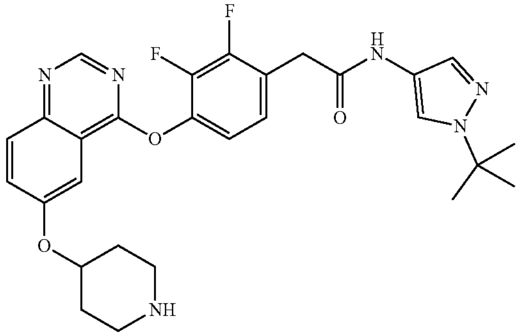 | N-(1-(tert-butyl)-1H-pyrazol-4-yl)-2-(2,3-difluoro-4-((6-(piperidin-4-yloxy) quinazolin-4-yl)oxy)phenyl) acetamide | (400 MHz, DMSO-$d_6$) δ 10.30 (s, 1H), 8.64 (s, 1H), 8.02-7.90 (m, 2H), 7.78-7.65 (m, 2H), 7.46 (s, 1H), 7.35-7.32 (m, 2H), 4.81-4.71 (m, 1H), 3.78 (s, 2H), 3.02-2.94 (m, 2H), 2.69-2.63 (m, 2H), 2.10-1.92 (m, 2H), 1.61-1.55 (m, 2H), 1.49 (s, 9H) | 537.2 $(M + H)^+$ |
| 170 | 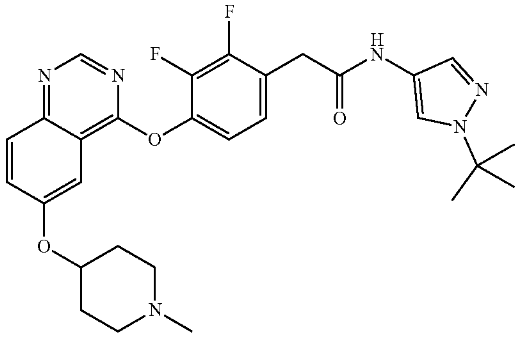 [SMILES: CN1CCC(Oc2ccc3ncnc(Oc4ccc(CC(=O)Nc5cnn(C(C)(C)C)c5)c(F)c4F)c3c2)CC1] | N-(1-(tert-butyl)-1H-pyrazol-4-yl)-2-(2,3-difluoro-4-((6-((1-methyl-piperidin-4-yl)oxy) quinazolin-4-yl)oxy)phenyl) acetamide | (400 MHz, DMSO-$d_6$) δ 10.31 (s, 1H), 8.64 (s, 1H), 7.98 (d, J = 9.1 Hz, 1H), 7.95 (s, 1H), 7.75-7.68 (m, 2H), 7.46 (s, 1H), 7.38-7.29 (m, 2H), 4.72 (dt, J = 8.3, 4.4 Hz, 1H), 3.78 (s, 2H), 2.70-2.58 (m, 2H), 2.31-2.21 (m, 2H), 2.20 (s, 3H), 2.07-1.98 (m, 2H), 1.74 (dtt, J = 12.3, 8.5, 3.5 Hz, 2H), 1.49 (s, 9H) | 551.1 $(M + H)^+$ |

-continued

| No. | Structure | Name | $^1$H NMR | Observed m/z |
|---|---|---|---|---|
| 171 | 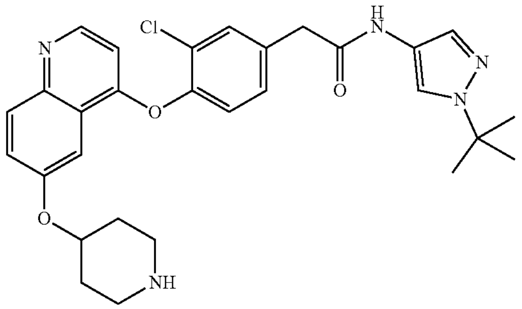 | N-(1-(tert-butyl)-1H-pyrazol-4-yl)-2-(3-chloro-4-((6-(piperidin-4-yloxy) quinolin-4-yl)oxy)phenyl) acetamide | (400 MHz, $CDCl_3$) δ 8.60 (d, J = 5.3 Hz, 1H), 8.16-8.07 (m, 2H), 7.68-7.61 (m, 2H), 7.53 (d, J = 2.1 Hz, 1H), 7.49-7.41 (m, 2H), 7.36 (dd, J = 8.4, 2.2 Hz, 1H), 7.22 (d, J = 8.3 Hz, 1H), 6.50 (d, J = 5.3 Hz, 1H), 4.91-4.87 (m, 1H), 3.72 (s, 2H), 3.47-3.37 (m, 2H), 3.33-3.23 (m, 2H), 2.29-2.21 (m, 4H), 1.56 (s, 9H) | 532.1 $(M-H)^-$ |
| 172 | 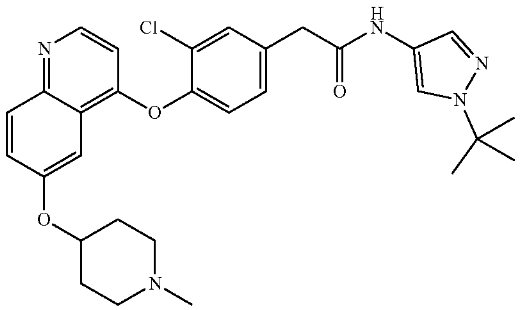 | N-(1-(tert-butyl)-1H-pyrazol-4-yl)-2-(3-chloro-4-((6-((1-methyl-piperidin-4-yl)oxy) quinolin-4-yl)oxy)phenyl) acetamide | (400 MHz, DMSO-$d_6$) δ 10.23 (s, 1H), 8.54 (d, J = 5.1 Hz, 1H), 8.01-7.91 (m, 2H), 7.65 (d, J = 1.3 Hz, 1H), 7.58 (d, J = 2.8 Hz, 1H), 7.50 (dd, J = 9.2, 2.8 Hz, 1H), 7.46 (s, 1H), 7.42-7.39 (m, 2H), 6.49 (d, J = 5.1 Hz, 1H), 4.59 (dt, J = 8.2, 4.1 Hz, 1H), 3.67 (s, 2H), 2.70-2.58 (m, 2H), 2.30-2.20 (m, 2H), 2.20 (s, 3H), 2.06-1.92 (m, 2H), 1.80-1.68 (m, 2H), 1.49 (s, 9H) | 546.2 $(M-H)^-$ |
| 185 | 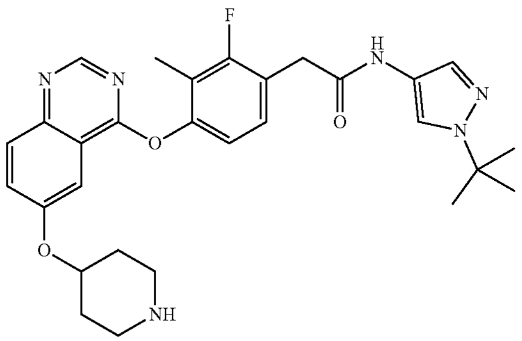 | N-(1-(tert-butyl)-1H-pyrazol-4-yl)-2-(2-fluoro-3-methyl-4-((6-(piperidin-4-yloxy) quinazolin-4-yl)oxy)phenyl) acetamide | (400 MHz, DMSO-d6) δ 12.06 (s, 1H), 10.59 (s, 1H), 8.58 (s, 1H), 7.95 (d, J = 9.9 Hz, 1H), 7.70-7.69 (m, 2H), 7.30 (t, J = 8.4 Hz, 1H), 7.11 (d, J = 8.3 Hz, 1H), 6.27 (s, 1H), 4.76 (d, J = 10.3 Hz, 1H), 3.71 (s, 2H), 3.10-2.90 (m, 2H), 2.77-2.58 (m, 2H), 2.10-1.92 (m, 5H), 1.66-1.48 (m, 2H), 1.25 (s, 9H) | 533.1 $(M+H)^+$ |
| 186 | 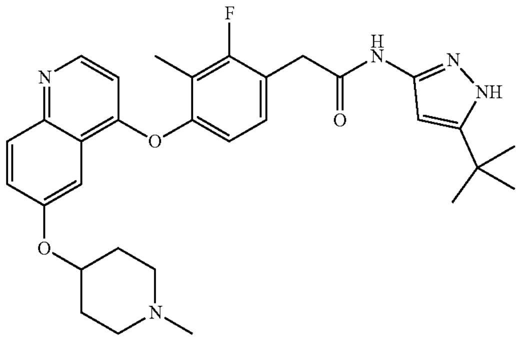 [SMILES: Cc1c(Oc2ccnc3ccc(OC4CCN(C)CC4)cc23)ccc(CC(=O)Nc2cc(C(C)(C)C)[nH]n2)c1F] | N-(5-(tert-butyl)-1H-pyrazol-3-yl)-2-(2-fluoro-3-methyl-4-((6-((1-methyl-piperidin-4-yl)oxy) quinazolin-4-yl)oxy)phenyl) acetamide | (400 MHz, DMSO-$d_6$) δ 12.06 (s, 1H), 10.59 (s, 1H), 8.58 (s, 1H), 8.00-7.89 (m, 1H), 7.71-7.69 (m, 2H), 7.30 (t, J = 8.3 Hz, 1H), 7.11 (d, J = 8.3 Hz, 1H), 6.29 (s, 1H), 4.70 (dd, J = 11.0, 3.8 Hz, 1H), 3.71 (s, 2H), 2.67-2.57 (m, 2H), 2.31-2.22 (m, 2H), 2.19 (s, 3H), 2.09-1.95 (m, 5H), 1.82-1.67 (m, 2H), 1.25 (s, 9H | 547.1 $(M+H)^+$ |

-continued

| No. | Structure | Name | $^1$H NMR | Observed m/z |
|---|---|---|---|---|
| 176 | 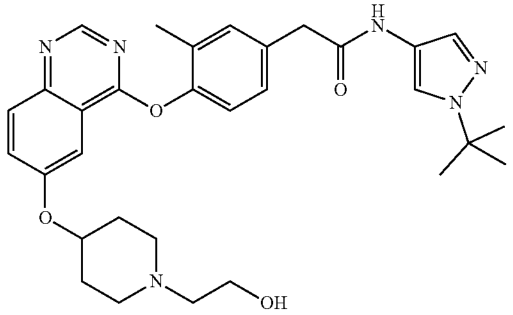 [SMILES: Cc1cc(CC(=O)Nc2cnn(C(C)(C)C)c2)ccc1Oc1ncnc2ccc(OC3CCN(CCO)CC3)cc12] | N-(1-(tert-butyl)-1H-pyrazol-4-yl)-2-(4-((6-((1-(2-hydroxyethyl)piperidin-4-yl)oxy)quinolin-4-yl)oxy)-3-methylphenyl)acetamide | (400 MHz, DMSO-$d_6$) δ 10.20 (s, 1H), 8.55 (s, 1H), 7.97-7.89 (m, 2H), 7.70-7.68 (m, 2H), 7.45 (s, 1H), 7.29 (d, J = 2.1 Hz, 1H), 7.26-7.16 (m, 2H), 4.70 (s, 1H), 4.42 (s, 1H), 3.58 (s, 2H), 3.51 (q, J = 6.0 Hz, 2H), 2.82-2.66 (m, 2H), 2.48-2.30 (m, 4H), 2.07 (s, 3H), 2.05-1.96 (m, 2H), 1.79-1.67 (m, 2H), 1.48 (s, 9H) | 559.1 $(M + H)^+$ |
| 177 | 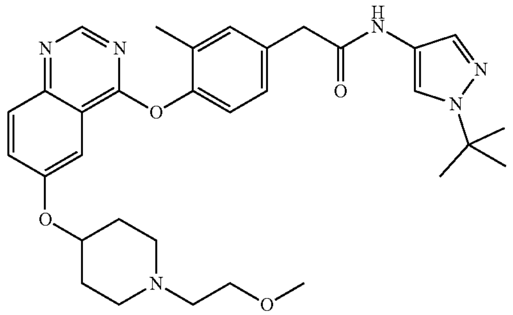 [SMILES: COCCN1CCC(Oc2ccc3ncnc(Oc4ccc(CC(=O)Nc5cnn(C(C)(C)C)c5)cc4C)c3c2)CC1] | N-(1-(tert-butyl)-1H-pyrazol-4-yl)-2-(4-((6-((1-(2-methoxyethyl)piperidin-4-yl)oxy)quinazolin-4-yl)oxy)-3-methylphenyl)acetamide | (400 MHz, DMSO-$d_6$) δ 10.20 (s, 1H), 8.55 (s, 1H), 7.97-7.90 (m, 2H), 7.70-7.68 (m, 2H), 7.45 (d, J = 0.7 Hz, 1H), 7.30 (d, J = 2.1 Hz, 1H), 7.28-7.22 (m, 1H), 7.19 (d, J = 8.2 Hz, 1H), 4.73-4.65 (m, 1H), 3.58 (s, 2H), 3.44 (t, J = 5.9 Hz, 2H), 3.24 (s, 3H), 2.80-2.69 (m, 2H), 2.52-2.49 (m, 2H), 2.40-2.30 (m, 2H), 2.08 (s, 3H), 2.05-1.98 (m, 2H), 1.77-1.66 (m, 2H), 1.49 (s, 9H) | 573.1 $(M + H)^+$ |
| 178 | 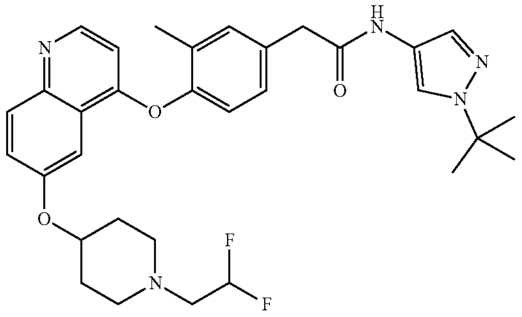 [SMILES: Cc1cc(CC(=O)Nc2cnn(C(C)(C)C)c2)ccc1Oc1ccnc2ccc(OC3CCN(CC(F)F)CC3)cc12] | N-(1-(tert-butyl)-1H-pyrazol-4-yl)-2-(4-((6-((1-(2,2-difluoroethyl)piperidin-4-yl)oxy)quinazolin-4-yl)oxy)-3-methylphenyl)acetamide | (400 MHz, DMSO-$d_6$) δ 10.22 (s, 1H), 8.55 (s, 1H), 8.02-7.90 (m, 2H), 7.77-7.67 (m, 2H), 7.46 (s, 1H), 7.33-7.16 (m, 3H), 6.14 (tt, J = 55.8, 4.3 Hz, 1H), 4.72 (dt, J = 8.0, 4.0 Hz, 1H), 3.58 (s, 2H), 2.87-2.70 (m, 4H), 2.54 (d, J = 3.0 Hz, 2H), 2.07 (s, 3H), 2.06-1.97 (m, 2H), 1.80-1.67 (m, 2H), 1.48 (s, 9H) | 579.1 $(M + H)^+$ |
| 187 | 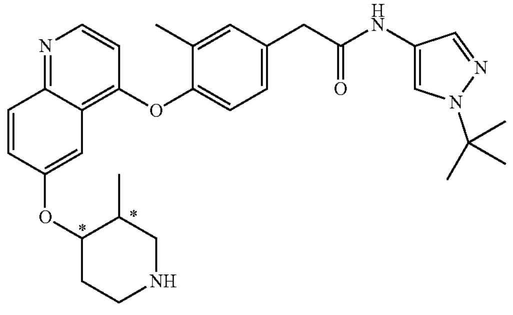 racemic mixture of trans isomers (retention time: 1.23 min, column: CHIRALPAK AS-3, 3.0 × 50 mm, 3 μm; mobile phase A: supercritical $CO_2$, mobile phase B: MeOH (0.1% DEA), 10-50% B in 4 min, flow rate: 2.0 mL/min, wavelength: 220 nm) | butyl)-1H-pyrazol-4-yl)-2-(3-methyl-4-((6-((3-methyl-piperidin-4-yl)oxy)quinolin-4-yl)oxy)phenyl)acetamide | (400 MHz, DMSO-$d_6$) δ 10.19 (s, 1H), 8.49 (d, J = 5.1 Hz, 1H), 7.96-7.94 (m, 2H), 7.62 (d, J = 2.8 Hz, 1H), 7.53-7.44 (m, 2H), 7.36 (d, J = 2.2 Hz, 1H), 7.28 (dd, J = 8.2, 2.2 Hz, 1H), 7.15 (d, J = 8.2 Hz, 1H), 6.39 (d, J = 5.2 Hz, 1H), 4.18 (td, J = 9.6, 4.0 Hz, 1H), 3.60 (s, 2H), 3.03-2.91 (m, 2H), 2.67-2.56 (m, 1H), 2.31 (dd, J = 12.7, 10.5 Hz, 1H), 2.12 (s, 3H), 2.08 (d, J = 3.7 Hz, 1H), 1.81-1.67 (m, 1H), 1.49 (s, 9H), 0.96 (d, J = 6.5 Hz, 3H) | 528.2 $(M + H)^+$ |

-continued

| No. | Structure | Name | $^1$H NMR | Observed m/z |
|---|---|---|---|---|
| 188 | 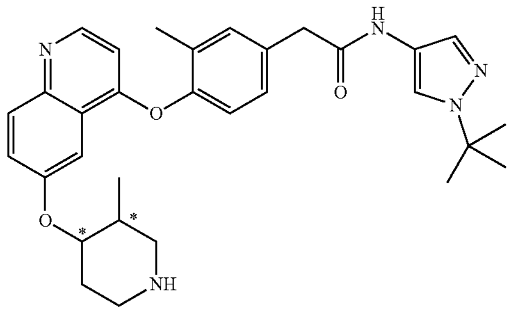 racemic mixture of cis isomers (retention time: 1.42 min, column: ChiralCel OJ-3, 4.6 x 50 mm, 3 μm; mobile phase A: supercritical $CO_2$, mobile phase B: MeOH (0.1% DEA), 10-50% B in 2 min, flow rate: 2.0 mL/min, wavelength: 220 nm) | N-(1-(tert-butyl)-1H-pyrazol-4-yl)-2-(3-methyl-4-((6-((-3-methyl-piperidin-4-yl)oxy) quinolin-4-yl)oxy)phenyl) acetamide | (400 MHz, DMSO-$d_6$) δ 10.21 (s, 1H), 8.49 (d, J = 5.1 Hz, 1H), 7.96-7.93 (m, 2H), 7.64 (d, J = 2.9 Hz, 1H), 7.51 (ddd, J = 9.2, 6.5, 2.8 Hz, 1H), 7.46 (d, J = 0.7 Hz, 1H), 7.36 (d, J = 2.2 Hz, 1H), 7.28 (dd, J = 8.3, 2.1 Hz, 1H), 7.16 (d, J = 8.2 Hz, 1H), 6.38 (d, J = 5.1 Hz, 1H), 4.73 (d, J = 3.6 Hz, 1H), 3.60 (s, 2H), 2.94-2.65 (m, 3H), 2.12 (s, 3H), 2.07-2.00 (m, 1H), 1.96-1.83 (m, 1H), 1.83-1.67 (m, 1H), 1.49 (s, 9H), 0.97 (d, J = 6.9 Hz, 3H) | 528.2 (M + H)$^+$ |
| 189 | 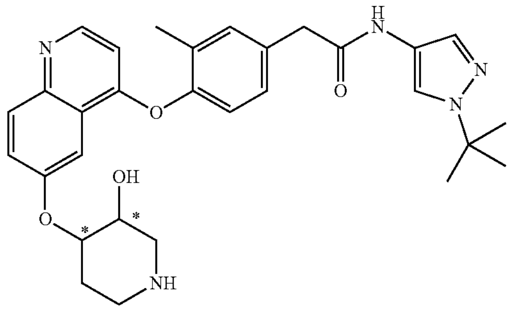 [SMILES: Cc1cc(CC(=O)Nc2cnn(C(C)(C)C)c2)ccc1Oc1ccnc2ccc(OC3CCNCC3O)cc12] racemic mixture of trans isomers | N-(1-(tert-butyl)-1H-pyrazol-4-yl)-2-(4-((6-((-3-hydroxy-piperidin-4-yl)oxy) quinolin-4-yl)oxy)-3-methylphenyl) acetamide | (300 MHz, DMSO-$d_6$) δ 10.20 (s, 1H), 8.48 (d, J = 5.1 Hz, 1H), 8.01-7.89 (m, 2H), 7.68 (d, J = 2.8 Hz, 1H), 7.50 (dd, J = 9.2, 2.8 Hz, 1H), 7.45 (d, J = 0.7 Hz, 1H), 7.35 (d, J = 2.2 Hz, 1H), 7.28 (dd, J = 8.2, 2.2 Hz, 1H), 7.15 (d, J = 8.2 Hz, 1H), 6.37 (d, J = 5.1 Hz, 1H), 5.08 (d, J = 5.0 Hz, 1H), 4.39-4.22 (m, 1H), 3.60 (s, 2H), 3.55-3.48 (m, 1H), 3.01 (dd, J = 12.3, 4.6 Hz, 1H), 2.85 (dt, J = 7.7, 3.9 Hz, 1H), 2.60-2.52 (m, 1H), 2.38 (dd, J = 12.4, 9.2 Hz, 1H), 2.11 (s, 3H), 2.08-1.97 (m, 1H), 1.48 (s, 9H) | 530.1 (M + H)$^+$ |
| 190 | 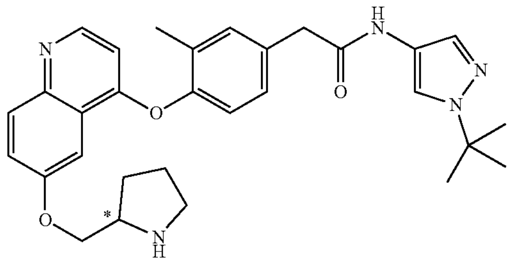 [SMILES: Cc1cc(CC(=O)Nc2cnn(C(C)(C)C)c2)ccc1Oc1ccnc2ccc(OCC3CCCN3)cc12] enantiomer 2 (retention time: 1.88 min, column: CHIRALPAK IB-N, 4.6 x 100 mm, 3 μm; mobile phase A: supercritical $CO_2$, mobile phase B: MeOH (0.1% DEA), 10-50% B in 2 min, flow rate: 4.0 mL/min, wavelength: 220 nm) | N-(1-(tert-butyl)-1H-pyrazol-4-yl)-2-(3-methyl-4-((6-(pyrrolidin-2-ylmethoxy) quinolin-4-yl)oxy)phenyl) acetamide | (400 MHz, DMSO-$d_6$) δ 10.20 (s, 1H), 8.49 (d, J = 5.1 Hz, 1H), 8.01-7.89 (m, 2H), 7.61 (d, J = 2.8 Hz, 1H), 7.52-7.42 (m, 2H), 7.36 (d, J = 2.2 Hz, 1H), 7.28 (dd, J = 8.2, 2.2 Hz, 1H), 7.16 (d, J = 8.2 Hz, 1H), 6.37 (d, J = 5.1 Hz, 1H), 3.99 (d, J = 6.2 Hz, 2H), 3.60 (s, 2H), 3.46 (t, J = 6.6 Hz, 1H), 2.85-2.80 (m, 2H), 2.12 (s, 3H), 1.88 (td, J = 13.2, 7.6 Hz, 1H), 1.73-1.66 (m, 2H), 1.57-1.51 (m, 1H), 1.49 (s, 9H) | 514.1 (M + H)$^+$ |

-continued

| No. | Structure | Name | $^1$H NMR | Observed m/z |
|---|---|---|---|---|
| 191 | 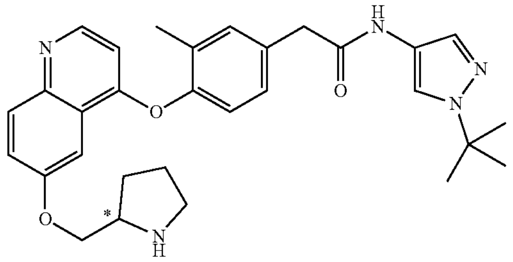 [SMILES: Cc1cc(CC(=O)Nc2cnn(C(C)(C)C)c2)ccc1Oc1ccnc2ccc(OCC3CCCN3)cc12] enantiomer 1 (retention time: 1.86 min, column: CHIRALPAK IB-N, 4.6 × 100 mm, 3 μm; mobile phase A: supercritical $CO_2$, mobile phase B: MeOH (0.1% DEA), 10-50% B in 2 min, flow rate: 4.0 mL/min, wavelength: 220 nm) | N-(1-(tert-butyl)-1H-pyrazol-4-yl)-2-(3-methyl-4-((6-(pyrrolidin-2-ylmethoxy) quinolin-4-yl)oxy)phenyl) acetamide | (400 MHz, DMSO-$d_6$) δ 10.20 (s, 1H), 8.49 (d, J = 5.1 Hz, 1H), 7.98-7.89 (m, 2H), 7.61 (d, J = 2.8 Hz, 1H), 7.52-7.42 (d, J = 9.6 Hz, 2H), 7.36 (d, J = 2.2 Hz, 1H), 7.28 (dd, J = 8.2, 2.2 Hz, 1H), 7.16 (d, J = 8.2 Hz, 1H), 6.37 (d, J = 5.1 Hz, 1H), 3.99 (d, J = 6.2 Hz, 2H), 3.60 (s, 2H), 3.46 (t, J = 6.5 Hz, 1H), 2.82 (dtd, J = 13.8, 9.7, 5.2 Hz, 2H), 2.12 (s, 3H), 1.93-1.82 (m, 1H), 1.79-1.61 (m, 2H), 1.49 (s, 9H) | 514.1 (M + H)$^+$ |
| 192 | 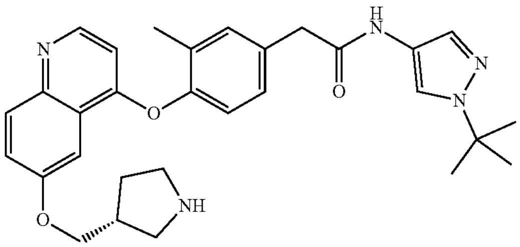 [SMILES: Cc1cc(CC(=O)Nc2cnn(C(C)(C)C)c2)ccc1Oc1ccnc2ccc(OC[C@@H]3CCNC3)cc12] | (R)-N-(1-(tert-butyl)-1H-pyrazol-4-yl)-2-(3-methyl-4-((6-(pyrrolidin-3-ylmethoxy) quinolin-4-yl)oxy)phenyl) acetamide | (300 MHz, DMSO-$d_6$) δ 10.28 (s, 1H), 8.50 (d, J = 5.1 Hz, 1H), 8.39 (s, 1H), 8.01-7.90 (m, 2H), 7.64 (d, J = 2.8 Hz, 1H), 7.49-7.47 (m, 2H), 7.36 (d, J = 2.1 Hz, 1H), 7.29 (dd, J = 8.1, 2.1 Hz, 1H), 7.15 (d, J = 8.2 Hz, 1H), 6.36 (d, J = 5.1 Hz, 1H), 4.21-4.12 (m, 2H), 3.61 (s, 2H), 3.30-3.02 (m, 3H), 2.80-2.70 (m, 1H), 2.11 (s, 3H), 2.10-1.99 (m, 1H), 1.77 (dd, J = 13.4, 6.9 Hz, 1H), 1.49 (s, 9H), 1.24 (s, 2H) | 514.1 (M + H)$^+$ |
| 193 | 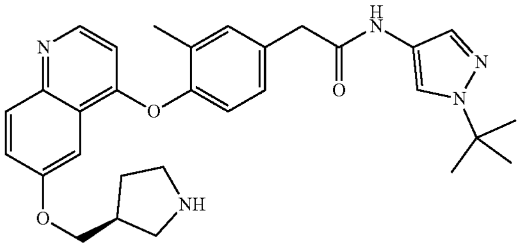 [SMILES: Cc1cc(CC(=O)Nc2cnn(C(C)(C)C)c2)ccc1Oc1ccnc2ccc(OC[C@H]3CCNC3)cc12] | (S)-N-(1-(tert-butyl)-1H-pyrazol-4-yl)-2-(3-methyl-4-((6-(pyrrolidin-3-ylmethoxy) quinolin-4-yl)oxy)phenyl) acetamide | (400 MHz, DMSO-$d_6$) δ 10.23 (s, 1H), 8.49 (d, J = 5.1 Hz, 1H), 7.95-7.93 (m, 2H), 7.61 (d, J = 2.9 Hz, 1H), 7.51-7.43 (m, 2H), 7.36 (d, J = 2.2 Hz, 1H), 7.29 (dd, J = 8.2, 2.2 Hz, 1H), 7.16 (d, J = 8.2 Hz, 1H), 6.36 (d, J = 5.1 Hz, 1H), 4.18-4.01 (m, 2H), 3.60 (s, 2H), 2.95-2.80 (m, 2H), 2.77-2.64 (m, 2H), 2.11 (s, 3H), 2.11-2.00 (bs, 1H), 1.94-1.72 (m, 2H), 1.49 (s, 9H) | 514.2 (M + H)$^+$ |
| 194 | 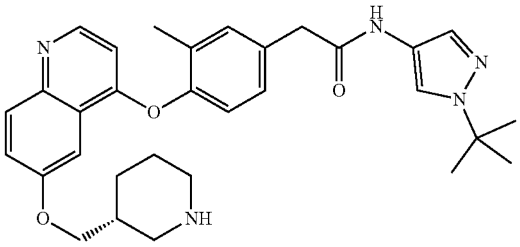 [SMILES: Cc1cc(CC(=O)Nc2cnn(C(C)(C)C)c2)ccc1Oc1ccnc2ccc(OC[C@@H]3CCCNC3)cc12] | (R)-N-(1-(tert-butyl)-1H-pyrazol-4-yl)-2-(3-methyl-4-((6-(piperidin-3-ylmethoxy) quinolin-4-yl)oxy)phenyl) acetamide | (400 MHz, DMSO-d6) § 10.21 (s, 1H), 8.49 (d, J = 5.1 Hz, 1H), 7.96-7.94 (s, 2H), 7.60 (d, J = 2.8 Hz, 1H), 7.52-7.40 (m, 2H), 7.36 (s, 1H), 7.29 (d, J = 8.2 Hz, 1H), 7.16 (d, J = 8.2 Hz, 1H), 6.36 (d, J = 5.1 Hz, 1H), 3.99 (d, J = 6.6 Hz, 2H), 3.60 (s, 2H), 3.13-3.04 (m, 1H), 2.90-2.80 (m, 1H), 2.49-2.34 (m, 2H), 2.11 (s, 3H), 2.01-1.80 (m, 2H), 1.65-1.55 (m, 1H), 1.49 (s, 9H), 1.43-1.35 (m, 1H), 1.32-1.20 (m, 1H) | 528.2 (M + H)$^+$ |

-continued

| No. | Structure | Name | $^1$H NMR | Observed m/z |
|---|---|---|---|---|
| 195 | 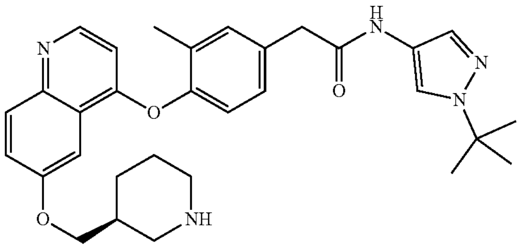 [SMILES: Cc1cc(CC(=O)Nc2cnn(C(C)(C)C)c2)ccc1Oc1ccnc2ccc(OC[C@H]3CCCNC3)cc12] | (S)-N-(1-(tert-butyl)-1H-pyrazol-4-yl)-2-(3-methyl-4-((6-(piperidin-3-ylmethoxy)quinolin-4-yl)oxy)phenyl)acetamide | (400 MHz, DMSO-$d_6$) δ 10.25 (s, 1H), 8.50 (d, J = 5.1 Hz, 1H), 7.96-7.94 (m, 2H), 7.62-7.60 (m, 1H), 7.48 (d, J = 7.2 Hz, 2H), 7.37 (s, 1H), 7.30 (d, J = 8.3 Hz, 1H), 7.16 (d, J = 8.1 Hz, 1H), 6.38 (d, J = 5.1 Hz, 1H), 3.99 (d, J = 6.5 Hz, 2H), 3.62 (s, 2H), 3.09 (dd, J = 12.0, 3.5 Hz, 1H), 2.90-2.79 (m, 1H), 2.42 (dt, J = 30.8, 11.1 Hz, 2H), 2.10 (s, 3H), 2.09-2.01 (m, 1H), 1.95 (ddd, J = 10.2, 6.6, 3.6 Hz, 1H), 1.89-1.81 (m, 1H), 1.65-1.56 (m, 1H), 1.50 (s, 9H), 1.45-1.36 (m, 1H), 1.32-1.20 (m, 1H) | 528.2 (M + H)$^+$ |
| 211 | 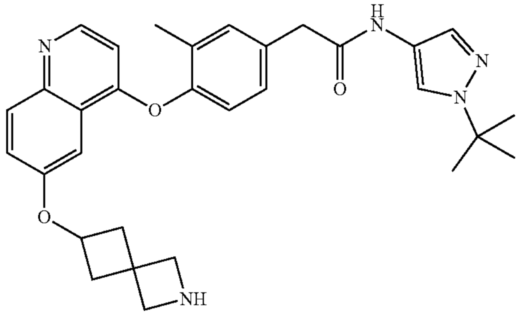 [SMILES: Cc1cc(CC(=O)Nc2cnn(C(C)(C)C)c2)ccc1Oc1ccnc2ccc(OC3CC4(CNC4)C3)cc12] | 2-(4-((6-((2-azaspiro[3.3]heptan-6-yl)oxy)quinolin-4-yl)oxy)-3-methyl-phenyl)-N-(1-(tert-butyl)-1H-pyrazol-4-yl)acetamide | (400 MHz, DMSO-$d_6$) δ 10.22 (s, 1H), 8.49 (d, J = 5.0 Hz, 1H), 7.94-7.92 (m, 2H), 7.53-7.32 (m, 4H), 7.28 (d, J = 8.4 Hz, 1H), 7.16 (d, J = 8.3 Hz, 1H), 6.40 (d, J = 5.0 Hz, 1H), 4.90-4.70 (m, 1H), 3.67-3.56 (m, 4H), 3.48 (s, 2H), 2.81-2.69 (s, 2H), 2.33-2.17 (s, 2H), 2.11 (s, 3H), 1.48 (s, 9H) | 526.1 (M + H)$^+$ |
| 220 | 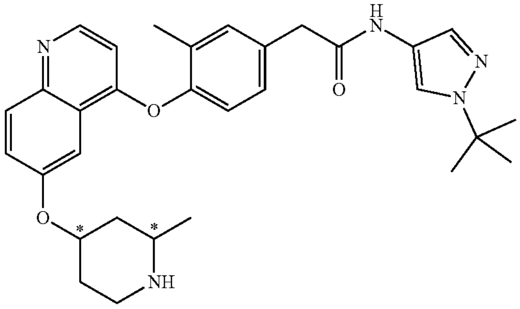 [SMILES: Cc1cc(CC(=O)Nc2cnn(C(C)(C)C)c2)ccc1Oc1ccnc2ccc(OC3CCNC(C)C3)cc12] racemic mixture of cis isomers | N-(1-(tert-butyl)-1H-pyrazol-4-yl)-2-(3-methyl-4-((6-((-2-methyl-piperidin-4-yl)oxy)quinolin-4-yl)oxy)phenyl)acetamide | (300 MHz, DMSO-$d_6$) δ 10.18 (s, 1H), 8.49 (d, J = 5.1 Hz, 1H), 7.97-7.89 (m, 2H), 7.61 (d, J = 2.8 Hz, 1H), 7.48-7.44 (m, 2H), 7.35 (d, J = 2.1 Hz, 1H), 7.27 (d, J = 7.7 Hz, 1H), 7.15 (d, J = 8.2 Hz, 1H), 6.40 (d, J = 5.1 Hz, 1H), 4.62-4.45 (m, 1H), 3.59 (s, 2H), 2.99 (d, J = 12.3 Hz, 1H), 2.69-2.56 (m, 2H), 2.12 (s, 3H), 2.10-1.96 (m, 2H), 1.48 (s, 9H), 1.41-1.32 (m, 1H), 1.10 (d, J = 11.3 Hz, 1H), 1.02 (d, J = 6.2 Hz, 3H) | 528.2 (M + H)$^+$ |
| 221 | 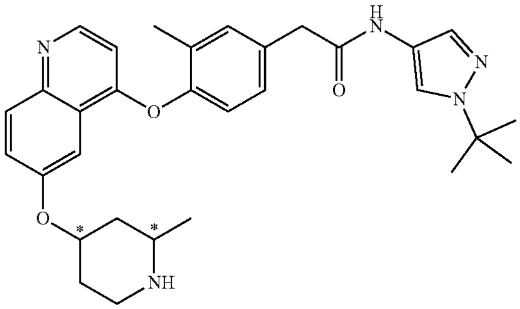 [SMILES: Cc1cc(CC(=O)Nc2cnn(C(C)(C)C)c2)ccc1Oc1ccnc2ccc(OC3CCNC(C)C3)cc12] racemic mixture of trans isomers | N-(1-(tert-butyl)-1H-pyrazol-4-yl)-2-(3-methyl-4-((6-((-2-methyl-piperidin-4-yl)oxy)quinolin-4-yl)oxy)phenyl)acetamide | (400 MHz, DMSO-$d_6$) δ 10.29 (s, 1H), 8.79 (d, J = 6.0 Hz, 1H), 8.18 (d, J = 9.2 Hz, 1H), 7.95-7.92 (m, 2H), 7.81 (dd, J = 9.3, 2.7 Hz, 1H), 7.47 (s, 1H), 7.42 (s, 1H), 7.34 (t, J = 9.1 Hz, 1H), 7.26 (d, J = 8.2 Hz, 1H), 6.68 (d, J = 6.0 Hz, 1H), 5.19 (s, 1H), 3.64 (s, 2H), 3.52 (s, 1H), 3.29-3.17 (m, 2H), 2.14-2.10 (m, 5H), 2.01 (t, J = 8.2 Hz, 1H), 1.85 (t, J = 13.5 Hz, 1H), 1.49 (s, 9H), 1.25 (d, J = 6.5 Hz, 3H) | 528.2 (M + H)$^+$ |

-continued

| No. | Structure | Name | $^1H$ NMR | Observed m/z |
|---|---|---|---|---|
| 222 | 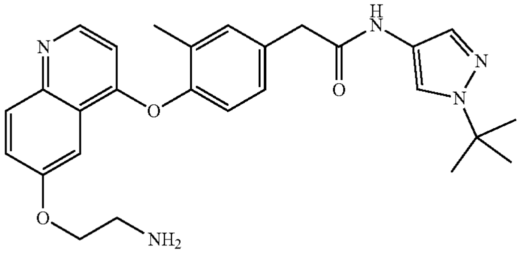 [SMILES: Cc1cc(CC(=O)Nc2cnn(C(C)(C)C)c2)ccc1Oc1ccnc2ccc(OCCN)cc12] | 2-(4-((6-(2-aminoethoxy) quinolin-4-yl)oxy)-3-methyl-phenyl)-N-(1-(tert-butyl)-1H-pyrazol-4-yl)acetamide | (400 MHz, DMSO-d6) § 10.20 (s, 1H), 8.49 (d, J = 5.1 Hz, 1H), 7.95-7.93 (m, 2H), 7.60 (d, J = 2.8 Hz, 1H), 7.51-7.46 (m, 1H), 7.45 (s, 1H), 7.35 (s, 1H), 7.28 (dd, J = 8.2, 2.3 Hz, 1H), 7.17 (d, J = 8.2 Hz, 1H), 6.37 (d, J = 5.1 Hz, 1H), 4.09 (t, J = 5.7 Hz, 2H), 3.60 (s, 2H), 2.95 (t, J = 5.7 Hz, 2H), 2.11 (s, 3H), 1.48 (s, 9H) | 472.2 $(M - H)^-$ |
| 223 | 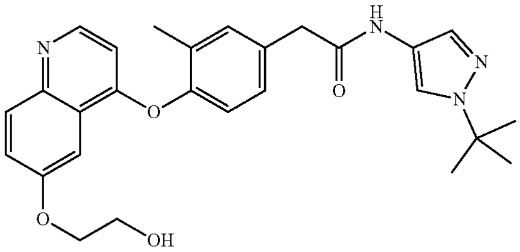 [SMILES: Cc1cc(CC(=O)Nc2cnn(C(C)(C)C)c2)ccc1Oc1ccnc2ccc(OCCO)cc12] | N-(1-(tert-butyl)-1H-pyrazol-4-yl)-2-(4-((6-(2-hydroxy-ethoxy) quinolin-4-yl)oxy)-3-methylphenyl) acetamide | (400 MHz, DMSO-$d_6$) δ 10.22 (s, 1H), 8.50 (d, J = 5.1 Hz, 1H), 7.97-7.94 (m, 2H), 7.62 (d, J = 2.9 Hz, 1H), 7.52-7.41 (m, 2H), 7.36 (d, J = 2.1 Hz, 1H), 7.29 (dd, J = 8.2, 2.2 Hz, 1H), 7.17 (d, J = 8.2 Hz, 1H), 6.38 (d, J = 5.1 Hz, 1H), 5.02-4.92 (m, 1H), 4.18 (t, J = 4.9 Hz, 2H), 3.81 (t, J = 4.7 Hz, 2H), 3.60 (s, 2H), 2.12 (s, 3H), 1.49 (s, 9H) | 475.0 $(M + H)^+$ |
| 224 | 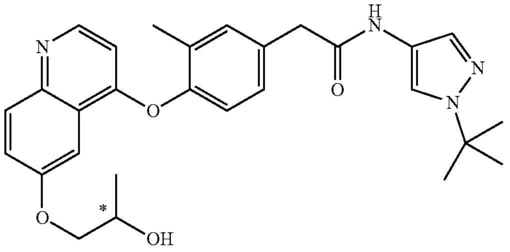 [SMILES: Cc1cc(CC(=O)Nc2cnn(C(C)(C)C)c2)ccc1Oc1ccnc2ccc(OCC(C)O)cc12] enantiomer 1 (retention time: 2.73 min, column: CHIRALPAK IC-3, 4.6 × 50 mm, 3 μm; mobile phase A: hexane (0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(4-((6-(2-hydroxy-propoxy) quinolin-4-yl)oxy)-3-methylphenyl) acetamide | (400 MHz, DMSO-d6) § 10.20 (s, 1H), 8.49 (d, J = 5.1 Hz, 1H), 7.97-7.93 (m, 2H), 7.61 (d, J = 2.8 Hz, 1H), 7.52-7.43 (m, 2H), 7.36 (d, J = 2.2 Hz, 1H), 7.28 (dd, J = 8.3, 2.2 Hz, 1H), 7.17 (d, J = 8.2 Hz, 1H), 6.37 (d, J = 5.1 Hz, 1H), 4.95 (d, J = 4.5 Hz, 1H), 4.05 (dt, J = 9.5, 5.0 Hz, 1H), 3.99 (d, J = 4.6 Hz, 2H), 3.60 (s, 2H), 2.11 (s, 3H), 1.49 (s, 9H), 1.20 (d, J = 6.1 Hz, 3H) | 489.2 $(M + H)^+$ |
| 225 | 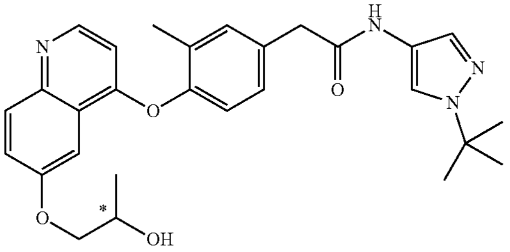 [SMILES: Cc1cc(CC(=O)Nc2cnn(C(C)(C)C)c2)ccc1Oc1ccnc2ccc(OCC(C)O)cc12] enantiomer 2 (retention time: 3.78 min, column: CHIRALPAK IC-3, 4.6 × 50 mm, 3 μm; mobile phase A: hexane (0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(4-((6-(2-hydroxy-propoxy) quinolin-4-yl)oxy)-3-methylphenyl) acetamide | (400 MHz, DMSO-$d_6$) δ 10.20 (s, 1H), 8.50 (d, J = 5.1 Hz, 1H), 7.97-7.93 (m, 2H), 7.61 (d, J = 2.9 Hz, 1H), 7.52-7.44 (m, 2H), 7.36 (d, J = 2.2 Hz, 1H), 7.29 (dd, J = 8.3, 2.2 Hz, 1H), 7.17 (d, J = 8.2 Hz, 1H), 6.37 (d, J = 5.1 Hz, 1H), 4.96 (d, J = 4.5 Hz, 1H), 4.05 (dt, J = 10.4, 5.2 Hz, 1H), 4.00 (dd, J = 5.3, 1.5 Hz, 2H), 3.61 (s, 2H), 2.12 (s, 3H), 1.49 (s, 9H), 1.21 (d, J = 6.1 Hz, 3H) | 489.2 $(M + H)^+$ |

-continued

| No. | Structure | Name | $^1$H NMR | Observed m/z |
|---|---|---|---|---|
| 226 | 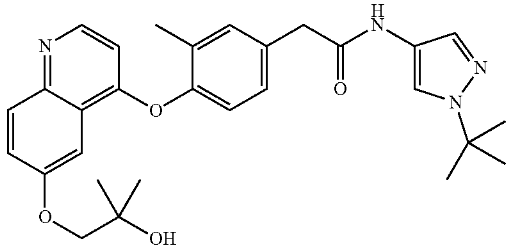 [SMILES: Cc1cc(CC(=O)Nc2cnn(C(C)(C)C)c2)ccc1Oc1ccnc2ccc(OCC(C)(C)O)cc12] | N-(1-(tert-butyl)-1H-pyrazol-4-yl)-2-(4-((6-(2-hydroxy-2-methyl-propoxy) quinolin-4-yl)oxy)-3-methylphenyl) acetamide | (400 MHz, DMSO-$d_6$) δ 10.22 (s, 1H), 8.49 (d, J = 5.1 Hz, 1H), 7.96-7.94 (dd, J = 5.0, 4.2 Hz, 2H), 7.60 (d, J = 2.8 Hz, 1H), 7.50 (dd, J = 9.2, 2.8 Hz, 1H), 7.46 (d, J = 0.8 Hz, 1H), 7.36 (d, J = 2.1 Hz, 1H), 7.29 (dd, J = 8.2, 2.2 Hz, 1H), 7.17 (d, J = 8.2 Hz, 1H), 6.36 (d, J = 5.1 Hz, 1H), 4.73 (s, 1H), 3.91 (s, 2H), 3.60 (s, 2H), 2.12 (s, 3H), 1.49 (s, 9H), 1.26 (s, 6H) | 503.1 $(M + H)^+$ |
| 227 | 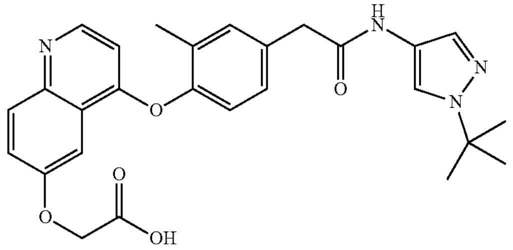 [SMILES: Cc1cc(CC(=O)Nc2cnn(C(C)(C)C)c2)ccc1Oc1ccnc2ccc(OCC(=O)O)cc12] | 2-((4-(4-(2-((1-(tert-butyl)-1H-pyrazol-4-yl)amino)-2-oxoethyl)-2-methyl-phenoxy) quinolin-6-yl)oxy)acetic acid | (400 MHz, DMSO-$d_6$) δ 10.21 (s, 1H), 8.49 (d, J = 5.1 Hz, 1H), 8.00-7.89 (m, 2H), 7.56-7.53 (m, 1H), 7.52-7.44 (m, 2H), 7.34 (d, J = 2.2 Hz, 1H), 7.27 (dd, J = 8.2, 2.2 Hz, 1H), 7.15 (d, J = 8.2 Hz, 1H), 6.36 (d, J = 5.1 Hz, 1H), 4.79 (s, 2H), 3.59 (s, 2H), 2.09 (s, 3H), 1.48 (s, 9H) | 489.0 $(M + H)^+$ |
| 228 | 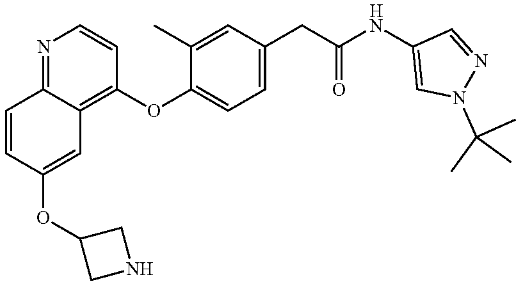 | 2-(4-((6-(azetidin-3-yloxy)quinol in-4-yl)oxy)-3-methyl-pheny 1)-N-(1-(tert-butyl)-1H-pyrazol-4-yl)acetamide | (400 MHz, DMSO-$d_6$) δ 10.19 (s, 1H), 8.50 (d, J = 4.0 Hz, 1H), 7.96 (d, J = 9.1 Hz, 1H), 7.94 (s, 1H), 7.45-7.43 (m, 2H), 7.37-7.32 (m, 2H), 7.27 (d, J = 8.7 Hz, 1H), 7.16 (d, J = 8.2 Hz, 1H), 6.41 (d, J = 5.1 Hz, 1H), 5.23-5.14 (m, 1H), 3.83 (t, J = 7.6 Hz, 2H), 3.62-3.53 (m, 4H), 2.11 (s, 3H), 1.48 (s, 9H) | 484.1 $(M - H)^-$ |
| 229 | 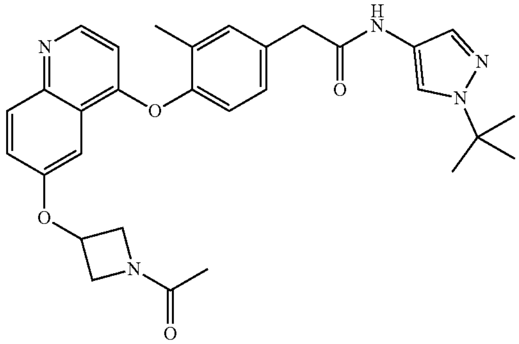 [SMILES: CC(=O)N1CC(Oc2ccc3nccc(Oc4ccc(CC(=O)Nc5cnn(C(C)(C)C)c5)cc4C)c3c2)C1] | 2-(4-((6-((1-acetylazetidin-3-yl)oxy) quinolin-4-yl)oxy)-3-methyl-phenyl)-N-(1-(tert-butyl)-1H-pyrazol-4-yl)acetamide | (400 MHz, DMSO-$d_6$) δ 10.20 (s, 1H), 8.53 (d, J = 5.1 Hz, 1H), 8.00 (d, J = 9.2 Hz, 1H), 7.94 (s, 1H), 7.48 (dd, J = 9.2, 2.9 Hz, 1H), 7.45 (s, 1H), 7.42 (d, J = 2.8 Hz, 1H), 7.36 (d, J = 2.2 Hz, 1H), 7.28 (dd, J = 8.3, 2.2 Hz, 1H), 7.17 (d, J = 8.2 Hz, 1H), 6.42 (d, J = 5.1 Hz, 1H), 5.26 (tt, J = 6.5, 3.7 Hz, 1H), 4.63 (ddd, J = 9.6, 6.3, 1.3 Hz, 1H), 4.34 (dd, J = 10.6, 6.4 Hz, 1H), 4.22-4.14 (m, 1H), 3.87 (dd, J = 10.3, 3.6 Hz, 1H), 3.60 (s, 2H), 2.12 (s, 3H), 1.80 (s, 3H), 1.48 (s, 9H) | 526.2 $(M - H)^-$ |
| 237 | 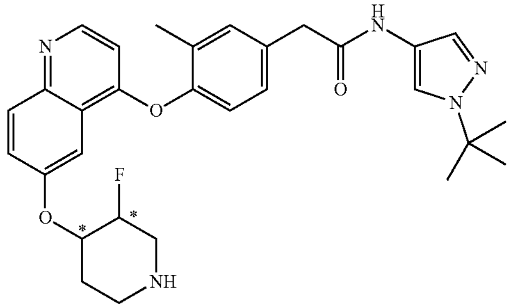 [SMILES: Cc1cc(CC(=O)Nc2cnn(C(C)(C)C)c2)ccc1Oc1ccnc2ccc(OC3CCNCC3F)cc12] racemic mixture of trans isomers | N-(1-(tert-butyl)-1H-pyrazol-4-yl)-2-(4-((6-((-3-fluoro-piperidin-4-yl)oxy) quinolin-4-yl)oxy)-3-methylphenyl) acetamide | (300 MHz, DMSO-$d_6$) δ 10.20 (s, 1H), 8.51 (d, J = 5.1 Hz, 1H), 7.97-7.94 (m, 2H), 7.73 (d, J = 2.8 Hz, 1H), 7.53 (dd, J = 9.2, 2.8 Hz, 1H), 7.46 (s, 1H), 7.41-7.34 (m, 1H), 7.29 (d, J = 8.2 Hz, 1H), 7.16 (d, J = 8.2 Hz, 1H), 6.39 (d, J = 5.1 Hz, 1H), 4.70 (ddd, J = 13.6, 9.5, 5.2 Hz, 2H), 4.49 (q, J = 8.2 Hz, 1H), 3.60 (s, 2H), 2.87 (d, J = 12.3 Hz, 2H), 2.69-2.56 (m, 2H), 2.25-2.15 (m, 1H), 2.12 (s, 3H), 1.49 (s, 9H) | 532.1 $(M + H)^+$ |

-continued

| No. | Structure | Name | $^1$H NMR | Observed m/z |
|---|---|---|---|---|
| 238 | 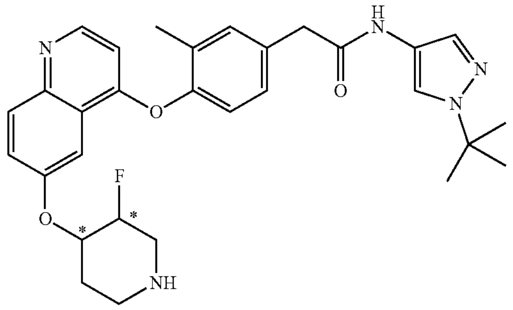 racemic mixture of cis isomers | N-(1-(tert-butyl)-1H-pyrazol-4-yl)-2-(4-((6-((-3-fluoro-piperidin-4-yl)oxy) quinolin-4-yl)oxy)-3-methylphenyl) acetamide | (300 MHz, DMSO-$d_6$) δ 10.20 (s, 1H), 8.51 (d, J = 5.1 Hz, 1H), 8.02-7.90 (m, 2H), 7.71 (d, J = 2.8 Hz, 1H), 7.53 (dd, J = 9.2, 2.8 Hz, 1H), 7.46 (s, 1H), 7.36 (d, J = 2.1 Hz, 1H), 7.28 (dd, J = 8.2, 2.2 Hz, 1H), 7.16 (d, J = 8.2 Hz, 1H), 6.39 (d, J = 5.1 Hz, 1H), 4.98-4.72 (m, 2H), 3.60 (s, 2H), 3.18-3.12 (m, 1H), 2.95-2.80 (m, 2H), 2.70-2.59 (m, 1H), 2.12 (s, 3H), 1.85 (s, 2H), 1.49 (s, 9H) | 532.1 $(M + H)^+$ |
| 307 | 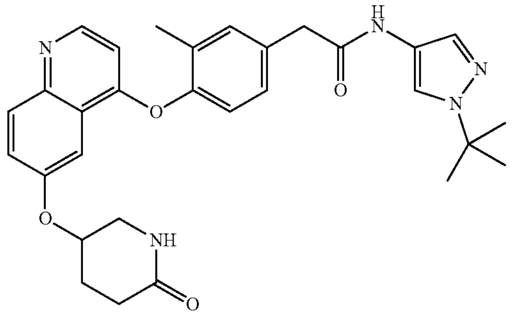 [SMILES: Cc1cc(CC(=O)Nc2cnn(C(C)(C)C)c2)ccc1Oc1ccnc2ccc(OC3CCC(=O)NC3)cc12] | N-(1-(tert-butyl)-1H-pyrazol-4-yl)-2-(3-methyl-4-((6-((6-oxopiperidin-3-yl)oxy) quinolin-4-yl)oxy)phenyl) acetamide | (400 MHz, DMSO-$d_6$) δ 10.22 (s, 1H), 8.51 (d, J = 5.1 Hz, 1H), 8.03-7.89 (m, 2H), 7.71 (d, J = 2.8 Hz, 1H), 7.58-7.43 (m, 3H), 7.36 (d, J = 2.2 Hz, 1H), 7.29 (dd, J = 8.3, 2.2 Hz, 1H), 7.16 (d, J = 8.2 Hz, 1H), 6.39 (d, J = 5.1 Hz, 1H), 5.05 (quint, J = 3.7 Hz, 1H), 3.61 (s, 2H), 3.55-3.50 (m, 1H), 3.37-3.35 (m, 1H), 2.40-2.18 (m, 2H), 2.11-2.07 (m, 5H), 1.48 (s, 9H) | 528.1 $(M + H)^+$ |
| 308 | 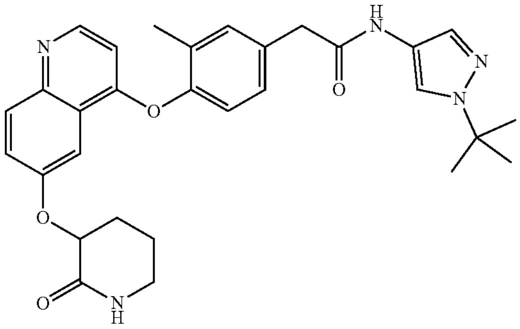 [SMILES: Cc1cc(CC(=O)Nc2cnn(C(C)(C)C)c2)ccc1Oc1ccnc2ccc(OC3CCCNC3=O)cc12] | N-(1-(tert-butyl)-1H-pyrazol-4-yl)-2-(3-methyl-4-((6-((2-oxopiperidin-3-yl)oxy) quinolin-4-yl)oxy)phenyl) acetamide | (400 MHz, DMSO-$d_6$) δ 10.19 (s, 1H), 8.49 (d, J = 5.1 Hz, 1H), 7.95-7.92 (m, 2H), 7.78-7.76 (m, 2H), 7.51 (dd, J = 9.2, 2.8 Hz, 1H), 7.45 (s, 1H), 7.35 (d, J = 2.2 Hz, 1H), 7.27 (dd, J = 8.2, 2.2 Hz, 1H), 7.15 (d, J = 8.2 Hz, 1H), 6.36 (d, J = 5.1 Hz, 1H), 5.05 (dd, J = 8.4, 5.6 Hz, 1H), 3.59 (s, 2H), 3.25-3.16 (m, 2H), 2.25-2.15 (m, 1H), 2.11 (s, 3H), 2.02-1.80 (m, 3H), 1.48 (s, 9H) | 528.1 $(M + H)^+$ |
| 409 | 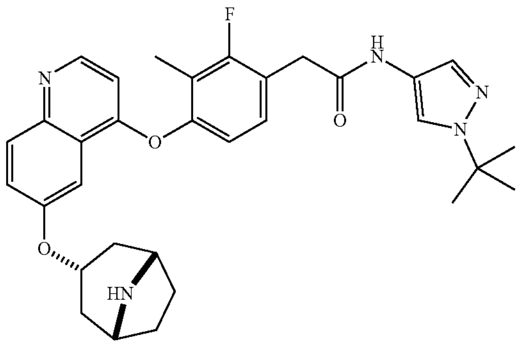 | 2-(4-((6-(((1R,3r,5S)-8-azabicyclo[3.2.1]octan-3-yl)oxy) quinolin-4-yl)oxy)-2-fluoro-3-methyl-phenyl)-N-(1-(tert-butyl)-1H-pyrazol-4-yl)acetamide | | 558.0 $(M + H)^+$ |

-continued

| No. | Structure | Name | $^1$H NMR | Observed m/z |
|---|---|---|---|---|
| 410 | 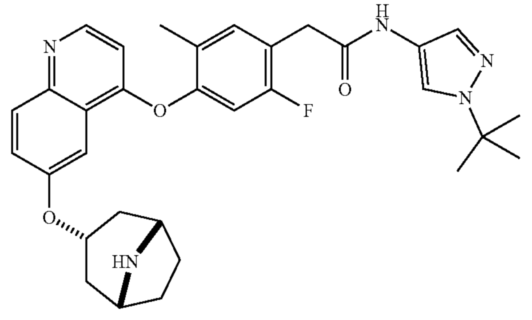 | 2-(4-((6-(((1R,3r,5S)-8-azabicyclo[3.2.1]octan-3-yl)oxy) quinolin-4-yl)oxy)-2-fluoro-5-methyl-phenyl)-N-(1-(tert-butyl)-1H-pyrazol-4-yl)acetamide | | 558.2 $(M + H)^+$ |

Example 26—Synthesis of N-(1-(tert-butyl)-1H-pyrazol-4-yl)-2-(2-fluoro-4-((6-morpholinoquinazolin-4-yl)oxy)phenyl)acetamide (Compound 14); Prepared According to General Scheme 17

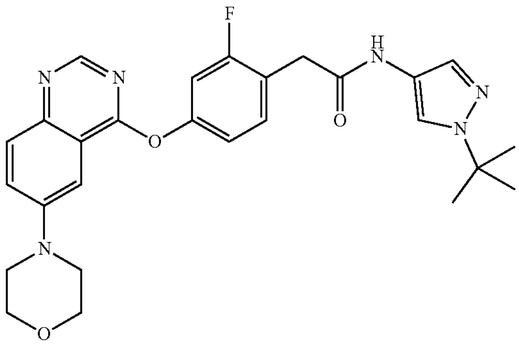 [SMILES: CC(C)(C)n1cc(NC(=O)Cc2ccc(Oc3ncnc4ccc(N5CCOCC5)cc34)cc2F)cn1]

Part I—Synthesis of N-(1-(tert-butyl)-1H-pyrazol-4-yl)-2-(2-fluoro-4-((6-iodoquinazolin-4-yl)oxy)phenyl)acetamide

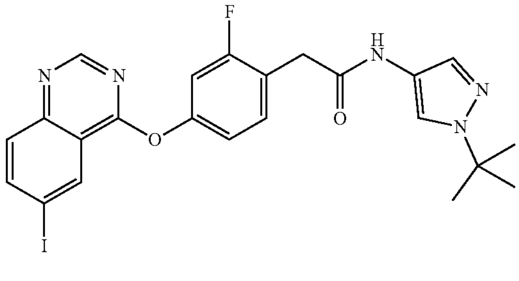 [SMILES: CC(C)(C)n1cc(NC(=O)Cc2ccc(Oc3ncnc4ccc(I)cc34)cc2F)cn1]

A solution of 4-chloro-6-iodoquinazoline (commercially available, 10.0 g, 34.4 mmol, 1.00 equiv.), N-(1-(tert-butyl)-1H-pyrazol-4-yl)-2-(2-fluoro-4-hydroxyphenyl)acetamide (10.0 g, 34.4 mmol, 1.00 equiv., can be synthesized as described in Part II of Example 9), and $K_3PO_4$ (21.92 g, 103 mmol, 3.00 equiv.) in 1,4-dioxane (200 mL) was heated to 60° C. for 3 h. Subsequently, water (100 mL) was added the product was extracted with EtOAc (3x30 mL). The combined organic phases were washed with brine (50 mL), dried over $Na_2SO_4$, and the solvent was removed under reduced pressure. The title compound was obtained as a yellow solid which was used in the next reaction without further purification.

Part II—Synthesis of N-(1-(tert-butyl)-1H-pyrazol-4-yl)-2-(2-fluoro-4-((6-morpholinoquinazolin-4-yl)oxy)phenyl)acetamide (Compound 14)

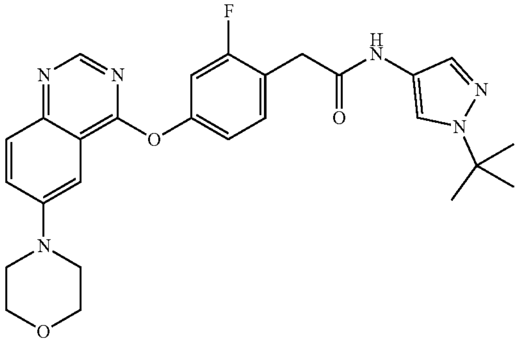 [SMILES: CC(C)(C)n1cc(NC(=O)Cc2ccc(Oc3ncnc4ccc(N5CCOCC5)cc34)cc2F)cn1]

RuPhos Pd G3 (30.7 mg, 0.037 mmol, 0.10 equiv.) was added to a solution of N-(1-(tert-butyl)-1H-pyrazol-4-yl)-2-(2-fluoro-4-((6-iodoquinazolin-4-yl)oxy)phenyl)acetamide (200 mg, 0.367 mmol, 1.00 equiv.), $Cs_2CO_3$ (239.7 mg, 0.734 mmol, 2.00 equiv.), morpholine (63.9 mg, 0.734 mmol, 2.00 equiv.) and RuPhos (17.1 mg, 0.037 mmol, 0.10 equiv.) in 1,4-dioxane (4 mL) under an inert atmosphere of nitrogen and the mixture was heated to 90° C. for 16 h. Subsequently, water (100 mL) was added, and the product was extracted with EtOAc (3x30 mL). The combined organic phases were washed with brine (50 mL) dried over $Na_2SO_4$, and the solvent was removed under reduced pressure. The crude product was purified by reversed-phase flash chromatography (column: C18 silica gel; mobile phase A: water (1% formic acid), mobile phase B: ACN, gradient: 10-40% B in 30 min; wavelength: 214 nm). The title compound was obtained as an off-white solid (75.1 mg, 41%). LCMS (ESI) calculated for $C_{27}H_{30}FN_6O_3$ $(M+H)^+$: 505.2, found: 505.3. $^1$H NMR (300 MHz, DMSO-$d_6$) δ 8.47 (s, 1H), 8.01 (s, 1H), 7.86 (d, J=2.1 Hz, 2H), 7.57 (s, 1H), 7.53 (s, 1H), 7.49 (t, J=8.4 Hz, 1H), 7.18-7.12 (m, 2H), 3.89 (t, J=4.8 Hz, 4H), 3.77 (s, 2H), 3.36 (t, J=4.9 Hz, 4H), 1.56 (s, 9H).

Example 27—Synthesis of N-(1-(tert-butyl)-1H-pyrazol-4-yl)-2-(2-fluoro-4-((6-(methylsulfonamido)quinolin-4-yl)oxy)phenyl)acetamide (Compound 68); Prepared According to General Scheme 17

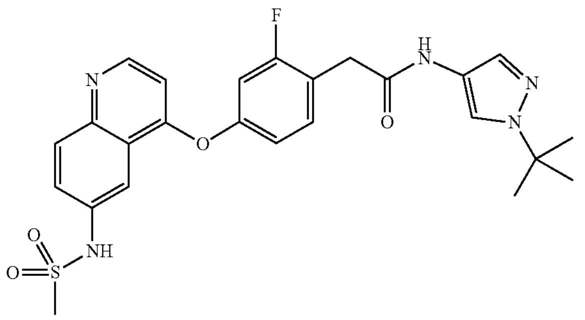 [SMILES: CC(C)(C)n1cc(NC(=O)Cc2ccc(Oc3ccnc4ccc(NS(C)(=O)=O)cc34)cc2F)cn1]

Methanesulfonamide (68.8 mg, 0.724 mmol, 1.20 equiv.), sodium trifluoroacetate (98.4 mg, 0.724 mmol, 1.20 equiv.), DBU (110.2 mg, 0.724 mmol, 1.20 equiv.), and [Pd(tBu-BrettPhos)(allyl)]OTf (23.5 mg, 0.030 mmol, 0.05 equiv.) were added to a solution of 2-(4-((6-bromoquinolin-4-yl)oxy)-2-fluorophenyl)-N-(1-(tert-butyl)-1H-pyrazol-4-yl)acetamide (300 mg, 0.603 mmol, 1.00 equiv., can be synthesized according to Part I in Example 32) in 2-methyltetrahydrofuran (3 mL) under an inert atmosphere of nitrogen. Subsequently, the reaction mixture was heated to 60° C. overnight. The solvent was removed under reduced pressure and the crude product was purified by reversed-phase flash chromatography (column: C18 silica gel; mobile phase A: water, mobile phase B: ACN, gradient: 20-50% B in 30 min; wavelength: 210 nm). The title compound was obtained as a white solid (27.9 mg, 8.9%). LCMS (ESI) calculated for $C_{25}H_{27}FN_5O_4S$ $(M+H)^+$: 512.2, found: 512.1. $^1H$ NMR (300 MHz, DMSO-$d_6$) 310.22 (s, 2H), 8.64 (d, J=5.1 Hz, 1H), 8.04-8.01 (m, 2H), 7.94 (s, 1H), 7.70 (d, J=9.5 Hz, 1H), 7.52 (t, J=8.5 Hz, 1H), 7.45 (s, 1H), 7.28 (d, J=10.5 Hz, 1H), 7.12 (d, J=8.4 Hz, 1H), 6.68 (d, J=5.2 Hz, 1H), 3.70 (s, 2H), 3.07 (s, 3H), 1.49 (s, 9H).

Example 28—Preparation of Additional 6-Nitrogen Substituted Quinoline and Quinazoline Compounds Compounds in the table below were prepared based on experimental procedures described in Examples 26 and 27 and the detailed description.

| No. | Structure | Name | $^1H$ NMR | Observed m/z |
|---|---|---|---|---|
| 152 | 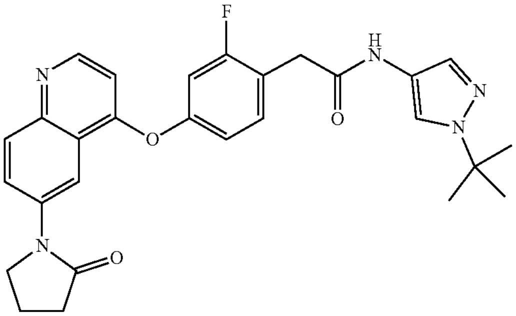 [SMILES: CC(C)(C)n1cc(NC(=O)Cc2ccc(Oc3ccnc4ccc(N5CCCC5=O)cc34)cc2F)cn1] | N-(1-(tert-butyl)-1H-pyrazol-4-yl)-2-(2-fluoro-4-((6-(2-oxopyrrolidin-1-yl)quinolin-4-yl)oxy)phenyl) acetamide | (400 MHz, DMSO-$d_6$) δ 10.22 (s, 1H), 8.66 (d, J = 5.1 Hz, 1H), 8.39 (d, J = 2.5 Hz, 1H), 8.26 (dd, J = 9.3, 2.5 Hz, 1H), 8.05 (d, J = 9.3 Hz, 1H), 7.94 (d, J = 0.7 Hz, 1H), 7.52 (t, J = 8.5 Hz, 1H), 7.45 (d, J = 0.7 Hz, 1H), 7.27 (dd, J = 10.5, 2.4 Hz, 1H), 7.12 (dd, J = 8.4, 2.4 Hz, 1H), 6.69 (d, J = 5.1 Hz, 1H), 4.00 (t, J = 7.0 Hz, 2H), 3.70 (s, 2H), 2.57 (t, J = 8.1 Hz, 2H), 2.12 (t, J = 7.5 Hz, 2H), 1.49 (s, 9H) | 502.1 $(M + H)^+$ |
| 153 | 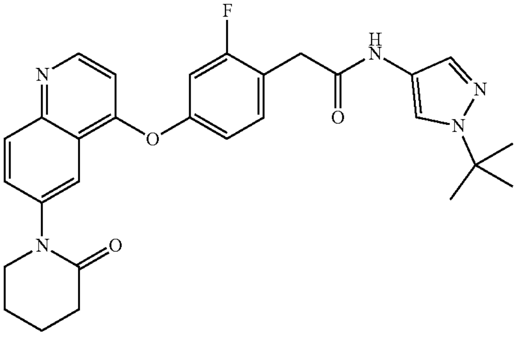 [SMILES: CC(C)(C)n1cc(NC(=O)Cc2ccc(Oc3ccnc4ccc(N5CCCCC5=O)cc34)cc2F)cn1] | N-(1-(tert-butyl)-1H-pyrazol-4-yl)-2-(2-fluoro-4-((6-(2-oxopiperidin-1-yl)quinolin-4-yl)oxy)phenyl) acetamide | (400 MHz, DMSO-$d_6$) δ 10.23 (s, 1H), 8.71 (d, J = 5.1 Hz, 1H), 8.13 (d, J = 2.4 Hz, 1H), 8.03 (d, J = 9.0 Hz, 1H), 7.94 (s, 1H), 7.76 (dd, J = 9.0, 2.4 Hz, 1H), 7.52 (t, J = 8.5 Hz, 1H), 7.45 (s, 1H), 7.29 (dd, J = 10.4, 2.4 Hz, 1H), 7.13 (dd, J = 8.3, 2.4 Hz, 1H), 6.69 (d, J = 5.1 Hz, 1H), 3.76 (t, J = 5.6 Hz, 2H), 3.70 (s, 2H), 2.45 (t, J = 6.3 Hz, 2H), 1.98-1.80 (m, 4H), 1.49 (s, 9H) | 516.2 $(M + H)^+$ |

-continued

| No. | Structure | Name | $^1$H NMR | Observed m/z |
|---|---|---|---|---|
| 154 | 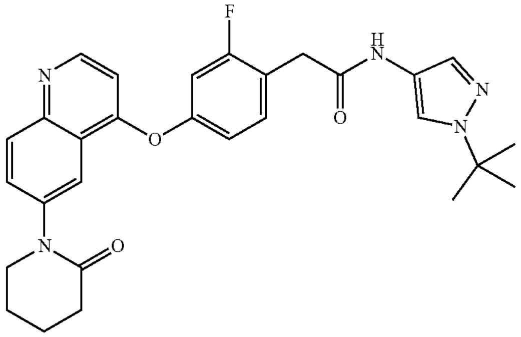 [SMILES: CC(C)(C)n1cc(NC(=O)Cc2ccc(Oc3ccnc4ccc(N5CCCCC5=O)cc34)cc2F)cn1] | N-(1-(tert-butyl)-1H-pyrazol-4-yl)-2-(2-fluoro-4-((6-(3-oxomorpholino)quinolin-4-yl)oxy)phenyl)acetamide | (400 MHz, DMSO-$d_6$) δ 10.23 (s, 1H), 8.72 (d, J = 5.1 Hz, 1H), 8.27 (d, J = 2.3 Hz, 1H), 8.07 (d, J = 9.0 Hz, 1H), 7.94 (d, J = 0.7 Hz, 1H), 7.89 (dd, J = 9.0, 2.4 Hz, 1H), 7.53 (t, J = 8.5 Hz, 1H), 7.45 (d, J = 0.7 Hz, 1H), 7.29 (dd, J = 10.5, 2.4 Hz, 1H), 7.14 (dd, J = 8.2, 2.5 Hz, 1H), 6.70 (d, J = 5.1 Hz, 1H), 4.27 (s, 2H), 4.04 (dd, J = 6.0, 4.0 Hz, 2H), 3.90 (dd, J = 6.1, 4.0 Hz, 2H), 3.70 (s, 2H), 1.49 (s, 9H) | 518.1 $(M + H)^+$ |
| 155 | 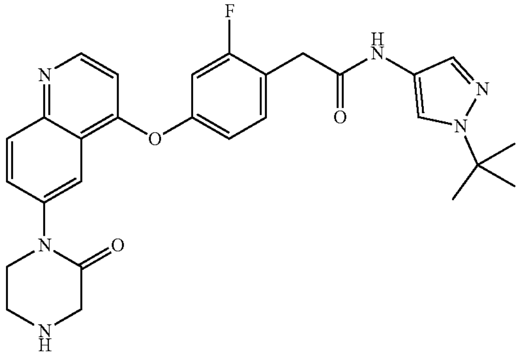 [SMILES: CC(C)(C)n1cc(NC(=O)Cc2ccc(Oc3ccnc4ccc(N5CCNCC5=O)cc34)cc2F)cn1] | N-(1-(tert-butyl)-1H-pyrazol-4-yl)-2-(2-fluoro-4-((6-(2-oxopiperazin-1-yl)quinolin-4-yl)oxy)phenyl)acetamide | (400 MHz, DMSO-$d_6$) δ 10.23 (s, 1H), 8.71 (d, J = 5.1 Hz, 1H), 8.17 (d, J = 2.3 Hz, 1H), 8.04 (d, J = 8.9 Hz, 1H), 7.93 (s, 1H), 7.81 (dd, J = 9.0, 2.4 Hz, 1H), 7.52 (t, J = 8.5 Hz, 1H), 7.45 (s, 1H), 7.29 (dd, J = 10.5, 2.4 Hz, 1H), 7.13 (dd, J = 8.4, 2.4 Hz, 1H), 6.70 (d, J = 5.1 Hz, 1H), 3.75 (t, J = 5.3 Hz, 2H), 3.70 (s, 2H), 3.44 (s, 2H), 3.07 (t, J = 5.4 Hz, 2H), 2.81 (s, 1H), 1.48 (s, 9H) | 517.1 $(M + H)^+$ |
| 156 | 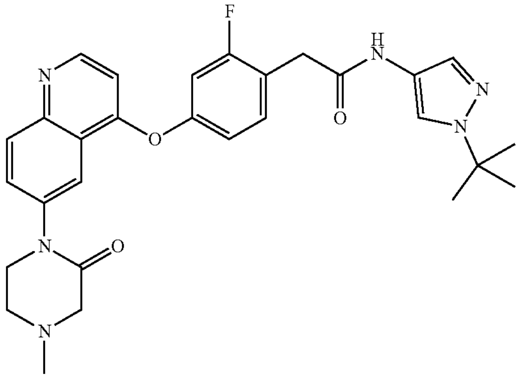 [SMILES: CN1CCN(c2ccc3nccc(Oc4ccc(CC(=O)Nc5cnn(C(C)(C)C)c5)c(F)c4)c3c2)C(=O)C1] | N-(1-(tert-butyl)-1H-pyrazol-4-yl)-2-(2-fluoro-4-((6-(4-methyl-2-oxopiperazin-1-yl)quinolin-4-yl)oxy)phenyl)acetamide | (400 MHz, DMSO-$d_6$) δ 10.23 (s, 1H), 8.72 (d, J = 5.1 Hz, 1H), 8.19 (d, J = 2.4 Hz, 1H), 8.05 (d, J = 9.0 Hz, 1H), 7.94 (d, J = 0.6 Hz, 1H), 7.82 (dd, J = 9.0, 2.4 Hz, 1H), 7.53 (t, J = 8.5 Hz, 1H), 7.45 (d, J = 0.6 Hz, 1H), 7.29 (dd, J = 10.5, 2.4 Hz, 1H), 7.14 (dd, J = 8.4, 2.4 Hz, 1H), 6.70 (d, J = 5.1 Hz, 1H), 3.81 (dd, J = 6.3, 4.5 Hz, 2H), 3.70 (s, 2H), 3.18 (s, 2H), 2.78 (t, J = 5.4 Hz, 2H), 2.31 (s, 3H), 1.49 (s, 9H) | 531.1 $(M + H)^+$ |

-continued

| No. | Structure | Name | $^1$H NMR | Observed m/z |
|---|---|---|---|---|
| 157 | 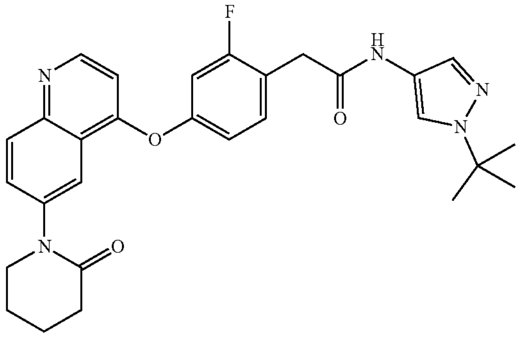 | N-(1-(tert-butyl)-1H-pyrazol-4-yl)-2-(2-fluoro-4-((6-(2-oxopyridin-1(2H)-yl)quinolin-4-yl)oxy)phenyl) acetamide | (400 MHz, DMSO-$d_6$) δ 10.23 (s, 1H), 8.80 (d, J = 5.1 Hz, 1H), 8.27 (d, J = 2.3 Hz, 1H), 8.15 (d, J = 8.9 Hz, 1H), 7.94 (d, J = 0.7 Hz, 1H), 7.87 (dd, J = 9.0, 2.4 Hz, 1H), 7.83 (ddd, J= 6.8, 2.1, 0.8 Hz, 1H), 7.61-7.50 (m, 2H), 7.45 (d, J = 0.7 Hz, 1H), 7.30 (dd, J = 10.4, 2.4 Hz, 1H), 7.19-7.12 (m, 1H), 6.77 (d, J = 5.1 Hz, 1H), 6.54 (dt, J = 9.1, 1.1 Hz, 1H), 6.39 (td, J = 6.7, 1.3 Hz, 1H), 3.70 (s, 2H), 1.48 (s, 9H) | 512.0 (M + H)$^+$ |
| 264 | 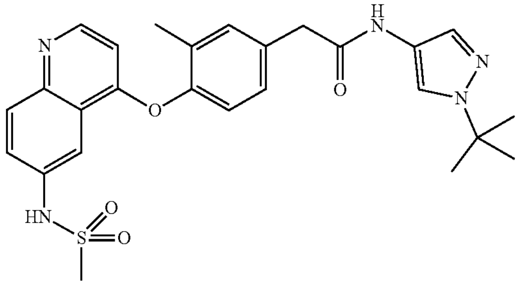 [SMILES: Cc1cc(CC(=O)Nc2cnn(C(C)(C)C)c2)ccc1Oc1ccnc2ccc(NS(C)(=O)=O)cc12] | N-(1-(tert-butyl)-1H-pyrazol-4-yl)-2-(3-methyl-4-((6-(methylsulfonamido) quinolin-4-yl)oxy)phenyl) acetamide | (400 MHz, DMSO-$d_6$) δ 10.19 (s, 1H), 8.56-8.54 (m, 1H), 8.07 (d, J = 2.5 Hz, 1H), 7.99 (d, J = 9.1 Hz, 1H), 7.94 (s, 1H), 7.66 (dd, J = 9.1, 2.5 Hz, 1H), 7.45 (s, 1H), 7.36 (d, J = 2.1 Hz, 1H), 7.29-7.25 (m, 1H), 7.16 (d, J = 8.2 Hz, 1H), 6.39 (d, J = 5.0 Hz, 1H), 3.60 (s, 2H), 3.05 (s, 3H), 2.11 (s, 3H), 1.48 (s, 9H) | 508.1 (M + H)$^+$ |
| 265 | 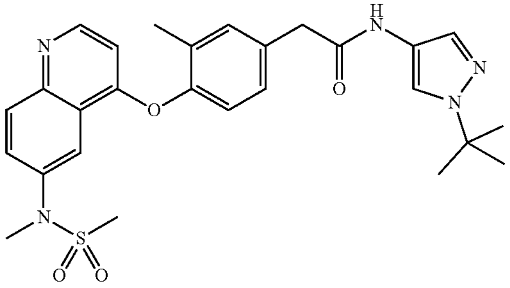 [SMILES: Cc1cc(CC(=O)Nc2cnn(C(C)(C)C)c2)ccc1Oc1ccnc2ccc(N(C)S(C)(=O)=O)cc12] | N-(1-(tert-butyl)-1H-pyrazol-4-yl)-2-(3-methyl-4-((6-(N-methylmethyl-sulfonamido) quinolin-4-yl)oxy)phenyl) acetamide | (300 MHz, DMSO-$d_6$) δ 10.19 (s, 1H), 8.65 (d, J = 5.1 Hz, 1H), 8.31 (d, J = 2.6 Hz, 1H), 8.05 (d, J = 9.1 Hz, 1H), 7.94 (s, 1H), 7.88 (dd, J = 9.1, 2.4 Hz, 1H), 7.45 (s, 1H), 7.37 (s, 1H), 7.30 (d, J = 8.8 Hz, 1H), 7.20 (d, J = 8.2 Hz, 1H), 6.43 (d, J = 5.2 Hz, 1H), 3.60 (s, 2H), 3.40 (s, 3H), 3.05 (s, 3H), 2.12 (s, 3H), 1.48 (s, 9H) | 522.2 (M + H)$^+$ |
| 266 | 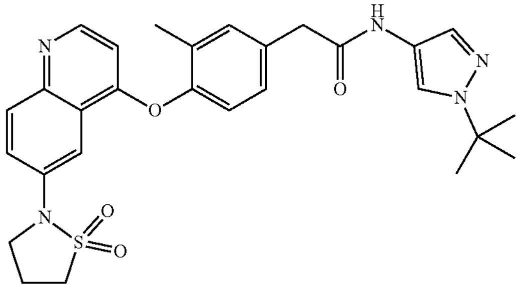 [SMILES: Cc1cc(CC(=O)Nc2cnn(C(C)(C)C)c2)ccc1Oc1ccnc2ccc(N3CCCS3(=O)=O)cc12] | N-(1-(tert-butyl)-1H-pyrazol-4-yl)-2-(4-((6-(1,1-dioxidoisothiazolidin-2-yl)quinolin-4-yl)oxy)-3-methylphenyl) acetamide | (400 MHz, DMSO-$d_6$) δ 10.19 (s, 1H), 8.57 (d, J = 5.1 Hz, 1H), 8.06 (d, J = 9.2 Hz, 1H), 7.95 (d, J = 0.7 Hz, 1H), 7.92 (d, J = 2.6 Hz, 1H), 7.81 (dd, J = 9.2, 2.7 Hz, 1H), 7.46 (d, J = 0.7 Hz, 1H), 7.37 (d, J = 2.2 Hz, 1H), 7.30 (dd, J = 8.2, 2.2 Hz, 1H), 7.19 (d, J = 8.2 Hz, 1H), 6.41 (d, J = 5.1 Hz, 1H), 3.95 (t, J = 6.5 Hz, 2H), 3.65-3.58 (m, 4H), 2.49-2.45 (m, 2H), 2.11 (s, 3H), 1.49 (s, 9H) | 534.1 (M + H)$^+$ |

-continued

| No. | Structure | Name | $^1$H NMR | Observed m/z |
|---|---|---|---|---|
| 277 | 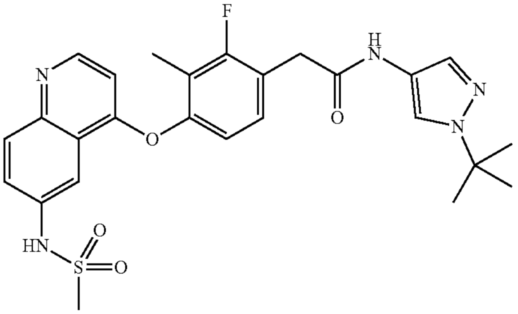 [SMILES: Cc1c(Oc2ccnc3ccc(NS(C)(=O)=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(methylsulfonamido)quinolin-4-yl)oxy)phenyl)acetamide | (400 MHz, DMSO-$d_6$) δ 10.22 (s, 2H), 8.60 (d, J = 5.1 Hz, 1H), 8.09 (d, J = 2.5 Hz, 1H), 8.03 (d, J = 9.0 Hz, 1H), 7.94 (d, J = 0.7 Hz, 1H), 7.71 (dd, J = 9.1, 2.5 Hz, 1H), 7.45 (d, J = 0.7 Hz, 1H), 7.35 (t, J = 8.4 Hz, 1H), 7.08 (d, J = 8.4 Hz, 1H), 6.49 (d, J = 5.1 Hz, 1H), 3.70 (s, 2H), 3.09 (s, 3H), 2.06 (d, J = 1.9 Hz, 3H), 1.49 (s, 9H) | 526.2 $(M + H)^+$ |
| 278 | 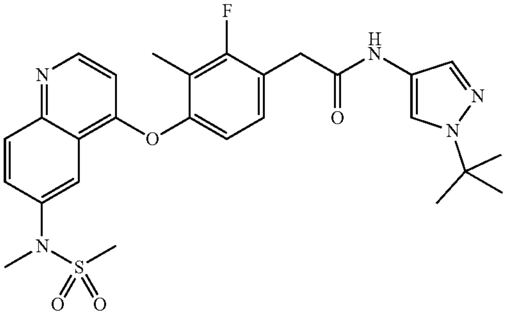 [SMILES: Cc1c(Oc2ccnc3ccc(N(C)S(C)(=O)=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(N-methylmethyl-sulfonamido)quinolin-4-yl)oxy)phenyl)acetamide | (400 MHz, DMSO-$d_6$) δ 10.23 (s, 1H), 8.69 (d, J = 5.1 Hz, 1H), 8.31 (d, J = 2.5 Hz, 1H), 8.07 (d, J = 9.1 Hz, 1H), 7.94 (s, 1H), 7.90 (dd, J = 9.1, 2.6 Hz, 1H), 7.46 (s, 1H), 7.37 (s, 1H), 7.12 (d, J = 8.4 Hz, 1H), 6.51 (d, J = 5.2 Hz, 1H), 3.71 (s, 2H), 3.41 (s, 3H), 3.05 (s, 3H), 2.06 (d, J = 1.9 Hz, 3H), 1.49 (s, 9H) | 540.2 $(M + H)^+$ |
| 279 | 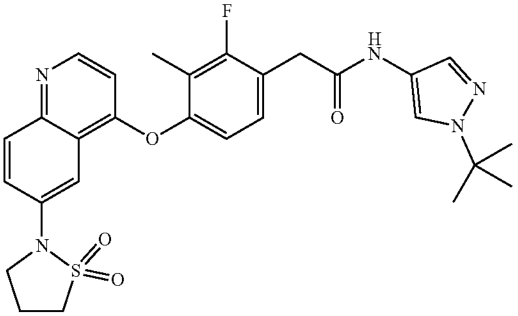 [SMILES: Cc1c(Oc2ccnc3ccc(N4CCCS4(=O)=O)cc23)ccc(CC(=O)Nc2cnn(C(C)(C)C)c2)c1F] | N-(1-(tert-butyl)-1H-pyrazol-4-yl)-2-(4-((6-(1,1-dioxidoisothiazolidin-2-yl)quinolin-4-yl)oxy)-2-fluoro-3-methylphenyl)acetamide | (400 MHz, DMSO-$d_6$) δ 10.22 (s, 1H), 8.60 (d, J = 5.1 Hz, 1H), 8.07 (d, J = 9.2 Hz, 1H), 7.94 (d, J = 0.7 Hz, 1H), 7.89 (d, J = 2.6 Hz, 1H), 7.82 (dd, J = 9.2, 2.7 Hz, 1H), 7.45 (d, J = 0.7 Hz, 1H), 7.36 (t, J = 8.4 Hz, 1H), 7.10 (d, J = 8.3 Hz, 1H), 6.49 (d, J = 5.1 Hz, 1H), 3.95 (t, J= 6.5 Hz, 2H), 3.70 (s, 2H), 3.62 (t, J = 7.3 Hz, 2H), 2.47 (d, J = 7.0 Hz, 2H), 2.05 (d, J = 1.9 Hz, 3H), 1.49 (s, 9H) | 552.2 $(M + H)^+$ |
| 290 | 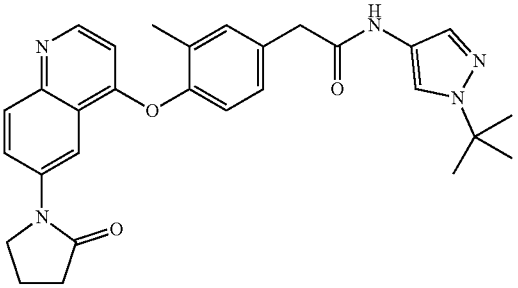 [SMILES: Cc1cc(CC(=O)Nc2cnn(C(C)(C)C)c2)ccc1Oc1ccnc2ccc(N3CCCC3=O)cc12] | N-(1-(tert-butyl)-1H-pyrazol-4-yl)-2-(3-methyl-4-((6-(2-oxopyrrolidin-1-yl)quinolin-4-yl)oxy)phenyl)acetamide | (400 MHz, DMSO-$d_6$) δ 10.20 (s, 1H), 8.58 (d, J = 5.1 Hz, 1H), 8.48 (d, J = 2.5 Hz, 1H), 8.25 (dd, J = 9.3, 2.5 Hz, 1H), 8.04 (d, J = 9.3 Hz, 1H), 7.95 (s, 1H), 7.46 (s, 1H), 7.37 (d, J = 2.1 Hz, 1H), 7.29 (dd, J = 8.3, 2.2 Hz, 1H), 7.19 (d, J = 8.2 Hz, 1H), 6.40 (d, J = 5.1 Hz, 1H), 4.02 (t, J = 7.0 Hz, 2H), 3.61 (s, 2H), 2.58 (t, J = 8.0 Hz, 2H), 2.16-2.08 (m, 5H), 1.49 (s, 9H) | 498.1 $(M + H)^+$ |

-continued

| No. | Structure | Name | $^1$H NMR | Observed m/z |
|---|---|---|---|---|
| 291 | 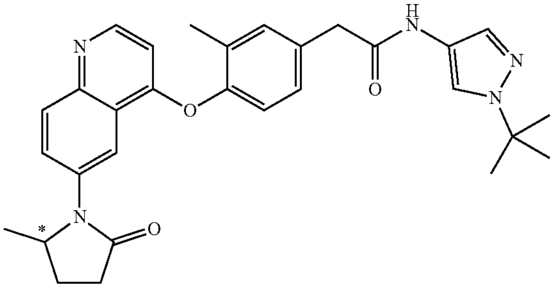 [SMILES: Cc1cc(CC(=O)Nc2cnn(C(C)(C)C)c2)ccc1Oc1ccnc2ccc(N3C(=O)CCC3C)cc12] enantiomer 1 (retention time: 1.21 min, column: CHIRALPAK IF-3, 4.6 × 50 mm, 3 μm; mobile phase A: hexane/DCM (3:1, 0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(3-methyl-4-((6-(2-methyl-5-oxopyrrolidin-1-yl)quinolin-4-yl)oxy)phenyl) acetamide | (400 MHz, DMSO-$d_6$) δ 10.21 (s, 1H), 8.61 (d, J = 5.1 Hz, 1H), 8.42 (d, J = 2.4 Hz, 1H), 8.05 (d, J = 9.1 Hz, 1H), 7.99-7.92 (m, 2H), 7.46 (s, 1H), 7.37 (d, J = 2.1 Hz, 1H), 7.29 (dd, J = 8.3, 2.2 Hz, 1H), 7.19 (d, J = 8.2 Hz, 1H), 6.41 (d, J = 5.2 Hz, 1H), 4.66-4.56 (m, 1H), 3.61 (s, 2H), 2.70-2.58 (m, 1H), 2.50-2.43 (m, 1H), 2.43-2.30 (m, 1H), 2.11 (s, 3H), 1.81-1.69 (m, 1H), 1.49 (s, 9H), 1.21 (d, J = 6.2 Hz, 3H) | 512.1 (M + H)$^+$ |
| 292 | 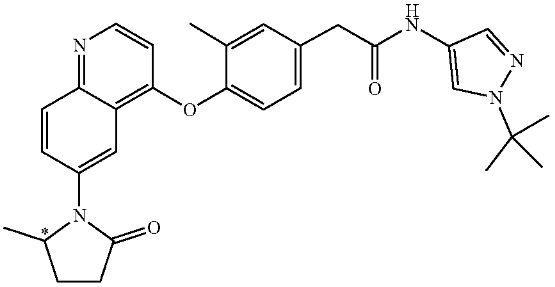 [SMILES: Cc1cc(CC(=O)Nc2cnn(C(C)(C)C)c2)ccc1Oc1ccnc2ccc(N3C(=O)CCC3C)cc12] enantiomer 2 (retention time: 1.71 min, column: CHIRALPAK IF-3, 4.6 × 50 mm, 3 μm; mobile phase A: hexane/DCM (3:1, 0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(3-methyl-4-((6-(2-methyl-5-oxopyrrolidin-1-yl)quinolin-4-yl)oxy)phenyl) acetamide | (400 MHz, DMSO-$d_6$) δ 10.21 (s, 1H), 8.61 (d, J = 5.1 Hz, 1H), 8.42 (d, J = 2.4 Hz, 1H), 8.05 (d, J = 9.1 Hz, 1H), 8.00-7.92 (m, 2H), 7.46 (s, 1H), 7.37 (d, J = 2.1 Hz, 1H), 7.29 (dd, J = 8.3, 2.2 Hz, 1H), 7.19 (d, J = 8.2 Hz, 1H), 6.41 (d, J = 5.1 Hz, 1H), 4.66-4.57 (m, 1H), 3.61 (s, 2H), 2.70-2.58 (m, 1H), 2.50-2.42 (m, 1H), 2.41-2.31 (m, 1H), 2.11 (s, 3H), 1.80-1.69 (m, 1H), 1.49 (s, 9H), 1.21 (d, J = 6.2 Hz, 3H) | 512.1 (M + H)$^+$ |
| 293 | 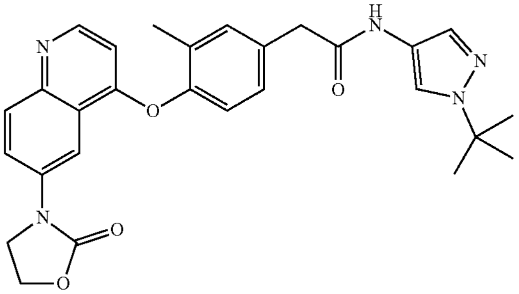 [SMILES: Cc1cc(CC(=O)Nc2cnn(C(C)(C)C)c2)ccc1Oc1ccnc2ccc(N3CCOC3=O)cc12] | N-(1-(tert-butyl)-1H-pyrazol-4-yl)-2-(3-methyl-4-((6-(2-oxooxazolidin-3-yl)quinolin-4-yl)oxy)phenyl) acetamide | (400 MHz, DMSO-$d_6$) δ 10.19 (s, 1H), 8.59 (d, J = 5.1 Hz, 1H), 8.33 (d, J = 2.5 Hz, 1H), 8.21 (dd, J = 9.3, 2.6 Hz, 1H), 8.07 (d, J = 9.3 Hz, 1H), 7.95 (d, J = 0.7 Hz, 1H), 7.46 (s, 1H), 7.37 (d, J = 2.2 Hz, 1H), 7.30 (dd, J = 8.4, 2.2 Hz, 1H), 7.19 (d, J = 8.3 Hz, 1H), 6.41 (d, J = 5.1 Hz, 1H), 4.51 (dd, J = 9.1, 6.7 Hz, 2H), 4.26 (dd, J = 9.1, 6.8 Hz, 2H), 3.61 (s, 2H), 2.11 (s, 3H), 1.49 (s, 9H) | 500.1 (M + H)$^+$ |

-continued

| No. | Structure | Name | $^1$H NMR | Observed m/z |
|---|---|---|---|---|
| 294 | 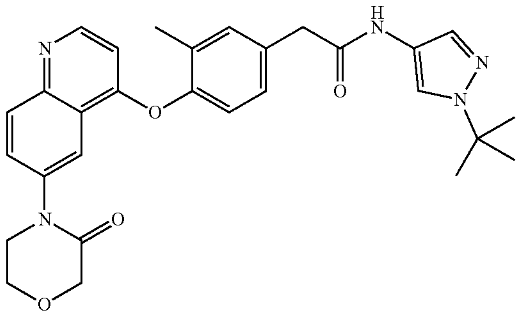 [SMILES: Cc1cc(CC(=O)Nc2cnn(C(C)(C)C)c2)ccc1Oc1ccnc2ccc(N3CCOCC3=O)cc12] | N-(1-(tert-butyl)-1H-pyrazol-4-yl)-2-(3-methyl-4-((6-(3-oxomorpholino) quinolin-4-yl)oxy)phenyl) acetamide | (400 MHz, DMSO-$d_6$) δ 10.19 (s, 1H), 8.65 (d, J = 5.1 Hz, 1H), 8.35 (d, J = 2.4 Hz, 1H), 8.06 (d, J = 9.0 Hz, 1H), 7.95 (s, 1H), 7.89 (dd, J = 9.0, 2.4 Hz, 1H), 7.46 (s, 1H), 7.37 (d, J = 2.1 Hz, 1H), 7.30 (dd, J = 8.2, 2.2 Hz, 1H), 7.19 (d, J = 8.2 Hz, 1H), 6.42 (d, J = 5.1 Hz, 1H), 4.28 (s, 2H), 4.05 (dd, J = 6.1, 3.9 Hz, 2H), 3.93 (dd, J = 6.0, 3.9 Hz, 2H), 3.61 (s, 2H), 2.12 (s, 3H), 1.49 (s, 9H) | 514.1 $(M + H)^+$ |
| 295 | 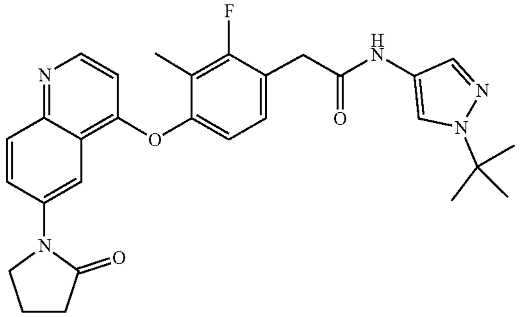 [SMILES: Cc1c(Oc2ccnc3ccc(N4CCCC4=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(2-oxopyrrolidin-1-yl)quinolin-4-yl)oxy)phenyl) acetamide | (300 MHz, DMSO-$d_6$) δ 10.21 (s, 1H), 8.61 (d, J = 5.2 Hz, 1H), 8.47 (d, J = 2.4 Hz, 1H), 8.33-8.22 (m, 1H), 8.05 (d, J = 9.2 Hz, 1H), 7.94 (s, 1H), 7.46 (s, 1H), 7.36 (t, J = 8.4 Hz, 1H), 7.08 (d, J= 8.3 Hz, 1H), 6.49 (d, J = 5.2 Hz, 1H), 4.02 (t, J = 7.0 Hz, 2H), 3.70 (s, 2H), 2.58 (t, J = 8.0 Hz, 2H), 2.14 (q, J = 7.5 Hz, 2H), 2.08-2.00 (m, 3H), 1.49 (s, 9H) | 516.1 $(M + H)^+$ |
| 296 | 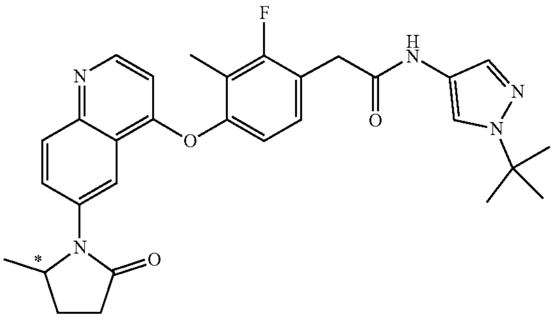 [SMILES: Cc1c(Oc2ccnc3ccc(N4C(=O)CCC4C)cc23)ccc(CC(=O)Nc2cnn(C(C)(C)C)c2)c1F] enantiomer 1 | N-(1-(tert-butyl)-1H-pyrazol-4-yl)-2-(2-fluoro-3-methyl-4-((6-(2-methyl-5-oxopyrrolidin-1-yl)quinolin-4-yl)oxy)phenyl) acetamide | (300 MHz, DMSO-$d_6$) δ 10.23 (s, 1H), 8.65 (d, J = 5.1 Hz, 1H), 8.42 (d, J = 2.4 Hz, 1H), 8.07 (d, J = 9.1 Hz, 1H), 8.02-7.92 (m, 2H), 7.46 (s, 1H), 7.37 (t, J = 8.4 Hz, 1H), 7.10 (d, J = 8.3 Hz, 1H), 6.50 (d, J = 5.1 Hz, 1H), 4.61 (dt, J = 12.3, 6.1 Hz, 1H), 3.71 (s, 2H), 2.65 (ddd, J = 16.1, 9.3, 6.6 Hz, 1H), 2.55-2.27 (m, 2H), 2.11-2.03 (m, 3H), 1.83-1.70 (m, 1H), 1.49 (s, 9H), 1.22 (d, J = 6.2 Hz, 3H) | 530.1 $(M + H)^+$ |
| 297 | 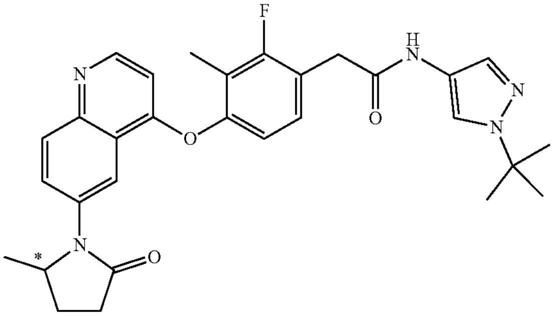 [SMILES: Cc1c(Oc2ccnc3ccc(N4C(=O)CCC4C)cc23)ccc(CC(=O)Nc2cnn(C(C)(C)C)c2)c1F] enantiomer 2 | N-(1-(tert-butyl)-1H-pyrazol-4-yl)-2-(2-fluoro-3-methyl-4-((6-(2-methyl-5-oxopyrrolidin-1-yl)quinolin-4-yl)oxy)phenyl) acetamide | (300 MHz, DMSO-$d_6$) δ 10.23 (s, 1H), 8.65 (d, J = 5.0 Hz, 1H), 8.42 (d, J = 2.3 Hz, 1H), 8.07 (d, J = 9.1 Hz, 1H), 8.02-7.92 (m, 2H), 7.46 (s, 1H), 7.37 (t, J = 8.4 Hz, 1H), 7.10 (d, J = 8.4 Hz, 1H), 6.50 (d, J = 5.1 Hz, 1H), 4.70-4.54 (m, 1H), 3.71 (s, 2H), 2.65 (ddd, J = 16.1, 9.4, 6.6 Hz, 1H), 2.55-2.27 (m, 2H), 2.06 (d, J = 1.9 Hz, 3H), 1.82-1.68 (m, 1H), 1.49 (s, 9H), 1.21 (d, J = 6.1 Hz, 3H) | 530.1 $(M + H)^+$ |

-continued

| No. | Structure | Name | $^1$H NMR | Observed m/z |
|---|---|---|---|---|
| 298 | 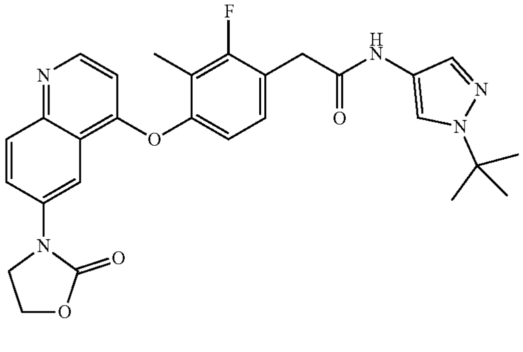 [SMILES: Cc1c(Oc2ccnc3ccc(N4CCOC4=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(2-oxooxazolidin-3-yl)quinolin-4-yl)oxy)phenyl) acetamide | (300 MHz, DMSO-$d_6$) δ 10.22 (s, 1H), 8.62 (d, J = 5.1 Hz, 1H), 8.31 (d, J = 2.5 Hz, 1H), 8.22 (dd, J = 9.3, 2.6 Hz, 1H), 8.09 (d, J = 9.3 Hz, 1H), 7.99-7.90 (m, 1H), 7.45 (d, J = 0.7 Hz, 1H), 7.35 (d, J = 8.4 Hz, 1H), 7.16-7.02 (m, 1H), 6.49 (d, J = 5.1 Hz, 1H), 4.51 (dd, J = 9.1, 6.7 Hz, 2H), 4.26 (dd, J = 9.1, 6.7 Hz, 2H), 3.70 (s, 2H), 2.05 (d, J = 2.0 Hz, 3H), 1.49 (s, 9H) | 518.0 (M + H)$^+$ |
| 317 | 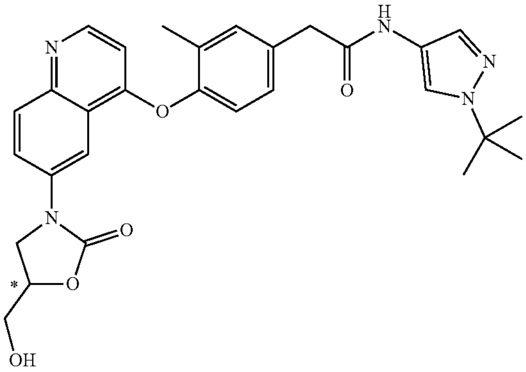 [SMILES: Cc1cc(CC(=O)Nc2cnn(C(C)(C)C)c2)ccc1Oc1ccnc2ccc(N3CC(CO)OC3=O)cc12] enantiomer 1 (retention time: 4.32 min, column: Lux Cellulose-4, 4.6 × 50 mm, 3 μm; mobile phase A: hexane (0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(4-((6-(5-(hydroxymethyl)-2-oxooxazolidin-3-yl)quinolin-4-yl)oxy)-3-methylphenyl) acetamide | (400 MHz, DMSO-$d_6$) δ 10.21 (s, 1H), 8.61 (d, J = 5.2 Hz, 1H), 8.32 (d, J = 2.6 Hz, 1H), 8.26 (dd, J = 9.3, 2.6 Hz, 1H), 8.08 (d, J = 9.3 Hz, 1H), 7.95 (s, 1H), 7.46 (d, J = 0.7 Hz, 1H), 7.37 (d, J = 2.2 Hz, 1H), 7.30 (dd, J = 8.2, 2.2 Hz, 1H), 7.19 (d, J = 8.2 Hz, 1H), 6.42 (d, J = 5.2 Hz, 1H), 5.27 (s, 1H), 4.78 (td, J = 6.0, 2.8 Hz, 1H), 4.29 (t, J = 9.0 Hz, 1H), 4.04 (dd, J = 8.8, 6.2 Hz, 1H), 3.73 (d, J = 11.8 Hz, 1H), 3.64-3.61 (m, 3H), 2.11 (s, 3H), 1.49 (s, 9H ) | 530.0 (M + H)$^+$ |

-continued

| No. | Structure | Name | $^1$H NMR | Observed m/z |
|---|---|---|---|---|
| 318 | 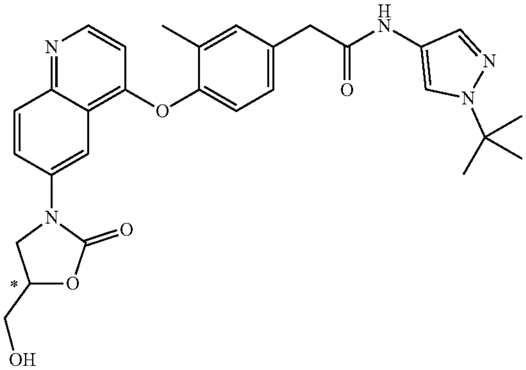 [SMILES: Cc1cc(CC(=O)Nc2cnn(C(C)(C)C)c2)ccc1Oc1ccnc2ccc(N3CC(CO)OC3=O)cc12] enantiomer 2 (retention time: 5.47 min, column: Lux Cellulose-4, 4.6 × 50 mm, 3 µm; mobile phase A: hexane (0.1% DEA), mobile phase B: EtOH, isocratic separation with 30% B, flow rate: 1.0 mL/min, wavelength: 254 nm) | N-(1-(tert-butyl)-1H-pyrazol-4-yl)-2-(4-((6-(5-(hydroxymethyl)-2-oxooxazolidin-3-yl)quinolin-4-yl)oxy)-3-methylphenyl) acetamide | (400 MHz, DMSO-$d_6$) δ 10.21 (s, 1H), 8.61 (d, J = 5.2 Hz, 1H), 8.33 (d, J = 2.6 Hz, 1H), 8.27 (dd, J = 9.3, 2.6 Hz, 1H), 8.08 (d, J = 9.3 Hz, 1H), 7.95 (s, 1H), 7.46 (d, J = 0.7 Hz, 1H), 7.38 (d, J = 2.2 Hz, 1H), 7.30 (dd, J = 8.2, 2.2 Hz, 1H), 7.20 (d, J = 8.2 Hz, 1H), 6.43 (d, J = 5.2 Hz, 1H), 5.27 (s, 1H), 4.78 (td, J = 6.0, 2.8 Hz, 1H), 4.29 (t, J = 9.0 Hz, 1H), 4.04 (dd, J = 8.8, 6.2 Hz, 1H), 3.73 (d, J = 11.8 Hz, 1H), 3.66-3.59 (m, 3H), 2.12 (s, 3H), 1.49 (s, 9H) | 530.1 $(M + H)^+$ |
| 319 | 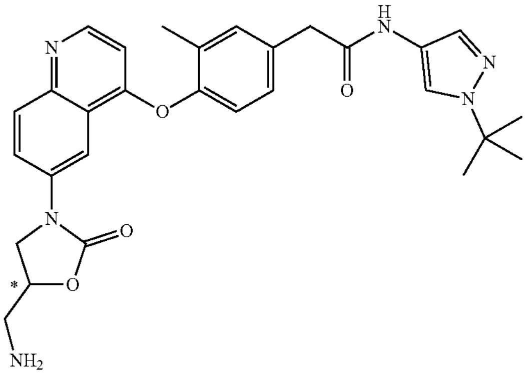 [SMILES: Cc1cc(CC(=O)Nc2cnn(C(C)(C)C)c2)ccc1Oc1ccnc2ccc(N3CC(CN)OC3=O)cc12] enantiomer 1 (retention time: 4.98 min, column: CHIRALPAK IE-3, 4.6 × 50 mm, 3 µm; mobile phase A: MTBE (0.1% DEA), mobile phase B: MeOH/DCM (1:1), isocratic separation with 30% B, flow rate: 1.0 mL/min, wavelength: 254 nm) | 2-(4-((6-(5-(aminomethyl)-2-oxooxazolidin-3-yl)quinolin-4-yl)oxy)-3-methylphenyl)-N-(1-(tert-butyl)-1H-pyrazol-4-yl)acetamide | (400 MHz, DMSO-$d_6$) δ 10.21 (s, 1H), 8.58 (d, J = 5.2 Hz, 1H), 8.32-8.22 (m, 2H), 8.07 (d, J = 9.2 Hz, 1H), 7.95 (s, 1H), 7.46 (s, 1H), 7.40-7.27 (m, 2H), 7.19 (d, J = 8.2 Hz, 1H), 6.39 (d, J = 5.1 Hz, 1H), 4.79-4.63 (m, 1H), 4.26 (t, J = 8.8 Hz, 1H), 4.12-4.04 (m, 1H), 3.61 (s, 2H), 2.96-2.81 (m, 2H), 2.11 (s, 3H), 1.49 (s, 9H) | 529.2 $(M + H)^+$ |

-continued

| No. | Structure | Name | $^1$H NMR | Observed m/z |
|---|---|---|---|---|
| 320 | 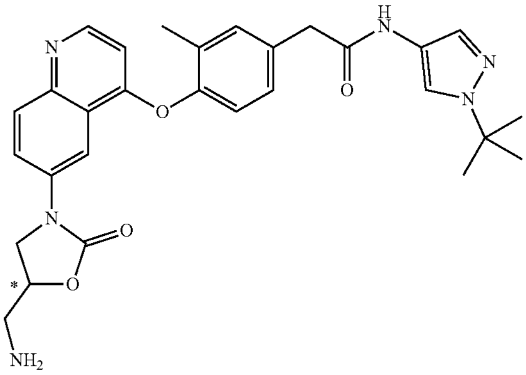 [SMILES: Cc1cc(CC(=O)Nc2cnn(C(C)(C)C)c2)ccc1Oc1ccnc2ccc(N3CC(CN)OC3=O)cc12] enantiomer 2 (retention time: 7.50 min, column: CHIRALPAK IE-3, 4.6 × 50 mm, 3 μm; mobile phase A: MTBE (0.1% DEA), mobile phase B: MeOH/DCM (1:1), isocratic separation with 30% B, flow rate: 1.0 mL/min, wavelength: 254 nm) | 2-(4-((6-(5-(aminomethyl)-2-oxooxazolidin-3-yl)quinolin-4-yl)oxy)-3-methylphenyl)-N-(1-(tert-butyl)-1H-pyrazol-4-yl)acetamide | (400 MHz, DMSO-$d_6$) δ 10.21 (s, 1H), 8.58 (d, J = 5.1 Hz, 1H), 8.32-8.22 (m, 2H), 8.07 (d, J = 9.3 Hz, 1H), 7.95 (s, 1H), 7.46 (s, 1H), 7.40-7.27 (m, 2H), 7.19 (d, J = 8.2 Hz, 1H), 6.40 (d, J = 5.1 Hz, 1H), 4.74-4.63 (m, 1H), 4.26 (t, J = 8.9 Hz, 1H), 4.12-4.00 (m, 1H), 3.61 (s, 2H), 2.96-2.80 (m, 2H), 2.11 (s, 3H), 1.49 (s, 9H) | 529.2 $(M + H)^+$ |
| 325 | 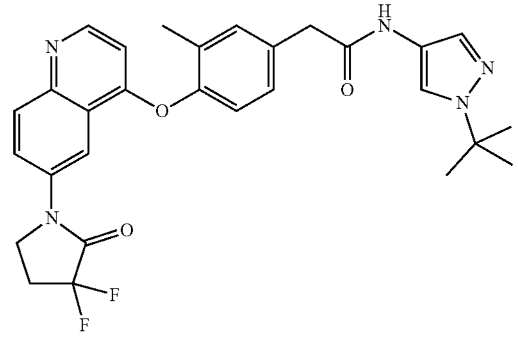 [SMILES: Cc1cc(CC(=O)Nc2cnn(C(C)(C)C)c2)ccc1Oc1ccnc2ccc(N3CCC(F)(F)C3=O)cc12] | N-(1-(tert-butyl)-1H-pyrazol-4-yl)-2-(4-((6-(3,3-difluoro-2-oxopyrrolidin-1-yl)quinolin-4-yl)oxy)-3-methylphenyl) acetamide | (400 MHz, DMSO-$d_6$) δ 10.20 (s, 1H), 8.68-8.62 (m, 2H), 8.23 (dd, J = 9.2, 2.5 Hz, 1H), 8.12 (d, J = 9.2 Hz, 1H), 7.94 (s, 1H), 7.45 (s, 1H), 7.37 (d, J = 2.1 Hz, 1H), 7.30 (dd, J = 8.2, 2.2 Hz, 1H), 7.20 (d, J = 8.2 Hz, 1H), 6.44 (d, J = 5.1 Hz, 1H), 4.16 (t, J = 6.5 Hz, 2H), 3.60 (s, 2H), 2.89-2.71 (m, 2H), 2.11 (s, 3H), 1.48 (s, 9H) | 534.1 $(M + H)^+$ |
| 326 | 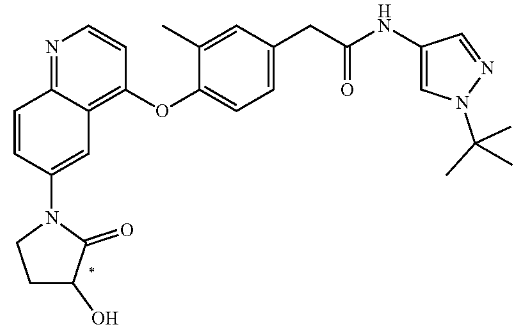 [SMILES: Cc1cc(CC(=O)Nc2cnn(C(C)(C)C)c2)ccc1Oc1ccnc2ccc(N3CCC(O)C3=O)cc12] enantiomer 1 (retention time: 1.56 min, column: CHIRALPAK IA-3, 4.6 × 50 mm, 3 μm; mobile phase A: hexane (0.1% DEA), mobile phase B: EtOH, isocratic separation with 50% B, flow rate: 1.0 mL/min, wavelength: 254 nm) | N-(1-(tert-butyl)-1H-pyrazol-4-yl)-2-(4-((6-(3-hydroxy-2-oxopyrrolidin-1-yl)quinolin-4-yl)oxy)-3-methylphenyl) acetamide | (400 MHz, DMSO-$d_6$) δ 10.21 (s, 1H), 8.59 (d, J = 5.1 Hz, 1H), 8.53 (d, J = 2.5 Hz, 1H), 8.28 (dd, J = 9.3, 2.6 Hz, 1H), 8.06 (d, J = 9.3 Hz, 1H), 7.95 (s, 1H), 7.46 (s, 1H), 7.37 (d, J = 2.1 Hz, 1H), 7.30 (dd, J = 8.3, 2.2 Hz, 1H), 7.19 (d, J = 8.2 Hz, 1H), 6.41 (d, J = 5.1 Hz, 1H), 5.85 (d, J = 5.9 Hz, 1H), 4.39 (td, J = 8.7, 5.8 Hz, 1H), 3.99-3.83 (m, 2H), 3.61 (s, 2H), 2.49-2.43 (m, 1H), 2.11 (s, 3H), 1.97-1.87 (m, 1H), 1.49 (s, 9H) | 514.0 $(M + H)^+$ |

-continued

| No. | Structure | Name | $^1$H NMR | Observed m/z |
| --- | --- | --- | --- | --- |
| 327 | 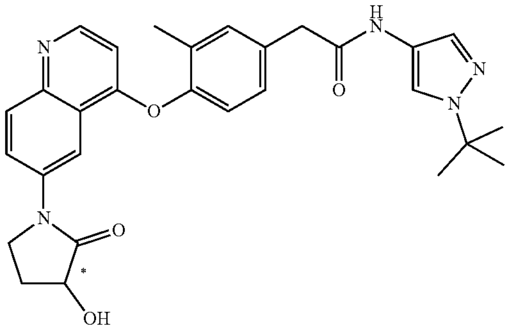 [SMILES: Cc1cc(CC(=O)Nc2cnn(C(C)(C)C)c2)ccc1Oc1ccnc2ccc(N3CCC(O)C3=O)cc12] enantiomer 2 (retention time: 2.19 min, column: CHIRALPAK IA-3, 4.6 x 50 mm, 3 μm; mobile phase A: hexane (0.1% DEA), mobile phase B: EtOH, isocratic separation with 50% B, flow rate: 1.0 mL/min, wavelength: 254 nm) | N-(1-(tert-butyl)-1H-pyrazol-4-yl)-2-(4-((6-(3-hydroxy-2-oxopyrrolidin-1-yl)quinolin-4-yl)oxy)-3-methylphenyl) acetamide | (400 MHz, DMSO-$d_6$) δ 10.21 (s, 1H), 8.59 (d, J = 5.1 Hz, 1H), 8.53 (d, J = 2.5 Hz, 1H), 8.28 (dd, J = 9.3, 2.6 Hz, 1H), 8.06 (d, J = 9.2 Hz, 1H), 7.95 (s, 1H), 7.46 (s, 1H), 7.37 (d, J = 2.2 Hz, 1H), 7.30 (dd, J = 8.2, 2.2 Hz, 1H), 7.19 (d, J = 8.2 Hz, 1H), 6.41 (d, J = 5.1 Hz, 1H), 5.85 (d, J = 5.9 Hz, 1H), 4.39 (td, J = 8.7, 5.7 Hz, 1H), 3.99-3.83 (m, 2H), 3.61 (s, 2H), 2.51-2.41 (m, 1H), 2.11 (s, 3H), 1.97-1.87 (m, 1H), 1.49 (s, 9H) | 514.0 $(M + H)^+$ |
| 414 | 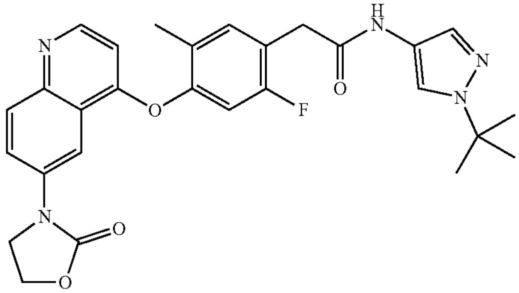 [SMILES: Cc1cc(CC(=O)Nc2cnn(C(C)(C)C)c2)c(F)cc1Oc1ccnc2ccc(N3CCOC3=O)cc12] | N-(1-(tert-butyl)-1H-pyrazol-4-yl)-2-(2-fluoro-5-methyl-4-((6-(2-oxooxazolidin-3-yl)quinolin-4-yl)oxy)phenyl) acetamide | | 518.5 $(M + H)^+$ |

Example 29—Synthesis of N-(1-(tert-butyl)-1H-pyrazol-4-yl)-2-(2-fluoro-4-((6-(methylsulfonyl) quinolin-4-yl)oxy)phenyl)acetamide (Compound 38); Prepared According to General Scheme 11

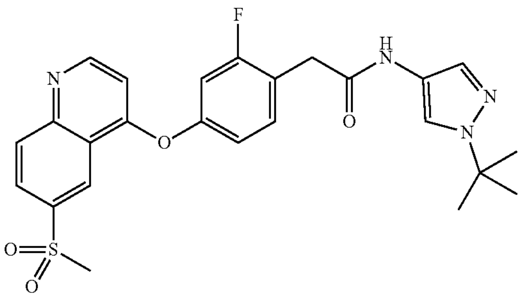 [SMILES: CC(C)(C)n1cc(NC(=O)Cc2ccc(Oc3ccnc4ccc(S(C)(=O)=O)cc34)cc2F)cn1]

$Cs_2CO_3$ (671.0 mg, 2.06 mmol, 2.00 equiv.), 4-chloro-6-(methylsulfonyl)quinoline (221 mg, 1.03 mmol, 1.00 equiv., can be synthesized as shown in Part II of Example 30), copper(I) iodide (78.5 mg, 0.412 mmol, 0.40 equiv.) and N,N-dimethylglycine (63.7 mg, 0.618 mmol, 0.60 equiv.) were added to a solution of N-(1-(tert-butyl)-1H-pyrazol-4-yl)-2-(2-fluoro-4-hydroxyphenyl)acetamide (300 mg, 1.03 mmol, 1.00 equiv., can be synthesized according to the synthesis described in Part II of Example 9) in 1,4-dioxane (5 mL) under an inert atmosphere of nitrogen. Subsequently, the reaction mixture was heated to 100° C. overnight. The solvent was removed under reduced pressure and the crude product was purified by reversed-phase flash chromatography (column: C18 silica gel; mobile phase A: water, mobile phase B: ACN, gradient: 10-50% B in 50 min; wavelength: 210 nm). The title compound was obtained as an off-white solid (133.4 mg, 25%). LCMS (ESI) calculated for $C_{25}H_{26}FN_4O_4S$ $(M+H)^+$: 497.2, found: 497.1. $^1$H NMR (300 MHz, DMSO-$d_6$) 310.23 (s, 1H), 8.91 (d, J=5.2 Hz, 1H), 8.85 (t, J=1.4 Hz, 1H), 8.29 (s, 1H), 8.28 (s, 1H), 7.94 (s, 1H), 7.56 (t, J=8.5 Hz, 1H), 7.45 (d, J=0.7 Hz, 1H), 7.37 (dd, J=10.5, 2.4 Hz, 1H), 7.21 (dd, J=8.5, 2.4 Hz, 1H), 6.83 (d, J=5.2 Hz, 1H), 3.72 (s, 2H), 3.38 (s, 3H), 1.49 (s, 9H).

Example 30—Synthesis of N-(1-(tert-butyl)-1H-pyrazol-4-yl)-2-(3-methyl-4-((6-(methylsulfonyl)quinolin-4-yl)oxy)phenyl)acetamide (Compound 86); Prepared According to General Scheme 11

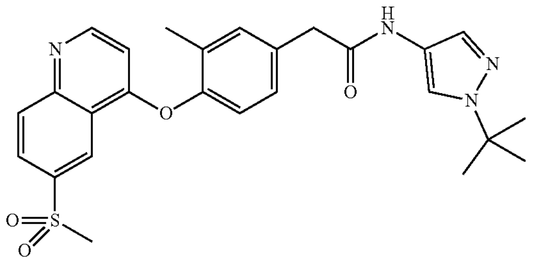 [SMILES: Cc1cc(CC(=O)Nc2cnn(C(C)(C)C)c2)ccc1Oc1ccnc2ccc(S(C)(=O)=O)cc12]

Part I—Synthesis of 4-chloro-6-(methylthio)quinoline

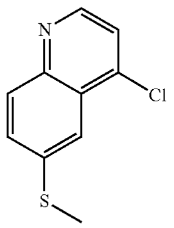

A solution of 6-bromo-4-chloroquinoline (commercially available, 50 g, 206 mmol, 1.00 equiv.), sodium thiomethoxide (28.9 g, 412 mmol, 2.00 equiv.), $Pd_2(dba)_3$ (4.72 g, 5.15 mmol, 0.025 equiv.), Xantphos (5.97 g, 10.3 mmol, 0.05 equiv.), and triethylamine (143 mmol, 1.03 mol, 5 equiv.) in 1,4-dioxane (300 mL) was heated to 80° C. for 5 h under an inert atmosphere of nitrogen. EtOAc was added and insoluble materials were filtered off. Next, the organic phase was washed with water and brine, dried over $Na_2SO_4$, and the solvent was removed under reduced pressure. EtOAc and hexanes were added (100 mL each), followed by silica gel (20 g). The slurry was stirred at room temperature for 30 min and the silica gel was subsequently filtered off and washed with EtOAc/hexanes (1:1). The solvent was removed under reduced pressure. The intended product was obtained as a red solid (43.5 g), which was used in the next reaction without further purification.

Part II—Synthesis of 4-chloro-6-(methylsulfonyl)quinoline

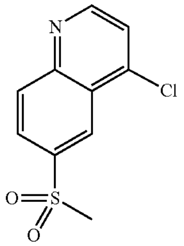

Oxone (139 g, 227 mmol, 1.1 equiv.) was added to a solution of 4-chloro-6-(methylthio)quinoline (43.2 g, 206 mmol, 1.00 equiv.) in THF (350 mL) and water (350 mL). The reaction mixture was stirred at room temperature for 2 h. Subsequently, water and EtOAc were added, and the organic phase was separated. The aqueous solution was neutralized with $K_2CO_3$ and extracted with EtOAc. The combined organic phases were washed with brine and dried over $Na_2SO_4$. The solvent was removed under reduced pressure. The obtained material was treated with DCM (200 mL) and hexanes (400 mL) to remove impurities. Next, the product was filtered off, washed with a small amount of EtOAc (ca. 40-50 mL) and hexanes and dried under reduced pressure. The intended product was obtained as a slightly yellowish solid (34.4 g, 69% yield), which was used in the next reaction without further purification.

Part III—Synthesis of 2-(4-hydroxy-3-methylphenyl)acetic Acid

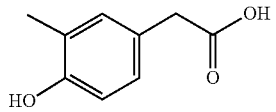

A solution of methyl 2-(4-hydroxy-3-methylphenyl)acetate (28.4 g, 158 mmol, 1.00 equiv.) and lithium hydroxide (9.44 g, 394 mmol, 2.50 equiv.) in THF (200 mL) and water (100 mL) was stirred at room temperature for 2 h. Subsequently, water was added, and the aqueous solution was washed with DCM. The pH was adjusted to 1-2 and the product was extracted with EtOAc. The combined organic phases were washed with brine, dried over $Na_2SO_4$, and the solvent was removed under reduced pressure. The intended product was obtained as a white solid (26.3 g, quantitative yield), which was used in the next reaction without further purification.

Part IV—Synthesis of N-(1-(tert-butyl)-1H-pyrazol-4-yl)-2-(4-hydroxy-3-methylphenyl)acetamide

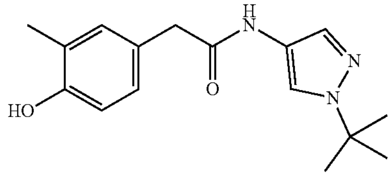 [SMILES: Cc1cc(CC(=O)Nc2cnn(C(C)(C)C)c2)ccc1O]

HATU (72.2 g, 190 mmol, 1.20 equiv.) was added to a solution of 2-(4-hydroxy-3-methylphenyl)acetic acid (26.3 g, 158 mmol, 1.00 equiv.), 1-tert-butylpyrazol-4-amine hydrochloride (30.6 g, 174 mmol, 1.10 equiv.), and DIPEA (82.7 mL, 474 mmol, 3.00 equiv.) in DMF (140 mL) and the mixture was stirred at room temperature for 2 h. Subsequently, water and EtOAc were added, and the organic phase was separated. The product was extracted with an aqueous NaOH solution. Subsequently, the pH was adjusted to 5-6 with HCl and the product was extracted with EtOAc. The organic phase was washed with brine, dried over $Na_2SO_4$, and the solvent was removed under reduced pressure. The residue was washed with EtOAc and dried under reduced pressure. The intended product was obtained as a white solid (27.1 g, 60%), which was used in the next reaction without further purification.

Part V—Synthesis of N-(1-(tert-butyl)-1H-pyrazol-4-yl)-2-(3-methyl-4-((6-(methylsulfonyl)quinolin-4-yl)oxy)phenyl)acetamide (Compound 86)

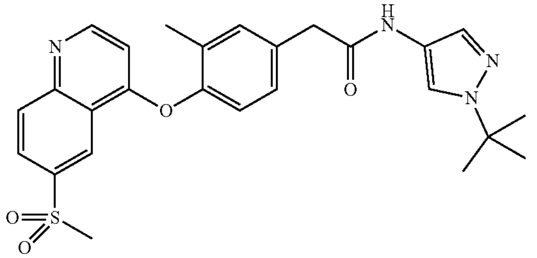 [SMILES: Cc1cc(CC(=O)Nc2cnn(C(C)(C)C)c2)ccc1Oc1ccnc2ccc(S(C)(=O)=O)cc12]

A solution of 4-chloro-6-methylsulfonylquinoline (22.8 g, 94.3 mmol, 1.00 equiv.), N-(1-tert-butylpyrazol-4-yl)-2-(4hydroxy-3-methylphenyl)acetamide (27.1 g, 94.3 mmol, 1.00 equiv.), DMAP (1.15 g, 9.43 mmol, 0.10 equiv.), and $K_2CO_3$ (19.5 g, 141 mmol, 1.50 equiv.) in DMF (90 mL) was heated to 120° C. for 3.5 h. More 4-chloro-6-methylsulfonylquinoline (2.28 g, 9.43 mmol, 0.10 equiv.) and $K_2CO_3$ (1.95 g, 14.1 mmol, 0.15 equiv.) were added and the heating was continued for another 1.5 h. Water and EtOAc were added, and the organic phase was separated. The organic phase was washed with water and the product was extracted with aqueous HCl (pH 1). The aqueous phase was washed with EtOAc and the pH was adjusted to 5-7. The product was extracted with EtOAc and the organic phase was washed with water, brine, dried over $Na_2SO_4$, and the solvent was removed under reduced pressure. The crude product was dissolved in DCM, and the organic solution was washed with an aqueous NaOH solution (pH 11-12) to remove remaining phenol starting material impurities. The organic phase was washed with brine, dried over $Na_2SO_4$, and the solvent was removed under reduced pressure. The residue was purified via column chromatography (DCM/MeOH 95:5). The intended product was obtained as a slightly yellowish solid (17.3 g, 37% yield). LCMS (ESI) calculated for $C_{26}H_{29}N_4O_4S$ $(M+H)^+$: 493.2, found: 493.1. $^1H$ NMR (400 MHz, DMSO-$d_6$) 310.20 (s, 1H), 8.91 (dd, J=1.9, 0.9 Hz, 1H), 8.84 (d, J=5.3 Hz, 1H), 8.29-8.27 (m, 2H), 7.95 (s, 1H), 7.46 (s, 1H), 7.39 (d, J=2.1 Hz, 1H), 7.32 (dd, J=8.3, 2.2 Hz, 1H), 7.23 (d, J=8.3 Hz, 1H), 6.55 (d, J=5.2 Hz, 1H), 3.62 (s, 2H), 3.39 (s, 3H), 2.14 (s, 3H), 1.49 (s, 9H).

Example 31—Synthesis of N-(1-(tert-butyl)-1H-pyrazol-4-yl)-2-(3-methyl-4-((6-((1-methylazetidin-3-yl)sulfonyl)quinolin-4-yl)oxy)phenyl)acetamide (Compound 149); Prepared According to General Scheme 11

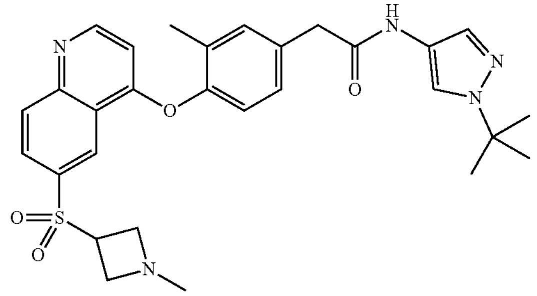 [SMILES: Cc1cc(CC(=O)Nc2cnn(C(C)(C)C)c2)ccc1Oc1ccnc2ccc(S(=O)(=O)C3CN(C)C3)cc12]

Part I—Synthesis of tert-butyl 3-((4-(4-(2-((1-(tert-butyl)-1H-pyrazol-4-yl)amino)-2-oxoethyl)-2-methylphenoxy)quinolin-6-yl)thio)azetidine-1-carboxylate

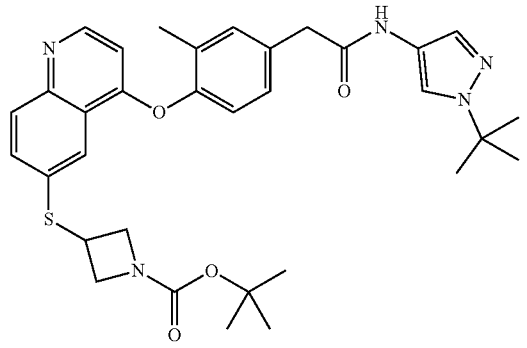 [SMILES: Cc1cc(CC(=O)Nc2cnn(C(C)(C)C)c2)ccc1Oc1ccnc2ccc(SC3CN(C(=O)OC(C)(C)C)C3)cc12]

A solution of 2-(4-((6-bromoquinolin-4-yl)oxy)-3-methylphenyl)-N-(1-(tert-butyl)-1H-pyrazol-4-yl)acetamide (1.00 g, 2.03 mmol, 1.00 equiv.), tert-butyl 3-mercaptoazetidine-1-carboxylate (767 mg, 4.05 mmol, 2.00 equiv., can be prepared according to the synthesis described in Part II of Example 43) triethylamine (1.03 g, 10.1 mmol, 5.00 equiv.), $Pd_2(dba)_3$ (371 mg, 0.405 mmol, 0.20 equiv.) and Xantphos (234.5 mg, 0.405 mmol, 0.2 equiv.) in 1,4-dioxane (10 mL) was heated to 80° C. for 1 h under an inert atmosphere of nitrogen. The solvent was removed under reduced pressure and the crude product was purified by column chromatography (petroleum ether/EtOAc 1:1). The title compound was obtained as a yellow solid (770 mg, 63%).

Part II—Synthesis of 2-(4-((6-(azetidin-3-ylthio)quinolin-4-yl)oxy)-3-methylphenyl)-N-(1-(tert-butyl)-1H-pyrazol-4-yl)acetamide

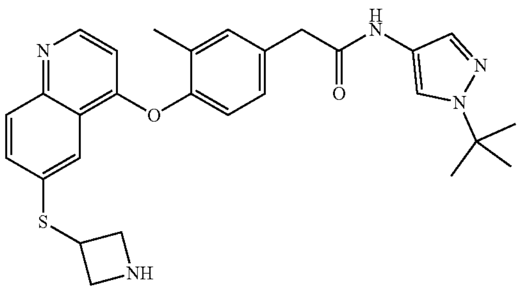 [SMILES: Cc1cc(CC(=O)Nc2cnn(C(C)(C)C)c2)ccc1Oc1ccnc2ccc(SC3CNC3)cc12]

A solution of HCl in 1,4-dioxane (4 M, 7 mL) was added to a solution of tert-butyl 3-((4-(4-(2-((1-(tert-butyl)-1H-pyrazol-4-yl)amino)-2-oxoethyl)-2-methylphenoxy)quinolin-6-yl)thio)azetidine-1-carboxylate carboxylate (700 mg, 1.16 mmol, 1.00 equiv.) in DCM (7 mL) and the mixture was stirred at room temperature for 30 min. Subsequently, the solvent was removed under reduced pressure. The title compound was obtained as a yellow solid (560 mg, 96%), which was used in the next reaction without further purification.

Part III—Synthesis of N-(1-(tert-butyl)-1H-pyrazol-4-yl)-2-(3-methyl-4-((6-((1-methylazetidin-3-yl)thio)quinolin-4-yl)oxy)phenyl)acetamide

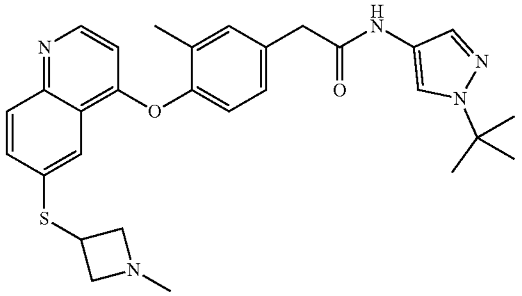 [SMILES: Cc1cc(CC(=O)Nc2cnn(C(C)(C)C)c2)ccc1Oc1ccnc2ccc(SC3CN(C)C3)cc12]

A solution of 2-(4-((6-(azetidin-3-ylthio)quinolin-4-yl)oxy)-3-methylphenyl)-N-(1-(tert-butyl)-1H-pyrazol-4-yl)acetamide (560 mg, 1.12 mmol, 1.00 equiv.), sodium acetate (458 mg, 5.58 mmol, 5.00 equiv.), formaldehyde (35% in water, 0.08 mL, 2.23 mmol, 2.00 equiv.), and palladium on carbon (119 mg, 20 wt. %) in MeOH (12 mL) was stirred at room temperature for 60 h under an atmosphere of hydrogen gas. Subsequently, the heterogeneous catalyst was filtered off and washed with MeOH (4×10 mL). The solvent was removed under reduced pressure and the crude product was purified by column chromatography (DCM/MeOH 10:1). The title compound was obtained as a yellow oil (330 mg, 57%).

Part IV—Synthesis of N-(1-(tert-butyl)-1H-pyrazol-4-yl)-2-(3-methyl-4-((6-((1-methylazetidin-3-yl)sulfonyl)quinolin-4-yl)oxy)phenyl)acetamide (Compound 149)

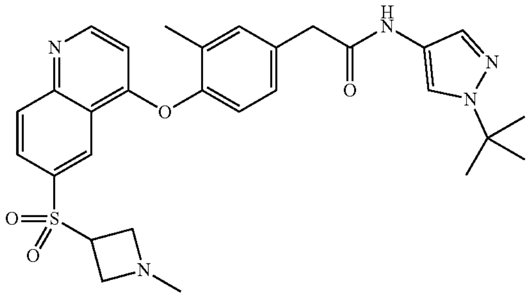 [SMILES: Cc1cc(CC(=O)Nc2cnn(C(C)(C)C)c2)ccc1Oc1ccnc2ccc(S(=O)(=O)C3CN(C)C3)cc12]

A solution of oxone (1.91 g, 3.11 mmol, 5.00 equiv.) in water (3.2 mL) was added to a solution of N-(1-(tert-butyl)-1H-pyrazol-4-yl)-2-(3-methyl-4-((6-((1-methylazetidin-3-yl)thio)quinolin-4-yl)oxy)phenyl)acetamide (320 mg, 0.621 mmol, 1.00 equiv.) in MeOH (3.2 mL) and the mixture was stirred at room temperature for 10 min. Insoluble byproducts were filtered off and washed with MeOH (2×2 mL). The solvent was removed under reduced pressure and the crude product was purified by reversed-phase flash chromatography (column: C18 silica gel; mobile phase A: water, mobile phase B: ACN, gradient: 20-60% B in 50 min; wavelength: 210 nm). The title compound was obtained as an off-white solid (77.6 mg, 23%). LCMS (ESI) calculated for $C_{29}H_{34}N_5O_4S$ $(M+H)^+$: 548.2, found: 548.3. $^1H$ NMR (300 MHz, DMSO-$d_6$) 310.20 (s, 1H), 8.92-8.80 (m, 2H), 8.32-8.11 (m, 2H), 7.95 (s, 1H), 7.46 (s, 1H), 7.40 (s, 1H), 7.35-7.23 (m, 2H), 6.58 (d, J=5.2 Hz, 1H), 4.57 (t, J=7.3 Hz, 1H), 3.62 (s, 2H), 3.58 (d, J=7.9 Hz, 4H), 2.31 (s, 3H), 2.14 (s, 3H), 1.49 (s, 9H).

Example 32—Synthesis of N-(1-(tert-butyl)-1H-pyrazol-4-yl)-2-(2-fluoro-4-((6-(methylsulfinyl)quinolin-4-yl)oxy)phenyl)acetamide (Compound 45); Prepared According to General Scheme 19

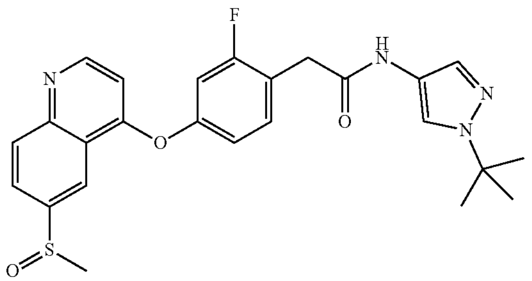 [SMILES: CS(=O)c1ccc2nccc(Oc3ccc(CC(=O)Nc4cnn(C(C)(C)C)c4)c(F)c3)c2c1]

Part I—Synthesis of 2-(4-((6-bromoquinolin-4-yl)oxy)-2-fluorophenyl)-N-(1-(tert-butyl)-1H-pyrazol-4-yl)acetamide

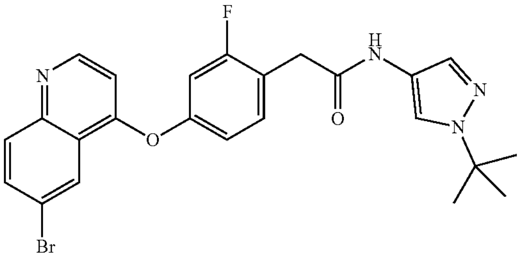 [SMILES: CC(C)(C)n1cc(NC(=O)Cc2ccc(Oc3ccnc4ccc(Br)cc34)cc2F)cn1]

N-(1-(tert-butyl)-1H-pyrazol-4-yl)-2-(2-fluoro-4-hydroxyphenyl)acetamide (2.88 g, 9.90 mmol, 1.20 equiv., can be synthesized according to the synthesis described in Part II of Example 9), copper(I) iodide (22.0 mg, 0.115 mmol, 0.014 equiv.), $Cs_2CO_3$ (5.37 g, 16.5 mmol, 2.00 equiv.), and 2,2,6,6-tetramethyl-3,5-heptanedione (21.3 mg, 0.115 mmol, 0.014 equiv.) were added to a solution of 6-bromo-4-chloroquinoline (commercially available, 2.00 g, 8.25 mmol, 1.00 equiv.) in DMF (20 mL) under an inert atmosphere of nitrogen. Subsequently, the reaction mixture was heated to 100° C. for 3 h. The reaction was quenched with water and the product was extracted with EtOAc (3×50 mL). The combined organic phases were washed with brine (3×10 mL), dried over $MgSO_4$ and the solvent was removed under reduced pressure. The crude product was purified by column chromatography (petroleum ether/EtOAc 1:1). The title compound was obtained as a light-yellow solid (2.0 g, 46%).

Part II—Synthesis of N-(1-(tert-butyl)-1H-pyrazol-4-yl)-2-(2-fluoro-4-((6-(methylthio)quinolin-4-yl)oxy)phenyl)acetamide

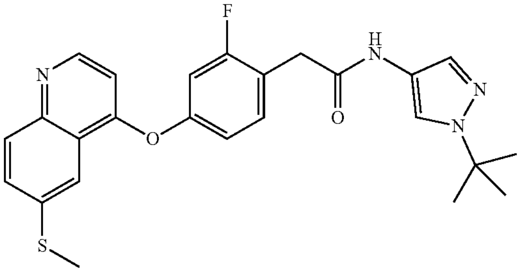 [SMILES: CSc1ccc2nccc(Oc3ccc(CC(=O)Nc4cnn(C(C)(C)C)c4)c(F)c3)c2c1]

Sodium thiomethoxide (0.36 g, 5.13 mmol, 1.50 equiv.), $Pd_2(dba)_3$ (0.63 g, 0.684 mmol, 0.20 equiv.), Xantphos (0.4 g, 0.684 mmol, 0.20 equiv.), and triethylamine (1.73 g, 17.1 mmol, 5.00 equiv.) were added to a solution of 2-(4-((6-bromoquinolin-4-yl)oxy)-2-fluorophenyl)-N-(1-(tert-butyl)-1H-pyrazol-4-yl)acetamide (1.7 g, 3.42 mmol, 1.00 equiv.) in 1,4-dioxane (17 mL) under an inert atmosphere of nitrogen. Subsequently, the reaction mixture was heated to 80° C. for 3 h. The reaction was quenched with water and the product was extracted with EtOAc (3×50 mL). The combined organic phases were washed with brine (10 mL), dried over $MgSO_4$ and the solvent was removed under reduced pressure. The crude product was purified by column chromatography (petroleum ether/EtOAc 1:1). The title compound was obtained as a light-yellow solid (1.43 g, 86%).

Part III—Synthesis of N-(1-(tert-butyl)-1H-pyrazol-4-yl)-2-(2-fluoro-4-((6-(methylsulfinyl)quinolin-4-yl)oxy)phenyl)acetamide (Compound 45)

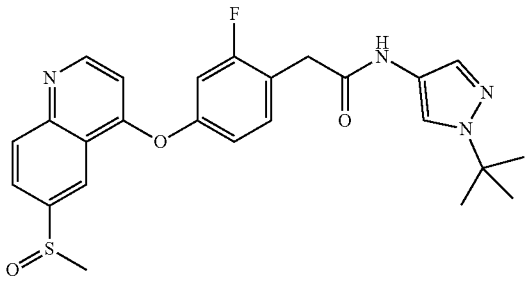 [SMILES: CS(=O)c1ccc2nccc(Oc3ccc(CC(=O)Nc4cnn(C(C)(C)C)c4)c(F)c3)c2c1]

A solution of $NaIO_4$ (276.3 mg, 1.29 mmol, 2.00 equiv.) in water (3 mL) was added dropwise to a solution of N-(1-(tert-butyl)-1H-pyrazol-4-yl)-2-(2-fluoro-4-((6-(methylthio)quinolin-4-yl)oxy)phenyl)acetamide (300 mg, 0.646 mmol, 1.00 equiv.) in THF (3 mL) at room temperature. Subsequently, the reaction mixture was stirred at room temperature for 60 h. The crude product was then purified by reversed-phase flash chromatography (column: C18 silica gel; mobile phase A: water, mobile phase B: ACN, gradient: 20-50% B in 30 min; wavelength: 210 nm). The title compound was obtained as a white solid (98.9 mg, 31%). LCMS (ESI) calculated for $C_{25}H_{25}FN_4NaO_3S$ $(M+Na)^+$: 503.2, found: 503.0. $^1H$ NMR (400 MHz, DMSO-$d_6$) δ 10.23 (s, 1H), 8.83 (d, J=5.2 Hz, 1H), 8.62 (d, J=2.0 Hz, 1H), 8.21 (d, J=8.8 Hz, 1H), 8.07 (dd, J=8.9, 2.0 Hz, 1H), 7.95 (s, 1H), 7.55 (t, J=8.5 Hz, 1H), 7.46 (s, 1H), 7.35 (dd, J=10.5, 2.4 Hz, 1H), 7.19 (dd, J=8.4, 2.4 Hz, 1H), 6.79 (d, J=5.2 Hz, 1H), 3.72 (s, 2H), 2.88 (s, 3H), 1.49 (s, 9H)

Example 33—Synthesis of N-(1-cyclopentyl-1H-pyrazol-4-yl)-2-(3-methyl-4-((6-(methylsulfonyl)quinolin-4-yl)oxy)phenyl)acetamide (Compound 214); Prepared According to General Scheme 3

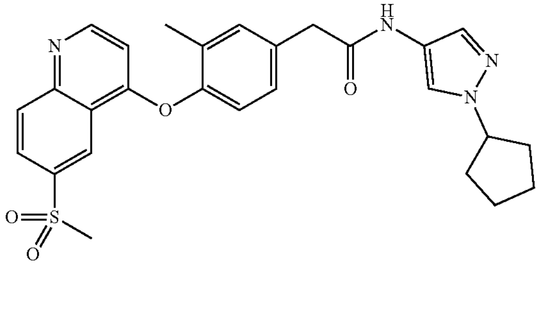 [SMILES: Cc1cc(CC(=O)Nc2cnn(C3CCCC3)c2)ccc1Oc1ccnc2ccc(S(C)(=O)=O)cc12]

Part I—Synthesis of 1-cyclopentyl-4-nitro-1H-pyrazole

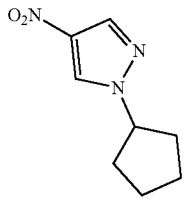 [SMILES: O=[N+]([O-])c1cnn(C2CCCC2)c1]

DEAD (6.01 g, 34.5 mmol, 1.30 equiv.) was added to a solution of 4-nitro-1H-pyrazole (3.00 g, 26.5 mmol, 1.00 equiv.), triphenylphosphine (8.35 g, 31.8 mmol, 1.20 equiv.), and cyclopentanol (2.51 g, 29.2 mmol, 1.10 equiv.) in THF (60 mL) at 0° C. and the mixture was stirred at this temperature for 2 h. Subsequently, a saturated aqueous solution of ammonium chloride (60 mL) was added, and the product was extracted with DCM (3×20 mL). The combined organic phases were dried over $Na_2SO_4$, and the solvent was removed under reduced pressure. The crude product was purified by column chromatography (petroleum ether/EtOAc 100:1). The title compound was obtained as a yellow oil (3.6 g, 74%).

Part II—Synthesis of 1-cyclopentyl-1H-pyrazol-4-amine

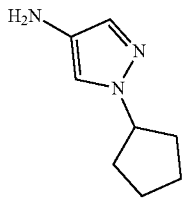

Palladium on carbon (30 mg, 10 wt. %) was added to a solution of 1-cyclopentyl-4-nitro-1H-pyrazole (300 mg, 1.66 mmol, 1.0 equiv.) in isopropanol (6 mL) and the mixture was stirred overnight at room temperature under an atmosphere of hydrogen. Subsequently, the heterogenous catalyst was filtered off and the solvent was removed under reduced pressure. The crude product was used in the next reaction without any further purification.

Part III—Synthesis of methyl 2-(3-methyl-4-((6-(methylsulfonyl)quinolin-4-yl)oxy)phenyl)acetate

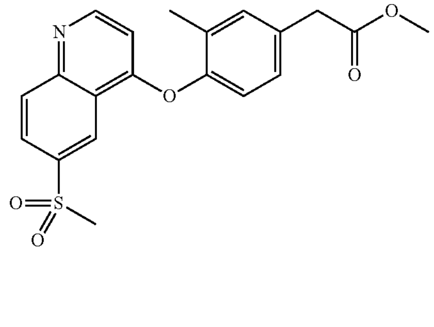 [SMILES: COC(=O)Cc1ccc(Oc2ccnc3ccc(S(C)(=O)=O)cc23)c(C)c1]

A solution of methyl 2-(4-hydroxy-3-methylphenyl)acetate (1.49 g, 8.28 mmol, 1.00 equiv.), 4-chloro-6-(methylsulfonyl)quinoline (2.0 g, 8.28 mmol, 1.00 equiv., can be synthesized as shown in Part II of Example 30), and $Cs_2CO_3$ (5.39 g, 16.6 mmol, 2.00 equiv.) in NMP (22 mL) was stirred at room temperature for 4 h. Subsequently, the mixture was filtered, and the crude product was purified by reversed-phase flash chromatography (column: C18 silica gel; mobile phase A: water (0.1% $NH_4HCO_3$), mobile phase B: ACN, gradient: 35-55% B in 40 min; wavelength: 210 nm). The title compound was obtained as a white solid (1.5 g, 47%).

Part IV—Synthesis of 2-(3-methyl-4-((6-(methylsulfonyl)quinolin-4-yl)oxy)phenyl)acetic Acid

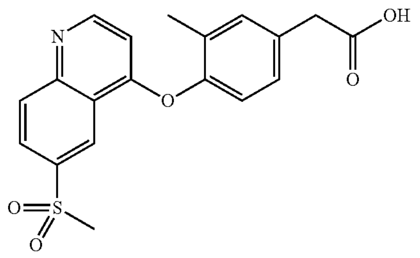 [SMILES: Cc1cc(CC(=O)O)ccc1Oc1ccnc2ccc(S(C)(=O)=O)cc12]

LiOH (0.15 g, 6.26 mmol, 2.00 equiv.) was added to a solution of methyl 2-(3-methyl-4-((6-(methylsulfonyl)quinolin-4-yl)oxy)phenyl)acetate (1.2 g, 3.11 mmol, 1.00 equiv.) in THF (12 mL) and water (12 mL) at 0° C. and the mixture was stirred at this temperature for 2 h. Subsequently, the pH of the solution was adjusted to 5 by the addition of hydrochloric acid (1 M) and the product was extracted with EtOAc (3×20 mL). The combined organic phases were washed with brine, dried over $Na_2SO_4$, and the solvent was removed under reduced pressure. The title compound was obtained as a white solid (1.1 g, 95%), which was used in the next reaction without further purification.

Part V—Synthesis of N-(1-cyclopentyl-1H-pyrazol-4-yl)-2-(3-methyl-4-((6-(methylsulfonyl)quinolin-4-yl)oxy)phenyl)acetamide (Compound 214)

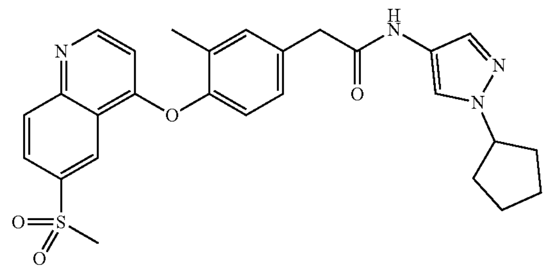 [SMILES: Cc1cc(CC(=O)Nc2cnn(C3CCCC3)c2)ccc1Oc1ccnc2ccc(S(C)(=O)=O)cc12]

Propylphosphonic anhydride (257 mg, 0.807 mmol, 1.50 equiv.) was added to a solution of 2-(3-methyl-4-((6-(methylsulfonyl)quinolin-4-yl)oxy)phenyl)acetic acid (200 mg, 0.538 mmol, 1.00 equiv.), 1-cyclopentyl-1H-pyrazol-4-amine (111 mg, 0.807 mmol, 1.50 equiv.) and DIPEA (348 mg, 2.69 mmol, 5.00 equiv.) in DMF (4 mL) at 0° C. and the mixture was stirred at this temperature for 1 h. Subsequently, the crude product was purified reversed-phase flash chromatography (column: C18 silica gel; mobile phase A: water (0.05% $(NH_4)_2CO_3$), mobile phase B: ACN, gradient: 25-55% B in 30 min; wavelength: 210 nm). The title compound was obtained as a white solid (48.4 mg, 17%). LCMS (ESI) calculated for $C_{27}H_{27}N_4O_4S$ $(M-H)^-$: 503.2, found: 503.1. $^1H$ NMR (400 MHz, DMSO-$d_6$) 310.21 (s, 1H), 8.90 (s, 1H), 8.83 (d, J=5.2 Hz, 1H), 8.28-8.26 (m, 2H), 7.90 (s, 1H), 7.43 (s, 1H), 7.39 (s, 1H), 7.31 (d, J=8.1 Hz, 1H), 7.23 (d, J=8.2 Hz, 1H), 6.55 (d, J=5.2 Hz, 1H), 4.69-4.57 (m, 1H), 3.61 (s, 2H), 3.38 (s, 3H), 2.14 (s, 3H), 2.09-1.97 (m, 2H), 1.93-1.82 (m, 2H), 1.81-1.68 (m, 2H), 1.67-1.54 (m, 2H).

Example 34—Synthesis of N-(1-(tert-butyl)-1H-pyrazol-4-yl)-2-(4-((6-(cyclobutylsulfonyl)quinolin-4-yl)oxy)-3-methylphenyl)acetamide (Compound 280); Prepared According to General Scheme 12

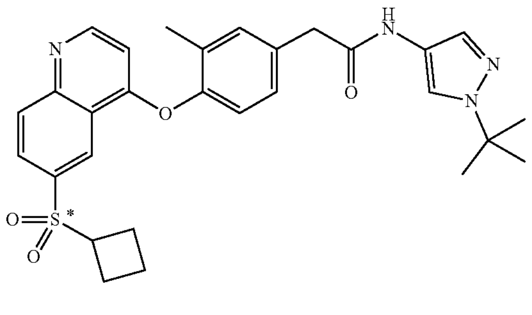

Part I—Synthesis of S-(4-chloroquinolin-6-yl) ethanethioate

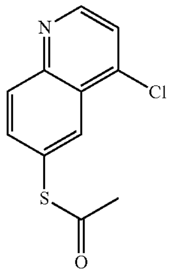

A solution of 6-bromo-4-chloroquinoline (50.0 g, 206 mmol, 1.00 equiv., commercially available), potassium thioacetate (47.1 g, 412 mmol, 2.00 equiv.), DIPEA (213 g, 1.65 mol, 8.00 equiv.), $Pd_2(dba)_3$ (5.93 g, 10.3 mmol, 0.05 equiv.), and XPhos (9.83 g, 20.6 mmol, 0.10 equiv.) in 1,4-dioxane (500 mL) was heated to 100° C. for 1 h under an inert atmosphere of nitrogen. Subsequently, EtOAc (300 mL) was added, and insoluble byproducts were filtered off. The organic phase was washed with eater (3×300 mL), dried over $Na_2SO_4$, and the solvent was removed under reduced pressure. The crude product was purified by column chromatography (gradient of petroleum ether to petroleum ether/EtOAc 9:1). The title compound was obtained as a white solid (11 g, 22%).

Part II—Synthesis of 4-chloro-6-(cyclobutylthio)quinoline

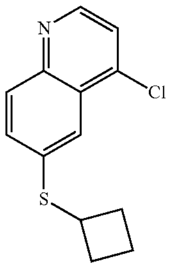 [SMILES: Clc1ccnc2ccc(SC3CCC3)cc12]

Iodocyclobutane (768 mg, 4.21 mmol, 1.00 equiv.) was added to a solution of S-(4-chloroquinolin-6-yl) ethanethioate (1.00 g, 4.21 mmol, 1.00 equiv.) and $K_2CO_3$ (1.16 g, 8.42 mmol, 2.00 equiv.) in MeOH (10 mL) and the mixture was stirred at room temperature for 1 h. Subsequently, insoluble byproducts were filtered off and the solvent was removed under reduced pressure. The crude product was purified by preparative HPLC (column: XB-C18; 50×250 mm, 10 μm; mobile phase A: water (10 mmol/L $NH_4HCO_3$), mobile phase B: ACN; flow rate: 100 mL/min; gradient: 35-55% B in 30 min; wavelength: 210 nm). The title compound was obtained as a yellow solid (512 mg, 49%).

Part III—Synthesis of 4-chloro-6-(cyclobutylsulfonyl)quinoline

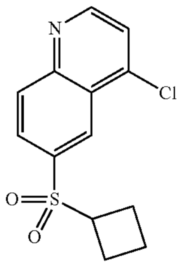 [SMILES: O=S(=O)(c1ccc2nccc(Cl)c2c1)C1CCC1]

mCPBA (311 mg, 3.60 mmol, 2.00 equiv.) was added to a solution of 4-chloro-6-(cyclobutylthio)quinoline (450 mg, 1.80 mmol, 1.00 equiv.) in DCM (9 mL) and the mixture was stirred at room temperature for 2 h. Subsequently, the crude product was purified by preparative HPLC (column: XBridge Prep OBD C18; 30×150 mm, 5 μm; mobile phase A: water (10 mmol/L $NH_4HCO_3$), mobile phase B: ACN; flow rate: 100 mL/min; gradient: 55-65% B in 20 min; wavelength: 220 nm). The title compound was obtained as a white solid (470 mg, 93%).

Part IV—Synthesis of N-(1-(tert-butyl)-1H-pyrazol-4-yl)-2-(4-((6-(cyclobutylsulfonyl)quinolin-4-yl)oxy)-3-methylphenyl)acetamide (Compound 280)

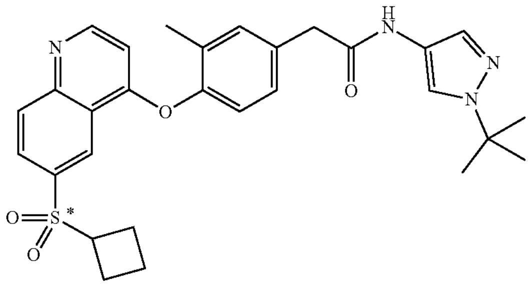

A solution of 4-chloro-6-(cyclobutylsulfonyl)quinoline (100 mg, 0.355 mmol, 1.00 equiv.), N-(1-(tert-butyl)-1H-pyrazol-4-yl)-2-(4-hydroxy-3-methylphenyl)acetamide (102 mg, 0.355 mmol, 1.00 equiv.), $Cs_2CO_3$ (232 mg, 0.710 mmol, 2.00 equiv.), CuI (67.6 mg, 0.355 mmol, 1.00 equiv.), and N,N-dimethylglycine (54.9 mg, 0.532 mmol, 1.50 equiv.) in 1,4-dioxane (5 mL) was heated to 100° C. overnight under an inert atmosphere of nitrogen. Subsequently, insoluble byproducts were filtered off and the crude product was purified by preparative PLC (column: XB-C18; 50×250 mm, 10 μm; mobile phase A: water (10 mmol/L $NH_4HCO_3$), mobile phase B: ACN; flow rate: 100 mL/min; gradient: 55175H B in 30 min; wavelength: 210 nm). The title compound was obtained as a yellow solid (35.7 mg, 190). LCMS (ESI) calculated for $C_{29}H_{33}N_4O_4S$ (M+H)l: 533.2, found: 533.2. $^1$H NMR (400 MHz, DMSO-$d_6$) 10.21 (s, 1H), 8.87-8.82 (m, 2H), 8.26 (d, J=8.9 Hz, 1H), 8.18 (dd, J=8.8, 2.1 Hz, 1H), 7.95 (s, 1H), 7.46 (s, 1H), 7.39 (s, 1H), 7.32 (d, J=8.2 Hz, 1H), 7.25 (d, J=8.2 Hz, 1H), 6.57 (d, J=5.3 Hz, 1H), 4.37-4.25 (m, 1H), 3.62 (s, 2H), 2.47-2.34 (m, 2H), 2.16 (ddd, J=7.1, 4.7, 2.2 Hz, 2H), 2.13 (s, 3H), 2.02-1.86 (m, 2H), 1.49 (s, 9H).

Example 35—Preparation of Additional Sulfone Compounds

Compounds in the table below were prepared based on experimental procedures described in Examples 30-34 and the detailed description.

| No. | Structure | Name | $^1$H NMR | Observed m/z |
|---|---|---|---|---|
| 40 | 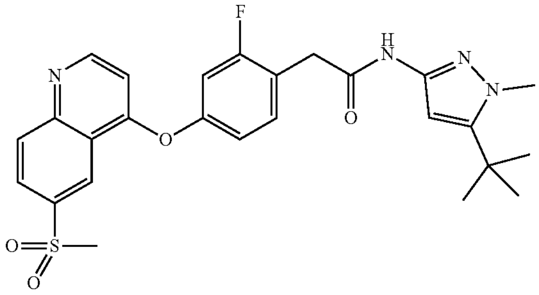 [SMILES: Cn1nc(NC(=O)Cc2ccc(Oc3ccnc4ccc(S(C)(=O)=O)cc34)cc2F)cc1C(C)(C)C] | N-(5-(tert-butyl)-1-methyl-1H-pyrazol-3-yl)-2-(2-fluoro-4-((6-(methylsulfonyl)quinolin-4-yl)oxy)phenyl)acetamide | (300 MHz, DMSO-$d_6$) δ 10.60 (s, 1H), 8.90 (d, J = 5.2 Hz, 1H), 8.85 (d, J = 1.5 Hz, 1H), 8.28 (d, J = 1.4 Hz, 2H), 7.55 (t, J = 8.5 Hz, 1H), 7.36 (dd, J = 10.4, 2.3 Hz, 1H), 7.21 (dd, J = 8.6, 2.4 Hz, 1H), 6.83 (d, J = 5.2 Hz, 1H), 6.30 (s, 1H), 3.80 (s, 3H), 3.73 (s, 2H), 3.38 (s, 3H), 1.31 (s, 9H) | 511.0 $(M + H)^+$ |
| 44 | 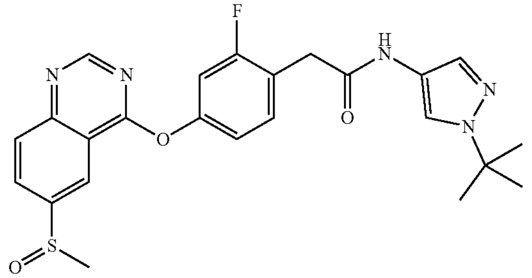 [SMILES: CS(=O)c1ccc2ncnc(Oc3ccc(CC(=O)Nc4cnn(C(C)(C)C)c4)c(F)c3)c2c1] | N-(1-(tert-butyl)-1H-pyrazol-4-yl)-2-(2-fluoro-4-((6-(methylsulfinyl)quinazolin-4-yl)oxy)phenyl)acetamide | (300 MHz, DMSO-$d_6$) δ 10.24 (s, 1H), 8.85 (s, 1H), 8.65 (s, 1H), 8.36-8.12 (m, 2H), 7.94 (d, J = 3.9 Hz, 1H), 7.59-7.13 (m, 4H), 3.70 (s, 2H), 2.90 (s, 3H), 1.48 (s, 9H) | 482.0 $(M + H)^+$ |
| 87 | 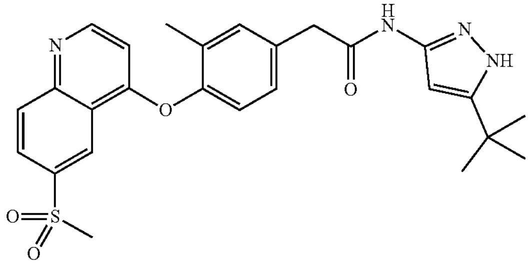 [SMILES: Cc1cc(CC(=O)Nc2cc(C(C)(C)C)[nH]n2)ccc1Oc1ccnc2ccc(S(C)(=O)=O)cc12] | N-(5-(tert-butyl)-1H-pyrazol-3-yl)-2-(3-methyl-4-((6-(methylsulfonyl)quinolin-4-yl)oxy)phenyl)acetamide | (400 MHz, DMSO-$d_6$) δ 12.04 (s, 1H), 10.56 (s, 1H), 8.91 (t, J = 1.3 Hz, 1H), 8.83 (d, J = 5.2 Hz, 1H), 8.31-8.21 (m, 2H), 7.40 (d, J = 2.2 Hz, 1H), 7.33 (dd, J = 8.2, 2.2 Hz, 1H), 7.23 (d, J = 8.2 Hz, 1H), 6.56 (d, J = 5.2 Hz, 1H), 6.29 (s, 1H), 3.64 (s, 2H), 3.38 (s, 3H), 2.14 (s, 3H), 1.24 (s, 9H) | 493.1 $(M + H)^+$ |

-continued

| No. | Structure | Name | $^1$H NMR | Observed m/z |
|---|---|---|---|---|
| 89 | 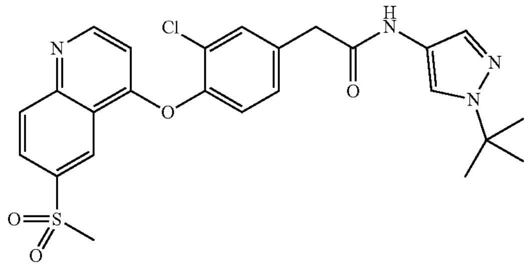 | N-(1-(tert-butyl)-1H-pyrazol-4-yl)-2-(3-chloro-4-((6-(methylsulfonyl)quinolin-4-yl)oxy)phenyl)acetamide | (300 MHz, DMSO-$d_6$) δ 10.26 (s, 1H), 8.89-8.87 (m, 2H), 8.31-8.30 (m, 2H), 7.96 (s, 1H), 7.69 (d, J = 2.0 Hz, 1H), 7.58-7.44 (m, 3H), 6.65 (d, J = 5.2 Hz, 1H), 3.70 (s, 2H), 3.40 (s, 3H), 1.49 (s, 9H) | 513.1 $(M + H)^+$ |
| 91 | 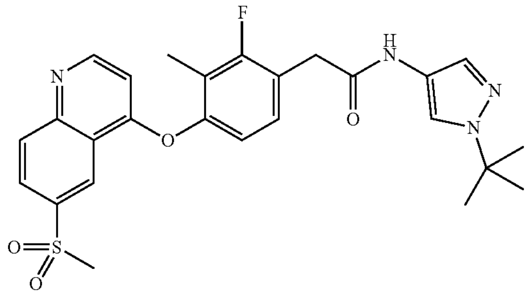 [SMILES: Cc1c(Oc2ccnc3ccc(S(C)(=O)=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(methylsulfonyl)quinolin-4-yl)oxy)phenyl)acetamide | (300 MHz, DMSO-$d_6$) δ 10.25 (s, 1H), 8.93-8.90 (m, 1H), 8.88 (d, J = 5.2 Hz, 1H), 8.31-8.29 (m, 2H), 7.95 (s, 1H), 7.47 (s, 1H), 7.40 (t, J = 8.4 Hz, 1H), 7.16 (d, J = 8.4 Hz, 1H), 6.64 (d, J = 5.2 Hz, 1H), 3.72 (s, 2H), 3.40 (s, 3H), 2.09 (s, 3H), 1.49 (s, 9H) | 511.0 $(M + H)^+$ |
| 93 | 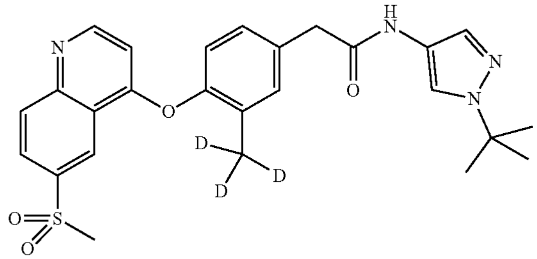 [SMILES: [2H]C([2H])([2H])c1cc(CC(=O)Nc2cnn(C(C)(C)C)c2)ccc1Oc1ccnc2ccc(S(C)(=O)=O)cc12] | N-(1-(tert-butyl)-1H-pyrazol-4-yl)-2-(3-(methyl-$d_3$)-4-((6-(methylsulfonyl)quinolin-4-yl)oxy)phenyl)acetamide | (300 MHz, DMSO-$d_6$) δ 10.20 (s, 1H), 8.93-8.90 (m, 1H), 8.84 (d, J = 5.2 Hz, 1H), 8.31-8.26 (m, 2H), 7.95 (s, 1H), 7.46 (s, 1H), 7.40 (d, J = 2.2 Hz, 1H), 7.31 (d, J = 2.3 Hz, 1H), 7.24 (d, J = 8.2 Hz, 1H), 6.56 (d, J = 5.2 Hz, 1H), 3.62 (s, 2H), 3.39 (s, 3H), 1.49 (s, 9H) | 494.1 $(M - H)^-$ |
| 97 | 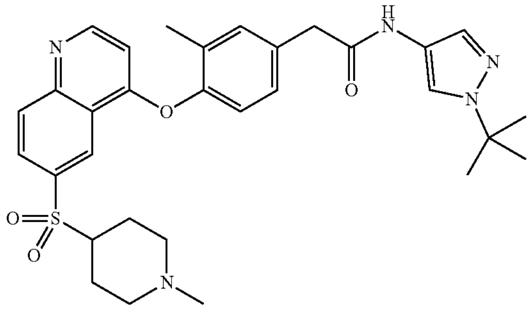 [SMILES: Cc1cc(CC(=O)Nc2cnn(C(C)(C)C)c2)ccc1Oc1ccnc2ccc(S(=O)(=O)C3CCN(C)CC3)cc12] | N-(1-(tert-butyl)-1H-pyrazol-4-yl)-2-(3-methyl-4-((6-((1-methylpiperidin-4-yl)sulfonyl)quinolin-4-yl)oxy)phenyl)acetamide | (400 MHz, DMSO-$d_6$) δ 10.25 (s, 1H), 8.88-8.85 (m, 2H), 8.31 (d, J = 8.8 Hz, 1H), 8.19 (dd, J = 8.9, 2.1 Hz, 1H), 7.95 (s, 1H), 7.47 (s, 1H), 7.40 (s, 1H), 7.33 (d, J = 8.3 Hz, 1H), 7.24 (d, J = 8.2 Hz, 1H), 6.59 (d, J = 5.3 Hz, 1H), 3.67 (d, J = 11.8 Hz, 1H), 3.62 (s, 2H), 3.51 (s, 2H), 2.71 (s, 2H), 2.61 (s, 3H), 2.14 (s, 3H), 2.09 (d, J = 12.8 Hz, 2H), 1.84 (t, J = 12.6 Hz, 2H), 1.49 (s, 9H) | 576.1 $(M + H)^+$ |
| 98 | 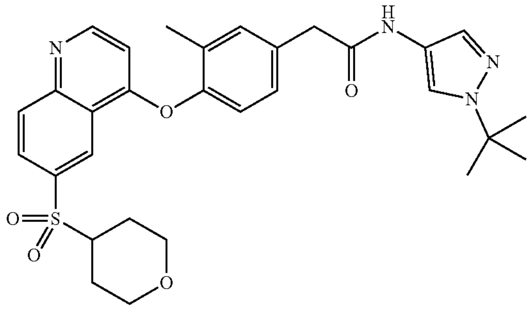 [SMILES: Cc1cc(CC(=O)Nc2cnn(C(C)(C)C)c2)ccc1Oc1ccnc2ccc(S(=O)(=O)C3CCOCC3)cc12] | N-(1-(tert-butyl)-1H-pyrazol-4-yl)-2-(3-methyl-4-((6-((tetrahydro-2H-pyran-4-yl)sulfonyl)quinolin-4-yl)oxy)phenyl)acetamide | (300 MHz, DMSO-$d_6$) δ 10.21 (s, 1H), 8.90-8.80 (m, 2H), 8.28 (d, J = 8.9 Hz, 1H), 8.17 (dd, J = 8.9, 2.1 Hz, 1H), 7.95 (s, 1H), 7.46 (s, 1H), 7.39 (s, 1H), 7.34-7.22 (m, 2H), 6.57 (d, J = 5.3 Hz, 1H), 3.97-3.87 (m, 2H), 3.81-3.73 (m, 1H), 3.62 (s, 2H), 3.30-3.24 (m, 2H), 2.14 (s, 3H), 1.84-1.73 (m, 2H), 1.69-1.57 (m, 2H), 1.49 (s, 9H) | 563.2 $(M + H)^+$ |

-continued

| No. | Structure | Name | $^1$H NMR | Observed m/z |
|---|---|---|---|---|
| 99 | 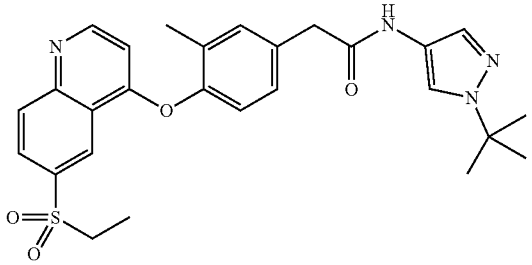 [SMILES: CCS(=O)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(4-((6-(ethylsulfonyl)quinolin-4-yl)oxy)-3-methylphenyl)acetamide | (300 MHz, DMSO-$d_6$) δ 10.21 (s, 1H), 8.91-8.80 (m, 2H), 8.31-8.19 (m, 2H), 7.95 (s, 1H), 7.46 (s, 1H), 7.39 (s, 1H), 7.34-7.20 (m, 2H), 6.56 (d, J = 5.2 Hz, 1H), 3.62 (s, 2H), 3.48 (q, J = 7.2 Hz, 2H), 2.14 (s, 3H), 1.49 (s, 9H), 1.18 (t, J = 7.3 Hz, 3H) | 529.2 $(M + Na)^+$ |
| 100 | 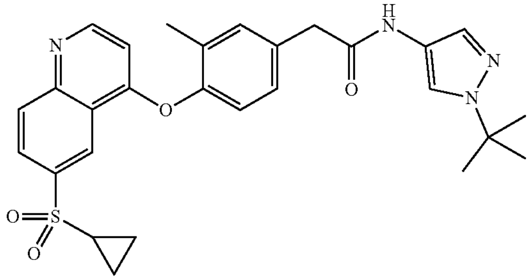 [SMILES: Cc1cc(CC(=O)Nc2cnn(C(C)(C)C)c2)ccc1Oc1ccnc2ccc(S(=O)(=O)C3CC3)cc12] | N-(1-(tert-butyl)-1H-pyrazol-4-yl)-2-(4-((6-(cyclopropylsulfonyl)quinolin-4-yl)oxy)-3-methylphenyl)acetamide | (300 MHz, DMSO-$d_6$) δ 10.21 (s, 1H), 8.93-8.80 (m, 2H), 8.32-8.19 (m, 2H), 7.95 (s, 1H), 7.46 (s, 1H), 7.39 (d, J = 2.1 Hz, 1H), 7.34-7.21 (m, 2H), 6.56 (d, J = 5.2 Hz, 1H), 3.62 (s, 2H), 3.07 (dt, J = 7.7, 4.6 Hz, 1H), 2.14 (s, 3H), 1.49 (s, 9H), 1.22 (q, J = 4.2, 3.6 Hz, 2H), 1.10 (dt, J = 7.7, 4.1 Hz, 2H) | 541.2 $(M + Na)^+$ |
| 101 | 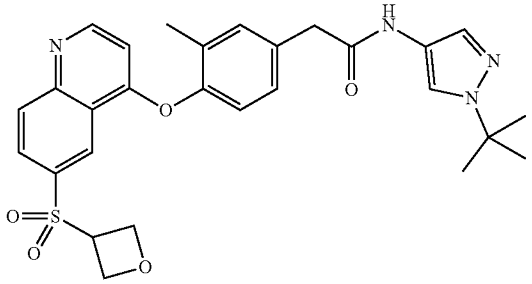 [SMILES: Cc1cc(CC(=O)Nc2cnn(C(C)(C)C)c2)ccc1Oc1ccnc2ccc(S(=O)(=O)C3COC3)cc12] | N-(1-(tert-butyl)-1H-pyrazol-4-yl)-2-(3-methyl-4-((6-(oxetan-3-ylsulfonyl)quinolin-4-yl)oxy)phenyl)acetamide | (300 MHz, DMSO-$d_6$) δ 10.20 (s, 1H), 8.90 (d, J = 1.6 Hz, 1H), 8.86 (d, J = 5.3 Hz, 1H), 8.26 (s, 1H), 8.24 (d, J = 1.9 Hz, 1H), 7.95 (s, 1H), 7.45 (s, 1H), 7.39 (s, 1H), 7.26-7.23 (m, 2H), 6.57 (d, J = 5.2 Hz, 1H), 5.15-5.07 (m, 1H), 4.84-4.78 (m, 4H), 3.61 (s, 2H), 2.14 (s, 3H), 1.49 (s, 9H) | 535.2 $(M + H)^+$ |
| 113 | 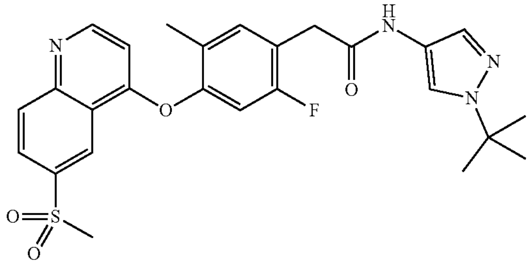 [SMILES: Cc1cc(CC(=O)Nc2cnn(C(C)(C)C)c2)c(F)cc1Oc1ccnc2ccc(S(C)(=O)=O)cc12] | N-(1-(tert-butyl)-1H-pyrazol-4-yl)-2-(2-fluoro-5-methyl-4-((6-(methylsulfonyl)quinolin-4-yl)oxy)phenyl)acetamide | (300 MHz, DMSO-$d_6$) δ 10.25 (s, 1H), 8.95-8.84 (m, 2H), 8.30-8.28 (m, 2H), 7.96 (s, 1H), 7.51-7.43 (m, 2H), 7.30 (d, J = 10.0 Hz, 1H), 6.65 (d, J = 5.2 Hz, 1H), 3.70 (s, 2H), 3.40 (s, 3H), 2.12 (s, 3H), 1.49 (s, 9H) | 510.9 $(M + H)^+$ |
| 125 | 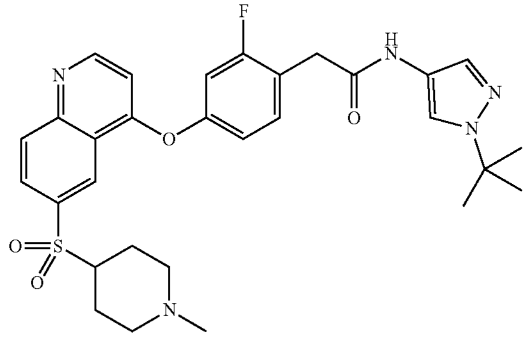 [SMILES: CN1CCC(S(=O)(=O)c2ccc3nccc(Oc4ccc(CC(=O)Nc5cnn(C(C)(C)C)c5)c(F)c4)c3c2)CC1] | N-(1-(tert-butyl)-1H-pyrazol-4-yl)-2-(2-fluoro-4-((6-((1-methylpiperidin-4-yl)sulfonyl)quinolin-4-yl)oxy)phenyl)acetamide | (300 MHz, DMSO-$d_6$) δ 10.24 (s, 1H), 8.94 (d, J = 5.2 Hz, 1H), 8.78 (s, 1H), 8.32 (d, J = 8.9 Hz, 1H), 8.19 (d, J = 9.2 Hz, 1H), 7.94 (s, 1H), 7.57 (t, J = 8.5 Hz, 1H), 7.47 (s, 1H), 7.37 (d, J = 8.4 Hz, 1H), 7.22 (d, J = 9.3 Hz, 1H), 6.87 (d, J = 5.2 Hz, 1H), 3.73 (s, 2H), 3.60-3.52 (m, 2H), 3.22-3.15 (m, 2H), 2.45 (s, 3H), 2.00 (d, J = 12.8 Hz, 2H), 1.82-1.68 (m, 2H), 1.49 (s, 9H) | 580.1 $(M + H)^+$ |

-continued

| No. | Structure | Name | $^1H$ NMR | Observed m/z |
|---|---|---|---|---|
| 127 | 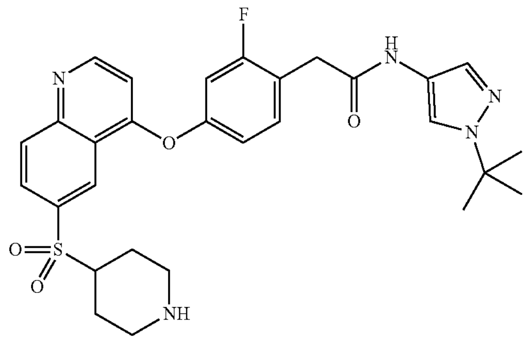 [SMILES: CC(C)(C)n1cc(NC(=O)Cc2ccc(Oc3ccnc4ccc(S(=O)(=O)C5CCNCC5)cc34)cc2F)cn1] | N-(1-(tert-butyl)-1H-pyrazol-4-yl)-2-(2-fluoro-4-((6-(piperidin-4-ylsulfonyl)quinolin-4-yl)oxy)phenyl)acetamide | (300 MHz, DMSO-$d_6$) δ 10.26 (s, 1H), 8.92 (d, J = 5.2 Hz, 1H), 8.75 (d, J = 2.0 Hz, 1H), 8.29 (d, J = 8.8 Hz, 1H), 8.17 (dd, J = 8.9, 2.1 Hz, 1H), 7.95 (s, 1H), 7.57 (t, J = 8.5 Hz, 1H), 7.46 (s, 1H), 7.39 (dd, J = 10.4, 2.4 Hz, 1H), 7.23 (dd, J = 8.3, 2.4 Hz, 1H), 6.85 (d, J = 5.2 Hz, 1H), 3.72 (s, 2H), 3.58-3.44 (m, 2H), 2.97 (d, J = 12.4 Hz, 2H), 2.41 (t, J = 11.9 Hz, 2H), 1.77 (d, J = 10.5 Hz, 2H), 1.49 (s, 9H), 1.45-1.37 (m, 2H) | 566.2 $(M + H)^+$ |
| 130 | 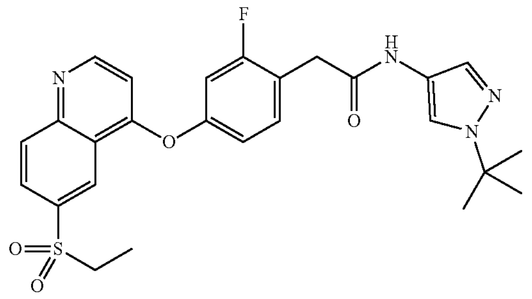 [SMILES: CCS(=O)(=O)c1ccc2nccc(Oc3ccc(CC(=O)Nc4cnn(C(C)(C)C)c4)c(F)c3)c2c1] | N-(1-(tert-butyl)-1H-pyrazol-4-yl)-2-(4-((6-(ethylsulfonyl)quinolin-4-yl)oxy)-2-fluorophenyl)acetamide | (300 MHz, DMSO-$d_6$) δ 10.23 (s, 1H), 8.91 (d, J = 5.2 Hz, 1H), 8.81 (d, J = 2.0 Hz, 1H), 8.32-8.17 (m, 2H), 7.94 (s, 1H), 7.56 (t, J = 8.5 Hz, 1H), 7.45 (s, 1H), 7.38 (dd, J = 10.5, 2.4 Hz, 1H), 7.22 (dd, J = 8.5, 2.3 Hz, 1H), 6.84 (d, J = 5.2 Hz, 1H), 3.72 (s, 2H), 3.47 (q, J = 7.3 Hz, 2H), 1.49 (s, 9H), 1.16 (t, J = 7.3 Hz, 3H) | 533.1 $(M + Na)^+$ |
| 131 | 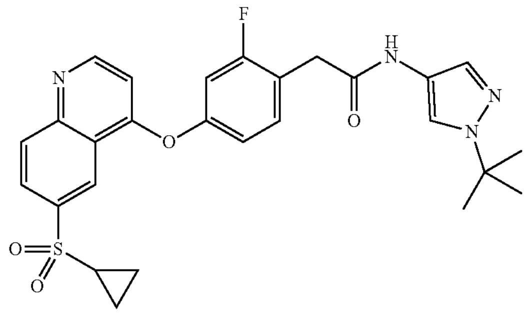 [SMILES: CC(C)(C)n1cc(NC(=O)Cc2ccc(Oc3ccnc4ccc(S(=O)(=O)C5CC5)cc34)cc2F)cn1] | N-(1-(tert-butyl)-1H-pyrazol-4-yl)-2-(4-((6-(cyclopropylsulfonyl) quinolin-4-yl)oxy)-2-fluorophenyl)acetamide | (400 MHz, DMSO-$d_6$) δ 10.23 (s, 1H), 8.91 (d, J = 5.2 Hz, 1H), 8.80 (d, J = 2.0 Hz, 1H), 8.32-8.22 (m, 2H), 7.94 (d, J = 0.7 Hz, 1H), 7.56 (t, J = 8.5 Hz, 1H), 7.45 (s, 1H), 7.38 (dd, J = 10.4, 2.4 Hz, 1H), 7.22 (dd, J = 8.3, 2.4 Hz, 1H), 6.84 (d, J = 5.2 Hz, 1H), 3.72 (s, 2H), 3.11-3.02 (m, 1H), 1.49 (s, 9H), 1.22 (dt, J = 6.1, 4.3 Hz, 2H), 1.11 (dt, J = 7.6, 3.7 Hz, 2H) | 523.2 $(M + H)^+$ |
| 132 | 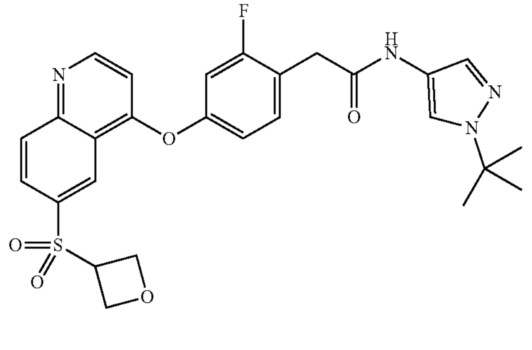 [SMILES: CC(C)(C)n1cc(NC(=O)Cc2ccc(Oc3ccnc4ccc(S(=O)(=O)C5COC5)cc34)cc2F)cn1] | N-(1-(tert-butyl)-1H-pyrazol-4-yl)-2-(2-fluoro-4-((6-(oxetan-3-ylsulfonyl)quinolin-4-yl)oxy)phenyl)acetamide | (300 MHz, DMSO-$d_6$) δ 10.24 (s, 1H), 8.93 (d, J = 5.2 Hz, 1H), 8.84 (d, J = 2.0 Hz, 1H), 8.35-8.18 (m, 2H), 7.94 (d, J = 0.7 Hz, 1H), 7.57 (t, J = 8.5 Hz, 1H), 7.46 (d, J = 0.7 Hz, 1H), 7.38 (dd, J = 10.4, 2.4 Hz, 1H), 7.22 (dd, J = 8.2, 2.4 Hz, 1H), 6.85 (d, J = 5.2 Hz, 1H), 5.11 (quint, J = 6.9 Hz, 1H), 4.81-4.79 (m, 4H), 3.72 (s, 2H), 1.49 (s, 9H) | 539.1 |

-continued

| No. | Structure | Name | $^1$H NMR | Observed m/z |
|---|---|---|---|---|
| 142 | 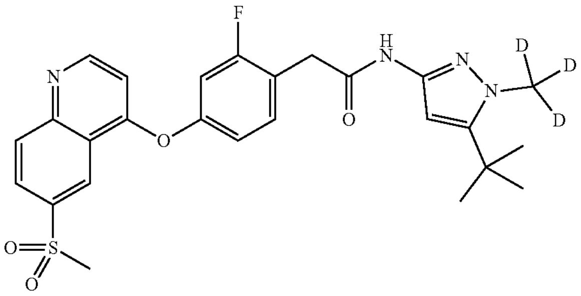 [SMILES: [2H]C([2H])([2H])n1nc(NC(=O)Cc2ccc(Oc3ccnc4ccc(S(C)(=O)=O)cc34)cc2F)cc1C(C)(C)C] | N-(5-(tert-butyl)-1-(methyl-d$_3$)-1H-pyrazol-3-yl)-2-(2-fluoro-4-((6-(methylsulfonyl)quinolin-4-yl)oxy)phenyl)acetamide | (400 MHz, MeOH-d$_4$) δ 9.01 (d, J = 2.1 Hz, 1H), 8.83 (d, J = 5.3 Hz, 1H), 8.33 - 8.22 (m, 2H), 7.55 (t, J = 8.3 Hz, 1H), 7.21-7.14 (m, 2H), 6.91 (d, J = 5.4 Hz, 1H), 6.36 (s, 1H), 3.82 (s, 2H), 3.26 (s, 3H), 1.38 (s, 9H) | 514.1 (M + H)$^+$ |
| 143 | 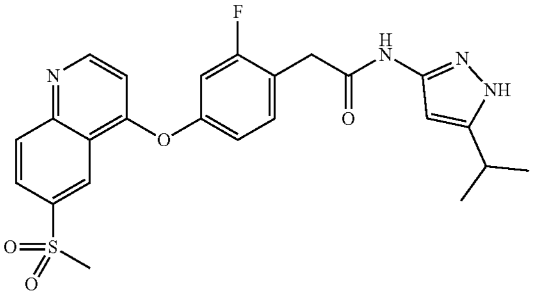 [SMILES: CC(C)c1cc(NC(=O)Cc2ccc(Oc3ccnc4ccc(S(C)(=O)=O)cc34)cc2F)n[nH]1] | 2-(2-fluoro-4-((6-(methylsulfonyl)quinolin-4-yl)oxy)phenyl)-N-(5-isopropyl-1H-pyrazol-3-yl)acetamide | (400 MHz, DMSO-d$_6$) δ 12.05 (s, 1H), 10.59 (s, 1H), 8.90 (d, J = 5.3 Hz, 1H), 8.85 (s, 1H), 8.29-8.27 (m, 2H), 7.56 (t, J = 8.5 Hz, 1H), 7.36 (dd, J = 10.4, 2.4 Hz, 1H), 7.21 (dd, J = 8.3, 2.5 Hz, 1H), 6.84 (d, J = 5.2 Hz, 1H), 6.28 (s, 1H), 3.75 (s, 2H), 3.37 (s, 3H), 2.89 (sept, J = 6.9 Hz, 1H), 1.19 (d, J = 6.9 Hz, 6H) | 483.2 (M + H)$^+$ |
| 144 | 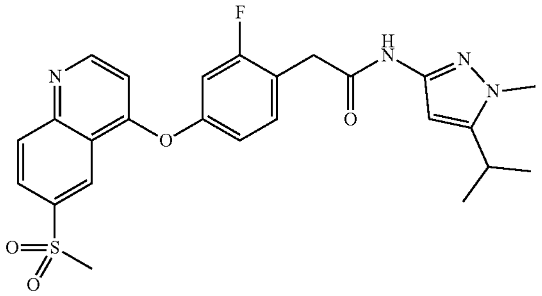 [SMILES: CC(C)c1cc(NC(=O)Cc2ccc(Oc3ccnc4ccc(S(C)(=O)=O)cc34)cc2F)nn1C] | 2-(2-fluoro-4-((6-(methylsulfonyl)quinolin-4-yl)oxy)phenyl)-N-(5-isopropyl-1-methyl-1H-pyrazol-3-yl)acetamide | (400 MHz, DMSO-d$_6$) δ 10.60 (s, 1H), 8.90 (d, J = 5.3 Hz, 1H), 8.85 (t, J = 1.4 Hz, 1H), 8.29-8.27 (m, 2H), 7.55 (t, J = 8.5 Hz, 1H), 7.36 (dd, J = 10.4, 2.4 Hz, 1H), 7.20 (dd, J = 8.4, 2.4 Hz, 1H), 6.83 (d, J = 5.2 Hz, 1H), 6.29 (s, 1H), 3.74 (s, 2H), 3.66 (s, 3H), 3.37 (s, 3H), 2.97 (sept, J = 6.9 Hz, 1H), 1.17 (d, J = 6.8 Hz, 6H) | 497.2 (M + H)$^+$ |
| 145 | 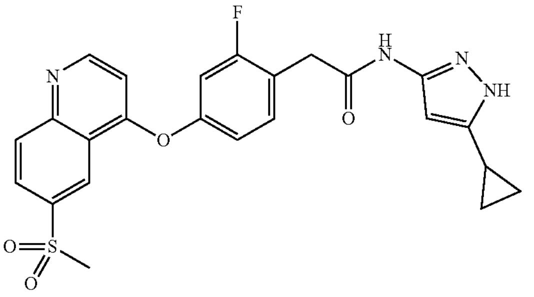 [SMILES: CS(=O)(=O)c1ccc2nccc(Oc3ccc(CC(=O)Nc4cc(C5CC5)[nH]n4)c(F)c3)c2c1] | N-(5-cyclopropyl-1H-pyrazol-3-yl)-2-(2-fluoro-4-((6-(methylsulfonyl)quinolin-4-yl)oxy)phenyl)acetamide | (400 MHz, DMSO-d$_6$) δ 12.08 (s, 1H), 10.58 (s, 1H), 8.91 (d, J = 5.2 Hz, 1H), 8.86 (t, J = 1.4 Hz, 1H), 8.30-8.28 (m, 2H), 7.56 (t, J = 8.5 Hz, 1H), 7.37 (dd, J = 10.3, 2.4 Hz, 1H), 7.21 (dd, J = 8.3, 2.4 Hz, 1H), 6.84 (d, J = 5.2 Hz, 1H), 6.16 (s, 1H), 3.75 (s, 2H), 3.38 (s, 3H), 1.88-1.80 (m, 1H), 0.94-0.87 (m, 2H), 0.69-0.61 (m, 2H | 481.1 (M + H)$^+$ |
| 146 | 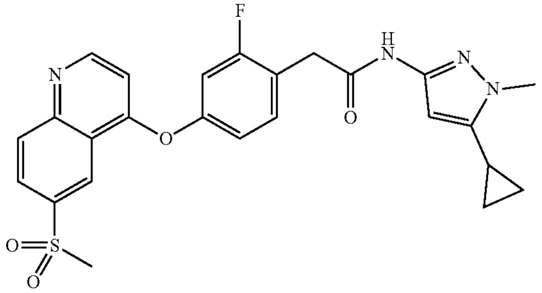 [SMILES: Cn1nc(NC(=O)Cc2ccc(Oc3ccnc4ccc(S(C)(=O)=O)cc34)cc2F)cc1C1CC1] | N-(5-cyclopropyl-1-methyl-1H-pyrazol-3-yl)-2-(2-fluoro-4-((6-(methylsulfonyl)quinolin-4-yl)oxy)phenyl)acetamide | (300 MHz, DMSO-d$_6$) δ 10.60 (s, 1H), 8.94-8.82 (m, 2H), 8.29-8.27 (m, 2H), 7.54 (t, J = 8.5 Hz, 1H), 7.36 (dd, J = 10.4, 2.4 Hz, 1H), 7.20 (dd, J = 8.4, 2.4 Hz, 1H), 6.83 (d, J = 5.2 Hz, 1H), 6.08 (s, 1H), 3.80-3.70 (m, 5H), 3.38 (s, 3H), 1.88-1.80 (m, 1H), 1.00-0.88 (m, 2H), 0.63-0.52 (m, 2H) | 495.0 (M + H)$^+$ |

-continued

| No. | Structure | Name | $^1$H NMR | Observed m/z |
|---|---|---|---|---|
| 147 | 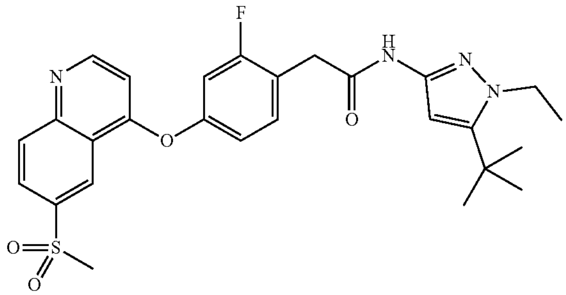 [SMILES: CCn1nc(NC(=O)Cc2ccc(Oc3ccnc4ccc(S(C)(=O)=O)cc34)cc2F)cc1C(C)(C)C] | N-(5-(tert-butyl)-1-ethyl-1H-pyrazol-3-yl)-2-(2-fluoro-4-((6-(methylsulfonyl)quinolin-4-yl)oxy)phenyl)acetamide | (300 MHz, DMSO-$d_6$) δ 10.66 (s, 1H), 8.90 (d, J = 5.2 Hz, 1H), 8.85 (t, J = 1.4 Hz, 1H), 8.29-8.27 (m, 2H), 7.55 (t, J = 8.5 Hz, 1H), 7.36 (dd, J = 10.4, 2.4 Hz, 1H), 7.25-7.14 (m, 1H), 6.83 (d, J = 5.2 Hz, 1H), 6.26 (s, 1H), 4.11 (q, J = 7.1 Hz, 2H), 3.73 (s, 2H), 3.37 (s, 3H), 1.35 (t, J = 7.3 Hz, 3H), 1.31 (s, 9H) | 525.1 (M + H)$^+$ |
| 148 | 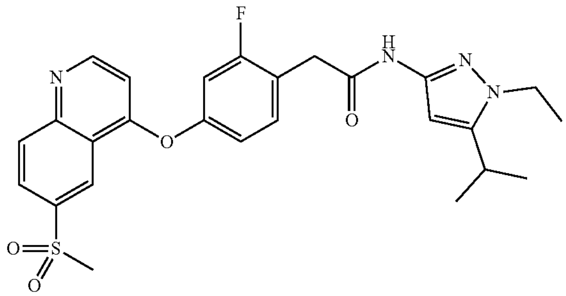 [SMILES: CCn1nc(NC(=O)Cc2ccc(Oc3ccnc4ccc(S(C)(=O)=O)cc34)cc2F)cc1C(C)C] | N-(1-ethyl-5-isopropyl-1H-pyrazol-3-yl)-2-(2-fluoro-4-((6-(methylsulfonyl)quinolin-4-yl)oxy)phenyl)acetamide | (400 MHz, DMSO-$d_6$) δ 10.66 (s, 1H), 8.90 (d, J = 5.2 Hz, 1H), 8.86 (t, J = 1.4 Hz, 1H), 8.30-8.28 (m, 2H), 7.56 (t, J = 8.5 Hz, 1H), 7.36 (dd, J = 10.4, 2.4 Hz, 1H), 7.21 (dd, J = 8.3, 2.4 Hz, 1H), 6.84 (d, J = 5.2 Hz, 1H), 6.29 (s, 1H), 3.97 (q, J = 7.2 Hz, 2H), 3.74 (s, 2H), 3.37 (s, 3H), 2.99 (sept, J = 6.8 Hz, 1H),1.31 (t, J = 7.1 Hz, 3H), 1.18 (d, J = 6.8 Hz, 6H) | 511.0 (M + H)$^+$ |
| 163 | 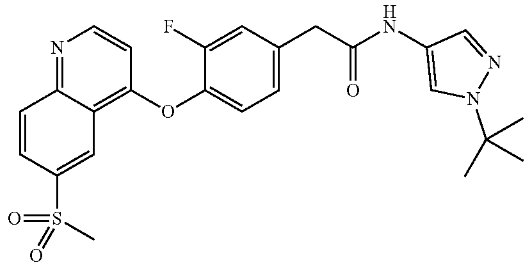 [SMILES: CC(C)(C)n1cc(NC(=O)Cc2ccc(Oc3ccnc4ccc(S(C)(=O)=O)cc34)c(F)c2)cn1] | N-(1-(tert-butyl)-1H-pyrazol-4-yl)-2-(3-fluoro-4-((6-(methylsulfonyl)quinolin-4-yl)oxy)phenyl)acetamide | (400 MHz, DMSO-$d_6$) δ 10.23 (s, 1H), 8.94-8.82 (m, 2H), 8.32-8.26 (m, 2H), 7.95 (d, J = 0.8 Hz, 1H), 7.59-7.43 (m, 3H), 7.36-7.28 (m, 1H), 6.77 (dd, J = 5.2, 1.2 Hz, 1H), 3.69 (s, 2H), 3.39 (s, 3H), 1.49 (s, 9H) | 497.1 (M + H)$^+$ |
| 164 | 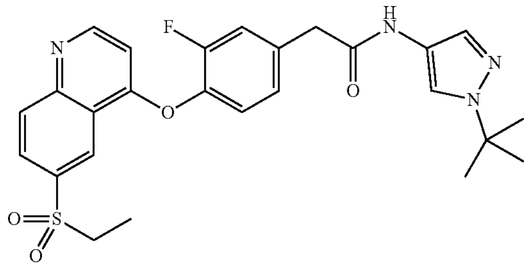 [SMILES: CCS(=O)(=O)c1ccc2nccc(Oc3ccc(CC(=O)Nc4cnn(C(C)(C)C)c4)cc3F)c2c1] | N-(1-(tert-butyl)-1H-pyrazol-4-yl)-2-(4-((6-(ethylsulfonyl)quinolin-4-yl)oxy)-3-fluorophenyl)acetamide | (300 MHz, DMSO-$d_6$) δ 10.24 (s, 1H), 8.90 (d, J = 5.2 Hz, 1H), 8.84 (d, J = 1.9 Hz, 1H), 8.34-8.20 (m, 2H), 7.95 (s, 1H), 7.60-7.43 (m, 3H), 7.32 (d, J = 8.3 Hz, 1H), 6.81-6.73 (m, 1H), 3.69 (s, 2H), 3.55-3.42 (m, 2H), 1.49 (s, 9H), 1.17 (t, J = 7.3 Hz, 3H) | 509.1 (M − H)$^-$ |
| 167 | 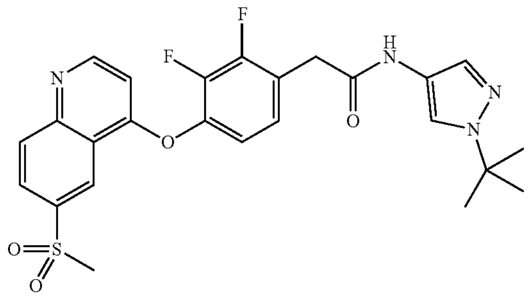 [SMILES: CC(C)(C)n1cc(NC(=O)Cc2ccc(Oc3ccnc4ccc(S(C)(=O)=O)cc34)c(F)c2F)cn1] | N-(1-(tert-butyl)-1H-pyrazol-4-yl)-2-(2,3-difluoro-4-((6-(methylsulfonyl)quinolin-4-yl)oxy)phenyl)acetamide | (400 MHz, DMSO-$d_6$) δ 10.28 (s, 1H), 8.93 (d, J = 5.2 Hz, 1H), 8.88 (d, J = 1.4 Hz, 1H), 8.32-8.29 (m, 2H), 7.94 (s, 1H), 7.46 (s, 1H), 7.41-7.38 (m, 2H), 6.90 (d, J = 5.2 Hz, 1H), 3.80 (s, 2H), 3.40 (s, 3H), 1.49 (s, 9H) | 515.0 (M + H)$^+$ |

-continued

| No. | Structure | Name | $^1$H NMR | Observed m/z |
|---|---|---|---|---|
| 168 | 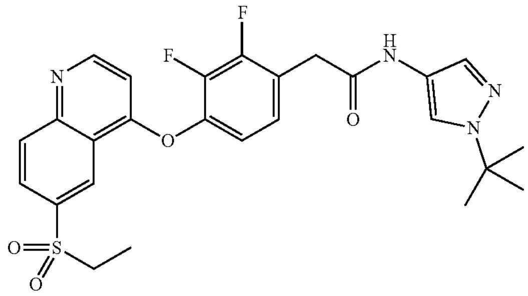 | N-(1-(tert-butyl)-1H-pyrazol-4-yl)-2-(4-((6-(ethylsulfonyl)quinolin-4-yl)oxy)-2,3-difluorophenyl)acetamide | (300 MHz, DMSO-$d_6$) δ 10.28 (s, 1H), 8.94 (d, J = 5.2 Hz, 1H), 8.88-8.77 (m, 1H), 8.37-8.20 (m, 2H), 7.95 (d, J = 0.7 Hz, 1H), 7.46 (d, J = 0.7 Hz, 1H), 7.43-7.35 (m, 2H), 6.91 (dd, J = 5.2, 1.2 Hz, 1H), 3.80 (s, 2H), 3.49 (q, J = 7.3 Hz, 2H), 1.49 (s, 9H), 1.17 (t, J = 7.3 Hz, 3H) | 529.1 $(M + H)^+$ |
| 173 | 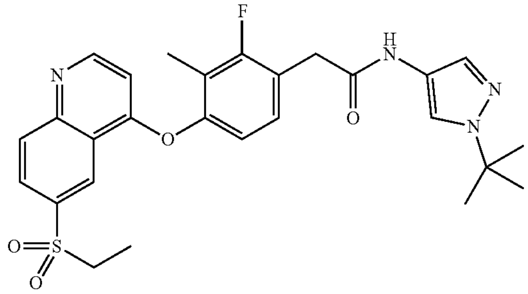 [SMILES: CCS(=O)(=O)c1ccc2nccc(Oc3ccc(CC(=O)Nc4cnn(C(C)(C)C)c4)c(F)c3C)c2c1] | N-(1-(tert-butyl)-1H-pyrazol-4-yl)-2-(4-((6-(ethylsulfonyl)quinolin-4-yl)oxy)-2-fluoro-3-methylphenyl)acetamide | (300 MHz, DMSO-$d_6$) δ 10.25 (s, 1H), 8.89-8.87 (m, 2H), 8.36-8.15 (m, 2H), 7.95 (d, J = 0.7 Hz, 1H), 7.46 (s, 1H), 7.40 (t, J = 8.4 Hz, 1H), 7.17 (d, J = 8.4 Hz, 1H), 6.65 (d, J = 5.2 Hz, 1H), 3.72 (s, 2H), 3.49 (q, J = 7.3 Hz, 2H), 2.08 (d, J = 1.9 Hz, 3H), 1.49 (s, 9H), 1.18 (t, J = 7.3 Hz, 3H) | 525.0 $(M + H)^+$ |
| 174 | 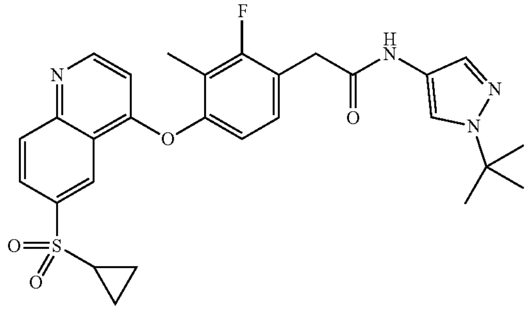 [SMILES: Cc1c(Oc2ccnc3ccc(S(=O)(=O)C4CC4)cc23)ccc(CC(=O)Nc2cnn(C(C)(C)C)c2)c1F] | N-(1-(tert-butyl)-1H-pyrazol-4-yl)-2-(4-((6-(cyclopropylsulfonyl) quinolin-4-yl)oxy)-2-fluoro-3-methylphenyl)acetamide | (300 MHz, DMSO-$d_6$) δ 10.23 (s, 1H), 8.93-8.85 (m, 2H), 8.34-8.22 (m, 2H), 7.95 (s, 1H), 7.46 (s, 1H), 7.40 (t, J = 8.4 Hz, 1H), 7.17 (d, J = 8.4 Hz, 1H), 6.66 (d, J = 5.2 Hz, 1H), 3.72 (s, 2H), 3.13-3.04 (m, 1H), 2.09 (s, 3H), 1.50 (s, 9H), 1.24 (s, 4H) | 537.0 $(M + H)^+$ |
| 175 | 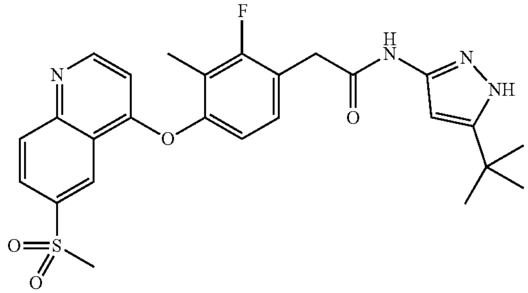 [SMILES: Cc1c(Oc2ccnc3ccc(S(C)(=O)=O)cc23)ccc(CC(=O)Nc2cc(C(C)(C)C)[nH]n2)c1F] | N-(5-(tert-butyl)-1H-pyrazol-3-yl)-2-(2-fluoro-3-methyl-4-((6-(methylsulfonyl)quinolin-4-yl)oxy)phenyl)acetamide | (300 MHz, DMSO-$d_6$) δ 12.06 (s, 1H), 10.61 (s, 1H), 8.93-8.82 (m, 2H), 8.30-8.28 (m, 2H), 7.39 (t, J = 8.4 Hz, 1H), 7.14 (d, J = 8.3 Hz, 1H), 6.64 (d, J = 5.2 Hz, 1H), 6.29 (s, 1H), 3.75 (s, 2H), 3.39 (s, 3H), 2.08 (s, 3H), 1.25 (s, 9H) | 511.0 $(M + H)^+$ |
| 198 | 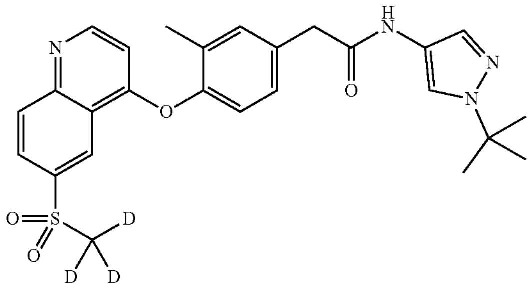 [SMILES: [2H]C([2H])([2H])S(=O)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(3-methyl-4-((6-((methyl-$d_3$)sulfonyl)quinolin-4-yl)oxy)phenyl)acetamide | (300 MHz, DMSO-$d_6$) δ 10.22 (s, 1H), 8.91 (s, 1H), 8.84 (d, J = 5.3 Hz, 1H), 8.29-8.25 (m, 2H), 7.96 (s, 1H), 7.46 (s, 1H), 7.40 (s, 1H), 7.36-7.28 (m, 1H), 7.28-7.21 (m, 1H), 6.56 (d, J = 5.2 Hz, 1H), 3.62 (s, 2H), 2.14 (s, 3H), 1.49 (s, 9H) | 518.2 $(M + Na)^+$ |

-continued

| No. | Structure | Name | $^1H$ NMR | Observed m/z |
|---|---|---|---|---|
| 199 | 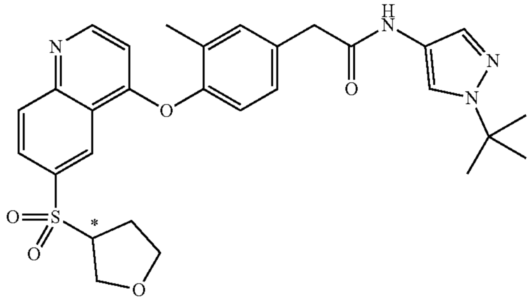 [SMILES: Cc1cc(CC(=O)Nc2cnn(C(C)(C)C)c2)ccc1Oc1ccnc2ccc(S(=O)(=O)C3CCOC3)cc12]<br>enantiomer 1<br>(retention time: 4.30 min; column: CHIRALPAK IC-3, 4.6 × 50 mm, 3 μm; mobile phase A: hexane/DCM (3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(3-methyl-4-((6-((tetrahydrofuran-3-yl)sulfonyl)quinolin-4-yl)oxy)phenyl)acetamide | (300 MHz, DMSO-$d_6$) δ 10.22 (s, 1H), 8.93-8.82 (m, 2H), 8.34-8.20 (m, 2H), 7.95 (d, J = 0.7 Hz, 1H), 7.46 (s, 1H), 7.39-7.25 (m, 3H), 6.58 (d, J = 5.2 Hz, 1H), 4.41 (dd, J = 9.0, 4.8 Hz, 1H), 4.10 (dd, J = 10.1, 4.6 Hz, 1H), 3.93-3.75 (m, 2H), 3.67-3.62 (m, 3H), 2.21 (q, J = 7.3 Hz, 2H), 2.14 (s, 3H), 1.49 (s, 9H) | 549.2 $(M + H)^+$ |
| 200 | 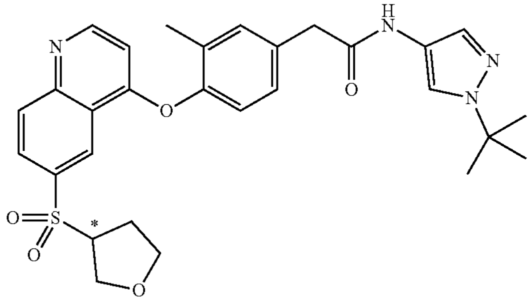 [SMILES: Cc1cc(CC(=O)Nc2cnn(C(C)(C)C)c2)ccc1Oc1ccnc2ccc(S(=O)(=O)C3CCOC3)cc12]<br>enantiomer 2<br>(retention time: 5.11 min; column: CHIRALPAK IC-3, 4.6 × 50 mm, 3 μm; mobile phase A: hexane/DCM (3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(3-methyl-4-((6-((tetrahydrofuran-3-yl)sulfonyl)quinolin-4-yl)oxy)phenyl)acetamide | (300 MHz, DMSO-$d_6$) δ 10.22 (s, 1H), 8.93-8.82 (m, 2H), 8.33-8.20 (m, 2H), 7.95 (d, J = 0.7 Hz, 1H), 7.46 (s, 1H), 7.39-7.25 (m, 3H), 6.57 (d, J = 5.2 Hz, 1H), 4.39 (dd, J = 9.0, 4.8 Hz, 1H), 4.09 (dd, J = 10.1, 4.7 Hz, 1H), 3.93-3.75 (m, 2H), 3.67-3.62 (m, 3H), 2.27-2.17 (m, 2H), 2.14 (s, 3H), 1.49 (s, 9H) | 549.2 $(M + H)^+$ |
| 201 | 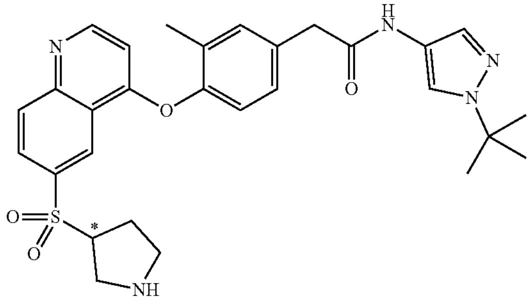 [SMILES: Cc1cc(CC(=O)Nc2cnn(C(C)(C)C)c2)ccc1Oc1ccnc2ccc(S(=O)(=O)C3CCNC3)cc12]<br>enantiomer 1<br>(retention time: 3.59 min; column: CHIRALPAK IF-3, 4.6 × 50 mm, 3 μm; mobile phase A: hexane/DCM (3:1, 0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(3-methyl-4-((6-(pyrrolidin-3-ylsulfonyl)quinolin-4-yl)oxy)phenyl)acetamide | (300 MHz, DMSO-$d_6$) δ 10.22 (s, 1H), 9.02-8.75 (m, 2H), 8.45-8.16 (m, 2H), 7.95 (s, 1H), 7.47 (s, 1H), 7.39 (s, 1H), 7.35-7.30 (m, 1H), 7.25 (d, J = 8.2 Hz, 1H), 6.57 (d, J = 5.3 Hz, 1H), 4.26-3.89 (m, 1H), 3.62 (s, 2H), 3.20-2.96 (m, 2H), 2.92-2.70 (m, 2H), 2.14 (s, 3H), 2.08-1.80 (m, 2H), 1.49 (s, 9H) | 548.0 $(M + H)^+$ |

-continued

| No. | Structure | Name | $^1$H NMR | Observed m/z |
|---|---|---|---|---|
| 202 | 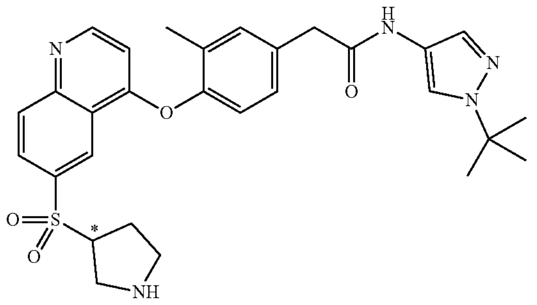 [SMILES: Cc1cc(CC(=O)Nc2cnn(C(C)(C)C)c2)ccc1Oc1ccnc2ccc(S(=O)(=O)C3CCNC3)cc12] enantiomer 2 (retention time: 5.07 min; column: CHIRALPAK IF-3, 4.6 × 50 mm, 3 μm; mobile phase A: hexane/DCM (3:1, 0.1% DEA), mobile phase B: EtOH, isocratic separation with 10% B, flow rate: 1.0 mL/min, wavelength: 254 nm) | N-(1-(tert-butyl)-1H-pyrazol-4-yl)-2-(3-methyl-4-((6-(pyrrolidin-3-ylsulfonyl)quinolin-4-yl)oxy)phenyl)acetamde | (300 MHz, DMSO-$d_6$) δ 10.22 (s, 1H), 8.96-8.73 (m, 2H), 8.38-8.12 (m, 2H), 7.96 (s, 1H), 7.47 (s, 1H), 7.39 (s, 1H), 7.36-7.22 (m, 2H), 6.57 (d, J = 5.2 Hz, 1H), 4.25-3.90 (m, 1H), 3.62 (s, 2H), 3.21-2.95 (m, 2H), 2.91-2.69 (m, 2H), 2.14 (s, 3H), 2.08-1.80 (m, 2H), 1.49 (s, 9H) | 548.0 $(M + H)^+$ |
| 203 | 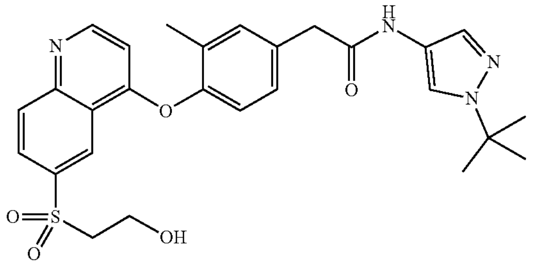 [SMILES: Cc1cc(CC(=O)Nc2cnn(C(C)(C)C)c2)ccc1Oc1ccnc2ccc(S(=O)(=O)CCO)cc12] | N-(1-(tert-butyl)-1H-pyrazol-4-yl)-2-(4-((6-((2-hydroxyethyl)sulfonyl)quinolin-4-yl)oxy)-3-methylphenyl)acetamide | (400 MHz, DMSO-$d_6$) δ 10.24 (s, 1H), 8.90 (d, J = 1.4 Hz, 1H), 8.83 (d, J = 5.2 Hz, 1H), 8.26-8.24 (m, 2H), 7.96 (s, 1H), 7.47 (s, 1H), 7.40 (d, J = 2.1 Hz, 1H), 7.33 (dd, J = 8.2, 2.2 Hz, 1H), 7.25 (d, J = 8.3 Hz, 1H), 6.55 (d, J = 5.3 Hz, 1H), 4.96 (t, J = 5.3 Hz, 1H), 3.79 (q, J = 5.8 Hz, 2H), 3.67-3.59 (m, 4H), 2.13 (s, 3H), 1.48 (s, 9H) | 523.1 $(M + H)^+$ |
| 204 | 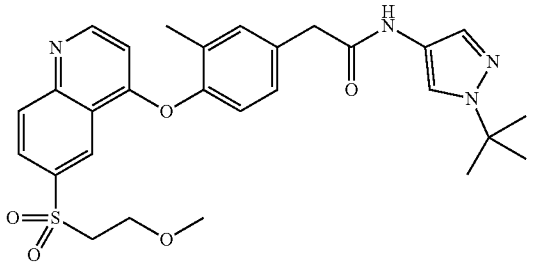 [SMILES: COCCS(=O)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(4-((6-((2-methoxyethyl)sulfonyl)quinolin-4-yl)oxy)-3-methylphenyl)acetamide | (300 MHz, DMSO-$d_6$) δ 10.21 (s, 1H), 8.92-8.80 (m, 2H), 8.25-8.23 (m, 2H), 7.95 (s, 1H), 7.46-7.24 (m, 4H), 6.55 (d, J = 5.2 Hz, 1H), 3.72-3.76 (m, 4H), 3.62 (s, 2H), 3.09 (s, 3H), 2.13 (s, 3H), 1.49 (s, 9H) | 537.1 $(M + H)^+$ |
| 205 | 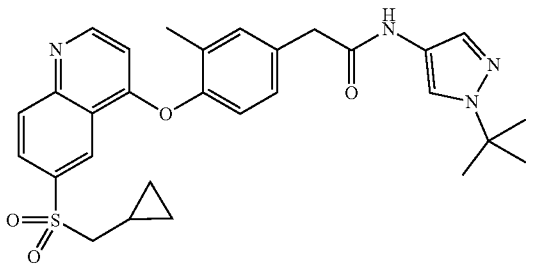 [SMILES: Cc1cc(CC(=O)Nc2cnn(C(C)(C)C)c2)ccc1Oc1ccnc2ccc(S(=O)(=O)CC3CC3)cc12] | N-(1-(tert-butyl)-1H-pyrazol-4-yl)-2-(4-((6-((cyclopropylmethyl)sulfonyl)quinolin-4-yl)oxy)-3-methylphenyl)acetamide | (400 MHz, DMSO-$d_6$) δ 10.21 (s, 1H), 8.90 (d, J = 1.9 Hz, 1H), 8.85 (d, J = 5.3 Hz, 1H), 8.29-8.19 (m, 2H), 7.95 (s, 1H), 7.46 (s, 1H), 7.39 (d, J = 2.1 Hz, 1H), 7.32 (dd, J = 8.3, 2.2 Hz, 1H), 7.25 (d, J = 8.2 Hz, 1H), 6.57 (d, J = 5.2 Hz, 1H), 3.62 (s, 2H), 3.45 (d, J = 7.2 Hz, 2H), 2.13 (s, 3H), 1.49 (s, 9H), 1.01-0.85 (m, 1H), 0.52-0.42 (m, 2H), 0.13 (dt, J = 6.3, 4.5 Hz, 2H) | 533.2 $(M + H)^+$ |

-continued

| No. | Structure | Name | $^1$H NMR | Observed m/z |
|---|---|---|---|---|
| 206 | 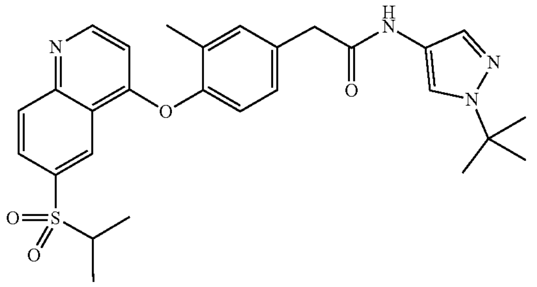 [SMILES: Cc1cc(CC(=O)Nc2cnn(C(C)(C)C)c2)ccc1Oc1ccnc2ccc(S(=O)(=O)C(C)C)cc12] | N-(1-(tert-butyl)-1H-pyrazol-4-yl)-2-(4-((6-(isopropylsulfonyl)quinolin-4-yl)oxy)-3-methylphenyl)acetamide | (300 MHz, DMSO-$d_6$) δ 10.20 (s, 1H), 8.89-8.78 (m, 2H), 8.27 (d, J = 8.9 Hz, 1H), 8.23-8.15 (m, 1H), 7.95 (d, J = 0.7 Hz, 1H), 7.46 (d, J = 0.7 Hz, 1H), 7.39 (s, 1H), 7.33-7.24 (m, 2H), 6.57 (d, J = 5.2 Hz, 1H), 3.63 (sept, J = 6.6 Hz, 1H), 3.62 (s, 2H), 2.13 (s, 3H), 1.49 (s, 9H), 1.24 (d, J = 6.6 Hz, 6H) | 521.1 $(M + H)^+$ |
| 212 | 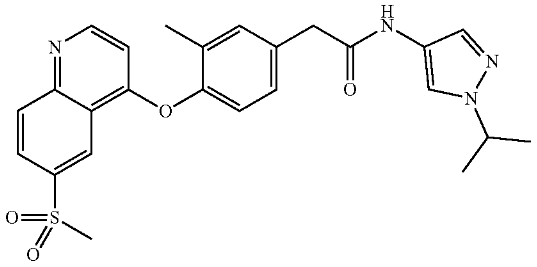 [SMILES: Cc1cc(CC(=O)Nc2cnn(C(C)C)c2)ccc1Oc1ccnc2ccc(S(C)(=O)=O)cc12] | N-(1-isopropyl-1H-pyrazol-4-yl)-2-(3-methyl-4-((6-(methylsulfonyl)quinolin-4-yl)oxy)phenyl)acetamide | (300 MHz, DMSO-$d_6$) δ 10.22 (s, 1H), 8.91 (s, 1H), 8.84 (d, J = 5.1 Hz, 1H), 8.31-8.24 (m, 2H), 7.91 (s, 1H), 7.43 (s, 1H), 7.39 (s, 1H), 7.32 (d, J = 8.1 Hz, 1H), 7.23 (d, J = 8.1 Hz, 1H), 6.55 (d, J = 5.1 Hz, 1H), 4.51-4.39 (m, 1H), 3.62 (s, 2H), 3.39 (s, 3H), 2.14 (s, 3H), 1.37 (d, J = 6.6 Hz, 1H) | 477.0 (M − H)− |
| 213 | 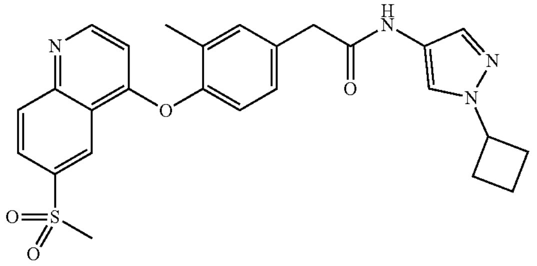 [SMILES: Cc1cc(CC(=O)Nc2cnn(C3CCC3)c2)ccc1Oc1ccnc2ccc(S(C)(=O)=O)cc12] | N-(1-cyclobutyl-1H-pyrazol-4-yl)-2-(3-methyl-4-((6-(methylsulfonyl)quinolin-4-yl)oxy)phenyl)acetamide | (300 MHz, DMSO-$d_6$) δ 10.22 (s, 1H), 8.91 (s, 1H), 8.84 (d, J = 5.2 Hz, 1H), 8.28-8.26 (m, 2H), 7.91 (s, 1H), 7.43-7.39 (m, 2H), 7.32 (d, J = 8.5 Hz, 1H), 7.23 (d, J = 8.2 Hz, 1H), 6.55 (d, J = 5.3 Hz, 1H), 4.44 (quint, J = 6.6 Hz, 1H), 3.62 (s, 2H), 3.39 (s, 3H), 2.50-2.30 (m, 4H), 2.14 (s, 3H), 1.85-1.65 (m, 2H) | 491.1 $(M + H)^+$ |
| 230 | 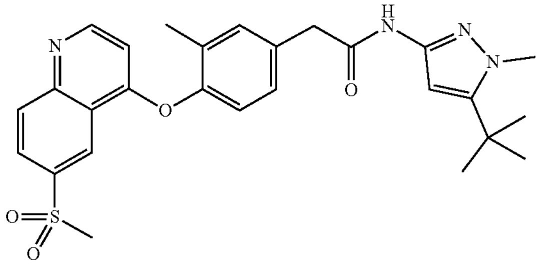 [SMILES: Cc1cc(CC(=O)Nc2cc(C(C)(C)C)n(C)n2)ccc1Oc1ccnc2ccc(S(C)(=O)=O)cc12] | N-(5-(tert-butyl)-1-methyl-1H-pyrazol-3-yl)-2-(3-methyl-4-((6-(methylsulfonyl)quinolin-4-yl)oxy)phenyl)acetamide | (400 MHz, DMSO-$d_6$) δ 10.59 (s, 1H), 8.91 (dd, J = 1.8, 0.9 Hz, 1H), 8.83 (d, J = 5.2 Hz, 1H), 8.28-8.26 (m, 2H), 7.39 (d, J = 2.1 Hz, 1H), 7.32 (dd, J = 8.3, 2.2 Hz, 1H), 7.23 (d, J = 8.2 Hz, 1H), 6.55 (d, J = 5.2 Hz, 1H), 6.32 (s, 1H), 3.80 (s, 3H), 3.62 (s, 2H), 3.39 (s, 3H), 2.13 (s, 3H), 1.31 (s, 9H) | 507.1 $(M + H)^+$ |
| 231 | 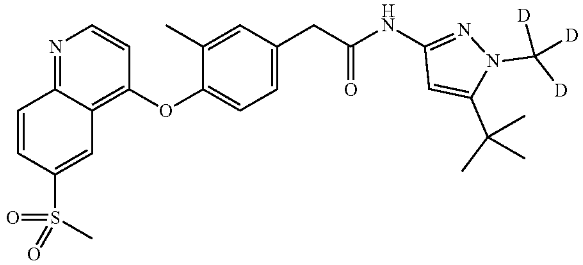 [SMILES: [2H]C([2H])([2H])n1nc(NC(=O)Cc2ccc(Oc3ccnc4ccc(S(C)(=O)=O)cc34)c(C)c2)cc1C(C)(C)C] | N-(5-(tert-butyl)-1-(methyl-$d_3$)-1H-pyrazol-3-yl)-2-(3-methyl-4-((6-(methylsulfonyl)quinolin-4-yl)oxy)phenyl)acetamide | (400 MHz, DMSO-$d_6$) δ 10.59 (s, 1H), 8.91 (dd, J = 1.9, 0.9 Hz, 1H), 8.83 (d, J = 5.2 Hz, 1H), 8.28-8.26 (m, 2H), 7.39 (s, 1H), 7.32 (dd, J = 8.3, 2.2 Hz, 1H), 7.23 (d, J = 8.2 Hz, 1H), 6.55 (d, J = 5.2 Hz, 1H), 6.32 (s, 1H), 3.62 (s, 2H), 3.39 (s, 3H), 2.13 (s, 3H), 1.31 (s, 9H) | 510.2 $(M + H)^+$ |

-continued

| No. | Structure | Name | $^1$H NMR | Observed m/z |
|---|---|---|---|---|
| 232 | 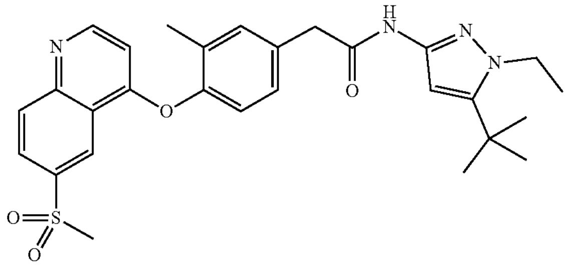 [SMILES: CCn1nc(NC(=O)Cc2ccc(Oc3ccnc4ccc(S(C)(=O)=O)cc34)c(C)c2)cc1C(C)(C)C] | N-(5-(tert-butyl)-1-ethyl-1H-pyrazol-3-yl)-2-(3-methyl-4-((6-(methylsulfonyl)quinolin-4-yl)oxy)phenyl)acetamide | (400 MHz, DMSO-$d_6$) δ 10.65 (s, 1H), 8.91 (dd, J = 1.9, 0.9 Hz, 1H), 8.83 (d, J = 5.2 Hz, 1H), 8.32-8.22 (m, 2H), 7.40 (d, J = 2.2 Hz, 1H), 7.32 (dd, J = 8.3, 2.2 Hz, 1H), 7.23 (d, J = 8.2 Hz, 1H), 6.55 (d, J = 5.2 Hz, 1H), 6.27 (s, 1H), 4.10 (q, J = 7.1 Hz, 2H), 3.62 (s, 2H), 3.39 (s, 3H), 2.14 (s, 3H), 1.34 (t, J = 7.1 Hz, 3H), 1.31 (s, 9H) | 521.4 (M + H)$^+$ |
| 233 | 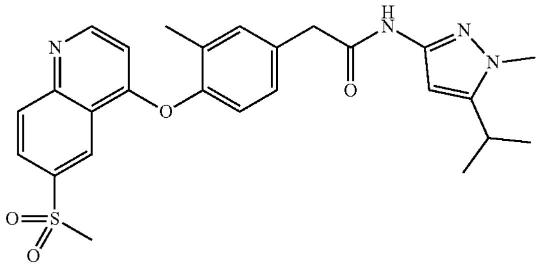 [SMILES: Cc1cc(CC(=O)Nc2cc(C(C)C)n(C)n2)ccc1Oc1ccnc2ccc(S(C)(=O)=O)cc12] | N-(5-isopropyl-1-methyl-1H-pyrazol-3-yl)-2-(3-methyl-4-((6-(methylsulfonyl)quinolin-4-yl)oxy)phenyl)acetamide | (400 MHz, DMSO-$d_6$) δ 10.60 (s, 1H), 8.91 (s, 1H), 8.83 (d, J = 5.2 Hz, 1H), 8.31-8.24 (m, 2H), 7.39 (s, 1H), 7.32 (d, J = 8.3 Hz, 1H), 7.23 (d, J = 8.2 Hz, 1H), 6.55 (d, J = 5.3 Hz, 1H), 6.30 (s, 1H), 3.66 (s, 3H), 3.63 (s, 2H), 3.39 (s, 3H), 2.97 (sept, J = 6.8 Hz, 1H), 2.14 (s, 3H), 1.17 (d, J = 6.8 Hz, 6H) | 493.1 (M + H)$^+$ |
| 234 | 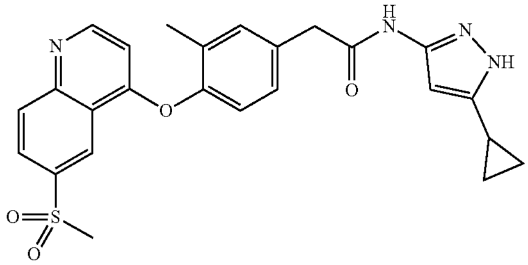 [SMILES: Cc1cc(CC(=O)Nc2cc(C3CC3)[nH]n2)ccc1Oc1ccnc2ccc(S(C)(=O)=O)cc12] | N-(5-cyclopropyl-1H-pyrazol-3-yl)-2-(3-methyl-4-((6-(methylsulfonyl)quinolin-4-yl)oxy)phenyl)acetamide | (300 MHz, DMSO-$d_6$) δ 12.06 (s, 1H), 10.54 (s, 1H), 8.91 (s, 1H), 8.83 (d, J = 5.2 Hz, 1H), 8.28-8.26 (m, 2H), 7.39 (s, 1H), 7.32 (d, J = 8.6 Hz, 1H), 7.22 (d, J = 8.2 Hz, 1H), 6.56 (d, J = 5.3 Hz, 1H), 6.15 (s, 1H), 3.63 (s, 2H), 3.38 (s, 3H), 2.13 (s, 3H), 1.91-1.78 (m, 1H), 0.94-0.84 (m, 2H), 0.65 (dt, J = 5.1, 3.0 Hz, 2H) | 477.1 (M + H)$^+$ |
| 235 | 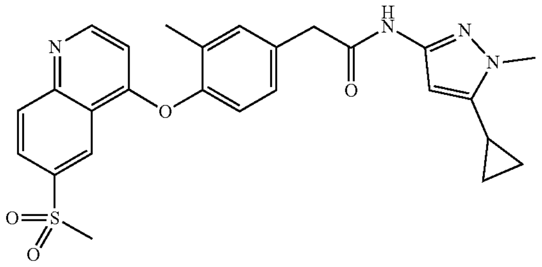 [SMILES: Cc1cc(CC(=O)Nc2cc(C3CC3)n(C)n2)ccc1Oc1ccnc2ccc(S(C)(=O)=O)cc12] | N-(5-cyclopropyl-1-methyl-1H-pyrazol-3-yl)-2-(3-methyl-4-((6-(methylsulfonyl)quinolin-4-yl)oxy)phenyl)acetamide | (400 MHz, DMSO-$d_6$) δ 10.59 (s, 1H), 8.90 (dd, J = 1.9, 0.9 Hz, 1H), 8.83 (d, J = 5.3 Hz, 1H), 8.29-8.27 (m, 2H), 7.38 (d, J = 2.1 Hz, 1H), 7.33-7.18 (m, 2H), 6.55 (d, J = 5.3 Hz, 1H), 6.09 (s, 1H), 3.72 (s, 3H), 3.61 (s, 2H), 3.39 (s, 3H), 2.13 (s, 3H), 1.85 (ddd, J = 13.4, 8.4, 5.0 Hz, 1H), 0.99-0.89 (m, 2H), 0.62-0.53 (m, 2H) | 491.1 (M + H)$^+$ |
| 236 | 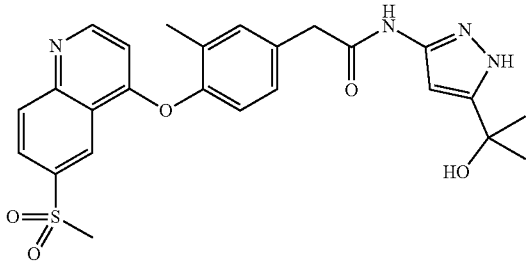 | N-(5-(2-hydroxypropan-2-yl)-1H-pyrazol-3-yl)-2-(3-methyl-4-((6-(methylsulfonyl)quinolin-4-yl)oxy)phenyl)acetamide | (300 MHz, DMSO-$d_6$) δ 12.06 (s, 1H), 10.58 (s, 1H), 8.91 (s, 1H), 8.84 (d, J = 5.2 Hz, 1H), 8.29-8.27 (m, 2H), 7.44-7.29 (m, 2H), 7.24 (d, J = 8.3 Hz, 1H), 6.56 (d, J = 5.3 Hz, 1H), 6.36 (s, 1H), 5.21 (s, 1H), 3.65 (s, 2H), 3.39 (s, 3H), 2.14 (s, 3H), 1.42 (s, 6H | 495.1 (M + H)$^+$ |

-continued

| No. | Structure | Name | $^1$H NMR | Observed m/z |
|---|---|---|---|---|
| 239 | 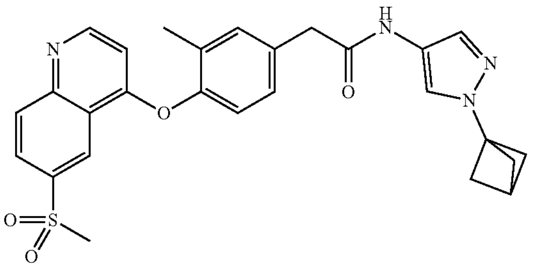 [SMILES: Cc1cc(CC(=O)Nc2cnn(C34CC(C3)C4)c2)ccc1Oc1ccnc2ccc(S(C)(=O)=O)cc12] | N-(1-(bicyclo[1.1.1]pentan-1-yl)-1H-pyrazol-4-yl)-2-(3-methyl-4-((6-(methylsulfonyl)quinolin-4-yl)oxy)phenyl)acetamide | (300 MHz, DMSO-$d_6$) δ 10.28 (s, 1H), 8.91 (s, 1H), 8.84 (d, J = 5.2 Hz, 1H), 8.29-8.27 (m, 2H), 7.91 (s, 1H), 7.46 (s, 1H), 7.39 (s, 1H), 7.32 (d, J = 8.5 Hz, 1H), 7.24 (d, J = 8.3 Hz, 1H), 6.55 (d, J = 5.2 Hz, 1H), 3.63 (s, 2H), 3.39 (s, 3H), 2.60 (s, 1H), 2.19 (s, 6H), 2.14 (s, 3H) | 503.1 (M + H)$^+$ |
| 240 | 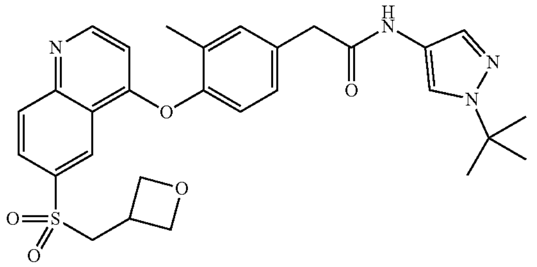 [SMILES: Cc1cc(CC(=O)Nc2cnn(C(C)(C)C)c2)ccc1Oc1ccnc2ccc(S(=O)(=O)CC3COC3)cc12] | N-(1-(tert-butyl)-1H-pyrazol-4-yl)-2-(3-methyl-4-((6-((oxetan-3-ylmethyl)sulfonyl) quinolin-4-yl)oxy)phenyl)acetamide | (400 MHz, DMSO-$d_6$) δ 10.21 (s, 1H), 8.93-8.73 (m, 2H), 8.34-8.14 (m, 2H), 7.96 (s, 1H), 7.46 (s, 1H), 7.40 (d, J = 2.1 Hz, 1H), 7.36-7.22 (m, 2H), 6.57 (d, J = 5.3 Hz, 1H), 4.57 (dd, J = 8.1, 6.0 Hz, 2H), 4.36 (t, J = 6.5 Hz, 2H), 3.95 (d, J = 7.4 Hz, 2H), 3.62 (s, 2H), 3.41 (quint, J = 7.5 Hz, 1H), 2.14 (s, 3H), 1.49 (s, 9H) | 549.1 (M + H)$^+$ |
| 241 | 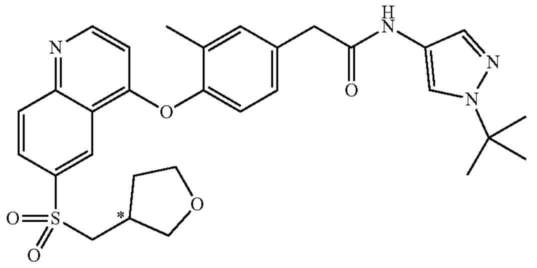 [SMILES: Cc1cc(CC(=O)Nc2cnn(C(C)(C)C)c2)ccc1Oc1ccnc2ccc(S(=O)(=O)CC3CCOC3)cc12] enantiomer 1 (retention time: 4.77 min; column: CHIRALPAK IF-3, 4.6 × 50 mm, 3 μm; mobile phase A: MTBE (0.1% DEA), mobile phase B: MeOH/DCM (1:1), isocratic separation with 10% B, flow rate: 1.0 mL/min, wavelength: 254 nm) | N-(1-(tert-butyl)-1H-pyrazol-4-yl)-2-(3-methyl-4-((6-(((tetrahydrofuran-3-yl)methyl)sulfonyl) quinolin-4-yl)oxy)phenyl)acetamide | (400 MHz, DMSO-$d_6$) δ 10.22 (s, 1H), 8.91 (d, J = 1.8 Hz, 1H), 8.85 (d, J = 5.3 Hz, 1H), 8.30-8.23 (m, 2H), 7.96 (s, 1H), 7.47 (s, 1H), 7.40 (d, J = 2.2 Hz, 1H), 7.32 (dd, J = 8.3, 2.2 Hz, 1H), 7.25 (d, J = 8.2 Hz, 1H), 6.57 (d, J = 5.3 Hz, 1H), 3.83 (dd, J = 8.6, 7.2 Hz, 1H), 3.74-3.56 (m, 6H), 2.58-2.51 (m, 1H), 2.14 (s,3H), 2.10-1.97 (m, 2H), 1.70-1.57 (m,1H), 1.49 (s, 9H) | 563.2 (M + H)$^+$ |
| 242 | 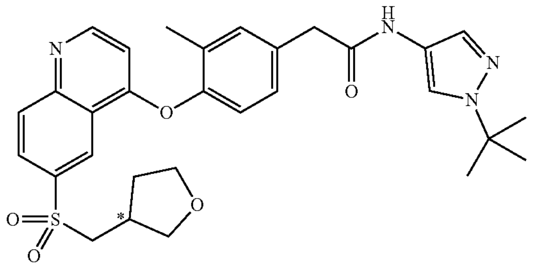 [SMILES: Cc1cc(CC(=O)Nc2cnn(C(C)(C)C)c2)ccc1Oc1ccnc2ccc(S(=O)(=O)CC3CCOC3)cc12] enantiomer 2 (retention time: 6.07 min; column: CHIRALPAK IF-3, 4.6 × 50 mm, 3 μm; mobile phase A: MTBE (0.1% DEA), mobile phase B: MeOH/DCM (1:1), isocratic separation with 10% B, flow rate: 1.0 mL/min, wavelength: 254 nm) | N-(1-(tert-butyl)-1H-pyrazol-4-yl)-2-(3-methyl-4-((6-(((tetrahydrofuran-3-yl)methyl)sulfonyl) quinolin-4-yl)oxy)phenyl)acetamide | (400 MHz, DMSO-$d_6$) δ 10.22 (s, 1H), 8.91 (d, J = 1.7 Hz, 1H), 8.85 (d, J = 5.2 Hz, 1H), 8.30-8.23 (m, 2H), 7.96 (s, 1H), 7.46 (s, 1H), 7.39 (d, J = 2.1 Hz, 1H), 7.32 (dd, J = 8.3, 2.2 Hz, 1H), 7.25 (d, J = 8.2 Hz, 1H), 6.57 (d, J = 5.3 Hz, 1H), 3.82 (dd, J = 8.6, 7.2 Hz, 1H), 3.73-3.57 (m, 6H), 2.55 (d, J = 7.3 Hz, 1H), 2.14 (s, 3H), 2.10-1.97 (m,1H), 1.70-1.57 (m, 1H), 1.49 (s, 9H) | 563.2 (M + H)$^+$ |

-continued

| No. | Structure | Name | $^1H$ NMR | Observed m/z |
|---|---|---|---|---|
| 243 | 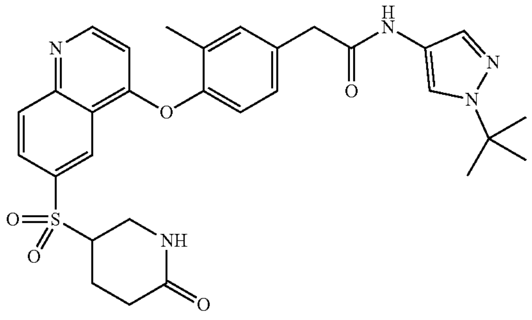 [SMILES: Cc1cc(CC(=O)Nc2cnn(C(C)(C)C)c2)ccc1Oc1ccnc2ccc(S(=O)(=O)C3CCC(=O)NC3)cc12] | N-(1-(tert-butyl)-1H-pyrazol-4-yl)-2-(3-methyl-4-((6-((6-oxopiperidin-3-yl)sulfonyl)quinolin-4-yl)oxy)phenyl)acetamide | (300 MHz, DMSO-$d_6$) δ 10.21 (s, 1H), 8.87-8.85 (m, 2H), 8.29 (d, J = 8.9 Hz, 1H), 8.21 (dd, J = 8.7, 2.2 Hz, 1H), 7.95 (s, 1H), 7.60 (s, 1H), 7.45 (s, 1H), 7.39 (s, 1H), 7.30 (s, 1H), 7.25 (d, J = 8.3 Hz, 1H), 6.58 (d, J = 5.2 Hz, 1H), 4.05-3.99 (m, 1H), 3.61 (s, 2H), 2.73 (dt, J = 4.2, 2.0 Hz, 1H), 2.27 (dt, J = 4.4, 2.0 Hz, 2H), 2.14 (s, 4H), 1.75 (s, 2H), 1.49 (s, 9H) | 576.0 (M + H)$^+$ |
| 248 | 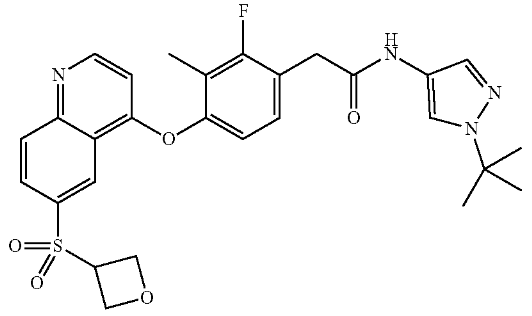 [SMILES: Cc1c(Oc2ccnc3ccc(S(=O)(=O)C4COC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(oxetan-3-ylsulfonyl)quinolin-4-yl)oxy)phenyl)acetamide | (400 MHz, DMSO-$d_6$) δ 10.25 (s, 1H), 8.93-8.87 (m, 2H), 8.30 (d, J = 8.9 Hz, 1H), 8.25 (dd, J = 8.8, 2.1 Hz, 1H), 7.95 (s, 1H), 7.46 (s, 1H), 7.40 (t, J = 8.4 Hz, 1H), 7.17 (d, J = 8.4 Hz, 1H), 6.66 (d, J = 5.3 Hz, 1H), 5.16-5.07 (m, 1H), 4.85-4.76 (m, 4H), 3.72 (s, 2H), 2.08 (d, J = 1.8 Hz, 3H), 1.49 (s, 9H) | 553.0 (M + H)$^+$ |
| 249 | 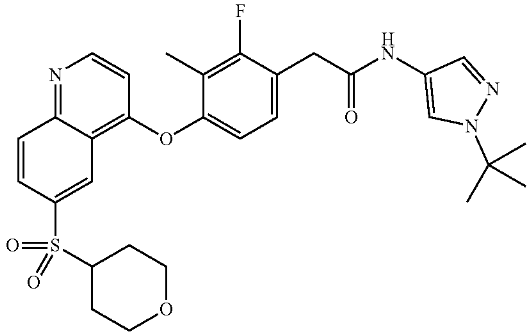 | N-(1-(tert-butyl)-1H-pyrazol-4-yl)-2-(2-fluoro-3-methyl-4-((6-((tetrahydro-2H-pyran-4-yl)sulfonyl)quinolin-4-yl)oxy)phenyl)acetamide | (400 MHz, DMSO-$d_6$) δ 10.25 (s, 1H), 8.89 (d, J = 5.2 Hz, 1H), 8.83 (d, J = 2.1 Hz, 1H), 8.30 (d, J = 8.9 Hz, 1H), 8.19 (dd, J = 8.9, 2.1 Hz, 1H), 7.95 (d, J = 0.7 Hz, 1H), 7.46 (d, J = 0.8 Hz, 1H), 7.40 (t, J = 8.4 Hz, 1H), 7.17 (d, J = 8.3 Hz, 1H), 6.66 (d, J = 5.2 Hz, 1H), 3.92 (dd, J = 11.4, 4.5 Hz, 2H), 3.78 (ddd, J = 11.9, 8.3, 3.8 Hz, 1H), 3.72 (s, 2H), 3.35-3.25 (m, 2H), 2.08 (d, J = 1.2 Hz, 3H), 1.80 (d, J = 12.3 Hz, 2H), 1.64 (qd, J = 12.4, 4.8 Hz, 2H), 1.49 (s, 9H) | 581.1 (M + H)+ |
| 250 | 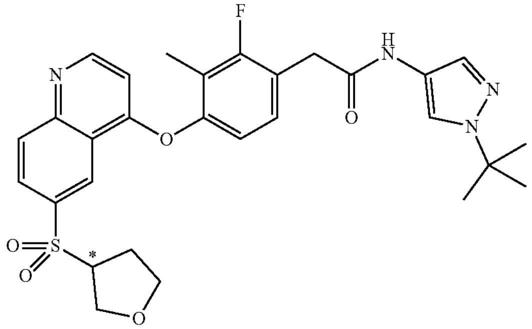 [SMILES: Cc1c(Oc2ccnc3ccc(S(=O)(=O)C4CCOC4)cc23)ccc(CC(=O)Nc2cnn(C(C)(C)C)c2)c1F] enantiomer 1 (retention time: 1.46 min; column: CHIRALPAK IF-3, 4.6 × 50 mm, 3 μm; mobile phase A: MTBE (0.1% DEA), mobile phase B: MeOH/DCM (1:1), isocratic separation with 30% B, flow rate: 1.0 mL/min, wavelength: 254 nm) | N-(1-(tert-butyl)-1H-pyrazol-4-yl)-2-(2-fluoro-3-methyl-4-((6-((tetrahydrofuran-3-yl)sulfonyl)quinolin-4-yl)oxy)phenyl)acetamide | (300 MHz, DMSO-$d_6$) δ 10.24 (s, 1H), 8.90-8.88 (m, 2H), 8.33-8.23 (m, 2H), 7.95 (s, 1H), 7.46 (s, 1H), 7.38 (d, J = 8.3 Hz, 1H), 7.23-7.11 (m, 1H), 6.65 (d, J = 5.2 Hz, 1H), 4.47-4.36 (m, 1H), 4.09 (dd, J = 10.1, 4.7 Hz, 1H), 3.92-3.79 (m, 2H), 3.72 (s, 2H), 3.69-3.61 (m, 1H), 2.28-2.16 (m, 2H), 2.08 (d, J = 1.9 Hz, 3H), 1.49 (s, 9H) | 567.0 (M + H)$^+$ |

-continued

| No. | Structure | Name | $^1$H NMR | Observed m/z |
|---|---|---|---|---|
| 251 | 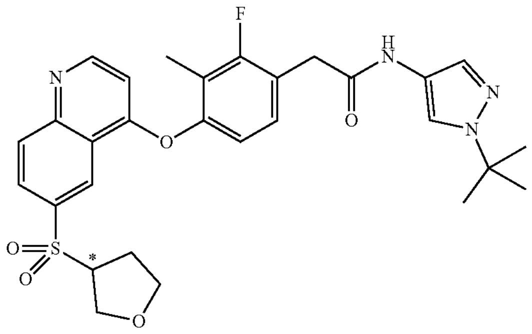 [SMILES: Cc1c(Oc2ccnc3ccc(S(=O)(=O)C4CCOC4)cc23)ccc(CC(=O)Nc2cnn(C(C)(C)C)c2)c1F] enantiomer 2 (retention time: 1.92min; column: CHIRALPAK IF-3, 4.6 x 50 mm, 3 µm; mobile phase A: MTBE (0.1% DEA), mobile phase B: MeOH/DCM (1:1), isocratic separation with 30% B, flow rate: 1.0 mL/min, wavelength: 254 nm) | N-(1-(tert-butyl)-1H-pyrazol-4-yl)-2-(2-fluoro-3-methyl-4-((6-((tetrahydrofuran-3-yl)sulfonyl)quinolin-4-yl)oxy)phenyl)acetamide | (300 MHz, DMSO-$d_6$) δ 10.24 (s, 1H), 8.90-8.88 (m, 2H), 8.34-8.21 (m, 2H), 7.95 (s, 1H), 7.46 (s, 1H), 7.39 (t, J = 8.4 Hz, 1H), 7.17 (d, J = 8.4 Hz, 1H), 6.65 (d, J = 5.2 Hz, 1H), 4.47-4.36 (m, 1H), 4.09 (dd, J = 10.1, 4.6 Hz, 1H), 3.91-3.77 (m, 2H), 3.72 (s, 2H), 3.69-3.62 (m, 1H), 2.28-2.13 (m, 2H), 2.08 (d, J = 1.9 Hz, 3H), 1.49 (s, 9H) | 567.0 (M + H)$^+$ |
| 281 | 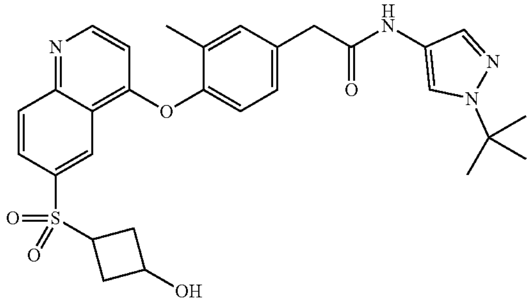 [SMILES: Cc1cc(CC(=O)Nc2cnn(C(C)(C)C)c2)ccc1Oc1ccnc2ccc(S(=O)(=O)C3CC(O)C3)cc12] | N-(1-(tert-butyl)-1H-pyrazol-4-yl)-2-(4-((6-((-3-hydroxycyclobutyl) sulfonyl)quinolin-4-yl)oxy)-3-methylphenyl)acetamide | (300 MHz, DMSO-$d_6$) δ 10.21 (s, 1H), 8.89-8.79 (m, 2H), 8.26 (d, J = 8.8 Hz, 1H), 8.15 (dd, J = 8.9, 2.1 Hz, 1H), 7.95 (s, 1H), 7.46 (s, 1H), 7.39 (d, J = 2.1 Hz, 1H), 7.32 (dd, J = 8.2, 2.2 Hz, 1H), 7.25 (d, J = 8.2 Hz, 1H), 6.57 (d, J = 5.2 Hz, 1H), 5.53 (d, J = 6.8 Hz, 1H), 4.03-3.96 (m, 1H), 3.87-3.70 (m, 1H), 3.62 (s, 2H), 2.46-2.31 (m, 2H), 2.22 (q, J = 10.1 Hz, 2H), 2.14 (s, 3H), 1.49 (s, 9H) | 549.1 (M + H)$^+$ |
| 282 | 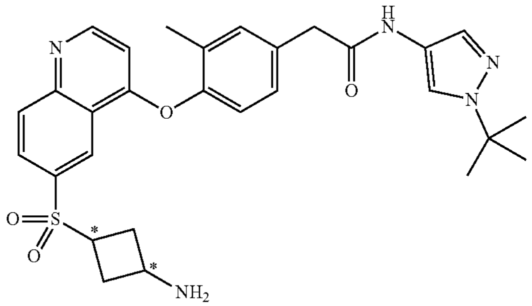 [SMILES: Cc1cc(CC(=O)Nc2cnn(C(C)(C)C)c2)ccc1Oc1ccnc2ccc(S(=O)(=O)C3CC(N)C3)cc12] diastereomer 1 (retention time: 3.43 min; column: CHIRALPAK IE-3, 4.6 x 50 mm, 3 µm; mobile phase A: MTBE (0.1% DEA), mobile phase B: EtOH, isocratic separation with 20% B, flow rate: 1.0 mL/min, wavelength: 254 nm) | 2-(4-((6-((-3-aminocyclobutyl)sulfonyl) quinolin-4-yl)oxy)-3-methylphenyl)-N-(1-(tert-butyl)-1H-pyrazol-4-yl)acetamide | (400 MHz, DMSO-$d_6$) δ 10.28 (s, 1H), 8.88-8.80 (m, 2H), 8.27 (d, J = 8.8 Hz, 1H), 8.21 (dd, J = 8.9, 2.1 Hz, 1H), 7.95 (s, 1H), 7.47 (s, 1H), 7.39 (d, J = 2.2 Hz, 1H), 7.32 (dd, J = 8.3, 2.2 Hz, 1H), 7.25 (d, J = 8.3 Hz, 1H), 6.57 (d, J = 5.2 Hz, 1H), 4.13 (s, 1H), 3.62 (s, 2H), 3.57-3.54 (m, 1H), 2.59 (ddt, J = 10.8, 8.0, 4.4 Hz, 2H), 2.13 (s, 3H), 2.09-2.01 (m, 2H), 1.49 (s, 9H) | 548.2 (M + H)$^+$ |

-continued

| No. | Structure | Name | $^1$H NMR | Observed m/z |
|---|---|---|---|---|
| 283 | 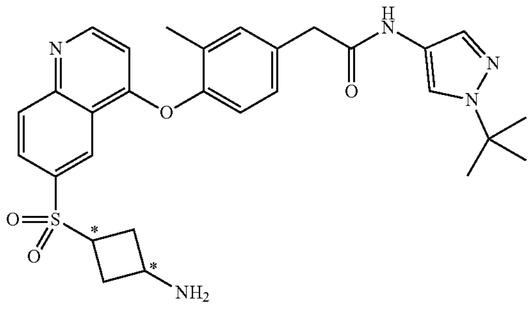 [SMILES: Cc1cc(CC(=O)Nc2cnn(C(C)(C)C)c2)ccc1Oc1ccnc2ccc(S(=O)(=O)C3CC(N)C3)cc12] diastereomer 2 (retention time: 4.45 min; column: CHIRALPAK IE-3, 4.6 × 50 mm, 3 μm; mobile phase A: MTBE (0.1% DEA), mobile phase B: EtOH, isocratic separation with 20% B, flow rate: 1.0 mL/min, wavelength: 254 nm) | 2-(4-((6-((-3-aminocyclobutyl)sulfonyl) quinolin-4-yl)oxy)-3-methylphenyl)-N-(1-(tert-butyl)-1H-pyrazol-4-yl)acetamide | (400 MHz, DMSO-$d_6$) δ 10.22 (s, 1H), 8.87-8.78 (m, 2H), 8.26 (d, J = 8.9 Hz, 1H), 8.14 (dd, J = 8.9, 2.1 Hz, 1H), 7.95 (d, J = 0.7 Hz, 1H), 7.46 (d, J = 0.7 Hz, 1H), 7.39 (d, J = 2.1 Hz, 1H), 7.35-7.28 (m, 1H), 7.25 (d, J = 8.2 Hz, 1H), 6.56 (d, J = 5.2 Hz, 1H), 3.89-3.80 (m, 1H), 3.61 (s, 2H), 3.23-3.20 (m, 1H), 2.32 (qd, J = 7.3, 2.6 Hz, 2H), 2.13 (s, 3H), 2.06 (qd, J = 9.2, 2.7 Hz, 2H), 1.49 (s, 9H) | 548.2 (M + H)$^+$ |
| 284 | 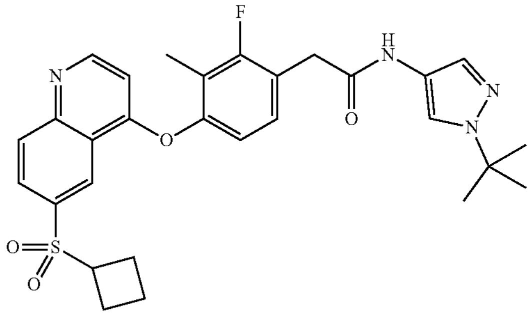 [SMILES: Cc1c(Oc2ccnc3ccc(S(=O)(=O)C4CCC4)cc23)ccc(CC(=O)Nc2cnn(C(C)(C)C)c2)c1F] | N-(1-(tert-butyl)-1H-pyrazol-4-yl)-2-(4-((6-(cyclobutylsulfonyl) quinolin-4-yl)oxy)-2-fluoro-3-methylphenyl)acetamide | (400 MHz, DMSO-$d_6$) δ 10.24 (s, 1H), 8.88 (d, J = 5.2 Hz, 1H), 8.83 (d, J = 2.1 Hz, 1H), 8.28 (d, J = 8.9 Hz, 1H), 8.19 (dd, J = 8.9, 2.1 Hz, 1H), 7.95 (d, J = 0.7 Hz, 1H), 7.48-7.43 (m, 1H), 7.39 (t, J = 8.4 Hz, 1H), 7.16 (d, J = 8.4 Hz, 1H), 6.65 (d, J = 5.2 Hz, 1H), 4.38-4.26 (m, 1H), 3.72 (s, 2H), 2.48-2.35 (m, 2H), 2.21-2.12 (m, 2H), 2.07 (s, 3H), 2.00-1.89 (m, 2H), 1.49 (s, 9H) | 551.2 (M + H)$^+$ |
| 285 | 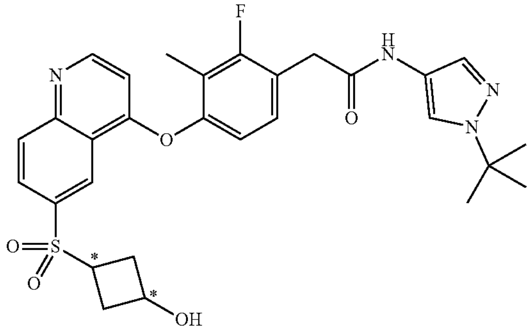 [SMILES: Cc1c(Oc2ccnc3ccc(S(=O)(=O)C4CC(O)C4)cc23)ccc(CC(=O)Nc2cnn(C(C)(C)C)c2)c1F] diastereomer 1 (retention time: 4.23 min; column: CHIRALPAK IE-3, 4.6 × 50 mm, 3 μm; mobile phase A: MTBE (0.1% DEA), mobile phase B: MeOH/DCM (1:1), isocratic separation with 10% B, flow rate: 1.0 mL/min, wavelength: 254 nm) | N-(1-(tert-butyl)-1H-pyrazol-4-yl)-2-(2-fluoro-4-((6-((-3-hydroxycyclobutyl) sulfonyl)quinolin-4-yl)oxy)-3-methylphenyl)acetamide | (300 MHz, DMSO-$d_6$) δ 10.23 (s, 1H), 8.88 (d, J = 5.2 Hz, 1H), 8.82 (d, J = 2.0 Hz, 1H), 8.28 (d, J = 8.9 Hz, 1H), 8.17 (dd, J = 8.8, 2.1 Hz, 1H), 7.95 (s, 1H), 7.46 (s, 1H), 7.40 (t, J = 8.4 Hz, 1H), 7.17 (d, J = 8.4 Hz, 1H), 6.65 (d, J = 5.2 Hz, 1H), 5.53 (s, 1H), 4.00 (s, 1H), 3.88-3.74 (m, 1H), 3.72 (s, 2H), 2.44-2.31 (m, 2H), 2.27-2.14 (m, 2H), 2.08 (d, J = 2.0 Hz, 3H), 1.49 (s, 9H) | 567.0 (M + H)$^+$ |

-continued

| No. | Structure | Name | $^1$H NMR | Observed m/z |
|---|---|---|---|---|
| 286 | 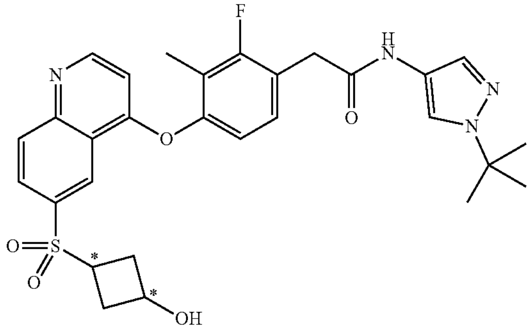 [SMILES: Cc1c(Oc2ccnc3ccc(S(=O)(=O)C4CC(O)C4)cc23)ccc(CC(=O)Nc2cnn(C(C)(C)C)c2)c1F] diastereomer 2 (retention time: 5.15 min; column: CHIRALPAK IE-3, 4.6 × 50 mm, 3 μm; mobile phase A: MTBE (0.1% DEA), mobile phase B: MeOH/DCM (1:1), isocratic separation with 10% B, flow rate: 1.0 mL/min, wavelength: 254 nm) | N-(1-(tert-butyl)-1H-pyrazol-4-yl)-2-(2-fluoro-4-((6-((-3-hydroxycyclobutyl) sulfonyl)quinolin-4-yl)oxy)-3-methylphenyl)acetamide | (300 MHz, DMSO-$d_6$) δ 10.25 (s, 1H), 8.92-8.75 (m, 2H), 8.32-8.15 (m, 2H), 7.95 (s, 1H), 7.50-7.32 (m, 2H), 7.16 (d, J = 8.5 Hz, 1H), 6.64 (d, J = 5.3 Hz, 1H), 5.48 (bs, 1H), 4.39-4.29 (m, 1H), 4.22-4.13 (m, 1H), 3.71 (s, 2H), 2.74-2.61 (m, 2H), 2.32-2.20 (m, 2H), 2.07 (s, 3H), 1.49 (s, 9H | 567.0 $(M + H)^+$ |
| 287 | 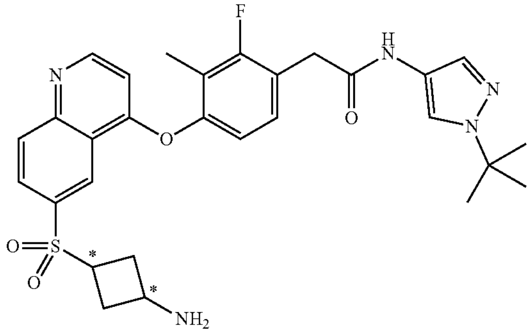 [SMILES: Cc1c(Oc2ccnc3ccc(S(=O)(=O)C4CC(N)C4)cc23)ccc(CC(=O)Nc2cnn(C(C)(C)C)c2)c1F] diastereomer 1 (retention time: 2.14 min; column: CHIRALPAK IE-3, 4.6 × 50 mm, 3 μm; mobile phase A: MTBE (0.1% DEA), mobile phase B: EtOH, isocratic separation with 30% B, flow rate: 1.0 mL/min, wavelength: 254 nm) | 2-(4-((6-((-3-aminocyclobutyl)sulfonyl)quinolin-4-yl)oxy)-2-fluoro-3-methylphenyl)-N-(1-(tert-butyl)-1H-pyrazol-4-yl)acetamide | (400 MHz, DMSO-$d_6$) δ 10.25 (s, 1H), 8.90-8.83 (m, 2H), 8.31-8.19 (m, 2H), 7.95 (s, 1H), 7.46 (s, 1H), 7.39 (t, J = 8.6 Hz, 1H), 7.17 (d, J = 8.3 Hz, 1H), 6.64 (d, J = 5.2 Hz, 1H), 4.27 - 4.09 (m, 1H), 3.71 (s, 2H), 3.57 (quint, J = 7.4 Hz, 1H), 2.64-2.56 (m, 2H), 2.09-2.01 (m, 5H), 1.49 (s, 9H) | 566.6 $(M + H)^+$ |
| 288 | 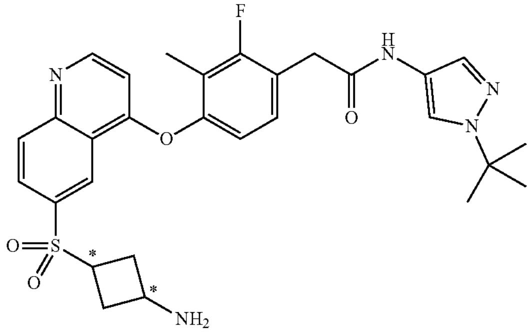 [SMILES: Cc1c(Oc2ccnc3ccc(S(=O)(=O)C4CC(N)C4)cc23)ccc(CC(=O)Nc2cnn(C(C)(C)C)c2)c1F] diastereomer 2 (retention time:2.68 min; column: CHIRALPAK IE-3, 4.6 × 50 mm, 3 μm; mobile phase A: MTBE (0.1% DEA), mobile phase B: EtOH, isocratic separation with 30% B, flow rate: 1.0 mL/min, wavelength: 254 nm) | 2-(4-((6-((-3-aminocyclobutyl) sulfonyl)quinolin-4-yl)oxy)-2-fluoro-3-methylphenyl)-N-(1-(tert-butyl)-1H-pyrazol-4-yl)acetamide | (400 MHz, DMSO-$d_6$) δ 10.24 (s, 1H), 8.88 (d, J = 5.3 Hz, 1H), 8.82 (d, J = 2.1 Hz, 1H), 8.29 (d, J = 8.8 Hz, 1H), 8.16 (dd, J = 8.9, 2.2 Hz, 1H), 7.95 (s, 1H), 7.46 (s, 1H), 7.40 (t, J = 8.4 Hz, 1H), 7.17 (d, J = 8.4 Hz, 1H), 6.66 (d, J = 5.2 Hz, 1H), 3.91 (t, J = 8.6 Hz, 1H), 3.72 (s, 2H), 2.37 (s, 3H), 2.15 (q, J = 9.5 Hz, 2H), 2.08 (d, J = 1.9 Hz, 3H), 1.49 (s, 9H) | 566.6 $(M + H)^+$ |

-continued

| No. | Structure | Name | $^1$H NMR | Observed m/z |
|---|---|---|---|---|
| 299 | 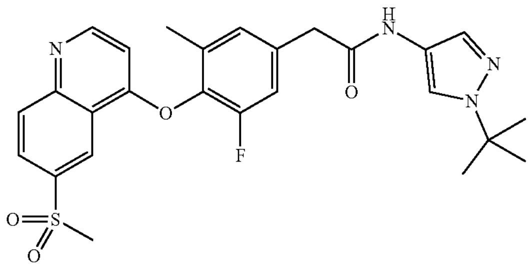 [SMILES: Cc1cc(CC(=O)Nc2cnn(C(C)(C)C)c2)cc(F)c1Oc1ccnc2ccc(S(C)(=O)=O)cc12] | N-(1-(tert-butyl)-1H-pyrazol-4-yl)-2-(3-fluoro-5-methyl-4-((6-(methylsulfonyl)quinolin-4-yl)oxy)phenyl)acetamide | (400 MHz, DMSO-$d_6$) δ 10.24 (s, 1H), 8.93 (dd, J = 1.8, 1.0 Hz, 1H), 8.88 (d, J = 5.2 Hz, 1H), 8.32 - 8.30 (m, 2H), 7.96 (s, 1H), 7.47 (s, 1H), 7.31 (dd, J = 11.1, 2.0 Hz, 1H), 7.24 (s, 1H), 6.66 (dd, J = 5.2, 1.2 Hz, 1H), 3.65 (s, 2H), 3.41 (s, 3H), 2.20 (s, 3H), 1.49 (s, 9H) | 511.1 $(M + H)^+$ |
| 306 | 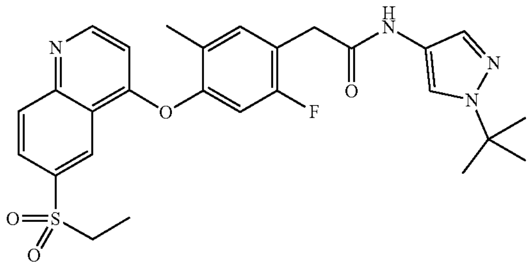 [SMILES: CCS(=O)(=O)c1ccc2nccc(Oc3cc(F)c(CC(=O)Nc4cnn(C(C)(C)C)c4)cc3C)c2c1] | N-(1-(tert-butyl)-1H-pyrazol-4-yl)-2-(4-((6-(ethylsulfonyl)quinolin-4-yl)oxy)-2-fluoro-5-methylphenyl)acetamide | (300 MHz, DMSO-$d_6$) δ 10.24 (s, 1H), 8.93-8.83 (m, 2H), 8.34-8.15 (m, 2H), 7.95 (s, 1H), 7.51-7.42 (m, 2H), 7.31 (d, J = 10.0 Hz, 1H), 6.66 (d, J = 5.2 Hz, 1H), 3.69 (s, 2H), 3.49 (m, 2H), 2.12 (s, 3H), 1.49 (s, 9H), 1.18 (t, J = 7.3 Hz, 3H) | 525.2 $(M + H)^+$ |
| 309 | 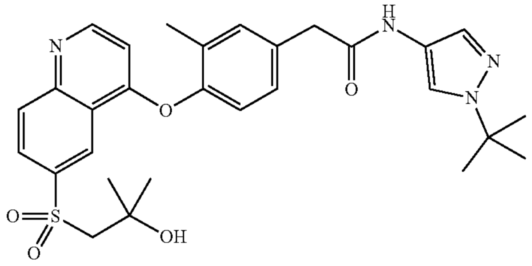 [SMILES: Cc1cc(CC(=O)Nc2cnn(C(C)(C)C)c2)ccc1Oc1ccnc2ccc(S(=O)(=O)CC(C)(C)O)cc12] | N-(1-(tert-butyl)-1H-pyrazol-4-yl)-2-(4-((6-((2-hydroxy-2-methylpropyl)sulfonyl)quinolin-4-yl)oxy)-3-methylphenyl)acetamide | (300 MHz, DMSO-$d_6$) δ 10.20 (s, 1H), 8.87 (s, 1H), 8.82 (d, J = 5.2 Hz, 1H), 8.24-8.22 (m, 2H), 7.95 (s, 1H), 7.46 (s, 1H), 7.39 (d, J = 1.7 Hz, 1H), 7.36-7.29 (m, 1H), 7.24 (d, J = 8.2 Hz, 1H), 6.54 (d, J = 6.0 Hz, 1H), 4.78 (s, 1H), 3.62 (s, 2H), 3.60 (s, 2H), 2.13 (s, 3H), 1.49 (s, 9H), 1.32 (s, 6H) | 551.2 $(M + H)^+$ |
| 310 | 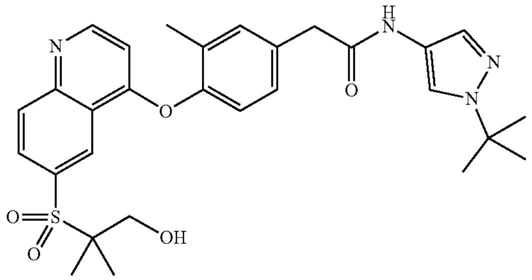 [SMILES: Cc1cc(CC(=O)Nc2cnn(C(C)(C)C)c2)ccc1Oc1ccnc2ccc(S(=O)(=O)C(C)(C)CO)cc12] | N-(1-(tert-butyl)-1H-pyrazol-4-yl)-2-(4-((6-((1-hydroxy-2-methylpropan-2-yl)sulfonyl)quinolin-4-yl)oxy)-3-methylphenyl)acetamide | (400 MHz, DMSO-$d_6$) δ 10.20 (s, 1H), 8.88-8.79 (m, 2H), 8.23 (d, J = 8.9 Hz, 1H), 8.16 (dd, J = 8.9, 2.1 Hz, 1H), 7.95 (s, 1H), 7.46 (s, 1H), 7.39 (d, J = 2.1 Hz, 1H), 7.32 (dd, J = 8.3, 2.1 Hz, 1H), 7.26 (d, J = 8.3 Hz, 1H), 6.58 (d, J = 5.2 Hz, 1H), 5.11 (t, J = 5.7 Hz, 1H), 3.64-3.57 (m, 4H), 2.10 (s, 3H), 1.49 (s, 9H), 1.28 (s, 6H) | 551.2 $(M + H)^+$ |
| 311 | 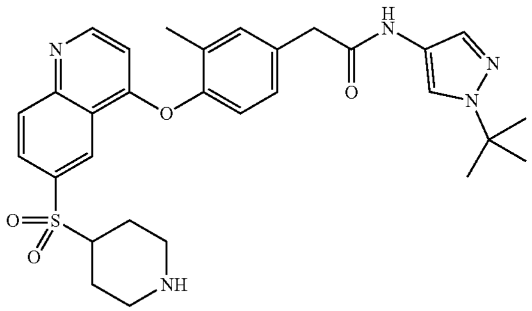 [SMILES: Cc1cc(CC(=O)Nc2cnn(C(C)(C)C)c2)ccc1Oc1ccnc2ccc(S(=O)(=O)C3CCNCC3)cc12] | N-(1-(tert-butyl)-1H-pyrazol-4-yl)-2-(3-methyl-4-((6-(piperidin-4-ylsulfonyl)quinolin-4-yl)oxy)phenyl)acetamide | (300 MHz, DMSO-$d_6$) δ 10.22 (s, 1H), 8.89-8.78 (m, 2H), 8.28 (d, J = 8.9 Hz, 1H), 8.17 (dd, J = 8.9, 2.1 Hz, 1H), 7.96 (s, 1H), 7.46 (s, 1H), 7.39 (d, J = 2.2 Hz, 1H), 7.37-7.21 (m, 2H), 6.58 (d, J = 5.2 Hz, 1H), 3.62 (s, 2H), 3.52 (m, 1H), 2.97 (d, J = 12.4 Hz, 2H), 2.41 (m, 2H), 2.14 (s, 3H), 1.79 (m, 2H), 1.49 (s, 9H), 1.48-1.40 (m, 2H) | 562.2 $(M + H)^+$ |

-continued

| No. | Structure | Name | $^{1}$H NMR | Observed m/z |
|---|---|---|---|---|
| 312 | 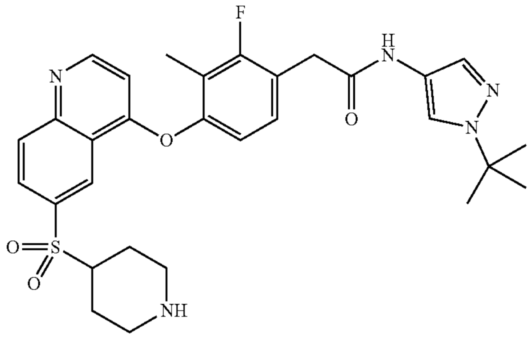 [SMILES: Cc1c(Oc2ccnc3ccc(S(=O)(=O)C4CCNCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(piperidin-4-ylsulfonyl)quinolin-4-yl)oxy)phenyl)acetamide | (400 MHz, DMSO-$d_6$) δ 10.26 (s, 1H), 8.89 (d, J = 5.2 Hz, 1H), 8.81 (d, J = 2.1 Hz, 1H), 8.29 (d, J = 8.9 Hz, 1H), 8.18 (dd, J = 8.9, 2.1 Hz, 1H), 7.95 (s, 1H), 7.47 (s, 1H), 7.40 (t, J = 8.4 Hz, 1H), 7.17 (d, J = 8.4 Hz, 1H), 6.66 (d, J = 5.2 Hz, 1H), 3.72 (s, 2H), 3.59-3.48 (m, 1H), 3.04-2.96 (m, 2H), 2.44 (m, 2H), 2.07 (s, 3H), 1.81 (d, J = 11.9 Hz, 2H), 1.49-1.43 (m, 11H) | 580.1 (M + H)$^+$ |
| 313 | 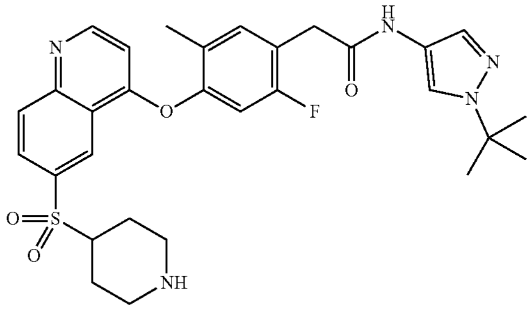 [SMILES: Cc1cc(CC(=O)Nc2cnn(C(C)(C)C)c2)c(F)cc1Oc1ccnc2ccc(S(=O)(=O)C3CCNCC3)cc12] | N-(1-(tert-butyl)-1H-pyrazol-4-yl)-2-(2-fluoro-5-methyl-4-((6-(piperidin-4-ylsulfonyl)quinolin-4-yl)oxy)phenyl)acetamide | (400 MHz, DMSO-$d_6$) δ 10.23 (s, 1H), 8.89 (d, J = 5.2 Hz, 1H), 8.80 (d, J = 2.0 Hz, 1H), 8.29 (d, J = 8.9 Hz, 1H), 8.17 (dd, J = 8.9, 2.1 Hz, 1H), 7.95 (s, 1H), 7.51-7.42 (m, 2H), 7.32 (d, J = 10.0 Hz, 1H), 6.67 (d, J = 5.2 Hz, 1H), 3.69 (s, 2H), 3.52 (m, 1H), 2.98 (m, 2H), 2.42 (m, 2H), 2.12 (s, 3H), 1.80 (d, J = 11.9 Hz, 2H), 1.50-1.35 (m, 11H) | 580.1 (M + H)$^+$ |
| 314 | 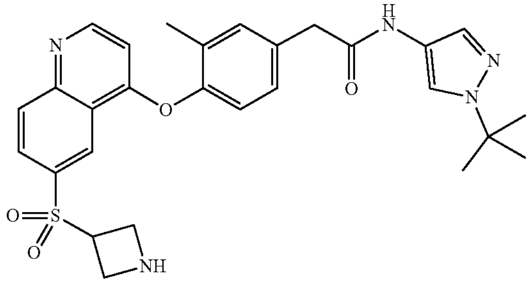 | 2-(4-((6-(azetidin-3-ylsulfonyl)quinolin-4-yl)oxy)-3-methylphenyl)-N-(1-(tert-butyl)-1H-pyrazol-4-yl)acetamide | (300 MHz, DMSO-$d_6$) δ 10.22 (s, 1H), 8.88-8.84 (m, 2H), 8.27 (d, J = 8.9 Hz, 1H), 8.20 (d, J = 8.8 Hz, 1H), 7.96 (s, 1H), 7.46 (s, 1H), 7.40 (s, 1H), 7.32 (d, J = 8.6 Hz, 1H), 7.25 (d, J= 8.1 Hz, 1H), 6.57 (d, J = 5.2 Hz, 1H), 4.72 (t, J = 7.3 Hz, 1H), 3.83 (t, J = 7.8 Hz, 2H), 3.58 (m, 4H), 2.11 (s, 3H), 1.49 (s, 9H) | 534.1 (M + H)$^+$ |
| 315 | 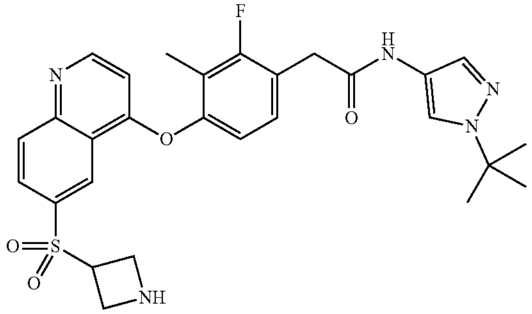 [SMILES: Cc1c(Oc2ccnc3ccc(S(=O)(=O)C4CNC4)cc23)ccc(CC(=O)Nc2cnn(C(C)(C)C)c2)c1F] | 2-(4-((6-(azetidin-3-ylsulfonyl)quinolin-4-yl)oxy)-2-fluoro-3-methylphenyl)-N-(1-(tert-butyl)-1H-pyrazol-4-yl)acetamide | (400 MHz, DMSO-$d_6$) δ 10.25 (s, 1H), 8.95-8.82 (m, 2H), 8.28 (d, J = 8.8 Hz, 1H), 8.21 (d, J = 8.2 Hz, 1H), 7.95 (s, 1H), 7.46 (s, 1H), 7.40 (t, J = 8.4 Hz, 1H), 7.17 (d, J = 8.3 Hz, 1H), 6.65 (d, J = 5.2 Hz, 1H), 3.73-3.71 (m, 3H), 3.51 (s, 4H), 2.07 (s, 3H), 1.49 (s, 9H) | 552.2 (M + H)$^+$ |
| 316 | 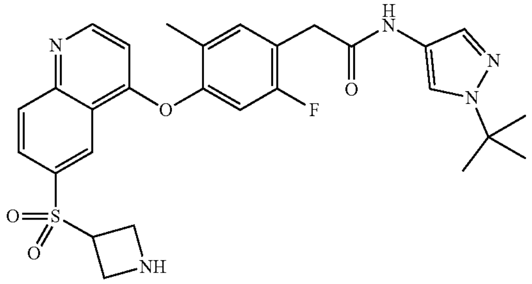 [SMILES: Cc1cc(CC(=O)Nc2cnn(C(C)(C)C)c2)c(F)cc1Oc1ccnc2ccc(S(=O)(=O)C3CNC3)cc12] | 2-(4-((6-(azetidin-3-ylsulfonyl)quinolin-4-yl)oxy)-2-fluoro-5-methylphenyl)-N-(1-(tert-butyl)-1H-pyrazol-4-yl)acetamide | (300 MHz, DMSO-$d_6$) δ 10.28 (s, 1H), 8.93-8.82 (m, 2H), 8.28 (d, J = 8.8 Hz, 1H), 8.21 (dd, J = 8.8, 1.9 Hz, 1H), 7.95 (s, 1H), 7.51-7.41 (m, 2H), 7.31 (d, J = 10.0 Hz, 1H), 6.66 (d, J = 5.2 Hz, 1H), 4.73 (s, 1H), 3.70 (s, 2H), 3.30-3.26 (m, 4H), 2.10 (s, 3H), 1.49 (s, 9H) | 574.1 (M + Na)$^+$ |

-continued

| No. | Structure | Name | $^1$H NMR | Observed m/z |
|---|---|---|---|---|
| 321 | 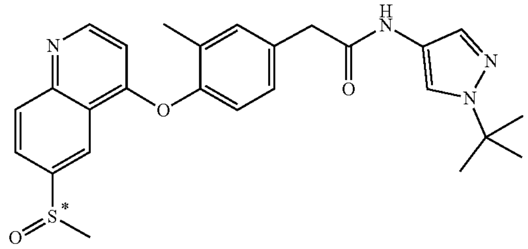 [SMILES: Cc1cc(CC(=O)Nc2cnn(C(C)(C)C)c2)ccc1Oc1ccnc2ccc(S(C)=O)cc12] enantiomer 1 (retention time: 5.93 min; column: CHIRALPAK IC-3, 4.6 × 50 mm, 3 μm; mobile phase A: hexane/DCM (3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(3-methyl-4-((6-(methylsulfinyl) quinolin-4-yl)oxy)phenyl)acetamide | (400 MHz, DMSO-$d_6$) δ 10.22 (s, 1H), 8.75 (d, J = 5.2 Hz, 1H), 8.68 (d, J = 2.0 Hz, 1H), 8.20 (d, J = 8.8 Hz, 1H), 8.06 (dd, J = 8.8, 2.0 Hz, 1H), 7.96 (s, 1H), 7.46 (s, 1H), 7.39 (d, J = 2.2 Hz, 1H), 7.31 (dd, J = 8.3, 2.2 Hz, 1H), 7.22 (d, J = 8.2 Hz, 1H), 6.50 (d, J = 5.2 Hz, 1H), 3.62 (s, 2H), 2.89 (s, 3H), 2.13 (s, 3H), 1.49 (s, 9H) | 477.2 $(M + H)^+$ |
| 322 | 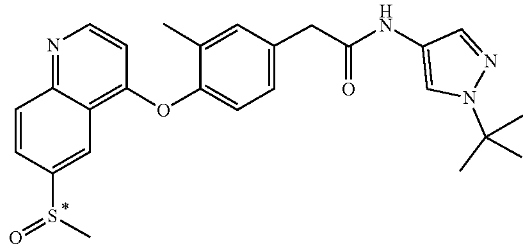 [SMILES: Cc1cc(CC(=O)Nc2cnn(C(C)(C)C)c2)ccc1Oc1ccnc2ccc(S(C)=O)cc12] enantiomer 2 (retention time: 7.83 min; column: CHIRALPAK IC-3, 4.6 × 50 mm, 3 μm; mobile phase A: hexane/DCM(3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(3-methyl-4-((6-(methylsulfinyl) quinolin-4-yl)oxy)phenyl)acetamide | (400 MHz, DMSO-$d_6$) δ 10.22 (s, 1H), 8.75 (d, J = 5.2 Hz, 1H), 8.68 (d, J = 2.0 Hz, 1H), 8.19 (d, J = 8.9 Hz, 1H), 8.06 (dd, J = 8.8, 2.1 Hz, 1H), 7.96 (s, 1H), 7.47 (s, 1H), 7.39 (d, J = 2.2 Hz, 1H), 7.31 (dd, J = 8.3, 2.2 Hz, 1H), 7.22 (d, J = 8.2 Hz, 1H), 6.50 (d, J = 5.2 Hz, 1H), 3.62 (s, 2H), 2.89 (s, 3H), 2.13 (s, 3H), 1.49 (s, 9H) | 477.2 $(M + H)^+$ |
| 323 | 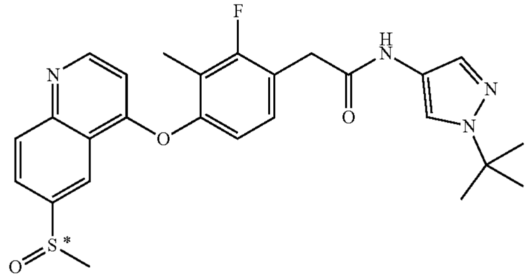 [SMILES: Cc1c(Oc2ccnc3ccc(S(C)=O)cc23)ccc(CC(=O)Nc2cnn(C(C)(C)C)c2)c1F] enantiomer 1 (retention time: 3.64 min; column: CHIRALPAK IA-3, 4.6 × 50 mm, 3 μm; mobile phase A: MTBE (0.1% DEA), mobile phase B: EtOH, isocratic separation with 15% B, flow rate: 1.0 mL/min, wavelength: 254 nm) | N-(1-(tert-butyl)-1H-pyrazol-4-yl)-2-(2-fluoro-3-methyl-4-((6-(methylsulfinyl)quinolin-4-yl)oxy)phenyl)acetamide | (400 MHz, DMSO-$d_6$) δ 10.24 (s, 1H), 8.79 (d, J = 5.2 Hz, 1H), 8.68 (d, J = 2.0 Hz, 1H), 8.22 (d, J = 8.9 Hz, 1H), 8.08 (dd, J = 8.8, 2.0 Hz, 1H), 7.95 (d, J = 0.7 Hz, 1H), 7.46 (d, J = 0.7 Hz, 1H), 7.39 (t, J = 8.3 Hz, 1H), 7.14 (d, J = 8.3 Hz, 1H), 6.59 (d, J = 5.2 Hz, 1H), 3.72 (s, 2H), 2.90 (s, 3H), 2.07 (d, J = 2.0 Hz, 3H), 1.49 (s, 9H) | 495.1 $(M + H)^+$ |
| 324 | 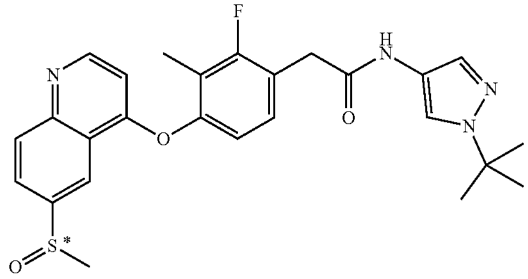 [SMILES: Cc1c(Oc2ccnc3ccc(S(C)=O)cc23)ccc(CC(=O)Nc2cnn(C(C)(C)C)c2)c1F] enantiomer 2 (retention time: 4.86 min; column: CHIRALPAK IA-3, 4.6 × 50 mm, 3 μm; mobile phase A: MTBE (0.1% DEA), mobile phase B: EtOH, isocratic separation with 15% B, flow rate: 1.0 mL/min, wavelength: 254 nm) | N-(1-(tert-butyl)-1H-pyrazol-4-yl)-2-(2-fluoro-3-methyl-4-((6-(methylsulfinyl)quinolin-4-yl)oxy)phenyl)acetamide | (400 MHz, DMSO-$d_6$) δ 10.25 (s, 1H), 8.79 (d, J = 5.2 Hz, 1H), 8.68 (d, J = 2.0 Hz, 1H), 8.22 (d, J = 8.9 Hz, 1H), 8.08 (dd, J = 8.8, 2.0 Hz, 1H), 7.95 (s, 1H), 7.46 (s, 1H), 7.39 (t, J = 8.4 Hz, 1H), 7.14 (d, J = 8.3 Hz, 1H), 6.59 (d, J = 5.2 Hz, 1H), 3.72 (s, 2H), 2.90 (s, 3H), 2.07 (d, J = 1.9 Hz, 3H), 1.49 (s, 9H) | 495.1 $(M + H)^+$ |

-continued

| No. | Structure | Name | $^1$H NMR | Observed m/z |
|---|---|---|---|---|
| 328 | 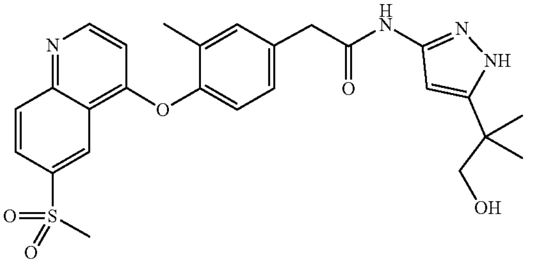 [SMILES: Cc1cc(CC(=O)Nc2cc(C(C)(C)CO)[nH]n2)ccc1Oc1ccnc2ccc(S(C)(=O)=O)cc12] | N-(5-(1-hydroxy-2-methylpropan-2-yl)-1H-pyrazol-3-yl)-2-(3-methyl-4-((6-(methylsulfonyl)quinolin-4-yl)oxy)phenyl)acetamide | (300 MHz, DMSO-$d_6$) δ 11.96 (s, 1H), 10.58 (s, 1H), 8.91 (t, J = 1.4 Hz, 1H), 8.84 (d, J = 5.2 Hz, 1H), 8.29-8.27 (m, 2H), 7.41 (s, 1H), 7.34 (d, J = 8.4 Hz, 1H), 7.23 (d, J = 8.2 Hz, 1H), 6.56 (d, J = 5.2 Hz, 1H), 6.32 (s, 1H), 4.81 (d, J = 5.5 Hz, 1H), 3.64 (s, 2H), 3.43 (s, 3H), 3.35(s, 2H), 2.14 (s, 3H), 1.18 (s, 6H) | 509.2 $(M + H)^+$ |
| 329 | 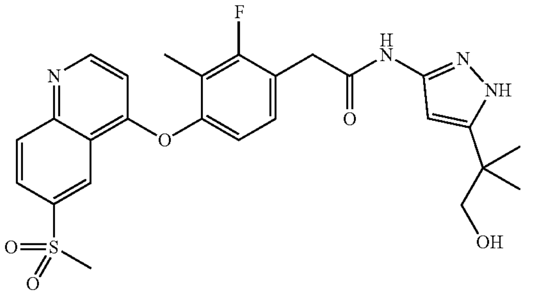 [SMILES: Cc1c(Oc2ccnc3ccc(S(C)(=O)=O)cc23)ccc(CC(=O)Nc2cc(C(C)(C)CO)[nH]n2)c1F] | 2-(2-fluoro-3-methyl-4-((6-(methylsulfonyl)quinolin-4-yl)oxy)phenyl)-N-(5-(1-hydroxy-2-methylpropan-2-yl)-1H-pyrazol-3-yl)acetamide | (300 MHz, DMSO-$d_6$) δ 11.97 (s, 1H), 10.61 (s, 1H), 8.95- 8.83 (m, 2H), 8.30-8.28 (m, 2H), 7.40 (t, J = 8.4 Hz, 1H), 7.15 (d, J = 8.2 Hz, 1H), 6.64 (d, J = 5.2 Hz, 1H), 6.31 (s, 1H), 4.81 (s, 1H), 3.75 (s, 2H), 3.43 (s, 3H), 3.35(s, 2H), 2.08 (d, J = 2.0 Hz, 3H), 1.19 (s, 6H) | 527.1 $(M + H)^+$ |
| 330 | 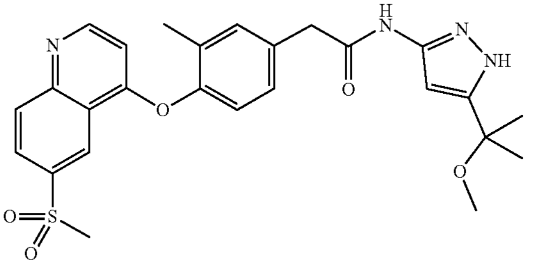 [SMILES: COC(C)(C)c1cc(NC(=O)Cc2ccc(Oc3ccnc4ccc(S(C)(=O)=O)cc34)c(C)c2)n[nH]1] | N-(5-(2-methoxypropan-2-yl)-1H-pyrazol-3-yl)-2-(3-methyl-4-((6-(methylsulfonyl)quinolin-4-yl)oxy)phenyl)acetamide | (400 MHz, DMSO-$d_6$) δ 12.29 (s, 1H), 10.66 (s, 1H), 8.91 (dd, J = 1.9, 0.9 Hz, 1H), 8.84 (d, J = 5.2 Hz, 1H), 8.32-8.22 (m, 2H), 7.41 (d, J = 2.1 Hz, 1H), 7.34 (dd, J = 8.3, 2.2 Hz, 1H), 7.24 (d, J = 8.3 Hz, 1H), 6.56 (d, J = 5.2 Hz, 1H), 6.44 (s, 1H), 3.66 (s, 2H), 3.39 (s, 3H), 2.96 (s, 3H), 2.14 (s, 3H), 1.45 (s, 6H) | 509.2 $(M + H)^+$ |
| 331 | 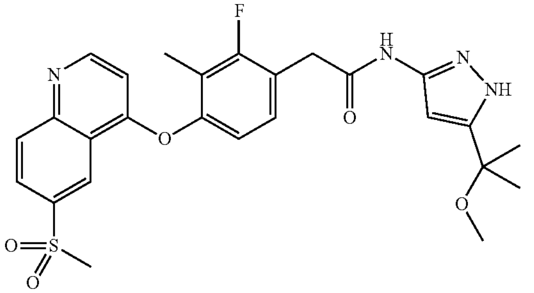 [SMILES: COC(C)(C)c1cc(NC(=O)Cc2ccc(Oc3ccnc4ccc(S(C)(=O)=O)cc34)c(C)c2F)n[nH]1] | 2-(2-fluoro-3-methyl-4-((6-(methylsulfonyl)quinolin-4-yl)oxy)phenyl)-N-(5-(2-methoxypropan-2-yl)-1H-pyrazol-3-yl)acetamide | (400 MHz, DMSO-$d_6$) δ 12.28 (s, 1H), 10.68 (s, 1H), 8.91 (t, J = 1.4 Hz, 1H), 8.87 (d, J = 5.3 Hz, 1H), 8.32-8.26 (m, 2H), 7.40 (t, J = 8.3 Hz, 1H), 7.15 (d, J = 8.5 Hz, 1H), 6.64 (d, J = 5.2 Hz, 1H), 6.43 (s, 1H), 3.76 (s, 2H), 3.39 (s, 3H), 2.96 (s, 3H), 2.08 (d, J = 1.7 Hz, 3H), 1.45 (s, 6H) | 527.2 $(M + H)^+$ |
| 332 | 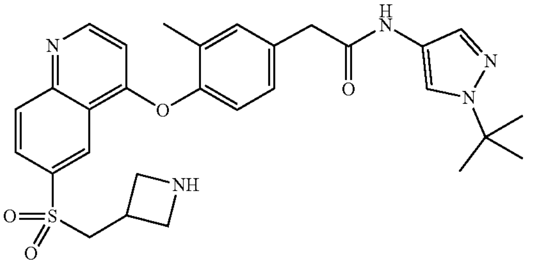 [SMILES: Cc1cc(CC(=O)Nc2cnn(C(C)(C)C)c2)ccc1Oc1ccnc2ccc(S(=O)(=O)CC3CNC3)cc12] | 2-(4-((6-((azetidin-3-ylmethyl)sulfonyl)quinolin-4-yl)oxy)-3-methylphenyl)-N-(1-(tert-butyl)-1H-pyrazol-4-yl)acetamide | (400 MHz, DMSO-$d_6$) δ 10.38-10.30 (m, 1H), 8.86 (s, 1H), 8.31 (d, J = 8.8 Hz, 1H), 8.22 (dd, J = 8.9, 2.1 Hz, 1H), 7.95 (s, 1H), 7.47 (s, 1H), 7.41 (d, J = 2.1 Hz, 1H), 7.34 (dd, J = 8.3, 2.2 Hz, 1H), 7.25 (d, J = 8.2 Hz, 1H), 6.58 (d, J = 5.2 Hz, 1H), 4.01-3.91 (m, 4H), 3.81 (t, J = 8.9 Hz, 2H), 3.63 (s, 2H), 3.15 (m, 1H), 2.14 (s, 3H), 1.49 (s, 9H) | 548.1 $(M + H)^+$ |

-continued

| No. | Structure | Name | $^1$H NMR | Observed m/z |
|---|---|---|---|---|
| 415 | 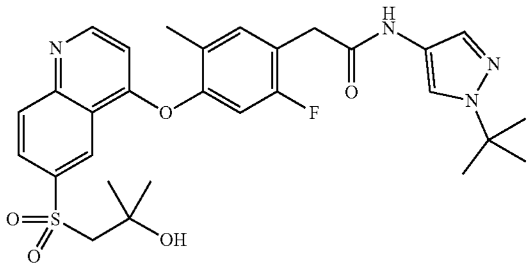 [SMILES: Cc1cc(CC(=O)Nc2cnn(C(C)(C)C)c2)c(F)cc1Oc1ccnc2ccc(S(=O)(=O)CC(C)(C)O)cc12] | N-(1-(tert-butyl)-1H-pyrazol-4-yl)-2-(2-fluoro-4-((6-((2-hydroxy-2-methylpropyl)sulfonyl) quinolin-4-yl)oxy)-5-methylphenyl)acetamide | | 569.1 $(M + H)^+$ |
| 416 | 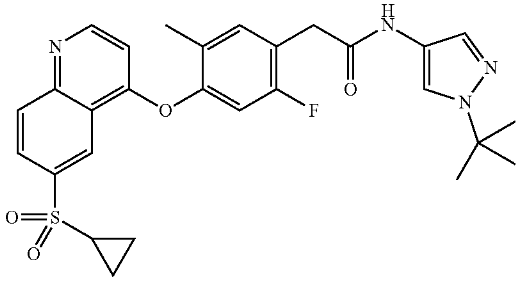 [SMILES: Cc1cc(CC(=O)Nc2cnn(C(C)(C)C)c2)c(F)cc1Oc1ccnc2ccc(S(=O)(=O)C3CC3)cc12] | N-(1-(tert-butyl)-1H-pyrazol-4-yl)-2-(4-((6-(cyclopropylsulfonyl) quinolin-4-yl)oxy)-2-fluoro-5-methylphenyl)acetamide | | 537.2 $(M + H)^+$ |
| 429 | 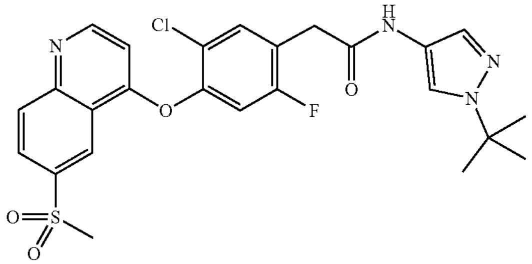 | N-(1-(tert-butyl)-1H-pyrazol-4-yl)-2-(5-chloro-2-fluoro-4-((6-(methylsulfonyl)quinolin-4-yl)oxy)phenyl)acetamide | (400 MHz, DMSO-$d_6$): δ 10.26 (d, J = 4.0 Hz, 1H), 8.95-8.86 (m, 2H), 8.32-8.30 (m, 2H), 7.95 (s, 1H), 7.82 (d, J = 7.4 Hz, 1H), 7.65 (d, J = 9.7 Hz, 1H), 7.47 (s, 1H), 6.77 (d, J = 5.2 Hz, 1H), 3.77 (s, 2H), 3.41 (s, 3H), 1.50 (s, 9H) | 531.0 $(M + H)^+$ |
| 430 | 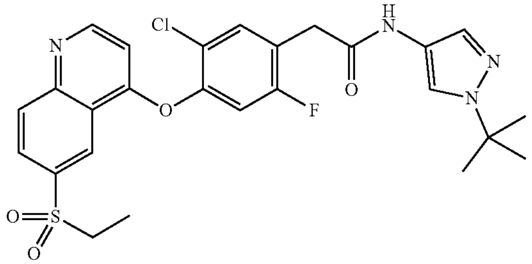 [SMILES: CCS(=O)(=O)c1ccc2nccc(Oc3cc(F)c(CC(=O)Nc4cnn(C(C)(C)C)c4)cc3Cl)c2c1] | N-(1-(tert-butyl)-1H-pyrazol-4-yl)-2-(5-chloro-4-((6-(ethylsulfonyl)quinolin-4-yl)oxy)-2-fluorophenyl)acetamide | | 545.0 $(M + H)^+$ |
| 432 | 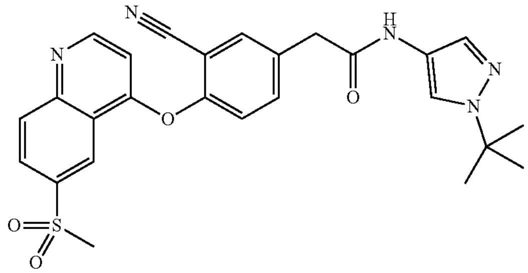 [SMILES: CC(C)(C)n1cc(NC(=O)Cc2ccc(Oc3ccnc4ccc(S(C)(=O)=O)cc34)c(C#N)c2)cn1] | N-(1-(tert-butyl)-1H-pyrazol-4-yl)-2-(3-cyano-4-((6-(methylsulfonyl)quinolin-4-yl)oxy)phenyl)acetamide | | 504.1 $(M + H)^+$ |

-continued

| No. | Structure | Name | $^1$H NMR | Observed m/z |
|---|---|---|---|---|
| 445 | 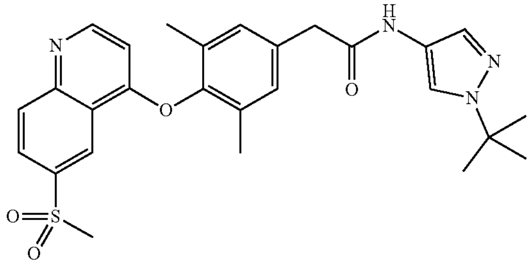 [SMILES: Cc1cc(CC(=O)Nc2cnn(C(C)(C)C)c2)cc(C)c1Oc1ccnc2ccc(S(C)(=O)=O)cc12] | N-(1-(tert-butyl)-1H-pyrazol-4-yl)-2-(3,5-dimethyl-4-((6-(methylsulfonyl) quinolin-4-yl)oxy)phenyl)acetamide | (400 MHz, DMSO-$d_6$): δ 10.19 (s, 1H), 8.95 (dd, J = 2.0, 0.9 Hz, 1H), 8.82 (d, J = 5.2 Hz, 1H), 8.34 - 8.21 (m, 2H), 7.95 (d, J = 0.7 Hz, 1H), 7.46 (d, J = 0.7 Hz, 1H), 7.21 (s, 2H), 6.45 (d, J = 5.2 Hz, 1H), 3.57 (s, 2H), 3.40 (s, 3H), 2.08 (s, 6H), 1.49 (s, 9H) | 505.1 $(M - H)^-$ |
| 446 | 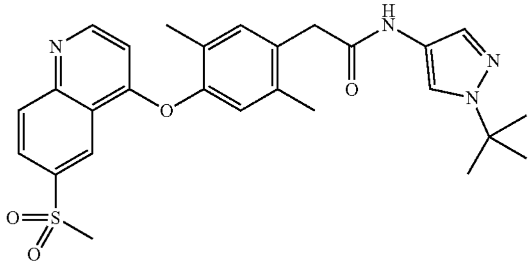 [SMILES: Cc1cc(Oc2ccnc3ccc(S(C)(=O)=O)cc23)c(C)cc1CC(=O)Nc1cnn(C(C)(C)C)c1] | N-(1-(tert-butyl)-1H-pyrazol-4-yl)-2-(2,5-dimethyl-4-((6-(methylsulfonyl)quinolin-4-yl)oxy)phenyl)acetamide | (400 MHz, DMSO-$d_6$): δ 10.15 (s, 1H), 8.93-8.88 (m, 1H), 8.85 (d, J = 5.2 Hz, 1H), 8.31 - 8.23 (m, 2H), 7.95 (s, 1H), 7.46 (s, 1H), 7.31 (s, 1H), 7.10 (s, 1H), 6.56 (d, J = 5.2 Hz, 1H), 3.64 (s, 2H), 3.39 (s, 3H), 2.30 (s, 3H), 2.09 (s, 3H), 1.49 (s, 9H) | 505.1 $(M - H)^-$ |
| 459 | 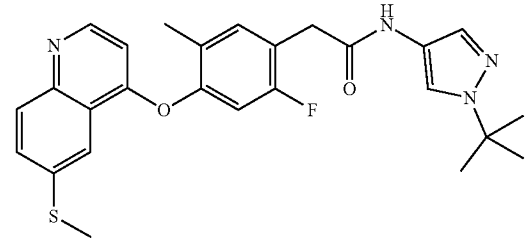 [SMILES: CSc1ccc2nccc(Oc3cc(F)c(CC(=O)Nc4cnn(C(C)(C)C)c4)cc3C)c2c1] | N-(1-(tert-butyl)-1H-pyrazol-4-yl)-2-(2-fluoro-5-methyl-4-((6-(methylthio)quinolin-4-yl)oxy)phenyl)acetamide | | 479.1 $(M + H)^+$ |
| 464 | 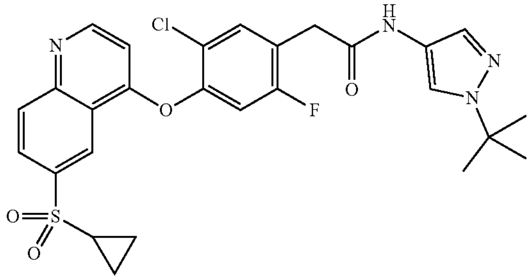 [SMILES: CC(C)(C)n1cc(NC(=O)Cc2cc(Cl)c(Oc3ccnc4ccc(S(=O)(=O)C5CC5)cc34)cc2F)cn1] | N-(1-(tert-butyl)-1H-pyrazol-4-yl)-2-(5-chloro-4-((6-(cyclopropylsulfonyl) quinolin-4-yl)oxy)-2-fluorophenyl)acetamide | (400 MHz, DMSO-$d_6$) δ 10.25 (s, 1H), 8.93 (d, J = 5.2 Hz, 1H), 8.83 (d, J = 1.9 Hz, 1H), 8.35-8.25 (m, 2H), 7.95 (s, 1H), 7.82 (d, J = 7.4 Hz, 1H), 7.67 (d, J = 9.7 Hz, 1H), 7.47 (s, 1H), 6.78 (d, J = 5.2 Hz, 1H), 3.77 (s, 2H), 3.09 (tt, J = 7.9, 4.8 Hz, 1H), 1.50 (s, 9H), 1.25-1.20 (m, 2H), 1.15-1.00 (m, 2H) | 557.0 $(M + H)^+$ |
| 472 | 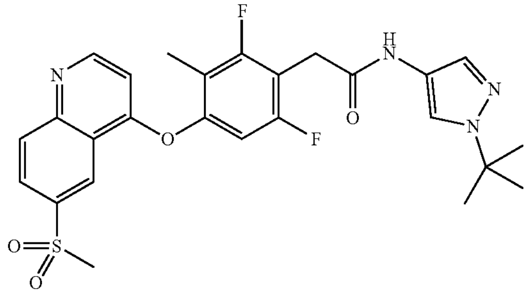 [SMILES: Cc1c(Oc2ccnc3ccc(S(C)(=O)=O)cc23)cc(F)c(CC(=O)Nc2cnn(C(C)(C)C)c2)c1F] | N-(1-(tert-butyl)-1H-pyrazol-4-yl)-2-(2,6-difluoro-3-methyl-4-((6-(methylsulfonyl)quinolin-4-yl)oxy)phenyl)acetamide | (300 MHz, DMSO-$d_6$) δ 10.30 (s, 1H), 8.95-8.87 (m, 2H), 8.33-8.29 (m, 2H), 7.94 (s, 1H), 7.46 (s, 1H), 7.28 (d, J = 9.6 Hz, 1H), 6.74 (d, J = 5.3 Hz, 1H), 3.75 (s, 2H), 3.45 (s, 3H), 2.06 (s, 3H), 1.49 (s, 9H) | 529.1 $(M + H)^+$ |

-continued

| No. | Structure | Name | $^1H$ NMR | Observed m/z |
|---|---|---|---|---|
| 473 | 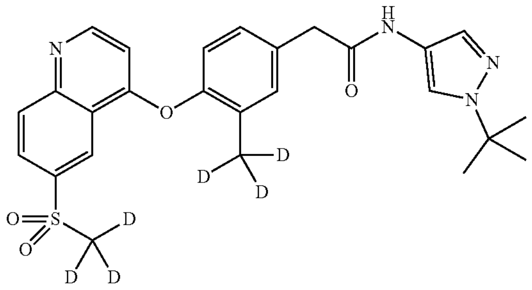 | N-(1-(tert-butyl)-1H-pyrazol-4-yl)-2-(3-chloro-5-methyl-4-((6-(methylsulfonyl)quinolin-4-yl)oxy)phenyl)acetamide | (300 MHz, DMSO-$d_6$) δ 10.24 (s, 1H), 8.93 (s, 1H), 8.86 (d, J = 5.4 Hz, 1H), 8.32-8.30 (m, 2H), 7.97 (s, 1H), 7.51-7.46 (m, 2H), 7.38 (s, 1H), 6.55 (d, J = 5.1 Hz, 1H), 3.66 (s, 2H), 3.41 (s, 3H), 2.19 (s, 3H), 1.50 (s, 9H) | 527.3 $(M + H)^+$ |
| 474 | 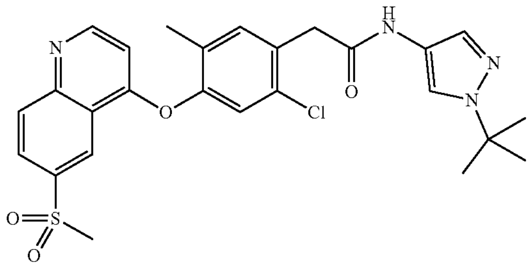 | N-(1-(tert-butyl)-1H-pyrazol-4-yl)-2-(2-chloro-5-methyl-4-((6-(methylsulfonyl)quinolin-4-yl)oxy)phenyl)acetamide | (300 MHz, DMSO-$d_6$) δ 10.21 (s, 1H), 8.93-8.87 (m, 2H), 8.35-8.25 (m, 2H), 7.95 (s, 1H), 7.52-7.47 (m, 3H), 6.64 (d, J = 5.1 Hz, 1H), 3.80 (s, 2H), 3.40 (s, 3H), 2.15 (s, 3H), 1.50 (s, 9H) | 527.2 $(M + H)^+$ |
| 485 | 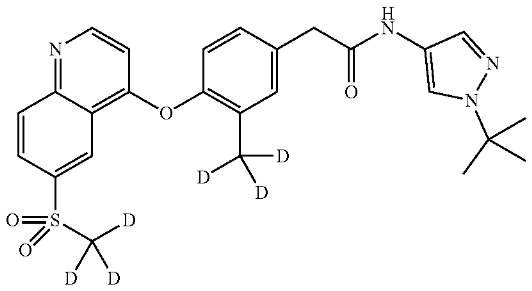 [SMILES: [2H]C([2H])([2H])c1cc(CC(=O)Nc2cnn(C(C)(C)C)c2)ccc1Oc1ccnc2ccc(S(=O)(=O)C([2H])([2H])[2H])cc12] | N-(1-(tert-butyl)-1H-pyrazol-4-yl)-2-(3-(methyl-d3)-4-((6-((methyl-$d_3$)sulfonyl)quinolin-4-yl)oxy)phenyl)acetamide | (400 MHz, DMSO-$d_6$) δ 10.21 (s, 1H), 8.91 (dd, J = 1.8, 0.9 Hz, 1H), 8.84 (d, J = 5.2 Hz, 1H), 8.33-8.23 (m, 2H), 7.96 (d, J = 0.7 Hz, 1H), 7.46 (d, J = 0.7 Hz, 1H), 7.40 (d, J = 2.2 Hz, 1H), 7.32 (dd, J = 8.3, 2.2 Hz, 1H), 7.24 (d, J = 8.2 Hz, 1H), 6.56 (d, J = 5.3 Hz, 1H), 3.62 (s, 2H), 1.49 (s, 9H) | 497.1 $(M + H)^+$ |
| 486 | 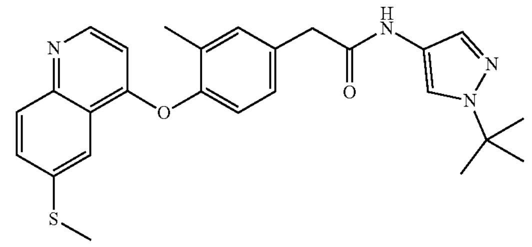 [SMILES: CSc1ccc2nccc(Oc3ccc(CC(=O)Nc4cnn(C(C)(C)C)c4)cc3C)c2c1] | N-(1-(tert-butyl)-1H-pyrazol-4-yl)-2-(3-methyl-4-((6-(methylthio)quinolin-4-yl)oxy)phenyl)acetamide | (300 MHz, DMSO-$d_6$) δ 10.19 (s, 1H), 8.57 (d, J = 5.1 Hz, 1H), 8.03 (d, J = 2.2 Hz, 1H), 7.96-7.93 (m, 2H), 7.72 (dd, J = 8.9, 2.2 Hz, 1H), 7.46 (s, 1H), 7.36 (d, J = 2.1 Hz, 1H), 7.29 (dd, J = 8.2, 2.2 Hz, 1H), 7.18 (d, J = 8.2 Hz, 1H), 6.40 (d, J = 5.1 Hz, 1H), 3.61 (s, 2H), 2.63 (s, 3H), 2.12 (s, 3H), 1.49 (s, 9H) | 461.1 $(M + H)^+$ |
| 518 | 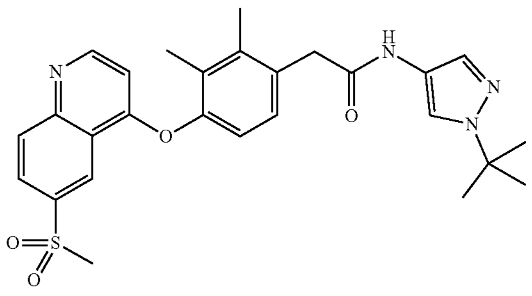 [SMILES: Cc1c(CC(=O)Nc2cnn(C(C)(C)C)c2)ccc(Oc2ccnc3ccc(S(C)(=O)=O)cc23)c1C] | N-(1-(tert-butyl)-1H-pyrazol-4-yl)-2-(2,3-dimethyl-4-((6-(methylsulfonyl)quinolin-4-yl)oxy)phenyl)acetamide | (300 MHz, DMSO-$d_6$) δ 10.17 (s, 1H), 8.92 (s, 1H), 8.84 (d, J = 5.2 Hz, 1H), 8.31-8.28 (m, 2H), 7.95 (s, 1H), 7.46 (s, 1H), 7.28 (d, J = 8.3 Hz, 1H), 7.10 (d, J = 8.3 Hz, 1H), 6.51 (d, J = 5.3 Hz, 1H), 3.72 (s, 2H), 3.39 (s, 3H), 2.29 (s, 3H), 2.08 (s, 3H), 1.49 (s, 9H) | 507.1 $(M + H)^+$ |

-continued

| No. | Structure | Name | $^1$H NMR | Observed m/z |
|---|---|---|---|---|
| 594 | 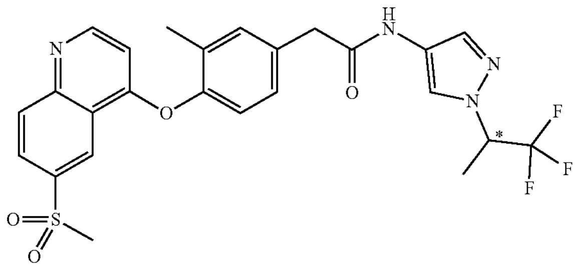 [SMILES: Cc1cc(CC(=O)Nc2cnn(C(C)C(F)(F)F)c2)ccc1Oc1ccnc2ccc(S(C)(=O)=O)cc12] enantiomer 1 (retention time: 2.63 min; column: CHIRALPAK ID-3, 4.6 x 50 mm, 3 µm; mobile phase A: MTBE (0.1% DEA), mobile phase B: isopropanol, isocratic separation with 10% B, flow rate: 1.0 mL/min, wavelength: 254 nm) | 2-(3-methyl-4-((6-(methylsulfonyl)quinolin-4-yl)oxy)phenyl)-N-(1-(1,1,1-trifluoropropan-2-yl)-1H-pyrazol-4-yl)acetamide | (400 MHz, DMSO-$d_6$) δ 10.36 (s, 1H), 8.95-8.90 (m, 1H), 8.84 (d, J = 5.2 Hz, 1H), 8.33-8.23 (m, 2H), 8.12 (s, 1H), 7.60 (s, 1H), 7.41 (d, J = 2.2 Hz, 1H), 7.33 (dd, J = 8.3, 2.2 Hz, 1H), 7.25 (d, J = 8.2 Hz, 1H), 6.57 (d, J = 5.2 Hz, 1H), 5.42-5.35 (m, 1H), 3.65 (s, 2H), 3.40 (s, 3H), 2.15 (s, 3H), 1.64 (d, J = 7.1 Hz, 3H) | 533.1 $(M + H)^+$ |
| 595 | 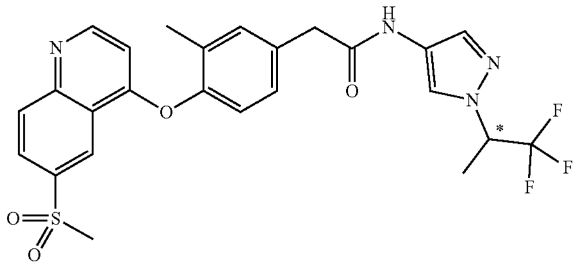 [SMILES: Cc1cc(CC(=O)Nc2cnn(C(C)C(F)(F)F)c2)ccc1Oc1ccnc2ccc(S(C)(=O)=O)cc12] enantiomer 2 (retention time: 3.42 min; column: CHIRALPAK ID-3, 4.6 x 50 mm, 3 µm; mobile phase A: MTBE (0.1% DEA), mobile phase B: isopropanol, isocratic separation with 10% B, flow rate: 1.0 mL/min, wavelength: 254 nm) | 2-(3-methyl-4-((6-(methylsulfonyl)quinolin-4-yl)oxy)phenyl)-N-(1-(1,1,1-trifluoropropan-2-yl)-1H-pyrazol-4-yl)acetamide | (400 MHz, DMSO-$d_6$) δ 10.36 (s, 1H), 8.95-8.90 (m, 1H), 8.84 (d, J = 5.2 Hz, 1H), 8.33-8.23 (m, 2H), 8.12 (s, 1H), 7.60 (s, 1H), 7.41 (d, J = 2.2 Hz, 1H), 7.33 (dd, J = 8.3, 2.2 Hz, 1H), 7.25 (d, J = 8.2 Hz, 1H), 6.57 (d, J = 5.2 Hz, 1H), 5.42-5.35 (m, 1H), 3.65 (s, 2H), 3.40 (s, 3H), 2.15 (s, 3H), 1.64 (d, J = 7.1 Hz, 3H) | 533.1 $(M + H)^+$ |
| 597 | 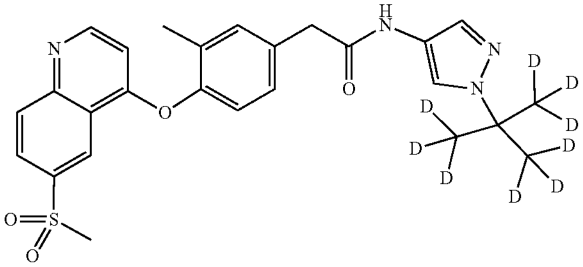 [SMILES: [2H]C([2H])([2H])C(n1cc(NC(=O)Cc2ccc(Oc3ccnc4ccc(S(C)(=O)=O)cc34)c(C)c2)cn1)(C([2H])([2H])[2H])C([2H])([2H])[2H]] | 2-(3-methyl-4-((6-(methylsulfonyl)quinolin-4-yl)oxy)phenyl)-N-(1-(2-(methyl-d3)propan-2-yl-1,1,1,3,3,3-d6)-1H-pyrazol-4-yl)acetamide | (300 MHz, DMSO-$d_6$) δ 10.22 (s, 1H), 8.92 (dd, J = 1.8, 0.9 Hz, 1H), 8.84 (d, J = 5.2 Hz, 1H), 8.32-8.25 (m, 2H), 7.95 (s, 1H), 7.47 (s, 1H), 7.40 (d, J = 2.1 Hz, 1H), 7.32 (dd, J = 8.3, 2.1 Hz, 1H), 7.24 (d, J = 8.2 Hz, 1H), 6.56 (d, J = 5.2 Hz, 1H), 3.63 (s, 2H), 3.40 (s, 3H), 2.14 (s, 3H) | 502.2 $(M + H)^+$ |

Example 36—Synthesis of 4-(4-(2-((1-(tert-butyl)-1H-pyrazol-4-yl)amino)-2-oxoethyl)-3-fluorophenoxy)-N,N-dimethylquinazoline-6-carboxamide (Compound 26); Prepared According to General Scheme 10

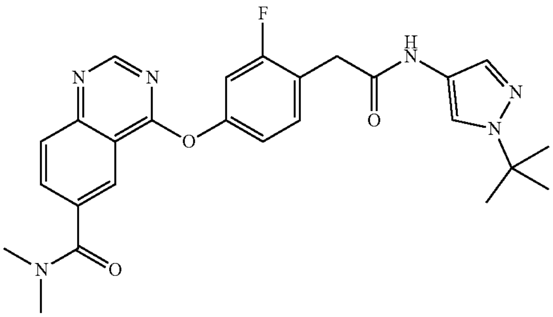 [SMILES: CN(C)C(=O)c1ccc2ncnc(Oc3ccc(CC(=O)Nc4cnn(C(C)(C)C)c4)c(F)c3)c2c1]

Part I—Synthesis of methyl 4-(4-(2-((1-(tert-butyl)-1H-pyrazol-4-yl)amino)-2-oxoethyl)-3-fluorophenoxy)quinazoline-6-carboxylate

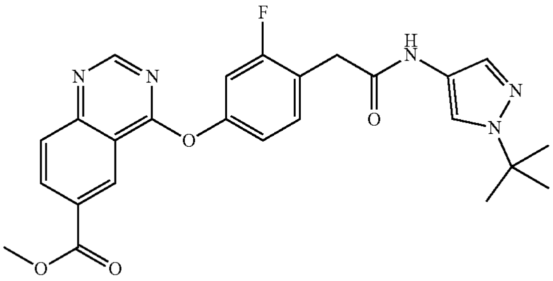 [SMILES: COC(=O)c1ccc2ncnc(Oc3ccc(CC(=O)Nc4cnn(C(C)(C)C)c4)c(F)c3)c2c1]

A solution of N-(1-(tert-butyl)-1H-pyrazol-4-yl)-2-(2-fluoro-4-hydroxyphenyl)acetamide (400 mg, 1.37 mmol, 1.00 equiv., can be synthesized as described in Part II of Example 9), methyl 4-chloroquinazoline-6-carboxylate (306 mg, 1.37 mmol, 1.00 equiv., commercially available), and DMAP (252 mg, 2.06 mmol, 1.50 equiv.) in chlorobenzene (4 mL) was heated to 150° C. for 3 h. Subsequently, the solvent was removed under reduced pressure and the crude product was purified by column chromatography (DCM/MeOH 10:1). The title compound was obtained as a light-yellow solid (211 mg, 31%).

Part II—Synthesis of 4-(4-(2-((1-(tert-butyl)-1H-pyrazol-4-yl)amino)-2-oxoethyl)-3-fluorophenoxy)quinazoline-6-carboxylic Acid

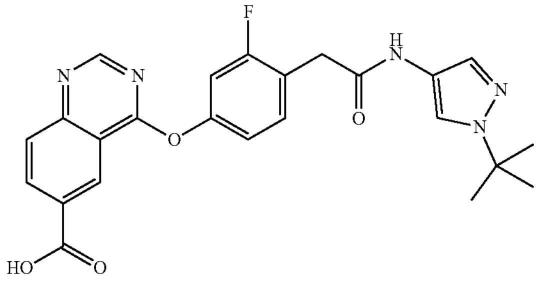 [SMILES: CC(C)(C)n1cc(NC(=O)Cc2ccc(Oc3ncnc4ccc(C(=O)O)cc34)cc2F)cn1]

A solution of lithium hydroxide (15.1 mg, 0.628 mmol, 2.00 equiv.) in water (0.3 mL) was added to a solution of 4-(4-(2-((1-(tert-butyl)-1H-pyrazol-4-yl)amino)-2-oxoethyl)-3-fluorophenoxy)quinazoline-6-carboxylate (150 mg, 0.314 mmol, 1.00 equiv.) in THF (3 mL) and the mixture was stirred at room temperature for 1 h. Subsequently, the crude product was purified by reversed-phase flash chromatography (column: C18 silica gel; mobile phase A: water, mobile phase B: ACN, gradient: 10-50% B in 40 min; wavelength: 210 nm). The title compound was obtained as a white solid (58 mg, 39%).

Part III—Synthesis of 4-(4-(2-((1-(tert-butyl)-1H-pyrazol-4-yl)amino)-2-oxoethyl)-3-fluorophenoxy)-N,N-dimethylquinazoline-6-carboxamide (Compound 26)

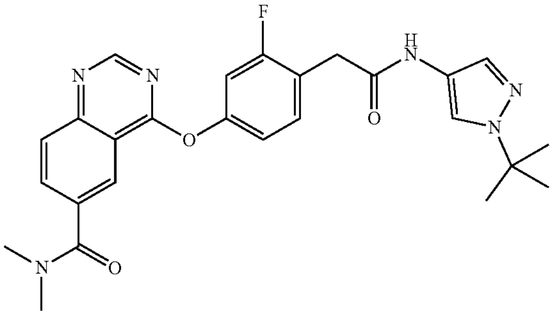 [SMILES: CN(C)C(=O)c1ccc2ncnc(Oc3ccc(CC(=O)Nc4cnn(C(C)(C)C)c4)c(F)c3)c2c1]

Dimethylamine (35.0 mg, 0.776 mmol, 1.20 equiv.), HATU (295 mg, 0.776 mmol, 1.20 equiv.), and DIPEA (251 mg, 1.94 mmol, 3.00 equiv.) were added to a solution of 4-(4-(2-((1-(tert-butyl)-1H-pyrazol-4-yl)amino)-2-oxoethyl)-3-fluorophenoxy)quinazoline-6-carboxylic acid (300 mg, 0.647 mmol, 1.00 equiv.) in DMF (3 mL) and the reaction mixture was stirred at room temperature for 2 h. Subsequently, water (15 mL) was added, and the product was extracted with EtOAc (3×5 mL). The combined organic phases were washed with brine (6×5 mL), dried over $Na_2SO_4$, and the solvent was removed under reduced pressure. The crude product was purified by reversed-phase flash chromatography (column: C18 silica gel; mobile phase A: water (1% $NH_4HCO_3$), mobile phase B: ACN, gradient: 35-65% B in 30 min; wavelength: 210 nm). The title compound was obtained as an off-white solid (80.5 mg, 25%). LCMS (ESI) calculated for $C_{26}H_{28}FN_6O_3(M+H)^+$:

491.2, found: 491.3. $^1$H NMR (400 MHz, DMSO-$d_6$) (10.25 (s, 1H), 8.80 (s, 1H), 8.36 (t, J=1.3 Hz, 1H), 8.08-8.04 (m, 2H), 7.94 (d, J=0.8 Hz, 1H), 7.50 (t, J=8.5 Hz, 1H), 7.45 (d, J=0.7 Hz, 1H), 7.36 (dd, J=10.5, 2.3 Hz, 1H), 7.21 (dd, J=8.4, 2.3 Hz, 1H), 3.70 (s, 2H), 3.06 (s, 3H), 2.99 (s, 3H), 1.49 (s, 9H).

Example 37—Synthesis of 4-(4-(2-((1-(tert-butyl)-1H-pyrazol-4-yl)amino)-2-oxoethyl)-5-fluoro-2-methylphenoxy)-N-methylquinoline-6-carboxamide (Compound 360); Prepared According to General Scheme 6

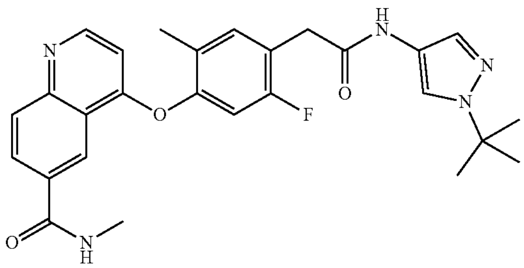 [SMILES: CNC(=O)c1ccc2nccc(Oc3cc(F)c(CC(=O)Nc4cnn(C(C)(C)C)c4)cc3C)c2c1]

Part I—Synthesis of methyl 2-(2-fluoro-5-methyl-4-(4,4,5,5-tetramethyl-1,3,2-dioxaborolan-2-yl)phenyl) acetate

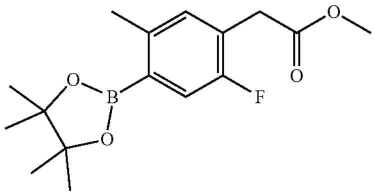

A solution of methyl 2-(4-bromo-2-fluoro-5-methylphenyl)acetate (26.0 g, 99.6 mmol, 1.00 equiv.), bis(pinacolato) diboron (50.6 g, 199 mmol, 2.00 equiv.), potassium acetate (29.3 g, 299 mmol, 3.00 equiv.), and Pd(dppf)$Cl_2$ (3.64 g, 4.98 mmol, 0.05 equiv.) in 1,4-dioxane (208 mL) was heated to 130° C. overnight under an inert atmosphere of nitrogen. The reaction mixture was used in the next reaction without any purification.

Part II—Synthesis of methyl 2-(2-fluoro-4-hydroxy-5-methylphenyl)acetate

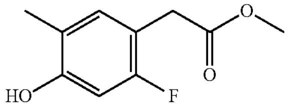

A solution of hydrogen peroxide in water (30%, 52 mL, 2.23 mol, 23.0 equiv.) was added dropwise to the solution of crude methyl 2-(2-fluoro-5-methyl-4-(4,4,5,5-tetramethyl-1,3,2-dioxaborolan-2-yl)phenyl)acetate (99.6 mmol, 1.00 equiv.) in 1,4-dioxane (208 mL) at 0° C. Subsequently, the mixture was stirred for 1 h at room temperature. The reaction was quenched through addition of a saturated aqueous solution of sodium thiosulfate. EtOAc (500 mL) was added, and the organic phase was washed with water (2×150 mL) and dried over $Na_2SO_4$. The solvent was removed under reduced pressure and the crude product was purified by column chromatography (petroleum ether/EtOAc 97:3). The title compound was obtained as a yellow oil (30 g).

Part III—Synthesis of 2-(2-fluoro-4-hydroxy-5-methylphenyl)acetic Acid

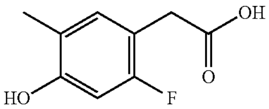

A solution of lithium hydroxide (7.27 g, 303 mmol, 2.00 equiv.) in water (150 mL) was added to a solution of methyl 2-(2-fluoro-4-hydroxy-5-methylphenyl)acetate (30.0 g, 152 mmol, 1.00 equiv.) in THF (150 mL) at 0° C. subsequently, the reaction mixture was stirred at room temperature for 1 h. The pH of the solution was adjusted to 2 by the addition of a citric acid solution and the product was extracted with EtOAc (500 mL). The organic phase was washed with water (2×200 mL), dried over $Na_2SO_4$, and the solvent was removed under reduced pressure. The title compound was obtained as a yellow solid (20 g), which was used in the next reaction without further purification.

Part IV—Synthesis of N-(1-(tert-butyl)-1H-pyrazol-4-yl)-2-(2-fluoro-4-hydroxy-5-methylphenyl)acetamide

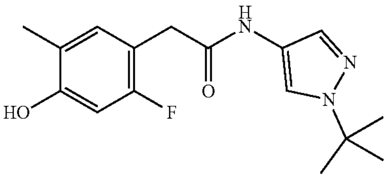 [SMILES: Cc1cc(CC(=O)Nc2cnn(C(C)(C)C)c2)c(F)cc1O]

PyBOP (10.2 g, 19.5 mmol, 1.50 equiv.) was added to a solution of 2-(2-fluoro-4-hydroxy-5-methylphenyl)acetic acid (2.40 g, 13.0 mmol, 1.00 equiv.), 1-(tert-butyl)-1H-pyrazol-4-amine (2.00 g, 14.3 mmol, 1.10 equiv.), and DIPEA (8.42 g, 65.2 mmol, 5.00 equiv.) in DMF (25 mL) at 0° C. Subsequently, the mixture was stirred at room temperature for 1 h. EtOAc (200 mL) was added, and the organic phase was washed with water (3×50 mL). The solvent was removed under reduced pressure and the crude product was purified by reversed-phase flash chromatography (column: C18 silica gel; mobile phase A: water (0.1% $NH_4HCO_3$), mobile phase B: ACN, gradient: 30-70% B in 20 min; wavelength: 210 nm). The title compound was obtained as a white solid (1.94 g, 53% over 4 steps).

Part V—Synthesis of 4-chloro-N-methylquinoline-6-carboxamide

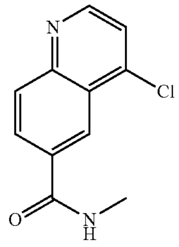

Methyl 4-chloroquinoline-6-carboxylate (1.50 g, 6.77 mmol, 1.00 equiv.) was added to a solution of methylamine in EtOH (33 wt. %, 30 mL) and the mixture was stirred at room temperature overnight. The crude product was purified by reversed-phase flash chromatography (column: C18 silica gel; mobile phase A: water (0.1% $NH_4HCO_3$), mobile phase B: ACN, gradient: 10-50% B in 20 min; wavelength: 210 nm). The title compound was obtained as a white solid (900 mg, 60%).

Part VI—Synthesis of 4-(4-(2-((1-(tert-butyl)-1H-pyrazol-4-yl)amino)-2-oxoethyl)-5-fluoro-2-methylphenoxy)-N-methylquinoline-6-carboxamide (Compound 360)

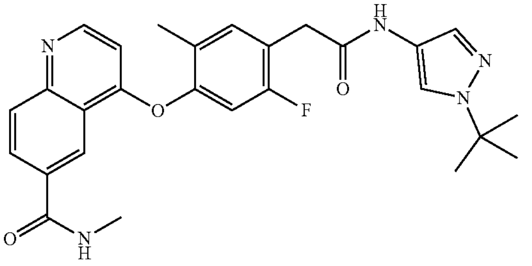 [SMILES: CNC(=O)c1ccc2nccc(Oc3cc(F)c(CC(=O)Nc4cnn(C(C)(C)C)c4)cc3C)c2c1]

A solution of N-(1-(tert-butyl)-1H-pyrazol-4-yl)-2-(2-fluoro-4-hydroxy-5-methylphenyl)acetamide (150 mg, 0.489 mmol, 1.00 equiv.), 4-chloro-N-methylquinoline-6-carboxamide (108 mg, 0.489 mmol, 1.00 equiv.), $Cs_2CO_3$ (319 mg, 0.978 mmol, 2.00 equiv.), CuI (37.3 mg, 0.196 mmol, 0.40 equiv.), and N,N-dimethylglycine (30.3 mg, 0.293 mmol, 0.60 equiv.) in 1,4-dioxane (1.5 mL) was heated to 90° C. for 6 h under an inert atmosphere of nitrogen. Subsequently, the crude product was purified by preparative HPLC (column: XSelect CSH Fluoro Phenyl; 30×150 mm, 5 μm; mobile phase A: water (10 mmol/L $NH_4HCO_3$), mobile phase B: ACN; flow rate: 60 mL/min; isocratic separation with 36% B for 13 min; wavelength: 220 nm, RT1: 11 min)). The title compound was obtained as a yellow solid (70 mg, 29%). LCMS (ESI) calculated for $C_{27}H_{29}FN_5O_3(M+H)^+$: 490.2, found: 490.1. $^1H$ NMR (400 MHz, DMSO-$d_6$) δ 10.23 (s, 1H), 8.89 (d, J=2.0 Hz, 1H), 8.83 (d, J=4.9 Hz, 1H), 8.76 (s, 1H), 8.25 (dd, J=8.8, 2.0 Hz, 1H), 8.10 (d, J=8.8 Hz, 1H), 7.95 (s, 1H), 7.48-7.43 (m, 2H), 7.27 (d, J=10.0 Hz, 1H), 6.54 (d, J=5.2 Hz, 1H), 3.69 (s, 2H), 2.87 (d, J=4.5 Hz, 3H), 2.11 (s, 3H), 1.49 (s, 9H).

Example 38—Preparation of Additional Amide Compounds

Compounds in the table below were prepared based on experimental procedures described in Examples 36 and 37 and the detailed description.

| No. | Structure | Name | $^1H$ NMR | Observed m/z |
|---|---|---|---|---|
| 24 | 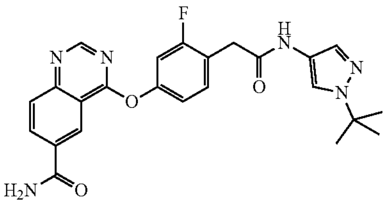 [SMILES: CC(C)(C)n1cc(NC(=O)Cc2ccc(Oc3ncnc4ccc(C(N)=O)cc34)cc2F)cn1] | 4-(4-(2-((1-(tert-butyl)-1H-pyrazol-4-yl)amino)-2-oxoethyl)-3-fluoro-phenoxy) quinazoline-6-carboxamide | (300 MHz, DMSO-$d_6$) δ 10.25 (s, 1H), 8.93 (s, 1H), 8.82 (s, 1H), 8.55-8.37 (m, 2H), 8.12-8.01 (m, 1H), 7.94 (s, 1H), 7.69 (s, 1H), 7.51-7.46 (m, 2H), 7.37 (d, J = 10.6 Hz, 1H), 7.22 (d, J = 8.3 Hz, 1H), 3.70 (s, 2H), 1.49 (s, 9H) | 463.2 $(M + H)^+$ |
| 25 | 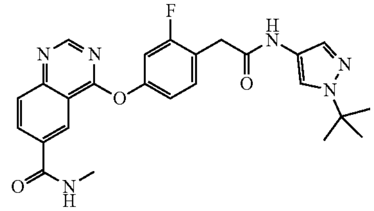 [SMILES: CNC(=O)c1ccc2ncnc(Oc3ccc(CC(=O)Nc4cnn(C(C)(C)C)c4)c(F)c3)c2c1] | 4-(4-(2-((1-(tert-butyl)-1H-pyrazol-4-yl)amino)-2-oxoethyl)-3-fluoro-phenoxy)-N-methyl-quinazoline-6-carboxamide | (400 MHz, DMSO-$d_6$) δ 10.26 (s, 1H), 8.92 (d, J = 4.6 Hz, 1H), 8.88 (d, J = 2.0 Hz, 1H), 8.81 (s, 1H), 8.45 (dd, J = 8.8, 2.0 Hz, 1H), 8.08 (d, J = 8.7 Hz, 1H), 7.94 (s, 1H), 7.51 (t, J = 8.5 Hz, 1H), 7.45 (s, 1H), 7.37 (dd, J = 10.4, 2.4 Hz, 1H), 7.22 (dd, J = 8.3, 2.4 Hz, 1H), 3.70 (s, 2H), 2.86 (d, J = 4.5 Hz, 3H), 1.49 (s, 9H) | 477.2 $(M + H)^+$ |

-continued

| No. | Structure | Name | $^1$H NMR | Observed m/z |
|---|---|---|---|---|
| 27 | 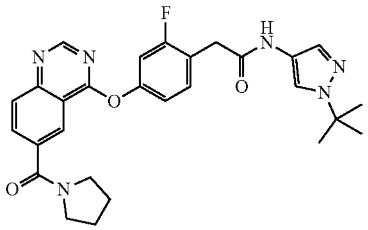 [SMILES: CC(C)(C)n1cc(NC(=O)Cc2ccc(Oc3ncnc4ccc(C(=O)N5CCCC5)cc34)cc2F)cn1] | N-(1-(tert-butyl)-1H-pyrazol-4-yl)-2-(2-fluoro-4-((6-(pyrrolidine-1-carbonyl)quinazolin-4-yl)oxy)phenyl)acetamide | (400 MHz, DMSO-$d_6$) δ 10.23 (s, 1H), 8.80 (s, 1H), 8.46 (d, J = 1.9 Hz, 1H), 8.15 (dd, J = 8.6, 1.9 Hz, 1H), 8.05 (d, J = 8.6 Hz, 1H), 7.93 (s, 1H), 7.49 (t, J = 8.5 Hz, 1H), 7.45 (s, 1H), 7.36 (dd, J = 10.5, 2.3 Hz, 1H), 7.21 (dd, J = 8.3, 2.4 Hz, 1H), 3.70 (s, 2H), 3.54 (t, J = 6.7 Hz, 2H), 3.47 (t, J = 6.4 Hz, 2H), 1.95-1.79 (m, 4H), 1.49 (s, 9H) | 517.3 $(M + H)^+$ |
| 207 | 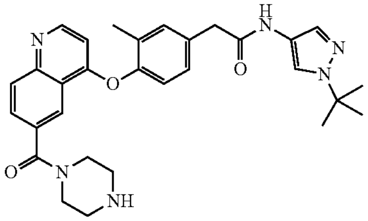 [SMILES: Cc1cc(CC(=O)Nc2cnn(C(C)(C)C)c2)ccc1Oc1ccnc2ccc(C(=O)N3CCNCC3)cc12] | N-(1-(tert-butyl)-1H-pyrazol-4-yl)-2-(3-methyl-4-((6-(piperazine-1-carbonyl)quinolin-4-yl)oxy)phenyl)acetamide | (300 MHz, DMSO-$d_6$) δ 10.20 (s, 1H), 8.71 (d, J = 5.1 Hz, 1H), 8.33 (d, J = 1.9 Hz, 1H), 8.08 (d, J = 8.7 Hz, 1H), 7.95 (s, 1H), 7.81 (dd, J = 8.6, 1.9 Hz, 1H), 7.45 (s, 1H), 7.37 (d, J = 2.1 Hz, 1H), 7.29 (dd, J = 8.2, 2.1 Hz, 1H), 7.20 (d, J = 8.2 Hz, 1H), 6.47 (d, J = 5.1 Hz, 1H), 3.60 (s, 4H), 3.34 (s, 2H), 2.82-2.62 (m, 4H), 2.12 (s, 3H), 1.49 (s, 9H) | 527.1 $(M + H)^+$ |
| 208 | 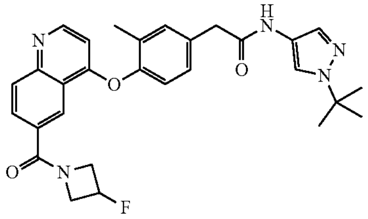 [SMILES: Cc1cc(CC(=O)Nc2cnn(C(C)(C)C)c2)ccc1Oc1ccnc2ccc(C(=O)N3CC(F)C3)cc12] | N-(1-(tert-butyl)-1H-pyrazol-4-yl)-2-(4-((6-(3-fluoro-azetidine-1-carbonyl)quinolin-4-yl)oxy)-3-methyl-phenyl)acetamide | (300 MHz, DMSO-$d_6$) δ 10.20 (s, 1H), 8.74 (d, J = 5.2 Hz, 1H), 8.62 (s, 1H), 8.11-7.99 (m, 2H), 7.95 (s, 1H), 7.45 (s, 1H), 7.37 (s, 1H), 7.30 (d, J = 8.4 Hz, 1H), 7.20 (d, J = 8.2 Hz, 1H), 6.48 (d, J = 5.2 Hz, 1H), 5.68-5.26 (m, 1H), 4.68-4.39 (m, 3H), 4.26-4.11 (m, 1H), 3.61 (s, 2H), 2.13 (s, 3H), 1.49 (s, 9H) | 516.1 $(M + H)^+$ |
| 209 | 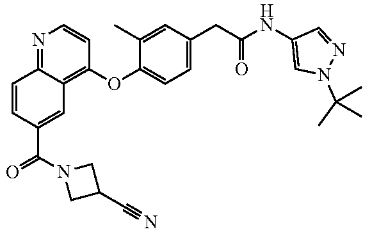 [SMILES: Cc1cc(CC(=O)Nc2cnn(C(C)(C)C)c2)ccc1Oc1ccnc2ccc(C(=O)N3CC(C#N)C3)cc12] | N-(1-(tert-butyl)-1H-pyrazol-4-yl)-2-(4-((6-(3-cyano-azetidine-1-carbonyl)quinolin-4-yl)oxy)-3-methyl-phenyl)acetamide | (300 MHz, DMSO-$d_6$) δ 10.23 (s, 1H), 8.83 (d, J = 5.5 Hz, 1H), 8.66 (d, J = 1.8 Hz, 1H), 8.19-8.06 (m, 2H), 7.95 (s, 1H), 7.46 (s, 1H), 7.40 (d, J = 2.1 Hz, 1H), 7.33 (dd, J = 8.2, 2.2 Hz, 1H), 7.24 (d, J = 8.2 Hz, 1H), 6.59 (d, J = 5.5 Hz, 1H), 4.72-4.54 (m, 2H), 4.48-4.21 (m, 2H), 3.95-3.83 (m, 1H), 3.62 (s, 2H), 2.14 (s, 3H), 1.49 (s, 9H) | 523.1 $(M + H)^+$ |
| 210 | 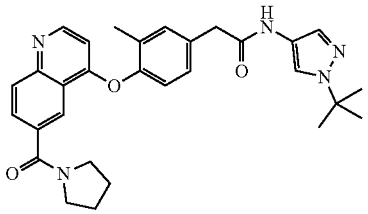 [SMILES: Cc1cc(CC(=O)Nc2cnn(C(C)(C)C)c2)ccc1Oc1ccnc2ccc(C(=O)N3CCCC3)cc12] | N-(1-(tert-butyl)-1H-pyrazol-4-yl)-2-(3-methyl-4-((6-(pyrrolidine-1-carbonyl)quinolin-4-yl)oxy)phenyl)acetamide | (300 MHz, DMSO-$d_6$) δ 10.23 (s, 1H), 8.71 (d, J = 5.1 Hz, 1H), 8.49 (s, 1H), 8.07 (d, J = 8.7 Hz, 1H), 8.00-7.90 (m, 2H), 7.46 (s, 1H), 7.37 (s, 1H), 7.35-7.27 (m, 1H), 7.20 (d, J = 8.2 Hz, 1H), 6.47 (d, J = 5.2 Hz, 1H), 3.61 (s, 2H), 3.57-3.46 (m, 4H), 2.12 (s, 3H), 1.87 (dq, J = 12.8, 6.6 Hz, 4H), 1.49 (s, 9H) | 512.1 $(M + H)^+$ |

-continued

| No. | Structure | Name | $^1$H NMR | Observed m/z |
| --- | --- | --- | --- | --- |
| 333 | 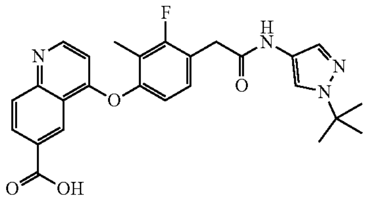 [SMILES: Cc1c(Oc2ccnc3ccc(C(=O)O)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy) quinoline-6-carboxylic acid | (400 MHz, DMSO-$d_6$) δ 10.24 (s, 1H), 8.98 (d, J = 2.0 Hz, 1H), 8.79 (d, J = 5.2 Hz, 1H), 8.30 (dd, J = 8.8, 2.0 Hz, 1H), 8.12 (d, J = 8.8 Hz, 1H), 7.95 (s, 1H), 7.46 (s, 1H), 7.38 (t, J = 8.3 Hz, 1H), 7.14 (d, J = 8.4 Hz, 1H), 6.56 (d, J = 5.2 Hz, 1H), 3.71 (s, 2H), 2.07 (d, J = 1.9 Hz, 3H), 1.49 (s, 9H) | 477.0 $(M + H)^+$ |
| 334 | 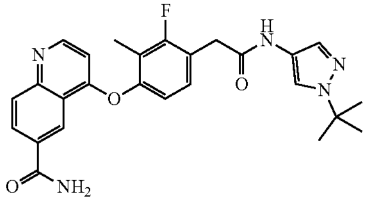 [SMILES: Cc1c(Oc2ccnc3ccc(C(N)=O)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy) quinoline-6-carboxamide | (300 MHz, DMSO-$d_6$) δ 10.25 (s, 1H), 8.95 (d, J = 2.0 Hz, 1H), 8.76 (d, J = 5.2 Hz, 1H), 8.37 (s, 1H), 8.29 (dd, J = 8.9, 2.0 Hz, 1H), 8.09 (d, J = 8.8 Hz, 1H), 7.95 (s, 1H), 7.61 (s, 1H), 7.46 (s, 1H), 7.38 (t, J = 8.4 Hz, 1H), 7.13 (d, J = 8.3 Hz, 1H), 6.54 (d, J = 5.2 Hz, 1H), 3.72 (s, 2H), 2.08 (d, J = 1.9 Hz, 3H), 1.49 (s, 9H) | 476.0 $(M + H)^+$ |
| 335 | 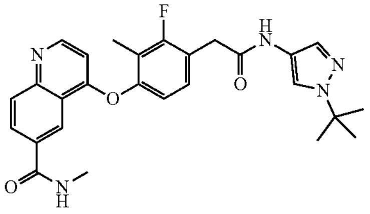 [SMILES: CNC(=O)c1ccc2nccc(Oc3ccc(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3-fluoro-2-methyl-phenoxy)-N-methyl-quinoline-6-carboxamide | (300 MHz, DMSO-$d_6$) δ 10.24 (s, 1H), 8.90 (d, J = 2.0 Hz, 1H), 8.83 (d, J = 4.9 Hz, 1H), 8.75 (d, J = 5.2 Hz, 1H), 8.25 (dd, J = 8.8, 2.0 Hz, 1H), 8.10 (d, J = 8.8 Hz, 1H), 7.95 (d, J = 0.7 Hz, 1H), 7.46 (d, J = 0.7 Hz, 1H), 7.38 (t, J = 8.4 Hz, 1H), 7.19-7.08 (m, 1H), 6.53 (d, J = 5.1 Hz, 1H), 3.72 (s, 2H), 2.86 (d, J = 4.4 Hz, 3H), 2.07 (d, J = 2.0 Hz, 3H), 1.49 (s, 9H) | 490.0 $(M + H)^+$ |
| 336 | 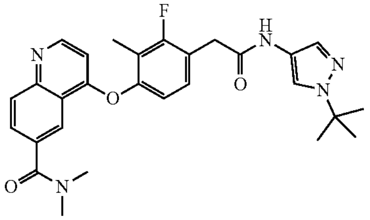 [SMILES: Cc1c(Oc2ccnc3ccc(C(=O)N(C)C)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N,N-dimethyl-quinoline-6-carboxamide | (400 MHz, DMSO-$d_6$) δ 10.24 (s, 1H), 8.75 (d, J = 5.1 Hz, 1H), 8.37 (d, J = 1.8 Hz, 1H), 8.09 (d, J = 8.7 Hz, 1H), 7.95 (s, 1H), 7.86 (dd, J = 8.7, 1.9 Hz, 1H), 7.46 (s, 1H), 7.37 (t, J = 8.4 Hz, 1H), 7.11 (dd, J = 8.4, 1.2 Hz, 1H), 6.56 (d, J = 5.1 Hz, 1H), 3.71 (s, 2H), 3.06 (s, 3H), 3.00 (s, 3H), 2.06 (s, 3H), 1.49 (s, 9H) | 504.2 $(M + H)^+$ |
| 337 | 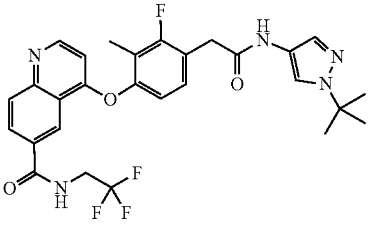 [SMILES: Cc1c(Oc2ccnc3ccc(C(=O)NCC(F)(F)F)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(2,2,2-trifluoroethyl) quinoline-6-carboxamide | (300 MHz, DMSO-$d_6$) δ 10.25 (s, 1H), 9.51 (t, J = 6.3 Hz, 1H), 8.99 (d, J = 2.0 Hz, 1H), 8.78 (d, J = 5.2 Hz, 1H), 8.30 (dd, J = 8.8, 2.0 Hz, 1H), 8.14 (d, J = 8.8 Hz, 1H), 7.95 (s, 1H), 7.46 (s, 1H), 7.40 (t, J = 8.4 Hz, 1H), 7.15 (d, J = 8.4 Hz, 1H), 6.55 (d, J = 5.2 Hz, 1H), 4.28-4.10 (m, 2H), 3.72 (s, 2H), 2.08 (d, J = 1.9 Hz, 3H), 1.50 (s, 9H) | 558.0 $(M + H)^+$ |

-continued

| No. | Structure | Name | $^1H$ NMR | Observed m/z |
|---|---|---|---|---|
| 338 | 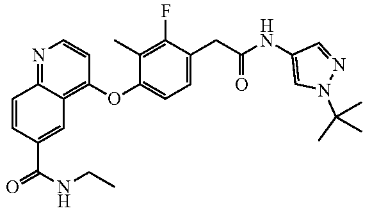 [SMILES: CCNC(=O)c1ccc2nccc(Oc3ccc(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3-fluoro-2-methyl-phenoxy)-N-ethylquinoline-6-carboxamide | (300 MHz, DMSO-$d_6$) δ 10.26 (s, 1H), 8.94-8.83 (m, 2H), 8.75 (d, J = 5.2 Hz, 1H), 8.27 (dd, J = 8.8, 2.0 Hz, 1H), 8.10 (d, J = 8.8 Hz, 1H), 7.96 (s, 1H), 7.46 (s, 1H), 7.39 (t, J = 8.5 Hz, 1H), 7.13 (d, J = 8.4 Hz, 1H), 6.52 (d, J = 5.2 Hz, 1H), 3.72 (s, 2H), 3.39 (q, J = 7.2 Hz, 2H), 2.08 (d, J = 2.0 Hz, 3H), 1.50 (s, 9H), 1.18 (t, J = 7.2 Hz, 3H) | 504.0 $(M + H)^+$ |
| 339 | 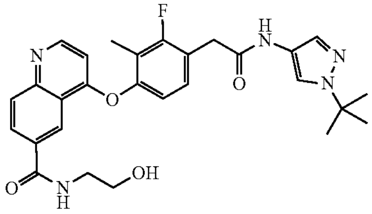 [SMILES: Cc1c(Oc2ccnc3ccc(C(=O)NCCO)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(2-hydroxyethyl) quinoline-6-carboxamide | (300 MHz, DMSO-$d_6$) δ 10.25 (s, 1H), 8.93 (s, 1H), 8.75 (d, J = 5.2 Hz, 1H), 8.27 (d, J = 10.6 Hz, 1H), 8.10 (d, J = 8.8 Hz, 1H), 7.96-7.94 (m, 2H), 7.46 (s, 1H), 7.13 (d, J = 7.9 Hz, 1H), 6.52 (d, J = 5.2 Hz, 1H), 4.92-4.83 (m, 1H), 3.72 (s, 2H), 3.60-3.52 (m, 4H), 2.08 (s, 3H), 1.49 (s, 9H) | 520.1 $(M + H)^+$ |
| 340 | 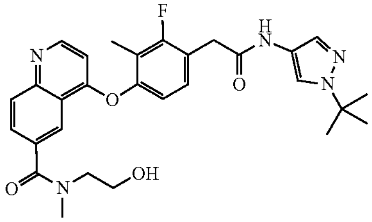 [SMILES: Cc1c(Oc2ccnc3ccc(C(=O)N(C)CCO)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(2-hydroxyethyl)-N-methyl-quinoline-6-carboxamide | (300 MHz, DMSO-$d_6$) δ 10.22 (s, 1H), 8.73 (d, J = 5.1 Hz, 1H), 8.38 (d, J = 1.8 Hz, 1H), 8.08 (d, J = 8.9 Hz, 1H), 7.94 (s, 1H), 7.85 (d, J = 8.6 Hz, 1H), 7.45 (s, 1H), 7.36 (t, J = 8.6 Hz, 1H), 7.11 (d, J = 8.3 Hz, 1H), 6.55 (d, J = 5.1 Hz, 1H), 4.84 (dt, J = 8.2, 4.0 Hz, 1H), 3.70 (s, 2H), 3.60-3.52 (m, 4H), 3.04 (s, 3H), 2.06 (d, J = 1.9 Hz, 3H), 1.49 (s, 9H) | 532.2 $(M - H)^-$ |
| 341 | 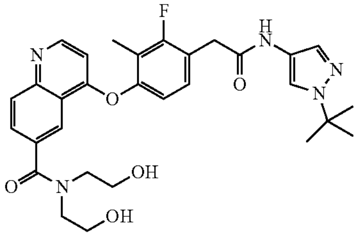 [SMILES: Cc1c(Oc2ccnc3ccc(C(=O)N(CCO)CCO)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N,N-bis(2-hydroxyethyl) quinoline-6-carboxamide | (300 MHz, DMSO-$d_6$) δ 10.22 (s, 1H), 8.73 (d, J = 5.2 Hz, 1H), 8.38 (d, J = 1.8 Hz, 1H), 8.08 (d, J = 8.7 Hz, 1H), 7.94 (s, 1H), 7.84 (dd, J = 8.7, 1.9 Hz, 1H), 7.45 (s, 1H), 7.36 (t, J = 8.4 Hz, 1H), 7.11 (d, J = 8.3 Hz, 1H), 6.54 (d, J = 5.1 Hz, 1H), 4.87-4.79 (m, 2H), 3.70 (s, 2H), 3.68-3.38 (m, 8H), 2.06 (d, J = 1.8 Hz, 3H), 1.49 (s, 9H) | 564.1 $(M + H)^+$ |
| 342 | 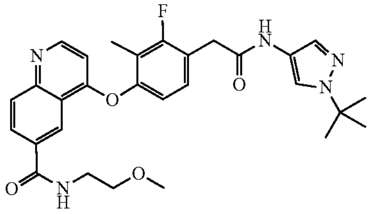 [SMILES: COCCNC(=O)c1ccc2nccc(Oc3ccc(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3-fluoro-2-methyl-phenoxy)-N-(2-methoxyethyl) quinoline-6-carboxamide | (400 MHz, DMSO-$d_6$) δ 10.24 (s, 1H), 8.98-8.90 (m, 2H), 8.76 (d, J = 5.2 Hz, 1H), 8.27 (dd, J = 8.8, 2.0 Hz, 1H), 8.10 (d, J = 8.8 Hz, 1H), 7.95 (s, 1H), 7.46 (s, 1H), 7.39 (t, J = 8.4 Hz, 1H), 7.13 (d, J = 8.4 Hz, 1H), 6.53 (d, J = 5.2 Hz, 1H), 3.72 (s, 2H), 3.53 (s, 4H), 3.31 (s, 3H), 2.08 (d, J = 1.9 Hz, 3H), 1.49 (s, 9H) | 534.1 $(M + H)^+$ |

-continued

| No. | Structure | Name | $^1$H NMR | Observed m/z |
|---|---|---|---|---|
| 343 | 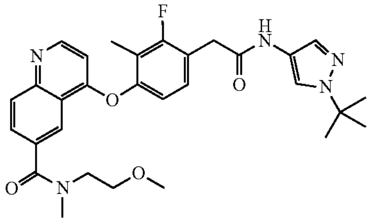 [SMILES: COCCN(C)C(=O)c1ccc2nccc(Oc3ccc(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3-fluoro-2-methyl-phenoxy)-N-(2-methoxyethyl)-N-methyl-quinoline-6-carboxamide | | 548.1 (M + H)+ |
| 344 | 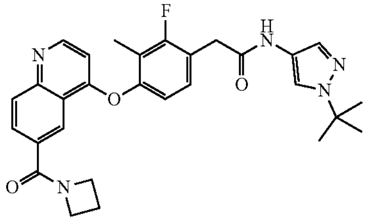 [SMILES: Cc1c(Oc2ccnc3ccc(C(=O)N4CCC4)cc23)ccc(CC(=O)Nc2cnn(C(C)(C)C)c2)c1F] | 2-(4-((6-(azetidine-1-carbonyl) quinolin-4-yl)oxy)-2-fluoro-3-methyl-phenyl)-N-(1-(tert-butyl)-1H-pyrazol-4-yl)acetamide | | 516.1 (M + H)+ |
| 345 | 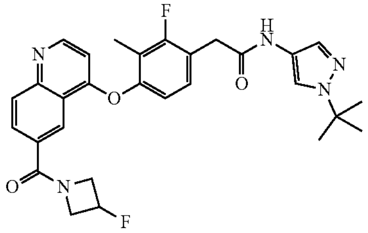 [SMILES: Cc1c(Oc2ccnc3ccc(C(=O)N4CC(F)C4)cc23)ccc(CC(=O)Nc2cnn(C(C)(C)C)c2)c1F] | N-(1-(tert-butyl)-1H-pyrazol-4-yl)-2-(2-fluoro-4-((6-(3-fluoro-azetidine-1-carbonyl) quinolin-4-yl)oxy)-3-methylphenyl) acetamide | | 534.0 (M + H)+ |
| 346 | 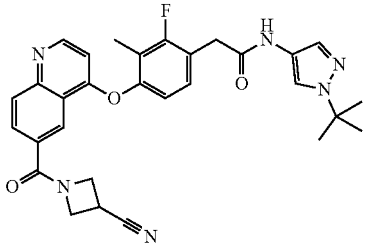 [SMILES: Cc1c(Oc2ccnc3ccc(C(=O)N4CC(C#N)C4)cc23)ccc(CC(=O)Nc2cnn(C(C)(C)C)c2)c1F] | N-(1-(tert-butyl)-1H-pyrazol-4-yl)-2-(4-((6-(3-cyano-azetidine-1-carbonyl) quinolin-4-yl)oxy)-2-fluoro-3-methylphenyl) acetamide | | 541.1 (M + H)+ |
| 347 | 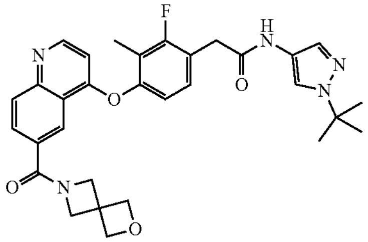 [SMILES: Cc1c(Oc2ccnc3ccc(C(=O)N4CC5(COC5)C4)cc23)ccc(CC(=O)Nc2cnn(C(C)(C)C)c2)c1F] | 2-(4-((6-(2-oxa-6-azaspiro[3.3] heptane-6-carbonyl) quinolin-4-yl)oxy)-2-fluoro-3-methyl-phenyl)-N-(1-(tert-butyl)-1H-pyrazol-4-yl)acetamide | | 558.1 (M + H)+ |

-continued

| No. | Structure | Name | $^1$H NMR | Observed m/z |
| --- | --- | --- | --- | --- |
| 348 | 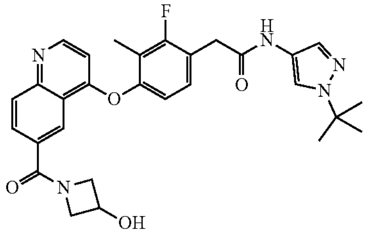 [SMILES: Cc1c(Oc2ccnc3ccc(C(=O)N4CC(O)C4)cc23)ccc(CC(=O)Nc2cnn(C(C)(C)C)c2)c1F] | N-(1-(tert-butyl)-1H-pyrazol-4-yl)-2-(2-fluoro-4-((6-(3-hydroxy-azetidine-1-carbonyl)quinolin-4-yl)oxy)-3-methyl-phenyl)acetamide | | 532.0 (M + H)+ |
| 349 | 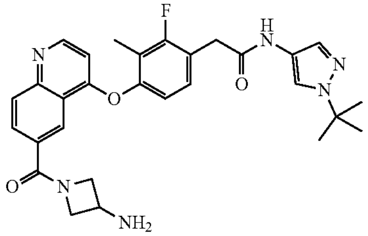 [SMILES: Cc1c(Oc2ccnc3ccc(C(=O)N4CC(N)C4)cc23)ccc(CC(=O)Nc2cnn(C(C)(C)C)c2)c1F] | 2-(4-((6-(3-amino-azetidine-1-carbonyl)quinolin-4-yl)oxy)-2-fluoro-3-methyl-phenyl)-N-(1-(tert-butyl)-1H-pyrazol-4-yl)acetamide | | 531.1 (M + H)+ |
| 350 | 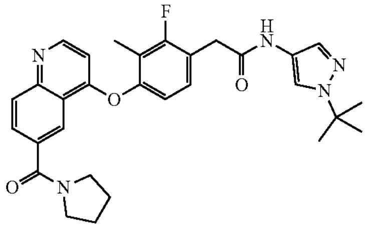 [SMILES: Cc1c(Oc2ccnc3ccc(C(=O)N4CCCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(pyrrolidine-1-carbonyl)quinolin-4-yl)oxy)phenyl)acetamide | | 530.1 (M + H)+ |
| 351 | 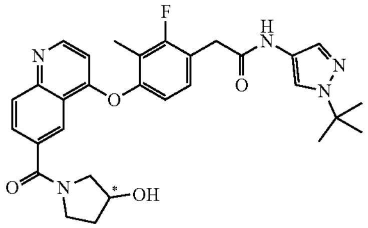 [SMILES: Cc1c(Oc2ccnc3ccc(C(=O)N4CCC(O)C4)cc23)ccc(CC(=O)Nc2cnn(C(C)(C)C)c2)c1F] enantiomer 1 (retention time: 2.42 min; column: CHIRALPAK IF-3, 4.6 x 50 mm, 3 μm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-4-((6-(3-hydroxy-pyrrolidine-1-carbonyl)quinolin-4-yl)oxy)-3-methyl-phenyl)acetamide | | 546.0 (M + H)+ |

-continued

| No. | Structure | Name | ¹H NMR | Observed m/z |
|---|---|---|---|---|
| 352 | 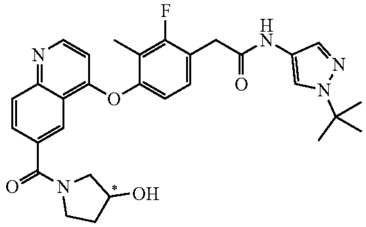 [SMILES: Cc1c(Oc2ccnc3ccc(C(=O)N4CCC(O)C4)cc23)ccc(CC(=O)Nc2cnn(C(C)(C)C)c2)c1F] enantiomer 2 (retention time: 2.89 min; column: CHIRALPAK IF-3, 4.6 x 50 mm, 3 μm; mobile phase A: MTBE (0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-4-((6-(3-hydroxy-pyrrolidine-1-carbonyl) quinolin-4-yl)oxy)-3-methyl-phenyl) acetamide | | 546.0 $(M + H)^+$ |
| 353 | 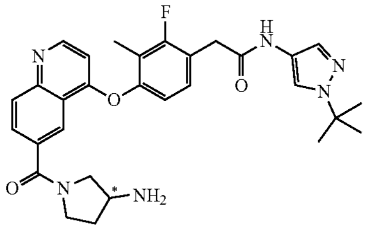 [SMILES: Cc1c(Oc2ccnc3ccc(C(=O)N4CCC(N)C4)cc23)ccc(CC(=O)Nc2cnn(C(C)(C)C)c2)c1F] enantiomer 1 (retention time: 2.90 min; column: CHIRALPAK IF-3, 4.6 x 50 mm, 3 μm; mobile phase A: MTBE (0.1% DEA), mobile phase B: MeOH/DCM (1:1), isocratic separation with 30% B, flow rate: 1.0 mL/min, wavelength: 254 nm) | 2-(4-((6-(3-amino-pyrrolidine-1-carbonyl) quinolin-4-yl)oxy)-2-fluoro-3-methyl-phenyl)-N-(1-(tert-butyl)-1H-pyrazol-4-yl)acetamide | | 545.0 $(M + H)^+$ |
| 354 | 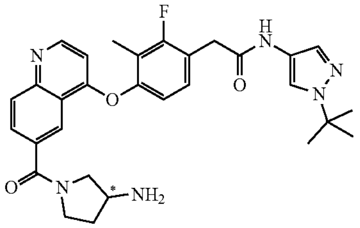 [SMILES: Cc1c(Oc2ccnc3ccc(C(=O)N4CCC(N)C4)cc23)ccc(CC(=O)Nc2cnn(C(C)(C)C)c2)c1F] enantiomer 2 (retention time: 3.69 min; column: CHIRALPAK IF-3, 4.6 x 50 mm, 3 μm; mobile phase A: MTBE (0.1% DEA), mobile phase B: MeOH/DCM (1:1), isocratic separation with 30% B, flow rate: 1.0 mL/min, wavelength: 254 nm) | 2-(4-((6-(3-amino-pyrrolidine-1-carbonyl) quinolin-4-yl)oxy)-2-fluoro-3-methyl-phenyl)-N-(1-(tert-butyl)-1H-pyrazol-4-yl)acetamide | | 567.2 $(M + Na)^+$ |

-continued

| No. | Structure | Name | $^1$H NMR | Observed m/z |
|---|---|---|---|---|
| 355 | 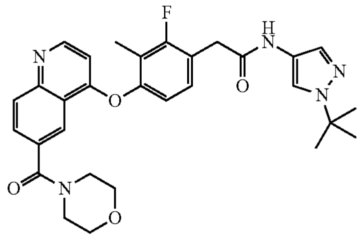 [SMILES: Cc1c(Oc2ccnc3ccc(C(=O)N4CCOCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(morpholine-4-carbonyl)quinolin-4-yl)oxy)phenyl)acetamide | | 546.1 $(M + H)^+$ |
| 356 | 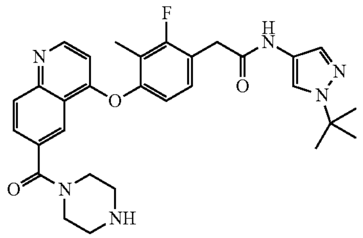 [SMILES: Cc1c(Oc2ccnc3ccc(C(=O)N4CCNCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(piperazine-1-carbonyl)quinolin-4-yl)oxy)phenyl)acetamide | | 545.1 $(M + H)^+$ |
| 357 | 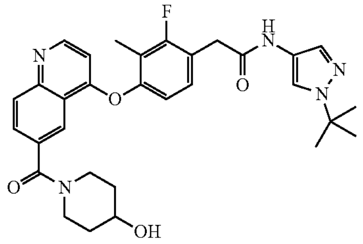 [SMILES: Cc1c(Oc2ccnc3ccc(C(=O)N4CCC(O)CC4)cc23)ccc(CC(=O)Nc2cnn(C(C)(C)C)c2)c1F] | N-(1-(tert-butyl)-1H-pyrazol-4-yl)-2-(2-fluoro-4-((6-(4-hydroxy-piperidine-1-carbonyl)quinolin-4-yl)oxy)-3-methyl-phenyl)acetamide | | 560.1 $(M + H)^+$ |
| 358 | 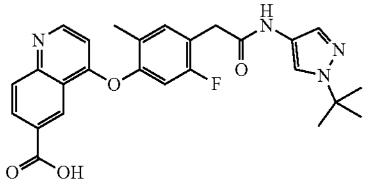 [SMILES: Cc1cc(CC(=O)Nc2cnn(C(C)(C)C)c2)c(F)cc1Oc1ccnc2ccc(C(=O)O)cc12] | 4-(4-(2-((1-(tert-butyl)-1H-pyrazol-4-yl)amino)-2-oxoethyl)-5-fluoro-2-methyl-phenoxy)quinoline-6-carboxylic acid | | 477.0 $(M + H)^+$ |
| 359 | 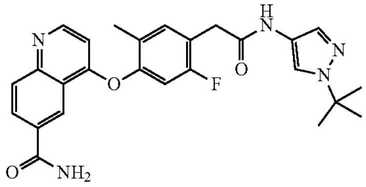 [SMILES: Cc1cc(CC(=O)Nc2cnn(C(C)(C)C)c2)c(F)cc1Oc1ccnc2ccc(C(N)=O)cc12] | 4-(4-(2-((1-(tert-butyl)-1H-pyrazol-4-yl)amino)-2-oxoethyl)-5-fluoro-2-methyl-phenoxy)quinoline-6-carboxamide | | 476.2 $(M + H)^+$ |
| 361 | 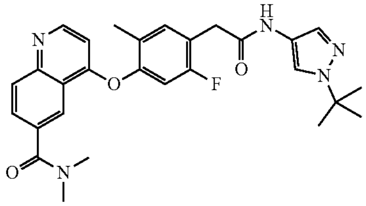 [SMILES: Cc1cc(CC(=O)Nc2cnn(C(C)(C)C)c2)c(F)cc1Oc1ccnc2ccc(C(=O)N(C)C)cc12] | 4-(4-(2-((1-(tert-butyl)-1H-pyrazol-4-yl)amino)-2-oxoethyl)-5-fluoro-2-methyl-phenoxy)-N,N-dimethyl-quinoline-6-carboxamide | | 504.1 $(M + H)^+$ |

-continued

| No. | Structure | Name | 1H NMR | Observed m/z |
|---|---|---|---|---|
| 362 | 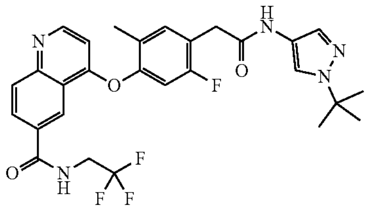 [SMILES: Cc1cc(CC(=O)Nc2cnn(C(C)(C)C)c2)c(F)cc1Oc1ccnc2ccc(C(=O)NCC(F)(F)F)cc12] | 4-(4-(2-((1-(tert-butyl)-1H-pyrazol-4-yl)amino)-2-oxoethyl)-5-fluoro-2-methyl-phenoxy)-N-(2,2,2-trifluoroethyl) quinoline-6-carboxamide | | 558.1 $(M + H)^+$ |
| 363 | 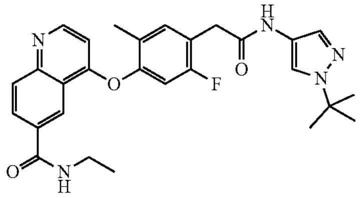 [SMILES: CCNC(=O)c1ccc2nccc(Oc3cc(F)c(CC(=O)Nc4cnn(C(C)(C)C)c4)cc3C)c2c1] | 4-(4-(2-((1-(tert-butyl)-1H-pyrazol-4-yl)amino)-2-oxoethyl)-5-fluoro-2-methyl-phenoxy)-N-ethyl-quinoline-6-carboxamide | | 504.1 $(M + H)^+$ |
| 364 | 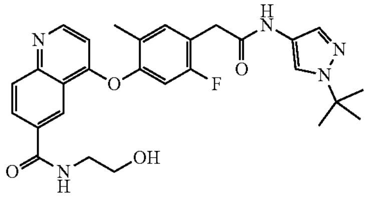 [SMILES: Cc1cc(CC(=O)Nc2cnn(C(C)(C)C)c2)c(F)cc1Oc1ccnc2ccc(C(=O)NCCO)cc12] | 4-(4-(2-((1-(tert-butyl)-1H-pyrazol-4-yl)amino)-2-oxoethyl)-5-fluoro-2-methyl-phenoxy)-N-(2-hydroxy-ethyl) quinoline-6-carboxamide | | 520.1 $(M + H)^+$ |
| 365 | 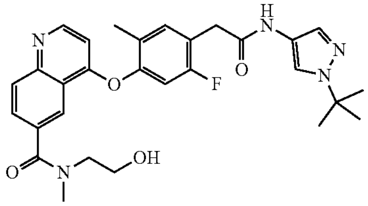 [SMILES: Cc1cc(CC(=O)Nc2cnn(C(C)(C)C)c2)c(F)cc1Oc1ccnc2ccc(C(=O)N(C)CCO)cc12] | 4-(4-(2-((1-(tert-butyl)-1H-pyrazol-4-yl)amino)-2-oxoethyl)-5-fluoro-2-methyl-phenoxy)-N-(2-hydroxy-ethyl)-N-methyl-quinoline-6-carboxamide | | 534.1 $(M + H)^+$ |
| 366 | 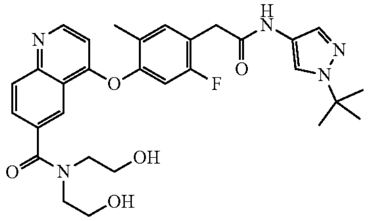 [SMILES: Cc1cc(CC(=O)Nc2cnn(C(C)(C)C)c2)c(F)cc1Oc1ccnc2ccc(C(=O)N(CCO)CCO)cc12] | 4-(4-(2-((1-(tert-butyl)-1H-pyrazol-4-yl)amino)-2-oxoethyl)-5-fluoro-2-methyl-phenoxy)-N,N-bis(2-hydroxyethyl) quinoline-6-carboxamide | | 564.1 $(M + H)^+$ |

-continued

| No. | Structure | Name | ¹H NMR | Observed m/z |
|---|---|---|---|---|
| 367 | 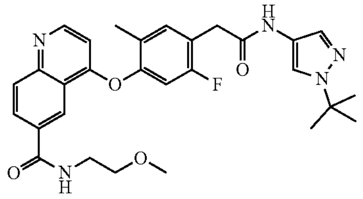 [SMILES: COCCNC(=O)c1ccc2nccc(Oc3cc(F)c(CC(=O)Nc4cnn(C(C)(C)C)c4)cc3C)c2c1] | 4-(4-(2-((1-(tert-butyl)-1H-pyrazol-4-yl)amino)-2-oxoethyl)-5-fluoro-2-methyl-phenoxy)-N-(2-methoxy-ethyl) quinoline-6-carboxamide | | 534.1 (M + H)+ |
| 368 | 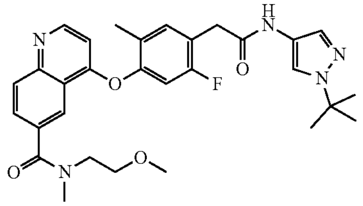 [SMILES: COCCN(C)C(=O)c1ccc2nccc(Oc3cc(F)c(CC(=O)Nc4cnn(C(C)(C)C)c4)cc3C)c2c1] | 4-(4-(2-((1-(tert-butyl)-1H-pyrazol-4-yl)amino)-2-oxoethyl)-5-fluoro-2-methyl-phenoxy)-N-(2-methoxy-ethyl)-N-methyl-quinoline-6-carboxamide | | 548.1 (M + H)+ |
| 369 | 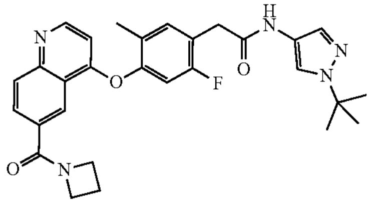 [SMILES: Cc1cc(CC(=O)Nc2cnn(C(C)(C)C)c2)c(F)cc1Oc1ccnc2ccc(C(=O)N3CCC3)cc12] | 2-(4-((6-(azetidine-1-carbonyl) quinolin-4-yl)oxy)-2-fluoro-5-methyl-phenyl)-N-(1-(tert-butyl)-1H-pyrazol-4-yl)acetamide | | 516.1 (M + H)+ |
| 370 | 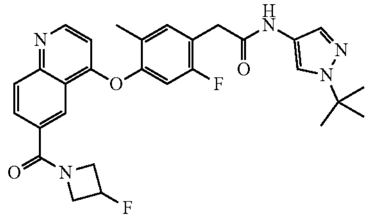 [SMILES: Cc1cc(CC(=O)Nc2cnn(C(C)(C)C)c2)c(F)cc1Oc1ccnc2ccc(C(=O)N3CC(F)C3)cc12] | N-(1-(tert-butyl)-1H-pyrazol-4-yl)-2-(2-fluoro-4-((6-(3-fluoro-azetidine-1-carbonyl) quinolin-4-yl)oxy)-5-methyl-phenyl) acetamide | | 534.1 (M + H)+ |
| 371 | 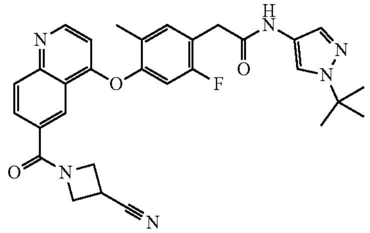 [SMILES: Cc1cc(CC(=O)Nc2cnn(C(C)(C)C)c2)c(F)cc1Oc1ccnc2ccc(C(=O)N3CC(C#N)C3)cc12] | N-(1-(tert-butyl)-1H-pyrazol-4-yl)-2-(4-((6-(3-cyano-azetidine-1-carbonyl) quinolin-4-yl)oxy)-2-fluoro-5-methyl-phenyl) acetamide | | 541.1 (M + H)+ |

-continued

| No. | Structure | Name | ¹H NMR | Observed m/z |
|---|---|---|---|---|
| 372 | 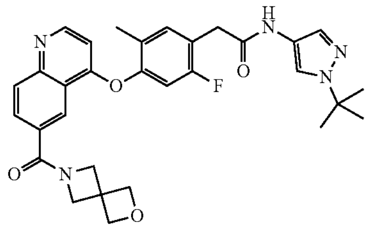 [SMILES: Cc1cc(CC(=O)Nc2cnn(C(C)(C)C)c2)c(F)cc1Oc1ccnc2ccc(C(=O)N3CC4(COC4)C3)cc12] | 2-(4-((6-(2-oxa-6-azaspiro[3.3]heptane-6-carbonyl)quinolin-4-yl)oxy)-2-fluoro-5-methyl-phenyl)-N-(1-(tert-butyl)-1H-pyrazol-4-yl)acetamide | | 558.1 $(M + H)^+$ |
| 373 | 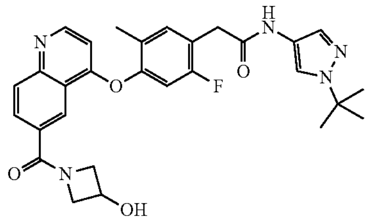 [SMILES: Cc1cc(CC(=O)Nc2cnn(C(C)(C)C)c2)c(F)cc1Oc1ccnc2ccc(C(=O)N3CC(O)C3)cc12] | N-(1-(tert-butyl)-1H-pyrazol-4-yl)-2-(2-fluoro-4-((6-(3-hydroxy-azetidine-1-carbonyl)quinolin-4-yl)oxy)-5-methylphenyl)acetamide | | 532.2 $(M + H)^+$ |
| 374 | 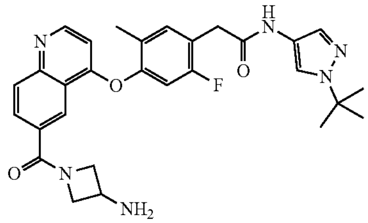 [SMILES: Cc1cc(CC(=O)Nc2cnn(C(C)(C)C)c2)c(F)cc1Oc1ccnc2ccc(C(=O)N3CC(N)C3)cc12] | 2-(4-((6-(3-amino-azetidine-1-carbonyl)quinolin-4-yl)oxy)-2-fluoro-5-methyl-phenyl)-N-(1-(tert-butyl)-1H-pyrazol-4-yl)acetamide | | 531.2 $(M + H)^+$ |
| 375 | 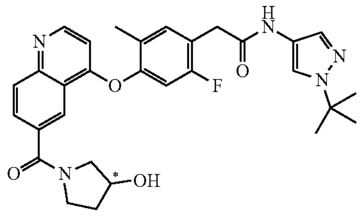 [SMILES: Cc1cc(CC(=O)Nc2cnn(C(C)(C)C)c2)c(F)cc1Oc1ccnc2ccc(C(=O)N3CCC(O)C3)cc12] enantiomer 1 (retention time: 1.59 min; column: Enantiocel C9-3, 4.6 × 50 mm, 3 μm; mobile phase A: supercritical $CO_2$, mobile phase B: MeOH (0.1% DEA), isocratic separation with 35% B, flow rate: 4.0 mL/min, wavelength: 220 nm) | N-(1-(tert-butyl)-1H-pyrazol-4-yl)-2-(2-fluoro-4-((6-(3-hydroxy-pyrrolidine-1-carbonyl)quinolin-4-yl)oxy)-5-methyl-phenyl)acetamide | | 546.2 $(M + H)^+$ |

-continued

| No. | Structure | Name | $^1$H NMR | Observed m/z |
|---|---|---|---|---|
| 376 | 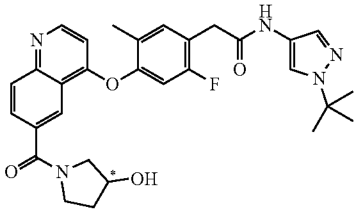 [SMILES: Cc1cc(CC(=O)Nc2cnn(C(C)(C)C)c2)c(F)cc1Oc1ccnc2ccc(C(=O)N3CCC(O)C3)cc12] enantiomer 2 (retention time: 2.03 min; column: Enantiocel C9-3, 4.6 x 50 mm, 3 µm; mobile phase A: supercritical $CO_2$, mobile phase B: MeOH (0.1% DEA), isocratic separation with 35% B, flow rate: 4.0 mL/min, wavelength: 220 nm) | N-(1-(tert-butyl)-1H-pyrazol-4-yl)-2-(2-fluoro-4-((6-(3-hydroxy-pyrrolidine-1-carbonyl) quinolin-4-yl)oxy)-5-methylphenyl) acetamide | | 546.2 $(M + H)^+$ |
| 377 | 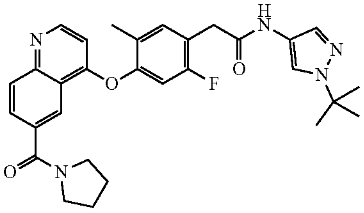 [SMILES: Cc1cc(CC(=O)Nc2cnn(C(C)(C)C)c2)c(F)cc1Oc1ccnc2ccc(C(=O)N3CCCC3)cc12] | N-(1-(tert-butyl)-1H-pyrazol-4-yl)-2-(2-fluoro-5-methyl-4-((6-(pyrrolidine-1-carbonyl) quinolin-4-yl) oxy)phenyl) acetamide | | 530.1 $(M + H)^+$ |
| 378 | 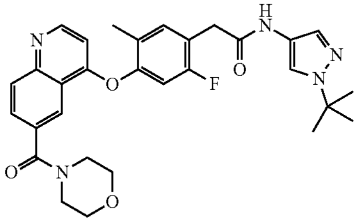 [SMILES: Cc1cc(CC(=O)Nc2cnn(C(C)(C)C)c2)c(F)cc1Oc1ccnc2ccc(C(=O)N3CCOCC3)cc12] | N-(1-(tert-butyl)-1H-pyrazol-4-yl)-2-(2-fluoro-5-methyl-4-((6-(morpholine-4-carbonyl) quinolin-4-yl) oxy)phenyl) acetamide | | 546.1 $(M + H)^+$ |
| 379 | 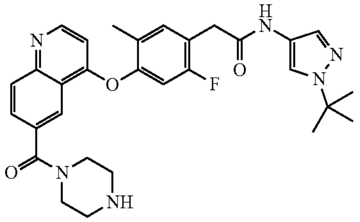 [SMILES: Cc1cc(CC(=O)Nc2cnn(C(C)(C)C)c2)c(F)cc1Oc1ccnc2ccc(C(=O)N3CCNCC3)cc12] | N-(1-(tert-butyl)-1H-pyrazol-4-yl)-2-(2-fluoro-5-methyl-4-((6-(piperazine-1-carbonyl) quinolin-4-yl) oxy)phenyl) acetamide | | 545.2 $(M + H)^+$ |
| 380 | 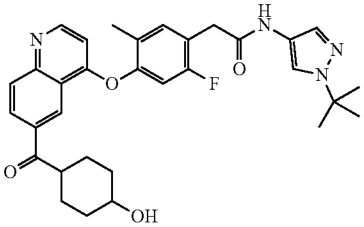 [SMILES: Cc1cc(CC(=O)Nc2cnn(C(C)(C)C)c2)c(F)cc1Oc1ccnc2ccc(C(=O)C3CCC(O)CC3)cc12] | N-(1-(tert-butyl)-1H-pyrazol-4-yl)-2-(2-fluoro-4-((6-(4-hydroxy-piperidine-1-carbonyl) quinolin-4-yl)oxy)-5-methyl-phenyl) acetamide | | 560.2 $(M + H)^+$ |

-continued

| No. | Structure | Name | $^1H$ NMR | Observed m/z |
|---|---|---|---|---|
| 384 | 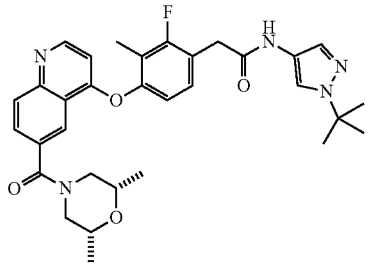 [SMILES: Cc1c(Oc2ccnc3ccc(C(=O)N4C[C@@H](C)O[C@@H](C)C4)cc23)ccc(CC(=O)Nc2cnn(C(C)(C)C)c2)c1F] | N-(1-(tert-butyl)-1H-pyrazol-4-yl)-2-(4-((6-((2R,6S)-2,6-dimethyl-morpholine-4-carbonyl) quinolin-4-yl)oxy)-2-fluoro-3-methyl-phenyl) acetamide | | 574.1 $(M + H)^+$ |
| 385 | 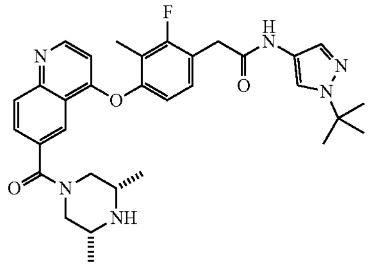 [SMILES: Cc1c(Oc2ccnc3ccc(C(=O)N4C[C@@H](C)N[C@@H](C)C4)cc23)ccc(CC(=O)Nc2cnn(C(C)(C)C)c2)c1F] | N-(1-(tert-butyl)-1H-pyrazol-4-yl)-2-(4-((6-((3R,5S)-3,5-dimethyl-piperazine-1-carbonyl) quinolin-4-yl)oxy)-2-fluoro-3-methylphenyl) acetamide | | 573.1 $(M + H)^+$ |
| 388 | 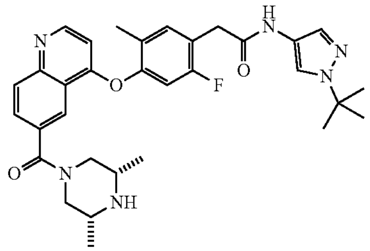 [SMILES: Cc1cc(CC(=O)Nc2cnn(C(C)(C)C)c2)c(F)cc1Oc1ccnc2ccc(C(=O)N3C[C@@H](C)N[C@@H](C)C3)cc12] | N-(1-(tert-butyl)-1H-pyrazol-4-yl)-2-(4-((6-((3R,5S)-3,5-dimethyl-piperazine-1-carbonyl) quinolin-4-yl)oxy)-2-fluoro-5-methyl-phenyl) acetamide | | 573.1 $(M + H)^+$ |
| 391 | 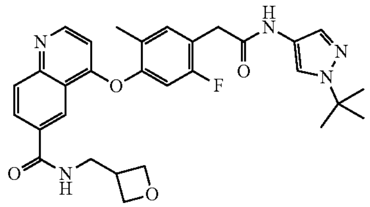 [SMILES: Cc1cc(CC(=O)Nc2cnn(C(C)(C)C)c2)c(F)cc1Oc1ccnc2ccc(C(=O)NCC3COC3)cc12] | 4-(4-(2-((1-(tert-butyl)-1H-pyrazol-4-yl)amino)-2-oxoethyl)-5-fluoro-2-methyl-phenoxy)-N-(oxetan-3-ylmethyl) quinoline-6-carboxamide | | 546.1 $(M + H)^+$ |
| 392 | 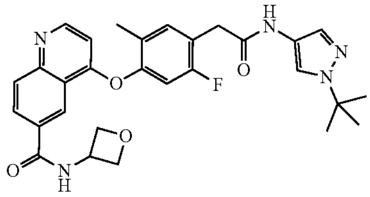 [SMILES: Cc1cc(CC(=O)Nc2cnn(C(C)(C)C)c2)c(F)cc1Oc1ccnc2ccc(C(=O)NC3COC3)cc12] | 4-(4-(2-((1-(tert-butyl)-1H-pyrazol-4-yl)amino)-2-oxoethyl)-5-fluoro-2-methyl-phenoxy)-N-(oxetan-3-yl)quinoline-6-carboxamide | | 532.1 $(M + H)^+$ |

-continued

| No. | Structure | Name | $^1$H NMR | Observed m/z |
|---|---|---|---|---|
| 393 | 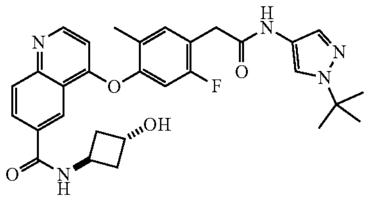 | 4-(4-(2-((1-(tert-butyl)-1H-pyrazol-4-yl)amino)-2-oxoethyl)-5-fluoro-2-methyl-phenoxy)-N-((1r,3r)-3-hydroxy-cyclobutyl) quinoline-6-carboxamide | | 546.2 $(M + H)^+$ |
| 394 | 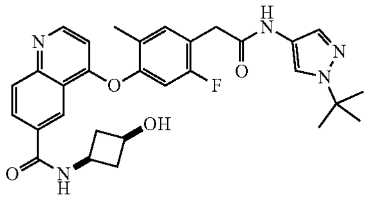 | 4-(4-(2-((1-(tert-butyl)-1H-pyrazol-4-yl)amino)-2-oxoethyl)-5-fluoro-2-methyl-phenoxy)-N-((1s,3s)-3-hydroxy-cyclobutyl) quinoline-6-carboxamide | | 546.2 $(M + H)^+$ |
| 395 | 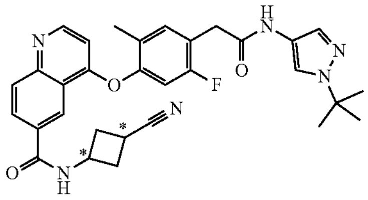 [SMILES: Cc1cc(CC(=O)Nc2cnn(C(C)(C)C)c2)c(F)cc1Oc1ccnc2ccc(C(=O)NC3CC(C#N)C3)cc12] diastereomer 2 (retention time: 2.41 min; column: CHIRALPAK ID-3, 4.6 x 50 mm, 3 μm; mobile phase A: MTBE (0.1% DEA), mobile phase B: EtOH, isocratic separation with 20% B, flow rate: 1.0 mL/min, wavelength: 254 nm) | 4-(4-(2-((1-(tert-butyl)-1H-pyrazol-4-yl)amino)-2-oxoethyl)-5-fluoro-2-methyl-phenoxy)-N-(-3-cyano-cyclobutyl) quinoline-6-carboxamide | | 555.2 $(M + H)^+$ |
| 396 | 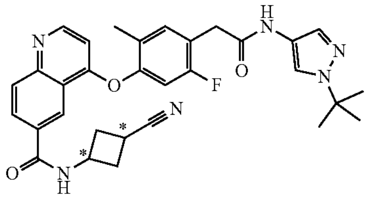 [SMILES: Cc1cc(CC(=O)Nc2cnn(C(C)(C)C)c2)c(F)cc1Oc1ccnc2ccc(C(=O)NC3CC(C#N)C3)cc12] diastereomer 1 (retention time: 1.60 min; column: CHIRALPAK ID-3, 4.6 x 50 mm, 3 μm; mobile phase A: MTBE (0.1% DEA), mobile phase B: EtOH, isocratic separation with 20% B, flow rate: 1.0 mL/min, wavelength: 254 nm) | 4-(4-(2-((1-(tert-butyl)-1H-pyrazol-4-yl)amino)-2-oxoethyl)-5-fluoro-2-methyl-phenoxy)-N-(-3-cyano-cyclobutyl) quinoline-6-carboxamide | | 555.2 $(M + H)^+$ |

-continued

| No. | Structure | Name | $^1$H NMR | Observed m/z |
|---|---|---|---|---|
| 397 | 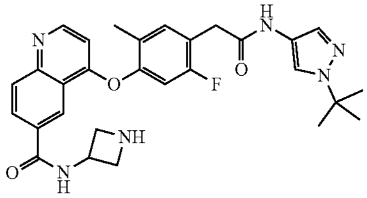 [SMILES: Cc1cc(CC(=O)Nc2cnn(C(C)(C)C)c2)c(F)cc1Oc1ccnc2ccc(C(=O)NC3CNC3)cc12] | N-(azetidin-3-yl)-4-(4-(2-((1-(tert-butyl)-1H-pyrazol-4-yl)amino)-2-oxoethyl)-5-fluoro-2-methyl-phenoxy) quinoline-6-carboxamide | | 531.1 (M + H)$^+$ |
| 398 | 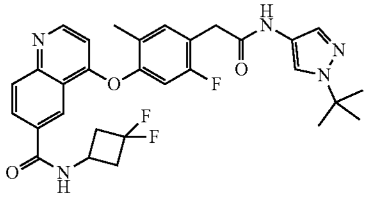 [SMILES: Cc1cc(CC(=O)Nc2cnn(C(C)(C)C)c2)c(F)cc1Oc1ccnc2ccc(C(=O)NC3CC(F)(F)C3)cc12] | 4-(4-(2-((1-(tert-butyl)-1H-pyrazol-4-yl)amino)-2-oxoethyl)-5-fluoro-2-methyl-phenoxy)-N-(3,3-difluoro-cyclobutyl) quinoline-6-carboxamide | | 566.1 (M + H)$^+$ |
| 399 | 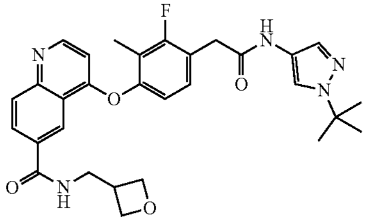 [SMILES: Cc1c(Oc2ccnc3ccc(C(=O)NCC4COC4)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(oxetan-3-ylmethyl) quinoline-6-carboxamide | | 546.1 (M + H)$^+$ |
| 400 | 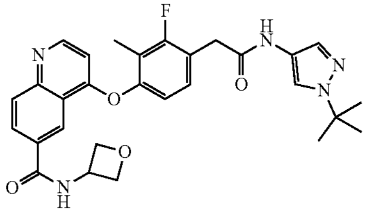 [SMILES: Cc1c(Oc2ccnc3ccc(C(=O)NC4COC4)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(oxetan-3-yl)quinoline-6-carboxamide | | 532.1 (M + H)$^+$ |
| 401 | 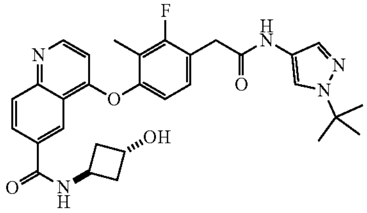 | 4-(4-(2-((1-(tert-butyl)-1H-pyrazol-4-yl)amino)-2-oxoethyl)-3-fluoro-2-methyl-phenoxy)-N-((1r,3r)-3-hydroxy-cyclobutyl) quinoline-6-carboxamide | | 546.1 (M + H)$^+$ |

-continued

| No. | Structure | Name | ¹H NMR | Observed m/z |
|---|---|---|---|---|
| 402 | 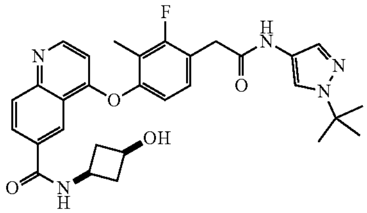 | 4-(4-(2-((1-(tert-butyl)-1H-pyrazol-4-yl)amino)-2-oxoethyl)-3-fluoro-2-methyl-phenoxy)-N-((1s,3s)-3-hydroxy-cyclobutyl) quinoline-6-carboxamide | | 546.1 (M + H)+ |
| 403 | 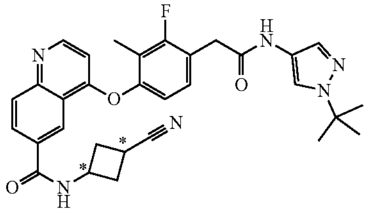 [SMILES: Cc1c(Oc2ccnc3ccc(C(=O)NC4CC(C#N)C4)cc23)ccc(CC(=O)Nc2cnn(C(C)(C)C)c2)c1F] diastereomer 1 (retention time: 1.77 min; column: CHIRALPAK ID-3, 4.6 x 50 mm, 3 µm; mobile phase A: MTBE (0.1% DEA), mobile phase B: EtOH, isocratic separation with 20% B, flow rate: 1.0 mL/min, wavelength: 254 nm) | 4-(4-(2-((1-(tert-butyl)-1H-pyrazol-4-yl)amino)-2-oxoethyl)-3-fluoro-2-methyl-phenoxy)-N-(-3-cyano-cyclobutyl) quinoline-6-carboxamide | | 555.1 (M + H)+ |
| 404 | 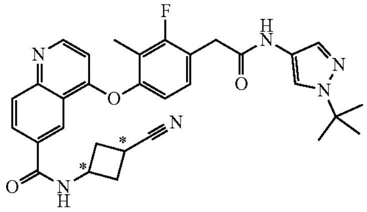 [SMILES: Cc1c(Oc2ccnc3ccc(C(=O)NC4CC(C#N)C4)cc23)ccc(CC(=O)Nc2cnn(C(C)(C)C)c2)c1F] diastereomer 2 (retention time: 2.66 min; column: CHIRALPAK ID-3, 4.6 x 50 mm, 3 µm; mobile phase A: MTBE (0.1% DEA), mobile phase B: EtOH, isocratic separation with 20% B, flow rate: 1.0 mL/min, wavelength: 254 nm) | 4-(4-(2-((1-(tert-butyl)-1H-pyrazol-4-yl)amino)-2-oxoethyl)-3-fluoro-2-methyl-phenoxy)-N-(-3-cyano-cyclobutyl) quinoline-6-carboxamide | | 555.2 (M + H)+ |
| 405 | 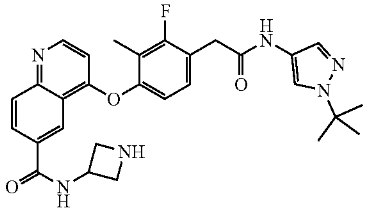 [SMILES: Cc1c(Oc2ccnc3ccc(C(=O)NC4CNC4)cc23)ccc(CC(=O)Nc2cnn(C(C)(C)C)c2)c1F] | N-(azetidin-3-yl)-4-(4-(2-((1-(tert-butyl)-1H-pyrazol-4-yl)amino)-2-oxoethyl)-3-fluoro-2-methyl-phenoxy) quinoline-6-carboxamide | | 531.2 (M + H)+ |

-continued

| No. | Structure | Name | $^1$H NMR | Observed m/z |
|---|---|---|---|---|
| 406 | 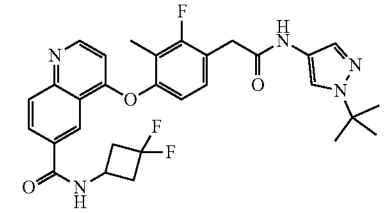 [SMILES: Cc1c(Oc2ccnc3ccc(C(=O)NC4CC(F)(F)C4)cc23)ccc(CC(=O)Nc2cnn(C(C)(C)C)c2)c1F] | 4-(4-(2-((1-(tert-butyl)-1H-pyrazol-4-yl)amino)-2-oxoethyl)-3-fluoro-2-methyl-phenoxy)-N-(3,3-difluoro-cyclobutyl) quinoline-6-carboxamide | | 566.0 (M + H)$^+$ |
| 434 | 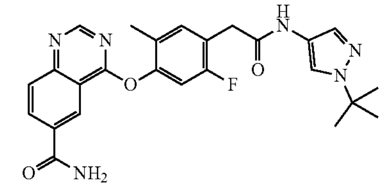 [SMILES: Cc1cc(CC(=O)Nc2cnn(C(C)(C)C)c2)c(F)cc1Oc1ncnc2ccc(C(N)=O)cc12] | 4-(4-(2-((1-(tert-butyl)-1H-pyrazol-4-yl)amino)-2-oxoethyl)-5-fluoro-2-methyl-phenoxy) quinazoline-6-carboxamide | (300 MHz, DMSO-$d_6$): δ 10.24 (s, 1H), 8.96 (d, J = 1.9 Hz, 1H), 8.80 (s, 1H), 8.49-8.45 (m, 2H), 8.08 (d, J = 8.8 Hz, 1H), 7.95 (s, 1H), 7.71 (s, 1H), 7.46 (s, 1H), 7.38 (d, J = 8.4 Hz, 1H), 7.29 (d, J = 10.1 Hz, 1H), 3.67 (s, 2H), 2.10 (s, 3H), 1.49 (s, 9H) | 477.2 (M + H)$^+$ |
| 438 | 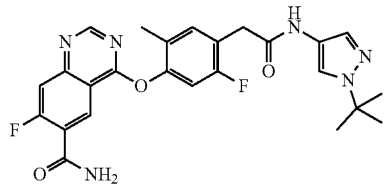 [SMILES: Cc1cc(CC(=O)Nc2cnn(C(C)(C)C)c2)c(F)cc1Oc1ncnc2cc(F)c(C(N)=O)cc12] | 4-(4-(2-((1-(tert-butyl)-1H-pyrazol-4-yl)amino)-2-oxoethyl)-5-fluoro-2-methyl-phenoxy)-7-fluoro-quinazoline-6-carboxamide | (300 MHz, DMSO-$d_6$): δ 10.24 (s, 1H), 8.79 (s, 1H), 8.68 (d, J = 7.6 Hz, 1H), 8.13 (s, 1H), 7.97-7.86 (m, 3H), 7.46 (s, 1H), 7.37 (d, J = 8.3 Hz, 1H), 7.27 (d, J = 10.0 Hz, 1H), 3.66 (s, 2H), 2.09 (s, 3H), 1.49 (s, 9H) | 495.1 (M + H)$^+$ |
| 439 | 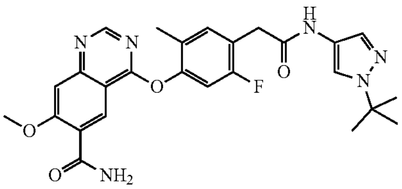 [SMILES: COc1cc2ncnc(Oc3cc(F)c(CC(=O)Nc4cnn(C(C)(C)C)c4)cc3C)c2cc1C(N)=O] | 4-(4-(2-((1-(tert-butyl)-1H-pyrazol-4-yl)amino)-2-oxoethyl)-5-fluoro-2-methyl-phenoxy)-7-methoxy-quinazoline-6-carboxamide | (300 MHz, DMSO-$d_6$): δ 10.23 (s, 1H), 8.69-8.66 (m, 2H), 7.94 (d, J = 0.7 Hz, 1H), 7.91 (s, 1H), 7.86-7.80 (m, 1H), 7.52 (s, 1H), 7.46 (s, 1H), 7.36 (d, J = 8.4 Hz, 1H), 7.25 (d, J = 10.0 Hz, 1H), 4.07 (s, 3H), 3.66 (s, 2H), 2.07 (s, 3H), 1.49 (s, 9H) | 507.2 (M + H)$^+$ |
| 447 | 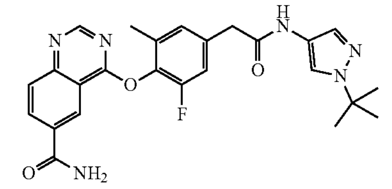 | 4-(4-(2-((1-(tert-butyl)-1H-pyrazol-4-yl)amino)-2-oxoethyl)-2-fluoro-6-methyl-phenoxy) quinazoline-6-carboxamide | (400 MHz, DMSO-$d_6$): δ 10.25 (s, 1H), 8.99 (d, J = 2.0 Hz, 1H), 8.81 (s, 1H), 8.51 (dd, J = 8.8, 2.0 Hz, 1H), 8.46 (s, 1H), 8.11 (d, J = 8.8 Hz, 1H), 7.95 (s, 1H), 7.72 (s, 1H), 7.47 (s, 1H), 7.22 (dd, J = 10.8, 2.0 Hz, 1H), 7.17 (d, J = 1.8 Hz, 1H), 3.62 (s, 2H), 2.19 (s, 3H), 1.49 (s, 9H) | 477.1 (M + H)$^+$ |
| 448 | 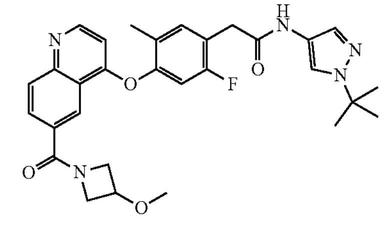 [SMILES: COC1CN(C(=O)c2ccc3nccc(Oc4cc(F)c(CC(=O)Nc5cnn(C(C)(C)C)c5)cc4C)c3c2)C1] | N-(1-(tert-butyl)-1H-pyrazol-4-yl)-2-(2-fluoro-4-((6-(3-meth-oxyazetidine-1-carbonyl) quinolin-4-yl)oxy)-5-methylphenyl) acetamide | | 546.2 (M + H)$^+$ |

-continued

| No. | Structure | Name | $^1H$ NMR | Observed m/z |
|---|---|---|---|---|
| 449 | 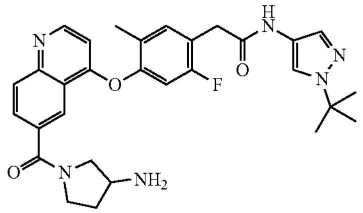 [SMILES: Cc1cc(CC(=O)Nc2cnn(C(C)(C)C)c2)c(F)cc1Oc1ccnc2ccc(C(=O)N3CCC(N)C3)cc12] | 2-(4-((6-(3-aminopyrrolidine-1-carbonyl)quinolin-4-yl)oxy)-2-fluoro-5-methylphenyl)-N-(1-(tert-butyl)-1H-pyrazol-4-yl)acetamide | | 545.1 $(M + H)^+$ |
| 450 | 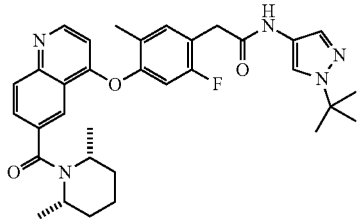 [SMILES: Cc1cc(CC(=O)Nc2cnn(C(C)(C)C)c2)c(F)cc1Oc1ccnc2ccc(C(=O)N3[C@H](C)CCC[C@@H]3C)cc12] | N-(1-(tert-butyl)-1H-pyrazol-4-yl)-2-(4-((6-((2S,6R)-2,6-dimethylpiperidine-1-carbonyl)quinolin-4-yl)oxy)-2-fluoro-5-methylphenyl)acetamide | | 572.4 $(M + H)^+$ |
| 451 | 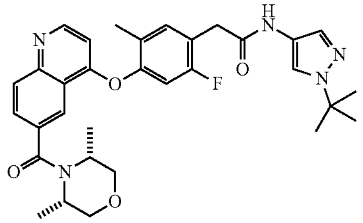 [SMILES: Cc1cc(CC(=O)Nc2cnn(C(C)(C)C)c2)c(F)cc1Oc1ccnc2ccc(C(=O)N3[C@H](C)COC[C@@H]3C)cc12] | N-(1-(tert-butyl)-1H-pyrazol-4-yl)-2-(4-((6-((3S,5R)-3,5-dimethylmorpholine-4-carbonyl)quinolin-4-yl)oxy)-2-fluoro-5-methylphenyl)acetamide | | 574.2 $(M + H)^+$ |
| 452 | 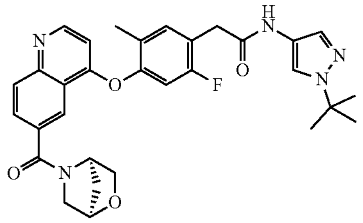 [SMILES: Cc1cc(CC(=O)Nc2cnn(C(C)(C)C)c2)c(F)cc1Oc1ccnc2ccc(C(=O)N3C[C@H]4C[C@@H]3CO4)cc12] | 2-(4-((6-((1R,4R)-2-oxa-5-azabicyclo[2.2.1]heptane-5-carbonyl)quinolin-4-yl)oxy)-2-fluoro-5-methylphenyl)-N-(1-(tert-butyl)-1H-pyrazol-4-yl)acetamide | | 558.2 $(M + H)^+$ |
| 453 | 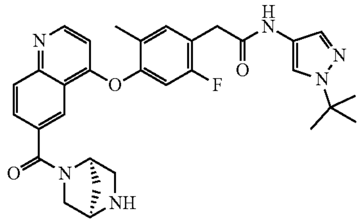 [SMILES: Cc1cc(CC(=O)Nc2cnn(C(C)(C)C)c2)c(F)cc1Oc1ccnc2ccc(C(=O)N3C[C@H]4C[C@@H]3CN4)cc12] | 2-(4-((6-((1R,4R)-2,5-diazabicyclo[2.2.1]heptane-2-carbonyl)quinolin-4-yl)oxy)-2-fluoro-5-methylphenyl)-N-(1-(tert-butyl)-1H-pyrazol-4-yl)acetamide | | 557.2 $(M + H)^+$ |

-continued

| No. | Structure | Name | $^1$H NMR | Observed m/z |
|---|---|---|---|---|
| 454 | 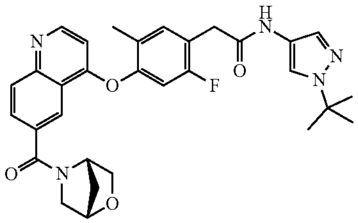 [SMILES: Cc1cc(CC(=O)Nc2cnn(C(C)(C)C)c2)c(F)cc1Oc1ccnc2ccc(C(=O)N3C[C@@H]4C[C@H]3CO4)cc12] | 2-(4-((6-((1S,4S)-2-oxa-5-azabicyclo[2.2.1]heptane-5-carbonyl)quinolin-4-yl)oxy)-2-fluoro-5-methyl-phenyl)-N-(1-(tert-butyl)-1H-pyrazol-4-yl)acetamide | | 558.2 (M + H)$^+$ |
| 455 | 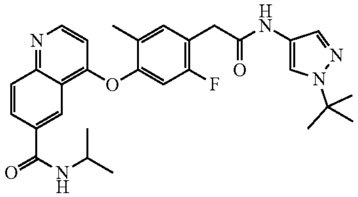 [SMILES: Cc1cc(CC(=O)Nc2cnn(C(C)(C)C)c2)c(F)cc1Oc1ccnc2ccc(C(=O)NC(C)C)cc12] | 4-(4-(2-((1-(tert-butyl)-1H-pyrazol-4-yl)amino)-2-oxoethyl)-5-fluoro-2-methyl-phenoxy)-N-isopropyl-quinoline-6-carboxamide | | 518.2 (M + H)$^+$ |
| 456 | 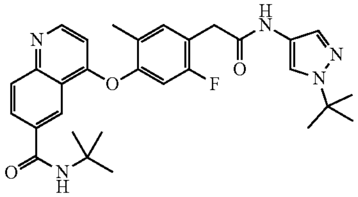 [SMILES: Cc1cc(CC(=O)Nc2cnn(C(C)(C)C)c2)c(F)cc1Oc1ccnc2ccc(C(=O)NC(C)(C)C)cc12] | N-(tert-butyl)-4-(4-(2-((1-(tert-butyl)-1H-pyrazol-4-yl)amino)-2-oxoethyl)-5-fluoro-2-methyl-phenoxy)quinoline-6-carboxamide | | 532.2 (M + H)$^+$ |
| 457 | 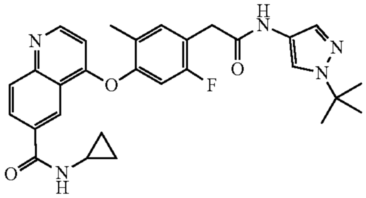 [SMILES: Cc1cc(CC(=O)Nc2cnn(C(C)(C)C)c2)c(F)cc1Oc1ccnc2ccc(C(=O)NC3CC3)cc12] | 4-(4-(2-((1-(tert-butyl)-1H-pyrazol-4-yl)amino)-2-oxoethyl)-5-fluoro-2-methyl-phenoxy)-N-cyclopropyl-quinoline-6-carboxamide | | 516.4 (M + H)$^+$ |
| 458 | 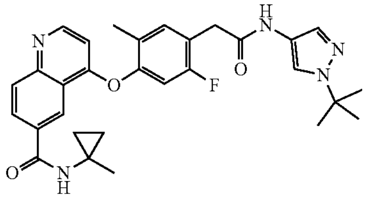 [SMILES: Cc1cc(CC(=O)Nc2cnn(C(C)(C)C)c2)c(F)cc1Oc1ccnc2ccc(C(=O)NC3(C)CC3)cc12] | 4-(4-(2-((1-(tert-butyl)-1H-pyrazol-4-yl)amino)-2-oxoethyl)-5-fluoro-2-methyl-phenoxy)-N-(1-methyl-cyclopropyl)quinoline-6-carboxamide | | 530.0 (M + H)$^+$ |

-continued

| No. | Structure | Name | ¹H NMR | Observed m/z |
|---|---|---|---|---|
| 435 | 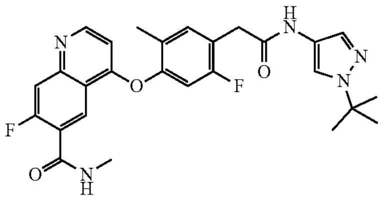 [SMILES: CNC(=O)c1cc2c(Oc3cc(F)c(CC(=O)Nc4cnn(C(C)(C)C)c4)cc3C)ccnc2cc1F] | 4-(4-(2-((1-(tert-butyl)-1H-pyrazol-4-yl)amino)-2-oxoethyl)-5-fluoro-2-methyl-phenoxy)-7-fluoro-N-methyl-quinoline-6-carboxamide | | 508.3 $(M + H)^+$ |
| 436 | 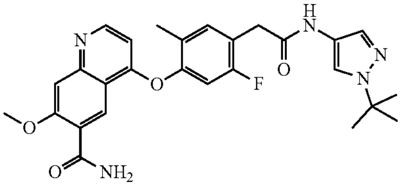 [SMILES: COc1cc2nccc(Oc3cc(F)c(CC(=O)Nc4cnn(C(C)(C)C)c4)cc3C)c2cc1C(N)=O] | 4-(4-(2-((1-(tert-butyl)-1H-pyrazol-4-yl)amino)-2-oxoethyl)-5-fluoro-2-methyl-phenoxy)-7-methoxy-quinoline-6-carboxamide | | 506.0 $(M + H)^+$ |
| 437 | 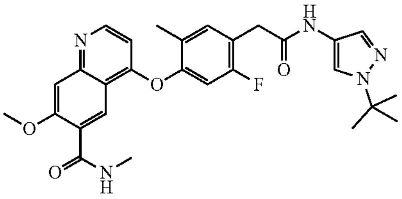 [SMILES: CNC(=O)c1cc2c(Oc3cc(F)c(CC(=O)Nc4cnn(C(C)(C)C)c4)cc3C)ccnc2cc1OC] | 4-(4-(2-((1-(tert-butyl)-1H-pyrazol-4-yl)amino)-2-oxoethyl)-5-fluoro-2-methyl-phenoxy)-7-methoxy-N-methyl-quinoline-6-carboxamide | | 520.1 $(M + H)^+$ |
| 440 | 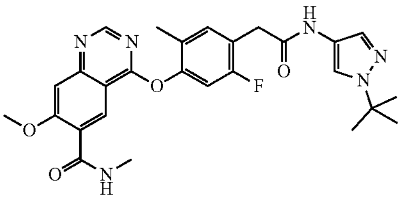 [SMILES: CNC(=O)c1cc2c(Oc3cc(F)c(CC(=O)Nc4cnn(C(C)(C)C)c4)cc3C)ncnc2cc1OC] | 4-(4-(2-((1-(tert-butyl)-1H-pyrazol-4-yl)amino)-2-oxoethyl)-5-fluoro-2-methyl-phenoxy)-7-methoxy-N-methyl-quinazoline-6-carboxamide | | 521.2 $(M + H)^+$ |
| 468 | 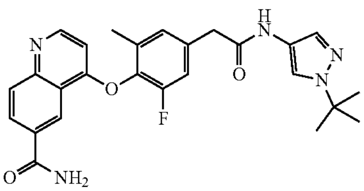 | 4-(4-(2-((1-(tert-butyl)-1H-pyrazol-4-yl)amino)-2-oxoethyl)-2-fluoro-6-methyl-phenoxy) quinoline-6-carboxamide | (400 MHz, DMSO-$d_6$) δ 10.25 (s, 1H), 8.96 (d, J = 2.0 Hz, 1H), 8.75 (d, J = 5.2 Hz, 1H), 8.39 (s, 1H), 8.29 (dd, J = 8.9, 2.0 Hz, 1H), 8.10 (d, J = 8.8 Hz, 1H), 7.96 (s, 1H), 7.61 (s, 1H), 7.47 (s, 1H), 7.29 (d, J = 11.1 Hz, 1H), 7.22 (s, 1H), 6.53 (d, J = 5.2 Hz, 1H), 3.65 (s, 2H), 2.19 (s, 3H), 1.49 (s, 9H) | 476.2 $(M + H)^+$ |

-continued

| No. | Structure | Name | $^1$H NMR | Observed m/z |
|---|---|---|---|---|
| 469 | 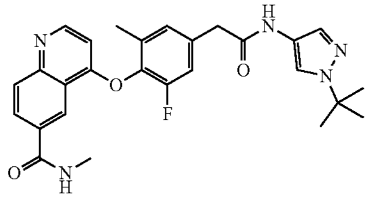 [SMILES: CNC(=O)c1ccc2nccc(Oc3c(C)cc(CC(=O)Nc4cnn(C(C)(C)C)c4)cc3F)c2c1] | 4-(4-(2-((1-(tert-butyl)-1H-pyrazol-4-yl)amino)-2-oxoethyl)-2-fluoro-6-methyl-phenoxy)-N-methyl-quinoline-6-carboxamide | (400 MHz, DMSO-$d_6$) δ 10.23 (s, 1H), 8.92 (d, J = 2.0 Hz, 1H), 8.84 (q, J = 4.5 Hz, 1H), 8.75 (d, J = 5.1 Hz, 1H), 8.26 (dd, J = 8.8, 2.1 Hz, 1H), 8.11 (d, J = 8.9 Hz, 1H), 7.96 (s, 1H), 7.47 (s, 1H), 7.30 (dd, J = 11.1, 2.0 Hz, 1H), 7.23 (s, 1H), 6.53 (dd, J = 5.2, 1.2 Hz, 1H), 3.65 (s, 2H), 2.87 (d, J = 4.4 Hz, 3H), 2.19 (s, 3H), 1.50 (s, 9H) | 490.1 $(M + H)^+$ |
| 470 | 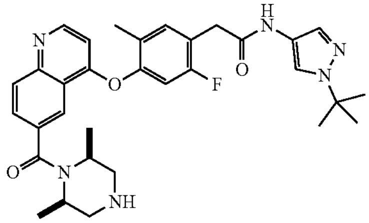 [SMILES: Cc1cc(CC(=O)Nc2cnn(C(C)(C)C)c2)c(F)cc1Oc1ccnc2ccc(C(=O)N3[C@H](C)CNC[C@@H]3C)cc12] | N-(1-(tert-butyl)-1H-pyrazol-4-yl)-2-(4-((6-((2R,6S)-2,6-dimethyl-piperazine-1-carbonyl) quinolin-4-yl)oxy)-2-fluoro-5-methylphenyl) acetamide | (300 MHz, DMSO-$d_6$) δ 10.22 (s, 1H), 8.74 (d, J = 5.1 Hz, 1H), 8.26 (d, J = 1.8 Hz, 1H), 8.10 (d, J = 8.6 Hz, 1H), 7.95 (s, 1H), 7.79 (dd, J = 8.6, 1.9 Hz, 1H), 7.46- 7.43 (m, 2H), 7.25 (d, J = 10.0 Hz, 1H), 6.57 (d, J = 5.1 Hz, 1H), 4.09 (s, 2H), 3.68 (s, 2H), 2.75 (s, 4H), 2.10 (s, 3H), 1.49 (s, 9H), 1.30 (d, J = 6.9 Hz, 6H) | 573.3 $(M + H)^+$ |
| 471 | 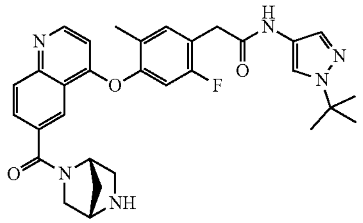 [SMILES: Cc1cc(CC(=O)Nc2cnn(C(C)(C)C)c2)c(F)cc1Oc1ccnc2ccc(C(=O)N3C[C@@H]4C[C@H]3CN4)cc12] | 2-(4-((6-((1S,4S)-2,5-diazabicyclo [2.2.1] heptane-2-carbonyl) quinolin-4-yl)oxy)-2-fluoro-5-methyl-phenyl)-N-(1-(tert-butyl)-1H-pyrazol-4-yl)acetamide | (300 MHz, DMSO-$d_6$) δ 10.27 (s, 1H), 8.76 (d, J = 5.2 Hz, 1H), 8.53 (s, 1H), 8.11 (t, J = 8.9 Hz, 1H), 7.97-7.91 (m, 2H), 7.47-7.44 (m, 2H), 7.24 (d, J = 9.9 Hz, 1H), 6.64-6.52 (m, 1H), 4.83 (s, 1H), 4.41 (s, 1H), 3.69 (s, 2H), 3.69-3.45 (m, 2H), 3.40-3.25 (m, 1H), 3.19-3.06 (m, 1H), 2.11 (s, 3H), 1.96-1.70 (m, 2H), 1.49 (s, 9H) | 557.1 $(M + H)^+$ |
| 487 | 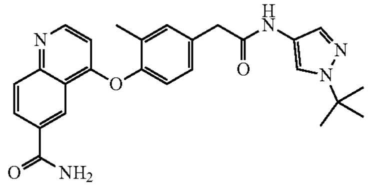 | 4-(4-(2-((1-(tert-butyl)-1H-pyrazol-4-yl)amino)-2-oxoethyl)-2-methyl-phenoxy) quinoline-6-carboxamide | (300 MHz, DMSO-$d_6$) δ 10.21 (s, 1H), 8.95 (s, 1H), 8.72 (d, J = 5.1 Hz, 1H), 8.35 (s, 1H), 8.27 (d, J = 6.6 Hz, 1H), 8.07 (d, J = 8.7 Hz, 1H), 7.95 (s, 1H), 7.58 (s, 1H), 7.46 (s, 1H), 7.39 (s, 1H), 7.31 (d, J = 2.1 Hz, 1H), 7.21 (d, J = 8.1 Hz, 1H), 6.45 (d, J = 5.4 Hz, 1H), 3.61 (s, 2H), 2.14 (s, 3H), 1.49 (s, 9H) | 458.2 $(M + H)^+$ |
| 488 | 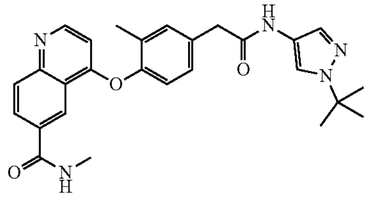 [SMILES: CNC(=O)c1ccc2nccc(Oc3ccc(CC(=O)Nc4cnn(C(C)(C)C)c4)cc3C)c2c1] | 4-(4-(2-((1-(tert-butyl)-1H-pyrazol-4-yl)amino)-2-oxoethyl)-2-methyl-phenoxy)-N-methyl-quinoline-6-carboxamide | (300 MHz, DMSO-$d_6$) δ 10.22 (s, 1H), 8.91 (d, J = 1.8, 1H), 8.82 (d, J = 4.5 Hz, 1H), 8.72 (d, J = 5.4 Hz, 1H), 8.24 (dd, J = 8.9, 2.1 Hz, 1H), 8.08 (d, J = 9.0 Hz, 1H), 7.96 (s, 1H), 7.47 (s, 1H), 7.39 (s, 1H), 7.31 (dd, J = 3.7, 1.8 Hz, 1H), 7.22 (d, J = 8.1 Hz, 1H), 6.44 (d, J = 5.1 Hz, 1H), 3.62 (s, 2H), 2.86 (d, J = 4.5 Hz, 3H), 2.14 (s, 3H), 1.49 (s, 9H) | 472.2 $(M + H)^+$ |

-continued

| No. | Structure | Name | $^1H$ NMR | Observed m/z |
|---|---|---|---|---|
| 491 | 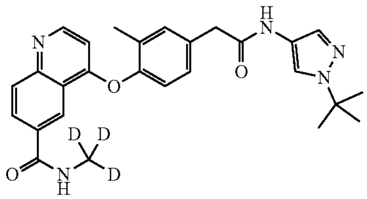 [SMILES: [2H]C([2H])([2H])NC(=O)c1ccc2nccc(Oc3ccc(CC(=O)Nc4cnn(C(C)(C)C)c4)cc3C)c2c1] | 4-(4-(2-((1-(tert-butyl)-1H-pyrazol-4-yl)amino)-2-oxoethyl)-2-methyl-phenoxy)-N-(methyl-$d_3$) quinoline-6-carboxamide | (300 MHz, DMSO-$d_6$) δ 10.21 (s, 1H), 8.90 (d, J = 1.8 Hz, 1H), 8.79 (s, 1H), 8.72 (d, J = 5.1 Hz, 1H), 8.24 (dd, J = 6.9 Hz, 1H), 8.08 (d, J = 8.7 Hz, 1H), 7.96 (s, 1H), 7.46 (s, 1H), 7.38 (s, 1H), 7.31 (dd, J = 8.1 Hz, 1H), 7.22 (d, J = 8.1 Hz, 1H), 6.45 (d, J = 5.4 Hz, 1H), 3.62 (s, 2H), 2.14 (s, 3H), 1.49 (s, 9H) | 475.2 $(M + H)^+$ |
| 492 | 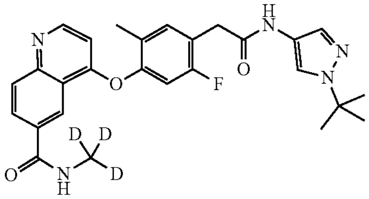 [SMILES: [2H]C([2H])([2H])NC(=O)c1ccc2nccc(Oc3cc(F)c(CC(=O)Nc4cnn(C(C)(C)C)c4)cc3C)c2c1] | 4-(4-(2-((1-(tert-butyl)-1H-pyrazol-4-yl)amino)-2-oxoethyl)-5-fluoro-2-methyl-phenoxy)-N-(methyl-$d_3$) quinoline-6-carboxamide | (300 MHz, DMSO-$d_6$) δ 10.23 (s, 1H), 8.89 (d, J = 2.0 Hz, 1H), 8.80 (s, 1H), 8.76 (d, J = 5.1 Hz, 1H), 8.25 (dd, J = 8.8 Hz, 1H), 8.10 (d, J = 8.8 Hz, 1H), 7.95 (d, J = 0.7 Hz, 1H), 7.53-7.40 (m, 2H), 7.26 (d, J = 10.1 Hz, 1H), 6.54 (d, J = 5.2 Hz, 1H), 3.69 (s, 2H), 2.11 (s, 3H), 1.49 (s, 9H) | 493.2 $(M + H)^+$ |
| 497 | 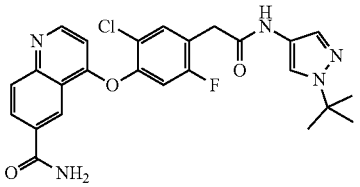 [SMILES: CC(C)(C)n1cc(NC(=O)Cc2cc(Cl)c(Oc3ccnc4ccc(C(N)=O)cc34)cc2F)cn1] | 4-(4-(2-((1-(tert-butyl)-1H-pyrazol-4-yl)amino)-2-oxoethyl)-2-chloro-5-fluoro-phenoxy) quinoline-6-carboxamide | (300 MHz, DMSO-$d_6$) δ 10.26 (s, 1H), 8.93 (d, J = 2.0 Hz, 1H), 8.80 (d, J = 5.1 Hz, 1H), 8.38 (s, 1H), 8.31 (dd, J = 8.8, 2.0 Hz, 1H), 8.11 (d, J = 8.8 Hz, 1H), 7.95 (s, 1H), 7.81 (d, J = 7.4 Hz, 1H), 7.67-7.57 (m, 2H), 7.47 (s, 1H), 6.63 (d, J = 5.2 Hz, 1H), 3.76 (s, 2H), 1.50 (s, 9H) | 496.1 $(M + H)^+$ |
| 498 | 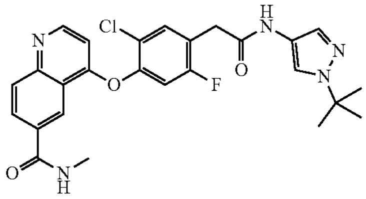 [SMILES: CNC(=O)c1ccc2nccc(Oc3cc(F)c(CC(=O)Nc4cnn(C(C)(C)C)c4)cc3Cl)c2c1] | 4-(4-(2-((1-(tert-butyl)-1H-pyrazol-4-yl)amino)-2-oxoethyl)-2-chloro-5-fluoro-phenoxy)-N-methyl-quinoline-6-carboxamide | (400 MHz, DMSO-$d_6$) δ 10.27 (s, 1H), 8.90-8.83 (m, 2H), 8.79 (d, J = 5.2 Hz, 1H), 8.27 (dd, J = 8.8, 2.1 Hz, 1H), 8.15-8.09 (m, 1H), 7.95 (d, J = 0.8 Hz, 1H), 7.81 (d, J = 7.4 Hz, 1H), 7.63 (d, J = 9.7 Hz, 1H), 7.46 (d, J = 0.7 Hz, 1H), 6.63 (d, J = 5.1 Hz, 1H), 3.76 (s, 2H), 2.86 (d, J = 4.5 Hz, 3H), 1.49 (s, 9H) | 510.1 $(M + H)^+$ |
| 499 | 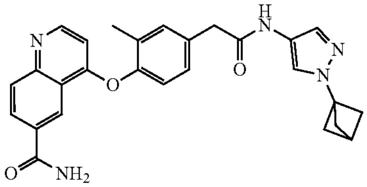 [SMILES: Cc1cc(CC(=O)Nc2cnn(C34CC(C3)C4)c2)ccc1Oc1ccnc2ccc(C(N)=O)cc12] | 4-(4-(2-((1-(bicyclo [1.1.1] pentan-1-yl)-1H-pyrazol-4-yl)amino)-2-oxoethyl)-2-methyl-phenoxy) quinoline-6-carboxamide | (400 MHz, DMSO-$d_6$) δ 10.28 (s, 1H), 8.95 (s, 1H), 8.72 (d, J = 5.2 Hz, 1H), 8.36 (s, 1H), 8.27 (d, J = 8.8 Hz, 1H), 8.07 (d, J = 8.8 Hz, 1H), 7.91 (s, 1H), 7.59 (s, 1H), 7.46 (s, 1H), 7.38 (s, 1H), 7.30 (d, J = 8.3 Hz, 1H), 7.22 (d, J = 8.3 Hz, 1H), 6.44 (d, J = 5.2 Hz, 1H), 3.63 (s, 2H), 2.60 (s, 1H), 2.20 (s, 6H), 2.13 (s, 3H) | 468.1 $(M + H)^+$ |

-continued

| No. | Structure | Name | $^1H$ NMR | Observed m/z |
|---|---|---|---|---|
| 500 | 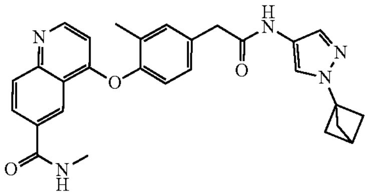 [SMILES: CNC(=O)c1ccc2nccc(Oc3ccc(CC(=O)Nc4cnn(C56CC(C5)C6)c4)cc3C)c2c1] | 4-(4-(2-((1-(bicyclo [1.1.1] pentan-1-yl)-1H-pyrazol-4-yl)amino)-2-oxoethyl)-2-methyl-phenoxy)-N-methyl-quinoline-6-carboxamide | (400 MHz, DMSO-$d_6$) δ 10.27 (s, 1H), 8.90 (d, J = 2.0 Hz, 1H), 8.81 (d, J = 4.7 Hz, 1H), 8.72 (d, J = 5.2 Hz, 1H), 8.24 (dd, J = 8.9, 2.0 Hz, 1H), 8.08 (d, J = 8.8 Hz, 1H), 7.91 (s, 1H), 7.46 (s, 1H), 7.38 (d, J = 2.1 Hz, 1H), 7.31 (dd, J = 8.2, 2.2 Hz, 1H), 7.22 (d, J = 8.2 Hz, 1H), 6.44 (d, J = 5.2 Hz, 1H), 3.63 (s, 2H), 2.86 (d, J = 4.5 Hz, 3H), 2.60 (s, 1H), 2.20 (s, 6H), 2.13 (s, 3H) | 482.2 $(M + H)^+$ |
| 501 | 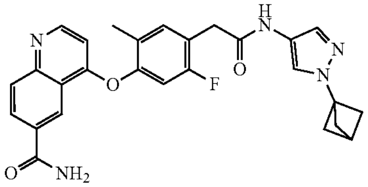 [SMILES: Cc1cc(CC(=O)Nc2cnn(C34CC(C3)C4)c2)c(F)cc1Oc1ccnc2ccc(C(N)=O)cc12] | 4-(4-(2-((1-(bicyclo [1.1.1] pentan-1-yl)-1H-pyrazol-4-yl)amino)-2-oxoethyl)-5-fluoro-2-methyl-phenoxy) quinoline-6-carboxamide | (400 MHz, DMSO-$d_6$) δ 10.30 (s, 1H), 8.96-8.91 (m, 1H), 8.76 (d, J = 5.2 Hz, 1H), 8.37 (s, 1H), 8.32-8.25 (m, 1H), 8.09 (d, J = 8.8 Hz, 1H), 7.90 (s, 1H), 7.60 (s, 1H), 7.47-7.44 (m, 2H), 7.26 (d, J = 10.0 Hz, 1H), 6.54 (d, J = 5.2 Hz, 1H), 3.70 (s, 2H), 2.60 (s, 1H), 2.20 (s, 6H), 2.11 (s, 3H) | 486.1 $(M + H)^+$ |
| 502 | 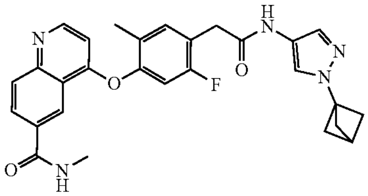 [SMILES: CNC(=O)c1ccc2nccc(Oc3cc(F)c(CC(=O)Nc4cnn(C56CC(C5)C6)c4)cc3C)c2c1] | 4-(4-(2-((1-(bicyclo [1.1.1] pentan-1-yl)-1H-pyrazol-4-yl)amino)-2-oxoethyl)-5-fluoro-2-methyl-phenoxy)-N-methyl-quinoline-6-carboxamide | (400 MHz, DMSO-$d_6$) δ 10.29 (s, 1H), 8.89 (d, J = 2.0 Hz, 1H), 8.82 (d, J = 4.7 Hz, 1H), 8.76 (d, J = 5.2 Hz, 1H), 8.25 (dd, J = 8.8, 2.1 Hz, 1H), 8.10 (d, J = 8.8 Hz, 1H), 7.90 (s, 1H), 7.49-7.42 (m, 2H), 7.26 (d, J = 10.0 Hz, 1H), 6.54 (d, J = 5.1 Hz, 1H), 3.70 (s, 2H), 2.87 (d, J = 4.5 Hz, 3H), 2.61 (s, 1H), 2.20 (s, 6H), 2.11 (s, 3H) | 500.1 $(M + H)^+$ |
| 503 | 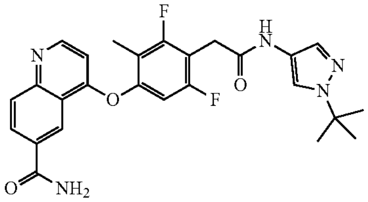 [SMILES: Cc1c(Oc2ccnc3ccc(C(N)=O)cc23)cc(F)c(CC(=O)Nc2cnn(C(C)(C)C)c2)c1F] | 4-(4-(2-((1-(tert-butyl)-1H-pyrazol-4-yl)amino)-2-oxoethyl)-3,5-difluoro-2-methyl-phenoxy) quinoline-6-carboxamide | (300 MHz, DMSO-$d_6$) δ 10.32 (s, 1H), 8.93 (d, J = 2.0 Hz, 1H), 8.79 (d, J = 5.1 Hz, 1H), 8.39 (s, 1H), 8.30 (dd, J = 8.8, 2.0 Hz, 1H), 8.11 (d, J = 8.8 Hz, 1H), 7.92 (s, 1H), 7.63 (s, 1H), 7.44 (s, 1H), 7.24 (dd, J = 9.8, 1.9 Hz, 1H), 6.63 (d, J = 5.2 Hz, 1H), 3.75 (s, 2H), 2.06 (s, 3H), 1.48 (s, 9H) | 494.1 $(M + H)^+$ |
| 504 | 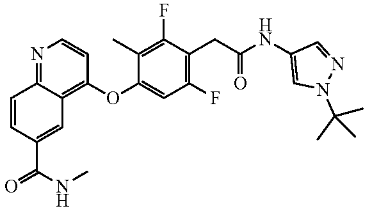 [SMILES: CNC(=O)c1ccc2nccc(Oc3cc(F)c(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3,5-difluoro-2-methyl-phenoxy)-N-methyl-quinoline-6-carboxamide | (400 MHz, DMSO-$d_6$) δ 10.46 (s, 1H), 9.15-9.09 (m, 2H), 9.07 (d, J = 1.9 Hz, 1H), 8.57 (dd, J = 8.8, 1.9 Hz, 1H), 8.44 (d, J = 8.9 Hz, 1H), 7.94 (s, 1H), 7.48 (s, 1H), 7.38 (dd, J = 9.4, 1.7 Hz, 1H), 7.03 (d, J = 6.2 Hz, 1H), 3.78 (s, 2H), 2.89 (d, J = 4.4 Hz, 3H), 2.08 (s, 3H), 1.49 (s, 9H) | 508.1 $(M + H)^+$ |

-continued

| No. | Structure | Name | $^1$H NMR | Observed m/z |
|---|---|---|---|---|
| 505 | 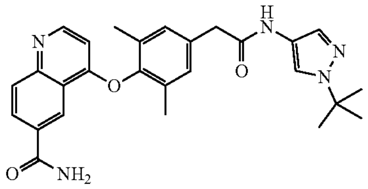 | 4-(4-(2-((1-(tert-butyl)-1H-pyrazol-4-yl)amino)-2-oxoethyl)-2,6-dimethyl-phenoxy) quinoline-6-carboxamide | (300 MHz, DMSO-$d_6$) δ 10.20 (s, 1H), 8.99 (d, J = 2.0 Hz, 1H), 8.70 (d, J = 5.1 Hz, 1H), 8.36 (s, 1H), 8.27 (dd, J = 8.8, 2.0 Hz, 1H), 8.08 (d, J = 8.8 Hz, 1H), 7.96 (s, 1H), 7.61 (s, 1H), 7.46 (s, 1H), 7.20 (s, 2H), 6.33 (d, J = 5.1 Hz, 1H), 3.58 (s, 2H), 2.08 (s, 6H), 1.49 (s, 9H) | 472.3 $(M + H)^+$ |
| 506 | 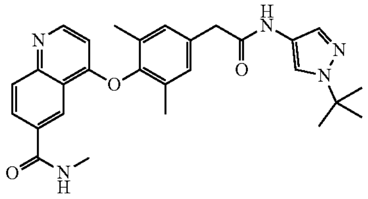 | 4-(4-(2-((1-(tert-butyl)-1H-pyrazol-4-yl)amino)-2-oxoethyl)-2,6-dimethyl-phenoxy)-N-methyl-quinoline-6-carboxamide | (300 MHz, DMSO-$d_6$) δ 10.20 (s, 1H), 8.95 (d, J = 2.0 Hz, 1H), 8.83 (d, J = 4.8 Hz, 1H), 8.70 (d, J = 5.1 Hz, 1H), 8.24 (dd, J = 8.8, 2.0 Hz, 1H), 8.09 (d, J = 8.8 Hz, 1H), 7.96 (d, J = 0.7 Hz, 1H), 7.46 (d, J = 0.7 Hz, 1H), 7.20 (s, 2H), 6.33 (d, J = 5.2 Hz, 1H), 3.58 (s, 2H), 2.87 (d, J = 4.5 Hz, 3H), 2.08 (s, 6H), 1.49 (s, 9H) | 486.3 $(M + H)^+$ |
| 509 | 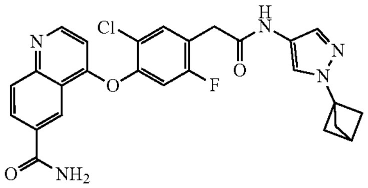 [SMILES: NC(=O)c1ccc2nccc(Oc3cc(F)c(CC(=O)Nc4cnn(C56CC(C5)C6)c4)cc3Cl)c2c1] | 4-(4-(2-((1-(bicyclo [1.1.1] pentan-1-yl)-1H-pyrazol-4-yl)amino)-2-oxoethyl)-2-chloro-5-fluoro-phenoxy) quinoline-6-carboxamide | (300 MHz, DMSO-$d_6$) δ 10.35 (s, 1H), 8.93 (d, J = 2.0 Hz, 1H), 8.80 (d, J = 5.1 Hz, 1H), 8.39 (s, 1H), 8.31 (dd, J = 8.9, 2.0 Hz, 1H), 8.11 (d, J = 8.8 Hz, 1H), 7.90 (s, 1H), 7.81 (d, J = 7.4 Hz, 1H), 7.63-7.60 (m 2H), 7.47 (s, 1H), 6.62 (d, J = 5.2 Hz, 1H), 3.77 (s, 2H), 2.60 (s, 1H), 2.20 (s, 6H) | 506.0 $(M + H)^+$ |
| 510 | 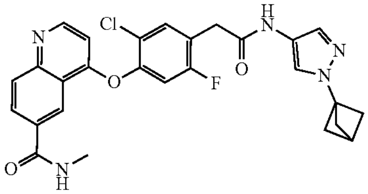 [SMILES: CNC(=O)c1ccc2nccc(Oc3cc(F)c(CC(=O)Nc4cnn(C56CC(C5)C6)c4)cc3Cl)c2c1] | 4-(4-(2-((1-(bicyclo [1.1.1] pentan-1-yl)-1H-pyrazol-4-yl)amino)-2-oxoethyl)-2-chloro-5-fluoro-phenoxy)-N-methyl-quinoline-6-carboxamide | (300 MHz, DMSO-$d_6$) δ 10.35 (s, 1H), 8.91-8.82 (m, 2H), 8.79 (d, J = 5.2 Hz, 1H), 8.27 (dd, J = 8.8, 2.0 Hz, 1H), 8.12 (d, J = 8.9 Hz, 1H), 7.90 (s, 1H), 7.81 (d, J = 7.4 Hz, 1H), 7.62 (d, J = 9.7 Hz, 1H), 7.47 (s, 1H), 6.63 (d, J = 5.1 Hz, 1H), 3.77 (s, 2H), 2.86 (d, J = 4.4 Hz, 3H), 2.59 (s, 1H), 2.20 (s, 6H) | 520.0 $(M + H)^+$ |
| 511 | 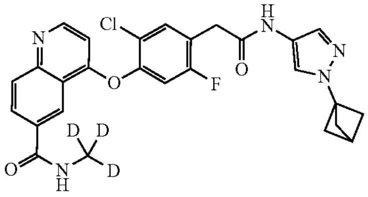 [SMILES: [2H]C([2H])([2H])NC(=O)c1ccc2nccc(Oc3cc(F)c(CC(=O)Nc4cnn(C56CC(C5)C6)c4)cc3Cl)c2c1] | 4-(4-(2-((1-(bicyclo [1.1.1] pentan-1-yl)-1H-pyrazol-4-yl)amino)-2-oxoethyl)-2-chloro-5-fluoro-phenoxy)-N-(methyl-$d_3$) quinoline-6-carboxamide | (300 MHz, DMSO-$d_6$) δ 10.34 (s, 1H), 8.88 (d, J = 2.0 Hz, 1H), 8.86-8.77 (m, 2H), 8.29 (dd, J = 8.8, 2.0 Hz, 1H), 8.13 (d, J = 8.8 Hz, 1H), 7.90 (s, 1H), 7.81 (d, J = 7.4 Hz, 1H), 7.62 (d, J = 9.7 Hz, 1H), 7.47 (s, 1H), 6.65 (d, J = 5.2 Hz, 1H), 3.78 (s, 2H), 2.60 (s, 1H), 2.20 (s, 6H) | 523.1 $(M + H)^+$ |

-continued

| No. | Structure | Name | $^1$H NMR | Observed m/z |
|---|---|---|---|---|
| 512 | 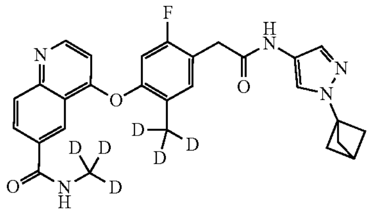 [SMILES: [2H]C([2H])([2H])NC(=O)c1ccc2nccc(Oc3cc(F)c(CC(=O)Nc4cnn(C56CC(C5)C6)c4)cc3C([2H])([2H])[2H])c2c1] | 4-(4-(2-((1-(bicyclo [1.1.1] pentan-1-yl)-1H-pyrazol-4-yl)amino)-2-oxoethyl)-5-fluoro-2-(methyl-$d_3$) phenoxy)-N-(methyl-$d_3$) quinoline-6-carboxamide | (400 MHz, DMSO-$d_6$) δ 10.33 (s, 1H), 8.89 (d, J = 2.0 Hz, 1H), 8.82 (s, 1H), 8.76 (d, J = 5.1 Hz, 1H), 8.33-8.21 (m, 1H), 8.10 (d, J = 8.8 Hz, 1H), 7.90 (s, 1H), 7.47-7.44 (d, J = 9.2 Hz, 2H), 7.27 (d, J = 10.0 Hz, 1H), 6.53 (d, J = 5.1 Hz, 1H), 3.70 (s, 2H), 2.60 (s, 1H), 2.20 (s, 6H) | 506.1 $(M + H)^+$ |
| 513 | 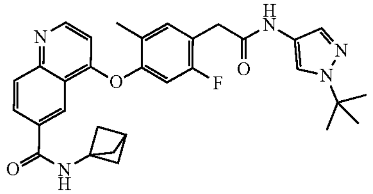 [SMILES: Cc1cc(CC(=O)Nc2cnn(C(C)(C)C)c2)c(F)cc1Oc1ccnc2ccc(C(=O)NC34CC(C3)C4)cc12] | N-(bicyclo [1.1.1]pentan-1-yl)-4-(4-(2-((1-(tert-butyl)-1H-pyrazol-4-yl)amino)-2-oxoethyl)-5-fluoro-2-methyl-phenoxy) quinoline-6-carboxamide | (300 MHz, DMSO-$d_6$) δ 10.24 (s, 1H), 9.38 (s, 1H), 8.90 (d, J = 2.0 Hz, 1H), 8.75 (d, J = 5.2 Hz, 1H), 8.24 (dd, J = 8.9, 2.0 Hz, 1H), 8.08 (d, J = 8.9 Hz, 1H), 7.95 (s, 1H), 7.51-7.40 (m, 2H), 7.26 (d, J = 10.0 Hz, 1H), 6.52 (d, J = 5.2 Hz, 1H), 3.69 (s, 2H), 2.49 (s, 1H), 2.14 (s, 6H), 2.10 (s, 3H), 1.49 (s, 9H) | 542.3 $(M + H)^+$ |
| 514 | 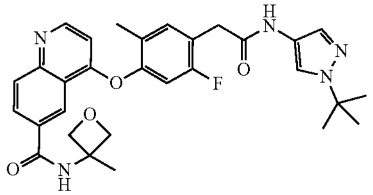 [SMILES: Cc1cc(CC(=O)Nc2cnn(C(C)(C)C)c2)c(F)cc1Oc1ccnc2ccc(C(=O)NC3(C)COC3)cc12] | 4-(4-(2-((1-(tert-butyl)-1H-pyrazol-4-yl)amino)-2-oxoethyl)-5-fluoro-2-methyl-phenoxy)-N-(3-methyl-oxetan-3-yl) quinoline-6-carboxamide | (300 MHz, DMSO-$d_6$) δ 10.24 (s, 1H), 9.29 (s, 1H), 8.92 (s, 1H), 8.77 (d, J = 5.2 Hz, 1H), 8.27 (d, J = 9.3 Hz, 1H), 8.12 (d, J = 8.7 Hz, 1H), 7.95 (s, 1H), 7.51-7.42 (m, 2H), 7.27 (d, J = 10.0 Hz, 1H), 6.53 (d, J = 5.2 Hz, 1H), 4.78 (d, J = 6.3 Hz, 2H), 4.42 (d, J = 6.2 Hz, 2H), 3.69 (s, 2H), 2.11 (s, 3H), 1.67 (s, 3H), 1.50 (s, 9H) | 546.2 $(M + H)^+$ |
| 515 | 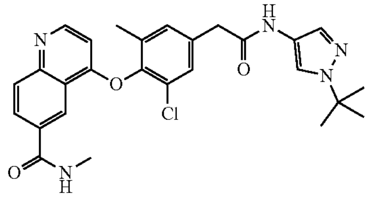 | 4-(4-(2-((1-(tert-butyl)-1H-pyrazol-4-yl)amino)-2-oxoethyl)-2-chloro-6-methyl-phenoxy)-N-methyl-quinoline-6-carboxamide | (300 MHz, DMSO-$d_6$) δ 10.24 (s, 1H), 9.00 (d, J = 1.9 Hz, 1H), 8.92-8.86 (m, 2H), 8.37 (dd, J = 8.8, 2.0 Hz, 1H), 8.18 (d, J = 8.9 Hz, 1H), 7.96 (d, J = 0.7 Hz, 1H), 7.53 (d, J = 2.1 Hz, 1H), 7.47 (d, J = 0.7 Hz, 1H), 7.39 (d, J = 2.0 Hz, 1H), 6.60 (d, J = 5.6 Hz, 1H), 3.66 (s, 2H), 2.87 (d, J = 4.5 Hz, 3H), 2.18 (s, 3H), 1.49 (s, 9H) | 506.3 $(M + H)^+$ |
| 516 | 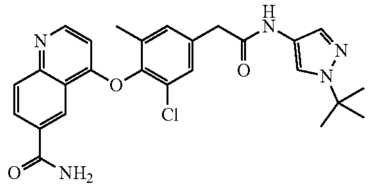 [SMILES: Cc1cc(CC(=O)Nc2cnn(C(C)(C)C)c2)cc(Cl)c1Oc1ccnc2ccc(C(N)=O)cc12] | 4-(4-(2-((1-(tert-butyl)-1H-pyrazol-4-yl)amino)-2-oxoethyl)-2-chloro-6-methyl-phenoxy) quinoline-6-carboxamide | (300 MHz, DMSO-$d_6$) δ 10.24 (s, 1H), 8.98 (d, J = 2.0 Hz, 1H), 8.74 (d, J = 5.2 Hz, 1H), 8.38 (s, 1H), 8.29 (dd, J = 8.8, 2.0 Hz, 1H), 8.10 (d, J = 8.8 Hz, 1H), 7.96 (d, J = 0.8 Hz, 1H), 7.63 (s, 1H), 7.50-7.46 (m, 2H), 7.41-7.32 (m, 1H), 6.41 (d, J = 5.2 Hz, 1H), 3.65 (s, 2H), 2.17 (s, 3H), 1.50 (s, 9H) | 492.3 $(M + H)^+$ |

-continued

| No. | Structure | Name | $^1$H NMR | Observed m/z |
|---|---|---|---|---|
| 517 | 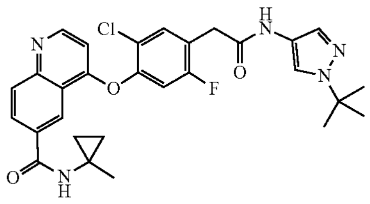 [SMILES: CC1(NC(=O)c2ccc3nccc(Oc4cc(F)c(CC(=O)Nc5cnn(C(C)(C)C)c5)cc4Cl)c3c2)CC1] | 4-(4-(2-((1-(tert-butyl)-1H-pyrazol-4-yl)amino)-2-oxoethyl)-2-chloro-5-fluoro-phenoxy)-N-(1-methyl-cyclopropyl) quinoline-6-carboxamide | (300 MHz, DMSO-$d_6$) δ 10.26 (s, 1H), 9.08 (s, 1H), 8.85 (d, J = 1.6 Hz, 1H), 8.78 (d, J = 5.2 Hz, 1H), 8.28-8.18 (m, 1H), 8.08 (d, J = 8.8 Hz, 1H), 7.95 (s, 1H), 7.80 (d, J = 7.5 Hz, 1H), 7.60 (d, J = 9.7 Hz, 1H), 7.46 (s, 1H), 6.60 (d, J = 5.1 Hz, 1H), 3.76 (s, 2H), 1.49 (s, 9H), 1.42 (s, 3H), 0.85-0.77 (m, 2H), 0.65 (t, J = 5.7 Hz, 2H) | 550.2 (M + H)$^+$ |
| 519 | 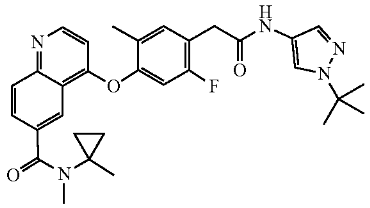 [SMILES: Cc1cc(CC(=O)Nc2cnn(C(C)(C)C)c2)c(F)cc1Oc1ccnc2ccc(C(=O)N(C)C3(C)CC3)cc12] | 4-(4-(2-((1-(tert-butyl)-1H-pyrazol-4-yl)amino)-2-oxoethyl)-5-fluoro-2-methyl-phenoxy)-N-methyl-N-(1-methyl-cyclopropyl) quinoline-6-carboxamide | (400 MHz, DMSO-$d_6$) δ 10.21 (s, 1H), 8.74 (d, J = 5.1 Hz, 1H), 8.35 (s, 1H), 8.08 (d, J = 8.7 Hz, 1H), 7.94 (d, J = 0.8 Hz, 1H), 7.83 (d, J = 8.7 Hz, 1H), 7.45 (d, J = 0.7 Hz, 1H), 7.43 (d, J = 8.4 Hz, 1H), 7.24 (d, J = 10.0 Hz, 1H), 6.57 (s, 1H), 3.67 (s, 2H), 3.02 (s, 3H), 2.09 (s, 3H), 1.49 (s, 9H), 1.42 (s, 3H), 0.84-0.36 (m, 4H) | 544.3 (M + H)$^+$ |
| 555 | 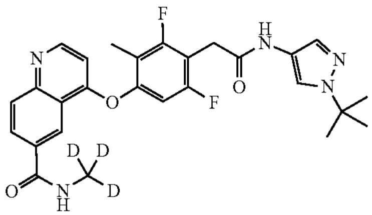 [SMILES: [2H]C([2H])([2H])NC(=O)c1ccc2nccc(Oc3cc(F)c(CC(=O)Nc4cnn(C(C)(C)C)c4)c(F)c3C)c2c1] | 4-(4-(2-((1-(tert-butyl)-1H-pyrazol-4-yl)amino)-2-oxoethyl)-3,5-difluoro-2-methyl-phenoxy)-N-(methyl-$d_3$) quinoline-6-carboxamide | (300 MHz, DMSO-$d_6$) δ 10.32 (s, 1H), 8.88 (d, J = 1.9 Hz, 1H), 8.85-8.75 (m, 2H), 8.27 (dd, J = 8.8, 1.9 Hz, 1H), 8.11 (d, J = 8.8 Hz, 1H), 7.95 (s, 1H), 7.46 (s, 1H), 7.24 (dd, J = 9.7, 1.9 Hz, 1H), 6.63 (d, J = 5.1 Hz, 1H), 3.75 (s, 2H), 2.05 (s, 3H), 1.49 (s, 9H) | 511.2 (M + H)$^+$ |
| 556 | 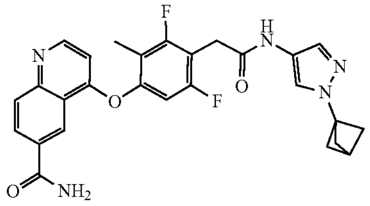 [SMILES: Cc1c(Oc2ccnc3ccc(C(N)=O)cc23)cc(F)c(CC(=O)Nc2cnn(C34CC(C3)C4)c2)c1F] | 4-(4-(2-((1-(bicyclo [1.1.1] pentan-1-yl)-1H-pyrazol-4-yl)amino)-2-oxoethyl)-3,5-difluoro-2-methyl-phenoxy) quinoline-6-carboxamide | (300 MHz, DMSO-$d_6$) δ 10.37 (s, 1H), 8.93 (d, J = 2.0 Hz, 1H), 8.79 (d, J = 5.2 Hz, 1H), 8.37 (s, 1H), 8.29 (dd, J = 8.9, 2.0 Hz, 1H), 8.10 (d, J = 8.8 Hz, 1H), 7.89 (s, 1H), 7.62 (s, 1H), 7.46 (s, 1H), 7.34-7.19 (m, 1H), 6.63 (d, J = 5.2 Hz, 1H), 3.75 (s, 2H), 2.60 (s, 1H), 2.20 (s, 6H), 2.06 (s, 3H) | 504.1 (M + H)$^+$ |
| 557 | 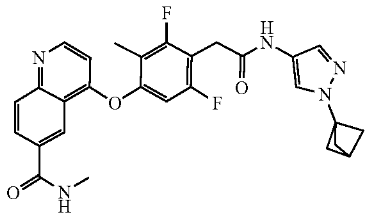 [SMILES: CNC(=O)c1ccc2nccc(Oc3cc(F)c(CC(=O)Nc4cnn(C56CC(C5)C6)c4)c(F)c3C)c2c1] | 4-(4-(2-((1-(bicyclo [1.1.1] pentan-1-yl)-1H-pyrazol-4-yl)amino)-2-oxoethyl)-3,5-difluoro-2-methyl-phenoxy)-N-methyl-quinoline-6-carboxamide | (300 MHz, DMSO-$d_6$) δ 10.39 (s, 1H), 8.95-8.81 (m, 3H), 8.31 (dd, J = 8.8, 2.0 Hz, 1H), 8.15 (d, J = 8.9 Hz, 1H), 7.89 (s, 1H), 7.47 (s, 1H), 7.27 (dd, J = 9.8, 1.9 Hz, 1H), 6.70 (d, J = 5.4 Hz, 1H), 3.76 (s, 2H), 2.87 (d, J = 4.4 Hz, 3H), 2.61 (s, 1H), 2.20 (s, 6H), 2.06 (s, 3H) | 518.1 (M + H)$^+$ |

-continued

| No. | Structure | Name | $^1$H NMR | Observed m/z |
|---|---|---|---|---|
| 558 | 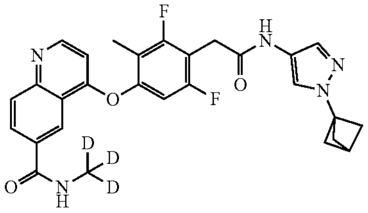 [SMILES: [2H]C([2H])([2H])NC(=O)c1ccc2nccc(Oc3cc(F)c(CC(=O)Nc4cnn(C56CC(C5)C6)c4)c(F)c3C)c2c1] | 4-(4-(2-((1-(bicyclo [1.1.1] pentan-1-yl)-1H-pyrazol-4-yl)amino)-2-oxoethyl)-3,5-difluoro-2-methyl-phenoxy)-N-(methyl-$d_3$) quinoline-6-carboxamide | (300 MHz, DMSO-$d_6$) δ 10.39 (s, 1H), 9.04-8.96 (m, 3H), 8.44 (dd, J = 8.9, 2.0 Hz, 1H), 8.27-8.20 (m, 1H), 7.88 (s, 1H), 7.48 (s, 1H), 7.36-7.24 (m, 1H), 6.90 (d, J = 5.9 Hz, 1H), 3.77 (s, 2H), 2.60 (s, 1H), 2.20 (s, 6H), 2.07 (s, 3H) | 521.0 $(M + H)^+$ |
| 559 | 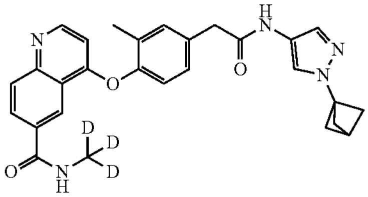 [SMILES: [2H]C([2H])([2H])NC(=O)c1ccc2nccc(Oc3ccc(CC(=O)Nc4cnn(C56CC(C5)C6)c4)cc3C)c2c1] | 4-(4-(2-((1-(bicyclo [1.1.1] pentan-1-yl)-1H-pyrazol-4-yl)amino)-2-oxoethyl)-2-methyl-phenoxy)-N-(methyl-$d_3$) quinoline-6-carboxamide | (400 MHz, DMSO-$d_6$) δ 10.28 (s, 1H), 8.90 (d, J = 1.9 Hz, 1H), 8.79 (s, 1H), 8.72 (d, J = 5.2 Hz, 1H), 8.24 (dd, J = 8.8, 2.0 Hz, 1H), 8.08 (d, J = 8.8 Hz, 1H), 7.91 (s, 1H), 7.46 (s, 1H), 7.38 (d, J = 2.1 Hz, 1H), 7.31 (dd, J = 8.3, 2.2 Hz, 1H), 7.22 (d, J = 8.3 Hz, 1H), 6.44 (d, J = 5.1 Hz, 1H), 3.63 (s, 2H), 2.60 (s, 1H), 2.20 (s, 6H), 2.13 (s, 3H) | 485.2 $(M + H)^+$ |
| 563 | 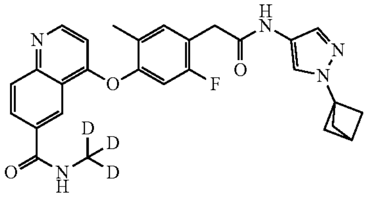 [SMILES: [2H]C([2H])([2H])NC(=O)c1ccc2nccc(Oc3cc(F)c(CC(=O)Nc4cnn(C56CC(C5)C6)c4)cc3C)c2c1] | 4-(4-(2-((1-(bicyclo [1.1.1] pentan-1-yl)-1H-pyrazol-4-yl)amino)-2-oxoethyl)-5-fluoro-2-methyl-phenoxy)-N-(methyl-$d_3$) quinoline-6-carboxamide | (400 MHz, DMSO-$d_6$) δ 10.30 (s, 1H), 8.89 (d, J = 1.9 Hz, 1H), 8.82-8.73 (m, 2H), 8.25 (dd, J = 8.8, 2.0 Hz, 1H), 8.10 (d, J = 8.8 Hz, 1H), 7.90 (s, 1H), 7.49-7.42 (m, 2H), 7.26 (d, J = 10.0 Hz, 1H), 6.54 (d, J = 5.2 Hz, 1H), 3.70 (s, 2H), 2.61 (s, 1H), 2.20 (s, 6H), 2.11 (s, 3H) | 503.2 $(M + H)^+$ |
| 587 | 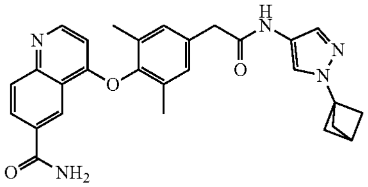 [SMILES: Cc1cc(CC(=O)Nc2cnn(C34CC(C3)C4)c2)cc(C)c1Oc1ccnc2ccc(C(N)=O)cc12] | 4-(4-(2-((1-(bicyclo [1.1.1] pentan-1-yl)-1H-pyrazol-4-yl)amino)-2-oxoethyl)-2,6-dimethyl-phenoxy) quinoline-6-carboxamide | (300 MHz, DMSO-$d_6$) δ 10.26 (s, 1H), 8.99 (d, J = 2.0 Hz, 1H), 8.70 (d, J = 5.1 Hz, 1H), 8.36 (s, 1H), 8.27 (dd, J = 8.8, 2.0 Hz, 1H), 8.08 (d, J = 8.9 Hz, 1H), 7.91 (s, 1H), 7.60 (s, 1H), 7.46 (s, 1H), 7.20 (s, 2H), 6.33 (d, J = 5.1 Hz, 1H), 3.59 (s, 2H), 2.60 (s, 1H), 2.20 (s, 6H), 2.08 (s, 6H) | 482.1 $(M + H)^+$ |
| 588 | 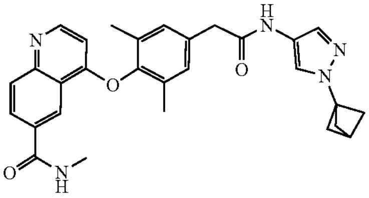 [SMILES: CNC(=O)c1ccc2nccc(Oc3c(C)cc(CC(=O)Nc4cnn(C56CC(C5)C6)c4)cc3C)c2c1] | 4-(4-(2-((1-(bicyclo [1.1.1] pentan-1-yl)-1H-pyrazol-4-yl)amino)-2-oxoethyl)-2,6-dimethyl-phenoxy)-N-methyl-quinoline-6-carboxamide | (300 MHz, DMSO-d6) δ 10.26 (s, 1H), 8.95 (d, J = 2.0 Hz, 1H), 8.82 (d, J = 4.7 Hz, 1H), 8.70 (d, J = 5.2 Hz, 1H), 8.24 (dd, J = 8.8, 2.0 Hz, 1H), 8.09 (d, J = 8.9 Hz, 1H), 7.91 (d, J = 0.7 Hz, 1H), 7.47 (d, J = 0.7 Hz, 1H), 7.20 (s, 2H), 6.33 (d, J = 5.1 Hz, 1H), 3.59 (s, 2H), 2.87 (d, J = 4.5 Hz, 3H), 2.60 (s, 1H), 2.20 (s, 6H), 2.08 (s, 6H) | 496.0 $(M + H)^+$ |

-continued

| No. | Structure | Name | $^1H$ NMR | Observed m/z |
| --- | --- | --- | --- | --- |
| 589 | 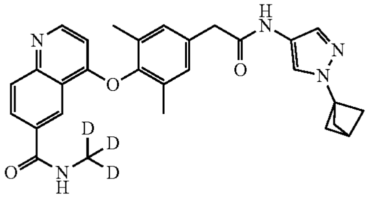 [SMILES: [2H]C([2H])([2H])NC(=O)c1ccc2nccc(Oc3c(C)cc(CC(=O)Nc4cnn(C56CC(C5)C6)c4)cc3C)c2c1] | 4-(4-(2-((1-(bicyclo[1.1.1]pentan-1-yl)-1H-pyrazol-4-yl)amino)-2-oxoethyl)-2,6-dimethyl-phenoxy)-N-(methyl-$d_3$)quinoline-6-carboxamide | 400 MHz, DMSO-$d_6$) δ 10.26 (s, 1H), 9.07 (d, J = 2.0 Hz, 1H), 8.99-8.88 (m, 2H), 8.51-8.42 (m, 1H), 8.23 (d, J = 8.8 Hz, 1H), 7.90 (s, 1H), 7.46 (s, 1H), 7.24 (s, 2H), 6.71-6.58 (m, 1H), 3.61 (s, 2H), 2.60 (s, 1H), 2.20 (s, 6H), 2.10 (s, 6H) | 499.1 $(M + H)^+$ |
| 590 | 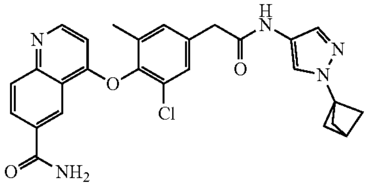 [SMILES: Cc1cc(CC(=O)Nc2cnn(C34CC(C3)C4)c2)cc(Cl)c1Oc1ccnc2ccc(C(N)=O)cc12] | 4-(4-(2-((1-(bicyclo[1.1.1]pentan-1-yl)-1H-pyrazol-4-yl)amino)-2-oxoethyl)-2-chloro-6-methyl-phenoxy)quinoline-6-carboxamide | (300 MHz, DMSO-$d_6$) δ 10.30 (s, 1H), 8.98 (d, J = 2.0 Hz, 1H), 8.74 (d, J = 5.2 Hz, 1H), 8.44-8.34 (m, 1H), 8.30 (dd, J = 8.8, 2.0 Hz, 1H), 8.10 (d, J = 8.8 Hz, 1H), 7.92 (d, J = 0.7 Hz, 1H), 7.62 (s, 1H), 7.50-7.47 (m, 2H), 7.40-7.32 (m, 1H), 6.41 (d, J = 5.2 Hz, 1H), 3.66 (s, 2H), 2.60 (s, 1H), 2.20 (s, 6H), 2.17 (s, 3H) | 502.2 $(M + H)^+$ |
| 591 | 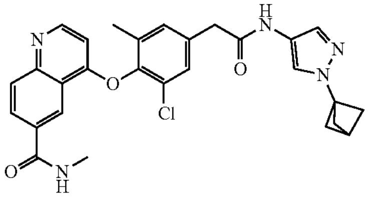 [SMILES: CNC(=O)c1ccc2nccc(Oc3c(C)cc(CC(=O)Nc4cnn(C56CC(C5)C6)c4)cc3Cl)c2c1] | 4-(4-(2-((1-(bicyclo[1.1.1]pentan-1-yl)-1H-pyrazol-4-yl)amino)-2-oxoethyl)-2-chloro-6-methyl-phenoxy)-N-methyl-quinoline-6-carboxamide | (300 MHz, DMSO-$d_6$) δ 10.31 (s, 1H), 8.93 (d, J = 2.0 Hz, 1H), 8.85-8.84 (m, 1H), 8.73 (d, J = 5.1 Hz, 1H), 8.26 (dd, J = 8.8, 2.0 Hz, 1H), 8.11 (d, J = 8.8 Hz, 1H), 7.92 (s, 1H), 7.53-7.45 (m, 2H), 7.40-7.33 (m, 1H), 6.41 (d, J = 5.1 Hz, 1H), 3.67 (s, 2H), 2.87 (d, J = 4.5 Hz, 3H), 2.60 (s, 1H), 2.20 (s, 6H), 2.16 (s, 3H) | 516.3 $(M + H)^+$ |
| 592 | 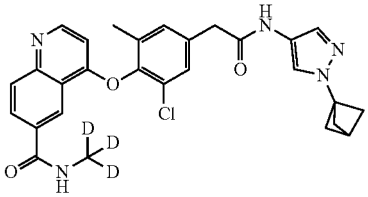 [SMILES: [2H]C([2H])([2H])NC(=O)c1ccc2nccc(Oc3c(C)cc(CC(=O)Nc4cnn(C56CC(C5)C6)c4)cc3Cl)c2c1] | 4-(4-(2-((1-(bicyclo[1.1.1]pentan-1-yl)-1H-pyrazol-4-yl)amino)-2-oxoethyl)-2-chloro-6-methyl-phenoxy)-N-(methyl-$d_3$)quinoline-6-carboxamide | (300 MHz, DMSO-$d_6$) δ 10.31 (s, 1H), 8.93 (d, J = 2.0 Hz, 1H), 8.82 (s, 1H), 8.73 (d, J = 5.1 Hz, 1H), 8.26 (dd, J = 8.8, 2.0 Hz, 1H), 8.11 (d, J = 8.8 Hz, 1H), 7.92 (s, 1H), 7.53-7.45 (m, 2H), 7.40-7.33 (m, 1H), 6.41 (d, J = 5.1 Hz, 1H), 3.67 (s, 2H), 2.60 (s, 1H), 2.20 (s, 6H), 2.16 (s, 3H) | 519.3 $(M + H)^+$ |
| 622 | 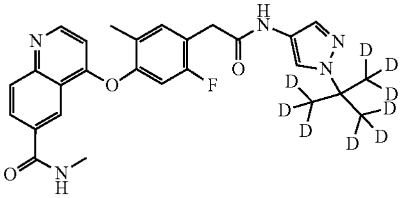 [SMILES: [2H]C([2H])([2H])C(n1cc(NC(=O)Cc2cc(C)c(Oc3ccnc4ccc(C(=O)NC)cc34)cc2F)cn1)(C([2H])([2H])[2H])C([2H])([2H])[2H]] | 4-(5-fluoro-2-methyl-4-(2-((1-(2-(methyl-$d_3$)propan-2-yl-1,1,1,3,3,3-$d_6$)-1H-pyrazol-4-yl)amino)-2-oxoethyl)phenoxy)-N-methyl-quinoline-6-carboxamide | (300 MHz, DMSO-$d_6$) δ 10.22 (s, 1H), 8.89 (d, J = 2.0 Hz, 1H), 8.82 (d, J = 4.8 Hz, 1H), 8.76 (d, J = 5.1 Hz, 1H), 8.25 (dd, J = 8.8, 2.0 Hz, 1H), 8.10 (d, J = 8.8 Hz, 1H), 7.94 (s, 1H), 7.50-7.41 (m, 2H), 7.26 (d, J = 10.0 Hz, 1H), 6.54 (d, J = 5.2 Hz, 1H), 3.69 (s, 2H), 2.87 (d, J = 4.6 Hz, 3H), 2.11 (s, 3H) | 499.3 $(M + H)^+$ |

Example 39—Synthesis of N-(1-(tert-butyl)-1H-pyrazol-4-yl)-2-(2-fluoro-4-((6-((methylsulfonyl)methyl)quinolin-4-yl)oxy)phenyl)acetamide (Compound 75); Prepared According to General Scheme 8

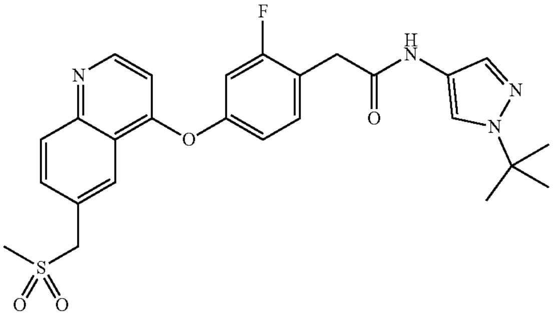 [SMILES: CC(C)(C)n1cc(NC(=O)Cc2ccc(Oc3ccnc4ccc(CS(C)(=O)=O)cc34)cc2F)cn1]

Part I—Synthesis of methyl(4-nitrobenzyl)sulfane

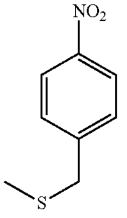

Sodium thiomethoxide (24.33 g, 347 mmol, 1.50 equiv.) was added to a solution of 1-(bromomethyl)-4-nitrobenzene (50.0 g, 231 mmol, 1.00 equiv.) in EtOH (500 mL) and the mixture was stirred at room temperature overnight. Subsequently, water was added, and the product was extracted with EtOAc. The organic phase was then washed with water, dried over $MgSO_4$, and the solvent was removed under reduced pressure. The crude product was purified by column chromatography (petroleum ether/EtOAc 100:1). The title compound was obtained as a light-yellow oil (29.1 g, 65%).

Part II—Synthesis of 4-((methylthio)methyl)aniline

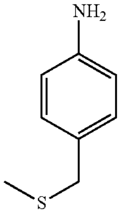

A solution of methyl(4-nitrobenzyl)sulfane (28.0 g, 153 mmol, 1.00 equiv.) and Pd/C (2.8 g, 10% w/w) in MeOH (280 mL) was heated to 30° C. overnight under an atmosphere of hydrogen. Subsequently, the solution was filtered, and the residue was washed with MeOH. The solvent was removed under reduced pressure and the crude product was purified by column chromatography (petroleum ether/EtOAc 2:1). The title compound was obtained as a light-yellow oil (20 g, 77%).

Part III—Synthesis of 2,2-dimethyl-5-(((4-((methylthio)methyl)phenyl)amino)methylene)-1,3-dioxane-4,6-dione

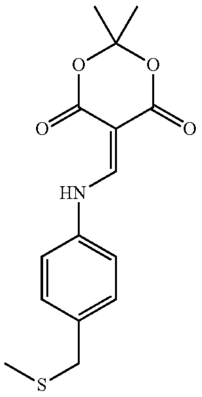 [SMILES: CSCc1ccc(NC=C2C(=O)OC(C)(C)OC2=O)cc1]

A solution of 4-((methylthio)methyl)aniline (25.0 g, 163 mmol, 1.00 equiv.), triethyl orthoformate (29.0 g, 196 mmol, 1.20 equiv.) and Meldrum's acid (28.22 g, 196 mmol, 1.20 equiv.) in EtOH (250 mL) was heated to 80° C. for 2 h under an inert atmosphere of nitrogen. After cooling to room temperature, the precipitated product was filtered off, washed with EtOH, and dried under reduced pressure. The crude title compound (35 g) was used in the next reaction without further purification.

Part IV—Synthesis of 6-((methylthio)methyl)quinolin-4-ol

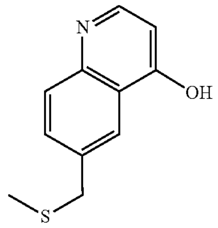

A solution of 2,2-dimethyl-5-(((4-((methylthio)methyl)phenyl)amino)methylene)-1,3-dioxane-4,6-dione (37.0 g, 120 mmol, 1.00 equiv.) in diphenyl ether (370 mL) was heated to 150° C. overnight under an inert atmosphere of nitrogen. Subsequently, water (100 mL) was added, and the organic phase was separated. The aqueous phase was extracted with MTBE (3×100 mL) and the solvent of the combined organic phases was removed under reduced pressure. The crude title compound (1.6 g) was used in the next reaction without further purification.

Part V—Synthesis of 4-chloro-6-((methylthio)methyl)quinoline

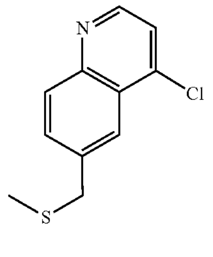

A solution of 6-((methylthio)methyl)quinolin-4-ol (1.5 g, 7.31 mmol, 1.00 equiv.) in phosphoryl chloride (15 mL) was heated to 100° C. for 2 h under an inert atmosphere of nitrogen. Subsequently, the solvent was removed under reduced pressure and the crude product was purified by reversed-phase flash chromatography (column: C18 silica gel; mobile phase A: water, mobile phase B: ACN, gradient: 10-50% B in 40 min; wavelength: 210 nm). The title compound was obtained as a light-yellow solid (680 mg, 1.9% over 3 steps).

Part VI—Synthesis of N-(1-(tert-butyl)-1H-pyrazol-4-yl)-2-(2-fluoro-4-((6-((methylthio)methyl)quinolin-4-yl)oxy)phenyl)acetamide

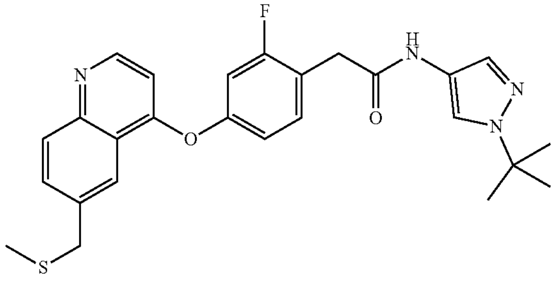 [SMILES: CSCc1ccc2nccc(Oc3ccc(CC(=O)Nc4cnn(C(C)(C)C)c4)c(F)c3)c2c1]

DMAP (491.5 mg, 4.02 mmol, 1.50 equiv.) and N-(1-(tert-butyl)-1H-pyrazol-4-yl)-2-(2-fluoro-4-hydroxyphenyl) acetamide (859.5 mg, 2.95 mmol, 1.10 equiv., can be synthesized according to the synthesis described in Part II of Example 9) were added to a solution of 4-chloro-6-((methylthio)methyl)quinoline (600 mg, 2.68 mmol, 1.00 equiv.) in chlorobenzene (6 mL) under an inert atmosphere of nitrogen. Subsequently, the mixture was heated to 150° C. for 1 h. The solvent was removed under reduced pressure and the crude product was purified by reversed-phase flash chromatography (column: C18 silica gel; mobile phase A: water, mobile phase B: ACN, gradient: 10-50% B in 40 min; wavelength: 210 nm). The title compound was obtained as a white solid (610 mg, 45%).

Part VII—Synthesis of N-(1-(tert-butyl)-1H-pyrazol-4-yl)-2-(2-fluoro-4-((6-((methylsulfonyl)methyl)quinolin-4-yl)oxy)phenyl)acetamide (Compound 75)

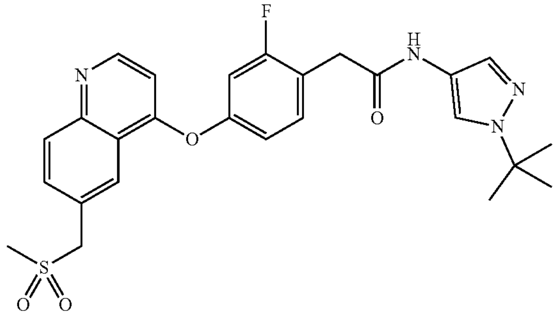 [SMILES: CC(C)(C)n1cc(NC(=O)Cc2ccc(Oc3ccnc4ccc(CS(C)(=O)=O)cc34)cc2F)cn1]

A solution of N-(1-(tert-butyl)-1H-pyrazol-4-yl)-2-(2-fluoro-4-((6-((methylthio)methyl)quinolin-4-yl)oxy)phenyl)acetamide (100 mg, 0.209 mmol, 1.00 equiv.) and oxone (105.4 mg, 0.627 mmol, 3.00 equiv.) in water/MeOH (1:1, 2 mL) was stirred at room temperature for 1 h. Subsequently, the crude product was purified by reversed-phase flash chromatography (column: C18 silica gel; mobile phase A: water, mobile phase B: ACN, gradient: 10-50% B in 40 min; wavelength: 210 nm). The title compound was obtained as a white solid (60.7 mg, 57%). LCMS (ESI) calculated for $C_{26}H_{27}FN_4NaO_4S$ $(M+H)^+$: 533.2, found: 533.2. $^1H$ NMR (300 MHz, DMSO-$d_6$) δ 10.23 (s, 1H), 8.75 (d, J=5.1 Hz, 1H), 8.37 (d, J=2.0 Hz, 1H), 8.07 (d, J=8.7 Hz, 1H), 7.94 (d, J=0.7 Hz, 1H), 7.85 (dd, J=8.7, 2.0 Hz, 1H), 7.53 (t, J=8.5 Hz, 1H), 7.45 (d, J=0.7 Hz, 1H), 7.32 (dd, J=10.5, 2.4 Hz, 1H), 7.16 (dd, J=8.5, 2.4 Hz, 1H), 6.71 (d, J=5.1 Hz, 1H), 4.79 (s, 2H), 3.70 (s, 2H), 2.97 (s, 3H), 1.49 (s, 9H).

Example 40—Synthesis of N-(1-(tert-butyl)-1H-pyrazol-4-yl)-2-(2-fluoro-5-methyl-4-((6-(piperidin-4-ylmethyl)quinolin-4-yl)oxy)phenyl)acetamide (Compound 408); Prepared According to General Scheme 22

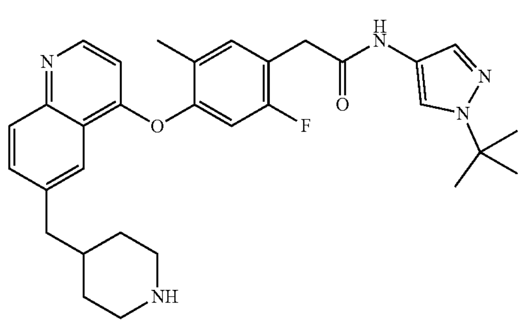 [SMILES: Cc1cc(CC(=O)Nc2cnn(C(C)(C)C)c2)c(F)cc1Oc1ccnc2ccc(CC3CCNCC3)cc12]

Part I—Synthesis of tert-butyl 4-((4-chloroquinolin-6-yl)methyl)piperidine-1-carboxylate

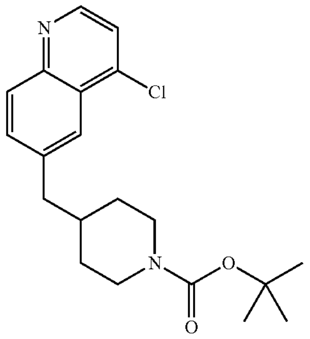 [SMILES: CC(C)(C)OC(=O)N1CCC(Cc2ccc3nccc(Cl)c3c2)CC1]

A solution of 6-bromo-4-chloroquinoline (1.00 g, 4.12 mmol, 1.00 equiv.), tert-butyl 4-((4,4,5,5-tetramethyl-1,3,2-dioxaborolan-2-yl)methyl)piperidine-1-carboxylate (1.61 g, 4.95 mmol, 1.20 equiv.), Pd(dppf)$Cl_2$ (0.30 g, 0.412 mmol, 0.10 equiv.), and $K_3PO_4$ (1.75 g, 8.25 mmol, 2.00 equiv.) in 1,4-dioxane was heated to 90° C. overnight under an inert atmosphere of nitrogen. The solvent was removed under reduced pressure and the crude product was purified by column chromatography (petroleum ether/EtOAc 5:1). The title compound was obtained as a yellow solid (1.3 g, 87%).

Part II—Synthesis of tert-butyl 4-((4-(4-(2-((1-(tert-butyl)-1H-pyrazol-4-yl)amino)-2-oxoethyl)-5-fluoro-2-methylphenoxy)quinolin-6-yl)methyl)piperidine-1-carboxylate

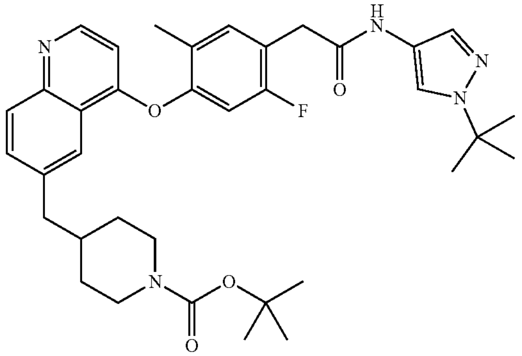 [SMILES: Cc1cc(CC(=O)Nc2cnn(C(C)(C)C)c2)c(F)cc1Oc1ccnc2ccc(CC3CCN(C(=O)OC(C)(C)C)CC3)cc12]

A solution of tert-butyl 4-((4-chloroquinolin-6-yl)methyl)piperidine-1-carboxylate (355 mg, 0.983 mmol, 1.50 equiv.), N-(1-(tert-butyl)-1H-pyrazol-4-yl)-2-(2-fluoro-4-hydroxy-5-methylphenyl)acetamide (200 mg, 0.655 mmol, 1.00 equiv., can be synthesized according to Part IV of Example 37), and $Cs_2CO_3$ (640 mg, 1.97 mmol, 3.00 equiv.) in NMP (4 mL) was heated to 130° C. for 3 h. Subsequently, the crude product was purified by reversed-phase flash chromatography (column: C18 silica gel; mobile phase A: water, mobile phase B: ACN, gradient: 10-50% B in 10 min; wavelength: 210 nm). The title compound was obtained as an off-white solid (103 mg, 24%).

Part III—Synthesis of N-(1-(tert-butyl)-1H-pyrazol-4-yl)-2-(2-fluoro-5-methyl-4-((6-(piperidin-4-ylmethyl)quinolin-4-yl)oxy)phenyl)acetamide (Compound 408)

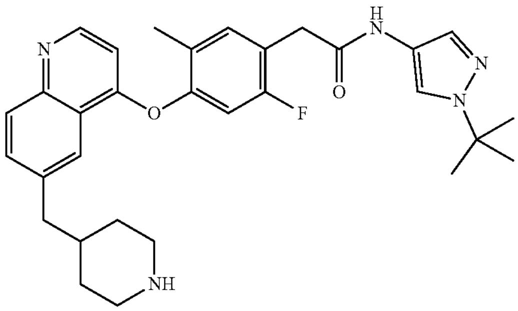

A solution of HCl in 1,4-dioxane (4 M, 2 mL) was added to a solution of tert-butyl 4-((4-(4-(2-((1-(tert-butyl)-1H-pyrazol-4-yl)amino)-2-oxoethyl)-5-fluoro-2-methylphenoxy)quinolin-6-yl)methyl)piperidine-1-carboxylate (200 mg, 0.318 mmol, 1.00 equiv.) in DCM (2 mL) and the mixture was stirred at room temperature for 30 min. Subsequently, the solvent was removed under reduced pressure. Water was added and the pH of the solution was brought to 8 through addition of a saturated, aqueous solution of $NaHCO_3$. The crude product was purified by reversed-phase flash chromatography (column: C18 silica gel; mobile phase A: water, mobile phase B: ACN, gradient: 10-50% B in 40 min; wavelength: 210 nm). The title compound was obtained as an off-white solid (102.2 mg, 60%). LCMS (ESI) calculated for $C_{31}H_{37}FN_5O_2(M+H)^+$: 530.3, found: 530.2.

Example 41—Preparation of Additional 6-Alkyl Substituted Quinoline and Quinazoline Compounds Compounds in the table below were prepared based on experimental procedures described in Example 40 and the detailed description.

| No. | Structure | Name | $^1$H NMR | Observed m/z |
|---|---|---|---|---|
| 252 | 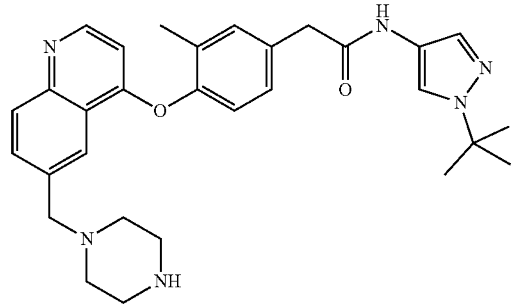 [SMILES: Cc1cc(CC(=O)Nc2cnn(C(C)(C)C)c2)ccc1Oc1ccnc2ccc(CN3CCNCC3)cc12] | N-(1-(tert-butyl)-1H-pyrazol-4-yl)-2-(3-methyl-4-((6-(piperazin-1-ylmethyl)quinolin-4-yl)oxy)phenyl) acetamide | (400 MHz, DMSO-$d_6$) δ 10.27 (s, 1H), 8.63 (d, J = 5.1 Hz, 1H), 8.26 (d, J = 1.9 Hz, 1H), 8.01 (d, J = 8.7 Hz, 1H), 7.95 (s, 1H), 7.81 (dd, J = 8.7, 1.9 Hz, 1H), 7.47 (s, 1H), 7.37 (d, J = 2.2 Hz, 1H), 7.29 (dd, J = 8.3, 2.2 Hz, 1H), 7.17 (d, J = 8.2 Hz, 1H), 6.40 (d, J = 5.1 Hz, 1H), 3.78 (s, 2H), 3.61 (s, 2H), 3.06 (t, J = 4.7 Hz, 4H), 2.67-2.57 (m, 4H), 2.11 (s, 3H), 1.49 (s, 9H) | 513.2 $(M + H)^+$ |
| 253 | 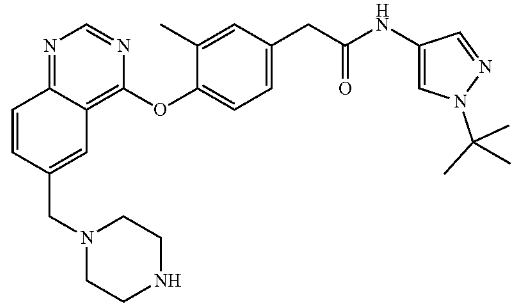 [SMILES: Cc1cc(CC(=O)Nc2cnn(C(C)(C)C)c2)ccc1Oc1ncnc2ccc(CN3CCNCC3)cc12] | N-(1-(tert-butyl)-1H-pyrazol-4-yl)-2-(3-methyl-4-((6-(piperazin-1-ylmethyl) quinazolin-4-yl)oxy)phenyl) acetamide | (400 MHz, DMSO-$d_6$) δ 10.22 (s, 1H), 8.66 (s, 1H), 8.27 (d, J = 1.8 Hz, 1H), 8.01 (dd, J = 8.6, 1.8 Hz, 1H), 7.97-7.95 (m, 2H), 7.45 (s, 1H), 7.30 (d, J = 2.0 Hz, 1H), 7.28-7.17 (m, 2H), 3.69 (s, 2H), 3.58 (s, 2H), 2.71 (t, J = 4.7 Hz, 4H), 2.37 (s, 4H), 2.08 (s, 3H), 1.49 (s, 9H) | 514.2 $(M + H)^+$ |
| 302 | 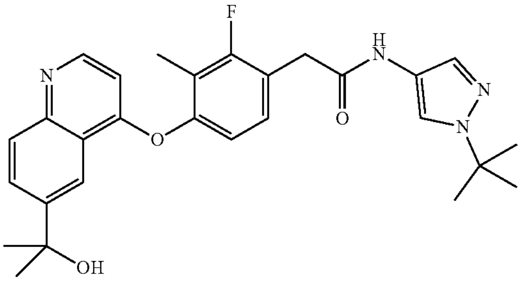 [SMILES: Cc1c(Oc2ccnc3ccc(C(C)(C)O)cc23)ccc(CC(=O)Nc2cnn(C(C)(C)C)c2)c1F] | N-(1-(tert-butyl)-1H-pyrazol-4-yl)-2-(2-fluoro-4-((6-(2-hydroxypropan-2-yl)quinolin-4-yl)oxy)-3-methylphenyl) acetamide | (300 MHz, DMSO-$d_6$) δ 10.23 (s, 1H), 8.63 (d, J = 5.1 Hz, 1H), 8.44 (d, J = 1.9 Hz, 1H), 8.03-7.86 (m, 3H), 7.45 (s, 1H), 7.36 (t, J = 8.3 Hz, 1H), 7.08 (d, J = 8.4 Hz, 1H), 6.45 (d, J = 5.1 Hz, 1H), 5.34 (s, 1H), 3.70 (s, 2H), 2.06 (s, 3H), 1.55 (s, 6H), 1.49 (s, 9H) | 491.1 $(M + H)^+$ |
| 303 | 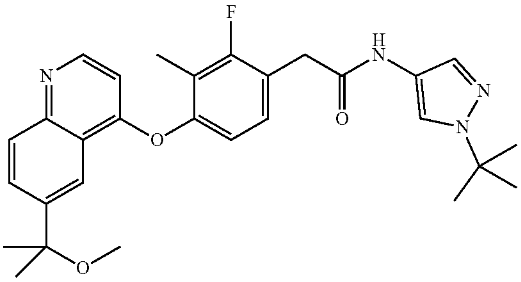 [SMILES: COC(C)(C)c1ccc2nccc(Oc3ccc(CC(=O)Nc4cnn(C(C)(C)C)c4)c(F)c3C)c2c1] | N-(1-(tert-butyl)-1H-pyrazol-4-yl)-2-(2-fluoro-4-((6-(2-methoxypropan-2-yl)quinolin-4-yl)oxy)-3-methylphenyl) acetamide | (300 MHz, DMSO-$d_6$) δ 10.23 (s, 1H), 8.67 (d, J = 5.1 Hz, 1H), 8.28 (d, J = 2.0 Hz, 1H), 8.05 (d, J = 8.9 Hz, 1H), 7.98 - 7.85 (m, 2H), 7.46 (s, 1H), 7.37 (t, J = 8.4 Hz, 1H), 7.11 (d, J = 8.3 Hz, 1H), 6.49 (d, J = 5.1 Hz, 1H), 3.71 (s, 2H), 3.07 (s, 3H), 2.07 (d, J = 1.9 Hz, 3H), 1.59 (s, 6H), 1.49 (s, 9H) | 505.1 $(M + H)^+$ |

-continued

| No. | Structure | Name | $^1$H NMR | Observed m/z |
|---|---|---|---|---|
| 304 | 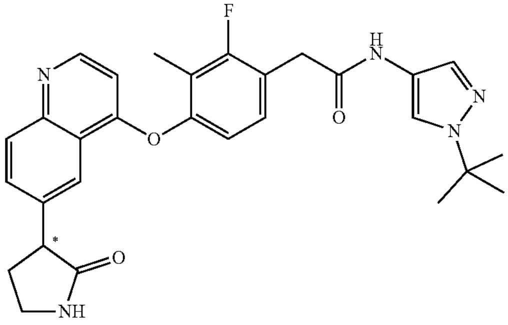 [SMILES: Cc1c(Oc2ccnc3ccc(C4CCNC4=O)cc23)ccc(CC(=O)Nc2cnn(C(C)(C)C)c2)c1F] enantiomer 1 (retention time: 2.02 min, column: CHIRALPAK IA-3, 4.6 × 50 mm, 3 μm; mobile phase A: hexane/DCM (3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-3-methyl-4-((6-(2-oxopyrrolidin-3-yl)quinolin-4-yl)oxy)phenyl) acetamide | (400 MHz, DMSO-$d_6$) δ 10.23 (s, 1H), 8.66 (d, J = 5.1 Hz, 1H), 8.22 (d, J = 2.0 Hz, 1H), 8.02 (d, J = 8.7 Hz, 1H), 7.96-7.94 (m, 2H), 7.73 (dd, J = 8.7, 2.0 Hz, 1H), 7.46 (s, 1H), 7.37 (t, J = 8.4 Hz, 1H), 7.09 (d, J = 8.3 Hz, 1H), 6.48 (d, J = 5.1 Hz, 1H), 3.89 (t, J = 9.2 Hz, 1H), 3.71 (s, 2H), 3.39 (d, J = 5.3 Hz, 2H), 2.61 (dd, J = 6.9, 3.4 Hz, 1H), 2.23 (dq, J = 12.6, 8.7 Hz, 1H), 2.07 (d, J = 1.9 Hz, 3H), 1.49 (s, 9H) | 514.2 $(M-H)^-$ |
| 305 | 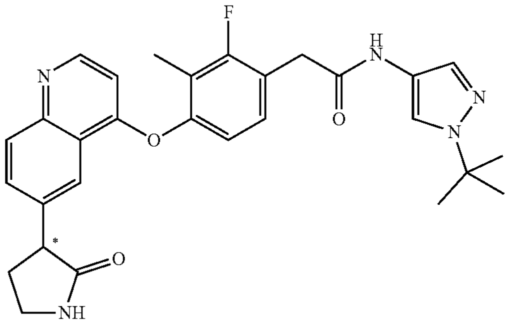 [SMILES: Cc1c(Oc2ccnc3ccc(C4CCNC4=O)cc23)ccc(CC(=O)Nc2cnn(C(C)(C)C)c2)c1F] enantiomer 2 (retention time: 4.92 min, column: CHIRALPAK IA-3, 4.6 × 50 mm, 3 μm; mobile phase A: hexane/DCM (3:1, 0.1% DEA), mobile phase B: EtOH, isocratic separation with 20% B, flow rate: 1.0 mL/min, wavelength: 254 nm) | N-(1-(tert-butyl)-1H-pyrazol-4-yl)-2-(2-fluoro-3-methyl-4-((6-(2-oxopyrrolidin-3-yl)quinolin-4-yl)oxy)phenyl) acetamide | (400 MHz, DMSO-$d_6$) δ 10.23 (s, 1H), 8.66 (d, J = 5.1 Hz, 1H), 8.22 (d, J = 2.0 Hz, 1H), 8.02 (d, J = 8.7 Hz, 1H), 7.96-7.94 (m, 2H), 7.73 (dd, J = 8.7, 2.0 Hz, 1H), 7.46 (s, 1H), 7.37 (t, J = 8.4 Hz, 1H), 7.09 (d, J = 8.3 Hz, 1H), 6.48 (d, J = 5.1 Hz, 1H), 3.89 (t, J = 9.2 Hz, 1H), 3.71 (s, 2H), 3.39 (d, J = 5.3 Hz, 2H), 2.61 (dd, J = 6.9, 3.4 Hz, 1H), 2.23 (dq, J = 12.6, 8.7 Hz, 1H), 2.07 (d, J = 1.9 Hz, 3H), 1.49 (s, 9H) | 514.1 $(M-H)^-$ |
| 407 | 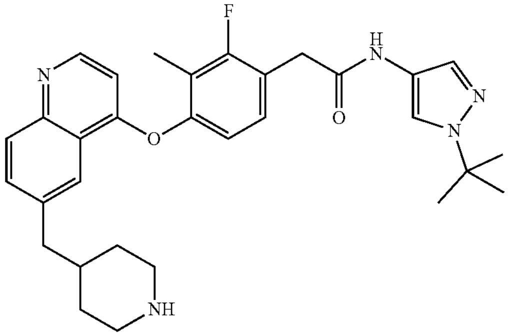 [SMILES: Cc1c(Oc2ccnc3ccc(CC4CCNCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(piperidin-4-ylmethyl) quinolin-4-yl)oxy)phenyl) acetamide | | 530.2 $(M+H)^+$ |

-continued

| No. | Structure | Name | $^1$H NMR | Observed m/z |
|---|---|---|---|---|
| 411 | 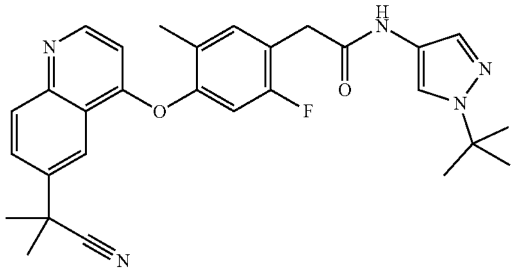 [SMILES: Cc1cc(CC(=O)Nc2cnn(C(C)(C)C)c2)c(F)cc1Oc1ccnc2ccc(C(C)(C)C#N)cc12] | N-(1-(tert-butyl)-1H-pyrazol-4-yl)-2-(4-((6-(2-cyanopropan-2-yl)quinolin-4-yl)oxy)-2-fluoro-5-methylphenyl) acetamide | | 500.5 (M + H)+ |
| 419 | 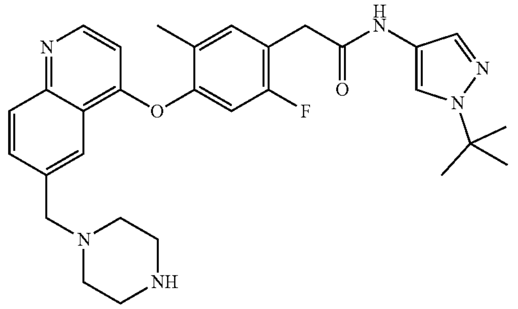 [SMILES: Cc1cc(CC(=O)Nc2cnn(C(C)(C)C)c2)c(F)cc1Oc1ccnc2ccc(CN3CCNCC3)cc12] | N-(1-(tert-butyl)-1H-pyrazol-4-yl)-2-(2-fluoro-5-methyl-4-((6-(piperazin-1-ylmethyl) quinolin-4-yl)oxy)phenyl) acetamide | | 531.3 (M + H)+ |
| 420 | 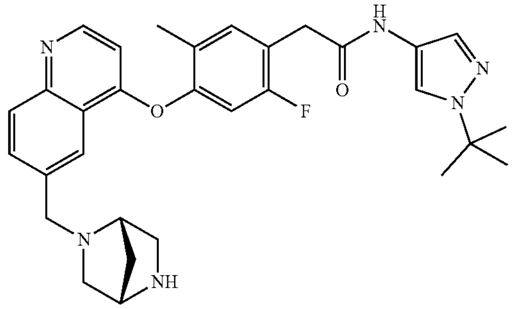 [SMILES: Cc1cc(CC(=O)Nc2cnn(C(C)(C)C)c2)c(F)cc1Oc1ccnc2ccc(CN3C[C@@H]4C[C@H]3CN4)cc12] | 2-(4-((6-(((1S,4S)-2,5-diazabicyclo[2.2.1] heptan-2-yl)methyl)quinolin-4-yl)oxy)-2-fluoro-5-methylphenyl)-N-(1-(tert-butyl)-1H-pyrazol-4-yl)acetamide | | 543.2 (M + H)+ |
| 421 | 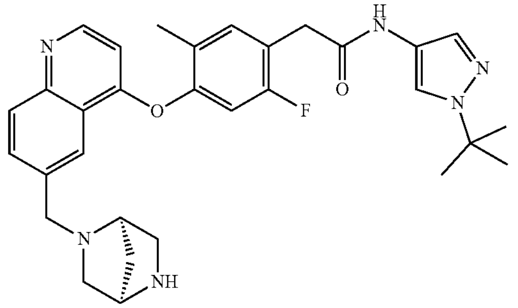 [SMILES: Cc1cc(CC(=O)Nc2cnn(C(C)(C)C)c2)c(F)cc1Oc1ccnc2ccc(CN3C[C@H]4C[C@@H]3CN4)cc12] | 2-(4-((6-(((1R,4R)-2,5-diazabicyclo[2.2.1] heptan-2-yl)methyl)quinolin-4-yl)oxy)-2-fluoro-5-methylphenyl)-N-(1-(tert-butyl)-1H-pyrazol-4-yl)acetamide | | 543.2 (M + H)+ |
| 422 | 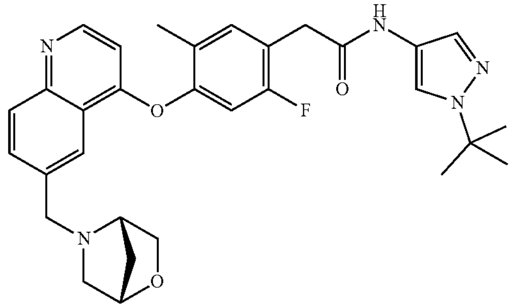 [SMILES: Cc1cc(CC(=O)Nc2cnn(C(C)(C)C)c2)c(F)cc1Oc1ccnc2ccc(CN3C[C@@H]4C[C@H]3CO4)cc12] | 2-(4-((6-(((1S,4S)-2-oxa-5-azabicyclo[2.2.1] heptan-5-yl)methyl)quinolin-4-yl)oxy)-2-fluoro-5-methylphenyl)-N-(1-(tert-butyl)-1H-pyrazol-4-yl)acetamide | | 544.2 (M + H)+ |

-continued

| No. | Structure | Name | ¹H NMR | Observed m/z |
|---|---|---|---|---|
| 423 | 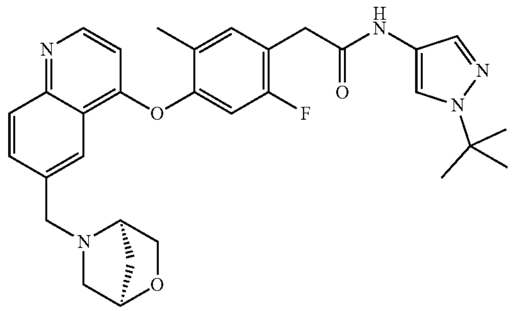 [SMILES: Cc1cc(CC(=O)Nc2cnn(C(C)(C)C)c2)c(F)cc1Oc1ccnc2ccc(CN3C[C@H]4C[C@@H]3CO4)cc12] | 2-(4-((6-(((1R,4R)-2-oxa-5-azabicyclo[2.2.1]heptan-5-yl)methyl)quinolin-4-yl)oxy)-2-fluoro-5-methylphenyl)-N-(1-(tert-butyl)-1H-pyrazol-4-yl)acetamide | | 544.2 (M + H)$^+$ |
| 433 | 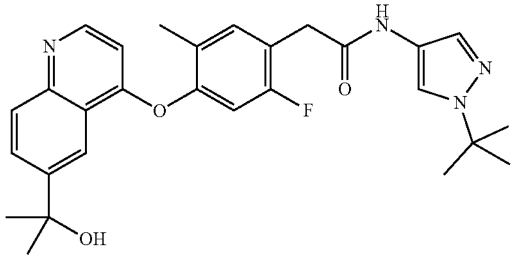 [SMILES: Cc1cc(CC(=O)Nc2cnn(C(C)(C)C)c2)c(F)cc1Oc1ccnc2ccc(C(C)(C)O)cc12] | N-(1-(tert-butyl)-1H-pyrazol-4-yl)-2-(2-fluoro-4-((6-(2-hydroxypropan-2-yl)quinolin-4-yl)oxy)-5-methylphenyl) acetamide | | 491.2 (M + H)$^+$ |
| 444 | 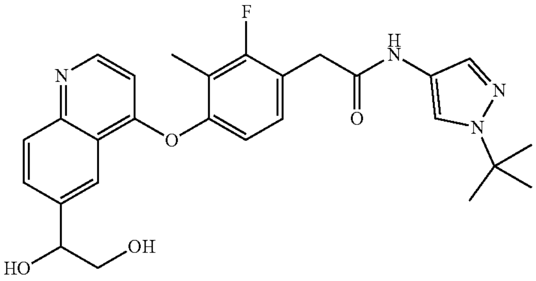 [SMILES: Cc1c(Oc2ccnc3ccc(C(O)CO)cc23)ccc(CC(=O)Nc2cnn(C(C)(C)C)c2)c1F] | N-(1-(tert-butyl)-1H-pyrazol-4-yl)-2-(4-((6-(1,2-dihydroxyethyl) quinolin-4-yl)oxy)-2-fluoro-3-methylphenyl) acetamide | | 493.1 (M + H)$^+$ |
| 560 | 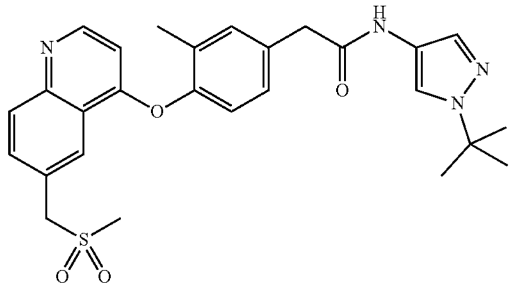 [SMILES: Cc1cc(CC(=O)Nc2cnn(C(C)(C)C)c2)ccc1Oc1ccnc2ccc(CS(C)(=O)=O)cc12] | N-(1-(tert-butyl)-1H-pyrazol-4-yl)-2-(3-methyl-4-((6-((methylsulfonyl) methyl)quinolin-4-yl)oxy)phenyl) acetamide | (300 MHz, DMSO-$d_6$) δ 10.24 (s, 1H), 8.68 (d, J = 5.2 Hz, 1H), 8.47 (s, 1H), 8.07 (d, J = 8.7 Hz, 1H), 7.96 (s, 1H), 7.85 (d, J = 8.8 Hz, 1H), 7.48 (s, 1H), 7.38 (s, 1H), 7.31 (d, J = 8.4 Hz, 1H), 7.21 (d, J = 8.2 Hz, 1H), 6.43 (d, J = 5.2 Hz, 1H), 4.81 (s, 2H), 3.62 (s, 2H), 3.00 (s, 3H), 2.10 (s, 3H), 1.48 (s, 9H) | 507.2 (M + H)$^+$ |
| 561 | 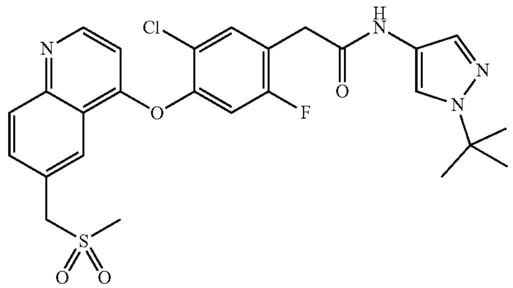 [SMILES: CC(C)(C)n1cc(NC(=O)Cc2cc(Cl)c(Oc3ccnc4ccc(CS(C)(=O)=O)cc34)cc2F)cn1] | N-(1-(tert-butyl)-1H-pyrazol-4-yl)-2-(5-chloro-2-fluoro-4-((6-((methylsulfonyl) methyl)quinolin-4-yl)oxy)phenyl) acetamide | (400 MHz, DMSO-$d_6$) δ 10.27 (s, 1H), 8.75 (d, J = 5.1 Hz, 1H), 8.42 (d, J = 2.0 Hz, 1H), 8.10 (d, J = 8.7 Hz, 1H), 7.95 (s, 1H), 7.87 (dd, J = 8.7, 2.0 Hz, 1H), 7.80 (d, J = 7.5 Hz, 1H), 7.63 (d, J = 9.7 Hz, 1H), 7.46 (s, 1H), 6.61 (d, J = 5.2 Hz, 1H), 4.82 (s, 2H), 3.76 (s, 2H), 2.99 (s, 3H), 1.49 (s, 9H) | 545.0 (M + H)$^+$ |

-continued

| No. | Structure | Name | $^1$H NMR | Observed m/z |
|---|---|---|---|---|
| 562 | 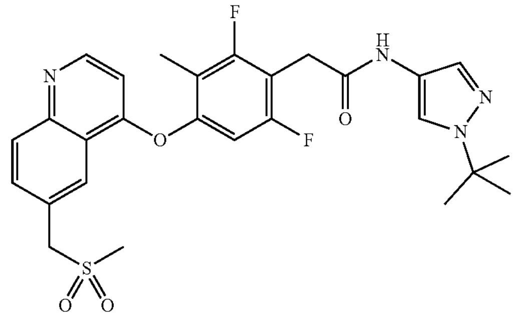 [SMILES: Cc1c(Oc2ccnc3ccc(CS(C)(=O)=O)cc23)cc(F)c(CC(=O)Nc2cnn(C(C)(C)C)c2)c1F] | N-(1-(tert-butyl)-1H-pyrazol-4-yl)-2-(2,6-difluoro-3-methyl-4-((6-((methylsulfonyl)methyl)quinolin-4-yl)oxy)phenyl)acetamide | (300 MHz, DMSO-$d_6$) δ 10.32 (s, 1H), 8.75 (d, J = 5.2 Hz, 1H), 8.44 (d, J = 2.0 Hz, 1H), 8.10 (d, J = 8.7 Hz, 1H), 7.95 (s, 1H), 7.93-7.83 (m, 1H), 7.47 (s, 1H), 7.24 (dd, J = 9.6, 1.9 Hz, 1H), 6.62 (d, J = 5.1 Hz, 1H), 4.81 (s, 2H), 3.74 (s, 2H), 3.00 (s, 3H), 2.06 (s, 3H), 1.49 (s, 9H) | 543.1 $(M + H)^+$ |
| 566 | 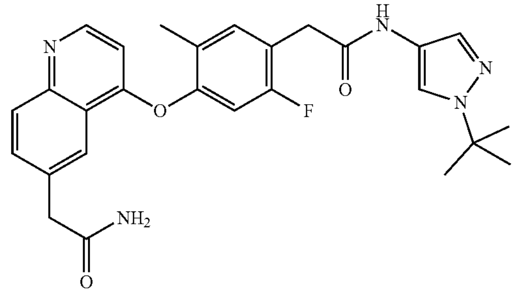 [SMILES: Cc1cc(CC(=O)Nc2cnn(C(C)(C)C)c2)c(F)cc1Oc1ccnc2ccc(CC(N)=O)cc12] | 2-(4-((6-(2-amino-2-oxoethyl)quinolin-4-yl)oxy)-2-fluoro-5-methylphenyl)-N-(1-(tert-butyl)-1H-pyrazol-4-yl)acetamide | (300 MHz, DMSO-$d_6$) δ 10.24 (s, 1H), 8.64 (d, J = 5.1 Hz, 1H), 8.23 (d, J = 2.0 Hz, 1H), 8.03-7.92 (m, 2H), 7.75 (dd, J = 8.6, 2.0 Hz, 1H), 7.64 (s, 1H), 7.46-7.42 (m, 2H), 7.22 (d, J = 10.1 Hz, 1H), 7.01 (s, 1H), 6.46 (d, J = 5.1 Hz, 1H), 3.68 (s, 2H), 3.65 (s, 2H), 2.09 (s, 3H), 1.49 (s, 9H) | 490.1 $(M + H)^+$ |
| 567 | 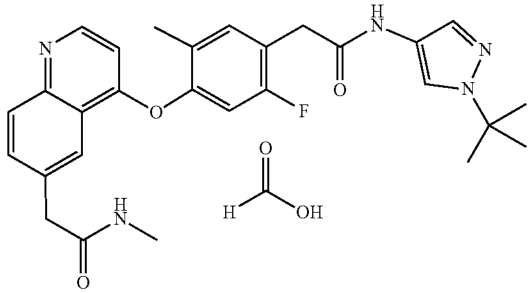 | N-(1-(tert-butyl)-1H-pyrazol-4-yl)-2-(2-fluoro-5-methyl-4-((6-(2-(methylamino)-2-oxoethyl)quinolin-4-yl)oxy)phenyl)acetamide formic acid salt | (400 MHz, DMSO-$d_6$) δ 10.21 (s, 1H), 8.64 (d, J = 5.1 Hz, 1H), 8.21 (d, J = 2.0 Hz, 1H), 8.08 (d, J = 4.9 Hz, 1H), 8.01-7.92 (m, 2H), 7.73 (dd, J = 8.7, 2.0 Hz, 1H), 7.48-7.40 (m, 2H), 7.20 (d, J = 10.0 Hz, 1H), 6.46 (d, J = 5.1 Hz, 1H), 6.03 (s, 1H), 3.67 (s, 2H), 3.66 (s, 2H), 2.60 (d, J = 4.6 Hz, 3H), 2.09 (s, 3H), 1.49 (s, 9H) | 504.2 $(M + H)^+$ |
| 568 | 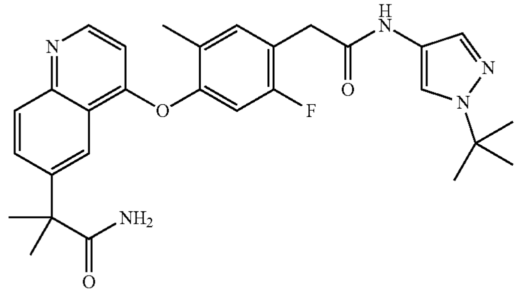 | 2-(4-(4-(2-((1-(tert-butyl)-1H-pyrazol-4-yl)amino)-2-oxoethyl)-5-fluoro-2-methylphenoxy)quinolin-6-yl)-2-methyl-propanamide | (400 MHz, DMSO-$d_6$) δ 10.21 (s, 1H), 8.65 (d, J = 5.1 Hz, 1H), 8.25 (d, J = 2.1 Hz, 1H), 7.99 (d, J = 9.0 Hz, 1H), 7.94 (d, J = 0.7 Hz, 1H), 7.80 (dd, J = 8.9, 2.2 Hz, 1H), 7.47-7.41 (m, 2H), 7.21 (d, J = 10.1 Hz, 1H), 7.09-7.05 (m, 2H), 6.47 (d, J = 5.1 Hz, 1H), 3.68 (s, 2H), 2.10 (s, 3H), 1.57 (s, 6H), 1.49 (s, 9H) | 518.2 $(M + H)^+$ |
| 569 | 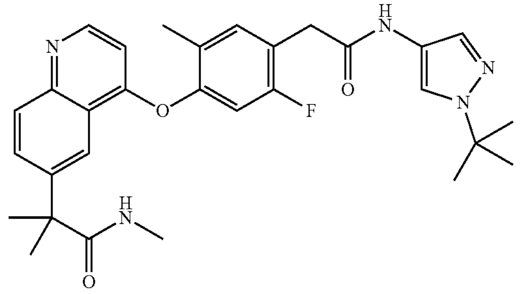 [SMILES: CNC(=O)C(C)(C)c1ccc2nccc(Oc3cc(F)c(CC(=O)Nc4cnn(C(C)(C)C)c4)cc3C)c2c1] | 2-(4-(4-(2-((1-(tert-butyl)-1H-pyrazol-4-yl)amino)-2-oxoethyl)-5-fluoro-2-methylphenoxy)quinolin-6-yl)-N,2-dimethyl-propanamide | (300 MHz, DMSO-$d_6$) δ 10.23 (s, 1H), 8.65 (d, J = 5.1 Hz, 1H), 8.21 (s, 1H), 8.04-7.92 (m, 2H), 7.75 (d, J = 9.0 Hz, 1H), 7.46-7.43 (m, 3H), 7.20 (d, J = 10.1 Hz, 1H), 6.50 (d, J = 5.1 Hz, 1H), 3.68 (s, 2H), 2.57 (d, J = 4.3 Hz, 3H), 2.10 (s, 3H), 1.58 (s, 6H), 1.49 (s, 9H) | 532.2 $(M + H)^+$ |

-continued

| No. | Structure | Name | $^1$H NMR | Observed m/z |
|---|---|---|---|---|
| 570 | 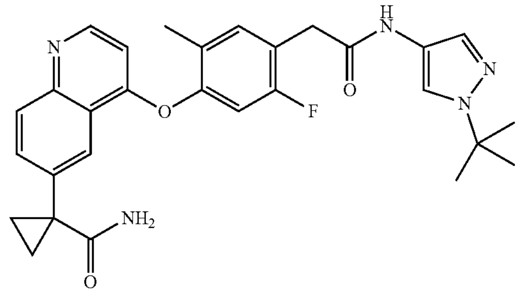 [SMILES: Cc1cc(CC(=O)Nc2cnn(C(C)(C)C)c2)c(F)cc1Oc1ccnc2ccc(C3(C(N)=O)CC3)cc12] | 1-(4-(4-(2-((1-(tert-butyl)-1H-pyrazol-4-yl)amino)-2-oxoethyl)-5-fluoro-2-methylphenoxy) quinolin-6-yl)cyclopropane-1-carboxamide | (300 MHz, DMSO-$d_6$) δ 10.23 (s, 1H), 8.67 (d, J = 5.1 Hz, 1H), 8.24 (d, J = 2.0 Hz, 1H), 8.14 (s, 1H), 8.05-7.92 (m, 2H), 7.79 (dd, J = 8.7, 2.1 Hz, 1H), 7.44 (d, J = 10.2 Hz, 1H), 7.18 (d, J = 10.0 Hz, 1H), 7.11 (s, 1H), 6.54-6.44 (m, 2H), 3.68 (s, 2H), 2.11 (s, 3H), 1.49 (s, 9H), 1.47-1.40 (m, 2H), 1.15-1.05 (m, 2H) | 516.1 $(M + H)^+$ |
| 571 | 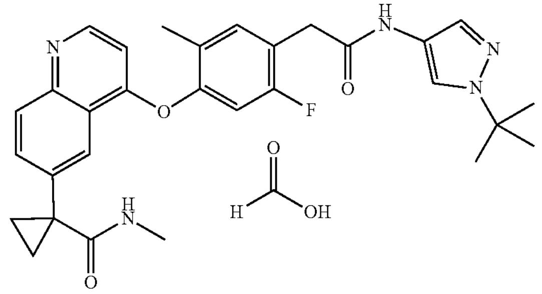 | 1-(4-(4-(2-((1-(tert-butyl)-1H-pyrazol-4-yl)amino)-2-oxoethyl)-5-fluoro-2-methylphenoxy) quinolin-6-yl)-N-methylcyclopropane-1-carboxamide formic acid salt | (300 MHz, DMSO-$d_6$) δ 10.20 (s, 1H), 8.67 (d, J = 5.2 Hz, 1H), 8.23 (d, J = 2.0 Hz, 1H), 8.16 (s, 1H), 8.01 (d, J = 8.7 Hz, 1H), 7.94 (s, 1H), 7.77 (dd, J = 8.7, 2.0 Hz, 1H), 7.44 (d, J = 10.9 Hz, 2H), 7.15 (d, J = 10.0 Hz, 1H), 6.90 (q, J = 4.4 Hz, 1H), 6.50 (d, J = 5.1 Hz, 1H), 3.68 (s, 2H), 2.53 (d, J = 4.3 Hz, 3H), 2.11 (s, 3H), 1.49 (s, 9H), 1.50-1.40 (m, 2H), 1.15-1.05 (m, 2H) | 530.2 $(M + H)^+$ |
| 572 | 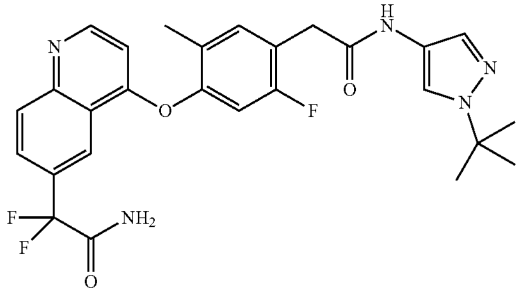 [SMILES: Cc1cc(CC(=O)Nc2cnn(C(C)(C)C)c2)c(F)cc1Oc1ccnc2ccc(C(F)(F)C(N)=O)cc12] | 2-(4-(4-(2-((1-(tert-butyl)-1H-pyrazol-4-yl)amino)-2-oxoethyl)-5-fluoro-2-methylphenoxy) quinolin-6-yl)-2,2-difluoroacetamide | (300 MHz, DMSO-$d_6$) δ 10.23 (s, 1H), 8.80 (d, J = 5.2 Hz, 1H), 8.58 (s, 2H), 8.25-8.12 (m, 2H), 8.04-7.92 (m, 2H), 7.50-7.41 (m, 2H), 7.30 (d, J = 10.0 Hz, 1H), 6.57 (d, J = 5.2 Hz, 1H), 3.69 (s, 2H), 2.10 (s, 3H), 1.49 (s, 9H) | 526.2 $(M + H)^+$ |
| 573 | 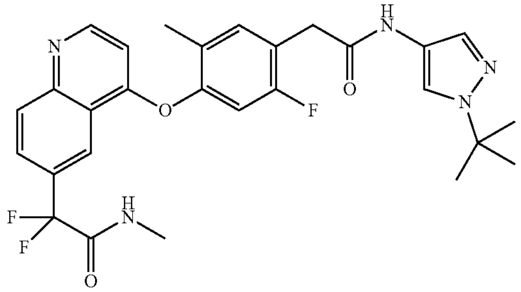 [SMILES: CNC(=O)C(F)(F)c1ccc2nccc(Oc3cc(F)c(CC(=O)Nc4cnn(C(C)(C)C)c4)cc3C)c2c1] | 2-(4-(4-(2-((1-(tert-butyl)-1H-pyrazol-4-yl)amino)-2-oxoethyl)-5-fluoro-2-methylphenoxy) quinolin-6-yl)-2,2-difluoro-N-methylacetamide | (300 MHz, DMSO-$d_6$) δ 10.24 (s, 1H), 9.16-9.08 (m, 1H), 8.80 (s, 1H), 8.56 (s, 1H), 8.19 (d, J = 8.8 Hz, 1H), 7.98-7.95 (m, 2H), 7.47-7.45 (m, 2H), 7.29 (d, J = 9.6 Hz, 1H), 6.57 (d, J = 5.4 Hz, 1H), 3.69 (s, 2H), 2.71 (s, 3H), 2.10 (s, 3H), 1.49 (s, 9H) | 540.2 $(M + H)^+$ |
| 603 | 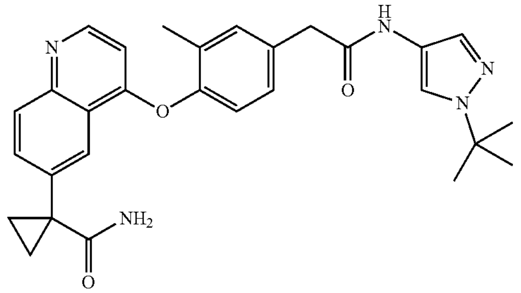 [SMILES: Cc1cc(CC(=O)Nc2cnn(C(C)(C)C)c2)ccc1Oc1ccnc2ccc(C3(C(N)=O)CC3)cc12] | 1-(4-(4-(2-((1-(tert-butyl)-1H-pyrazol-4-yl)amino)-2-oxoethyl)-2-methylphenoxy) quinolin-6-yl)cyclopropane-1-carboxamide | (400 MHz, DMSO-$d_6$) δ 10.21 (s, 1H), 8.62 (d, J = 5.1 Hz, 1H), 8.26 (d, J = 2.1 Hz, 1H), 8.03-7.93 (m, 2H), 7.78 (dd, J= 8.7, 2.0 Hz, 1H), 7.46 (s, 1H), 7.37 (d, J = 2.2 Hz, 1H), 7.29 (dd, J = 8.4, 2.2 Hz, 1H), 7.16 (d, J = 8.2 Hz, 1H), 7.10 (s, 1H), 6.51 (s, 1H), 6.39 (d, J = 5.1 Hz, 1H), 3.61 (s, 2H), 2.13 (s, 3H), 1.49 (s, 9H), 1.45-1.43 (m, 2H), 1.13-1.11 (m, 2H) | 498.1 $(M + H)^+$ |

-continued

| No. | Structure | Name | $^1$H NMR | Observed m/z |
|---|---|---|---|---|
| 604 | 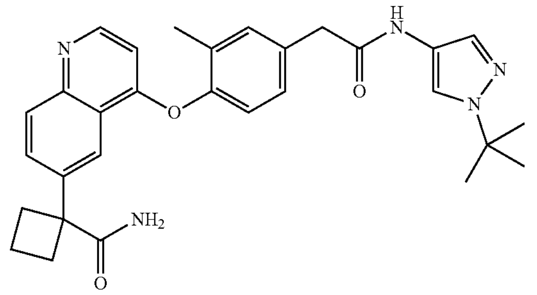 [SMILES: Cc1cc(CC(=O)Nc2cnn(C(C)(C)C)c2)ccc1Oc1ccnc2ccc(C3(C(N)=O)CCC3)cc12] | 1-(4-(4-(2-((1-(tert-butyl)-1H-pyrazol-4-yl)amino)-2-oxoethyl)-2-methylphenoxy) quinolin-6-yl)cyclobutane-1-carboxamide | (400 MHz, DMSO-$d_6$) δ 10.22 (s, 1H), 8.61 (d, J = 5.1 Hz, 1H), 8.28 (d, J = 2.0 Hz, 1H), 8.16 (s, 1H), 8.03-7.94 (m, 2H), 7.78 (dd, J = 8.8, 2.1 Hz, 1H), 7.47 (s, 1H), 7.41-7.35 (m, 1H), 7.30 (dd, J = 8.2, 2.2 Hz, 1H), 7.19 (d, J = 8.2 Hz, 1H), 7.01 (s, 1H), 6.38 (d, J = 5.1 Hz, 1H), 3.62 (s, 2H), 2.82 (tt, J = 8.3, 4.8 Hz, 2H), 2.47 (dd, J = 11.1, 8.1 Hz, 2H), 2.13 (s, 3H), 1.98-1.75 (m, 2H), 1.48 (s, 9H) | 534.2 $(M + H)^+$ |
| 605 | 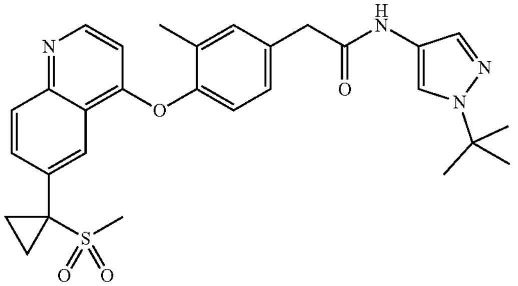 [SMILES: Cc1cc(CC(=O)Nc2cnn(C(C)(C)C)c2)ccc1Oc1ccnc2ccc(C3(S(C)(=O)=O)CC3)cc12] | N-(1-(tert-butyl)-1H-pyrazol-4-yl)-2-(3-methyl-4-((6-(1-(methylsulfonyl) cyclopropyl) quinolin-4-yl)oxy)phenyl) acetamide | (300 MHz, DMSO-$d_6$) δ 10.22 (s, 1H), 8.69 (d, J = 5.1 Hz, 1H), 8.54 (s, 1H), 8.06 (d, J = 8.8 Hz, 1H), 7.99-7.96 (m, 2H), 7.47 (s, 1H), 7.38 (s, 1H), 7.31 (d, J = 8.5 Hz, 1H), 7.21 (d, J = 8.2 Hz, 1H), 6.44 (d, J = 5.1 Hz, 1H), 3.62 (s, 2H), 2.95 (s, 3H), 2.10 (s, 3H), 1.80-1.63 (m, 2H), 1.60-1.35 (m, 11H) | 533.2 $(M + H)^+$ |
| 606 | 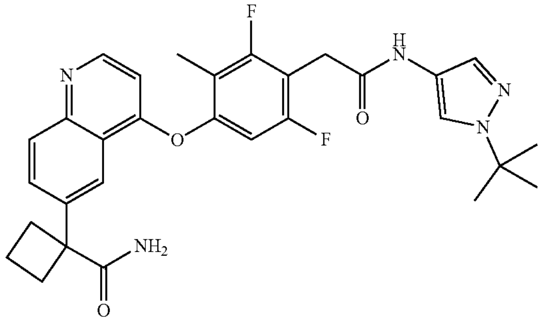 [SMILES: Cc1c(Oc2ccnc3ccc(C4(C(N)=O)CCC4)cc23)cc(F)c(CC(=O)Nc2cnn(C(C)(C)C)c2)c1F] | 1-(4-(4-(2-((1-(tert-butyl)-1H-pyrazol-4-yl)amino)-2-oxoethyl)-3,5-difluoro-2-methylphenoxy) quinolin-6-yl)cyclobutane-1-carboxamide | (300 MHz, DMSO-$d_6$) δ 10.29 (s, 1H), 8.68 (d, J = 5.1 Hz, 1H), 8.25 (d, J = 2.1 Hz, 1H), 8.02 (d, J = 8.8 Hz, 1H), 7.94 (d, J = 0.8 Hz, 1H), 7.85-7.76 (m, 1H), 7.46 (d, J = 0.8 Hz, 1H), 7.36 (s, 1H), 7.25-7.18 (m, 1H), 7.00 (s, 1H), 6.56 (d, J = 5.1 Hz, 1H), 3.74 (s, 2H), 2.89-2.75 (m, 2H), 2.50-2.41 (m, 2H), 2.04 (s, 3H), 1.98-1.70 (m, 2H), 1.49 (s, 9H) | 548.2 $(M + H)^+$ |
| 607 | 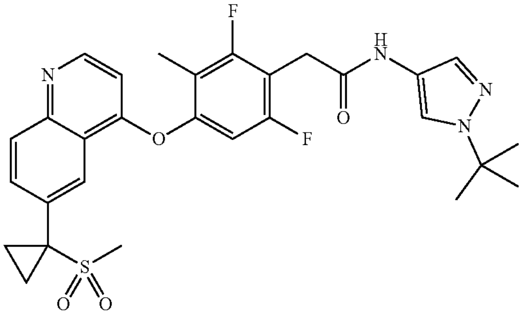 [SMILES: Cc1c(Oc2ccnc3ccc(C4(S(C)(=O)=O)CC4)cc23)cc(F)c(CC(=O)Nc2cnn(C(C)(C)C)c2)c1F] | N-(1-(tert-butyl)-1H-pyrazol-4-yl)-2-(2,6-difluoro-3-methyl-4-((6-(1-(methylsulfonyl) cyclopropyl) quinolin-4-yl)oxy)phenyl) acetamide | (300 MHz, DMSO-$d_6$) δ 10.30 (s, 1H), 8.76 (d, J = 5.2 Hz, 1H), 8.51 (d, J = 2.0 Hz, 1H), 8.09 (d, J = 8.8 Hz, 1H), 8.00 (dd, J = 8.7, 2.0 Hz, 1H), 7.94 (d, J = 0.7 Hz, 1H), 7.46 (d, J = 0.7 Hz, 1H), 7.23 (dd, J = 9.8, 1.8 Hz, 1H), 6.62 (d, J = 5.2 Hz, 1H), 3.74 (s, 2H), 2.96 (s, 3H), 2.04 (s, 3H), 1.80-1.70 (m, 2H), 1.56-1.43 (m, 11H) | 569.2 $(M + H)^+$ |

-continued

| No. | Structure | Name | $^1H$ NMR | Observed m/z |
|---|---|---|---|---|
| 609 | 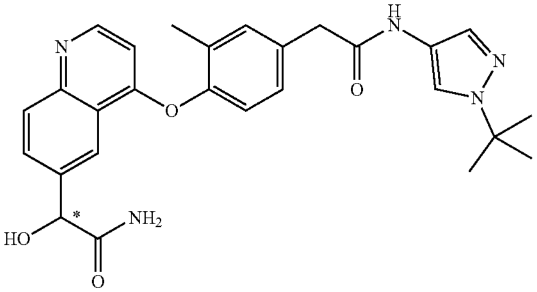 [SMILES: Cc1cc(CC(=O)Nc2cnn(C(C)(C)C)c2)ccc1Oc1ccnc2ccc(C(O)C(N)=O)cc12] enantiomer 1 (retention time: 2.05 min; column: CHIRALPAK ID-3, 4.6 × 50 mm, 3 μm; mobile phase A: MTBE (0.1% DEA), mobile phase B: EtOH, isocratic separation with 20% B, flow rate: 1.0 mL/min, wavelength: 254 nm) | 2-(4-((6-(2-amino-1-hydroxy-2-oxoethyl)quinolin-4-yl)oxy)-3-methylphenyl)-N-(1-(tert-butyl)-1H-pyrazol-4-yl)acetamide | (400 MHz, DMSO-$d_6$) δ 10.25 (s, 1H), 8.71 (d, J = 5.5 Hz, 1H), 8.48 (s, 1H), 8.05 (d, J = 8.8 Hz, 1H), 7.98-7.95 (m, 2H), 7.62 (s, 1H), 7.46 (s, 1H), 7.40 (d, J = 2.2 Hz, 1H), 7.33-7.31 (m, 2H), 7.29-7.19 (m, 1H), 6.48 (d, J = 5.4 Hz, 1H), 6.38 (s, 1H), 5.16 (s, 1H), 3.62 (s, 2H), 2.13 (s, 3H), 1.49 (s, 9H) | 488.2 $(M + H)^+$ |
| 615 | 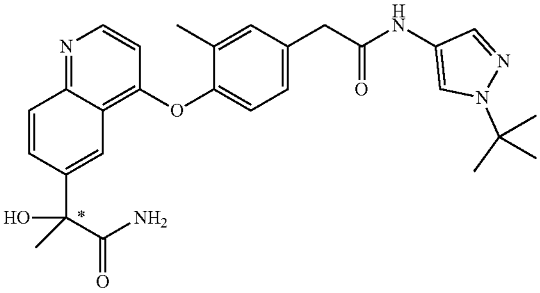 [SMILES: Cc1cc(CC(=O)Nc2cnn(C(C)(C)C)c2)ccc1Oc1ccnc2ccc(C(C)(O)C(N)=O)cc12] enantiomer 1 (retention time: 2.92 min; column: CHIRALPAK ID-3, 4.6 × 50 mm, 3 μm; mobile phase A: MTBE (0.1% DEA), mobile phase B: isopropanol, isocratic separation with 20% B, flow rate: 1.0 mL/min, wavelength: 254 nm) | 2-(4-(4-(2-((1-(tert-butyl)-1H-pyrazol-4-yl)amino)-2-oxoethyl)-2-methylphenoxy)quinolin-6-yl)-2-hydroxy-propanamide | (300 MHz, DMSO-$d_6$) δ 10.21 (s, 1H), 8.62 (d, J = 5.1 Hz, 1H), 8.57-8.50 (m, 1H), 8.06-7.92 (m, 3H), 7.46-7.44 (m, 2H), 7.38 (d, J = 2.1 Hz, 1H), 7.30 (dd, J = 8.3, 2.1 Hz, 1H), 7.24-7.14 (m, 2H), 6.37 (d, J = 5.1 Hz, 1H), 6.27 (s, 1H), 3.61 (s, 2H), 2.10 (s, 3H), 1.73 (s, 3H), 1.49 (s, 9H) | 502.2 $(M + H)^+$ |

-continued

| No. | Structure | Name | $^1$H NMR | Observed m/z |
|---|---|---|---|---|
| 616 | 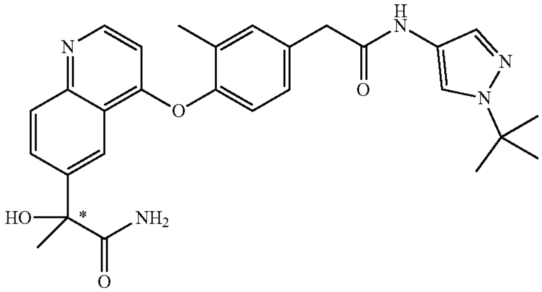 [SMILES: Cc1cc(CC(=O)Nc2cnn(C(C)(C)C)c2)ccc1Oc1ccnc2ccc(C(C)(O)C(N)=O)cc12] enantiomer 2 (retention time: 4.44 min; column: CHIRALPAK ID-3, 4.6 x 50 mm, 3 μm; mobile phase A: MTBE (0.1% DEA), mobile phase B: isopropanol, isocratic separation with 20% B, flow rate: 1.0 mL/min, wavelength: 254 nm) | 2-(4-(4-(2-((1-(tert-butyl)-1H-pyrazol-4-yl)amino)-2-oxoethyl)-2-methylphenoxy)quinolin-6-yl)-2-hydroxy-propanamide | (300 MHz, DMSO-$d_6$) δ 10.21 (s, 1H), 8.62 (d, J = 5.1 Hz, 1H), 8.53 (d, J = 1.8 Hz, 1H), 8.06-7.93 (m, 3H), 7.46-7.44 (m, 2H), 7.38 (s, 1H), 7.30 (d, J = 8.1 Hz, 1H), 7.24-7.14 (m, 2H), 6.37 (d, J = 5.2 Hz, 1H), 6.27 (s, 1H), 3.61 (s, 2H), 2.12 (s, 3H), 1.73 (s, 3H), 1.49 (s, 9H) | 502.2 $(M + H)^+$ |

Example 42—Synthesis of N-(1-(tert-butyl)-1H-pyrazol-4-yl)-2-(2-fluoro-5-methyl-4-((6-(4-methylpyridazin-3-yl)quinolin-4-yl)oxy)phenyl)acetamide (Compound 460); Prepared According to General Scheme 14

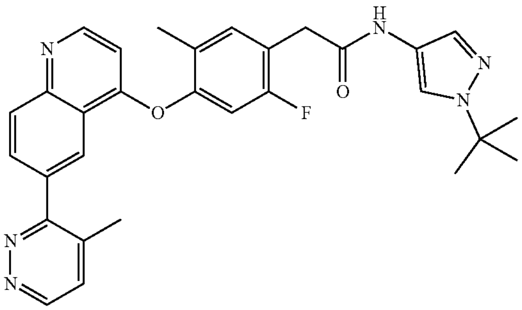 [SMILES: Cc1cc(CC(=O)Nc2cnn(C(C)(C)C)c2)c(F)cc1Oc1ccnc2ccc(-c3nnccc3C)cc12]

Part I—Synthesis of 4-chloro-6-(4,4,5,5-tetramethyl-1,3,2-dioxaborolan-2-yl)quinoline

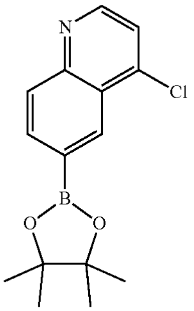 [SMILES: CC1(C)OB(c2ccc3nccc(Cl)c3c2)OC1(C)C]

A solution of 6-bromo-4-chloroquinoline (commercially available, 5.0 g, 20.6 mmol, 1.0 equiv.), bis(pinacolato) diboron (6.28 g, 24.7 mmol, 1.20 equiv.), potassium acetate (4.05 g, 41.2 mmol, 2.00 equiv.), and Pd(dppf)$Cl_2$ (754 mg, 1.03 mmol, 0.05 equiv.) in 1,4-dioxane (50 mL) was heated to 80° C. for 3 h. The solvent was removed under reduced pressure and the crude product was purified by column chromatography (petroleum ether/EtOAc 1:1). The title compound was obtained as a brown solid (5.0 g, 84%).

Part II—Synthesis of 4-chloro-6-(4-methylpyridazin-3-yl)quinoline

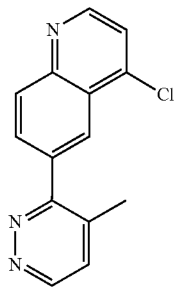 [SMILES: Cc1ccnnc1-c1ccc2nccc(Cl)c2c1]

A solution of 4-chloro-6-(4,4,5,5-tetramethyl-1,3,2-dioxaborolan-2-yl)quinoline (1.0 g, 3.45 mmol, 1.00 equiv.), 3-chloro-4-methylpyridazine (0.53 g, 4.14 mmol, 1.20 equiv.), $Cs_2CO_3$ (2.25 g, 6.91 mmol, 2.00 equiv.) and Pd(dppf)$Cl_2$ (126 mg, 0.173 mmol, 0.05 equiv.) in 1,4-dioxane (10 mL) and water (2 mL) was heated to 80° C. for 2 h. Subsequently, the crude product was purified by reversed-phase flash chromatography (column: C18 silica gel; mobile phase A: water (0.1% formic acid), mobile phase B: ACN, gradient: 10-80% B in 10 min; wavelength: 254 nm). The obtained material was extracted with diethyl ether (3×150 mL) and the combined organic phases were washed with water (150 mL) and dried over $Na_2SO_4$. The solvent was removed under reduced pressure. The title compound was obtained as a brown solid (600 mg, 68%).

Part III—Synthesis of N-(1-(tert-butyl)-1H-pyrazol-4-yl)-2-(2-fluoro-5-methyl-4-((6-(4-methylpyridazin-3-yl)quinolin-4-yl)oxy)phenyl)acetamide (Compound 460)

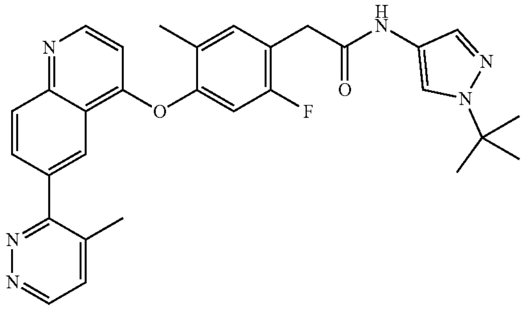 [SMILES: Cc1cc(CC(=O)Nc2cnn(C(C)(C)C)c2)c(F)cc1Oc1ccnc2ccc(-c3nnccc3C)cc12]

A solution of 4-chloro-6-(4-methylpyridazin-3-yl)quinoline (200 mg, 0.782 mmol, 1.00 equiv.), N-(1-(tert-butyl)-1H-pyrazol-4-yl)-2-(2-fluoro-4-hydroxy-5-methylphenyl) acetamide (287 mg, 0.938 mmol, 1.20 equiv., can be synthesized according to Part IV of Example 37) and $Cs_2CO_3$ (119 mg, 1.56 mmol, 2.00 equiv.) in DMA (2 mL) was heated to 100° C. for 3 h. Subsequently, the crude product was purified by reversed-phase flash chromatography (column: C18 silica gel; mobile phase A: water (0.1% formic acid), mobile phase B: ACN, gradient: 10-80% B in 20 min; wavelength: 254 nm). The title compound was obtained as a pink solid (198 mg, 48%). LCMS (ESI) calculated for $C_{30}H_{30}FN_6O_2(M+H)^+$: 525.2, found: 525.4. $^1H$ NMR (300 MHz, DMSO-$d_6$) (310.20 (s, 1H), 9.15 (d, J=5.2 Hz, 1H), 8.78 (d, J=5.2 Hz, 1H), 8.58 (d, J=1.9 Hz, 1H), 8.19 (d, J=8.7 Hz, 1H), 8.11 (dd, J=8.7, 2.0 Hz, 1H), 7.94 (d, J=0.7 Hz, 1H), 7.76-7.68 (m, 1H), 7.49-7.39 (m, 2H), 7.26 (d, J=10.1 Hz, 1H), 6.59 (d, J=5.2 Hz, 1H), 3.68 (s, 2H), 2.49 (s, 3H), 2.11 (s, 3H), 1.49 (s, 9H).

Example 43—Synthesis of N-(1-(tert-butyl)-1H-pyrazol-4-yl)-2-(3-methyl-4-((6-(4-methyl-3-oxo-3,4-dihydropyrazin-2-yl)quinolin-4-yl)oxy)phenyl) acetamide (Compound 461); Prepared According to General Scheme 14

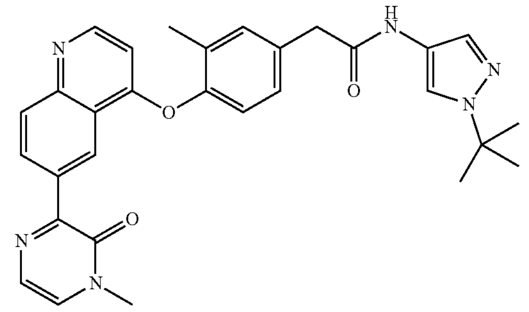 [SMILES: Cc1cc(CC(=O)Nc2cnn(C(C)(C)C)c2)ccc1Oc1ccnc2ccc(-c3nccn(C)c3=O)cc12]

Part I—Synthesis of 3-chloro-1-methylpyrazin-2(1H)-one

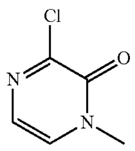

Dimethyl sulfate (724 mg, 5.75 mmol, 1.50 equiv.) was added to a solution of 3-chloropyrazin-2(1H)-one (500 mg, 3.83 mmol, 1.00 equiv.), and $K_2CO_3$ (1.06 g, 7.66 mmol, 2.00 equiv.) in ACN (10 mL) and the mixture was heated to 70° C. for 3 h. Subsequently, insoluble byproducts were filtered off and the crude product was purified by column chromatography (gradient of petroleum ether to petroleum ether/EtOAc 1:1). The title compound was obtained as an off-white solid (450 mg, 81%).

Part II—Synthesis of 2-(4-((6-bromoquinolin-4-yl)oxy)-3-methylphenyl)-N-(1-(tert-butyl)-1H-pyrazol-4-yl)acetamide

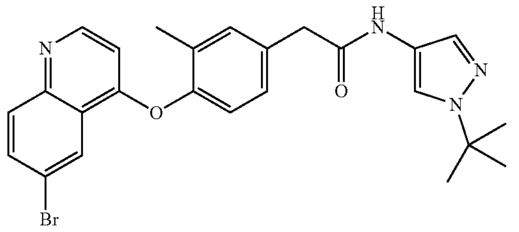 [SMILES: Cc1cc(CC(=O)Nc2cnn(C(C)(C)C)c2)ccc1Oc1ccnc2ccc(Br)cc12]

A solution of N-(1-(tert-butyl)-1H-pyrazol-4-yl)-2-(4-hydroxy-3-methylphenyl)acetamide (2.0 g, 6.96 mmol, 1.00 equiv., can be synthesized as shown in Part II of Example 30), 6-bromo-4-chloroquinoline (commercially available, 1.69 g, 6.96 mmol, 1.00 equiv.), $Cs_2CO_3$ (4.54 g, 13.9 mmol, 2.00 equiv.), CuI (0.27 g, 1.39 mmol, 0.20 equiv.), and N,N-dimethylglycine (0.22 g, 2.09 mmol, 0.30 equiv.) in DMF (20 mL) was heated to 80° C. for 3 h under an inert atmosphere of nitrogen. Subsequently, the crude product was purified by reversed-phase flash chromatography (column: C18 silica gel; mobile phase A: water (0.1% $NH_4HCO_3$), mobile phase B: ACN, gradient: 20-60% B in 30 min; wavelength: 210 nm). The title compound was obtained as a brown oil (1.98 g, 55%).

Part III—Synthesis of N-(1-(tert-butyl)-1H-pyrazol-4-yl)-2-(3-methyl-4-((6-(4,4,5,5-tetramethyl-1,3,2-dioxaborolan-2-yl)quinolin-4-yl)oxy)phenyl)acetamide

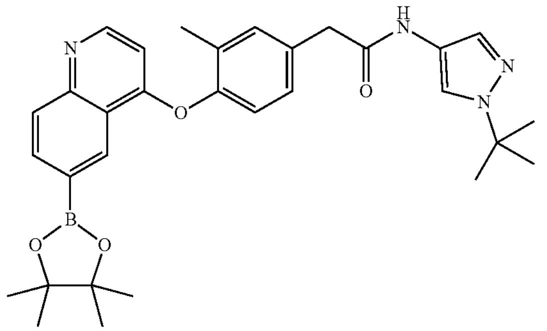 [SMILES: Cc1cc(CC(=O)Nc2cnn(C(C)(C)C)c2)ccc1Oc1ccnc2ccc(B3OC(C)(C)C(C)(C)O3)cc12]

A solution of 2-(4-((6-bromoquinolin-4-yl)oxy)-3-methylphenyl)-N-(1-(tert-butyl)-1H-pyrazol-4-yl)acetamide (5.00 g, 10.1 mmol, 1.00 equiv.), bis(pinacolato)diboron (3.09 g, 12.2 mmol, 1.20 equiv.), potassium acetate (2.98 g, 30.4 mmol, 3.00 equiv.), and Pd(dppf)$Cl_2$ (1.11 g, 1.52 mmol, 0.15 equiv.) in 1,4-dioxane (80 mL) was heated to 80° C. for 1 h under an inert atmosphere of nitrogen. Subsequently, insoluble byproducts were filtered off and the crude product was purified by column chromatography (gradient of petroleum ether to petroleum ether/EtOAc 1:1). The title compound was obtained as a green solid (2.4 g, 43%).

Part IV—Synthesis of N-(1-(tert-butyl)-1H-pyrazol-4-yl)-2-(3-methyl-4-((6-(4-methyl-3-oxo-3,4-dihydropyrazin-2-yl)quinolin-4-yl)oxy)phenyl)acetamide (Compound 461)

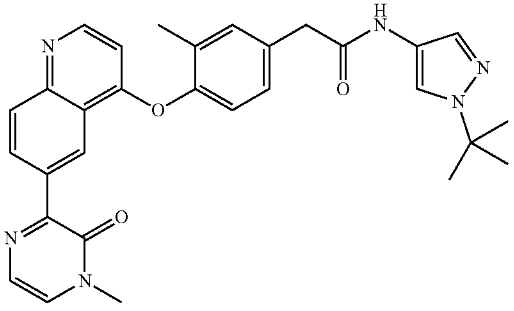 [SMILES: Cc1cc(CC(=O)Nc2cnn(C(C)(C)C)c2)ccc1Oc1ccnc2ccc(-c3nccn(C)c3=O)cc12]

A solution of N-(1-(tert-butyl)-1H-pyrazol-4-yl)-2-(3-methyl-4-((6-(4,4,5,5-tetramethyl-1,3,2-dioxaborolan-2-yl)quinolin-4-yl)oxy)phenyl)acetamide (300 mg, 0.555 mmol, 1.00 equiv.), 3-chloro-1-methylpyrazin-2(1H)-one (80.2 mg, 0.555 mmol, 1.00 equiv.), Pd(dppf)$Cl_2$ (22.6 mg, 0.028 mmol, 0.05 equiv.), and $Cs_2CO_3$ (271.3 mg, 0.833 mmol, 1.50 equiv.) in 1,4-dioxane (3 mL) and water (0.3 mL) was heated to 100° C. for 1 h under an inert atmosphere of nitrogen. Subsequently, insoluble byproducts were filtered off and the crude product was purified by preparative HPLC (column: Xselect CSH C18 OBD; 30×150 mm, 5 μm; mobile phase A: water (50 mmol/L $NH_4HCO_3$), mobile phase B: ACN; flow rate: 60 mL/min; gradient: 30-34% B in 15 min; wavelength: 220 nm; RT1: 11 min). The title compound was obtained as an off-white solid (140 mg, 48%). LCMS (ESI) calculated for $C_{30}H_{31}N_6O_3$ $(M+H)^+$: 523.3, found: 523.2. $^1H$ NMR (400 MHz, DMSO-$d_6$) δ 10.21 (s, 1H), 9.65 (d, J=2.0 Hz, 1H), 8.69-8.62 (m, 2H), 8.06 (d, J=9.0 Hz, 1H), 7.96 (d, J=0.7 Hz, 1H), 7.84 (d, J=4.1 Hz, 1H), 7.58 (d, J=4.1 Hz, 1H), 7.47 (d, J=0.7 Hz, 1H), 7.38 (d, J=2.1 Hz, 1H), 7.31 (dd, J=8.3, 2.2 Hz, 1H), 7.22 (d, J=8.3 Hz, 1H), 6.42 (d, J=5.2 Hz, 1H), 3.62 (s, 2H), 3.59 (s, 3H), 2.13 (s, 3H), 1.49 (s, 9H).

Example 44—Preparation of Additional 6-Heteroaryl Substituted Quinoline and Quinazoline Compounds Compounds in the table below were prepared based on experimental procedures described in Examples 42 and 43 and the detailed description.

| No. | Structure | Name | ¹H NMR | Observed m/z |
|---|---|---|---|---|
| 244 | 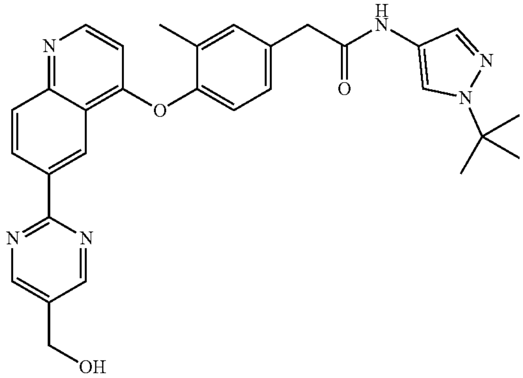 [SMILES: Cc1cc(CC(=O)Nc2cnn(C(C)(C)C)c2)ccc1Oc1ccnc2ccc(-c3ncc(CO)cn3)cc12] | N-(1-(tert-butyl)-1H-pyrazol-4-yl)-2-(4-((6-(5-(hydroxymethyl)pyrimidin-2-yl)quinolin-4-yl)oxy)-3-methylphenyl)acetamide | (400 MHz, DMSO-$d_6$) δ 10.22 (s, 1H), 9.45 (s, 1H), 8.93 (s, 2H), 8.81 (dd, J = 8.9, 2.0 Hz, 1H), 8.71 (d, J = 5.1 Hz, 1H), 8.16 (d, J = 8.9 Hz, 1H), 7.96 (s, 1H), 7.47 (s, 1H), 7.39 (s, 1H), 7.34-7.29 (m, 1H), 7.24 (d, J = 8.3 Hz, 1H), 6.44 (d, J = 5.2 Hz, 1H), 5.54 (t, J = 5.6 Hz, 1H), 4.64 (d, J = 5.6 Hz, 2H), 3.62 (s, 2H), 2.15 (s, 3H), 1.49 (s, 9H) | 523.1 $(M + H)^+$ |
| 245 | 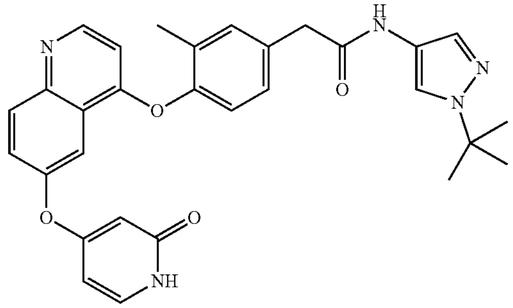 | N-(1-(tert-butyl)-1H-pyrazol-4-yl)-2-(3-methyl-4-((6-(2-oxo-1,2-dihydropyridin-3-yl)quinolin-4-yl)oxy)phenyl)acetamide | (400 MHz, DMSO-$d_6$) δ 11.93 (s, 1H), 10.20 (s, 1H), 8.83 (d, J = 2.0 Hz, 1H), 8.63 (d, J = 5.2 Hz, 1H), 8.16 (dd, J = 8.9, 2.0 Hz, 1H), 8.02 (d, J = 8.9 Hz, 1H), 7.95 (s, 1H), 7.90 (dd, J = 7.0, 2.1 Hz, 1H), 7.51-7.42 (m, 2H), 7.37 (d, J = 2.1 Hz, 1H), 7.30 (dd, J = 8.3, 2.1 Hz, 1H), 7.20 (d, J = 8.2 Hz, 1H), 6.44-6.30 (m, 2H), 3.61 (s, 2H), 2.12 (s, 3H), 1.49 (s, 9H) | 508.1 $(M + H)^+$ |
| 246 | 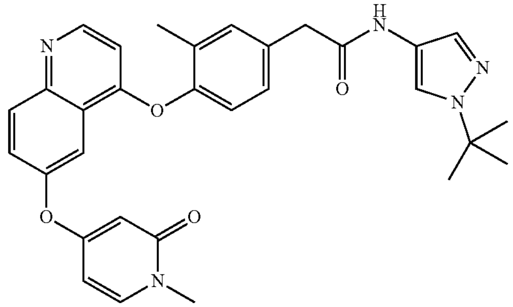 | N-(1-(tert-butyl)-1H-pyrazol-4-yl)-2-(3-methyl-4-((6-(1-methyl-2-oxo-1,2-dihydropyridin-3-yl)quinolin-4-yl)oxy)phenyl)acetamide | (400 MHz, DMSO-$d_6$) δ 10.21 (s, 1H), 8.82 (d, J = 2.0 Hz, 1H), 8.63 (d, J = 5.2 Hz, 1H), 8.13 (dd, J = 8.9, 2.1 Hz, 1H), 8.02 (d, J = 8.9 Hz, 1H), 7.96 (d, J = 0.7 Hz, 1H), 7.88-7.81 (m, 2H), 7.46 (d, J = 0.7 Hz, 1H), 7.37 (d, J = 2.1 Hz, 1H), 7.30 (dd, J = 8.4, 2.2 Hz, 1H), 7.20 (d, J = 8.2 Hz, 1H), 6.42-6.39 (m, 2H), 3.61 (s, 2H), 3.56 (s, 3H), 2.12 (s, 3H), 1.49 (s, 9H) | 522.1 $(M + H)^+$ |
| 247 | 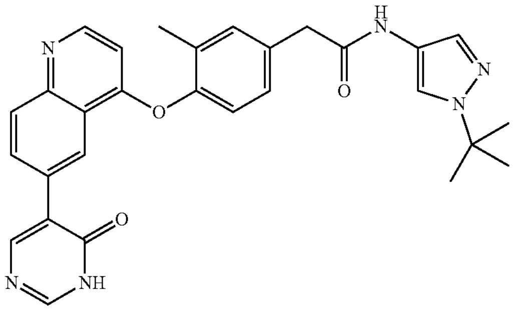 [SMILES: Cc1cc(CC(=O)Nc2cnn(C(C)(C)C)c2)ccc1Oc1ccnc2ccc(-c3cnc[nH]c3=O)cc12] | N-(1-(tert-butyl)-1H-pyrazol-4-yl)-2-(3-methyl-4-((6-(3-oxo-3,4-dihydropyrazin-2-yl)quinolin-4-yl)oxy)phenyl)acetamide | (400 MHz, DMSO-$d_6$) δ 12.67 (s, 1H), 10.20 (s, 1H), 9.63 (d, J = 2.0 Hz, 1H), 8.74-8.62 (m, 2H), 8.05 (d, J = 9.0 Hz, 1H), 7.95 (s, 1H), 7.59-7.52 (m, 2H), 7.45 (s, 1H), 7.37 (d, J = 2.1 Hz, 1H), 7.30 (dd, J = 8.3, 2.2 Hz, 1H), 7.22 (d, J = 8.2 Hz, 1H), 6.42 (d, J = 5.2 Hz, 1H), 3.61 (s, 2H), 2.12 (s, 3H), 1.48 (s, 9H) | 509.1 $(M + H)^+$ |

-continued

| No. | Structure | Name | $^1$H NMR | Observed m/z |
|---|---|---|---|---|
| 424 | 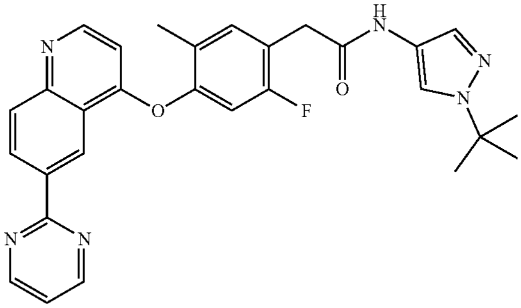 [SMILES: Cc1cc(CC(=O)Nc2cnn(C(C)(C)C)c2)c(F)cc1Oc1ccnc2ccc(-c3ncccn3)cc12] | N-(1-(tert-butyl)-1H-pyrazol-4-yl)-2-(2-fluoro-5-methyl-4-((6-(pyrimidin-2-yl)quinolin-4-yl)oxy)phenyl) acetamide | | 511.1 $(M + H)^+$ |
| 425 | 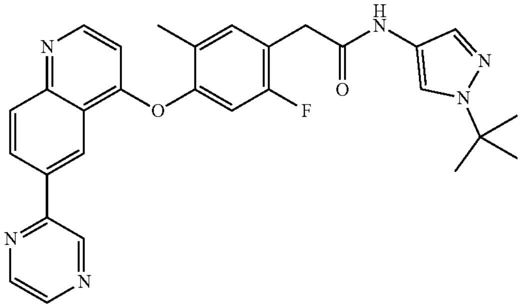 [SMILES: Cc1cc(CC(=O)Nc2cnn(C(C)(C)C)c2)c(F)cc1Oc1ccnc2ccc(-c3cnccn3)cc12] | N-(1-(tert-butyl)-1H-pyrazol-4-yl)-2-(2-fluoro-5-methyl-4-((6-(pyrazin-2-yl)quinolin-4-yl)oxy)phenyl) acetamide | | 511.1 $(M + H)^+$ |
| 426 | 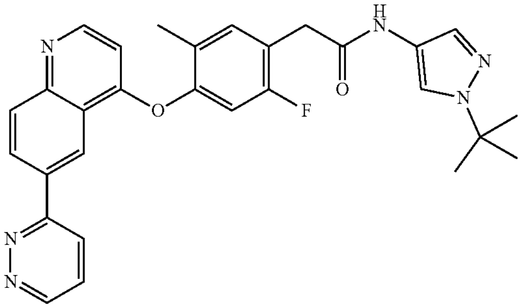 [SMILES: Cc1cc(CC(=O)Nc2cnn(C(C)(C)C)c2)c(F)cc1Oc1ccnc2ccc(-c3cccnn3)cc12] | N-(1-(tert-butyl)-1H-pyrazol-4-yl)-2-(2-fluoro-5-methyl-4-((6-(pyridazin-3-yl)quinolin-4-yl)oxy)phenyl) acetamide | | 511.2 $(M + H)^+$ |
| 427 | 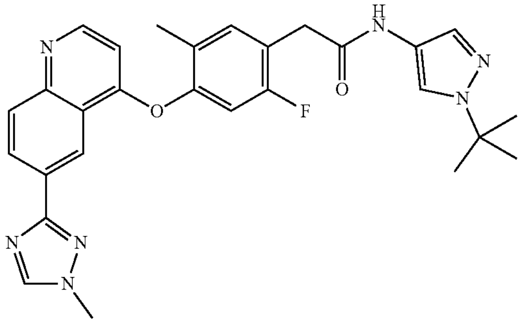 [SMILES: Cc1cc(CC(=O)Nc2cnn(C(C)(C)C)c2)c(F)cc1Oc1ccnc2ccc(-c3ncn(C)n3)cc12] | N-(1-(tert-butyl)-1H-pyrazol-4-yl)-2-(2-fluoro-5-methyl-4-((6-(1-methyl-1H-1,2,4-triazol-3-yl)quinolin-4-yl)oxy)phenyl) acetamide | | 514.2 $(M + H)^+$ |
| 428 | 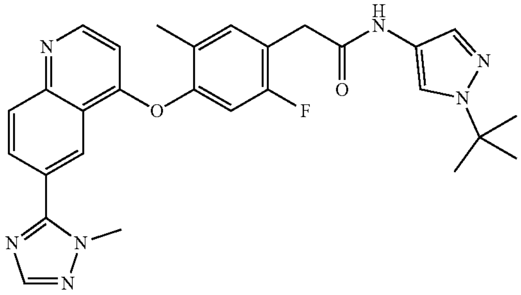 [SMILES: Cc1cc(CC(=O)Nc2cnn(C(C)(C)C)c2)c(F)cc1Oc1ccnc2ccc(-c3ncnn3C)cc12] | N-(1-(tert-butyl)-1H-pyrazol-4-yl)-2-(2-fluoro-5-methyl-4-((6-(1-methyl-1H-1,2,4-triazol-5-yl)quinolin-4-yl)oxy)phenyl) acetamide | | 514.0 $(M + H)^+$ |

-continued

| No. | Structure | Name | $^1$H NMR | Observed m/z |
|---|---|---|---|---|
| 475 | 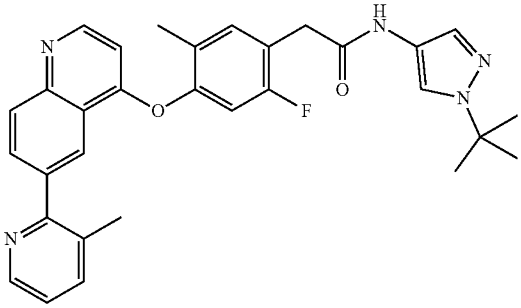 | N-(1-(tert-butyl)-1H-pyrazol-4-yl)-2-(2-fluoro-5-methyl-4-((6-(3-methylpyridin-2-yl)quinolin-4-yl)oxy)phenyl) acetamide | (300 MHz, DMSO-$d_6$) δ 10.20 (s, 1H), 8.72 (d, J = 5.1 Hz, 1H), 8.57 (d, J = 3.6 Hz, 1H), 8.49 (d, J = 1.5 Hz, 1H), 8.14-8.07 (m, 2H), 7.94 (s, 1H), 7.79 (d, J = 7.5 Hz, 1H), 7.46-7.35 (m, 3H), 7.24 (dd, J = 9.9, 2.4 Hz, 1H), 6.56 (d, J = 5.1, 2.5 Hz, 1H), 3.67 (s, 2H), 2.43 (s, 3H), 2.10 (s, 3H), 1.48 (s, 9H) | 524.4 $(M + H)^+$ |
| 476 | 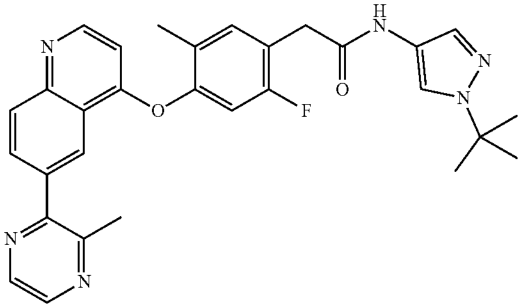 | N-(1-(tert-butyl)-1H-pyrazol-4-yl)-2-(2-fluoro-5-methyl-4-((6-(3-methylpyrazin-2-yl)quinolin-4-yl)oxy)phenyl) acetamide | (300 MHz, DMSO-$d_6$) δ 10.22 (s, 1H), 8.76 (d, J = 5.1 Hz, 1H), 8.68-8.56 (m, 3H), 8.22-8.08 (m, 2H), 7.95 (s, 1H), 7.47-7.43 (m, 2H), 7.26 (d, J = 10.0 Hz, 1H), 6.58 (d, J = 5.2 Hz, 1H), 3.68 (s, 2H), 2.67 (s, 3H), 2.11 (s, 3H), 1.49 (s, 9H) | 525.1 $(M + H)^+$ |
| 477 | 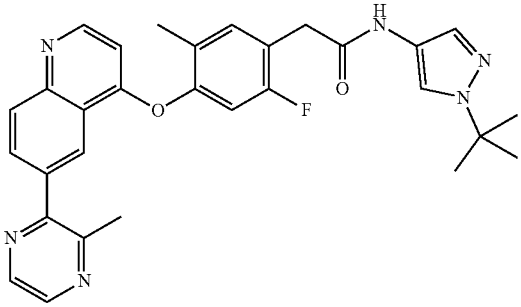 | N-(1-(tert-butyl)-1H-pyrazol-4-yl)-2-(2-fluoro-5-methyl-4-((6-(5-methylpyrimidin-4-yl)quinolin-4-yl)oxy)phenyl) acetamide | (300 MHz, DMSO-$d_6$) δ 10.22 (s, 1H), 9.17 (s, 1H), 8.84-8.74 (m, 2H), 8.66 (t, J = 1.4 Hz, 1H), 8.19-8.15 (m, 2H), 7.95 (s, 1H), 7.46-7.43 (m, 2H), 7.26 (d, J = 10.0 Hz, 1H), 6.59 (d, J = 5.2 Hz, 1H), 3.68 (s, 2H), 2.47 (s, 3H), 2.11 (s, 3H), 1.49 (s, 9H) | 525.1 $(M + H)^+$ |
| 478 | 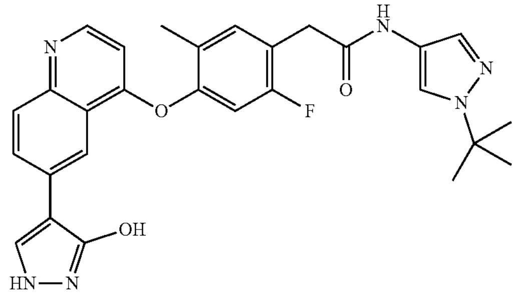 [SMILES: Cc1cc(CC(=O)Nc2cnn(C(C)(C)C)c2)c(F)cc1Oc1ccnc2ccc(-c3c[nH]nc3O)cc12] | N-(1-(tert-butyl)-1H-pyrazol-4-yl)-2-(2-fluoro-4-((6-(3-hydroxy-1H-pyrazol-4-yl)quinolin-4-yl)oxy)-5-methylphenyl) acetamide | (400 MHz, DMSO-$d_6$) δ 10.19 (s, 1H), 8.68 (d, J = 2.0 Hz, 1H), 8.57 (d, J = 5.1 Hz, 1H), 8.23-8.12 (m, 2H), 7.98-7.95 (m, 2H), 7.49-7.40 (m, 2H), 7.21 (d, J = 10.0 Hz, 1H), 6.44 (d, J = 5.1 Hz, 1H), 3.68 (s, 2H), 2.10 (s, 3H), 1.50 (s, 9H) | 515.2 $(M + H)^+$ |
| 479 | 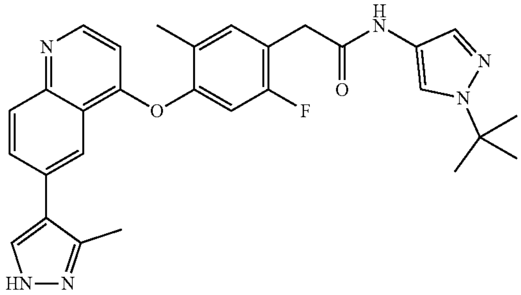 [SMILES: Cc1cc(CC(=O)Nc2cnn(C(C)(C)C)c2)c(F)cc1Oc1ccnc2ccc(-c3c[nH]nc3C)cc12] | N-(1-(tert-butyl)-1H-pyrazol-4-yl)-2-(2-fluoro-5-methyl-4-((6-(3-methyl-1H-pyrazol-4-yl)quinolin-4-yl)oxy)phenyl) acetamide | (400 MHz, DMSO-$d_6$) δ 12.81 (s, 1H), 10.20 (s, 1H), 8.64 (d, J = 5.1 Hz, 1H), 8.30 (d, J = 2.0 Hz, 1H), 8.06-7.94 (m, 4H), 7.49-7.40 (m, 2H), 7.22 (d, J = 10.0 Hz, 1H), 6.54 (d, J = 5.1 Hz, 1H), 3.68 (s, 2H), 2.47 (s, 3H), 2.12 (s, 3H), 1.49 (s, 9H) | 513.2 $(M + H)^+$ |

-continued

| No. | Structure | Name | $^1$H NMR | Observed m/z |
|---|---|---|---|---|
| 480 | 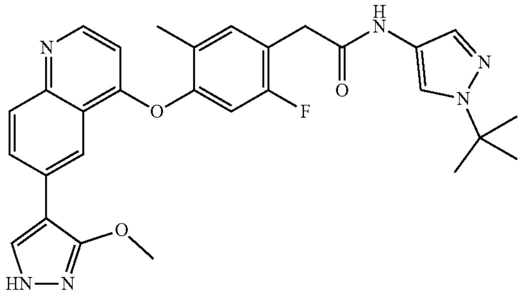 [SMILES: COc1n[nH]cc1-c1ccc2nccc(Oc3cc(F)c(CC(=O)Nc4cnn(C(C)(C)C)c4)cc3C)c2c1] | N-(1-(tert-butyl)-1H-pyrazol-4-yl)-2-(2-fluoro-4-((6-(3-methoxy-1H-pyrazol-4-yl)quinolin-4-yl)oxy)-5-methylphenyl) acetamide | (400 MHz, DMSO-$d_6$) δ 12.25 (s, 1H), 10.21 (s, 1H), 8.63-8.56 (m, 2H), 8.30 (d, J = 1.8 Hz, 1H), 8.14 (dd, J = 8.9, 2.0 Hz, 1H), 8.02-7.92 (m, 2H), 7.49-7.41 (m, 2H), 7.22 (d, J = 10.0 Hz, 1H), 6.50 (d, J = 5.1 Hz, 1H), 3.97 (s, 3H), 3.68 (s, 2H), 2.12 (s, 3H), 1.50 (s, 9H) | 529.2 $(M + H)^+$ |
| 481 | 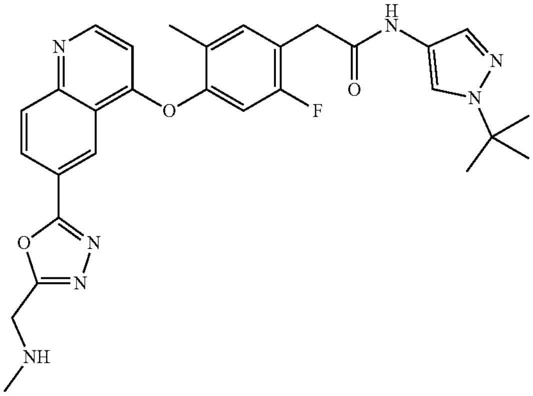 [SMILES: CNCc1nnc(-c2ccc3nccc(Oc4cc(F)c(CC(=O)Nc5cnn(C(C)(C)C)c5)cc4C)c3c2)o1] | N-(1-(tert-butyl)-1H-pyrazol-4-yl)-2-(2-fluoro-5-methyl-4-((6-(5-((methylamino) methyl)-1,3,4-oxadiazol-2-yl)quinolin-4-yl)oxy)phenyl) acetamide | (400 MHz, DMSO-$d_6$) δ 10.24 (s, 1H), 8.93 (d, J = 2.1 Hz, 1H), 8.81 (d, J = 5.2 Hz, 1H), 8.42 (dd, J = 8.9, 2.0 Hz, 1H), 8.25 (d, J = 8.8 Hz, 1H), 7.95 (s, 1H), 7.50-7.44 (m, 2H), 7.30 (d, J = 10.0 Hz, 1H), 6.60 (d, J = 5.2 Hz, 1H), 4.00 (s, 2H), 3.70 (s, 2H), 2.35 (s, 3H), 2.12 (s, 3H), 1.50 (s, 9H) | 544.2 $(M + H)^+$ |
| 482 | 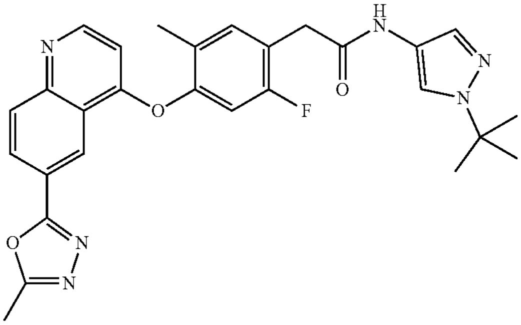 [SMILES: Cc1nnc(-c2ccc3nccc(Oc4cc(F)c(CC(=O)Nc5cnn(C(C)(C)C)c5)cc4C)c3c2)o1] | N-(1-(tert-butyl)-1H-pyrazol-4-yl)-2-(2-fluoro-5-methyl-4-((6-(5-methyl-1,3,4-oxadiazol-2-yl)quinolin-4-yl)oxy)phenyl) acetamide | (300 MHz, DMSO-$d_6$) δ 10.23 (s, 1H), 8.90 (s, 1H), 8.80 (d, J = 5.1 Hz, 1H), 8.39 (d, J = 8.9 Hz, 1H), 8.23 (d, J = 8.9 Hz, 1H), 7.95 (s, 1H), 7.47-7.45 (m, 2H), 7.30 (d, J = 10.1 Hz, 1H), 6.59 (d, J = 5.1 Hz, 1H), 3.69 (s, 2H), 2.65 (s, 3H), 2.12 (s, 3H), 1.50 (s, 9H) | 515.1 $(M + H)^+$ |
| 483 | 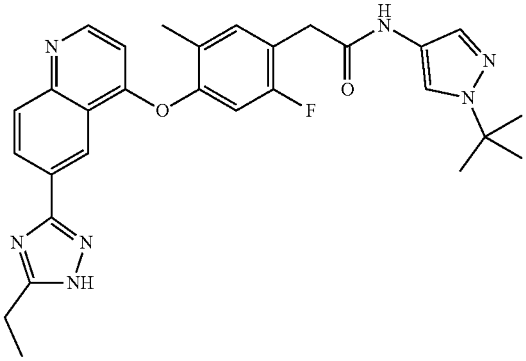 [SMILES: CCc1nc(-c2ccc3nccc(Oc4cc(F)c(CC(=O)Nc5cnn(C(C)(C)C)c5)cc4C)c3c2)n[nH]1] | N-(1-(tert-butyl)-1H-pyrazol-4-yl)-2-(4-((6-(5-ethyl-1H-1,2,4-triazol-3-yl)quinolin-4-yl)oxy)-2-fluoro-5-methylphenyl) acetamide | (300 MHz, DMSO-$d_6$) δ 13.89 (s, 1H), 10.24 (s, 1H), 8.96 (s, 1H), 8.70 (d, J = 5.2 Hz, 1H), 8.44 (dd, J = 8.8, 2.0 Hz, 1H), 8.11 (d, J = 8.8 Hz, 1H), 7.96 (s, 1H), 7.50-7.42 (m, 2H), 7.28 (d, J = 10.0 Hz, 1H), 6.50 (d, J = 5.1 Hz, 1H), 3.69 (s, 2H), 2.81 (q, J = 7.7 Hz, 2H), 2.12 (s, 3H), 1.50 (s, 9H), 1.31 (t, J = 7.5 Hz, 3H) | 528.2 $(M + H)^+$ |

-continued

| No. | Structure | Name | $^1H$ NMR | Observed m/z |
|---|---|---|---|---|
| 484 | 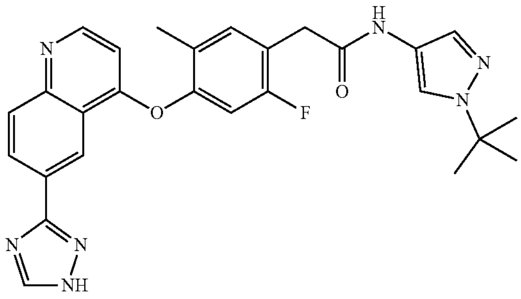 [SMILES: Cc1cc(CC(=O)Nc2cnn(C(C)(C)C)c2)c(F)cc1Oc1ccnc2ccc(-c3nc[nH]n3)cc12] | 2-(4-((6-(1H-1,2,4-triazol-3-yl)quinolin-4-yl)oxy)-2-fluoro-5-methylphenyl)-N-(1-(tert-butyl)-1H-pyrazol-4-yl)acetamide | (300 MHz, DMSO-$d_6$) δ 14.40 (s, 1H), 10.24 (s, 1H), 9.02 (s, 1H), 8.72 (d, J = 5.1 Hz, 1H), 8.60 (s, 1H), 8.47 (dd, J = 8.8, 1.9 Hz, 1H), 8.15 (d, J = 8.8 Hz, 1H), 7.96 (s, 1H), 7.51-7.42 (m, 2H), 7.28 (d, J = 10.1 Hz, 1H), 6.54 (d, J = 5.1 Hz, 1H), 3.69 (s, 2H), 2.13 (s, 3H), 1.50 (s, 9H) | 500.1 $(M + H)^+$ |
| 507 | 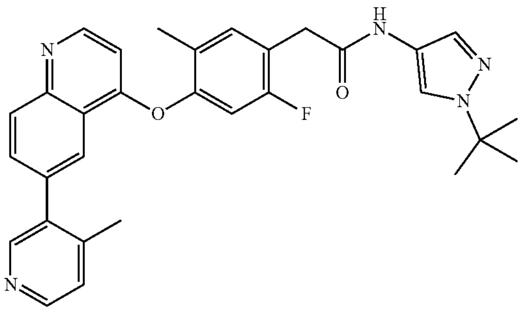 | N-(1-(tert-butyl)-1H-pyrazol-4-yl)-2-(2-fluoro-5-methyl-4-((6-(4-methylpyridin-3-yl)quinolin-4-yl)oxy)phenyl) acetamide | (400 MHz, DMSO-$d_6$) δ 10.20 (s, 1H), 8.75 (d, J = 5.1 Hz, 1H), 8.58-8.48 (m, 2H), 8.31 (d, J = 2.1 Hz, 1H), 8.15 (d, J = 8.7 Hz, 1H), 7.97-7.87 (m, 2H), 7.48-7.38 (m, 3H), 7.24 (d, J = 10.0 Hz, 1H), 6.58 (d, J = 5.1 Hz, 1H), 3.68 (s, 2H), 2.35 (s, 3H), 2.11 (s, 3H), 1.49 (s, 9H) | 524.1 $(M + H)^+$ |
| 508 | 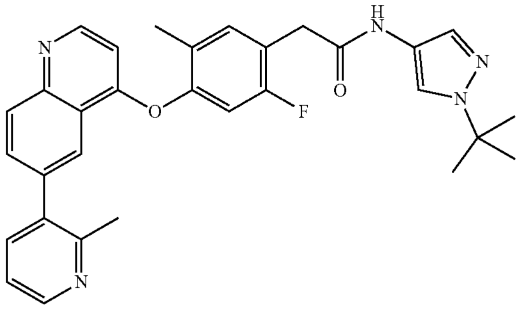 [SMILES: Cc1cc(CC(=O)Nc2cnn(C(C)(C)C)c2)c(F)cc1Oc1ccnc2ccc(-c3cccnc3C)cc12] | N-(1-(tert-butyl)-1H-pyrazol-4-yl)-2-(2-fluoro-5-methyl-4-((6-(2-methylpyridin-3-yl)quinolin-4-yl)oxy)phenyl) acetamide | (400 MHz, DMSO-$d_6$) δ 10.22 (s, 1H), 8.74 (t, J = 4.6 Hz, 1H), 8.53 (s, 1H), 8.30 (m, 1H), 8.14 (dd, J = 8.8, 3.8 Hz, 1H), 7.92-7.79 (m, 3H), 7.45-7.35 (m, 2H), 7.39-7.22 (m, 2H), 6.58 (d, J = 4.7 Hz, 1H), 3.66 (s, 2H), 3.49 (s, 3H), 2.08 (s, 3H), 1.47 (s, 9H) | 524.2 $(M + H)^+$ |
| 520 | 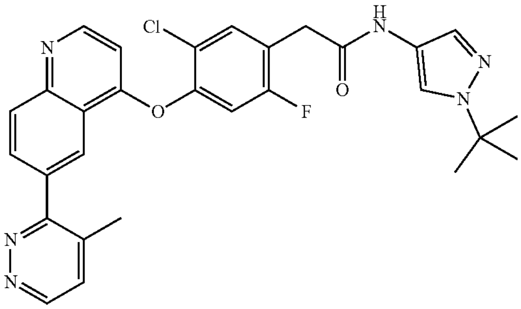 | N-(1-(tert-butyl)-1H-pyrazol-4-yl)-2-(5-chloro-2-fluoro-4-((6-(4-methylpyridazin-3-yl)quinolin-4-yl)oxy)phenyl) acetamide | (300 MHz, DMSO-$d_6$) δ 10.25 (s, 1H), 9.16 (d, J = 5.1 Hz, 1H), 8.82 (d, J = 5.2 Hz, 1H), 8.56 (d, J = 1.9 Hz, 1H), 8.21 (d, J = 8.7 Hz, 1H), 8.13 (dd, J = 8.7, 2.0 Hz, 1H), 7.95 (s, 1H), 7.79 (d, J = 7.5 Hz, 1H), 7.73 (d, J = 5.2 Hz, 1H), 7.62 (d, J = 9.8 Hz, 1H), 7.46 (s, 1H), 6.68 (d, J = 5.1 Hz, 1H), 3.75 (s, 2H), 2.44 (s, 3H), 1.49 (s, 9H) | 545.1 $(M + H)^+$ |

-continued

| No. | Structure | Name | $^1$H NMR | Observed m/z |
|---|---|---|---|---|
| 521 | 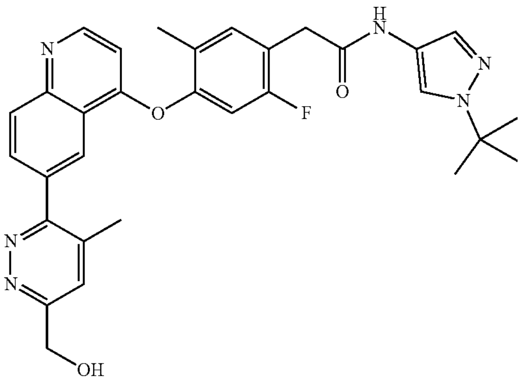 [SMILES: Cc1cc(CC(=O)Nc2cnn(C(C)(C)C)c2)c(F)cc1Oc1ccnc2ccc(-c3nnc(CO)cc3C)cc12] | N-(1-(tert-butyl)-1H-pyrazol-4-yl)-2-(2-fluoro-4-((6-(6-(hydroxymethyl)-4-methylpyridazin-3-yl)quinolin-4-yl)oxy)-5-methylphenyl) acetamide | (300 MHz, DMSO-$d_6$) δ 10.23 (s, 1H), 8.78 (d, J = 5.2 Hz, 1H), 8.58 (d, J = 2.1 Hz, 1H), 8.19 (d, J = 8.7 Hz, 1H), 8.10 (dd, J = 8.7, 2.0 Hz, 1H), 7.95 (s, 1H), 7.73 (s, 1H), 7.50-7.40 (m, 2H), 7.26 (d, J = 10.0 Hz, 1H), 6.59 (d, J = 5.2 Hz, 1H), 5.72 (t, J = 5.9 Hz, 1H), 4.83 (d, J = 5.0 Hz, 2H), 3.68 (s, 2H), 2.45 (s, 3H), 2.11 (s, 3H), 1.49 (s, 9H) | 555.1 (M + H)$^+$ |
| 522 | 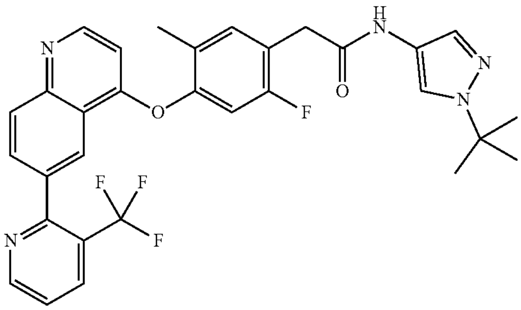 [SMILES: Cc1cc(CC(=O)Nc2cnn(C(C)(C)C)c2)c(F)cc1Oc1ccnc2ccc(-c3ncccc3C(F)(F)F)cc12] | N-(1-(tert-butyl)-1H-pyrazol-4-yl)-2-(2-fluoro-5-methyl-4-((6-(3-(trifluoromethyl) pyridin-2-yl)quinolin-4-yl)oxy)phenyl) acetamide | (400 MHz, DMSO-$d_6$) δ 10.21 (s, 1H), 8.99 (dd, J = 4.7, 1.6 Hz, 1H), 8.78 (d, J = 5.2 Hz, 1H), 8.45 (d, J = 2.0 Hz, 1H), 8.40 (dd, J = 8.1, 1.6 Hz, 1H), 8.16 (d, J = 8.7 Hz, 1H), 7.97 (d, J = 2.1 Hz, 1H), 7.94 (s, 1H), 7.74 (dd, J = 8.1, 4.7 Hz, 1H), 7.48-7.40 (m, 2H), 7.27 (d, J = 10.0 Hz, 1H), 6.59 (d, J = 5.2 Hz, 1H), 3.68 (s, 2H), 2.08 (s, 3H), 1.49 (s, 9H) | 578.2 (M + H)$^+$ |
| 523 | 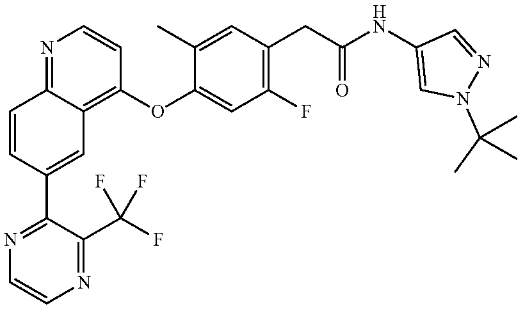 [SMILES: Cc1cc(CC(=O)Nc2cnn(C(C)(C)C)c2)c(F)cc1Oc1ccnc2ccc(-c3nccnc3C(F)(F)F)cc12] | N-(1-(tert-butyl)-1H-pyrazol-4-yl)-2-(2-fluoro-5-methyl-4-((6-(3-(trifluoromethyl) pyrazin-2-yl)quinolin-4-yl)oxy)phenyl) acetamide | (400 MHz, DMSO-$d_6$) δ 10.22 (s, 1H), 9.12 (d, J = 2.4 Hz, 1H), 8.94 (d, J = 2.4 Hz, 1H), 8.80 (d, J = 5.2 Hz, 1H), 8.57 (d, J = 2.0 Hz, 1H), 8.20 (d, J = 8.7 Hz, 1H), 8.03 (dd, J = 8.7, 2.0 Hz, 1H), 7.94 (s, 1H), 7.48-7.40 (m, 2H), 7.28 (d, J = 9.9 Hz, 1H), 6.61 (d, J = 5.2 Hz, 1H), 3.68 (s, 2H), 2.09 (s, 3H), 1.49 (s, 9H) | 579.1 (M + H)$^+$ |
| 524 | 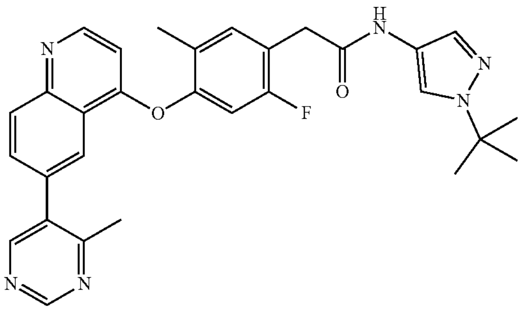 | N-(1-(tert-butyl)-1H-pyrazol-4-yl)-2-(2-fluoro-5-methyl-4-((6-(4-methylpyrimidin-5-yl)quinolin-4-yl)oxy)phenyl) acetamide | (400 MHz, DMSO-$d_6$) δ 10.22 (s, 1H), 9.12 (s, 1H), 8.81-8.74 (m, 2H), 8.41 (d, J = 2.0 Hz, 1H), 8.17 (d, J = 8.7 Hz, 1H), 8.01-7.92 (m, 2H), 7.48-7.40 (m, 2H), 7.24 (d, J = 9.9 Hz, 1H), 6.59 (d, J= 5.2 Hz, 1H), 3.68 (s, 2H), 2.54 (s, 3H), 2.11 (s, 3H), 1.49 (s, 9H) | 525.1 (M + H)$^+$ |

-continued

| No. | Structure | Name | ¹H NMR | Observed m/z |
|---|---|---|---|---|
| 525 | 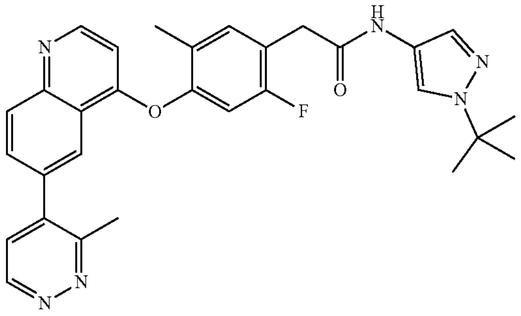 [SMILES: Cc1cc(CC(=O)Nc2cnn(C(C)(C)C)c2)c(F)cc1Oc1ccnc2ccc(-c3ccnnc3C)cc12] | N-(1-(tert-butyl)-1H-pyrazol-4-yl)-2-(2-fluoro-5-methyl-4-((6-(3-methylpyridazin-4-yl)quinolin-4-yl)oxy)phenyl) acetamide | (300 MHz, DMSO-$d_6$) δ 10.24 (s, 1H), 9.22 (d, J = 5.1 Hz, 1H), 8.78 (d, J = 5.2 Hz, 1H), 8.44 (d, J = 2.0 Hz, 1H), 8.18 (d, J = 8.7 Hz, 1H), 8.04-7.92 (m, 2H), 7.73 (d, J = 5.1 Hz, 1H), 7.46-7.42 (m, 2H), 7.25 (d, J = 10.0 Hz, 1H), 6.59 (d, J = 5.2 Hz, 1H), 3.68 (s, 2H), 2.70 (s, 3H), 2.11 (s, 3H), 1.49 (s, 9H) | 525.1 $(M + H)^+$ |
| 526 | 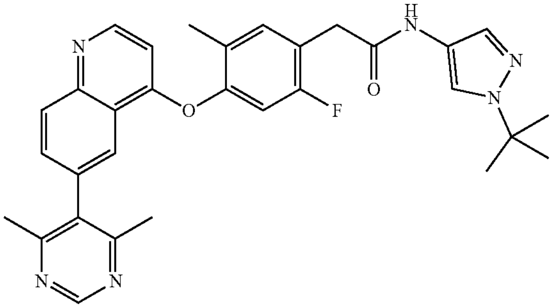 [SMILES: Cc1cc(CC(=O)Nc2cnn(C(C)(C)C)c2)c(F)cc1Oc1ccnc2ccc(-c3c(C)ncnc3C)cc12] | N-(1-(tert-butyl)-1H-pyrazol-4-yl)-2-(4-((6-(4,6-dimethylpyrimidin-5-yl)quinolin-4-yl)oxy)-2-fluoro-5-methylphenyl) acetamide | (400 MHz, DMSO-$d_6$) δ 10.22 (s, 1H), 8.95 (s, 1H), 8.76 (d, J = 5.1 Hz, 1H), 8.30-8.25 (m, 1H), 8.18 (dd, J = 8.7, 0.6 Hz, 1H), 7.94 (s, 1H), 7.79 (dd, J = 8.7, 2.0 Hz, 1H), 7.48-7.39 (m, 2H), 7.26 (d, J = 10.0 Hz, 1H), 6.59 (d, J = 5.1 Hz, 1H), 3.67 (s, 2H), 2.26 (s, 6H), 2.09 (s, 3H), 1.49 (s, 9H) | |

Example 45—Synthesis of N-(1-(tert-butyl)-1H-pyrazol-4-yl)-2-(2-fluoro-4-((6-sulfamoylquinolin-4-yl)oxy)phenyl)acetamide (Compound 46); Prepared According to General Scheme 25

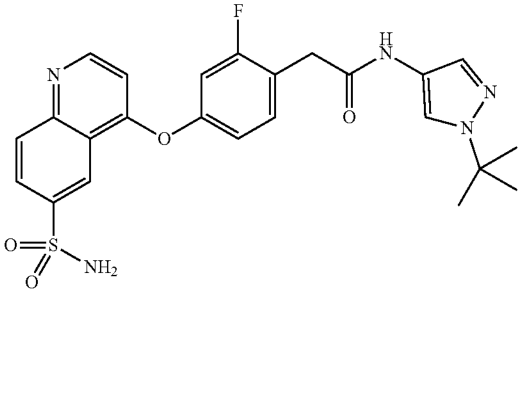 [SMILES: CC(C)(C)n1cc(NC(=O)Cc2ccc(Oc3ccnc4ccc(S(N)(=O)=O)cc34)cc2F)cn1]

Part I—Synthesis of 4-(4-(2-((1-(tert-butyl)-1H-pyrazol-4-yl)amino)-2-oxoethyl)-3-fluorophenoxy) quinoline-6-sulfinic Acid

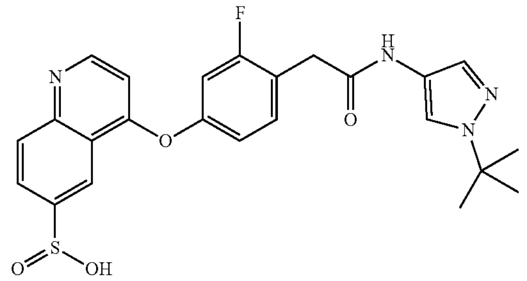 [SMILES: CC(C)(C)n1cc(NC(=O)Cc2ccc(Oc3ccnc4ccc(S(=O)O)cc34)cc2F)cn1]

$Pd(OAc)_2$ (0.23 g, 1.01 mmol, 0.10 equiv.) and di(1-adamantyl)-n-butylphosphine (0.54 g, 1.51 mmol, 0.15 equiv.) were added to a solution of 2-(4-((6-bromoquinolin-4-yl)oxy)-2-fluorophenyl)-N-(1-(tert-butyl)-1H-pyrazol-4-yl)acetamide (5.0 g, 10.1 mmol, 1.00 equiv., can be made according to Example 32, part I), DABSO (2.42 g, 10.1 mmol, 1.00 equiv.) and triethylamine (3.05 g, 30.2 mmol, 3.00 equiv.) in isopropanol (100 mL) under an inert atmosphere of nitrogen. The mixture was heated to 75° C. for 16 h. Subsequently, the solvent was removed under reduced pressure and the crude product was purified by column chromatography (DCM/MeOH 50:1 to 2:1). The title compound was obtained as a brown solid (1.2 g, 20%).

Part II—Synthesis of N-(1-(tert-butyl)-1H-pyrazol-4-yl)-2-(2-fluoro-4-((6-sulfamoylquinolin-4-yl)oxy)phenyl)acetamide (Compound 46)

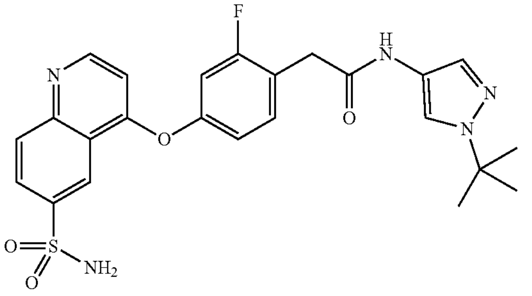 [SMILES: CC(C)(C)n1cc(NC(=O)Cc2ccc(Oc3ccnc4ccc(S(N)(=O)=O)cc34)cc2F)cn1]

A solution of 4-(4-(2-((1-(tert-butyl)-1H-pyrazol-4-yl)amino)-2-oxoethyl)-3-fluorophenoxy)quinoline-6-sulfinic acid (300 mg, 0.622 mmol, 1.00 equiv.), hydroxylamine-O-sulfonic acid (140.7 mg, 1.24 mmol, 2.00 equiv.), and sodium acetate (102.0 mg, 1.24 mmol, 2.00 equiv.) in THF/water (1:1, 8 mL) was stirred at room temperature overnight. Subsequently, the solvent was removed under reduced pressure and the crude product was purified by reversed-phase flash chromatography (column: C18 silica gel; mobile phase A: water, mobile phase B: ACN, gradient: 10-30% B in 30 min; wavelength: 210 nm). The title compound was obtained as a white solid (45.3 mg, 15%). LCMS (ESI) calculated for $C_{24}H_{25}FN_5O_4S$ $(M+H)^+$: 498.2, found: 498.1. $^1H$ NMR (300 MHz, DMSO-$d_6$) 310.23 (s, 1H), 8.86 (d, J=5.2 Hz, 1H), 8.77 (s, 1H), 8.27-8.16 (m, 2H), 7.94 (s, 1H), 7.61-7.52 (m, 2H), 7.46 (s, 1H), 7.36 (d, J=11.1 Hz, 1H), 7.20 (d, J=9.4 Hz, 1H), 6.81 (d, J=5.3 Hz, 1H), 3.72 (s, 2H), 1.49 (s, 9H).

Example 46—Synthesis of N-(1-(tert-butyl)-1H-pyrazol-4-yl)-2-(3-methyl-4-((6-(pyrrolidin-1-ylsulfonyl)quinolin-4-yl)oxy)phenyl)acetamide (Compound 257); Prepared According to General Scheme 24

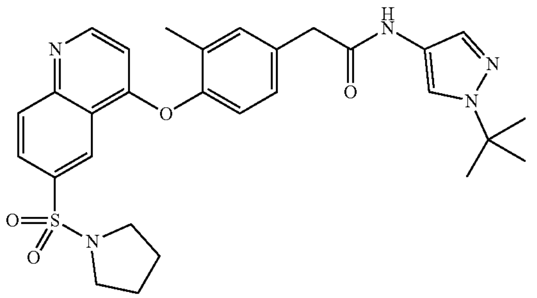 [SMILES: Cc1cc(CC(=O)Nc2cnn(C(C)(C)C)c2)ccc1Oc1ccnc2ccc(S(=O)(=O)N3CCCC3)cc12]

Part I—Synthesis of 4-chloro-6-(pyrrolidin-1-ylsulfonyl)quinoline

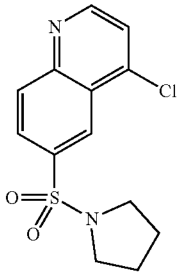 [SMILES: O=S(=O)(c1ccc2nccc(Cl)c2c1)N1CCCC1]

Pyrrolidine (0.73 g, 10.3 mmol, 1.50 equiv.) and pyridine (1.63 g, 20.6 mmol, 3.00 equiv.) were added to a solution of 4-chloroquinoline-6-sulfonyl chloride (1.80 g, 6.87 mmol, 1.00 equiv.) in DCM (18 mL) and the mixture was stirred at room temperature for 2 h. Subsequently, the reaction was quenched by the addition of a mixture of water and ice and the product was extracted with EtOAc (3×10 mL). The combined organic phases were dried over $Na_2SO_4$. The solvent was removed under reduced pressure and the crude product was triturated with petroleum ether. The title compound was obtained as a yellow solid (720 mg), which was used in the next reaction without further purification.

Part II—Synthesis of N-(1-(tert-butyl)-1H-pyrazol-4-yl)-2-(3-methyl-4-((6-(pyrrolidin-1-ylsulfonyl)quinolin-4-yl)oxy)phenyl)acetamide (Compound 257)

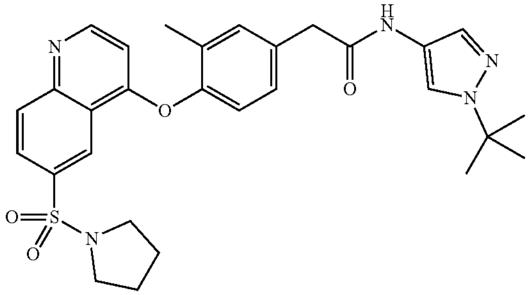 [SMILES: Cc1cc(CC(=O)Nc2cnn(C(C)(C)C)c2)ccc1Oc1ccnc2ccc(S(=O)(=O)N3CCCC3)cc12]

A solution of 4-chloro-6-(pyrrolidin-1-ylsulfonyl)quinoline (300 mg, 1.01 mmol, 1.00 equiv.), N-(1-(tert-butyl)-1H-pyrazol-4-yl)-2-(4-hydroxy-3-methylphenyl)acetamide (290 mg, 1.01 mmol, 1.00 equiv.), and DMAP (247 mg, 2.02 mmol, 2.00 equiv.) in chlorobenzene (3 mL) was heated to 130° C. overnight. Subsequently, the crude product was purified by preparative HPLC (column: YMC-Actus Triart C18 ExRS; 30×250 mm, 5 μm; mobile phase A: water (10 mmol/L $NH_4HCO_3$), mobile phase B: ACN; flow rate: 25 mL/min; gradient: 43-45% B in 13 min; wavelength: 220 nm). The title compound was obtained as a white solid (140.2 mg, 25%). LCMS (ESI) calculated for $C_{29}H_{34}N_5O_4S$ $(M+H)^+$: 548.2, found: 548.1. $^1H$ NMR (400 MHz, DMSO-$d_6$) δ 10.20 (s, 1H), 8.83 (d, J=5.2 Hz, 1H), 8.73 (d, J=2.0 Hz, 1H), 8.27-8.13 (m, 2H), 7.95 (s, 1H), 7.46 (s, 1H), 7.39 (d, J=2.1 Hz, 1H), 7.34-7.20 (m, 2H), 6.57 (d, J=5.2 Hz, 1H), 3.62 (s, 2H), 3.25-3.20 (m, 4H), 2.13 (s, 3H), 1.73-1.65 (m, 4H), 1.49 (s, 9H).

Example 47—Preparation of Additional Sulfonamides Compounds

Compounds in the table below were prepared based on experimental procedures described in Examples 45 and 46 and the detailed description.

| No. | Structure | Name | $^1$H NMR | Observed m/z |
|---|---|---|---|---|
| 118 | 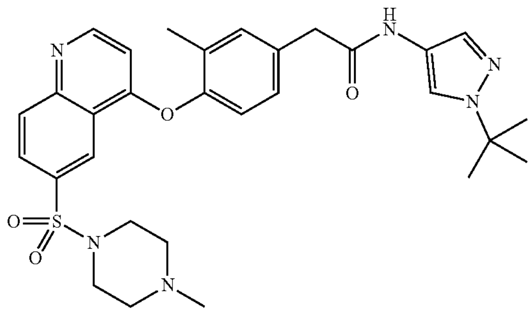 | N-(1-(tert-butyl)-1H-pyrazol-4-yl)-2-(3-methyl-4-((6-((4-methylpiperazin-1-yl)sulfonyl)quinolin-4-yl)oxy)phenyl)acetamide | (300 MHz, DMSO-$d_6$) δ 10.21 (s, 1H), 8.84 (d, J = 5.3 Hz, 1H), 8.69 (d, J = 2.1 Hz, 1H), 8.26 (d, J = 8.8 Hz, 1H), 8.07 (dd, J = 8.9, 2.1 Hz, 1H), 7.95 (s, 1H), 7.46 (s, 1H), 7.39 (d, J = 2.0 Hz, 1H), 7.34-7.22 (m, 2H), 6.58 (d, J = 5.2 Hz, 1H), 3.62 (s, 2H), 3.02 (t, J = 6.0 Hz, 4H), 2.38 (t, J = 6.0 Hz, 4H), 2.13 (s, 6H), 1.49 (s, 9H) | 577.2 $(M + H)^+$ |
| 119 | 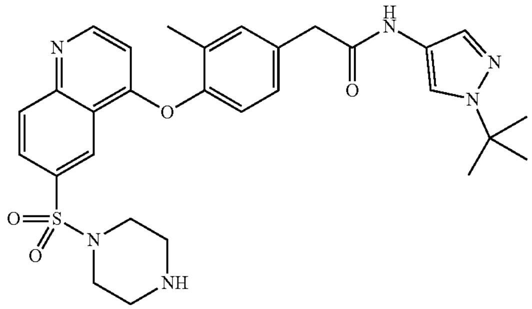 | N-(1-(tert-butyl)-1H-pyrazol-4-yl)-2-(3-methyl-4-((6-(piperazin-1-ylsulfonyl)quinolin-4-yl)oxy)phenyl)acetamide | (300 MHz, DMSO-$d_6$) δ 10.25 (s, 1H), 8.84 (d, J = 5.2 Hz, 1H), 8.67 (s, 1H), 8.27 (d, J = 8.7 Hz, 1H), 8.07 (d, J = 9.1 Hz, 1H), 7.95 (s, 1H), 7.57-7.19 (m, 4H), 6.57 (d, J = 5.1 Hz, 1H), 3.62 (s, 2H), 2.90 (s, 4H), 2.73 (s, 4H), 2.12 (s, 3H), 1.48 (s, 9H) | 563.2 $(M + H)^+$ |
| 126 | 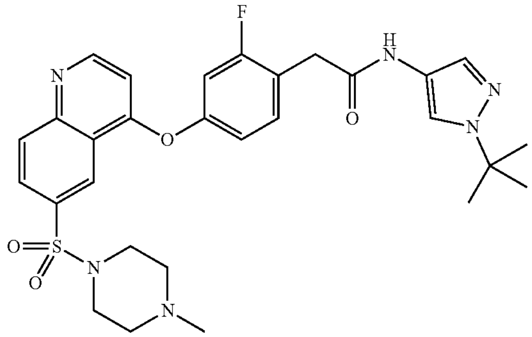 [SMILES: CN1CCN(S(=O)(=O)c2ccc3nccc(Oc4ccc(CC(=O)Nc5cnn(C(C)(C)C)c5)c(F)c4)c3c2)CC1] | N-(1-(tert-butyl)-1H-pyrazol-4-yl)-2-(2-fluoro-4-((6-((4-methylpiperazin-1-yl)sulfonyl)quinolin-4-yl)oxy)phenyl)acetamide | (300 MHz, DMSO-$d_6$) δ 10.22 (s, 1H), 8.91 (d, J = 5.2 Hz, 1H), 8.61 (d, J = 2.0 Hz, 1H), 8.28 (d, J = 8.9 Hz, 1H), 8.11-8.04 (m, 1H), 7.93 (s, 1H), 7.54 (d, J = 8.4 Hz, 1H), 7.45 (s, 1H), 7.38 (d, J = 10.4 Hz, 1H), 7.22 (d, J = 10.2 Hz, 1H), 6.86 (d, J = 5.3 Hz, 1H), 3.71 (s, 2H), 3.01 (s, 3H), 2.45-2.35 (m, 6H), 2.18-2.12 (m, 2H), 1.49 (s, 9H) | 581.2 $(M + H)^+$ |
| 128 | 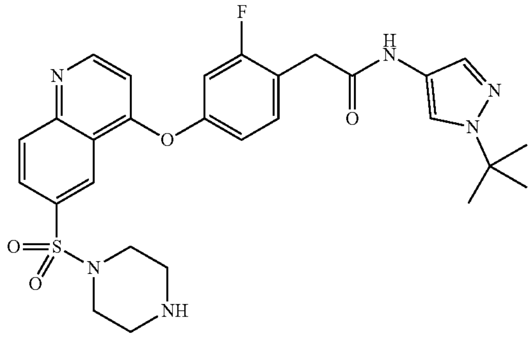 | N-(1-(tert-butyl)-1H-pyrazol-4-yl)-2-(2-fluoro-4-((6-(piperazin-1-ylsulfonyl)quinolin-4-yl)oxy)phenyl)acetamide | (300 MHz, DMSO-$d_6$) δ 10.23 (s, 1H), 8.91 (d, J = 5.2 Hz, 1H), 8.60 (d, J = 2.1 Hz, 1H), 8.28 (d, J = 8.9 Hz, 1H), 8.07 (dd, J = 8.9, 2.1 Hz, 1H), 7.94 (s, 1H), 7.56 (t, J = 8.5 Hz, 1H), 7.46 (s, 1H), 7.38 (dd, J = 10.4, 2.4 Hz, 1H), 7.22 (dd, J = 8.4, 2.4 Hz, 1H), 6.86 (d, J = 5.2 Hz, 1H), 3.72 (s, 2H), 2.89 (t, J = 4.8 Hz, 4H), 2.73 (t, J = 4.8 Hz, 4H), 1.49 (s, 9H) | 567.2 $(M + H)^+$ |

-continued

| No. | Structure | Name | $^1$H NMR | Observed m/z |
|---|---|---|---|---|
| 254 | 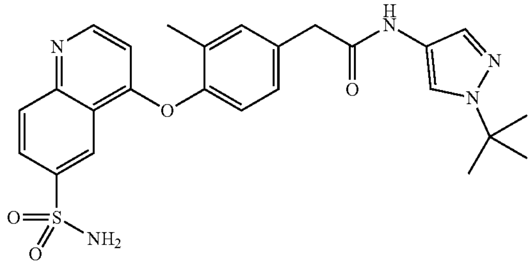 [SMILES: Cc1cc(CC(=O)Nc2cnn(C(C)(C)C)c2)ccc1Oc1ccnc2ccc(S(N)(=O)=O)cc12] | N-(1-(tert-butyl)-1H-pyrazol-4-yl)-2-(3-methyl-4-((6-sulfamoylquinolin-4-yl)oxy)phenyl) acetamide | (300 MHz, DMSO-$d_6$) δ 10.22 (s, 1H), 8.83 (d, J = 2.0 Hz, 1H), 8.79 (d, J = 5.2 Hz, 1H), 8.24-8.14 (m, 2H), 7.95 (d, J = 0.6 Hz, 1H), 7.62 (s, 2H), 7.46 (d, J = 0.7 Hz, 1H), 7.39 (d, J = 2.1 Hz, 1H), 7.31 (dd, J = 8.3, 2.2 Hz, 1H), 7.23 (d, J = 8.2 Hz, 1H), 6.52 (d, J = 5.1 Hz, 1H), 3.62 (s, 2H), 2.13 (s, 3H), 1.49 (s, 9H) | 494.0 $(M + H)^+$ |
| 255 | 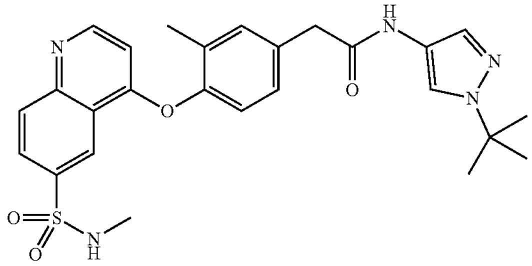 [SMILES: CNS(=O)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(3-methyl-4-((6-(N-methylsulfamoyl) quinolin-4-yl)oxy)phenyl) acetamide | (400 MHz, DMSO-$d_6$) δ 10.21 (s, 1H), 8.81-8.78 (m, 2H), 8.24 (d, J = 8.9 Hz, 1H), 8.11 (dd, J = 8.8, 2.1 Hz, 1H), 7.95 (s, 1H), 7.74 (q, J = 4.9 Hz, 1H), 7.45 (s, 1H), 7.38 (d, J = 2.1 Hz, 1H), 7.31 (dd, J = 8.3, 2.1 Hz, 1H), 7.24 (d, J = 8.2 Hz, 1H), 6.53 (d, J = 5.1 Hz, 1H), 3.61 (s, 2H), 2.48 (d, J = 4.8 Hz, 3H), 2.13 (s, 3H), 1.48 (s, 9H) | 508.1 $(M + H)^+$ |
| 256 | 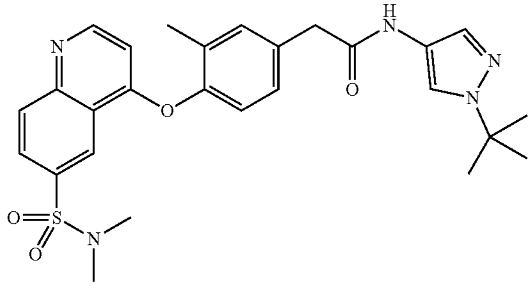 [SMILES: Cc1cc(CC(=O)Nc2cnn(C(C)(C)C)c2)ccc1Oc1ccnc2ccc(S(=O)(=O)N(C)C)cc12] | N-(1-(tert-butyl)-1H-pyrazol-4-yl)-2-(4-((6-(N,N-dimethylsulfamoyl) quinolin-4-yl)oxy)-3-methylphenyl) acetamide | (400 MHz, DMSO-$d_6$) δ 10.20 (s, 1H), 8.84 (d, J = 5.2 Hz, 1H), 8.70 (d, J = 2.0 Hz, 1H), 8.26 (d, J = 8.9 Hz, 1H), 8.10 (dd, J = 8.9, 2.1 Hz, 1H), 7.95 (s, 1H), 7.46 (s, 1H), 7.39 (d, J = 2.1 Hz, 1H), 7.32 (dd, J = 8.2, 2.2 Hz, 1H), 7.25 (d, J = 8.2 Hz, 1H), 6.58 (d, J = 5.2 Hz, 1H), 3.62 (s, 2H), 2.72 (s, 6H), 2.13 (s, 3H), 1.49 (s, 9H) | 522.1 $(M + H)^+$ |
| 258 | 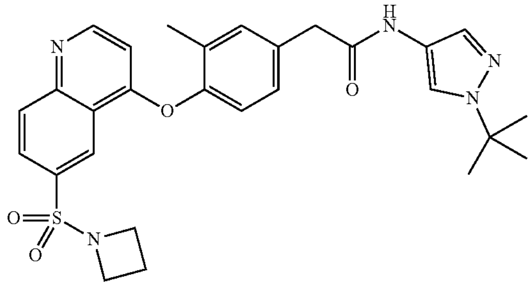 [SMILES: Cc1cc(CC(=O)Nc2cnn(C(C)(C)C)c2)ccc1Oc1ccnc2ccc(S(=O)(=O)N3CCC3)cc12] | 2-(4-((6-(azetidin-1-ylsulfonyl)quinolin-4-yl)oxy)-3-methylphenyl)-N-(1-(tert-butyl)-1H-pyrazol-4-yl)acetamide | (400 MHz, DMSO-$d_6$) δ 10.20 (s, 1H), 8.86 (d, J = 5.2 Hz, 1H), 8.74 (d, J = 2.0 Hz, 1H), 8.31 (d, J = 8.9 Hz, 1H), 8.15 (dd, J = 8.8, 2.1 Hz, 1H), 7.95 (d, J = 0.9 Hz, 1H), 7.46 (d, J = 0.7 Hz, 1H), 7.39 (d, J = 2.1 Hz, 1H), 7.32 (dd, J = 8.3, 2.2 Hz, 1H), 7.26 (d, J = 8.2 Hz, 1H), 6.59 (d, J = 5.3 Hz, 1H), 3.78 (t, J = 7.6 Hz, 4H), 3.62 (s, 2H), 2.14 (s, 3H), 2.07-1.98 (m, 2H), 1.49 (s, 9H) | 534.1 $(M + H)^+$ |
| 259 | 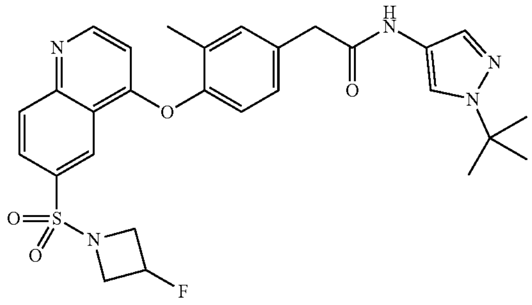 [SMILES: Cc1cc(CC(=O)Nc2cnn(C(C)(C)C)c2)ccc1Oc1ccnc2ccc(S(=O)(=O)N3CC(F)C3)cc12] | N-(1-(tert-butyl)-1H-pyrazol-4-yl)-2-(4-((6-((3-fluoroazetidin-1-yl)sulfonyl)quinolin-4-yl)oxy)-3-methylphenyl) acetamide | (400 MHz, DMSO-$d_6$) δ 10.20 (s, 1H), 8.86 (d, J = 5.2 Hz, 1H), 8.77 (d, J = 2.1 Hz, 1H), 8.30 (d, J = 8.9 Hz, 1H), 8.18 (dd, J = 8.9, 2.1 Hz, 1H), 7.95 (s, 1H), 7.46 (s, 1H), 7.39 (d, J = 2.1 Hz, 1H), 7.34-7.23 (m, 2H), 6.59 (d, J = 5.2 Hz, 1H), 5.22 (dddd, J = 57.2, 9.4, 6.2, 3.5 Hz, 1H), 4.17 (ddd, J = 20.9, 10.6, 5.9 Hz, 2H), 3.87 (ddd, J = 24.1, 10.6, 3.2 Hz, 2H), 3.62 (s, 2H), 2.14 (s, 3H), 1.49 (s, 9H) | 552.1 $(M + H)^+$ |

-continued

| No. | Structure | Name | $^1$H NMR | Observed m/z |
|---|---|---|---|---|
| 260 | 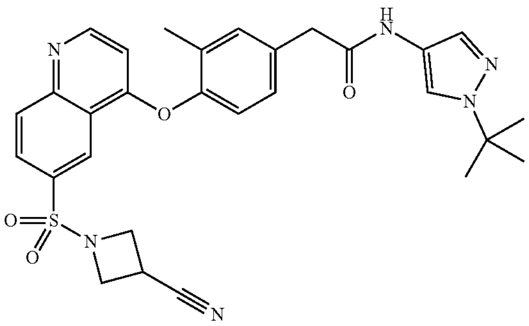 [SMILES: Cc1cc(CC(=O)Nc2cnn(C(C)(C)C)c2)ccc1Oc1ccnc2ccc(S(=O)(=O)N3CC(C#N)C3)cc12] | N-(1-(tert-butyl)-1H-pyrazol-4-yl)-2-(4-((6-((3-cyanoazetidin-1-yl)sulfonyl)quinolin-4-yl)oxy)-3-methylphenyl) acetamide | (400 MHz, DMSO-$d_6$) δ 10.21 (s, 1H), 8.87 (d, J = 5.2 Hz, 1H), 8.78 (d, J = 2.1 Hz, 1H), 8.32 (d, J = 8.9 Hz, 1H), 8.18 (dd, J = 8.9, 2.2 Hz, 1H), 7.95 (s, 1H), 7.46 (s, 1H), 7.39 (d, J = 2.2 Hz, 1H), 7.31 (d, J = 2.1 Hz, 1H), 7.25 (d, J = 8.3 Hz, 1H), 6.60 (d, J = 5.2 Hz, 1H), 4.09 (t, J = 8.7 Hz, 2H), 3.99 (dd, J = 8.5, 5.8 Hz, 2H), 3.69-3.64 (m, 1H), 3.62 (s, 2H), 2.14 (s, 3H), 1.49 (s, 9H) | 559.1 $(M + H)^+$ |
| 261 | 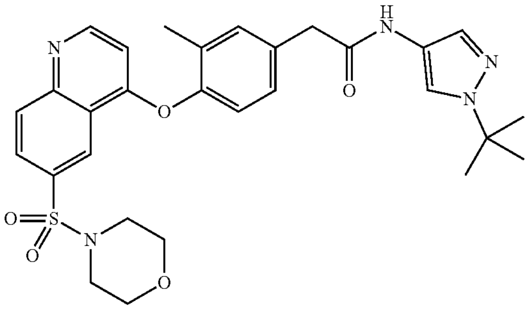 | N-(1-(tert-butyl)-1H-pyrazol-4-yl)-2-(3-methyl-4-((6-(morpholinosulfonyl) quinolin-4-yl)oxy)phenyl) acetamide | (400 MHz, DMSO-$d_6$) δ 10.19 (s, 1H), 8.85 (d, J = 5.2 Hz, 1H), 8.69 (d, J = 2.1 Hz, 1H), 8.27 (d, J = 8.9 Hz, 1H), 8.08 (dd, J = 8.9, 2.2 Hz, 1H), 7.94 (d, J = 0.7 Hz, 1H), 7.46 (d, J = 0.7 Hz, 1H), 7.38 (d, J = 2.1 Hz, 1H), 7.31 (dd, J = 8.3, 2.1 Hz, 1H), 7.25 (d, J = 8.2 Hz, 1H), 6.58 (d, J = 5.2 Hz, 1H), 3.65 (dd, J = 5.6, 3.8 Hz, 4H), 3.61 (s, 2H), 3.05-2.96 (m, 4H), 2.13 (s, 3H), 1.49 (s, 9H) | 564.1 $(M + H)^+$ |
| 262 | 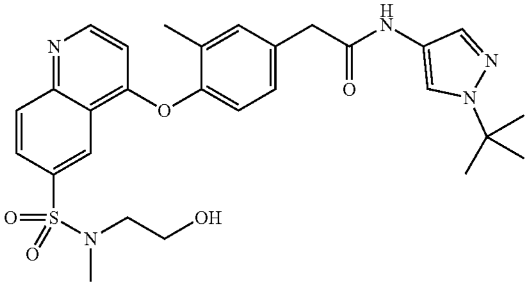 [SMILES: Cc1cc(CC(=O)Nc2cnn(C(C)(C)C)c2)ccc1Oc1ccnc2ccc(S(=O)(=O)N(C)CCO)cc12] | N-(1-(tert-butyl)-1H-pyrazol-4-yl)-2-(4-((6-(N-(2-hydroxyethyl)-N-methylsulfamoyl) quinolin-4-yl)oxy)-3-methylphenyl) acetamide | (400 MHz, DMSO-$d_6$) δ 10.21 (s, 1H), 8.82 (d, J = 5.2 Hz, 1H), 8.72 (d, J = 2.1 Hz, 1H), 8.24 (d, J = 8.9 Hz, 1H), 8.12 (dd, J = 8.9, 2.1 Hz, 1H), 7.95 (s, 1H), 7.46 (s, 1H), 7.39 (d, J = 2.1 Hz, 1H), 7.34-7.29 (m, 1H), 7.25 (d, J = 8.2 Hz, 1H), 6.56 (d, J = 5.2 Hz, 1H), 4.82 (t, J = 5.4 Hz, 1H), 3.62 (s, 2H), 3.55 (q, J = 5.8 Hz, 2H), 3.14 (t, J = 6.0 Hz, 2H), 2.83 (s, 3H), 2.13 (s, 3H), 1.49 (s, 9H) | 552.0 $(M + H)^+$ |
| 263 | 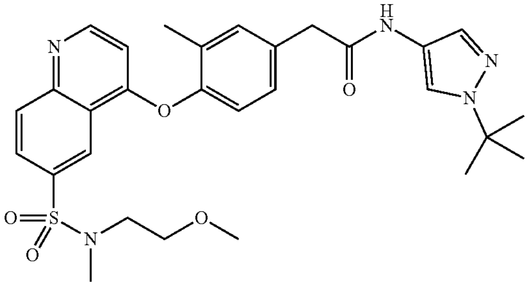 [SMILES: COCCN(C)S(=O)(=O)c1ccc2nccc(Oc3ccc(CC(=O)Nc4cnn(C(C)(C)C)c4)cc3C)c2c1] | N-(1-(tert-butyl)-1H-pyrazol-4-yl)-2-(4-((6-(N-(2-methoxyethyl)-N-methylsulfamoyl) quinolin-4-yl)oxy)-3-methylphenyl) acetamide | (400 MHz, DMSO-$d_6$) δ 10.21 (s, 1H), 8.82 (d, J = 5.3 Hz, 1H), 8.73 (d, J = 2.1 Hz, 1H), 8.24 (d, J = 8.9 Hz, 1H), 8.12 (dd, J = 8.9, 2.1 Hz, 1H), 7.95 (d, J = 0.7 Hz, 1H), 7.49-7.44 (m, 1H), 7.39 (d, J = 2.2 Hz, 1H), 7.34-7.29 (m, 1H), 7.25 (d, J = 8.2 Hz, 1H), 6.56 (d, J = 5.2 Hz, 1H), 3.62 (s, 2H), 3.48 (t, J = 5.4 Hz, 2H), 3.28 (t, J = 5.4 Hz, 2H), 3.20 (s, 3H), 2.82 (s, 3H), 2.13 (s, 3H), 1.49 (s, 9H) | |
| 267 | 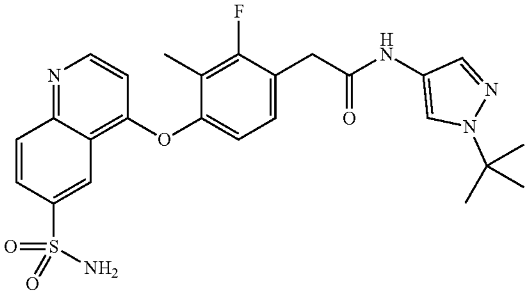 [SMILES: Cc1c(Oc2ccnc3ccc(S(N)(=O)=O)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-sulfamoylquinolin-4-yl)oxy)phenyl) acetamide | (400 MHz, DMSO-$d_6$) δ 10.24 (s, 1H), 8.88-8.78 (m, 2H), 8.27-8.17 (m, 2H), 7.95 (s, 1H), 7.63 (s, 2H), 7.46 (s, 1H), 7.39 (t, J = 8.4 Hz, 1H), 7.14 (d, J = 8.4 Hz, 1H), 6.61 (d, J = 5.2 Hz, 1H), 3.72 (s, 2H), 2.08 (d, J = 1.9 Hz, 3H), 1.49 (s, 9H) | 512.0 $(M + H)^+$ |

-continued

| No. | Structure | Name | $^1$H NMR | Observed m/z |
|---|---|---|---|---|
| 268 | 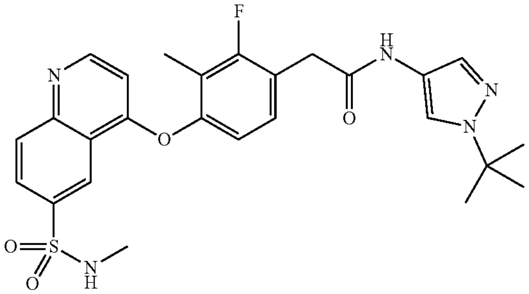 [SMILES: CNS(=O)(=O)c1ccc2nccc(Oc3ccc(CC(=O)Nc4cnn(C(C)(C)C)c4)c(F)c3C)c2c1] | N-(1-(tert-butyl)-1H-pyrazol-4-yl)-2-(2-fluoro-3-methyl-4-((6-(N-methylsulfamoyl)quinolin-4-yl)oxy)phenyl)acetamide | (400 MHz, DMSO-$d_6$) δ 10.23 (s, 1H), 8.84 (d, J = 5.2 Hz, 1H), 8.78 (d, J = 2.1 Hz, 1H), 8.26 (d, J = 8.8 Hz, 1H), 8.13 (dd, J = 8.9, 2.1 Hz, 1H), 7.95 (s, 1H), 7.76 (d, J = 5.2 Hz, 1H), 7.46 (s, 1H), 7.39 (t, J = 8.4 Hz, 1H), 7.16 (d, J = 8.4 Hz, 1H), 6.63 (d, J = 5.2 Hz, 1H), 3.72 (s, 2H), 2.49 (s, 3H), 2.08 (d, J = 1.9 Hz, 3H), 1.49 (s, 9H) | 526.0 $(M + H)^+$ |
| 269 | 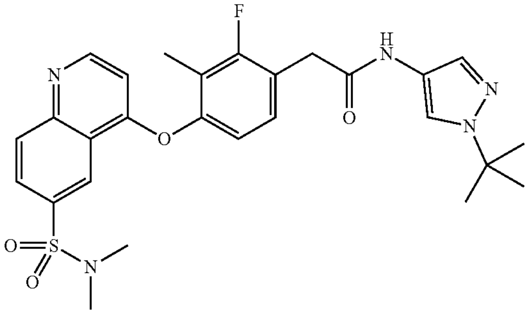 [SMILES: Cc1c(Oc2ccnc3ccc(S(=O)(=O)N(C)C)cc23)ccc(CC(=O)Nc2cnn(C(C)(C)C)c2)c1F] | N-(1-(tert-butyl)-1H-pyrazol-4-yl)-2-(4-((6-(N,N-dimethylsulfamoyl)quinolin-4-yl)oxy)-2-fluoro-3-methylphenyl)acetamide | (400 MHz, DMSO-$d_6$) δ 10.22 (s, 1H), 8.87 (d, J = 5.2 Hz, 1H), 8.69 (d, J = 2.0 Hz, 1H), 8.28 (d, J = 8.9 Hz, 1H), 8.11 (dd, J = 8.9, 2.1 Hz, 1H), 7.94 (d, J = 0.7 Hz, 1H), 7.46 (d, J = 0.7 Hz, 1H), 7.39 (t, J = 8.4 Hz, 1H), 7.21-7.13 (m, 1H), 6.65 (d, J = 5.2 Hz, 1H), 3.71 (s, 2H), 2.72 (s, 6H), 2.07 (d, J = 2.0 Hz, 3H), 1.49 (s, 9H) | 540.1 $(M + H)^+$ |
| 270 | 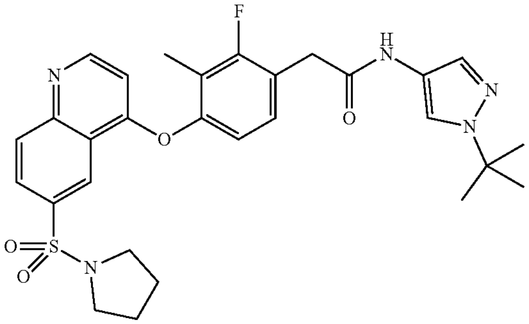 [SMILES: Cc1c(Oc2ccnc3ccc(S(=O)(=O)N4CCCC4)cc23)ccc(CC(=O)Nc2cnn(C(C)(C)C)c2)c1F] | N-(1-(tert-butyl)-1H-pyrazol-4-yl)-2-(2-fluoro-3-methyl-4-((6-(pyrrolidin-1-ylsulfonyl)quinolin-4-yl)oxy)phenyl)acetamide | (300 MHz, DMSO-$d_6$) δ 10.23 (s, 1H), 8.86 (d, J = 5.2 Hz, 1H), 8.73 (d, J = 2.0 Hz, 1H), 8.26 (d, J = 8.9 Hz, 1H), 8.17 (dd, J = 8.9, 2.1 Hz, 1H), 7.95 (d, J = 0.7 Hz, 1H), 7.46 (s, 1H), 7.39 (t, J = 8.4 Hz, 1H), 7.16 (dd, J = 8.4, 1.3 Hz, 1H), 6.66 (d, J = 5.2 Hz, 1H), 3.72 (s, 2H), 3.30-3.18 (m, 4H), 2.08 (d, J = 2.5 Hz, 3H), 1.82-1.64 (m, 4H), 1.49 (s, 9H) | 566.1 $(M + H)^+$ |
| 271 | 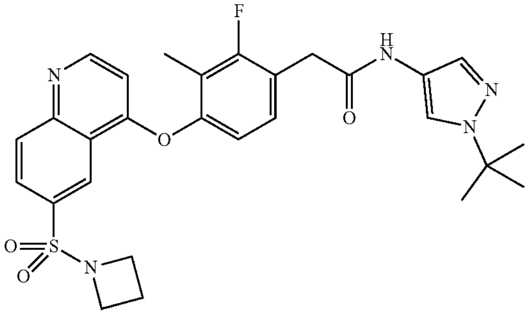 [SMILES: Cc1c(Oc2ccnc3ccc(S(=O)(=O)N4CCC4)cc23)ccc(CC(=O)Nc2cnn(C(C)(C)C)c2)c1F] | 2-(4-((6-(azetidin-1-ylsulfonyl)quinolin-4-yl)oxy)-2-fluoro-3-methylphenyl)-N-(1-(tert-butyl)-1H-pyrazol-4-yl)acetamide | (300 MHz, DMSO-$d_6$) δ 10.23 (s, 1H), 8.89 (d, J = 5.2 Hz, 1H), 8.73 (d, J = 2.0 Hz, 1H), 8.32 (d, J = 8.9 Hz, 1H), 8.16 (dd, J = 8.9, 2.1 Hz, 1H), 7.94 (s, 1H), 7.46 (s, 1H), 7.39 (t, J = 8.4 Hz, 1H), 7.17 (d, J = 8.4 Hz, 1H), 6.67 (d, J = 5.2 Hz, 1H), 3.78 (t, J = 7.6 Hz, 4H), 3.71 (s, 2H), 2.08 (d, J = 2.0 Hz, 3H), 2.02 (t, J = 7.6 Hz, 2H), 1.49 (s, 9H) | 552.0 $(M + H)^+$ |

-continued

| No. | Structure | Name | ¹H NMR | Observed m/z |
|---|---|---|---|---|
| 272 | 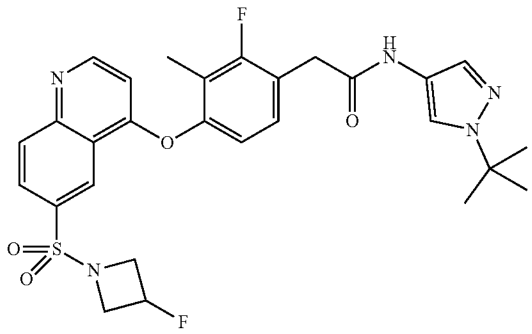 [SMILES: Cc1c(Oc2ccnc3ccc(S(=O)(=O)N4CC(F)C4)cc23)ccc(CC(=O)Nc2cnn(C(C)(C)C)c2)c1F] | N-(1-(tert-butyl)-1H-pyrazol-4-yl)-2-(2-fluoro-4-((6-((3-fluoroazetidin-1-yl)sulfonyl)quinolin-4-yl)oxy)-3-methylphenyl) acetamide | (300 MHz, DMSO-$d_6$) δ 10.23 (s, 1H), 8.89 (d, J = 5.2 Hz, 1H), 8.84-8.75 (m, 1H), 8.32 (d, J = 8.9 Hz, 1H), 8.20 (dd, J = 8.9, 2.1 Hz, 1H), 7.94 (s, 1H), 7.46 (s, 1H), 7.39 (t, J = 8.4 Hz, 1H), 7.17 (d, J = 8.2 Hz, 1H), 6.64 (dd, J = 18.1, 5.2 Hz, 1H), 5.37-5.02 (m, 1H), 4.17 (ddd, J = 20.9, 10.5, 5.8 Hz, 2H), 3.96-3.80 (m, 2H), 3.71 (s, 2H), 2.08 (d, J = 2.1 Hz, 3H), 1.49 (s, 9H) | 570.1 $(M + H)^+$ |
| 273 | 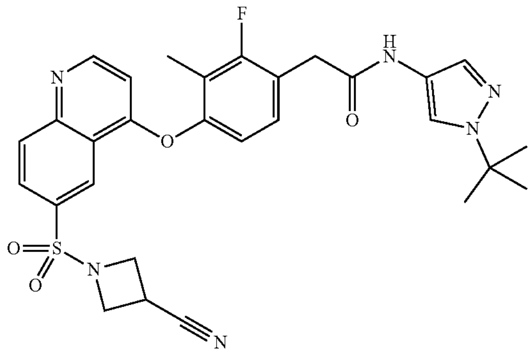 [SMILES: Cc1c(Oc2ccnc3ccc(S(=O)(=O)N4CC(C#N)C4)cc23)ccc(CC(=O)Nc2cnn(C(C)(C)C)c2)c1F] | N-(1-(tert-butyl)-1H-pyrazol-4-yl)-2-(4-((6-((3-cyanoazetidin-1-yl)sulfonyl)quinolin-4-yl)oxy)-2-fluoro-3-methylphenyl) acetamide | (300 MHz, DMSO-$d_6$) δ 10.23 (s, 1H), 8.90 (d, J = 5.2 Hz, 1H), 8.77 (d, J = 2.1 Hz, 1H), 8.33 (d, J = 8.9 Hz, 1H), 8.19 (dd, J = 8.9, 2.2 Hz, 1H), 7.95 (d, J = 0.7 Hz, 1H), 7.46 (d, J = 0.7 Hz, 1H), 7.40 (t, J = 8.4 Hz, 1H), 7.16 (d, J = 8.4 Hz, 1H), 6.68 (d, J = 5.2 Hz, 1H), 4.09 (t, J = 8.7 Hz, 2H), 3.99 (dd, J = 8.5, 5.8 Hz, 2H), 3.72 (s, 2H), 3.64 (ddd, J = 8.8, 5.8, 3.1 Hz, 1H), 2.08 (d, J = 1.9 Hz, 3H), 1.49 (s, 9H) | 577.2 $(M + H)^+$ |
| 274 | 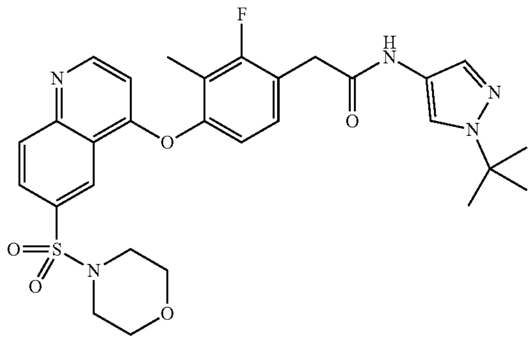 | N-(1-(tert-butyl)-1H-pyrazol-4-yl)-2-(2-fluoro-3-methyl-4-((6-(morpholinosulfonyl) quinolin-4-yl)oxy)phenyl) acetamide | (400 MHz, DMSO-$d_6$) δ 10.23 (s, 1H), 8.89 (d, J = 5.2 Hz, 1H), 8.69 (d, J = 2.1 Hz, 1H), 8.29 (d, J = 8.9 Hz, 1H), 8.09 (dd, J = 8.9, 2.1 Hz, 1H), 7.95 (d, J = 0.7 Hz, 1H), 7.46 (d, J = 0.7 Hz, 1H), 7.39 (t, J = 8.4 Hz, 1H), 7.17 (d, J = 8.4 Hz, 1H), 6.67 (d, J = 5.3 Hz, 1H), 3.72 (s, 2H), 3.66 (t, J = 4.7 Hz, 4H), 3.01 (t, J = 4.6 Hz, 4H), 2.08 (s, 3H), 1.49 (s, 9H) | 582.2 $(M + H)^+$ |
| 275 | 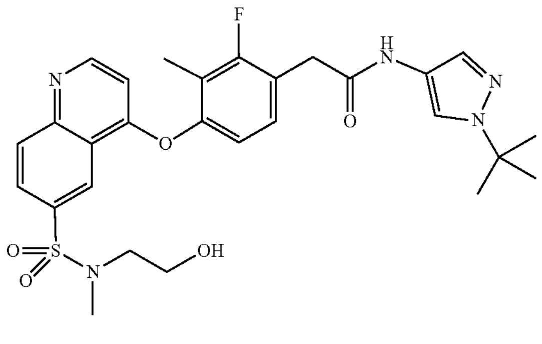 [SMILES: Cc1c(Oc2ccnc3ccc(S(=O)(=O)N(C)CCO)cc23)ccc(CC(=O)Nc2cnn(C(C)(C)C)c2)c1F] | N-(1-(tert-butyl)-1H-pyrazol-4-yl)-2-(2-fluoro-4-((6-(N-(2-hydroxyethyl)-N-methylsulfamoyl) quinolin-4-yl)oxy)-3-methylphenyl) acetamide | (300 MHz, DMSO-$d_6$) δ 10.23 (s, 1H), 8.86 (d, J = 5.2 Hz, 1H), 8.72 (d, J = 2.0 Hz, 1H), 8.26 (d, J = 8.9 Hz, 1H), 8.13 (dd, J = 8.9, 2.2 Hz, 1H), 7.95 (s, 1H), 7.46 (s, 1H), 7.39 (t, J = 8.4 Hz, 1H), 7.17 (d, J = 8.5 Hz, 1H), 6.65 (d, J = 5.2 Hz, 1H), 4.82 (t, J = 5.5 Hz, 1H), 3.72 (s, 2H), 3.55 (q, J = 5.9 Hz, 2H), 3.15 (t, J = 6.0 Hz, 2H), 2.83 (s, 3H), 2.08 (s, 3H), 1.50 (s, 9H) | 570.0 $(M + H)^+$ |

-continued

| No. | Structure | Name | $^1H$ NMR | Observed m/z |
|---|---|---|---|---|
| 276 | 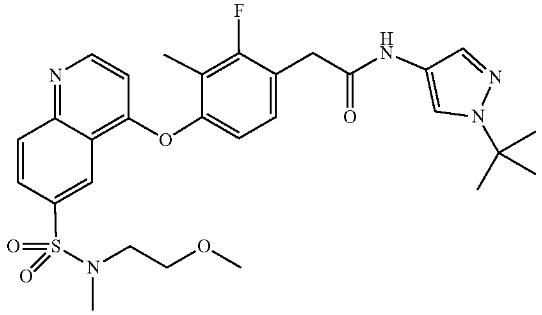 [SMILES: COCCN(C)S(=O)(=O)c1ccc2nccc(Oc3ccc(CC(=O)Nc4cnn(C(C)(C)C)c4)c(F)c3C)c2c1] | N-(1-(tert-butyl)-1H-pyrazol-4-yl)-2-(2-fluoro-4-((6-(N-(2-methoxyethyl)-N-methylsulfamoyl)quinolin-4-yl)oxy)-3-methylphenyl)acetamide | (300 MHz, DMSO-$d_6$) δ 10.22 (s, 1H), 8.85 (d, J = 5.2 Hz, 1H), 8.72 (d, J = 2.0 Hz, 1H), 8.25 (d, J = 8.9 Hz, 1H), 8.13 (dd, J = 8.9, 2.1 Hz, 1H), 7.94 (d, J = 0.7 Hz, 1H), 7.46 (d, J = 0.7 Hz, 1H), 7.39 (t, J = 8.4 Hz, 1H), 7.20-7.09 (m, 1H), 6.64 (d, J = 5.2 Hz, 1H), 3.71 (s, 2H), 3.48 (t, J = 5.4 Hz, 2H), 3.32 (s, 3H), 3.28 (t, J = 5.4 Hz, 2H), 2.82 (s, 3H), 2.07 (s, 3H), 1.49 (s, 9H) | 584.1 $(M + H)^+$ |
| 386 | 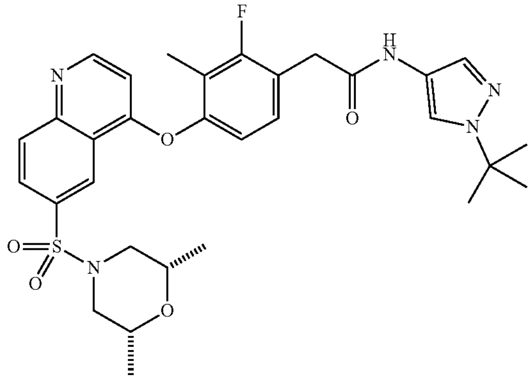 [SMILES: Cc1c(Oc2ccnc3ccc(S(=O)(=O)N4C[C@@H](C)O[C@@H](C)C4)cc23)ccc(CC(=O)Nc2cnn(C(C)(C)C)c2)c1F] | N-(1-(tert-butyl)-1H-pyrazol-4-yl)-2-(4-((6-(((2R,6S)-2,6-dimethylmorpholino)sulfonyl)quinolin-4-yl)oxy)-2-fluoro-3-methylphenyl)acetamide | | 610.0 $(M + H)^+$ |
| 387 | 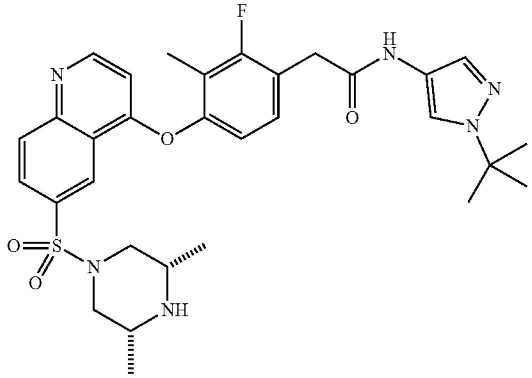 [SMILES: Cc1c(Oc2ccnc3ccc(S(=O)(=O)N4C[C@@H](C)N[C@@H](C)C4)cc23)ccc(CC(=O)Nc2cnn(C(C)(C)C)c2)c1F] | N-(1-(tert-butyl)-1H-pyrazol-4-yl)-2-(4-((6-(((3R,5S)-3,5-dimethylpiperazin-1-yl)sulfonyl)quinolin-4-yl)oxy)-2-fluoro-3-methylphenyl)acetamide | | 609.1 $(M + H)^+$ |
| 389 | 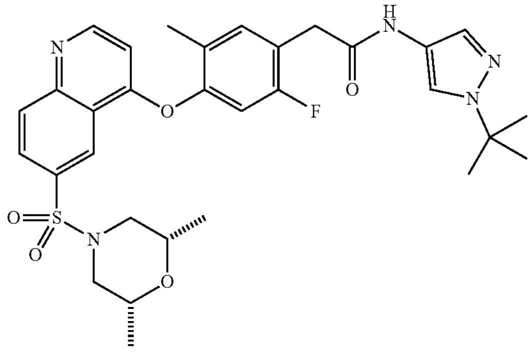 [SMILES: Cc1cc(CC(=O)Nc2cnn(C(C)(C)C)c2)c(F)cc1Oc1ccnc2ccc(S(=O)(=O)N3C[C@@H](C)O[C@@H](C)C3)cc12] | N-(1-(tert-butyl)-1H-pyrazol-4-yl)-2-(4-((6-(((2R,6S)-2,6-dimethylmorpholino)sulfonyl)quinolin-4-yl)oxy)-2-fluoro-5-methylphenyl)acetamide | | 610.1 $(M + H)^+$ |

-continued

| No. | Structure | Name | $^1$H NMR | Observed m/z |
|---|---|---|---|---|
| 390 | 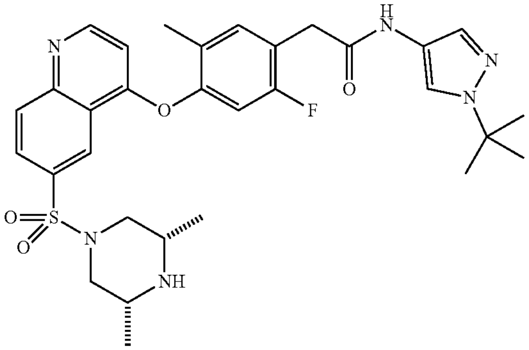 [SMILES: Cc1cc(CC(=O)Nc2cnn(C(C)(C)C)c2)c(F)cc1Oc1ccnc2ccc(S(=O)(=O)N3C[C@@H](C)N[C@@H](C)C3)cc12] | N-(1-(tert-butyl)-1H-pyrazol-4-yl)-2-(4-((6-(((3R,5S)-3,5-dimethylpiperazin-1-yl)sulfonyl)quinolin-4-yl)oxy)-2-fluoro-5-methylphenyl) acetamide | | 609.1 (M + H)$^+$ |

Example 48—RIPK2 Inhibition

RIPK2 inhibition was measured as follows:

Materials: RIPK2 enzyme was purchased from Carna (catalogue number 09-128). The V9102 ADP-Glo Kinase Assay (including ultrapure ATP, 10 mM) was purchased from Promega. Native swine MBP was used as the substrate for the reaction and was purchased from SignalChem Biotech (catalogue number M42-51N). Assay buffer used for the assay consisted of the following components: $MgCl_2$ (final concentration of 10 mM), Brij-35 (0.01%), DTT (final concentration of 2 mM), BSA (0.05%), EGTA (final concentration of 1 mM), and HEPE (pH 7.5 at final concentration of 50 mM).

Method: In a 384 well plate, 10 nL of test compound was dispensed using Echo550 and mixed with RIPK2 enzyme (final concentration of 5 nM) in assay buffer for 30 minutes at room temperature. Subsequently, ATP (final concentration of 150 μM) and MBP (final concentration of 0.02 μg/μL) were dissolved in assay buffer, added, and the mixture was incubated for 180 min at room temperature. Then ADP-Glo reagent was added and incubated for 60 min at room temperature. Last, Kinase Detection Reagent was added to the mixture and incubated for 60 min. The resulting luminescent signal was measured with an Envision reader to determine the amount of ADP produced. All plates contained vehicle controls (10 nL DMSO only) as a reference for the high control (0% kinase inhibition), and wells with no RIPK2 enzyme as reference for low control (100% kinase inhibition). Data were analyzed to determine the percent inhibition of ADP production in the presence of test compound using both low and high controls. Percent inhibition of test compound=100−(test compound RLU (relative luminescence units)−low control RLU)/(high control RLU−low control RLU). 4-parametric curve fit was used to determine the test compound concentration that results in 50% of RIPK2 kinase inhibition. The results are shown in Table 4.

TABLE 4

| Compound Number | RIPK2 $IC_{50}$ (nM) |
|---|---|
| 1 | 5.6 |
| 2 | <2.5 |
| 3 | <2.5 |
| 4 | 61.9 |

TABLE 4-continued

| Compound Number | RIPK2 $IC_{50}$ (nM) |
|---|---|
| 5 | 99.7 |
| 6 | 9.0 |
| 7 | 24.0 |
| 8 | 7.6 |
| 9 | 21.8 |
| 10 | 43.5 |
| 11 | 70.7 |
| 12 | 11.6 |
| 13 | 3.5 |
| 14 | 23.7 |
| 15 | 34.9 |
| 16 | 9.3 |
| 17 | 27.4 |
| 18 | 7.9 |
| 19 | 4.2 |
| 20 | 10.4 |
| 21 | 36.6 |
| 22 | 23.9 |
| 23 | 14.4 |
| 24 | 7.4 |
| 25 | 4.3 |
| 26 | 21.0 |
| 27 | 19.2 |
| 28 | 12.7 |
| 29 | 5.2 |
| 30 | 7.2 |
| 31 | 19.8 |
| 32 | 13.7 |
| 33 | 85.4 |
| 34 | 33.3 |
| 35 | 29.6 |
| 36 | 4.7 |
| 37 | 7.8 |
| 38 | <2.5 |
| 39 | <2.5 |
| 40 | <2.5 |
| 41 | 7.6 |
| 42 | 5.5 |
| 43 | 4.8 |
| 44 | 26.2 |
| 45 | <2.5 |
| 46 | <2.5 |
| 47 | 3.9 |
| 48 | 9.2 |
| 49 | 18.5 |
| 50 | 15.4 |
| 51 | 18.7 |
| 52 | 54.1 |
| 53 | 224.9 |
| 54 | 54.1 |
| 55 | 24.5 |
| 56 | 4.9 |

TABLE 4-continued

| Compound Number | RIPK2 $IC_{50}$ (nM) |
|---|---|
| 57 | <2.5 |
| 58 | 3.7 |
| 59 | 41.5 |
| 60 | 45.7 |
| 61 | 13.3 |
| 62 | 13.2 |
| 63 | 37.3 |
| 64 | 67.5 |
| 65 | <2.5 |
| 66 | <2.5 |
| 67 | <2.5 |
| 68 | <2.5 |
| 69 | 6.9 |
| 70 | 5.1 |
| 71 | 9.1 |
| 72 | <2.5 |
| 73 | 3.2 |
| 74 | 4.0 |
| 75 | <2.5 |
| 76 | <2.5 |
| 77 | <2.5 |
| 78 | 13.4 |
| 79 | <2.5 |
| 80 | 3.5 |
| 81 | <2.5 |
| 82 | <2.5 |
| 83 | <2.5 |
| 84 | 9.3 |
| 85 | 5.1 |
| 86 | <2.5 |
| 87 | <2.5 |
| 88 | <2.5 |
| 89 | <2.5 |
| 90 | 2.9 |
| 91 | <2.5 |
| 92 | <2.5 |
| 93 | <2.5 |
| 94 | <2.5 |
| 95 | <2.5 |
| 96 | <2.5 |
| 97 | <2.5 |
| 98 | <2.5 |
| 99 | <2.5 |
| 100 | <2.5 |
| 101 | <2.5 |
| 102 | <2.5 |
| 103 | <2.5 |
| 104 | <2.5 |
| 105 | <2.5 |
| 106 | <2.5 |
| 107 | <2.5 |
| 108 | 11.3 |
| 109 | 3.9 |
| 110 | <2.5 |
| 111 | 36.4 |
| 112 | 20.8 |
| 113 | <2.5 |
| 114 | <2.5 |
| 115 | <2.5 |
| 116 | <2.5 |
| 117 | <2.5 |
| 118 | <2.5 |
| 119 | <2.5 |
| 120 | <2.5 |
| 121 | <2.5 |
| 122 | <2.5 |
| 123 | <2.5 |
| 124 | <2.5 |
| 125 | <2.5 |
| 126 | <2.5 |
| 127 | <2.5 |
| 128 | <2.5 |
| 129 | 4.4 |
| 130 | <2.5 |
| 131 | <2.5 |
| 132 | <2.5 |
| 133 | 10.9 |

TABLE 4-continued

| Compound Number | RIPK2 $IC_{50}$ (nM) |
|---|---|
| 134 | <2.5 |
| 135 | <2.5 |
| 136 | <2.5 |
| 137 | <2.5 |
| 138 | 5.2 |
| 139 | 3.2 |
| 140 | 7.4 |
| 141 | 10.3 |
| 142 | <2.5 |
| 143 | <2.5 |
| 144 | <2.5 |
| 145 | 3.1 |
| 146 | <2.5 |
| 147 | <2.5 |
| 148 | <2.5 |
| 149 | <2.5 |
| 150 | 4.1 |
| 151 | <2.5 |
| 152 | <2.5 |
| 153 | 2.7 |
| 154 | <2.5 |
| 155 | 2.5 |
| 156 | 4.5 |
| 157 | 5.2 |
| 158 | <2.5 |
| 159 | <2.5 |
| 160 | <2.5 |
| 161 | <2.5 |
| 162 | <2.5 |
| 163 | <2.5 |
| 164 | <2.5 |
| 165 | <2.5 |
| 166 | <2.5 |
| 167 | <2.5 |
| 168 | <2.5 |
| 169 | <2.5 |
| 170 | <2.5 |
| 171 | <2.5 |
| 172 | <2.5 |
| 173 | <2.5 |
| 174 | <2.5 |
| 175 | <2.5 |
| 176 | 4.0 |
| 177 | <2.5 |
| 178 | 5.0 |
| 179 | <2.5 |
| 180 | <2.5 |
| 181 | <2.5 |
| 182 | <2.5 |
| 183 | <2.5 |
| 184 | 3.0 |
| 185 | <2.5 |
| 186 | <2.5 |
| 187 | <2.5 |
| 188 | <2.5 |
| 189 | <2.5 |
| 190 | <2.5 |
| 191 | <2.5 |
| 192 | <2.5 |
| 193 | <2.5 |
| 194 | <2.5 |
| 195 | <2.5 |
| 196 | <2.5 |
| 197 | <2.5 |
| 198 | <2.5 |
| 199 | <2.5 |
| 200 | <2.5 |
| 201 | <2.5 |
| 202 | <2.5 |
| 203 | <2.5 |
| 204 | <2.5 |
| 205 | <2.5 |
| 206 | <2.5 |
| 207 | <2.5 |
| 208 | <2.5 |
| 209 | <2.5 |
| 210 | <2.5 |

TABLE 4-continued

| Compound Number | RIPK2 $IC_{50}$ (nM) |
|---|---|
| 211 | <2.5 |
| 212 | <2.5 |
| 213 | <2.5 |
| 214 | <2.5 |
| 215 | <2.5 |
| 216 | <2.5 |
| 217 | <2.5 |
| 218 | <2.5 |
| 219 | <2.5 |
| 220 | <2.5 |
| 221 | <2.5 |
| 222 | <2.5 |
| 223 | <2.5 |
| 224 | <2.5 |
| 225 | <2.5 |
| 226 | <2.5 |
| 227 | <2.5 |
| 228 | 5.9 |
| 229 | <2.5 |
| 230 | <2.5 |
| 231 | <2.5 |
| 232 | <2.5 |
| 233 | <2.5 |
| 234 | <2.5 |
| 235 | <2.5 |
| 236 | <2.5 |
| 237 | <2.5 |
| 238 | <2.5 |
| 239 | <2.5 |
| 240 | <2.5 |
| 241 | <2.5 |
| 242 | <2.5 |
| 243 | <2.5 |
| 244 | <2.5 |
| 245 | <2.5 |
| 246 | 3.8 |
| 247 | <2.5 |
| 248 | <2.5 |
| 249 | <2.5 |
| 250 | <2.5 |
| 251 | <2.5 |
| 252 | <2.5 |
| 253 | <2.5 |
| 254 | <2.5 |
| 255 | <2.5 |
| 256 | <2.5 |
| 257 | <2.5 |
| 258 | <2.5 |
| 259 | <2.5 |
| 260 | 2.5 |
| 261 | <2.5 |
| 262 | <2.5 |
| 263 | <2.5 |
| 264 | <2.5 |
| 265 | <2.5 |
| 266 | <2.5 |
| 267 | <2.5 |
| 268 | <2.5 |
| 269 | <2.5 |
| 270 | <2.5 |
| 271 | <2.5 |
| 272 | <2.5 |
| 273 | <2.5 |
| 274 | <2.5 |
| 275 | <2.5 |
| 276 | <2.5 |
| 277 | <2.5 |
| 278 | <2.5 |
| 279 | <2.5 |
| 280 | <2.5 |
| 281 | <2.5 |
| 282 | <2.5 |
| 283 | <2.5 |
| 284 | <2.5 |
| 285 | <2.5 |
| 286 | <2.5 |
| 287 | <2.5 |

TABLE 4-continued

| Compound Number | RIPK2 $IC_{50}$ (nM) |
|---|---|
| 288 | <2.5 |
| 289 | 4.3 |
| 290 | <2.5 |
| 291 | <2.5 |
| 292 | <2.5 |
| 293 | <2.5 |
| 294 | <2.5 |
| 295 | <2.5 |
| 296 | <2.5 |
| 297 | <2.5 |
| 298 | <2.5 |
| 299 | <2.5 |
| 300 | <2.5 |
| 301 | <2.5 |
| 302 | <2.5 |
| 303 | <2.5 |
| 304 | <2.5 |
| 305 | <2.5 |
| 306 | <2.5 |
| 307 | <2.5 |
| 308 | <2.5 |
| 309 | <2.5 |
| 310 | <2.5 |
| 311 | <2.5 |
| 312 | <2.5 |
| 313 | <2.5 |
| 314 | <2.5 |
| 315 | <2.5 |
| 316 | <2.5 |
| 317 | <2.5 |
| 318 | <2.5 |
| 319 | <2.5 |
| 320 | <2.5 |
| 321 | <2.5 |
| 322 | <2.5 |
| 323 | <2.5 |
| 324 | <2.5 |
| 325 | <2.5 |
| 326 | <2.5 |
| 327 | <2.5 |
| 328 | <2.5 |
| 329 | <2.5 |
| 330 | <2.5 |
| 331 | <2.5 |
| 332 | <2.5 |
| 333 | <2.5 |
| 334 | <2.5 |
| 335 | <2.5 |
| 336 | <2.5 |
| 337 | <2.5 |
| 338 | <2.5 |
| 339 | <2.5 |
| 340 | <2.5 |
| 341 | <2.5 |
| 342 | <2.5 |
| 343 | <2.5 |
| 344 | <2.5 |
| 345 | <2.5 |
| 346 | <2.5 |
| 347 | <2.5 |
| 348 | <2.5 |
| 349 | <2.5 |
| 350 | <2.5 |
| 351 | <2.5 |
| 352 | <2.5 |
| 353 | <2.5 |
| 354 | <2.5 |
| 355 | <2.5 |
| 356 | <2.5 |
| 357 | <2.5 |
| 358 | <2.5 |
| 359 | <2.5 |
| 360 | <2.5 |
| 361 | <2.5 |
| 362 | <2.5 |
| 363 | <2.5 |
| 364 | <2.5 |

TABLE 4-continued

| Compound Number | RIPK2 $IC_{50}$ (nM) |
|---|---|
| 365 | <2.5 |
| 366 | <2.5 |
| 367 | <2.5 |
| 368 | <2.5 |
| 369 | <2.5 |
| 370 | <2.5 |
| 371 | <2.5 |
| 372 | <2.5 |
| 373 | <2.5 |
| 374 | <2.5 |
| 375 | <2.5 |
| 376 | <2.5 |
| 377 | <2.5 |
| 378 | <2.5 |
| 379 | <2.5 |
| 380 | <2.5 |
| 381 | <2.5 |
| 382 | <2.5 |
| 383 | <2.5 |
| 384 | <2.5 |
| 385 | <2.5 |
| 386 | <2.5 |
| 387 | <2.5 |
| 388 | <2.5 |
| 389 | 2.9 |
| 390 | <2.5 |
| 391 | <2.5 |
| 392 | <2.5 |
| 393 | <2.5 |
| 394 | <2.5 |
| 395 | <2.5 |
| 396 | <2.5 |
| 397 | <2.5 |
| 398 | <2.5 |
| 399 | <2.5 |
| 400 | <2.5 |
| 401 | <2.5 |
| 402 | <2.5 |
| 403 | <2.5 |
| 404 | <2.5 |
| 405 | <2.5 |
| 406 | <2.5 |
| 407 | <2.5 |
| 408 | <2.5 |
| 409 | <2.5 |
| 410 | <2.5 |
| 411 | <2.5 |
| 412 | <2.5 |
| 413 | <2.5 |
| 414 | <2.5 |
| 415 | <2.5 |
| 416 | <2.5 |
| 417 | <2.5 |
| 418 | <2.5 |
| 419 | <2.5 |
| 420 | <2.5 |
| 421 | <2.5 |
| 422 | <2.5 |
| 423 | <2.5 |
| 424 | <2.5 |
| 425 | <2.5 |
| 426 | <2.5 |
| 427 | <2.5 |
| 428 | <2.5 |
| 429 | <2.5 |
| 430 | <2.5 |
| 431 | <2.5 |
| 432 | 2.8 |
| 433 | <2.5 |
| 434 | 3.0 |
| 435 | <2.5 |
| 436 | <2.5 |
| 437 | <2.5 |
| 438 | 3.5 |
| 439 | <2.5 |
| 440 | <2.5 |
| 441 | <2.5 |

TABLE 4-continued

| Compound Number | RIPK2 $IC_{50}$ (nM) |
|---|---|
| 442 | <2.5 |
| 443 | <2.5 |
| 444 | <2.5 |
| 445 | <2.5 |
| 446 | 21.4 |
| 447 | <2.5 |
| 448 | <2.5 |
| 449 | <2.5 |
| 450 | <2.5 |
| 451 | <2.5 |
| 452 | <2.5 |
| 453 | <2.5 |
| 454 | <2.5 |
| 455 | <2.5 |
| 456 | <2.5 |
| 457 | <2.5 |
| 458 | <2.5 |
| 459 | <2.5 |
| 460 | <2.5 |
| 462 | <2.5 |
| 463 | <2.5 |
| 464 | <2.5 |
| 465 | <2.5 |
| 466 | <2.5 |
| 467 | <2.5 |
| 468 | <2.5 |
| 469 | <2.5 |
| 470 | <2.5 |
| 471 | <2.5 |
| 472 | <2.5 |
| 473 | <2.5 |
| 474 | 8.1 |
| 475 | 4.2 |
| 476 | <2.5 |
| 477 | <2.5 |
| 478 | <2.5 |
| 479 | <2.5 |
| 480 | <2.5 |
| 481 | <2.5 |
| 482 | <2.5 |
| 483 | <2.5 |
| 484 | <2.5 |
| 485 | <2.5 |
| 486 | <2.5 |
| 487 | <2.5 |
| 488 | <2.5 |
| 489 | <2.5 |
| 490 | <2.5 |
| 491 | <2.5 |
| 492 | <2.5 |
| 493 | <2.5 |
| 494 | <2.5 |
| 495 | <2.5 |
| 496 | <2.5 |
| 497 | <2.5 |
| 498 | <2.5 |
| 499 | <2.5 |
| 500 | <2.5 |
| 501 | <2.5 |
| 502 | <2.5 |
| 503 | <2.5 |
| 504 | <2.5 |
| 505 | <2.5 |
| 506 | <2.5 |
| 507 | <2.5 |
| 508 | <2.5 |
| 509 | <2.5 |
| 510 | <2.5 |
| 511 | <2.5 |
| 512 | <2.5 |
| 513 | <2.5 |
| 514 | <2.5 |
| 515 | <2.5 |
| 516 | <2.5 |
| 517 | <2.5 |
| 518 | <2.5 |
| 519 | <2.5 |

TABLE 4-continued

| Compound Number | RIPK2 $IC_{50}$ (nM) |
|---|---|
| 520 | <2.5 |
| 521 | <2.5 |
| 522 | 8.6 |
| 523 | 4.9 |
| 524 | <2.5 |
| 525 | <2.5 |
| 526 | <2.5 |
| 527 | <2.5 |
| 528 | <2.5 |
| 529 | <2.5 |
| 530 | <2.5 |
| 531 | <2.5 |
| 532 | <2.5 |
| 533 | <2.5 |
| 534 | <2.5 |
| 535 | <2.5 |
| 536 | <2.5 |
| 537 | <2.5 |
| 538 | <2.5 |
| 539 | <2.5 |
| 540 | <2.5 |
| 541 | <2.5 |
| 542 | <2.5 |
| 543 | <2.5 |
| 544 | <2.5 |
| 545 | <2.5 |
| 546 | <2.5 |
| 547 | <2.5 |
| 548 | <2.5 |
| 549 | <2.5 |
| 550 | <2.5 |
| 551 | <2.5 |
| 552 | <2.5 |
| 553 | <2.5 |
| 554 | <2.5 |
| 555 | <2.5 |
| 556 | <2.5 |
| 557 | <2.5 |
| 558 | <2.5 |
| 559 | <2.5 |
| 560 | <2.5 |
| 561 | <2.5 |
| 562 | <2.5 |
| 563 | <2.5 |
| 564 | <2.5 |
| 565 | <2.5 |
| 566 | <2.5 |
| 567 | <2.5 |
| 568 | <2.5 |
| 569 | <2.5 |
| 570 | 2.7 |
| 571 | 2.9 |
| 572 | <2.5 |
| 573 | <2.5 |
| 574 | <2.5 |
| 575 | <2.5 |
| 576 | <2.5 |
| 577 | <2.5 |
| 578 | <2.5 |
| 579 | <2.5 |
| 580 | <2.5 |
| 581 | <2.5 |
| 582 | <2.5 |
| 583 | <2.5 |
| 584 | <2.5 |
| 585 | <2.5 |
| 586 | <2.5 |
| 587 | <2.5 |
| 588 | <2.5 |
| 589 | <2.5 |
| 590 | <2.5 |
| 591 | <2.5 |
| 592 | 2.8 |
| 593 | <2.5 |
| 594 | <2.5 |
| 595 | <2.5 |
| 596 | <2.5 |

TABLE 4-continued

| Compound Number | RIPK2 $IC_{50}$ (nM) |
|---|---|
| 597 | <2.5 |
| 598 | <2.5 |
| 599 | <2.5 |
| 600 | <2.5 |
| 601 | <2.5 |
| 602 | <2.5 |
| 603 | <2.5 |
| 604 | <2.5 |
| 605 | <2.5 |
| 606 | 3.8 |
| 607 | 3.5 |
| 608 | 2.5 |
| 609 | <2.5 |
| 610 | <2.5 |
| 611 | <2.5 |
| 612 | <2.5 |
| 613 | <2.5 |
| 614 | <2.5 |
| 615 | 2.8 |
| 616 | <2.5 |
| 617 | <2.5 |
| 618 | <2.5 |
| 619 | <2.5 |
| 620 | <2.5 |
| 621 | <2.5 |
| 622 | <2.5 |

Example 49—Inhibition of Human NOD2 Signaling

Materials: Human NOD32-expressing 1TEK293 cells, HEK-Blue™-hNOD2 cells, were developed by Invivogen (catalogue number: hkb-hnod2) using co-transfection of the human NOD2 gene and an optimized secreted embryonic alkaline phosphatase (SEAP) reporter gene into HTEK293 cells. The cell maintenance medium consisted of DMEM (Giboc, 21063-029), heat inactivated FBS, penicillin (100 U/mL), streptomycin (100 μg/mL), Normocin (100 μg/mL), Blasticidin (30 μg/mL), and Zeocin (100 μg/mL). HEK-Blue™-hNOD2 cells were transferred to assay medium consisting of DMEM (Giboc, 21063-029), heat inactivated FBS, penicillin (100 U/mL) and streptomycin (100 μg/mL) prior to stimulation. Stimulation with a NOD2 ligand, L18-MDP (Invivogen, catalogue number: tlrl-lmdp) activated NF-κB and AP-1 which induced the production of SEAP. Levels of SEAP were determined with HEK-Blue™ Detection (referred to as QUANTI-Blue solution), a cell culture medium that allows for real-time detection of SEAP. QUANTI-Blue solution was prepared by adding 1 mL of QB reagent and 1 mL of QB buffer to 98 mL of sterile $H_2O$. Test compounds were prepared into a 10 mM DMSO solution and were serially diluted into 10 points using a 3-fold dilution in a 384 well plate using a TECAN EVO200.

Method: In a 384 well plate, 40 nL of test compound was dispensed using Echo550. HEK-Blue™-hNOD2 cells (Invivogen) were prepared into a cell suspension and 40 μL of the cell suspension (12500 cells per well) was dispensed into the 384 well plate. To activate NOD2 signaling, 40 nL of L18-MDP (final concentration of 0.5 ng/mL) was added and the plate was incubated at 37° C. in a $CO_2$ incubator for 24 hours. After the 24-hour incubation, 5 μL of the induced HEK-Blue hNOD2 cell supernatant was transferred to a new 384-well plate, centrifuged, and 45 μL of QUANTI-Blue solution was added per well and incubated for 3 hours at 37° C. SEAP levels were measured using an Ensight at 620 nm. Percent inhibition of NOD2 signaling was determined using the following equation: (high control−test compound signal)/(High control−low control)×100. The reaction high control was determined using wells with DMSO, cells, L18-MDP, and QUANTI-Blue solution. The reaction low control was determined using wells with DMSO, cells, and QUANTI-Blue solution. 4-parametric curve fit was used to determine the test compound concentration that results in 50% reduction of L18-MDP-driven human NOD2 signaling. The results are shown in Table 5.

Using the assay described above, inhibition of hNOD2 signaling was also evaluated for GSK 2983559 (Haile at al., *J. Med. Chem.* 2019, 62, 14, 6482-6494), a known RIPK2 kinase inhibitor:

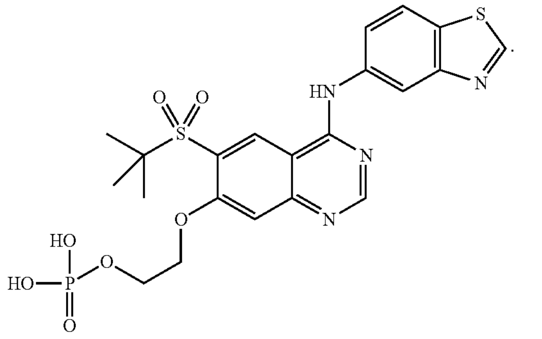 [SMILES: CC(C)(C)S(=O)(=O)c1cc2c(Nc3ccc4scnc4c3)ncnc2cc1OCCOP(=O)(O)O]

Unlike the RIPK2 scaffolding inhibitors of the present disclosure that exhibit desirable hNOD2 inhibition $IC_{50}$ values (see Table 5), hNOD2 inhibition $IC_{50}$ for GSK 2983559 was determined to be greater than 10 μM.

Example 50—Inhibition of TNF-Alpha Secretion in Human Whole Blood

Materials: Assay medium consisted of RPMI 1640 medium (catalogue number: 11875119) and 10% heat inactivated FBS (Cytvia). U-PLEX Biomarker Assay (cat #K15067L-4) to detect levels of TNF-alpha was purchased from Meso Scale Discovery. Heparinized whole blood from healthy donors/volunteers was obtained through Research Blood Components, LLC.

Method: Priming of human whole blood with IFN-gamma (catalogue number: 285-IF-100) followed by stimulation with a NOD2 ligand, L18-MDP (Invivogen, catalogue number: tlrl-lmdp), resulted in secretion of TNF-alpha. Test compounds were prepared into a 10 mM DMSO solution and serially diluted into 9 points using a 3-fold dilution in a 96 well plate. A 10× working stock solution of recombinant human IFN-gamma (final concentration of 10 ng/mL) was prepared in assay medium and used to prepare a 10× solution of test compound. 20 μL of 10×IFN-gamma and test compound (or DMSO control) was added to a 96-well plate. 160 μL of heparinized whole blood obtained from healthy donors was dispensed into individual wells of the 96-well plate and placed on a plate shaker (150 rpm) and incubated for 60 min at 37° C. in a $CO_2$ incubator. Subsequently, 20 μL of L18-MDP (final concentration of 100 ng/mL) was added to the appropriate wells and further incubated for 16 hours on a plate shaker (150 rpm) at 37° C. in a $CO_2$ incubator. The final concentration of DMSO was 0.05% (v/v) in all wells. After incubation, 100 μL of DPBS was added per well, mixed by shaking at 500 rpm for 2 minutes, followed by centrifugation (400×g for 10 minutes) and collection of supernatants. TNF-alpha in supernatants was measured using MSD immunoassay (MesoScale Discovery). 4-parametric curve fit was used to determine the test compound concentration that results in 50% reduction of TNF-alpha concentration in supernatant relative to assay controls. The results are shown in Table 6.

Example 51—Inhibition of the Interaction of RIPK2 with XIAP

An assay measuring the RIPK2 and XIAP protein-protein interaction was generated using the NanoBRET protein: protein interaction system (Promega) which measures the energy transfer from a bioluminescent protein donor (NanoLuc fusion protein) to a fluorescent protein acceptor (Halotag fusion protein). In this assay, the C-terminus of full-length XIAP was appended with the NanoLuc fusion protein and the N-terminus of full-length RIPK2 was appended with the HaloTag fusion protein. Assay medium consisted of Opti-MEM I reduced serum medium with no phenol red plus 4% heat inactivated FBS. Transfection reagents were combined in a microfuge tube as follows: 400 μL of assay medium, 8 μL of vector with N-terminus of RIPK2 HaloTag fusion protein (vector concentration at 1 μg/μL), 0.8 μL of vector with C-terminus of XIAP NanoLuc fusion protein (vector concentration at 1 μg/μL), and 24 μL of FuGENE HD transfection reagent (Promega, catalogue number E2312). NanoBRET Nano-Glo Detection System was purchased from Promega (catalogue number N1663) and contained the HaloTag NanoBRET 618 ligand and NanoBRET Nano-Glo substrate. Test compounds were prepared into a 10 mM DMSO solution and were serially diluted into 10 points using a 3-fold dilution in a 384 well plate using a TECAN EV0200.

Method: HEK293T cells were transfected with the RIPK2 HaloTag fusion and XIAP NanoLuc fusion vectors in suspension. Briefly, a 16 mL cell suspension of HEK293T cells (final density of 125 000 cells/mL) in assay medium was prepared in a 50 mL tube. Transfection reagents were pre-mixed and incubated at room temperature for 30 minutes. Then the total transfection reagent mixture was added dropwise to the 16 mL cell suspension and mixed gently. 40 μL of the cells and transfection reagent suspension was plated into a white 384 well plate and incubated at 37° C. in a $CO_2$ incubator for 24 hours. The next day, transfected cells were first treated with test compound (total volume of 40 nL) and incubated for 2 hours followed by addition of the HaloTag NanoBRET 618 ligand (100 nM, total volume of 40 nL) and again incubated for 2 hours. Lastly, a 3× solution of NanoBRET Nano-Glo substrate in Opti-MEM I reduced serum media (no phenol red; 20 μL total volume) was added to each well and incubated for 2-3 minutes at room temperature. The plate was then measured using 460 nm filter (donor emission) and 618 nm filter (acceptor emission) in an EnVision multimode plate reader (PerkinElmer). The NanoBRET ratio values were determined by dividing the acceptor emission value by the donor emission value for each sample. 4-parametric curve fit was used to determine the test compound concentration that results in 500 reduction of the RIPK2 and XIAP protein-protein interaction relative to assay controls. The results are shown in Table 7.

Using the assay described above, inhibition of the RIPK2 and XIAP protein-protein interaction was also evaluated for GSK 2983559. Unlike the RTPK2 scaffolding inhibitors of the present disclosure, GSK 2983559 showed no inhibition of the RTPK2 and XIAP protein-protein interaction.

TABLE 5

| Compound Number | hNOD2 $IC_{50}$ (nM) |
|---|---|
| 8 | 11.4 |
| 20 | 21.7 |
| 38 | 9.0 |
| 43 | 39.3 |
| 78 | 32.7 |
| 82 | 1.9 |
| 83 | 5.9 |
| 84 | 19.2 |
| 86 | 0.7 |
| 91 | 0.5 |
| 92 | 6.6 |
| 99 | 0.3 |
| 113 | 2.2 |
| 174 | 0.2 |
| 179 | 38.1 |
| 182 | 2.0 |
| 197 | 4.0 |
| 215 | 3.2 |
| 239 | 2.9 |
| 253 | 7.2 |
| 299 | 3.4 |
| 306 | 1.3 |
| 359 | 0.5 |
| 360 | 0.2 |
| 413 | 2.5 |
| 429 | 1.6 |
| 441 | 0.2 |
| 442 | 0.2 |
| 443 | 1.1 |
| 462 | 7.5 |
| 463 | 4.0 |
| 464 | 0.5 |
| 465 | 0.2 |
| 466 | 2.5 |
| 467 | 1.7 |
| 468 | 2.1 |
| 469 | 1.6 |
| 470 | 1.1 |
| 471 | 9.9 |
| 472 | 0.3 |
| 473 | 7.8 |
| 474 | 95.6 |
| 475 | 54.0 |
| 476 | 5.9 |
| 477 | 5.4 |
| 478 | 26.0 |
| 479 | 1.4 |
| 480 | 0.8 |
| 481 | 4.2 |
| 482 | 0.3 |
| 483 | 0.6 |
| 484 | 0.4 |
| 485 | 0.3 |
| 486 | 1.8 |
| 487 | 0.3 |
| 488 | 0.2 |
| 489 | 0.1 |
| 490 | 0.1 |
| 491 | 0.1 |
| 492 | 3.7 |
| 493 | 0.2 |
| 494 | 0.4 |
| 495 | 0.5 |
| 496 | 0.5 |
| 497 | 0.6 |
| 498 | 0.4 |
| 499 | 1.1 |
| 500 | 0.4 |
| 501 | 2.2 |
| 502 | 0.8 |
| 503 | 0.2 |
| 504 | 0.2 |
| 505 | 3.5 |
| 506 | 2.2 |
| 507 | 0.3 |
| 508 | 2.5 |
| 509 | 14.2 |

TABLE 5-continued

| Compound Number | hNOD2 $IC_{50}$ (nM) |
|---|---|
| 510 | 8.4 |
| 511 | 8.0 |
| 512 | 2.4 |
| 513 | 3.1 |
| 514 | 1.5 |
| 515 | 1.4 |
| 516 | 1.0 |
| 517 | 2.7 |
| 518 | 1.5 |
| 519 | 0.6 |
| 520 | 0.7 |
| 521 | 2.2 |
| 522 | 25.8 |
| 523 | 18.5 |
| 524 | 0.7 |
| 525 | 5.5 |
| 526 | 16.1 |
| 527 | 0.7 |
| 528 | 0.8 |
| 529 | 14.3 |
| 530 | 21.5 |
| 531 | 41.6 |
| 532 | 16.9 |
| 533 | 10.4 |
| 534 | 6.0 |
| 535 | 0.8 |
| 536 | 0.7 |
| 537 | 0.4 |
| 538 | 0.2 |
| 539 | 1.2 |
| 540 | 0.5 |
| 541 | 0.3 |
| 542 | 0.2 |
| 543 | 1.2 |
| 544 | 2.0 |
| 545 | 1.8 |
| 546 | 1.4 |
| 547 | 1.3 |
| 548 | 0.9 |
| 549 | 18.2 |
| 550 | 11.0 |
| 551 | 1.7 |
| 552 | 1.7 |
| 553 | 5.6 |
| 554 | 4.9 |
| 555 | 0.1 |
| 556 | 0.9 |
| 557 | 0.3 |
| 558 | 0.7 |
| 559 | 1.0 |
| 560 | 8.9 |
| 561 | 15.4 |
| 562 | 1.2 |
| 563 | 1.9 |
| 564 | 10.8 |
| 565 | 6.9 |
| 566 | 11.1 |
| 567 | 9.8 |
| 568 | 24.4 |
| 569 | 10.4 |
| 570 | 10.5 |
| 571 | 4.5 |
| 572 | 1.1 |
| 573 | 1.0 |
| 574 | 3.2 |
| 575 | 2.2 |
| 576 | 5.2 |
| 577 | 2.0 |
| 578 | 0.7 |
| 579 | 0.8 |
| 580 | 1.2 |
| 581 | 1.2 |
| 582 | 0.6 |
| 583 | 1.2 |
| 584 | 1.3 |
| 585 | 0.9 |
| 586 | 0.6 |

TABLE 5-continued

| Compound Number | hNOD2 $IC_{50}$ (nM) |
|---|---|
| 587 | 28.6 |
| 588 | 36.0 |
| 589 | 48.6 |
| 590 | 31.2 |
| 591 | 46.7 |
| 592 | 80.2 |
| 593 | 6.7 |
| 594 | 27.0 |
| 595 | 19.3 |
| 596 | 0.7 |
| 597 | 1.3 |
| 598 | 2.3 |
| 599 | 1.7 |
| 600 | 1.4 |
| 601 | 1.4 |
| 602 | 8.0 |
| 603 | 2.5 |
| 604 | 12.4 |
| 605 | 15.6 |
| 606 | 0.8 |
| 607 | 6.1 |
| 608 | 1.6 |
| 609 | 46.3 |
| 610 | 2.1 |
| 611 | 0.9 |
| 612 | 3.6 |
| 613 | 4.6 |
| 614 | 3.7 |
| 615 | 17.5 |
| 616 | 22.4 |
| 617 | 1.1 |
| 618 | 0.3 |
| 619 | 1.4 |
| 620 | 6.7 |
| 621 | 11.7 |
| 622 | 2.0 |

TABLE 6

| Compound Number | Human Whole Blood TNFα $IC_{50}$ (nM) |
|---|---|
| 8 | 103 |
| 20 | 12 |
| 38 | 5 |
| 43 | 5 |
| 78 | 7 |
| 82 | 4 |
| 83 | 3 |
| 84 | 4 |
| 86 | 9 |
| 91 | 6 |
| 92 | 40 |
| 99 | 8 |
| 113 | 14 |
| 174 | 2 |
| 179 | 6 |
| 182 | 14 |
| 197 | 24 |
| 215 | 55 |
| 239 | 37 |
| 253 | 7 |
| 299 | 49 |
| 306 | 8 |
| 359 | 4 |
| 360 | 7 |
| 413 | 13 |
| 429 | 18 |
| 441 | 6 |
| 442 | 7 |
| 443 | 83 |

TABLE 6-continued

| Compound Number | Human Whole Blood TNFα $IC_{50}$ (nM) |
|---|---|
| 465 | 2.6 |
| 468 | 8.4 |
| 472 | 4.1 |
| 492 | 5.9 |
| 543 | 3 |
| 544 | 4.5 |
| 545 | 5.9 |
| 546 | 4 |
| 559 | 2 |

TABLE 7

| Compound Number | NanoBRET Scaffolding $IC_{50}$ (nM) |
|---|---|
| 8 | 6 |
| 20 | 144 |
| 38 | 54 |
| 43 | 218 |
| 78 | 37 |
| 82 | 6 |
| 83 | 29 |
| 84 | 37 |
| 86 | 12 |
| 91 | 12 |
| 92 | 132 |
| 99 | 15 |
| 113 | 33 |
| 174 | 5 |
| 179 | 465 |
| 182 | 18 |
| 197 | 93 |
| 215 | 39 |
| 239 | 20 |
| 253 | 174 |
| 299 | 73 |
| 359 | 14 |
| 360 | 8 |
| 413 | 27 |
| 429 | 44 |
| 441 | 8 |
| 442 | 3 |
| 443 | 11 |
| 464 | 7.5 |
| 465 | 4.2 |
| 466 | 48.0 |
| 467 | 30.2 |
| 468 | 69.1 |
| 469 | 6.6 |
| 470 | 13.1 |
| 471 | 1023.1 |
| 472 | 13.3 |
| 473 | 171.0 |
| 474 | 620.5 |
| 476 | 52.1 |
| 477 | 38.7 |
| 479 | 5.8 |
| 481 | 4.5 |
| 482 | 4.6 |
| 487 | 47.5 |
| 488 | 3.4 |
| 489 | 7.1 |
| 490 | 24.2 |
| 492 | 22.0 |
| 494 | 20.5 |
| 495 | 70.8 |
| 496 | 127.0 |
| 497 | 10.8 |
| 498 | 13.7 |
| 499 | 21.9 |

TABLE 7-continued

| Compound Number | NanoBRET Scaffolding $IC_{50}$ (nM) |
|---|---|
| 500 | 7.4 |
| 501 | 62.9 |
| 502 | 17.5 |
| 503 | 63.1 |
| 504 | 3.4 |
| 505 | 128.0 |
| 506 | 73.6 |
| 509 | 188.7 |
| 510 | 172.1 |
| 512 | 57.6 |
| 513 | 34.4 |
| 515 | 170.4 |
| 516 | 102.8 |
| 517 | 311.4 |
| 518 | 26.9 |
| 523 | 132.9 |
| 529 | 75.0 |
| 530 | 94.3 |
| 543 | 77.5 |
| 544 | 123.2 |
| 545 | 183.6 |
| 546 | 203.7 |
| 547 | 153.0 |
| 548 | 108.0 |
| 551 | 87.1 |
| 552 | 60.9 |
| 555 | 7.3 |
| 556 | 42.1 |
| 557 | 35.1 |
| 558 | 57.3 |
| 559 | 95.8 |
| 560 | 300.7 |
| 562 | 61.1 |
| 563 | 176.2 |
| 566 | 459.0 |
| 568 | 179.0 |
| 572 | 37.2 |
| 581 | 61.4 |
| 582 | 36.3 |
| 583 | 42.4 |
| 584 | 44.6 |
| 585 | 29.3 |

Example 52—In Vivo Inhibition of Monocyte Chemoattractant Protein-1 (MCP-1)

The compounds of the disclosure were tested for their ability to inhibit RTPK2 activity in vivo, as measured by plasma levels of cytokine MCP-1. C57BL/6 mice were dosed orally with the compounds of the disclosure one hour prior to intra-peritoneal administration of muramyldipeptide (MDP), a NOD2 agonist. Intraperitoneal (i.p.) injection of MDP in mice induces an increase in circulating levels of proinflammatory cytokines, such as MCP-1, in a RIPK2-dependent manner. This acute mouse MDP challenge represents a screening model to measure the ability of compounds to inhibit RIPK2 in vivo.

Materials: Female C57BL/6 mice (6-13 weeks of age) were purchased from the Jackson Laboratory. All mice were maintained under a 12 h light/dark cycle and had food and water ad libitum. Muramyldipeptide (MDP) was purchased from Invivogen (catalog No. tlrl-mdp; lot No. 6231-43-02). Mouse MCP-1 was measured using U-PLEX MSD kit (Meso Scale Discovery (MSD), catalog No. K15069M-2). Carboxymethyl cellulose was purchased from Sigma-Aldrich (catalog No. C5678-500 ml), Tween80 was purchased from Sigma-Aldrich (catalog No. P1754-500 ml), (Hydroxypropyl)-β-cyclodextrin (HP-β-CD) was purchased from Sigma-Aldrich (catalog No. C332607-500G), PBS was purchased from Thermo Fisher Scientific (catalog No. 14190250).

Methods:

Oral Dosing Formulation

The vehicle was prepared by mixing carboxymethyl cellulose and Tween80 to achieve a final solution of 0.5% CMC or 20% HP-β-CD in water. The compounds of the disclosure were weighed out and mixed with the vehicle to yield final working suspensions. Working suspensions of the compounds were prepared once at the beginning of the study, and vortexed and sonicated prior to each dosing to ensure the material was in fine suspension.

Oral Dosing and MDP Administration

Mice were acclimated to the facility for at least 5 days before the start of the study. On day 0, mice were weighed and assigned to groups in a balanced manner to achieve similar average weight across the groups at the start of the study. Oral dosing (p.o.) with the compounds of the disclosure was administered as shown in Table 8. On day 0, hour −1 (1 hours before MDP injection), all mice were given a single p.o. dose with vehicle or a compound of the disclosure. At hour 0 (1 hour after dosing), mice were injected intraperitoneally (IP) with 8 mpk MDP in PBS. Two hours after MDP injection (3 hours after drug treatment), blood was collected via cardiac puncture for all mice into EDTA microtainer collection tubes. Plasma was prepared from blood and stored at −80° C.

Measurement of Plasma MCP-1

MCP-1 levels in mouse plasma were measured using U-PLEX MSD kit according to manufacturer's instructions. A single analysis was performed for each sample. Concentrations were determined relative to a standard calibration curve, and total analyte levels in pg/mL.

The MCP-1 data in pg/mL were normalized in GraphPad Prism 9.2 using the normalize function and entering the 0% and 100% inhibition control groups for the study. 0% inhibition was defined as mean MCP-1 pg/mL in MDP vehicle group, and 100% inhibition was defined as mean MCP-1 pg/mL in the unstimulated vehicle group.

The results are shown in Table 8. In mice treated with MDP, compounds 38, 91, 113, 86, 99, 359, 360, and 581 inhibited production (greater than 50% inhibition) of the cytokine MCP-1.

TABLE 8

| Compound Number | % MCP-1 inhibition | Dose, mg/kg |
|---|---|---|
| 38 | 99 | 10 |
| 83 | no effect | 3 |
| 91 | 99 | 3 |
| 113 | 82 | 10 |
| 86 | 101 | 3 |
| 99 | 111 | 3 |
| 359 | 88 | 10 |
| 360 | 93 | 10 |
| 581 | 75 | 3 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula:

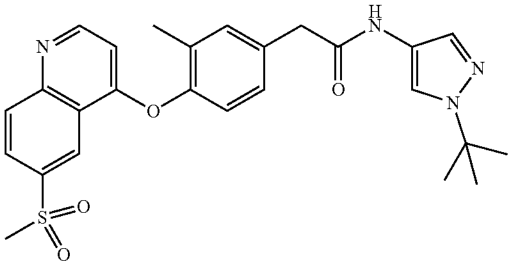 [SMILES: Cc1cc(CC(=O)Nc2cnn(C(C)(C)C)c2)ccc1Oc1ccnc2ccc(S(C)(=O)=O)cc12]

or a pharmaceutically acceptable salt thereof.

2. The compound of claim 1, wherein the compound is an HCl salt of the compound represented by the following structural formula:

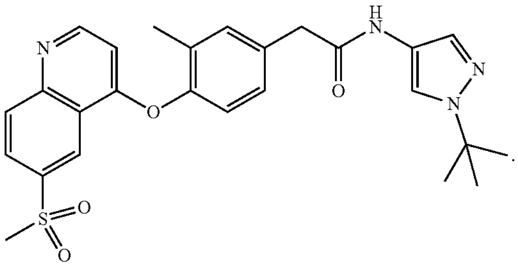 [SMILES: Cc1cc(CC(=O)Nc2cnn(C(C)(C)C)c2)ccc1Oc1ccnc2ccc(S(C)(=O)=O)cc12]

3. A pharmaceutical composition comprising a compound of claim 1 or a pharmaceutically acceptable salt thereof and a pharmaceutically acceptable excipient.

4. A method of treating inflammatory bowel disease (IBD), comprising administering to a subject in need thereof a therapeutically effective amount of a compound represented by the following structural formula:

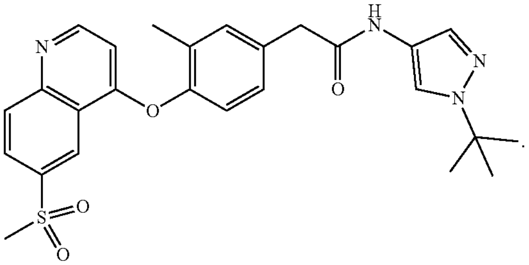 [SMILES: Cc1cc(CC(=O)Nc2cnn(C(C)(C)C)c2)ccc1Oc1ccnc2ccc(S(C)(=O)=O)cc12]

or a pharmaceutically acceptable salt thereof.

5. The method of claim 4, wherein the compound is an HCl salt of the compound represented by the following structural formula:

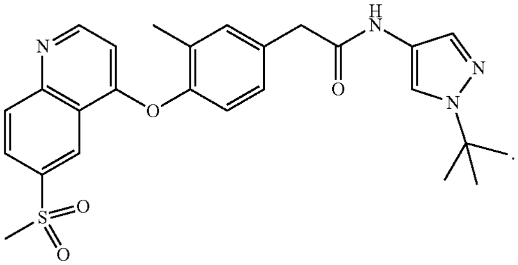 [SMILES: Cc1cc(CC(=O)Nc2cnn(C(C)(C)C)c2)ccc1Oc1ccnc2ccc(S(C)(=O)=O)cc12]

6. The method of claim 4, wherein the IBD is selected from ulcerative colitis, Crohn's disease, early-onset IBD, and extraintestinal IBD.

7. The method of claim 4, wherein the IBD is ulcerative colitis.

8. The method of claim 4, further comprising administering a therapeutically effective amount of an anti-integrin agent.

9. The method of claim 8, wherein the anti-integrin agent is vedolizumab.

10. The method of claim 4, further comprising administering a therapeutically effective amount of a Janus kinase (JAK) inhibitor.

11. The method of claim 10, wherein the JAK inhibitor is tofacitinib.

* * * * *